US010022453B2

(12) United States Patent
Lerchen et al.

(10) Patent No.: US 10,022,453 B2
(45) Date of Patent: Jul. 17, 2018

(54) ANTIBODY DRUG CONJUGATES (ADCS) WITH KINESIN SPINDEL PROTEIN (KSP)

(71) Applicant: BAYER PHARMA AKTIENGESELLSCHAFT, Berlin (DE)

(72) Inventors: Hans-Georg Lerchen, Leverkusen (DE); Sven Wittrock, Lyons (FR); Nils Griebenow, Dormagen (DE); Beatrix Stelte-Ludwig, Wülfrath (DE); Anette Sommer, Berlin (DE); Sandra Berndt, Hohen Neuendorf (DE); Christoph Mahlert, Wuppertal (DE); Mario Lobell, Wuppertal (DE); Carsten Terjung, Bochum (DE); Simone Greven, Dormagen (DE); Yolanda Cancho Grande, Leverkusen (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/105,486

(22) PCT Filed: Dec. 10, 2014

(86) PCT No.: PCT/EP2014/077144
§ 371 (c)(1),
(2) Date: Jun. 16, 2016

(87) PCT Pub. No.: WO2015/096982
PCT Pub. Date: Jul. 2, 2015

(65) Prior Publication Data
US 2016/0346402 A1    Dec. 1, 2016

(30) Foreign Application Priority Data

Dec. 23, 2013    (EP) .................................... 13199358
May 30, 2014    (EP) .................................... 14170585

(51) Int. Cl.
| | | |
|---|---|---|
| A61K 38/00 | (2006.01) | |
| A61K 47/48 | (2006.01) | |
| C07D 403/12 | (2006.01) | |
| C07D 231/12 | (2006.01) | |
| C07D 233/64 | (2006.01) | |
| C07D 403/14 | (2006.01) | |
| C07D 405/12 | (2006.01) | |
| C07D 413/12 | (2006.01) | |
| C07D 207/335 | (2006.01) | |
| C07C 53/18 | (2006.01) | |
| C07D 207/337 | (2006.01) | |

(Continued)

(52) U.S. Cl.
CPC .... *A61K 47/48561* (2013.01); *A61K 47/6803* (2017.08); *A61K 47/6811* (2017.08); *A61K 47/6849* (2017.08); *A61K 47/6851* (2017.08); *C07C 53/18* (2013.01); *C07D 207/335* (2013.01); *C07D 207/337* (2013.01); *C07D 231/12* (2013.01); *C07D 233/64* (2013.01); *C07D 403/12* (2013.01); *C07D 403/14* (2013.01); *C07D 405/12* (2013.01); *C07D 413/12* (2013.01); *C07K 5/06052* (2013.01); *C07K 5/1016* (2013.01); *C07K 16/2863* (2013.01); *C07K 16/2875* (2013.01); *C07K 16/32* (2013.01); *C07K 2317/24* (2013.01); *C07K 2317/565* (2013.01); *C07K 2317/75* (2013.01); *C07K 2317/92* (2013.01)

(58) Field of Classification Search
CPC ........ A61K 47/48384; A61K 47/48415; A61K 47/48561; A61K 47/48569; C07C 53/18; C07D 207/335; C07D 207/337; C07D 231/12; C07D 233/64; C07D 403/12; C07D 403/14; C07D 405/12; C07D 413/12; C07K 16/28
See application file for complete search history.

(56) References Cited

U.S. PATENT DOCUMENTS 4,474,893 A    10/1984 Reading
4,714,681 A    12/1987 Reading
(Continued)

FOREIGN PATENT DOCUMENTS

EP    0 586 002 A2    3/1994
EP    0 712 863 A1    5/1996
(Continued)

OTHER PUBLICATIONS

Ausubel et al., "Current Protocols in Molecular Biology," Green Publishing Associates, Inc. / John Wiley & Sons, Inc., ringbou edition (Dec. 4, 2003), (4755 pages).
International Search Report (PCT/ISA/210) dated Apr. 29, 2015, by the European Patent Office as the International Searching Authority for International Application No. PCT/EP2014/077144.
Written Opinion (PCT/ISA/237) dated Apr. 29, 2015, by the European Patent Office as the International Searching Authority for International Application No. PCT/EP2014/077144.
Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag), (6 pages).
(Continued)

*Primary Examiner* — Marcela M Cordero Garcia
(74) *Attorney, Agent, or Firm* — Buchanan, Ingersoll & Rooney PC

(57) ABSTRACT

The present application relates to novel antibody drug conjugates (ADCs), to active metabolites of these ADCs, to processes for preparing these ADCs, to the use of these ADCs for the treatment and/or prophylaxis of diseases and to the use of these ADCs for preparing medicaments for treatment and/or prevention of diseases, in particular hyperproliferative and/or angiogenic disorders such as, for example, cancer diseases. Such treatments can be carried out as monotherapy or else in combination with other medicaments or further therapeutic measures.

39 Claims, 7 Drawing Sheets

(51) Int. Cl.
*C07K 5/062* (2006.01)
*C07K 5/107* (2006.01)
*C07K 16/28* (2006.01)
*C07K 16/32* (2006.01)
*A61K 47/68* (2017.01)

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,925,648 A | 5/1990 | Hansen et al. | |
| 5,270,163 A | 12/1993 | Gold et al. | |
| 5,573,920 A | 11/1996 | Randle | |
| 5,601,819 A | 2/1997 | Wong et al. | |
| 7,318,924 B2 | 1/2008 | McKenzie et al. | |
| 7,465,449 B2 | 12/2008 | Violette et al. | |
| 7,598,350 B2 | 10/2009 | Liu et al. | |
| 7,628,986 B2 | 12/2009 | Weber et al. | |
| 7,662,581 B1 | 2/2010 | Bussiere et al. | |
| 8,821,850 B2 * | 9/2014 | Yurkovetskiy | A61K 47/48692 424/78.17 |
| 2006/0009472 A1 | 1/2006 | Wang et al. | |
| 2007/0037853 A1 | 2/2007 | Barsanti et al. | |
| 2007/0264253 A1 | 11/2007 | Liu et al. | |
| 2008/0021079 A1 | 1/2008 | Zhou et al. | |
| 2008/0207589 A1 | 8/2008 | Boyce et al. | |
| 2009/0175796 A1 | 7/2009 | Raitano et al. | |
| 2009/0258016 A1 | 10/2009 | Wang et al. | |
| 2011/0003791 A1 | 1/2011 | Boyce et al. | |
| 2012/0189623 A1 | 7/2012 | Boyce et al. | |
| 2013/0017196 A1 | 1/2013 | Wang et al. | |

FOREIGN PATENT DOCUMENTS

| | | |
|---|---|---|
| EP | 0 719 859 A1 | 7/1996 |
| EP | 1 900 750 A1 | 3/2008 |
| EP | 1 911 766 A1 | 4/2008 |
| WO | 90/00786 A1 | 1/1990 |
| WO | 91/00360 A1 | 1/1991 |
| WO | 91/05871 A1 | 5/1991 |
| WO | 92/05793 A1 | 4/1992 |
| WO | 92/08802 A1 | 5/1992 |
| WO | 92/15683 A1 | 9/1992 |
| WO | 93/17715 A1 | 9/1993 |
| WO | 97/08320 A1 | 3/1997 |
| WO | 97/35616 A1 | 10/1997 |
| WO | 99/47554 A1 | 9/1999 |
| WO | 01/09192 A1 | 2/2001 |
| WO | 01/62931 A2 | 8/2001 |
| WO | 02/12501 A2 | 2/2002 |
| WO | 02/077033 A1 | 10/2002 |
| WO | 02/088170 A2 | 11/2002 |
| WO | 02/092771 A2 | 11/2002 |
| WO | 02/100348 A2 | 12/2002 |
| WO | 03/040979 A1 | 5/2003 |
| WO | 03/049527 A2 | 6/2003 |
| WO | 03/060064 A2 | 7/2003 |
| WO | 03/083041 A2 | 10/2003 |
| WO | 03/106495 A2 | 12/2003 |
| WO | 2004/056847 A2 | 7/2004 |
| WO | 2004/091375 A2 | 10/2004 |
| WO | 2004/100873 A2 | 11/2004 |
| WO | WO 2004/100873 A2 | 11/2004 |
| WO | 2005/009369 A2 | 2/2005 |
| WO | 2005/010151 A2 | 2/2005 |
| WO | 2005/051922 A1 | 6/2005 |
| WO | 2005/056606 A2 | 6/2005 |
| WO | 2005/081711 A2 | 9/2005 |
| WO | 2005/081854 A2 | 9/2005 |
| WO | 2005/090407 A1 | 9/2005 |
| WO | 2006/002236 A1 | 1/2006 |
| WO | 2006/002326 A2 | 1/2006 |
| WO | WO 2006/002236 A1 | 1/2006 |
| WO | 2006/044825 A2 | 4/2006 |
| WO | 2006/060737 A2 | 6/2006 |
| WO | 2006/062779 A2 | 6/2006 |
| WO | 2006/066896 A2 | 6/2006 |
| WO | 2006/074418 A2 | 7/2006 |
| WO | 2006/089232 A2 | 8/2006 |
| WO | 2006/100036 A1 | 9/2006 |
| WO | 2007/021794 A1 | 2/2007 |
| WO | WO 2007/021794 A1 | 2/2007 |
| WO | 2007/024536 A2 | 3/2007 |
| WO | 2007/038637 A2 | 4/2007 |
| WO | 2007/070538 A2 | 6/2007 |
| WO | 2008/004834 A1 | 1/2008 |
| WO | 2008/028686 A2 | 3/2008 |
| WO | 2008/031056 A2 | 3/2008 |
| WO | 2008036688 A2 | 3/2008 |
| WO | 2008/047242 A2 | 4/2008 |
| WO | 2008/070593 A2 | 6/2008 |
| WO | 2008/086122 A2 | 7/2008 |
| WO | 2008/092117 A2 | 7/2008 |
| WO | WO 2008/086122 A2 | 7/2008 |
| WO | 2008/140603 A2 | 11/2008 |
| WO | 2009/020933 A2 | 2/2009 |
| WO | 2009/023265 A1 | 2/2009 |
| WO | 2009/026274 A1 | 2/2009 |
| WO | 2009/033094 A2 | 3/2009 |
| WO | 2009/068204 A1 | 6/2009 |
| WO | 2009/080829 A1 | 7/2009 |
| WO | 2009/080830 A1 | 7/2009 |
| WO | 2009/123894 A2 | 10/2009 |
| WO | 2009/140177 A2 | 11/2009 |
| WO | 2010/022736 A2 | 3/2010 |
| WO | WO2010/084186 * 7/2010 | ........... C07D 233/64 |
| WO | 2011/044368 A1 | 4/2011 |
| WO | 01/88138 A1 | 11/2011 |
| WO | 2012/143499 A2 | 10/2012 |
| WO | 2012/171020 A1 | 12/2012 |

OTHER PUBLICATIONS

Brown et al., "TWEAK Binding to the Fn14 Cysteine-Rich Domain Depends on Charged Residues Located in Both the A1 and D2 Modules," Biochemical Journal, (Jul. 2006), vol. 397, No. 2, pp. 297-304.

Clackson et al., "Making Antibody Fragments using Phage Display Libraries," Nature, (Aug. 15, 1991), vol. 352, No. 6336, pp. 624-628.

Culp et al., "Antibodies to TWEAK Receptor Inhibit Human Tumor Growth Through Dual Mechanisms," Clinical Cancer Research, (Jan. 15, 2010), vol. 16, No. 2, pp. 497-508.

Delfourne et al., "Synthesis and in Vitro Antitumor Activity of Phenanthrolin-7-one Derivatives, Analogues of the Marine Pyridoacridine Alkaloids Ascididemin and Meridine:Structure-Activity Relationship," Journal of Medicinal Chemistry, (2003), vol. 46, No. 16, pp. 3536-3545.

Donohue et al., "TWEAK Is an Endothelial Cell Growth and Chemotactic Factor That Also Potentiates FGF-2 and VEGF-A Mitogenic Activity," Arteriosclerosis, Thrombosis, and Vascular Biology, (Apr. 2003), vol. 23, Issue 4, pp. 594-600.

Doronina et al., "Development of Potent Monoclonal Antibody Auristatin Conjugates for Cancer Therapy," Nature Biotechnology, (Jul. 2003), vol. 21, No. 7, pp. 778-784.

Dubowchik et al., "Cathepsin B-Sensitive Dipeptide Prodrugs. 1. A Model Study of Structural Requirements for Efficient Release of Doxorubicin," Bioorganic & Medicinal Chemistry Letters, (1998), vol. 8, No-23, pp. 3341-3346.

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chemistry, (2002), vol. 13, No. 4, pp. 855-869.

Ducry et al., "Antibody-Drug Conjugates: Linking Cytotoxic Payloads to Monoclonal Antibodies," Bioconjugate Chemistry, (2010), vol. 21, No. 1, pp. 5-13.

Gebauer et al., "Engineered Protein Scaffolds as Next-Generation Antibody Therapeutics," Current Opinion in Chemical Biology, (2009), vol. 13, No. 3, pp. 245-255.

(56) References Cited

OTHER PUBLICATIONS

Harlow et al., (Monoclonal Antibodies: A Laboratory Manual, Cold Spring Harbor Laboratory Press (19881, Paul [Ed.]); Fundamental Immunology, (Lippincott Williams & Wilkins (1998), (9 pages).
Hoet et al., "Generation of High-Affinity Human Antibodies by Combining Donor-Derived and Synthetic Complementarity-Determining-Region Diversity," Nature Biotechnology, (Mar. 2005), vol. 23, No. 3, pp. 344-348.
Hoogenboom, "Selecting and Screening Recombinant Antibody Libraries," Nature Biotechnology, (Sep. 2005), vol. 23, No. 9, pp. 1105-1116.
Junutula et al., "Site-Specific Conjugation of a Cytotoxic Drug to an Antibody Improves the Therapeutic Index," Nature Biotechnology, (Aug. 2008), vol. 26, No. 8, pp. 925-932.
Kabat et al., "Sequences of Proteins of Immunological Interest," 5th Ed. Public Health Service, National Institutes of Health, Bethesda, MD. (1991), vol. 1, (12 pages).
Keefe et al., "Aptamers as Therapeutics," Nature Reviews Drug Discovery, (Jul. 2010), vol. 9, No. 7, pp. 537-550.
Kostelny et al., "Formation of a Bispecific Antibody by the use of Leucine Zippers," The Journal of Immunology, (Mar. 1, 1992), vol. 148, No. 5, pp. 1547-1553.
Lambert, "Drug-Conjugated Monoclonal Antibodies for the Treatment of Cancer," Current Opinion in Pharmacology, (2005), vol. 5, No. 5, pp. 543-549.
Lonberg et al., "Human Antibodies from Transgenic Mice," International reviews of immunology, (1995), vol. 13, No. 1, pp. 65-93.
Mayer et al., "Small Molecule Inhibitor of Mitotic Spindle Bipolarity Identified in a Phenotype-Based Screen," Science, (Oct. 29, 1999), vol. 286, No. 5441, pp. 971-974.
Michaelson et al., "Development of an Fn14 Agonistic Antibody as an Anti-Tumor Agent," mAbs, (Jul.-Aug. 2011), vol. 3 Issue 4, pp. 362-375.
Nakayama et al., "Characterization of Murine TWEAK and its Receptor (Fn14) by Monoclonal Antibodies," Biochemical and Biophysical Research Communications, (2003), vol. 306, Issue 4, pp. 819-825.
Nuttall et al., "Display Scaffolds: Protein Engineering for Novel Therapeutics," Current Opinion in Pharmacology, (2008), vol. 8, No. 5, pp. 609-615.
Tao et al., "Induction of Apoptosis by Inhibitor of the Mitotic Kinesin KSP Requires both Activation of the Spindle Assembly Checkpoint and Mitotic Slippage," Cancer Cell, (Jul. 2005), vol. 8, No. 1, pp. 49-59.
Tom et al., Kapitel 12 in Methods Express: Expression Systems herausgegeben von Micheal R. Dyson and Yves Durocher, Scion Publishing Ltd, 2007 (siehe AK-Beispiel 1), (32 pages).
Troutman et al., "Novel Experimental Parameters to Quantify the Modulation of Absorptive and Secretory Transport of Compounds by P-Glycoprotein in Cell Culture Models of Intestinal Epithelium," Pharmaceutical Research, (Aug. 2003), vol. 20, No. 8, pp. 1210-1224.
Tutt et al., "Trispecific F(ab')3 Derivatives that use Cooperative Signaling Via the TCR/CD3 Complex and CD2 to Activate and Redirect Resting Cytotoxic T Cells," The Journal of Immunology, (Jul. 1, 1991), vol. 147, No. 1, pp. 60-69.
Wiley et al., "A Novel TNF Receptor Family Member Binds TWEAK and Is Implicated in Angiogenesis," Immunity (Nov. 2001), vol. 15, Issue 5, pp. 837-846.
Wu et al., "Arming Antibodies: Prospects and Challenges for Immunoconjugates," Nature Biotechnology, (Sep. 2005), vol. 23, No. 9, pp. 1137-1146.
Notification of Transmittal of the International Search Report (Forms PCT/ISA/220 and PCT/ISA/210) and the Written Opinion of the International Searching Authority (Form PCT/ISA/237) dated Apr. 29, 2015, by the European Patent Office in corresponding International Application No. PCT/EP2014/077144 with English Translation of the International Search Report and Written Opinion of the International Searching Authority. (23 pages).
Olsson et al., "Human-Human Monoclonal Antibody-Producing Hybridomas: Technical Aspects," Methods in Enzymology, (1983), vol. 92, pp. 3-16.
Pellegrini et al., "Structure of the Extracellular Domains of Human and Xenopus Fn14: Implications in the Evolution of TWEAK and Fn14 Interactions," The FEBS Journal, (2013), vol. 280, No. 8, pp. 1818-1829.
Peterson et al., "Cathepsin Substrates as Cleavable Peptide Linkers in Bioconjugates, Selected from a Fluorescence Quench Combinatorial Library," Bioconjugate Chemistry, (1998), vol. 9, No. 5, pp. 618-626.
Polson et al., "Antibody-Drug Conjugates Targeted to CD79 for the Treatment of non-Hodgkin Lymphoma," Blood, (Jul. 15, 2007), vol. 110, No. 2, pp. 616-623.
Polson et al., "Antibody-Drug Conjugates for the Treatment of Non-Hodgkin's Lymphom: Target and Linker-Drug Selection," Cancer Research, (Mar. 15, 2009), vol. 69, No. 6, pp. 2358-2364.
Queen et al., "A Humanized Antibody that Binds to the Interleukin 2 Receptor," Proceedings of the National Academy of Sciences of the United States of America, (Dec. 1989), vol. 86, No. 24, pp. 10029-10033.
Sambrook et al., (Molecular Cloning: A Laboratory Manual, (Second Edition, Cold Spring Harbor Laboratory Press; Cold Spring Harbor, N.Y.; 1989) vol. 1-3), (12 pages).
Schinkel et al., "Absence of the mdr1a P-Glycoprotein in Mice Affects Tissue Distribution and Pharmacokinetics of Dexamethasone, Digoxin, and Cyclosporin A," The Journal of Clinical Investigation, (Oct. 1995), vol. 96, No. 4, pp. 1698-1705.
Schwab et al., "Comparision of in Vitro P-Glycoprotein Screening Assays: Recommendations for Their Use in Drug Discovery," Journal of Medicinal Chemistry, (2003), vol. 46, No. 9, pp. 1716-1725.
Senter, "Potent Antibody Drug Conjugates for Cancer Therapy," Current Opinion in Chemical Biology, (2009), vol. 13, No. 3, pp. 235-244.
Söderlind et al., "Recombining Germline-Derived CDR Sequences for Creating Diverse Single-Framework Antibody Libraries," Nature Biotechnology, (Aug. 2000), vol. 18, No. 8, pp. 852-856.

\* cited by examiner

Fig. 1:

```
         34        40         50         60        68
Human    APCSRGSSWSADLDKCMDCASCRARPHSDFCLGCA
Rat      APCSSGSSWSADLDKCMDCASCPARPHSDFCLGCA
Mac      APCSHGSSWSADLDKCMDCASCRARPHSDFCLGCS
Pig      TPCSRGSSWSADLDKCMDCASCPARPHSDFCLGCA
Mouse    SPCSSGSSWSADLDKCMDCASCPARPHSDFCLGCA
Dog      TPCPRGSSWSADLDKCMDCASCRARPHSDFCLGCT
              ^         ^
```

A

B

ANTIBODY DRUG CONJUGATES (ADCS) WITH KINESIN SPINDLE PROTEIN (KSP)

INTRODUCTION AND STATE OF THE ART

The invention relates to antibody drug conjugates (ADCs) of kinesin spindle protein inhibitors, to active metabolites of these ADCs, to processes for preparing these ADCs, to the use of these ADCs for the treatment and/or prophylaxis of diseases and to the use of these ADCs for preparing medicaments for treatment and/or prevention of diseases, in particular hyperproliferative and/or angiogenic disorders such as, for example, cancer diseases. Such treatments can be carried out as monotherapy or else in combination with other medicaments or further therapeutic measures.

Cancer diseases are the consequence of uncontrolled cell growth of the most diverse tissues. In many cases, the new cells penetrate into existing tissue (invasive growth), or they metastase into remote organs. Cancer diseases occur in the most diverse organs and often have tissue-specific courses of the disease. The term cancer as a generic term therefore describes a large group of defined diseases of various organs, tissue and cell types.

Tumours in early stages can possibly be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins with one or more active compound molecules are known, in particular in the form of antibody drug conjugates (ADCs) in which an internalising antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophor molecules are attached via a polymeric linker to an antibody. As possible toxophors, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject of a number of patent applications (e.g. WO2006/044825; WO2006/002236; WO2005/051922; WO2006/060737; WO03/060064; WO03/040979; and WO03/049527). However, since KSP unfolds its action only during a relatively short period of time during the mitosis phase, KSP inhibitors have to be present in a sufficiently high concentration during these initial phases.

SUMMARY OF THE INVENTION

Against this background it is an object of the present invention to provide substances which, after administration at a relatively low concentration, unfold apoptotic action and may therefore be of benefit for cancer therapy.

To achieve this object, the invention provides conjugates of a binder or derivatives thereof with one or more active compound molecules, the active compound molecule being a kinesin spindle protein inhibitor (KSP inhibitor) attached to the binder via a linker L. The binder is preferably a binder protein or peptide, particularly preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2090, or the anti-EGFR antibodies cetuximab or nimotuzumab.

The inventors have found a number of ways to attach the binder to the KSP inhibitor in order to achieve the object mentioned above.

According to the invention, the kinesin spindle protein inhibitors may have the substructure I(sub) below:

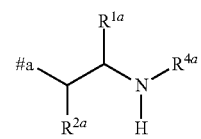

I(sub)

where
a represents a bond to the remainder of the molecule;
$R^{1a}$ represents H or $-(CH_2)_{0-3}Z$, where Z represents —H, halogen, $-OY^3$, $-SY^3$, $-NHY^3$, $-CO-NY^1Y^2$ or $-CO-OY^3$,
where $Y^1$ and $Y^2$ independently of one another represent H, $NH_2$, $-(CH_2CH_2O)_{0-3}-(CH_2)_{0-3}Z'$ (e.g. $-(CH_2)_{0-3}Z'$) or $-CH(CH_2W)Z'$, and $Y^3$ represents H or $-(CH_2)_{0-3}Z'$, where $Z'$ represents H, $SO_3H$, $NH_2$, COOH, $-NH-CO-CH_2-CH_2-CH(NH_2)COOH$ or $-(CO-NH-CHY^4)_{1-3}COOH$, where W represents H or OH, where $Y^4$ independently of one another represents straight-chain or branched $C_{1-6}$-alkyl which is optionally substituted by $-NHCONH_2$, or represents aryl or benzyl which are optionally substituted by $-NH_2$;
$R^{2a}$ and $R^{4a}$ independently of one another represent H, $-CO-CHY^4-NHY^5$ or $-(CH_2)_{0-3}Z$, or $R^{2a}$ and $R^{4a}$ together represent (with formation of a pyrrolidine ring) $-CH_2-CHR^{10}-$ or $-CHR^{10}-CH_2-$, where $R^{10}$ represents H, $NH_2$, COOH, $SO_3H$, SH or OH, and where Z represents $-H$, $-OY^3$, $-SY^3$, $-NHY^3$, $-CO-NY^1Y^2$ or $-CO-OY^3$,
where $Y^1$ and $Y^2$ independently of one another represent H, $NH_2$ or $-(CH_2)_{0-3}Z'$, and $Y^3$ represents H or $-(CH_2)_{0-3}Z'$, where $Z'$ represents H, $SO_3H$, $NH_2$ or COOH;

where $Y^4$ independently of one another represents straight-chain or branched $C_{1-6}$-alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched $C_{1-6}$-alkyl.

According to the invention, the kinesin spindle protein inhibitor may be attached to the binder via a linker by substitution of a hydrogen atom at $R^{1a}$, $R^{2a}$, $R^{4a}$ or $R^{10}$.

The KSP inhibitor which is attached to this binder (or the KSP inhibitors, since frequently more than one KSP inhibitor is attached to the binder), is preferably a compound of the formula (Ia) or (IIa) below:

Formula (Ia):

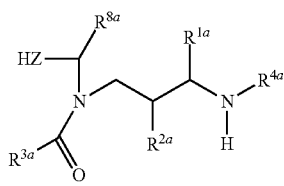

(Ia)

where
$R^{1a}$ represents H, -MOD or —(CH$_2$)$_{0-3}$Z, where Z represents —H, halogen, —OY$^3$, —SY$^3$, —NHY$^3$, —CO—NY$^1$Y$^2$ or —CO—OY$^3$,
where $Y^1$ and $Y^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and $Y^3$ represents H or —(CH$_2$)$_{0-3}$Z', where Z' represents H, SO$_3$H, NH$_2$, COOH, —NH—CO—CH$_2$—CH$_2$—CH(NH$_2$)COOH or —(CO—NH—CHY$^4$)$_{1-3}$COOH, where W represents H or OH,
where $Y^4$ independently of one another represents straight-chain or branched $C_{1-6}$-alkyl which is optionally substituted by —NHCONH$_2$, or represents aryl or benzyl which are optionally substituted by —NH$_2$;
$R^{2a}$ and $R^{4a}$ independently of one another represent H, —CO—CHY$^4$—NHY$^5$ or —(CH$_2$)$_{0-3}$Z, or $R^{2a}$ and $R^{4a}$ together (with formation of a pyrrolidine ring) represent —CH$_2$—CHR$^{10}$— or —CHR$^{10}$—CH$_2$—, where $R^{10}$ represents H, SO$_3$H, NH$_2$, COOH, SH or OH,
where Z represents —H, halogen, —OY$^3$, —SY$^3$, NHY$^3$, —CO—NY$^1$Y$^2$ or —CO—OY$^3$,
where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;
where $Y^4$ independently of one another represents straight-chain or branched $C_{1-6}$ alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched $C_{1-6}$-alkyl;
$R^{3a}$ represents -MOD or an optionally substituted alkyl, cycloalkyl, aryl, heteroaryl, heteroalkyl or heterocycloalkyl group,
preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z' and $Y^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents $C_{1-10}$-alkyl);
$R^{8a}$ represents $C_{1-10}$-alkyl or —(CH$_2$)$_{0-2}$—(HZ$^2$), where HZ$^2$ represents a 4- to 7-membered heterocycle having up to two heteroatoms selected from the group consisting of N, O and S; HZ represents a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen;
where -MOD represents —(NR$^{10}$)$_n$-(G1)$_o$-G2-H, where $R^{10}$ represents H or $C_1$-$C_3$-alkyl;
G1 represents —NHCO—, —CONH— or

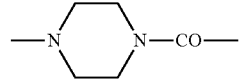

(where, if G1 represents —NHCO— or

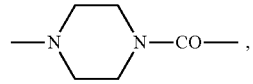

$R^{10}$ does not represent NH$_2$);
n is 0 or 1;
o is 0 or 1; and
G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, $C_1$-$C_{10}$-alkyl, $C_2$-$C_{10}$-alkenyl or $C_2$-$C_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, $C_1$-$C_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;
where the kinesin spindle protein inhibitor is attached to the linker by substitution of a hydrogen atom at $R^{1a}$, $R^{2a}$, $R^{3a}$, $R^{4a}$, $R^{8a}$ or $R^{10}$ optionally via one of the substituents of HZ, in particular via $R^{1a}$, $R^{2a}$, $R^{3a}$, $R^{4a}$ or $R^{10}$,
and the salts, solvates and salts of the solvates thereof.

Formula (IIa):

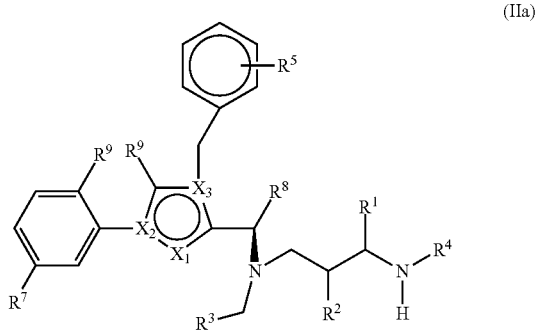

where
$X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH, $X_2$ represents N and $X_3$ represents C
(with $X_1$ representing CH, $X_2$ representing C and $X_3$ representing N being preferred);
$R^1$ represents H, —L-#$^1$, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH,
where Y$^4$ independently of one another represents straight-chain or branched C$_{1-6}$-alkyl which is optionally substituted by —NHCONH$_2$, or represents aryl or benzyl which are optionally substituted by —NH$_2$;
$R^2$ represents —L-#$^1$, H, -MOD, —CO—CHY$^4$—NHY$^5$ or —(CH$_2$)$_{0-3}$Z, or $R^2$ and $R^4$ together (with formation of a pyrrolidine ring) represent —CH$_2$—CHR$^{10}$— or —CHR$^{10}$—CH$_2$—, where R$^{10}$ represents L-#$^1$, H, NH$_2$, SO$_3$H, COOH, SH, or OH;
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
$R^4$ represents —L-#$^1$, H, —CO—CHY$^4$—NHY$^5$ or —(CH$_2$)$_{0-3}$Z,
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
or $R^2$ and $R^4$ together (with formation of a pyrrolidine ring) represent —CH$_2$—CHR$^{10}$— or —CHR$^{10}$—CH$_2$—, where R$^{10}$ represents L-#1, H, NH$_2$, SO$_3$H, COOH, SH or OH;
A represents CO, SO, SO$_2$, SO$_2$NH or CNNH;
$R^3$ represents —L-#$^1$, -MOD or an optionally substituted alkyl, cycloalkyl, aryl, heteroaryl, heteroalkyl, heterocycloalkyl group, preferably —L-#$^1$ or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents C$_{1-10}$-alkyl);
$R^5$ represents —L-#$^1$, H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
$R^6$ and $R^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br),
$R^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, CO$_2$H or NH$_2$ or;
where one or none of the substituents $R^1$, $R^2$, $R^3$, $R^4$ $R^5$, $R^8$ and $R^{10}$ represents or (in the case of $R^8$) contains —L-#$^1$,
L represents the linker and #$^1$ represents the bond to the binder or derivative thereof, where -MOD represents —(NR$^{10}$)$_n$-(G1)$_o$-G2-H, where
$R^{10}$ represents H or C$_1$-C$_3$-alkyl;
G1 represents —NHCO—, —CONH— or

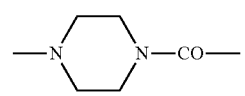

(where, if G1 represents —NHCO— or

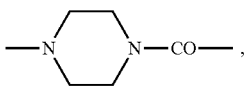

R$^{10}$ does not represent NH$_2$);
n is 0 or 1;
o is 0 or 1; and
G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

and the salts, solvates and salts of the solvates thereof.

The conjugates according to the invention can have chemically labile linkers, enzymatically labile linkers or stable linkers. Particular preference is given to stable linkers and linkers which can be cleaved by cathepsin.

The invention furthermore provides processes for preparing the conjugates according to the invention, and also precursors and intermediates for the preparation.

The preparation of the conjugates according to the invention regularly comprises the following steps:
(i) Preparation of a linker precursor which optionally carries protective groups and has a reactive group which is capable of coupling to the binder;
(ii) Conjugation of the linker precursor to the derivative, which optionally carries protective groups, of a low-molecular weight KSP inhibitor (preferably a KSP inhibitor having the substructure I(sub), particularly preferably of formula (Ia) and in particular of formula (IIa), where in these formulae there is as yet no bond to a linker), giving a reactive KSP inhibitor/linker conjugate which optionally carries protective groups;
(iii) Removal of any protective groups present in the KSP inhibitor/linker conjugate and
(iv) Conjugation of the binder to the KSP inhibitor/linker conjugate, giving the binder/KSP inhibitor conjugate according to the invention.

Attachment of the reactive group may also take place after the construction of an optionally protected KSP inhibitor/linker precursor conjugate.

Depending on the linker, succinimide-linked ADCs may, after conjugation, be converted according to Scheme 26 into the open-chain succinamides, which have an advantageous stability profile.

As illustrated above, conjugation of the linker precursor to a low-molecular weight KSP inhibitor may take place by substitution of a hydrogen atom at R$^{1a}$, R$^{2a}$, R$^{4a}$ or R$^{10}$ in substructure I(sub), R$^{1a}$, R$^{2a}$, R$^{3a}$, R$^{4a}$, R$^{8a}$ or R$^{10}$ in formula (Ia), or R$^1$, R$^2$, R$^3$, R$^4$, R$^5$, R$^8$ or R$^{10}$ in formula (IIa) by the linker. In the synthesis steps prior to the conjugation, any functional groups present may also be present in protected form. Prior to the conjugation step, these protective groups are removed by known methods of peptide chemistry. Conjugation can take place chemically by various routes, as shown in an exemplary manner in Schemes 7 to 31 in the examples. In particular, it is optionally possible to modify the low-molecular weight KSP inhibitor for conjugation to the linker, for example by introduction of protective groups or leaving groups to facilitate substitution.

In particular, the invention provides novel low-molecular weight KSP inhibitors which may optionally be conjugated to a binder. These KSP inhibitors or their binder conjugates have the following general formula (IIIa):

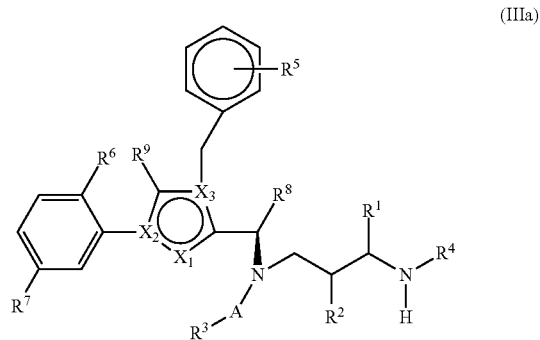

(IIIa)

where
X$_1$ represents N, X$_2$ represents N and X$_3$ represents C; or
X$_1$ represents N, X$_2$ represents C and X$_3$ represents N; or
X$_1$ represents CH or CF, X$_2$ represents C and X$_3$ represents N; or
X$_1$ represents NH, X$_2$ represents C and X$_3$ represents C; or
X$_1$ represents CH, X$_2$ represents N and X$_3$ represents C
(with X$_1$ representing CH, X$_2$ representing C and X$_3$ representing N being preferred);
R$^1$ represents H, -L-BINDER, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH,
where Y$^4$ independently of one another represents straight-chain or branched C$_{1-6}$-alkyl which is optionally substituted by —NHCONH$_2$, or represents aryl or benzyl which are optionally substituted by —NH$_2$;
R$^2$ represents -L-BINDER, H, -MOD, —CO—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—, where R$^{10}$ represents L-#$^1$, H, NH$_2$, SO$_3$H, COOH, SH, or OH;
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y⁴ independently of one another represents straight-chain or branched $C_{1-6}$ alkyl which is optionally substituted by —NHCONH₂, or represents aryl or benzyl which are optionally substituted by —NH₂, and Y⁵ represents H or —CO—CHY⁶—NH₂, where Y⁶ represents straight-chain or branched $C_{1-6}$-alkyl;

R⁴ represents -L-BINDER, H, —CO—CHY⁴—NHY⁵ or —(CH₂)$_{0-3}$Z, where Z represents —H, halogen, —OY³, —SY³, NHY³, —CO—NY¹Y² or —CO—OY³, where Y¹ and Y² independently of one another represent H, NH₂ or —(CH₂)$_{0-3}$Z', and Y³ represents H or —(CH₂)$_{0-3}$Z', where Z' represents H, SO₃H, NH₂ or COOH;

where Y⁴ independently of one another represents straight-chain or branched $C_{1-6}$ alkyl which is optionally substituted by —NHCONH₂, or represents aryl or benzyl which are optionally substituted by —NH₂, and Y⁵ represents H or —CO—CHY⁶—NH₂, where Y⁶ represents straight-chain or branched $C_{1-6}$-alkyl;

or R² and R⁴ together (with formation of a pyrrolidine ring) represent —CH₂—CHR¹⁰— or —CHR¹⁰—CH₂—, where R¹⁰ represents -L-BINDER, H, NH₂, SO₃H, COOH, SH or OH;

A represents CO, SO, SO₂, SO₂NH or CNNH;

R³ represents -L-BINDER, -MOD or an optionally substituted alkyl, cycloalkyl, aryl, heteroaryl, heteroalkyl, heterocycloalkyl group, preferably -L-BINDER, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO₂—NH-alkyl groups, 1-3 —NH-alkyl groups, 1-3 —N(alkyl)₂ groups, 1-3 —NH₂ groups or 1-3 —(CH₂)$_{0-3}$Z groups, where Z represents —H, halogen, —OY³, —SY³, —NHY³, —CO—NY¹Y² or —CO—OY³, where Y¹ and Y² independently of one another represent H, NH₂ or —(CH₂)$_{0-3}$Z' and Y³ represents H, —(CH₂)$_{0-3}$—CH(NHCOCH₃)Z', —(CH₂)$_{0-3}$—CH(NH₂)Z' or —(CH₂)$_{0-3}$Z', where Z' represents H, SO₃H, NH₂ or COOH (where "alkyl" preferably represents $C_{1-10}$-alkyl);

R⁵ represents -L-BINDER, H, NH₂, NO₂, halogen (in particular F, Cl, Br), —CN, CF₃, —OCF₃, —CH₂F, —CH₂F, SH or —(CH₂)$_{0-3}$Z, where Z represents —H, —OY³, —SY³, halogen, NHY³, —CO—NY¹Y² or —CO—OY³, where Y¹ and Y² independently of one another represent H, NH₂ or —(CH₂)$_{0-3}$Z', and Y³ represents H or —(CH₂)$_{0-3}$Z', where Z' represents H, SO₃H, NH₂ or COOH;

R⁸ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —(CH₂)$_{0-2}$—(HZ²), where HZ² represents a 4- to 7-membered heterocycle having up to two heteroatoms selected from the group consisting of N, O and S (preferably oxetane), where each of these groups may be substituted by —OH, CO₂H or NH₂ or -L-BINDER;

where L represents a linker and BINDER represents a binder or a derivative thereof, where the binder may optionally be attached to a plurality of active compound molecules, where at most one representative of R¹, R², R³, R⁴, R⁵, R⁸ and R¹⁰ represents -L-binder;

R⁶ and R⁷ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, NO₂, NH₂, COOH or halogen (in particular F, Cl, Br), where -MOD represents —(NR¹⁰)$_n$-(G1)$_o$-G2-H, where R¹⁰ represents H or $C_1$-$C_3$-alkyl;

G1 represents —NHCO—, —CONH— or

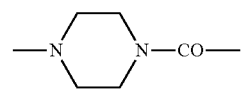

(where, if G1 represents —NHCO— or

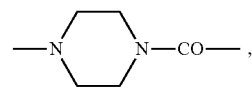

R¹⁰ does not represent NH₂);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, SO₂, —NR$^y$—, —NR$^y$CO—, CONR$^y$—, —NR$^y$NR$^y$—, —SO₂NR$^y$NR$^y$—, —CONR$^y$NR$^y$— (where R$^y$ represents H, phenyl, $C_1$-$C_{10}$-alkyl, $C_2$-$C_{10}$-alkenyl or $C_2$-$C_{10}$-alkynyl, each of which may be substituted by —NHCONH₂, —COOH, —OH, —NH₂, NH—CNNH₂, sulphonamide, sulphone, sulphoxide or sulphonic acid), —CO—, —CR$^z$=N—O— (where R$^x$ represents H, $C_1$-$C_3$-alkyl or phenyl), where the hydrocarbon chain including any side chains may be substituted by —NHCONH₂, —COOH, —OH, —NH₂, NH—CNNH₂, sulphonamide, sulphone, sulphoxide or sulphonic acid, where the group -MOD preferably has at least one group —COOH;

and the salts, solvates and salts of the solvates thereof.

DESCRIPTION OF THE FIGURES

FIG. 1: Alignment of the TWEAKR cysteine-rich domain (amino acids 34 to 68) of various species. (The numbers show the amino acid position in full-length constructs including the signal sequences; SEQ ID NO: 169).

B— Amino acid sequence of the extracellular domain: It has been published that the amino acid 64 is essential for TWEAK ligand binding; and the amino acid 47 is essential for binding of the antibodies according to the invention, as was determined here.

Figure 3:
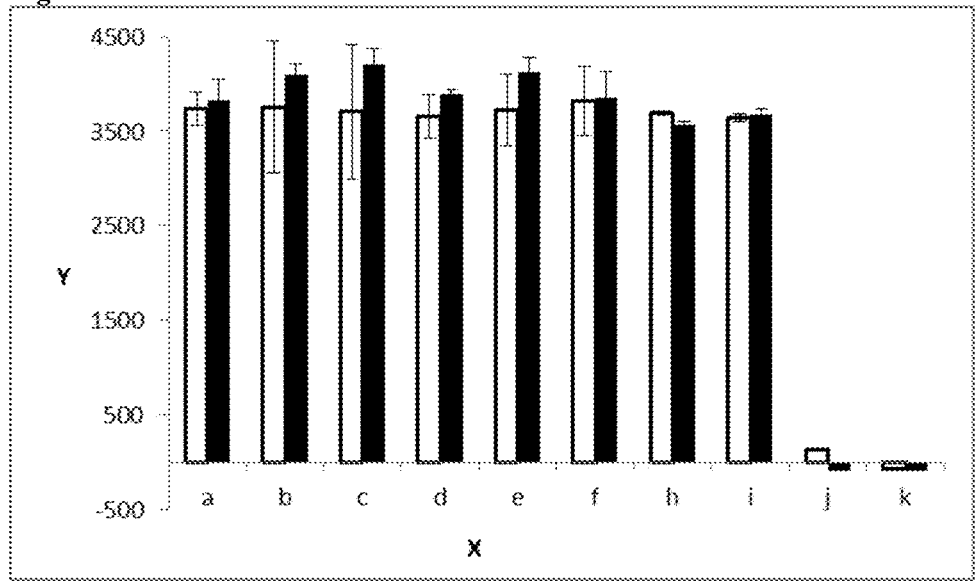

FIG. 3: Interaction of the TWEAKR ectodomain with antibodies and reference antibodies. What is shown is the result of an ELISA with TWEAKR-Fc fusion protein coating (TPP-2202, 1 µg/ml) and with 0.08 µg/ml (open bars) and 0.03 µ/ml (solid bars) of biotinylated IgG as soluble binding partner. Detection was carried out using streptavidin-HRP and Amplex Red substrate. Y is the "ELISA signal intensity [Rfu]"; X are the "tested antibody constructs": a is "TPP-2090"; b is "TPP-2084"; c is "PDL-192(TPP-1104)"; d is "P4A8(TPP-1324)"; e is "P3G5(TPP-2195)"; f is "136.1 (TPP-2194)"; h is "ITEM1"; i is "ITEM4"; j is a mouse isotype control; k is a human isotype control. All antibodies examined show saturated binding at a concentration of 80 ng/ml.

Figure 4:
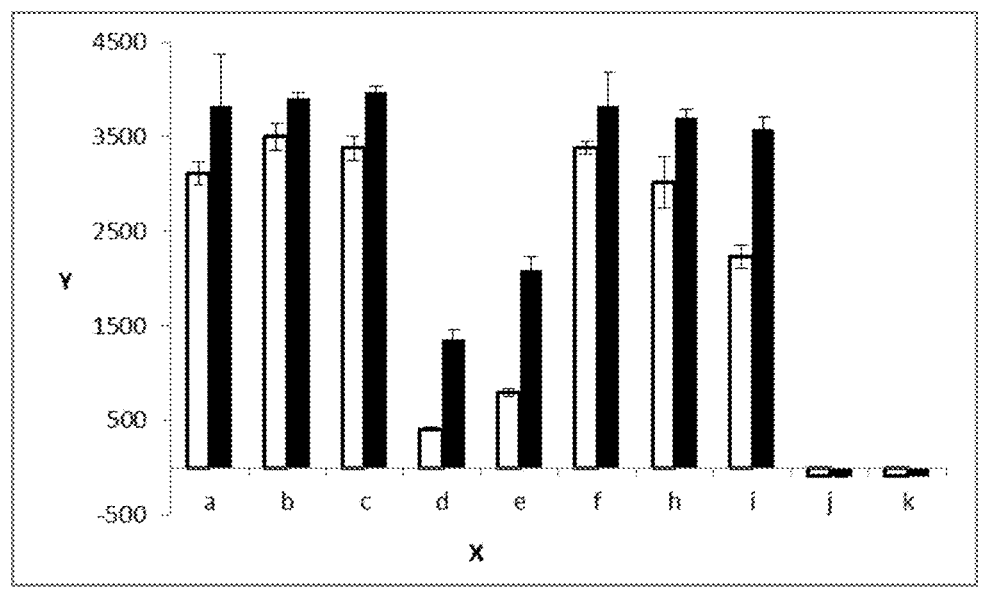

FIG. 4: Interaction of the cysteine-rich domain of TWEAKR with antibodies according to the invention and reference antibodies. What is shown is the result of an ELISA with TWEAKR (34-68)-Fc fusion protein coating (TPP-2203, 1 µg/ml) and 0.08 µg/ml (open bars) and 0.3 µ/ml (solid bars) of biotinylated IgG as soluble binding partner. Detection was carried out using streptavidin-HRP and Amplex Red substrate. X are the "antibody constructs tested": a is "TPP-2090"; b is "TPP-2084"; c is "PDL-192 (TPP-1104)"; d is "P4A8(TPP-1324)"; e is "P3G5(TPP-2195)"; f is "136.1(TPP-2194)"; h is "ITEM1"; i is "ITEM4"; j is a mouse isotype control; k is a human isotype control. All antibodies examined show saturated binding at a concentration of 80 ng/ml.

Figure 5:
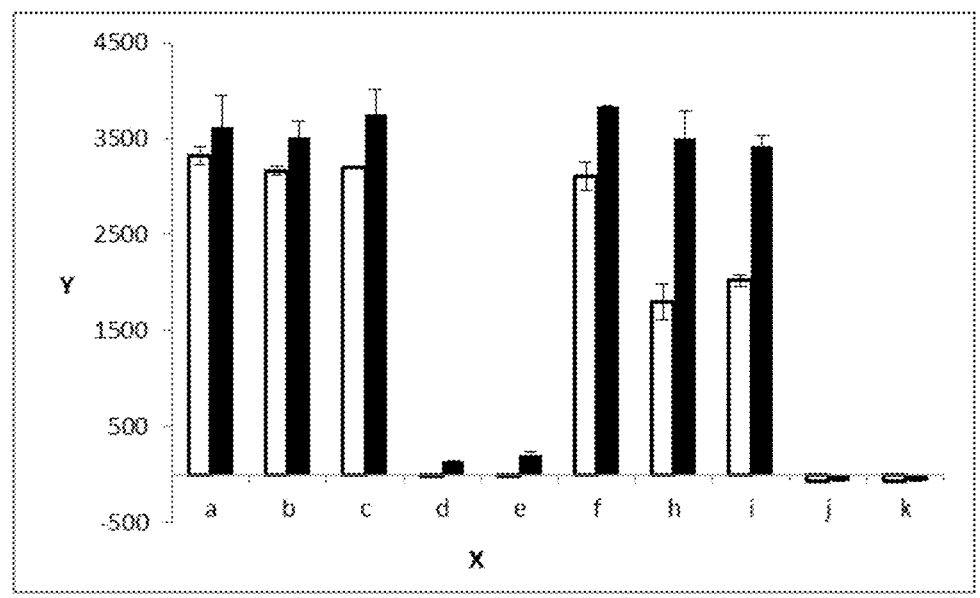

FIG. 5: Interaction of TWEAKR (28-68) with antibodies according to the invention and reference antibodies. What is shown is the result of an ELISA with TWEAKR (28-68)-HIS coating (TTP-1984, 1 µg/ml) and 0.08 µg/ml (open bars) and 0.3 µ/ml (solid bars) of biotinylated IgG as soluble binding partner. Detection was carried out using streptavidin-HRP and Amplex Red substrate. X are the "antibody constructs tested": a is "TPP-2090"; b is "TPP-2084"; c is "PDL-192(TPP-1104)"; d is "P4A8(TPP-1324)"; e is "P3G5 (TPP-2195)"; f is "136.1(TPP-2194)"; h is "ITEM1"; i is "ITEM4"; j is a mouse isotype control; k is a human isotype control. All antibodies examined show saturated binding at a concentration of 80 ng/ml.

Figure 6:
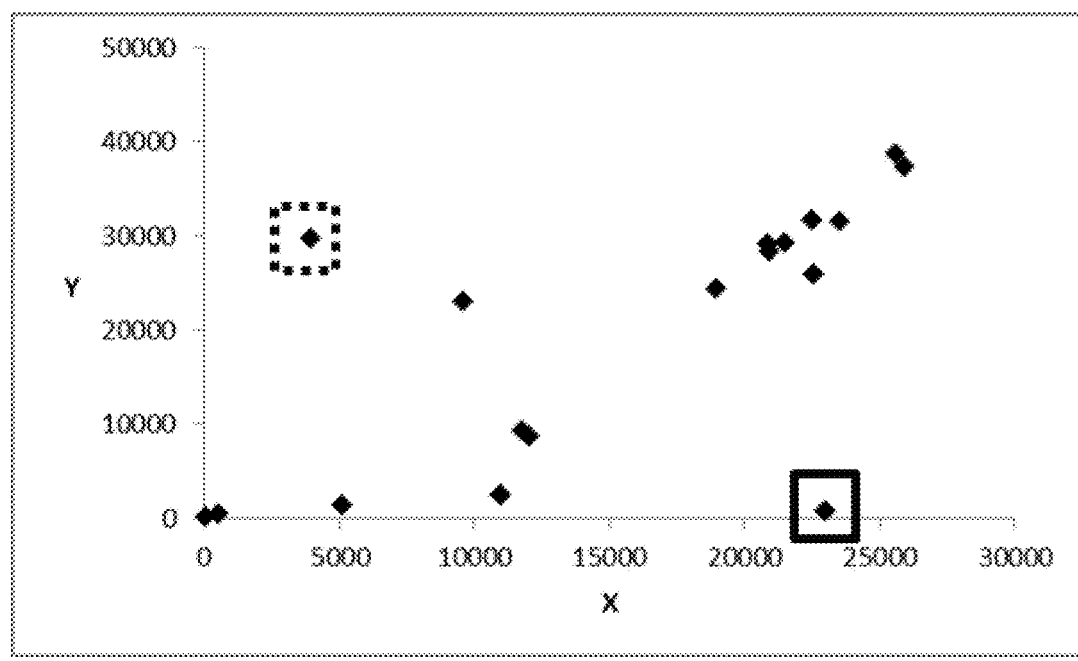
Figure 6:
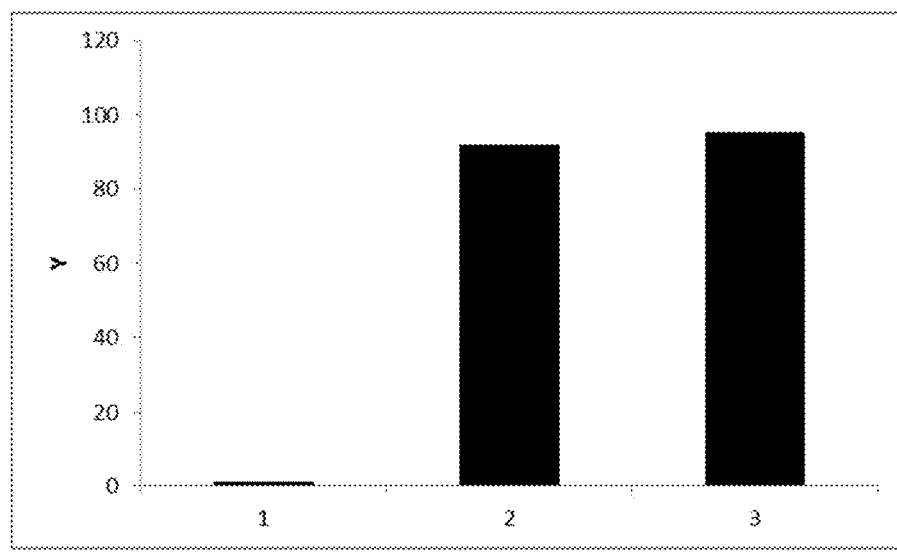

FIG. 6: A— Alanine scan of the cysteine-rich domain Muteins of TWEAKR(34-68)-Fc were analysed for PDL-192(TPP-1104) (X)- and TPP-2090 (Y)-binding. S37A, R38A, S40A, W42A, S43A, D45A, D47A, K48A, D51A, S54A, R56A, R58A, P59A, H60A, S61A, D62A, F63A and L65A muteins were expressed in HEK293 cells (black diamonds). PFL192(TPP-1104) and TPP-2090 were coated (1 µg/ml) and an 8-fold diluted supernatant of the HEK293 fermentation broth was added for TWEAKR protein binding. X is the "ELISA intensity of the PDL-192/TTP-1104) interaction [Rfu]", Y is the "ELISA intensity of the TPP-2090 interaction [Rfu]". TPP-2090 (Y) shows reduced binding for the D74A-TWEAKR mutein (closed box), and PDL-192(TPP-1104) (X) shows reduced binding to R56A (spotted box).

B—Y is the "binding in % normalized to the wild-type binding signal [%]", 1 is "TPP-2090"; 2 is "PDL-192(TPP-1104)"; 3 is "P4A8(TPP-1324)". (1 µg/ml), the TWEAKR variant was added at 250 ng/ml, detection was via anti-HIS HRP. Compared to the wild-typ construct, TTP-2090 shows less than 5% binding.

Figure 7:
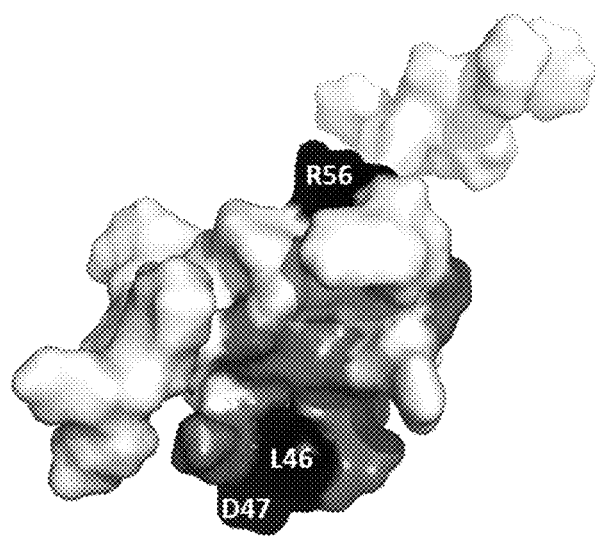

FIG. 7: NMR structure of the TWEAKR ectodomain as published by Pellegrini et al. (FEBS 280:1818-1829). TWEAK binding depends on L46 (Pellegrini et al.), TTP-2090 binding depends on D47 and PDL-192 binds to R56. PDL-192 binds opposite the TWEAK ligand binding site, TPP-2090 binds directly to the TWEAK ligand site.

DETAILED DESCRIPTION OF THE INVENTION

The invention provides conjugates of a binder or derivative thereof with one or more active compound molecules, the active compound molecule being a kinesin spindle protein inhibitor (KSP inhibitor) attached to the binder via a linker L.

The conjugate according to the invention can be represented by the general formula

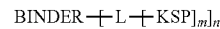

where BINDER represents the binder, preferably an antibody, L represents the linker, KSP represents the KSP inhibitor, m represents a number from 1 to 2, preferably 1, and n represents a number from 1 to 50, preferably from 1.2 to 20 and particularly preferably from 2 to 8. Here, m is the number of KSP inhibitors per linker and n a mean of the number of KSP inhibitor/linker conjugates per BINDER. The sum of all KSP present in the conjugate is thus the product of m and n. KSP-L preferably has the formula (I) or (II) shown above. The binder is preferably a binder peptide or protein such as, for example, an antibody. Furthermore, the linker is preferably attached to different amino acids of the binder peptide or protein or derivative thereof. Particular preference is given to binding to different cysteine residues of the binder.

Binders which can be used according to the invention, KSP inhibitors which can be used according to the invention and linkers which can be used according to the invention which can be used in combination without any limitation are described below. In particular, the binders represented in each case as preferred or particularly preferred can be employed in combination with the KSP inhibitors represented in each case as preferred or particularly preferred, optionally in combination with the linkers represented in each case as preferred or particularly preferred.

KSP Inhibitors and their Binder Conjugates

Low-molecular weight KSP inhibitors are known, for example, from WO2006/044825; WO2006/002236; WO2005/051922; WO2006/060737; WO03/060064; WO03/040979; and WO03/049527.

As a rule, KSP inhibitors have the following substructure I(sub):

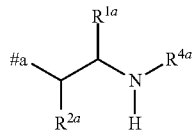

where
a represents a bond to the remainder of the molecule;
$R^{1a}$ represents H or —$(CH_2)_{0-3}$Z, where Z represents —H, halogen, $NHY^3$, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_2)_{0-3}Z'$, where Z' represents H, $SO_3H$, $NH_2$, COOH, —NH—CO—$CH_2$—$CH_2$—$CH(NH_2)$COOH or —(CO—NH—$CHY^4)_{1-3}$COOH, where W represents H or OH,
where $Y^4$ independently of one another represents straight-chain or branched $C_{1-6}$-alkyl which is optionally substituted by —$NHCONH_2$, or represents aryl or benzyl which are optionally substituted by —$NH_2$;
$R^{2a}$ and $R^{4a}$ independently of one another represent H, —CO—$CHY^4$—$NHY^5$ or —$(CH_2)_{0-3}$Z, or $R^{2a}$ and $R^{4a}$ together (with formation of a pyrrolidine ring) represent —$CH_2$—$CHR^{10}$— or —$CHR^{10}$—$CH_2$—, where $R^{10}$ represents H, $NH_2$, COOH, $SO_3H$, SH or OH,
where Z represents —H, —$OY^3$, —$SY^3$, $NHY^3$, —CO—$NY^1Y^2$ or —CO—$OY^3$,
where $Y^1$ and $Y^2$ independently of one another represent H, $NH^2$ or —$(CH_2)_{0-3}Z'$, and $Y^3$ represents H or —$(CH_2)_{0-3}Z'$, where Z' represents H, $SO_3H$, $NH_2$ or COOH,
where $Y^4$ independently of one another represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl.

Particularly frequently encountered is the following substructure II(sub)

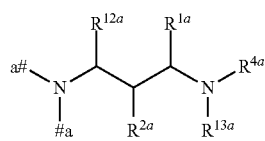

where #a, $R^{1a}$, $R^{2a}$, $R^{4a}$ have the same meaning as in I(sub) and $R^{12a}$ and $R^{13a}$ represent H or $R^{12a}$ and $R^{13a}$ together (with formation of a piperidine ring) represent —$CH_2$—$CHR^{10}$— or —$CHR^{10}$—$CH_2$—, where $R^{10}$ represents H, $NH_2$, COOH, $SO_3H$, SH or OH;
where Z represents —H, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2CH_2O)_{0-3}$—$(CH_2)_{0-3}Z'$ (e.g. —$(CH_2)_{0-3}Z'$), and $Y^3$ represents H or —$(CH_2)_{0-3}Z'$, where Z' represents H, $SO_3H$, $NH_2$, COOH or —(CO—NH—$CHY^4)_{1-3}$COOH, where $Y^4$ independently of one another represents straight-chain or branched $C_{1-6}$-alkyl which is optionally substituted by —$NHCONH_2$, or represents aryl or benzyl which are optionally substituted by —$NH_2$.

In particular, a number of KSP inhibitors have the substructure II(sub) where $R^{1a}$, $R^{2a}$, $R^{4a}$, $R^{12a}$ and $R^{13a}$ represent H.

According to the invention, use may be made of KSP inhibitors of the substructure I(sub) or the substructure II(sub). The KSP inhibitors which are used in accordance with the invention also include, for example, ispinesib (Cytokinetics/GSK), MK-0731 (Merck), AZD4877 (AstraZeneca), ARRY-520 (Array BioPharma) and ARQ 621 (ArQule).

KSP inhibitors which are preferred in accordance with the invention have the following basic structure:

Formula (I)

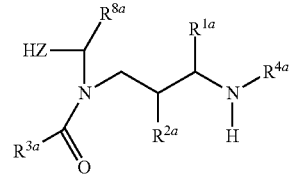

where
$R^{1a}$ represents H, -MOD or —$(CH_2)_{0-3}$Z, where Z represents —H, halogen, —$OY^3$, —$SY^3$, —$NHY^3$, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_2)_{0-3}Z'$, where Z' represents H, $SO_3H$, $NH_2$, COOH, —NH—CO—$CH_2$—$CH_2$—$CH(NH_2)$COOH or —(CO—NH—$CHY^4)_{1-3}$COOH, where W represents H or OH,
where $Y^4$ independently of one another represents straight-chain or branched $C_{1-6}$-alkyl which is optionally substituted by —$NHCONH_2$, or represents aryl or benzyl which are optionally substituted by —$NH_2$;
$R^{2a}$ and $R^{4a}$ independently of one another represent H, —CO—$CHY^4$—$NHY^5$ or —$(CH_2)_{0-3}$Z, or $R^{2a}$ and $R^{4a}$ together (with formation of a pyrrolidine ring) represent —$CH_2$—$CHR^{10}$— or —$CHR^{10}$—$CH_2$—, where $R^{10}$ represents H, $SO_3H$, $NH_2$, COOH, SH or OH,
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;
where $Y^4$ independently of one another represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl.
$R^{3a}$ represents -MOD or an optionally substituted alkyl, cycloalkyl, aryl, heteroaryl, heteroalkyl or heterocycloalkyl group,
preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents C$_{1-10}$-alkyl);
R$^{8a}$ represents C$_{1-10}$-alkyl;
HZ represents a mono- or bicyclic heterocycle which may be substituted by one or more substituents selected from the group consisting of halogen, C$_{1-10}$-alkyl groups, C$_{6-10}$-aryl groups and C$_{6-10}$-aralkyl groups which may optionally be substituted by halogen;
where -MOD represents —(NR$^{10}$)$_n$-(G1)$_o$-G2-H, where R$^{10}$ represents H or C$_1$-C$_3$-alkyl;
G1 represents —NHCO—, —CONH— or

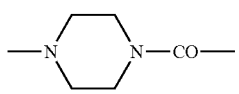

(where, if G1 represents —NHCO— or

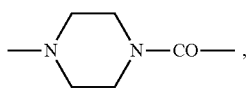

R$^{10}$ does not represent NH$_2$);
n is 0 or 1;
o is 0 or 1; and
G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;
and the salts, solvates and salts of the solvates thereof.
According to the invention, such a kinesin spindle protein inhibitor can be attached to the linker by substitution of a hydrogen atom at R$^{1a}$, R$^{2a}$, R$^{3a}$, R$^{4a}$, R$^{8a}$ or R$^{10}$ or optionally via one of the substituents of HZ, in particular via R$^{1a}$, R$^{2a}$, R$^{3a}$, R$^{4a}$ or R$^{10}$.

The substituents of the formula (I) preferably have the following meanings, where these preferred meanings are preferably combined with one another:
R$^{1a}$ preferably represents H or —(CH$_2$)$_{0-3}$Z, where Z represents —H, halogen, —OY$^3$, —SY$^3$, —NHY$^3$, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, SO$_3$H, NH$_2$, COOH, —NH—CO—CH$_2$—CH$_2$—CH(NH$_2$)COOH or —(CO—NH—CHY$^4$)$_{1-3}$COOH, where W represents H or OH,
where Y$^4$ independently of one another represents straight-chain or branched C$_{1-6}$-alkyl which is optionally substituted by —NHCONH$_2$, or represents aryl or benzyl which are optionally substituted by —NH$_2$;
R$^{2a}$ and R$^{4a}$ independently of one another preferably represent H, —COCHY$^4$—NHY$^5$ or —(CH$_2$)$_{0-3}$Z, or R$^{2a}$ and R$^{4a}$ together (with formation of a pyrrolidine ring) represent —CH$_2$—CHR$^{10}$— or —CHR$^{10}$—CH$^2$—, where R$^{10}$ represents H, SO$_3$H, NH$_2$, COOH, SH or OH,
where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$^2$)$_{0-3}$Z', and Y$^3$ represents H or —(CH$_2$)$_{0-3}$Z', where Z' represents H, SO$_3$H, NH$_2$ or COOH, where Y$^4$ independently of one another represents straight-chain or branched C$_{1-6}$-alkyl which is optionally substituted by —NHCONH$_2$, or represents aryl or benzyl which are optionally substituted by —NH$_2$ and Y$^5$ represents H or —CO—CHY$^6$—NH$_2$, where Y$^6$ represents straight-chain or branched C$_{1-6}$-alkyl.
R$^3$ preferably represents an optionally substituted alkyl, aryl, heteroaryl, heteroalkyl, heterocycloalkyl group, preferably —L-#$^1$ or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents C$_{1-10}$-alkyl).
R$^{8a}$ preferably represents C$_{1-10}$-alkyl.
HZ preferably represents a mono- or bicyclic heterocycle which may be substituted by one or more substituents selected from the group consisting of halogen, C$_{1-10}$-alkyl groups, C$_{6-10}$-aryl groups and C$_{6-10}$-aralkyl groups which may optionally be substituted by halogen.
C$_{1-10}$-Alkyl in the context of the invention (i.e. in the formula above and also in the formulae that follow) represents a straight-chain or branched alkyl radical having 1 to 10 carbon atoms. Examples which may be mentioned as being preferred are: methyl, ethyl, n-propyl, isopropyl, n-butyl, isobutyl, 1-methylpropyl and tert-butyl.

$C_{6-10}$-Aryl- in the context of the invention represents a mono- or bicyclic aromatic homocycle, for example phenyl and naphthyl.

$C_{6-10}$-Aralkyl group in the context of the invention represents a monocyclic aromatic homocycle, by way of example phenyl, to which a $C_1$-$C_4$-alkyl group is attached. An exemplary $C_{6-10}$-aralkyl group is benzyl.

$C_{5-10}$-Heteroaryl in the context of the invention represents a mono- or bicyclic aromatic heterocycle having a total of 6 to 10 ring atoms, where the ring(s) contains/contain one or two ring heteroatoms from the group consisting of N, O, S, SO and $SO_2$ and which is attached via a ring carbon atom or optionally a ring nitrogen atom. Examples which may be mentioned are pyridyl, furanyl, pyrimidyl, imidazolyl, thienyl, thiophenyl, isoxazoyl, isothiazoyl, 1,2,3-oxadiazoyl, furazanyl, 1,2,3-triazoyl, 1,2,4-triazoyl, pyridazyl, pyrrolyl, triazinyl, indolyl, quinolinyl, quinazolinyl, 1,3-benzodioxol, isoindolyl, indazolyl, 1H-pyrazolo[3,4-d]pyrimidyl, benzotriazolyl, isoquinolinyl, cinolinyl, phthalazinyl, pteridinyl, naphthyridinyl, benzimidazolinyl, benzothiazolinyl, benzoxazolinyl, 3,4-methylenedioxyphenyl and benzo[6]furanyl.

Mono- or bicyclic heterocycle in the context of the invention represents a mono- or bicyclic heterocycle having a total of 5 to 10 ring carbon atoms, where the ring(s) contains/contain one to three ring heteroatoms from the group consisting of N, O, S, SO and $SO_2$ and which is attached via a ring carbon atom or optionally a ring nitrogen atom. Examples which may be mentioned are piperidyl, pyrrolinyl, morpholinyl, 3,4-methylenedioxyphenyl and tetrahydrofuranyl.

Halogen atom in the context of the invention represents F, Cl, Br or I.

By substitution of a hydrogen atom at $R^{1a}$, $R^{2a}$, $R^{4a}$ or $R^{10}$ in substructure I(sub) or substructure II(sub), or $R^{1a}$, $R^{2a}$, $R^{3a}$, $R^{4a}$, $R^{8a}$ or $R^{10}$ at HZ in formula (I), the compound of the formula (I) may be attached to a linker in a manner known to the person of average skill. Particularly preferably, the substitution of the hydrogen atom takes place at $R^{1a}$, $R^{2a}$, $R^{3a}$, $R^{4a}$ or at the pyrrolidine ring formed by $R^{2a}$ and $R^{4a}$. This conjugation can take place chemically by various routes, as shown in an exemplary manner in Schemes 7 to 31 in the examples. In particular, it is optionally possible to modify the low-molecular weight KSP inhibitor for the conjugation to the linker, for example by introducing protective groups or leaving groups to facilitate substitution (such that in the reaction said leaving group, and not a hydrogen atom, is substituted by the linker). The KSP inhibitor— linker molecules obtained in this manner (where the linker has a reactive group for coupling to the binder) can then be reacted with the binder to give a binder conjugate according to the invention. In the experimental section, this procedure is illustrated in an exemplary manner by a large number of examples.

Preferred for $R^{1a}$ are H, —COOH, —CONHNH$_2$, —(CH$_2$)$_{1-3}$NH$_2$, —CONZ"(CH$_2$)$_{1-3}$NH$_2$ and —CONZ"CH$_2$COOH, where Z" represents H or NH$_2$.

Preferred for $R^{2a}$ and $R^{4a}$ are H, or $R^{2a}$ and $R^{4a}$ together (with formation of a pyrrolidine ring) represent CH$_2$—CHR$^{10}$— or —CHR$^{10}$—CH$_2$—, where $R^{10}$ represents H.

Preferred for $R^{3a}$ is $C_{1-10}$-alkyl-, which may be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl is preferably $C_{1-3}$-alkyl).

Preferred for $R^{8a}$ is a branched $C_{1-5}$-alkyl group, preferably methyl, ethyl, n-propyl, isopropyl, n-butyl, isobutyl, 1-methylpropyl and tert-butyl.

Preferred for HZ is a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen.

Particularly preferably, HZ is a substituted pyrrole, pyrazole, imidazole, quinazoline or dihydroquinazoline which is substituted in the ortho-position (with respect to the substituents with R1a etc.) by an optionally substituted benzyl group. Furthermore, the substituted pyrrole, pyrazole, imidazole or quinazoline can preferably be substituted by oxo (in the case of dihydroquinazoline) or a phenyl group substituted by 1 or 2 halogen atoms. Particularly preferably, HZ is a substituted pyrrole.

A KSP inhibitor which is preferably used is ispinesib. A further preferred KSP inhibitor is Arry-520.

Other particularly preferred compounds have the formula (IIa) or (II) below:

Formula (IIa)

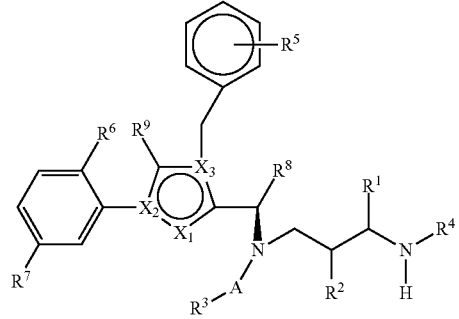

(IIa)

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH or CF, $X_2$ represents N and $X_3$ represents C;

(with $X_1$ representing CH, $X_2$ representing C and $X_3$ representing N being preferred);

$R^1$ represents H, —L-#$^1$, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH, where Y$^4$ independently of one another represents straight-chain or branched $C_{1-6}$-alkyl which is optionally substituted by —NHCONH$_2$, or represents aryl or benzyl which are optionally substituted by —NH$_2$;

$R^2$ represents —L-#$^1$, H, -MOD, —CO—CHY$^4$—NHY$^5$ or —(CH$_2$)$_{0-3}$Z, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

R$^4$ represents —L-#$^1$, H, —CO—CHY$^4$—NHY$^5$ or —(CH$_2$)$_{0-3}$Z, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

or R$^2$ and R$^4$ together (with formation of a pyrrolidine ring) represent —CH$_2$—CHR$^{10}$— or —CHR$^{10}$—CH$_2$—, where R$^{10}$ represents L-#$^1$, H, NH$_2$, SO$_3$H, COOH, SH or OH;

A represents CO, SO, SO$_2$, SO$_2$NH or CNNH;

R$^3$ represents —L-#$^1$, -MOD or an optionally substituted alkyl, cycloalkyl, aryl, heteroaryl, heteroalkyl, heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH((CH$_2$CH$_2$O)$_{1-20}$H) groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" is preferably C$_{1-10}$-alkyl);

R$^5$ represents —L-#$^1$, H, -MOD, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br), R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S (preferably oxetane), where each of these groups may be substituted by —OH, CO$_2$H or NH$_2$ or L-#$^1$;

where one or none of the substituents R$^1$, R$^2$, R$^3$, R$^4$ R$^5$, R$^8$ and R$^{10}$ represents (or in the case of R$^8$ contains) —L-#$^1$, L represents the linker and #$^1$ represents the bond to the binder or derivative thereof, R$^9$ represents H, F, CH$_3$, CF$_3$, CH$_2$F or CHF$_2$;

where -MOD represents —(NR$^{10}$)$_n$-(G1)$_o$-G2-H, where R$^{10}$ represents H or C$_1$-C$_3$-alkyl;

G1 represents —NHCO—, —CONH— or

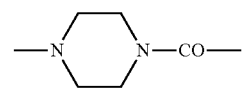

(where, if G1 represents —NHCO— or

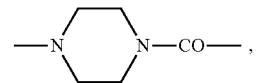

R$^{10}$ does not represent NH$_2$);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

and the salts, solvates and salts of the solvates thereof.

Formula (II):

(II)

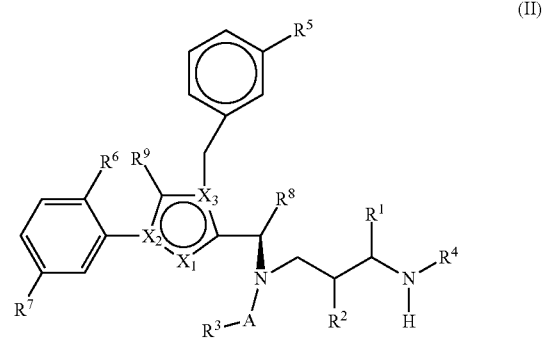

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C $R^1$ represents H, —L-#$^1$ or —(CH$_2$)$_{0-3}$Z, where Z represents —H, —NHY$^3$, —OY$^3$, —SY$^3$, halogen, —CO—NY$^1$Y$^2$ or —CO—OY$^3$, where $Y^1$ and $Y^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and $Y^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH;

where $Y^4$ independently of one another represents straight-chain or branched C$_{1-6}$-alkyl which is optionally substituted by —NHCONH$_2$, or represents aryl or benzyl which are optionally substituted by —NH$_2$;

$R^2$ and $R^4$ independently of one another represent H, —L-#$^1$, —CO—CHY$^4$—NHY$^5$ or —(CH$_2$)$_{0-3}$Z, or $R^2$ and $R^4$ together (with formation of a pyrrolidine ring) represent —CH$_2$—CHR$^{10}$— or —CHR$^{10}$—CH$_2$—, where $R^{10}$ represents H, —L-#$^1$, NH$_2$, SO$_3$H, COOH, SH or OH, where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where $Y^4$ independently of one another represents straight-chain or branched C$_{1-6}$-alkyl which is optionally substituted by —NHCONH$_2$ or represents aryl or benzyl which are optionally substituted by —NH$_2$, where $Y^4$ independently of one another represents straight-chain or branched C$_{1-6}$-alkyl which is optionally substituted by —NHCONH$_2$ or represents aryl or benzyl which are optionally substituted by —NH$_2$ and $Y^5$ represents H or —CO—CHY$^6$—NH$_2$, where $Y^6$ represents straight-chain or branched C$_{1-6}$-alkyl;

A represents CO, SO, SO$_2$, SO$_2$NH or CNNH;

$R^3$ represents an optionally substituted alkyl, aryl, heteroaryl, heteroalkyl, heterocycloalkyl group, preferably —L-#$^1$ or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z' and $Y^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

$R^5$ represents H, F, NH$_2$, NO$_2$, halogen, SH or —(CH$_2$)$_{0-3}$Z, where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

$R^6$ and $R^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen, $R^8$ represents (optionally fluorinated) C$_{1-10}$-alkyl, (optionally fluorinated) C$_{4-10}$-cycloalkyl or optionally substituted oxetane; and $R^9$ represents H, F, CH$_3$, CF$_3$, CH$_2$F or CHF$_2$;

and the salts, solvates and salts of the solvates thereof.

By substitution of a hydrogen atom at $R^1$, $R^2$, $R^3$, $R^4$, $R^5$ or $R^8$ or at the pyrrolidine ring ($R^{10}$) formed by $R^2$ and $R^4$, in a manner known to the person of average skill the compound of the formula (IIa) or (II) in which none of the substituents $R^1$, $R^2$, $R^3$, $R^4$, $R^5$, $R^8$ and $R^{10}$ represents —L-#$^1$ may be attached to a linker. This gives conjugates of the formula (IIa) or (II) where one of the substituents $R^1$, $R^2$, $R^3$, $R^4$, $R^5$, $R^8$ or $R^{10}$ represents —L-#$^1$, L represents the linker and #$^1$ represents the bond to the binder or the derivative thereof. If the KSP inhibitor according to formula (IIa) or (II) is conjugated with a binder, one of the substituents $R^1$, $R^2$, $R^3$, $R^4$, $R^5$, $R^8$ or $R^{10}$ thus represents —L-#$^1$, where L represents the linker and #$^1$ represents the bond to the binder or the derivative thereof. That is in the case of the conjugates one of the substituents $R^1$, $R^2$, $R^3$, $R^4$, $R^5$, $R^8$ and $R^{10}$ represents —L-#$^1$, where —L-#$^1$ is attached to the binder, for example an antibody. With particular preference, one of the substituents $R^1$ and $R^3$ represents —L-#$^1$. The binder is preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2090, or the anti-EGFR antibodies cetuximab or nimotuzumab.

Instead of —L-#$^1$, it is also possible for the group —L-#$^3$ to be present in the compound, where L represents the linker and #$^3$ represents the reactive group for binding to the binder or the derivative thereof. Compounds comprising —L-#$^3$ are reactive compounds which react with the binder or the derivative thereof. #$^3$ is preferably a group which reacts with an amino or thiol group with formation of a covalent bond, preferably with the cysteine residue in a protein. The cysteine residue in a protein may of course be present naturally in the protein, may be introduced by biochemical methods or, preferably, may be generated by prior reduction of disulphides of the binder.

The compounds of the formula (IIa) or (II) in which one of the substituents $R^1$, $R^2$, $R^3$, $R^4$, $R^5$ and $R^{10}$ represents —L-#$^1$ and in which $X_1$ represents N, $X_2$ represents N and $X_3$ represents C;

$X_1$ represents CH or CF, $X_2$ represents C and $X_3$ represents N;

$X_1$ represents NH, $X_2$ represents C and $X_3$ represents C; or $X_1$ represents CH, $X_2$ represents N and $X_3$ represents C are particularly preferred, in particular those in which $X_1$ represents N, $X_2$ represents N and $X_3$ represents C; or $X_1$ represents CH, $X_2$ represents C and $X_3$ represents N.

Particular preference is given to compounds in which $X_1$ represents CH, $X_2$ represents C and $X_3$ represents N.

For A, preference is given to CO (carbonyl).

Preferred for $R^1$ are —L-#$^1$, H, —COOH, —CONHNH$_2$, —(CH$_2$)$_{1-3}$NH$_2$, —CONZ"(CH$_2$)$_{1-3}$ NH$_2$ and —CONZ"CH$_2$COOH, where Z" represents H or NH$_2$.

Preferred for $R^2$ and $R^4$ are H, —L-#$^1$, or $R^2$ and $R^4$ together (with formation of a pyrrolidine ring) represent CH$_2$—CHR$^{10}$— or —CHR$^{10}$—CH$_2$—, where $R^{10}$ represents H or —L-#$^1$.

Preferred for $R^3$ is —L-#$^1$ or $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl is preferably $C_{1-3}$-alkyl).

Preferred for $R^5$ is —L-#$^1$, H or F.

Preferred for $R^6$ and $R^7$, independently of one another, are H, (optionally fluorinated) $C_{1-3}$-alkyl, (optionally fluorinated) $C_{2-4}$-alkenyl, (optionally fluorinated) $C_{2-4}$-alkynyl, hydroxy or halogen, Preferred for $R^8$ is a branched $C_{1-5}$-alkyl group, in particular a group of the formula —C(CH$_3$)$_2$—(CH$_2$)$_{0-2}$—R$_{y'}$, where R$_{y'}$ represents —H, —OH, CO$_2$H, NH$_2$ or —L-#$^1$. Particular preference is given to the group of the formula —C(CH$_3$)$_2$—(CH$_2$)—R$_{y'}$, where R$_{y'}$ represents —H or —L-#$^1$.

Preferred for $R^9$ is H or F.

Particular preference is given to compounds of the formula (IIa) or (II) in which none or one of the substituents $R^1$, $R^2$, $R^3$, $R^4$, $R^5$, $R^8$ and $R^{10}$ represents —L-#$^1$, and
in which
$X_1$ represents N, $X_2$ represents N and $X_3$ represents C;
$X_1$ represents CH or CF, $X_2$ represents C and $X_3$ represents N;
$X_1$ represents NH, $X_2$ represents C and $X_3$ represents C; or
$X_1$ represents CH, $X_2$ represents N and $X_3$ represents C
A represents CO (carbonyl);
$R^1$ represents H, —COOH, —CONHNH$_2$, —(CH$_2$)$_{1-3}$ NH$_2$, —CONZ"(CH$_2$)$_{1-3}$ NH$_2$ and —CONZ"CH$_2$COOH, where Z" represents H or NH$_2$;
$R^2$ and $R^4$ represent H or $R^2$ and $R^4$ together (with formation of a pyrrolidine ring) represent —CH$_2$—CHR$^{10}$— or —CHR$^{10}$—CH$_2$—, where $R^{10}$ represents H or —L-#$^1$;
$R^3$ represents a phenyl group which may be mono- or polysubstituted by halogen (in particular F) or optionally fluorinated $C_{1-3}$-alkyl, or represents an optionally fluorinated $C_{1-10}$-alkyl group which may optionally be substituted by —OY$^4$, —SY$^4$, —O—CO—Y$^4$, —O—CO—NH—Y$^4$, NH—CO—Y$^4$, —NH—CO—NH—Y$^4$, S(O)$_n$—Y$^4$ (where n represents 0, 1 or 2), —SO$_2$—NH—Y$^4$, NH—Y$^4$ or N(Y$^4$)$_2$, where Y$^4$ represents H, phenyl (optionally mono- or polysubstituted by halogen (in particular F) or optionally fluorinated $C_{1-3}$-alkyl), or alkyl (where the alkyl group may be substituted by —OH, —COOH, and/or —NHCO—$C_{1-3}$-alkyl and where alkyl preferably represents $C_{1-3}$-alkyl);
where particularly preferably $R^3$ may be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl preferably means $C_{1-3}$-alkyl)
$R^5$ represents H or F;
$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ represents a branched $C_{1-5}$-alkyl group; and
$R^9$ represents H or F.

Furthermore, it is preferred when (alone or in combination)
$R^1$ represents —L-#$^1$, COOH or H,
$R^2$ and $R^4$ independently of one another represent —L-#$^1$ or H or $R^2$ and $R^4$ together (with formation of a pyrrolidine ring) represent —CH$_2$—CHR$^{10}$— or —CHR$^{10}$—CH$_2$—, or where $R^{10}$ represents H or —L-#$^1$,
A represents CO,
$R^3$ represents —(CH$_2$)OH, —CH(CH$_3$)OH, —CH$_2$SCH$_2$CH(COOH)NHCOCH$_3$, —CH(CH$_3$)OCH$_3$, a phenyl group which may be substituted by 1-3 halogen atoms, 1-3 amino groups or 1-3 alkyl groups (which may optionally be halogenated), or represents —L-#$^1$,
$R^5$ represents —L-#$^1$ or H,
$R^6$ and $R^7$ independently of one another represent H, $C_{1-3}$-alkyl or halogen; in particular, $R^6$ and $R^7$ represent F;
$R^8$ represents $C_{1-4}$-alkyl (preferably tert-butyl); and/or
$R^9$ represents H,
where one of the substituents $R^1$, $R^2$, $R^3$, $R^4$, $R^5$ and $R^{10}$ represents —L-#$^1$.

Additionally, in accordance with the invention it is preferred when
$R^1$ represents —L-#$^1$, COOH or H,
$R^2$ and $R^4$ independently of one another represent —L-#$^1$ or H or $R^2$ and $R^4$ together (with formation of a pyrrolidine ring) represent —CH$_2$—CHR$^{10}$— or —CHR$^{10}$—CH$_2$—, where $R^{10}$ represents H or —L-#$^1$,
A represents CO,
$R^3$ represents —(CH$_2$)OH, —CH(CH$_3$)OH, —CH$_2$SCH$_2$CH(COOH)NHCOCH$_3$, —CH(CH$_3$)OCH$_3$, a phenyl group which may be substituted by 1-3 halogen atoms, 1-3 amino groups or 1-3 alkyl groups (which may optionally be halogenated), or represents —L-#$^1$,
$R^5$ represents —L-#$^1$ or H,
$R^6$ and $R^7$ independently of one another represent H, $C_{1-3}$-alkyl or halogen; in particular, $R^6$ and $R^7$ represent F;
$R^8$ represents $C_{1-4}$-alkyl (preferably tert-butyl); and
$R^9$ represents H,
where one of the substituents $R^1$, $R^2$, $R^3$, $R^4$, $R^5$ and $R^{10}$ represents —L-#$^1$.

Other particularly preferred compounds have the formula (IIIa) or (III) below:

Formula (IIIa)

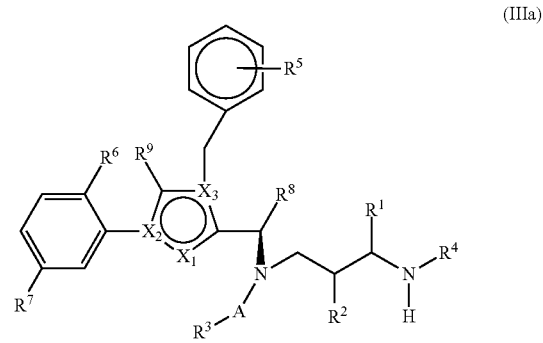

(IIIa)

where
$X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH, $X_2$ represents N and $X_3$ represents C
(with $X_1$ representing CH, $X_2$ representing C and $X_3$ representing N being preferred);
$R^1$ represents H, -L-BINDER, -MOD or —$(CH_2)_{0-3}$Z, where Z represents —H, —$NHY^3$, —$OY^3$, —$SY^3$, halogen, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}$Z' (e.g. —$(CH_2)_{0-3}$Z') or —CH($CH_2$W)Z', and $Y^3$ represents H or —$(CH_3)_{0-3}$Z', where Z' represents H, $NH_2$, $SO_3H$, —COOH, —NH—CO—$CH_2$—$CH_2$—CH($NH_2$)COOH or —(CO—NH—$CHY^4)_{1-3}$COOH, where W represents H or OH,
where $Y^4$ independently of one another represents straight-chain or branched $C_{1-6}$-alkyl which is optionally substituted by —$NHCONH_2$, or represents aryl or benzyl which are optionally substituted by —$NH_2$;
$R^2$ represents H, -L-BINDER, -MOD, —CO—$CHY^4$—$NHY^5$ or —$(CH_2)_{0-3}$Z, where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
$R^4$ represents H, -L-BINDER, —CO—$CHY^4$—$NHY^5$ or —$(CH_2)_{0-3}$Z,
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
or $R^2$ and $R^4$ together (with formation of a pyrrolidine ring) represent —$CH_2$—$CHR^{10}$— or —$CHR^{10}$—$CH_2$—, where $R^{10}$ represents -L-BINDER, H, $NH_2$, $SO_3H$, COOH, SH or OH;
A represents CO, SO, $SO_2$, $SO_2NH$ or CNNH;
$R^3$ represents -L-BINDER, -MOD or an optionally substituted alkyl, cycloalkyl, aryl, heteroaryl, heteroalkyl, heterocycloalkyl group, preferably —L-#$^1$ or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —$(CH_2)_{0-3}$Z groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}$Z' and $Y^3$ represents H, —$(CH_2)_{0-3}$—CH($NHCOCH_3$)Z', —$(CH_2)_{0-3}$—CH($NH_2$)Z' or —$(CH_2)_{0-3}$Z', where Z' represents H, $SO_3H$, $NH_2$ or COOH
(where "alkyl" preferably represents $C_{1-10}$-alkyl);
$R^5$ represents -L-BINDER, H, $NH_2$, $NO_2$, halogen (in particular F, Cl, Br), —CN, $CF_3$, —$OCF_3$, —$CH_2F$, —$CH_2F$, SH or —$(CH_2)_{0-3}$Z, where Z represents —H, —$OY^3$, —$SY^3$, halogen, $NHY^3$, —CO—$NY^1Y^2$ or —CO—$OY^3$,
where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br),
$R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —$(CH_2)_{0-2}$—($HZ^2$), where $HZ^2$ represents a 4- to 7-membered heterocycle having up to two heteroatoms selected from the group consisting of N, O and S, where each of these groups may be substituted by —OH, $CO_2H$ or $NH_2$ or -L-BINDER;
$R^9$ represents H, F, $CH_3$, $CF_3$, $CH_2F$ or $CHF_2$;
where -MOD represents —($NR^{10})_n$-(G1)$_o$-G2-H, where
$R^{10}$ represents H or $C_1$-$C_3$-alkyl;
G1 represents —NHCO—, —CONH— or

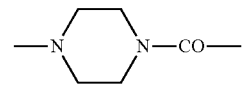

(where, if G1 represents —NHCO— or

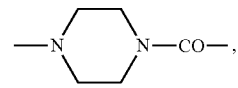

$R^{10}$ does not represent $NH_2$);
n is 0 or 1;
o is 0 or 1; and
G2 represents a straight-chain and/or branched hydrocarbon group which has 1 to 10 carbon atoms and which may be interrupted once or more than once by one or more of the groups —O—, —S—, —SO—, $SO_2$, —$NR^y$—, —$NR^y$CO—, —$CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —CO—, —$CR^x$=N—O— (where $R^x$ represents H, $C_1$-$C_3$- alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

and the salts, solvates and salts of the solvates thereof.

In the case of binder conjugates of the KSP inhibitors of the formula (IIIa), at most one representative of $R^1$, $R^2$, $R^3$ $R^4$, $R^5$, $R^8$ and $R^{10}$ (alternatively to one of the conditions given above) may represent -L-BINDER, where L represents a linker and BINDER represents a binder or a derivative thereof, where the binder may optionally be attached to a plurality of active compound molecules.

Formula (III)

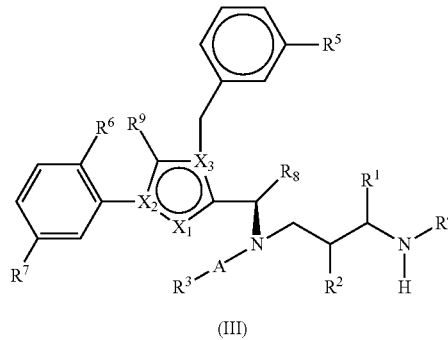

(III)

where $X_1$ represent N, $X_2$ represents N and $X_3$ represents C, or $X_1$ represents CH, $X_2$ represents C and $X_3$ represents N or $X_1$ represents NH, $X_2$ represents C and $X_3$ represents C, or $X_1$ represents CH, $X_2$ represents N and $X_3$ represents C;

$R^1$ represents -L-BINDER, H or —(CH$_2$)$_{0-3}$Z, where Z represents —H, —NHY$^3$, —OY$^3$, —SY$^3$, halogen, —CO—NY$^1$Y$^2$ or —CO—OY$^3$, where $Y^1$ and $Y^2$ independently of one another represent H, NH$_2$, —(CH$_2$CH$_2$O)$_{0-3}$—(CH$_2$)$_{0-3}$Z' or —CH(CH$_2$W)Z', and $Y^3$ represents H or —(CH$_2$)$_{0-3}$Z', where Z' represents H, NH$_2$, SO$_3$H, COOH, —NH—CO—CH$_2$—CH$_2$—CH(NH$_2$) COOH or —(CO—NH—CHY$^4$)$_{1-3}$COOH; where W represents H or OH;

where $Y^4$ independently of one another represents straight-chain or branched C$_{1-6}$-alkyl which is optionally substituted by —NHCONH$_2$, or represents aryl or benzyl which are optionally substituted by —NH$_2$;

$R^2$ and $R^4$ independently of one another represent -L-BINDER, H, —CO—CHY$^4$—NHY$^5$ or —(CH$_2$)$_{0-3}$Z, or $R^2$ and $R^4$ together (with formation of a pyrrolidine ring) represent —CH$_2$—CHR$^{10}$— or —CHR$^{10}$—CH$_2$—, where $R^{10}$ represents L-#$^1$, H, NH$_2$, SO$_3$H, COOH, SH or OH, where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where $Y^4$ independently of one another represents straight-chain or branched C$_{1-6}$ alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched C$_{1-6}$-alkyl;

A represents CO, SO, SO$_2$, SO$_2$NH or CNNH;

$R^3$ represents -L-BINDER or an optionally substituted alkyl, aryl, heteroaryl, heteroalkyl, heterocycloalkyl group, preferably —L-#$^1$, or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z' and $Y^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

$R^5$ represents -L-BINDER, H, F, NH$_2$, NO$_2$, halogen, SH or —(CH$_2$)$_{0-3}$Z, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where L represents a linker and BINDER represents a binder or a derivative thereof, where the binder may optionally be attached to a plurality of active compound molecules, $R^6$ and $R^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen, $R^8$ represents (optionally fluorinated) C$_{1-10}$-alkyl, (optionally fluorinated) C$_{4-10}$-cycloalkyl or optionally substituted oxetane; and $R^9$ represents H, F, CH$_3$, CF$_3$, CH$_2$F or CHF$_2$;

and the salts, solvates and salts of the solvates thereof.

Furthermore, preference according to the invention is given to the following KSP inhibitors and their binder conjugates:

Formula (IIIb):

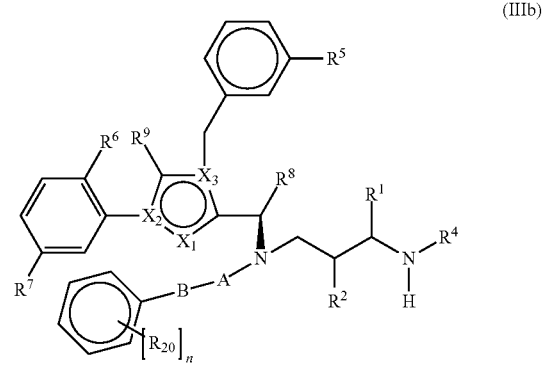

(IIIb)

where $X_1$, $X_2$, $X_3$ have the same meaning as in formula (IIIa) or (III) (where preferably $X_1$ represents CH, $X_2$ represents C and $X_3$ represent N), $R^1$, $R^2$, $R^4$, $R^5$, $R^6$, $R^7$, $R^8$ and $R^9$ have the same meaning as in formula (IIIa) or (III), A represents CO, B represents a single bond, —O—CH$_2$— or —CH$_2$—O— and $R^{20}$ represents NH$_2$, F, CF$_3$ or CH$_3$ and n represents 0, 1 or 2.

Formula (IIIc)

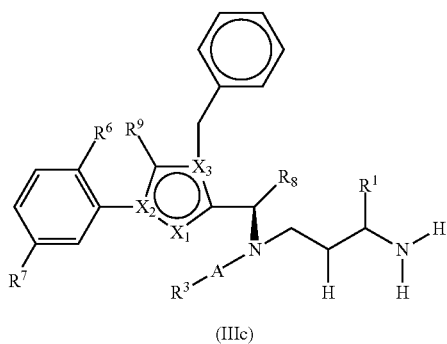

(IIIc)

where $X_1$, $X_2$, $X_3$ have the same meaning as in formula (IIIa) or (III) (where preferably $X_1$ represents CH, $X_2$ represents C and $X_3$ represents N), A, $R^1$, $R^3$, $R^6$, $R^7$, $R^8$ and $R^9$ have the same meaning as in formula (IIIa) or (III), A preferably represents CO and $R^3$ represents —$CH_2OH$, —$CH_2OCH_3$, $CH(CH_3)OH$ or $CH(CH_3)OCH_3$.

Formula (IIId):

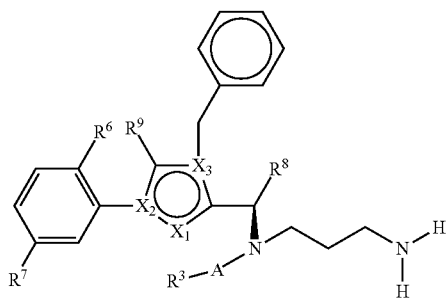

(IIId)

where $X_1$, $X_2$, $X_3$ have the same meaning as in formula (IIIa) or (III) (where preferably $X_1$ represents CH, $X_2$ represents C and $X_3$ represents N), A, $R^3$, $R^6$, $R^7$, $R^8$ and $R^9$ have the same meaning as in formula (IIIa) or (III), where A preferably represents CO and $R^3$ represents —$CH_2$—$S_x$—$(CH_2)_{0-4}$—$CHY^5$—COOH, where x is 0 or 1 and $Y^5$ represents H or $NHY^6$, where $Y^6$ represents H or —$COCH_3$.

Formula (IIIe)

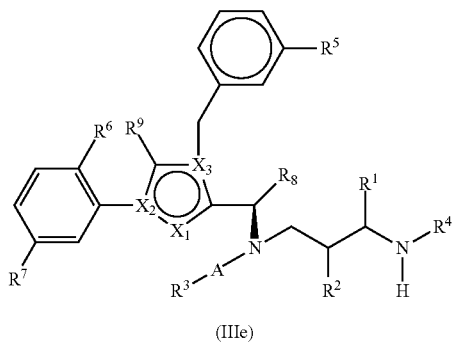

(IIIe)

where $X_1$ represents CH, $X_2$ represents C and $X_3$ represents N, A, $R^3$, $R^6$, $R^7$, $R^8$ and $R^9$ have the same meaning as in formula (IIIa) or (III) and $R^1$ represents -L-BINDER.

Furthermore, it is preferred when in the compounds of the formulae (III), (IIIa), (IIIb), (IIIc), (IIId) and (IIIe) (alone or in combination):

Z represents Cl or Br;

$R^1$ represents —$(CH_2)_{0-3}Z$, where Z represents —CO—$NY^1Y^2$, where $Y^2$ represents —$(CH_2CH_2O)_{0-3}$—$(CH_2)_{0-3}Z'$ and $Y^1$ represents H, $NH_2$ or —$(CH_2CH_2O)_{0-3}$—$(CH_2)_{0-3}Z'$;

$Y^1$ represents H, $Y^2$ represents —$(CH_2CH_2O)_3$—$CH_2CH_2Z'$ and $Z'$ represents —COOH;

$Y^1$ represents H, $Y^2$ represents —$CH_2CH_2Z'$ and $Z'$ represents —$(CONHCHY^4)_2COOH$;

$Y^1$ represents H, $Y^2$ represents —$CH_2CH_2Z'$, $Z'$ represents —$(CONHCHY^4)_2COOH$ and one of the $Y^4$ radicals represents i-propyl and the other —$(CH_2)_3$—$NHCONH_2$;

$Y^1$ represents H, $Y^2$ represents —$CH_2CH_2Z'$, $Z'$ represents —$(CONHCHY^4)_2COOH$ and one of the $Y^4$ radicals represents —$CH_3$ and the other —$(CH_2)_3$—$NHCONH_2$;

$Y^4$ represents straight-chain or branched $C_{1-6}$-alkyl which is optionally substituted by —$NHCONH_2$;

at least one $Y^4$ representative is selected from the group consisting of i-propyl and —$CH_3$;

$Y^1$ represents H, $Y^2$ represents —$CH_2CH_2Z'$, $Z'$ represents —$CONHCHY^4COOH$ and $Y^4$ represents aryl or benzyl which are optionally substituted by —$NH_2$;

$Y^4$ represents aminobenzyl;

$R^2$ represents —$(CH_2)_{0-3}Z$ and Z represents —$SY^3$;

$R^4$ represents —CO—$CHY^4$—$NHY^5$ and $Y^5$ represents H;

$R^4$ represents —CO—$CHY^4$—$NHY^5$ and $Y^5$ represents —CO—$CHY^6$—$NH_2$;

$Y^4$ represents straight-chain or branched $C_{1-6}$-alkyl which is optionally substituted by —$NHCONH_2$.

Furthermore, it is preferred when $R^1$, $R^2$ or $R^3$ in formula (IIa) or (IIIa) represents -MOD, in particular when $R^4$ represents —L-#$^1$ or -L-BINDER (in particular when -L is a cleavable linker which cleaves directly at —N—$R^4$ or —N—L-#$^1$ or -L-BINDER, such that $R^4$ or L is replaced by H).

Particularly preferably, $R^3$ represents -MOD and $R^1$ or $R^4$ represents —L-#$^1$ or -L-BINDER, where -MOD represents —$(NR^{10})_n$-$(G1)_o$-G2-H, where $R^{10}$ represents H or $C_1$-$C_3$-alkyl;

G1 represents —NHCO—, —CONH— or

(where, if G1 represents —NHCO— or

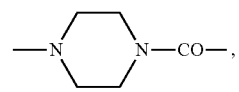

$R^{10}$ does not represent $NH_2$);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —CO—, —$CR^x$=N—O— (where $R^x$ represents H, $C_1$-$C_3$-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, where the group -MOD preferably has at least one group —COOH;

Particularly preferably, the group -MOD has a (preferably terminal) —COOH group, for example in a betaine group. Preferably, the group -MOD has the formula —$CH_2$—$S_x$—$(CH_2)_{0-4}$—$CHY^5$—COOH where x is 0 or 1, and $Y^5$ represents H or $NHY^6$, where $Y^6$ represents H or —$COCH_3$.

Other particularly preferred compounds have the formula (IV) below:

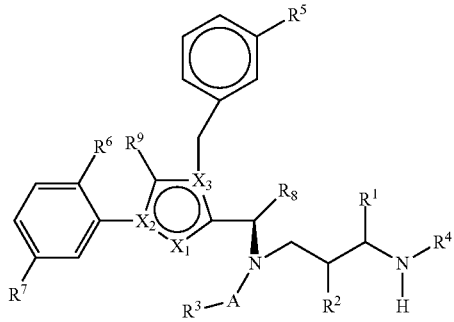

where
$X_1$ represents N, $X_2$ represents C and $X_3$ represents N;
$R^1$ represents -L-BINDER, H or —$(CH_2)_{0-3}Z$, where Z represents —H, —$NHY^3$, —$OY^3$, —$SY^3$, halogen, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}Z'$ or —$CH(CH_2W)Z'$, and $Y^3$ represents H or —$(CH_2)_{0-3}Z'$, where $Z'$ represents H, $NH_2$, $SO_3H$, COOH, —NH—CO—$CH_2$—$CH_2$—$CH(NH_2)$COOH or —$(CO-NH-CHY^4)_{1-3}$COOH;
where $Y^4$ independently of one another represents straight-chain or branched $C_{1-6}$-alkyl which is optionally substituted by —$NHCONH_2$, or represents aryl or benzyl which are optionally substituted by —$NH_2$;
$R^2$ and $R^4$ independently of one another represent -L-BINDER, H, —CO—$CHY^4$—$NHY^5$ or —$(CH_2)_{0-3}Z$, or
$R^2$ and $R^4$ together (with formation of a pyrrolidine ring) represent —$CH_2$—$CHR^{10}$— or —$CHR^x$—$CH_2$—, where $R^{10}$ represents L-#$^1$, H, $NH_2$, $SO_3H$, COOH, SH or OH,
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;

where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

A represents CO, SO, $SO_2$, $SO_2NH$ or CNNH;
$R^3$ represents -L-BINDER, an optionally substituted alkyl, aryl, heteroaryl, heteroalkyl, heterocycloalkyl group or —$CH_2$—$S_x$—$(CH_2)_{0-4}$—$CHY^5$—COOH, where x is 0 or 1, and $Y^5$ represents H or $NHY^6$, where $Y^6$ represents H or —$COCH_3$, preferably -L-BINDER or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z'$, —$(CH_2)_{0-3}$—$CH(NH_2)Z'$ or —$(CH_2)_{0-3}Z'$, where $Z'$ represents H, $SO_3H$, $NH_2$ or COOH
(where "alkyl" preferably represents $C_{1-10}$-alkyl);
$R^5$ represents -L-BINDER, H, F, $NH_2$, $NO_2$, halogen, SH or —$(CH_2)_{0-3}Z$, where Z represents —H, halogen, —$OY^3$, —$SY^3$, —$NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;
where L represents a linker and BINDER represents a binder or a derivative thereof, where the binder may optionally be attached to a plurality of active compound molecules,
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen,
$R^8$ represents (optionally fluorinated) $C_{1-10}$-alkyl, (optionally fluorinated) $C_{4-10}$-cycloalkyl or optionally substituted oxetane; and
$R^9$ represents H, F, $CH_3$, $CF_3$, $CH_2F$ or $CHF_2$;
and the salts, solvates and salts of the solvates thereof;
with the proviso that $R^1$, $R^2$ and $R^4$ do not simultaneously represent H.

Furthermore, it is preferred when in the formula (IIa), (II), (III), (IIIa), (IIIb), (IIIc), (IIId), (IIIe) or (IV) (alone or in combination):
Z represents Cl or Br;
$R^1$ represents —$(CH_2)_{0-3}Z$, where Z represents —CO—$NY^1Y^2$, where $Y^2$ represents —$(CH_2CH_2O)_{0-3}$—$(CH_2)_{0-3}Z'$ and $Y^1$ represents H, $NH_2$ or —$(CH_2CH_2O)_{0-3}$—$(CH_2)_{0-3}Z'$;
$Y^1$ represents H, $Y^2$ represents —$(CH_2CH_2O)_3$—$CH_2CH_2Z'$ and $Z'$ represents —COOH;
$Y^1$ represents H, $Y^2$ represents —$CH_2CH_2Z'$ and $Z'$ represents —$(CONHCHY^4)_2$COOH;
$Y^1$ represents H, $Y^2$ represents —$CH_2CH_2Z'$, $Z'$ represents —$(CONHCHY^4)_2$COOH and one $Y^4$ representative represents i-propyl and the other represents —$(CH_2)_3$—$NHCONH_2$;

$Y^1$ represents H, $Y^2$ represents —$CH_2CH_2Z'$, $Z'$ represents —$(CONHCHY^4)_2COOH$ and one $Y^4$ representative represents —$CH_3$ and the other represents —$(CH_2)_3$—$NHCONH_2$;

$Y^4$ represents straight-chain or branched $C_{1-6}$-alkyl which is optionally substituted by —$NHCONH_2$;

at least one $Y^4$ representative is selected from the group consisting of i-propyl and —$CH_3$;

$Y^1$ represents H, $Y^2$ represents —$CH_2CH_2Z'$, $Z'$ represents —$CONHCHY^4COOH$ and $Y^4$ represents aryl or benzyl which are optionally substituted by —$NH_2$;

$Y^4$ represents aminobenzyl;

$R^2$ represents —$(CH_2)_{0-3}Z$ and Z represents —$SY^3$;

$R^4$ represents —CO—$CHY^4$—$NHY^5$ and $Y^5$ represents H;

$R^4$ represents —CO—$CHY^4$—$NHY^5$ and $Y^5$ represents —CO—$CHY^6$—$NH_2$;

$Y^4$ represents straight-chain or branched $C_{1-6}$-alkyl which is optionally substituted by —$NHCONH_2$.

Preference is furthermore given to compounds of the formula (IIa), (II), (III), (IIIa) or (IV)
where
$X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH or CF, $X_2$ represents N and $X_3$ represents C;
(with $X_1$ representing CH, $X_2$ representing C and $X_3$ representing N being preferred);

$R^1$ represents H, —L-#$^1$ or -L-BINDER, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_3)_{0-3}Z'$, where $Z'$ represents H, $NH_2$, $SO_3H$, COOH, —NH—CO—$CH_2$—$CH_2$—$CH(NH_2)COOH$ or —$(CO—NH—CHY^4)_{1-3}COOH$, where W represents H or OH, where $Y^4$ independently of one another represents straight-chain or branched $C_{1-6}$-alkyl which is optionally substituted by —$NHCONH_2$, or represents aryl or benzyl which are optionally substituted by —$NH_2$;

$R^2$ represents H, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;

where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H;

A represents CO, SO, $SO_2$, $SO_2NH$ or CNNH;

$R^3$ represents —L-#$^1$ or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —$SO_2$—NH-alkyl groups, 1-3 —NH-alkyl groups, 1-3 —N(alkyl)$_2$ groups, 1-3 —NH(($CH_2CH_2O)_{1-20}H$) groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z'$, —$(CH_2)_{0-3}$—$CH(NH_2)Z'$ or —$(CH_2)_{0-3}Z'$, where $Z'$ represents H, $SO_3H$, $NH_2$ or COOH (where "alkyl" is preferably $C_{1-10}$-alkyl);

$R^5$ represents H, -MOD, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where $Z'$ represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br), $R^8$ represents (optionally fluorinated) $C_{1-10}$-alkyl, (optionally fluorinated) $C_{2-10}$-alkenyl, (optionally fluorinated) $C_{2-10}$-alkynyl or (optionally fluorinated) $C_{4-10}$-cycloalkyl;

where one or none of the substituents $R^1$ and $R^3$ represents —L-#$^1$ or -L-BINDER, L represents the linker and #$^1$ represents the bond to the binder or derivative thereof and BINDER represents the binder, $R^9$ represents H, F, $CH_3$, $CF_3$, $CH_2F$ or $CHF_2$;

where -MOD represents —$(NR^{10})_n$-(G1)$_o$-G2-H, where $R^{10}$ represents H or $C_1$-$C_3$-alkyl;

G1 represents —NHCO—, —CONH— or

—N⟨     ⟩N—CO—

(where, if G1 represents —NHCO— or

—N⟨     ⟩N—CO—, $R^{10}$ does not represent $NH_2$);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —$NHCONH_2$, —COOH, —OH, —$NH_2$, NH—$CNNH_2$, sulphonamide, sulphone, sulphoxide or sulphonic acid), —CO—, —$CR^x$=N—O— (where $R^x$ represents H, $C_1$-$C_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

and the salts, solvates and salts of the solvates thereof.

Preference is furthermore given to compounds of the formula (IIa), (II), (III), (IIIa) or (IV) in which $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH or CF, $X_2$ represents N and $X_3$ represents C;

(with $X_1$ representing CH, $X_2$ representing C and $X_3$ representing N being preferred);

$R^1$ represents H, —L-#$^1$ or -L-BINDER, -MOD or —(CH$_2$)$_{0-3}$Z, where Z represents —H, —NHY$^3$, —OY$^3$, —SY$^3$, halogen, —CO—NY$^1$Y$^2$ or —CO—OY$^3$, where $Y^1$ and $Y^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and $Y^3$ represents H or —(CH$_3$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH, where $Y^4$ independently of one another represents straight-chain or branched $C_{1-6}$-alkyl which is optionally substituted by —NHCONH$_2$, or represents aryl or benzyl which are optionally substituted by —NH$_2$;

$R^2$ represents H, —CO—CHY$^4$—NHY$^5$ or —(CH$_2$)$_{0-3}$Z, where Z represents —H, halogen, —OY$^3$, —SY$^3$, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

where $Y^4$ independently of one another represents straight-chain or branched $C_{1-6}$ alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched $C_{1-6}$-alkyl;

$R^4$ represents H;

A represents CO, SO, SO$_2$, SO$_2$NH or CNNH;

$R^3$ represents —L-#$^1$ or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH((CH$_2$CH$_2$O)$_{1-20}$H) groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, NH$_2$ or —(CH$_2$)$_{0-3}$Z' and $Y^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" is preferably $C_{1-10}$-alkyl);

$R^5$ represents H, -MOD, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;

$R^6$ and $R^7$ independently of one another represent H or halogen (in particular F, Cl, Br), $R^8$ represents (optionally fluorinated) $C_{1-10}$-alkyl;

where one or none of the substituents $R^1$ and $R^3$ represents —L-#$^1$ or -L-BINDER, L represents the linker and #$^1$ represents the bond to the binder or derivative thereof and BINDER represents the binder, $R^9$ represents H, F, CH$_3$, CF$_3$, CH$_2$F or CHF$_2$;

where -MOD represents —CH$_2$—S$_x$—(CH$_2$)$_{0-4}$—CHY$^5$—COOH where x is 0 or 1, and $Y^5$ represents H or NHY$^6$, where $Y^6$ represents H or —COCH$_3$, and the salts, solvates and salts of the solvates thereof.

Preference is furthermore given to the following compounds which may optionally be present together with an acid such as, for example, trifluoroacetic acid. These compounds may be attached via the positions corresponding to the positions $R^1$, $R^2$, $R^3$ $R^4$, $R^5$, $R^8$ and $R^{10}$, in particular $R^1$ and $R^3$, via a linker to a binder (where a hydrogen atom is substituted by the linker):

N-(3-aminopropyl)-N-{(1R)-1-[4-benzyl-1-(2,5-difluorophenyl)-1H-pyrazol-3-yl]-2,2-dimethylpropyl}-2-hydroxyacetamide;

N-(3-aminopropyl)-N-{(1R)-1-[1-benzyl-4-(2,5-difluorophenyl)-1H-pyrrol-2-yl]-2,2-dimethylpropyl}-2-hydroxyacetamide;

(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1);

N-(3-aminopropyl)-N-{(1S)-1-[1-benzyl-4-(2,5-difluorophenyl)-1H-pyrrol-2yl]-2,2-dimethylpropyl}acetamide;

(15S,19R)-15-amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oic acid;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N$^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N$^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-amino-L-phenylalanine;

N-{(1R)-1-[1-(3-aminobenzyl)-4-(2,5-difluorophenyl)-1H-imidazol-2-yl]-2,2-dimethylpropyl}-N-(3-aminopropyl)-2-hydroxyacetamide (1:1);

(2S)-2-amino-4-[{(1R)-1-[1-benzyl-4-(2,5-difluorophenyl)-1H-imidazol-2-yl]-2,2-dimethylpropyl}(glycoloyl)amino]butanoic acid;

N-[(3S)-3-amino-4-hydrazino-4-oxobutyl]-N-{(1R)-1-[1-benzyl-4-(2,5-difluorophenyl)-1H-imidazol-2-yl]-2,2-dimethylpropyl}-2-hydroxyacetamide (1:1);

N-{(1R)-1-[1-benzyl-4-(2,5-difluorophenyl)-1H-imidazol-2-yl]-2,2-dimethylpropyl}-N-[(3S)-3,4-diaminobutyl]-2-hydroxyacetamide (1:1);

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanine;

(2S)-2-amino-N-(2-aminoethyl)-4-[{(1R)-1-[1-benzyl-4-(2,5-difluorophenyl)-1H-imidazol-2-yl]-2,2-dimethylpropyl}(glycoloyl)amino]butanamide (2:1);

(1-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}hydrazino)acetic acid;

N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1);

4-amino-N-(3-aminopropyl)-N-{(1R)-1-[1-benzyl-4-(2,5-difluorophenyl)-1H-imidazol-2-yl]-2,2-dimethylpropyl}benzamide (2:1);

N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

N-(3-aminopropyl)-N-{(1S)-1-[1-benzyl-4-(2,5-difluorophenyl)-1H-pyrrol-2-yl]-2,2-dimethylpropyl}-2-hydroxyacetamide;

S-(1-{2-[(N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-2,5-dioxopyrrolidin-3-yl]-L-cysteine;

N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N5-carbamoyl-L-ornithinamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-2,5-dioxopyrrolidin-3-yl]-L-cysteine;

N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N5-carbamoyl-L-ornithinamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

N-[6-(3-{[(2R)-2-amino-2-carboxyethyl]sulphanyl}-2,5-dioxopyrrolidin-1-yl)hexanoyl]-L-valyl-N5-carbamoyl-L-ornithyl-N6-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine;

S-[1-(2-{[2-({(2S)-2-amino-4-[{(1R)-1-[4-benzyl-1-(2,5-difluorophenyl)-1H-pyrrol-2-yl]-2,2-dimethylpropyl}(glycoloyl)amino]butanoyl}amino)ethyl]amino}-2-oxoethyl)-2,5-dioxopyrrolidin-3-yl]-L-cysteine;

S-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-L-cysteine;

S-{1-[6-({2-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}hydrazino)-6-oxohexyl]-2,5-dioxopyrrolidin-3-yl}-L-cysteine;

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl) {(1R)-1-[1-benzyl-4-(2,5-difluorophenyl)-1H-pyrrol-2-yl]-2,2-dimethylpropyl}amino]-2-oxoethyl}homocysteine;

S-{(3R/S)-1-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-2,5-dioxopyrrolidin-3-yl}-L-cysteine;

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl) {(1R)-1-[1-benzyl-4-(2,5-difluorophenyl)-1H-imidazol-2-yl]-2,2-dimethylpropyl}amino]-2-oxoethyl}homocysteine;

S-[(3R/S)-1-(2-{[6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)hexanoyl]amino}ethyl)-2,5-dioxopyrrolidin-3-yl]-L-cysteine;

S-{1-[2-({[(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine;

S-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine;

N6-(N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-D-alanyl)-L-lysine;

N6-(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N2-{N-[6-(3-{[(2R)-2-amino-2-carboxyethyl]sulphanyl}-2,5-dioxopyrrolidin-1-yl)hexanoyl]-L-valyl-L-alanyl}-L-lysine;

N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine;

N6-(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine;

N-(3-aminopropyl)-N-{(1R)-1-[4-benzyl-1-(2,5-difluorophenyl)-1H-pyrazol-3-yl]-2,2-dimethylpropyl}acetamide;

N-(3-aminopropyl)-N-{(1R)-1-[4-benzyl-1-(2,5-difluorophenyl)-1H-pyrazol-3-yl]2,2-dimethylpropyl}-2-methoxyacetamide;

N-(3-aminopropyl)-N-{(1R)-1-[4-benzyl-1-(2,5-difluorophenyl)-1H-pyrazol-3-yl]-2,2-dimethylpropyl}-2,4-difluorobenzamide;

N-(3-aminopropyl)-N-{(1R)-1-[4-benzyl-1-(2,5-difluorophenyl)-1H-pyrazol-3-yl]-2,2-dimethylpropyl}-4-methylbenzamide;

N-(3-aminopropyl)-N-{(1R)-1-[4-benzyl-1-(2,5-difluorophenyl)-1H-pyrazol-3-yl]-2,2-dimethylpropyl}-2-ethoxyacetamide;

N-(3-aminopropyl)-N-{(1R)-1-[1-benzyl-4-(2,5-difluorophenyl)-1H-pyrrol-2-yl]-2,2-dimethylpropyl}-3,3,3-trifluoropropanamide;
N-(3-aminopropyl)-N-{(1R)-1-[1-benzyl-4-(2,5-difluorophenyl)-1H-pyrrol-2-yl]-2,2-dimethylpropyl}-4-fluorobenzamide;
N-(3-aminopropyl)-N-{(1R)-1-[1-benzyl-4-(2,5-difluorophenyl)-1H-pyrrol-2-yl]-2,2-dimethylpropyl}acetamide;
N-(3-aminopropyl)-N-{(1R)-1-[1-benzyl-4-(2,5-difluorophenyl)-1H-pyrrol-2-yl]-2,2-dimethylpropyl}-4-(trifluoromethyl)benzamide;
N-(3-aminopropyl)-N-{(1R)-1-[4-benzyl-1-(2,5-difluorophenyl)-1H-pyrazol-3-yl]-2,2-dimethylpropyl}-2-ethoxyacetamide;
N-(3-aminopropyl)-N-{(1R)-1-[4-benzyl-1-(2,5-difluorophenyl)-1H-pyrazol-3-yl]-2,2-dimethylpropyl}-2-ethoxyacetamide;
(2S)-2-amino-4-[{(1R)-1-[1-benzyl-4-(2,5-difluorophenyl)-1H-pyrrol-2-yl]-2,2-dimethylpropyl}(glycoloyl)amino]butanoic acid;
(2S)-2-amino-N-(2-aminoethyl)-4-[{(1R)-1-[1-benzyl-4-(2,5-difluorophenyl)-1H-pyrrol-2-yl]-2,2-dimethylpropyl}(glycoloyl)amino]butanamide;
4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid;
4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid;
N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanine;
N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-serine;
N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-alanine;
N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}glycine;
N-(3-aminopropyl)-N-{(1R)-1-[1-benzyl-4-(2,5-difluorophenyl)-1H-pyrrol-2-yl]-2,2-dimethylpropyl}-4-methylbenzamide;
N-(3-aminopropyl)-N-{(1R)-1-[1-benzyl-4-(2,5-difluorophenyl)-1H-pyrrol-2-yl]-2,2-dimethylpropyl}-4-(methylsulphanyl)benzamide;
(2S)—N-(3-aminopropyl)-N-{(1R)-1-[1-benzyl-4-(2,5-difluorophenyl)-1H-pyrrol-2-yl]-2,2-dimethylpropyl}-2-hydroxypropanamide;
N-(3-aminopropyl)-N-{(1R)-1-[1-benzyl-4-(2,5-difluorophenyl)-1H-pyrrol-2-yl]-2,2-dimethylpropyl}-2-(methylsulphanyl)acetamide;
(2S)—N-(3-aminopropyl)-N-{(1R)-1-[4-benzyl-1-(2,5-difluorophenyl)-1H-pyrazol-3-yl]-2,2-dimethylpropyl}-2-hydroxypropanamide;
methyl 4-[(3-aminopropyl){(1R)-1-[1-benzyl-4-(2,5-difluorophenyl)-1H-pyrrol-2-yl]-2,2-dimethylpropyl}amino]-4-oxobutanoate;
4-[(3-aminopropyl){(1R)-1-[1-benzyl-4-(2,5-difluorophenyl)-1H-pyrrol-2-yl]-2,2-dimethylpropyl}amino]-4-oxobutanoic acid;
(2R)-22-[(3R/S)-3-{[(2R)-2-amino-2-carboxyethyl]sulphanyl}-2,5-dioxopyrrolidin-1-yl]-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-4,20-dioxo-7,10, 13,16-tetraoxa-3, 19-diazadocosan-1-oic acid;
4-amino-N-(3-aminopropyl)-N-{(1R)-1-[4-benzyl-1-(2,5-difluorophenyl)-1H-pyrazol-3-yl]-2,2-dimethylpropyl}benzamide;
N-acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine;
N-acetyl-S-[2-({3-(L-alanylamino)propyl}{(1R)-1-[1-benzyl-4-(2,5-difluorophenyl)-1H-pyrrol-2-yl]-2,2-dimethylpropyl}amino)-2-oxoethyl]-L-cysteine;
(2S)—N-(3-aminopropyl)-N-{(1R)-1-[1-benzyl-4-(2,5-difluorophenyl)-1H-pyrrol-2-yl]-2,2-dimethylpropyl}tetrahydrofuran-2-carboxamide;
3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)propanoic acid;
S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine;
4-amino-N-(3-aminopropyl)-N-{(1R)-1-[1-benzyl-4-(2,5-difluorophenyl)-1H-pyrrol-2-yl]-2,2-dimethylpropyl}benzamide;
4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid;
4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic acid.

Particular preference according to the invention is given to the following compounds of the formulae V, VI and VII, where $R^1$, $R^2$, $R^3$, $R^4$ and $R^5$ have the meanings mentioned above (as mentioned, for example for formula (IIa) or (IIIa)):

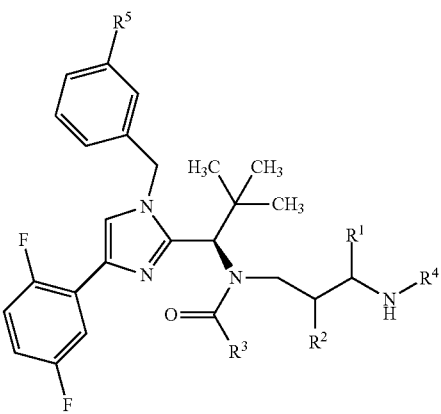

Formula V

Formula VI

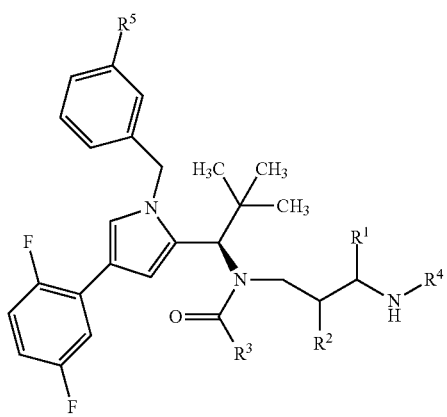

Formula VII

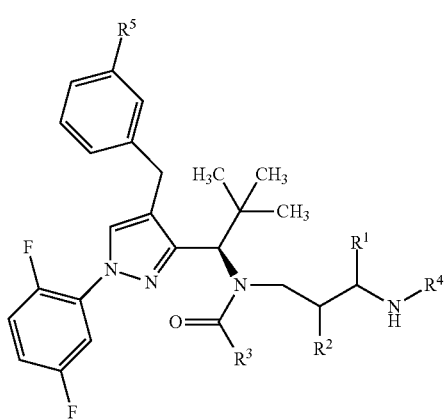

Particular preference is given to the compounds of the formulae V, VI, VII where $R^1$ and $R^5$ represent H or —L-#$^1$; $R^2$ and $R^4$ independently of one another represent —L-#$^1$ or H or $R^2$ and $R^4$ together (with formation of a pyrrolidine ring) represent —CH$_2$—CHR$^{10}$— or —CHR$^{10}$—CH$_2$—, $R^{10}$ represents H or —L-#$^1$; and $R^3$ represents CH$_2$OH, CH(CH$_3$)OH or —L-#$^1$, where one of the substituents $R^1$, $R^2$, $R^3$, $R^4$, $R^5$ and $R^{10}$ represents —L-#$^1$. Especially preferred are the corresponding compounds of the formula VI.

Linkers

The literature discloses various options for covalently coupling (conjugating) organic molecules to binders such as, for example antibodies (see, for example, K. Lang and J. W. Chin. *Chem. Rev.* 2014, 114, 4764-4806, M. Rashidian et al. *Bioconjugate Chem.* 2013, 24, 1277-1294). Preference according to the invention is given to conjugation of the KSP inhibitors to an antibody via one or more sulphur atoms of cysteine residues of the antibody which are either already present as free thiols or generated by reduction of disulphide bridges, and/or via one or more NH groups of lysine residues of the antibody. However, it is also possible to attach the KSP inhibitor to the antibody via tyrosine residues, via glutamine residues, via residues of unnatural amino acids, via free carboxyl groups or via sugar residues of the antibody. For coupling, use is made of linkers. Linkers can be categorized into the group of the linkers which can be cleaved in vivo and the group of the linkers which are stable in vivo (see L. Ducry and B. Stump, *Bioconjugate Chem.* 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as cathepsin or plasmin, or glyosidases such as, for example, β-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo are in particular the 2-8-oligopeptide group, especially a dipeptide group or glycoside. Peptide cleavage sites are disclosed in *Bioconjugate Chem.* 2002, 13, 855-869, and *Bioorganic & Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

Linkers which are stable in vivo are distinguished by a high stability (less than 5% metabolites after 24 hours in plasma) and do not have the chemically or enzymatically in vivo cleavable groups mentioned above.

The linker -L- preferably has one of the basic structures (i) to (iv) below:

(i) —(CO)$_m$—SG1-L1-L2-
(ii) —(CO)$_m$-L1-SG-L1-L2-
(iii) —(CO)$_m$-L1-L2-
(iv) —(CO)$_m$-L1 —SG-L2 where m is 0 or 1; SG is a (chemically or enzymatically) in vivo cleavable group (in particular disulphide, hydrazone, acetal and aminal; or a 2-8-oligopeptide group which can be cleaved by cathepsin or plasmin), SG1 is an oligopeptide group or preferably a dipeptide group, L1 independently of one another represent in vivo stable organic groups, and L2 represents a coupling group to the binder or a single bond. Here, coupling is preferably to a cysteine residue or a lysine residue of the binder. Alternatively, coupling can be to a tyrosine residue, glutamine residue or to an unnatural amino acid of the binder. The unnatural amino acids may contain, for example, aldehyde or keto groups (such as, for example, formylglycine) or azide or alkyne groups (see Lan & Chin, Cellular Incorporation of Unnatural Amino Acids and Bioorthogonal Labeling of Proteins, Chem. Rev. 2014, 114, 4764-4806).

Particular preference according to the invention is given to the basic linker structure (iii), in particular when the binder is an anti-TWEAKR antibody or an anti-EGFR antibody. Via metabolization, the administration of a conjugate according to the invention having a basic linker structure (iii) and coupling of the linker to a cysteine or lysine residue of the binder protein or peptide leads to cysteine or lysine derivatives of the formulae below:

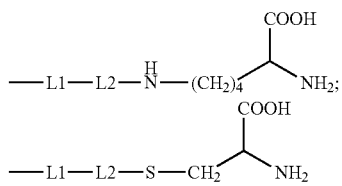

where L1 is in each case attached to the low-molecular weight KSP inhibitor, for example a compound of the formula (I), (IIa), (II), (III), (IIIa), (IIIb), (IIIc), (IIId), (IIIe) or (IV).

Preference according to the invention is also given to the basic linker structures (ii) and (iv), in particular when attachment is at position (iii), in particular when group L1 has one of the following structures:

(a)  —NH—$(CH_2)_{0-4}$—$(CHCH_3)_{0-4}$—$CHY^5$—CO—$Y^7$, where $Y^5$ represents H or $NHY^6$, where $Y^6$ represents H or —$COCH_3$, and $Y^7$ represents a single bond or —NH—$(CH_2)_{0-4}$—$CHNH_2$—CO—, so that after cleavage the corresponding structure —NH—$(CH_2)_{0-4}$—$(CHCH_3)_{0-4}$—$CHY^5$—COOH or —NH—$(CH_2)_{0-4}(CHCH_3)_{0-4}$—$CHY^5$—CO—NH—$(CH_2)_{0-4}$—$CHNH_2$—COOH is obtained.

(b) —$CH_2$—$S_x$—$(CH_2)_{0-4}$—$CHY^5$—CO—, where x is 0 or 1, and $Y^5$ represents H or $NHY^6$, where $Y^6$ represents H or —$COCH_3$, such that after cleavage the corresponding structure —$CH_2$—$S_x$—$(CH_2)_{0-4}$—$CHY^5$—COOH is obtained.

This embodiment is preferred when L1 is attached in each case to the low-molecular weight KSP inhibitor, for example a compound of the formula (I), (IIa), (II), (III), (IIIa), (IIIb), (IIIc), (IIId), (IIIe) or (IV), in particular at position $R_4$. The binder is preferably an anti-TWEAKR antibody or an anti-EGFR antibody.

If the linker is attached to a cysteine side chain or a cysteine residue, L2 is preferably derived from a group which reacts with the sulphhydryl group of the cysteine. These include haloacetyls, maleimides, aziridines, acryloyls, arylating compounds, vinylsulphones, pyridyl disulphides, TNB thiols and disulphide-reducing agents. These groups generally react in an electrophilic manner with the sulphhydryl bond, forming a sulphide (e.g. thioether) or disulphide bridge. Preference is given to stable sulphide bridges. L2 is preferably

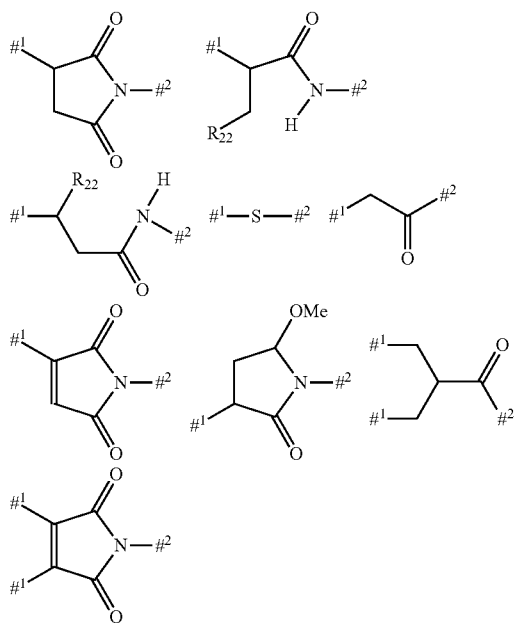

where
$\#^1$ denotes the point of attachment to the sulphur atom of the binder,
$\#^2$ denotes the point of attachment to group L1, and
$R_{22}$ represents COOH, COOR, COR, CONHR, $CONR_2$ (where R in each case represents $C_{1-3}$-alkyl), $CONH_2$, preferably COOH.

Particularly preferred for L2 is:

Formula A3

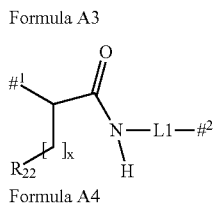

Formula A4

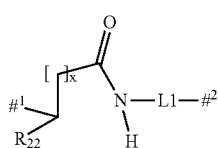

where $\#^1$ denotes the point of attachment to the sulphur atom of the binder, $\#^2$ denotes the point of attachment to the active compound, x represents 1 or 2, and $R_{22}$ represents COOH, COOR, COR, CONHR (where R in each case represents $C_{1-3}$-alkyl), $CONH_2$, preferably COOH. It is preferred when x=1 and $R_{22}$ represents COOH.

In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A3 or A4. Here, the structures of the formula A3 or A4 are generally present together, preferably in a ratio of from 60:40 to 40:60, based on the number of bonds to the binder. The remaining bonds are then present as the structure

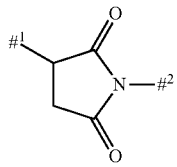

According to the invention, L1 is preferably represented by the formula $\#^1$—$(NR^{10})_n$-$(G1)_o$-G2-$\#^2$ where
$R^{10}$ represents H, $NH_2$ or $C_1$-$C_3$-alkyl;
G1 represents —NHCO—, —CONH— or

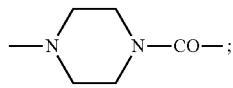

($R^{10}$ is preferably not $NH_2$, if G1 represents NHCO or

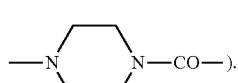).

n is 0 or 1;
o is 0 or 1; and

G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, SO$_2$, —C(NH)NR$^y$—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, C$_1$-C$_3$-alkyl or phenyl) and/or a 3- to 10-membered aromatic or non-aromatic heterocycle having up to 4 heteroatoms selected from the group consisting of N, O and S, —SO— or —SO$_2$— (preferably


), where the hydrocarbon chain including any side chains may be substituted by —NHCONH$_2$, —COOH, —OH, —NH$_2$, NH—CNNH$_2$, sulphonamide, sulphone, sulphoxide or sulphonic acid.

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH— and a 5- to 10-membered aromatic or non-aromatic heterocycle having up to 4 heteroatoms selected from the group consisting of N, O and S, or —SO— (preferably


), where the side chains, if present, may be substituted by —NHCONH$_2$, —COOH, —OH, —NH$_2$, NH—CNNH$_2$, sulphonamide, sulphone, sulphoxide or sulphonic acid.

G2 preferably represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH—, —CH$^x$=N—O— (where R$^x$ represents H, C$_1$-C$_3$-alkyl or phenyl) and a 3- to 10-membered, for example 5- to 10-membered, aromatic or non-aromatic heterocycle having up to 4 heteroatoms selected from the group consisting of N, O and S, —SO— or —SO$_2$— (preferably

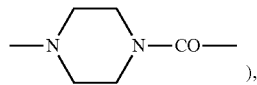

), where the hydrocarbon chain including the side chains, if present, may be substituted by —NHCONH$_2$, —COOH, —OH, —NH$_2$, NH—CNNH$_2$, sulphonamide, sulphone, sulphoxide or sulphonic acid.

Further interrupting groups in G2 are preferably

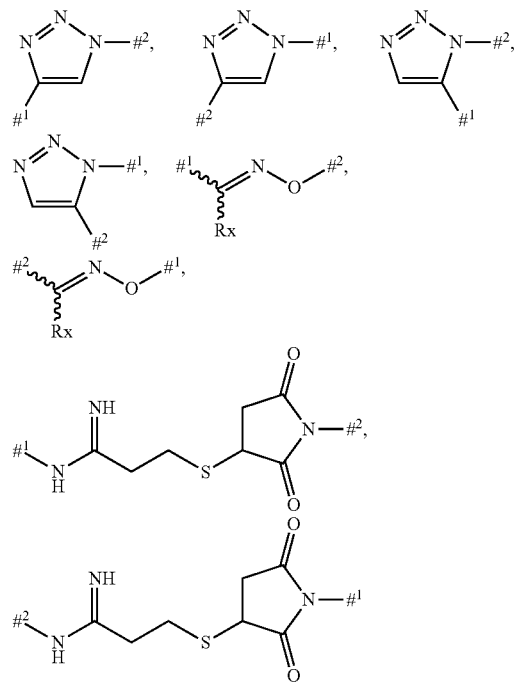

where Rx represents H, C$_1$-C$_3$-alkyl or phenyl.

Here, #$^1$ is the bond to the KSP inhibitor and #$^2$ is the bond to the coupling group to the binder (e.g. L2).

A straight-chain or branched hydrocarbon chain of arylen groups and/or straight-chain and/or branched and/or cyclic alkylene groups generally comprises a α,ω-divalent alkyl radical having the respective number of carbon atoms stated. Examples which may be mentioned as being preferred are: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene).

However, the alkylene groups in the hydrocarbon chain may also be branched, i.e. one or more hydrogen atoms of the straight-chain alkylene groups mentioned above may optionally be substituted by C$_{1-10}$-alkyl groups, thus forming side chains. The hydrocarbon chain may furthermore contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon group. In turn, in the cyclic alkylene groups and the arylene groups, too, one or more hydrogen atoms may optionally be substituted by C$_{1-10}$-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The side chains, if present, may be substituted by —NHCONH$_2$, —COOH, —OH, —NH$_2$, NH—CNNH$_2$, sulphonamide, sulphone, sulphoxide or sulphonic acid.

The hydrocarbon chain may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH— and a 5- to 10-membered aromatic or non-aromatic heterocycle having up to 4 heteroatoms selected from the group consisting of N, O and S, —SO— or —SO$_2$— (preferably
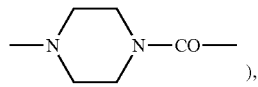
),
Further interrupting groups in G2 are preferably
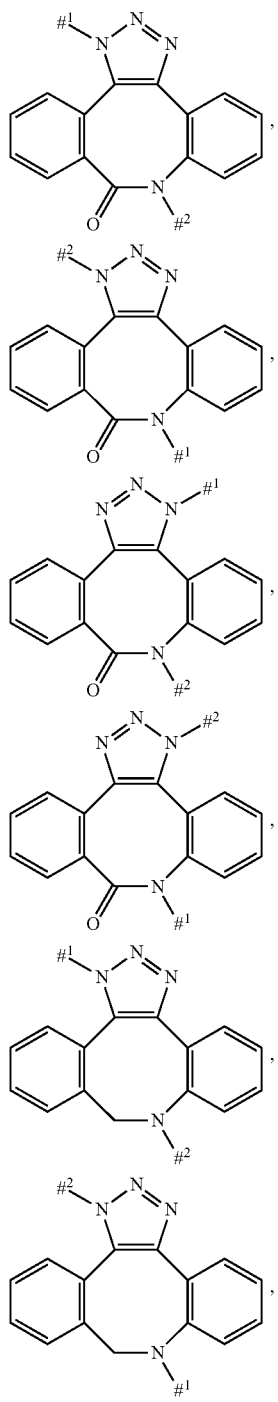
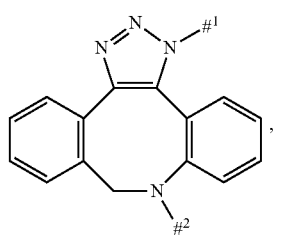
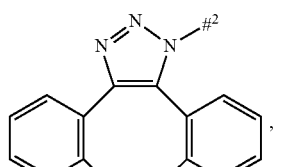
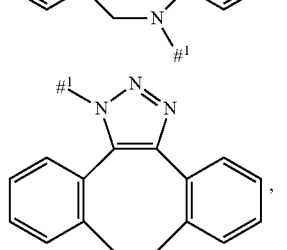
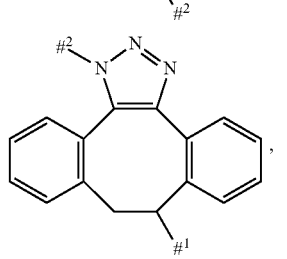
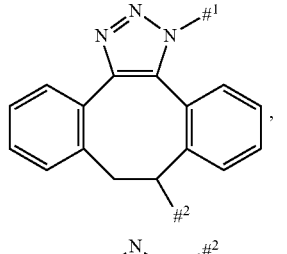
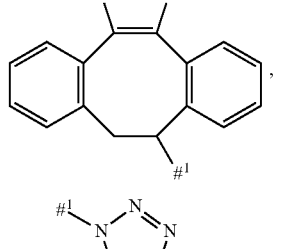
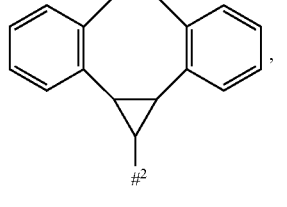

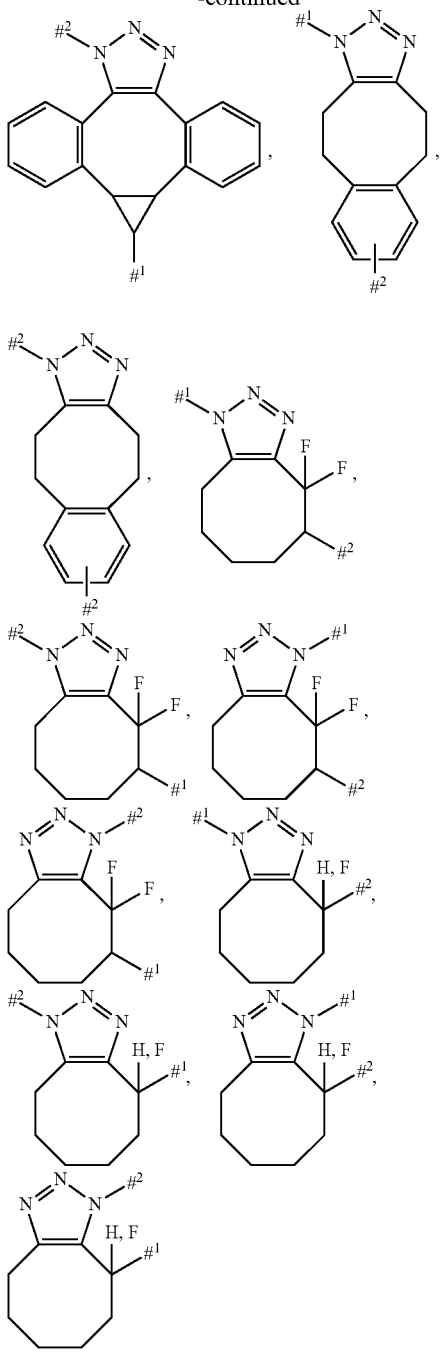

Preferably, the linker corresponds to the formula below:

§-(CO)$_m$-L1-L2-§§ where
m is 0 or 1;
§ represents the bond to the active compound molecule and
§§ represents the bond to the binder peptide or protein, and
L1 and L2 have the meaning given above.
Particularly preferably, L1 has the formula —NR$^{11}$B—,
where
R$^{11}$ represents H or NH$_2$;
B represents —[(CH$_2$)$_x$—(X$^4$)$_y$]w-(CH$_2$)$_z$—,
w=0 to 20;
x=0 to 5;
x=0 to 5;
y=0 or 1;
z=0 to 5; and
X$^4$ represents —O—, —CONH—, —NHCO— or

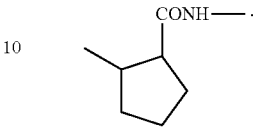

Linkers L which are preferred in accordance with the invention have the formula below:

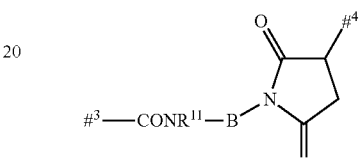

where
$^3$ represents the bond to the active compound molecule,
$^4$ represents the bond to the binder peptide or protein,
R$^{11}$ represents H or NH$_2$;
B represents —[(CH$_2$)$_x$—(X$^4$)$_y$]$_w$—(CH$_2$)$_z$—
w=0 to 20;
x=0 to 5;
y=0 or 1;
z=1 to 5; and
X$^4$ represents —O—, —CONH—, —NHCO— or

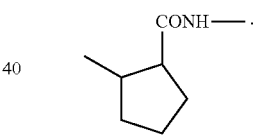

The linkers mentioned above are especially preferred in conjugates of the formula (I) or (II) in which the linker couples by substitution of a hydrogen atom at R$^1$ or in combination with a cleavable linker SG1 at R$^4$, i.e. R$^1$ represents —L-#$^1$ or R$^4$ represents -SG1—L-#$^1$, where #$^1$ represents the bond to the binder.

Preference in accordance with the invention is furthermore given to the linkers below: In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A5 or A6:

Formula A5

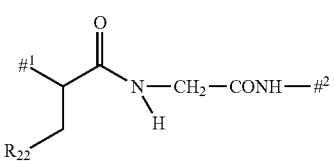

-continued

Formula A6

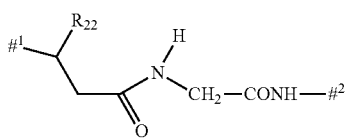

where
¹ denotes the point of attachment to the sulphur atom of the binder,
² denotes the point of attachment to group L1, and
$R_{22}$ represents COOH, COOR, COR, CONHR (where R in each case represents C1-3-alkyl), $CONH_2$, preferably COOH.

Here, the structures of the formula A5 or A6 are generally present together, preferably in a ratio of from 60:40 to 40:60, based on the number of bonds to the binder. The remaining bonds are then present as the structure

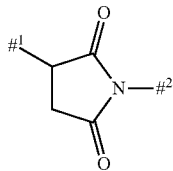

Other linkers -L- attached to a cysteine side chain or cysteine residue have the formula below:

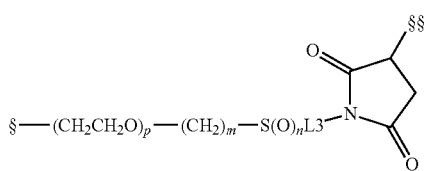

where
§ represents the bond to the active compound molecule and
§§ represents the bond to the binder peptide or protein,
m is 0, 1, 2 or 3;
n is 0, 1 or 2;
p is 0 to 20; and
L3 represents

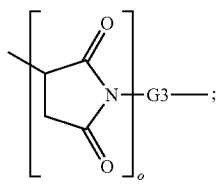

where
o is 0 or 1;
and
G3 represents a straight-chain or branched hydrocarbon chain having 1 to 100 carbon atoms from arylene groups and/or straight-chain and/or cyclic alkylene groups and which may be interrupted once or more than once by one or more of the groups —O—, —S—, —SO—, $SO_2$, —NH—, —CO—, —NHCO—, —CONH—, —NMe—, —NHNH—, —$SO_2$NHNH—, —CONHNH— and a 3- to 10-membered (preferably 5- to 10-membered) aromatic or non-aromatic heterocycle having up to 4 heteroatoms selected from the group consisting of N, O and S, —SO— or $SO_2$ (preferably

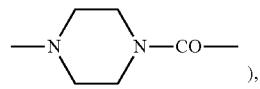

), where the side chains, if present, may be substituted by —$NHCONH_2$, —COOH, —OH, —$NH_2$, NH—$CNNH_2$, sulphonamide, sulphone, sulphoxide or sulphonic acid.

In the formula above, preferably
m is 1;
p is 0;
n is 0;
and L3 represents

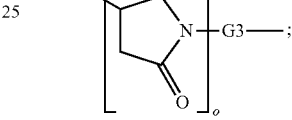

where
o is 0 or 1; and
G3 represents —$(CH_2CH_2O)_s(CH_2)_t(CONH)_uCH_2CH_2O)_v(CH_2)_w$—, where
s, t, v and w each independently of one another are from 0 to 20 and u is 0 or 1.

Preferred groups L1 in the formula §-$(CO)_m$-L1-L2-§§ above are those below, where r in each case independently of one another represents a number from 0 to 20, preferably from 0 to 15, particularly preferably from 1 to 20, especially preferably from 2 to 10:

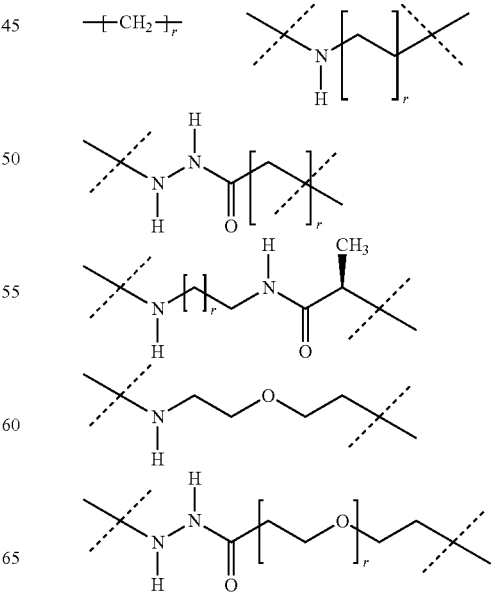

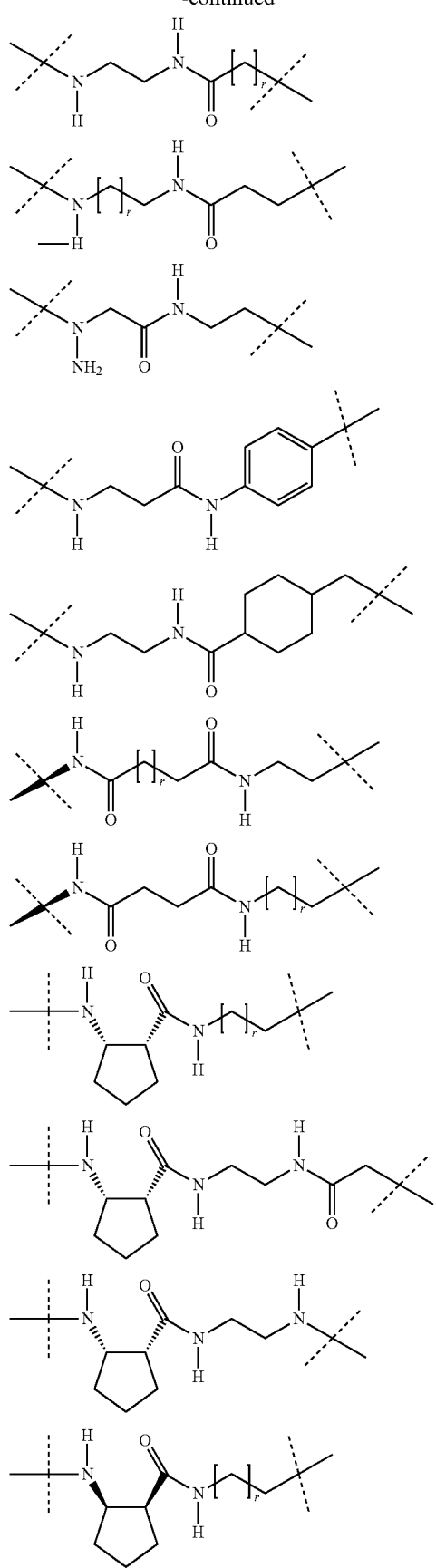
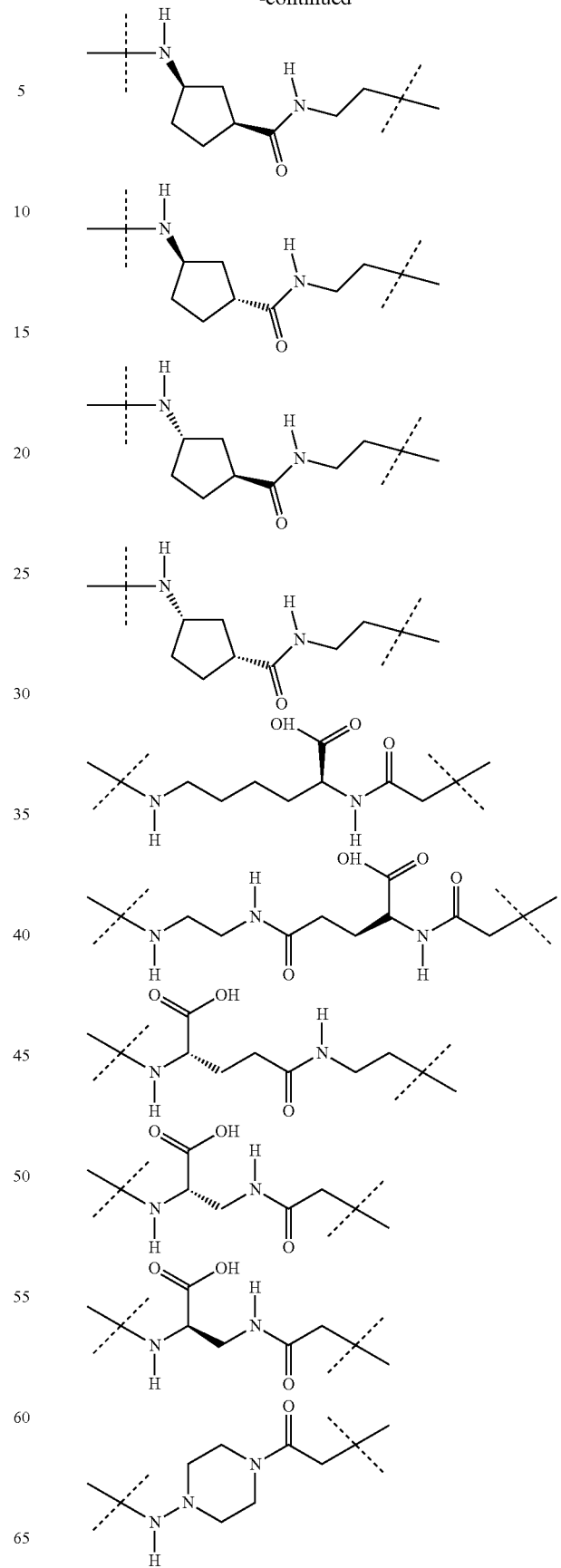

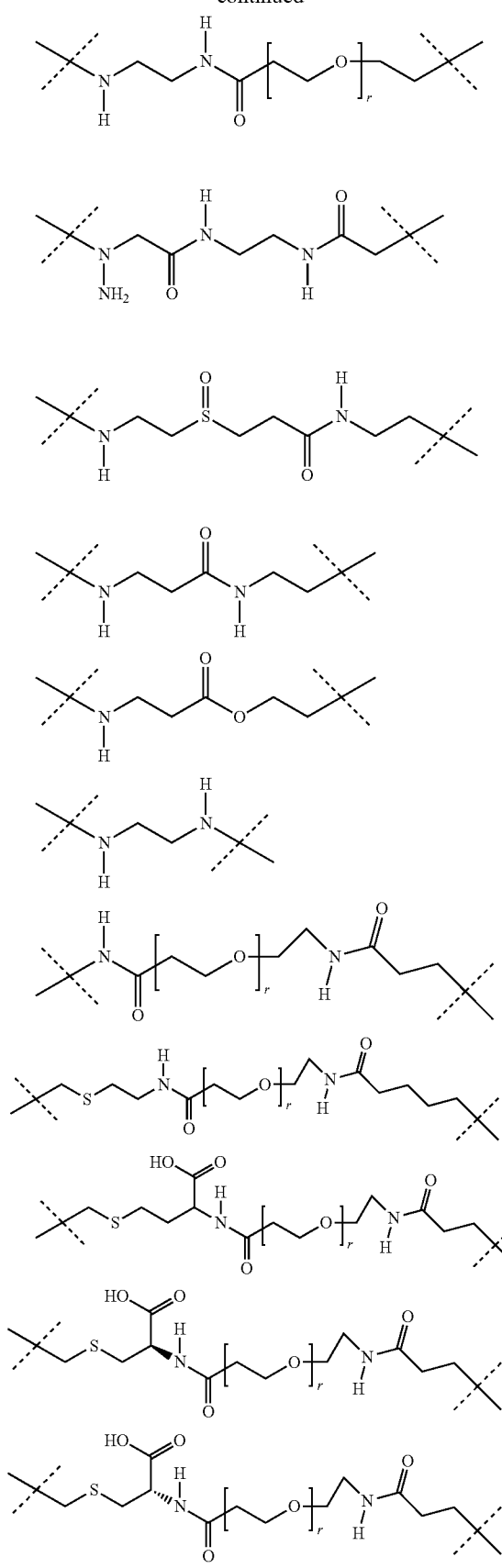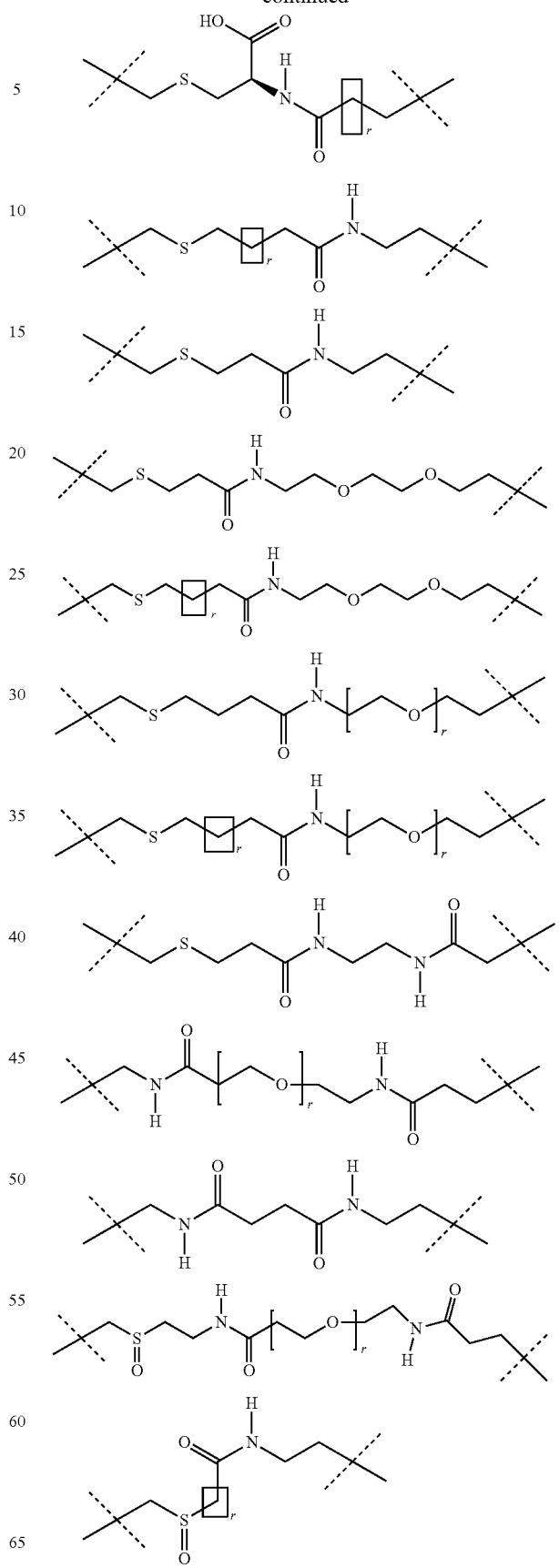

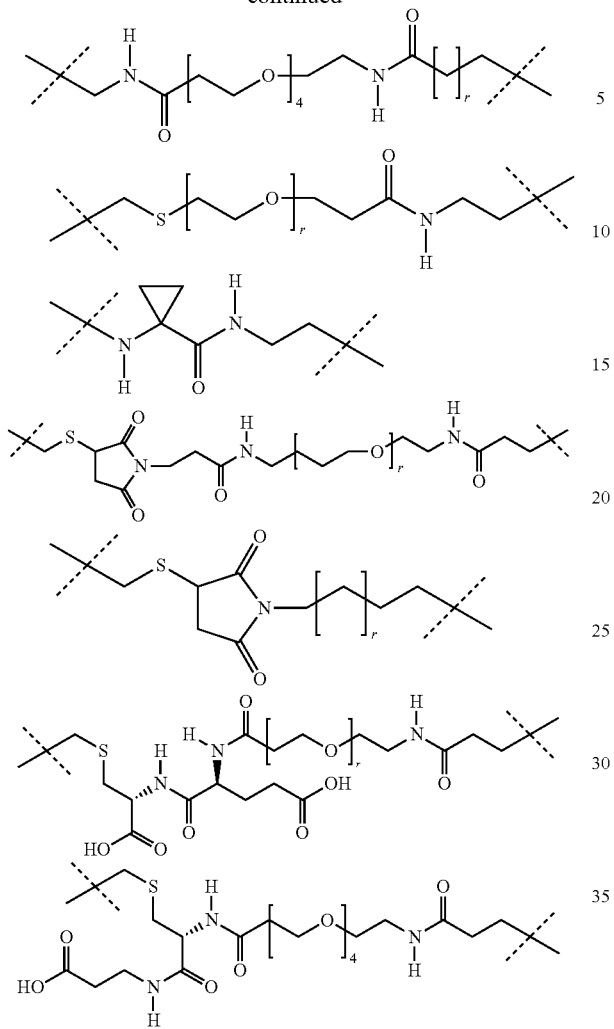
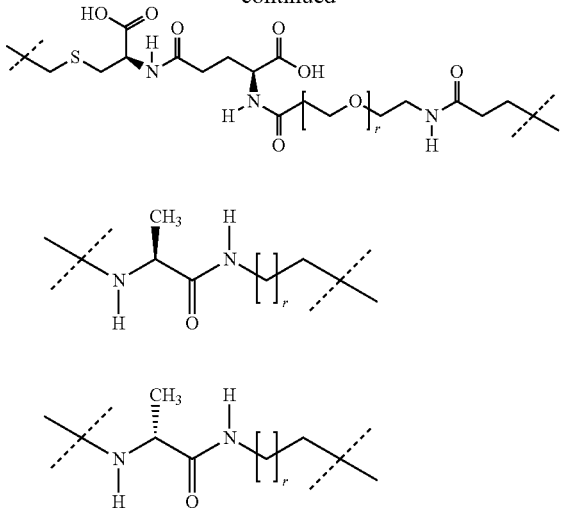

Further examples of L1 are given in Table C, in which this group is highlighted in a box.

Examples of a linker moiety L1 are given in Tables A and A' below. The table furthermore states with which group L2 these examples of L1 are preferably combined, and also the preferred coupling point ($R^1$-$R^5$) and the preferred value for m, this is whether there is a carbonyl group in front of L1 or not (cf. §-(CO)$_m$-L1-L2-§§). These linkers are preferably coupled to a cysteine residue. The first column furthermore states the example numbers for the cetuximab ADCs in which the linkers in question are used, but which likewise apply in each row for ADCs with other antibodies. If L2 is a succinimide or derived therefrom, this imide may also be fully or partially in the form of the hydrolysed open-chain succinamide, as described above. Depending on L1, this hydrolysis to open-chain succinamides may be more or less pronounced or not present at all.

TABLE A

| Ex. | Subst. | m | L1 | L2 |
|---|---|---|---|---|
| 2 | $R^1$ | 1 | | |
| 3 | $R^1$ | 1 | | |
| 4 | $R^1$ | 1 | | |

TABLE A-continued

| Ex. | Subst. | m | L1 | L2 |
|---|---|---|---|---|
| 5 | R¹ | 1 | (structure) | (succinimide) |
| 6 | R¹ | 1 | (structure) | (succinimide) |
| 7 | R¹ | 1 | (structure) | (succinimide) See note ** |
| 9 | R¹ | 1 | (structure) | (succinimide) |
| 10 | R¹ | 1 | (structure) | (succinimide) |
| 11 | R¹ | 1 | (structure) | (succinimide) |
| 12 | R¹ | 1 | (structure) | (succinimide) |
| 13 | R¹ | 1 | (structure) | (succinimide) |

TABLE A-continued
| Ex. | Subst. | m | L1 | L2 |
|---|---|---|---|---|
| 19 | R¹ | 1 | 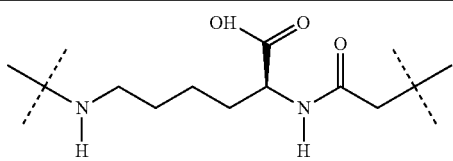 | 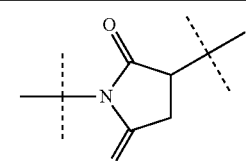<br>See note ** |
| 20 | R¹ | 1 | 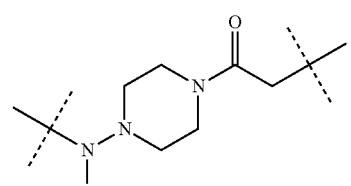 | 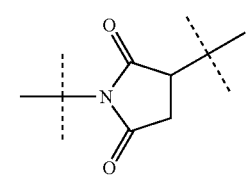<br>See note ** |
| 21/176 | R¹ | 1 | 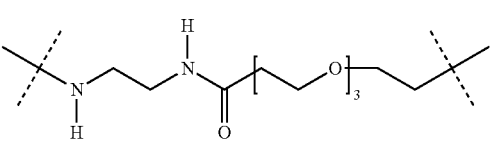 | 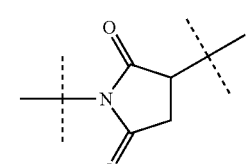 |
| 22 | R¹ | 1 | 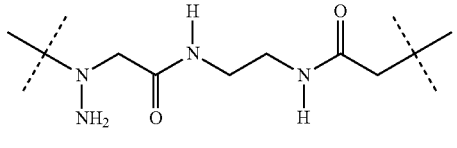 | 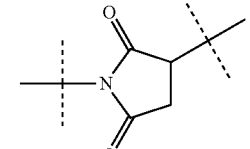<br>See note ** |
| 30 | R¹ | 1 | 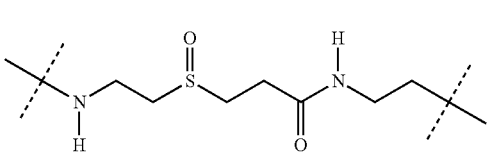 | 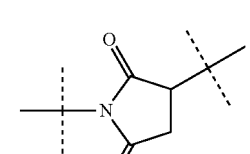 |
| 32 | R¹ | 1 | 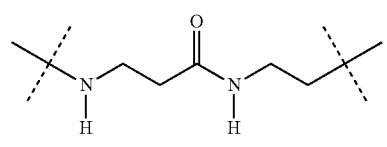 | 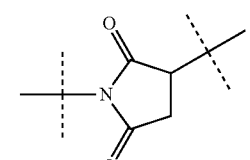 |
| 33 | R¹ | 1 | 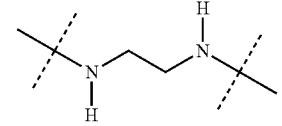 | 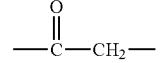 |
| 37 | R²—R⁴* | 0 | 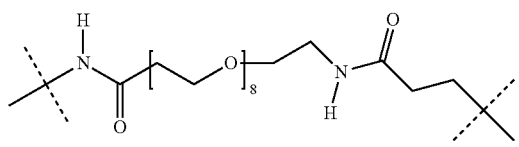 | 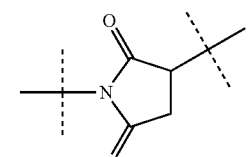 |

TABLE A-continued

| Ex. | Subst. | m | L1 | L2 |
|---|---|---|---|---|
| 38 | R³ | 0 | [structure: -CH2-S-CH2CH2-NH-C(O)-(CH2-CH2-O)8-CH2CH2-NH-C(O)-CH2CH2-] | [maleimide/succinimide structure] |
| 40 | R²—R⁴* | 0 | [structure: -CH2-NH-C(O)-(CH2-O)8-CH2CH2-NH-C(O)-CH2CH2-] | [maleimide/succinimide structure] |
| 41 | R³ | 0 | [structure: -CH2-S(=O)-CH2CH2-NH-C(O)-(CH2-CH2-O)8-CH2CH2-NH-C(O)-CH2CH2-] | [maleimide/succinimide structure] |
| 42 | R²—R⁴* | 1 | [structure: -C(CH3)2-NH-CH2CH2-] | [maleimide/succinimide structure] |
| 44 | R²—R⁴* | 0 | [structure: -CH2-NH-C(O)-(CH2-O)4-CH2CH2-NH-C(O)-CH2CH2-] | [maleimide/succinimide structure] |
| 48 | R³ | 0 | [structure: -CH2-S-(CH2CH2-O)4-CH2CH2-C(O)-NH-CH2CH2-] | [maleimide/succinimide structure] |
| 49 | R³ | 0 | [structure: -CH2-S-(CH2CH2-O)4-CH2CH2-C(O)-NH-CH2CH2-] | [maleimide/succinimide structure] |
| 50 | R¹ | 1 | [structure: cyclopropane with NH and C(O)NH-] | [maleimide/succinimide structure] |
| 51 | R² | 0 | [structure: -CH2-S-(succinimide)-N-CH2-C(O)-NH-(CH2CH2-O)3-CH2CH2-NH-C(O)-CH2CH2-] | [maleimide/succinimide structure] |

TABLE A-continued

| Ex. | Subst. | m | L1 | L2 |
|---|---|---|---|---|
| 52 | R² | 0 | | |
| 53 | R² | 0 | | |
| 54 | R² | 0 | | |
| 56 | R¹ | 1 | | |
| 57 | R¹ | 1 | | |

*R² and R⁴ form a pyrrolidine ring which is substituted by the linker.
**With particular preference, the linkers L1 given in these rows are attached to a linker L2 selected from:

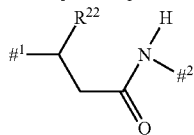

Formula A7 and/or

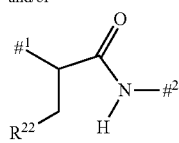

Formula A8 where $\#^1$ denotes the point of attachment to the sulphur atom of the binder, $\#^2$ denotes the point of attachment to group L1, $R_{22}$ preferably represents COOH. In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A7 or A8. Here, the structures of the formula A7 or A8 are generally present together, preferably in a ratio of from 60:40 to 40:60, based on the number of bonds to the binder. The remaining bonds are then present as the structure

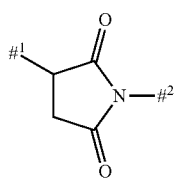

TABLE A'

| Ex. | Subst. | m | L1 | L2 |
|---|---|---|---|---|
| 105 | R¹ | 1 | (structure: N-H–CH(COOH)–CH2CH2–C(=O)–NH–CH2CH2–C(CH3)3) | (structure: succinimide N-linked with tBu) |
| 111 | R¹ | 1 | (structure: NH–cyclopentyl–C(=O)–NH–CH2CH2–C(CH3)3) | (succinimide) |
| 114 | R¹ | 1 | (structure: NH–cyclopentyl–C(=O)–NH–CH2CH2–C(CH3)3) | (succinimide) |
| 119/158 | R¹ | 1 | (structure: NH–CH2CH2–NH) | —C(=O)—CH2— |
| 120 | R¹ | 1 | (structure: NH–cyclopentyl–C(=O)–NH–CH2CH2–C(CH3)3) | (succinimide) |
| 123/157/125 | R¹ | 1 | (structure: NH–cyclopentyl–C(=O)–NH–CH2CH2–C(CH3)3) | (succinimide) |
| 138/142 | R³ | 0 | (structure: S–CH2CH2–CH(COOH)–NH–C(=O)–CH2–(OCH2CH2)4–NH–C(=O)–CH2CH2–C(CH3)3) | (succinimide) |
| 141/143 | R³ | 0 | (structure: S–(CH2)4–C(=O)–NH–CH2CH2–C(CH3)3) | (succinimide) |

TABLE A'-continued

| Ex. | Subst. | m | L1 | L2 |
|---|---|---|---|---|
| 144 | R³ | 0 | (heptyl chain) | (succinimide) |
| 147 | R³ | 0 | –CH₂–S–(CH₂)₃–C(O)–NH–(CH₂CH₂O)₂–CH₂CH₂– | (succinimide) |
| 148 | R³ | 0 | –CH₂–S(O)–(CH₂)₄–C(O)–NH–(CH₂)₂– | (succinimide) |
| 175 | R¹ | 1 | –N(H)–CH₂CH₂–N(H)–C(O)–(CH₂)₅– | (succinimide) |
| 177 | R¹ | 1 | –N(H)–(cyclopentane-1,2-diyl)–C(O)–NH–CH₂CH₂–NH–C(O)–CH₂– | (succinimide) See note ** |
| 178 | R¹ | 1 | –N(H)–(cyclopentane-1,2-diyl)–C(O)–NH–CH₂CH₂–N(H)– | –C(O)–CH₂– |
| 179 | R¹ | 1 | –N(H)–(CH₂)₆– | (succinimide) |
| 180 | R¹ | 1 | –N(H)–CH₂CH₂–NH–C(O)–CH₂CH₂–CH(COOH)–NH–C(O)–CH₂– | (succinimide) See note ** |

TABLE A'-continued

| Ex. | Subst. | m | L1 | L2 |
|---|---|---|---|---|
| 192 | R¹ | 1 | (structure: Dap with COOH, NH, and amide linker) | (succinimide structure) See note ** |
| 193 | R¹ | 1 | (structure: Dap with COOH, NH, and amide linker) | (succinimide structure) See note ** |
| 195 | R¹ | 0 | (structure: succinic diamide linker) | (succinimide structure) |
| 196 | R¹ | 1 | (structure: β-alanine ester linker) | (succinimide structure) |
| 208/199 | R¹ | 1 | (structure: ethylenediamine amide linker) | (structure: substituted succinamic acid) and (structure: substituted succinamic acid isomer) See note *** |
| 208/199 | R¹ | 1 | (structure: ethylenediamine amide linker) | (structure: substituted succinamic acid) |
| 208/199 | R¹ | 1 | (structure: ethylenediamine amide linker) | (structure: substituted succinamic acid) |

TABLE A'-continued

| Ex. | Subst. | m | L1 | L2 |
|---|---|---|---|---|
| 204 | R¹ | 1 | | |
| 209/226 | R³ | 0 | | |
| 210 | R³ | 0 | | |
| 211 | R³ | 0 | | |
| 212 | R³ | 0 | | |
| 213 | R³ | 0 | | See note ** |
| 214 | R³ | 0 | | |
| 216 | R³ | 0 | | |

TABLE A'-continued
| Ex. | Subst. | m | L1 | L2 |
|---|---|---|---|---|
| 217 | R³ | 0 | 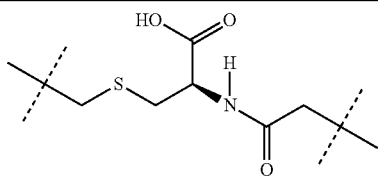 | 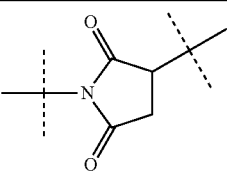\nSee note ** |
| 218 | R³ | 0 | 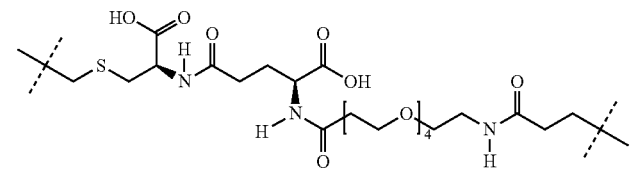 | 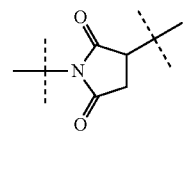 |
| 238 | R² | 0 | 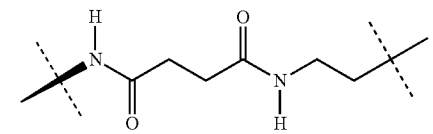 | 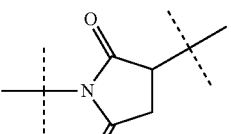 |
|  | R¹ | 1 | 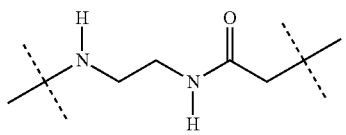 | 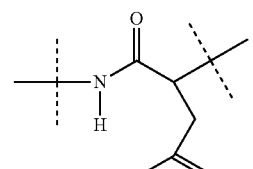\nwhere R₂₂ = —OH\nor —NH₂ |
|  | R¹ | 1 | 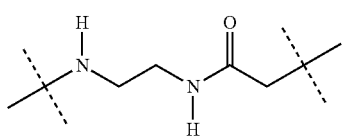 | 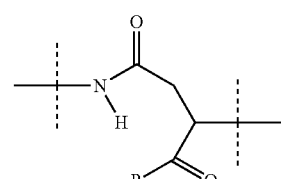\nwhere R₂₂ = —OH\nor —NH₂ |
| 234 | R¹ | 1 | 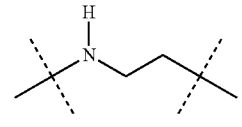 | 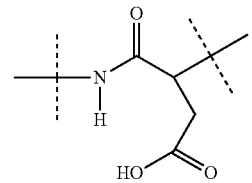\nand\n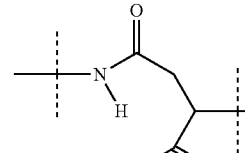\nSee note *** |

TABLE A'-continued

| Ex. | Subst. | m | L1 | L2 |
|---|---|---|---|---|
| 234 | R¹ | 1 | (structure: -N(H)-CH₂-C(CH₃)₂-) | (structure: -NH-C(O)-CH(-)-CH₂-COOH) |
| 234 | R¹ | 1 | (structure: -N(H)-CH₂-C(CH₃)₂-) | (structure: -NH-C(O)-CH₂-CH(-)-COOH) |
| 236 | R¹ | 1 | (structure: -N(H)-CH(COOH)-CH₂-CH₂-NH-C(O)-) | (structure: -NH-C(O)-CH(-)-CH₂-COOH) and (structure: -NH-C(O)-CH₂-CH(-)-COOH) See note *** |
| 236 | R¹ | 1 | (structure: -N(H)-CH(COOH)-CH₂-CH₂-NH-C(O)-) | (structure: -NH-C(O)-CH(-)-CH₂-COOH) |
| 236 | R¹ | 1 | (structure: -N(H)-CH(COOH)-CH₂-CH₂-NH-C(O)-) | (structure: -NH-C(O)-CH₂-CH(-)-COOH) |

TABLE A'-continued

| Ex. | Subst. | m | L1 | L2 |
|---|---|---|---|---|
| 237 | R³ | 0 | (structure) | (structure) and (structure) See note *** |
| 237 | R³ | 0 | (structure) | (structure) |
| 237 | R³ | 0 | (structure) | (structure) |
| 239 | R³ | 0 | (structure) | (structure) and (structure) See note *** |
| 239 | R³ | 0 | (structure) | (structure) |

TABLE A'-continued

| Ex. | Subst. | m | L1 | L2 |
|---|---|---|---|---|
| 239 | R³ | 0 | (structure: dashed-CH2-S-CH2-CH(COOH)-NH-C(=O)-C(CH3)3-dashed) | (structure: dashed-N(H)-C(=O)-CH2-CH(COOH)-dashed, tert-butyl branch) |
| 240 | R³ | 0 | (structure: dashed-CH2-S-CH2CH2-C(=O)-NH-CH2CH2-NH-C(=O)-C(CH3)2-dashed) | (structure: dashed-N(H)-C(=O)-CH(...)-CH2-COOH-dashed) and (second structure similar) See note *** |
| 240 | R³ | 0 | (structure: dashed-CH2-S-CH2CH2-C(=O)-NH-CH2CH2-NH-C(=O)-C(CH3)2-dashed) | (structure: dashed-N(H)-C(=O)-CH-CH2-COOH-dashed) |
| 240 | R³ | 0 | (structure: dashed-CH2-S-CH2CH2-C(=O)-NH-CH2CH2-NH-C(=O)-C(CH3)2-dashed) | (structure: dashed-N(H)-C(=O)-CH(...)-CH2-COOH-dashed) |
| 241 | R¹ | 1 | (structure: dashed-NH-CH2CH2-NH-C(=O)-CH2-NH-dashed) | —C(=O)—CH2— |

TABLE A'-continued

| Ex. | Subst. | m | L1 | L2 |
|---|---|---|---|---|
| 242 | R¹ | 1 | (NH-propyl-NH-C(O)-CH2- linker) | aspartyl-type linker with HOOC branch; and isomer (See note ***) |
| 242 | R¹ | 1 | (NH-propyl-NH-C(O)-CH2- linker) | aspartyl-type linker with HOOC branch |
| 242 | R¹ | 1 | (NH-propyl-NH-C(O)-CH2- linker) | aspartyl-type linker with HOOC branch |
| 243 | R¹ | 1 | (NH-CH2CH2-O-CH2CH2-NH-C(O)-CH2- linker) | aspartyl-type linker with HOOC branch; and isomer (See note ***) |
| 243 | R¹ | 1 | (NH-CH2CH2-O-CH2CH2-NH-C(O)-CH2- linker) | aspartyl-type linker with HOOC branch |

TABLE A'-continued

| Ex. | Subst. | m | L1 | L2 |
|---|---|---|---|---|
| 243 | R¹ | 1 | –NH-CH₂CH₂-O-CH₂CH₂-NH-C(O)-CH₂CH₂– | –NH-C(O)-CH₂-CH(COOH)– |
| 244 | R3 | 0 | –S-CH(NH₂)-C(O)-NH-CH₂CH₂-NH-C(O)-(CH₂)₅– | succinimide (N-substituted 2,5-dioxopyrrolidin-3-yl) |
| 245 | R1 | 0 | –NH-C(O)-CH₂CH₂-C(O)-NH-CH₂CH₂-NH-C(O)-CH₂CH₂– | –NH-C(O)-CH₂-CH(COOH)– and –NH-C(O)-CH(COOH)-CH₂– |

See note ***

| 245 | R1 | 0 | –NH-C(O)-CH₂CH₂-C(O)-NH-CH₂CH₂-NH-C(O)-CH₂CH₂– | –NH-C(O)-CH₂-CH(COOH)– |
| 245 | R1 | 0 | –NH-C(O)-CH₂CH₂-C(O)-NH-CH₂CH₂-NH-C(O)-CH₂CH₂– | –NH-C(O)-CH(COOH)-CH₂– |
| 247 | R1 | 1 | –NH-CH₂CH₂-NH-C(O)-CH₂CH₂– | –NH-C(O)-CH(COOCH₃)-CH₂– |

TABLE A'-continued

| Ex. | Subst. | m | L1 | L2 |
|---|---|---|---|---|
| 248 | R1 | 1 | 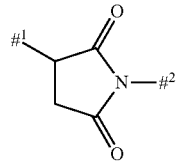 | 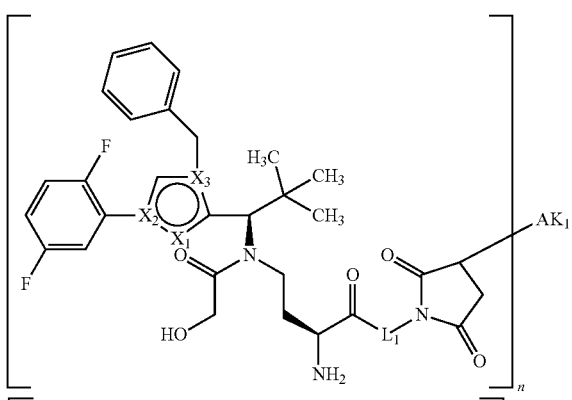 |

\*\*: See note \*\* for Table A.
\*\*\*: When this structure L2 is present, there may simultaneously be a structure L2 of the formula below:

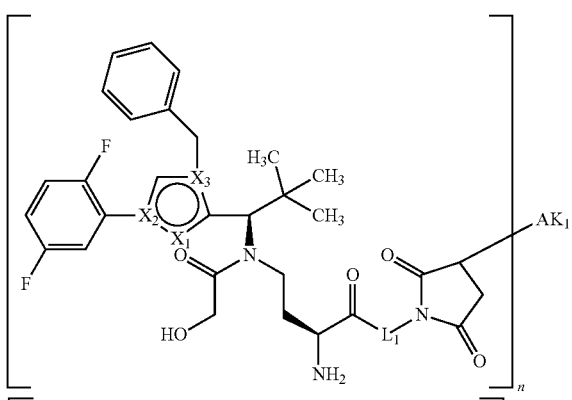

Examples of conjugates having corresponding linkers have the following structures, where $X_1$, $X_2$, $X_3$ and L1 have the meanings given above, L2 and L3 have the same meaning as L1, $AK_1$ represents an antibody attached via a cysteine residue and n is a number from 1 to 10. With particular preference, AK1 is a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2090, or the anti-EGFR antibodies cetuximab or nimotuzumab.

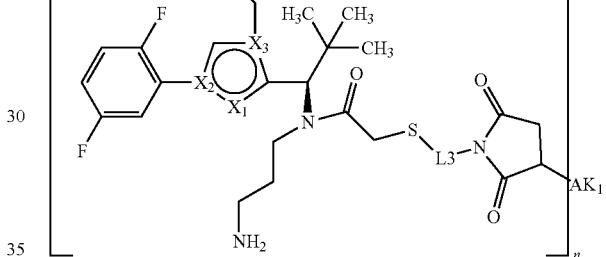

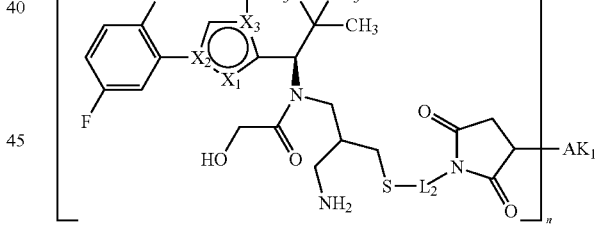

If the linker is attached to a lysine side chain or a lysine residue, it preferably has the formula below:

-§-(SG)$_x$-L4-CO-§§ where
§ represents the bond to the active compound molecule and
§§ represents the bond to the binder peptide or protein,
x represents 0 or 1,
SG represents a cleavable group, preferably a 2-8 oligopeptide, particularly preferably a dipeptide, and
L4 represents a single bond or a group —(CO)$_y$-G4-, where y represents 0 or 1, and
G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—,

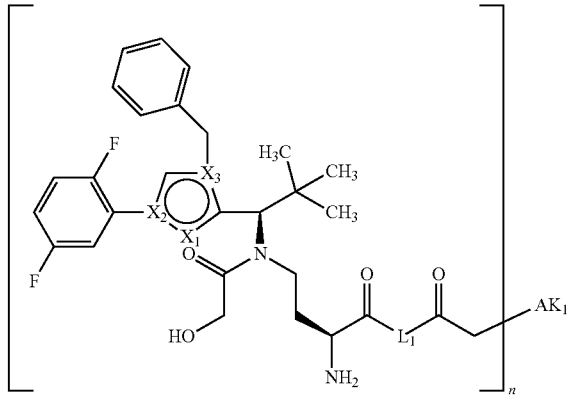

—NMe—, —NHNH—, —SO₂NHNH—, —CONHNH—
and a 5- to 10-membered aromatic or non-aromatic heterocycle having up to 4 heteroatoms selected from the group consisting of N, O and S, —SO— or —SO2- (preferably

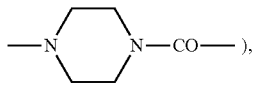
), where the side chains, if present, may be substituted by —NHCONH₂, —COOH, —OH, —NH₂, NH—CNNH₂, sulphonamide, sulphone, sulphoxide or sulphonic acid. Table B below gives examples of linkers to a lysine residue. The table furthermore gives the preferred coupling point (R¹-R⁵). The first column furthermore states the example numbers in which the corresponding linkers are used.

TABLE B lysine linker
-§-(SG)ₓ—L4—CO-§§

| Ex. | Subst. | (SG)ₓ—L4 |
|---|---|---|
| 1A | R¹ | single bond |
| 58/194 | R⁴ | (structure) |

Examples of conjugates having corresponding linkers have the following structures, where X₁, X₂, X₃ and L4 have the meaning given above, AK₂ represents an antibody attached via a lysine residue and n is a number from 1 to 10. With particular preference, AK₂ is a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2090, or the anti-EGFR antibodies cetuximab or nimotuzumab.

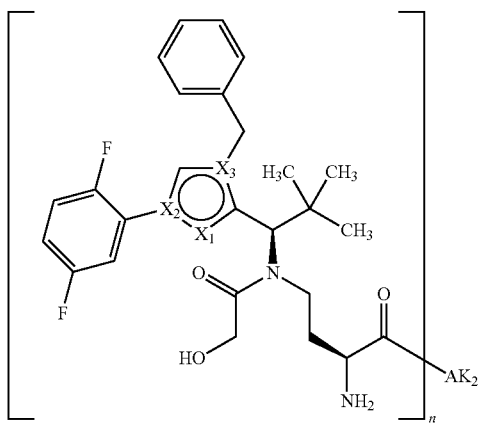

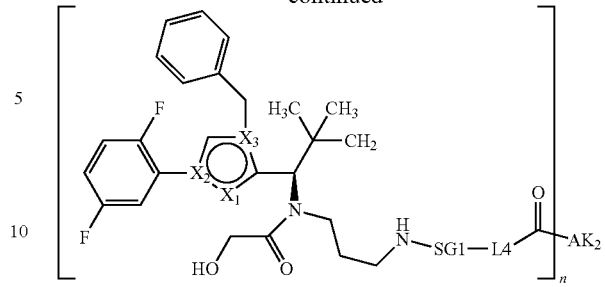

Preference according to the invention is furthermore given to the basic structure (i), (ii) or (iv), where SG1 or SG represents a group which can be cleaved by cathepsin and L1 and L2 have the meanings given above. Particular preference is given to the following groups:

-Val-Ala-CONH— (hereby cleavage of the amide bond at the C-terminal amide of alanine)
—NH-Val-Lys-CONH— (cleavage of the amide bond at the C-terminal amide of lysine)
—NH-Val-Cit-CONH— (cleavage of the amide bond at the C-terminal amide of citrulline)
—NH-Phe-Lys-CONH (cleavage of the amide bond at the C-terminal amide of lysine)
—NH-Ala-Lys-CONH— (cleavage of the amide bond at the C-terminal amide of lysine)
—NH-Ala-Cit-CONH— (cleavage of the amide bond at the C-terminal amide of citrulline)

SG1 or SG is particularly preferably

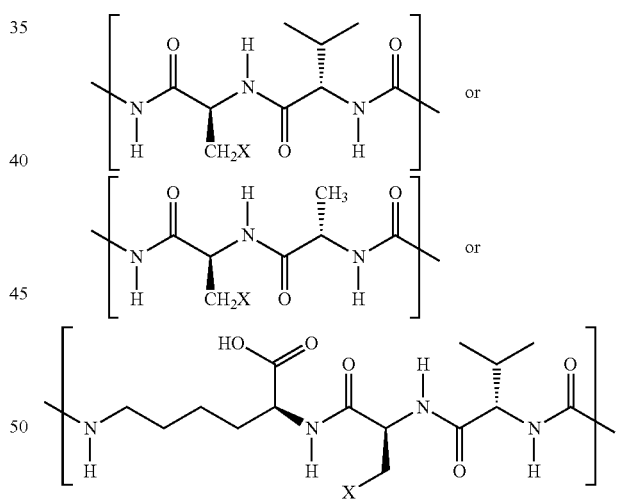

where X represents H or a $C_{1-10}$-alkyl group which may optionally be substituted by —NHCONH₂, —COOH, —OH, NH₂, —NH—CNNH₂ or sulphonic acid.

Table C below gives examples of a linker moiety —SG1-L1- or -L1-SG-L1-, where SG1 and SG are groups which can be cleaved by cathepsin. Table C furthermore states with which group L2 these examples of —SG1-L1- and -L1-SG-L1- are preferably combined, and also the preferred coupling point (R¹-R⁵) and the preferred value for m, thus whether there is a carbonyl group in front of L1 or not (cf. §-(CO)ₘ-L1-L2-§§). These linkers are preferably coupled to a cysteine residue. The first column furthermore states the example numbers, given in an exemplary manner for cetuximab ADCs, in which corresponding linkers are used. They apply in the same manner to the corresponding ADCs with other antibodies. The L1 group is highlighted in a box. However, these groups L1 can be replaced by one of the groups L1 given for formula §-(CO)$_m$-L1-L2-§§ above. If L2 is a succinamide or derived therefrom, this amide may also be fully or partially in the form of the hydrolysed open-chain succinamide, as described above.

TABLE C

| Ex. | Sub St. | m | —SG1—L1— or —L1—SG—L1— | L2 |
|---|---|---|---|---|
| 8A/163A | R$^1$ | 1 | 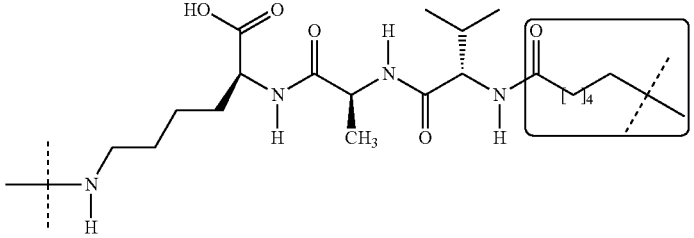 | 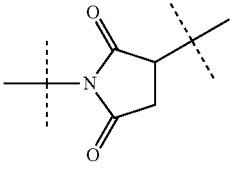 |
| 14A | R$^1$ | 1 | 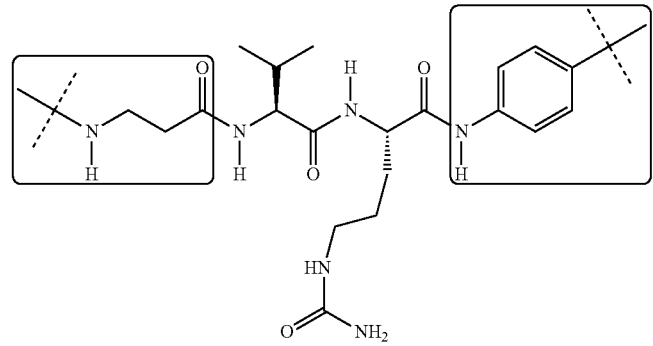 | 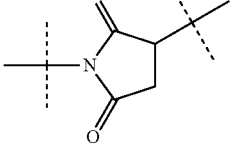 |
| 15A | R$^1$ | 1 | 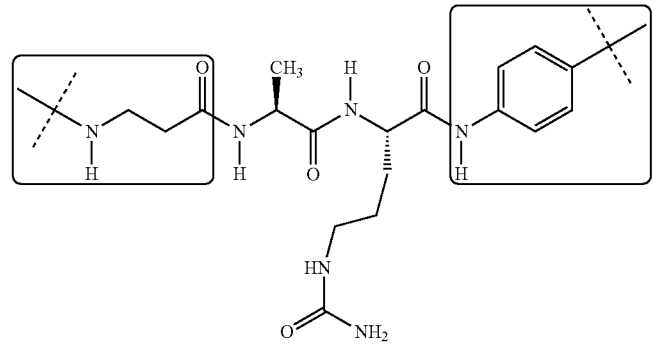 | 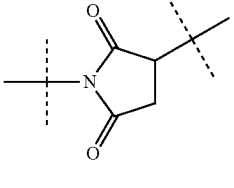 |
| 16A | R$^1$ | 1 | 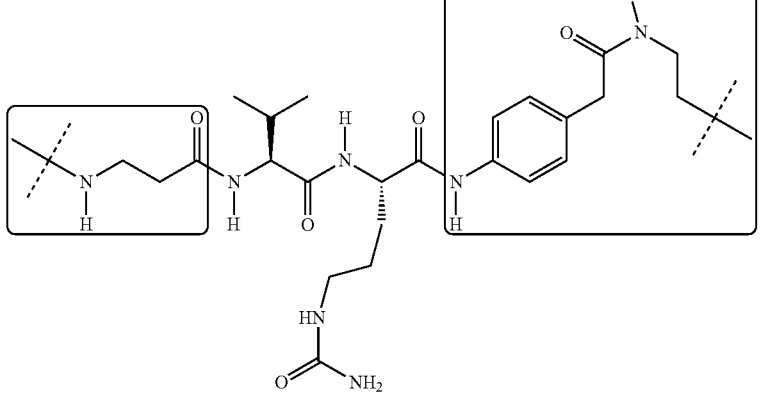 | 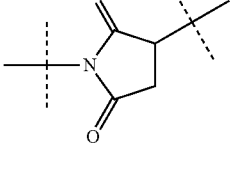 |

TABLE C-continued
| Ex. | Sub St. | m | —SG1—L1— or —L1—SG—L1— | L2 |
|---|---|---|---|---|
| 17A/168A | R¹ | 1 | 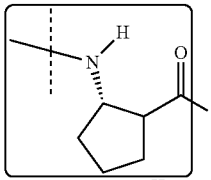 | 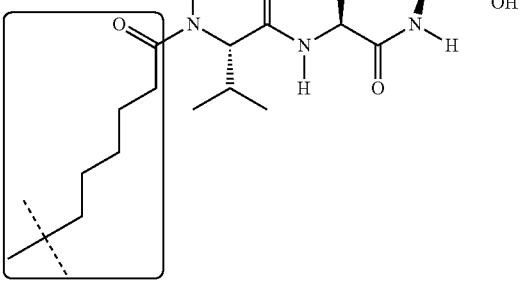 |
| 18A | R¹ | 1 | 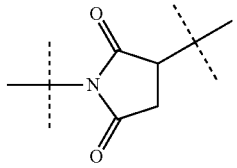 | 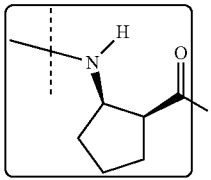 |
| 23A/164A | R¹ | 1 | 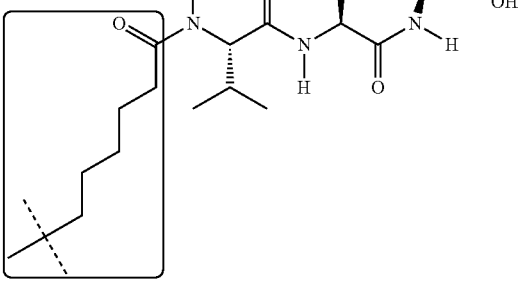 | 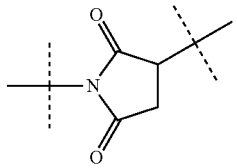 |
| 24A | R¹ | 1 | 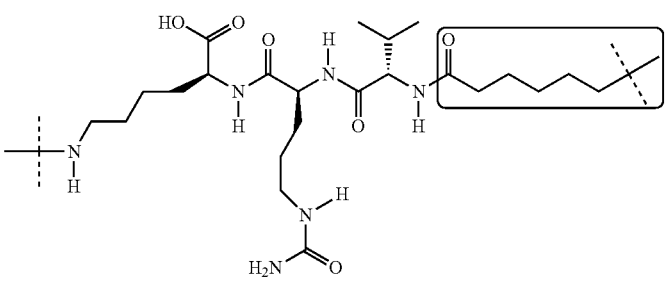 | 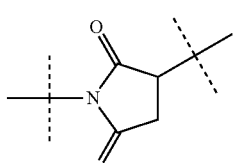 |

TABLE C-continued
| Ex. | Sub St. | m | —SG1—L1— or —L1—SG—L1— | L2 |
|---|---|---|---|---|
| 25A | R¹ | 1 | 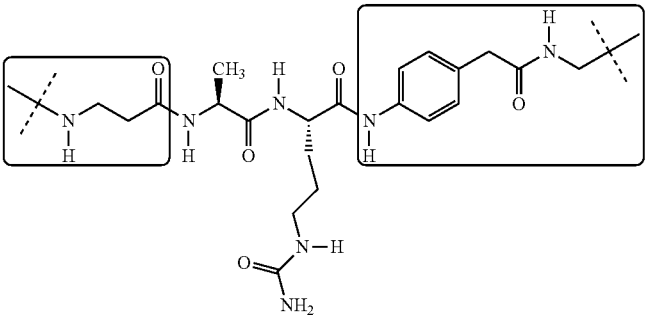 | 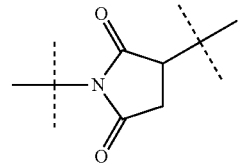 |
| 26A | R¹ | 1 | 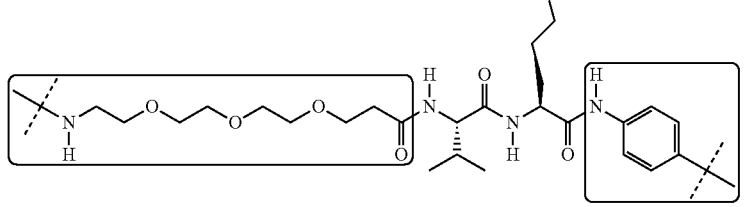 | 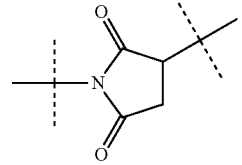 |
| 27A | R¹ | 1 | 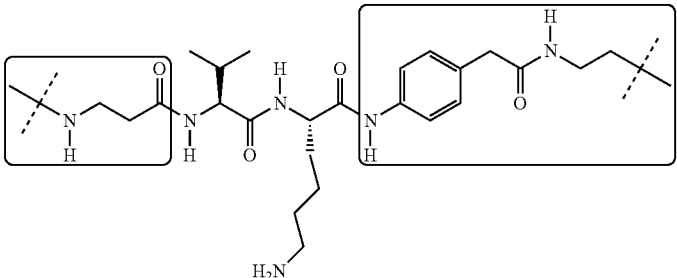 | 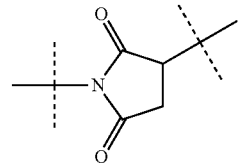 |
| 28A | R¹ | 1 | 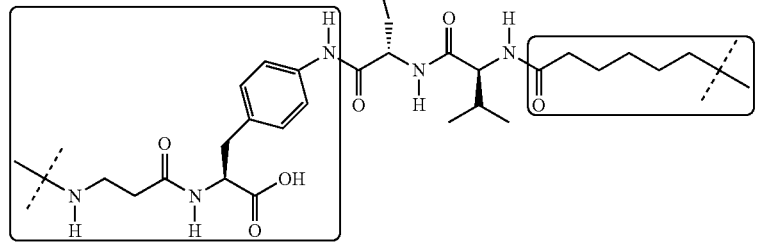 | 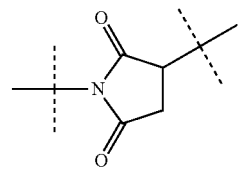 |
| 29A | R¹ | 1 | 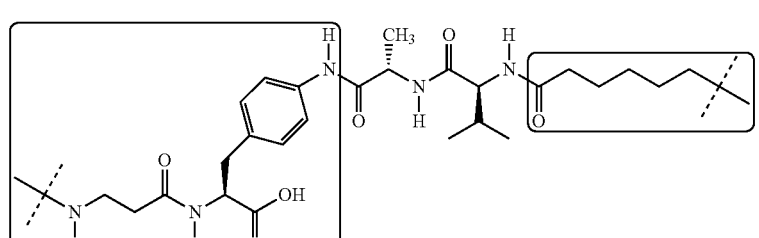 | 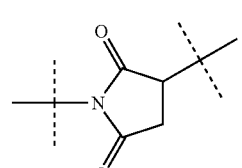 |

TABLE C-continued

| Ex. | Sub St. | m | —SG1—L1— or —L1—SG—L1— | L2 |
|---|---|---|---|---|
| 31A | R⁵(m) | 0 | | |
| 34A | R¹ | 1 | | |
| 35A | R⁴ | 0 | | |
| 36A | R⁴ | 0 | | |
| 39A/215A | R⁴ | 0 | | |
| 43A | R⁴ | 0 | | |

TABLE C-continued

| Ex. | Sub St. | m | —SG1—L1— or —L1—SG—L1— | L2 |
|---|---|---|---|---|
| 45A | R⁴ | 0 | | |
| 46A | R⁴ | 0 | | |
| 47A | R⁴ | 0 | | |
| 55A | R³ | 0 | | |
| 55B | R³ | 0 | | |

TABLE C-continued
| Ex. | Sub St. | m | —SG1—L1— or —L1—SG—L1— | L2 |
|---|---|---|---|---|
| 110 A/ 156 A | R¹ | 1 | 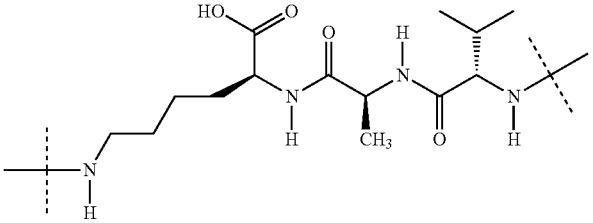 | 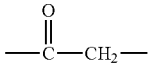 |
| 128 A | R¹ | 1 | 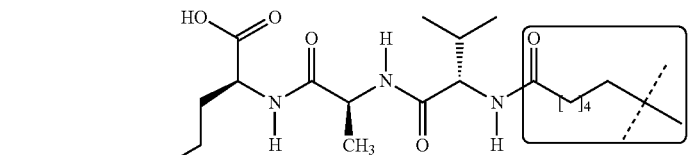 | 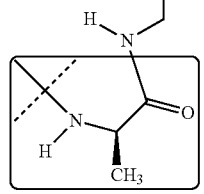 |
| 129 A/ 167 A | R¹ | 1 | 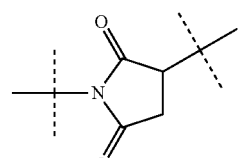 | 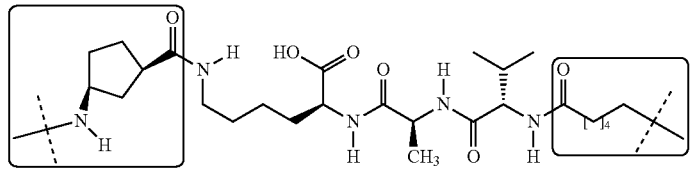 |
| 150 | R³ | 0 | 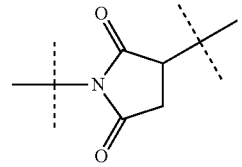 | 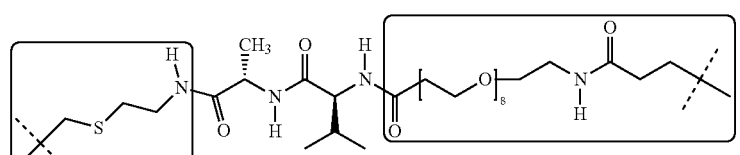 |
| 154 A/ 155 A/ 160 | R¹ | 1 | 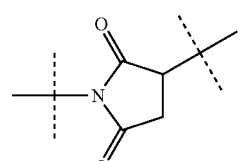 | 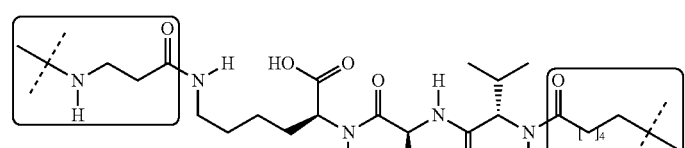 |
| 165 A | R¹ | 1 | 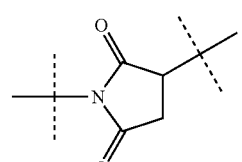 | 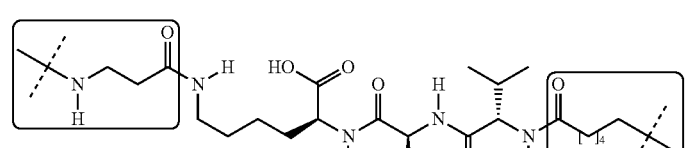 |

US 10,022,453 B2
TABLE C-continued
| Ex. | Sub St. | m | —SG1—L1— or —L1—SG—L1— | L2 |
|---|---|---|---|---|
| 166 A | R¹ | 1 | 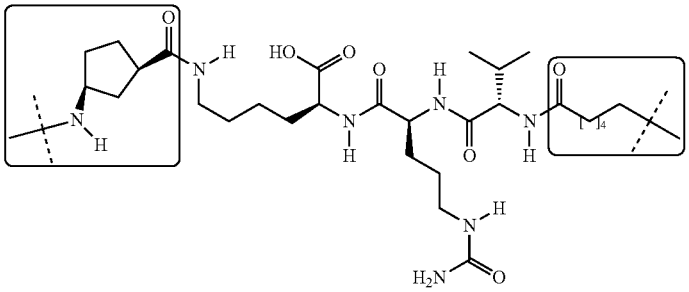 | 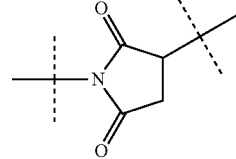 |
| 169 A | R¹ | 1 | 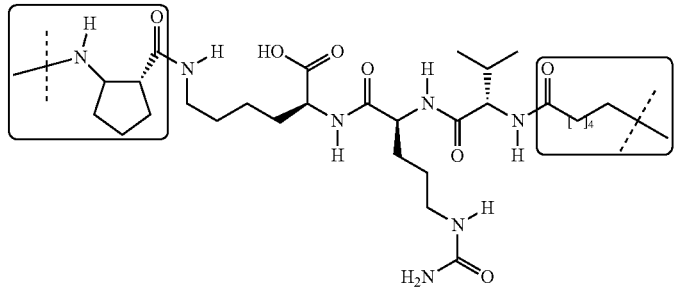 | 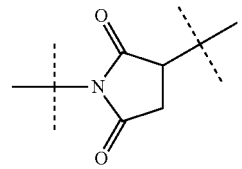 |
| 170 A | R¹ | 1 | 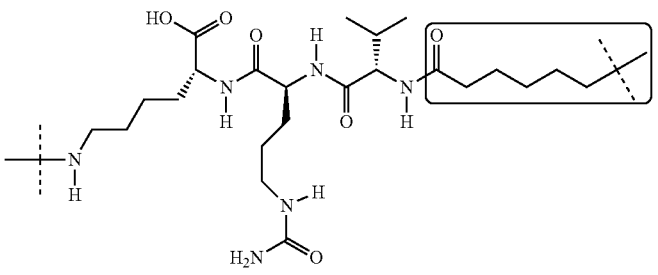 | 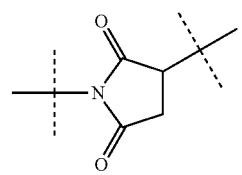 |
| 171 A | R¹ | 1 | 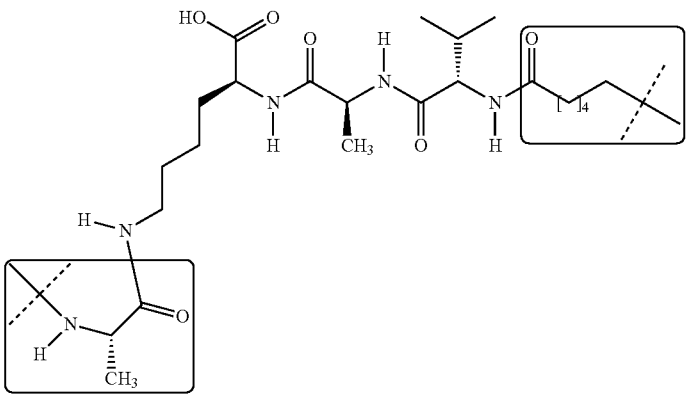 | 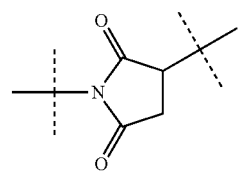 |

TABLE C-continued
| Ex. | Sub St. | m | —SG1—L1— or —L1—SG—L1— | L2 |
|---|---|---|---|---|
| 172A/ 173A/ 174A | R¹ | 1 | 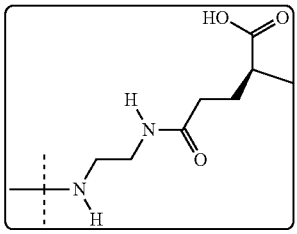 | 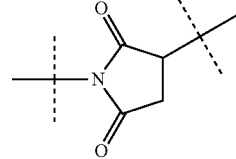 |
| 205A | R¹ | 1 | 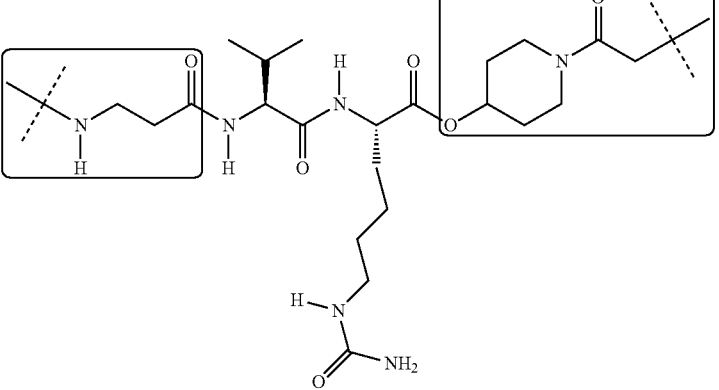 | 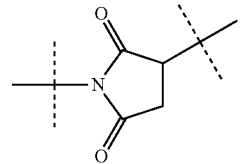 |
| 206A | R¹ | 1 | 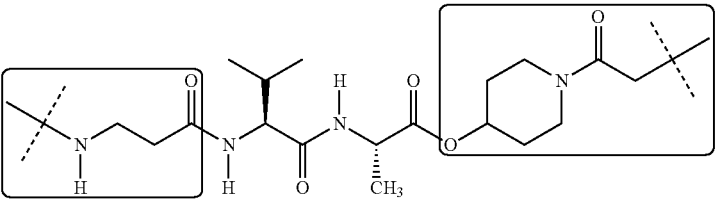 | 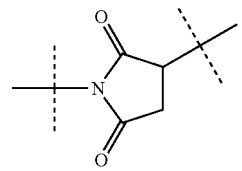 |
| 207A | R¹ | 1 | 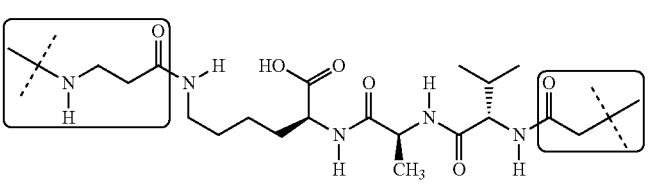 | 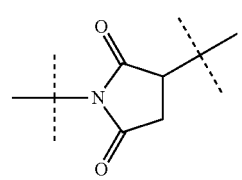 |

TABLE C-continued

| Ex. | Sub St. | m | —SG1—L1— or —L1—SG—L1— | L2 |
|---|---|---|---|---|
| 235 A | R³ | 0 | 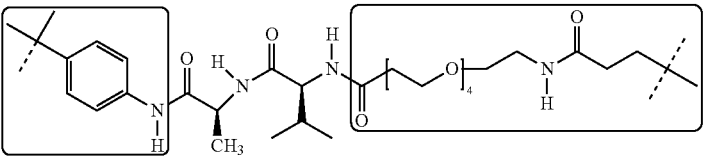 | 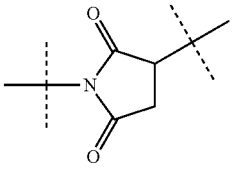 |

Examples of conjugates having basic structure (i) have the following structure, where $X_1$, $X_2$ and $X_3$ have the meanings given above, L4 has the same meaning as L1, $AK_1$ represents an antibody attached via a cysteine residue and n is a number from 1 to 10. Particularly preferably, $AK_1$ is an anti-TWEAKR antibody, in particular an anti-TWEAKR antibody which binds specifically to amino acid D in position 47 (D47) of TWEAKR (SEQ ID NO:169), in particular the anti-TWEAKR antibody TPP-2090.

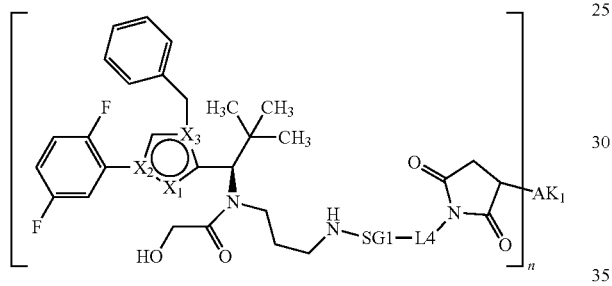

KSP Inhibitor— Linker-Intermediates and Preparation of the Conjugates

The conjugates according to the invention are prepared by initially providing the low-molecular weight KSP inhibitor with a linker. The intermediate obtained in this manner is then reacted with the binder (preferably antibody).

Preferably, for coupling to a cysteine residue, one of the compounds below is reacted with the cysteine-containing binder such as an antibody, which is optionally partially reduced for this purpose:

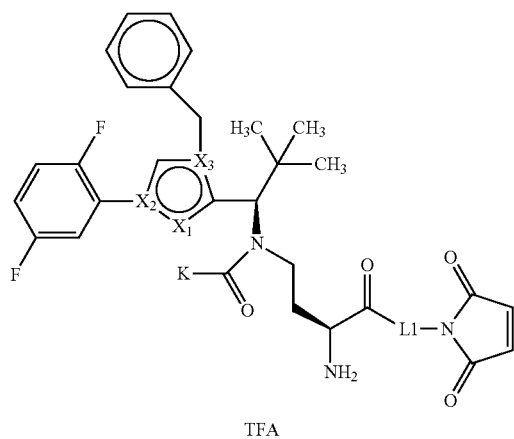

TFA

-continued

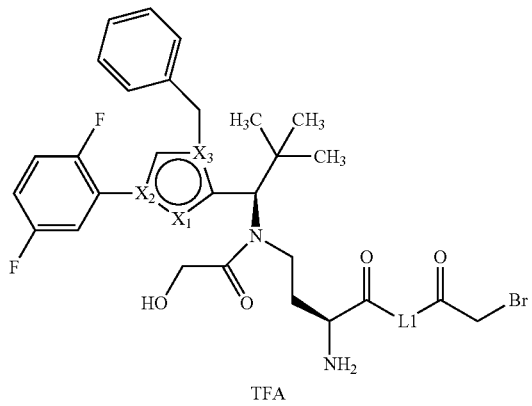

TFA

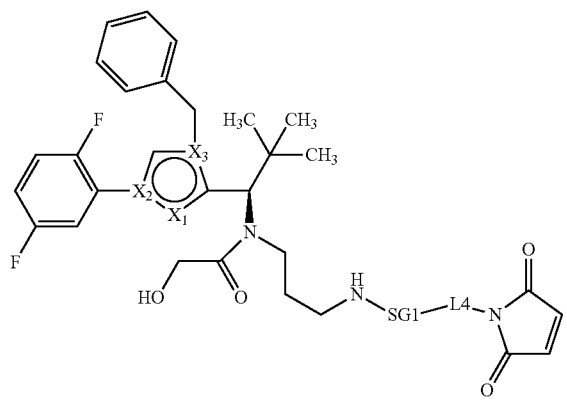

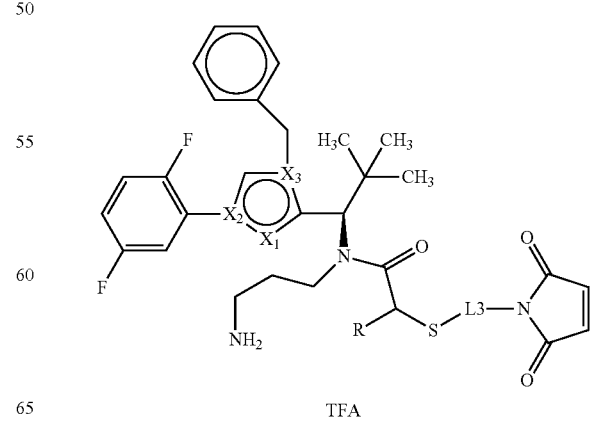

TFA

109
-continued
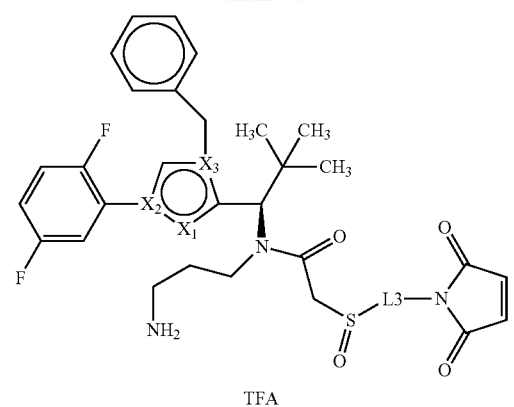
TFA
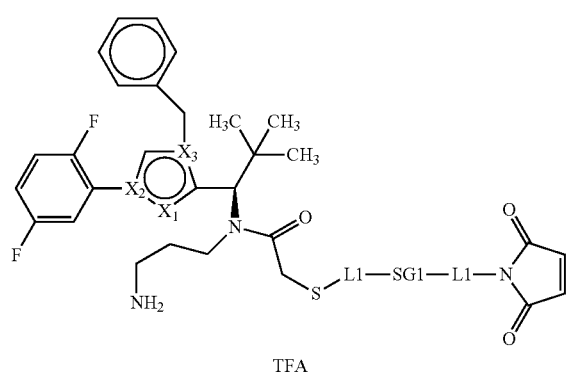
TFA
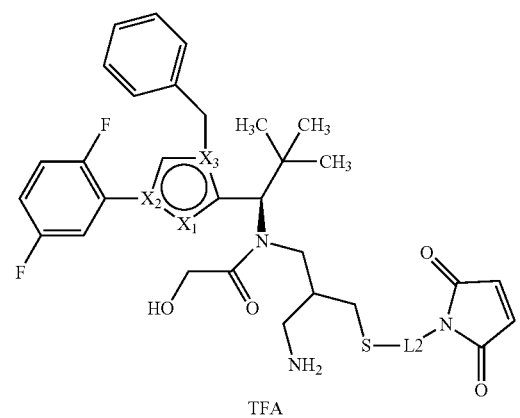
TFA
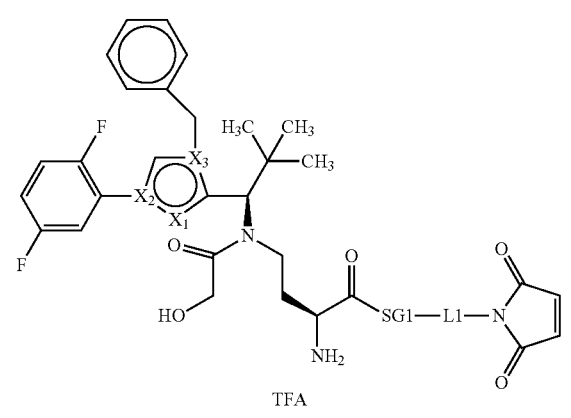
TFA
110
-continued
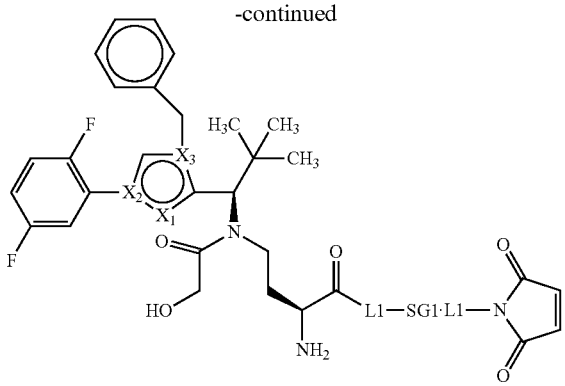
TFA
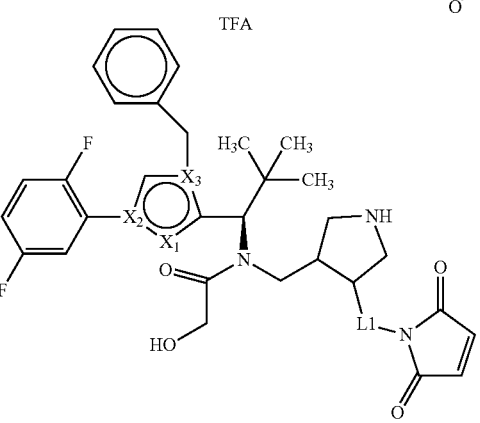
TFA
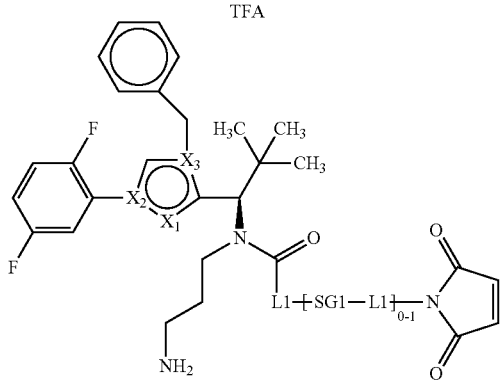
TFA
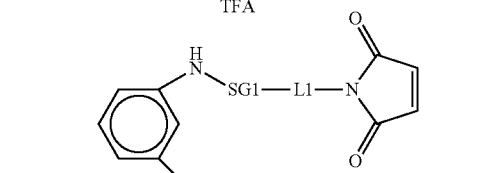
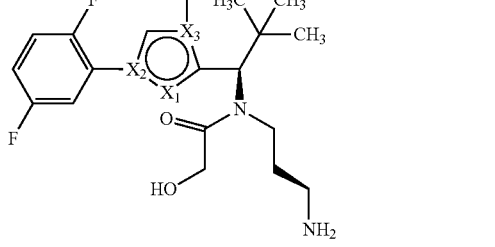
TFA
where R represents —H or —COOH,
where K represents straight-chain or branched $C_1$-$C_6$ alkyl which is optionally substituted by $C_1$-$C_6$-alkoxy or —OH, and where $X_1$, $X_2$, $X_3$, SG1, L1, L2, L3 and L4 have the same meaning as described above.

The compound may be employed, for example, in the form of its trifluoroacetic acid salt. For the reaction with the binder such as, for example, the antibody, the compound is preferably used in a 2- to 12-fold molar excess with respect to the binder.

Preferably, for coupling to a lysine residue, one of the compounds below is reacted with the lysine-containing binder such as an antibody:

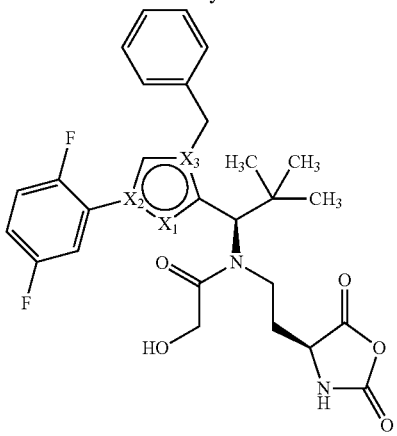

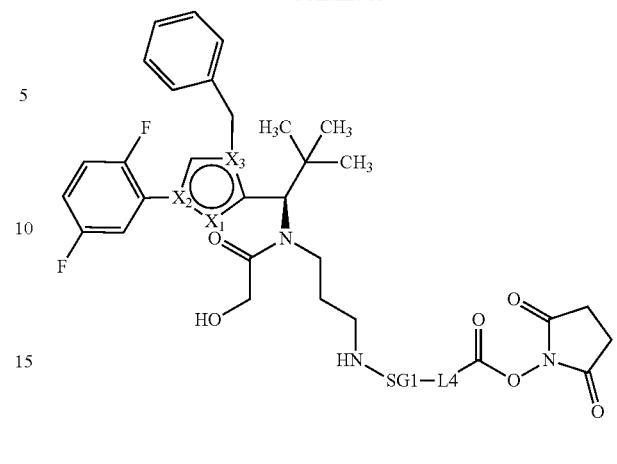

where $X_1$, $X_2$, $X_3$ have the same meaning as in formula (II) and L4 has the same meaning as L1 and L1 has the same meaning as described above.

For an intermediate coupling to a cysteine residue, the reactions can be illustrated as follows:

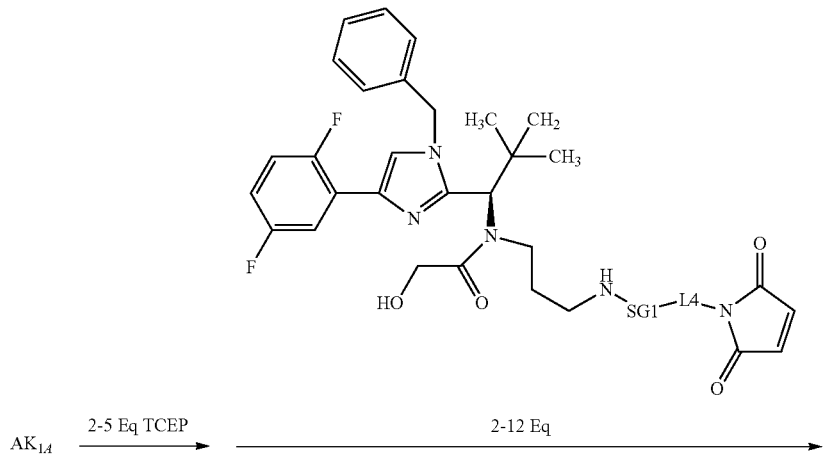

$AK_{1A}$ $\xrightarrow{\text{2-5 Eq TCEP}}$ $\xrightarrow{\text{2-12 Eq}}$

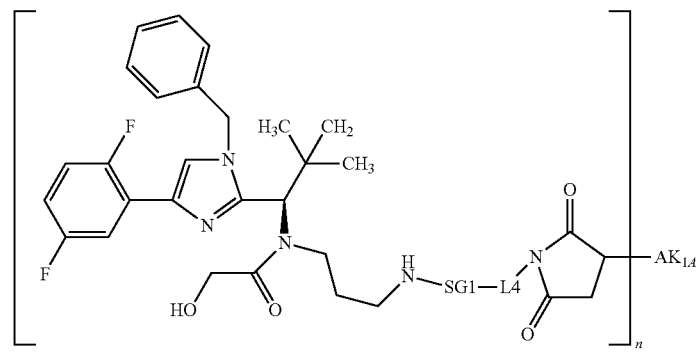

-continued
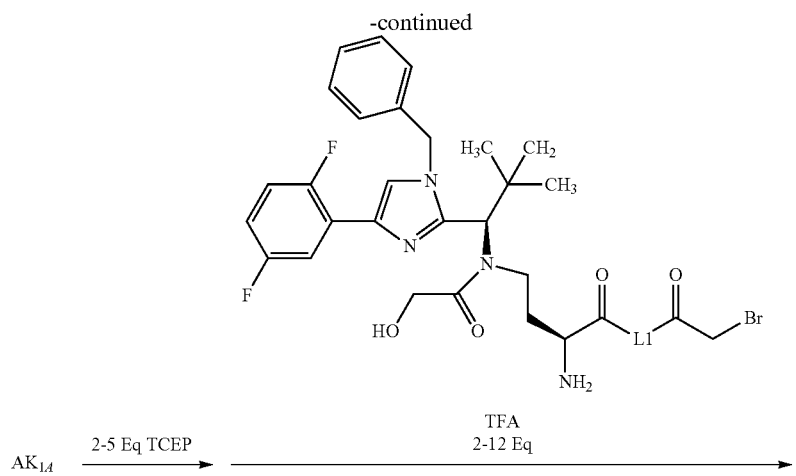
AK$_{1A}$ $\xrightarrow{\text{2-5 Eq TCEP}}$ $\xrightarrow[\text{2-12 Eq}]{\text{TFA}}$
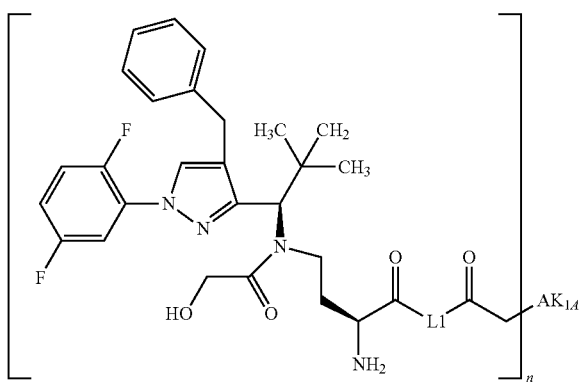
The other intermediates and other antibodies can be reacted correspondingly.
For an intermediate coupling to a lysine radical, the reaction can be illustrated as follows:
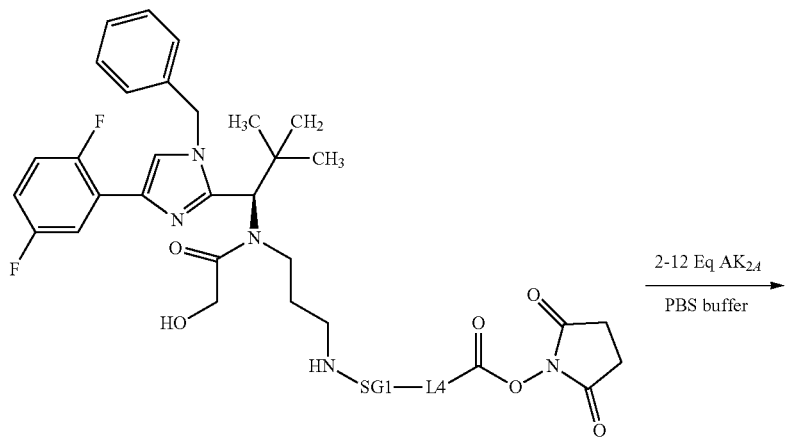

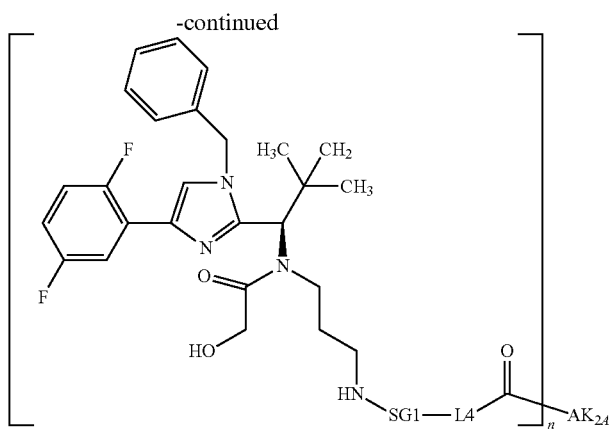
In accordance with the invention, this gives the following conjugates:
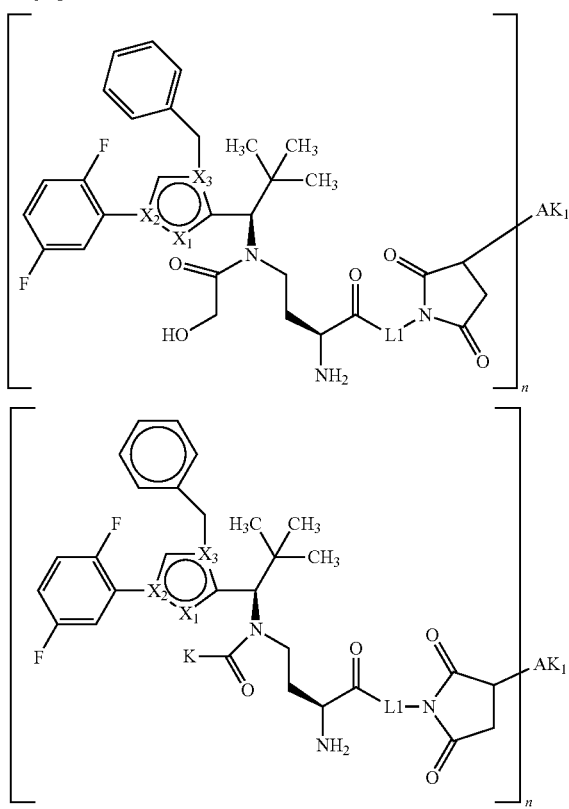
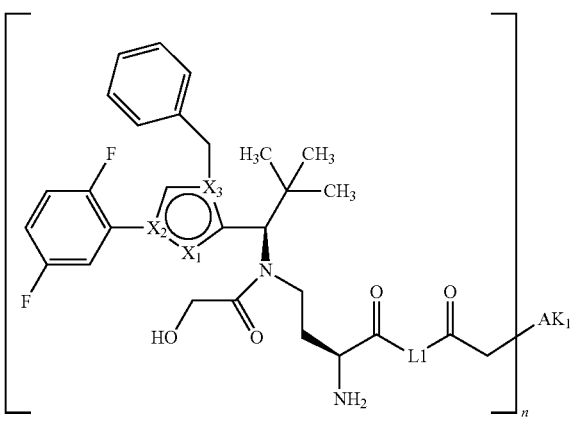
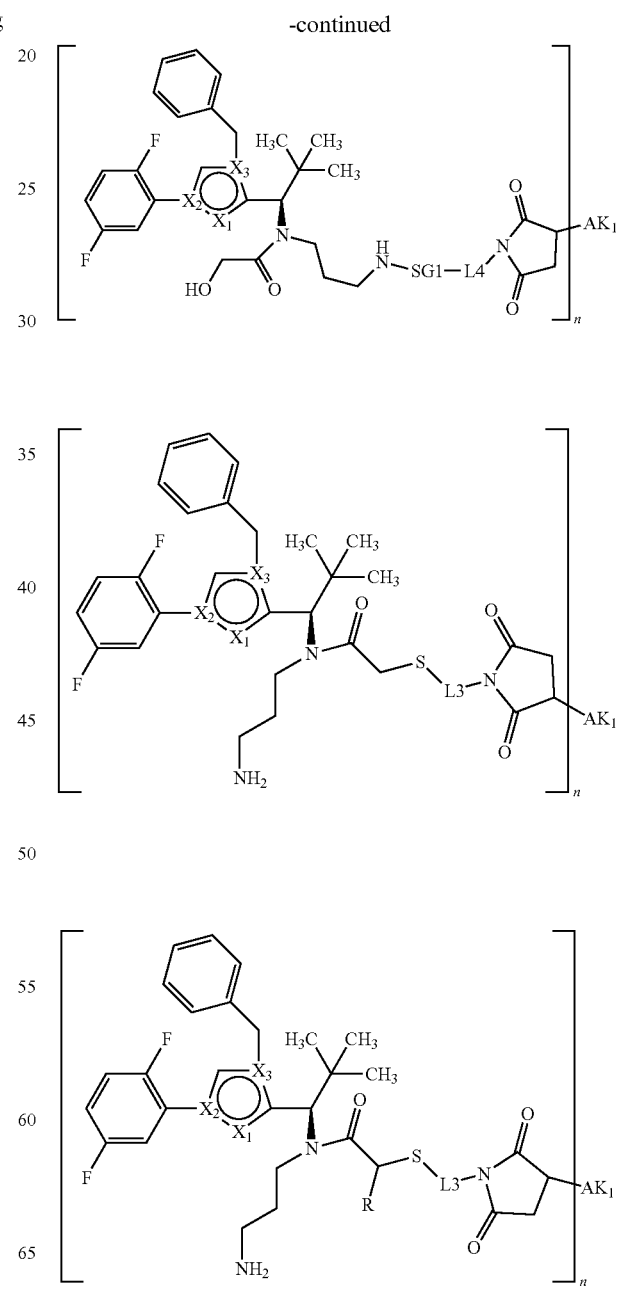

117
-continued
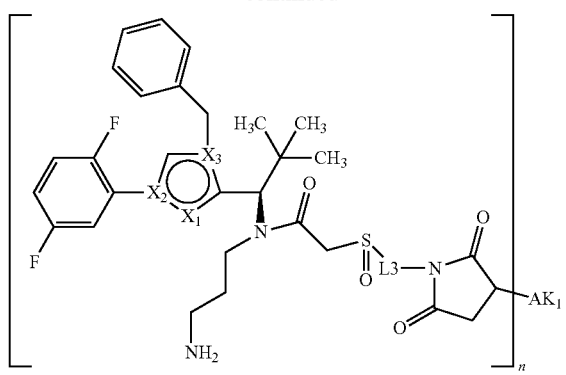
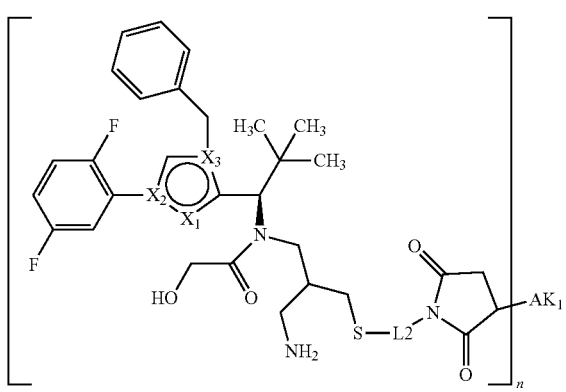
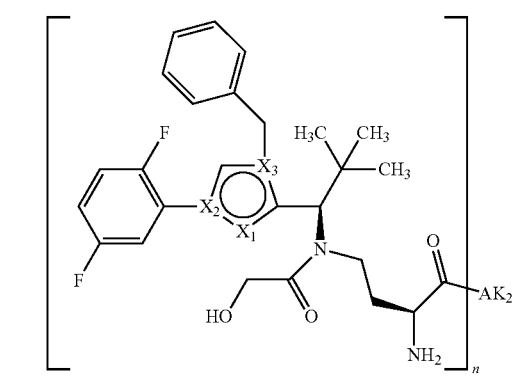
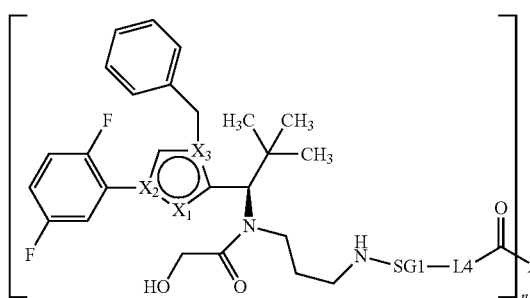
118
-continued
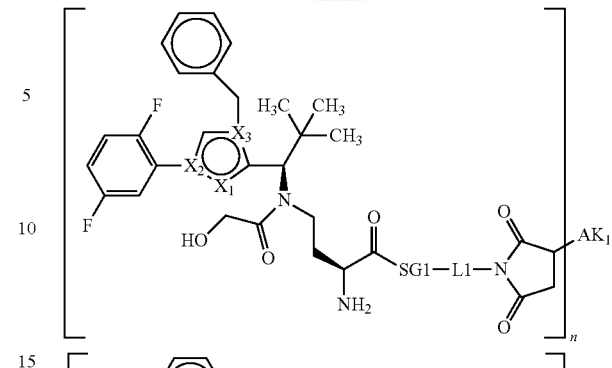
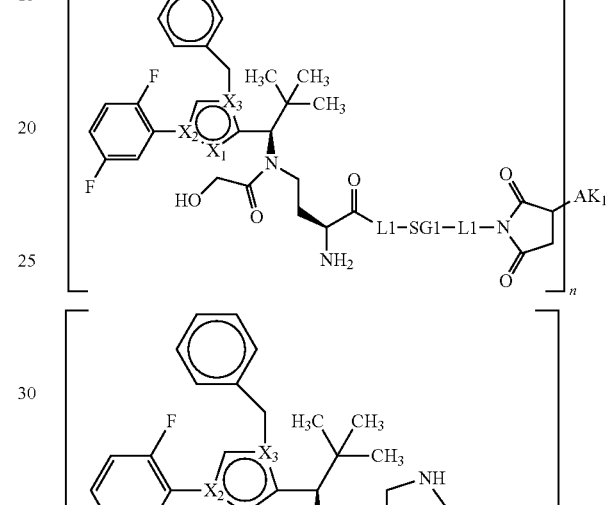
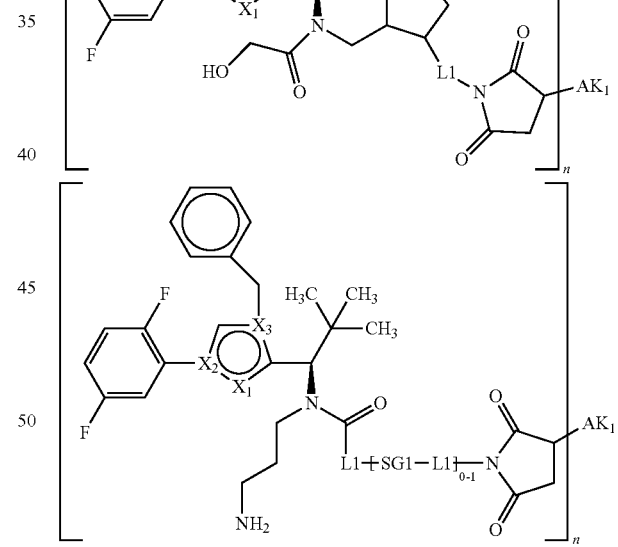
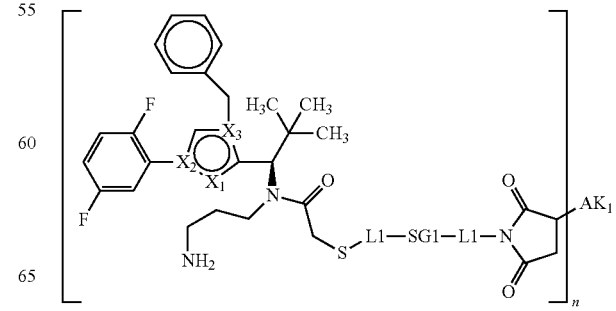

-continued

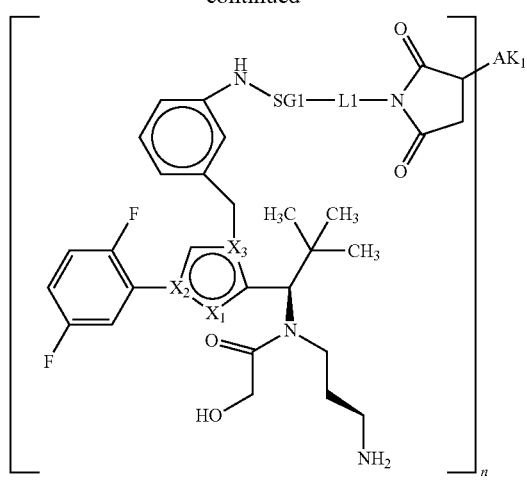

Depending on the linker, succinimide-linked ADCs may, after conjugation, be converted into the open-chain succinamides, which have an advantageous stability profile.

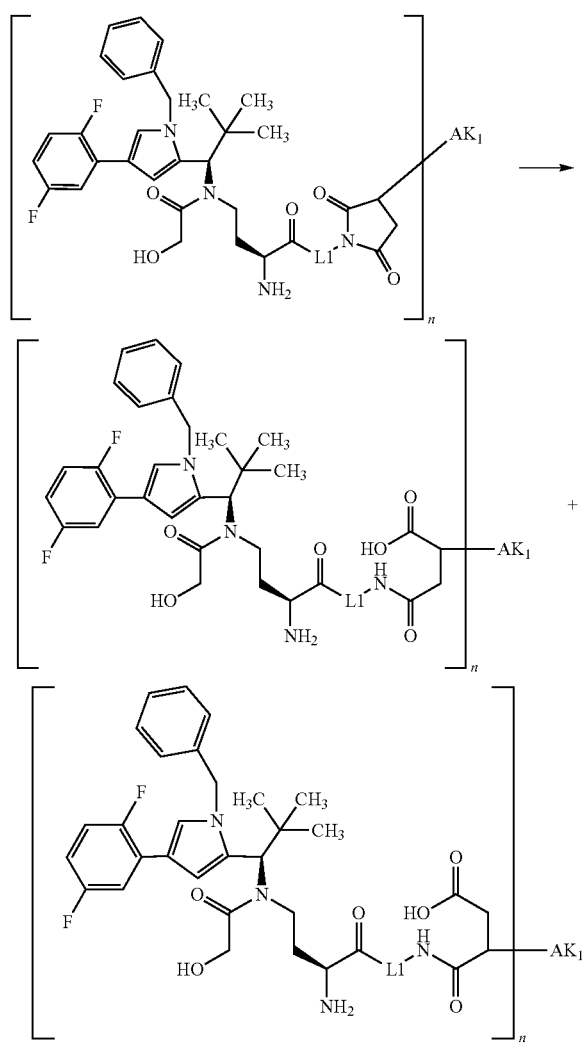

This reaction (ring opening) can be carried out at pH 7.5 to 9, preferably at pH 8, at a temperature of from 25° C. to 37° C., for example by stirring. The preferred stirring time is 8 to 30 hours.

In the above formulae, $X_1$, $X_2$, $X_3$ have the same meaning as in formula (II), SG1 and L1 have the same meaning as described above and L2, L3 and L4 have the same meaning as L1; R and K have the same meaning as described above. AK1 is an antibody coupled via a cysteine residue, and AK2 is an antibody coupled via a lysine residue. With particular preference, AK1 and AK2 are anti-TWEAKR antibodies, in particular antibodies which bind specifically to amino acid D in position 47 (D47) of TWEAKR (SEQ ID NO:169), in particular the anti-TWEAKR antibody TPP-2090.

Binders

In the broadest sense, the term "binder" is understood to mean a molecule which binds to a target molecule present at a certain target cell population to be addressed by the binder/active compound conjugate. The term binder is to be understood in its broadest meaning and also comprises, for example, lectins, proteins capable of binding to certain sugar chains, and phospholipid-binding proteins. Such binders include, for example, high-molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies and antibody fragments or antibody mimetics such as, for example, affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The literature also discloses various options of covalent coupling (conjugation) of organic molecules to antibodies. Preference according to the invention is given to the conjugation of the toxophores to the antibody via one or more sulphur atoms of cysteine residues of the antibody and/or via one or more NH groups of lysine residues of the antibody. However, it is also possible to bind the toxophor to the antibody via free carboxyl groups or via sugar residues of the antibody.

A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, attached to the cell, which is located at the outside of a cell, or the part of a target molecule which is located at the outside of a cell, i.e. a binder may bind on an intact cell to its extracellular target molecule. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The binder can be attached to the linker via a bond. Attachment of the binder can be via a heteroatom of the binder. Heteroatoms according to the invention of the binder which can be used for attachment are sulphur (in one embodiment via a sulphhydryl group of the binder), oxygen (according to the invention by means of a carboxyl or hydroxyl group of the binder) and nitrogen (in one embodiment via a primary or secondary amine group or amide group of the binder). These heteroatoms may be present in the natural binder or are introduced by chemical methods or methods of molecular biology. According to the invention, the attachment of the binder to the toxophor has only a minor effect on the binding activity of the binder with respect to the target molecule. In a preferred embodiment, the attachment has no effect on the binding activity of the binder with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monocvlonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophor (see Junutula et al. Nat Biotechnol. 2008 August; 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Soderlind et al., Nature Biotech. 2000, 18:853-856.

The term "humanized" or "chimeric" antibody describes antibodies consisting of a non-human and a human portion of the sequence. In these antibodies, part of the sequences of the human immunoglobulin (recipient) are replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recepient nor in the donor, which were introduced during the optimization of the antibody. In the case of chimeric antibodies, the variable domains of the donor immunoglobulin are fused with the constant regions of a human antibody.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ]

and [my/μ.]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')2 and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; or Kostelny et al., 1992, J. Immunol. 148: 1547 1553). An F(ab')2 or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al. U.S. Pat. No. 4,816,567 or Boss et al. U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or Phage Display Technologien (Clackson et al., Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with smaller Kd values than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany) Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells.

In a preferred embodiment, the target molecule is a selective cancer target molecule.

In a particularly preferred embodiment, the target molecule is a protein.

In one embodiment, the target molecule is an extracellular target molecule. In a preferred embodiment, the extracellular target molecule is a protein.

Cancer target molecules are known to those skilled in the art. Examples of these are listed below.

Examples of cancer target molecules are:

(1) EGF receptor (NCBI reference sequence NP_005219.2), SEQ ID NO: 213 (1210 amino acids):

```
>gi|29725609|ref|NP_005219.2|EGFR receptor
precursor [Homo sapiens]
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA
```

The extracellular domain is marked by underlining (2) mesothelin (SwissProt reference Q13421-3), SEQ ID NO: 214 (622 amino acids):

```
>sp|Q13421-3|MSLN_HUMAN isoform 2 of mesothelin
OS = Homo sapiens GN = MSLN
MALPTARPLLGSCGTPALGSLLFLLFSLGWVQPSRTLAGETGQEAAPLDG
VLANPPNISSLSPRQLLGFPCAEVSGLSTERVRELAVALAQKNVKLSTEQ
LRCLAHRLSEPPEDLDALPLDLLLFLNPDAFSGPQACTRFFSRITKANVD
LLPRGAPERQRLLPAALACWGVRGSLLSEADVRALGGLACDLPGRFVAES
AEVLLPRLVSCPGPLDQDQQEAARAALQGGGPPYGPPSTWSVSTMDALRG
LLPVLGQPIIRSIPQGIVAAWRQRSSRDPSWRQPERTILRPRFRREVEKT
ACPSGKKAREIDESLIFYKKWELEACVDAALLATQMDRVNAIPFTYEQLD
VLKHKLDELYPQGYPESVIQHLGYLFLKMSPEDIRKWNVTSLETLKALLE
VNKGHEMSPQVATLIDRFVKGRGQLDKDTLDTLTAFYPGYLCSLSPEELS
SVPPSSIWAVRPQDLDTCDPRQLDVLYPKARLAFQNMNGSEYFVKIQSFL
GGAPTEDLKALSQQNVSMDLATFMKLRTDAVLPLTVAEVQKLLGPHVEGL
```

KAEERHRPVRDWILRQRQDDLDTLGLGLQGGIPNGYLVLDLSMQEALSGT

PCLLGPGPVLTVLALLLASTLA where mesothelin is encoded by amino acids 296-598. Amino acids 37-286 are coding for the megakaryocyte-potentiating factor. Mesothelin is anchored in the cell membrane via a GPI anchor and is localized extracellularly.

(3) carboanhydrase IX (SwissProt reference Q16790), SEQ ID NO: 215 (459 amino acids):

>sp|Q16790|CAH9_HUMAN carbonic anhydrase
9 OS = Homo sapiens GN = CA9 PE = 1 SV = 2
MAPLCPSPWLPLLIPAPAPGLTVQLLLSLLLLVPVHP<u>QRLPRMQEDSPLG</u>

<u>GGSSGEDDPLGEEDLPSEEDSPREEDPPGEEDLPGEEDLPGEEDLPEVKP</u>

<u>KSEEEGSLKLEDLPTVEAPGDPQEPQNNAHRDKEGDDQSHWRYGGDPPWP</u>

<u>RVSPACAGRFQSPVDIRPQLAAFCPALRPLELLGFQLPPLPELRLRNNGH</u>

<u>SVQLTLPPGLEMALGPGREYRALQLHLHWGAAGRPGSEHTVEGHRFPAEI</u>

<u>HVVHLSTAFARVDEALGRPGGLAVLAAFLEEGPEENSAYEQLLSRLEEIA</u>

<u>EEGSETQVPGLDISALLPSDFSRYFQYEGSLTTPPCAQGVIWTVFNQTVM</u>

<u>LSAKQLHTLSDTLWGPGDSRLQLNFRATQPLNGRVIEASFPAGVDSSPRA</u>

<u>AEPVQLNSCLAAGD</u>ILALVFGLLFAVTSVAFLVQMRRQHRRGTKGGVSYR

PAEVAETGA

The extracellular domain is marked by underlining (4) C4.4a (NCBI reference sequence NP_055215.2; synonym LYPD3), SEQ ID NO: 216 (346 amino acids):

>gi|93004088|ref|NP_055215.2|ly6/PLAUR domain-
containing protein 3-precursor [Homo sapiens]
MDPARKAGAQAMIWTAGWLLLLLLRGGAQA<u>LECYSCVQKADDGCSPNKMK</u>

<u>TVKCAPGVDVCTEAVGAVETIHGQFSLAVRGCGSGLPGKNDRGLDLHGLL</u>

<u>AFIQLQQCAQDRCNAKLNLTSRALDPAGNESAYPPNGVECYSCVGLSREA</u>

<u>CQGTSPPVVSCYNASDHVYKGCFDGNVTLTAANVTVSLPVRGCVQDEFCT</u>

<u>RDGVTGPGFTLSGSCCQGSRCNSDLRNKTYFSPRIPPLVRLPPPEPTTVA</u>

<u>STTSVTTSTSAPVRPTSTTKPMPAPTSQTPRQGVEHEASRDEEPRLTGGA</u>

<u>AGHQDRSNSGQYPAKGGPQQPHNKGC</u>VAPTAGLAALLLAVAAGVLL

The mature extracellular domain is marked by underlining (5) CD52 (NCBI reference sequence NP_001794.2), SEQ ID NO: 217

>gi|68342030|ref|NP_001794.2|CAMPATH-1 antigen-
precursor [Homo sapiens]
MKRFLFLLLTISLLVMVQIQTGLSGQNDTSQTSSPSASSNISGGIFLFFV

ANAIIHLFCFS (6) Her2 (NCBI reference sequence NP_004439.2), SEQ ID NO: 218

>gi|54792096|ref|NP_004439.2|receptor tyrosine-
protein kinase erbB-2 isoform a [Homo sapiens]
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV (7) CD20 (NCBI reference sequence NP_068769.2), SEQ ID NO: 219

>gi|23110987|ref|NP_068769.2|B-lymphocyte
antigen CD20 [Homo sapiens]
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP (8) the lymphocyte activation antigen CD30 (SwissProt ID P28908), SEQ ID NO: 220

>gi|68348711|ref|NP_001234.2|tumor necrosis
factor receptor superfamily member 8
isoform 1-precursor [Homo sapiens]
MRVLLAALGLLFLGALRAFPQDRPFEDTCHGNPSHYYDKAVRRCCYRCPM

GLFPTQQCPQRPTDCRKQCEPDYYLDEADRCTACVTCSRDDLVEKTPCAW

NSSRVCECRPGMFCSTSAVNSCARCFFHSVCPAGMIVKFPGTAQKNTVCE

PASPGVSPACASPENCKEPSSGTIPQAKPTPVSPATSSASTMPVRGGTRL

AQEAASKLTRAPDSPSSVGRPSSDPGLSPTQPCPEGSGDCRKQCEPDYYL

DEAGRCTACVSCSRDDLVEKTPCAWNSSRTCECRPGMICATSATNSRARC

VPYPICAAETVTKPQDMAEKDTTFEAPPLGTQPDCNPTPENGEAPASTSP

TQSLLVDSQASKTLPIPTSAPVALSSTGKPVLDAGPVLFWVILVLVVVG

SSAFLLCHRRACRKRIRQKLHLCYPVQTSQPKLELVDSRPRRSSTQLRSG

ASVTEPVAEERGLMSQPLMETCHSVGAAYLESLPLQDASPAGGPSSPRDL

PEPRVSTEHTNNKIEKIYIMKADTVIVGTVKAELPEGRGLAGPAEPELEE

ELEADHTPHYPEQETEPPLGSCSDVMLSVEEEGKEDPLPTAASGK (9) the lymphocyte adhesion molecule CD22 (SwissProt ID P20273), SEQ ID NO: 221

>gi|157168355|ref|NP_001762.2|B-cell receptor
CD22 isoform 1-precursor [Homo sapiens]
MHLLGPWLLLLVLEYLAFSDSSKWVFEHPETLYAWEGACVWIPCTYRALD

GDLESFILFHNPEYNKNTSKFDGTRLYESTKDGKVPSEQKRVQFLGDKNK

NCTLSIHPVHLNDSGQLGLRMESKTEKWMERIHLNVSERPFPPHIQLPPE

IQESQEVTLTCLLNFSCYGYPIQLQWLLEGVPMRQAAVTSTSLTIKSVFT

RSELKFSPQWSHHGKIVTCQLQDADGKFLSNDTVQLNVKHTPKLEIKVTP

SDAIVREGDSVTMTCEVSSSNPEYTTVSWLKDGTSLKKQNTFTLNLREVT

KDQSGKYCCQVSNDVGPGRSEEVFLQVQYAPEPSTVQILHSPAVEGSQVE

FLCMSLANPLPTNYTWYHNGKEMQGRTEEKVHIPKILPWHAGTYSCVAEN

ILGTGQRGPGAELDVQYPPKKVTTVIQNPMPIREGDTVTLSCNYNSSNPS

VTRYEWKPHGAWEEPSLGVLKIQNVGWDNTTIACAACNSWCSWASPVALN

VQYAPRDVRVRKIKPLSEIHSGNSVSLQCDFSSSHPKEVQFFWEKNGRLL

GKESQLNFDSISPEDAGSYSCWVNNSIGQTASKAWTLEVLYAPRRLRVSM

SPGDQVMEGKSATLTCESDANPPVSHYTWFDWNNQSLPYHSQKLRLEPVK

VQHSGAYWCQGTNSVGKGRSPLSTLTVYYSPETIGRRVAVGLGSCLAILI

LAICGLKLQRRWKRTQSQQGLQENSSGQSFFVRNKKVRRAPLSEGPHSLG

CYNPMMEDGISYTTLRFPEMNIPRTGDAESSEMQRPPPDCDDTVTYSALH

KRQVGDYENVIPDFPEDEGIHYSELIQFGVGERPQAQENVDYVILKH

(10) the myloid cell surface antigen CD33 (SwissProt ID P20138), SEQ ID NO: 222

>gi|130979981|ref|NP_001763.3|myeloid cell surface
antigen CD33 isoform 1-precursor [Homo sapiens]
MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDGSGK

QETRAGVVHGAIGGAGVTALLALCLCLIFFIVKTHRRKAARTAVGRNDTH

PTTGSASPKHQKKSKLHGPTETSSCSGAAPTVEMDEELHYASLNFHGMNP

SKDTSTEYSEVRTQ

(11) the transmembrane glycoprotein NMB (SwissProt ID Q14956), SEQ ID NO: 223

>gi|52694752|ref|NP_001005340.1|transmembrane
glycoprotein NMB isoform a-precursor [Homo sapiens]
MECLYYFLGFLLLAARLPLDAAKRFHDVLGNERPSAYMREHNQLNGWSSD

ENDWNEKLYPVWKRGDMRWKNSWKGGRVQAVLTSDSPALVGSNITFAVNL

IFPRCQKEDANGNIVYEKNCRNEAGLSADPYVYNWTAWSEDSDGENGTGQ

SHHNVFPDGKPFPHHPGWRRWNFIYVFHTLGQYFQKLGRCSVRVSVNTAN

VTLGPQLMEVTVYRRHGRAYVPIAQVKDVYVVTDQIPVFVTMFQKNDRNS

SDETFLKDLPIMFDVLIHDPSHFLNYSTINYKWSFGDNTGLFVSTNHTVN

HTYVLNGTFSLNLTVKAAAPGPCPPPPPPPRPSKPTPSLATTLKSYDSNT

PGPAGDNPLELSRIPDENCQINRYGHFQATITIVEGILEVNIIQMTDVLM

PVPWPESSLIDFVVTCQGSIPTEVCTIISDPTCEITQNTVCSPVDVDEMC

LLTVRRTFNGSGTYCVNLTLGDDTSLALTSTLISVPDRDPASPLRMANSA

LISVGCLAIFVTVISLLVYKKHKEYNPIENSPGNVVRSKGLSVFLNRAKA

VFFPGNQEKDPLLKNQEFKGVS

(12) the adhesion molecule CD56 (SwissProt ID P13591), SEQ ID NO: 224

>gi|94420689|ref|NP_000606.3|neural cell
adhesion molecule 1 isoform 1 [Homo sapiens]
MLQTKDLIWTLFFLGTAVSLQVDIVPSQGEISVGESKFFLCQVAGDAKDK

DISWFSPNGEKLTPNQQRISVVWNDDSSSTLTIYNANIDDAGIYKCVVTG

EDGSESEATVNVKIFQKLMFKNAPTPQEFREGEDAVIVCDVVSSLPPTII

WKHKGRDVILKKDVRFIVLSNNYLQIRGIKKTDEGTYRCEGRILARGEIN

FKDIQVIVNVPPTIQARQNIVNATANLGQSVTLVCDAEGFPEPTMSWTKD

GEQIEQEEDDEKYIFSDDSSQLTIKKVDKNDEAEYICIAENKAGEQDATI

HLKVFAKPKITYVENQTAMELEEQVTLTCEASGDPIPSITWRTSTRNISS

EEKTLDGHMVVRSHARVSSLTLKSIQYTDAGEYICTASNTIGQDSQSMYL

EVQYAPKLQGPVAVYTWEGNQVNITCEVFAYPSATISWFRDGQLLPSSNY

SNIKIYNTPSASYLEVTPDSENDFGNYNCTAVNRIGQESLEFILVQADTP

SSPSIDQVEPYSSTAQVQFDEPEATGGVPILKYKAEWRAVGEEVWHSKWY

DAKEASMEGIVTIVGLKPETTYAVRLAALNGKGLGEISAASEFKTQPVQG

EPSAPKLEGQMGEDGNSIKVNLIKQDDGGSPIRHYLVRYRALSSEWKPEI

RLPSGSDHVMLKSLDWNAEYEVYVVAENQQGKSKAAHFVFRTSAQPTAIP

ANGSPTSGLSTGAIVGILIVIFVLLLVVVDITCYFLNKCGLFMCIAVNLC

GKAGPGAKGKDMEEGKAAFSKDESKEPIVEVRTEEERTPNHDGGKHTEPN

ETTPLTEPEKGPVEAKPECQETETKPAPAEVKTVPNDATQTKENESKA

(13) the surface molecule CD70 (SwissProt ID P32970), SEQ ID NO: 225

```
>gi|4507605|ref|NP_001243.1|CD70
antigen [Homo sapiens]
MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

CTIASQRLTPLARGDTLCTNLTGTLLPSRNTDETFFGVQWVRP
```

(14) the surface molecule CD74 (SwissProt ID PO4233), SEQ ID NO: 226

```
>gi|10835071|ref|NP_004346.1|HLA
class II histocompatibility antigen
gamma chain isoform b [Homo sapiens]
MHRRRSRSCREDQKPVMDDQRDLISNNEQLPMLGRRPGAPESKCSRGALY

TGFSILVTLLLAGQATTAYFLYQQQGRLDKLTVTSQNLQLENLRMKLPKP

PKPVSKMRMATPLLMQALPMGALPQGPMQNATKYGNMTEDHVMHLLQNAD

PLKVYPPLKGSFPENLRHLKNTMETIDWKVFESWMHHWLLFEMSRHSLEQ

KPTDAPPKESLELEDPSSGLGVTKQDLGPVPM
```

(15) the B-lymphocyte antigen CD19 (SwissProt ID P15391), SEQ ID NO: 227

```
>gi|296010921|ref|NP_001171569.1|B-lymphocyte
antigen CD19 isoform 1-precursor [Homo sapiens]
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLAGSQS

YEDMRGILYAAPQLRSIRGQPGPNHEEDADSYENMDNPDGPDPAWGGGGR

MGTWSTR
```

(16) the surface protein mucin-1 (SwissProt ID P15941), SEQ ID NO: 228

```
>gi|65301117|ref|NP_002447.4|mucin-1
isoform 1-precursor [Homo sapiens]
MTPGTQSPFFLLLLLTVLTVVTGSGHASSTPGGEKETSATQRSSVPSSTE

KNALSTGVSFFFLSFHISNLQFNSSLEDPSTDYYQELQRDISEMFLQIYK

QGGFLGLSNIKFRPGSVVVQLTLAFREGTINVHDVETQFNQYKTEAASRY

NLTISDVSVSDVPFPFSAQSGAGVPGWGIALLVLVCVLVALAIVYLIALA

VCQCRRKNYGQLDIFPARDTYHPMSEYPTYHTHGRYVPPSSTDRSPYEKV

SAGNGGSSLSYTNPAVAATSANL
```

(17) the surface protein CD138 (SwissProt ID P18827), SEQ ID NO: 229

```
>gi|29568086|ref|NP_002988.3|syndecan-1-precursor
[Homo sapiens]
MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA
```

(18) the integrin alphaV (Genbank Accession No.: NP_002201.1), SEQ ID NO: 230

```
>gi|4504763|ref|NP_002201.1|integrin
alpha-V isoform 1-precursor [Homo sapiens]
MAFPPRRRLRLGPRGLPLLLSGLLLPLCRAFNLDVDSPAEYSGPEGSYFG

FAVDFFVPSASSRMFLLVGAPKANTTQPGIVEGGQVLKCDWSSTRRCQPI

EFDATGNRDYAKDDPLEFKSHQWFGASVRSKQDKILACAPLYHWRTEMKQ

EREPVGTCFLQDGTKTVEYAPCRSQDIDADGQGFCQGGFSIDFTKADRVL

LGGPGSFYWQGQLISDQVAEIVSKYDPNVYSIKYNNQLATRTAQAIFDDS

YLGYSVAVGDFNGDGIDDFVSGVPRAARTLGMVYIYDGKNMSSLYNFTGE

QMAAYFGFSVAATDINGDDYADVFIGAPLFMDRGSDGKLQEVGQVSVSLQ

RASGDFQTTKLNGFEVFARFGSAIAPLGDLDQDGFNDIAIAAPYGGEDKK

GIVYIFNGRSTGLNAVPSQILEGQWAARSMPPSFGYSMKGATDIDKNGYP

DLIVGAFGVDRAILYRARPVITVNAGLEVYPSILNQDNKTCSLPGTALKV

SCFNVRFCLKADGKGVLPRKLNFQVELLLDKLKQKGAIRRALFLYSRSPS

HSKNMTISRGGLMQCEELIAYLRDESEFRDKLTPITIFMEYRLDYRTAAD

TTGLQPILNQFTPANISRQAHILLDCGEDNVCKPKLEVSVDSDQKKIYIG

DDNPLTLIVKAQNQGEGAYEAELIVSIPLQADFIGVVRNNEALARLSCAF

KTENQTRQVVCDLGNPMKAGTQLLAGLRFSVHQQSEMDTSVKFDLQIQSS

NLFDKVSPVVSHKVDLAVLAAVEIRGVSSPDHIFLPIPNWEHKENPETEE

DVGPVVQHIYELRNNGPSSFSKAMLHLQWPYKYNNNTLLYILHYDIDGPM

NCTSDMEINPLRIKISSLQTTEKNDTVAGQGERDHLITKRDLALSEGDIH

TLGCGVAQCLKIVCQVGRLDRGKSAILYVKSLLWTETFMNKENQNHSYSL

KSSASFNVIEFPYKNLPIEDITNSTLVTTNVTWGIQPAPMPVPWVIILA

VLAGLLLLAVLVFVMYRMGFFKRVRPPQEEQEREQLQPHENGEGNSET
```

(19) the teratocarcinoma-derived growth factor 1 protein TDGF1 (Genbank Accession No.: NP_003203.1), SEQ ID NO: 231

```
>gi|4507425|ref|NP_003203.1|teratocarcinoma-derived
growth factor 1 isoform 1-precursor [Homo sapiens]
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS
```

-continued
FYGRNCEHDVRKENCGSVPHDTWLPKKCSLCKCWHGQLRCFPQAFLPGCD

GLVMDEHLVASRTPELPPSARTTTFMLVGICLSIQSYY

(20) the prostate-specific membrane antigen PSMA (Swiss Prot ID: Q04609), SEQ ID NO: 232

>gi|4758398|ref|NP_004467.1|glutamate
carboxypeptidase 2 isoform 1 [Homo sapiens]
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLVYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVR

SFGTLKKEGWRPRRTILFASWDAEEFGLLGSTEWAEENSRLLQERGVAYI

NADSSIEGNYTLRVDCTPLMYSLVHNLTKELKSPDEGFEGKSLYESWTKK

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMKHPQEMKTYSVSFDSLFSAVKNFTEIASKFSERL

QDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA

(21) the tyrosine protein kinase EPHA2 (Swiss Prot ID: P29317), SEQ ID NO: 233

>gi|32967311|ref|NP_004422.2|ephrin
type-A receptor 2-precursor [Homo sapiens]
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIMGQFSHHNIIRLEGVISKYKPMMIITEYMENGAL

DKFLREKDGEFSVLQLVGMLRGIAAGMKYLANMNYVHRDLAARNILVNSN

LVCKVSDFGLSRVLEDDPEATYTTSGGKIPIRWTAPEAISYRKFTSASDV

WSFGIVMWEVMTYGERPYWELSNHEVMKAINDGFRLPTPMDCPSAIYQLM

MQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVR

LPGHQKRIAYSLLGLKDQVNTVGIPI

(22) the surface protein SLC44A4 (Genbank Accession No: NP_001171515), SEQ ID NO: 234

>gi|295849282|ref|NP_001171515.1|choline
transporter-like protein 4 isoform 2 [Homo sapiens]
MGGKQRDEDDEAYGKPVKYDPSFRGPIKNRSCTDVICCVLFLLFILGYIV

VGIVAWLYGDPRQVLYPRNSTGAYCGMGENKDKPYLLYFNIFSCILSSNI

ISVAENGLQCPTPQTVITSLQQELCPSFLLPSAPALGRCFPWTNVTPPAL

PGITNDTTIQQGISGLIDSLNARDISVKIFEDFAQSWYWILVALGVALVL

SLLFILLLRLVAGPLVLVLILGVLGVLAYGIYYCWEEYRVLRDKGASISQ

LGFTTNLSAYQSVQETWLAALIVLAVLEAILLLMLIFLRQRIRIAIALLK

EASKAVGQMMSTMFYPLVTFVLLLICIAYWAMTALYLATSGQPQYVLWAS

NISSPGCEKVPINTSCNPTAHLVNSSCPGLMCVFQGYSSKGLIQRSVFNL

QIYGVLGLFWTLNWVLALGQCVLAGAFASFYWAFHKPQDIPTFPLISAFI

RTLRYHTGSLAFGALILTLVQIARVILEYIDHKLRGVQNPVARCIMCCFK

CCLWCLEKFIKFLNRNAYIMIAIYGKNFCVSAKNAFMLLMRNIVRVVVLD

KVTDLLLFFGKLLVVGGVGVLSFFFFSGRIPGLGKDFKSPHLNYYWLPIM

TSILGAYVIASGFFSVFGMCVDTLFLCFLEDLERNNGSLDRPYYMSKSLL

KILGKKNEAPPDNKKRKK

(23) the surface protein BMPR1B (SwissProt: 000238)
(24) the transport protein SLC7A5 (SwissProt: Q01650)
(25) the epithelial prostate antigen STEAP1 (SwissProt: Q9UHE8)
(26) the ovarial carcinoma antigen MUC16 (SwissProt: Q8WXI7)
(27) the transport protein SLC34A2 (SwissProt: O95436)
(28) the surface protein SEMA5b (SwissProt: Q9P283)
(29) the surface protein LYPD1 (SwissProt: Q8N2G4)
(30) the endothelin receptor type B EDNRB (SwissProt: P24530)
(31) the ring finger protein RNF43 (SwissProt: Q68DV7)
(32) the prostate carcinoma-associated protein STEAP2 (SwissProt: Q8NFT2)
(33) the cation channel TRPM4 (SwissProt: Q8TD43)
(34) the complement receptor CD21 (SwissProt: P20023)
(35) the B-cell antigen receptor complex-associated protein CD79b (SwissProt: P40259)
(36) the cell adhesion antigen CEACAM6 (SwissProt: P40199)
(37) the dipeptidase DPEP1 (SwissProt: P16444)
(38) the interleukin receptor IL20Ralpha (SwissProt: Q9UHF4)
(39) the proteoglycan BCAN (SwissProt: Q96GW7)
(40) the ephrin receptor EPHB2 (SwissProt: P29323)
(41) the prostate stem cell-associated protein PSCA (Genbank Accession No: NP_005663.2)
(42) the surface protein LHFPL3 (SwissProt: Q86UP9)
(43) the receptor protein TNFRSF13C (SwissProt: Q96RJ3)
(44) the B-cell antigen receptor complex-associated protein CD79a (SwissProt: P11912)

(45) the receptor protein CXCR5 (SwissProt: P32302)
(46) the ion channel P2X5 (SwissProt: Q93086)
(47) the lymphocyte antigen CD180 (SwissProt: Q99467)
(48) the receptor protein FCRL1 (SwissProt: Q96LA6)
(49) the receptor protein FCRL5 (SwissProt: Q96RD9)
(50) the MHC class II molecule Ia antigen HLA-DOB (Genbank Accession No: NP_002111.1)
(51) the T-cell protein VTCN1 (SwissProt: Q7Z7D3)
(52) TWEAKR (SEQ ID NO:169 (protein); SEQ ID NO:170 (DNA).
(53) the lymphocyte antigen CD37 (Swiss Prot: P11049)
(54) the FGF receptor 2; FGFR2 (Gene ID: 2263; official symbol: FGFR2). The FGFR2 receptor occurs in different splice variants (alpha, beta, IIIb, IIIc). All splice variants may act as target molecule.
(55) the transmembrane glycoprotein B7H3 (CD276; Gene ID: 80381.
(56) the B cell receptor BAFFR (CD268; Gene ID: 115650)
(57) the receptor protein ROR 1 (Gene ID: 4919)
(58) the surface receptor IL3RA (CD123; Gene ID: 3561)
(59) the CXC chemokine receptor CXCR5 (CD185; Gene ID 643)
(60) the receptor protein syncytin (Gene ID 30816)

In a preferred subject matter of the invention, the cancer target molecule is selected from the group consisting of the cancer target molecules (1)-(60), in particular (1), (6) and (52).

In a further particularly preferred subject matter of the invention, the binder binds to an extracellular cancer target molecule which is selected from the group consisting of the cancer target molecules (1)-(60), in particular (1), (6) and (52).

In a further particularly preferred subject matter of the invention, the binder binds specifically to an extracellular cancer target molecule which is selected from the group consisting of the cancer target molecules (1)-(60), in particular (1), (6) and (52). In a preferred embodiment the binder is, after binding to its extracellular target molecule on the target cell, internalized by the target cell as a result of the binding. This causes the binder/active compound conjugate, which may be an immunoconjugate or an ADC, to be taken up by the target cell. The binder is then processed, preferably intracellularly, with preference lysosomally.

In one embodiment the binder is a binding protein. In a preferred embodiment the binder is an antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')2 and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression.

Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (1988, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Anti-EGFR Antibodies

Examples of antibodies which bind the cancer target molecules EGFR are cetuximab (INN number 7906), panitumumab (INN number 8499) and nimotuzumab (INN number 8545). Cetuximab (Drug Bank Accession Number DB00002) is a chimeric anti-EGFR1 antibody which is produced in SP2/0 mouse myeloma cells and is sold by ImClone Systems Inc/Merck KgaA/Bristol-Myers Squibb Co. Cetuximab is indicated for the treatment of metastasizing, EGFR expressing, colorectal carcinoma with wild type K-Ras gene. It has an affinity of $10^{-10}$ M.

Sequence:

```
Cetuximab Light Chain (kappa), SEQ ID NO: 235:
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV
```

```
DNALQSGNSQESVTEQDSKDSTYSLSSTLTLSKADYEKHKVYACEVTHQG

LSSPVTKSFNRGEC

Cetuximab Heavy Chain, SEQ ID NO: 236:
QVQLKQSGPGLVQPSQSLSITCTVSGFSLTNYGVHWVRQSPGKGLEWLGV

IWSGGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Panitumumab (INN number 8499) (Drug Bank Accession Number DB01269) is a recombinant monoclonal human IgG2 antibody which binds specifically to the human EGF receptor 1 and is sold by Abgenix/Amgen. Panitumumab originates from the immunization of transgenic mice (Xeno-Mouse). These mice are capable of producing human immunoglobulin (light and heavy chains). A specific B-cell clone was selected which produces antibodies against EGFR, and this clone was immortalized with CHO cells (Chinese hamster ovary cells). These cells are now used for the production of a 100% human antibody. Panitumumab is indicated for the treatment of EGFR-expressing, metastasizing colorectal carcinoma, which is resistant to chemotherapeutic treatment with fluoropyrimidine, oxaliplatin and irinotecan. It has an affinity of $10^{-11}$ M.
Sequence:

```
Panitumumab Light Chain (kappa), SEQ ID NO: 237:
DIQMTQSPSSLSASVGDRVTITCQASQDISNYLNWYQQKPGKAPKLLIYD

ASNLETGVPSRFSGSGSGTDFTFTISSLQPEDIATYFCQHFDHLPLAFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Panitumumab Heavy Chain, SEQ ID NO: 238:
QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD

RVTGAFDIWGQGTMVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPG
```

Nimotuzumab (INN number 8545) (EP 00586002, EP 00712863) is a humanized monoclonal IgG1 antibody which binds specifically to the human EGF receptor 1 and is sold by YM BioScienecs Inc. (Mississauga Canada). It is produced in non-secreting NS0 cells (mammalian cell line). Nimotuzumab is approved for the treatment of head-and-neck tumours, highly malignant astrocytoma and glioblastoma multiforms (not in EU and US) and pancreatic carcinoma (Orphan drug, EMA). It has an affinity of 10 M.

```
Nimotuzumab Light Chain, SEQ ID NO: 239:
DIQMTQSPSSLSASVGDRVTITCRSSQNIVHSNGNTYLDWYQQTPGKAPK

LLIYKVSNRFSGVPSRFSGSGSGTDFTFTISSLQPEDIATYYCFQYSHVP

WTFGQGTKLQITRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Nimotuzumab Heavy Chain, SEQ ID NO: 240:
QVQLQQSGAEVKKPGSSVKVSCKASGYTFTNYYIYWVRQAPGQGLEWIGG

INPTSGGSNFNEKFKTRVTITADESSTTAYMELSSLRSEDTAFYFCTRQG

LWFDSDGRGFDFWGQGTTVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

Further embodiments of EGFR antibodies are as follows:
- Zalutumumab/2F8/HuMax-EGFr, from Genmab A/S (WO 02/100348, WO 2004/056847, INN number 8605)
- Necitumumab/11F8, ImClone/IMC-11F8, from ImClone Systems Inc. [Eli Lilly & Co] (WO 2005/090407 (EP 01735348-A1, US 2007/0264253-A1, U.S. Pat. No. 7,598,350, WO 2005/090407-A1), INN number 9083)
- Matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (Matuzumab))
- RG-7160/GA-201/GA201/R-7160/R7160/RG7160/RO-4858696/RO-5083945/R04858696/R05083945, from Glycart Biotechnology AG (Roche Holding AG) (WO 2010/112413-A1, WO 2010/115554)
- GT-MAB 5.2-GEX/CetuGEX, from Glycotope GmbH (WO 2008/028686-A2 (EP 01900750-A1, EP 01911766-A1, EP 02073842-A2, US 2010/0028947-A1)
- ISU-101, from Isu Abxis Inc (ISU Chemical Co Ltd)/Scancell (WO 2008/004834-A1)
- ABT-806/mAb-806/ch-806/anti-EGFR monoclonal antibody 806, from Ludwig Institute for Cancer Research/Abbott/Life Science Pharmaceuticals (WO 02/092771, WO 2005/081854 and WO 2009/023265)
- SYM-004 (consists of two chimeric IgG1 antibodies (992 and 1024)), from Symphogen A/S (WO 2010/022736-A2)
- MR1-1/MR1-1KDEL, from IVAX Corp (Teva Pharmaceutical Industries Ltd) (Duke University), (patent: WO2001/062931-A2)
- Antibody against the deletion mutant, EGFRvIII, from Amgen/Abgenix (WO 2005/010151, U.S. Pat. No. 7,628,986)

SC-100, from Scancell Ltd (WO 01/088138-A1)
MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)
anti-EGFR-Mab, from Xencor (WO 2005/056606)
DXL-1218/anti-EGFR monoclonal antibody (cancer), InNexus, from InNexus Biotechnology Inc, Pharmaprojects PH048638

In a preferred embodiment, the anti-EGFR antibodies are selected from the group consisting of cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a particularly preferred embodiment the anti-EGFR antibodies are selected from the group consisting of cetuximab, panitumumab, nimotuzumab, zalutumumab, necitumumab and matuzumab.

The person skilled in the art knows of processes which can be used to prepare further antibodies, from the CDR regions of the abovementioned antibodies by means of sequence variations, these further antibodies having a similar or better affinity and/or specificity for the target molecule.

In a further embodiment, the anti-EGFR antibodies or antigen-binding antibody fragments are selected from the group consisting of antibodies or antigen-binding antibody fragments comprising the three CDR regions of the light chain and the three CDR regions of the heavy chain of one of the following antibodies: cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a further embodiment, the anti-EGFR antibodies or antigen-binding antibody fragments are selected from the group consisting of antibodies or antigen-binding antibody fragments comprising three CDR regions of the light chain and the three CDR regions of the heavy chain of one of the following antibodies: cetuximab, panitumumab, nimotuzumab, zalutumumab, necitumumab, matuzumab. By reference, these antibodies and antigen-binding fragments thereof are incorporated herein, and they can be used in the context of the present invention.

Anti-Carboanhydrase IX Antibodies

Examples of antibodies which bind the cancer target molecule carbonahydrase IX are described in WO 2007/070538-A2 (e.g. Claims 1-16).

In a preferred embodiment the anti-carboanhydrase IX antibodies or antigen-binding antibody fragments are selected from the group consisting of anti-carboanhydrase IX antibodies or antigen-binding antibody fragments 3ee9 (claim 4 (a) in WO 2007/070538-A2), 3ef2 (claim 4 (b) in WO2007/070538-A2), 1e4 (claim 4 (c) in WO 2007/070538-A2), 3a4 (claim 4 (d) in WO 2007/070538-A2), 3ab4 (claim 4 (e) in WO 2007/070538-A2), 3ah10 (claim 4 (f) in WO 2007/070538-A2), 3bb2 (claim 4 (g) in WO 2007/070538-A2), 1aa1 (claim 4 (h) in WO 2007/070538-A2), 5a6 (claim 4 (i) in WO 2007/070538-A2) and 5aa3 (claim 4 (j) in WO 2007/070538-A2).

Anti-C4.4a Antibodies:

According to the invention, use may be made of C4.4a antibodies.

Examples of C4.4a antibodies and antigen-binding fragments are described in WO 2012/143499 A2. By reference, all antibodies of WO 2012/143499 A2 are hereby incorporated into the description of the present invention, and they can be used in the present invention. The sequences of the antibodies are given in Table 1 of WO 2012/143499 A2, where each row shows the respective CDR amino acid sequences of the variable light chain or the variable heavy chain of the antibody listed in column 1.

In one embodiment, the anti-C4.4a antibodies or antigen-binding antibody fragments thereof are, after binding to a cell expressing C4.4a, internalized by the cell.

In a further embodiment, the anti-C4.4a antibodies or antigen-binding antibody fragments comprise at least one, two or three CDR amino acid sequences of an antibody listed in Table 1 of WO 2012/143499 A2 or Table 2 of WO 2012/143499 A2. Preferred embodiments of such antibodies are likewise listed in WO 2012/143499 A2 and incorporated herein by reference.

Anti-HER2 Antibodies:

An example of an antibody binding to the cancer target molecule Her2 is trastuzumab (Genentech). Trastuzumab is a humanized antibody used inter alia for the treatment of breast cancer.

Further examples of antibodies binding to HER2 are, in addition to trastuzumab (INN 7637, CAS No.: RN: 180288-69-1) and Pertuzumab (CAS No.: 380610-27-5), the antibodies disclosed in WO 2009/123894-A2, WO 200/8140603-A2 or in WO 2011/044368-A2. An example of an anti-HER2 conjugate is trastuzumab-emtansine (INN-No. 9295). By reference, these antibodies and antigen-binding fragments thereof are incorporated herein, and they can be used in the context of the present invention.

Anti-CD20 Antibodies:

An example of an antibody binding to the cancer target molecule CD20 is rituximab (Genentech). Rituximab (CAS Number: 174722-31-7) is a chimeric antibody used for the treatment of non-Hodgkin lymphoma. By reference, these antibodies and antigen-binding fragments thereof are incorporated herein, and they can be used in the context of the present invention.

Anti-CD52 Antibodies:

An example of an antibody binding to the cancer target molecule CD52 is alemtuzumab (Genzyme). Alemtuzumab (CAS Number: 216503-57-0) is a humanized antibody used for the treatment of chronic lymphocytic leukaemia. By reference, these antibodies and antigen-binding fragments thereof are incorporated herein, and they can be used in the context of the present invention.

Anti-Mesothelin Antibodies:

Examples of anti-mesothelin antibodies are described, for example, in WO 2009/068204. By reference, all antibodies described in WO 2009/068204 are hereby incorporated into the present description, such that these antibodies can be used in the context of the invention disclosed herein.

The anti-mesothelin antibodies used in accordance with the invention are also notable preferably for an invariant binding to mesothelin. Invariant binding is characterized, for example, in that the antibody used in accordance with the invention binds to an epitope of mesothelin which cannot be masked by a further extracellular protein. Such a further extracellular protein is, for example, the protein ovarian cancer antigen 125 (CA125). Antibodies which are used with preference are characterized in that their binding to mesothelin is not blocked by CA125.

Anti-CD30 Antibodies

Examples of antibodies which bind the cancer target molecule CD30 and can be used for the treatment of cancer, for example Hodgkin lymphoma, are brentuximab, iratumumab and antibodies disclosed in WO 2008/092117, WO 2008/036688 or WO 2006/089232. An example of an anti-CD30 conjugate is brentuximab vedotin (INN No. 9144). By reference, these antibodies and antigen-binding fragments thereof are incorporated herein, and they can be used in the context of the present invention.

Anti-CD22 Antibodies

Examples of antibodies which bind the cancer target molecule CD22 and can be used for the treatment of cancer, for example lymphoma, are inotuzumab and epratuzumab. Examples of anti-CD22 conjugates are inotuzumab ozagamycin (INN No. 8574) or anti-CD22-MMAE and anti-CD22-MC-MMAE (CAS RN: 139504-50-0 and 474645-27-7, respectively). By reference, these antibodies and antigen-binding fragments thereof are incorporated herein, and they can be used in the context of the present invention.

Anti-CD33 Antibodies

Examples of antibodies which bind the cancer target molecule CD33 and can be used for the treatment of cancer, for example leukaemia, are gemtuzumab and lintuzumab (INN 7580). An example of an anti-CD33 conjugate is gemtuzumab-ozagamycin. By reference, these antibodies and antigen-binding fragments thereof are incorporated herein, and they can be used in the context of the present invention.

Anti-NMB Antibodies

An example of an antibody which binds the cancer target molecule NMB and can be used for the treatment of cancer, for example melanoma or breast cancer, is glembatumumab (INN 9199). An example of an anti-NMB conjugate is glembatumumab vedotin (CAS RN: 474645-27-7). By reference, these antibodies and antigen-binding fragments thereof are incorporated herein, and they can be used in the context of the present invention.

Anti-CD56 Antibodies

An example of an antibody which binds the cancer target molecule CD56 and can be used for the treatment of cancer, for example multiple myeloma, small-cell lung carcinoma, MCC or ovarial carcinoma is lorvotuzumab. An example of an anti-CD56 conjugate is lorvotuzumab mertansine (CAS RN: 139504-50-0). By reference, these antibodies and antigen-binding fragments thereof are incorporated herein, and they can be used in the context of the present invention.

Anti-CD70 Antibodies

Examples of antibodies which bind the cancer target molecule CD70 and can be used for the treatment of cancer, for example non-Hodgkin lymphoma or renal cell cancer, are disclosed in WO 2007/038637-A2 and WO 2008/070593-A2. An example of an anti-CD70 conjugate is SGN-75 (CD70 MMAF). By reference, these antibodies and antigen-binding fragments thereof are incorporated herein, and they can be used in the context of the present invention.

Anti-CD74 Antibodies

An example of an antibody which binds the cancer target molecule CD74 and can be used for the treatment of cancer, for example multiple myeloma, is milatuzumab. An example of an anti-CD74 conjugate is milatuzumab-doxorubicin (CAS RN: 23214-92-8). By reference, these antibodies and antigen-binding fragments thereof are incorporated herein, and they can be used in the context of the present invention.

Anti-CD19 Antibodies

An example of an antibody which binds the cancer target molecule CD19 and can be used for the treatment of cancer, for example non-Hodgkin lymphoma, is disclosed in WO 2008/031056-A2. Further antibodies and examples of an anti-CD19 conjugate (SAR3419) are disclosed in WO 2008/047242-A2. By reference, these antibodies and antigen-binding fragments thereof are incorporated herein, and they can be used in the context of the present invention.

Anti-Mucin Antibodies

Examples of antibodies which bind the cancer target molecule mucin-1 and can be used for the treatment of cancer, for example non-Hodgkin lymphoma, are clivatuzumab and the antibodies disclosed in WO 2003/106495-A2, WO 2008/028686-A2. Examples of anti-mucin conjugates are disclosed in WO 2005/009369-A2. By reference, these antibodies and antigen-binding fragments thereof are incorporated herein, and they can be used in the context of the present invention.

Anti-CD138 Antibodies

Examples of antibodies which bind the cancer target molecule CD138 and conjugates thereof, which can be used for the treatment of cancer, for example multiple myeloma, are disclosed in WO 2009/080829-A1, WO 2009/080830-A1. By reference, these antibodies and antigen-binding fragments thereof are incorporated herein, and they can be used in the context of the present invention.

Anti-Integrin-alphaV Antibodies

Examples of antibodies which bind the cancer target molecule integrin alphaV and can be used for the treatment of cancer, for example melanoma, sarcoma or carcinoma, are intetumumab (CAS RN: 725735-28-4), abciximab (CAS RN: 143653-53-6), etaracizumab (CAS RN: 892553-42-3) and the antibodies disclosed in U.S. Pat. No. 7,465,449, EP 719859-A1, WO 2002/012501-A1 and WO2006/062779-A2. Examples of anti-integrin AlphaV conjugates are intetumumab-DM4 and other ADCs disclosed in WO 2007/024536-A2. By reference, these antibodies and antigen-binding fragments thereof are incorporated herein, and they can be used in the context of the present invention.

Anti-TDGF1 Antibodies

Examples of antibodies which bind the cancer target molecule TDGF1 and can be used for the treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2. By reference, these antibodies and antigen-binding fragments thereof are incorporated herein, and they can be used in the context of the present invention.

Anti-PSMA Antibodies

Examples of antibodies which bind the cancer target molecule PSMA and can be used for the treatment of cancer, for example prostate carcinoma, are the antibodies disclosed in WO 97/35616-A1, WO 99/47554-A1, WO 01/009192-A1 and WO2003/034903. Examples of anti-PSMA conjugates are disclosed in WO 2009/026274-A1 and WO 2007/002222. By reference, these antibodies and antigen-binding fragments thereof are incorporated herein, and they can be used in the context of the present invention.

Anti-EPHA2 Antibodies

Examples of antibodies which bind the cancer target molecule EPHA2 and can be used for preparing a conjugate and for the treatment of cancer are disclosed in WO 2004/091375-A2. By reference, these antibodies and antigen-binding fragments thereof are incorporated herein, and they can be used in the context of the present invention.

Anti-SLC44A4 Antibodies

Examples of antibodies which bind the cancer target molecule SLC44A4 and can be used for preparing a conjugate and for the treatment of cancer, for example pancreas or prostate carcinoma, are disclosed in WO2009/033094-A2 and US2009/0175796-A1. By reference, these antibodies and antigen-binding fragments thereof are incorporated herein, and they can be used in the context of the present invention.

Anti-HLA-DOB Antibodies

An example of an antibody binding to the cancer target molecule HLA-DOB is the antibody Lym-1 (CAS RN: 301344-99-0) which can be used for the treatment of cancer, for example non-Hodgkin lymphoma. Examples of anti-HLA-DOB conjugates are disclosed, for example, in WO 2005/081711-A2. By reference, these antibodies and antigen-binding fragments thereof are incorporated herein, and they can be used in the context of the present invention.

Anti-VTCN1 Antibodies

Examples of antibodies which bind the cancer target molecule VTCN1 and can be used for preparing a conjugate and for the treatment of cancer, for example ovarial carcinoma, pancreas, lung or breast cancer, are disclosed in WO 2006/074418-A2. By reference, these antibodies and antigen-binding fragments thereof are incorporated herein, and they can be used in the context of the present invention.

Anti-FGFR2 Antibodies

According to the invention, use may be made of anti-FGFR2 antibodies.

Examples of anti-FGFR2 antibodies and antigen-binding fragments are described in WO2013076186. By reference, all antibodies of WO2013076186 are hereby incorporated into the description of the present invention, and they can be used in the present invention. The sequences of the antibodies are shown in Table 9 and Table 10 of WO2013076186. Preference is given to antibodies, antigen-binding fragments and variants of the antibodies derived from the antibodies referred to as M048-D01 and M047-D08. Preferred anti-FGFR2 bind to the various splice variants known of FGFR2.

In one embodiment, the anti-FGFR2 antibodies or antigen-binding antibody fragments thereof are, after binding to a cell expressing FGFR2, internalized by the cell.

In a further embodiment, the anti-FGFR2 antibodies or antigen-binding antibody fragments comprise at least one, two or three CDR amino acid sequences of an antibody listed in Table 9 or Table 10 of WO2013076186. Preferred embodiments of such antibodies are likewise listed in WO2013076186 and incorporated herein by reference.

Anti-TWEAKR Antibodies

In a preferred embodiment, when an anti-TWEAKR antibody or an antigen-binding fragment thereof is used in the processes according to the present invention, this antibody or fragment is selected from those described below. In addition, antibodies which bind to TWEAKR are known to the person skilled in the art, see, for example, WO2009/020933(A2) or WO2009140177 (A2).

The invention relates in particular to conjugates with antibodies or antigen-binding antibody fragments thereof or variants thereof which lead to strong activation of the TWEAKR (SEQ ID NO:169 (protein); SEQ ID NO:170 (DNA)), resulting in a strong induction of apoptosis in various cancer cells overexpressing TWEAKR.

The agonistic activity of TWEAKR with regard to the induction of apoptosis and inhibition of the proliferation of the anti-TWEAKR antibodies already described (e.g. PDL-192) is limited and does not reach the efficacy of the endogenous ligand TWEAK. This lack of agonistic activity is not based on reduced affinity, since these antibodies bind at the TWEAKR with affinities which, compared to the endogenous ligand TWEAK, are in a similar range (Michaelson J S et al, MAbs. 2011 July-August; 3(4):362-75; Culp P A et al, Clin Cancer Res. 2010 Jan. 15; 16(2):497-508), and even antibodies having a higher binding affinity do not necessarily display a more effective signalling activity (Culp P A, et al, Clin Cancer Res. 2010 Jan. 15; 16(2):497-508). In addition, it has been shown that the antitumour activity of the antibodies already described depends on the Fc effector function, and it was shown that ADCC plays an important role for the in-vivo efficacy in mouse models.

Generation of the Anti-TWEAKR Antibodies

A complete human antibody phage library (Hoet R M et al, Nat Biotechnol 2005; 23(3):344-8) was employed to isolate TWEAKR-specific human monoclonal antibodies of the present invention by protein panning (Hoogenboom H. R., Nat Biotechnol 2005; 23(3):1105-16) using dimeric Fc-fused extracellular domains of human and mouse TWEAKR as immobilized target. 11 different Fab phages were identified, and the corresponding antibodies were cloned into a mammalian EgG expression vector which provides the CH2-CH3 domains missing in the soluble FAb. Following identification of preferred antibodies, these were expressed as full-length IgGs. These constructs were expressed, for example, transiently in mammalian cells as described by Tom et al., Chapter 12 in Methods Express: Expression Systems edited by Micheal R. Dyson and Yves Durocher, Scion Publishing Ltd, 2007 (see AK-Example 1). The antibodies were purified by protein-A chromatography and characterized further by their binding affinity to soluble monomeric TWEAKR using ELISA and BIAcore analysis, as described in AK-Example 2. To determine the cell binding characteristics of the anti-TWEAKR antibodies, binding was tested by flow cytometry on a number of cell lines (HT29, HS68, HS578). NFiB reporter gene assays were carried out to examine the agonistic activity of all 11 antibodies identified (human IgG1). The antibody having the highest in vitro activity (TPP-883) was selected for further activity and affinity maturation (see AK-Example 1 for details). A single substitution variant having improved agonistic activity was detected: G102T of CDR-H3. In the end, 7 variants were selected based on increased affinity compared to the best single substitution variant G102T. The corresponding DNA thereof was cloned into a mammalian IgG expression vector and examined for functional activity in the NF-kappaB reporter gene assay mentioned above. Finally, the sequences obtained were compared with human germ line sequences, and deviations without any significant effect on the affinity and the efficacy were adapted. The following antibodies were obtained by antibody library screening and by affinity and/or activity maturation. "TPP-2090", "TPP-2149", "TPP-2093", "TPP-2148", "TPP-2084", "TPP-2077", "TPP-1538", "TPP-883", "TPP-1854", "TPP-1853", "TPP-1857" and "TPP-1858".

Antibodies of the invention can furthermore be obtained by methods known in the art such as antibody phage display screening (see, for example, Hoet R M et al., Nat Biotechnol 2005; 23(3):344-8), the well-established hybridoma technology (see, for example, Köhler and Milstein Nature. 1975 Aug. 7; 256(5517):495-7) or immunization of mice, inter alia immunization of hMAb mice (e.g. VelocImmune Mouse®).

Particular Embodiments of Anti-TWEAKR Antibodies

One embodiment of the invention is the provision of antibodies or antigen-binding antibody fragments thereof or variants thereof showing strong induction of caspase 3/7 in one or more TWEAKR-expressing cell lines. In a preferred embodiment, the one or more TWEAKR-expressing cell line(s) is/are present in the group consisting of WiDr, A253, NCI-H322, HT29 and 786-0. "Induction of caspase 3/7" can be measured by customary methods known in the art, including those described herein. In one embodiment, the "induction of caspase 3/7" is determined in accordance with the present invention using the activity determination with capase 3/7 solution (Promega, #G8093) and reading the luminescence on a VICTOR V (Perkin Elmer). At the end of the incubation time, the caspase 3/7 activity was determined and the induction factor of caspase 3/7 was determined in comparison to untreated cells. An antibody is said to show "strong induction" of caspase 3/7 when the induction factor is greater than 1.2, preferably greater than 1.5, even more preferably greater than 1.8, even more preferably greater than 2.1, even more preferably greater than 2.5. What is provided are anti-TWEAKR antibodies leading to stronger induction of caspase 3/7 in HT29 cells compared to agonistic antibodies already described [e.g. PDL-192(TPP-1104), P4A8(TPP-1324), 136.1(TPP-2194)] and also compared to 300 ng/ml recombinant human TWEAK. This strong activity of inducing caspase 3/7 in cancer cells was also observed in WiDr, A253, NIC-H322 and 786-0 cells where in most experiments the antibodies of the invention examined induced higher factors of change compared to the reference antibodies [PDL-192(TPP-1104), P4A8(TPP-1324)] and to 300 ng/ml TWEAK. Some antibodies of the invention bind to the TWEAKR only with moderate affinity (>10 nM) which is clearly less than the affinity of the endogenous ligand TWEAK, and also less compared to other known agonistic antibodies. This property offers further possible advantages such as, for example, potentially deeper penetration into the tumour.

In this regard, one embodiment of the invention is the provision of antibodies or antigen-binding antibody fragments thereof binding specifically to a TWEAKR at a novel epitope characterized by selective binding to aspartate (D) at position 47 (D47) of TWEAKR (SEQ ID NO:169; see also FIG. 1). The dependencies identified for certain TWEAKR amino acids for antibody interaction correlate with the agonistic activity determined for these antibodies. The native ligand TWEAK shows an effective activation of the TWEAKR and binds depending on leucine 46 in the cysteine-rich domain of TWEAKR (Pellegrini et al, FEBS 280: 1818-1829). P4A8 displays a very low agonistic activity and interacts at least partially with domains outside of the cysteine-rich domain of TWEAKR. PDL-192 displays a moderate agonistic activity and binds depending on R56 to the cysteine-rich domain, but opposite the TWEAK ligand site. Antibodies of the present invention (e.g. TPP-2090) bind depending on D47, and TWEAK binds depending on L46. Thus, TWEAK binds to a similar but different binding site (FIG. 7). Accordingly, the antibodies of the present invention displaying strong agonistic activity bind to a novel epitope (D47-dependent) for antibodies associated with very high agonistic activity.

The amino acid at position 47 (D47) of TWEAKR (SEQ ID NO:169) is considered to be critical for binding of the antibodies according to the invention, which means that the antibody binds specifically to the D at position 47 (D47) of TWEAKR (SEQ ID NO:169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal by modification of this residue into alanine, as described in AK-Example 2 and FIG. 6. Alternatively, an antibody binds specifically to the D at position 47 (D47) of TWEAKR (SEQ ID NO:169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal for TPP-2614 compared to TPP-2203. Preferably, an antibody binds specifically to the D at position 47 (D47) of TWEAKR (SEQ ID NO:169) when the antibody loses more than 80% of its ELISA signal for TPP-2614 compared to TPP-2203.

In the present application, reference is made to the following preferred antibodies of the invention, as shown in the table below: "TPP-2090", "TPP-2149", "TPP-2093", "TPP-2148", "TPP-2084", "TPP-2077", "TPP-1538", "TPP-883", "TPP-1854", "TPP-1853", "TPP-1857", "TPP-1858".

TABLE

| | Protein sequences of the antibodies: | | | | | | | | | |
|---|---|---|---|---|---|---|---|---|---|---|
| | SEQ ID NO: IgG1 light chain | SEQ ID NO: IgG1 heavy chain | SEQ ID NO: L-CDR1 | SEQ ID NO: L-CDR2 | SEQ ID NO: L-CDR3 | SEQ ID NO: H-CDR1 | SEQ ID NO: H-CDR2 | SEQ ID NO: H-CDR3 | SEQ ID NO: VL protein | SEQ ID NO: VH protein |
| Anti-TWEAKR antibodies according to the invention: | | | | | | | | | | |
| TPP-2090 | 1 | 2 | 3 | 4 | 5 | 6 | 7 | 8 | 9 | 10 |
| TPP-2149 | 11 | 12 | 13 | 14 | 15 | 16 | 17 | 18 | 19 | 20 |
| TPP-2093 | 21 | 22 | 23 | 24 | 25 | 26 | 27 | 28 | 29 | 30 |
| TPP-2148 | 31 | 32 | 33 | 34 | 35 | 36 | 37 | 38 | 39 | 40 |
| TPP-2084 | 41 | 42 | 43 | 44 | 45 | 46 | 47 | 48 | 49 | 50 |
| TPP-2077 | 51 | 52 | 53 | 54 | 55 | 56 | 57 | 58 | 59 | 60 |
| TPP-1538 | 61 | 62 | 63 | 64 | 65 | 66 | 67 | 68 | 69 | 70 |
| TPP-883 | 71 | 72 | 73 | 74 | 75 | 76 | 77 | 78 | 79 | 80 |
| TPP-1854 | 81 | 82 | 83 | 84 | 85 | 86 | 87 | 88 | 89 | 90 |
| TPP-1853 | 91 | 92 | 93 | 94 | 95 | 96 | 97 | 98 | 99 | 100 |
| TPP-1857 | 101 | 102 | 103 | 104 | 105 | 106 | 107 | 108 | 109 | 110 |
| TPP-1858 | 111 | 112 | 113 | 114 | 115 | 116 | 117 | 118 | 119 | 120 |
| Comparative antibodies: | | | | | | | | | | |
| P3G5(TPP-2195) | 121 | 122 | | | | | | | | |
| 136.1(TPP-2194) | 123 | 124 | | | | | | | | |
| P4A8(TPP-1324) | 125 | 126 | | | | | | | | |
| PDL-192(TPP-1104) | 127 | 128 | | | | | | | | |
| 18.3.3(TPP-2193) | 129 | 130 | | | | | | | | |
| P2D3(TPP-2196) | 131 | 132 | | | | | | | | |

TPP-2090 is: an antibody which comprises a region of the heavy chain corresponding to SEQ ID NO: 2 and a region of the light chain corresponding to SEQ ID NO: 1.

TPP-2149 is: an antibody which comprises a region of the heavy chain corresponding to SEQ ID NO: 12 and a region of the light chain corresponding to SEQ ID NO: 11.

TPP-2093 is: an antibody which comprises a region of the heavy chain corresponding to SEQ ID NO: 22 and a region of the light chain corresponding to SEQ ID NO: 21.

TPP-2148 is: an antibody which comprises a region of the heavy chain corresponding to SEQ ID NO: 32 and a region of the light chain corresponding to SEQ ID NO: 31.

TPP-2084 is: an antibody which comprises a region of the heavy chain corresponding to SEQ ID NO: 42 and a region of the light chain corresponding to SEQ ID NO: 41.

TPP-2077 is: an antibody which comprises a region of the heavy chain corresponding to SEQ ID NO: 52 and a region of the light chain corresponding to SEQ ID NO: 51.

TPP-1538 is: an antibody which comprises a region of the heavy chain corresponding to SEQ ID NO: 62 and a region of the light chain corresponding to SEQ ID NO: 61.

TPP-883 is: an antibody which comprises a region of the heavy chain corresponding to SEQ ID NO: 72 and a region of the light chain corresponding to SEQ ID NO: 71.

TPP-1854 is: an antibody which comprises a region of the heavy chain corresponding to SEQ ID NO: 82 and a region of the light chain corresponding to SEQ ID NO: 81.

TPP-1853 is: an antibody which comprises a region of the heavy chain corresponding to SEQ ID NO: 92 and a region of the light chain corresponding to SEQ ID NO: 91.

TPP-1857 is: an antibody which comprises a region of the heavy chain corresponding to SEQ ID NO: 102 and a region of the light chain corresponding to SEQ ID NO: 101.

TPP-1858 is: an antibody which comprises a region of the heavy chain corresponding to SEQ ID NO: 112 and a region of the light chain corresponding to SEQ ID NO: 111.

TPP-2090 is: an antibody which comprises a variable region of the heavy chain corresponding to SEQ ID NO: 10 and a variable region of the light chain corresponding to SEQ ID NO: 9.

TPP-2149 is: an antibody which comprises a variable region of the heavy chain corresponding to SEQ ID NO: 20 and a variable region of the light chain corresponding to SEQ ID NO: 19.

TPP-2093 is: an antibody which comprises a variable region of the heavy chain corresponding to SEQ ID NO: 30 and a variable region of the light chain corresponding to SEQ ID NO: 29.

TPP-2148 is: an antibody which comprises a variable region of the heavy chain corresponding to SEQ ID NO: 40 and a variable region of the light chain corresponding to SEQ ID NO: 39.

TPP-2084 is: an antibody which comprises a variable region of the heavy chain corresponding to SEQ ID NO: 50 and a variable region of the light chain corresponding to SEQ ID NO: 49.

TPP-2077 is: an antibody which comprises a variable region of the heavy chain corresponding to SEQ ID NO: 60 and a variable region of the light chain corresponding to SEQ ID NO: 59.

TPP-1538 is: an antibody which comprises a variable region of the heavy chain corresponding to SEQ ID NO: 70 and a variable region of the light chain corresponding to SEQ ID NO: 69.

TPP-883 is: an antibody which comprises a variable region of the heavy chain corresponding to SEQ ID NO: 80 and a variable region of the light chain corresponding to SEQ ID NO: 79.

TPP-1854 is: an antibody which comprises a variable region of the heavy chain corresponding to SEQ ID NO: 90 and a variable region of the light chain corresponding to SEQ ID NO: 89.

TPP-1853 is: an antibody which comprises a variable region of the heavy chain corresponding to SEQ ID NO: 100 and a variable region of the light chain corresponding to SEQ ID NO: 99.

TPP-1857 is: an antibody which comprises a variable region of the heavy chain corresponding to SEQ ID NO: 110 and a variable region of the light chain corresponding to SEQ ID NO: 109.

TPP-1858 is: an antibody which comprises a variable region of the heavy chain corresponding to SEQ ID NO: 120 and a variable region of the light chain corresponding to SEQ ID NO: 119.

TABLE

| DNA sequences of antibodies according to the invention | | |
|---|---|---|
| Antibody | SEQ ID NO: IgG1 light chain | SEQ ID NO: IgG1 heavy chain |
| Antibodies according to the invention: | | |
| TPP-2090 | 177 | 178 |
| TPP-2149 | 179 | 180 |
| TPP-2093 | 181 | 182 |
| TPP-2148 | 183 | 184 |
| TPP-2084 | 185 | 186 |
| TPP-2077 | 187 | 188 |
| TPP-1538 | 189 | 190 |
| TPP-883 | 191 | 192 |
| TPP-1854 | 193 | 194 |
| TPP-1853 | 195 | 196 |
| TPP-1857 | 197 | 198 |
| TPP-1858 | 199 | 200 |
| Comparative antibodies: | | |
| P3G5 (TPP-2195) | 201 | 202 |
| 136.1 (TPP-2194) | 203 | 204 |
| Antibodies according to the invention: | | |
| P4A8 (TPP-1324) | 205 | 206 |
| PDL-192 (TPP-1104) | 207 | 208 |
| 18.3.3 (TPP-2193) | 209 | 210 |
| P2D3 (TPP-2196) | 211 | 212 |

Preferred embodiments of the anti-TWEAKR antibody are those below:

1. An anti-TWEAKR antibody or an antigen-binding fragment thereof which binds specifically to the D at position 47 (D47) of the TWEAKR (SEQ ID NO:169).
2. The antibody or an antigen-binding fragment thereof according to embodiment 1 where the antibody is an agonistic antibody.

3. The antibody or an antigen-binding fragment thereof according to embodiment 1 or 2 which comprises:
a variable heavy chain comprising:
   (a) a CDR1 of the heavy chain encoded by an amino acid sequence comprising the formula PYPMX (SEQ ID NO: 171), where X is I or M;
   (b) a CDR2 of the heavy chain encoded by an amino acid sequence comprising the formula YISPSGGXTHYADSVKG (SEQ ID NO: 172), where X is S or K; and
   (c) a CDR3 of the heavy chain encoded by an amino acid sequence comprising the formula GGD-TYFDYFDY (SEQ ID NO: 173);
   and a variable light chain comprising:
   (a) a CDR1 of the light chain encoded by an amino acid sequence comprising the formula RASQSISXYLN (SEQ ID NO: 174), where X is G or S;
   (b) a CDR2 of the light chain encoded by an amino acid sequence comprising the formula XASSLQS (SEQ ID NO: 175), where X is Q, A or N; and
   (c) a CDR3 of the light chain encoded by an amino acid sequence comprising the formula QQSYXXPXIT (SEQ ID NO: 176), where X at position 5 is T or S, X at position 6 is T or S and X at position 8 is G or F.
4. The antibody or an antigen-binding fragment thereof according to any of the preceding embodiments, comprising:
   a. a variable heavy chain comprising the variable CDR1 sequence of the heavy chain, as shown in SEQ ID NO: 6, the variable CDR2 sequence of the heavy chain, as shown in SEQ ID NO: 7 and the variable CDR3 sequence of the heavy chain, as shown in SEQ ID NO: 8, and also
      a variable light chain comprising the variable CDR1 sequence of the light chain shown in SEQ ID NO: 3, the variable CDR2 sequence of the light chain shown in SEQ ID NO: 4 and the variable CDR3 sequence of the light chain shown in SEQ ID NO: 5 or
   b. a variable heavy chain comprising the variable CDR1 sequence of the heavy chain, as shown in SEQ ID NO: 16, the variable CDR2 sequence of the heavy chain, as shown in SEQ ID NO: 17, the variable CDR3 sequence of the heavy chain, as shown in SEQ ID NO:18, and also
      a variable light chain comprising the variable CDR1 sequence of the light chain shown in SEQ ID NO: 13, the variable CDR2 sequence of the light chain shown in SEQ ID NO: 14 and the variable CDR3 sequence of the light chain shown in SEQ ID NO:15 or
   c. a variable heavy chain comprising the variable CDR1 sequence of the heavy chain, as shown in SEQ ID NO: 26, the variable CDR2 sequence of the heavy chain, as shown in SEQ ID NO: 27, the variable CDR3 sequence of the heavy chain, as shown in SEQ ID NO:28, and also
      a variable light chain comprising the variable CDR1 sequence of the light chain shown in SEQ ID NO: 23, the variable CDR2 sequence of the light chain shown in SEQ ID NO: 24 and the variable CDR3 sequence of the light chain shown in SEQ ID NO:25 or
   d. a variable heavy chain comprising the variable CDR1 sequence of the heavy chain, as shown in SEQ ID NO: 36, the variable CDR2 sequence of the heavy chain, as shown in SEQ ID NO: 37, the variable CDR3 sequence of the heavy chain, as shown in SEQ ID NO:38, and also
      a variable light chain comprising the variable CDR1 sequence of the light chain shown in SEQ ID NO: 33, the variable CDR2 sequence of the light chain shown in SEQ ID NO: 34 and the variable CDR3 sequence of the light chain shown in SEQ ID NO:35 or
   e. a variable heavy chain comprising the variable CDR1 sequence of the heavy chain, as shown in SEQ ID NO: 46, the variable CDR2 sequence of the heavy chain, as shown in SEQ ID NO: 47, the variable CDR3 sequence of the heavy chain, as shown in SEQ ID NO:48, and also
      a variable light chain comprising the variable CDR1 sequence of the light chain shown in SEQ ID NO: 43, the variable CDR2 sequence of the light chain shown in SEQ ID NO: 44 and the variable CDR3 sequence of the light chain shown in SEQ ID NO:45 or
   f. a variable heavy chain comprising the variable CDR1 sequence of the heavy chain, as shown in SEQ ID NO: 56, the variable CDR2 sequence of the heavy chain, as shown in SEQ ID NO: 57, the variable CDR3 sequence of the heavy chain, as shown in SEQ ID NO:58, and also
      a variable light chain comprising the variable CDR1 sequence of the light chain shown in SEQ ID NO: 53, the variable CDR2 sequence of the light chain shown in SEQ ID NO: 54 and the variable CDR3 sequence of the light chain shown in SEQ ID NO:55 or
   g. a variable heavy chain comprising the variable CDR1 sequence of the heavy chain, as shown in SEQ ID NO: 66, the variable CDR2 sequence of the heavy chain, as shown in SEQ ID NO: 67, the variable CDR3 sequence of the heavy chain, as shown in SEQ ID NO:68, and also
      a variable light chain comprising the variable CDR1 sequence of the light chain shown in SEQ ID NO: 63, the variable CDR2 sequence of the light chain shown in SEQ ID NO: 64 and the variable CDR3 sequence of the light chain shown in SEQ ID NO:65 or
   h. a variable heavy chain comprising the variable CDR1 sequence of the heavy chain, as shown in SEQ ID NO: 76, the variable CDR2 sequence of the heavy chain, as shown in SEQ ID NO: 77, the variable CDR3 sequence of the heavy chain, as shown in SEQ ID NO:78, and also
      a variable light chain comprising the variable CDR1 sequence of the light chain shown in SEQ ID NO: 73, the variable CDR2 sequence of the light chain shown in SEQ ID NO: 74 and the variable CDR3 sequence of the light chain shown in SEQ ID NO:75 or
   i. a variable heavy chain comprising the variable CDR1 sequence of the heavy chain, as shown in SEQ ID NO: 86, the variable CDR2 sequence of the heavy chain, as shown in SEQ ID NO: 87, the variable CDR3 sequence of the heavy chain, as shown in SEQ ID NO:88, and also
      a variable light chain comprising the variable CDR1 sequence of the light chain shown in SEQ ID NO: 83, the variable CDR2 sequence of the light chain shown in SEQ ID NO: 84 and the variable CDR3 sequence of the light chain shown in SEQ ID NO:85 or j. a variable heavy chain comprising the variable CDR1 sequence of the heavy chain, as shown in SEQ ID NO: 96, the variable CDR2 sequence of the heavy chain, as shown in SEQ ID NO: 97, the variable CDR3 sequence of the heavy chain, as shown in SEQ ID NO:98, and also a variable light chain comprising the variable CDR1 sequence of the light chain shown in SEQ ID NO: 93, the variable CDR2 sequence of the light chain shown in SEQ ID NO: 94 and the variable CDR3 sequence of the light chain shown in SEQ ID NO:95 or k. a variable heavy chain comprising the variable CDR1 sequence of the heavy chain, as shown in SEQ ID NO: 106, the variable CDR2 sequence of the heavy chain, as shown in SEQ ID NO: 107, the variable CDR3 sequence of the heavy chain, as shown in SEQ ID NO:108, and also a variable light chain comprising the variable CDR1 sequence of the light chain shown in SEQ ID NO: 103, the variable CDR2 sequence of the light chain shown in SEQ ID NO: 104 and the variable CDR3 sequence of the light chain shown in SEQ ID NO:105 or l. a variable heavy chain comprising the variable CDR1 sequence of the heavy chain, as shown in SEQ ID NO: 116, the variable CDR2 sequence of the heavy chain, as shown in SEQ ID NO: 117, the variable CDR3 sequence of the heavy chain, as shown in SEQ ID NO:118, and also a variable light chain comprising the variable CDR1 sequence of the light chain shown in SEQ ID NO: 113, the variable CDR2 sequence of the light chain shown in SEQ ID NO: 114 and the variable CDR3 sequence of the light chain shown in SEQ ID NO:115.

5. The antibody or the antigen-binding fragment thereof according to any of the preceding embodiments, comprising:
    a. a variable sequence of the heavy chain, as shown in SEQ ID NO:10, and also a variable sequence of the light chain, as shown in SEQ ID NO:9, or
    b. a variable sequence of the heavy chain, as shown in SEQ ID NO:20, and also a variable sequence of the light chain, as shown in SEQ ID NO:19, or
    c. a variable sequence of the heavy chain, as shown in SEQ ID NO:30, and also a variable sequence of the light chain, as shown in SEQ ID NO:29, or
    d. a variable sequence of the heavy chain, as shown in SEQ ID NO:40, and also a variable sequence of the light chain, as shown in SEQ ID NO:39, or
    e. a variable sequence of the heavy chain, as shown in SEQ ID NO:50, and also a variable sequence of the light chain, as shown in SEQ ID NO:49, or
    f. a variable sequence of the heavy chain, as shown in SEQ ID NO:60, and also a variable sequence of the light chain, as shown in SEQ ID NO:59, or
    g. a variable sequence of the heavy chain, as shown in SEQ ID NO:70, and also a variable sequence of the light chain, as shown in SEQ ID NO:69, or
    h. a variable sequence of the heavy chain, as shown in SEQ ID NO:80, and also a variable sequence of the light chain, as shown in SEQ ID NO:79, or
    i. a variable sequence of the heavy chain, as shown in SEQ ID NO:90, and also a variable sequence of the light chain, as shown in SEQ ID NO:89, or
    j. a variable sequence of the heavy chain, as shown in SEQ ID NO:100, and also a variable sequence of the light chain, as shown in SEQ ID NO:99, or
    k. a variable sequence of the heavy chain, as shown in SEQ ID NO:110, and also a variable sequence of the light chain, as shown in SEQ ID NO:109, or
    l. a variable sequence of the heavy chain, as shown in SEQ ID NO:120, and also a variable sequence of the light chain, as shown in SEQ ID NO:119.

6. The antibody according to any of the preceding embodiments which is an IgG antibody.

7. The antibody according to any of the preceding embodiments, comprising:
    a. a sequence of the heavy chain, as shown in SEQ ID NO:2, and also a sequence of the light chain, as shown in SEQ ID NO:1, or
    b. a sequence of the heavy chain, as shown in SEQ ID NO:12, and also a sequence of the light chain, as shown in SEQ ID NO:11, or
    c. a sequence of the heavy chain, as shown in SEQ ID NO:22, and also a sequence of the light chain, as shown in SEQ ID NO:21, or
    d. a sequence of the heavy chain, as shown in SEQ ID NO:32, and also a sequence of the light chain, as shown in SEQ ID NO:31, or
    e. a sequence of the heavy chain, as shown in SEQ ID NO:42, and also a sequence of the light chain, as shown in SEQ ID NO:41, or
    f. a sequence of the heavy chain, as shown in SEQ ID NO:52, and also a sequence of the light chain, as shown in SEQ ID NO:51, or
    g. a sequence of the heavy chain, as shown in SEQ ID NO:62, and also a sequence of the light chain, as shown in SEQ ID NO:61, or
    h. a sequence of the heavy chain, as shown in SEQ ID NO:72, and also a sequence of the light chain, as shown in SEQ ID NO:71, or
    i. a sequence of the heavy chain, as shown in SEQ ID NO:82, and also a sequence of the light chain, as shown in SEQ ID NO:81, or
    j. a sequence of the heavy chain, as shown in SEQ ID NO:92, and also a sequence of the light chain, as shown in SEQ ID NO:91, or
    k. a sequence of the heavy chain, as shown in SEQ ID NO:102, and also a sequence of the light chain, as shown in SEQ ID NO:101, or
    l. a sequence of the heavy chain, as shown in SEQ ID NO:112, and also a sequence of the light chain, as shown in SEQ ID NO:111.

8. The antigen-binding fragment according to any of the preceding embodiments or an antigen-binding fragment of an antibody according to any of the preceding embodiments which is an scFv, Fab, Fab' fragment or a F(ab')2 fragment.

9. The antibody or the antigen-binding fragment according to any of the preceding embodiments which is a monoclonal antibody or an antigen-binding fragment thereof.

10. The antibody or the antigen-binding fragment according to any of the preceding embodiments which is a human, humanized or chimeric antibody or an antigen-binding fragment.

Particular preference is given to the anti-TWEAKR antibody TPP-2090.

Isotopes, Salts, Solvates, Isotopic Variants

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

In addition, the present invention also encompasses prodrugs of the compounds according to the invention. The term "prodrugs" here denotes compounds which may themselves be biologically active or inactive, but are converted (for example by metabolic or hydrolytic means) to inventive compounds during their residence time in the body.

PARTICULAR EMBODIMENTS

The following embodiments are particularly preferred:

Embodiment A

An ADC of the formula

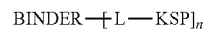

where KSP-L- is a compound of the formula (II), (IIa), (IIb), (IIc), (IId), (IIe) below or the formula (IIf) below, the binder is an anti-TWEAKR antibody (particularly preferably an anti-TWEAKR antibody which binds specifically to amino acid D in position 47 (D47) of TWEAKR (SEQ ID NO:169), especially the anti-TWEAK R antibody TPP-2090), and n is a number from 1 to 10:

formula (IIf)

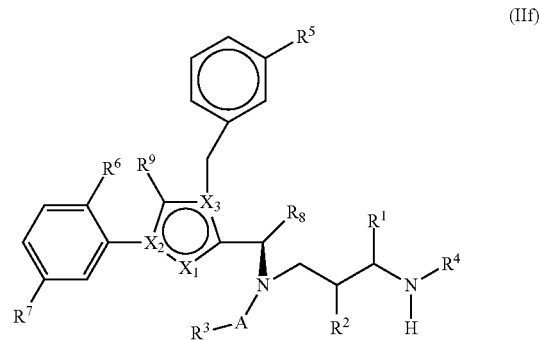

(IIf)

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents CO (carbonyl);
$R^1$ represents —L-#$^1$, H, —COOH, —CONHNH$_2$, —(CH$_2$)$_{1-3}$NH$_2$, —CONZ"(CH$_2$)$_{1-3}$ NH$_2$ and —CONZ"CH$_2$COOH, where Z" represents H or NH$_2$;
$R^2$ and $R^4$ represent H or —L-#$^1$, or $R^2$ and $R^4$ together (with formation of a pyrrolidine ring) represent —CH$_2$—CHR$^{10}$— or —CHR$^{10}$—CH$_2$—, where R$^{10}$ represents H or —L-#$^1$;
$R^3$ represents —L-#$^1$ or a C$_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl is preferably C$_{1-3}$-alkyl);
$R^5$ represents —L-#$^1$, H or F;

$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;

$R^8$ represents a branched $C_{1-5}$-alkyl group which may be substituted by —L-#$^1$; and $R^9$ represents H or F, where one of the substituents $R^1$, $R^2$, $R^3$, $R^4$, $R^5$, $R^8$ and $R^{10}$ represents —L-#$^1$, and -L- represents the linker and #$^1$ represents the bond to the antibody, and salts, solvates and salts of the solvates of the ADC.

The linker is preferably a linker

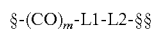

where
m is 0 or 1;
§ represents the bond to KSP and
§§ represents the bond to the antibody, and
L2 represents

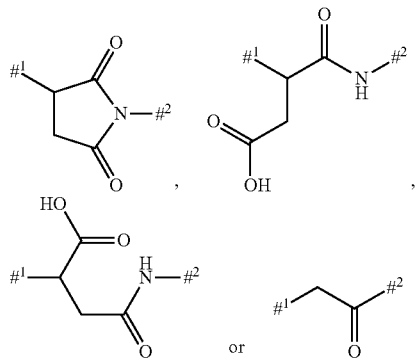

where
$^1$ denotes the point of attachment to the sulphur atom of the antibody,
$^2$ denotes the point of attachment to group L1,
and L1 is represented by formula

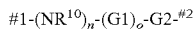

where
$R^{10}$ represents H, $NH_2$ or $C_1$-$C_3$-alkyl;
G1 represents —NHCO— or

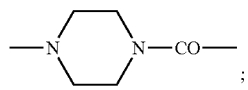

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe—, —NHNH—, —$SO_2$NHNH—, —CONHNH— and a 3- to 10-membered aromatic or non-aromatic heterocycle having up to 4 heteroatoms selected from the group consisting of N, O and S, or —SO— (preferably

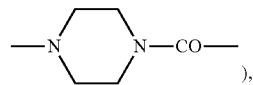

where the side chains, if present, may be substituted by —$NHCONH_2$, —COOH, —OH, —$NH_2$, NH—$CNNH_2$, sulphonamide, sulphone, sulphoxide or sulphonic acid.

Here, #$^1$ is the bond to the KSP inhibitor and #$^2$ is the bond to the coupling group to the binder (e.g. L2).

Embodiment B

An ADC of the formula

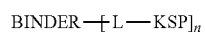

where KSP-L- is a compound of the formula (II), (IIa), (IIb), (IIc), (IId), (IIe), (IIe), (IIf) below or of the formula (IIg) below, the binder is an antibody and n is a number from 1 to 10:

formula (IIg)

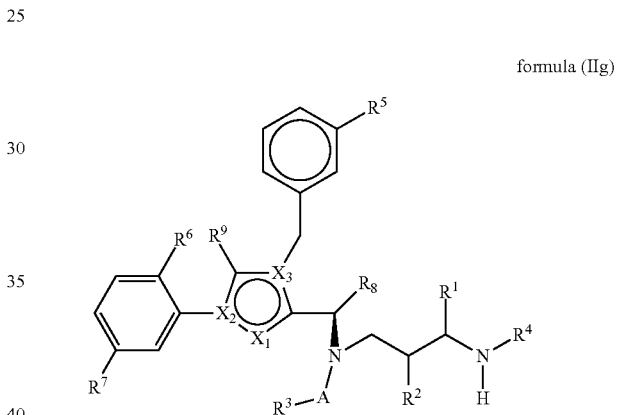

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents CO (carbonyl);
$R^1$ represents —L-#$^1$, H, —COOH, —$CONHNH_2$, —$(CH_2)_{1-3}NH_2$, —CONZ"$(CH_2)_{1-3}$ $NH_2$ and —CONZ"$CH_2$COOH, where Z" represents H or $NH_2$;
$R^2$ and $R^4$ represent H or —L-#$^1$, or $R^2$ and $R^4$ together (with formation of a pyrrolidine ring) represent —$CH_2$—$CHR^{10}$— or —$CHR^{10}$—$CH_2$—, where $R^{10}$ represents H or —L-#$^1$;
$R^3$ represents —L-#$^1$ or a $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH-alkyl, NH-alkyl, N(alkyl)$_2$ or $NH_2$ (where alkyl is preferably $C_{1-3}$-alkyl);
$R^5$ represents —L-#$^1$, H or F;
$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ represents a branched $C_{1-5}$-alkyl group; and
$R^9$ represents H or F, where one of the substituents $R^1$, $R^2$, $R^3$, $R^4$, $R^5$ and $R^{10}$ represents —L-#$^1$, and
-L- represents the linker and #$^1$ represents the bond to the antibody,
where -L- is represented by §-(CO)$_m$-L1-L2-§§ where
m is 0 or 1;
§ represents the bond to KSP and
§§ represents the bond to the antibody, and
L2 represents

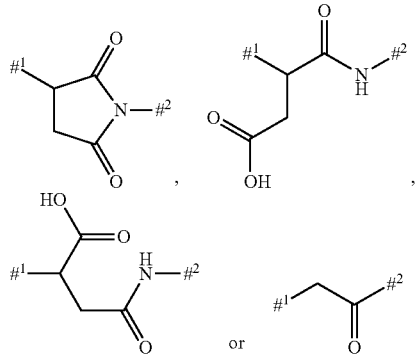

where
$^1$ denotes the point of attachment to the sulphur atom of the antibody,
$^2$ denotes the point of attachment to group L1,
and L1 is represented by formula

$^1$—(NR$^{10}$)$_n$-(G1)$_o$-G2-#$^2$ where
$R^{10}$ represents H, NH$_2$ or C$_1$-C$_3$-alkyl;
G1 represents —NHCO— or

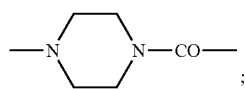

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH— and a 3- to 10-membered aromatic or non-aromatic heterocycle having up to 4 heteroatoms selected from the group consisting of N, O and S, or —SO— (preferably

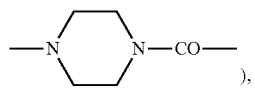

where the side chains, if present, may be substituted by —NHCONH$_2$, —COOH, —OH, —NH$_2$, NH—CNNH$_2$, sulphonamide, sulphone, sulphoxide or sulphonic acid, #$^1$ is the bond to the KSP inhibitor and #$^2$ is the bond to the coupling group to the antibody (e.g. L2), and salts, solvates and salts of the solvates of the ADC.

Embodiment C

An ADC of the formula

BINDER—[L—KSP]$_n$ where KSP-L- is a compound having the substructure I(sub) below, the binder is an anti-TWEAKR antibody (particularly preferably an anti-TWEAKR antibody which binds specifically to amino acid D in position 47 (D47) of TWEAKR (SEQ ID NO:169), especially the anti-TWEAK R antibody TPP-2090), anti-HER2 antibody or anti-EGRF antibody (preferably nimotuzumab), and n is a number from 1 to 10:

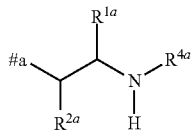

where
a represents a bond to the remainder of the molecule;
$R^{1a}$ represents —L-#$^1$, H or —(CH$_2$)$_{0-3}$Z, where Z represents —H, halogen, —NHY$^3$, —CO—NY$^1$Y$^2$ or —CO—OY$^3$,
where Y$^1$ and Y$^2$ independently of one another represent H, NH$_2$ or —(CH$_2$CH$_2$O)$_{0-3}$—(CH$_2$)$_{0-3}$Z', and Y$^3$ represents H or —(CH$_2$)$_{0-3}$Z', where Z' represents H, SO$_3$H, NH$_2$, COOH or —(CO—NH—CHY$^4$)$_{1-3}$ COOH, where Y$^4$ independently of one another represents straight-chain or branched C$_{1-6}$-alkyl which is optionally substituted by —NHCONH$_2$, or represents aryl or benzyl which are optionally substituted by —NH$_2$;
$R^{2a}$ and $R^{4a}$ independently of one another represent H, —L-#$^1$, —CO—CHY$^4$—NHY$^5$ or —(CH$_2$)$_{0-3}$Z, or
$R^{2a}$ and $R^{4a}$ together represent (with formation of a pyrrolidine ring) —CH$_2$—CHR$^{10}$— or —CHR$^{10}$—CH$_2$—, where R$^{10}$ represents —L-#$^1$, H, NH$_2$, COOH, SO$_3$H, SH or OH, and where Z represents —H, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH,
where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
where one of the substituents $R^{1a}$, $R^{2a}$, $R^{4a}$ or $R^{10}$ represents —L-#$^1$,
-L- represents the linker and #$^1$ represents the bond to the antibody,
where -L- is represented by §-(CO)$_m$-L1-L2-§§ where
m is 0 or 1;

§ represents the bond to KSP and
§§ represents the bond to the antibody, and
L2 represents

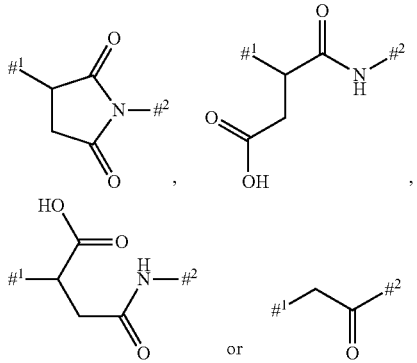

where
¹ denotes the point of attachment to the sulphur atom of the antibody,
² denotes the point of attachment to group L1,
and L1 is represented by formula

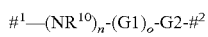

where
$R^{10}$ represents H, $NH_2$ or $C_1$-$C_3$-alkyl;
G1 represents —NHCO— or

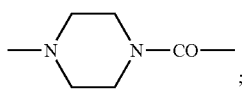

;

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe—, —NHNH—, —$SO_2$NHNH—, —CONHNH— and a 3- to 10-membered aromatic or non-aromatic heterocycle having up to 4 heteroatoms selected from the group consisting of N, O and S, or —SO— (preferably

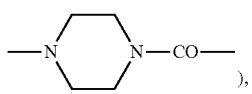

), where the side chains, if present, may be substituted by —$NHCONH_2$, —COOH, —OH, —$NH_2$, NH—$CNNH_2$, sulphonamide, sulphone, sulphoxide or sulphonic acid, #¹ is the bond to the KSP inhibitor and #² is the bond to the coupling group to the antibody (e.g. L2), and salts, solvates and salts of the solvates of the ADC.

Embodiment D

An ADC of the formula

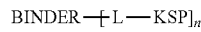

where KSP-L- is a compound of the formula (II), (IIa), (IIb), (IIc), (IId), (IIe), (IIf), (IIg) below or of the formula (IIh) below, the binder is an antibody and n is a number from 1 to 10:

formula (IIh):

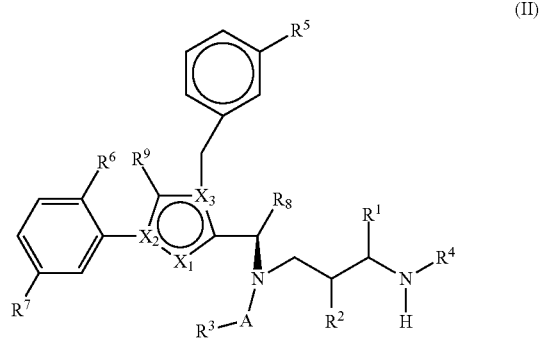

(II)

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents CO (carbonyl);
$R^1$ represents —L-#¹;
$R^2$ and $R^4$ represent H, or $R^2$ and $R^4$ together (with formation of a pyrrolidine ring) represent —$CH_2$—$CHR^{10}$— or —$CHR^{10}$—$CH_2$—, where $R^{10}$ represents H;
$R^3$ represents $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH-alkyl, NH-alkyl, $N(alkyl)_2$ or $NH_2$ (where alkyl is preferably $C_{1-3}$-alkyl), or -MOD;
where -MOD represents —$(NR^{10})^n$-$(G1)_o$-G2-H, where
$R^{10}$ represents H or $C_1$-$C_3$-alkyl;
G1 represents —NHCO—, —CONH— or

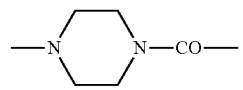

(where, if G1 represents —NHCO— or

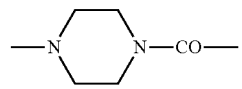

, $R^{10}$ does not represent $NH_2$);
n is 0 or 1;
o is 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CH$_2$=N—O— (where Rx represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

R$^5$ represents H or F;
R$^6$ and R$^7$ independently of one another represent H, (optionally fluorinated) C$_{1-3}$-alkyl, (optionally fluorinated) C$_{2-4}$-alkenyl, (optionally fluorinated) C$_{2-4}$-alkynyl, hydroxy or halogen;
R$^8$ represents a branched C$_{1-5}$-alkyl group; and
R$^9$ represents H or F,
where -L- represents the linker and #$^1$ represents the bond to the antibody,
where -L- is represented by §-(CO)$_m$-L1-L2-§§ where
m is 0 or 1;
§ represents the bond to KSP and
§§ represents the bond to the antibody, and
L2 represents

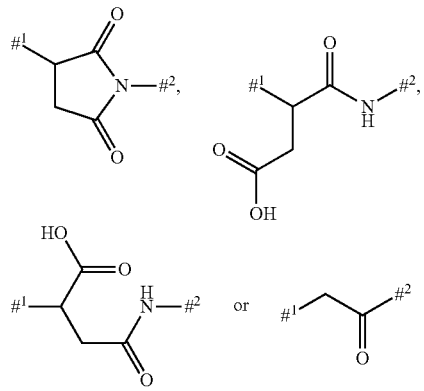

where
$^1$ denotes the point of attachment to the sulphur atom of the antibody,
$^2$ denotes the point of attachment to group L1,
and L1 is represented by formula

$^1$—(NR$^{10}$)$_n$-(G1)$_o$-G2-#$^2$ where
R$_{10}$ represents H, NH$_2$ or C$_1$-C$_3$-alkyl;
G1 represents —NHCO— or

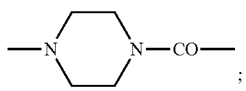

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH—, —CH$_2$=N—O— (where R$^x$ represents H, C$_1$-C$_3$-alkyl or phenyl) and a 3- to 10-membered aromatic or non-aromatic heterocycle having up to 4 heteroatoms selected from the group consisting of N, O and S, —SO— or —SO$_2$— (preferably

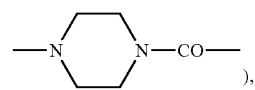

where the hydrocarbon chain including the side chains, if present, may be substituted by —NHCONH$_2$, —COOH, —OH, —NH$_2$, NH—CNNH$_2$, sulphonamide, sulphone, sulphoxide or sulphonic acid.
$^1$ is the bond to the KSP inhibitor and #$^2$ is the bond to the coupling group to the antibody (e.g. L2),
and salts, solvates and salts of the solvates of the ADC.

Embodiment E

An ADC of the formula

BINDER—[L—KSP]$_n$ where KSP-L- is a compound having the substructure I(sub) below, the binder is nimutuzumab and n is a number from 1 to 10:

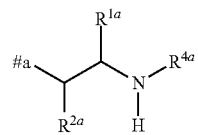

where
a represents a bond to the remainder of the molecule;
R$^{1a}$ represents —L-#$^1$, H or —(CH$_2$)$_{0-3}$Z, where Z represents —H, halogen, —NHY$^3$, —CO—NY$^1$Y$^2$ or —CO—OY$^3$,
where Y$^1$ and Y$^2$ independently of one another represent H, NH$_2$ or —(CH$_2$CH$_2$O)$_{0-3}$—(CH$_2$)$_{0-3}$Z', and Y$^3$ represents H or —(CH$_2$)$_{0-3}$Z', where Z' represents H, SO$_3$H, NH$_2$, COOH or —(CO—NH—CHY$^4$)$_{1-3}$ COOH, where Y$^4$ independently of one another represents straight-chain or branched C$_{1-6}$-alkyl which is optionally substituted by —NHCONH$_2$, or represents aryl or benzyl which are optionally substituted by —NH$_2$;
R$^{2a}$ and R$^{4a}$ independently of one another represent H, —L-#1, —CO—CHY$^4$—NHY$^5$ or —(CH$_2$)$_{0-3}$Z, or
R$^{2a}$ and R$^{4a}$ together represent (with formation of a pyrrolidine ring) —CH$_2$—CHR$^{10}$— or —CHR$^{10}$—CH$_2$—, where R$^{10}$ represents —L-#1, H, NH$_2$, COOH, SO₃H, SH or OH, and where Z represents —H, —CO—NY¹Y² or —CO—OY³,
where Y¹ and Y² independently of one another represent H, NH₂ or —(CH₂)₀₋₃Z', and Y³ represents H or —(CH₂)₀₋₃Z', where Z' represents H, SO₃H, NH₂ or COOH,
where Y⁴ independently of one another represents straight-chain or branched C₁₋₆ alkyl which is optionally substituted by —NHCONH₂, or represents aryl or benzyl which are optionally substituted by —NH₂, and Y⁵ represents H or —CO—CHY⁶—NH₂, where Y⁶ represents straight-chain or branched C₁₋₆-alkyl;
where one of the substituents R¹ᵃ, R²ᵃ, R⁴ᵃ or R¹⁰ represents —L-#¹,
-L- represents the linker and #¹ represents the bond to the antibody,
where -L- is represented by

§-(CO)ₘ-L1-L2-§§ where
m is 0 or 1;
§ represents the bond to KSP and
§§ represents the bond to the antibody, and
L2 represents

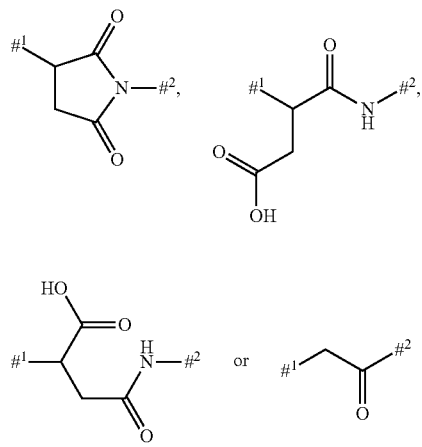

where
¹ denotes the point of attachment to the sulphur atom of the antibody,
² denotes the point of attachment to group L1,
and L1 is represented by formula

¹—(NR¹⁰)ₙ-(G1)ₒ-G2-#² where
R¹⁰ represents H, NH₂ or C₁-C₃-alkyl;
G1 represents —NHCO— or

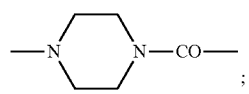

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NHCO—, —CONH—, —NMe—, —NHNH—, —SO₂NHNH—, —CONHNH— and a 3- to 10-membered aromatic or non-aromatic heterocycle having up to 4 heteroatoms selected from the group consisting of N, O and S, or —SO— (preferably

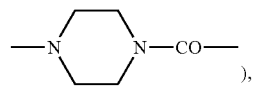), where the side chains, if present, may be substituted by —NHCONH₂, —COOH, —OH, —NH₂, NH—CNNH₂, sulphonamide, sulphone, sulphoxide or sulphonic acid, #¹ is the bond to the KSP inhibitor and #² is the bond to the coupling group to the antibody (e.g. L2), and salts, solvates and salts of the solvates of the ADC.

In this embodiment, KSP-L- particularly preferably has the formula (IIi) below:

formula (IIi):

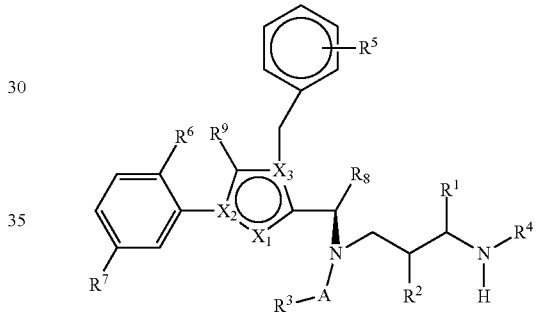

(IIi)

where
X₁ represents N, X₂ represents N and X₃ represents C; or
X₁ represents N, X₂ represents C and X₃ represents N; or
X₁ represents CH or CF, X₂ represents C and X₃ represents N; or
X₁ represents NH, X₂ represents C and X₃ represents C; or
X₁ represents CH, X₂ represents N and X₃ represents C (with X₁ representing CH, X₂ representing C and X₃ representing N being preferred);
R¹ represents H, -MOD or —(CH₂)₀₋₃Z, where Z represents —H, —NHY³, —OY³, —SY³, halogen, —CO—NY¹Y² or —CO—OY³,
where Y¹ and Y² independently of one another represent H, NH₂, —(CH₂CH₂O)₀₋₃—(CH₂)₀₋₃Z' (e.g. —(CH₂)₀₋₃Z') or —CH(CH₂W)Z', and Y³ represents H or —(CH₂)₀₋₃Z', where Z' represents H, NH₂, SO₃H, COOH, —NH—CO—CH₂—CH₂—CH(NH₂)COOH or —(CO—NH—CHY⁴)₁₋₃COOH, where W represents H or OH,
where Y⁴ independently of one another represents straight-chain or branched C₁₋₆-alkyl which is optionally substituted by —NHCONH₂, or represents aryl or benzyl which are optionally substituted by —NH₂;
R² represents H, -MOD, —CO—CHY⁴—NHY⁵ or —(CH₂)₀₋₃Z, or R² and R⁴ together (with formation of a pyrrolidine ring) represent —CH$_2$—CHR$^{10}$— or —CHR$^{10}$—CH$^2$—, where R$^{10}$ represents H, NH$_2$, SO$_3$H, COOH, SH, or OH;

where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

R$^4$ represents H, —CO—CHY$^4$—NHY$^5$ or —(CH$_2$)$_{0-3}$Z, preferably H, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

or R$^2$ and R$^4$ together (with formation of a pyrrolidine ring) represent —CH$_2$—CHR$^{10}$— or —CHR$^{10}$—CH$_2$—, where R$^{10}$ represents H, NH$_2$, SO$_3$H, COOH, SH or OH;

A represents CO, SO, SO$_2$, SO$_2$NH or CNNH;

R$^3$ represents —L-#$^1$,

R$^5$ represents H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br), R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, CO$_2$H or NH$_2$;

L represents the linker and #$^1$ represents the bond to the binder or derivative thereof, where -MOD represents —(NR$^{10}$)$_n$-(G1)$_o$-G2-H, where R$^{10}$ represents H or C$_1$-C$_3$-alkyl;

G1 represents —NHCO—, —CONH— or

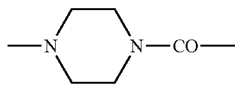

(where, if G1 represents —NHCO— or

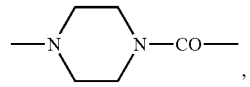

R$^{10}$ does not represent NH$_2$);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NR$^y$—, —NR$^y$CO—, CONR$^y$—, —NR$^y$NR$^y$—, —SO$_2$NR$^y$NR$^y$—, —CONR$^y$NR$^y$— (where R$^y$ represents H, phenyl, C$_1$-C$_{10}$-alkyl, C$_2$-C$_{10}$-alkenyl or C$_2$-C$_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —CH$_2$=N—O— (where R$^x$ represents H, C$_1$-C$_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where the group -MOD preferably has at least one group —COOH;

and the salts, solvates and salts of the solvates thereof.

Embodiment F

Compounds of the general formula:

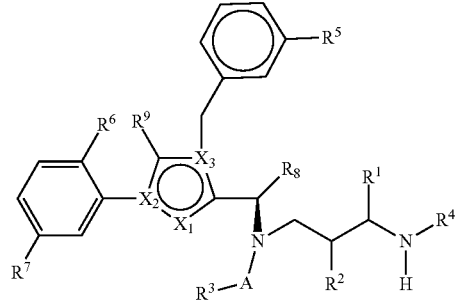

(III)

where

X$_1$ represents N, X$_2$ represents N and X$_3$ represents C, or X$_1$ represents CH, X$_2$ represents C and X$_3$ represents N;

R$^1$ represents H or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH; where W represents H or OH;

where Y$^4$ independently of one another represents straight-chain or branched C$_{1-6}$-alkyl which is optionally substituted by —NHCONH$_2$, or represents aryl or benzyl which are optionally substituted by —NH$_2$;

R$^2$ and R$^4$ independently of one another represent H, —CO—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—, where R$^{10}$ represents H, NH$_2$, SO$_3$H, COOH, SH or OH, where Z represents —H, halogen, —OY$^3$, —SY$^3$, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
A represents CO, SO, SO$_2$, SO$_2$NH or CNNH;
R$^3$ represents an optionally substituted alkyl, aryl, heteroaryl, heteroalkyl, heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH
(where "alkyl" preferably represents C$_{1-10}$-alkyl);
R$^5$ represents H, F, NH$_2$, NO$_2$, halogen, SH or —(CH$_2$)$_{0-3}$Z, where Z represents —H, halogen, —OY$^3$, —SY$^3$, —NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen,
R$^8$ represents (optionally fluorinated) C$_{1-10}$-alkyl, (optionally fluorinated) C$_{4-10}$-cycloalkyl or optionally substituted oxetane; and
R$^9$ represents H, F, CH$_3$, CF$_3$, CH$_2$F or CHF$_2$;
and the salts, solvates and salts of the solvates thereof.

Embodiment G

The invention also provides binder/active compound of the general formula below:

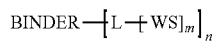

where BINDER represents the binder (preferably: antibody) or a derivative thereof (preferably: cysteine residue), preferably an antibody, L represents the linker, WS represents the active compound, preferably a KSP inhibitor such as, for example, a KSP inhibitor according to the invention of one of the formulae (II), (IIa), (IIb), (IIc), (IId), (IIe), (IIf), (IIg) or (IIh), m represents a number from 1 to 2, preferably 1, and n represents a number from 1 to 50, preferably from 1.2 to 20 and particularly preferably from 2 to 8, where L has one of the structures below. Here, m is the number of active compound molecules per linker and n a mean of the number of active compound/linker conjugates per BINDER. The sum of all WS present in a conjugate molecule is therefore the product of m and n.

WS is an active compound which has local or systemic therapeutic action in animals, preferably in humans. These active compounds generally have a molecular weight below 5 kDa, preferably below 1.5 kDa. Preferred active compounds are antiproliferative substances, for example cytotoxic or cytostatic substances. Preferred active compounds are cytotoxic substances, inhibitors of angiogenesis, cell cycle inhibitors, PI3 kinase or m-TOR inhibitors, inhibitors of the MAPK signalling cascade pathway, HDAC inhibitors, proteasome inhibitors, PARP inhibitors, Wnt/Hedgehog signal cascade path inhibitors and RNA polymerase inhibitors. Cytotoxic substances are, inter alia, DNA-binding or intercalating substances, DNA-alkylating substances, microtubulin-stabilizing substances or -destabilizing substances, platinum compounds and topoisomerase I inhibitors. Exemplary DNA-binding substances are, for example, anthracyclins such as doxorubicin or daunorubicin). Exemplary DNA-alkylating substances are, for example, calicheamicins, temozolomide or cyclophosphamide and derivatives. Exemplary microtubulin-stabilizing or -destabilizing substances are, for example, taxanes such as paclitaxel, docetaxel, maytansinoides and auristatins, tubulysines, vinca alkaloids, epothilones and derivatives thereof. Examples of maytansinoides are maytansins, maytansinols, DM-1 and DM-4 (see, for example, US patent U.S. Pat. No. 5,208,020). Examples of auristatins are auristatin E, monomethylauristatin E (MMAE), auristatin F, monomethylauristatin F (MMAF) and dolastin (see, inter alia, WO 09/117531, WO 2005/081711, WO 04/010957; WO02/088172 or WO01/24763). Examples of vinca alkaloids are vincristine and vinblastine. Examples of epothilones are epothilone A, B, C, D, E or F (see, inter alia, WO 98/13375; WO2004/005269; WO 2008/138561; WO 2009/002993; WO 2009/055562; WO 2009/012958; WO2009/026177; WO 2009/134279; WO 2010/033733; WO2010/034724; WO 2011/017249; WO2011/057805). Examples of platinum compounds are cisplatin and carboplatin. Examples of topoisomerase I inhibitors are camptothecin and derivatives. Examples of inhibitors of angiogenesis are MetAP2 inhibitors such as, for example, fumagillol. Examples of cell cycle inhibitors are CDK inhibitors (e.g. BMS-387032 or PD0332991), Rho kinase inhibitors such as, for example, GSK429286, PLK inhibitors such as, for example, volasertib, aurora kinase inhibitors such as, for example, AZD1152 or MLN805Z. Examples of inhibitors of the MAPK signalling cascade pathway are inter alia MEK inhibitors (e.g. PD0325901), Ras inhibitors, JNK inhibitors, B-Raf inhibitors (e.g. SB590885) or p38 MAPK inhibitors (e.g. SB202190). Examples of HDAC inhibitors are belinostat and givinostat. Examples of PARP inhibitors are iniparib and olaparib. Examples of RNA polymerase inhibitors are amatoxins such as, for example, alpha-amantin, amanin and amanullin. Particularly preferred active compounds are vinca alkaloids, auristatins, maytansinoides, tubulysins, duocarmycins, kinase inhibitors, MEK inhibitors and KSP inhibitors.

Here, L represents one of the formulae A3 and A4 below

Formula A3

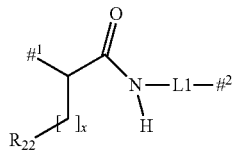

Formula A4

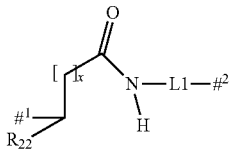

where #¹ denotes the point of attachment to the sulphur atom of the binder, #² denotes the point of attachment to the active compound, x represents 1 or 2, and $R_{22}$ represents COOH, COOR, COR (where R in each case represents $C_{1-3}$-alkyl), $CONH_2$, Br, preferably COOH.

L1 has the same meaning as above. Preferably, -L1-#² is represented by the formula below:

³—$(NR^{10})_n$-$(G1)_o$-G2-#² where
³ denotes the point of attachment to the nitrogen atom,
$R^{10}$ represents H, $NH_2$ or $C_1$-$C_3$-alkyl;
G1 represents —NHCO—, —CONH— or

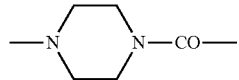

(where, if G1 represents NHCO or

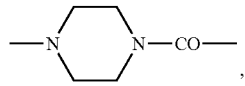

$R^{10}$ does not represent $NH_2$),
n is 0 or 1;
o is 0 or 1; and
G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, $SO_2$, —$NR^y$—, —$NR^yCO$—, —$C(NH)NR^y$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CH_2$=N—O— (where $R^x$ represents H, $C_1$-$C_3$-alkyl or phenyl) and/or a 3- to 10-membered aromatic or non-aromatic heterocycle having up to 4 heteroatoms selected from the group consisting of N, O and S, —SO— or —$SO_2$— (preferably

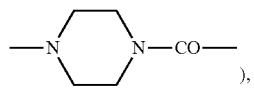

where the hydrocarbon chain including any side chains may be substituted by $NHCONH_2$, —COOH, —OH, —$NH_2$, NH—$CNNH_2$, sulphonamide, sulphone, sulphoxide or sulphonic acid.

Further interrupting groups in G2 are preferably

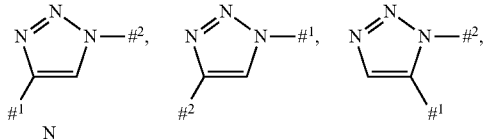

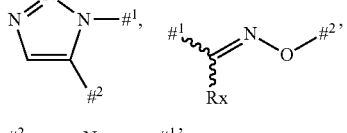

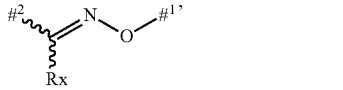

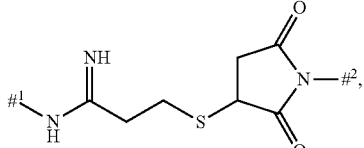

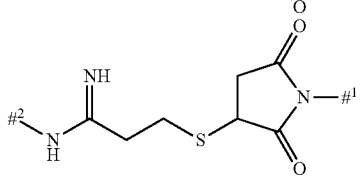

where Rx represents H, $C_1$-$C_3$-alkyl or phenyl.

In the conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder) as one of the two structures of the formula A3 or A4.

The conjugates with the linkers of formula A3 or A4 can be obtained by coupling the binders to the appropriate bromine derivatives of the formulae A3' and A4', respectively, below:

Formula A3'

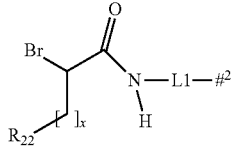

Formula A4'

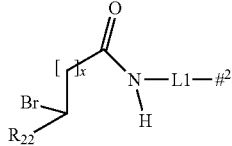

These bromine derivatives of the formula A3' or A4' can be obtained by reacting $HOOCCH_2CHBrCOOR_{22}$ or $HOOCCHBrCH_2COOR_{22}$ with an amine group of the binder, as illustrated in an exemplary manner in Schemes 30 to 32 below.

Scheme 30:
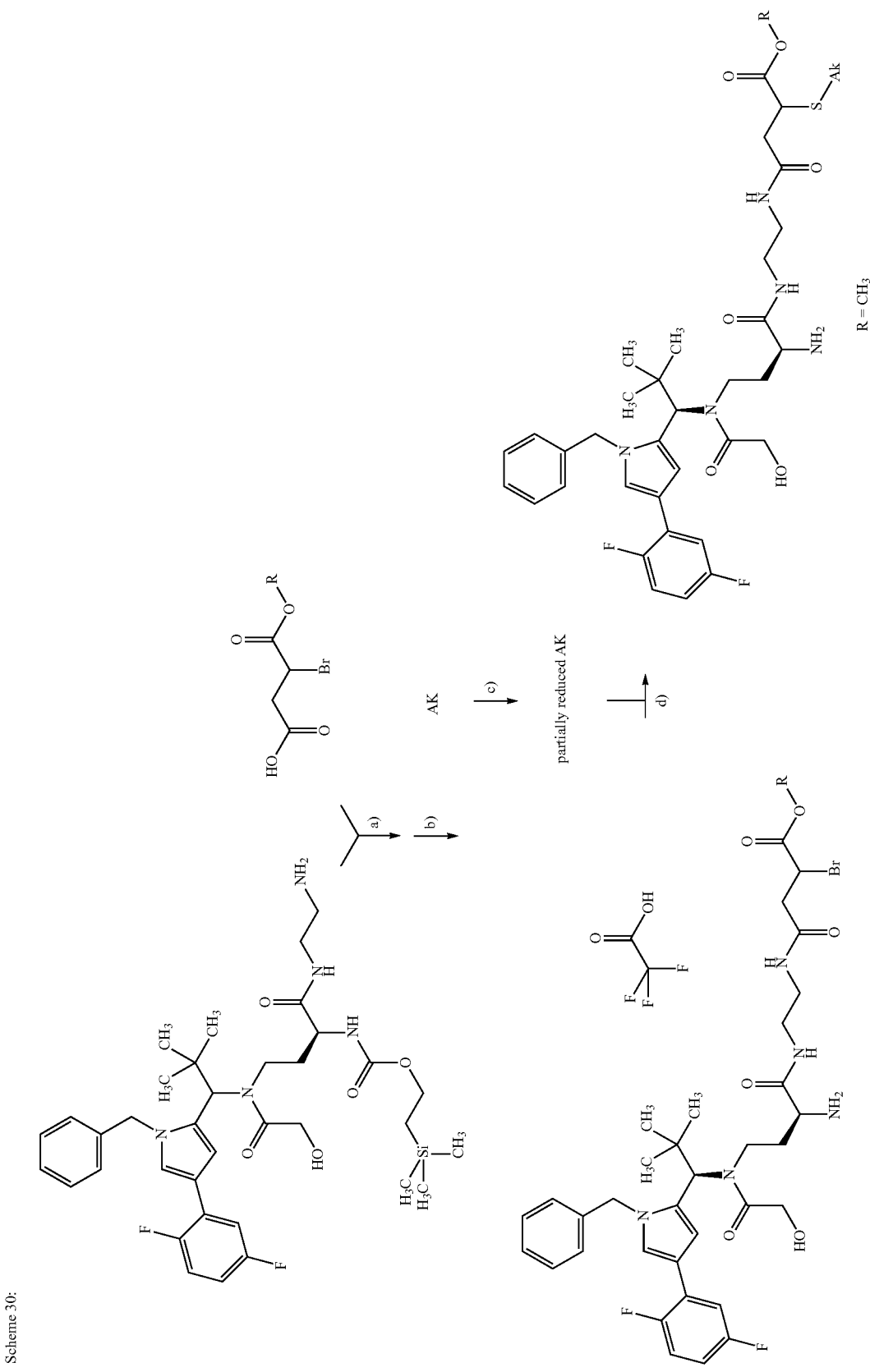
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 31:

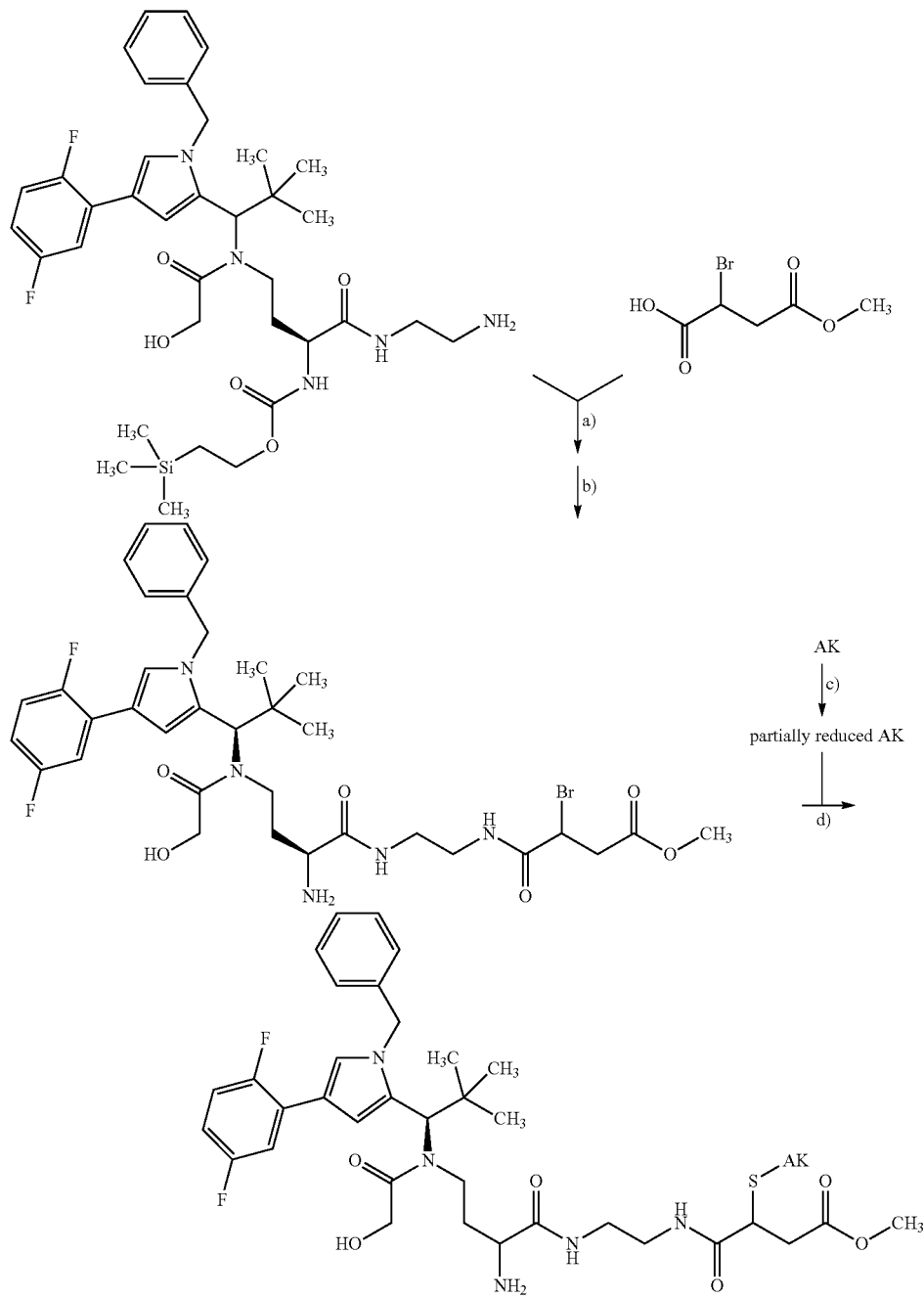

[a]: 2-bromo-1-ethylpyridinium tetrafluoroborate (BEP), DCM, pyridine, RT; b) zinc chloride, trifluoroethanol, 50° C., EDTA; c) 3-4 equivalents OF TCEP, PBS buffer; d) PBS buffer, 20 h RT.]

Embodiment H

The invention also provides binder/active compound of the general formula below:

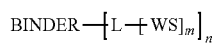

where BINDER represents the binder (preferably: antibody) or a derivative thereof (preferably: cysteine residue), preferably an antibody, L represents the linker, WS represents the active compound, preferably a KSP inhibitor such as, for example, a KSP inhibitor according to the invention of one of the formulae (II), (IIa), (III) or (IIIa), m represents a number from 1 to 2, preferably 1, and n represents a number from 1 to 50, preferably from 1.2 to 20 and particularly preferably from 2 to 8, where L has one of the structures below. Here, m is the number of active compound molecules per linker and n a mean of the number of active compound/linker conjugates per BINDER. The sum of all WS present in a conjugate molecule is therefore the product of m and n.

Here, L represents:

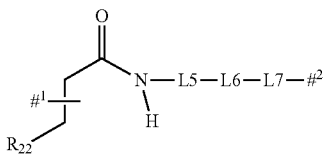
Formula A where $\#^1$ denotes the point of attachment to the sulphur atom of the binder, $\#^2$ denotes the point of attachment to the active compound and $R_{22}$ represents COOH, COOR, COR (where R in each case represents $C_{1-3}$-alkyl), $CONH_2$, Br, preferably COOH. The link to the sulphur atom of the binder may thus have one of the structures below:

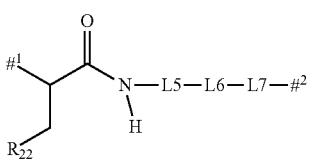
Formula A1

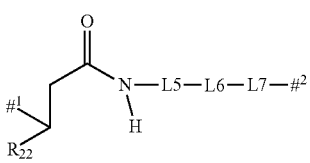
Formula A2

In the case of active compound/binder conjugates containing more than one active compound molecule WS per active compound/binder conjugate, both structures according to the formulae A1 and/or A2 may be present in an active compound/binder conjugate. Since the active compound/binder conjugates according to the invention may be mixtures of different active compound/binder conjugates, it is also possible for this mixture to comprise both active compound/binder conjugates of formula A1 or formula A2 and those of formula A1 and A2.

L5 is a group selected from $-(CH_2)_m-(CHR^S)_n-(OCH_2CH_2)_o-(X)_p-(CH_2)_q-$, where m, n, o, p and q independently of one another have the following values: m=0-10; n=0 or 1; o=0-10; p=0 or 1; and q=0-10, where m+n+o=1-15, preferably 1-6. X represents a 5- or 6-membered aromatic or nonaromatic hetero- or homocycle, preferably $-C_6H_4-$ or $-C_6H_{10}-$. $R^S$ represents an acid group, preferably $-COOH$ or $SO_3H$.

L6 is a group selected from $-CONH-$, $-OCONH-$, $-NHCO-$, $-NHCOO-$,

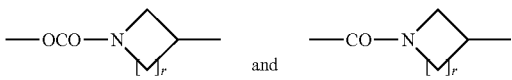
and where r is 1, 2 or 3.

L7 is a single bond or a group selected from a straight-chain or branched hydrocarbon chain which has 1 to 100 (preferably 1 to 10) carbon atoms from arylene groups and/or straight-chain and/or branched and/or cyclic alkylene groups and which may be interrupted once or more than once by one or more of the groups $-O-$, $-S-$, $-SO-$, $SO_2$, $-NR^y-$, $-NR^yCO-$, $-C(NH)NR^y-$, $CONR^y-$, $-NR^yNR^y-$, $-SO_2NR^yNR^y-$, $-CONR^yNR^y-$ (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, $-COOH$, $-OH$, $-NH_2$, $NH-CNNH_2$, sulphonamide, sulphone, sulphoxide or sulphonic acid), $-CO-$, $-CH_2=N-O-$ (where $R^x$ represents H, $C_1$-$C_3$-alkyl or phenyl) and/or a 3- to 10-membered, preferably 5- to 10-membered aromatic or non-aromatic heterocycle having up to 4 heteroatoms selected from the group consisting of N, O and S, $-SO-$ or $-SO_2-$ (preferably

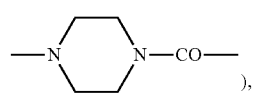

where the hydrocarbon chain including any side chains may be substituted by $-NHCONH_2$, $-COOH$, $-OH$, $-NH_2$, $NH-CNNH_2$, sulphonamide, sulphone, sulphoxide or sulphonic acid.

L5 is preferably a group $-(CH_2)_m-(CHR^S)_n-(OCH_2CH_2)_o-(X)_p-(CH_2)_q-$, where m=1-3, n=0, o=0-7, p=0 and q=0 or 1. Particular preference is given to a group $-(CH_2)_n-(CHR^S)_m-(OCH_2CH_2)_o-(X)_p-(CH_2)_q-$, where m=1 or 2, n=0, o=0 or 1, p=0 and q=0 or 1.

L6 is preferably a group selected from $-CONH-$ and $-NHCO-$.

L7 is preferably a single bond or $-[(CH_2)_x-(X^4)_y]w-(CH_2)_z-$, where
w=0 to 20;
x=0 to 5;
y=0 or 1;
z=1 to 5; and
$X^4$ represents $-O-$, $-CONH-$, $-NHCO-$ or

Particularly preferably, L7 is a single bond or a group $-[(CH_2)_x-NHCO-]$, where x=1 to 5.

Particularly preferably, -L5-L6-L7- represents $-(CH_2)_m-(CHR^S)_n-(OCH_2CH_2)_o-(X)_p-(CH_2)_q-$ NHCO-$[(CH_2)_x-NHCO-]$, where m=1 or 2, n=0, o=0 or 1, p=0, and q=0 or 1, and x=1-5.

However, it is also possible that these two structures are jointly present in the conjugate according to the invention.

According to the invention, these binder/active compound conjugates can be prepared from the compounds of the formula $$BINDER-[L-[WS]_m]_n$$

where L has the formula A' below:

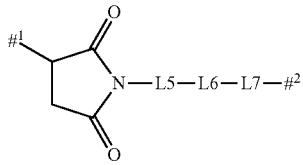

Formula A'

Preferably, the conversion of A' into A is carried out by stirring in a pH buffer having a pH of from 7.5 to 8.5, preferably 8, at a temperature below 37° C., preferably from 10 to 25° C., over a period of up to 40 hours, preferably 1 to 15 hours.

Embodiment I

An antibody conjugate of the formula

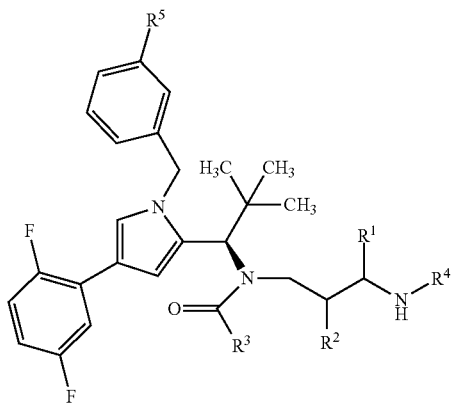

where
$R^2$, $R^4$ and $R^5$ represent H;
$R^3$ represents —CH$_2$OH;
$R^1$ represents -L1-L2-BINDER, where
L1 represents

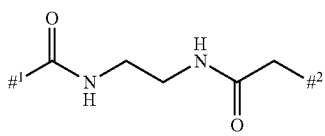

where #$^2$ represents the attachment to L2 and #$^1$ represents the attachment to the other attachment;
and L2 represents one or both of the structure of the formulae A5 and A6 below:

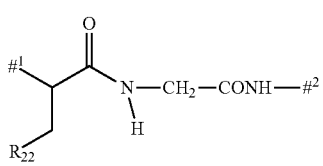

Formula A5

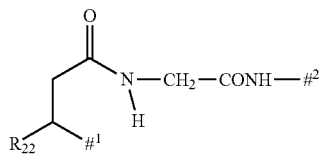

Formula A6 where
$^1$ denotes the point of attachment to the sulphur atom of the binder,
$^2$ denotes the point of attachment to group L1, and
$R_{22}$ represents COOH, COOR, COR, CONHR (where R in each case represents C1-3-alkyl), CONH$_2$, preferably COOH.

In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder) particularly preferably as one of the two structures of the formula A5 or A6.

Here, the structures of the formula A5 or A6 are generally present together, preferably in a ratio of from 60:40 to 40:60, based on the number of bonds to the binder. The remaining bonds are then present as the structure

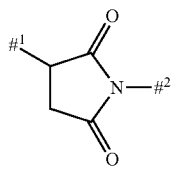

The binder is preferably a binder protein or peptide, particularly preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO:169), in particular the anti-TWEAKR antibody TPP-2090, or the anti-EGFR antibodies cetuximab or nimotuzumab. As an alternative to the binder, a cysteine residue may also be present.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of soft tissue (inter alia soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative blood diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds according to the invention for the treatment and/or prevention of disorders, in particular the disorders mentioned above.

The present invention further provides for the use of the compounds according to the invention for producing a medicament for the treatment and/or prevention of disorders, in particular the disorders mentioned above.

The present invention further provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with one or more other pharmacologically active substances, provided that this combination does not lead to undesirable and unacceptable side effects. The present invention furthermore therefore provides medicaments containing at least one of the compounds according to the invention and one or more further active compounds, in particular for treatment and/or prevention of the abovementioned disorders.

For example, the compounds of the present invention can be combined with known anti-hyper-proliferative, cytostatic or cytotoxic substances for the treatment of cancer diseases. Examples of suitable combination active compounds include:

131I-chTNT, abarelix, abiraterone, aclarubicin, afatinib, aflibercept, aldesleukin, alemtuzumab, alisertib, alitretinoin, alpharadin (radium-223 chloride), altretamine, aminoglutethimide, AMP-514, amrubicin, amsacrine, anastrozole, arglabin, arsenic trioxide, asparaginase, AT9283, axitinib, azacitidine, basiliximab, belotecan, bendamustin, bevacizumab, bexaroten, bicalutamide, bisantrene, bleomycin, BMS-936559, bosutinib, bortezomib, brentuximab vedotin, buserelin, busulfan, cabazitaxel, cabozantinib, calcium folinate, calcium levofolinate, capecitabine, carboplatin, carfilzomib (proteasome inhibitor), carmofur, carmustine, catumaxomab, celecoxib, celmoleukin, cetuximab, chlorambucil, chlormadinone, chlormethine, cisplatin, cladribine, clodronic acid, clofarabine, copanlisib, crisantaspase, crizotinib, cyclophosphamide, CYC116, cyproterone, cytarabine, dacarbazine, dactinomycin, darbepoetin-alfa, dabrafenib, danusertib, dasatinib, daunorubicin, decitabine, degarelix, denileukin-diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, ENMD-2076, enocitabine, epirubicin, epitiostanol, epoetin-alfa, epoetin-beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab-tiuxetan, ibrutinib, idarubicin, ifosfamide, imatinib, imiquimod, INCB24360, improsulfan, interferon-alfa, interferon-beta, interferon-gamma, ipilimumab, irinotecan, ixabepilone, lambrolizumab, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, methylaminolevulinate, methyltestosterone, mifamurtide, miltefosine, miriplatin, mitobronitol, mitoguazone, mitolactol, mitomycin, mitotane, mitoxantrone, MLN-8054, Mps1 inhibitors (disclosed in WO2013/087579, in particular Example 01.01, WO2014/131739, in particular Example 2), nedaplatin, nelarabine, nemorubicin, nilotinib, nilutamide, nimotuzumab, nimustine, nitracrine, nivolumab, NMS-P715, NMS-P937, ofatumumab, omeprazole, oprelvekin, oxaliplatin, p53 gene therapy, paclitaxel, palbociclib, palifermin, palladium-103 seed, pamidronic acid, panitumumab, pazopanib, pegaspargase, PEG-epoetin-beta (methoxy-PEG-epoetin-beta), pegfilgrastim, Peg-interferon-alfa-2b, pemetrexed, pentazocin, pentostatin, peplomycin, perfosfamide, picibanil, pirarubicin, plerixafor, plicamycin, poliglusam, polyestradiol phosphate, polysaccharide-K, ponatinib, porfimer-sodium, pralatrexate, prednimustine, procarbazine, quinagolide, R763, raloxifene, raltitrexed, ranimustine, razoxane, refametinib, regorafenib, risedronic acid, rituximab, romidepsin, romiplostim, roninciclib, ruxolitinib, sargramostim, sipuleucel-T, sizofiran, sobuzoxane, sodium glycididazole, SNS-314, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, TKM-PLK1, tioguanine, tocilizumab, topotecan, toremifene, tositumomab, tozasertib, trabectedin, trametinib, trastuzumab, trastuzumab emtansine, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbin, volasertib, vorinostat, vorozol, XL228, yttrium-90 glass microbeads, zinostatin, zinostatin-stimalamer, zoledronic acid, zorubicin.

In addition, the compounds of the present invention can be combined, for example, with binders which, by way of example, can bind to the following targets: OX-40, CD137/4-1BB, DR3, IDO1/IDO2, LAG-3, CD40.

In addition, the compounds according to the invention can also be used in combination with radiotherapy and/or surgical intervention.

Generally, the following aims can be pursued with the combination of compounds of the present invention with other cytostatically or cytotoxically active agents:

improved efficacy in slowing the growth of a tumour, in reducing its size or even in the complete elimination thereof, compared with treatment with an individual active compound;

the possibility of using the chemotherapeutics used in a lower dosage than in the case of monotherapy;

the possibility of a more tolerable therapy with fewer side effects compared with individual administration;

the possibility of treatment of a broader spectrum of tumour diseases;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example parenterally, possibly inhalatively or as implants or stents.

The compounds according to the invention can be administered in suitable administration forms for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of from about 0.001 to 1 mg/kg, preferably about 0.01 to 0.5 mg/kg, of body weight to achieve effective results.

It may nevertheless be necessary where appropriate to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

Synthesis Routes:

Exemplary for the working examples, the schemes below show exemplary synthesis routes leading to the working examples:

Scheme 1: Synthesis of cysteine-linked ADCs

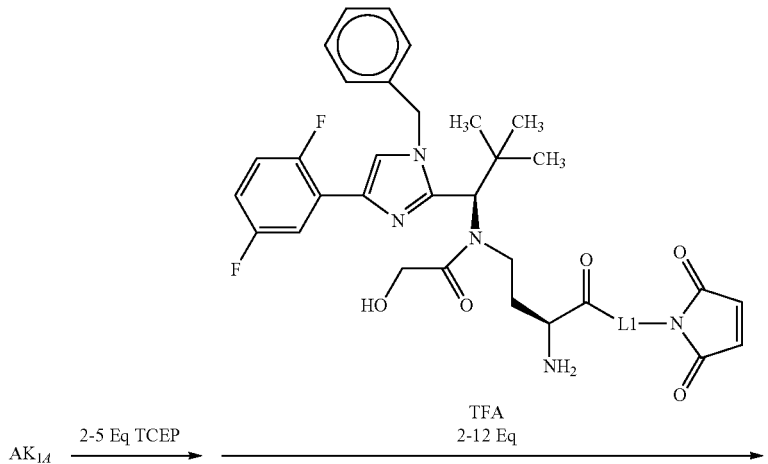

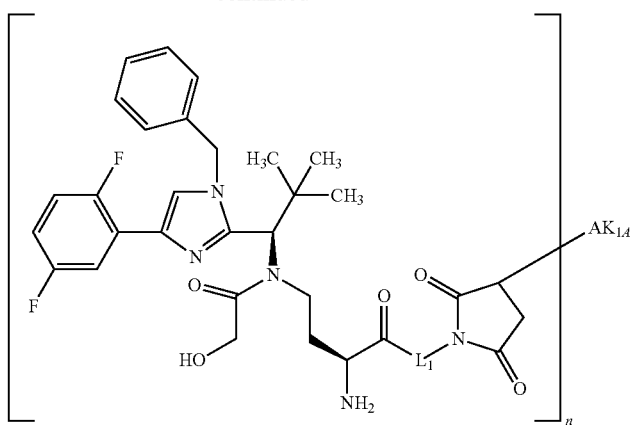
Scheme 2: Synthesis of cysteine-linked ADCs
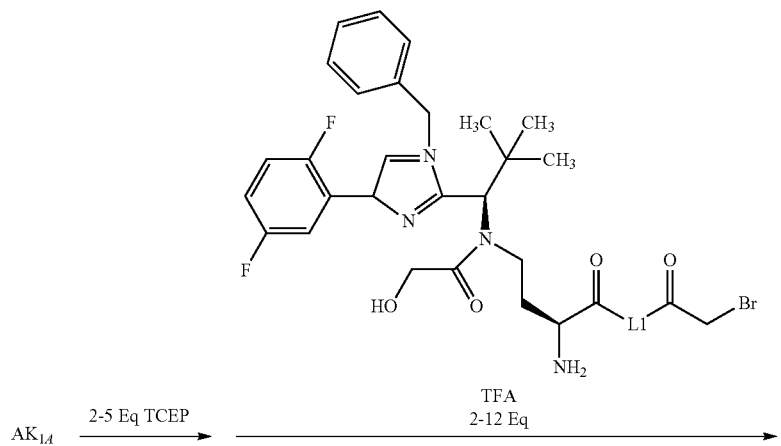
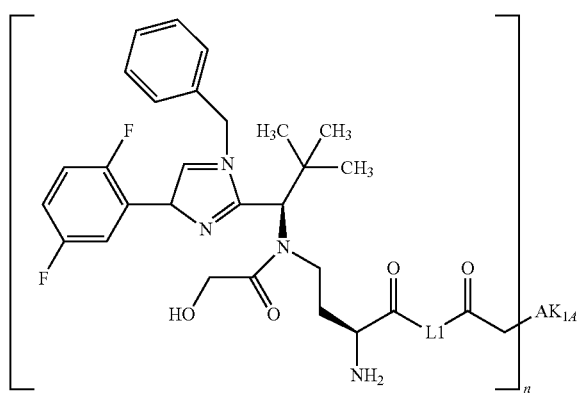

Scheme 3: Synthesis of cysteine-linked ADCs
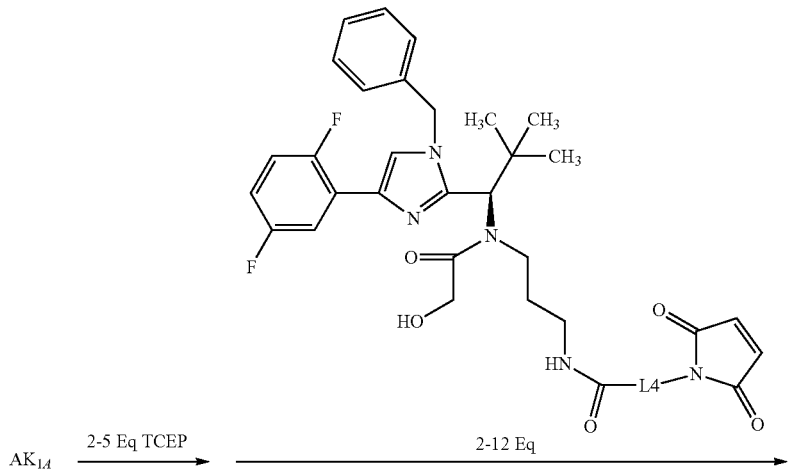
AK$_{1A}$ $\xrightarrow{\text{2-5 Eq TCEP}}$ $\xrightarrow{\text{2-12 Eq}}$
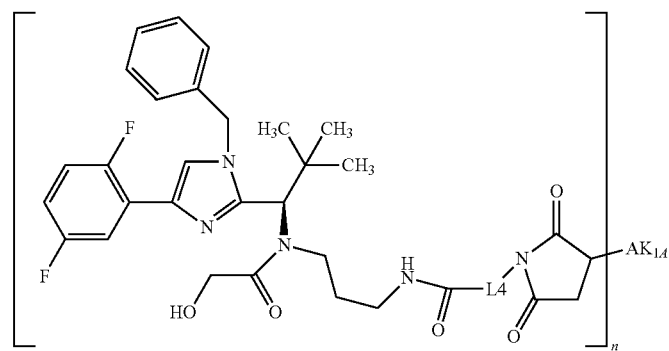
Scheme 4: Synthesis of cysteine-linked ADCs
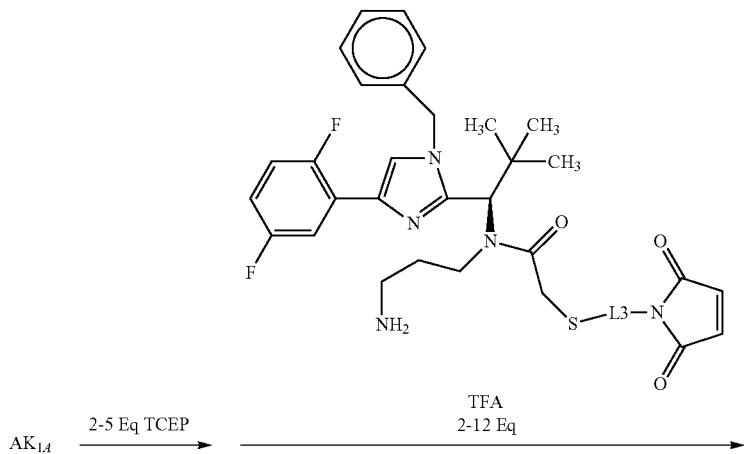
AK$_{1A}$ $\xrightarrow{\text{2-5 Eq TCEP}}$ $\xrightarrow[\text{2-12 Eq}]{\text{TFA}}$ 187 188
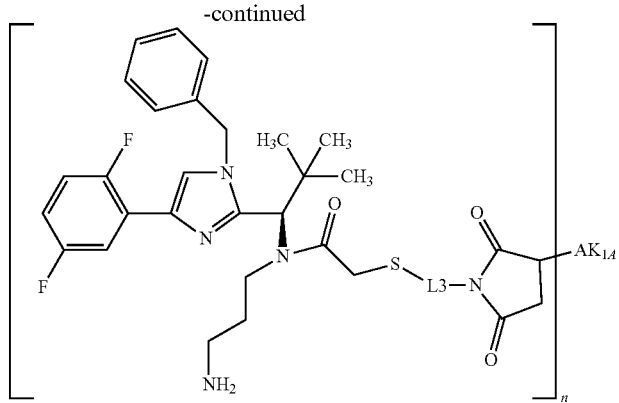
Scheme 5: Synthesis of lysine-linked ADCs
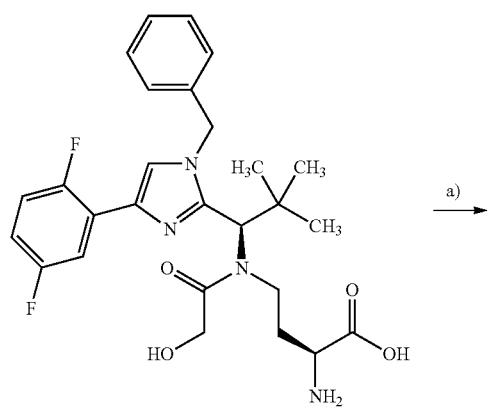
a) triphosgene, THF, under argon
Scheme 6: Synthesis of lysine-linked ADCs
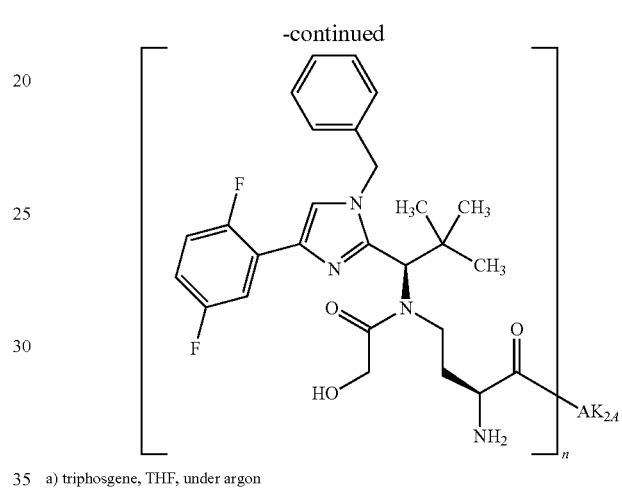
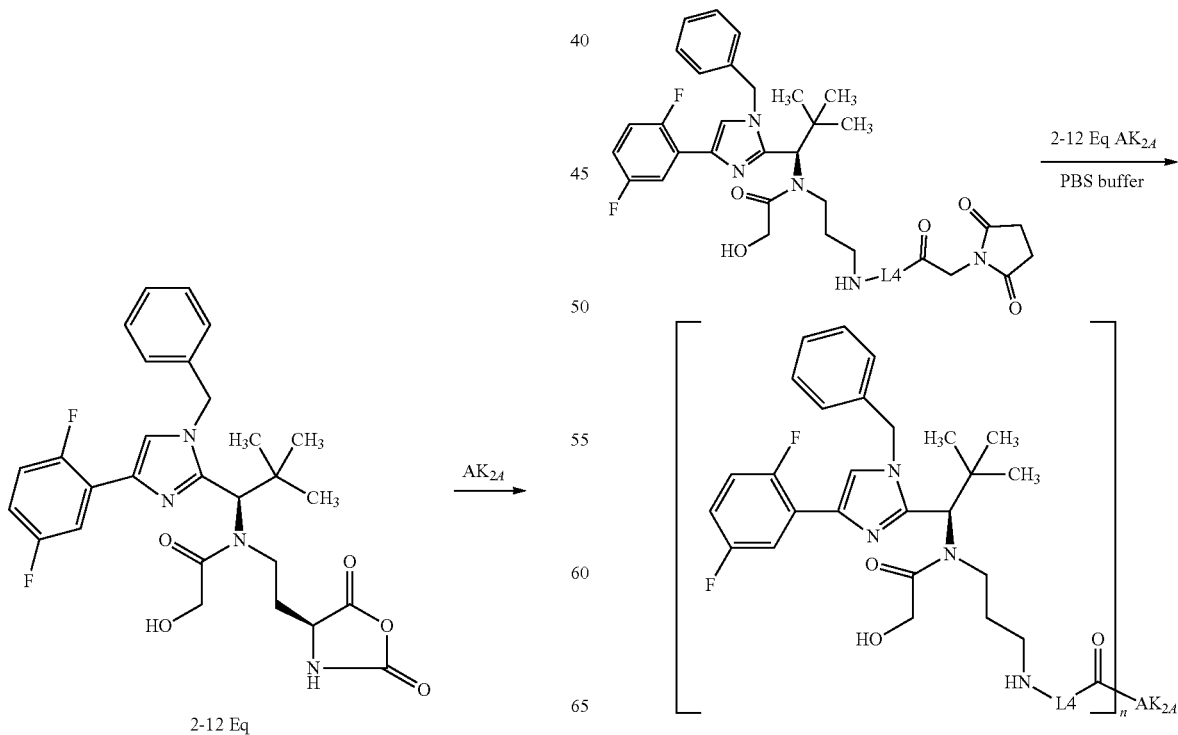

Scheme 7
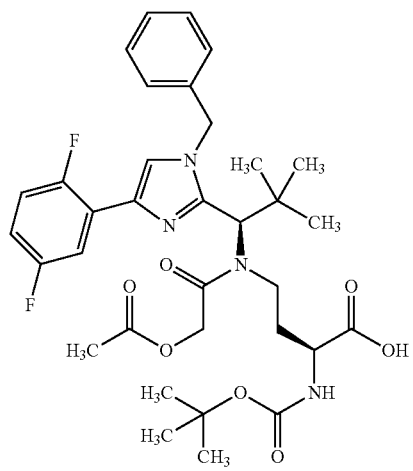
a) ↓
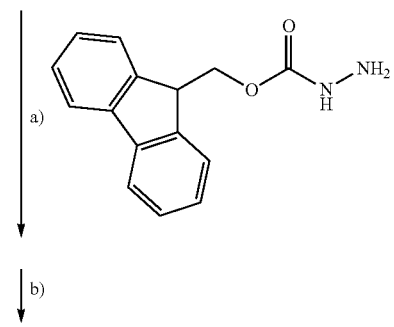
b) ↓
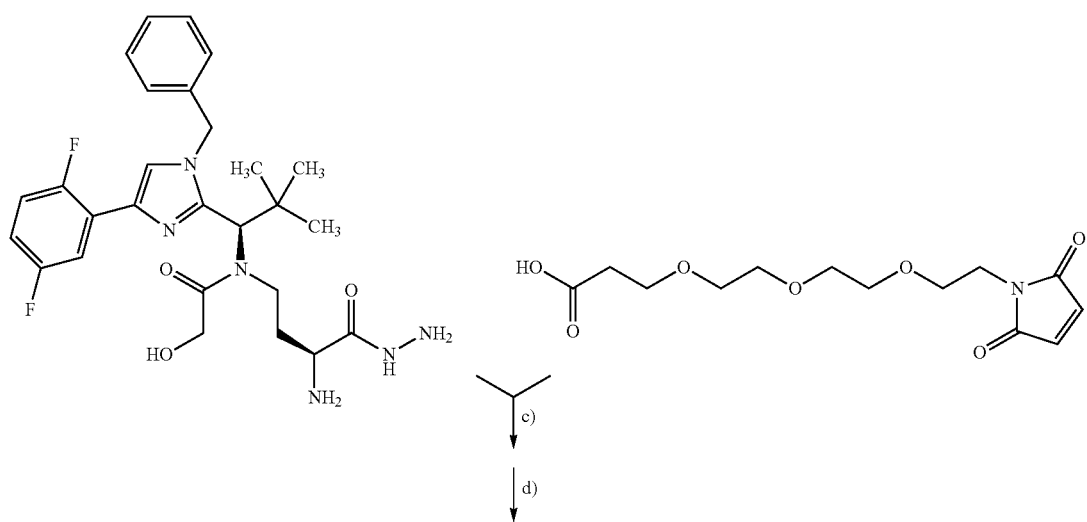
c) ↓
d) ↓

-continued
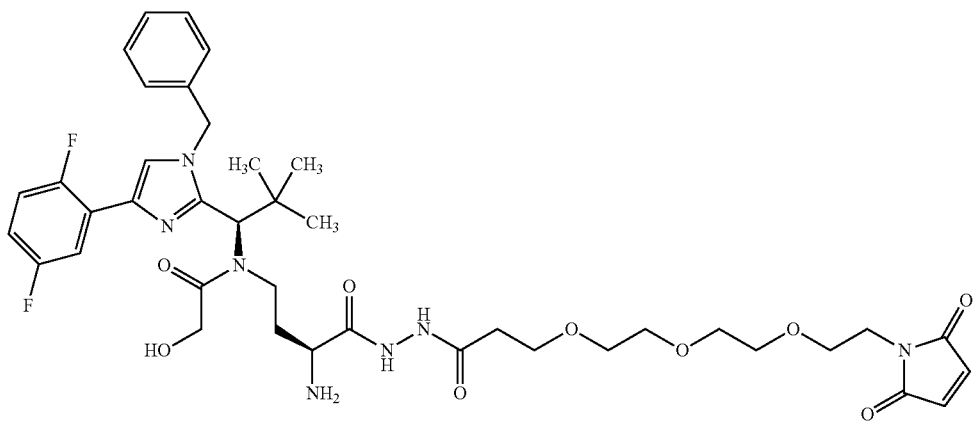
[a]: EDCI, HOBT, diisopropylethylamine, RT; b) ethanol, piperidine, methylamine, water, RT; c) HATU, diisopropylethylamine, RT; d) TFA, DCM, RT]
Scheme 8
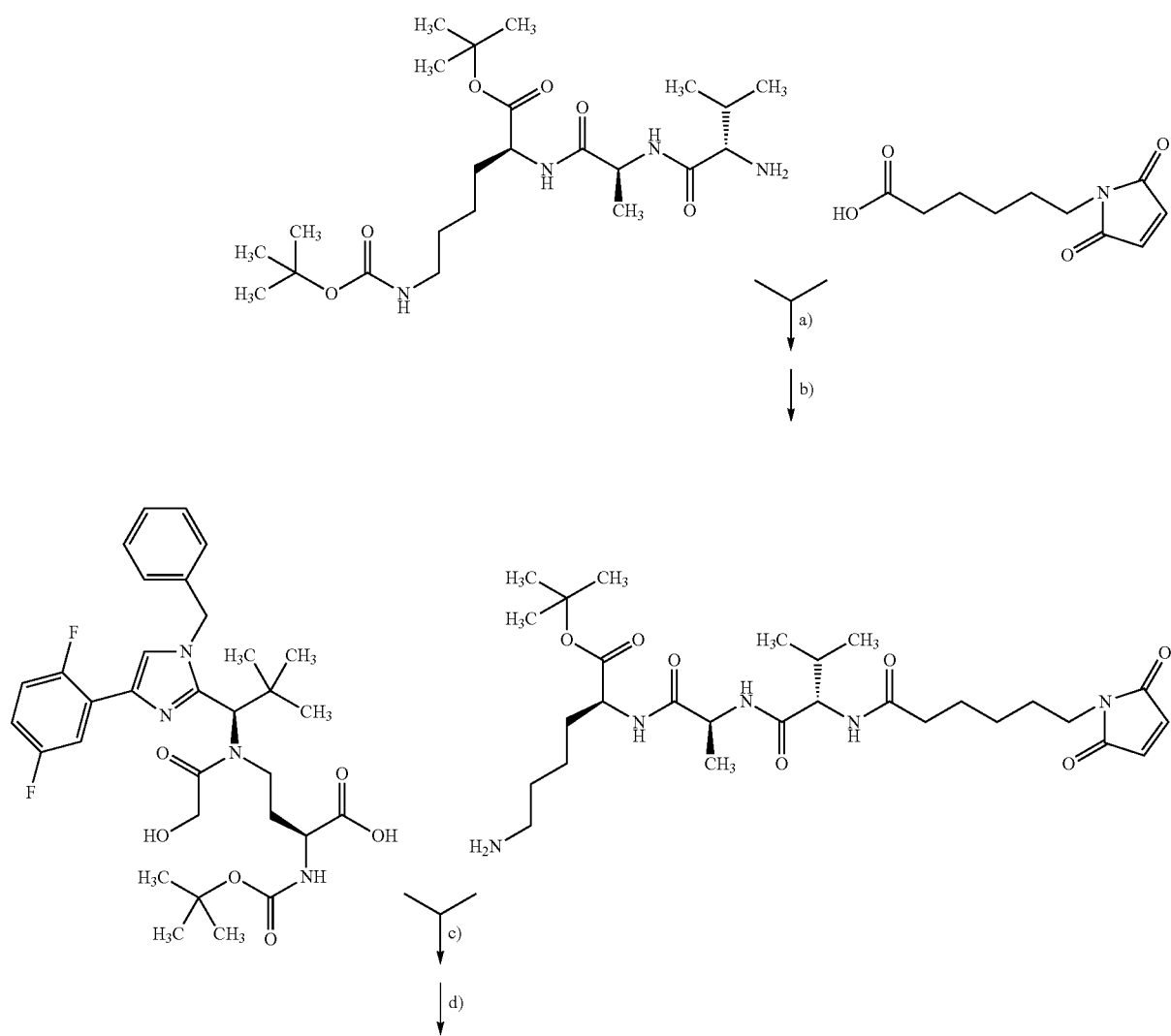

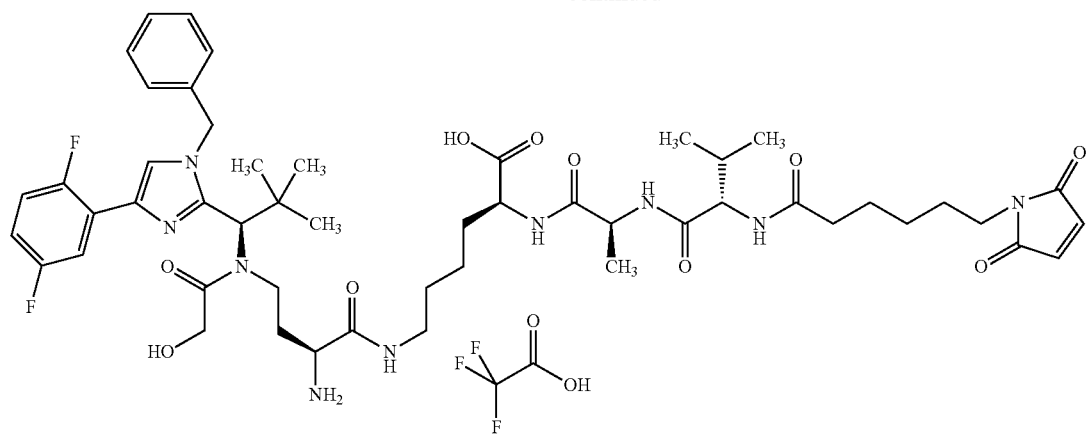
[a): for example EDCI, HOBT, diisopropylethylamine, DMF, RT; b) for example DCM/TFA 20:1, RT; c) for example HATU, diisopropylethylamine, DMF, RT; d) for example TFA, DCM, RT]
Scheme 9
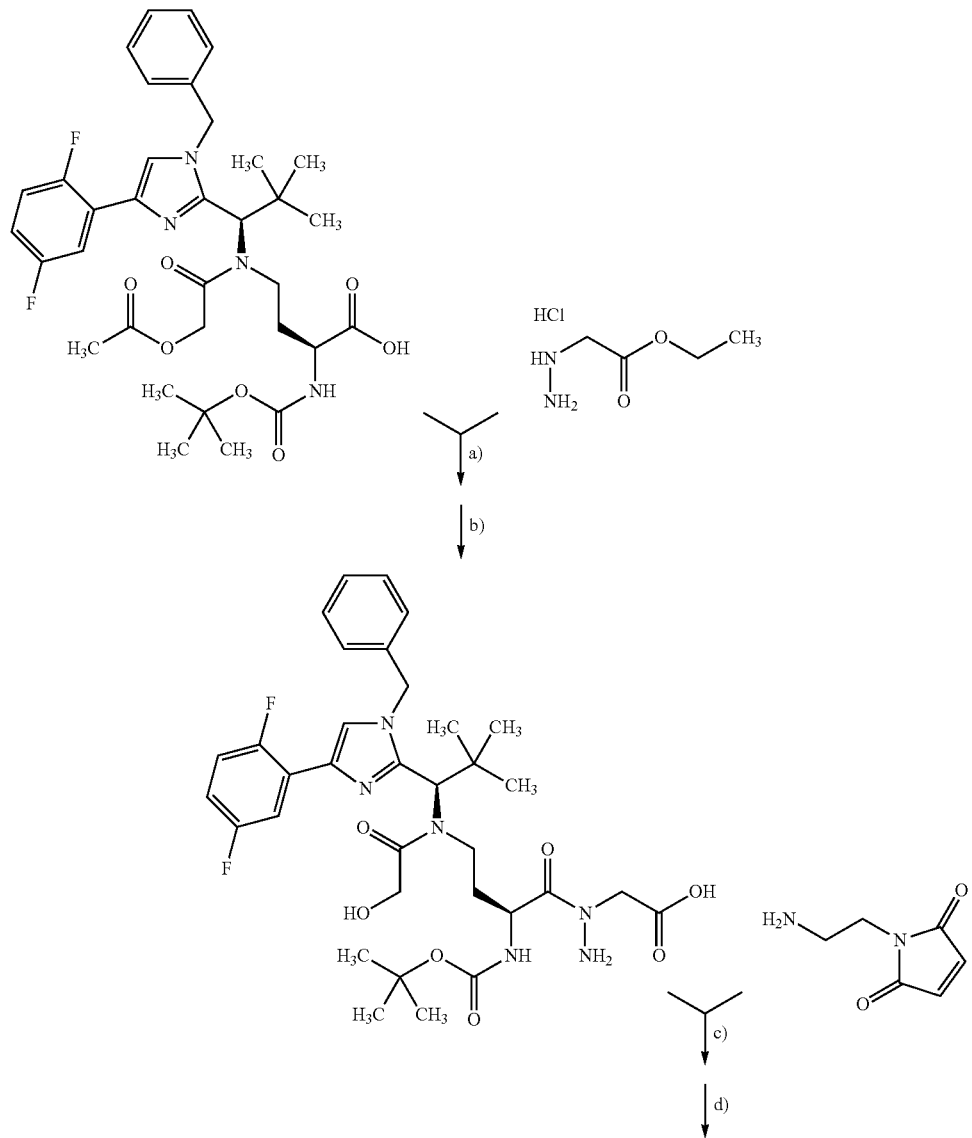

-continued
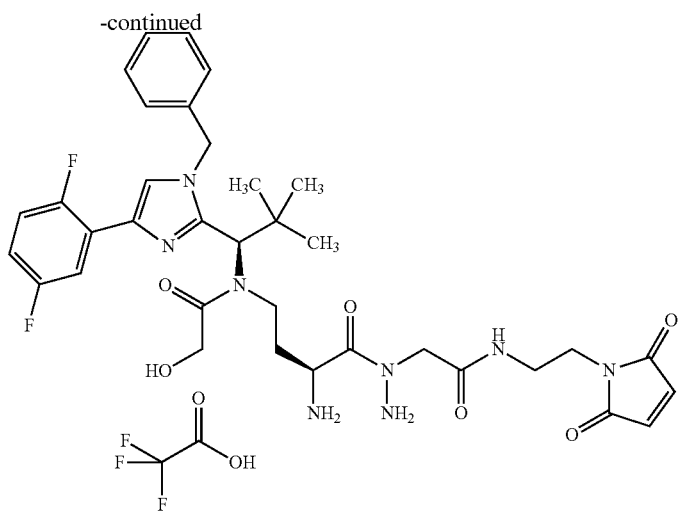
[a): for example 2-bromo-1-ethylpyridinium tetrafluoroborate, diisopropylethylamine, DCM, RT; b) for example 2M LiOH solution, THF, water, RT, HPLC separation of the regiosisomers; c) for example EDCI, HOBT, diisopropylethylamine, DMF, RT; d) for example TFA, DCM, RT]

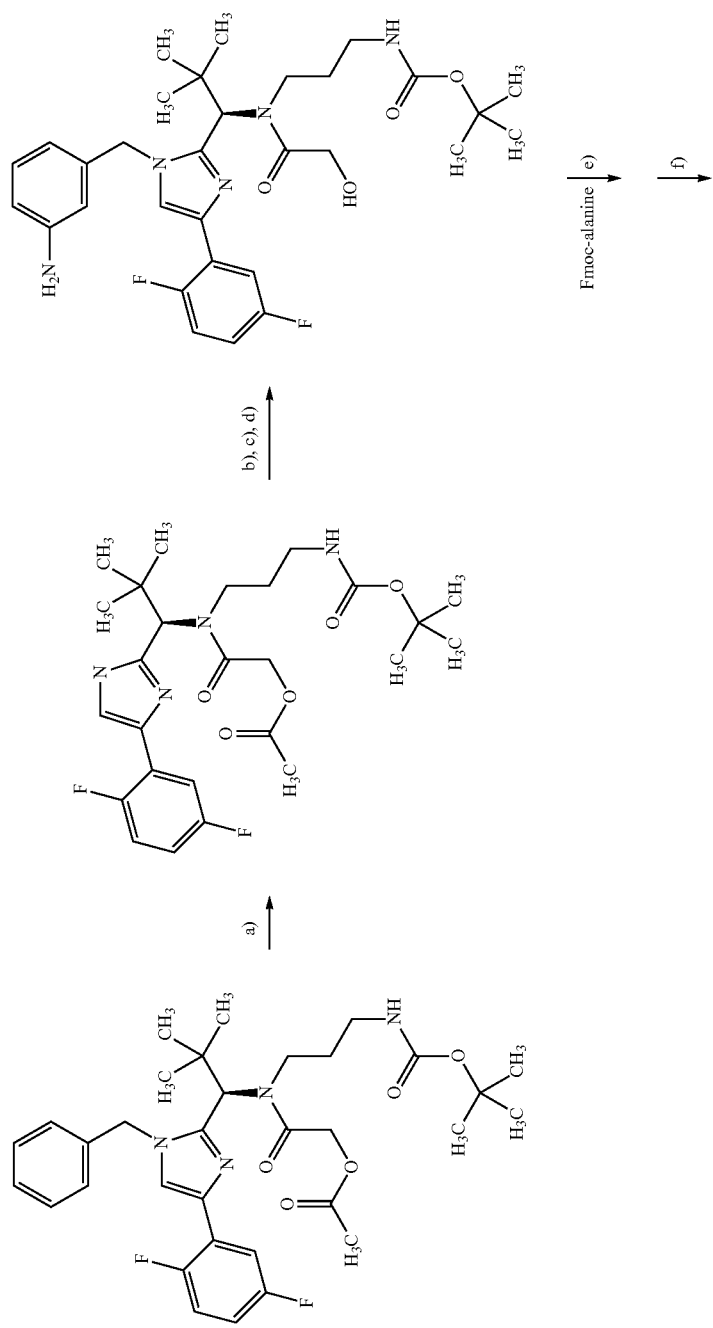
Scheme 10

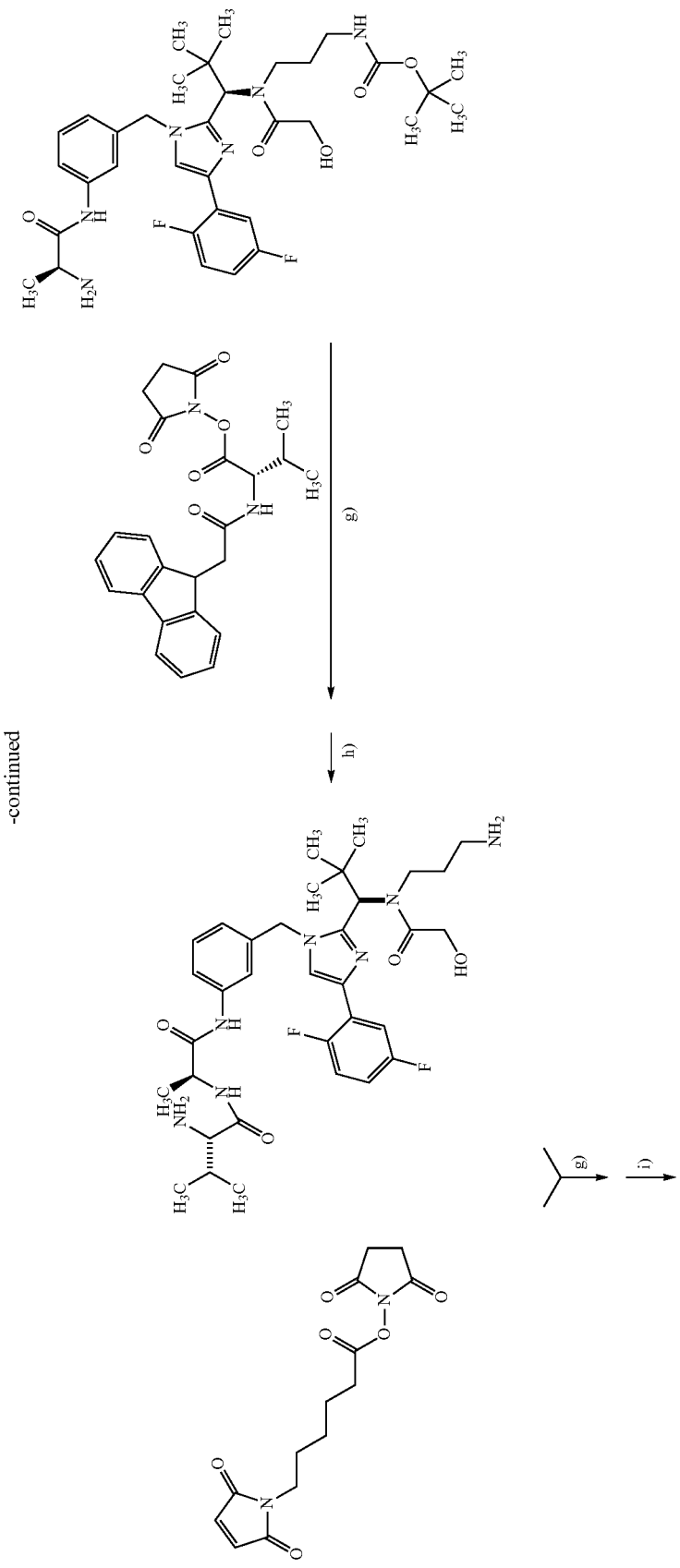

-continued

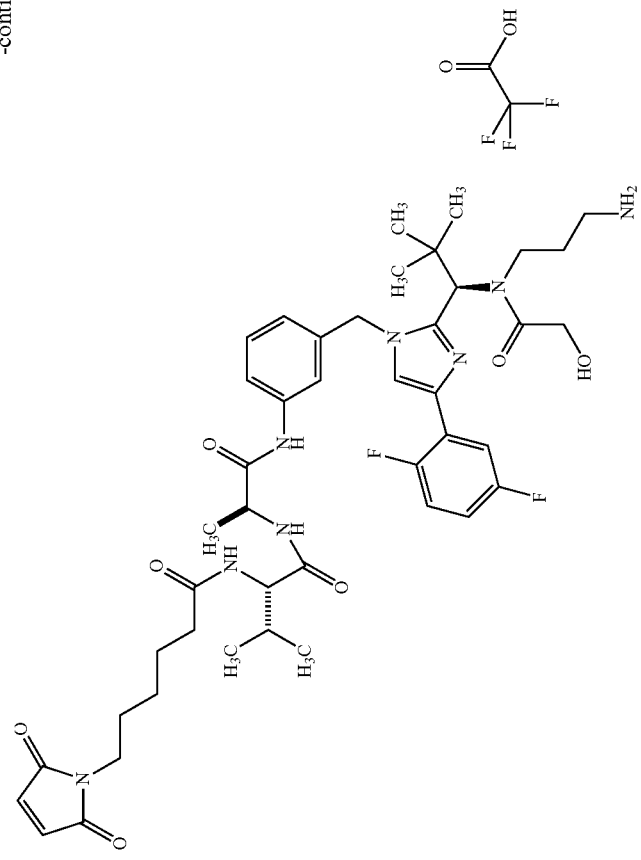

[a]: for example H₂, Pd—C, EtOH, RT; b) for example p-nitrobenzyl bromide, K₂CO₃, DMF; c) for example ethanol, 40% strength methylamine solution in water, 50° C.; d) for example disodium dithionite, THF, water, 50° C.; e) for example HATU, diisopropylethylamine, DMF, RT; f) for example piperidine, 40% strength methylamine solution in water, ethanol, 50° C.; g) for example diisopropylethylamine, DMF, RT; h) for example piperidine, DMF, RT; i) TFA, DCM, RT]

203 204
Scheme 11
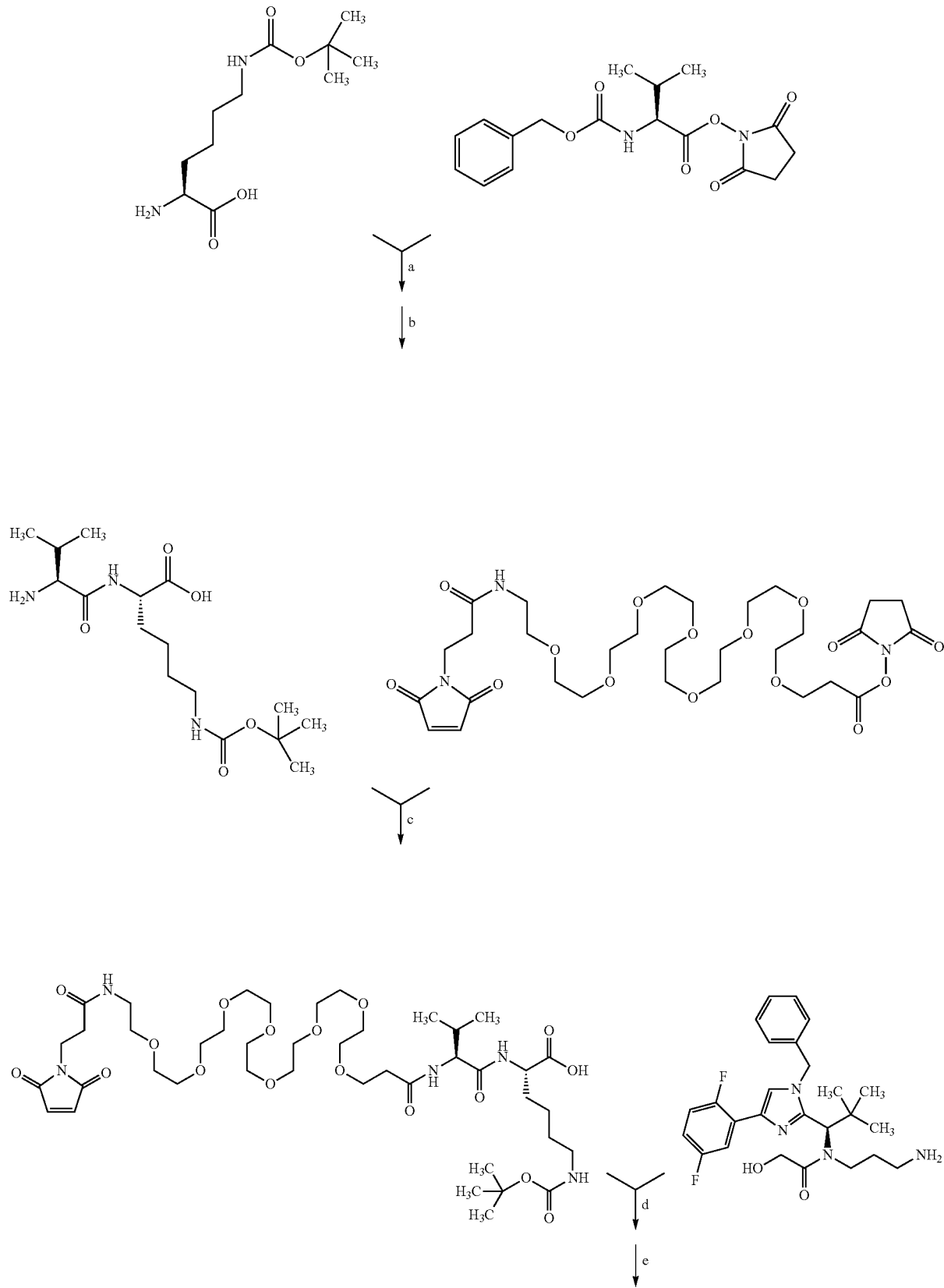

-continued
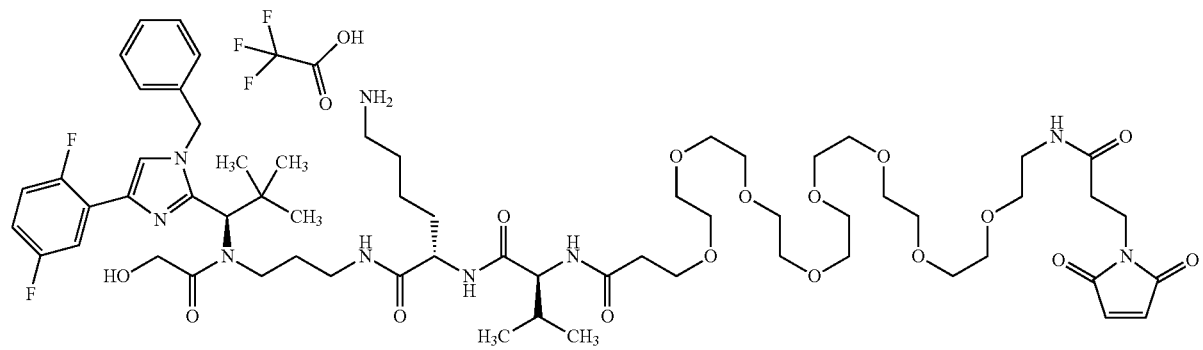
[a): for example Et₃N, DMF, RT; b) for example H₂, Pd—C,EtOH/ethyl acetate/THF (1:1:1), RT; c) for example 4-methylmorpholine, DMF, RT; d) for example HATU, HOAt, diisopropylethylamine, DMF, RT; e) for example TFA, RT]
Scheme 12
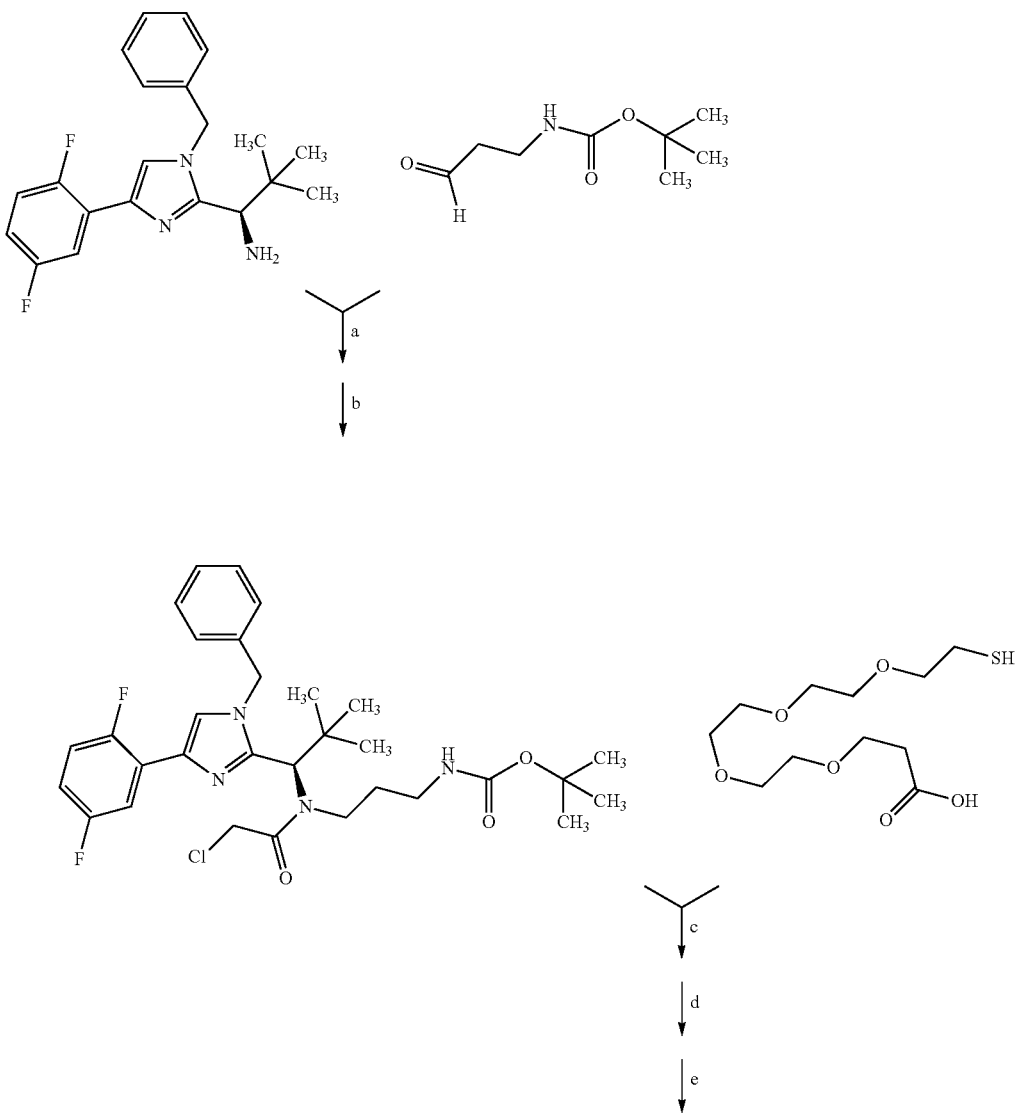

-continued
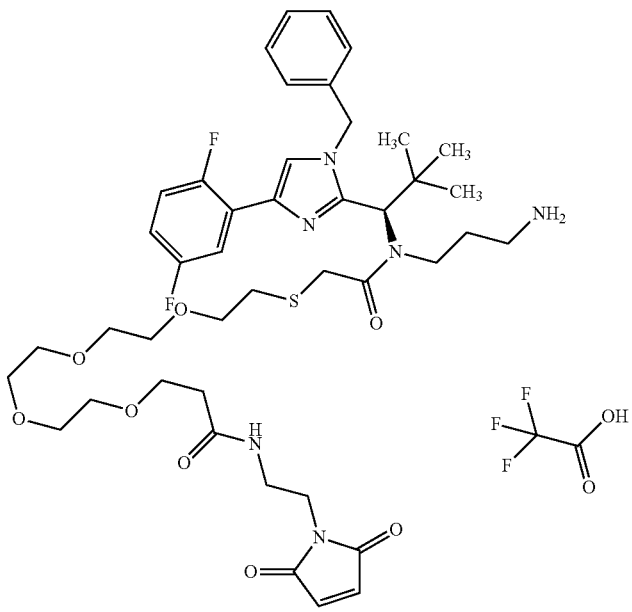
[a): for example NaBH(OAc)$_3$, HOAc, dichloromethane, RT; b) for example chloroacetyl chloride, NEt$_3$, DCM, RT; c) for example Cs$_2$CO$_3$, DMF, 50° C.; d) for example 1-(2-aminoethyl)-1H-pyrrole-2,5-dione hydrochloride (1:1), T3P$^{(R)}$, diisopropylethylamine, MeCN, RT; e) for example TFA, RT]
Scheme 13
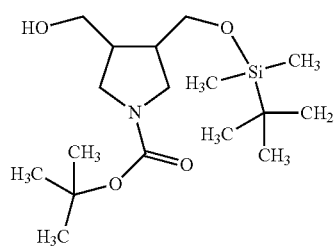
↓ a, b
↓ c, d
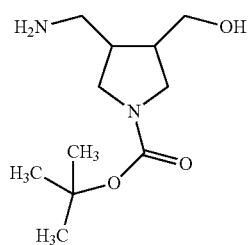
↓ e, f 209                              210
-continued
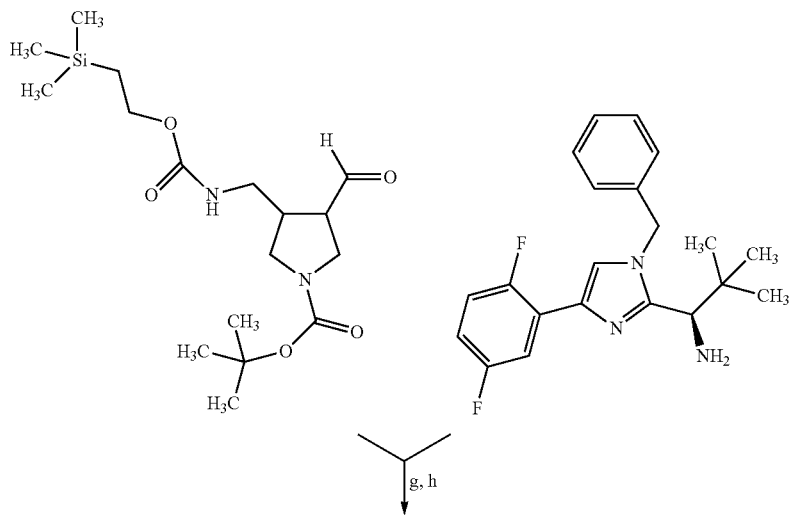
g, h
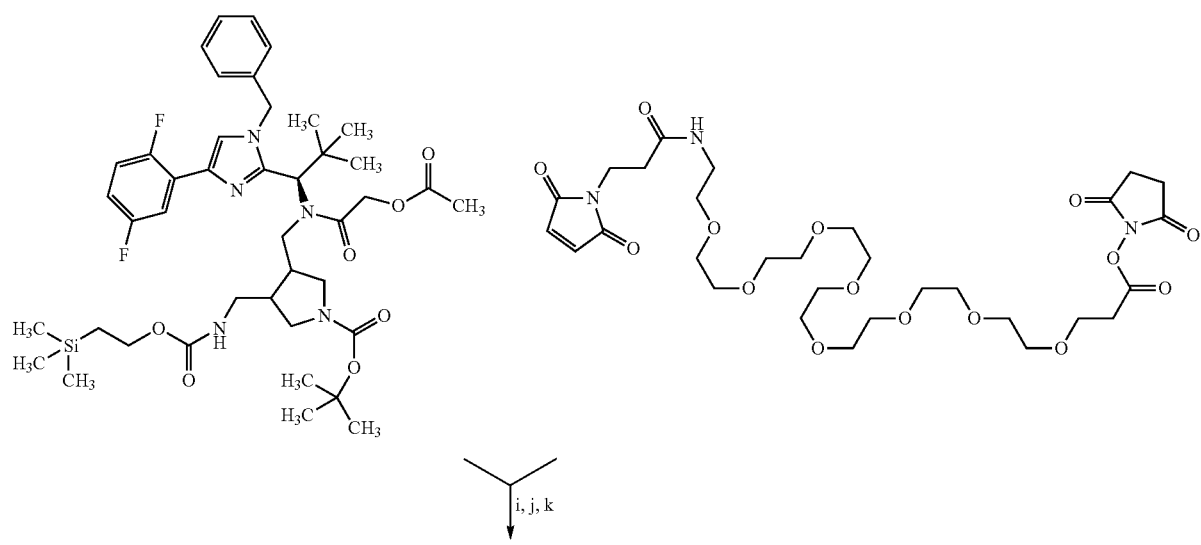
i, j, k -continued

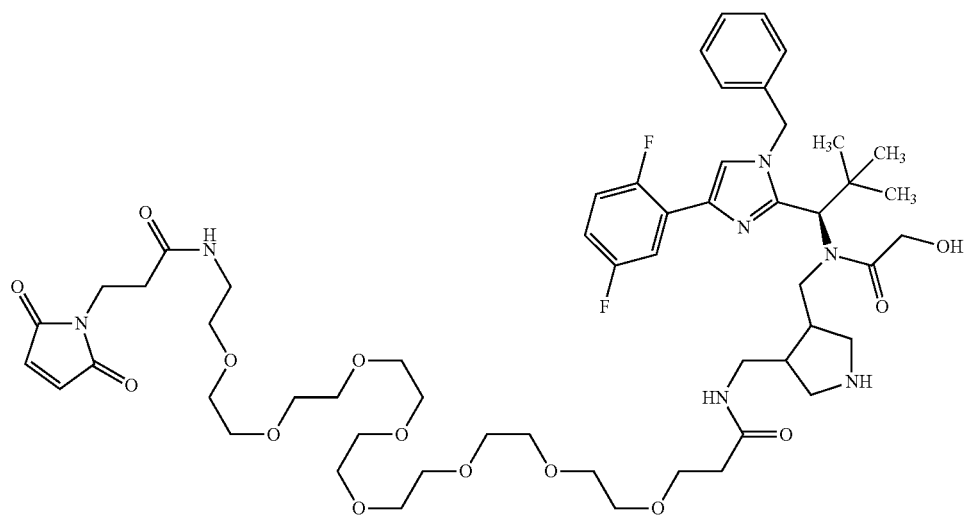

[a): for example methanesulphonic chloride, NEt₃, dichloromethane, 0° C.;
b) for example NaN₃, DMF, 40° C.;
c) for example H₂, Pd—C, EtOH/ethyl acetate (1:1), RT;
d) for example TBAF, THF, RT;
e) for example 1-({[2-trimethylsilyl)ethoxy]carbonyl}oxy)pyrrolidine-2,5-dione, NEt₃, CaCO₃, 1-4-dioxane, RT;
f) for example N-chlorosuccinimide, TEMPO, tetra-n-butylammonium chloride, chloroform, 0.05 N potassium carbonate/0.05 N sodium bicarbonate solution (1:1);
g) for example NaBH(OAc)₃, HOAc, dichloromethane, RT;
h) for example chloroacetyl chloride, NEt₃, DCM, RT;
i) for example TBAF, THF, water, RT;
j) for example 4-methylmorpholine, DMF, RT;
k) for example TFA, RT]

Scheme 14

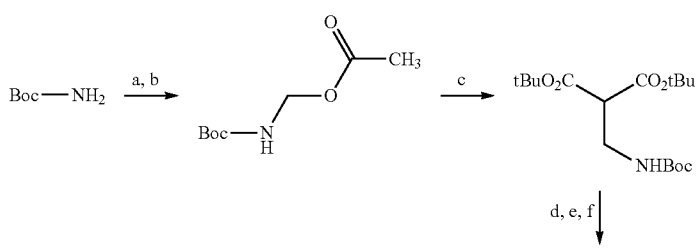

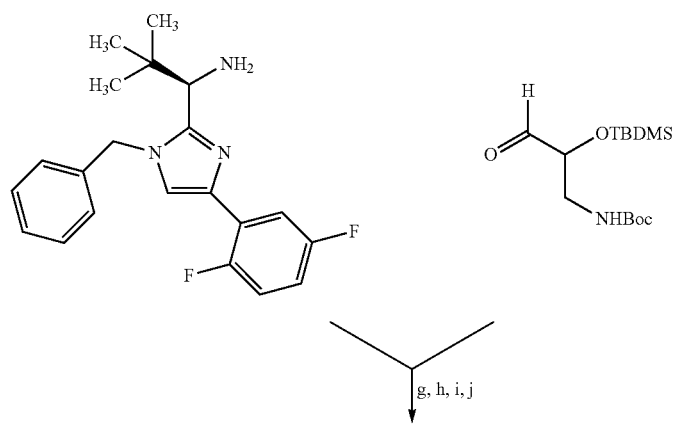

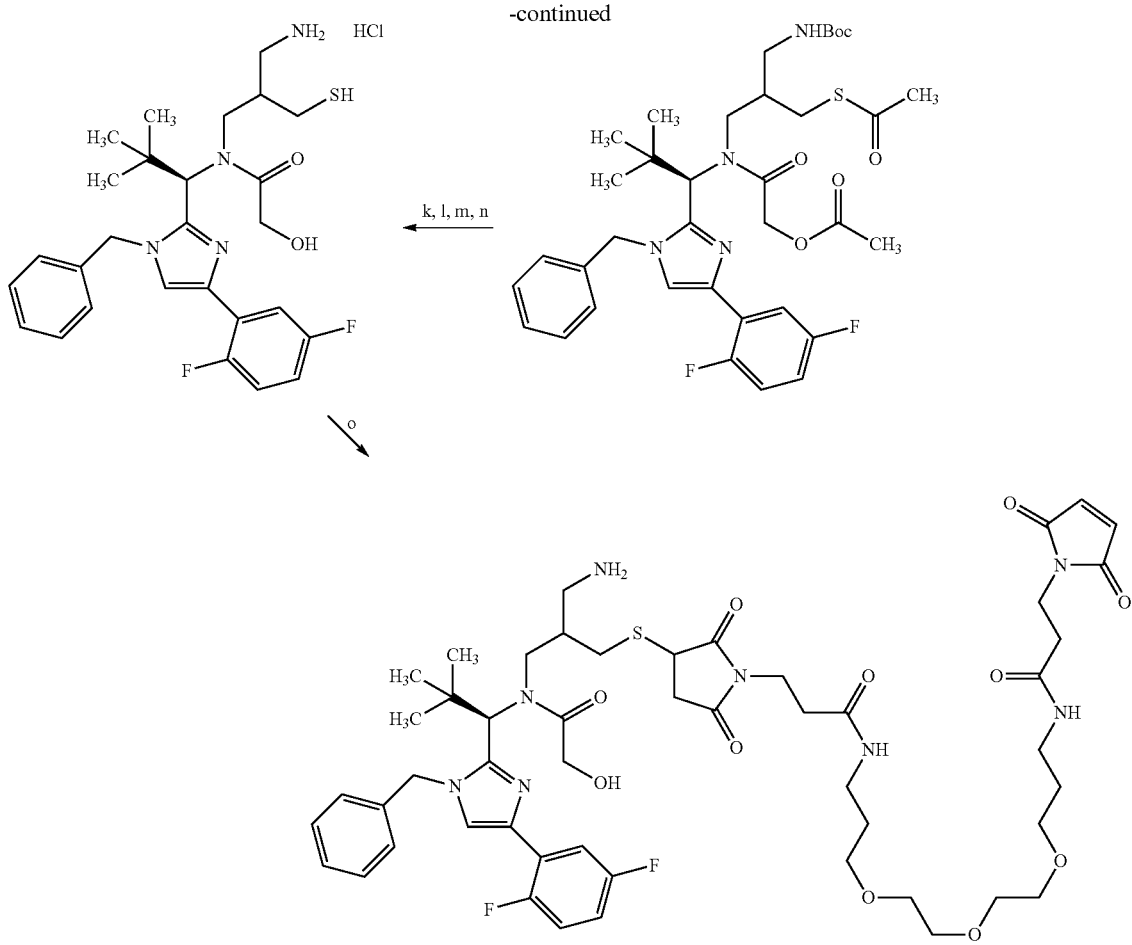

[a) for example formaldehyde, Na$_2$CO$_3$, water, RT;
b) for example Ac$_2$O, pyridine, THF, RT;
c) for example di-tert-butyl malonate, KOtBu, THF, RT;
d) for example LiBH$_4$, THF, RT;
e) for example TBDMSCl, imidazole, DCM, RT;
f) for example Dess-Martin periodinane, DCM;
g) for example sodium triacetoxyborohydride, AcOH, DCM, RT;
h) for example nBu$_4$NF, THF, RT;
i) for example SOCl$_2$, THF, RT;
j) for example AcSK, nBu$_4$NI, DMF, 90° C.;
k) for example NaOH, MeOH, THF, RT;
l) for example TCEP, dioxane, RT;
m) for example separation of the epimers;
n) for example 6N hydrochloric acid, THF, RT
o) for example Mal-dPEG(3)-Mal, PBS buffer, ACN, RT]

Scheme 15

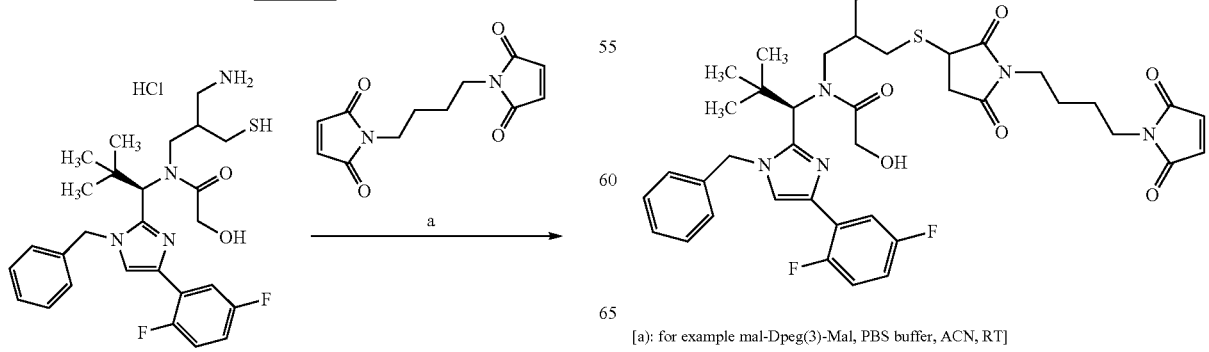

[a): for example mal-Dpeg(3)-Mal, PBS buffer, ACN, RT]

Scheme 16

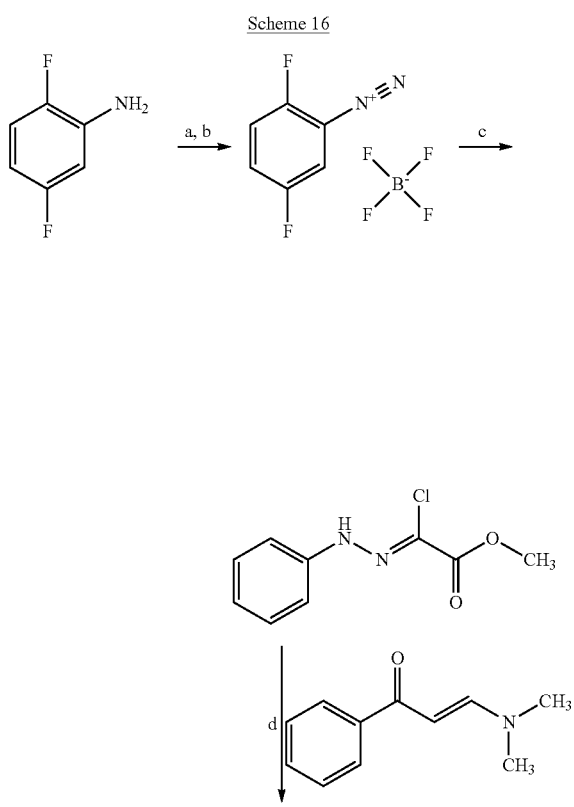
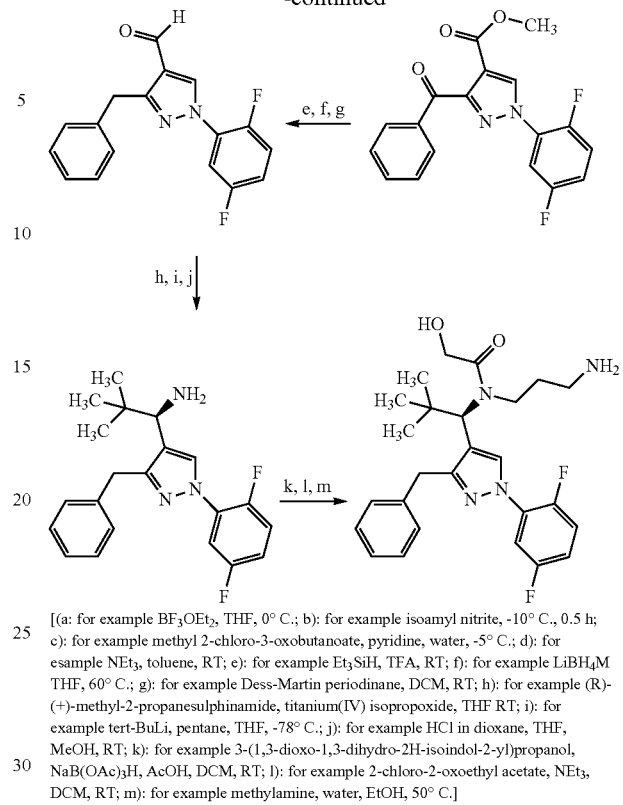

[(a: for example BF$_3$OEt$_2$, THF, 0° C.; b): for example isoamyl nitrite, -10° C., 0.5 h; c): for example methyl 2-chloro-3-oxobutanoate, pyridine, water, -5° C.; d): for esample NEt$_3$, toluene, RT; e): for example Et$_3$SiH, TFA, RT; f): for example LiBH$_4$M THF, 60° C.; g): for example Dess-Martin periodinane, DCM, RT; h): for example (R)-(+)-methyl-2-propanesulphinamide, titanium(IV) isopropoxide, THF RT; i): for example tert-BuLi, pentane, THF, -78° C.; j): for example HCl in dioxane, THF, MeOH, RT; k): for example 3-(1,3-dioxo-1,3-dihydro-2H-isoindol-2-yl)propanol, NaB(OAc)$_3$H, AcOH, DCM, RT; l): for example 2-chloro-2-oxoethyl acetate, NEt$_3$, DCM, RT; m): for example methylamine, water, EtOH, 50° C.]

Scheme 17

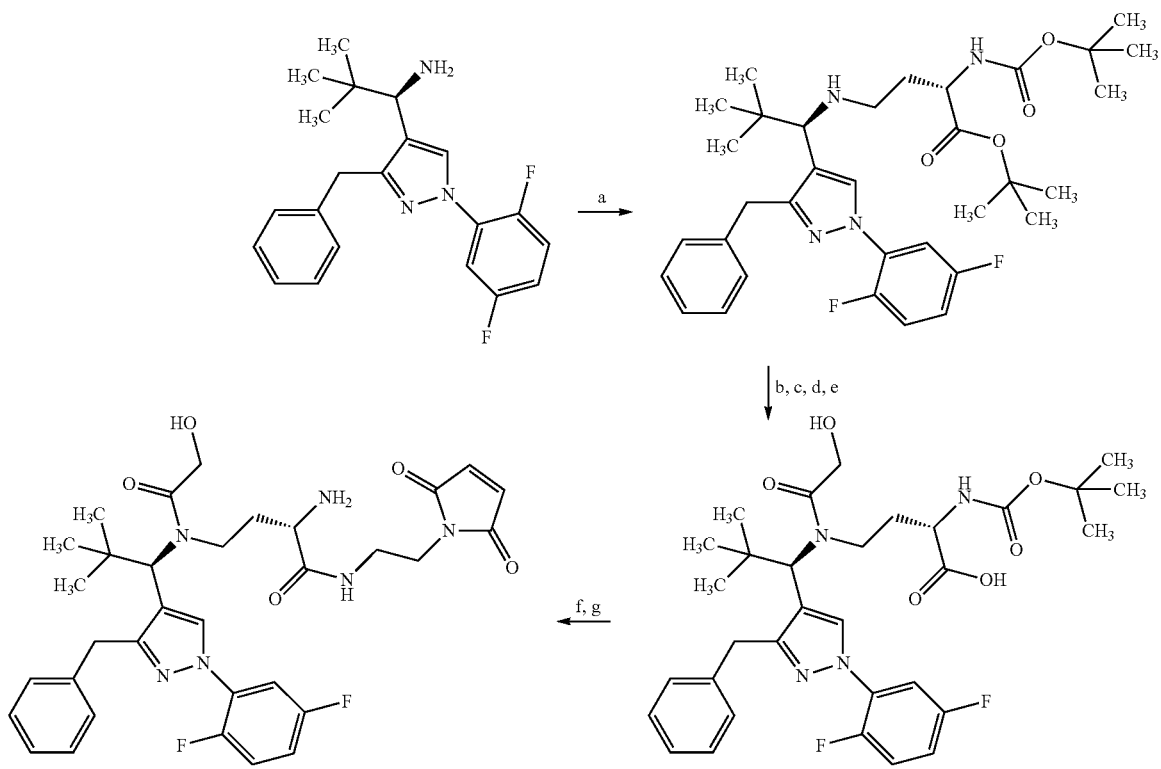

[a): for example tert-butyl N-(tert-butoxycarbonyl)-5-oxo-L-norvalinate, NaB(OAc)$_3$H, AcOH, DCM, RT; b): for example 2-chloro-oxoethyl acetate, NEt$_3$,DCM, RT; c): for example methylamine, water, EtOH, 60° C.; d): for example THF, DCM, 50° C.; e): for example Boc$_2$O, NEt$_3$, DCM, RT; f): for example trifluoroacetic acid/1-(2-aminoethyl)-1H-pyyrole-2,3-dione (1:1), HATU, diisopropylethylamine, DMF, RT; f): for example TFA, DCM, RT]

Scheme 18: Synthesis of cysteine-linked ADCs
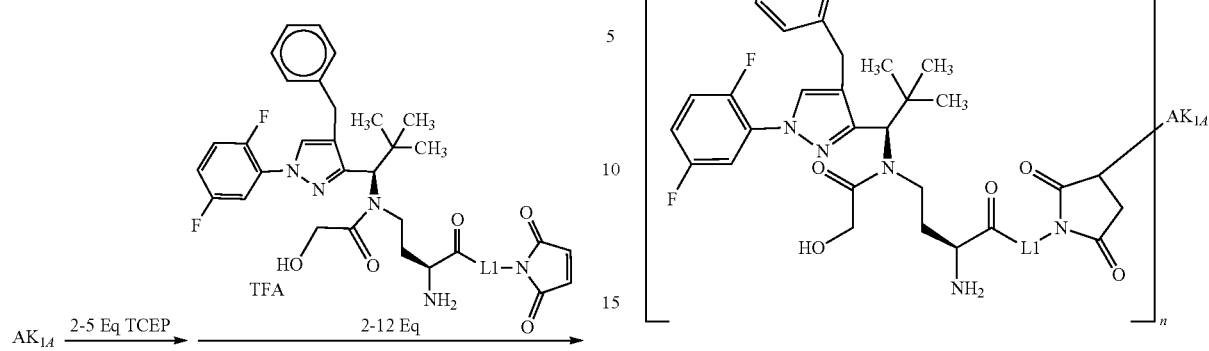
Scheme 19: Synthesis of cysteine-linked ADCs
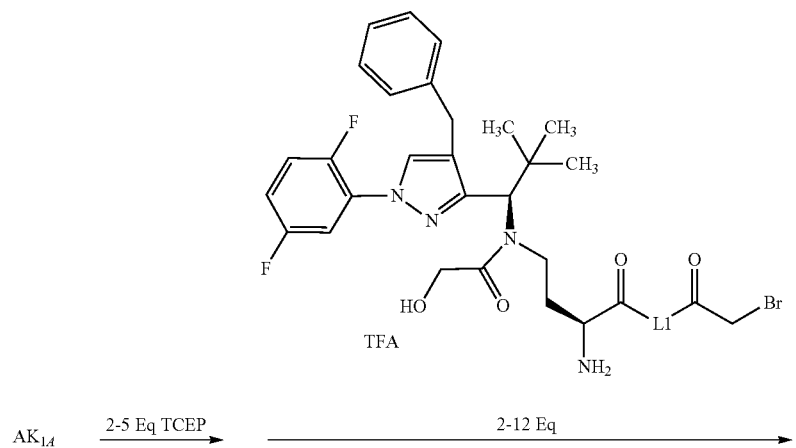
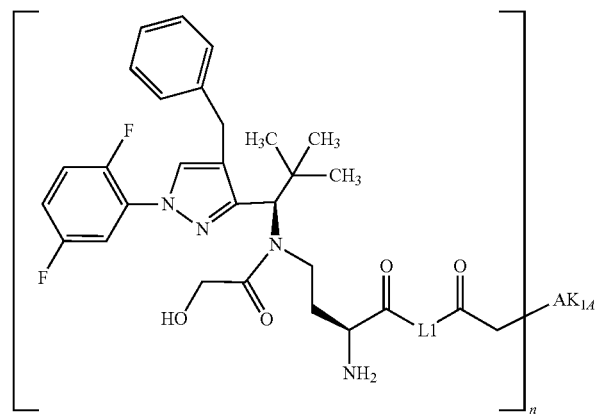

Scheme 20: Synthesis of cysteine-linked ADCs
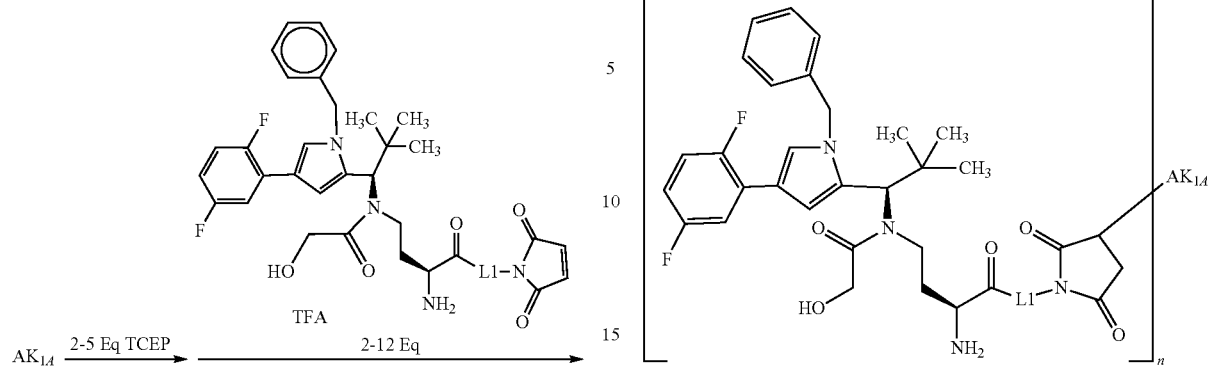
Scheme 21: Synthesis of cysteine-linked ADCs
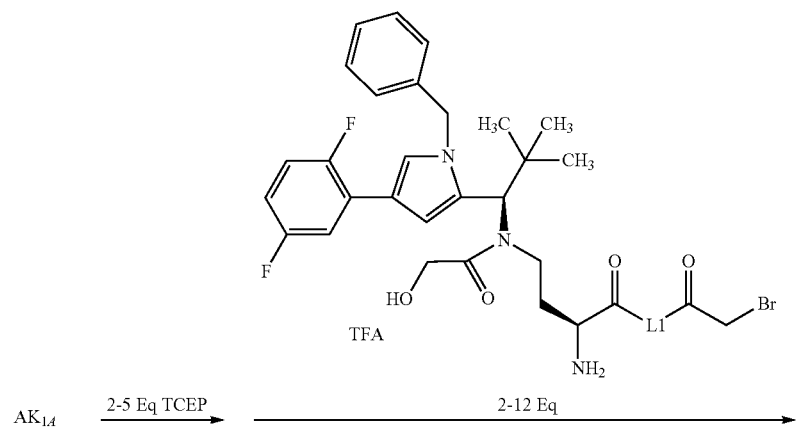
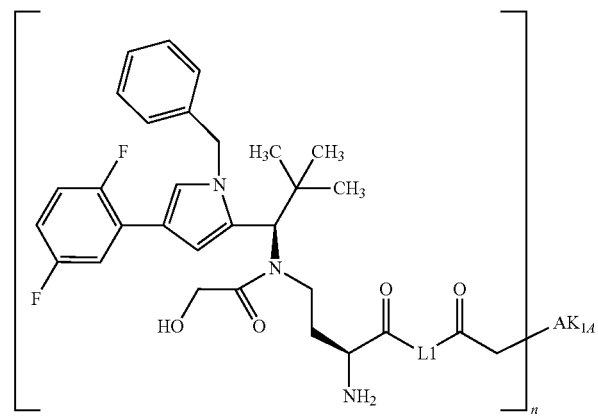

Scheme 22
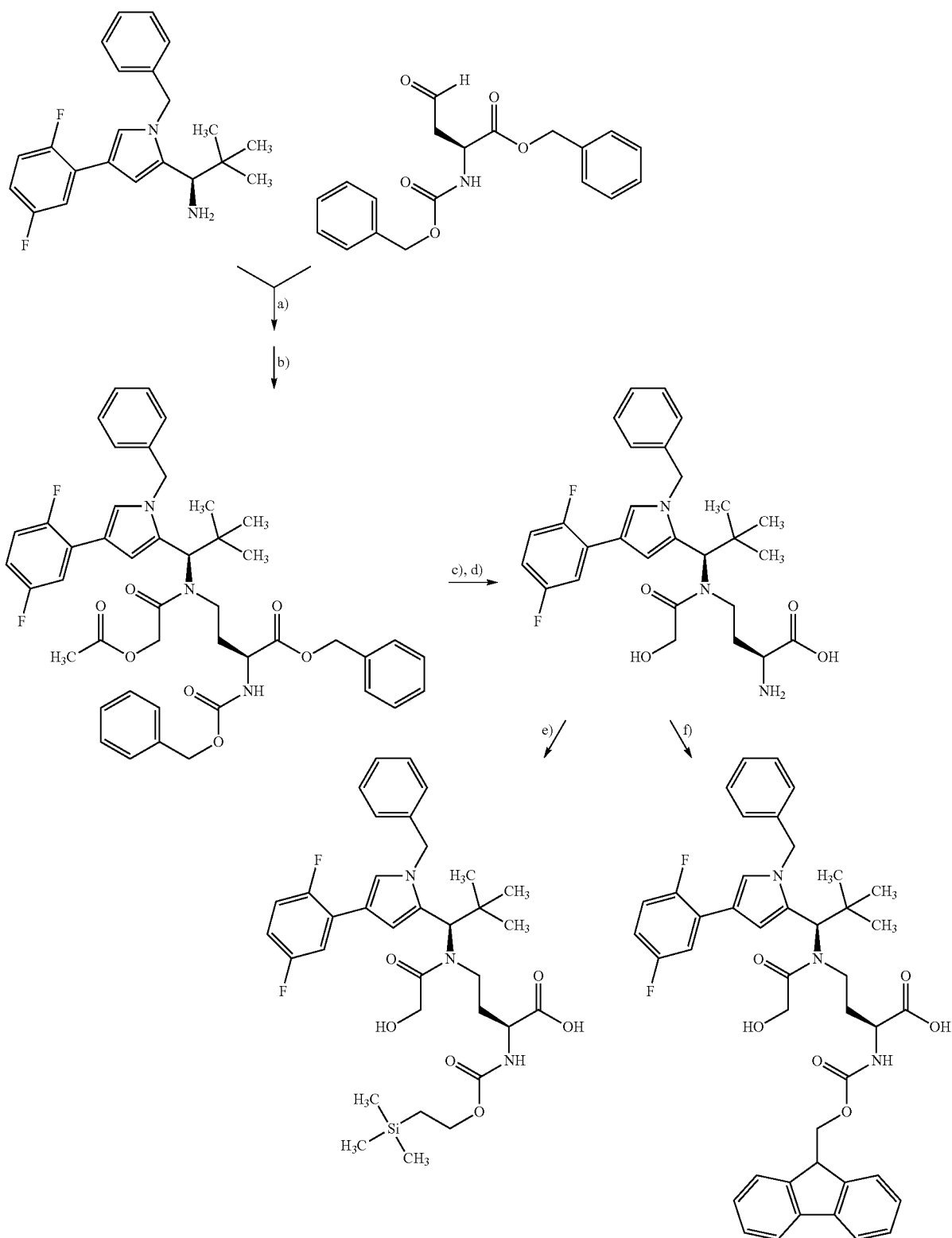
[a) for example sodium triacetoxyborohydride, acetic acid, DCM, RT;
b) for example acetoxyacetyl chloride, NEt₃, DCM, RT;
c) for example LiOH, THF/water, RT;
d) for example H₂, Pd—C, EtOH, RT;
e) for example Teoc-OSu, NEt₃, dioxane, RT;
f) for example Fmoc—Cl, diisopropylethylamine, dioxane/water 2:1, RT]

Scheme 23
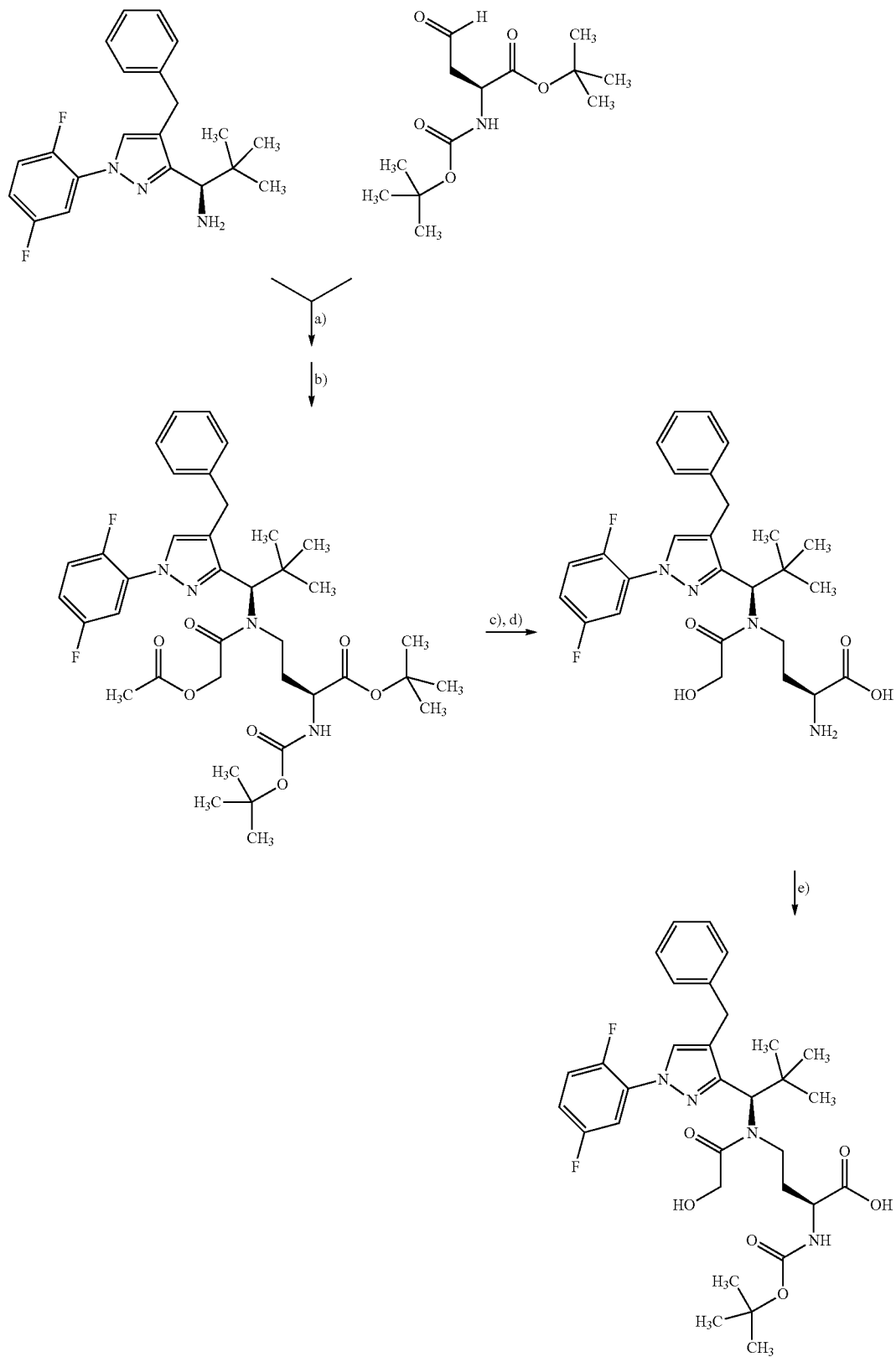
[a): for example sodium triacetoxyborohydride, acetic acid, DCM, RT; b) for example acetoxyacetyl chloride, NEt$_3$, DCM, RT; c) for example LiOH, methanol, RT; d) for example TFA, DCM, RT; e) for example Boc$_2$O, diisopropylethylamine, DCM, RT]

Scheme 24
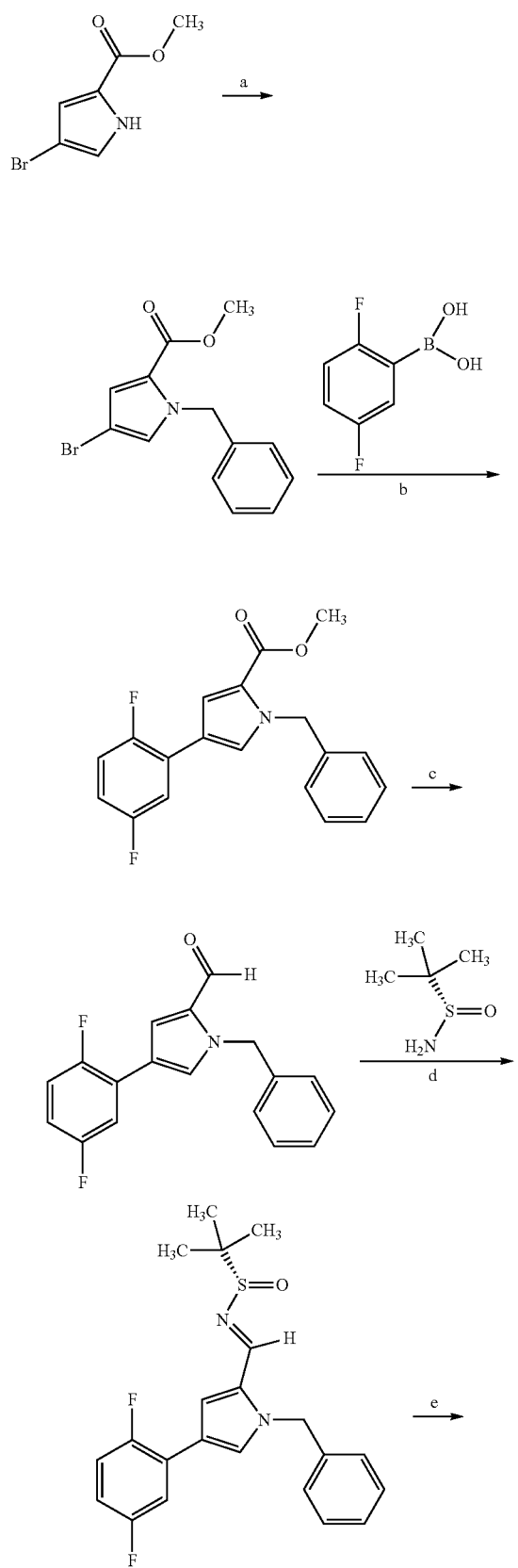
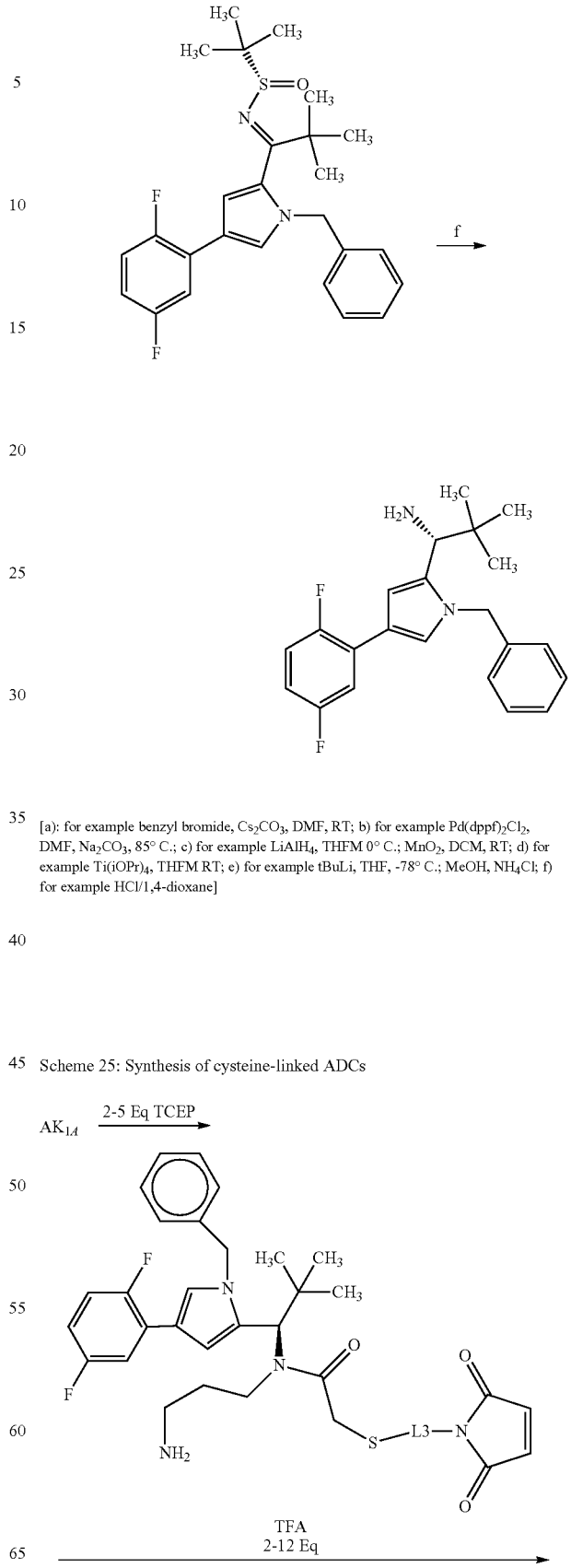
[a): for example benzyl bromide, Cs$_2$CO$_3$, DMF, RT; b) for example Pd(dppf)$_2$Cl$_2$, DMF, Na$_2$CO$_3$, 85° C.; c) for example LiAlH$_4$, THFM 0° C.; MnO$_2$, DCM, RT; d) for example Ti(iOPr)$_4$, THFM RT; e) for example tBuLi, THF, -78° C.; MeOH, NH$_4$Cl; f) for example HCl/1,4-dioxane]
Scheme 25: Synthesis of cysteine-linked ADCs

227
-continued
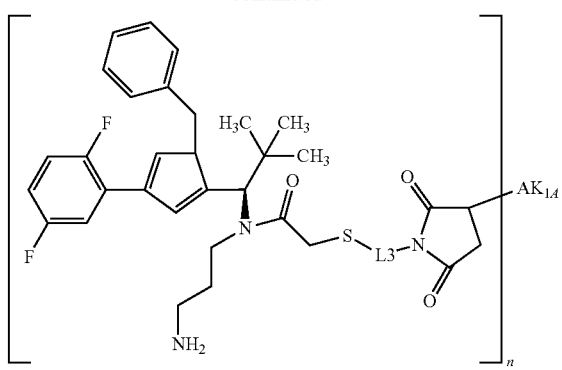
228
-continued
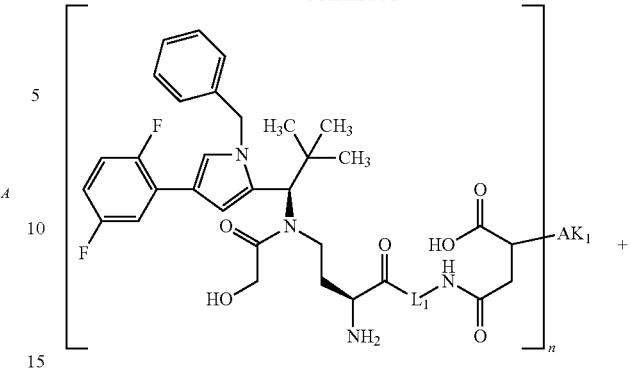
+
Scheme 26: Synthesis of cysteine-linked ADCs via hydrolysed succinamides
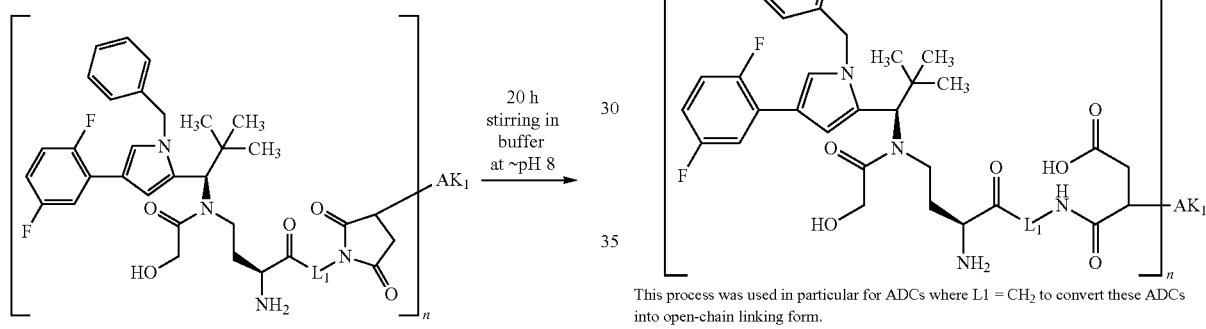
This process was used in particular for ADCs where L1 = CH₂ to convert these ADCs into open-chain linking form.
Scheme 27:
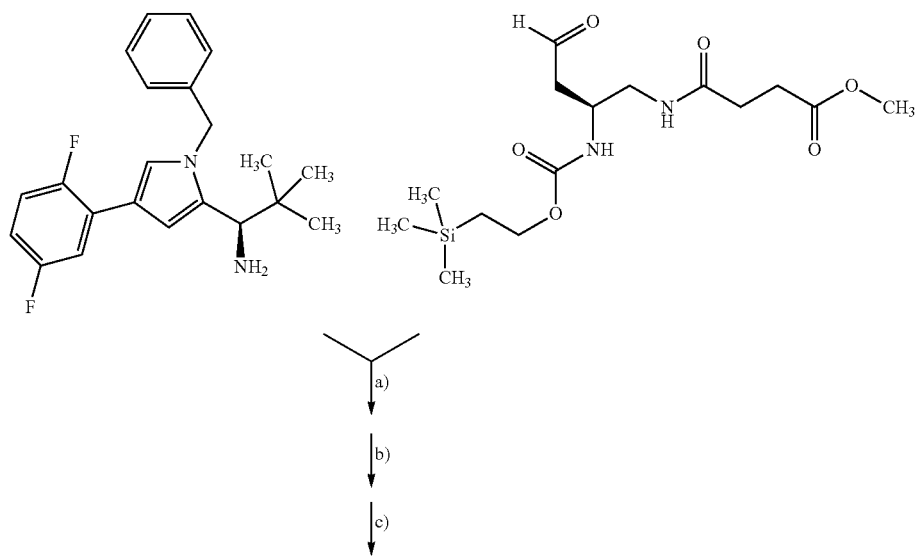

-continued
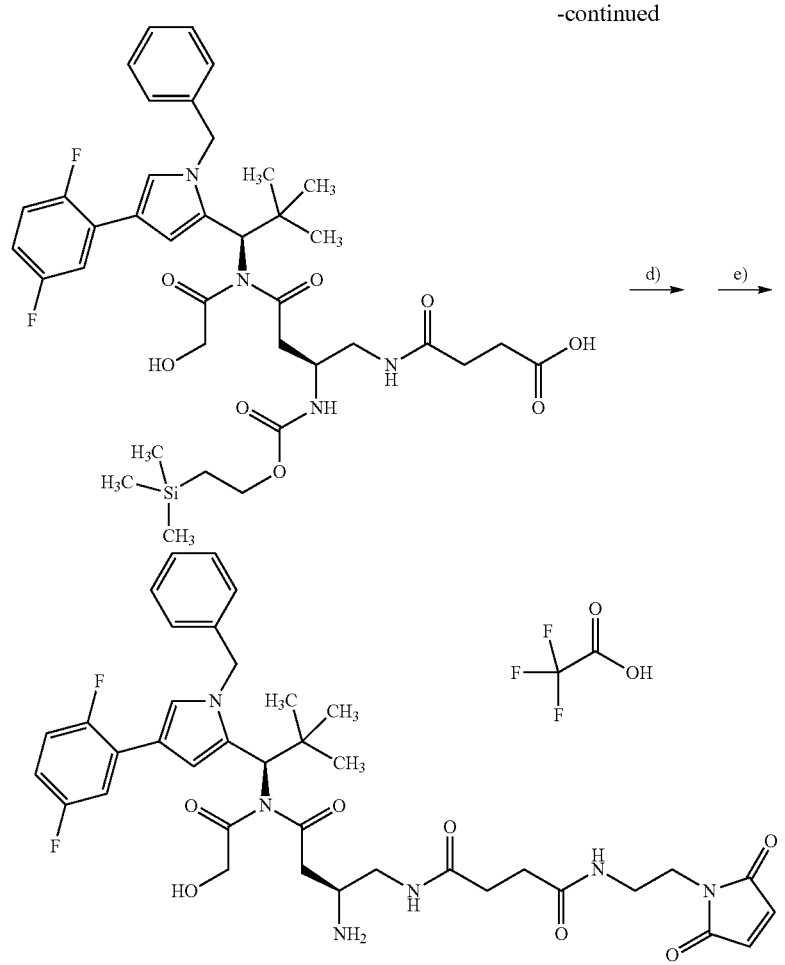
[a): sodium triacetoxyborohydride, acetic acid, DCM, RT; b) acetoxyacetyl chloride, diisopropylethylamine, DCM, RT; c) LiOH, MeOH, RT; d) trifluoroacetic acid/1-(2-aminoethyl)-1H-pyrrole-2,5-dione (1:1) HATU, DMF, diisopropylethylamine, RT; e) zinc chloride, trifluoroethanol, 50° C., EDTA.]
Scheme 28:
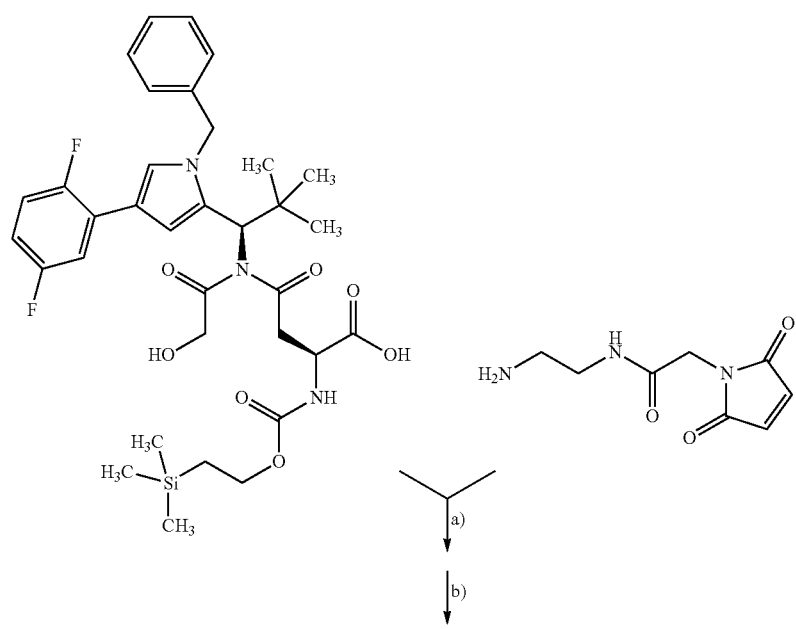

-continued
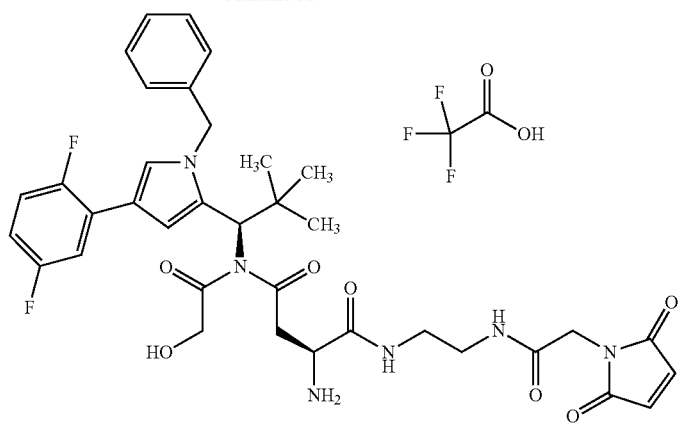
[a): HATU, DMF, diisopropylethylamine, RT; b) zinc chloride, trifluoroethanol, 50° C., EDTA.]
Scheme 29:
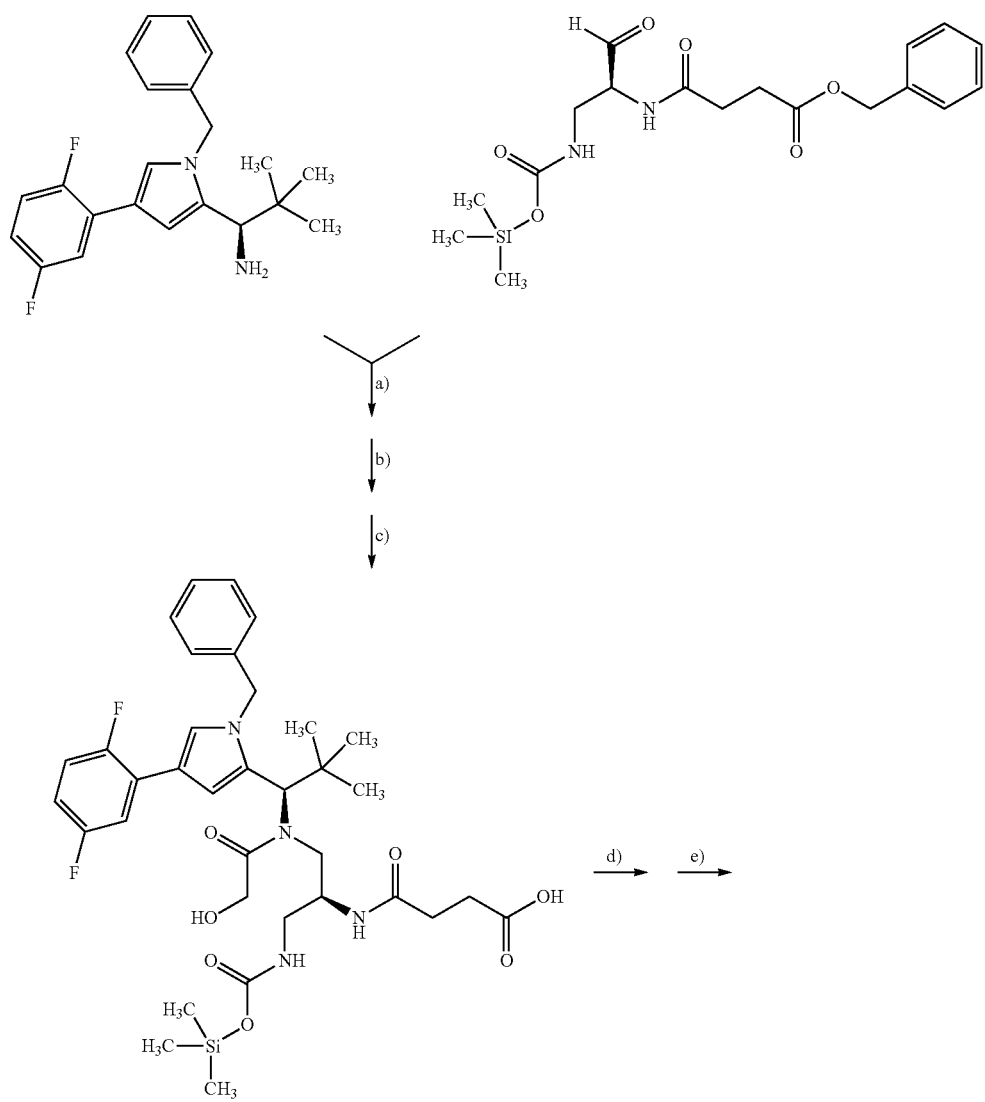

-continued
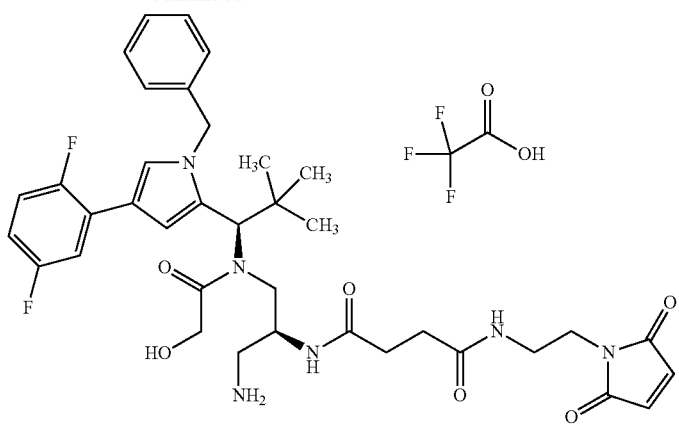
[a): sodium triacetoxyborohydride, acetic acid, DCM, RT; b) acetoxyacetyl chloride, triethylamine, DCM, RT; c) LiOH, MeOH, RT; d) trifluoroacetic acid/1-(2-aminoethyl)-1H-pyrrole-2,5-dione (1:1) HATU, DMF, diisopropylethylamine, RT; e) zinc chloride, trifluoroethanol, 50° C., EDTA.]
Scheme 30:
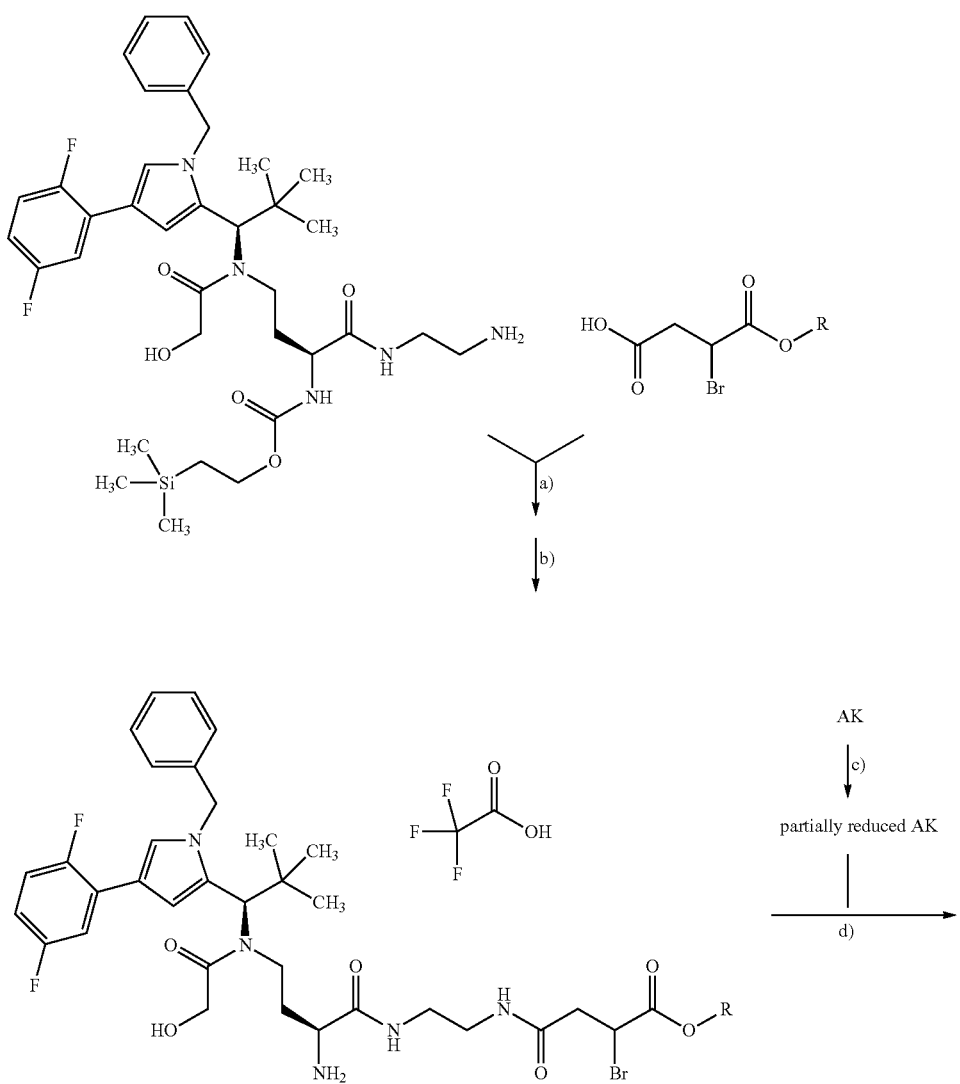

-continued
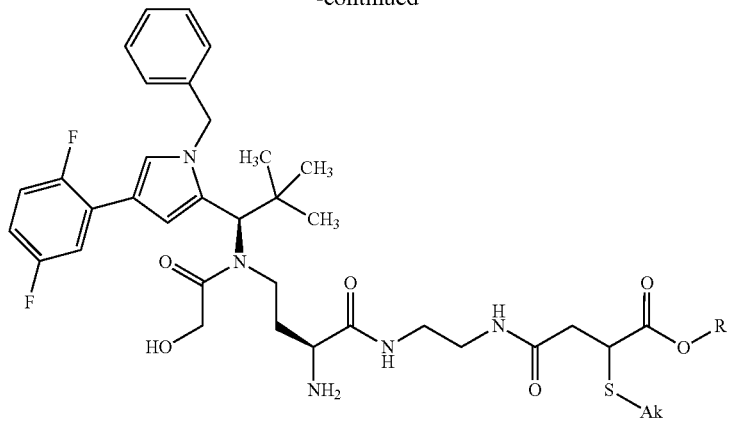
R = CH₃
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS suffer, 20 h RT.]
Scheme 31:
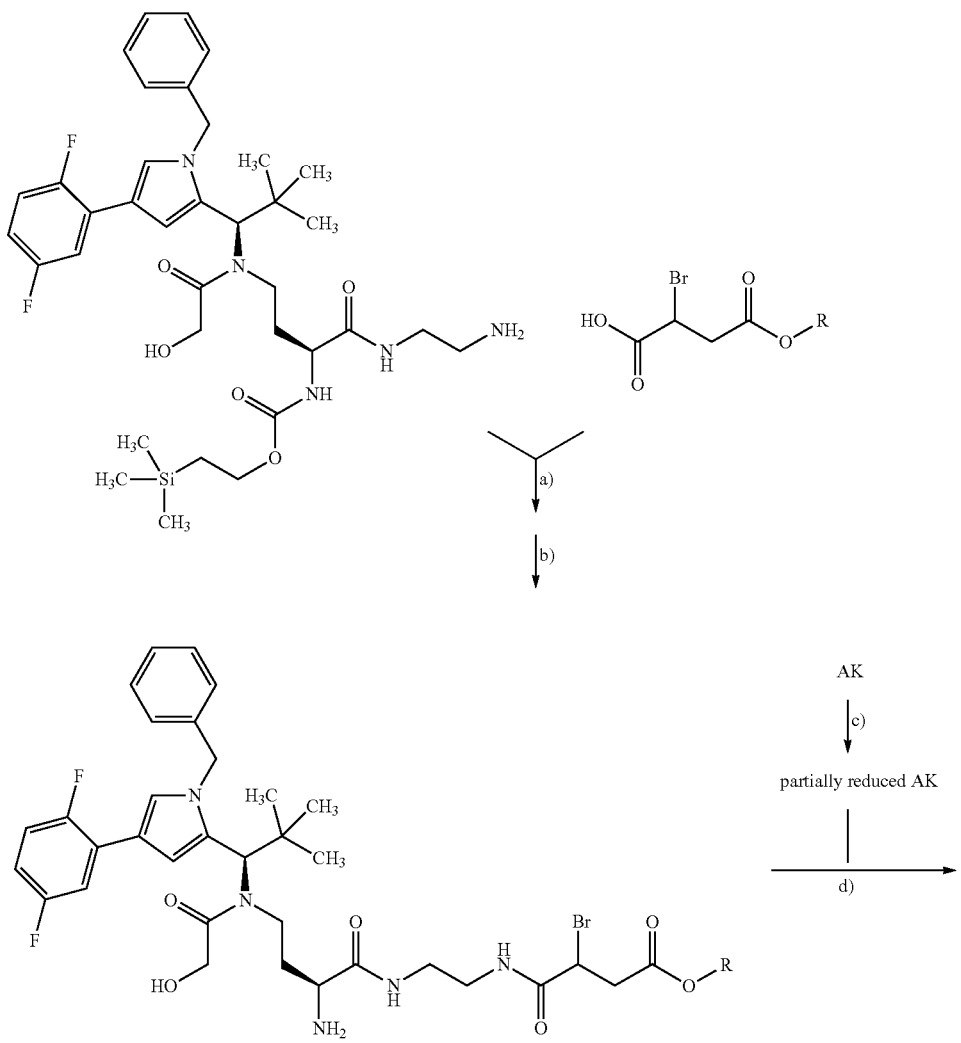

-continued

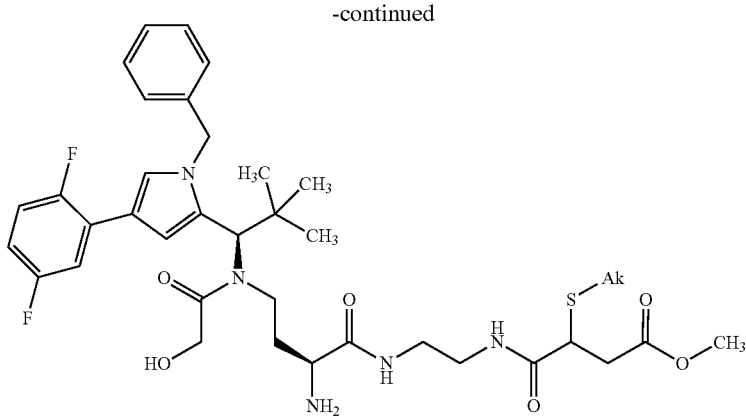

[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS suffer, 20 h RT.]

A. Examples

Abbreviations and Acronyms

A431NS human tumour cell line
A549 human tumour cell line
ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
CI chemical ionization (in MS)
d doublet (in NMR)
d day(s)
TLC thin-layer chromatography
DCI direct chemical ionization (in MS)
dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, PBS Dulbecco's phosphate-buffered salt solution
PBS=DPBS=D-PBS, pH 7.4, from Sigma, No D8537 composition:
0.2 g KCl
0.2 g $KH_2PO_4$ (anhyd)
8.0 g NaCl
1.15 g $Na_2HPO_4$ (anhyd)
made up ad 1 l with $H_2O$
dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS) ESI-MicroTofq ESI-MicroTofq (name of the mass spectrometer with Tof=time of flight and q=quadrupol)
FCS foetal calf serum
Fmoc (9H-fluoren-9-ylmethoxy)carbonyl
GTP guanosine-5'-triphosphate
h hour(s)
HATU O-(7-azabenzotriazol-1-yl)-N,N,N',N'-tetramethyluronium hexafluorophosphate
HCT-116 human tumour cell line
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure high-performance liquid chromatography
HT29 human tumour cell line
$IC_{50}$ half-maximal inhibitory concentration
i.m. intramuscularly, administration into the muscle
i.v. intravenously, administration into the vein
conc. concentrated
LC-MS liquid chromatography-coupled mass spectroscopy
LLC-PK1 cells Lewis lung carcinoma pork kidney cell line
L-MDR human MDR1 transfected LLC-PK1 cells
m multiplet (in NMR)
MDR1 multidrug resistance protein 1
MeCN acetonitrile
min minute(s)
MS mass spectrometry
MTT 3-(4,5-dimethylthiazol-2-yl)-2,5-diphenyl-2H-tetrazolium bromide
NCI-H292 human tumour cell line
NCI-H520 human tumour cell line
NMM N-methylmorpholine
NMP N-methyl-2-pyrrolidinone
NMR nuclear magnetic resonance spectrometry
NMRI mouse strain, originates from the Naval Medical Research Institute (NMRI)
NSCLC non small cell lung cancer
PBS phosphate-buffered salt solution
Pd/C palladium on activated carbon P-gp P-gycoprotein, a transporter protein
PNGaseF enzyme for cleaving sugar
quant. quantitative (in yield)
quart quartet (in NMR)
quint quintet (in NMR)
$R_f$ retention index (in TLC)
RT room temperature
$R_t$ retention time (in HPLC)
s singlet (in NMR)
s.c. subcutaneously, administration under the skin
SCC-4 human tumour cell line
SCC-9 human tumour cell line
SCID mice test mice with severe combined immunodeficiency
t triplet (in NMR)
TBAF tetra-n-butylammonium fluoride
TEMPO (2,2,6,6-tetramethylpiperidin-1-yl)oxyl
tert. tertiary
TFA trifluoroacetic acid
THF tetrahydrofuran
T3P® 2,4,6-tripropyl-1,3,5,2,4,6-trioxatriphosphinane 2,4,6-trioxide
UV ultraviolet spectrometry
v/v ratio by volume (of a solution)
Z benzyloxycarbonyl If, in the context of the present disclosure, no temperature is given in the description of a reaction, room temperature should always be assumed.

HPLC and LC-MS Methods:

Method 1 (LC-MS):
Instrument: Waters ACQUITY SQD UPLC system; column: Waters Acquity UPLC HSS T3 1.8µ 50×1 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm Method 2 (LC-MS):
MS instrument type: Waters Synapt G2S; UPLC instrument type: Waters Acquity I-CLASS; column: Waters, BEH300, 2.1×150 mm, C18 1.7 µm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm Method 3 (LC-MS):
MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm Method 4 (LC-MS):
MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm Method 5 (LC-MS):
Instrument: Waters ACQUITY SQD UPLC system; column: Waters Acquity UPLC HSS T3 1.8µ50×1 mm; mobile phase A: 1 l of water+0.25 ml of 99% strength formic acid; mobile phase B: 1 l of acetonitrile+0.25 ml of 99% strength formic acid; gradient: 0.0 min 95% A→6.0 min 5% A→7.5 min 5% A oven: 50° C.; flow rate: 0.35 ml/min; UV detection: 210-400 nm Method 6 (LC-MS):
Instrument: Micromass Quattro Premier with Waters UPLC Acquity; column: Thermo Hypersil GOLD 1.9µ 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 7 (LC-MS):
Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid; mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm Method 8 (LC-MS):
MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm Method 9: LC-MS-Prep Purification Method for Examples 181-191 (Method LIND-LC-MS-Prep)
MS instrument: Waters; HPLC instrument: Waters (column Waters X-Bridge C18, 19 mm×50 mm, 5 µm, mobile phase A: water+0.05% ammonia, mobile phase B: acetonitrile (ULC) with gradient; flow rate: 40 ml/min; UV detection: DAD; 210-400 nm).

or:

MS instrument: Waters; HPLC instrument: Waters (column Phenomenex Luna 5 µC18(2) 100A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).

Method 10: LC-MS Analysis Method for Examples 181-191 (LIND_SQD_SB_AQ)
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm Method 11 (HPLC):

Instrument: HP1100 Series

Column: Merck Chromolith SpeedROD RP-18e, 50-4.6 mm, Cat. No. 1.51450.0001, precolumn Chromolith Guard Cartridge Kit, RP-18e, 5-4.6 mm, Cat. No. 1.51470.0001

Gradient: flow rate 5 ml/min injection volume 5 µl solvent A: $HClO_4$ (70% strength) in water (4 ml/l)

solvent B: acetonitrile start 20% B 0.50 min 20% B 3.00 min 90% B 3.50 min 90% B 3.51 min 20% B
4.00 min 20% B
column temperature: 40° C.
Wavelength: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates

Intermediate C1

Trifluoroacetic acid-(1R)-1-[1-benzyl-4-(2,5-difluorophenyl)-1H-imidazol-2-yl]-2,2-dimethylpropan-1-amine (1:1)

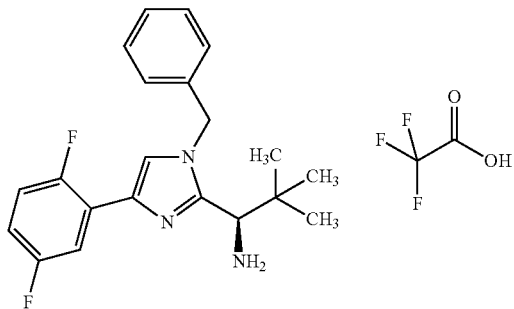 [SMILES: CC(C)(C)[C@@H](N)c1nc(-c2cc(F)ccc2F)cn1Cc1ccccc1 ; O=C(O)C(F)(F)F]

The title compound was prepared as described in WO2006/002326.

Intermediate C2 tert-Butyl (2S)-4-({(1R)-1-[1-benzyl-4-(2,5-difluorophenyl)-1H-imidazol-2-yl]-2,2-dimethylpropyl}amino)-2-[(tert-butoxycarbonyl)amino]butanoate

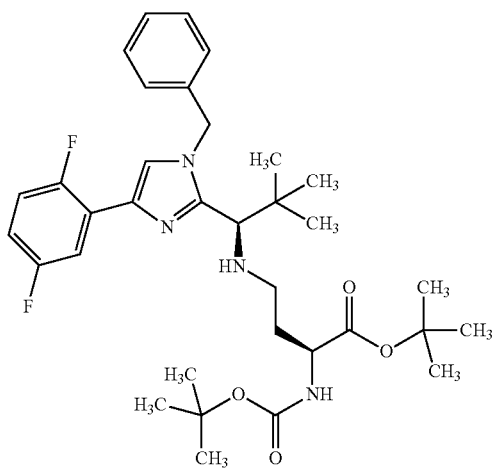 [SMILES: CC(C)(C)OC(=O)N[C@@H](CCN[C@@H](c1nc(-c2cc(F)ccc2F)cn1Cc1ccccc1)C(C)(C)C)C(=O)OC(C)(C)C]

4.22 g (14.5 mmol) of tert-butyl N-(tert-butoxycarbonyl)-L-homoserinate were dissolved in 180 ml of dichloromethane, and 3.5 ml of pyridine and 9.2 g (21.7 mmol) of 1,1,1-triacetoxy-llambda$^5$,2-benziodoxol-3(1H)-one were then added. The reaction was stirred at RT for 1 h and then diluted with 500 ml of dichloromethane and extracted twice with 10% strength sodium thiosulphate solution and then extracted successively twice with 5% strength citric acid and twice with 10% strength sodium bicarbonate solution. The organic phase was separated off, dried over magnesium sulphate and then dried under reduced pressure. The residue was taken up in diethyl ether, and HCl (solution in diethyl ether) was added. The precipitate was filtered off and the filtrate was then concentrated and lyophilized from acetonitrile/water. This gave 3.7 g (93%) of tert-butyl (2S)-2-[(tert-butoxycarbonyl)amino]-4-oxobutanoate which were used without further purification for the next step. ($R_f$: 0.5 (DCM/methanol 95/5).

3.5 g (9.85 mmol) of Intermediate C1 were dissolved in 160 ml of DCM, and 3.13 g (14.77 mmol) of sodium triacetoxyborohydride and 0.7 ml of acetic acid were added. After 5 min of stirring at RT, 3.23 g (11.85 mmol) of tert-butyl (2S)-2-[(tert-butoxycarbonyl)amino]-4-oxobutanoate were added and the reaction was stirred at RT for a further 30 min. The solvent was then evaporated under reduced pressure and the residue was taken up in acetonitrile/water. The precipitated solid was filtered off and dried, giving 5.46 g (84%) of the title compound.

HPLC (Method 11): $R_t$=2.5 min;
LC-MS (Method 1): $R_t$=1.13 min; MS (ESIpos): m/z=613 (M+H)$^+$.

Intermediate C3

(2S)-4-[(Acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoic acid

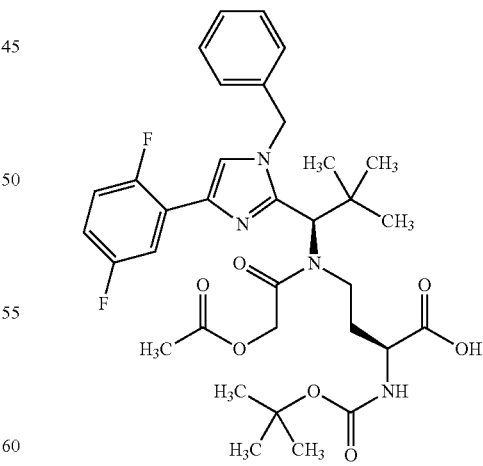

5.46 g (8.24 mmol) of Intermediate C2 were dissolved in 160 ml of DCM, and 4.8 ml of triethylamine and 2.2 ml (20.6 mmol) of acetoxyacetyl chloride then were added. The reaction was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 (M+H)$^+$.

1 g (1.36 mmol) of this intermediate was dissolved in 20 ml of DCM, and 20 ml of TFA were added. After 5 h of stirring at RT, the mixture was concentrated and the residue was triturated twice with n-pentane. In each case, the n-pentane was decanted off and the solid that remained was dried under high vacuum. This gave 1.1 g of (2S)-4-[(acetoxyacetyl){(1R)-1-[1-benzyl-4-(2,5-difluorophenyl)-1H-imidazol-2-yl]-2,2-dimethylpropyl}amino]-2-aminobutanoic acid/trifluoroacetic acid (1:1). LC-MS (Method 1): $R_t$=0.93 min; MS (ESIpos): m/z=557 (M+H)$^+$.

0.91 g (1.57 mmol) of this intermediate were dissolved in 70 ml of DCM, and 3.43 g (15.7 mmol) of di-tert-butyl dicarbonate and 4.1 ml of N,N-diisopropylethylamine were added. After 30 min of stirring at RT, the reaction was diluted with DCM and extracted with 5% strength citric acid. The organic phase was dried over sodium sulphate and concentrated. The residue was triturated twice with n-pentane and in each case the n-pentane was decanted off. The solid that remained was lyophilized from acetonitrile/water 1:1, giving 1.11 g of the title compound.

HPLC (Method 11): $R_t$=2.55 min;
LC-MS (Method 1): $R_t$=1.3 min; MS (ESIpos): m/z=657 (M+H)$^+$.

Intermediate C4

(2S)-2-Amino-4-[{(1R)-1-[1-benzyl-4-(2,5-difluorophenyl)-1H-imidazol-2-yl]-2,2-dimethylpropyl}(glycoloyl)amino]butanoic acid/trifluoroacetic acid (1:1)

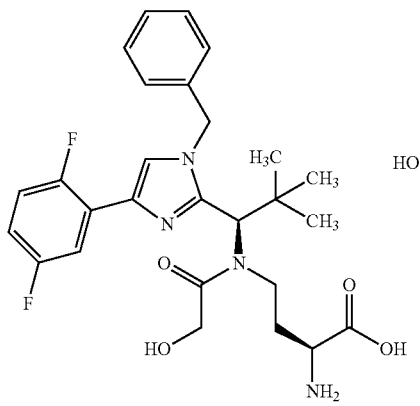

5.46 g (8.24 mmol) of Intermediate C2 were dissolved in 160 ml of DCM, and 4.8 ml of triethylamine and 2.2 ml (20.6 mmol) of acetoxyacetyl chloride were added. The reaction was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 (M+H)$^+$.

1.5 g (2.035 mmol) of this intermediate were taken up in 50 ml of ethanol, and 5.8 ml of a 40% strength solution of methanamine in water was added. The reaction was stirred at 50° C. for 4 h and then concentrated. The residue was taken up in DCM and washed twice with water. The organic phase was dried over magnesium sulphate and then concentrated.

The residue was dried under high vacuum. This gave 1.235 mg of this intermediate, which were reacted further without further purification.

1.235 mg (1.5 mmol) of this intermediate were dissolved in 15 ml of DCM, and 15 ml of TFA were added. After 4 h of stirring at RT, the mixture was concentrated. The residue was purified by preparative HPLC. The appropriate fractions were concentrated and the residue was lyophilized from acetonitrile. This gave 1.04 g (quant) of the title compound.

HPLC (Method 11): $R_t$=1.9 min;
LC-MS (Method 1): $R_t$=0.89 min; MS (ESIpos): m/z=515 (M+H)$^+$.

Intermediate C5

(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoic acid

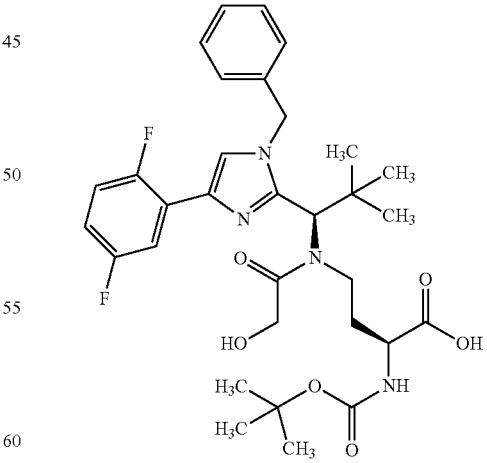

0.9 g (1.24 mmol) of Intermediate C4 was dissolved in 60 ml of DCM, and 2.7 g (12.5 mmol) of di-tert-butyl dicarbonate and 3.3 ml of N,N-diisopropylethylamine were added. After 45 min of stirring at RT, the reaction was

Intermediate C6

Trifluoroacetic acid/tert-butyl {(2S)-4-[{(1R)-1-[1-benzyl-4-(2,5-difluorophenyl)-1H-imidazol-2-yl]-2,2-dimethylpropyl}(glycoloyl)amino]-1-hydrazino-1-oxobutan-2-yl}carbamate (1:1)

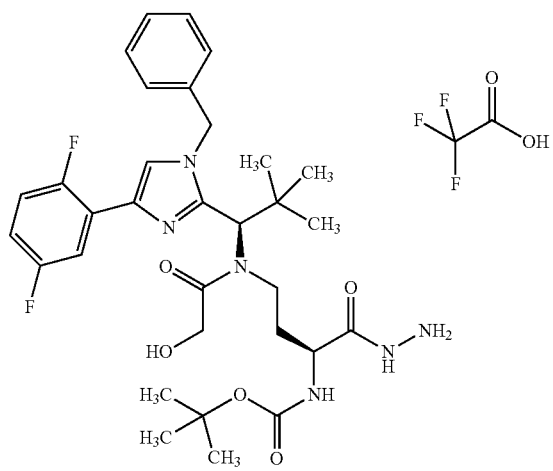 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NN ; O=C(O)C(F)(F)F]

150 mg (0.16 mmol) of Intermediate C3 were dissolved in 21 ml of DMF, and then 37.2 mg (0.19 mmol) of N-(3-dimethylaminopropyl)-N′-ethylcarbodiimide hydrochloride (EDC), 37 mg (0.243 mmol) of 1-hydroxybenzotriazole, 85 μl of N,N-diisopropylethylamine and finally 45 mg (0.18 mmol) of commercially available 9H-fluoren-9-ylmethyl hydrazinecarboxylate were added. The reaction was stirred at RT overnight and then concentrated under reduced pressure. The residue was purified by preparative HPLC. The appropriate fractions were concentrated and the residue was lyophilized from acetonitrile/water. This gave 60 mg (41% of theory) of the protected intermediate.

HPLC (Method 11): $R_t$=2.9 min;
LC-MS (Method 1): $R_t$=1.47 min; MS (ESIpos): m/z=893 (M+H)$^+$.

60 mg (0.067 mmol) of this intermediate were dissolved in 19 ml of ethanol, and 681 μl of piperidine and 386 μl of a 40% strength solution of methanamine in water were added. The reaction was stirred at 50° C. for 18 h and then concentrated. The residue was taken up in acetonitrile/water 2:1 and adjusted to pH 2 with TFA. The mixture was then concentrated and the residue was purified by preparative HPLC. The appropriate fractions were concentrated and the residue was lyophilized from acetonitrile/water.

This gave 25 mg (51% of theory) of the title compound.
HPLC (Method 11): $R_t$=2.2 min;
LC-MS (Method 1): $R_t$=1.27 min; MS (ESIpos): m/z=629 (M+H)$^+$.

Intermediate C7

1-{(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoyl}hydrazino)acetic acid/trifluoroacetic acid (1:1)

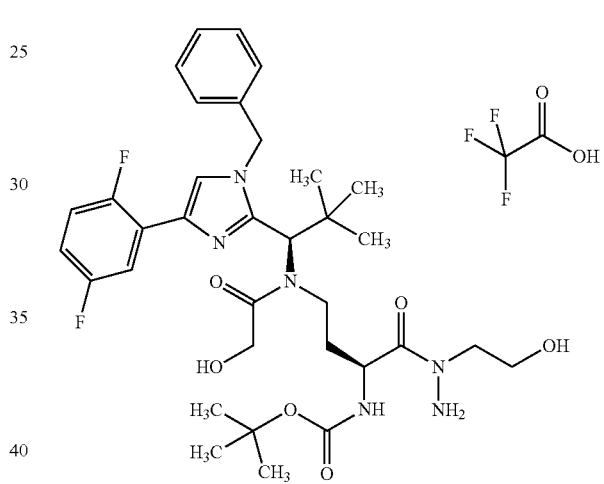

0.2 g (0.305 mmol) of intermediate C3 were dissolved in 80 ml of DCM, 0.125 g (0.46 mmol) of 2-bromo-1-ethylpyridinium tetrafluoroborate (BEP), 94 mg (0.61 mmol) of commercially available ethylhydrazinoacetate hydrochloride and 159 μl of N,N-diisopropylethylamine were added and the mixture was then stirred at RT for 1 h. Ethyl acetate and water were then added to the reaction mixture, and the phases were separated. The organic phase was extracted with saturated sodium chloride solution and then dried over magnesium sulphate, filtered and concentrated. The residue was dried under reduced pressure and reacted further without purification. To this end, it was taken up in 20 ml of tetrahydrofuran, and 10 ml of water and 3.2 ml of a 2N lithium hydroxide solution were added. The reaction was stirred at RT for 1 h and then adjusted to pH 7 using TFA. The reaction was then concentrated and the residue was purified by preparative HPLC. In this manner, the title compound was separated from its earlier eluting regioisomer. Combination of the corresponding fractions, lyophilization and drying gave 19.7 g (8% of theory over 2 steps) of the title compound as a colourless foam.

Previously concentrated and the residue was taken up in diethyl ether, and n-pentane was added until the mixture started to get cloudy. The reaction was cooled to 0° C. and then decanted. Once more, n-pentane was added to the residue and the mixture was decanted. The solid that remained was lyophilized from acetonitrile/water 1:1, giving 0.95 g (quant) of the title compound.

HPLC (Method 11): $R_t$=2.5 min;
LC-MS (Method 1): $R_t$=1.27 min; MS (ESIpos): m/z=615 (M+H)$^+$.

HPLC (Method 11): $R_t$=2.4 min;

LC-MS (Method 1): $R_t$=1.22 min; MS (ESIpos): m/z=687 (M+H)$^+$.

Structural assignment of the regiosisomers was carried out in a separate experiment after separation of the regioisomers at the protected intermediate stage by NMR spectroscopy. The protected intermediate ethyl (1-{(2S)-4-[(acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoyl}hydrazino)acetate of the title compound had the 1H NMR spectrum below:

$^1$H NMR (500 MHz, DMSO-d$_6$): δ=7.8 (m, 2H), 7.4-7.2 (m, 6H), 7.08 (m, 1H), 6.73 (d, 1H), 5.6 (s, 1H), 5.25 and 4.89 (2d, 2H), 4.89 and 4.77 (2d, 2H), 4.62 (t, 1H), 4.32 and 3.78 (2d, 2H), 4.1 (t, 2H), 3.62-3.47 (m), 2.13 (s, 3H), 1.41 and 0.72 (2m, 2H), 1.3 (s, 9H), 1.18 (t, 3H), 0.92 (s, 9H).

Intermediate C8

N-{(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoyl}-beta-alanine 293 mg (0.41 mmol) of Intermediate C3 were dissolved in 25 ml of DMF, and then 144 mg (0.75 mmol) of N-(3-dimethylaminopropyl)-N'-ethylcarbodiimide hydrochloride (EDC), 128 mg (0.83 mmol) of 1-hydroxybenzotriazole, 218 µl of N,N-diisopropylethylamine and finally 70 mg (0.5 mmol) of commercially available 3-methoxy-3-oxopropan-1-aminium chloride were added. The reaction was stirred at RT for 4 h and then concentrated under reduced pressure. The residue was purified by preparative HPLC. The appropriate fractions were concentrated and the residue was dried under high vacuum. This gave 177 mg (53% of theory) of the protected intermediate.

HPLC (Method 11): $R_t$=2.6 min;

LC-MS (Method 1): $R_t$=1.33 min; MS (ESIpos): m/z=742 (M+H)$^+$.

177 mg (0.22 mmol) of this intermediate were taken up in 20 ml of methanol, and 2.8 ml of 2N lithium hydroxide solution were added. The reaction was stirred at RT for 18 h. The mixture was then concentrated, the residue was taken up in water and the solution was adjusted to pH 5 using 5% strength citric acid. The mixture was then extracted twice with DCM and the organic phase was dried over magnesium sulphate and concentrated. The residue was finally lyophilized from acetonitrile/water, giving 133 mg (81% of theory) of the title compound.

HPLC (Method 11): $R_t$=2.3 min;

LC-MS (Method 3): $R_t$=7.4 min; MS (ESIpos): m/z=686 (M+H)$^+$.

Intermediate C9

(6S)-6-{2-[{(1R)-1-[1-Benzyl-4-(2,5-difluorophenyl)-1H-imidazol-2-yl]-2,2-dimethylpropyl}(glycoloyl)amino]ethyl}-2,2-dimethyl-4,7-dioxo-3,11,14,17-tetraoxa-5,8-diazaicosan-20-oic acid

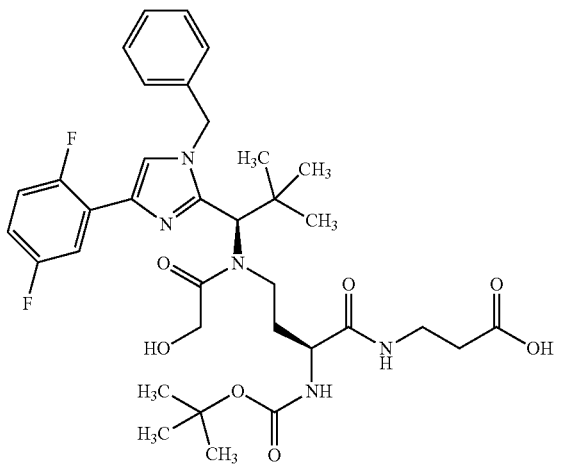 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NCCC(=O)O]

In the first step, 70 mg (0.114 mmol) of Intermediate C5 were coupled with 32 mg (0.114 mmol) of tert-butyl 3-{2-[2-(2-aminoethoxy)ethoxy]ethoxy}propanoate in 15 ml of DMF in the presence of 44 mg (0.228 mmol) of 1-(3-dimethylaminopropyl)-3-ethylcarbodiimide hydrochloride, 35 mg (0.228 mmol) of 1-hydroxy-1H-benzotriazole hydrate and 60 µl of N,N-diisopropylethylamine.

The reaction was stirred at RT overnight and the product was purified by preparative HPLC. This gave 33 mg (33% of theory) of the protected intermediate. This was stirred with 1.1 ml of trifluoroacetic acid in 11 ml of dichloromethane for 1 h giving, after work-up, 26 mg (98%) of the fully deprotected compound.

Finally, the intermediate was taken up in 2 ml of DCM and the tert-butoxycarbonyl protective group was introduced by twice adding in each case 10 mg of di-tert-butyl dicarbonate and 79 µl of N,N-diisopropylethylamine with stirring at RT for 3 days. Purification of the product by preparative HPLC gave 16.4 mg (66% of theory) of the title compound.

HPLC (Method 11): $R_t$=2.3 min;
LC-MS (Method 1): $R_t$=1.22 min; MS (ESIpos): m/z=818 (M+H)$^+$.

Intermediate C10 tert-Butyl {3-[{(1R)-1-[1-(3-aminobenzyl)-4-(2,5-difluorophenyl)-1H-imidazol-2-yl]-2,2-dimethylpropyl}(glycoloyl)amino]propyl}carbamate

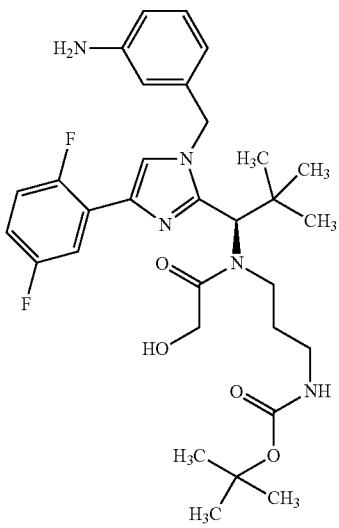 [SMILES: CC(C)(C)OC(=O)NCCCN(C(=O)CO)[C@@H](c1nc(-c2cc(F)ccc2F)cn1Cc1cccc(N)c1)C(C)(C)C]

The title compound was prepared from Intermediate C1 over 6 steps: In the first step, 1 g (2.77 mmol) of Intermediate C1 and 0.864 g (5 mmol) of tert-butyl (3-oxopropyl)carbamate were combined in 100 ml of methanol, and 400 ml of acetic acid and 1.288 g (13.9 mmol) of borane-pyridine complex were added. The reaction was stirred at RT for 3 days. The mixture was then concentrated under reduced pressure and the residue was purified by flash chromatography on silica gel (mobile phase: dichloromethane/ethyl acetate 9:1→dichloromethane/methanol 95:5). Concentration of the appropriate fractions and drying under high vacuum gave 1.255 g (80% of theory) of the N-alkylated intermediate.

LC-MS (Method 1): $R_t$=1.0 min; MS (ESIpos): m/z=513 (M+H)$^+$.

1.255 g (2.2 mmol) of this intermediate were dissolved in 50 ml of DCM, and 1.2 ml of triethylamine and 0.52 ml (4.85 mmol) of acetoxyacetyl chloride were then added. The reaction was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by preparative HPLC.

This gave 593 mg (41% of theory) of the acylated intermediate.

LC-MS (Method 1): $R_t$=1.4 min; MS (ESIpos): m/z=613 (M+H)$^+$.

993 mg (0.91 mmol) of this intermediate were dissolved in 100 ml of ethanol and, after addition of 60 mg of 10% palladium on activated carbon, hydrogenated under standard hydrogen pressure at RT for 3 min. The catalyst was then filtered off and the solvent was removed under reduced pressure. This gave 494 mg (91% of theory) of the debenzylated imidazole derivative as a virtually colourless oil.

LC-MS (Method 1): $R_t$=1.17 min; MS (ESIpos): m/z=523 (M+H)$^+$.

150 mg (0.25 mmol) of this intermediate were initially charged in 15 ml of DMF, and 69.2 mg (0.5 mmol) of potassium carbonate were added. After 15 min of stirring at RT, 60 mg (0.28 mmol) of p-nitrobenzyl bromide were added and the mixture was stirred overnight. The solvent was then removed under reduced pressure, and the residue was taken up in ethyl acetate and extracted with saturated sodium bicarbonate solution. The organic phase was washed with saturated sodium chloride solution, concentrated on a rotary evaporator and purified by preparative HPLC. The appropriate fractions were concentrated on a rotary evaporator and the residue was lyophilized from 1,4-dioxane. This gave 169 mg (quant.) of the intermediate.

LC-MS (Method 1): $R_t$=1.39 min; MS (ESIpos): m/z=658 (M+H)$^+$.

165 mg (0.251 mmol) of this intermediate were taken up in 30 ml of ethanol, and 0.35 ml of a 40% strength aqueous solution of methanamine was added. The reaction was stirred at 50° C. for 5 h, and the same amount of the methylamine solution was then added again. After 10 h of stirring, the reaction was concentrated under reduced pressure. The distillate was redistilled twice with diethyl ether and the residue was then lyophilized from acetonitrile/water. This gave 148 mg (89% of theory) of this intermediate.

LC-MS (Method 6): $R_t$=2.97 min; MS (ESIpos): m/z=616 (M+H)$^+$.

98 mg (0.15 mmol) of the precursor were dissolved in 15 ml of THF, and a solution of 569 mg (3.27 mmol) of disodium dithionite in 6 ml of water was then added at RT. After 8 h of stirring at 50° C., the same amount of dithionite— dissolved in 1 ml of H$_2$O— was added again. After a further 16 hours of stirring at 50° C., the reaction was cooled to RT and extracted with ethyl acetate. The organic phase was concentrated and the residue was purified by preparative HPLC. Lyophilization of the residue from 1,4-dioxane gave 44.5 mg (47% of theory) of the title compound.

LC-MS (Method 1): $R_t$=1.24 min; MS (ESIpos): m/z=586 (M+H)$^+$.

Intermediate C11

R/S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetate (1:1)

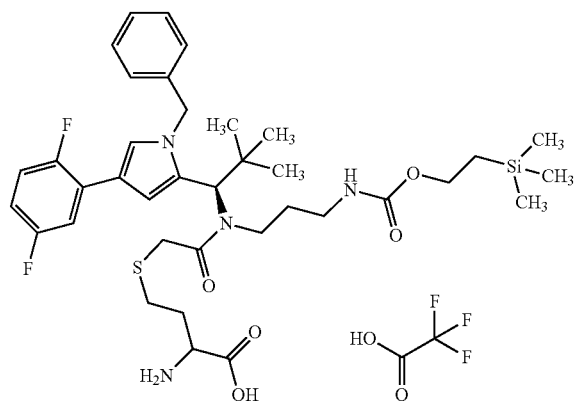 [SMILES: CC(C)(C)[C@H](c1cc(-c2cc(F)ccc2F)cn1Cc1ccccc1)N(CCCNC(=O)OCC[Si](C)(C)C)C(=O)CSCCC(N)C(=O)O ; O=C(O)C(F)(F)F]

990.0 mg (2.79 mmol) of (1R)-1-[1-benzyl-4-(2,5-difluorophenyl)-1H-pyrrol-2-yl]-2,2-dimethylpropan-1-amine were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min 698.1 mg (3.21 mmol) of 2-(trimethylsilyl)ethyl (3-oxopropyl)carbamate (Intermediate L58) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified using silica gel (mobile phase: dichloromethane/methanol 100:2). The solvents were evaporated under reduced pressure and the residue was dried under high vacuum. This gave 1.25 g (73% of theory) of the compound 2-(trimethylsilyl)ethyl [34 (1R)-1-[1-benzyl-4-(2,5-difluorophenyl)-1H-pyrrol-2-yl]-2,2-dimethylpropyl amino)propyl]carbamate.

LC-MS (Method 1): $R_t$=1.09 min; MS (ESIpos): m/z=556 (M+H)$^+$.

151.4 mg (1.5 mmol) of triethylamine and 161.6 mg (1.43 mmol) of chloroacetyl chloride were added to 400.0 mg (0.65 mmol) of 2-(trimethylsilyl)ethyl [34 (1R)-1-[1-benzyl-4-(2,5-difluorophenyl)-1H-pyrrol-2-yl]-2,2-dimethylpropyl amino)propyl]carbamate. The reaction mixture was stirred at RT overnight. Ethyl acetate was added to the reaction mixture and the organic phase was washed three times with water and once with saturated NaCl solution. The organic phase was dried over magnesium sulphate and the solvent was evaporated under reduced pressure. The residue was purified using silica gel (mobile phase: cyclohexane/ethyl acetate 3:1). The solvents were evaporated under reduced pressure and the residue was dried under high vacuum. This gave 254.4 mg (57% of theory) of the compound 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate.

LC-MS (Method 1): $R_t$=1.49 min; MS (ESIneg): m/z=676 (M+HCOO$^-$)$^-$.

117.4 mg (0.19 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propy}carbamate were dissolved in 10.0 ml of isopropanol, and 928.4 µl of 1M NaOH and 50.2 mg (0.37 mmol) of DL-homocysteine were added. The reaction mixture was stirred at 50° C. for 4.5 h. Ethyl acetate was added to the reaction mixture and the organic phase was washed with saturated sodium bicarbonate solution and sat. NaCl solution. The organic phase was dried over magnesium sulphate and the solvent was evaporated under reduced pressure. The residue was purified by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 75.3 mg (48% of theory) of the title compound.

LC-MS (Method 1): $R_t$=1.24 min; MS (ESIpos): m/z=731 (M+H)$^+$.

$^1$H NMR (400 MHz, DMSO-d$_6$): δ [ppm]=0.03 (s, 9H), 0.40 (m, 1H), 0.75-0.91 (m, 11H), 1.30 (m, 1H), 1.99-2.23 (m, 2H), 2.63-2.88 (m, 4H), 3.18-3.61 (m, 5H), 3.79-4.10 (m, 3H), 4.89 (d, 1H), 4.89 (d, 1H), 5.16 (d, 1H), 5.56 (s, 1H), 6.82 (m, 1H), 6.91 (s, 1H), 6.97 (m, 1H), 7.13-7.38 (m, 6H), 7.49 (s, 1H), 7.63 (m, 1H), 8.26 (s, 3H).

Intermediate C12

R/S-[(8S)-11-{(1R)-1-[1-Benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine

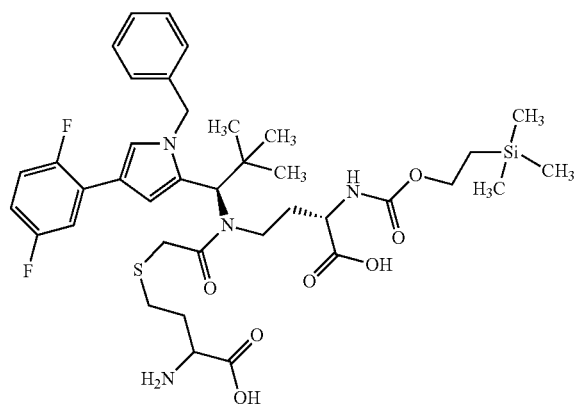 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CSCCC(N)C(=O)O]

The synthesis was carried out analogously to the synthesis of Intermediate C11 using methyl (2S)-4-oxo-2-({[2-(trimethylsilyl)ethoxy]carbonyl}amino)butanoate (Intermediate L57) and Intermediate C52 as starting materials.

LC-MS (Method 1): $R_t$=1.18 min; MS (ESIpos): m/z=775 (M+H)$^+$.

Intermediate C13

9-{(1R)-1-[1-Benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid

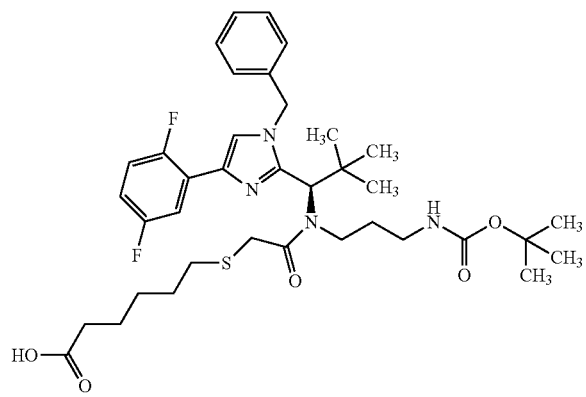 [SMILES: CC(C)(C)OC(=O)NCCCN(C(=O)CSCCCCCC(=O)O)[C@@H](c1nc(-c2cc(F)ccc2F)cn1Cc1ccccc1)C(C)(C)C]

90.0 mg (0.15 mmol) of intermediate C16 and 43.6 mg (0.23 mmol) of 6-(acetylsulphanyl)hexanoic acid were dissolved in 9.0 ml of methanol, and a drop of water and 73.9 mg (0.54 mmol) of potassium carbonate were added. The reaction mixture was stirred at 50° C. for 4 h and then diluted with ethyl acetate. The organic phase was washed with water/saturated NaCl solution and saturated NaCl solution and subsequently dried over magnesium sulphate. The solvent was evaporated under reduced pressure and the residue was chromatographed on silica gel (mobile phase: dichloromethane/methanol=100:2). The solvents were evaporated under reduced pressure and the residue was dried under high vacuum. This gave the title compound in 83% of theory.

LC-MS (Method 1): $R_t$=1.44 min; MS (ESIpos): m/z=701 (M+H)$^+$.

Intermediate C14

R/S-[2-({(1R)-1-[1-Benzyl-4-(2,5-difluorophenyl)-1H-imidazol-2-yl]-2,2-dimethylpropyl}{3-[(tert-butoxycarbonyl)amino]propyl}amino)-2-oxoethyl]homocysteine

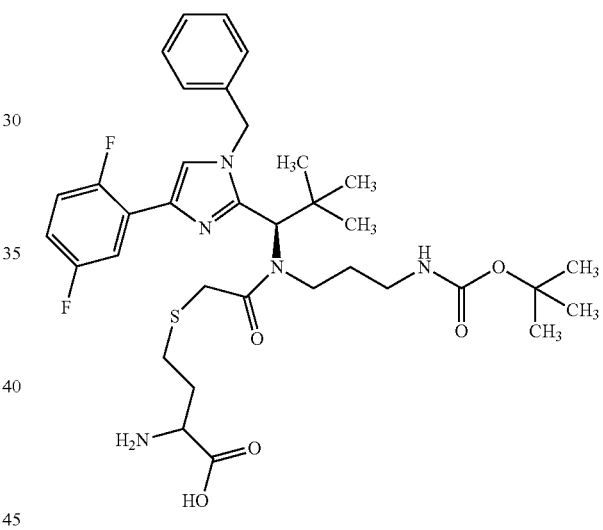

100.0 mg (0.17 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate (Intermediate C16) were initially charged in 4.0 ml of isopropanol, and 276.5 mg (0.85 mmol) of 1 M NaOH solution and 45.9 mg (0.34 mmol) of D/L-homocysteine were added. The reaction mixture was stirred at 50° C. for 1 h. The reaction mixture was diluted with ethyl acetate. The organic phase was washed with saturated sodium bicarbonate solution and sat. NaCl solution. Drying was over magnesium sulphate, and the solvent was evaporated under reduced pressure. The residue was purified by preparative RP-HPLC (column: Reprosil 250×40; 10μ, flow rate: 50 ml/min, MeCN/water). The solvents were evaporated under reduced pressure and the residue was dried under high vacuum.

This gave 92.6 mg (66% of theory) of the title compound.

LC-MS (Method 1): $R_t$=1.07 min; MS (ESIpos): m/z=688 (M+H)$^+$.

Intermediate C15 tert-Butyl [3-({(1R)-1-[1-benzyl-4-(2,5-difluorophenyl)-1H-imidazol-2-yl]-2,2-dimethylpropyl}amino)propyl]carbamate

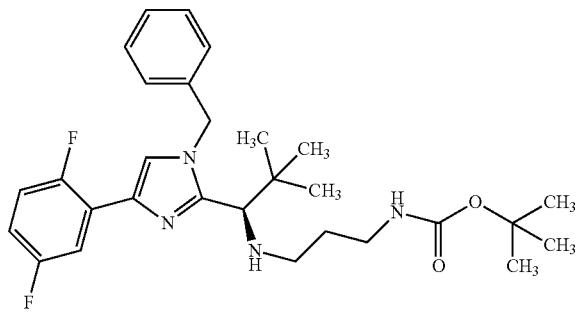 [SMILES: CC(C)(C)OC(=O)NCCCN[C@@H](c1nc(-c2cc(F)ccc2F)cn1Cc1ccccc1)C(C)(C)C]

750.0 mg (2.11 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were dissolved in 15.0 ml of dichloromethane, and 626.0 mg (2.95 mmol) of sodium triacetoxyborohydride and 139 µl (2.43 mmol) of HOAc were added and the mixture was stirred at RT for 5 min 420.3 mg (2.43 mmol) of tert-butyl (3-oxopropyl)carbamate (synthesis according to literature procedure J. Med. Chem. 2003, 46, 3536) were then added, and the mixture was stirred at RT overnight. Ethyl acetate was added and the reaction mixture was extracted twice with saturated sodium carbonate solution. The organic phase was washed with sat. NaCl solution and dried over magnesium sulphate. The solvent was evaporated under reduced pressure and the residue was chromatographed on silica gel (mobile phase: cyclohexane/ethyl acetate=4:1). The solvents were evaporated under reduced pressure and the residue was dried under high vacuum. This gave 881.0 mg (82% of theory) of the title compound.

LC-MS (Method 1): $R_t$=1.07 min; MS (ESIpos): m/z=513 [M+H]$^+$.

Intermediate C16 tert-Butyl {3-[{(1R)-1-[1-benzyl-4-(2,5-difluorophenyl)-1H-imidazol-2-yl]-2,2-dimethylpropyl}(chloroacetyl)amino]propyl}carbamate

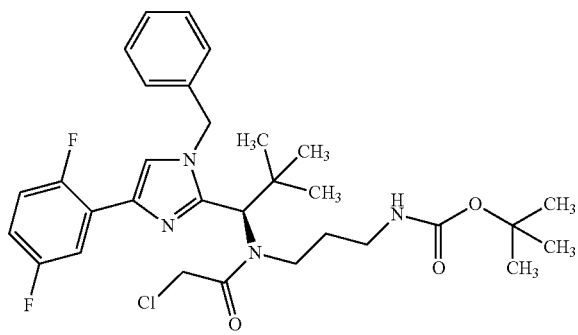 [SMILES: CC(C)(C)OC(=O)NCCCN(C(=O)CCl)[C@@H](c1nc(-c2cc(F)ccc2F)cn1Cc1ccccc1)C(C)(C)C]

373.4 mg (0.73 mmol) of tert-butyl [3-({(1R)-1-[1-benzyl-4-(2,5-difluorophenyl)-1H-imidazol-2-yl]-2,2-dimethylpropyl}amino)propyl]carbamate (Intermediate C15) were initially charged in 5.0 ml of dichloromethane, and 169.5 mg (1.68 mmol) of triethylamine and 181.0 mg (1.60 mmol) of chloroacetyl chloride were added. The reaction mixture was stirred at RT overnight, ethyl acetate was then added and the mixture was extracted repeatedly with water. The organic phase was washed with sat. NaCl solution and dried over magnesium sulphate. The solvent was evaporated under reduced pressure and the residue was chromatographed on silica gel (mobile phase: dichloromethane/methanol=100:0.5). The solvents were evaporated under reduced pressure and the residue was dried under high vacuum. This gave 336.0 mg (75% of theory) of the title compound.

LC-MS (Method 1): $R_t$=1.48 min; MS (ESIpos): m/z=589 [M+H]$^+$.

Intermediate C17

9-{(1R)-1-[1-Benzyl-4-(2,5-difluorophenyl)-1H-imidazol-2-yl]-2,2-dimethylpropyl}-2,2-dimethyl-4,10-dioxo-3,15,18,21,24-pentaoxa-12-thia-5,9-diazaheptacosan-27-oic acid

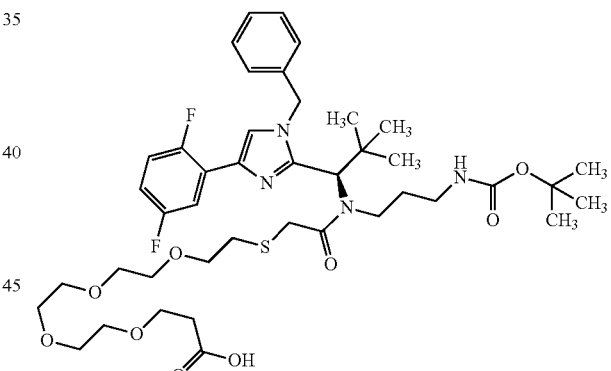

50.0 mg (0.09 mmol) of tert-butyl {3-[{(1R)-1-[1-benzyl-4-(2,5-difluorophenyl)-1H-imidazol-2-yl]-2,2-dimethylpropyl}(chloracetyl)amino]propyl}carbamate (Intermediate C16) were initially charged in 2.0 ml of DMF, and 69.1 mg (0.21 mmol) of caesium carbonate and 28.8 mg (0.10 mmol) of 1-sulphanyl-3,6,9,12-tetraoxapentadecan-15-oic acid were added. The mixture was stirred at 50° C. overnight. Water was added and the reaction mixture was purified directly by preparative RP-HPLC (column: Reprosil 250× 30; 10µ, flow rate: 50 ml/min, MeCN/water). The solvents were evaporated under reduced pressure and the residue was dried under high vacuum. This gave 25.1 mg (35% of theory) of the title compound.

LC-MS (Method 1): $R_t$=1.42 min; MS (ESIpos): m/z=835 [M+H]$^+$.

Intermediate C18 tert-Butyl [22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazapentacosan-25-yl] carbamate

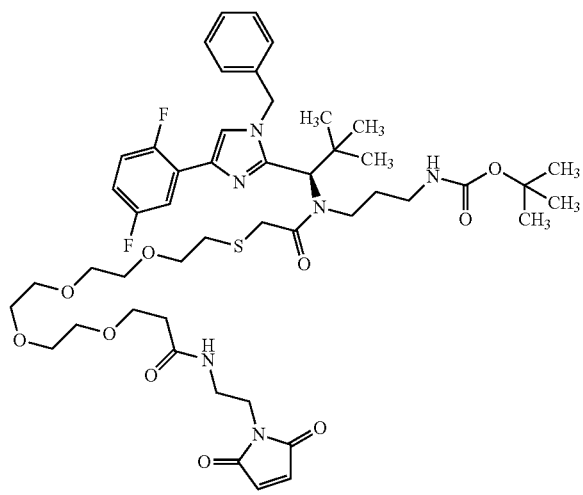 [SMILES: CC(C)(C)OC(=O)NCCCN(C(=O)CSCCOCCOCCOCCOCCC(=O)NCCN1C(=O)C=CC1=O)[C@@H](c1nc(-c2cc(F)ccc2F)cn1Cc1ccccc1)C(C)(C)C]

21.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3,15,18,21,24-pentaoxa-12-thia-5,9-diazaheptacosan-27-oic acid (Intermediate C17) and 5.8 mg (0.0.3 mmol) of 1-(2-aminoethyl)-1H-pyrrole-2,5-dione hydrochloride (1:1) were initially charged in 1.0 ml of acetonitrile, and 26.1 mg (0.20 mmol) of N,N-diisopropylethylamine and 20.9 mg (0.03 mmol) of T3P (50% in ethyl acetate) were added. The mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 19.7 mg (79% of theory) of the title compound.

LC-MS (Method 1): $R_t$=1.42 min; MS (ESIpos): m/z=835 [M+H]$^+$.

Intermediate C19 tert-Butyl (13-{(1R)-1-[1-benzyl-4-(2,5-difluorophenyl)-1H-imidazol-2-yl]-2,2-dimethylpropyl}-2,2-dimethyl-6,12-dioxo-5-oxa-10-thia-7,13-diaza-2-silahexadecan-16-yl)carbamate

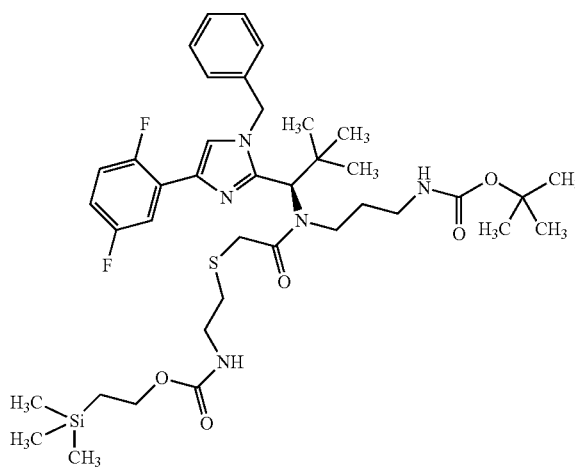 [SMILES: CC(C)(C)OC(=O)NCCCN(C(=O)CSCCNC(=O)OCC[Si](C)(C)C)[C@@H](c1nc(-c2cc(F)ccc2F)cn1Cc1ccccc1)C(C)(C)C]

58.5 mg (0.10 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate (Intermediate C16) were initially charged in 2.0 ml of DMF, and 44.0 mg (0.20 mmol) of 2-(trimethylsilyl)ethyl (2-sulphanylethyl) carbamate (Intermediate L39) and 64.7 mg (0.20 mmol) of caesium carbonate were added. The mixture was stirred at 50° C. for 4 h. The reaction was repeated with 46.6 mg (0.079 mmol) of Intermediate C16. The two reaction mixtures were combined and purified directly by preparative RP-HPLC (column: Reprosil 250×30; 10μ, flow rate: 50 ml/min, MeCN/water). The solvents were evaporated under reduced pressure and the residue was dried under high vacuum. This gave 98.0 mg (71% of theory) of the title compound.

LC-MS (Method 1): $R_t$=1.62 min; MS (ESIpos): m/z=774 [M+H]$^+$.

Intermediate C20

Trifluoroacetic acid/tert-butyl [3-({[(2-aminoethyl)sulphanyl]acetyl}{(1R)-1-[1-benzyl-4-(2,5-difluorophenyl)-1H-imidazol-2-yl]-2,2-dimethylpropyl}amino)propyl]carbamate

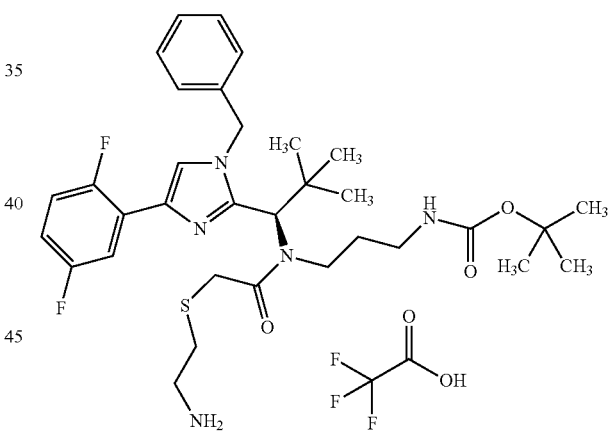

98.0 mg (0.13 mmol) of tert-butyl (13-{(1R)-1-[1-benzyl-4-(2,5-difluorophenyl)-1H-imidazol-2-yl]-2,2-dimethylpropyl}-2,2-dimethyl-6,12-dioxo-5-oxa-10-thia-7,13-diaza-2-silahexadecan-16-yl)carbamate (Intermediate C19) were initially charged in 2.0 ml of DMF/tert-butanol (9:1), and 96.2 mg (0.63 mmol) of CsF were added. The mixture was stirred at 90° C. for 16 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 57.1 mg (61% of theory) of the title compound. The compound also comprises the corresponding sulphoxide.

LC-MS (Method 1): $R_t$=1.08 min; MS (ESIpos): m/z=630 [M+H]$^+$.

Intermediate C21 tert-Butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-3,31,37-trioxo-7,10,13,16,19,22,25,28-octaoxa-35-thia-4,32,38-triazahentetracontan-41-yl]carbamate

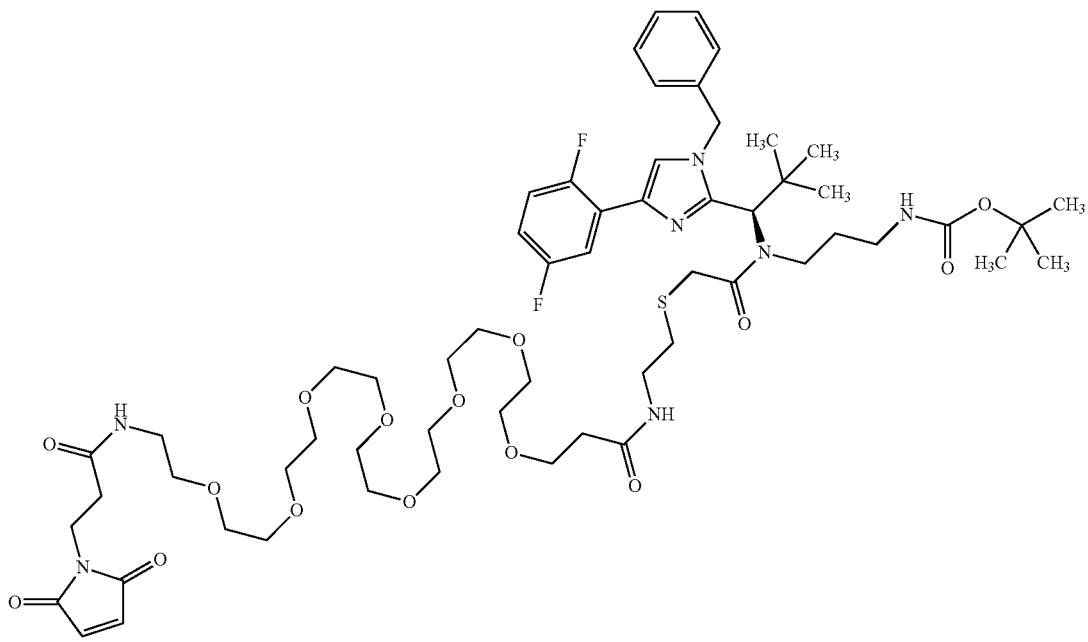 [SMILES: CC(C)(C)OC(=O)NCCCN(C(=O)CSCCNC(=O)CCOCCOCCOCCOCCOCCOCCOCCOCCNC(=O)CCN1C(=O)C=CC1=O)[C@@H](c1nc(-c2cc(F)ccc2F)cn1Cc1ccccc1)C(C)(C)C]

57.1 mg (0.08 mmol) of trifluoroacetic acid/tert-butyl [3-({[(2-aminoethyl)sulphanyl]acetyl}{(1R)-1-[1-benzyl-4-(2,5-difluorophenyl)-1H-imidazol-2-yl]-2,2-dimethylpropyl}amino)propyl]carbamate (Intermediate C20) were initially charged in 3.0 ml of DMF, and 53.0 mg (0.08 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 15.5 mg (0.15 mmol) of triethylamine were added. The mixture was stirred at RT for 16 h. The reaction mixture was purified directly by preparative RP-HPLC (column: Reprosil 250× 30; 10μ, flow rate: 50 ml/min, MeCN/water). The solvents were evaporated under reduced pressure and the residue was lyophilized. This gave 49.7 mg (49% of theory) of the title compound.

LC-MS (Method 1): $R_t$=1.34 min; MS (ESIpos): m/z=1204 [M+H]$^+$.

Intermediate C22 tert-Butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-35-oxido-3,31,37-trioxo-7,10,13,16,19,22,25,28-octaoxa-35lambda4-thia-4,32,38-triazahentetracontan-41-yl]carbamate

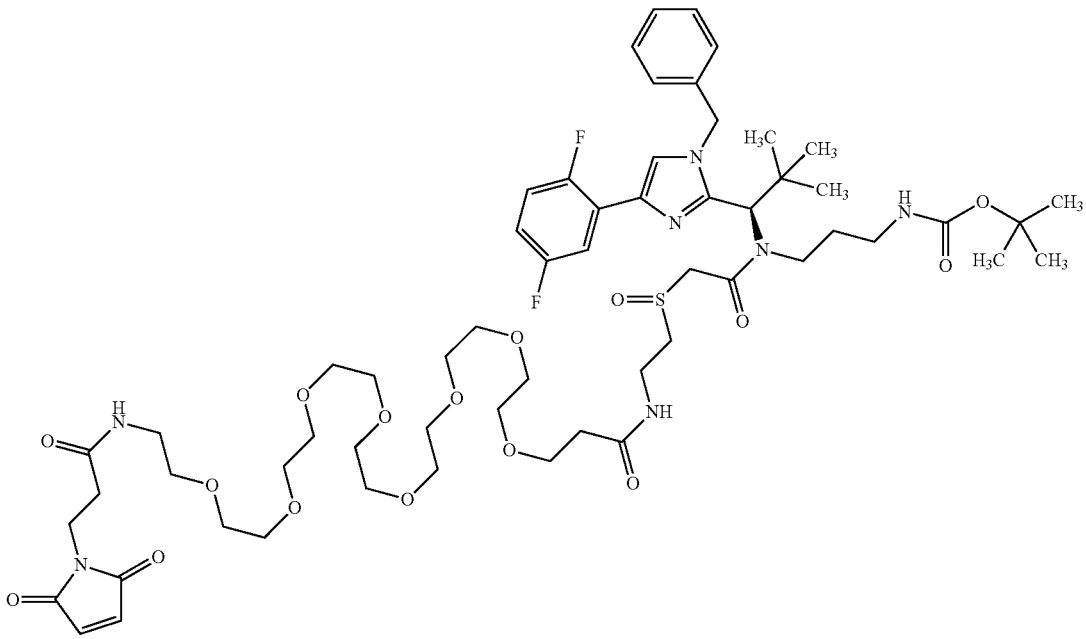 [SMILES: CC(C)(C)OC(=O)NCCCN(C(=O)CS(=O)CCNC(=O)CCOCCOCCOCCOCCOCCOCCOCCOCCNC(=O)CCN1C(=O)C=CC1=O)[C@@H](c1nc(-c2cc(F)ccc2F)cn1Cc1ccccc1)C(C)(C)C]

The title compound was formed as a by-product in the synthesis of Intermediate C21. This gave 15.5 mg (15% of theory) of the title compound.

LC-MS (Method 1): $R_t$=1.25 min; MS (ESIpos): m/z=1220 [M+H]$^+$.

Intermediate C23 tert-Butyl 3-amino-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate Mixture of Stereoisomers.

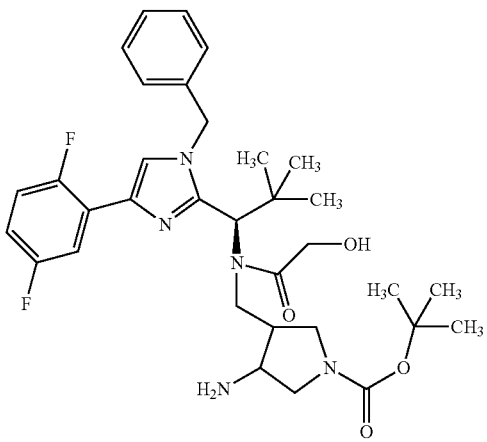 [SMILES: CC(C)(C)OC(=O)N1CC(N)C(CN(C(=O)CO)[C@@H](c2nc(-c3cc(F)ccc3F)cn2Cc2ccccc2)C(C)(C)C)C1]

411.2 mg (1.15 mmol) of tert-butyl 3-formyl-4-({[2-(trimethylsilyl)ethoxy]carbonyl}amino)pyrrolidine-1-carboxylate (Intermediate L28) and 339.7 mg (0.96 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were initially charged in 6.0 ml of dichloromethane, and 68.9 mg (1.15 mmol) of HOAc were added and the mixture was stirred at RT for 1 h. 405.2 mg (1.91 mmol) of sodium triacetoxyborohydride were added and the mixture was stirred at RT for 2 h. The solvent was evaporated under reduced pressure and ethyl acetate and water were added to the residue. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 40 ml/min, petroleum ether/ethyl acetate). The solvents were evaporated under reduced pressure and the residue was dried under high vacuum. This gave 541.5 mg (81% of theory) of the compound tert-butyl 3-[({(1R)-1-[1-benzyl-4-(2,5-difluorophenyl)-1H-imidazol-2-yl]-2,2-dimethylpropyl}amino)methyl]-4-({[2-(trimethylsilyl)ethoxy]carbonyl}amino)pyrrolidine-1-carboxylate.

LC-MS (Method 1): $R_t$=1.24 and 1.29 min; MS (ESIpos): m/z=698 [M+H]$^+$.

541.5 mg (0.78 mmol) of tert-butyl 3-[({(1R)-1-[1-benzyl-4-(2,5-difluorophenyl)-1H-imidazol-2-yl]-2,2-dimethylpropyl}amino)methyl]-4-({[2-(trimethylsilyl)ethoxy]carbonyl}amino)pyrrolidine-1-carboxylate were dissolved in 13.0 ml of dichloromethane, and 180.6 mg (1.78 mmol) of triethylamine were added. The reaction solution was cooled to 0° C., 233.1 mg (1.71 mmol) of acetoxyacetyl chloride were added and the mixture was stirred at RT for 16 h. Another 180.6 mg (1.78 mmol) of triethylamine and 233.1 mg (1.71 mmol) of acetoxyacetyl chloride were added, and the mixture was stirred at RT for another 80 h. The solvent was evaporated under reduced pressure and the residue was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 40 ml/min, petroleum ether/ethyl acetate). The solvents were evaporated under reduced pressure and the residue was dried under high vacuum. This gave 529.2 mg (86% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[2-(trimethylsilyl)ethoxy]carbonyl}amino)pyrrolidine-1-carboxylate.

LC-MS (Method 1): $R_t$=1.53 and 1.56 min; MS (ESIpos): m/z=798 [M+H]$^+$.

529.2 mg (0.66 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[2-(trimethylsilyl)ethoxy]carbonyl}amino)pyrrolidine-1-carboxylate were initially charged in 10.0 ml of DMF/tert-butanol (9:1), and 503.7 mg (3.32 mmol) of CsF were added. The reaction mixture was stirred at 90° C. for 16 h. The reaction mixture was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified using Biotage Isolera (silica gel, column 50 g SNAP, flow rate 25 ml/min, dichloromethane/methanol). The solvents were evaporated under reduced pressure and the residue was dried under high vacuum. This gave 172.4 mg (40% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-aminopyrrolidine-1-carboxylate.

LC-MS (Method 1): $R_t$=1.05 and 1.35 min; MS (ESIpos): m/z=654 [M+H]$^+$.

172.4 mg (0.26 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-aminopyrrolidine-1-carboxylate were initially charged in 4.5 ml of methanol/water (2:1), and 80.2 mg (0.58 mmol) potassium carbonate were added and the mixture was stirred at RT for 16 h. The reaction mixture was partitioned between water and ethyl acetate. The aqueous phase was extracted three times with ethyl acetate. The combined organic phases were washed once with sat. NaCl solution and dried over magnesium sulphate. The solvent was evaporated under reduced pressure and the residue was purified by preparative RP-HPLC (column: Reprosil 250×30; 10μ, flow rate: 50 ml/min, MeCN/water). The solvents were evaporated under reduced pressure and the residue was dried under high vacuum. This gave 116.0 mg (72% of theory) of the title compound.

LC-MS (Method 1): $R_t$=1.01 min and 1.03 min; MS (ESIpos): m/z=612 [M+H]$^+$.

Intermediate C24

Trifluoroacetic acid/tert-butyl 3-(aminomethyl)-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (1:1)

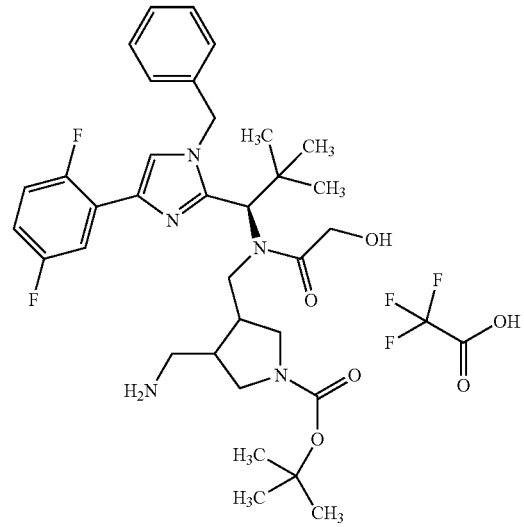

26.8 mg of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were dissolved in 3.0 ml of dichloromethane, and 5.2 mg (0.09 mmol) of HOAc and 22.4 mg (0.11 mmol) of sodium triacetoxyborohydride were added and the mixture was stirred at RT for 5 min 62.4 mg (0.09 mmol) of tert-butyl 3-formyl-4-[({[2-(trimethylsilyl)ethoxy]carbonyl}amino)methyl]pyrrolidine-1-carboxylate (Intermediate L29) were added and the mixture was stirred at RT overnight. The solvent was evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 57.6 mg (91% of theory) of the compound trifluoroacetic acid/tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate.

LC-MS (Method 1): $R_t$=1.25 and 1.27 min; MS (ESIpos): m/z=712 [M+H]$^+$.

77.0 mg (0.11 mmol) of tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate were initially charged in 1.5 ml of dichloromethane, and 21.9 mg (0.22 mmol) of triethylamine were added. At 0° C., 29.5 mg (0.22 mmol) of acetoxyacetyl chloride were then added and the reaction mixture was stirred at RT overnight. The solvent was evaporated under reduced pressure and the residue was taken up in ethyl acetate. The organic phase was washed in each case once with water, saturated sodium bicarbonate solution and sat. NaCl solution. After drying over magnesium sulphate, the solvent was evaporated under reduced pressure. The reaction was repeated with 77.0 mg (0.11 mmol) of tert-butyl 3-[({(1R)-1-[1-benzyl-4-(2,5-difluorophenyl)-1H-imidazol-2-yl]-2,2-dimethylpropyl}amino)methyl]-4-[({[2-(trimethylsilyl)ethoxy]carbonyl}amino)methyl]pyrrolidine-1-carboxylate. The combined residues were purified on silica gel (mobile phase: cyclohexane/ethyl acetate=2:1). This gave 171.1 mg (85% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-[({[2-(trimethylsilyl)ethoxy]carbonyl}amino)methyl]pyrrolidine-1-carboxylate.

LC-MS (Method 1): $R_t$=1.56 and 1.57 min; MS (ESIpos): m/z=812 [M+H]$^+$.

30.0 mg (0.04 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-[({[2-(trimethylsilyl)ethoxy]carbonyl}amino)methyl]pyrrolidine-1-carboxylate were initially charged in 0.5 ml of TBAF solution (1M in THF). The mixture was stirred at RT overnight. The solvent was evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 25.0 mg (92% of theory) of the title compound.

LC-MS (Method 1): $R_t$=0.98 min; MS (ESIpos): m/z=626 [M+H]$^+$.

Intermediate C25

4-{[{(1R)-1-[1-Benzyl-4-(2,5-difluorophenyl)-1H-imidazol-2-yl]-2,2-dimethylpropyl}(glycoloyl)amino]methyl}-1-(tert-butoxycarbonyl)pyrrolidine-3-carboxylic acid

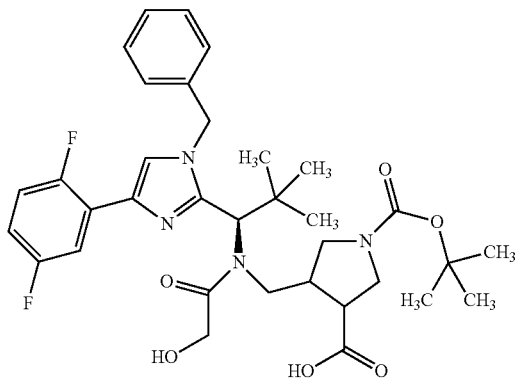 [SMILES: CC(C)(C)OC(=O)N1CC(CN(C(=O)CO)[C@@H](c2nc(-c3cc(F)ccc3F)cn2Cc2ccccc2)C(C)(C)C)C(C(=O)O)C1]

171.4 mg (0.48 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C1) were initially charged in 4.0 ml of dichloromethane, and 248.5 mg (0.72 mmol) of tert-butyl 3-({[tert-butyl(dimethyl)silyl]oxy}methyl)-4-formylpyrrolidine-1-carboxylate (Intermediate L30) and 34.8 mg (0.58 mmol) of HOAc were added. The reaction mixture was stirred at RT for 1 h. 204.4 mg (0.97 mmol) of sodium triacetoxyborohydride were added and the mixture was stirred at RT for 60 h. The solvent was removed under reduced pressure and the residue was purified using Biotage Isolera (silica gel, column 25 g SNAP, flow rate 25 ml/min, petroleum ether/ethyl acetate). The solvents were evaporated under reduced pressure and the residue was dried under high vacuum. This gave 267.0 mg (77% of theory) of the compound tert-butyl 3-[({(1R)-1-[1-benzyl-4-(2,5-difluorophenyl)-1H-imidazol-2-yl]-2,2-dimethylpropyl}amino)methyl]-4-([tert-butyl(dimethyl)silyl]oxy methyl)pyrrolidine-1-carboxylate.

LC-MS (Method 1): $R_t$=1.49 min; MS (ESIpos): m/z=683 [M+H]$^+$.

267.0 mg (0.39 mmol) of tert-butyl 3-[({(1R)-1-[1-benzyl-4-(2,5-difluorophenyl)-1H-imidazol-2-yl]-2,2-dimethylpropyl}amino)methyl]-4-({[tert-butyl(dimethyl)silyl]oxy}methyl)pyrrolidine-1-carboxylate were dissolved in 5.0 ml of dichloromethane, and 91.0 mg (0.90 mmol) of triethylamine were added and the mixture was cooled to 0° C. 117.4 mg (0.86 mmol) of acetoxyacetyl chloride were added, and the mixture was stirred at RT for 16 h. Another 593.4 mg (5.87 mmol) of triethylamine and 427.0 mg (3.13 mmol) of acetoxyacetyl chloride were added, and the mixture was stirred at RT for another 10 h. The solvent was evaporated under reduced pressure and the residue was purified by preparative RP-HPLC (column: Reprosil 250×30; 10µ, flow rate: 50 ml/min, MeCN/water). The solvents were then evaporated under reduced pressure and the residue was dried under high vacuum. This gave 216.3 mg (71% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[tert-butyl(dimethyl)silyl]oxy}methyl)pyrrolidine-1-carboxylate.

LC-MS (Method 1): $R_t$=1.70 and 1.72 min; MS (ESIpos): m/z=783 [M+H]$^+$.

216.3 mg (0.28 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-({[tert-butyl(dimethyl)silyl]oxy}methyl)pyrrolidine-1-carboxylate were initially charged in 4.0 ml of THF, and 16.6 mg (0.28 mmol) of HOAc and 361.1 mg (1.38 mmol) of TBAF solution (1M in THF) were added. The reaction solution was stirred at RT for 4 h. The solvent was evaporated under reduced pressure and the residue was purified by preparative RP-HPLC (column: Reprosil 250×30; 10µ, flow rate: 50 ml/min, MeCN/water). The solvents were then evaporated under reduced pressure and the residue was dried under high vacuum. This gave 94.0 mg (51% of theory) of the compound tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-(hydroxymethyl)pyrrolidine-1-carboxylate.

LC-MS (Method 1): $R_t$=1.34 min; MS (ESIpos): m/z=669 [M+H]$^+$.

52.0 mg (0.08 mmol) of tert-butyl 3-{[(acetoxyacetyl){(1R)-1-[1-benzyl-4-(2,5-difluorophenyl)-1H-imidazol-2-yl]-2,2-dimethylpropyl}amino]methyl}-4-(hydroxymethyl)pyrrolidine-1-carboxylate were initially charged in 4.0 ml of PBS buffer/acetonitrile (9:1), and 1.2 mg (0.01 mmol) of TEMPO were added. 14.1 mg (0.16 mmol) of sodium chlorite in 1.0 ml of water and 115.8 µl of (0.16 mmol) 10% strength sodium hypochlorite solution were then added simultaneously. The reaction mixture was stirred at RT for 16 h. The reaction mixture was poured into a 10% strength sodium sulphite solution, and ethyl acetate was added. The aqueous phase was extracted three times with ethyl acetate and the combined organic phases were washed once with saturated NaCl solution and dried over magnesium sulphate. The solvent was evaporated under reduced pressure and the residue was used for the next synthesis step without further purification.

LC-MS (Method 1): $R_t$=1.34 min; MS (ESIpos): m/z=683 [M+H]$^+$.

103.0 mg (0.15 mmol) of 4-{[(acetoxyacetyl){(1R)-1-[1-benzyl-4-(2,5-difluorophenyl)-1H-imidazol-2-yl]-2,2-dimethylpropyl}amino]methyl}-1-(tert-butoxycarbonyl)pyrrolidin-3-carboxylic acid were initially charged in 4.5 ml of methanol/water (2:1), and 45.9 mg (0.33 mmol) potassium carbonate were added and the mixture was stirred at RT for 3 h. The reaction mixture was partitioned between water and ethyl acetate. The aqueous phase was extracted three times with ethyl acetate and the combined organic phases were washed once with saturated NaCl solution and dried over magnesium sulphate. The solvent was evaporated under reduced pressure and the title compound was used for the next synthesis step without further purification.

LC-MS (Method 1): $R_t$=1.35 min; MS (ESIpos): m/z=641 [M+H]$^+$.

Intermediate C26 tert-Butyl [3-({(1R)-1-[1-benzyl-4-(2,5-difluorophenyl)-1H-imidazol-2-yl]-2,2-dimethylpropyl}amino)-2-({[tert-butyl(dimethyl)silyl]oxy}methyl)propyl]carbamate

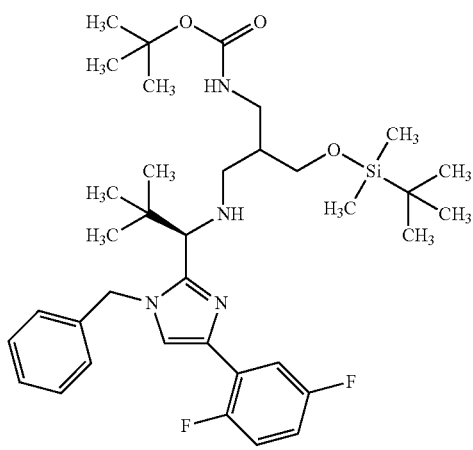 [SMILES: CC(C)(C)OC(=O)NCC(CN[C@@H](c1nc(-c2cc(F)ccc2F)cn1Cc1ccccc1)C(C)(C)C)CO[Si](C)(C)C(C)(C)C]

590 mg (1.69 mmol) of sodium triacetoxyborohydride and 155 µl (2.70 mmol, 162 mg) of acetic acid were initially charged in 30 ml of dichloromethane, and the mixture was stirred at RT for 30 min 600 mg (1.687 mmol) of (1R)-1-[1-benzyl-4-(2,5-difluorophenyl)-1H-imidazol-2-yl]-2,2-dimethylpropan-1-amine (obtained from trifluoroacetic acid/(1R)-1-[1-benzyl-4-(2,5-difluorophenyl)-1H-imidazol-2-yl]-2,2-dimethylpropan-1-amine (1:1) by extraction with 1N aqueous sodium hydroxide solution) and 750 mg (2.362 mmol) of tert-butyl (3-{[tert-butyl(dimethyl)silyl]oxy}-2-formylpropyl)carbamate dissolved in 40 ml of dichloromethane were then added dropwise. The mixture was stirred at RT for 2 h. Ethyl acetate was then added, the mixture was washed with saturated sodium carbonate solution and the organic phase was concentrated. The residue was separated by preparative HPLC (mobile phase: ACN/water, gradient). This gave 510 mg (46% of theory) of the target compound as a diastereomer mixture.

Isomer 1:
LC-MS (Method 1): $R_t$=1.36 min (51%); MS (EIpos): m/z=657 [M+H]$^+$.
Isomer 2:
LC-MS (Method 1): $R_t$=1.41 min (49%); MS (EIpos): m/z=657 [M+H]$^+$.

Intermediate C27

2-({(1R)-1-[1-Benzyl-4-(2,5-difluorophenyl)-1H-imidazol-2-yl]-2,2-dimethylpropyl}{3-[(tert-butoxycarbonyl)amino]-2-({[tert-butyl(dimethyl)silyl]oxy}methyl)propyl}amino)-2-oxoethyl acetate

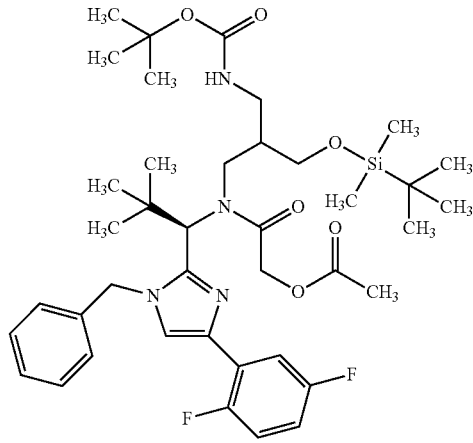 [SMILES: CC(=O)OCC(=O)N(CC(CNC(=O)OC(C)(C)C)CO[Si](C)(C)C(C)(C)C)[C@@H](c1nc(-c2cc(F)ccc2F)cn1Cc1ccccc1)C(C)(C)C]

510 mg (0,776 mmol) of tert-butyl [3-({(1R)-1-[1-benzyl-4-(2,5-difluorophenyl)-1H-imidazol-2-yl]-2,2-dimethylpropyl}amino)-2-({[tert-butyl(dimethyl)silyl]oxy}methyl)propyl]carbamate were initially charged in 30 ml of dichloromethane, and 181 mg (249 µl, 1.786 mmol) of triethylamine and 219 mg (1.553 mmol) of 2-chloro-2-oxoethyl acetate were added. The reaction mixture was stirred at RT for 2 h and then washed with saturated sodium bicarbonate solution. The organic phase was dried over sodium sulfate and concentrated on a rotary evaporator. The residue was separated by preparative HPLC (mobile phase: ACN/water, gradient). This gave 290 mg (49% of theory) of the target compound as an epimer mixture.

Isomer 1:
LC-MS (Method 1): $R_t$=1.70 min; MS (EIpos): m/z=757 [M+H]$^+$.
Isomer 2:
LC-MS (Method 1): $R_t$=1.72 min; MS (EIpos): m/z=757 [M+H]$^+$.

Intermediate C28

2-({(1R)-1-[1-Benzyl-4-(2,5-difluorophenyl)-1H-imidazol-2-yl]-2,2-dimethylpropyl}{3-[(tert-butoxycarbonyl)amino]-2-(hydroxymethyl)propyl}amino)-2-oxoethyl acetate

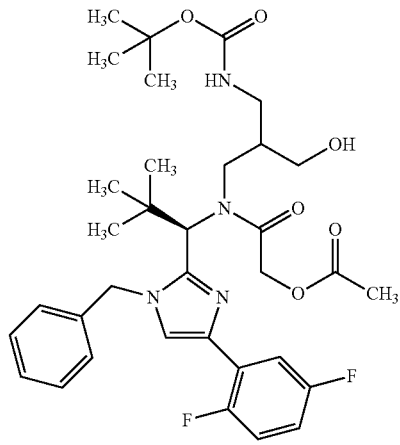 [SMILES: CC(=O)OCC(=O)N(CC(CO)CNC(=O)OC(C)(C)C)[C@@H](c1nc(-c2cc(F)ccc2F)cn1Cc1ccccc1)C(C)(C)C]

285 mg (0.376 mmol) of 2-({(1R)-1-[1-benzyl-4-(2,5-difluorophenyl)-1H-imidazol-2-yl]-2,2-dimethylpropyl}{3-[(tert-butoxycarbonyl)amino]-2-({[tert-butyl(dimethyl)silyl]oxy}methyl)propyl}amino)-2-oxoethyl acetate were dissolved in 5 ml of THF. 452 µl (0.452 mmol) of a 1 M solution of tetra-n-butylammonium fluoride in THF were added, and the reaction mixture was stirred at RT for 3 h. The reaction mixture was separated by preparative HPLC (mobile phase: ACN/water, gradient) and lyophilized. This gave 214 mg (81% of theory, purity according to LC/MS=92%) of the target compound as an epimer mixture.
Isomer 1:
LC-MS (Method 1): $R_t$=1.37 min; MS (EIpos): m/z=643 [M+H]$^+$.
Isomer 2:
LC-MS (Method 1): $R_t$=1.40 min; MS (EIpos): m/z=643 [M+H]$^+$.

Intermediate C29

2-([3-(Acetylsulphanyl)-2-{[(tert-butoxycarbonyl)amino]methyl}propyl]{(1R)-1-[1-benzyl-4-(2,5-difluorophenyl)-1H-imidazol-2-yl]-2,2-dimethylpropyl}amino)-2-oxoethyl acetate

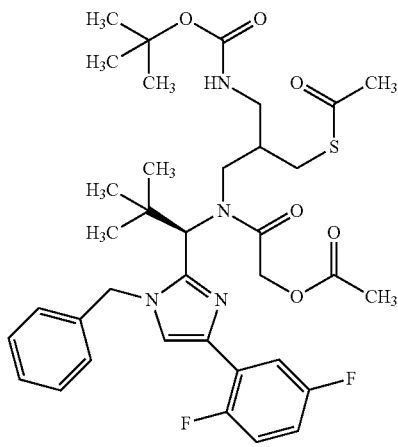 [SMILES: CC(=O)OCC(=O)N(CC(CNC(=O)OC(C)(C)C)CSC(C)=O)[C@@H](c1nc(-c2cc(F)ccc2F)cn1Cc1ccccc1)C(C)(C)C]

210 mg (0.301 mmol) of 2-({(1R)-1-[1-benzyl-4-(2,5-difluorophenyl)-1H-imidazol-2-yl]-2,2-dimethylpropyl}{3-[(tert-butoxycarbonyl)amino]-2-(hydroxymethyl)propyl}amino)-2-oxoethyl acetate were initially charged in 8 ml of absolute THF, 178 mg (1.503 mmol, 109 µl) of thionyl chloride dissolved in 8 ml of absolute THF were added dropwise at RT and the mixture was stirred at RT for 40 min. The reaction mixture was concentrated on a rotary evaporator and dried under high vacuum. The residue was taken up in 16 ml of absolute DMF, 172 mg (1.503 mmol) of potassium thioacetate and 133 mg (0.361 mmol) of tetra-n-butylammonium iodide were added and the mixture was stirred at 90° C. for 2 h. After cooling, water was added and the mixture was extracted with ethyl acetate. The organic phase was concentrated on a rotary evaporator and the residue was purified by preparative HPLC (mobile phase: ACN/water, gradient) and lyophilized. This gave 155 mg (69% of theory, purity according to LC/MS=94%) of the target compound as an epimer mixture.
Isomer 1:
LC-MS (Method 1): $R_t$=1.50 min; MS (EIpos): m/z=701 [M+H]$^+$.
Isomer 2:
LC-MS (Method 1): $R_t$=1.51 min; MS (EIpos): m/z=701 [M+H]$^+$.

Intermediate C30

Di-tert-butyl [disulphanediylbis(2-{[{(1R)-1-[1-benzyl-4-(2,5-difluorophenyl)-1H-imidazol-2-yl]-2,2-dimethylpropyl}(glycoloyl)amino]methyl}propan-3,1-diyl)]biscarbamate

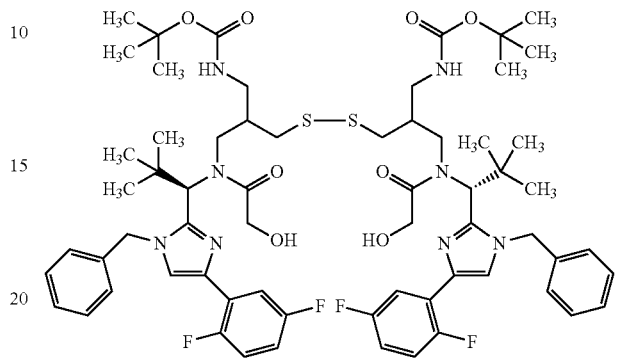

1.220 g (1.010 mmol, purity according to LC/MS=58%) of 2-([3-(acetylsulphanyl)-2-{[(tert-butoxycarbonyl)amino]methyl}propyl]{(1R)-1-[1-benzyl-4-(2,5-difluorophenyl)-1H-imidazol-2-yl]-2,2-dimethylpropyl}amino)-2-oxoethyl acetate were initially charged in 30 ml of THF and 30 ml of methanol, 10 ml of a 1 N aqueous sodium hydroxide solution were added and the mixture was stirred at RT for 2 h. Water was added and the reaction mixture was extracted with dichloromethane. The organic phase was dried over sodium sulfate and concentrated on a rotary evaporator. The residue was purified by preparative HPLC (mobile phase: ACN/water, gradient). This gave 390 mg (54% of theory, purity according to LC/MS=86%) of the target compound as a diastereomer mixture.
Isomers:
LC-MS (Method 1): $R_t$=1.81 min; MS (EIpos): m/z=1232 [M+H]$^+$.

Intermediate C31 tert-Butyl 3-[{(1R)-1-[1-benzyl-4-(2,5-difluorophenyl)-1H-imidazol-2-yl]-2,2-dimethylpropyl}(glycoloyl)amino]-2-(sulphanylmethyl)propyl}carbamate

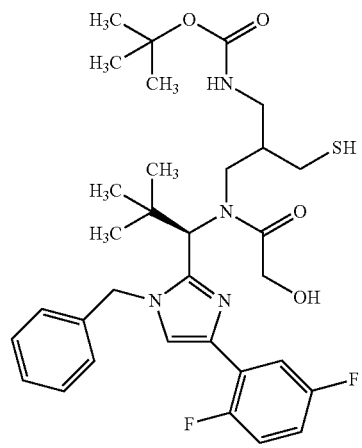 [SMILES: CC(C)(C)OC(=O)NCC(CS)CN(C(=O)CO)[C@@H](c1nc(-c2cc(F)ccc2F)cn1Cc1ccccc1)C(C)(C)C]

390 mg (0.272 mmol, purity according to LC/MS=86%) of di-tert-butyl [disulphanediylbis(2-{[{(1R)-1-[1-benzyl-4-(2,5-difluorophenyl)-1H-imidazol-2-yl]-2,2-dimethylpropyl}(glycoloyl)amino]methyl}propan-3,1-diyl)]biscarbamate were taken up in 20 ml of 1,4-dioxane and 10 ml of PBS buffer, and 234 mg (0.817 mmol) of 3,3',3"-phosphanetriyltripropanoic acid hydrochloride (1:1) were added. The mixture was stirred at RT for 16 h. The reaction mixture was then concentrated on a rotary evaporator and triturated with dichloromethane, and the filtrate was concentrated and dried under high vacuum. The residue was dissolved in 8 ml of isopropanol and purified by chiral chromatography (column: 250×30 mm filled with Daicel Chiralpak AZ-H, mobile phase: isohexane/isopropanol=90:10). This gave two fractions of the target compound. Fraction 1 contained 181.2 mg (50% of theory) of Isomer 1 and fraction 2 yielded 90.2 mg (25% of theory) of Isomer 2.

Isomer 1:
Chiral HPLC (column: 250×4.6 mm, filled with Diacel Chiralpak AZ-H, mobile phase: isohexane. ethanol 90:10): $R_t$=6.98 min
LC-MS (Method 1): $R_t$=1.47 min; MS (EIpos): m/z=617 [M+H]$^+$.

Isomer 2:
Chiral HPLC (column: 250×4.6 mm, filled with Diacel Chiralpak AZ-H, mobile phase: isohexane. ethanol 90:10): $R_t$=9.39 min
LC-MS (Method 1): $R_t$=1.47 min; MS (EIpos): m/z=617 [M+H]$^+$.

Intermediate C32

N-[3-Amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1)

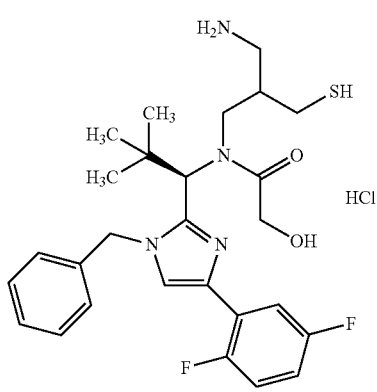 [SMILES: CC(C)(C)[C@H](c1nc(-c2cc(F)ccc2F)cn1Cc1ccccc1)N(CC(CN)CS)C(=O)CO ; Cl]

123 mg (199.42 µmol) of tert-butyl {3-[{(1R)-1-[1-benzyl-4-(2,5-difluorophenyl)-1H-imidazol-2-yl]-2,2-dimethylpropyl}(glycoloyl)amino]-2-(sulphanylmethyl)propyl}carbamate (Isomer 1) were dissolved in 2 ml of THF and stirred with 10 ml of semiconcentrated hydrochloric acid at RT for 1 h. The reaction solution was degassed under argon and then lyophilized. This gave 108 mg (98% of theory) of the target compound.

Isomer 1
LC-MS (Method 1): $R_t$=0.95 min; MS (EIpos): m/z=517 [M+H]$^+$.

Intermediate C33

N-[3-Amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2)

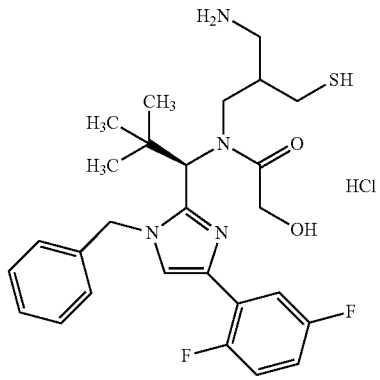 [SMILES: CC(C)(C)[C@H](c1nc(-c2cc(F)ccc2F)cn1Cc1ccccc1)N(CC(CN)CS)C(=O)CO ; Cl]

123 mg (199.42 µmol) of tert-butyl {3-[{(1R)-1-[1-benzyl-4-(2,5-difluorophenyl)-1H-imidazol-2-yl]-2,2-dimethylpropyl}(glycoloyl)amino]-2-(sulphanylmethyl)propy}carbamate (Isomer 2) were dissolved in 2 ml of THF and stirred with 10 ml of semiconcentrated hydrochloric acid at RT for 1 h. The reaction solution was degassed under argon and then lyophilized. This gave 58 mg (63% of theory, purity according to LC/MS=91%) of the target compound.

Isomer 2
LC-MS (METHOD 1): $R_t$=0.97 min; MS (ESIpos): m/z=517 [M+H]$^+$.

Intermediate C34 tert-Butyl [3-({(1R)-1-[1-benzyl-4-(2,5-difluorophenyl)-1H-imidazol-2-yl]-2,2-dimethylpropyl}amino)propyl]carbamate

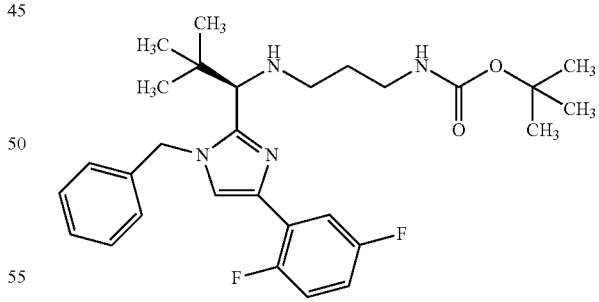

3.790 g (10.02 mmol) of (1R)-1-[1-benzyl-4-(2,5-difluorophenyl)-1H-imidazol-2-yl]-2,2-dimethylpropan-1-amine (obtained from trifluoroacetic acid/(1R)-1-[1-benzyl-4-(2,5-difluorophenyl)-1H-imidazol-2-yl]-2,2-dimethylpropan-1-amine (1:1) by extraction with 1N aqueous sodium hydroxide solution), 3.186 g (15.04 mmol) of sodium triacetoxyborohydride and 690 µl (12.03 mmol, 722 mg) were initially charged in 100 ml of dichloromethane. The mixture was stirred at RT for 5 min 4.687 g (27.06 mmol) of tert-butyl (3-oxopropyl)carbamate were then added, and the mixture was stirred at RT for 16 h. The reaction mixture was diluted with dichloromethane and washed with saturated sodium bicarbonate solution. The organic phase was dried over sodium sulphate and concentrated on a rotary evaporator. The residue was purified by chromatography on silica gel (mobile phase: dichloromethane/ethyl acetate, gradient=4:1→1:1). This gave 2.57 g (48% of theory, purity according to LC/MS=96%) of the target compound.

LC-MS (Method 1): $R_t$=1.00 min; MS (EIpos): m/z=513 [M+H]$^+$.

Intermediate C35 tert-Butyl {3-[{(1R)-1-[1-benzyl-4-(2,5-difluorophenyl)-1H-imidazol-2-yl]-2,2-dimethylpropyl}(4-nitrobenzoyl)amino]propyl}carbamate

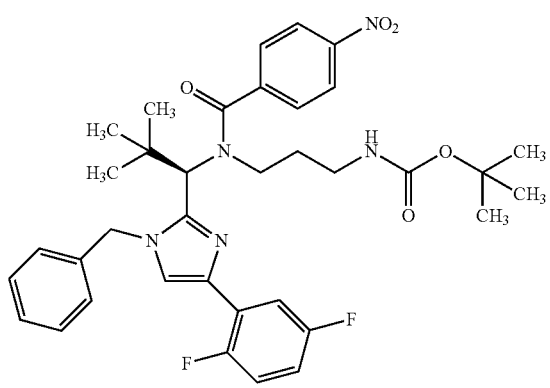 [SMILES: CC(C)(C)OC(=O)NCCCN(C(=O)c1ccc([N+](=O)[O-])cc1)[C@@H](c1nc(-c2cc(F)ccc2F)cn1Cc1ccccc1)C(C)(C)C]

200 mg (0.38 mmol) of tert-butyl [3-({(1R)-1-[1-benzyl-4-(2,5-difluorophenyl)-1H-imidazol-2-yl]-2,2-dimethylpropyl}amino)propyl]carbamate were initially charged in 9 ml of absolute dichloromethane, and 120 μl (0.86 mmol, 87 mg) of triethylamine were added at RT. At RT, 83 mg (0.45 mmol) of 4-nitrobenzoyl chloride dissolved in 1 ml of absolute dichloromethane were added dropwise, and the mixture was stirred at RT for 1 h. Water was added, and the mixture was concentrated on a rotary evaporator. The residue was purified by preparative HPLC (mobile phase: ACN/water+0.1% TFA, gradient) and dried. This gave 181 mg (73% of theory) of the target compound.

LC-MS (Method 1): $R_t$=1.47 min; MS (EIpos): m/z=662 [M+H]$^+$.

Intermediate C36 tert-Butyl {3-[(4-aminobenzoyl){(1R)-1-[1-benzyl-4-(2,5-difluorophenyl)-1H-imidazol-2-yl]-2,2-dimethylpropyl}amino]propyl}carbamate

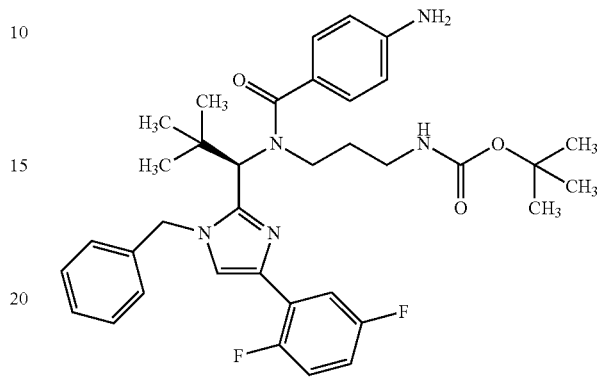

170 mg (0.26 mmol) of tert-butyl {3-[{(1R)-1-[1-benzyl-4-(2,5-difluorophenyl)-1H-imidazol-2-yl]-2,2-dimethylpropyl}(4-nitrobenzoyl)amino]propyl}carbamate were initially charged in 10 ml of acetic acid. 143 mg (2.57 mmol) of iron powder were added, and the mixture was stirred at 50° C. for 16 h. After cooling, water was added and the mixture was extracted with ethyl acetate. The organic phase was dried over sodium sulphate and concentrated on a rotary evaporator. The residue was dried under HV. This gave 154 mg (77% of theory, purity according to LC/MS=82%) of the target compound.

LC-MS (Method 5): $R_t$=4.73 min; MS (EIpos): m/z=632 [M+H]$^+$.

Intermediate C37

N-[19-(2,5-Dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-imidazol-2-yl]-2,2-dimethylpropyl}{3-[(tert-butoxycarbonyl)amino]propyl}carbamoyl)phenyl]-L-alaninamide

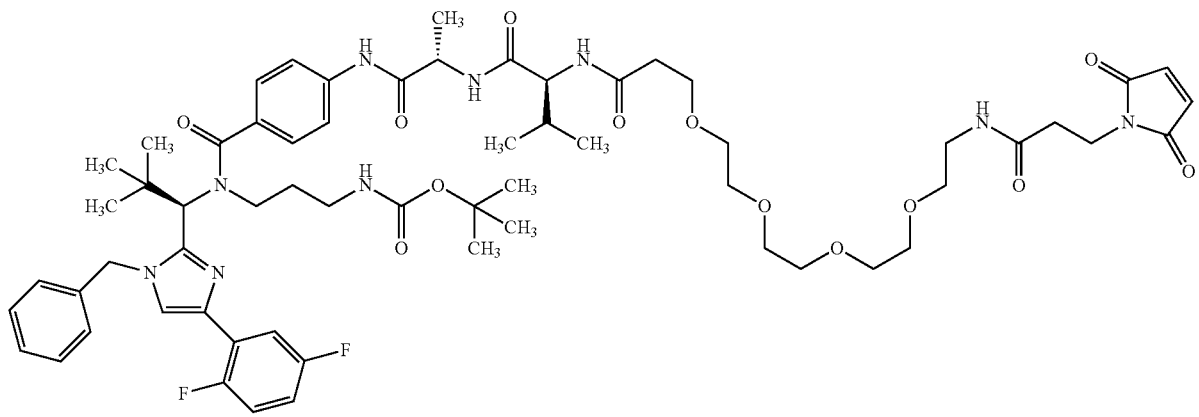 [SMILES: CC(C)[C@H](NC(=O)CCOCCOCCOCCOCCNC(=O)CCN1C(=O)C=CC1=O)C(=O)N[C@@H](C)C(=O)Nc1ccc(C(=O)N(CCCNC(=O)OC(C)(C)C)[C@@H](c2nc(-c3cc(F)ccc3F)cn2Cc2ccccc2)C(C)(C)C)cc1]

38.6 mg (0.05 mmol, LC/MS purity=82%) of tert-butyl {3-[(4-aminobenzoyl){(1R)-1-[1-benzyl-4-(2,5-difluorophenyl)-1H-imidazol-2-yl]-2,2-dimethylpropyl}amino]propyl}carbamate were dissolved in absolute DMF, and 24.8 mg (0.06 mmol) of HATU and 13.0 mg (0.10 mmol) of N,N-diisopropylethylamine were added. The mixture was stirred at RT for 5 min, 63 mg (0.06 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine were added and the mixture was stirred at RT for 3 h. 7.5 mg (0.06 mmol) of 3H-[1,2,3]triazolo[4,5-b]pyridin-3-ol (HOAt) were added, and the mixture was stirred for 16 h. 19.1 mg (0.05 mmol) of HATU were added, and the mixture was stirred at 50° C. for 2 h. After cooling, the reaction mixture was purified directly by preparative HPLC (mobile phase: ACN/water+0.1% TFA, gradient). This gave 6.5 mg (9% of theory, purity according to LC/MS=83%) of the target compound.

LC-MS (Method 2): $R_t$=7.89 min; MS (EIpos): m/z=1200.6 $[M+H]^+$.

Intermediate C38

2-[3-({(1R)-1-[1-Benzyl-4-(2,5-difluorophenyl)-1H-imidazol-2-yl]-2,2-dimethylpropyl}amino)propyl]-1H-isoindole-1,3(2H)-dione

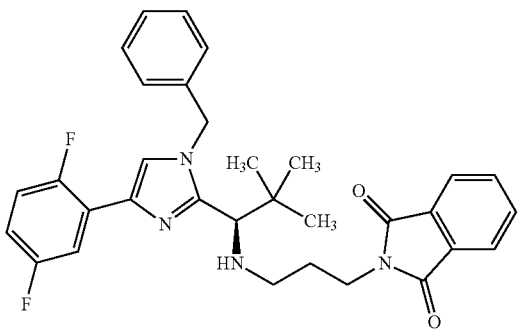 [SMILES: CC(C)(C)[C@@H](NCCCN1C(=O)c2ccccc2C1=O)c1nc(-c2cc(F)ccc2F)cn1Cc1ccccc1]

300.0 mg (0.84 mmol) of 2-[3-({(1R)-1-[1-benzyl-4-(2,5-difluorophenyl)-1H-imidazol-2-yl]-2,2-dimethylpropyl}amino)propyl]-1H-isoindole-1,3(2H)-dione (Intermediate C1) were initially charged in 4.0 ml of dichloromethane, and 58.3 mg (0.97 mmol) of HOAc and 250.4 mg (1.18 mmol) of sodium triacetoxyborohydride were added and the mixture was stirred at RT for 5 min 197.2 mg (0.97 mmol) of 3-(1,3-dioxo-1,3-dihydro-2H-isoindol-2-yl)propanal were added. The reaction mixture was stirred at RT overnight. The reaction mixture was diluted with ethyl acetate and the organic phase washed twice with saturated sodium carbonate solution and once with saturated NaCl solution. After drying over magnesium sulphate, the solvent was evaporated under reduced pressure and the residue was purified on silica gel (mobile phase: ethyl acetate/cyclohexane 1:5). The solvents were evaporated under reduced pressure and the residue was dried under high vacuum. This gave 333.3 mg (70%) of the title compound.

LC-MS (Method 1): $R_t$=1.05 min; MS (ESIpos): m/z=543 $[M+H]^+$.

Intermediate C39

2-({(1R)-1-[1-Benzyl-4-(2,5-difluorophenyl)-1H-imidazol-2-yl]-2,2-dimethylpropyl}[3-(1,3-dioxo-1,3-dihydro-2H-isoindol-2-yl)propyl]amino)-2-oxoethyl acetate

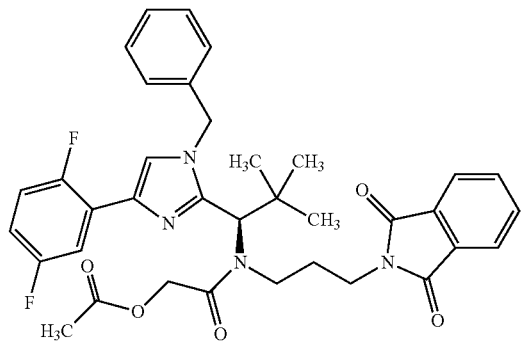 [SMILES: CC(=O)OCC(=O)N(CCCN1C(=O)c2ccccc2C1=O)[C@@H](c1nc(-c2cc(F)ccc2F)cn1Cc1ccccc1)C(C)(C)C]

332.3 mg (0.61 mmol) of 2-[3-({(1R)-1-[1-benzyl-4-(2,5-difluorophenyl)-1H-imidazol-2-yl]-2,2-dimethylpropyl}amino)propyl]-1H-isoindole-1,3(2H)-dione (Intermediate C38) were initially charged in 8.0 ml of dichloromethane, and 142.5 mg (1.35 mmol) of triethylamine were added. At 0° C., 184.0 mg (1.35 mmol) of acetoxyacetyl chloride were added, and the reaction mixture was stirred at RT overnight. The reaction mixture was diluted with ethyl acetate and the organic phase washed twice with saturated sodium bicarbonate solution and once with sat. NaCl solution. After drying over magnesium sulphate, the solvent was evaporated under reduced pressure and the residue was purified on silica gel (mobile phase: ethyl acetate/cyclohexane 1:3). The solvents were evaporated under reduced pressure and the residue was dried under high vacuum. This gave 367.1 mg (63%) of the title compound.

LC-MS (Method 1): $R_t$=1.42 min; MS (ESIpos): m/z=643 $[M+H]^+$.

Intermediate C40

N-(3-Aminopropyl)-N-{(1R)-1-[1-benzyl-4-(2,5-difluorophenyl)-1H-imidazol-2-yl]-2,2-dimethylpropyl}-2-hydroxyacetamide

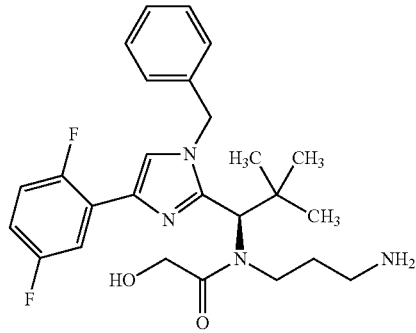 [SMILES: CC(C)(C)[C@H](c1nc(-c2cc(F)ccc2F)cn1Cc1ccccc1)N(CCCN)C(=O)CO]

583.1 mg (0.91 mmol) of 2-({(1R)-1-[1-benzyl-4-(2,5-difluorophenyl)-1H-imidazol-2-yl]-2,2-dimethylpropyl}[3-(1,3-dioxo-1,3-dihydro-2H-isoindol-2-yl)propyl]amino)-2-oxoethyl acetate (Intermediate C39) were initially charged in 15.0 ml of ethanol, and 1.41 g (18.15 mmol) of methanamine (40% in water) were added. The reaction mixture was stirred at 50° C. overnight. The solvent was evaporated under reduced pressure and the residue co-distilled three times with toluene. The residue was purified on silica gel (mobile phase: dichloromethane/methanol=100:5). The solvents were evaporated under reduced pressure and the residue was dried under high vacuum. This gave 324.9 mg (73%) of the title compound.

LC-MS (Method 1): $R_t$=0.97 min; MS (ESIpos): m/z=471 [M+H]$^+$.

Intermediate C41

Trifluoroacetic acid/L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1)

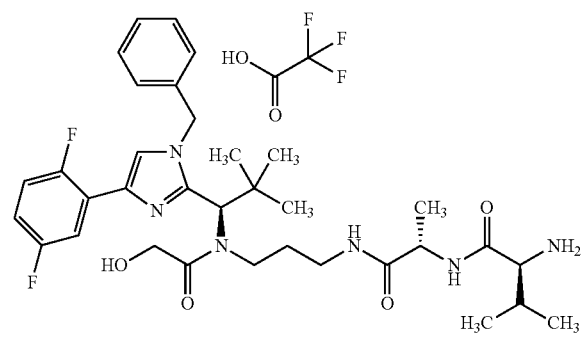

50.0 mg (0.11 mol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) and 30.4 mg (0.11 mmol) of 2,5-dioxopyrrolidin-1-yl-N-(tert-butoxycarbonyl)-L-alaninate were initially charged in 2.0 ml of DMF, and 32.2 mg (0.32 mmol) of 4-methylmorpholine were added. The reaction mixture was stirred at RT overnight. 19.1 mg (0.32 mmol) of HOAc were added, and the reaction mixture purified directly by preparative RP-HPLC (column: Reprosil 250×30; 10μ, flow rate: 50 ml/min, MeCN/water). The solvents were evaporated under reduced pressure and the residue was dried under high vacuum. This gave 38.0 mg (56%) of the compound tert-butyl [(2S)-1-({3-[{(1R)-1-[1-benzyl-4-(2,5-difluorophenyl)-1H-imidazol-2-yl]-2,2-dimethylpropyl}(glycoloyl)amino]propyl}amino)-1-oxopropan-2-yl]carbamate.

LC-MS (Method 1): $R_t$=1.26 min; MS (ESIpos): m/z=642 [M+H]$^+$.

33.6 mg (0.05 mmol) of tert-butyl [(2S)-1-({3-[{(1R)-1-[1-benzyl-4-(2,5-difluorophenyl)-1H-imidazol-2-yl]-2,2-dimethylpropyl}(glycoloyl)amino]propyl}amino)-1-oxopropan-2-yl]carbamate were initially charged in 3.0 ml of dichloromethane. 119.4 mg (1.05 mmol) of TFA were added and the reaction mixture was stirred at RT overnight. The solvent was evaporated under reduced pressure and the residue was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 32.8 mg (96%) of the compound trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1).

LC-MS (Method 1): $R_t$=0.93 min; MS (ESIpos): m/z=542 [M+H]$^+$.

29.5 mg (0.05 mmol) of trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1) and 14.1 mg (0.05 mmol) of 2,5-dioxopyrrolidin-1-yl-N-(tert-butoxycarbonyl)-L-valinate were initially charged in 1.0 ml of DMF, and 18.2 mg (0.18 mmol) of 4-methylmorpholine were added. The reaction mixture was stirred at RT overnight and purified directly by preparative RP-HPLC (column: Reprosil 250×30; 10μ, flow rate: 50 ml/min, MeCN/water). The solvents were evaporated under reduced pressure and the residue was dried under high vacuum. This gave 23.1 mg (69%) of the compound N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide LC-MS (Method 1): $R_t$=1.30 min; MS (ESIpos): m/z=741 [M+H]$^+$.

19.4 mg (0.03 mmol) of N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide were dissolved in 1.5 ml of dichloromethane, and 59.7 mg (0.52 mmol) of TFA were added. The reaction mixture was stirred at RT overnight. 119.4 mg (1.04 mmol) of TFA were added, and the mixture was once more stirred at RT overnight. The solvent was evaporated under reduced pressure and the residue was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 19.2 mg (97%) of the title compound.

LC-MS (Method 1): $R_t$=0.96 min; MS (ESIpos): m/z=641 [M+H]$^+$.

Intermediate C42

2,5-Difluorobenzenediazonium tetrafluoroborate

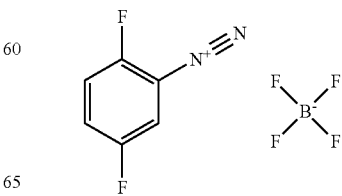

3.00 g (21.16 mmol, 2.68 ml) of boron trifluoride-diethyl ether complex were initially charged, and 1.37 g (10.58 mmol) of 2,5-difluoroaniline dissolved in 27 ml of absolute THF were slowly added dropwise at 0° C. At −10° C., a solution of 1.61 g (13.75 mmol, 1.85 ml) of isoamyl nitrite dissolved in 3 ml of absolute THF was added dropwise, and stirring was continued at the same temperature for 30 min 15 ml of diethyl ether were added and the precipitated diazonium salt was filtered off, washed with a little diethyl ether and dried under high vacuum. This gave 2.27 g of the target compound (94% of theory).

LC-MS (Method 6): $R_t$=0.24 min; MS (ESIpos): m/z=141 [M]$^+$.

$^1$H NMR (400 MHz, DMSO-d$_6$): δ [ppm]=8.11-8.17 (m, 1H), 8.36-8.43 (m, 1H), 8.69-8.73 (m, 1H).

Intermediate C43

Methyl chloro[2-(2,5-difluorophenyl)hydrazinylidene]acetate

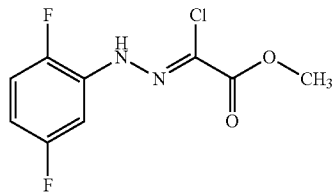 [SMILES: COC(=O)/C(Cl)=N/Nc1cc(F)ccc1F]

Under an atmosphere of argon, 3.63 g (24.13 mmol) of methyl 2-chloro-3-oxobutanoate were initially charged in 100 ml of water, and 48.90 g (618.19 mmol, 50.00 ml) of pyridine were added at −5° C. and the mixture was stirred at this temperature for 10 min t −5° C., 5.00 g (21.94 mmol) of 2,5-difluorobenzenediazonium tetrafluoroborate were then added, resulting in the formation of an orange suspension. The mixture was stirred at this temperature for 30 min and the reaction was diluted with water and extracted three times with dichloromethane. The combined organic phases were washed with saturated sodium chloride solution, dried over sodium sulphate, concentrated on a rotary evaporator and dried under high vacuum. This gave 5.52 g of the target compound (97% of theory, purity according to LC/MS=96%).

LC-MS (Method 1): $R_t$=1.03 min; MS (ESIpos): m/z=249 [M+H]$^+$.

$^1$H NMR (400 MHz, DMSO-d$_6$): δ [ppm]=3.85 (s, 3H), 6.88-6.94 (m, 1H), 7.16-7.21 (m, 1H), 7.31-7.37 (m, 1H), 10.00 (s, 1H).

Intermediate C44

Methyl 4-benzoyl-1-(2,5-difluorophenyl)-1H-pyrazole-3-carboxylate

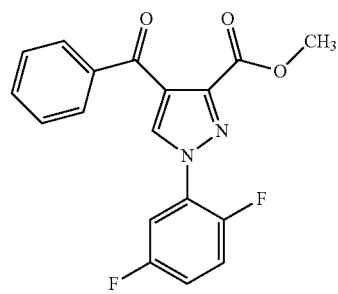 [SMILES: COC(=O)c1nn(-c2cc(F)ccc2F)cc1C(=O)c1ccccc1]

3.50 g (13.52 mmol) of methyl chloro[2-(2,5-difluorophenyl)hydrazinyliden]acetate (purity according to LC/MS 96%) were dissolved in 9 ml of absolute toluene, 2.61 g (14.87 mmol) of (2E)-3-(dimethylamino)-1-phenylprop-2-en-1-one and 3.01 g (29.73 mmol), 4.14 ml) of triethylamine were added and the mixture was stirred at room temperature for 16 h. The reaction mixture was concentrated on a rotary evaporator and the residue separated by preparative HPLC (mobile phase: ACN/water with 0.1% formic acid, gradient). This gave 1.79 g (39% of theory) of the target compound.

LC-MS (Method 1): $R_t$=1.07 min; MS (ESIpos): m/z=343 [M+H]$^+$.

$^1$H NMR (400 MHz, DMSO-d$_6$): δ [ppm]=3.86 (s, 3H), 7.44-7.50 (m, 1H), 7.55-7.72 (m, 4H), 7.81-7.87 (m, 3H), 8.80 (d, 1H).

Intermediate C45

[4-Benzyl-1-(2,5-difluorophenyl)-1H-pyrazol-3-yl]methanol

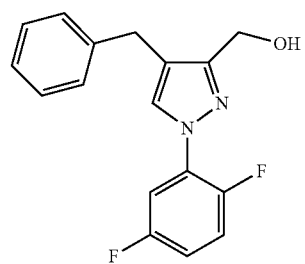 [SMILES: OCc1nn(-c2cc(F)ccc2F)cc1Cc1ccccc1]

3.18 g (8.92 mmol) of methyl 4-benzoyl-1-(2,5-difluorophenyl)-1H-pyrazole-3-carboxylate (purity according to LC/MS=96%) were initially charged in 50 ml of trifluoroacetic acid, 8.74 g (75.13 mmol, 12 ml) of triethylsilane were added dropwise and the mixture was stirred at room temperature for 1 h. The reaction mixture was concentrated on a rotary evaporator and dried under high vacuum. The residue obtained was taken up in 120 ml of absolute THF, and 2.89 g (33.63 mmol, 33.63 ml) of borane-tetrahydrofuran complex were added dropwise at 0° C. The mixture was stirred at RT overnight. Owing to the low conversion, another 12.33 ml (12.33 mmol) of a 1M lithium borohydride solution in THF were added. The mixture was stirred at room temperature for 1 h, at 60° C. for 30 min and at 80° C. for 2 h. At 0° C., the reaction was carefully quenched with 60 ml of saturated sodium bicarbonate solution. The mixture was extracted twice with in each case 100 ml of ethyl acetate, the combined organic phases were dried over sodium sulphate and concentrated on a rotary evaporator and the residue was dried under high vacuum. This gave 2.67 g (76% of theory, purity=96%) of the target compound.

LC-MS (Method 3): $R_t$=2.79 min; MS (ESIpos): m/z=329 [M+H]$^+$.

$^1$H NMR (400 MHz, DMSO-d$_6$): δ [ppm]=3.91 (s, 2H), 4.45 (d, 2H), 6.51 (s, 1H), 7.18-7.23 (m, 2H), 7.27-7.32 (m, 4H), 7.46-7.53 (m, 1H), 7.60-7.65 (m, 1H), 7.95 (d, 1H).

Intermediate C46

4-Benzyl-1-(2,5-difluorophenyl)-1H-pyrazole-3-carbaldehyde

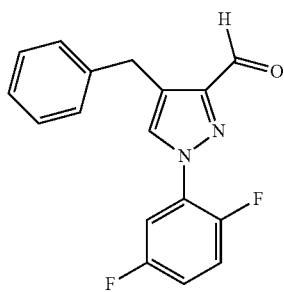 [SMILES: O=Cc1nn(-c2cc(F)ccc2F)cc1Cc1ccccc1]

2.66 g (8.50 mmol) of [4-benzyl-1-(2,5-difluorophenyl)-1H-pyrazol-3-yl]methanol (purity 96%) were dissolved in 150 ml of dichloromethane, and 4.33 g (10.20 mmol) of Dess-Martin periodinane were added a little at a time. The mixture was stirred at room temperature for 2 h, 100 ml of a semiconcentrated sodium bicarbonate solution and 100 ml of a 10% strength sodium thiosulphate solution were then added and the mixture was stirred for 20 min. The organic phase was separated off, dried over sodium sulphate and concentrated under high vacuum. This gave 2.35 g (88% of theory, purity=95%) of the target compound.

LC-MS (Method 7): $R_t$=1.49 min; MS (ESIpos): m/z=299 [M+H]$^+$.

$^1$H NMR (400 MHz, DMSO-d$_6$): δ [ppm]=4.12 (s, 2H), 7.17-7.21 (m, 1H), 7.27-7.31 (m, 4H), 7.37-7.42 (m, 1H), 7.57-7.62 (m, 1H), 7.75-7.78 (m, 1H), 8.22 (d, 1H), 10.06 (s, 1H).

Intermediate C47

(1R)-1-[4-Benzyl-1-(2,5-difluorophenyl)-1H-pyrazol-3-yl]-2,2-dimethylpropan-1-amine

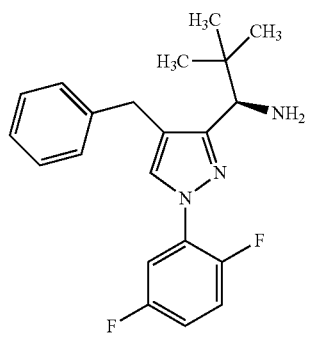 [SMILES: CC(C)(C)[C@@H](N)c1nn(-c2cc(F)ccc2F)cc1Cc1ccccc1]

2.35 g (7.56 mmol) of 4-benzyl-1-(2,5-difluorophenyl)-1H-pyrazole-3-carbaldehyde were dissolved in 25 ml of absolute THF, and 1.10 g (9.08 mmol) of (R)-(+)-2-methyl-2-propanesulphinamide and 4.73 g (16.64 mmol) of titanium (IV) isopropoxide were added. The reaction mixture was stirred at room temperature for 16 h, and 20 ml of a saturated sodium chloride solution and 30 ml of ethyl acetate were added. About 3 g of kieselguhr were then added, and the mixture was boiled under reflux for 1 h. The mixture was filtered and the organic phase was separated from the filtrate. The aqueous phase was extracted with ethyl acetate and the combined organic phases were washed with saturated sodium chloride solution, dried over sodium sulphate, concentrated on a rotary evaporator and dried under high vacuum. The residue was used further without further purification.

Under an atmosphere of argon, the residue was dissolved in 60 ml of absolute THF and cooled to −78° C., and 14.5 ml (23.24 mmol) of a solution of tert-butyllithium in pentane (c=1.6 mol/1) were added dropwise. The reaction was stirred at −78° C. for 3 h and then quenched with 5 ml of methanol and 15 ml of a saturated ammonium chloride solution. With stirring, the reaction mixture was allowed to warm to room temperature (about 30 min.). The mixture was extracted with ethyl acetate and the organic phase was extracted with saturated sodium chloride solution, concentrated on a rotary evaporator and dried under high vacuum. The residue was used further without further purification.

The residue was taken up in 30 ml of THF and 6 ml of methanol, 6 ml (24.00 mmol) of a 4N hydrogen chloride solution in dioxane were added and the mixture was stirred at room temperature for 1 h. 15 ml of saturated sodium carbonate solution were then added, and the mixture was extracted with ethyl acetate. The organic phase was separated off, concentrated on a rotary evaporator and dried under high vacuum. The residue was separated by preparative HPLC (mobile phase: ACN/water, gradient). This gave two fractions of the target compound. The first fraction yielded 1.31 g (72% of theory, LC/MS purity=97%) and the second 0.37 g (17% of theory, LC/MS purity=83%) of product.

LC-MS (Method 1): $R_t$=0.88 min; MS (ESIpos): m/z=356 [M+H]$^+$.

$^1$H NMR (400 MHz, DMSO-d$_6$): δ [ppm]=0.91 (s, 9H), 1.71 (s, 2H), 3.59 (s, 1H), 3.87 (s, 2H), 7.17-7.32 (m, 6H), 7.45-7.51 (m, 1H), 7.61-7.65 (m, 1H), 7.84(s br, 1H).

Intermediate C48 tert-Butyl (2S)-4-({(1R)-1-[4-benzyl-1-(2,5-difluorophenyl)-1H-pyrazol-3-yl]-2,2-dimethylpropyl}amino)-2-[(tert-butoxycarbonyl)amino]butanoate

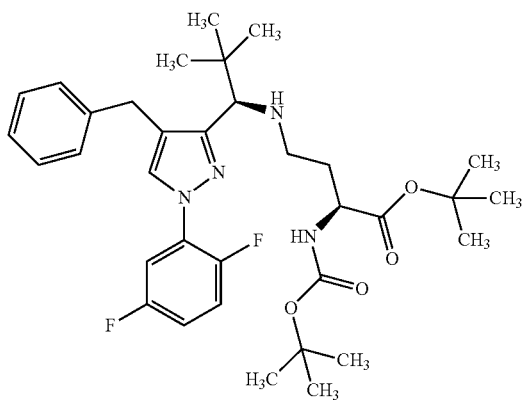 [SMILES: CC(C)(C)OC(=O)N[C@@H](CCN[C@@H](c1nn(-c2cc(F)ccc2F)cc1Cc1ccccc1)C(C)(C)C)C(=O)OC(C)(C)C]

1.28 g (3.35 mmol, LC/MS purity 93%) of (1R)-1-[4-benzyl-1-(2,5-difluorophenyl)-1H-pyrazol-3-yl]-2,2-dimethylpropan-1-amine were dissolved in 100 ml of absolute dichloromethane, and 261 mg (4.35 mmol, 250 μl) of acetic acid and 1.14 g (4.34 mmol) of sodium triacetoxyborohydride were added at room temperature followed after 5 min of stirring by 1.19 g (4.35 mmol) of tert-butyl (2S)-2-[(tert-butoxycarbonyl)amino]-4-oxobutanoate. The mixture was stirred at room temperature for 15 min, concentrated on a rotary evaporator, taken up in acetonitrile and water and purified by preparative HPLC (mobile phase: ACN/water+ 0.1% TFA, gradient). This gave 1.64 g (80% of theory) of the target compound.

LC-MS (Method 1): $R_t$=1.10 min; MS (ESIpos): m/z=613 [M+H]$^+$.

$^1$H NMR (400 MHz, DMSO-d$_6$): δ [ppm]=1.01 (s, 9H), 1.32 (s, 9H), 1.35 (s, 9H), 1.80-1.89 (m, 1H), 2.01-2.11 (m, 1H), 2.54-2.71 (m, 2H), 3.75-3.81 (m, 1H), 3.90 (s, 2H), 4.18 (d, 1H), 7.13 (d, 1H), 7.20-7.24 (m, 1H), 7.28-7.34 (m, 5H), 7.52-7.58 (m, 1H), 7.76-7.80 (m, 1H), 8.10 (s br, 1H), 8.23 (s br, 1H).

Intermediate C49

(2S)-4-[{(1R)-1-[4-Benzyl-1-(2,5-difluorophenyl)-1H-pyrazol-3-yl]-2,2-dimethylpropyl}(glycoloyl)amino]-2-[(tert-butoxycarbonyl)amino]butanoic acid

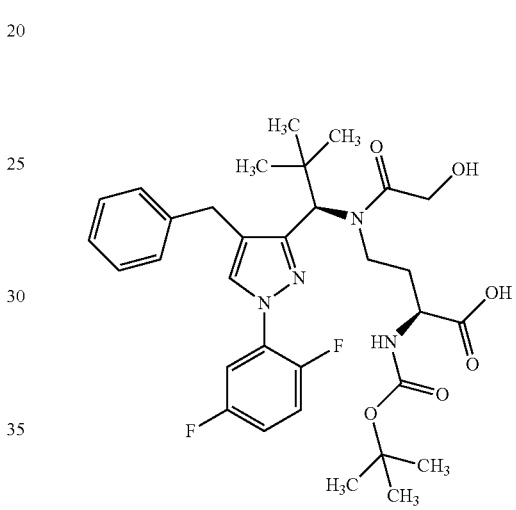

225 mg (0.37 mmol) of tert-butyl (2S)-4-({(1R)-1-[4-benzyl-1-(2,5-difluorophenyl)-1H-pyrazol-3-yl]-2,2-dimethylpropyl}amino)-2-[(tert-butoxycarbonyl)amino]butanoate were dissolved in 10 ml of absolute dichloromethane, and 156 mg (1.54 mmol) of triethylamine were added. At 0° C., 125 mg (0.92 mmol) of acetoxyacetyl chloride were added, and the mixture was stirred at RT for 16 h. Another 251 mg (1.84 mmol) of acetoxyacetyl chloride and 186 mg (1.84 mmol) of triethylamine were added, and the mixture was stirred at RT for 3 h. A little dichloromethane was added and the mixture was washed with saturated sodium bicarbonate solution and saturated sodium chloride solution. The organic phase was dried over sodium sulphate, concentrated on a rotary evaporator and dried under high vacuum. The residue was taken up in 10 ml of ethanol, 0.91 ml (12.67 mmol) of a 40% strength aqueous methylamine solution was added and the mixture was stirred at 50° C. for 3 h. The mixture was concentrated on a rotary evaporator, the residue was taken up in dichloromethane and the organic phase was washed twice with water. The organic phase was dried over sodium sulphate, concentrated on a rotary evaporator and dried under high vacuum. The residue was taken up in 2 ml of dichloromethane, 2 ml (25.96 mmol) of trifluoroacetic acid were added and the mixture was stirred at 50° C. for 4 h. The mixture was concentrated on a rotary evaporator and the residue was dried under high vacuum. The residue was taken up in 10 ml of absolute dichloromethane, 298 mg (2.95 mmol) of triethylamine and 429 mg (1.97 mmol) of di-tert-butyl dicarbonate were added and the mixture was stirred at RT for 1 h. The mixture was concentrated on a rotary evaporator and the residue was purified by preparative HPLC (mobile phase: ACN/water, gradient). This gave 62 mg (27% of theory) of the target compound.

LC-MS (Method 1): $R_t$=1.32 min; MS (ESIpos): m/z=615 [M+H]$^+$.

$^1$H NMR (400 MHz, DMSO-d$_6$): δ [ppm]=0.91 (s, 9H), 1.32 (s, 9H), 2.64-2.72 (m, 4H), 3.50-3.58 (m, 1H), 3.72 (dd, 2H), 4.07-4.22 (m, 2H), 4.47-4.54 (m, 1H), 5.75 (s, 1H), 6.84-6.89 (m, 1H), 7.15-7.30 (m, 6H), 7.47-7.53 (m, 1H), 7.70-7.75 (m, 1H), 8.09-8.13 (m, 1H), 11.66 (s br, 1H).

Intermediate C50 tert-Butyl [(2S)-4-[{(1R)-1-[4-benzyl-1-(2,5-difluorophenyl)-1H-pyrazol-3-yl]-2,2-dimethylpropyl}(glycoloyl)amino]-1-{[2-(2,5-dioxo-2,5-dihydro-1H-pyrrol-1-yl)ethyl]amino}-1-oxobutan-2-yl]carbamate

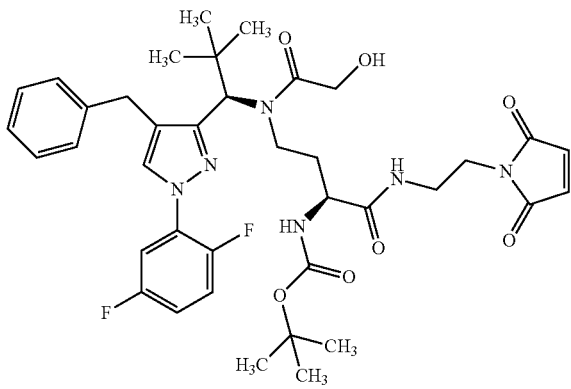 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)NCCN1C(=O)C=CC1=O]

mg (0.1 mmol) of (2S)-4-[{(1R)-1-[4-benzyl-1-(2,5-difluorophenyl)-1H-pyrazol-3-yl]-2,2-dimethylpropyl}(glycoloyl)amino]-2-[(tert-butoxycarbonyl)amino]butanoic acid were dissolved in 10 ml of absolute DMF, and 74 mg (0.20 mmol) of HATU were added. 74 mg (0.29 mmol) of trifluoroacetic acid/1-(2-aminoethyl)-1H-pyrrole-2,5-dione (1:1) were dissolved separately in 2 ml of absolute DMF, 38 mg (0.29 mmol) of N,N-diisopropylethylamine were added and the mixture was added dropwise to the reaction mixture. The reaction was stirred at RT for 3 d. The mixture was purified directly by preparative HPLC mobile phase: ACN/water+0.1% TFA, gradient). This gave 9.3 mg (13% of theory) of the target compound.

LC-MS (Method 1): $R_t$=1.34 min; MS (ESIpos): m/z=737 [M+H]$^+$.

Intermediate C51

N-{(2S)-4-[{(1R)-1-[4-Benzyl-1-(2,5-difluorophenyl)-1H-pyrazol-3-yl]-2,2-dimethylpropyl}(glycoloyl)amino]-2-[(tert-butoxycarbonyl)amino]butanoyl}-beta-alanine

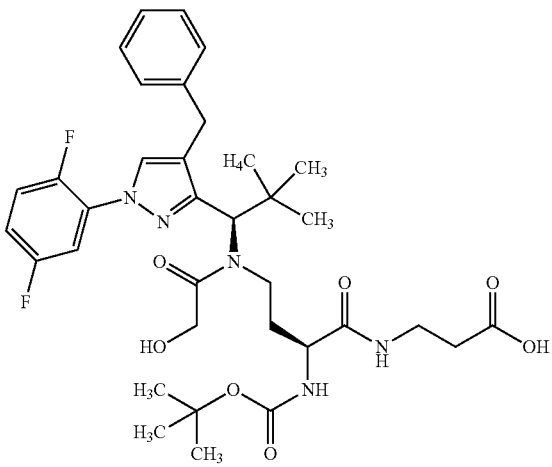 [SMILES: CC(C)(C)OC(=O)N[C@@H](CCN(C(=O)CO)[C@@H](c1nn(-c2cc(F)ccc2F)cc1Cc1ccccc1)C(C)(C)C)C(=O)NCCC(=O)O]

First, Intermediate C47 was reductively alkylated with benzyl N-{(2S)-2-[(tert-butoxycarbonyl)amino]-4-oxobutanoyl}-beta-alaninate analogously to Intermediate C2. The secondary amino group was then acylated with 2-chloro-2-oxoethyl acetate as described for Intermediate C27, and the two ester groups were then hydrolysed with 2M lithium hydroxide solution in methanol. This gave 23 mg of the title compound.

LC-MS (Method 1): $R_t$=1.24 min; MS (ESIpos): m/z=686 (M+H)$^+$.

Intermediate C52

(1R)-1-[1-Benzyl-4-(2,5-difluorophenyl)-1H-pyrrol-2-yl]-2,2-dimethylpropan-1-amine

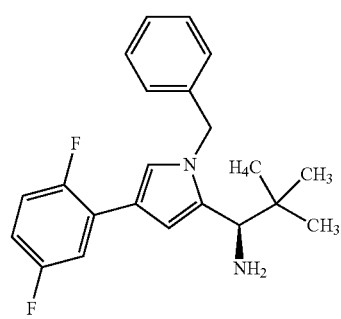 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate. The two combined reactions were purified by preparative RP-HPLC (column: Daiso 300×100; 10μ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1'-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was purified on silica gel (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese(IV) oxide were added and the mixture was stirred at RT for 48 h. Another 2.20 g (21.47 mmol) of manganese(IV) oxide were added and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphonamide were initially charged in 403.0 ml of absolute THF, and 7.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)—N-{(E/Z)-[1-benzyl-4-(2,5-difluorophenyl)-1H-pyrrol-2-yl]methylene}-2-methylpropane-2-sulphinamide were initially charged in absolute THF under argon and cooled to -78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 [M+H]$^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 $[M-NH_2]^+$, 709 $[2M+H]^+$.

$^1$H NMR (400 MHz, DMSO-$d_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C53

(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic acid

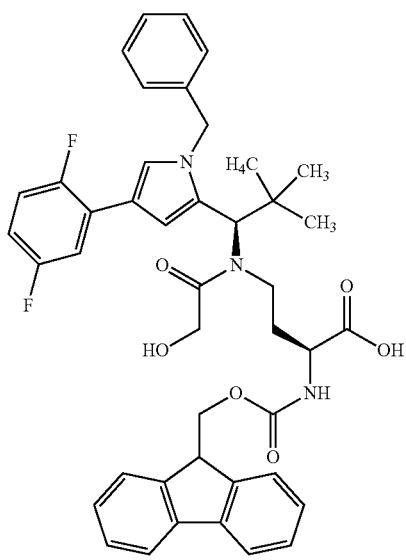 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)O)C(=O)CO]

First, Intermediate C52 was reductively alkylated with benzyl (2S)-2-{[(benzyloxy)carbonyl]amino}-4-oxobutanoate analogously to C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine LC-MS (Method 1): $R_t$=1.37 min; MS (ESIpos): m/z=734 $(M-H)^-$.

Intermediate C54

N-[(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoyl]-beta-alanine

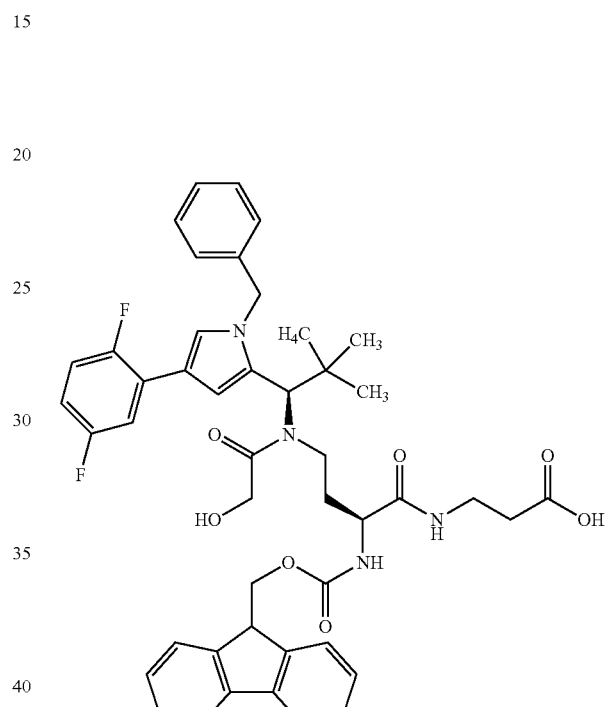

First, Intermediate C52 was reductively alkylated with benzyl N-[(2S)-2-{[(benzyloxy)carbonyl]amino}-4-oxobutanoyl]-beta-alaninate analogously to Intermediate C2. The secondary amino group was then acylated with 2-chloro-2-oxoethyl acetate as described for Intermediate C27. The intermediate obtained in this manner was dissolved in ethanol, palladium on carbon (10%) was added and the mixture was hydrogenated at RT with hydrogen under standard pressure for 1 h. The two ester groups were then hydrolysed with 2M lithium hydroxide solution in methanol. The deprotected compound was taken up in dioxane/water 2:1 and in the last step the Fmoc protective group was introduced using 9H-fluoren-9-ylmethyl chlorocarbonate in the presence of N,N-diisopropylethylamine. This gave 48 mg of the title compound.

LC-MS (Method 1): $R_t$=1.38 min; MS (ESIpos): m/z=807 $(M+H)^+$.

Intermediate C55

2-[3-({(1R)-1-[4-Benzyl-1-(2,5-difluorophenyl)-1H-pyrazol-3-yl]-2,2-dimethylpropyl}amino)propyl]-1H-isoindole-1,3(2H)-dione

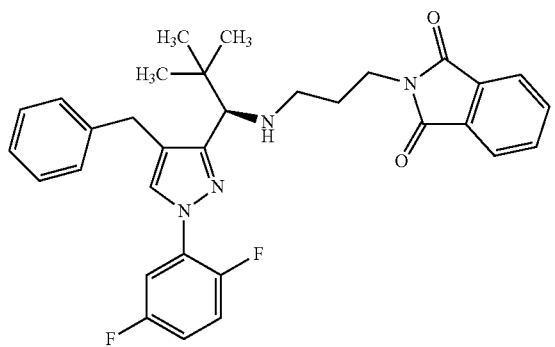 [SMILES: CC(C)(C)[C@@H](NCCCN1C(=O)c2ccccc2C1=O)c1nn(-c2cc(F)ccc2F)cc1Cc1ccccc1]

340 mg (0.96 mmol) of (1R)-1-[4-benzyl-1-(2,5-difluorophenyl)-1H-pyrazol-3-yl]-2,2-dimethylpropan-1-amine were dissolved in 7 ml of absolute DCM, and 69 mg (1.15 mmol, 60 µl) acetic acid and 284 mg (1.34 mmol) of sodium triacetoxyborohydride were added at RT. The mixture was stirred for 15 min, and 233 mg (1.15 mmol) of 3-(1,3-dioxo-1,3-dihydro-2H-isoindol-2-yl)propanal were then added. The mixture was stirred at RT for 4.5 h. Another 233 mg (1.15 mmol) of 3-(1,3-dioxo-1,3-dihydro-2H-isoindol-2-yl)propanal, 69 mg (1.15 mmol, 60 µl) acetic acid and 284 mg (1.34 mmol) of sodium triacetoxyborohydride were added, and the mixture was stirred at RT for 7 h. Ethyl acetate was added and the reaction mixture was washed with saturated sodium carbonate solution. The organic phase was concentrated and the residue was purified twice by preparative HPLC [1.) mobile phase: ACN/water+0.1% TFA, gradient; 2.) mobile phase: ACN/water+1% TFA+1.0% NEt$_3$)]. This gave 108 mg (21% of theory) of the target compound.

LC-MS (Method 1): R$_t$=0.96 min; MS (ESIpos): m/z=543 [M+H]$^+$.

Intermediate C56

2-({(1R)-1-[4-Benzyl-1-(2,5-difluorophenyl)-1H-pyrazol-3-yl]-2,2-dimethylpropyl}[3-(1,3-dioxo-1,3-dihydro-2H-isoindol-2-yl)propyl]amino)-2-oxoethyl acetate

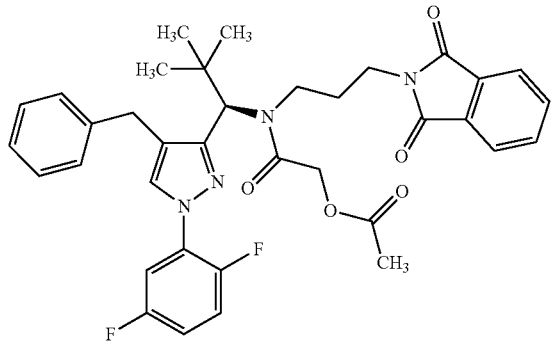 [SMILES: CC(=O)OCC(=O)N(CCCN1C(=O)c2ccccc2C1=O)[C@@H](c1nn(-c2cc(F)ccc2F)cc1Cc1ccccc1)C(C)(C)C]

102 mg (0.19 mmol) of 2-[3-({(1R)-1-[4-benzyl-1-(2,5-difluorophenyl)-1H-pyrazol-3-yl]-2,2-dimethylpropyl}amino)propyl]-1H-isoindole-1,3(2H)-dione were initially charged in 2 ml of absolute DCM, and 44 mg (0.43 mmol) of triethylamine were added at RT. At 0° C., 31 mg (0.23 mmol) of 2-chloro-2-oxoethyl acetate dissolved in 1 ml of absolute DCM were added. The mixture was stirred at RT for 40 min Another 26 mg of 2-chloro-2-oxoethyl acetate dissolved in 0.5 ml of absolute DCM and 19 mg (0.19 mmol) of triethylamine were added, and the mixture was stirred at RT for 60 min Water was added, the mixture was concentrated on a rotary evaporator and the residue was purified by preparative HPLC(mobile phase: ACN/water+0.1% TFA, gradient). This gave 106 mg (88% of theory) of the target compound.

LC-MS (Method 1): R$_t$=1.37 min; MS (ESIpos): m/z=643 [M+H]$^+$.

Intermediate C57

Trifluoroacetic acid/tert-butyl {(2S)-1-[(2-aminoethyl)amino]-4-[{(1R)-1-[4-benzyl-1-(2,5-difluorophenyl)-1H-pyrazol-3-yl]-2,2-dimethylpropyl}(glycoloyl)amino]-1-oxobutan-2-yl}carbamate (1:1)

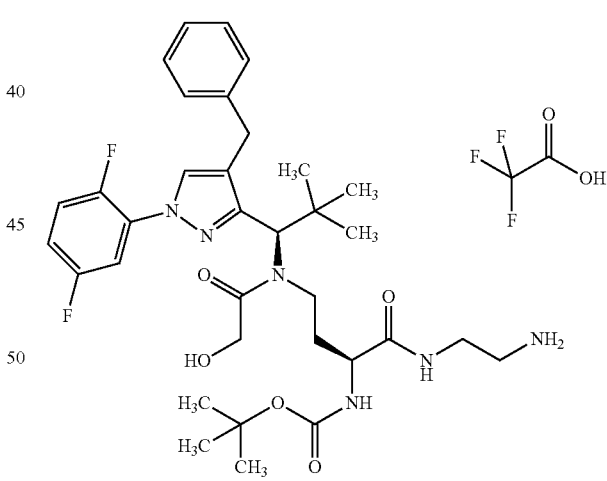

The title compound was prepared according to standard methods by coupling Intermediate C49 with 9H-fluoren-9-ylmethyl (2-aminoethyl)carbamate in the presence of HATU and subsequent removal of the Fmoc protective group with piperidine. This gave 14 mg of the title compound (40% of theory over 2 steps).

LC-MS (Method 1): R$_t$=0.98 min; MS (ESIpos): m/z=657 (M+H)$^+$.

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

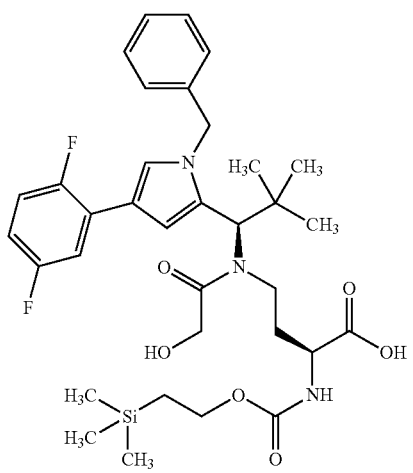 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

First, Intermediate C52 was reductively alkylated with benzyl (2S)-2-{[(benzyloxy)carbonyl]amino}-4-oxobutanoate analogously to Intermediate C2. First, Intermediate C52 was reductively alkylated with benzyl (2S)-2-{[(benzyloxy)carbonyl]amino}-4-oxobutanoate analogously to C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h.

500 mg (0.886 mmol) of this fully deprotected intermediate were taken up in 60 ml of dioxane, and 253 mg (0.975 mmol) of 1-({[2-(trimethylsilyl)ethoxy]carbonyl}oxy)pyrrolidine-2,5-dione and 198 µl of triethylamine were added. After 24 h of stirring at RT, the reaction was concentrated and the residue was purified by preparative HPLC. Combination of the appropriate fractions, concentration under reduced pressure and drying under high vacuum gave 312 mg (50% of theory) of the title compound.

LC-MS (Method 5): $R_t$=4.61 min; MS (ESIpos): m/z=658 (M+H)$^+$.

Intermediate C59

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

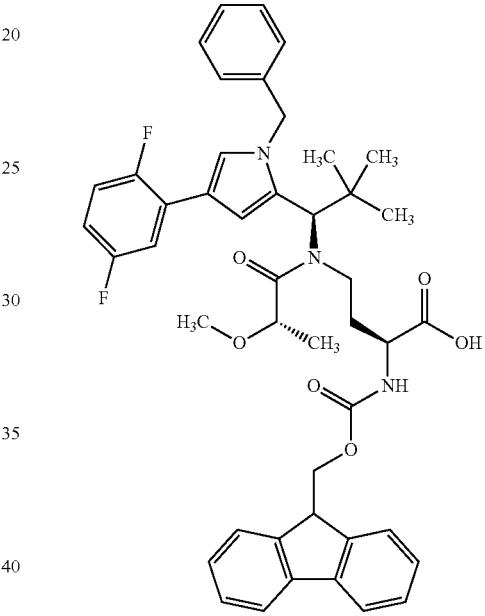

Initially, the secondary amino group of benzyl (2S)-4-({(1R)-1-[1-benzyl-4-(2,5-difluorophenyl)-1H-pyrrol-2-yl]-2,2-dimethylpropyl} amino)-2-[(benzyloxy)carbonyl]amino}butanoate was acylated with (2S)-2-methoxypropanoyl chloride (intermediate of Intermediate C53) in the presence of triethylamine as described for Intermediate C53. The intermediate obtained was taken up in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine LC-MS (Method 1): $R_t$=1.39 min; MS (ESIpos): m/z=764 (M−H)$^-$.

Intermediate C60

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

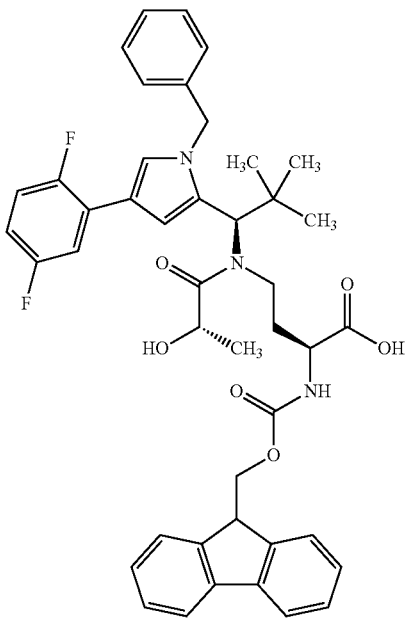 [SMILES: C[C@H](O)C(=O)N(CC[C@H](NC(=O)OCC1c2ccccc2-c2ccccc21)C(=O)O)[C@@H](c1cc(-c2cc(F)ccc2F)cn1Cc1ccccc1)C(C)(C)C]

The synthesis was carried out analogously to Intermediate C53.

LC-MS (Method 1): $R_t$=1.41 min; MS (ESIpos): m/z=750 (M+H)$^+$.

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

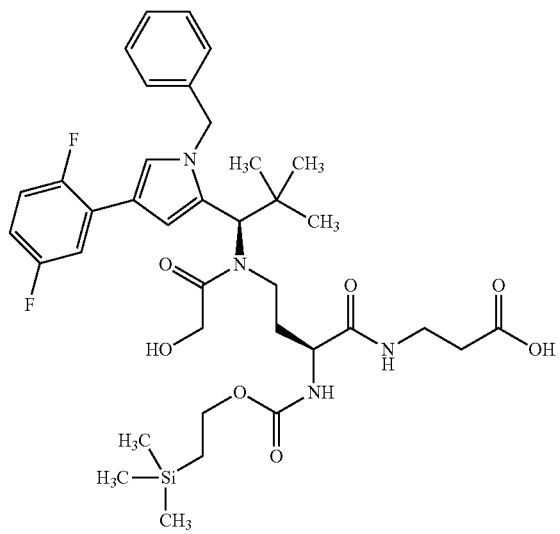 [SMILES: CC(C)(C)[C@H](c1cc(-c2cc(F)ccc2F)cn1Cc1ccccc1)N(CC[C@H](NC(=O)OCC[Si](C)(C)C)C(=O)NCCC(=O)O)C(=O)CO]

The title compound was prepared by coupling 60 mg (0.091 mmol) of Intermediate C58 with methyl β-alaninate, followed by ester cleavage with 2M lithium hydroxide solution. This gave 67 mg (61% of theory) of the title compound over 2 steps.

LC-MS (Method 1): $R_t$=1.29 min; MS (ESIpos): m/z=729 (M+H)$^+$.

Intermediate C62

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alanine

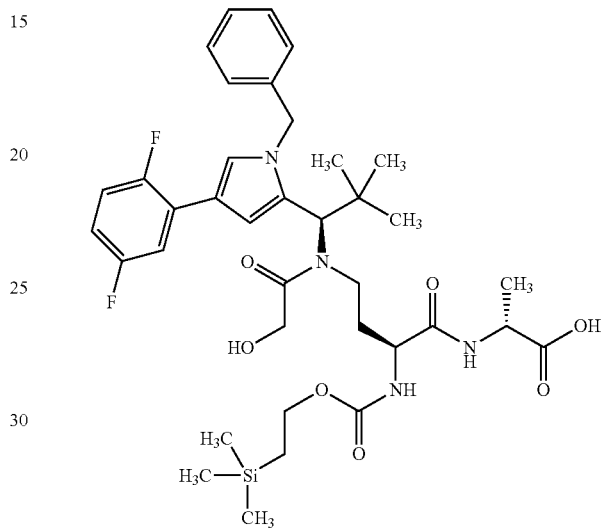

The title compound was prepared analogously to Intermediate C61 from Intermediate C58 and methyl D-alaninate.

LC-MS (Method 1): $R_t$=1.32 min; MS (ESIpos): m/z=729 (M+H)$^+$.

Intermediate C63

Trifluoroacetic acid/tert-butyl {(2S)-1-[(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate (1:1)

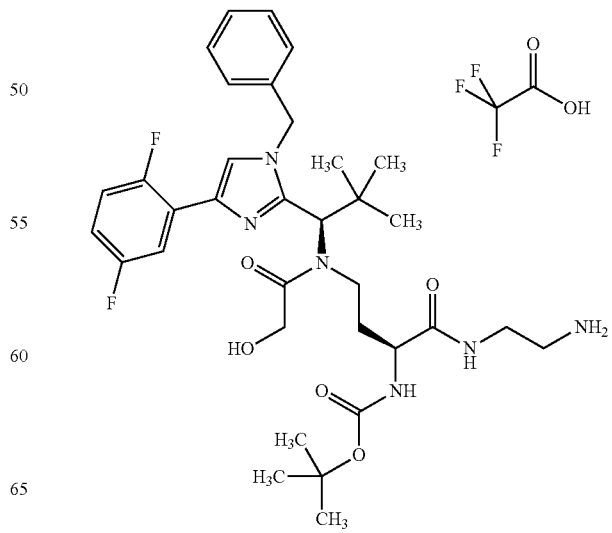

The synthesis of this intermediate began in the first step with the coupling of 50 mg (0.075 mmol) of Intermediate C3 with 26.2 mg (0.082 mmol) of 9H-fluoren-9-ylmethyl (2-aminoethyl)carbamate hydrochloride (1:1) in the presence of 28.7 mg (0.15 mmol) of 1-(3-dimethylaminopropyl)-3-ethyl carbodiimide hydrochloride, 22.9 mg (0.15 mmol) of 1-hydroxy-1H-benzotriazole hydrate and 39 µl of N,N-diisopropylethylamine After 18 h of stirring at RT, the mixture was concentrated and the residue was purified by preparative HPLC. This gave 45 mg (65% of theory) of this intermediate. LC-MS (Method 1): $R_t$=1.51 min; MS (ESIpos): m/z=921 (M+H)$^+$.

45 mg (0.049 mmol) of this intermediate were taken up in 10 ml of ethanol, and 176 µl of a 40% strength solution of methanamine in water were added. The reaction was stirred at 50° C., with the same amount of methanamine solution being added after 6 h and after 9 h. After a further 14 h of stirring at 50° C., another 700 µl of the methanamine solution were added, and after a further 20 h of stirring the mixture was finally concentrated. The residue was taken up in DCM and washed with water. The organic phase was concentrated and the residue was purified by preparative HPLC. Concentration of the appropriate fractions and drying of the residue under high vacuum gave 32 mg (99% of theory) of tert-butyl {(2S)-1-[(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate.

LC-MS (Method 1): $R_t$=0.95 min; MS (ESIpos): m/z=657 (M+H)$^+$.

Intermediate C64

Trifluoroacetic acid/2-(trimethylsilyl)ethyl {(2S)-1-[(2-aminoethyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}carbamate (1:1)

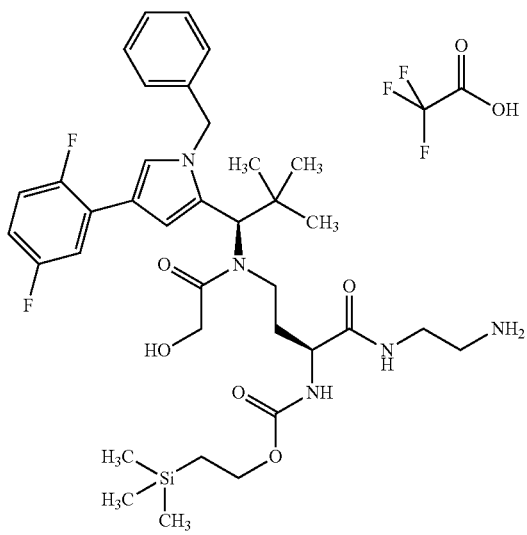 [SMILES: CC(C)(C)[C@H](c1cc(-c2cc(F)ccc2F)cn1Cc1ccccc1)N(CC[C@H](NC(=O)OCC[Si](C)(C)C)C(=O)NCCN)C(=O)CO ; O=C(O)C(F)(F)F]

The title compound was prepared from Intermediate C58 analogously to Intermediate C63.

HPLC (Method 11): $R_t$=2.4 min;
LC-MS (Method 1): $R_t$=1.01 min; MS (ESIpos): m/z=700 (M+H)$^+$.

Intermediate C65

(8S)-8-{2-[{(1R)-1-[1-Benzyl-4-(2,5-difluorophenyl)-1H-pyrrol-2-yl]-2,2-dimethylpropyl}-(glycoloyl)amino]ethyl}-2,2-dimethyl-6,11-dioxo-5-oxa-7,10-diaza-2-silatetradecan-14-oic acid

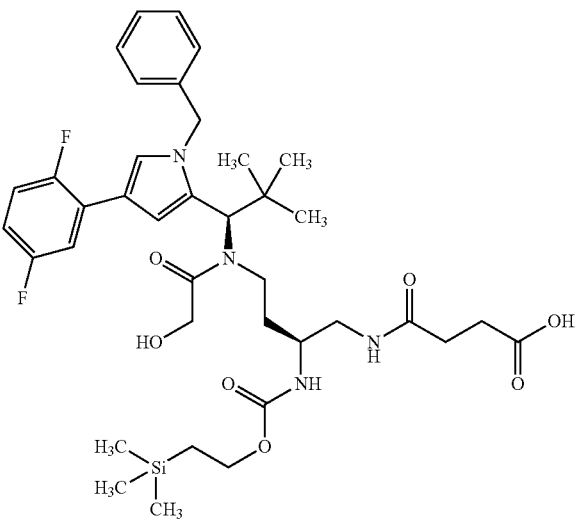 [SMILES: CC(C)(C)[C@H](c1cc(-c2cc(F)ccc2F)cn1Cc1ccccc1)N(CC[C@@H](CNC(=O)CCC(=O)O)NC(=O)OCC[Si](C)(C)C)C(=O)CO]

215 mg (0.59 mmol) of Intermediate L66 were initially charged in 25 ml of dichloromethane, and 377 mg (0.89 mmol) of Dess-Martin periodinane and 144 µl (1.78 mmol) of pyridine were added. The mixture was stirred at RT for 30 min. The reaction was then diluted with 300 ml of dichloromethane and the organic phase was washed in each case twice with 10% strength $Na_2S_2O_3$ solution, 10% strength citric acid solution and saturated sodium bicarbonate solution. The organic phase was dried over magnesium sulphate and the solvent was evaporated under reduced pressure. This gave 305 mg of the aldehyde which was reacted without further purification.

175 mg (0.49 mmol) of Intermediate C52 were dissolved in 50 ml of dichloromethane, and 147 mg (0.69 mmol) of sodium triacetoxyborohydride and 32.5 µl of acetic acid were added. After 5 min of stirring at RT, 214 mg (0.593 mmol) of the aldehyde described above were added, and the reaction was stirred at RT overnight. Here, instead of the expected product, 2-(trimethylsilyl)ethyl [(2S)-4-({(1R)-1-[1-benzyl-4-(2,5-difluorophenyl)-1H-pyrrol-2-yl]-2,2-dimethylpropyl}amino)-1-(2,5-dioxopyrrolidin-1-yl)butan-2-yl]carbamate was formed. Since this imide can also be converted into the title compound, the reaction was concentrated and the residue was purified by preparative HPLC. After combination of the appropriate imide-containing fractions, the solvent was evaporated under reduced pressure and the residue was dried under high vacuum. This gave 195 mg (58%) of the imide named above.

LC-MS (Method 5): $R_t$=3.32 min; MS (ESIpos): m/z=667 (M+H)$^+$.

65 mg (97.5 µmol) of this imide were taken up in 15 ml of dichloromethane, and 367 µl (3.4 mmol) of acetoxyacetyl chloride and 595 µl of N,N-diisopropylethylamine were added. After 30 min of stirring at RT, the reaction was concentrated without heating under reduced pressure and the residue was purified by preparative HPLC. The appropriate fractions were combined giving, after evaporation of the solvents and drying under high vacuum, 28 mg (37% of theory) of (8S)-11-{(1R)-1-[1-benzyl-4-(2,5-difluorophenyl)-1H-pyrrol-2-yl]-2,2-dimethylpropyl}-8-[(2,5-dioxopyrrolidin-1-yl)methyl]-2,2-dimethyl-6,12-dioxo-5-oxa-7,11-diaza-2-silatridecan-13-yl acetate.

LC-MS (Method 1): $R_t$=1.44 min; MS (ESIpos): m/z=767 (M+H)$^+$.

28 mg (37 μmol) of this intermediate were dissolved in 3 ml of methanol, and 548 μl of a 2M lithium hydroxide solution were added. After 10 min of stirring at RT, the reaction was adjusted to pH 4 with trifluoroacetic acid and then concentrated. The residue was purified by preparative HPLC. The appropriate fractions were combined, the solvent was evaporated and the residue was dried under high vacuum, giving 26 mg (96% of theory) of the title compound as a white solid.

LC-MS (Method 1): $R_t$=1.33 min; MS (ESIpos): m/z=743 (M+H)$^+$.

Intermediate C66

2-(Trimethylsilyl)ethyl [(2S)-4-[{(1R)-1-[1-benzyl-4-(2,5-difluorophenyl)-1H-pyrrol-2-yl]-2,2-dimethylpropyl}(glycoloyl)amino]-1-{[2-(glycylamino)ethyl]amino}-1-oxobutan-2-yl]carbamate

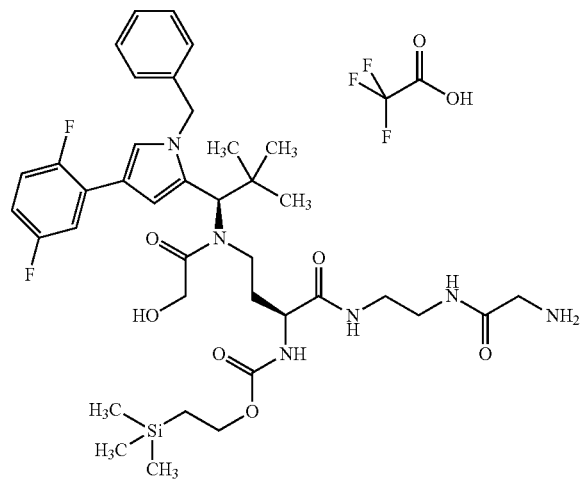 [SMILES: CC(C)(C)[C@H](c1cc(-c2cc(F)ccc2F)cn1Cc1ccccc1)N(CC[C@H](NC(=O)OCC[Si](C)(C)C)C(=O)NCCNC(=O)CN)C(=O)CO ; O=C(O)C(F)(F)F]

First, trifluoroacetic acid/benzyl {2[(2-aminoethyl)amino]-2-oxoethyl}carbamate (1:1) was prepared from N-[(benzyloxy)carbonyl]glycine and tert-butyl (2-aminoethyl)carbamate according to classical methods of peptide chemistry (HATU coupling and Boc removal).

13 mg (0.036 mmol) of this Intermediate and 25 mg (0.033 mmol) of Intermediate C58 were taken up in 3 ml of DMF, and 19 mg (0.05 mmol) of HATU and 17 μl of N,N-diisopropylethylamine were added.

After 10 min of stirring at RT, the mixture was concentrated and the residue was purified by preparative HPLC. This gave 17.8 mg (60% of theory) of the intermediate.

LC-MS (Method 1): $R_t$=1.36 min; MS (ESIpos): m/z=891 (M+H)$^+$.

17 mg (0.019 mmol) of this intermediate were dissolved in 10 ml of ethanol, palladium on carbon (10%) was added and the mixture was hydrogenated at RT with hydrogen at standard pressure for 2 h. The catalyst was filtered off, the solvents were evaporated under reduced pressure and the residue was dried under high vacuum. This gave 9 mg (62% of theory) of the title compound.

LC-MS (Method 1): $R_t$=1.03 min; MS (ESIpos): m/z=757 (M+H)$^+$.

Intermediate C67

9H-Fluoren-9-ylmethyl [3-({(1R)-1-[1-benzyl-4-(2,5-difluorophenyl)-1H-pyrrol-2-yl]-2,2-dimethylpropyl}amino)propyl]carbamate

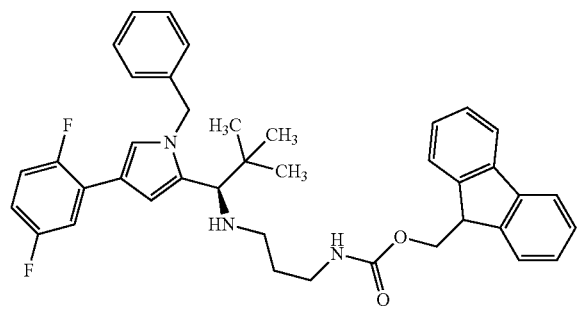 [SMILES: CC(C)(C)[C@@H](NCCCNC(=O)OCC1c2ccccc2-c2ccccc21)c1cc(-c2cc(F)ccc2F)cn1Cc1ccccc1]

605.3 mg (1.71 mmol) of (1R)-1-[1-benzyl-4-(2,5-difluorophenyl)-1H-pyrrol-2-yl]-2,2-dimethylpropan-1-amine (Intermediate C52) were initially charged in 10.0 ml of dichloromethane, and 506.7 mg (2.39 mmol) of sodium triacetoxyborohydride and 117.9 mg (1.96 mmol) of acetic acid were added and the mixture was stirred at RT for 5 min 580.0 mg (1.96 mmol) of 9H-fluoren-9-ylmethyl (3-oxopropyl)carbamate (Intermediate L70) dissolved in 10.0 ml of dichloromethane were added and the reaction mixture stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified on silica gel (mobile phase: cyclohexane/ethyl acetate 3:1). The solvents were evaporated under reduced pressure and the residue was dried under high vacuum. This gave 514.7 mg (46% of theory) of the title compound.

LC-MS (Method 1): $R_t$=1.10 min; MS (ESIpos): m/z=634 (M+H)$^+$.

Intermediate C68 tert-Butyl [3-({(1R)-1-[4-benzyl-1-(2,5-difluorophenyl)-1H-pyrazol-3-yl]-2,2-dimethylpropyl}amino)propyl]carbamate

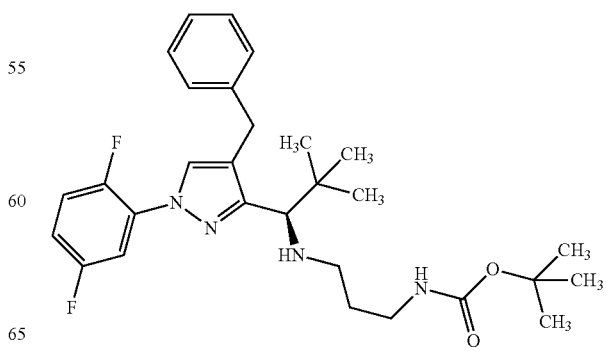

The synthesis was carried out analogously to the synthesis of the compound Intermediate C67.

1000.0 mg (2.81 mmol) of (1R)-1-[4-benzyl-1-(2,5-difluorophenyl)-1H-pyrazol-3-yl]-2,2-dimethylpropan-1-amine (Intermediate C47)

835.0 mg (3.94 mmol) of sodium triacetoxyborohydride 194.0 mg (3.24 mmol) of acetic acid 560.0 mg (3.24 mmol) of tert-butyl (3-oxopropyl)carbamate This gave 695.8 mg (48% of theory) of the title compound.

LC-MS (Method 1): $R_t$=1.02 min; MS (ESIpos): m/z=513 (M+H)$^+$.

Intermediate C69

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid

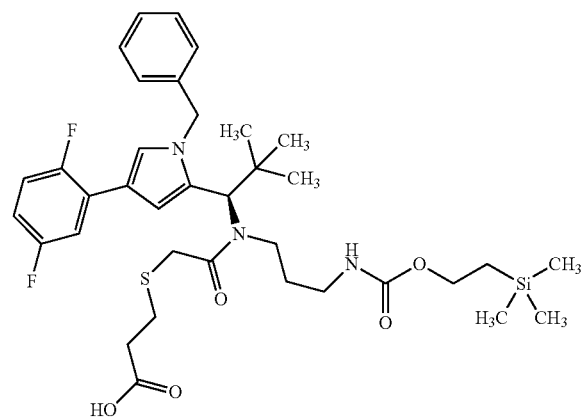 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)O]

117.0 mg (0.19 mmol) of (2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) and 21.6 mg (0.20 mmol) of 3-sulphanylpropanoic acid were initially charged in 3.0 ml of methanol, 89.5 mg (0.65 mmol) of potassium carbonate were added and the mixture was stirred at 50° C. for 4 h. The reaction mixture was diluted with ethyl acetate and the organic phase was washed with water and saturated NaCl solution. The organic phase was dried over magnesium sulphate, the solvent was evaporated under reduced pressure and the residue was dried under high vacuum. The residue was used without further purification in the next step of the synthesis. This gave 106.1 mg (73% of theory) of the title compound.

LC-MS (Method 1): $R_t$=1.42 min; MS (ESIneg): m/z=700 (M−H)$^−$.

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

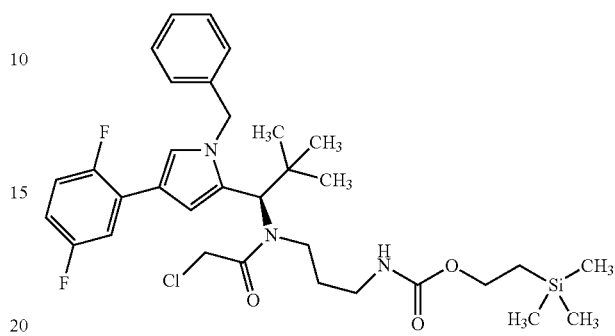

908.1 mg (1.63 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): $R_t$=1.53 min; MS (ESIneg): m/z=676 (M+HCOO$^−$)$^−$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1)

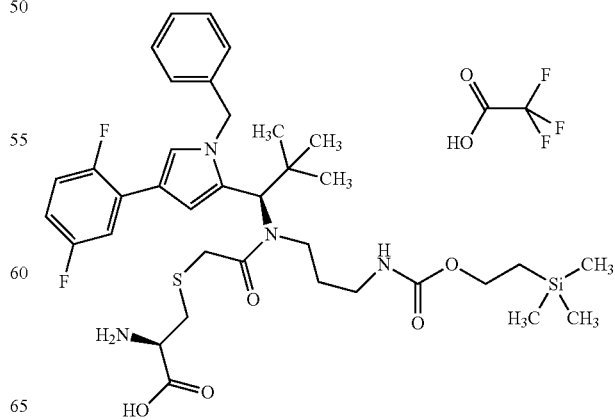

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): $R_t$=1.20 min; MS (ESIpos): m/z=717 (M+H)$^+$.

Intermediate C72

(9S)-9-{[{(1R)-1-[1-Benzyl-4-(2,5-difluorophenyl)-1H-pyrrol-2-yl]-2,2-dimethylpropyl}(glycoloyl)amino]methyl}-2,2-dimethyl-6,11-dioxo-5-oxa-7,10-diaza-2-silatetradecan-14-oic acid

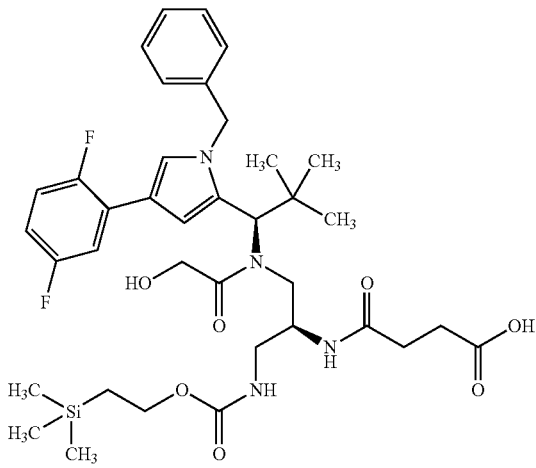 [SMILES: CC(C)(C)[C@H](c1cc(-c2cc(F)ccc2F)cn1Cc1ccccc1)N(C[C@H](CNC(=O)OCC[Si](C)(C)C)NC(=O)CCC(=O)O)C(=O)CO]

90 mg (0.212 mmol) of Intermediate L72 were initially charged in 6 ml of dichloromethane, and 86 µl (1.06 mmol) of pyridine and 135 mg (0.318 mmol) of Dess-Martin periodinane were added. The mixture was stirred at RT for 30 min. The reaction was then diluted with 30 ml of dichloromethane and the organic phase was washed twice with 10% strength $Na_2S_2O_3$ solution and once with 5% strength citric acid solution. The organic phase was dried over magnesium sulphate and the solvent was evaporated under reduced pressure. The aldehyde obtained in this manner was reacted without further purification.

63 mg (0.177 mmol) of Intermediate C52 were dissolved in 15 ml of dichloromethane, and 52.4 mg (0.247 mmol) of sodium triacetoxyborohydride and 20.2 µl of acetic acid were added. After 5 min of stirring at RT, 89.6 mg (0.212 mmol) of the aldehyde described above were added, and the reaction was stirred at RT for 20 min. The reaction was concentrated under reduced pressure and the residue was purified by preparative HPLC. After combination of the appropriate fractions, the solvent was evaporated under reduced pressure and the residue was lyophilized from acetonitrile/water. This gave 71 mg (53% of theory over 2 steps) of benzyl (9R)-9-[({(1R)-1-[1-benzyl-4-(2,5-difluorophenyl)-1H-pyrrol-2-yl]-2,2-dimethylpropyl}amino)methyl]-2,2-dimethyl-6,11-dioxo-5-oxa-7,10-diaza-2-silatetradecan-14-oate.

LC-MS (Method 1): $R_t$=1.21 min; MS (ESIpos): m/z=761 (M+H)$^+$.

70 mg (92 µmol) of this intermediate were taken up in 15 ml of dichloromethane, the mixture was cooled to 10° C. and 54 µl of triethylamine and 25.5 µl (0.23 mmol) of acetoxyacetyl chloride were added. After 1 h of stirring at RT, the same amounts of acid chloride and triethylamine were added, and once more after a further hour of stirring at RT. The reaction was then stirred at RT for a further 30 min and then concentrated under reduced pressure, and the residue was purified by preparative HPLC. The appropriate fractions were combined giving, after evaporation of the solvents and lyophilization of the residue from acetonitrile/water, 46.5 mg (59% of theory) of the acylated intermediate.

LC-MS (Method 1): $R_t$=1.53 min; MS (ESIpos): m/z=861 (M+H)$^+$.

46 mg (53 µmol) of this intermediate were dissolved in 5 ml of methanol, and 2.7 ml of a 2M lithium hydroxide solution were added. After 10 min of stirring at RT, the reaction was adjusted to pH 3-4 with acetic acid and then diluted with 15 ml of water. The aqueous phase was extracted with ethyl acetate and the organic phase was dried over magnesium sulphate and concentrated. The residue was lyophilized from acetonitrile/water giving, after drying of the residue under high vacuum, 37 mg (90% of theory) of the title compound as a white solid.

LC-MS (Method 1): $R_t$=1.32 min; MS (ESIpos): m/z=729 (M+H)$^+$.

Intermediate C73

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine

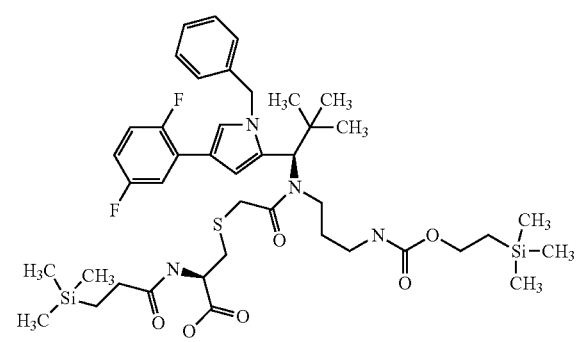

619 mg (0.86 mmol) of S-(11-{(1R)-1-[1-benzyl-4-(2,5-difluorophenyl)-1H-pyrrol-2-yl]-2,2-dimethylpropyl}-2,2- dimethyl-6,12-dioxo-5-oxa-7,11-diaza-2-silatridecan-13-yl)-L-cysteine/trifluoroacetic acid (1:1) (Intermediate C71) were initially charged in 8.8 ml of dichloromethane, and 87 mg (0.86 mmol) of triethylamine and 224 mg (0.86 mmol) of N-[2-(trimethylsilyl)ethoxycarbonyloxy]pyrrolidine-2,5-dione were added. After 1 h, 45 mg (0.17 mmol) of N-[2-(trimethylsilyl)ethoxycarbonyloxy]pyrrolidine-2,5-dione were added. The reaction mixture was stirred at RT for 1 h. The mixture was concentrated under reduced pressure, the residue was taken up in dichloromethane and the organic phase was then washed twice with water and a saturated sodium bicarbonate solution. The organic phase was dried over magnesium sulphate, concentrated on a rotary evaporator and dried under high vacuum. The residue was used further without further purification. This gave 602 mg (71%, purity 87%) of the title compound.

LC-MS (Method 1): $R_t$=1.58 min; MS (ESIpos): m/z=861 (M+H)$^+$.

Intermediate L1

Trifluoroacetic acid/N-(2-aminoethyl)-2-(2,5-dioxo-2,5-dihydro-1H-pyrrol-1-yl)acetamide (1:1)

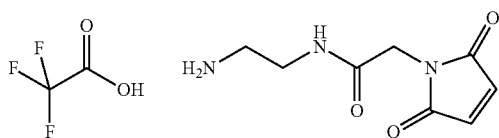 [SMILES: O=C(O)C(F)(F)F ; NCCNC(=O)CN1C(=O)C=CC1=O]

The title compound was prepared by classical methods of peptide chemistry from commercially available (2,5-dioxo-2,5-dihydro-1H-pyrrol-1-yl)acetic acid and tert-butyl (2-aminoethyl)carbamate.

HPLC (Method 11): $R_t$=0.19 min;
LC-MS (Method 1): $R_t$=0.17 min; MS (ESIpos): m/z=198 (M+H)$^+$.

Intermediate L2

Trifluoroacetic acid/rel-(1R,2S)-2-amino-N-[2-(2,5-dioxo-2,5-dihydro-1H-pyrrol-1-yl)ethyl]cyclopentanecarboxamide (1:1)

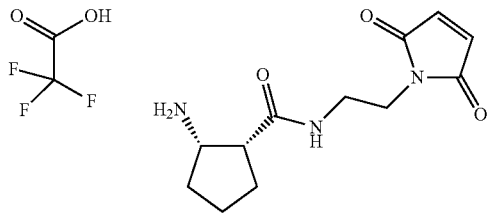 [SMILES: O=C(O)C(F)(F)F ; N[C@H]1CCC[C@H]1C(=O)NCCN1C(=O)C=CC1=O]

The title compound was prepared from 50 mg (0.214 mmol) of commercially available cis-2-[(tert-butoxycarbonyl)amino]-1-cyclopentanecarboxylic acid and 60 mg (0.235 mmol) of likewise commercially available trifluoroacetic acid/1-(2-aminoethyl)-1H-pyrrole-2,5-dione (1:1) by coupling with EDC/HOBT and subsequent deprotection with TFA. This gave 36 mg (38% of theory over 2 steps) of the title compound.

HPLC (Method 11): $R_t$=0.2 min;
LC-MS (Method 1): $R_t$=0.17 min; MS (ESIpos): m/z=252 (M+H)$^+$.

Intermediate L3

Trifluoroacetic acid/(1S,2R)-2-amino-N-[2-(2,5-dioxo-2,5-dihydro-1H-pyrrol-1-yl)ethyl]cyclopentanecarboxamide (1:1)

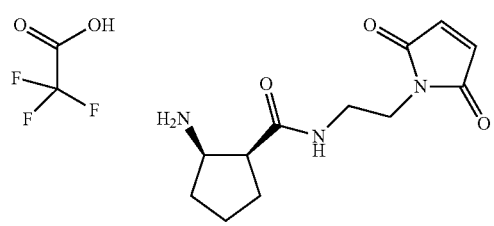 [SMILES: O=C(O)C(F)(F)F ; N[C@@H]1CCC[C@@H]1C(=O)NCCN1C(=O)C=CC1=O]

The title compound was prepared from 50 mg (0.214 mmol) of commercially available (1S,2R)-2-[(tert-butoxycarbonyl)amino]cyclopentanecarboxylic acid with 72 mg (0.283 mmol) of likewise commercially available trifluoroacetic acid/1-(2-aminoethyl)-1H-pyrrole-2,5-dione (1:1) by coupling with EDC/HOBT and subsequent deprotection with TFA. This gave 13 mg (16% of theory over 2 steps) of the title compound.

HPLC (Method 11): $R_t$=0.2 min;
LC-MS (Method 1): $R_t$=0.2 min; MS (ESIpos): m/z=252 (M+H)$^+$.

Intermediate L4

Trifluoroacetic acid/N-(2-aminoethyl)-4-(2,5-dioxo-2,5-dihydro-1H-pyrrol-1-yl)cyclohexanecarboxamide (1:1)

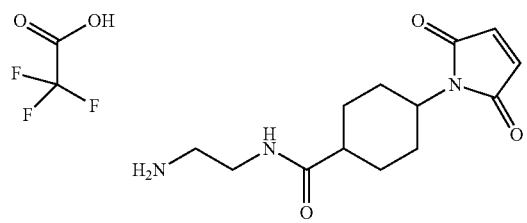 [SMILES: O=C(O)C(F)(F)F ; NCCNC(=O)C1CCC(N2C(=O)C=CC2=O)CC1]

The title compound was prepared by classical methods of peptide chemistry from commercially available 1-[(4-{[(2,5-dioxopyrrolidin-1-yl)oxy]carbonyl}cyclohexyl)methyl]-1H-pyrrole-2,5-dione and tert-butyl (2-aminoethyl)carbamate.

HPLC (Method 11): $R_t$=0.26 min;
LC-MS (Method 1): $R_t$=0.25 min; MS (ESIpos): m/z=280 (M+H)$^+$.

Intermediate L5

Trifluoroacetic acid/N-[4-(2,5-dioxo-2,5-dihydro-1H-pyrrol-1-yl)phenyl]-beta-alaninamide (1:1)

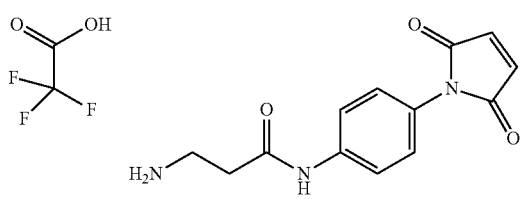 [SMILES: O=C(O)C(F)(F)F ; NCCC(=O)Nc1ccc(N2C(=O)C=CC2=O)cc1]

The title compound was prepared by classical methods of peptide chemistry from commercially available 1-(4-aminophenyl)-1H-pyrrole-2,5-dione and N-(tert-butoxycarbonyl)-beta-alanine.

HPLC (Method 11): $R_t$=0.22 min;
LC-MS (Method 1): $R_t$=0.22 min; MS (ESIpos): m/z=260 (M+H)$^+$.

Intermediate L6

Trifluoroacetic acid/tert-butyl-N-[6-(2,5-dioxo-2,5-dihydro-1H-pyrrol-1-yl)hexanoyl]-L-valyl-L-alanyl-L-lysinate (1:1)

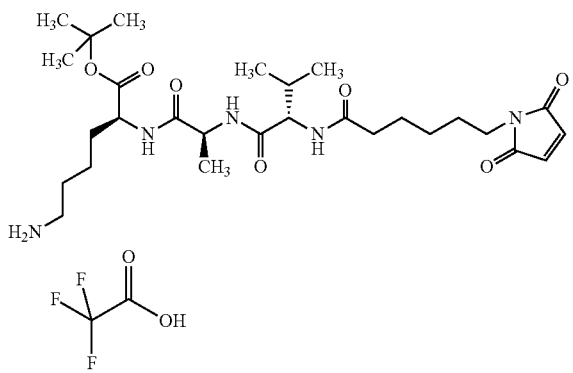

The title compound was prepared by initially coupling, in the presence of EDC/HOBT, commercially available 6-(2,5-dioxo-2,5-dihydro-1H-pyrrol-1-yl)hexanoic acid with the partially protected peptide tert-butyl L-valyl-L-alanyl-N6-(tert-butoxycarbonyl)-L-lysinate, prepared by classical methods of peptide chemistry. This was followed by deprotection at the amino group under gentle conditions by stirring in 5% strength trifluoroacetic acid in DCM at RT, which gave the title compound in a yield of 37%.

HPLC (Method 11): $R_t$=1.29 min;
LC-MS (Method 1): $R_t$=0.62 min; MS (ESIpos): m/z=566 (M+H)$^+$.

Intermediate L7

Trifluoroacetic acid/beta-alanyl-L-valyl-$N^5$-carbamoyl-N-[4-(2,5-dioxo-2,5-dihydro-1H-pyrrol-1-yl)phenyl]-L-ornithinamide (1:1)

The title compound was prepared according to classical methods of peptide chemistry from commercially available 1-(4-aminophenyl)-1H-pyrrole-2,5-dione by sequential coupling with N2-(tert-butoxycarbonyl)-N5-carbamoyl-L-ornithine in the presence of HATU, deprotection with TFA, coupling with 2,5-dioxopyrrolidin-1-yl N-(tert-butoxycarbonyl)-L-valinate, deprotection with TFA, coupling with 2,5-dioxopyrrolidin-1-yl N-(tert-butoxycarbonyl)-beta-alaninate and another deprotection with TFA. This gave 32 mg of the title compound.

HPLC (Method 11): $R_t$=0.31 min;
LC-MS (Method 1): $R_t$=0.47 min; MS (ESIpos): m/z=516 (M+H)$^+$.

Intermediate L8

Trifluoroacetic acid/L-alanyl-$N^5$-carbamoyl-N-[4-(2,5-dioxo-2,5-dihydro-1H-pyrrol-1-yl)phenyl]-L-ornithinamide (1:1)

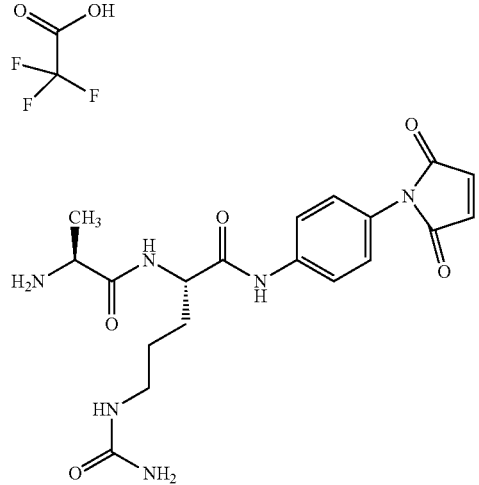

The title compound was prepared according to classical methods of peptide chemistry from commercially available 1-(4-aminophenyl)-1H-pyrrole-2,5-dione by sequential coupling with $N^2$-(tert-butoxycarbonyl)-$N^5$-carbamoyl-L-ornithine in the presence of HATU, deprotection with TFA, coupling with 2,5-dioxypyrrolidin-1-yl N-(tert-butoxycarbonyl)-L-alaninate and another deprotection with TFA. This gave 171 mg of the title compound.

HPLC (Method 11): $R_t$=0.23 min;

LC-MS (Method 7): $R_t$=0.3 min; MS (ESIpos): m/z=417 (M+H)$^+$.

Intermediate L9

Trifluoroacetic acid/beta-alanyl-L-valyl-$N^5$-carbamoyl-N-[4-(2-methoxy-2-oxoethyl)phenyl]-L-ornithinamide (1:1)

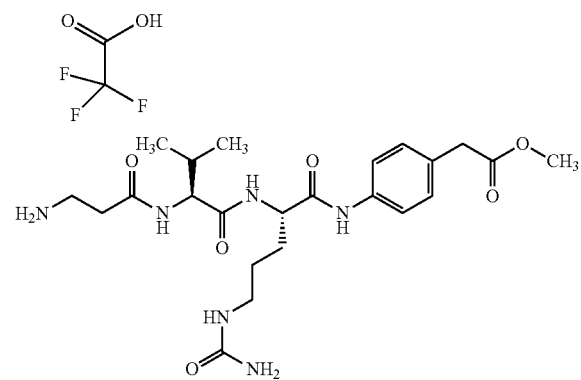

The title compound was prepared analogously to Intermediate L7 from commercially available methyl (4-aminophenyl)acetate. This gave 320 mg of the title compound.

HPLC (Method 11): $R_t$=0.45 min;

LC-MS (Method 1): $R_t$=0.48 min; MS (ESIpos): m/z=493 (M+H)$^+$.

Intermediate L10

N-[6-(2,5-Dioxo-2,5-dihydro-1H-pyrrol-1-yl) hexanoyl]-L-valyl-L-alanyl-rel-$N^6$-{[(1R,2S)-2-aminocyclopentyl]carbonyl}-L-lysine/trifluoroacetic acid (1:2)

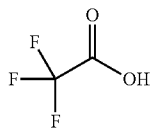

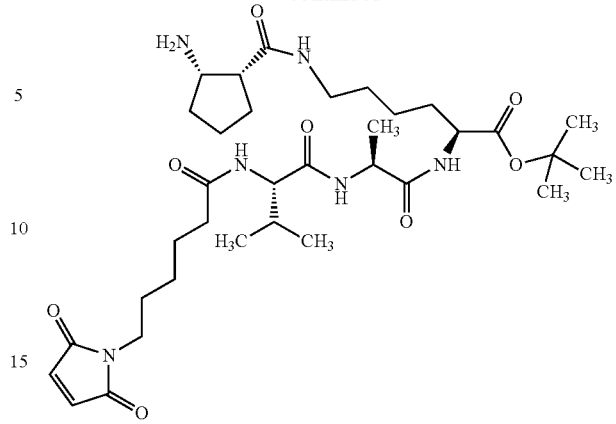

The title compound was prepared from Intermediate L6 by coupling with cis-2-[(tert-butoxycarbonyl)amino]-1-cyclopentanecarboxylic acid with EDC/HOBT and subsequent deprotection with TFA. This gave 12 mg (52% of theory over 2 steps) of the title compound.

HPLC (Method 11): $R_t$=1.45 min;

LC-MS (Method 1): $R_t$=0.73 min; MS (ESIpos): m/z=677 (M+H)$^+$.

Intermediate L11

N-[6-(2,5-Dioxo-2,5-dihydro-1H-pyrrol-1-yl) hexanoyl]-L-valyl-L-alanyl-$N^6$-{[(1S,2R)-2-aminocyclopentyl]carbonyl}-L-lysine/trifluoroacetic acid (1:2)

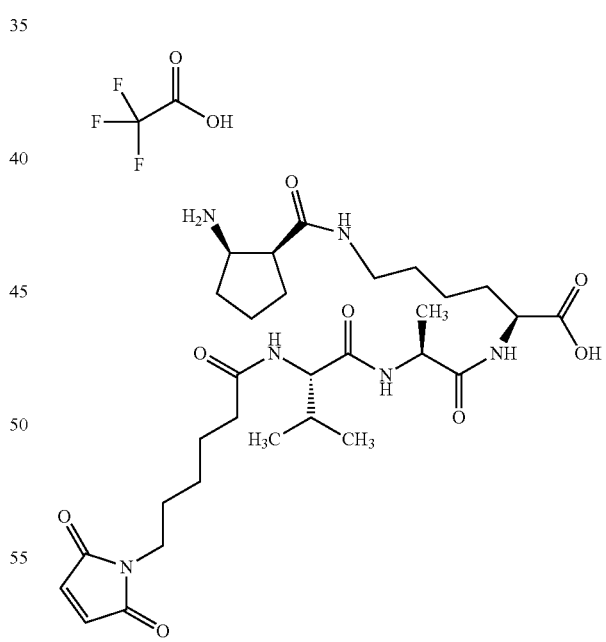

The title compound was prepared from Intermediate L6 by coupling with (1S,2R)-2-[(tert-butoxycarbonyl)amino] cyclopentanecarboxylic acid with EDC/HOBT and subsequent deprotection with TFA. This gave 11 mg (39% of theory over 2 steps) of the title compound.

HPLC (Method 11): $R_t$=1.45 min;

LC-MS (Method 1): $R_t$=0.74 min; MS (ESIpos): m/z=677 (M+H)$^+$.

Intermediate L12

Trifluoroacetic acid/1-[2-(2-aminoethoxy)ethyl]-1H-pyrrole-2,5-dione (1:1)

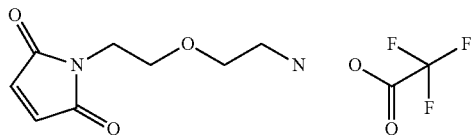

381 mg (2.46 mmol) of methyl 2,5-dioxo-2,5-dihydro-1H-pyrrole-1-carboxylate were added to 228 mg (1.12 mmol) of tert-butyl [2-(2-aminoethoxy)ethyl]carbamate dissolved in 7 ml of dioxane/water 1:1. 1.2 ml of a saturated sodium bicarbonate solution were then added and the reaction was stirred at RT.

After a total of 5 days of stirring and 2 further additions of the same amounts of the sodium bicarbonate solution, the reaction was worked up by acidification with trifluoroacetic acid, concentration on a rotary evaporator and purification by preparative HPLC. The appropriate fractions were combined, the solvent was removed under reduced pressure and the residue was lyophilized from acetonitrile/water 1:1. The residue was taken up in 3 ml of dichloromethane, and 1 ml of trifluoroacetic acid was added. After 15 min of stirring at RT, the solvent was removed under reduced pressure and the residue was lyophilized from acetonitrile/water 1:1. This gave 70 mg (67% of theory over 2 steps) of the title compound as a resinous residue.

HPLC (Method 11): $R_t$=0.2 min;
LC-MS (Method 1): $R_t$=0.18 min; MS (ESIpos): m/z=185 (M+H)$^+$.

Intermediate L13

Trifluoroacetic acid/tert-butyl N2-[(2,5-dioxo-2,5-dihydro-1H-pyrrol-1-yl)acetyl]-L-lysinate (1:1)

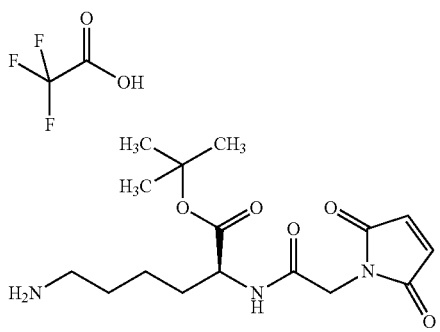

The title compound was prepared by coupling of (2,5-dioxo-2,5-dihydro-1H-pyrrol-1-yl)acetic acid with tert-butyl N6-(tert-butoxycarbonyl)-L-lysinate hydrochloride (1:1) in the presence of EDC/HOBT and subsequent gentle removal of the tert-butoxycarbonyl protective group analogously to Intermediate L6.

HPLC (Method 11): $R_t$=0.42 min;
LC-MS (Method 1): $R_t$=0.43 min; MS (ESIpos): m/z=340 (M+H)$^+$.

Intermediate L14

Trifluoroacetic acid/1-[2-(4-aminopiperazin-1-yl)-2-oxoethyl]-1H-pyrrole-2,5-dione (1:1)

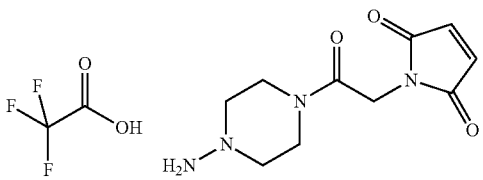 [SMILES: O=C(O)C(F)(F)F ; NN1CCN(C(=O)CN2C(=O)C=CC2=O)CC1]

The title compound was prepared analogously to Intermediate L2 over 2 steps from tert-butyl piperazin-1-ylcarbamate and (2,5-dioxo-2,5-dihydro-1H-pyrrol-1-yl)acetic acid.

HPLC (Method 11): $R_t$=0.2 min;
LC-MS (Method 3): $R_t$=0.25 min; MS (ESIpos): m/z=239 (M+H)$^+$.

Intermediate L15

Trifluoroacetic acid/N-(2-aminoethyl)-3-(2-{2-[2-(2,5-dioxo-2,5-dihydro-1H-pyrrol-1-yl)ethoxy]ethoxy}ethoxy)propanamide (1:1)

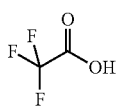

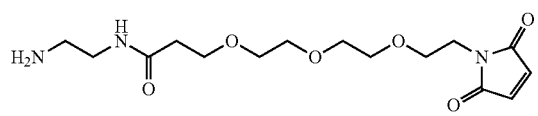

2.93 g (10.58 mmol) of tert-butyl 3-{2-[2-(2-aminoethoxy)ethoxy]ethoxy}propanoate were dissolved in 100 ml of dioxane/water 1:1, and 3.28 g (21.15 mmol) of methyl 2,5-dioxo-2,5-dihydro-1H-pyrrole-1-carboxylate and a saturated sodium bicarbonate solution were added until a pH of 6-7 had been reached. The solution was stirred at RT for 30 min and the 1,4-dioxane was then evaporated under reduced pressure. 200 ml of water were then added, and the mixture was extracted three times with in each case 300 ml of ethyl acetate. The organic extracts were combined, dried over magnesium sulphate and filtered. Concentration gave tert-butyl 3-(2-{2-[2-(2,5-dioxo-2,5-dihydro-1H-pyrrol-1-yl)ethoxy]ethoxy}ethoxy)propanoate as a brown oil which was then dried under high vacuum.

HPLC (Method 11): $R_t$=1.5 min;
LC-MS (Method 3): $R_t$=0.88 min; MS (ESIpos): m/z=375 (M+NH$_4$)$^+$.

This intermediate was converted by standard methods (deprotection with TFA, coupling with tert-butyl (2-aminoethyl)carbamate and another deprotection with TFA) into the title compound.

HPLC (Method 11): $R_t$=0.2 min;
LC-MS (Method 3): $R_t$=0.25 min; MS (ESIpos): m/z=344 (M+H)$^+$.

Intermediate L16

N-[6-(2,5-Dioxo-2,5-dihydro-1H-pyrrol-1-yl)hexanoyl]-L-valyl-N⁵-carbamoyl-L-ornithine

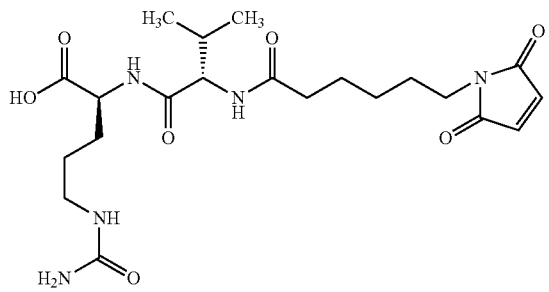 [SMILES: CC(C)[C@H](NC(=O)CCCCCN1C(=O)C=CC1=O)C(=O)N[C@@H](CCCNC(N)=O)C(=O)O]

535 mg (1.73 mmol) of commercially available 1-{6-[(2,5-dioxopyrrolidin-1-yl)oxy]-6-oxohexyl}-1H-pyrrole-2,5-dione and 930 ml of N,N-diisopropylethylamine were added to a solution of 266 mg (1.33 mmol) of L-valyl-N⁵-carbamoyl-L-ornithine in 24 ml of DMF. The reaction was treated in an ultrasonic bath for 24 h and then concentrated to dryness under reduced pressure. The residue that remained was purified by preparative HPCL and gave, after concentration of the appropriate fractions and drying of the residue under high vacuum, 337 mg (50% of theory) of the title compound.

HPLC (Method 11): $R_t$=0.4 min;
LC-MS (Method 3): $R_t$=0.58 min; MS (ESIpos): m/z=468 (M+H)⁺.

Intermediate L17

Trifluoroacetic acid/tert-butyl N-[6-(2,5-dioxo-2,5-dihydro-1H-pyrrol-1-yl)hexanoyl]-L-valyl-N⁵-carbamoyl-L-ornithyl-L-lysinate (1:1)

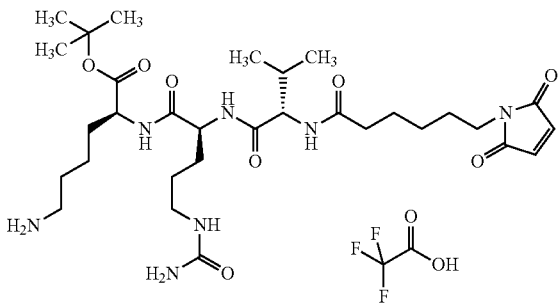 [SMILES: CC(C)[C@H](NC(=O)CCCCCN1C(=O)C=CC1=O)C(=O)N[C@@H](CCCNC(N)=O)C(=O)N[C@@H](CCCCN)C(=O)OC(C)(C)C ; O=C(O)C(F)(F)F]

The title compound was prepared by initially coupling 172 mg (0.37 mmol) of Intermediate L16 and 125 mg (0.37 mmol) of tert-butyl N6-(tert-butoxycarbonyl)-L-lysinate hydrochloride (1:1) in the presence of EDC/HOBT and N,N-diisopropylethylamine and then deprotecting the amino group under gentle conditions by stirring for 2 h in 10% strength trifluoroacetic acid in DCM at RT. Freeze-drying from acetonitrile/water gave 194 mg (49% of theory) of the title compound over 2 steps.

HPLC (Method 11): $R_t$=1.1 min;
LC-MS (Method 1): $R_t$=0.58 min; MS (ESIpos): m/z=652 (M+H)⁺.

Intermediate L18

Trifluoroacetic acid/beta-alanyl-L-alanyl-N⁵-carbamoyl-N-[4-(2-methoxy-2-oxoethyl)phenyl]-L-ornithinamide (1:1)

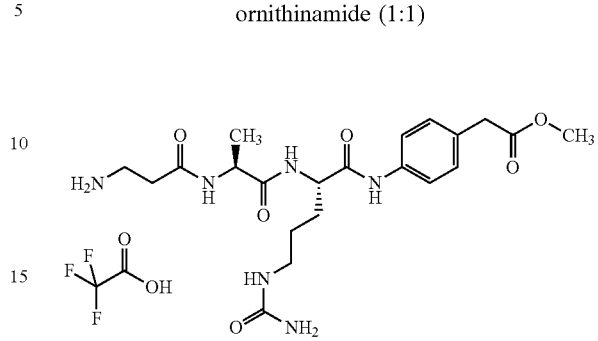

The title compound was prepared from methyl (4-aminophenyl)acetate analogously to Intermediate L7 sequentially according to classical methods of peptide chemistry by linking N²-(tert-butoxycarbonyl)-N⁵-carbamoyl-L-ornithine in the presence of HATU, deprotection with TFA, coupling with 2,5-dioxopyrrolidin-1-yl N-(tert-butoxycarbonyl)-L-alaninate, deprotection with TFA, coupling with 2,5-dioxopyrrolidin-1-yl N-(tert-butoxycarbonyl)-beta-alaninate and another deprotection with TFA. This gave 330 mg of the title compound.

HPLC (Method 11): $R_t$=0.29 min;
LC-MS (Method 1): $R_t$=0.41 min; MS (ESIpos): m/z=465 (M+H)⁺.

Intermediate L19

Trifluoroacetic acid/L-alanyl-N⁵-carbamoyl-N-(4-{[(2,5-dioxo-2,5-dihydro-1H-pyrrol-1-yl)acetyl]amino}phenyl)-L-ornithinamide (1:1)

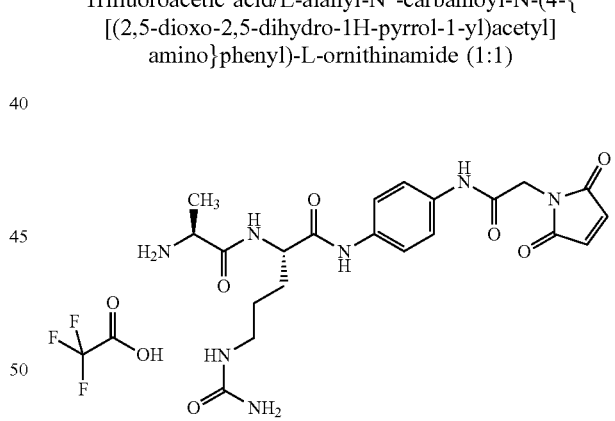

The title compound was prepared from 1,4-phenylenediamine sequentially according to classical methods of peptide chemistry. In the first step, 942 mg (8.72 mmol) of 1,4-phenylenediamine were monoacylated with 0.8 g (2.9 mmol) of N²-(tert-butoxycarbonyl)-N⁵-carbamoyl-L-ornithine in the presence of HATU and N,N-diisopropylethylamine. In the second step, in an analogous manner, the second anilinic amino group was acylated with (2,5-dioxo-2,5-dihydro-1H-pyrrol-1-yl)acetic acid in the presence of HATU and N,N-diisopropylethylamine Deprotection with TFA, coupling with 2,5-dioxopyrrolidin-1-yl N-(tert-butoxycarbonyl)-L-alaninate and another deprotection with TFA then gave, in 3 further synthesis steps, the title compound, 148 mg of which were obtained by this route.

LC-MS (Method 1): $R_t$=0.21 min; MS (ESIpos): m/z=474 (M+H)$^+$.

LC-MS (Method 4): $R_t$=0.2 min; MS (ESIpos): m/z=474 (M+H)$^+$.

Intermediate L20

Trifluoroacetic acid/L-valyl-N$^5$-carbamoyl-N-[4-(2,5-dioxo-2,5-dihydro-1H-pyrrol-1-yl)phenyl]-L-ornithinamide (1:1)

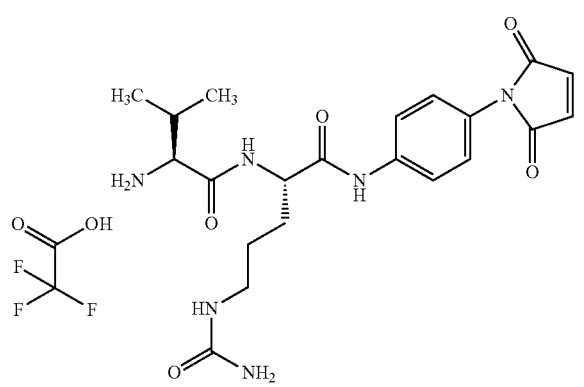 [SMILES: O=C(O)C(F)(F)F ; CC(C)[C@H](N)C(=O)N[C@@H](CCCNC(N)=O)C(=O)Nc1ccc(N2C(=O)C=CC2=O)cc1]

The title compound was prepared according to classical methods of peptide chemistry analogously to Intermediate L8 from commercially available 1-(4-aminophenyl)-1H-pyrrole-2,5-dione by sequential coupling with N$^2$-(tert-butoxycarbonyl)-N$^5$-carbamoyl-L-ornithine in the presence of HATU, deprotection with TFA, coupling with 2,5-dioxypyrrolidin-1-yl N-(tert-butoxycarbonyl)-L-valinate and another deprotection with TFA. This gave 171 mg of the title compound.

HPLC (Method 11): $R_t$=0.28 min;

LC-MS (Method 1): $R_t$=0.39 min; MS (ESIpos): m/z=445 (M+H)$^+$.

Intermediate L21

L-Valyl-N$^6$-(tert-butoxycarbonyl)-N-[4-(2-methoxy-2-oxoethyl)phenyl]-L-lysinamide

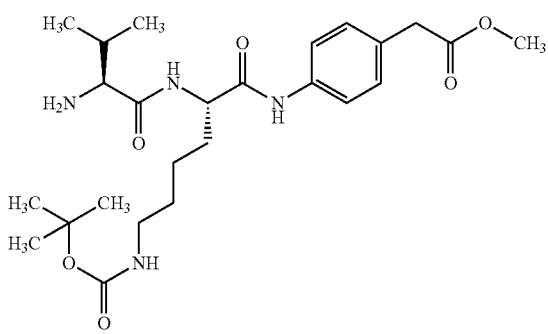 [SMILES: COC(=O)Cc1ccc(NC(=O)[C@H](CCCCNC(=O)OC(C)(C)C)NC(=O)[C@@H](N)C(C)C)cc1]

The title compound was prepared according to classical methods of peptide chemistry from commercially available 0.42 g (2.56 mmol) of methyl (4-aminophenyl)acetate by sequential coupling with N$^6$-(tert-butoxycarbonyl)-N$^2$-[(9H-fluoren-9-ylmethoxy)carbonyl]-L-lysine in the presence of HATU and N,N-diisopropylethylamine, deprotection with piperidine, coupling with 2,5-dioxopyrrolidin-1-yl N-[(benzyloxy)carbonyl]-L-valinate in the presence of N,N-diisopropylethylamine and subsequent hydrogenolytic removal of the benzyloxycarbonyl protective group over 10% palladium on activated carbon. This gave 360 mg (32% of theory over 4 steps) of the title compound.

HPLC (Method 11): $R_t$=1.5 min;

LC-MS (Method 1): $R_t$=0.73 min; MS (ESIpos): m/z=493 (M+H)$^+$.

Intermediate L22

Trifluoroacetic acid/N-[(9H-fluoren-9-ylmethoxy)carbonyl]-L-valyl-N-{4-[(2S)-2-amino-3-methoxy-3-oxopropyl]phenyl}-N$^5$-carbamoyl-L-ornithinamide (1:1)

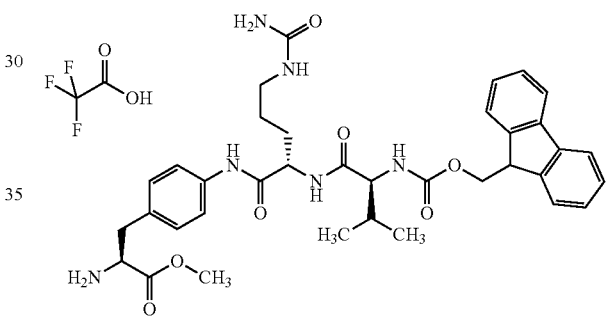

The title compound was prepared from N-(tert-butoxycarbonyl)-4-nitro-L-phenylalanine sequentially according to classical methods of peptide chemistry. 2.5 g (8.06 mmol) of this starting material were in the first step initially converted into the caesium salt and then with iodomethane in DMF into the methyl ester.

Hydrogenolytically in methanol over 10% palladium on activated carbon, the nitro group was then converted into an amino group.

The amino group generated in this manner was then acylated with N$^5$-carbamoyl-N$^2$-[(9H-fluoren-9-ylmethoxy)carbonyl]-L-ornithine in DMF in the presence of HATU and N,N-diisopropylethylamine. In the next step, the Fmoc group was removed with piperidine in DMF.

Coupling was then carried out in DMF with N-[(9H-fluoren-9-ylmethoxy)carbonyl]-L-valine in the presence of 1-(3-dimethylaminopropyl)-3-ethylcarbodiimide hydrochloride, 1-hydroxy-1H-benzotriazole hydrate and N,N-diisopropylethylamine and finally removal of the tert-butoxycarbonyl group with trifluoroacetic acid.

HPLC (Method 11): $R_t$=1.6 min;

LC-MS (Method 1): $R_t$=0.77 min; MS (ESIpos): m/z=673 (M+H)$^+$.

Intermediate L23

Trifluoroacetic acid/N-[2-(2,5-dioxo-2,5-dihydro-1H-pyrrol-1-yl)ethyl]-beta-alaninamide (1:1)

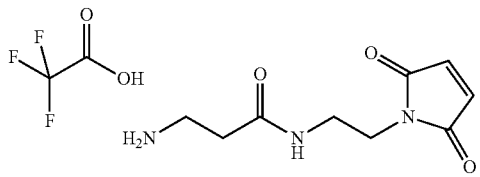 [SMILES: O=C(O)C(F)(F)F ; NCCC(=O)NCCN1C(=O)C=CC1=O]

The title compound was prepared from commercially available trifluoroacetic acid/1-(2-aminoethyl)-1H-pyrrole-2,5-dione (1:1) by coupling with N-(tert-butoxycarbonyl)-beta-alanine in the presence of EDCl/HOBT and N,N-diisopropylethylamine and subsequent deprotection with trifluoroacetic acid.

HPLC (Method 11): $R_t$=0.19 min

Intermediate L24

Trifluoroacetic acid 1-amino-N-[2-(2,5-dioxo-2,5-dihydro-1H-pyrrol-1-yl)ethyl]cyclopropanecarboxamide (1:1)

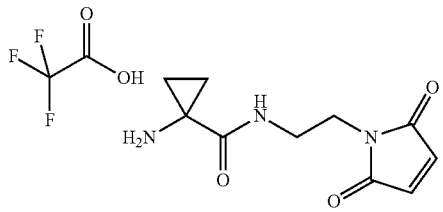

114 mg (0.67 mmol) of commercially available 1-[(tert-butoxycarbonyl)amino]cyclopropane-carboxylic acid were dissolved in 25 ml of DCM, 110 mg (0.623 mmol) of commercially available trifluoroacetic acid/1-(2-aminoethyl)-1H-pyrrole-2,5-dione (1:1) and 395 µl of N,N-diisopropylethylamine were added and the mixture was cooled to −10° C. 217 mg (0.793 mmol) of 2-bromo-1-ethylpyridinium tetrafluoroborate were then added, and the mixture was stirred at RT for 2 h. The mixture was then diluted with ethyl acetate and extracted successively with 10% strength citric acid, saturated sodium bicarbonate solution and saturated sodium chloride solution, then dried over magnesium sulphate and concentrated. Drying under high vacuum gave 152 mg of the protected intermediate.

These were then taken up in 10 ml of DCM and deprotected with 1 ml of trifluoroacetic acid. Lyophilization from acetonitrile/water gave 158 mg (71% of theory over 2 steps) of the title compound.

HPLC (Method 11): $R_t$=0.19 min

LC-MS (Method 3): $R_t$=0.98 min; MS (ESIpos): m/z=224 (M+H)⁺.

Intermediate L25

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-L-alanine

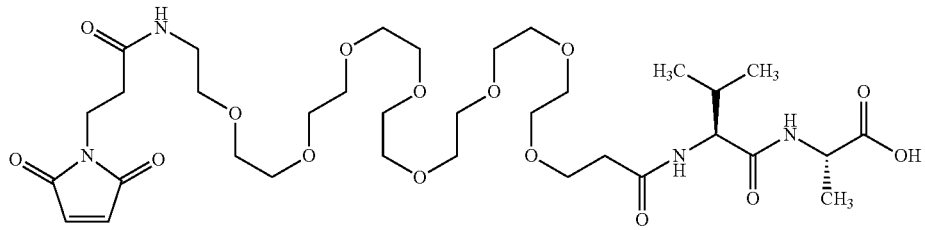 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)O]

31.4 mg (0.17 mmol) of valyl-L-alanine were dissolved in 3.0 ml of DMF, and 115.0 mg (0.17 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 33.7 mg (0.0.33 mmol) of triethylamine were added. The mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 74.1 mg (58% of theory) of the title compound.

LC-MS (Method 1): $R_t$=0.61 min; MS (ESIpos): m/z=763 [M+H]⁺.

Intermediate L26

L-Valyl-N⁶-(tert-butoxycarbonyl)-L-lysine

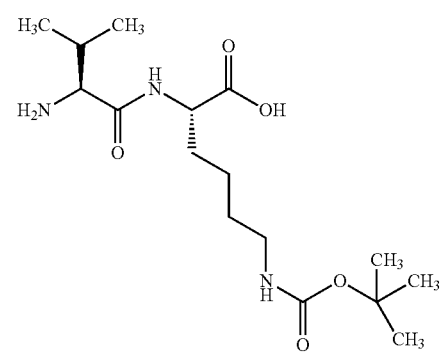 [SMILES: CC(C)[C@H](N)C(=O)N[C@@H](CCCCNC(=O)OC(C)(C)C)C(=O)O]

600.0 mg (1.58 mmol) of N²-[(benzyloxy)carbonyl]-N⁶-(tert-butoxycarbonyl)-L-lysine were suspended in 25.0 ml of water/ethanol/THF (1:1:0.5), palladium on carbon (10%) was added and the mixture was hydrogenated at RT with hydrogen under standard pressure for 5 h. The catalyst was filtered off and the solvents were evaporated under reduced pressure. The compound obtained was used in the next step without further purification.

LC-MS (Method 1): $R_t$=0.42 min; MS (ESIpos): m/z=247 [M+H]$^+$.

180 mg (0.73 mmol) of $N^6$-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction solution was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 294.1 mg (76% of theory) of N-[(benzyloxy)carbonyl]-L-valyl-$N^6$-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-$N^6$-(tert-butoxycarbonyl)-L-lysine were initially charged in 20.0 ml of ethyl acetate/ethanol/THF (1:1:1), and 27.2 mg of palladium on activated carbon were added. The mixture was hydrogenated with hydrogen at RT under standard pressure for 5 h. The mixture was filtered off with the aid of Celite® and the filter cake was washed with ethyl acetate/ethanol/THF (1:1:1). The solvents were evaporated under reduced pressure and the residue was dried under high vacuum. The title compound (182 mg, 72% of theory) was used in the next reaction step without further purification.

LC-MS (Method 1): $R_t$=0.53 min; MS (ESIpos): m/z=346 [M+H]$^+$.

Intermediate L27

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine

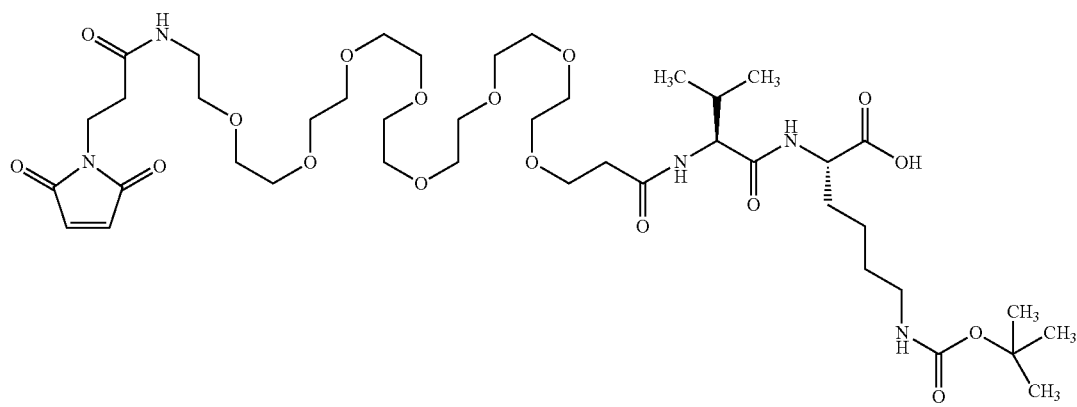 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

30 mg (0.07 mmol) of L-valyl-N6-(tert-butoxycarbonyl)-L-lysine (Intermediate L26) and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were initially charged in 1.5 ml of DMF, and 6.8 mg (0.07 mmol) of 4-methylmorpholine were added. The reaction solution was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 [M+H]$^+$.

Intermediate L28 tert-Butyl 3-formyl-4-({[2-(trimethylsilyl)ethoxy]carbonyl}amino)pyrrolidine-1-carboxylate

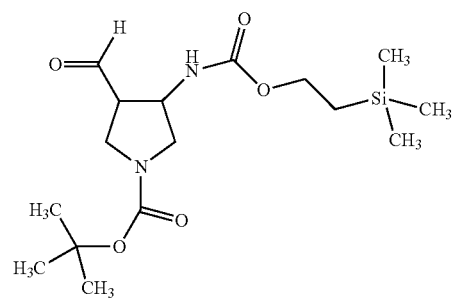 [SMILES: CC(C)(C)OC(=O)N1CC(C=O)C(NC(=O)OCC[Si](C)(C)C)C1]

461.7 mg (1.15 mmol) of 1-tert-butyl 3-ethyl-4-({[2-(trimethylsilyl)ethoxy]carbonyl}amino)pyrrolidine-1,3-dicarboxylate (this compound was prepared according to the literature procedure of WO 2006/066896) were initially charged in 5.0 ml of absolute dichloromethane and the mixture was cooled to −78° C. 326.2 mg (2.29 mmol) of diisobutylaluminum hydride solution (1 M in THF) were then slowly added dropwise and the mixture was stirred at −78° C. for 2 h (monitored by thin-layer chromatography (petroleum ether/ethyl acetate=3:1). 1.3 g (4.59 mmol) of potassium sodium tartrate dissolved in 60 ml of water were added dropwise and the reaction mixture was allowed to warm to RT. Ethyl acetate was added to the reaction mixture and the aqueous phase was extracted three times with ethyl acetate. The combined organic phases were washed once with sat. NaCl solution and dried over magnesium sulphate. The solvent was evaporated under reduced pressure and the residue was dried under high vacuum. This gave 629.0 mg of the title compound as a crude product which was used immediately without further purification in the next reaction step.

Intermediate L29 tert-Butyl 3-formyl-4-[({[2-(trimethylsilyl)ethoxy]carbonyl}amino)methyl]pyrrolidine-1-carboxylate
Mixture of diastereomers

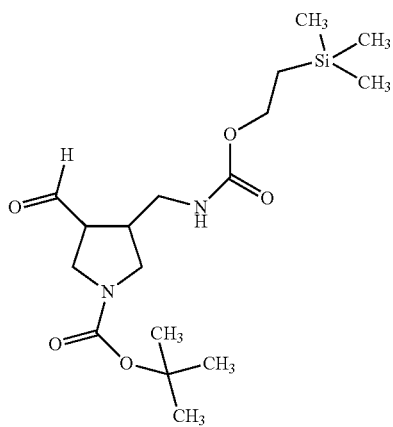 [SMILES: CC(C)(C)OC(=O)N1CC(C=O)C(CNC(=O)OCC[Si](C)(C)C)C1]

807.1 mg (2.34 mmol) of tert-butyl 3-({[tert-butyl(dimethyl)silyl]oxy}methyl)-4-(hydroxymethyl)pyrrolidine-1-carboxylate (prepared according to the literature procedure of WO 2006/100036) were initially charged in 8.0 ml of dichloromethane, and 236.4 mg (2.34 mmol) of triethylamine were added. At 0° C., 267.6 mg (2.34 mmol) of methanesulphonyl chloride were added dropwise, and the reaction mixture stirred at RT overnight. A further 133.8 mg (1.17 mmol) of methanesulphonyl chloride and 118.2 mg (1.17 mmol) of triethylamine were added. The reaction mixture was stirred at RT overnight. The mixture was diluted with dichloromethane and the organic phase was washed in each case once with saturated sodium bicarbonate solution, 5% strength potassium hydrogen sulphate solution and saturated NaCl solution. After drying over magnesium sulphate, the solvent was evaporated under reduced pressure and the residue was purified on Biotage Isolera (silica gel, column 50 g SNAP, flow rate 66 ml/min, cyclohexane/ethyl acetate). The solvents were evaporated under reduced pressure and the residue was dried under high vacuum. This gave 402.0 mg (41% of theory) of the compound tert-butyl 3-({[tert-butyl(dimethyl)silyl]oxy}methyl)-4-{[(methylsulphonyl)oxy]methyl}pyrrolidine-1-carboxylate.

LC-MS (Method 1): $R_t$=1.38 min; MS (ESIpos): m/z=424 [M+H]$^+$.

400.0 mg (0.94 mmol) of tert-butyl 3-({[tert-butyl(dimethyl)silyl]oxy}methyl)-4-{[(methylsulphonyl)oxy]methyl}pyrrolidine-1-carboxylate were initially charged in 5.0 ml of DMF, and 98.2 mg (1.51 mmol) of sodium azide were added. The reaction mixture was stirred at 40° C. for 10 h. Another 30.7 mg (0.47 mmol) of sodium azide were then added, and the mixture was stirred at 40° C. for a further 10 h. Ethyl acetate was added and the organic phase was washed repeatedly with water. After drying of the organic phase over magnesium sulphate, the solvent was evaporated under reduced pressure and the residue was dried under high vacuum. This gave 309.5 mg (89% of theory) of the compound tert-butyl 3-(azidomethyl)-4-({[tert-butyl(dimethyl)silyl]oxy}methyl)pyrrolidine-1-carboxylate. The compound was used without further purification in the next step of the synthesis.

LC-MS (Method 1): $R_t$=1.50 min; MS (ESIpos): m/z=371 [M+H]$^+$.

250 mg (0.68 mmol) of tert-butyl 3-(azidomethyl)-4-({[tert-butyl(dimethyl)silyl]oxy}methyl)pyrrolidine-1-carboxylate were dissolved in 10.0 ml of ethyl acetate/ethanol (1:1), and 25.0 mg of palladium on activated carbon (10%) were added. The mixture was hydrogenated with hydrogen at RT under standard pressure for 8 h. The reaction was filtered through Celite® and the filter cake was washed thoroughly with ethyl acetate. The solvent was evaporated under reduced pressure and the residue was dried under high vacuum. This gave 226.2 mg (82% of theory) of the compound tert-butyl 3-(aminomethyl)-4-({[tert-butyl(dimethyl)silyl]oxy}methyl)pyrrolidine-1-carboxylate. The compound was used without further purification in the next step of the synthesis.

LC-MS (Method 1): $R_t$=0.89 min; MS (ESIpos): m/z=345 [M+H]$^+$.

715.0 mg (2.08 mmol) of tert-butyl 3-(aminomethyl)-4-({[tert-butyl(dimethyl)silyl]oxy}methyl)pyrrolidine-1-carboxylate were dissolved in 15.0 ml of THF, and 2.28 ml (2.28 mmol) of TBAF solution (1M in THF) were added. The reaction mixture was stirred at RT overnight. The solvent was evaporated under reduced pressure and the residue (1.54 g) used without further purification in the next step of the synthesis.

LC-MS (Method 1): $R_t$=0.41 min; MS (ESIpos): m/z=231 [M+H]$^+$.

1.54 g (4.88 mmol) of tert-butyl 3-(aminomethyl)-4-(hydroxymethyl)pyrrolidine-1-carboxylate were initially charged in 1,4-dioxane, and 541.8 mg (4.88 mmol) of calcium chloride (anhydrous) and 488.6 mg (4.88 mmol) of calcium carbonate were added and the mixture was stirred vigorously. 592.8 mg (5.86 mmol) of triethylamine and 1.52 g (5.86 mmol) of 1-({[2-(trimethylsilyl)ethoxy]carbonyl}oxy)pyrrolidine-2,5-dione were then added and the reaction mixture stirred at RT overnight. 644.9 mg (10.7 mmol) of HOAc and ethyl acetate were added. The organic phase was washed twice with water and once with saturated NaCl solution. After drying over magnesium sulphate, the solvent was evaporated under reduced pressure and the residue was purified on silica gel (mobile phase: dichloromethane/methanol=100:1). The solvents were evaporated under reduced pressure and the residue was dried under high vacuum. This gave 346.9 mg (19% of theory) of the compound tert-butyl 3-(hydroxymethyl)-4-[({[2-(trimethylsilyl)ethoxy]carbonyl}amino)methyl]pyrrolidine-1-carboxylate.

LC-MS (Method 1): $R_t$=1.08 min; MS (ESIpos): m/z=375 [M+H]$^+$.

804.0 mg (2.15 mmol) of tert-butyl 3-(hydroxymethyl)-4-[({[2-(trimethylsilyl)ethoxy]carbonyl}amino)methyl]pyrrolidine-1-carboxylate were initially charged in 20.0 ml of chloroform and 20.0 ml of 0.05 N potassium carbonate/0.05 N sodium bicarbonate solution (1:1). 59.7 mg (0.22 mmol) of tetra-n-butylammonium chloride, 429.9 mg (3.22 mmol) of N-chlorosuccinimide and 33.5 mg (0.22 mmol) of TEMPO were then added and the reaction mixture was stirred vigorously at RT overnight. The organic phase was separated off and freed from the solvent under reduced pressure. The residue was purified on silica gel (mobile phase: cyclohexane/ethyl acetate=3:1). This gave 517.0 mg (46% of theory) of the title compound.

LC-MS (Method 1): $R_t$=1.13 min; MS (ESIpos): m/z=373 [M+H]$^+$.

Intermediate L30 tert-Butyl 3-({[tert-butyl(dimethyl)silyl]oxy}methyl)-4-formylpyrrolidine-1-carboxylate Mixture of Stereoisomers

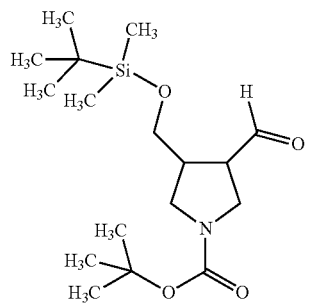 [SMILES: CC(C)(C)OC(=O)N1CC(C=O)C(CO[Si](C)(C)C(C)(C)C)C1]

250.0 mg (0.72 mmol) of tert-butyl 3-({[tert-butyl(dimethyl)silyl]oxy}methyl)-4-(hydroxymethyl)pyrrolidine-1-carboxylate (the compound was prepared according to the literature procedure of WO2006/100036) were initially charged in 12.5 ml of dichloromethane/DMSO (4:1), and 219.6 mg (2.17 mmol) of triethylamine were added. At 2° C., 345.5 mg (2.17 mmol) of sulphur trioxide-pyridine complex were added a little at a time and the mixture was stirred at 2° C. for 3 h. Another 345.5 mg (2.17 mmol) of sulphur trioxide-pyridine complex were added a little at a time and the mixture was stirred at RT for 17 h. The reaction mixture was partitioned between dichloromethane and water. The aqueous phase was extracted three times with dichloromethane and the combined organic phases were washed once with water and dried over magnesium sulphate. The solvent was evaporated under reduced pressure and the residue was dried under high vacuum. The residue was used without further purification in the next step of the synthesis (thin-layer chromatography: petroleum ether/ethyl acetate 7:3).

Intermediate L31

Di-tert-butyl {[(tert-butoxycarbonyl)amino]methyl}malonate

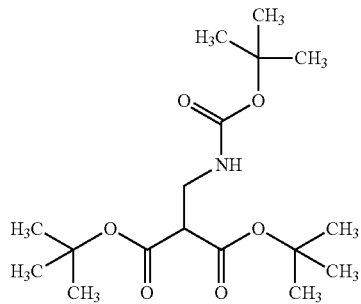 [SMILES: CC(C)(C)OC(=O)NCC(C(=O)OC(C)(C)C)C(=O)OC(C)(C)C]

57.2 g (488.27 mmol) of tert-butyl carbamate, 51.2 ml (683.57 mmol) of a 37% strength solution of formaldehyde in water and 25.9 g (244.13 mmol) of sodium carbonate were added to 600 ml of water. The mixture was warmed until a solution was formed and then stirred at RT for 16 h. The suspension formed was extracted with 500 ml of dichloromethane and the organic phase was separated off, washed with saturated sodium chloride solution and dried over sodium sulphate. The mixture was concentrated on a rotary evaporator and the residue was dried under high vacuum, giving a crystalline solid. The residue was taken up in 1000 ml of absolute THF, and a mixture of 322 ml (3.414 mol) of acetic anhydride and 138 ml (1.707 mol) of pyridine was added dropwise at RT. The reaction mixture was stirred at RT for 16 h and then concentrated on a rotary evaporator, with the water bath at room temperature. The residue was taken up in diethyl ether and washed three times with a saturated sodium bicarbonate solution and once with a saturated sodium chloride solution. The organic phase was dried over sodium sulphate and concentrated on a rotary evaporator and the residue was dried under high vacuum for 2 d. The residue was taken up in 2000 ml of absolute THF, and 456 ml (456.52 mmol) of a 1 M solution of potassium tert-butoxide in THF were added with ice cooling. The mixture was stirred at 0° C. for 20 min, and 100.8 g (456.52 mmol) of di-tert-butyl malonate dissolved in 200 ml of absolute THF were then added dropwise. The mixture was stirred at RT for 48 h, and water was then added. The reaction mixture was concentrated on a rotary evaporator and taken up in 500 ml of ethyl acetate. The mixture was washed with 500 ml of water and 100 ml of a saturated sodium chloride solution and the organic phase was dried over sodium sulphate. The organic phase was concentrated on a rotary evaporator and the residue was dried under high vacuum. The residue was purified by filtration through silica gel (mobile phase: cyclohexane/ethyl acetate, gradient=30:1→5:1). This gave 37.07 g (22% of theory) of the target compound.

LC-MS (Method 6): $R_t$=2.87 min; MS (ESIpos): m/z=346 [M+H]$^+$.

Intermediate L32 tert-Butyl [3-hydroxy-2-(hydroxymethyl)propyl]carbamate

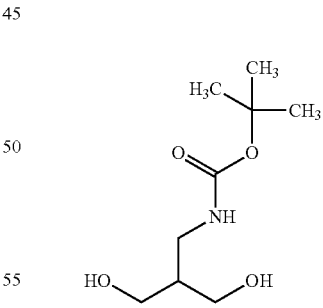

37.0 g (107.11 mmol) of di-tert-butyl (acetoxymethyl)malonate were dissolved in 1000 ml of absolute THF, and 535.5 ml (1071.10 mmol) of a 2 M solution of lithium borohydride in THF were added dropwise with ice cooling. 19.3 ml (1071.10 mmol) of water were added dropwise and the mixture was stirred at RT for 4.5 h. The reaction mixture was concentrated on a rotary evaporator and dried under high vacuum. The residue was taken up in 1500 ml of ethyl acetate, 100 ml of water were added and the mixture was stirred with water cooling (slightly exothermic) for 30 min.

The organic phase was separated off and the aqueous phase was extracted twice with 500 ml of ethyl acetate. The organic phase was concentrated on a rotary evaporator and the residue was dried under high vacuum. This gave 20.7 g (94% of theory) of the target compound.

LC-MS (Method 6): $R_t$=1.49 min; MS (EIpos): m/z=106 $[M—C_5H_8O_2]^+$.

Intermediate L33 tert-Butyl [3-{[tert-butyl(dimethyl)silyl]oxy}-2-(hydroxymethyl)propyl]carbamate

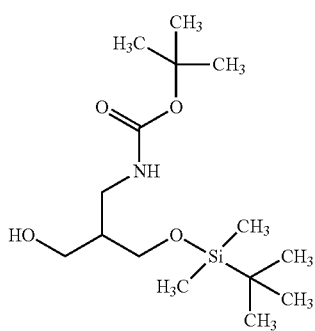

20.00 g (97.44 mmol) of tert-butyl [3-hydroxy-2-(hydroxymethyl)propyl]carbamate were dissolved in 1000 ml of absolute dichloromethane, and 6.63 g (97.44 mmol) of imidazole and 16.16 g (107.18 mmol) of tert-butyl(chloro)dimethylsilane were added at RT. The reaction mixture was stirred at RT for 16 h and washed with semiconcentrated sodium chloride solution. The aqueous phase was extracted with ethyl acetate and the combined organic phases were dried over sodium sulphate, concentrated on a rotary evaporator and dried under high vacuum. This gave 28.50 g (92% of theory) of the target compound.

$^1$H NMR (400 MHz, DMSO-$d_6$): δ [ppm]=0.02 (s, 6H), 0.86 (s, 9H), 1.37 (s, 9H), 1.58-1.73 (m, 1H), 2.91 (q, 2H), 3.33-3.36 [m, (2H, obscured)], 3.53-3.58 (m, 2H), 6.65-6.72 (m, 1H).

Intermediate L34 tert-Butyl (3-{[tert-butyl(dimethyl)silyl]oxy}-2-formylpropyl)carbamate

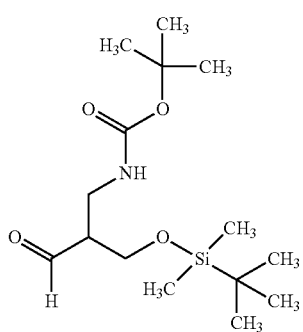 [SMILES: CC(C)(C)OC(=O)NCC(C=O)CO[Si](C)(C)C(C)(C)C]

12.65 g (39.591 mmol) of tert-butyl [3-{[tert-butyl(dimethyl)silyl]oxy}-2-(hydroxy-methyl)propyl]carbamate were dissolved in 200 ml of dichloromethane, and 19.31 g (45.53 mmol) of Dess-Martin periodinane dissolved in 150 ml of dichloromethane were added dropwise at RT. The mixture was stirred at room temperature for 2 h, 250 ml of a semiconcentrated sodium bicarbonate solution and 250 ml of a 10% strength sodium thiosulphate solution were then added and the mixture was stirred for 20 min. The organic phase was separated off and the aqueous phase was extracted with ethyl acetate. The combined organic phases were washed with 300 ml of water, dried over sodium sulphate, concentrated on a rotary evaporator and dried under high vacuum. This gave 11.35 g (90% of theory) of the target compound.

$^1$H NMR (400 MHz, DMSO-$d_6$): δ [ppm]=0.02 (s, 6H), 0.84(s, 9H), 1.36 (s, 9H), 1.48-1.51 (m, 1H), 3.08-3.32 [m, (1H, obscured)], 3.50-3.58 (m, 2H), 3.81-3.91 (m, 1H), 6.71 (t, 1H), 9.60 (d, 1H).

Intermediate L35 tert-Butyl (3-oxopropyl)carbamate

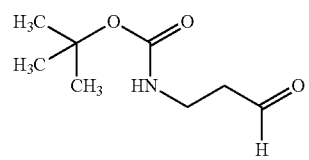

The title compound was prepared according to a method known from the literature (e.g. Jean Bastide et al. J. Med. Chem. 2003, 46(16), 3536-3545).

Intermediate L36

N-[(Benzyloxy)carbonyl]-L-valyl-N5-carbamoyl-L-ornithine

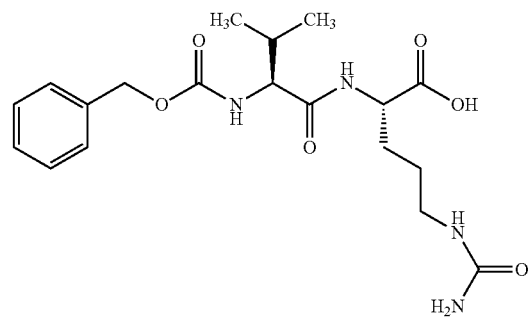 [SMILES: CC(C)[C@H](NC(=O)OCc1ccccc1)C(=O)N[C@@H](CCCNC(N)=O)C(=O)O]

100 mg (0.57 mmol) of $N^5$-carbamoyl-L-ornithine were taken up in 4.0 ml of DMF, and 0.08 ml (0.57 mmol) of triethylamine was added. 199.0 mg (0.57 mmol) of 2,5-dioxopyrrolidin-1-yl N-[(benzyloxy)carbonyl]-L-valine and 0.08 ml (0.57 mmol) of triethylamine were then added. The mixture was stirred at RT for 48 h. The reaction mixture was purified directly by preparative RP-HPLC (column: Reprosil 250×30; 10µ, flow rate: 50 ml/min, MeCN/water with 0.1% TFA). The solvents were evaporated under reduced pressure and the residue was dried under high vacuum. This gave 75.7 mg (33% of theory) of the title compound.

LC-MS (Method 1): $R_t$=0.69 min; MS (ESIpos): m/z=409 [M+H]$^+$.

Intermediate L37

L-Valyl-N$^5$-carbamoyl-L-ornithine

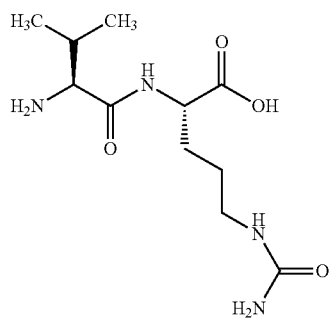 [SMILES: CC(C)[C@H](N)C(=O)N[C@@H](CCCNC(N)=O)C(=O)O]

75.7 mg (0.19 mmol) of Intermediate L36 were suspended in 25 ml of water/ethanol/THF, and 7.5 mg of palladium on activated carbon (10%) were added and the mixture was hydrogenated at RT with hydrogen under standard pressure for 4.5 h. The catalyst was filtered off and the reaction mixture was freed from the solvent under reduced pressure and dried under high vacuum. The residue was used for the next step without further purification. This gave 64.9 mg (93% of theory) of the title compound.

LC-MS (Method 6): $R_t$=0.25 min; MS (ESIpos): m/z=275 [M+H]$^+$.

Intermediate L38

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N$^5$-carbamoyl-L-ornithine 38.3 mg (0.14 mmol) of Intermediate L37 were initially charged in 3.0 ml of DMF, and 96.4 mg (0.14 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 39.0 µl (0.28 mmol) of triethylamine were added. The mixture was stirred at RT overnight. 16.0 µl (0.28 mmol) of HOAc were then added, and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 58.9 mg (45% of theory) of the title compound.

LC-MS (Method 1): $R_t$=0.61 min; MS (ESIpos): m/z=849 [M+H]$^+$.

Intermediate L39

2-(Trimethylsilyl)ethyl (2-sulphanylethyl)carbamate

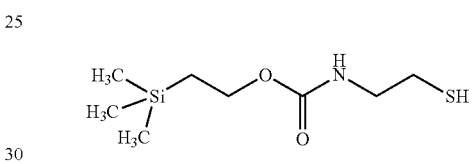

300 mg (2.64 mmol) of 2-aminoethanethiol hydrochloride (1:1) were initially charged in 3.0 ml of dichloromethane, and 668.0 mg (6.60 mmol) of triethylamine and 719.1 mg (2.77 mmol) of 1-({[2-(trimethylsilyl)ethoxy]carbonyl}oxy)pyrrolidine-2,5-dione were added. The mixture was stirred at RT for 2 days (monitored by thin-layer chromatography: dichloromethane/methanol=100:1.5). Ethyl acetate was added and the reaction mixture was washed three times with water. The organic phase was washed twice with saturated NaCl solution and dried over magnesium sulphate. The solvent was evaporated under reduced pressure and the residue was dried under high vacuum. The compound was used without further purification in the next step of the synthesis.

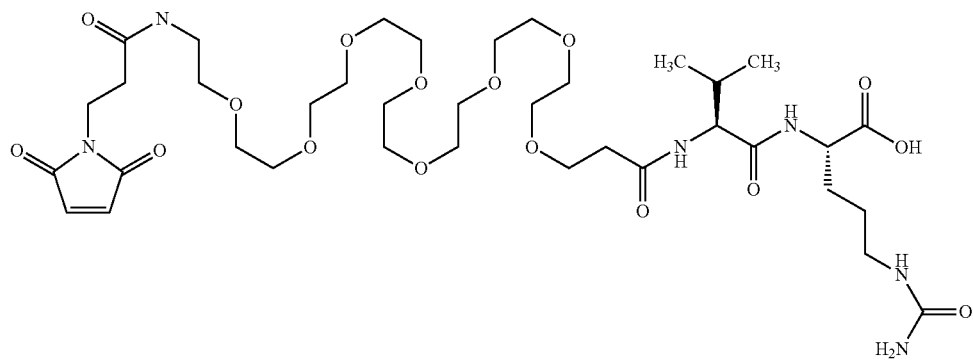 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)O]

Intermediate L40

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-$N^6$-(tert-butoxycarbonyl)-L-lysine

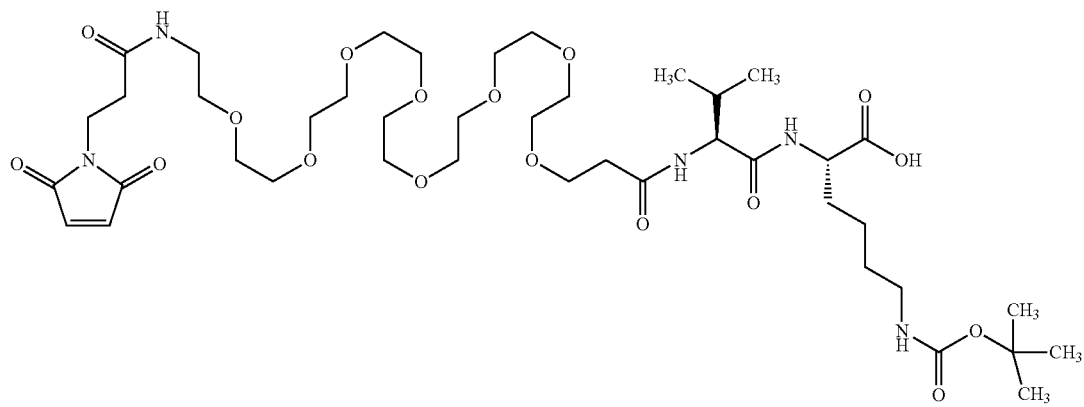 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of $N^2$-[(benzyloxy)carbonyl]-$N^6$-(tert-butoxycarbonyl)-L-lysine were hydrogenated in 25.0 ml of water/ethanol/THF (1:1:0.5) using palladium on carbon (10%) at RT under standard pressure with hydrogen. The compound $N^6$-(tert-butoxycarbonyl)-L-lysine is used without further purification in the next step of the synthesis.

LC-MS (Method 1): $R_t$=0.99 min; MS (ESIpos): m/z=247 [M+H]⁺.

180.0 g (0.73 mmol) of $N^6$-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 294.1 mg (76% of theory) of the compound N-[(benzyloxy)carbonyl]-L-valyl-$N^6$-(tert-butoxycarbonyl)-L-lysine.

LC-MS (Method 1): $R_t$=0.97 min; MS (ESIpos): m/z=480 [M+H]⁺.

272.2 mg (0.57 mmol) of N-[(benzyloxy)carbonyl]-L-valyl-$N^6$-(tert-butoxycarbonyl)-L-lysine were dissolved in 20 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-$N^6$-(tert-butoxycarbonyl)-L-lysine.

LC-MS (Method 1): $R_t$=0.53 min; MS (ESIpos): m/z=346 [M+H]⁺.

30.0 mg (0.07 mmol) of L-valyl-N6-(tert-butoxycarbonyl)-L-lysine and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 [M+H]⁺.

Intermediate L41

N-[19-(2,5-Dioxo-2,5-dihydro-1H-pyrrol-1-yl)-17-oxo-4,7,10,13-tetraoxa-16-azanonadecan-1-oyl]-L-valyl-N6-(tert-butoxycarbonyl)-L-lysine

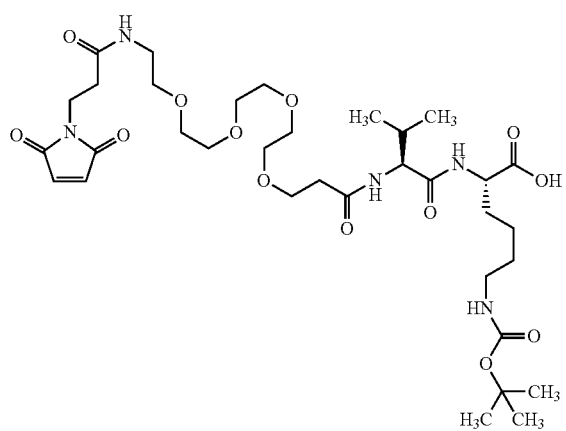 [SMILES: CC(C)[C@H](NC(=O)CCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of $N^2$-[(benzyloxy)carbonyl]-$N^6$-(tert-butoxycarbonyl)-L-lysine were hydrogenated in 25.0 ml of water/ethanol/THF (1:1:0.5) using palladium on carbon (10%) at RT under standard pressure with hydrogen. The compound $N^6$-(tert-butoxycarbonyl)-L-lysine is used without further purification in the next step of the synthesis.

LC-MS (Method 1): $R_t$=0.99 min; MS (ESIpos): m/z=247 [M+H]$^+$.

180.0 g (0.73 mmol) of $N^6$-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction mixture was purified directly by preparative RP-HPLC (column: Reprosil 250×30; 10μ, flow rate: 50 ml/min, MeCN/water, 0.1% TFA). The solvents were then evaporated under reduced pressure and the residue was dried under high vacuum. This gave 294.1 mg (76% of theory) of the compound N-[(benzyloxy)carbonyl]-L-valyl-$N^6$-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-$N^6$-(tert-butoxycarbonyl)-L-lysine were dissolved in 20.0 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-$N^6$-(tert-butoxycarbonyl)-L-lysine.

LC-MS (Method 1): $R_t$=0.53 min; MS (ESIpos): m/z=346 [M+H]$^+$.

30.0 mg (0.07 mmol) of L-valyl-N6-(tert-butoxycarbonyl)-L-lysine and 34.3 mg (0.07 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 40.6 mg (82% of theory) of the title compound.

LC-MS (Method 1): $R_t$=0.73 min; MS (ESIpos): m/z=744 [M+H]$^+$.

Intermediate L42

N-[19-(2,5-Dioxo-2,5-dihydro-1H-pyrrol-1-yl)-17-oxo-4,7,10,13-tetraoxa-16-azanonadecan-1-oyl]-L-valyl-$N^5$-carbamoyl-L-ornithine

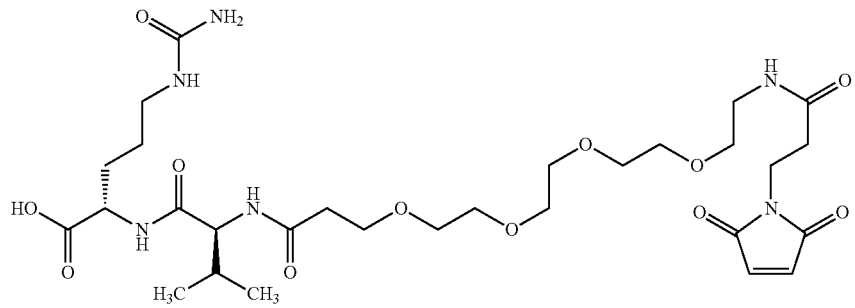 [SMILES: CC(C)[C@H](NC(=O)CCOCCOCCOCCOCCNC(=O)CCN1C(=O)C=CC1=O)C(=O)N[C@@H](CCCNC(N)=O)C(=O)O]

50.0 mg (0.18 mmol) of L-valyl-$N^5$-carbamoyl-L-ornithine (Intermediate L37) were initially charged in DMF, and 93.6 mg (0.18 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 36.9 mg (0.37 mmol) of triethylamine were added. The reaction mixture was stirred at RT overnight. 21.9 mg (0.37 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 20.6 mg (14% of theory) of the title compound.

LC-MS (Method 1): $R_t$=0.55 min; MS (ESIpos): m/z=673 [M+H]$^+$.

Intermediate L43

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-$N^5$-carbamoyl-L-ornithine

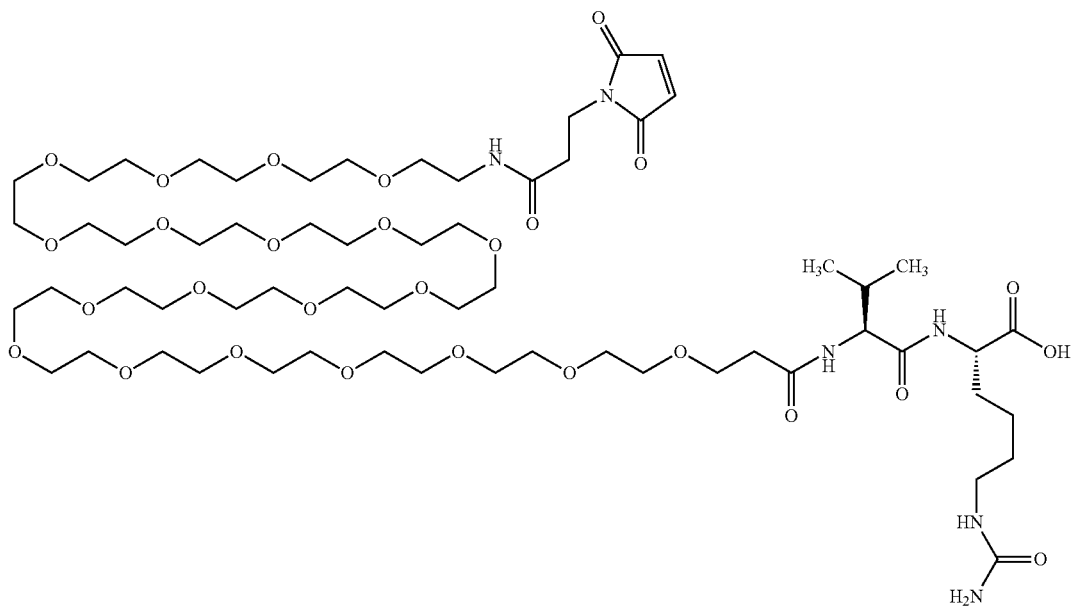 [SMILES: CC(C)[C@H](NC(=O)CCOCCOCCOCCOCCOCCOCCOCCOCCOCCOCCOCCOCCOCCOCCOCCOCCOCCOCCOCCOCCNC(=O)CCN1C(=O)C=CC1=O)C(=O)N[C@@H](CCCCNC(N)=O)C(=O)O]

11.3 mg (0.04 mmol) of L-valyl-$N^5$-carbamoyl-L-ornithine (Intermediate L37) were initially charged in DMF, and 50.0 mg (0.04 mmol) of 3-(2,5-dioxo-2,5-dihydro-1H-pyrrol-1-yl)-N-{63-[(2,5-dioxopyrrolidin-1-yl)oxy]-63-oxo-3,6,9,12,15,18,21,24,27,30,33,36,39,42,45,48,51,54,57,60-icosaoxatrihexacont-1-yl}propanamide and 8.3 mg (0.08 mmol) of triethylamine were added. The reaction mixture was stirred at RT overnight. 4.9 mg (0.08 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 15.8 mg (20% of theory) of the title compound.

LC-MS (Method 4): $R_t$=0.94 min; MS (ESIpos): m/z=1377 [M+H]$^+$.

Intermediate L44

N-[19-(2,5-Dioxo-2,5-dihydro-1H-pyrrol-1-yl)-17-oxo-4,7,10,13-tetraoxa-16-azanonadecan-1-oyl]-L-valyl-L-alanine

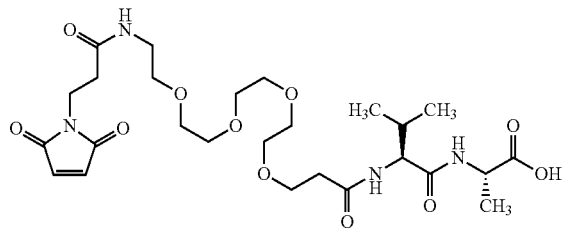 [SMILES: CC(C)[C@H](NC(=O)CCOCCOCCOCCOCCNC(=O)CCN1C(=O)C=CC1=O)C(=O)N[C@@H](C)C(=O)O]

73.3 mg (0.39 mmol) of L-valyl-L-alanine were dissolved in 7.0 ml of DMF, and 200.0 mg (0.39 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 78.8 mg (0.78 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 103.3 mg (45% of theory) of the title compound.

LC-MS (Method 1): $R_t$=0.58 min; MS (ESIpos): m/z=587 [M+H]$^+$.

Intermediate L45 tert-Butyl (2S)-2-[(tert-butoxycarbonyl)amino]-4-oxobutanoate

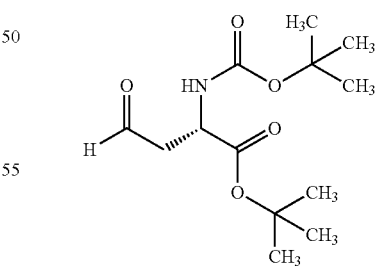

2.00 g (7.26 mmol) of tert-butyl N-(tert-butoxycarbonyl)-L-homoserinate were dissolved in 90 ml of dichloromethane, and 1.76 ml of pyridine and 4.62 g (10.90 mmol) of 1,1,1-triacetoxy-1lambda$^5$,2-benziodoxol-3(1H)-on (Dess-Martin periodinane) were then added. The reaction was stirred at RT for 2 h and then diluted with 200 ml of dichloromethane and extracted twice with 10% strength sodium thiosulphate solution and then successively twice with 5% strength citric acid and twice with saturated sodium bicarbonate solution. The organic phase was separated off, dried over sodium sulphate and then dried under reduced pressure. 100 ml of diethyl ether and cyclohexane (v/v=1:1) were added to the residue, resulting in the formation of a white precipitate. This was filtered off with suction. The filtrate was concentrated on a rotary evaporator and dried under high vacuum, giving 1.74 g (88% of theory) of the target compound as a light-yellow oil.

LC-MS (Method 1): $R_t$=0.85 min; MS (ESIpos): m/z=274 [M+H]$^+$.

$^1$H NMR (400 MHz, DMSO-d$_6$): δ [ppm]=1.38 (s, 18H), 2.64-2.81 (m, 2H), 4.31-4.36 (m, 1H), 7.23 (d, 1H), 9.59 (s, 1H).

Intermediate L46

Trifluoroacetic acid/tert-butyl N-[2-(2,5-dioxo-2,5-dihydro-1H-pyrrol-1-yl)ethyl]-L-glutaminate (1:1)

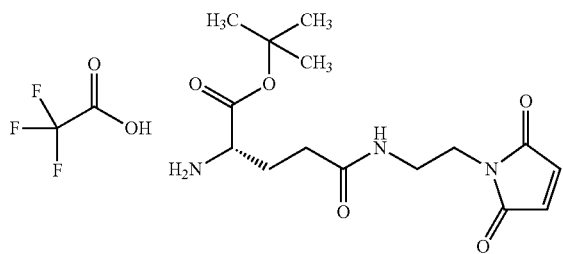 [SMILES: O=C(O)C(F)(F)F ; CC(C)(C)OC(=O)[C@@H](N)CCC(=O)NCCN1C(=O)C=CC1=O]

The title compound was prepared by first coupling 200 mg (0.79 mmol) of trifluoroacetic acid/1-(2-aminoethyl)-1H-pyrrole-2,5-dione (1:1) with 263 mg (0.87 mmol) of (4S)-5-tert-butoxy-4-[(tert-butoxycarbonyl)amino]-5-oxopentanoic acid/trifluoroacetic acid (1:1) in the presence of EDC/HOBT and N,N-diisopropylethylamine and then deprotecting the amino group under gentle conditions by stirring for 1 h in 10% strength trifluoroacetic acid in DCM at RT. Freeze-drying from acetonitrile/water gave 85 mg (20% of theory) of the title compound over 2 steps.

LC-MS (Method 1): $R_t$=0.37 min; MS (ESIpos): m/z=326 [M+H]$^+$.

Intermediate L47

Trifluoroacetic acid/beta-alanyl-L-alanyl-N$^5$-carbamoyl-N-[4-(2,5-dioxo-2,5-dihydro-1H-pyrrol-1-yl)phenyl]-L-ornithinamide (1:1)

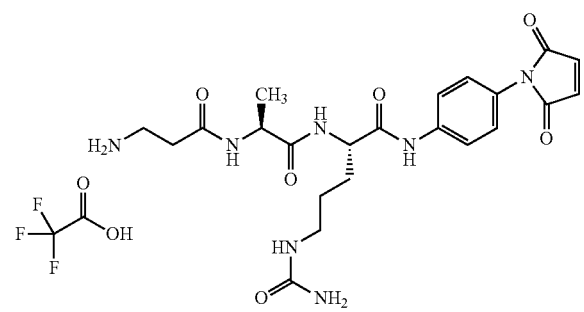 [SMILES: O=C(O)C(F)(F)F ; C[C@H](NC(=O)CCN)C(=O)N[C@@H](CCCNC(N)=O)C(=O)Nc1ccc(N2C(=O)C=CC2=O)cc1]

The title compound was prepared by coupling Intermediate L8 with 2,5-dioxopyrrolidin-1-yl N-(tert-butoxycarbonyl)-beta-alaninate and subsequent deprotection with TFA.

LC-MS (Method 3): $R_t$=1.36 min; MS (ESIpos): m/z=488 (M+H)$^+$.

Intermediate L48

Trifluoroacetic acid/(1R,2S)-2-amino-N-[2-(2,5-dioxo-2,5-dihydro-1H-pyrrol-1-yl)ethyl]cyclopentanecarboxamide (1:1)

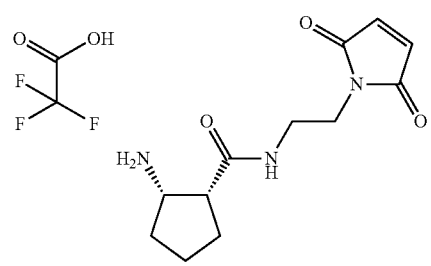 [SMILES: O=C(O)C(F)(F)F ; N[C@H]1CCC[C@H]1C(=O)NCCN1C(=O)C=CC1=O]

The title compound was prepared from commercially available (1R,2S)-2-[(tert-butoxycarbonyl)amino]cyclopentanecarboxylic acid analogously to Intermediate L2.

LC-MS (Method 3): $R_t$=1.22 min; MS (ESIpos): m/z=252 (M+H)$^+$.

Intermediate L49

Trifluoroacetic acid/tert-butyl-N-(bromoacetyl)-L-valyl-L-alanyl-L-lysinate (1:1)

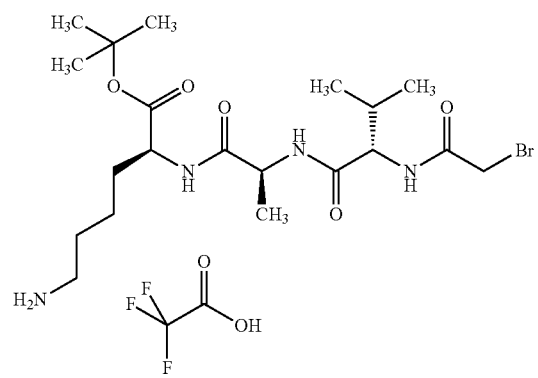

The title compound was prepared by first coupling commercially available bromoacetic anhydride with then partially protected peptide tert-butyl L-valyl-L-alanyl-N$^6$-(tert-butoxycarbonyl)-L-lysinate, prepared according to classical methods of peptide chemistry, in the presence of N,N-diisopropylethylamine in dichloromethane. This was followed by deprotection at the amino group under gentle conditions by stirring in 10% strength trifluoroacetic acid in DCM at RT, giving the title compound in 49% yield over 2 steps.

LC-MS (Method 1): $R_t$=1.09 min; MS (ESIpos): m/z=593 and 595 (M+H)$^+$.

Intermediate L50

Trifluoroacetic acid/(1S,3R)-3-amino-N-[2-(2,5-dioxo-2,5-dihydro-1H-pyrrol-1-yl)ethyl]cyclopentanecarboxamide (1:1)

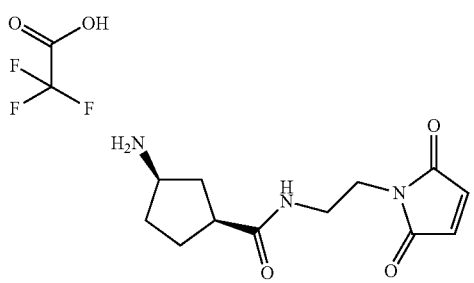 [SMILES: O=C(O)C(F)(F)F ; N[C@@H]1CC[C@H](C(=O)NCCN2C(=O)C=CC2=O)C1]

The title compound was prepared from commercially available (1S,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.2 min;

LC-MS (Method 3): $R_t$=0.88 min; MS (ESIpos): m/z=252 (M+H)$^+$.

Intermediate L51

Trifluoroacetic acid/(1R,3R)-3-amino-N-[2-(2,5-dioxo-2,5-dihydro-1H-pyrrol-1-yl)ethyl]cyclopentanecarboxamide (1:1)

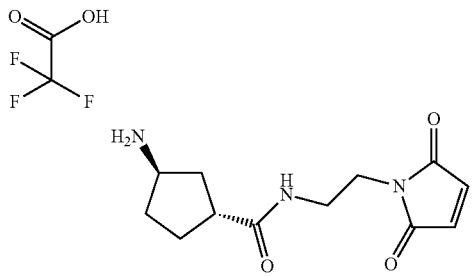 [SMILES: O=C(O)C(F)(F)F ; N[C@@H]1CC[C@@H](C(=O)NCCN2C(=O)C=CC2=O)C1]

The title compound was prepared from commercially available (1R,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.98 min; MS (ESIpos): m/z=250 (M–H)$^-$.

Intermediate L52

Trifluoroacetic acid/N-(2-aminoethyl)-2-bromoacetamide (1:1)

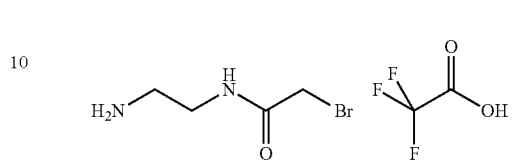

420 mg (2.62 mmol) of tert-butyl (2-aminoethyl)carbamate were taken up in 50 ml of dichloromethane, and 817 mg (3.15 mmol) of bromoacetic anhydride and 913 μl (5.24 mmol) of N,N-diisopropylethylamine were added. The reaction was stirred at RT for 1 h and then dried under reduced pressure. The residue was purified by preparative HPLC.

This gave 577 mg of the protected intermediate which were then taken up in 50 ml of dichloromethane, and 10 ml of trifluoroacetic acid were added. After 1 h of stirring at RT, the reaction was concentrated under reduced pressure and the residue was lyophilized from acetonitrile/water. This gave 705 mg (65% of theory) of the title compound.

LC-MS (Method 3): $R_t$=0.34 min; MS (ESIpos): m/z=181 and 183 (M+H)$^+$.

Intermediate L53

Trifluoroacetic acid/(1S,3S)-3-amino-N-[2-(2,5-dioxo-2,5-dihydro-1H-pyrrol-1-yl)ethyl]cyclopentanecarboxamide (1:1)

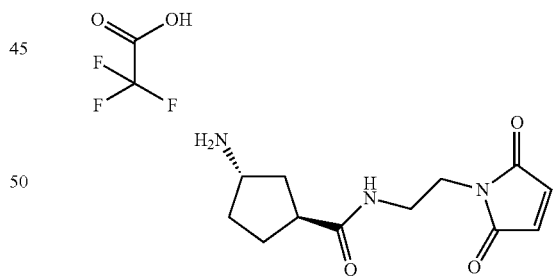

The title compound was prepared from commercially available (1S,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.19 min;

LC-MS (Method 3): $R_t$=0.88 min; MS (ESIpos): m/z=250 (M–H)$^-$.

Intermediate L54

Trifluoroacetic acid/(1R,3S)-3-amino-N-[2-(2,5-dioxo-2,5-dihydro-1H-pyrrol-1-yl)ethyl]cyclopentanecarboxamide (1:1)

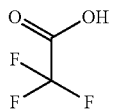
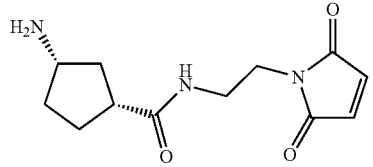

The title compound was prepared from commercially available (1R,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.89 min; MS (ESIpos): m/z=252 (M+H)$^+$.

Intermediate L55

Trifluoroacetic acid/tert-butyl-$N^6$-D-alanyl-$N^2$-{N-[6-(2,5-dioxo-2,5-dihydro-1H-pyrrol-1-yl)-hexanoyl]-L-valyl-L-alanyl}-L-lysinate (1:1)

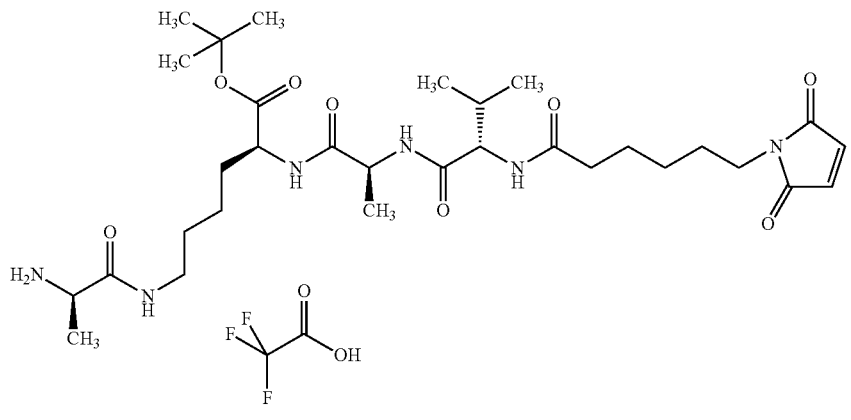 [SMILES: CC(C)[C@H](NC(=O)CCCCCN1C(=O)C=CC1=O)C(=O)N[C@@H](C)C(=O)N[C@@H](CCCCNC(=O)[C@@H](C)N)C(=O)OC(C)(C)C ; O=C(O)C(F)(F)F]

The title compound was prepared by first coupling Intermediate L6 with N-(tert-butoxycarbonyl)-D-alanine in the presence of HATU, followed by deprotection at the amino group under gentle conditions by stirring for 90 minutes in 5% strength trifluoroacetic acid in DCM at RT.

HPLC (Method 11): $R_t$=1.35 min;
LC-MS (Method 1): $R_t$=0.67 min; MS (ESIpos): m/z=637 (M+H)$^+$.

Intermediate L56

Trifluoroacetic acid/tert-butyl-N-[6-(2,5-dioxo-2,5-dihydro-1H-pyrrol-1-yl)hexanoyl]-L-valyl-L-alanyl-$N^6$-{[(1R,3S)-3-aminocyclopentyl]carbonyl}-L-lysinate (1:1)

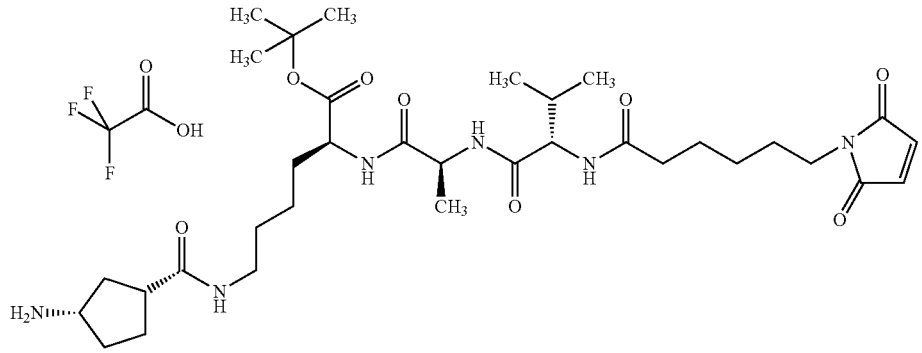

The title compound was prepared by first coupling Intermediate L6 with (1R,3S)-3-[(tert-butoxycarbonyl)amino]cyclopentanecarboxylic acid in the presence of HATU, followed by deprotection at the amino group under gentle conditions by stirring for 15 minutes in 25% strength trifluoroacetic acid in DCM at RT.

HPLC (Method 11): $R_t$=1.4 min;
LC-MS (Method 1): $R_t$=0.7 min; MS (ESIpos): m/z=677 (M+H)$^+$.

Intermediate L57

Methyl (2S)-4-oxo-2-({[2-(trimethylsilyl)ethoxy]carbonyl}amino)butanoate

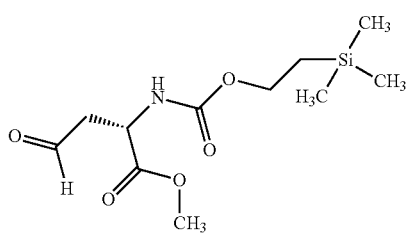 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10μ, flow rate: 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid.

LC-MS (Method 1): $R_t$=0.89 min; MS (ESIneg): m/z=290 (M-H)$^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C. and 205.8 mg (2.04 mmol) of 4-methylmorpholine and 277.9 mg (2.04 mmol) of isobutyl chloroformate were added. The precipitate was filtered off after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed in each case once with saturated sodium bicarbonate solution and saturated NaCl solution. The organic phase was dried over magnesium sulphate, the solvent was evaporated under reduced pressure and the residue was dried under high vacuum. This gave 515.9 mg (91% of theory) of the compound methyl N-[{2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength $Na_2S_2O_3$ solution, 10% strength citric acid solution and saturated sodium bicarbonate solution. The organic phase was dried over magnesium sulphate and the solvent was evaporated under reduced pressure. This gave 565.7 mg (97% of theory) of the title compound.

$^1$H NMR (400 MHz, DMSO-$d_6$): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L58

2-(Trimethylsilyl)ethyl (3-oxopropyl)carbamate

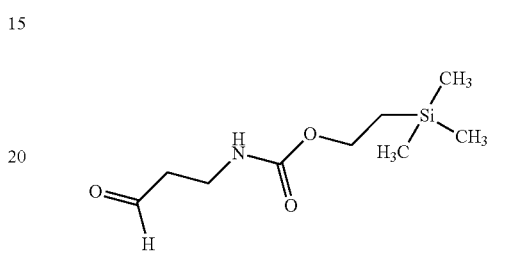

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure.

The residue 2-(trimethylsilyl)ethyl (3-hydroxypropyl)carbamate (996.4 mg, 79% of theory) was dried under high vacuum and used without further purification in the next step of the synthesis.

807.0 mg (3.68 mmol) of 2-(trimethylsilyl)ethyl (3-hydroxypropyl)carbamate were initially charged in 15.0 ml of chloroform and 15.0 ml of 0.05 N potassium carbonate/0.05 N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L59

Trifluoroacetic acid/1-{2-[2-(2-aminoethoxy)ethoxy]ethyl}-1H-pyrrole-2,5-dione (1:1)

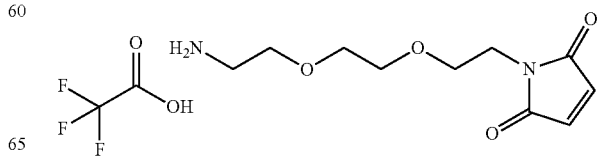

300.0 mg (0.91 mmol) of tert-butyl (2-{2-[2-(2,5-dioxo-2,5-dihydro-1H-pyrrol-1-yl)ethoxy]ethoxy}ethyl)carbamate were initially charged in dichloromethane, 4.2 g (36.54 mmol) of TFA were added and the mixture was stirred at RT for 1 h (monitored by TLC: dichloromethane/methanol 10:1). The volatile components were evaporated under reduced pressure and the residue was co-distilled four times with dichloromethane. The residue was dried under high vacuum and used without further purification in the next step of the synthesis.

LC-MS (Method 1): $R_t$=0.19 min; MS (ESIpos): m/z=229 $(M+H)^+$.

Intermediate L60

6-(2,5-Dioxo-2,5-dihydro-1H-pyrrol-1-yl)hexanoyl chloride

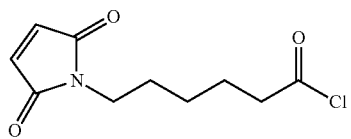 [SMILES: O=C(Cl)CCCCCN1C(=O)C=CC1=O]

200.0 mg (0.95 mmol) of 6-(2,5-dioxo-2,5-dihydro-1H-pyrrol-1-yl)hexanoic acid were dissolved in 4.0 ml of dichloromethane, and 338.0 mg (2.84 mmol) of thionyl chloride were added. The reaction mixture was stirred at RT for 3 h, and 1 drop of DMF was then added. The mixture was stirred for another 1 h. The solvent was evaporated under reduced pressure and the residue was co-distilled three times with dichloromethane. The crude product was used without further purification in the next step of the synthesis.

Intermediate L61

Trifluoroacetic acid/2-(trimethylsilyl)ethyl-N-[6-(2,5-dioxo-2,5-dihydro-1H-pyrrol-1-yl)hexanoyl]-L-valyl-L-alanyl-L-lysinate (1:1)

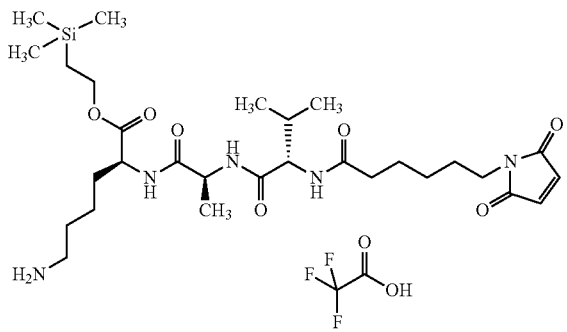 [SMILES: CC(C)[C@H](NC(=O)CCCCCN1C(=O)C=CC1=O)C(=O)N[C@@H](C)C(=O)N[C@@H](CCCCN)C(=O)OCC[Si](C)(C)C ; O=C(O)C(F)(F)F]

First, the tripeptide derivative 2-trimethylsilyl)ethyl-L-valyl-L-alanyl-$N^6$-(tert-butoxycarbonyl)-L-lysinate was prepared from $N^2$-[(benzyloxy)carbonyl]-$N^6$-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis). The title compound was prepared by coupling this partially protected peptide derivative with commercially available 6-(2,5-dioxo-2,5-dihydro-1H-pyrrol-1-yl)hexanoic acid in the presence of HATU and N,N-diisopropylethylamine. This was followed by deprotection at the amino group under gentle conditions by stirring for 2.5 hours in 5% strength trifluoroacetic acid in DCM at RT with retention of the ester protective group. Work-up and purification by preparative HPLC gave 438 mg of the title compound.

HPLC (Method 11): $R_t$=1.69 min;
LC-MS (Method 1): $R_t$=0.78 min; MS (ESIpos): m/z=610 $(M+H)^+$.

Intermediate L62

Trifluoroacetic acid/2-(trimethylsilyl)ethyl-N-[6-(2,5-dioxo-2,5-dihydro-1H-pyrrol-1-yl)hexanoyl]-L-valyl-$N^5$-carbamoyl-L-ornithyl-L-lysinate (1:1)

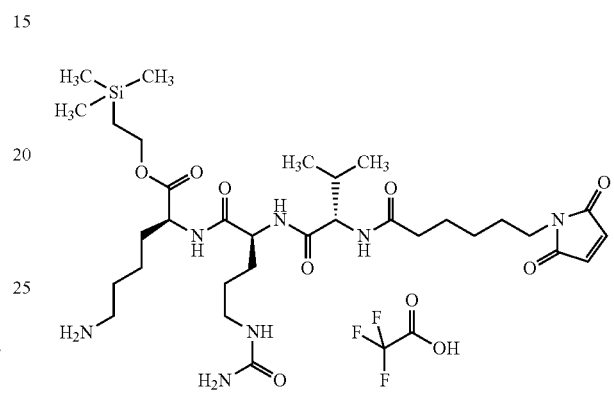

First, 2-(trimethylsilyl)ethyl $N^6$-(tert-butoxycarbonyl)-L-lysinate was prepared from $N^2$-[(benzyloxy)carbonyl]-$N^6$-(tert-butoxycarbonyl)-L-lysine according to classical methods of peptide chemistry. 148 mg (0.43 mmol) of this Intermediate were then coupled in the presence of 195 mg (0.51 mmol) of HATU and 149 μl of N,N-diisopropylethylamine with 200 mg (0.43 mmol) of Intermediate L16. After concentration and purification of the residue by preparative HPLC, the protected intermediate was taken up in 20 ml of DCM and the tert-butoxycarbonyl protective group was removed by addition of 2 ml of trifluoroacetic acid and 1 h of stirring at RT. Concentration and lyophilization of the residue from acetonitrile/water gave 254 mg (63% of theory over 2 steps).

HPLC (Method 11): $R_t$=1.51 min;
LC-MS (Method 1): $R_t$=0.68 min; MS (ESIpos): m/z=696 $(M+H)^+$.

Intermediate L63

(4S)-4-{[(2S)-2-{[(2S)-2-{[6-(2,5-Dioxo-2,5-dihydro-1H-pyrrol-1-yl)hexanoyl]amino}-3-methylbutanoyl]amino}propanoyl]amino}-5-oxo-5-[2-(trimethylsilyl)ethoxy]pentanoic acid

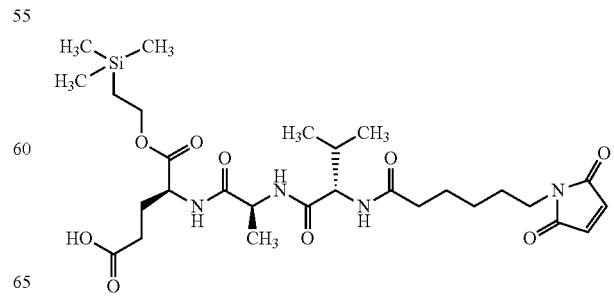

First, the tripeptide derivative (4S)-4-{[(2S)-2-{[(2S)-2-amino-3-methylbutanoyl]amino}propanoyl]amino}-5-oxo-5-[2-(trimethylsilyl)ethoxy]pentanoic acid was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, coupling with N-[(benzyloxy)carbonyl]-L-valyl-L-alanine in the presence of HATU and hydrogenolysis in methanol over 10% palladium on activated carbon). The title compound was prepared by coupling of this partially protected peptide derivative with commercially available 1-{6-[(2,5-dioxopyrrolidin-1-yl)oxy]-6-oxohexyl}-1H-pyrrole-2,5-dione. Work-up and purification by preparative HPLC gave 601 mg of the title compound.

LC-MS (Method 1): R$_t$=0.96 min; MS (ESIpos): m/z=611 (M+H)$^+$.

Intermediate L64

(4S)-4-{[(2,5-Dioxo-2,5-dihydro-1H-pyrrol-1-yl)acetyl]amino}-5-oxo-5-[2-(trimethylsilyl)ethoxy]pentanoic acid

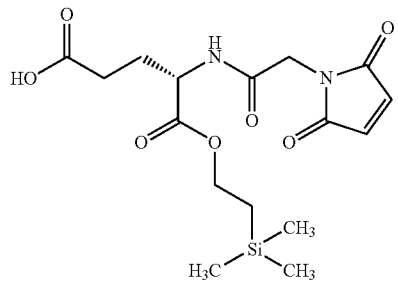 [SMILES: C[Si](C)(C)CCOC(=O)[C@H](CCC(=O)O)NC(=O)CN1C(=O)C=CC1=O]

The title compound was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, hydrogenolytic cleavage of the benzyl ester in methanol over 10% palladium on activated carbon and coupling with 1-{2-[(2,5-dioxopyrrolidin-1-yl)oxy]-2-oxoethyl}-1H-pyrrole-2,5-dione in the presence of N,N-diisopropylethylamine)

LC-MS (Method 1): R$_t$=0.84 min; MS (ESIpos): m/z=385 (M+H)$^+$.

Intermediate L65

Trifluoroacetic acid/2-(trimethylsilyl)ethyl-3-{[(benzyloxy)carbonyl]amino}-L-alaninate (1:1)

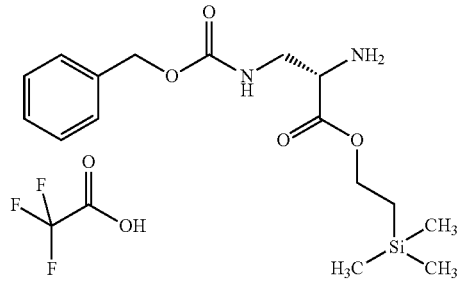

The title compound was prepared from 3-{[(benzyloxy)carbonyl]amino}-N-(tert-butoxycarbonyl)-L-alanine according to classical methods of peptide chemistry (esterification with 2-(trimethylsilylethanol using EDCI/DMAP and removal of the Boc protective group with trifluoroacetic acid. This gave 373 mg (79% of theory over 2 steps) of the title compound.

LC-MS (Method 1): R$_t$=0.72 min; MS (ESIpos): m/z=339 (M+H)$^+$.

Intermediate L66

Methyl (8S)-8-(2-hydroxyethyl)-2,2-dimethyl-6,11-dioxo-5-oxa-7,10-diaza-2-silatetradecan-14-oate

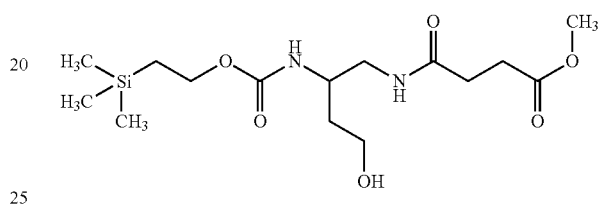

1000 mg (2.84 mmol) of (3S)-3-{[(benzyloxy)carbonyl]amino}-4-[(tert-butoxycarbonyl)amino]butanoic acid were initially charged in 10.0 ml of 1,2-dimethoxyethane, and 344.4 mg (3.4 mmol) of 4-methylmorpholine and 504 mg (3.69 mmol) of isobutyl chloroformate were added. After 10 min of stirring at RT, the reaction was cooled to 5° C. and 161 mg (4.26 mmol) of sodium borohydride dissolved in 3 ml of water were added a little at a time with vigorous stirring. After 1 h, the same amount of sodium borohydride was added again and the reaction was then slowly warmed to RT. 170 ml of water were added and the reaction was then extracted four times with in each case 200 ml of ethyl acetate. The phases were separated and the organic phase was washed once with citric acid and then with saturated sodium bicarbonate solution. The organic phase was dried over magnesium sulphate, the solvent was evaporated under reduced pressure and the residue was dried under high vacuum. This gave 760 mg (78% of theory) of the compound benzyl tert-butyl [(2S)-4-hydroxybutane-1,2-diyl]biscarbamate.

LC-MS (Method 1): R$_t$=0.84 min; MS (ESIpos): m/z=339 (M+H)$^+$.

760 mg (2.16 mmol) of this intermediate dissolved in 13 ml of hydrogen chloride/dioxane were stirred at RT for 20 min. The reaction was then concentrated to 5 ml, and diethyl ether was added. The precipitate was filtered off and lyophilized from acetonitrile/water 1:1.

The product obtained in this manner was dissolved in 132 ml of DMF, and 345.5 mg (2.35 mmol) of 4-methoxy-4-oxobutanoic acid, 970 mg (2.55 mmol) of HATU and 1025 µl of N,N-diisopropylethylamine were added. The mixture was stirred at RT for 5 min. The solvent was removed under reduced pressure and the residue that remained was purified by preparative HPLC. The appropriate fractions were combined and the acetonitrile was evaporated under reduced pressure. The aqueous phase that remained was extracted twice with ethyl acetate and the organic phase was then concentrated and dried under high vacuum.

The intermediate obtained in this manner was taken up in methanol and hydrogenated over 10% palladium on activated carbon at RT under hydrogen standard pressure for 1 h. The catalyst was then filtered off and the solvent was removed under reduced pressure.

247 mg of this deprotected compound were taken up in 20 ml of DMF, and 352 mg (1.36 mmol) of 1-({[2-(trimethylsilyl)ethoxy]carbonyl}oxy)pyrrolidine-2,5-dione and 592 μl of N,N-diisopropylethylamine were added. The reaction mixture was stirred at RT for 1 h and then concentrated, and the residue was purified by preparative HPLC. The solvents were then evaporated under reduced pressure and the residue was dried under high vacuum. This gave, over these 5 reaction steps, 218 mg of the title compound in a total yield of 21%.

LC-MS (Method 1): $R_t$=0.74 min; MS (ESIpos): m/z=363 (M+H)$^+$.

Intermediate L67

Trifluoroacetic acid/2-(2,5-dioxo-2,5-dihydro-1H-pyrrol-1-yl)ethyl-beta-alaninate (1:1)

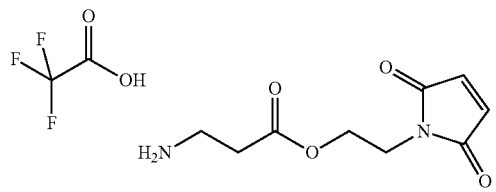 [SMILES: O=C(O)C(F)(F)F ; NCCC(=O)OCCN1C(=O)C=CC1=O]

The title compound was prepared from 50 mg (0.354 mmol) of commercially available 1-(2-hydroxyethyl)-1H-pyrrole-2,5-dione by coupling with 134 mg (0.71 mmol) of N-(tert-butoxycarbonyl)-beta-alanine in 10 ml of dichloromethane in the presence of 1.5 equivalents of EDCI and 0.1 equivalent of 4-N,N-dimethylaminopyridine and subsequent deprotection with trifluoroacetic acid.

Yield: 56 mg (48% of theory over 2 stages)

LC-MS (Method 3): $R_t$=1.15 min; MS (ESIpos): m/z=213 (M+H)$^+$.

Intermediate L68

Trifluoroacetic acid/N-(2-aminoethyl)-2-(2,5-dioxo-2,5-dihydro-1H-pyrrol-1-yl)propanamide (1:1)

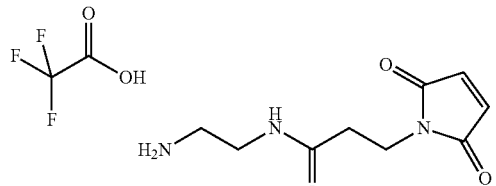

The title compound was prepared analogously to Intermediate L1 according to classical methods of peptide chemistry from commercially available (2,5-dioxo-2,5-dihydro-1H-pyrrol-1-yl)propanoic acid and tert-butyl (2-aminoethyl)carbamate.

LC-MS (Method 1): $R_t$=0.17 min; MS (ESIpos): m/z=212 (M+H)$^+$.

Intermediate L69

Trifluoroacetic acid/1-[(benzyloxy)carbonyl]piperidin-4-yl-L-valyl-N$^5$-carbamoyl-L-ornithinate (1:1)

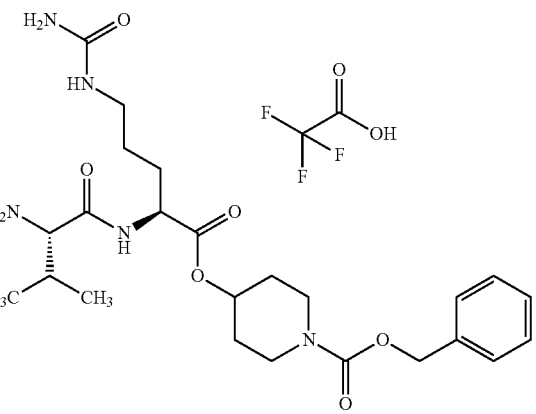

The title compound was prepared by classical methods of peptide chemistry from commercially available benzyl 4-hydroxypiperidine-1-carboxylate by esterification with N$^2$-(tert-butoxycarbonyl)-N$^5$-carbamoyl-L-ornithine using EDCI/DMAP, subsequent Boc removal with TFA, followed by coupling with N-[(tert-butoxy)carbonyl]-L-valine in the presence of HATU and N,N-diisopropylethylamine and finally another Boc removal with TFA.

LC-MS (Method 1): $R_t$=0.62 min; MS (ESIpos): m/z=492 (M+H)$^+$.

Intermediate L70

9H-Fluoren-9-ylmethyl (3-oxopropyl)carbamate

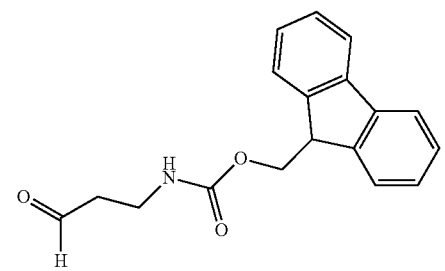 [SMILES: O=CCCNC(=O)OCC1c2ccccc2-c2ccccc21]

1000.0 mg (3.36 mmol) of 9H-fluoren-9-ylmethyl (3-hydroxypropyl)carbamate were initially charged in 15.0 ml of chloroform and 15.0 ml of 0.05 N potassium carbonate/0.05 N sodium bicarbonate solution (1:1). 93.5 mg (0.34 mmol) of tetra-n-butylammonium chloride, 673.6 mg (5.04 mmol) of N-chlorosuccinimide and 52.5 mg (0.34 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and purified on silica gel (mobile phase: cyclohexane/ethyl acetate 3:1-1:1). The solvents were evaporated under reduced pressure and the residue was dried under high vacuum. This gave 589.4 mg (58% of theory) of the title compound.

LC-MS (Method 6): $R_t$=2.15 min; MS (ESIpos): m/z=296 (M−H)⁺.

Intermediate L71 tert-Butyl [4-(chlorocarbonyl)phenyl]carbamate

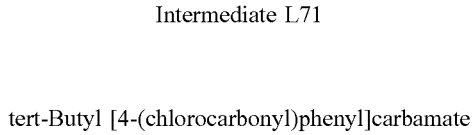

100.0 mg (0.42 mmol) of 4-[(tert-butoxycarbonyl)amino]benzoic acid were initially charged in 2.0 ml of dichloromethane, and 64.2 mg (0.51 mmol) of oxalyl chloride were added. The reaction mixture was stirred at RT for 30 min (monitored by TLC: dichloromethane/methanol). Another 192.6 mg (1.53 mmol) of oxalyl chloride and 1 drop of DMF were then added and the mixture was stirred at RT for 1 h. The solvent was evaporated under reduced pressure and the residue was co-distilled repeatedly with dichloromethane. The residue was used without further purification in the next step of the synthesis.

Intermediate L72

Benzyl (9S)-9-(hydroxymethyl)-2,2-dimethyl-6,11-dioxo-5-oxa-7,10-diaza-2-silatetradecan-14-oate

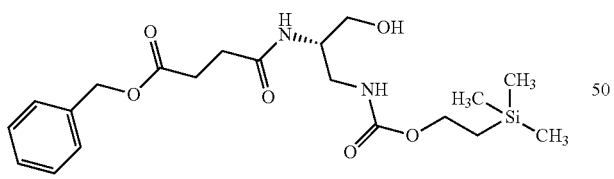

The title compound was prepared from commercially available benzyl tert-butyl [(2S)-3-hydroxypropan-1,2-diyl]biscarbamate according to classical methods of peptide chemistry by hydrogenolytic removal of the Z protective group, subsequent coupling with 4-(benzyloxy)-4-oxobutanoic acid in the presence of EDCI/HOBT, followed by removal of the Boc protective group with TFA and finally by reaction with 1-({[2-(trimethylsilyl)ethoxy]carbonyl}oxy)pyrrolidine-2,5-dione in the presence of triethylamine LC-MS (Method 1): $R_t$=0.94 min; MS (ESIpos): m/z=425 [M+H]+.

Intermediate L73

N-(2-Aminoethyl)-6-(2,5-dioxo-2,5-dihydro-1H-pyrrol-1-yl)hexanamide

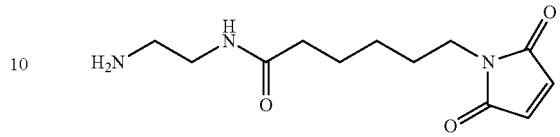

395.5 mg (1.87 mmol) of 6-(2,5-dioxo-2,5-dihydro-1H-pyrrol-1-yl)hexanoic acid, 1.21 g (9.36 mmol) of N,N-diisopropylethylamine and 854.3 mg (2.25 mmol) of HATU were added to a solution of 300 mg (1.87 mmol) of tert-butyl (2-aminoethyl)carbamate in 20 ml of dimethylformamide. The reaction mixture was stirred at RT for 5 minutes. After concentration of the mixture, the residue was taken up in DCM and washed with water. The organic phase was washed with brine, dried over magnesium sulphate, filtered off and concentrated. This gave 408 mg (33%, purity 53%) of the title compound which were used without further purification.

LC-MS (Method 1): $R_t$=0.75 min; MS (ESIpos): m/z=354 (M+H)⁺.

1 ml of TFA was added to a solution of tert-butyl (2-{[6-(2,5-dioxo-2,5-dihydro-1H-pyrrol-1-yl)hexanoyl]amino}ethyl)carbamate (408 mg, 0.365 mmol) of in 7 ml of dichloromethane. The reaction mixture was stirred at RT for 0.5 h. The reaction mixture was concentrated under reduced pressure and the residue was co-distilled twice with dichloromethane. The residue was used further without further purification. This gave 384 mg (94%, purity 57%) of the title compound.

LC-MS (Method 1): $R_t$=0.26 min; MS (ESIpos): m/z=254 (M+H)⁺.

Intermediate F1

N-{(1R)-1-[1-Benzyl-4-(2,5-difluorophenyl)-1H-imidazol-2-yl]-2,2-dimethylpropyl}-N-{2-[(4S)-2,5-dioxo-1,3-oxazolidin-4-yl]ethyl}-2-hydroxyacetamide

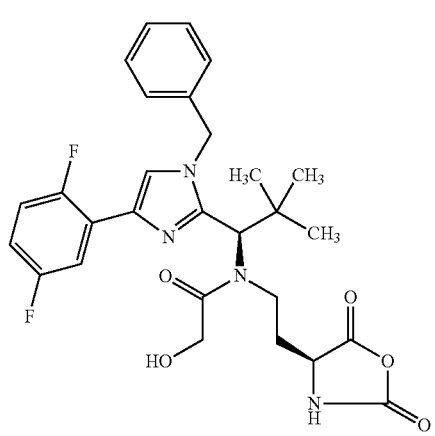 [SMILES: CC(C)(C)[C@H](c1nc(-c2cc(F)ccc2F)cn1Cc1ccccc1)N(CC[C@@H]1NC(=O)OC1=O)C(=O)CO]

Under argon, 77 mg (0.14 mmol) of (2S)-2-amino-4-[{(1R)-1-[1-benzyl-4-(2,5-difluorophenyl)-1H-imidazol-2-yl]-2,2-dimethylpropyl}(glycoloyl)amino]butanoic acid hydrochloride (1:1) (Intermediate C4) were dissolved in THF. 2 mg of activated carbon and 27.5 mg (0.14 mmol) of triphosgene were then added, and the reaction was then stirred at 50° C. for 10 min After two more additions of in each case 27.5 mg of triphosgene and 30 min of stirring at RT, the reaction was complete.

The activated carbon was filtered off through a syringe filter and the solvent was then removed under reduced pressure. Acetonitrile was added, and the mixture was once more concentrated under reduced pressure. This gave 72 mg (95%) of the title compound which were used without further purification for the ADC coupling.

HPLC (Method 11): $R_t$=2.28 min;
LC-MS (Method 1): $R_t$=1.2 min; MS (ESIpos): m/z=541 (M+H)$^+$.

Intermediate F2

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[2-(2,5-dioxo-2,5-dihydro-1H-pyrrol-1-yl)ethyl]butanamide (1:1)

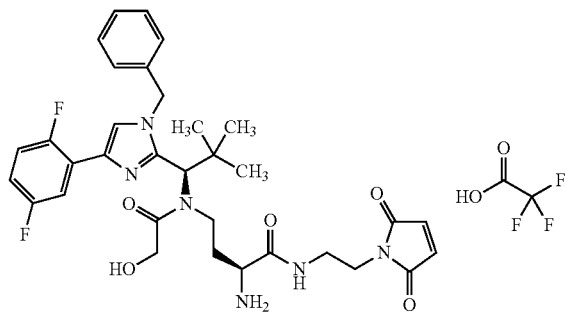 [SMILES: CC(C)(C)[C@H](c1nc(-c2cc(F)ccc2F)cn1Cc1ccccc1)N(CC[C@H](N)C(=O)NCCN1C(=O)C=CC1=O)C(=O)CO ; O=C(O)C(F)(F)F]

55 mg (0.089 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were taken up in 12 ml of DMF, and 68 mg (0.268 mmol) of commercially available trifluoroacetic acid/1-(2-aminoethyl)-1H-pyrrole-2,5-dione (1:1), 34.3 mg (0.18 mmol) of 1-(3-dimethylaminopropyl)-3-ethylcarbodiimide hydrochloride, 27.4 mg (0.18 mmol) of 1-hydroxy-1H-benzotriazole hydrate and 47 µl (0.27 mmol) of N,N-diisopropylethylamine were added in succession. The mixture was stirred at RT overnight. The solvent was removed under reduced pressure and the residue that remained was purified by preparative HPLC. The appropriate fractions were concentrated giving, after lyophilization from 1,4-dioxane, 20 mg (30% of theory) of the title compound.

HPLC (Method 11): $R_t$=2.48 min;
LC-MS (Method 1): $R_t$=1.29 min; MS (ESIpos): m/z=737 (M+H)$^+$.

20 mg (0.027 mmol) of this intermediate were taken up in 5 ml of dichloromethane, 1 ml of trifluoroacetic acid was added and the mixture was stirred at RT for 1 h. The reaction mixture was then concentrated under reduced pressure and the residue that remained was lyophilised from acetonitrile/water 1:1. This gave 19 mg (95% of theory) of the title compound.

HPLC (Method 11): $R_t$=2.0 min;
LC-MS (Method 1): $R_t$=0.9 min; MS (ESIpos): m/z=637 (M+H)$^+$.
$^1$H NMR (500 MHz, DMSO-$d_6$): δ=8.28 (t, 1H), 7.9-8.1 (m, 3H), 7.7-7.8 (m, 2H), 7.2-7.4 (m, 6H) 7.0-7.1 (m, 3H), 5.7 (s, 1H), 5.0 and 5.3 (2d, 2H), 4.08 and 4.25 (2d, 2H), 3.3-3.65 (m, 5H), 3.1-3.25 (m, 2H), 0.75 and 1.45 (2m, 2H), 0.9 (s, 9H).

Intermediate F3

Trifluoroacetic acid/N-[(3S)-3-amino-4-{2-[6-(2,5-dioxo-2,5-dihydro-1H-pyrrol-1-yl)hexanoyl]hydrazino}-4-oxobutyl]-N-(1R)-1-[1-benzyl-4-(2,5-difluorophenyl)-1H-imidazol-2-yl]-2,2-dimethylpropyl -2-hydroxyacetamide (1:1)

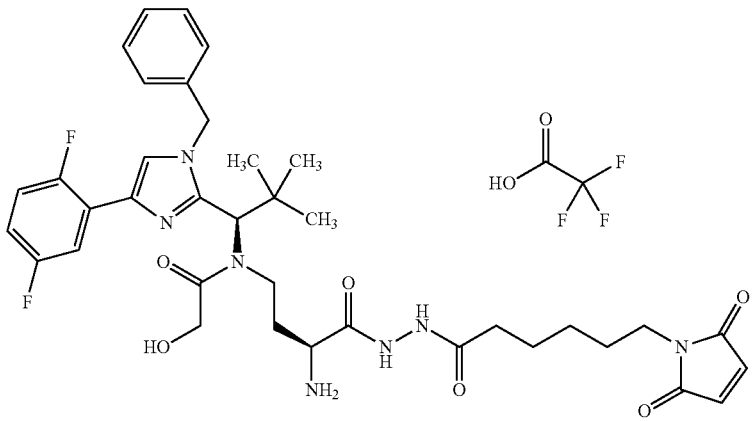 [SMILES: CC(C)(C)[C@H](c1nc(-c2cc(F)ccc2F)cn1Cc1ccccc1)N(CC[C@H](N)C(=O)NNC(=O)CCCCCN1C(=O)C=CC1=O)C(=O)CO ; O=C(O)C(F)(F)F]

13 mg (0.021 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were taken up in 5 ml of DMF, and 33 mg (86 µmol) of O-(7-azabenzotriazol-1-yl)-N,N,N',N'-tetramethyluronium hexafluorophosphate, 15 µl of N,N-diisopropylethylamine and 22 mg (64 µmol) of commercially available 6-(2,5-dioxo-2,5-dihydro-1H-pyrrol-1-yl)hexanehydrazide were then added. The reaction mixture was stirred at RT for 1 h. The mixture was then concentrated under high vacuum and the residue that remained was purified by preparative HPLC. This gave 9.5 mg (53% of theory) of the protected intermediate as a colourless foam.

HPLC (Method 11): $R_t$=2.1 min;

LC-MS (Method 1): $R_t$=1.33 min; MS (ESIpos): m/z=822 (M+H)$^+$.

9.5 mg (0.011 mmol) of this intermediate were taken up in 3 ml of dichloromethane, 1 ml of trifluoroacetic acid was added and the mixture was stirred at RT for 2 h. The reaction mixture was then concentrated under reduced pressure and the residue that remained was lyophilised from acetonitrile/water 1:1. This gave 7 mg (70% of theory) of the title compound.

HPLC (Method 11): $R_t$=1.75 min;

LC-MS (Method 1): $R_t$=0.91 min; MS (ESIpos): m/z=722 (M+H)$^+$.

Intermediate F4

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(6-{[(2R)-2-(2,5-dioxo-2,5-dihydro-1H-pyrrol-1-yl)propanoyl]amino}hexyl)butanamide (1:1)

amine, coupled with (2R)-2-(2,5-dioxo-2,5-dihydro-1H-pyrrol-1-yl)propanoyl chloride which had been prepared from the free acid using thionyl chloride. In the last step, the Boc protective group was removed with trifluoroacetic acid in DCM. This gave 1.1 mg (3% over 4 steps) of the title compound.

HPLC (Method 11): $R_t$=1.83 min;

LC-MS (Method 1): $R_t$=0.96 min; MS (ESIpos): m/z=764 (M+H)$^+$.

Intermediate F5

Trifluoroacetic acid/(2S)-2-amino-4-[{(1R)-1-[1-benzyl-4-(2,5-difluorophenyl)-1H-imidazol-2-yl]-2,2-dimethylpropyl}(propionyl)amino]-N-{2-[2-(2,5-dioxo-2,5-dihydro-1H-pyrrol-1-yl)ethoxy]ethyl}butanamide (1:1)

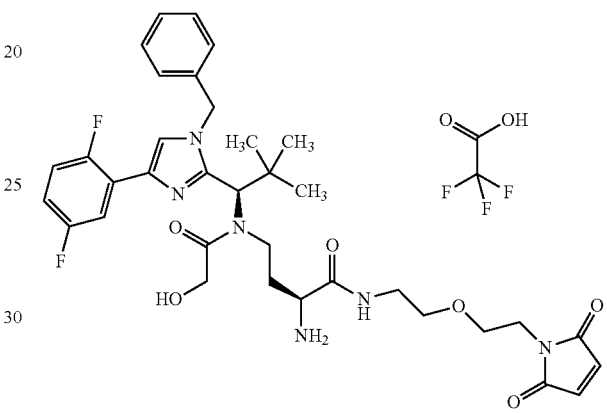

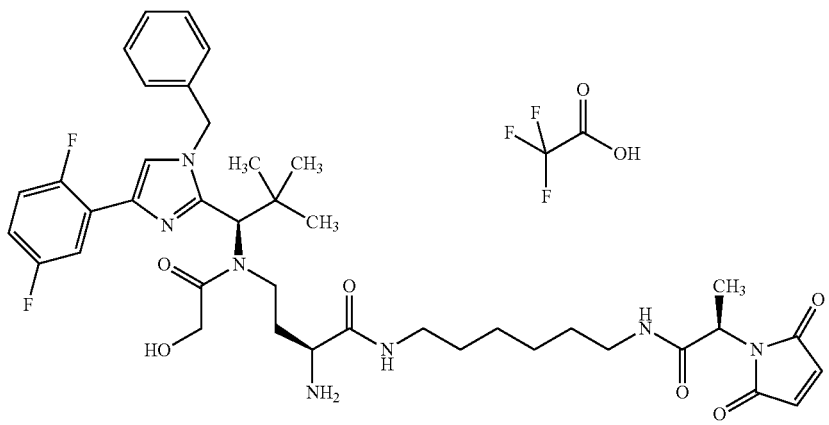 [SMILES: C[C@H](C(=O)NCCCCCCNC(=O)[C@@H](N)CCN(C(=O)CO)[C@@H](c1nc(-c2cc(F)ccc2F)cn1Cc1ccccc1)C(C)(C)C)N1C(=O)C=CC1=O ; O=C(O)C(F)(F)F]

First, 30 mg (0.049 mmol) of (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (Intermediate C5) were coupled analogously to Intermediate F3 with trifluoroacetic acid/9H-fluoren-9-ylmethyl-(6-aminohexyl) carbamate (1:1) in the presence of HATU. Then the Fmoc protective group was removed with piperidine according to standard methods. This amine component was then, in the presence of N,N-diisopropylethyl- The title compound was prepared analogously to Intermediate F2 from 16 mg (0.026 mmol) of Intermediate C5 and 8.5 mg (0.03 mmol) of Intermediate L12. This gave 3 mg (13% of theory over 2 steps) of the title compound.

HPLC (Method 11): $R_t$=2.0 min;

LC-MS (Method 1): $R_t$=0.96 min; MS (ESIpos): m/z=681 (M+H)$^+$.

Intermediate F6

Trifluoroacetic acid/N-[(16S)-16-amino-1-(2,5-dioxo-2,5-dihydro-1H-pyrrol-1-yl)-12,15-dioxo-3,6,9-trioxa-13,14-diazaoctadecan-18-yl]-N-{(1R)-1-[1-benzyl-4-(2,5-difluorophenyl)-1H-imidazol-2-yl]-2,2-dimethylpropyl}-2-hydroxyacetamide (1:1)

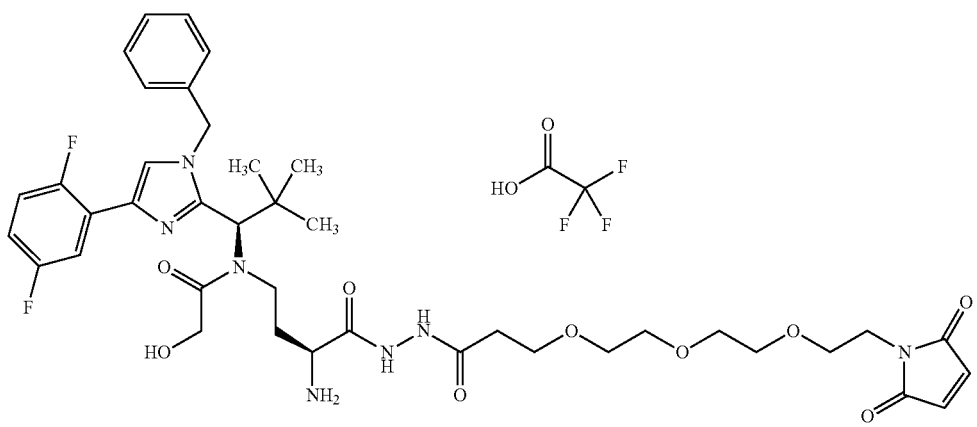 [SMILES: CC(C)(C)[C@H](c1nc(-c2cc(F)ccc2F)cn1Cc1ccccc1)N(CC[C@H](N)C(=O)NNC(=O)CCOCCOCCOCCN1C(=O)C=CC1=O)C(=O)CO ; O=C(O)C(F)(F)F]

8 mg (12.7 µmol) of trifluoroacetic acid/tert-butyl {(2S)-4-[{(1R)-1-[1-benzyl-4-(2,5-difluorophenyl)-1H-imidazol-2-yl]-2,2-dimethylpropyl}(glycoloyl)amino]-1-hydrazino-1-oxobutan-2-yl}carbamate (1:1) (Intermediate C6) were taken up in 8 ml of DMF, and 6 mg (19 µmol) of commercially available 3-(2-{2-[2-(2,5-dioxo-2,5-dihydro-1H-pyrrol-1-yl)ethoxy]ethoxy}ethoxy)propanoic acid, 5.8 mg (15 µmol) of O-(7-azabenzotriazol-1-yl)-N,N,N',N'-tetramethyluronium hexafluorophosphate (HATU) and 7 µl (38 µmol) of N,N-diisopropylethylamine were added. The mixture was stirred at RT for 15 min. The solvent was then removed under reduced pressure and the residue was taken up in acetonitrile/water 1:1 and adjusted to pH 2 with trifluoroacetic acid. Purification was by preparative HPLC. Combination of the appropriate fractions, concentration and freeze-drying from acetonitrile/water 1:1 gave 5 mg (41% of theory) of the Boc-protected intermediate. Removal of the Boc group with trifluoroacetic acid afforded 4 mg (32% of theory over 2 steps) of the title compound.

HPLC (Method 11): $R_t$=1.89 min;

LC-MS (Method 1): $R_t$=0.89 min; MS (ESIpos): m/z=812 (M+H)$^+$.

Intermediate F7

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

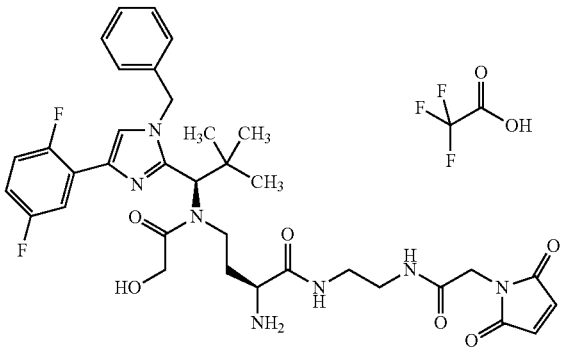 [SMILES: CC(C)(C)[C@H](c1nc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

The title compound was prepared analogously to Intermediate F2 from 25 mg (0.037 mmol) of Intermediate C5 and 35 mg (0.112 mmol) of Intermediate L1. This gave 14.4 mg (29% of theory over 2 steps) of the title compound.

HPLC (Method 11): $R_t$=2.0 min;

LC-MS (Method 1): $R_t$=0.9 min; MS (ESIpos): m/z=694 (M+H)$^+$.

$^1$H NMR (500 MHz, DMSO-$d_6$): δ=8.2 (m, 1H), 7.9-8.1 (m, 3H), 7.7-7.8 (m, 2H), 7.2-7.4 (m, 6H), 7.0-7.12 (m, 3H), 5.7 (s, 1H), 4.95 and 5.3 (2d, 2H), 4.1 and 4.25 (2d, 2H), 4.0 (s, 2H), 3.3-3.65 (m, 5H), 3.0-3.15 (m, 2H), 0.7 and 1.45 (2m, 2H), 0.88 (s, 9H).

Intermediate F8

N-[6-(2,5-Dioxo-2,5-dihydro-1H-pyrrol-1-yl)hexanoyl]-L-valyl-L-alanyl-N6-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic acid (1:1)

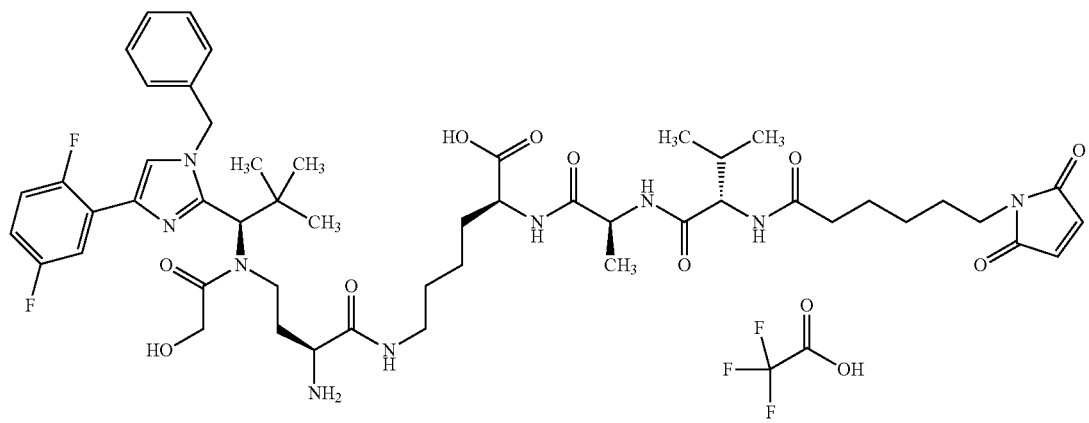 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F2 from 10 mg (0.016 mmol) of Intermediate C5 and 13 mg (0.018 mmol) of Intermediate L6. This gave 10 mg (49% of theory over 2 steps) of the title compound.

HPLC (Method 11): $R_t$=1.97 min;
LC-MS (Method 1): $R_t$=0.93 min; MS (ESIpos): m/z=1006 (M+H)$^+$.

Intermediate F9

Trifluoroacetic acid/N-{(3S)-3-amino-4-[1-(2-{[2-(2,5-dioxo-2,5-dihydro-1H-pyrrol-1-yl)ethyl]amino}-2-oxoethyl)hydrazino]-4-oxobutyl}-N-{(1R)-1-[1-benzyl-4-(2,5-difluorophenyl)-1H-imidazol-2-yl]-2,2-dimethylpropyl}-2-hydroxyacetamide (1:1)

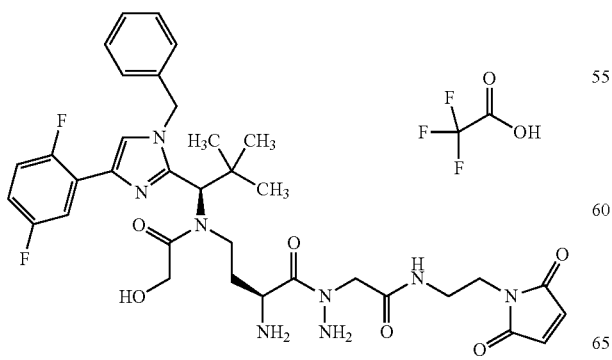

The title compound was prepared analogously to Intermediate F2 from 1.5 mg (0.002 mmol) of Intermediate C7 and 0.95 mg (0.004 mmol) of commercially available trifluoroacetic acid/1-(2-aminoethyl)-1H-pyrrole-2,5-dione (1:1). This gave 1.1 mg (52% of theory over 2 steps) of the title compound.

HPLC (Method 11): $R_t$=1.9 min;
LC-MS (Method 1): $R_t$=0.89 min; MS (ESIpos): m/z=709 (M+H)$^+$.

Intermediate F10

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(3-{[4-(2,5-dioxo-2,5-dihydro-1H-pyrrol-1-yl)phenyl]amino}-3-oxopropyl)butanamide (1:1)

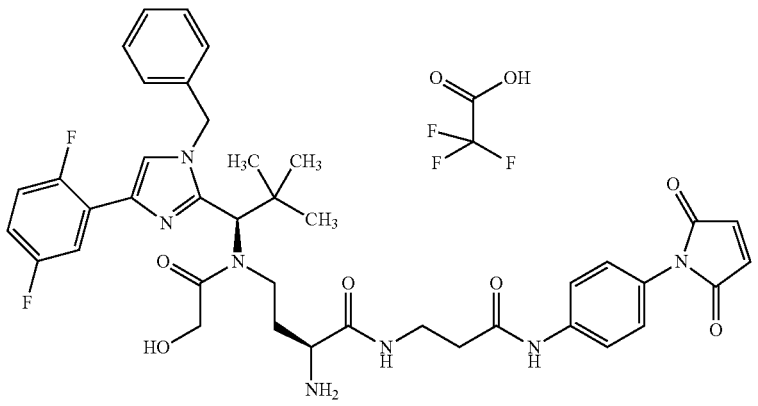 [SMILES: CC(C)(C)[C@H](c1nc(-c2cc(F)ccc2F)cn1Cc1ccccc1)N(CC[C@H](N)C(=O)NCCC(=O)Nc1ccc(N2C(=O)C=CC2=O)cc1)C(=O)CO ; O=C(O)C(F)(F)F]

The title compound was prepared analogously to Intermediate F2 from 14 mg (0.022 mmol) of Intermediate C5 and 10 mg (0.025 mmol) of Intermediate L5. This gave 4.5 mg (22% of theory over 2 steps) of the title compound.

HPLC (Method 11): $R_t$=2.0 min;

LC-MS (Method 1): $R_t$=0.93 min; MS (ESIpos): m/z=756 (M+H)$^+$.

Intermediate F11

Trifluoroacetic acid/N-[2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]-4-(2,5-dioxo-2,5-dihydro-1H-pyrrol-1-yl)cyclohexanecarboxamide (1:1)

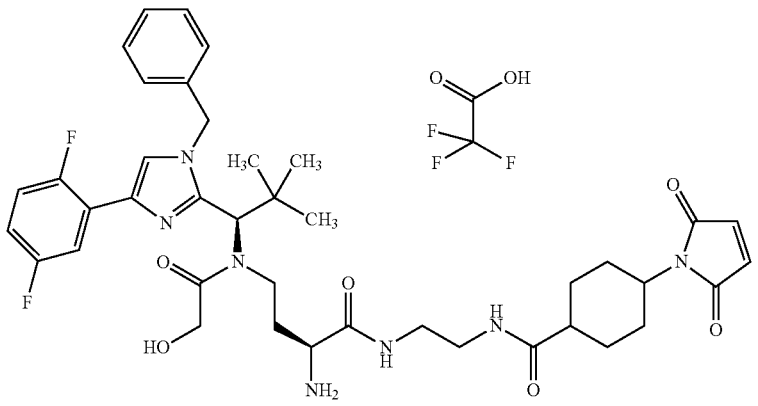 [SMILES: CC(C)(C)[C@H](c1nc(-c2cc(F)ccc2F)cn1Cc1ccccc1)N(CC[C@H](N)C(=O)NCCNC(=O)C1CCC(N2C(=O)C=CC2=O)CC1)C(=O)CO ; O=C(O)C(F)(F)F]

The title compound was prepared analogously to Intermediate F2 from 12 mg (0.019 mmol) of Intermediate C5 and 10 mg (0.021 mmol) of Intermediate L4. This gave 7 mg (38% of theory over 2 steps) of the title compound.

HPLC (Method 11): $R_t$=2.04 min;

LC-MS (Method 1): $R_t$=0.93 min; MS (ESIpos): m/z=776 (M+H)$^+$.

Intermediate F12

Trifluoroacetic acid/(1R,2S)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

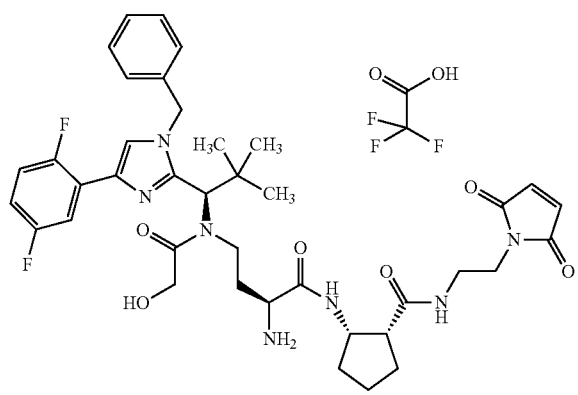 [SMILES: CC(C)(C)[C@H](c1nc(-c2cc(F)ccc2F)cn1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared analogously to Intermediate F2 from 43 mg (0.071 mmol) of Intermediate C5 and 30 mg (0.071 mmol) of Intermediate L2. At the stage of the Boc-protected intermediate, the diastereomers formed were separated by preparative HPLC (Chromatorex C18-10/125×30/12 ml/min) The stereochemistry of the separated diastereomers was assigned by comparison with the individual diastereomer prepared in an analogous manner from commercially available (1S,2R)-2-[(tert-butoxycarbonyl)amino]cyclopentanecarboxylic acid:

Fraction 1: 1S2R Diastereomer

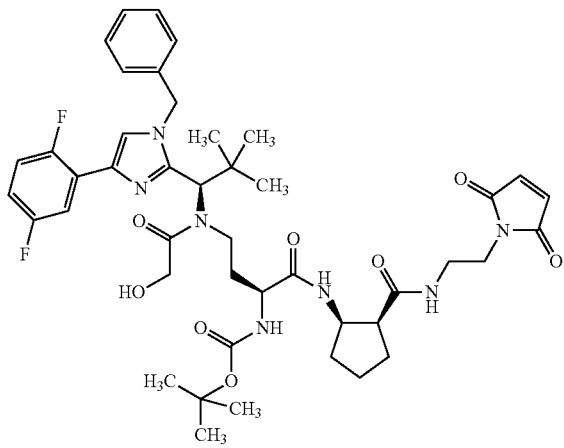 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)N[C@@H]1CCC[C@@H]1C(=O)NCCN1C(=O)C=CC1=O]

Yield: 13 mg (22%)
HPLC (Method 11): $R_t$=2.52 min;
LC-MS (Method 1): $R_t$=1.31 min; MS (ESIpos): m/z=848 (M+H)$^+$.

Fraction 2: 1R2S diastereomer

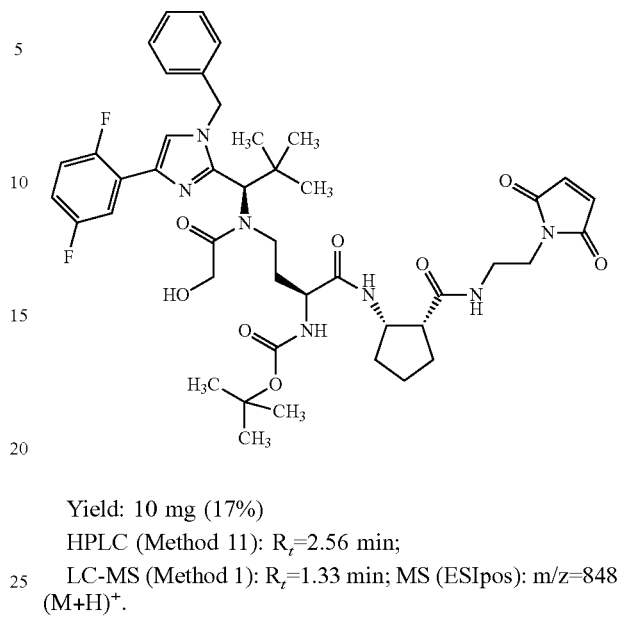

Yield: 10 mg (17%)
HPLC (Method 11): $R_t$=2.56 min;
LC-MS (Method 1): $R_t$=1.33 min; MS (ESIpos): m/z=848 (M+H)$^+$.

The deprotection of 10 mg (0.011 mmol) of the 1R2S diastereomer with TFA then yielded 8 mg (75% of theory) of the title compound.
HPLC (Method 11): $R_t$=2.04 min;
LC-MS (Method 1): $R_t$=0.92 min; MS (ESIpos): m/z=748 (M+H)$^+$.

Intermediate F13

Trifluoroacetic acid/(1S,2R)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

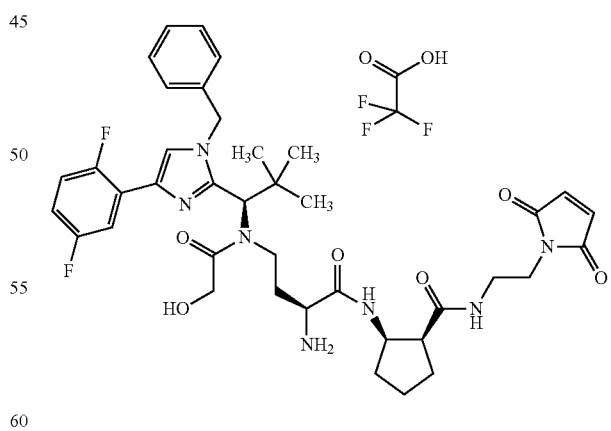

The synthesis was carried out analogously to Intermediate F13 and the title compound was obtained by deprotection of the 1 S2R diastereomer.
HPLC (Method 11): $R_t$=2.1 min;
LC-MS (Method 1): $R_t$=0.94 min; MS (ESIpos): m/z=748 (M+H)$^+$.

Intermediate F14

Trifluoroacetic acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N$^5$-carbamoyl-N-[4-(2,5-dioxo-2,5-dihydro-1H-pyrrol-1-yl)phenyl]-L-ornithinamide (1:1)

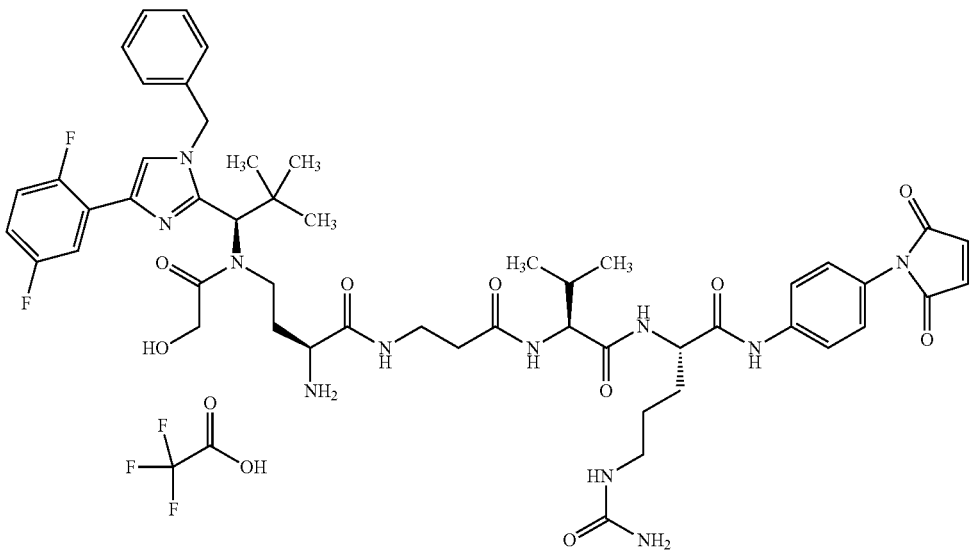 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

The title compound was prepared coupling of 20 mg (0.028 mmol) of Intermediate C5 and 18 mg (0.028 mmol) of Intermediate L7 in the presence of HATU and subsequent deblocking with TFA. This gave 15 mg (49% of theory over 2 steps) of the title compound.

HPLC (Method 11): $R_t$=1.97 min;

LC-MS (Method 1): $R_t$=0.91 min; MS (ESIpos): m/z=1012 (M+H)$^+$.

Intermediate F15

Trifluoroacetic acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N5-carbamoyl-N-[4-(2,5-dioxo-2,5-dihydro-1H-pyrrol-1-yl)phenyl]-L-ornithinamide (1:1)

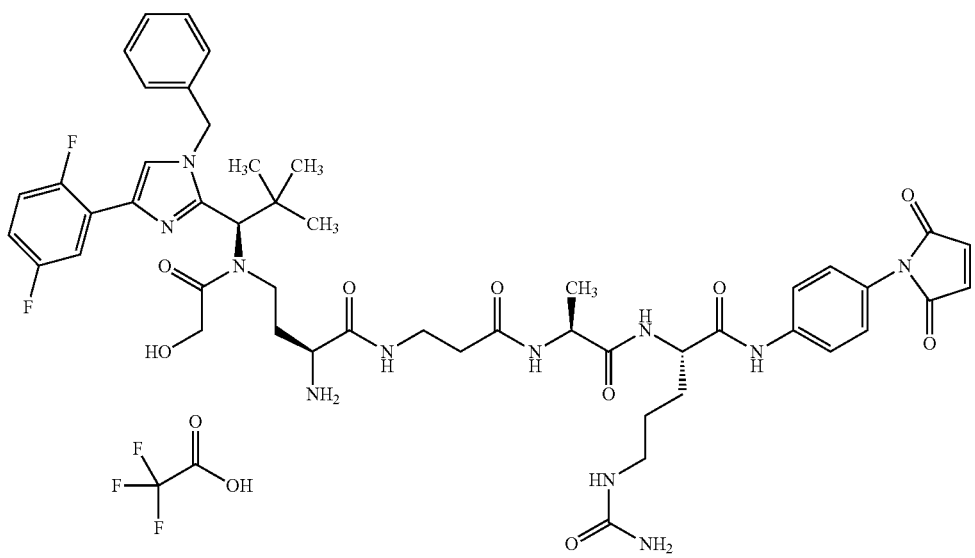 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

This Intermediate was prepared by coupling of 15 mg (0.022 mmol) of Intermediate C8 and 14 mg (0.026 mmol) of Intermediate L8 in the presence of HATU and subsequent deblocking with TFA. This gave 7 mg (27% of theory over 2 steps) of the title compound.

HPLC (Method 11): $R_t$=1.85 min;

LC-MS (Method 1): $R_t$=0.87 min; MS (ESIpos): m/z=984 (M+H)$^+$.

Intermediate F16

Trifluoroacetic acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-$N^5$-carbamoyl-N-[4-(2-{[2-(2,5-dioxo-2,5-dihydro-1H-pyrrol-1-yl)ethyl]amino}-2-oxoethyl)phenyl]-L-ornithinamide (1:1)

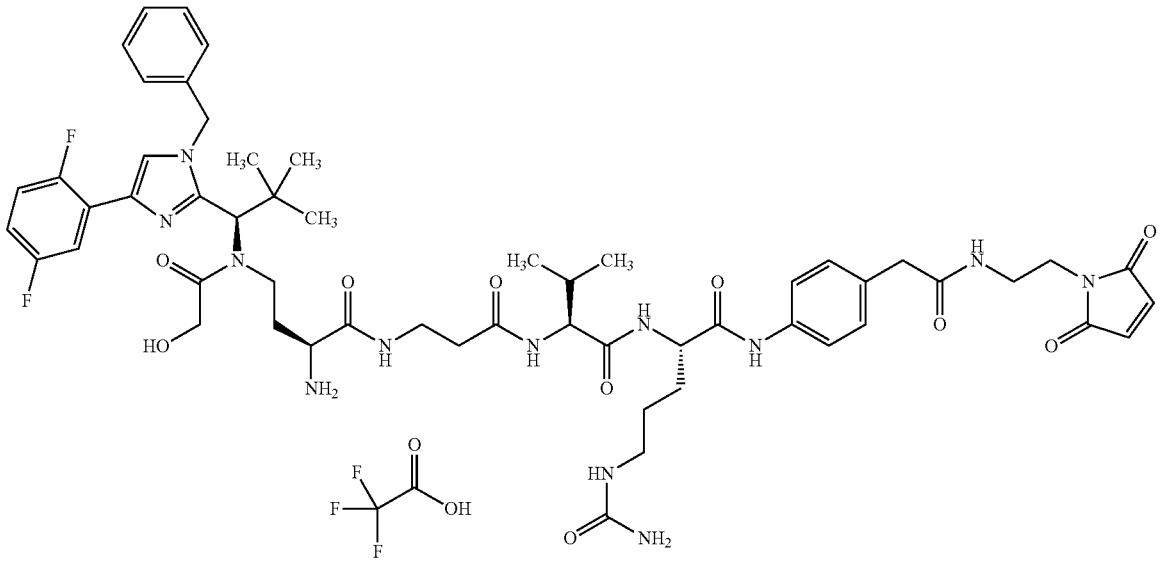 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)C=CC2=O)cc1 ; O=C(O)C(F)(F)F]

First, 20 mg (0.03 mmol) of Intermediate C3 were coupled analogously to Intermediate F3 with trifluoroacetic acid/beta-alanyl-L-valyl-N5-carbamoyl-N-[4-(2-methoxy-2-oxoethyl)phenyl]-L-ornithinamide (1:1) (Intermediate L9) in the presence of HATU (Yield: 15 mg (44% of theory). 26 mg (0.023 mmol) of this intermediate N-{(2S)-4-[(acetoxyacetyl){(1R)-1-[1-benzyl-4-(2,5-difluorophenyl)-1H-imidazol-2-yl]-2,2-dimethylpropyl}amino]-2-[(tert-butoxycarbonyl)amino]butanoyl}-beta-alanyl-L-valyl-N5-carbamoyl-N-[4-(2-methoxy-2-oxoethyl)phenyl]-L-ornithinamide were dissolved in 5 ml of methanol, 1 ml of a 2M lithium hydroxide solution were added and the reaction was stirred at RT for 90 min. The solvent was then removed under reduced pressure, the residue was taken up in acetonitrile/water and the mixture was adjusted to pH 2 using TFA. The mixture was then concentrated again giving, after purification of the residue by preparative HPLC, 20 mg (81%) of the carboxyl compound.

This intermediate was then taken up in 5 ml of DMF and coupled with 6 mg (0.022 mmol) of commercially available trifluoroacetic acid/1-(2-aminoethyl)-1H-pyrrole-2,5-dione (1:1) in the presence of 8.4 mg (0.022 mmol) of HATU and 16 μl of N,N-diisopropylethylamine Purification by preparative HPLC gave 17 mg (76% of theory) of the protected intermediate. These were taken up in 3 ml of DCM, and 1 ml of TFA was added. After 45 min of stirring at RT, the mixture was concentrated and the residue was digested with diethyl ether. Filtration with suction and drying of the residue under high vacuum yielded 15 mg (81%) of the title compound.

HPLC (Method 11): $R_t$=1.9 min;

LC-MS (Method 1): $R_t$=0.9 min; MS (ESIpos): m/z=1097 (M+H)$^+$.

Intermediate F17

N-[6-(2,5-Dioxo-2,5-dihydro-1H-pyrrol-1-yl)hexanoyl]-L-valyl-L-alanyl-$N^6$-{[(1R,2S)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic acid (1:1)

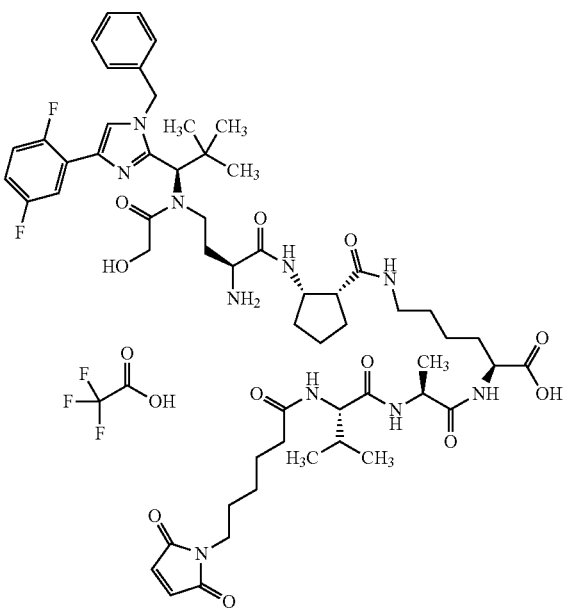 [SMILES: CC(C)[C@H](NC(=O)CCCCCN1C(=O)C=CC1=O)C(=O)N[C@@H](C)C(=O)N[C@@H](CCCCNC(=O)[C@@H]1CCC[C@@H]1NC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F12 from 6 mg (0.01 mmol) of Intermediate C5 and 8 mg (0.01 mmol) of Intermediate L10. At the stage of the Boc-protected intermediate, the diastereomers formed were separated by preparative HPLC (Chromatorex C18-10/125× 30/12 ml/min) The stereochemistry of the separated diastereomers was assigned by comparison with the individual diastereomer prepared in an analogous manner from commercially available (1S,2R)-2-[(tert-butoxycarbonyl)amino]cyclopentanecarboxylic acid:

Fraction 1: 1S2R diastereomer

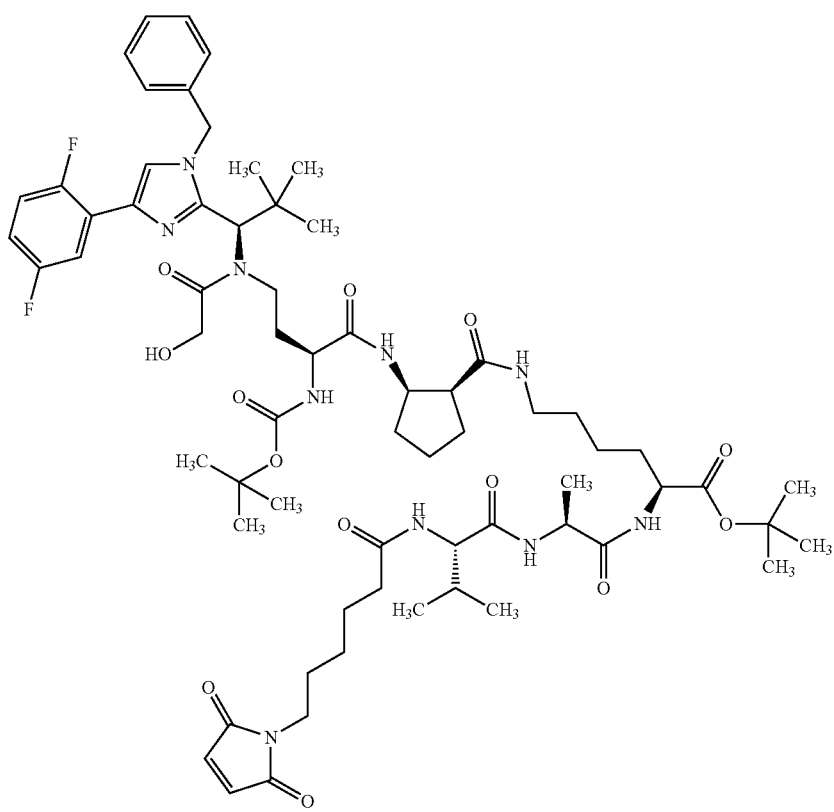 [SMILES: CC(C)[C@H](NC(=O)CCCCCN1C(=O)C=CC1=O)C(=O)N[C@@H](C)C(=O)N[C@@H](CCCCNC(=O)[C@H]1CCC[C@H]1NC(=O)[C@H](CCN(C(=O)CO)[C@@H](c1nc(-c2cc(F)ccc2F)cn1Cc1ccccc1)C(C)(C)C)NC(=O)OC(C)(C)C)C(=O)OC(C)(C)C]

Yield: 1 mg
HPLC (Method 11): $R_t$=2.73 min;
LC-MS (Method 1): $R_t$=1.37 min; MS (ESIpos): m/z=1274 (M+H)$^+$.

Fraction 2: 1R2S diastereomer

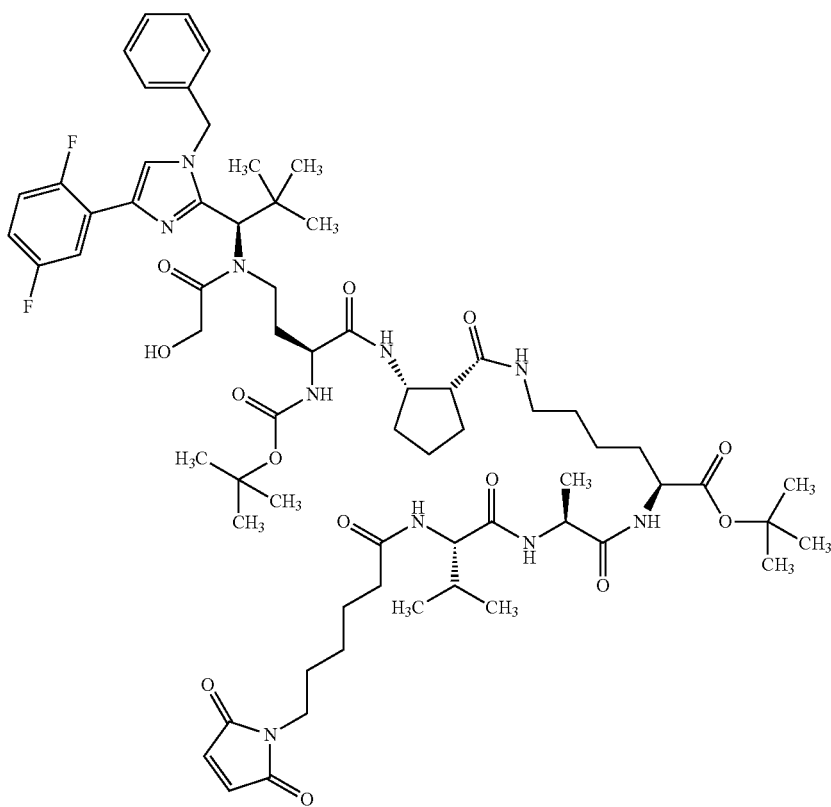

Yield: 0.7 mg

HPLC (Method 11): $R_t$=2.81 min;

LC-MS (Method 1): $R_t$=1.41 min; MS (ESIpos): m/z=1274 (M+H)$^+$.

Complete deprotection of 0.7 mg (0.001 mmol) of the 1R2S diastereomer was achieved by dissolution in 1 ml of DCM, addition of 1 ml of TFA and 1 h of stirring at RT. Concentration under reduced pressure and lyophilization of the residue from acetonitrile/water gave 0.68 mg (94% of theory) of the title compound.

HPLC (Method 11): $R_t$=2.1 min;

LC-MS (Method 1): $R_t$=0.97 min; MS (ESIpos): m/z=1117 (M+H)$^+$.

Intermediate F18

N-[6-(2,5-Dioxo-2,5-dihydro-1H-pyrrol-1-yl)hexanoyl]-L-valyl-L-alanyl-N$^6$-{[(1S,2R)-2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic acid (1:1)

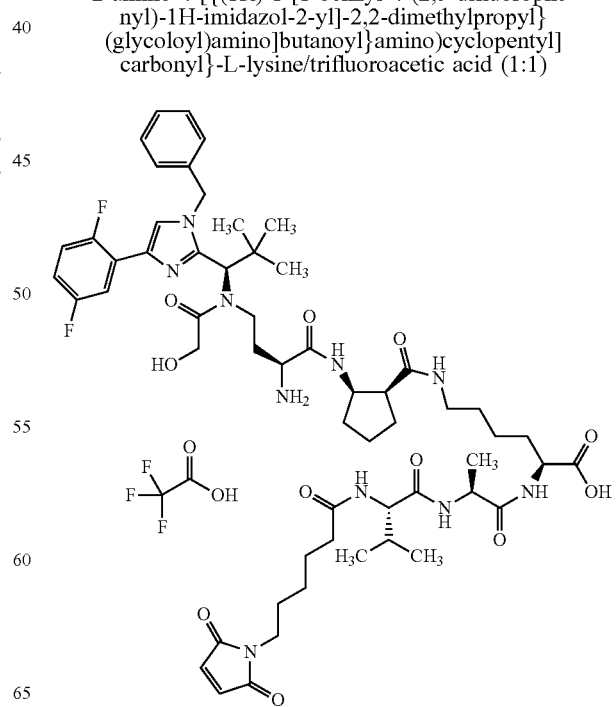

The title compound was prepared analogously to Intermediate F17 from 8.9 mg (0.014 mmol) of Intermediate C5 and 13 mg (0.014 mmol) of Intermediate L11.

HPLC (Method 11): $R_t$=2.2 min;

LC-MS (Method 1): $R_t$=1.01 min; MS (ESIpos): m/z=1117 (M+H)⁺.

Intermediate F19

N⁶-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-N²-[(2,5-dioxo-2,5-dihydro-1H-pyrrol-1-yl)acetyl]-L-lysine/ trifluoroacetic acid (1:1)

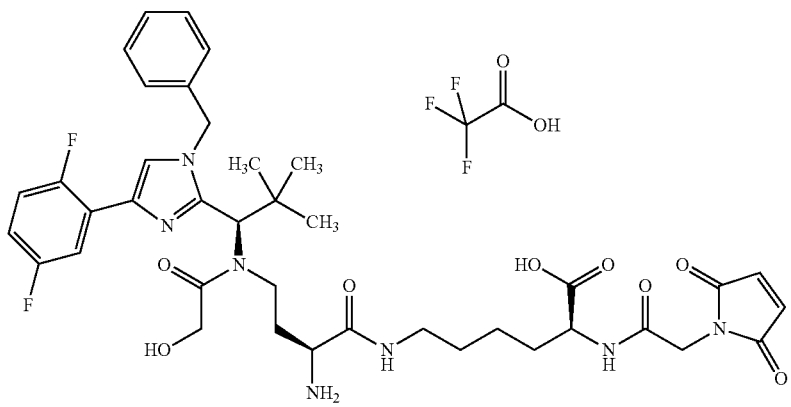 [SMILES: CC(C)(C)[C@H](c1nc(-c2cc(F)ccc2F)cn1Cc1ccccc1)N(CC[C@H](N)C(=O)NCCCC[C@H](NC(=O)CN1C(=O)C=CC1=O)C(=O)O)C(=O)CO ; O=C(O)C(F)(F)F]

The title compound was prepared analogously to Intermediate F2 by coupling of 25 mg (0.041 mmol) of Intermediate C5 with 55 mg (0.122 mmol) of Intermediate L13 and subsequent deprotection.

HPLC (Method 11): $R_t$=1.84 min;

LC-MS (Method 1): $R_t$=0.88 min; MS (ESIpos): m/z=780 (M+H)⁺.

The title compound was prepared analogously to Intermediate F2 by coupling of 10 mg (0.015 mmol) of Intermediate C5 with 55 mg (0.122 mmol) of Intermediate L14 and subsequent deprotection.

HPLC (Method 11): $R_t$=1.9 min;

LC-MS (Method 1): $R_t$=0.87 min; MS (ESIpos): m/z=735 (M+H)⁺.

Intermediate F20

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{4-[(2,5-dioxo-2,5-dihydro-1H-pyrrol-1-yl)acetyl]piperazin-1-yl}butanamide (1:1)

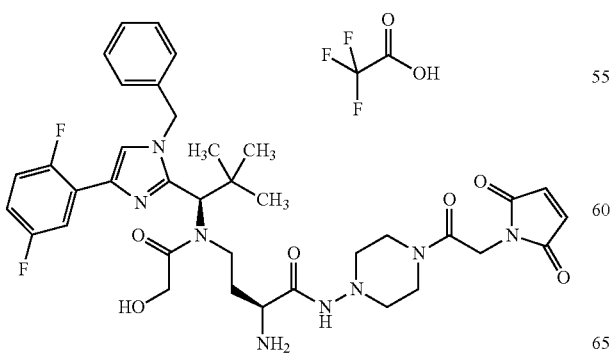

Intermediate F21

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[1-(2,5-dioxo-2,5-dihydro-1H-pyrrol-1-yl)-12-oxo-3,6,9-trioxa-13-azapentadecan-15-yl]butanamide (1:1)

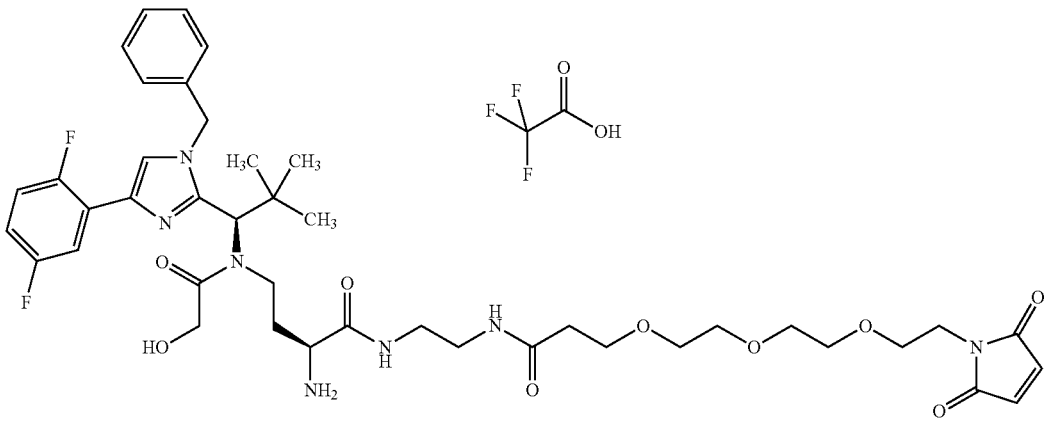 [SMILES: CC(C)(C)[C@H](c1nc(-c2cc(F)ccc2F)cn1Cc1ccccc1)N(CC[C@H](N)C(=O)NCCNC(=O)CCOCCOCCOCCN1C(=O)C=CC1=O)C(=O)CO ; O=C(O)C(F)(F)F]

The title compound was prepared analogously to Intermediate F2 by coupling of 10 mg (0.015 mmol) of Intermediate C5 with 7 mg (0.015 mmol) of Intermediate L15 and subsequent deprotection.

LC-MS (Method 1): $R_t$=0.89 min; MS (ESIpos): m/z=840 (M+H)$^+$.

Intermediate F22

Trifluoroacetic acid/N-[(3S)-3-amino-4-(1-{2-[(2-{[(2,5-dioxo-2,5-dihydro-1H-pyrrol-1-yl)acetyl]amino}ethyl)amino]-2-oxoethyl}hydrazino)-4-oxobutyl]-N-{(1R)-1-[1-benzyl-4-(2,5-difluorophenyl)-1H-imidazol-2-yl]-2,2-dimethylpropyl}-2-hydroxyacetamide (1:1)

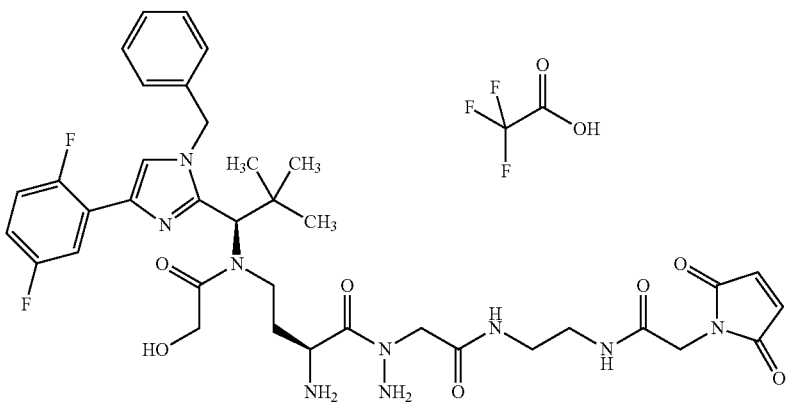 [SMILES: CC(C)(C)[C@H](c1nc(-c2cc(F)ccc2F)cn1Cc1ccccc1)N(CC[C@H](N)C(=O)N(N)CC(=O)NCCNC(=O)CN1C(=O)C=CC1=O)C(=O)CO ; O=C(O)C(F)(F)F]

The title compound was prepared analogously to Intermediate F9 by coupling of 13.7 mg (0.017 mmol) of Intermediate C7 with 5.9 mg (0.017 mmol) of Intermediate L1 and subsequent deprotection.

HPLC (Method 11): $R_t$=2.3 min;
LC-MS (Method 1): $R_t$=1.2 min; MS (ESIpos): m/z=866 (M+H)$^+$.

Intermediate F23

N-[6-(2,5-Dioxo-2,5-dihydro-1H-pyrrol-1-yl)hexanoyl]-L-valyl-N⁵-carbamoyl-L-ornithyl-N⁶-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic acid (1:1)

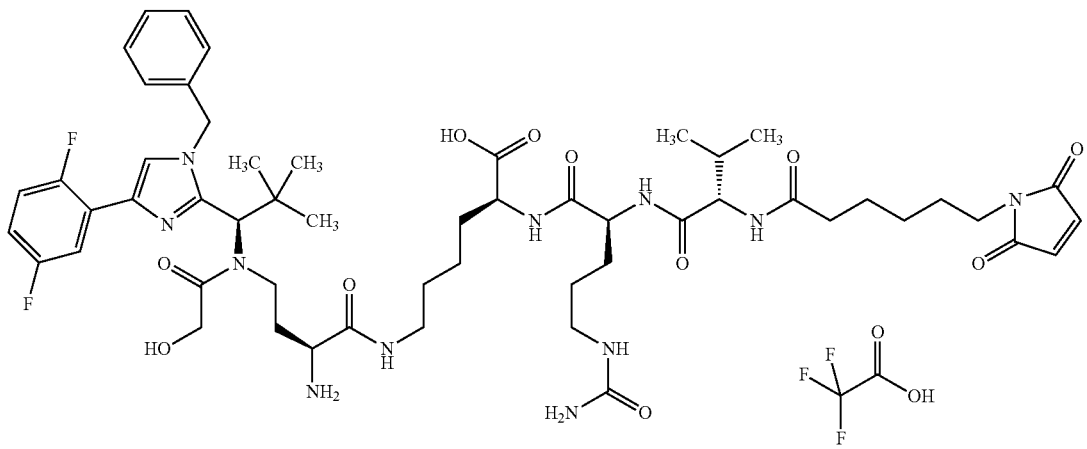 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F2 by coupling of 10 mg (0.016 mmol) of Intermediate C5 with 16.8 mg (0.016 mmol) of Intermediate L17 in the presence of EDC/HOBT and N,N-diisopropylethylamine and subsequent deprotection.

HPLC (Method 11): $R_t$=1.9 min;

LC-MS (Method 1): $R_t$=0.9 min; MS (ESIpos): m/z=1092 (M+H)⁺.

Intermediate F24

Trifluoroacetic acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N⁵-carbamoyl-N-[4-(2-{[2-(2,5-dioxo-2,5-dihydro-1H-pyrrol-1-yl)ethyl]amino}-2-oxoethyl)phenyl]-L-ornithinamide (1:1)

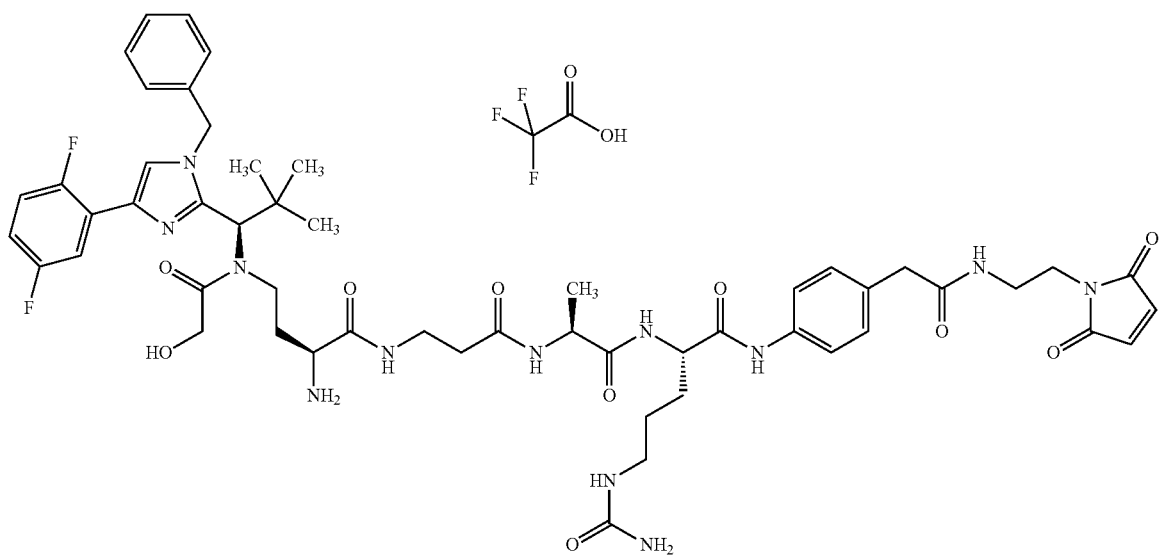 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)C=CC2=O)cc1 ; O=C(O)C(F)(F)F]

The preparation of the title compound was carried out analogously to Intermediate F16:

First, 30 mg (0.046 mmol) of Intermediate C3 were coupled analogously to Intermediate F3 with Intermediate L18 in the presence of HATU (Yield: 25 mg (47% of theory).

27 mg (0.024 mmol) of this intermediate were dissolved in 5 ml of methanol, 1 ml of a 2M lithium hydroxide solution was added and the mixture was stirred at RT for 30 min, resulting in the cleavage of both the methyl ester and the acetyl group. The solvent was then removed under reduced pressure, the residue was taken up in acetonitrile/water and the mixture was adjusted to pH 2 using TFA. The mixture was then concentrated again giving, after purification of the residue by preparative HPLC, 15 mg (58%) of the carboxyl compound.

This intermediate was then taken up in 3 ml of DMF and coupled with 4.4 mg (0.017 mmol) of commercially available trifluoroacetic acid/1-(2-aminoethyl)-1H-pyrrole-2,5-dione (1:1) in the presence of 6.5 mg (0.017 mmol) of HATU and 12 µl of N,N-diisopropylethylamine Purification by preparative HPLC gave 12 mg (72% of theory) of the protected intermediate. These were taken up in 2 ml of DCM, and 1 ml of TFA was added. After 30 min of stirring at RT, the mixture was concentrated and lyophilized from acetonitrile/water 1:1. Drying of the residue under high vacuum afforded 11 mg (91%) of the title compound.

LC-MS (Method 1): $R_t$=0.83 min; MS (ESIpos): m/z=1069 (M+H)$^+$.

Intermediate F25

Trifluoroacetic acid/N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N$^5$-carbamoyl-N-(4-{[(2,5-dioxo-2,5-dihydro-1H-pyrrol-1-yl)acetyl]amino}phenyl)-L-ornithinamide (1:1)

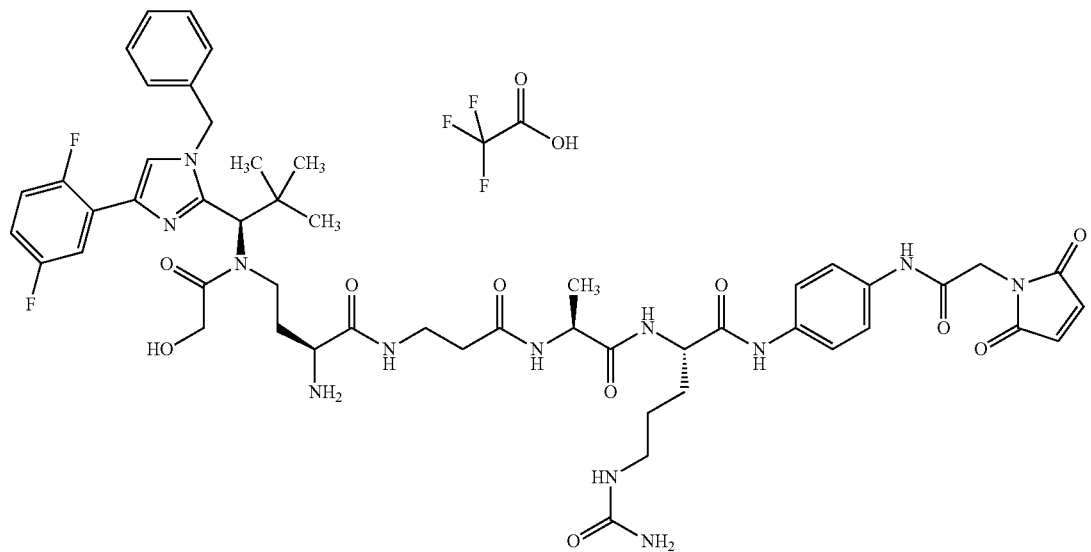 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(NC(=O)CN2C(=O)C=CC2=O)cc1 ; O=C(O)C(F)(F)F]

This intermediate was prepared by coupling of 9.6 mg (0.014 mmol) of Intermediate C8 with 10.8 mg (0.015 mmol) of Intermediate L19 in the presence of 6.4 mg (0.017 mmol) of HATU and 72 µl of N,N-diisopropylethylamine and subsequent deblocking with TFA. This gave 5 mg (31% of theory over 2 steps) of the title compound.

HPLC (Method 11): $R_t$=1.8 min;

LC-MS (Method 1): $R_t$=0.85 min; MS (ESIpos): m/z=1041 (M+H)$^+$.

Intermediate F26

Trifluoroacetic acid/N-{(15S,19R)-15-amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oyl}-L-valyl-$N^5$-carbamoyl-N-[4-(2,5-dioxo-2,5-dihydro-1H-pyrrol-1-yl)phenyl]-L-ornithinamide (1:1)

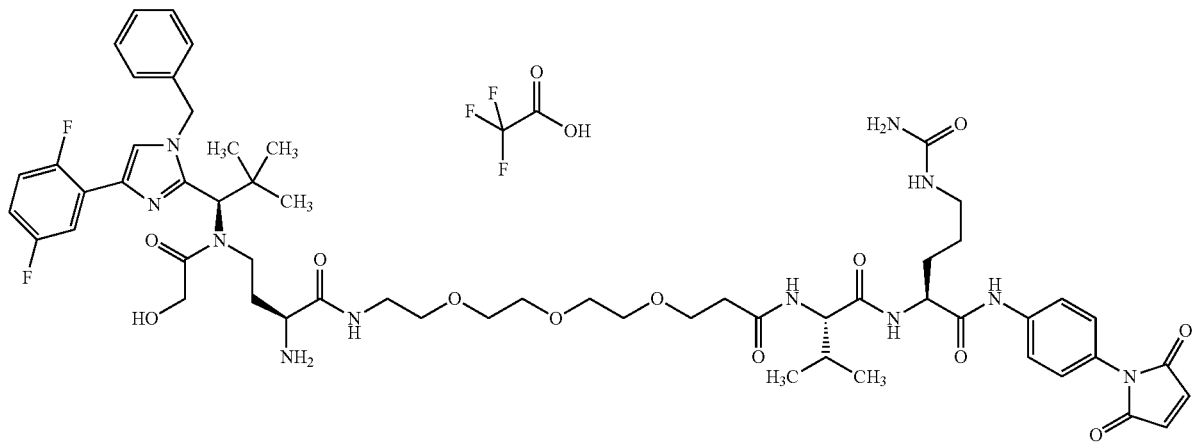 [SMILES: CC(C)[C@H](NC(=O)CCOCCOCCOCCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

This intermediate was prepared by coupling of 16.4 mg (0.02 mmol) of Intermediate C9 with 11.2 mg (0.02 mmol) of Intermediate L20 in the presence of 8 mg (0.04 mmol) of 1-(3-dimethylaminopropyl)-3-ethylcarbodiimide hydrochloride, 6 mg (0.04 mmol) of 1-hydroxy-1H-benzotriazole hydrate and 11 μl (0.06 mmol) of N,N-diisopropylethylamine and subsequent deblocking with TFA. This gave 10 mg (37% of theory over 2 steps) of the title compound.

HPLC (Method 11): $R_t$=2.0 min;

LC-MS (Method 1): $R_t$=0.91 min; MS (ESIpos): m/z=1144 (M+H)$^+$.

Intermediate F27

Trifluoroacetic acid/N-{(2S)-2-amino-4-{[(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N-[4-(2-{[2-(2,5-dioxo-2,5-dihydro-1H-pyrrol-1-yl)ethyl]amino}-2-oxoethyl)phenyl]-L-lysinamide (2:1)

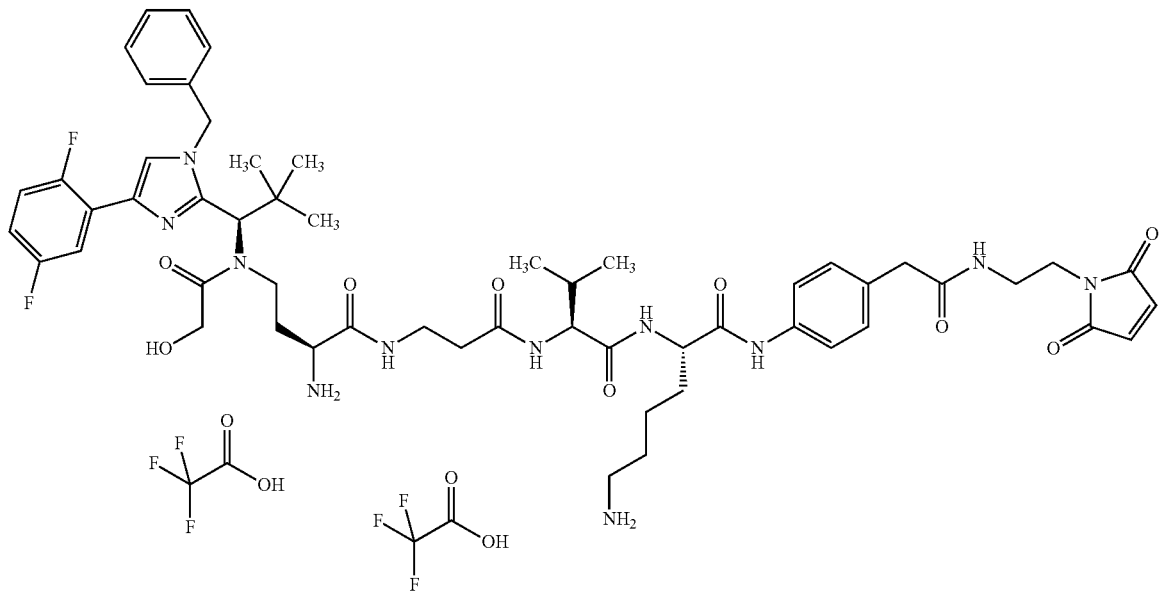 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCCN)C(=O)Nc1ccc(CC(=O)NCCN2C(=O)C=CC2=O)cc1 ; O=C(O)C(F)(F)F ; O=C(O)C(F)(F)F]

This intermediate was prepared over 4 steps:

In the first step, 20 mg (0.028 mmol) of Intermediate C8 were coupled with 16.7 mg (0.031 mmol) of Intermediate L21 in the presence of 11 mg (0.057 mmol) of 1-(3-dimethylaminopropyl)-3-ethylcarbodiimide hydrochloride, 8.7 mg (0.057 mmol) of 1-hydroxy-1H-benzotriazole hydrate and 15 µl (0.085 mmol) of N,N-diisopropylethylamine in 5 ml of DMF. After 4 days of stirring at RT, the reaction was concentrated and the product was purified by preparative HPLC. Yield: 18 mg (54.5% of theory).

18 mg (0.016 mmol) of this intermediate were dissolved in 4 ml of methanol, 194 µl of a 2M lithium hydroxide solution were added and the reaction was stirred at RT overnight. Another 116 µl of lithium hydroxide solution were then added, and the reaction was stirred at RT for a further 4 h. The solvent was then removed under reduced pressure, the residue was taken up in water and the reaction was then adjusted to pH 5 with 5% strength citric acid. The mixture was extracted twice with dichloromethane and the organic phase was dried over sodium sulphate. The organic phase was then filtered and concentrated and the residue was dried under high vacuum. This gave 10.5 mg (58%) of the carboxyl compound.

10.5 mg (0.009 mmol) of this intermediate were then taken up in 4 ml of DMF and coupled with 3 mg (0.012 mmol) of commercially available trifluoroacetic acid/1-(2-aminoethyl)-1H-pyrrole-2,5-dione (1:1) in the presence of 3.5 mg (0.018 mmol) of 1-(3-dimethylaminopropyl)-3-ethylcarbodiimide hydrochloride, 2.8 mg (0.018 mmol) of 1-hydroxy-1H-benzotriazole hydrate and 6 µl of N,N-diisopropylethylamine After stirring overnight, the same amount of coupling reagents were added again and the reaction was stirred at RT for a further 3 days. The mixture was then concentrated and the product was purified by preparative HPLC. Yield: 6 mg (52% of theory).

6 mg (0.005 mmol) of this intermediate were then deprotected in 3 ml of DCM with 1 ml of trifluoroacetic acid. Lyophilization from acetonitrile/water gave 6 mg (83% of theory) of the title compound.

HPLC (Method 11): $R_t$=1.84 min;
LC-MS (Method 4): $R_t$=0.93 min; MS (ESIpos): m/z=1068 (M+H)$^+$.

Intermediate F28

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-({N-[6-(2,5-dioxo-2,5-dihydro-1H-pyrrol-1-yl)hexanoyl]-L-valyl-N$^5$-carbamoyl-L-ornithyl}amino)-L-phenylalanine/trifluoroacetic acid (1:1)

This intermediate was prepared over 5 steps:

In the first step, 40 mg (0.058 mmol) of Intermediate C8 were coupled with 46 mg (0.058 mmol) of Intermediate L22 in the presence of 44.3 mg (0.117 mmol) of HATU and 30 µl of N,N-diisopropylethylamine After 1 h of stirring at RT, the reaction was concentrated and the product was purified by preparative HPLC. Yield: 53 mg (62.5% of theory).

In the next step, the Fmoc group was removed with 0.6 ml of piperidine in 3 ml of DMF. After 1 h of stirring at RT, the reaction was concentrated and the product was purified by preparative HPLC. Yield: 42 mg (82% of theory).

To cleave the methyl ester, 42 mg (0.033 mmol) of this intermediate were dissolved in 2 ml of THF and 1 ml of water, 330 µl of a 2M lithium hydroxide solution were added and the reaction was stirred at RT for 1 h.

The reaction was then neutralized with TFA and concentrated and the residue was purified by preparative HPLC. Drying under high vacuum gave 32 mg (78%) of the carboxyl compound.

32 mg (0.026 mmol) of this intermediate were then coupled in 2.3 ml of DMF with 14.6 mg (0.047 mmol) of commercially available 1-{6-[(2,5-dioxopyrrolidin-1-yl)oxy]-6-oxohexyl}-1H-pyrrole-2,5-dione in the presence of 18 µl of N,N-diisopropylethylamine After a 4-hour treatment in an ultrasonic bath, the reaction was concentrated and the product was purified by preparative HPLC Yield: 20.4 mg (60% of theory).

In the last step, 20.4 mg (0.016 mmol) of this intermediate were deprotected in DCM with trifluoroacetic acid. Lyophilization from acetonitrile/water gave 20 mg (85% of theory) of the title compound.

HPLC (Method 11): $R_t$=1.9 min;
LC-MS (Method 5): $R_t$=2.84 min; MS (ESIpos): m/z=1197 (M+H)$^+$.

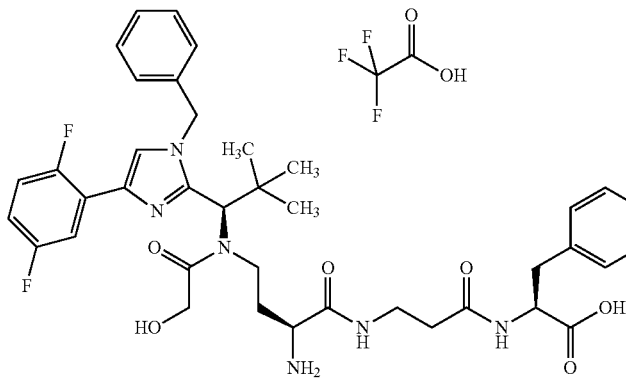
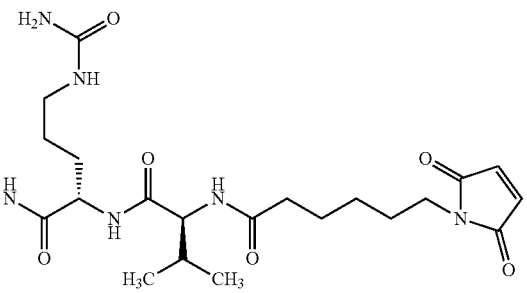

Intermediate F29

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-({N-[6-(2,5-dioxo-2,5-dihydro-1H-pyrrol-1-yl)hexanoyl]-L-valyl-L-alanyl}amino)-L-phenylalanine/trifluoroacetic acid (1:1)

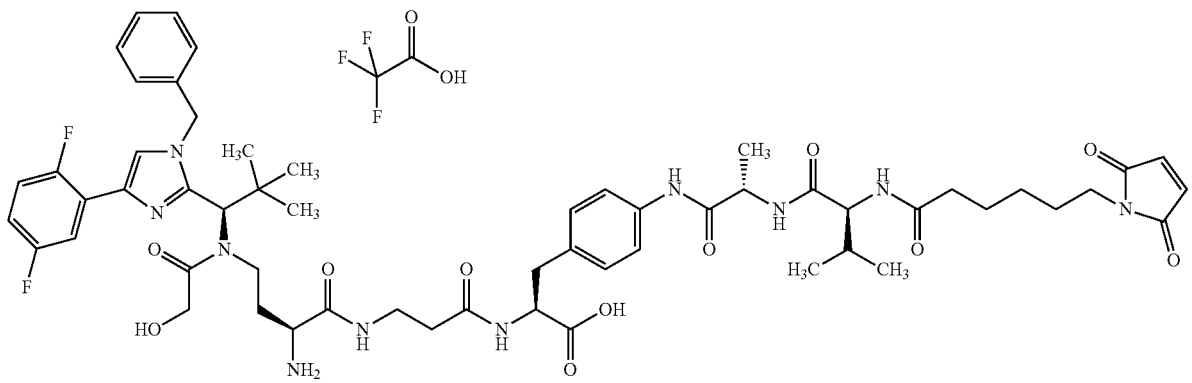 [SMILES: CC(C)[C@H](NC(=O)CCCCCN1C(=O)C=CC1=O)C(=O)N[C@@H](C)C(=O)Nc1ccc(C[C@H](NC(=O)CCNC(=O)[C@@H](N)CCN(C(=O)CO)[C@@H](c2nc(-c3cc(F)ccc3F)cn2Cc2ccccc2)C(C)(C)C)C(=O)O)cc1 ; O=C(O)C(F)(F)F]

The preparation of the title compound was carried out analogously to Intermediate F28.

HPLC (Method 11): $R_t$=2.0 min;
LC-MS (Method 1): $R_t$=0.92 min; MS (ESIpos): m/z=1111 (M+H)$^+$.

Intermediate F30

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{2-1[(3-{[2-(2,5-dioxo-2,5-dihydro-1H-pyrrol-1-yl)ethyl]amino}-3-oxopropyl)sulphinyl]ethyl}butanamide (1:1)

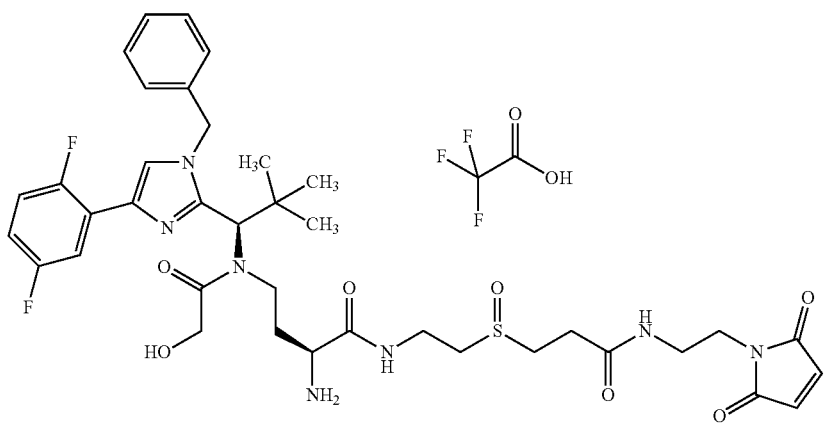 [SMILES: CC(C)(C)[C@H](c1nc(-c2cc(F)ccc2F)cn1Cc1ccccc1)N(CC[C@H](N)C(=O)NCCS(=O)CCC(=O)NCCN1C(=O)C=CC1=O)C(=O)CO ; O=C(O)C(F)(F)F]

This intermediate was prepared over 4 steps:

In the first step, 37.5 mg (0.055 mmol) of Intermediate C3 were coupled with 15 mg (0.066 mmol) of commercially available methyl 3-[(2-aminoethyl)sulphanyl]propanoate hydrochloride (1:1) in DMF in the presence of 25 mg (0.066 mmol) of HATU and 29 μl of N,N-diisopropylethylamine After 15 min of stirring at RT, the coupling reagents were added again. The reaction was stirred at RT for another 15 min and then concentrated and the product was purified by preparative HPLC. Yield: 21 mg (48% of theory).

LC-MS (Method 1): $R_t$=1.41 min; MS (ESIpos): m/z=802 (M+H)$^+$.

To cleave the methyl ester, 21 mg (0.026 mmol) of this intermediate were dissolved in 5 ml of methanol, 655 μl of a 2M lithium hydroxide solution were added and the reaction was stirred at RT overnight. During this time, partial oxidation at the sulphur occurred. The reaction was concentrated and the residue was taken up in water and then adjusted to pH 3 with acetic acid. The mixture was extracted twice with 50 ml of ethyl acetate and the organic phase was then dried over magnesium sulphate, filtered and concentrated. The mixture obtained after drying of the residue under high vacuum was used without further purification in the next step for coupling with 8.4 mg (0.033 mmol) of commercially available trifluoroacetic acid/1-(2-aminoethyl)-1H-pyrrole-2,5-dione (1:1) in the presence of 11.6 mg (0.031 mmol) of HATU and 22 μl of N,N-diisopropylethylamine. The reaction was stirred at RT for 5 min and then concentrated. The residue was taken up in ethyl acetate and the solution was extracted with 5% strength citric acid and then with water. The organic phase was then dried over magnesium sulphate, filtered and concentrated. The mixture obtained after drying of the residue under high vacuum was used without further purification in the next step.

22 mg of this crude material were then dissolved in 2 ml of DCM and deprotected with 0.5 ml of trifluoroacetic acid. After 10 min of stirring at RT, the reaction was concentrated and the residue was purified by preparative HPLC. Drying under high vacuum gave 2.1 mg of the title compound.

HPLC (Method 11): $R_t$=1.8 min;

LC-MS (Method 1): $R_t$=0.83 min; MS (ESIpos): m/z=784 (M+H)$^+$.

Intermediate F31

Trifluoroacetic acid/N-[6-(2,5-dioxo-2,5-dihydro-1H-pyrrol-1-yl)hexanoyl]-L-valyl-N-(3-{[2-{(1R)-1-[(3-aminopropyl)(glycoloyl)amino]-2,2-dimethylpropyl}-4-(2,5-difluorophenyl)-1H-imidazol-1-yl]methyl}phenyl)-L-alaninamide (1:1)

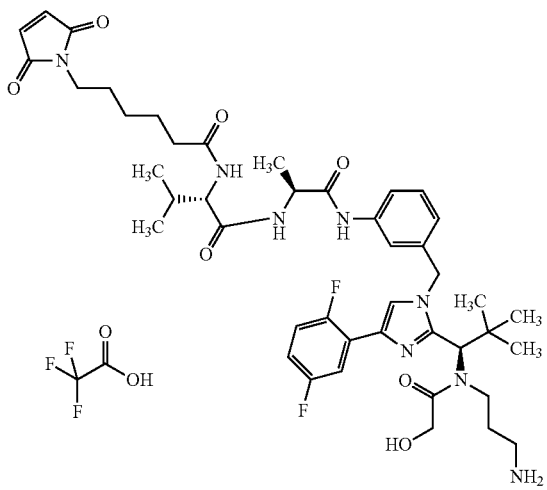 [SMILES: CC(C)[C@H](NC(=O)CCCCCN1C(=O)C=CC1=O)C(=O)N[C@@H](C)C(=O)Nc1cccc(Cn2cc(-c3cc(F)ccc3F)nc2[C@H](N(CCCN)C(=O)CO)C(C)(C)C)c1 ; O=C(O)C(F)(F)F]

This intermediate was synthesized from Intermediate C10 over 6 steps using classical methods of peptide chemistry.

In the first step, 42 mg (0.066 mmol) of Intermediate C10 were coupled with 20.7 mg (0.066 mmol) of N-[(9H-fluoren-9-ylmethoxy)carbonyl]-L-alanine in 5 ml of DMF in the presence of 100 mg (0.266 mmol) of HATU and 46 μl of N,N-diisopropylethylamine. The reaction was stirred at RT overnight and the product was purified by preparative HPLC. This gave 16 mg (27% of theory) of the N-acylated compound and 9 mg (12% of theory) of the N-, O-bisacylated compound.

The deprotection of the N-acylated compound was carried out in DMF with piperidine. The bisacylated compound was treated in ethanol both with piperidine and with an aqueous solution of methylamine. In both cases, tert-butyl (3-{[(1R)-1-{1-[3-(L-alanylamino)benzyl]-4-(2,5-difluorophenyl)-1H-imidazol-2-yl}-2,2-dimethylpropyl](glycoloyl)amino}propyl)carbamate was formed, and purification by preparative HPLC gave 13 mg in a purity of 95%.

LC-MS (Method 1): $R_t$=0.95 min; MS (ESIpos): m/z=657 (M+H)$^+$.

13 mg (0.019 mmol) of this intermediate were coupled in 2 ml of DMF with 9.1 mg (0.021 mmol) of 2,5-dioxopyrrolidin-1-yl N-[(9H-fluoren-9-ylmethoxy)carbonyl]-L-valinate in the presence of 7 μl of N,N-diisopropylethylamine After 20 h of stirring at RT, the mixture was concentrated and the residue was purified by preparative HPLC. Lyophilization from 1,4-dioxane/water gave 10 mg (54% of theory).

The subsequent removal of the Fmoc protective group with piperidine in DMF gave 9 mg (quant.) of the partially deprotected intermediate.

9 mg (0.01 mmol) of this intermediate were then coupled in 2 ml of DMF with 3.2 mg (0.01 mmol) of commercially available 1-{6-[(2,5-dioxopyrrolidin-1-yl)oxy]-6-oxohexyl}-1H-pyrrole-2,5-dione in the presence of 5 μl of N,N-diisopropylethylamine After stirring at RT overnight, the reaction was concentrated and the product was purified by preparative HPLC. Lyophilization from acetonitrile/water and a few drops of 1,4-dioxane afforded 3 mg (32% of theory) which were deprotected in the last step in 2 ml of DCM with 0.5 ml of trifluoroacetic acid. Lyophilization from acetonitrile/water gave 3.8 mg (quant.) of the title compound.

HPLC (Method 11): $R_t$=1.9 min;

LC-MS (Method 1): $R_t$=0.89 min; MS (ESIpos): m/z=849 (M+H)$^+$.

Intermediate F32

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

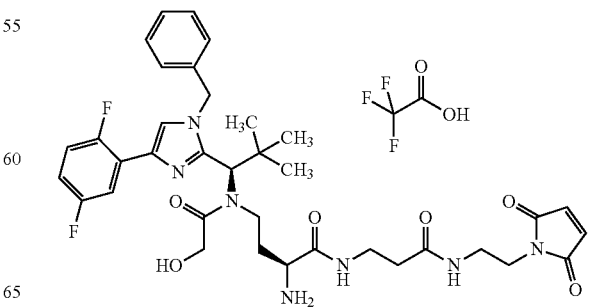

This intermediate was prepared by coupling of 15 mg (0.041 mmol) of Intermediate C5 with 16.8 mg (0.027 mmol) of Intermediate L23 in the presence of 10.5 mg (0.055 mmol) of 1-(3-dimethylaminopropyl)-3-ethylcarbodiimide hydrochloride, 8.4 mg (0.055 mmol) of 1-hydroxy-1H-benzotriazole hydrate and 14 μl (0.08 mmol) of N,N-diisopropylethylamine and subsequent deblocking with TFA. This gave 3.4 mg (15% of theory over 2 steps) of the title compound.

HPLC (Method 11): $R_t$=1.9 min;
LC-MS (Method 1): $R_t$=0.85 min; MS (ESIpos): m/z=708 (M+H)$^+$.

Intermediate F33

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-{2-[(bromoacetyl)amino]ethyl}butanamide (1:1)

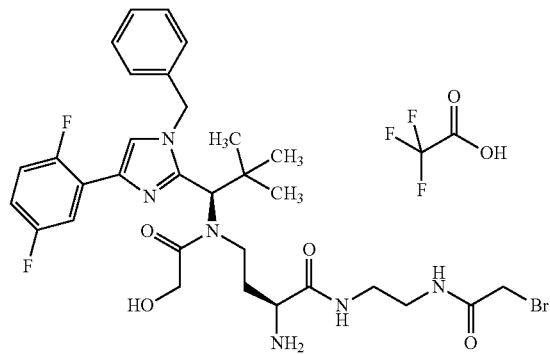 [SMILES: CC(C)(C)[C@H](c1nc(-c2cc(F)ccc2F)cn1Cc1ccccc1)N(CC[C@H](N)C(=O)NCCNC(=O)CBr)C(=O)CO ; O=C(O)C(F)(F)F]

The synthesis of this intermediate began in the first step with the coupling of 50 mg (0.075 mmol) of Intermediate C3 with 26.2 mg (0.082 mmol) of 9H-fluoren-9-ylmethyl (2-aminoethyl)carbamate hydrochloride (1:1) in the presence of 28.7 mg (0.15 mmol) of 1-(3-dimethylaminopropyl)-3-ethyl carbodiimide hydrochloride, 22.9 mg (0.15 mmol) of 1-hydroxy-1H-benzotriazole hydrate and 39 μl of N,N-diisopropylethylamine After 18 h of stirring at RT, the mixture was concentrated and the residue was purified by preparative HPLC. This gave 45 mg (65% of theory) of this intermediate.

LC-MS (Method 1): $R_t$=1.51 min; MS (ESIpos): m/z=921 (M+H)$^+$.

45 mg (0.049 mmol) of this intermediate were taken up in 10 ml of ethanol, and 176 μl of a 40% strength solution of methanamine in water were added. The reaction was stirred at 50° C., with the same amount of methanamine solution being added after 6 h and after 9 h. After a further 14 h of stirring at 50° C., another 700 μl of the methanamine solution were added, and after a further 20 h of stirring the mixture was finally concentrated. The residue was taken up in DCM and washed with water. The organic phase was concentrated and the residue was purified by preparative HPLC. Concentration of the appropriate fractions and drying of the residue under high vacuum gave 32 mg (99% of theory) of tert-butyl{(2S)-[4(2-aminoethyl)amino]-4-[{(1R)-1-[1-benzyl-4-(2,5-difluorophenyl)-1H-imidazol-2-yl]-2,2-dimethylpropyl}(glycoloyl)amino]-1-oxobutan-2-yl}carbamate.

LC-MS (Method 1): $R_t$=0.95 min; MS (ESIpos): m/z=657 (M+H)$^+$.

8.3 mg (0.013 mmol) of this intermediate were dissolved in 4 ml of dichloromethane, and 3.3 mg (0.013 mmol) of bromoacetic anhydride and 2 μl of N,N-diisopropylethylamine were added. After 1 h of stirring at RT, the mixture was concentrated and the residue was purified by preparative HPLC. The appropriate fractions were concentrated and the residue was lyophilized from acetonitrile/water. The residue was taken up in 1 ml of dichloromethane and deprotected with 0.5 ml of trifluoroacetic acid. Concentration and lyophilization from acetonitrile/water gave 1.1 mg (9% of theory over 2 steps) of the title compound.

HPLC (Method 11): $R_t$=1.9 min;
LC-MS (Method 1): $R_t$=0.88 min; MS (ESIpos): m/z=677/679 (M+H)$^+$.

Intermediate F34

Trifluoroacetic acid/N-{(2S)-2-amino-4-{[(1R)-1-[1-benzyl-4-(2,5-difluorophenyl)-1H-imidazol-2-yl]-2,2-dimethylpropyl}(glycoloyl)amino]butanoyl}-L-alanyl-N$^5$-carbamoyl-N-[4-(2,5-dioxo-2,5-dihydro-1H-pyrrol-1-yl)phenyl]-L-ornithinamide (1:1)

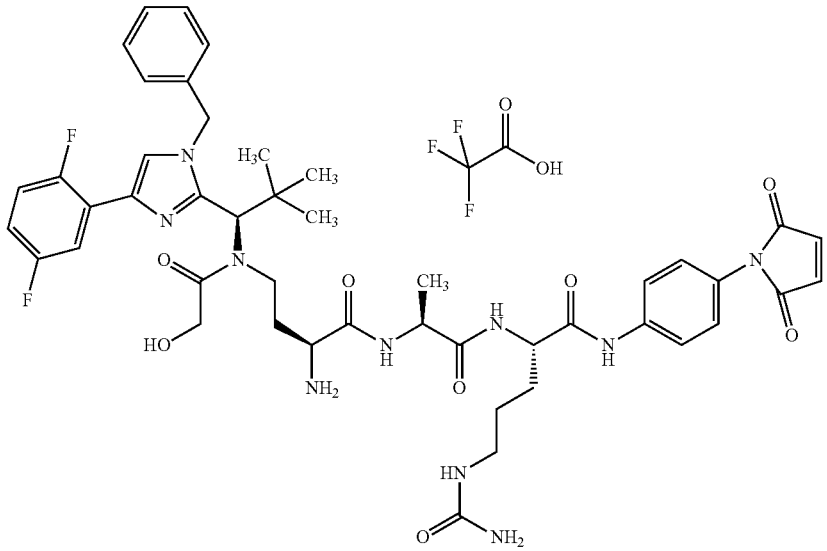 [SMILES: C[C@H](NC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

This intermediate was prepared by coupling of 14 mg (0.022 mmol) of Intermediate C5 with 12.7 mg (0.024 mmol) of Intermediate L8 in the presence of 9.9 mg (0.026 mmol) of HATU and 19 µl of N,N-diisopropylethylamine. The reaction was stirred at RT for 30 min and the product was purified by preparative HPLC and then lyophilized from acetonitrile/water.

The intermediate obtained was taken up in 3 ml of dichloromethane and deblocked with 1 ml of trifluoroacetic acid. After 30 min of stirring at RT, the reaction was concentrated and the residue was lyophilized from acetonitrile/water. This gave 8.2 mg (36% of theory over 2 steps) of the title compound.

HPLC (Method 11): $R_t$=1.8 min;
LC-MS (Method 1): $R_t$=0.87 min; MS (ESIpos): m/z=913 (M-FH)$^+$.

Intermediate F35

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide

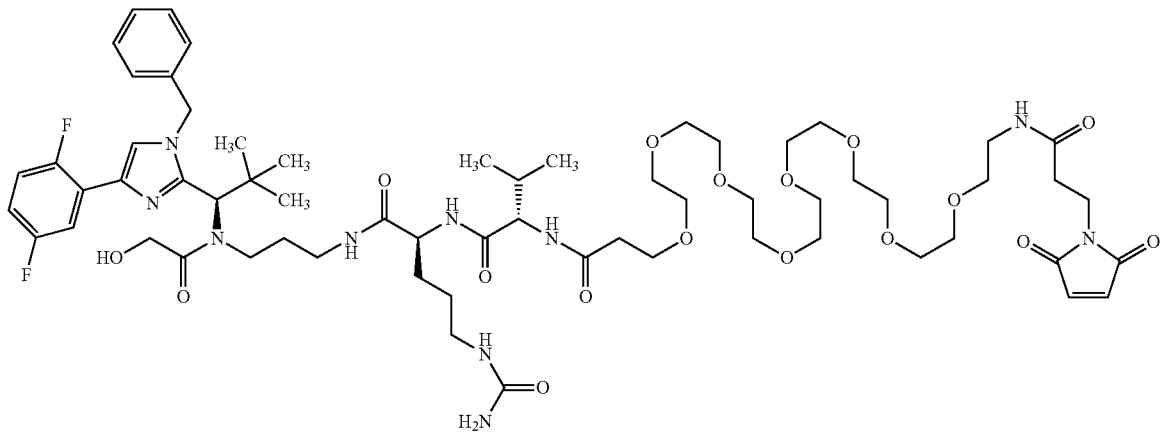 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)NCCCN(C(=O)CO)[C@@H](c1nc(-c2cc(F)ccc2F)cn1Cc1ccccc1)C(C)(C)C]

Under argon and at 0° C., 57.3 mg (0.07 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N$^5$-carbamoyl-L-ornithine (Intermediate L38), 9.2 mg (0.07 mmol) of HOAt and 32 mg (0.08 mmol) of HATU were added to 31.8 mg (0.07 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) in 4.0 ml of DMF. 23.5 µl (0.14 mmol) of N,N-diisopropylethylamine were then added, and the reaction was stirred at RT overnight. 7.7 µl of HOAc were added, and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 33.4 mg (38% of theory) of the title compound.

LC-MS (Method 1): $R_t$=1.12 min; MS (ESIpos): m/z=651 [M+2H]$^{2+}$.

Intermediate F36

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

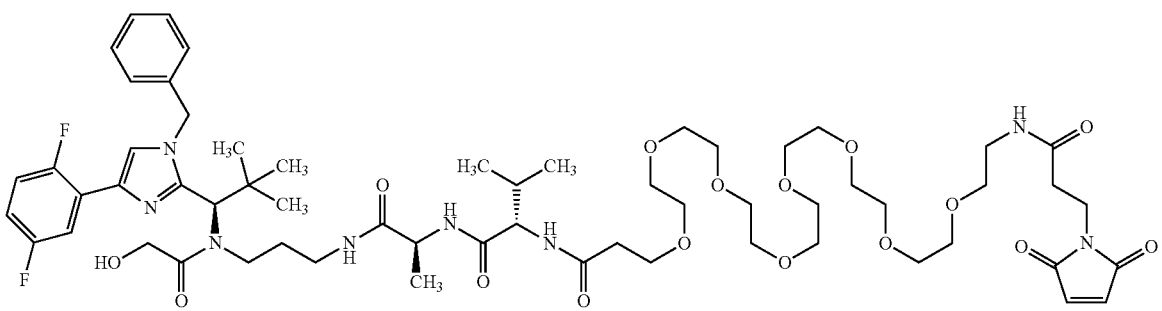 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)[C@@H](c1nc(-c2cc(F)ccc2F)cn1Cc1ccccc1)C(C)(C)C]

The synthesis of the title compound was carried out analogously to the preparation of Intermediate F35. 15.4 mg (0.03 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40).

25.0 mg (0.03 mmol) of N-[31-(2,5-doxo-2,5-dihydro-1H-pyrrol-1-yl)-29-oxo-4,7,10,13,16,19,22,25-octaoxa-28-azahentriacontan-1-oyl]-L-valyl-L-alanine (Intermediate L25).

This gave 10.7 mg (27% of theory) of the title compound.
LC-MS (Method 1): $R_t$=1.13 min; MS (ESIpos): m/z=1215 [M+H]$^+$.

Intermediate F37

Trifluoroacetic acid/N-(4-{[{(1R)-1-[1-benzyl-4-(2,5-difluorophenyl)-1H-imidazol-2-yl]-2,2-dimethylpropyl}(glycoloyl)amino]methyl}pyrrolidin-3-yl)-31-(2,5-dioxo-2,5-dihydro-1H-pyrrol-1-yl)-29-oxo-4,7,10,13,16,19,22,25-octaoxa-28-azahentriacontan-1-amide (1:1)

Mixture of Diastereomers.

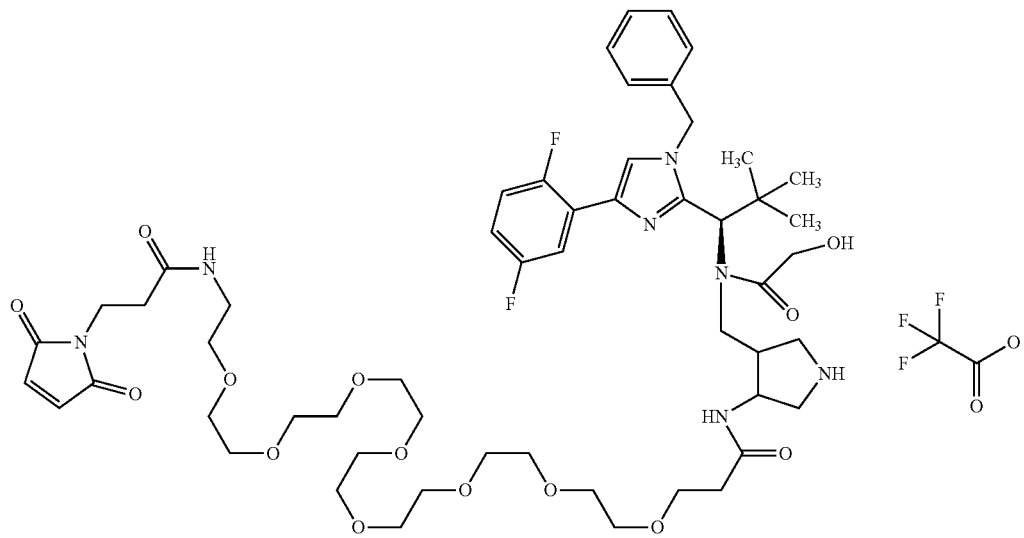 [SMILES: CC(C)(C)[C@H](c1nc(-c2cc(F)ccc2F)cn1Cc1ccccc1)N(CC1CNCC1NC(=O)CCOCCOCCOCCOCCOCCOCCOCCOCCNC(=O)CCN1C(=O)C=CC1=O)C(=O)CO ; O=C(O)C(F)(F)F]

The compound tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[31-(2,5-dioxo-2,5-dihydro-1H-pyrrol-1-yl)-29-oxo-4,7,10,13,16,19,22,25-octaoxa-28-azahentriacontan-1-oyl]amino}pyrrolidine-1-carboxylate was prepared analogously to the synthesis of Intermediate C21.

8.0 (0.01 mmol) and 13.0 mg (0.02 mmol), respectively, of tert-butyl 3-amino-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (Intermediate C23).

9.0 mg (0.01 mmol) and 14.7 mg (0.02 mmol), respectively, of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide.

Yield (both reactions combined):

10.5 mg (42%) diastereomer 1

11.6 mg (46%) diastereomer 2

The title compound was prepared analogously to the synthesis of Intermediate F38.

10.5 mg (0.01 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-{[31-(2,5-dioxo-2,5-dihydro-1H-pyrrol-1-yl)-29-oxo-4,7,10,13,16,19,22,25-octaoxa-28-azahentriacontan-1-oyl]amino}pyrrolidine-1-carboxylate (Diastereomer 1)

60.6 mg (0.54 mmol) of TFA.

This gave 7.4 mg (70% of theory) of the title compound.

LC-MS (Method 1): $R_t$=1.09 min; MS (ESIpos): m/z=1086 [M+H]$^+$.

Intermediate F38

Trifluoroacetic acid/N-(3-aminopropyl)-N-{(1R)-1-[1-benzyl-4-(2,5-difluorophenyl)-1H-imidazol-2-yl]-2,2-dimethylpropyl}-37-(2,5-dioxo-2,5-dihydro-1H-pyrrol-1-yl)-7,35-dioxo-10,13,16,19,22,25,28,31-octaoxa-3-thia-6,34-diazaheptatriacontan-1-amide (1:1)

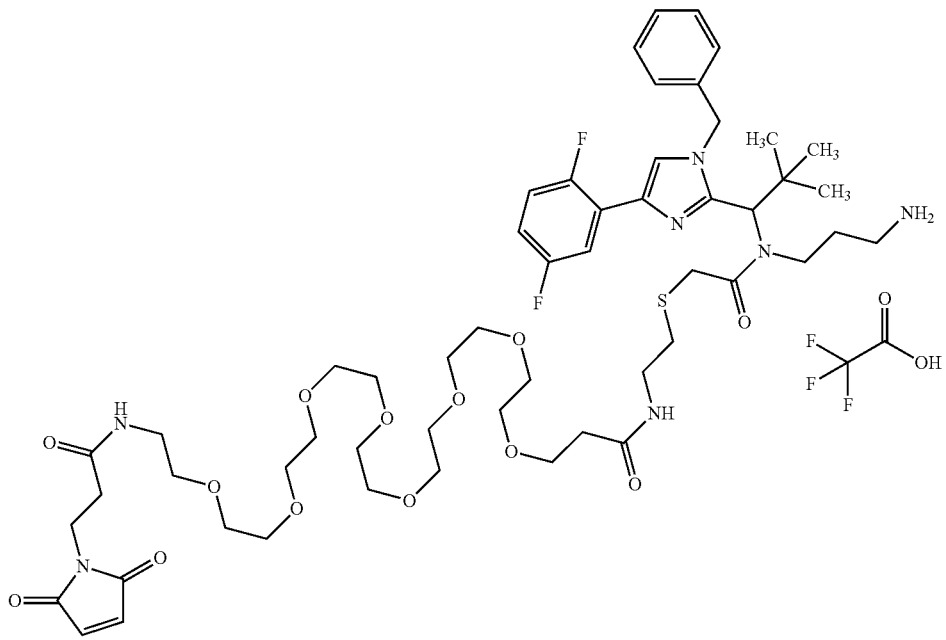

24.8 mg (0.02 mmol) of tert-butyl [38-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-3,31,37-trioxo-7,10,13,16,19,22,25,28-octaoxa-35-thia-4,32,38-triazahentetracontan-41-yl]carbamate (Intermediate C21) were initially charged in 1.0 ml of dichloromethane, and 85.8 mg (0.75 mmol) of TFA were added. The mixture was stirred at RT for 16 h. The solvent was evaporated under reduced pressure and the residue was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 23.0 mg (95% of theory) of the title compound.

LC-MS (Method 1): $R_t$=0.96 min; MS (ESIpos): m/z=1104 [M+H]$^+$.

Intermediate F39

N-[19-(2,5-Dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

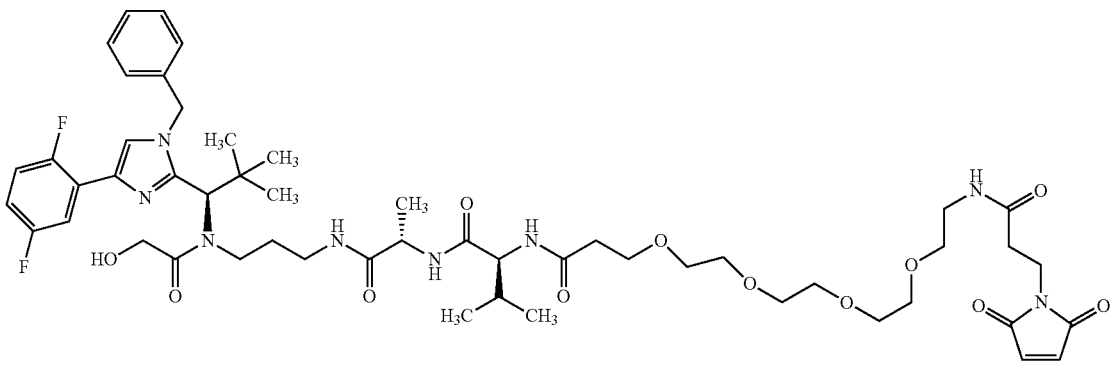 [SMILES: CC(C)[C@H](NC(=O)CCOCCOCCOCCOCCNC(=O)CCN1C(=O)C=CC1=O)C(=O)N[C@@H](C)C(=O)NCCCN(C(=O)CO)[C@@H](c1nc(-c2cc(F)ccc2F)cn1Cc1ccccc1)C(C)(C)C]

The title compound was prepared analogously to the synthesis of Intermediate F35. 56.1 mg (0.10 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine (Intermediate L44).

45.0 mg (0.10 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40).

This gave 20.9 mg (21% of theory) of the title compound.

LC-MS (Method 1): $R_t$=1.16 min; MS (ESIpos): m/z=1040 [M+H]$^+$.

Intermediate F40

Trifluoroacetic acid/N-[(4-{[{(1R)-1-[1-benzyl-4-(2,5-difluorophenyl)-1H-imidazol-2-yl]-2,2-dimethylpropyl}(glycoloyl)amino]methyl}pyrrolidin-3-yl)methyl]-31-(2,5-dioxo-2,5-dihydro-1H-pyrrol-1-yl)-29-oxo-4,7,10,13,16,19,22,25-octaoxa-28-azahentriacontan-1-amide (1:1)

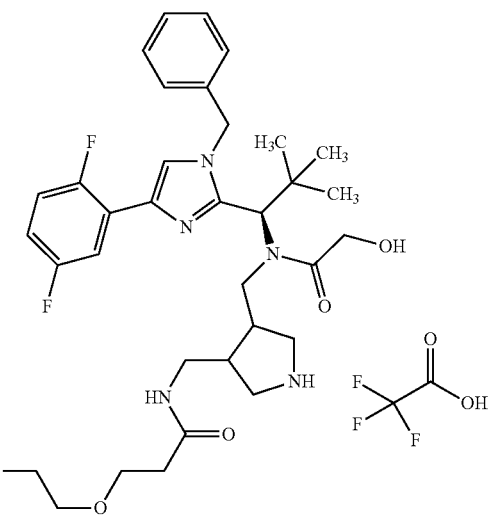

tert-Butyl 3-{[{(1R)-1-[1-benzyl-4-(2,5-difluorophenyl)-1H-imidazol-2-yl]-2,2-dimethylpropyl}(glycoloyl)amino]methyl}-4-[33-(2,5-dioxo-2,5-dihydro-1H-pyrrol-1-yl)-3,31-dioxo-6,9,12,15,18,21,24,27-octaoxa-2,30-diazatritriacont-1-yl]pyrrolidine-1-carboxylate was prepared analogously to the synthesis of Intermediate C21.

25.0 mg (0.04 mmol) of trifluoroacetic acid/tert-butyl 3-(aminomethyl)-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (1:1) (Intermediate C24).

27.6 mg (0.04 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide.

Yield: 20.6 mg (39% of theory)

LC-MS (Method 1): $R_t$=1.23 min; MS (ESIpos): m/z=1200 [M+H]$^+$.

The title compound was prepared analogously to the synthesis of Intermediate F37.

26.1 mg (0.02 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-[33-(2,5-dioxo-2,5-dihydro-1H-pyrrol-1-yl)-3,31-dioxo-6,9,12,15,18,21,24,27-octaoxa-2,30-diazatritriacont-1-yl]pyrrolidine-1-carboxylate.

90.6 mg (0.80 mmol) of TFA.

This gave 22.9 mg (95% of theory) of the title compound.

LC-MS (Method 1): $R_t$=0.91 and 0.92 min; MS (ESIpos): m/z=1100 [M+H]$^+$.

Intermediate F41

Trifluoroacetic acid/N-(3-aminopropyl)-N-{(1R)-1-[1-benzyl-4-(2,5-difluorophenyl)-1H-imidazol-2-yl]-2,2-dimethylpropyl}-37-(2,5-dioxo-2,5-dihydro-1H-pyrrol-1-yl)-7,35-dioxo-10,13,16,19,22,25,28,31-octaoxa-3-thia-6,34-diazaheptatriacontan-1-amide 3-oxide (1:1)

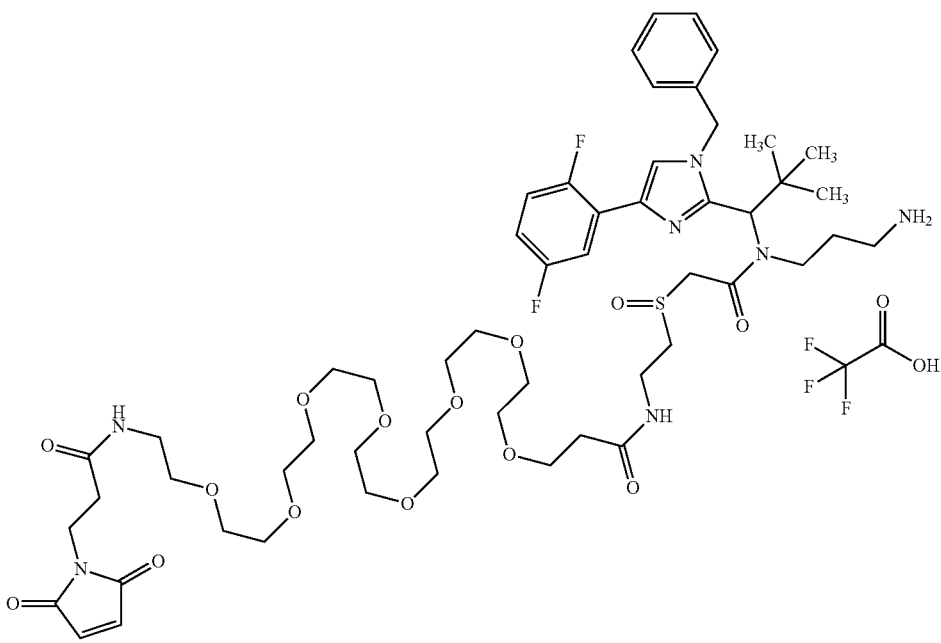

The title compound was prepared analogously to Intermediate F38 from 15.5 mg (0.01 mmol) of Intermediate C22. This gave 4.0 mg (27% of theory) of the title compound.

LC-MS (Method 1): $R_t$=0.90 min; MS (ESIpos): m/z=1120 [M+H]$^+$.

Intermediate F42

Trifluoroacetic acid/4-{[{(1R)-1-[1-benzyl-4-(2,5-difluorophenyl)-1H-imidazol-2-yl]-2,2-dimethylpropyl}(glycoloyl)amino]methyl}-N[2-(2,5-dioxo-2,5-dihydro-1H-pyrrol-1-yl)ethyl]pyrrolidine-3-carboxamide (1:1)

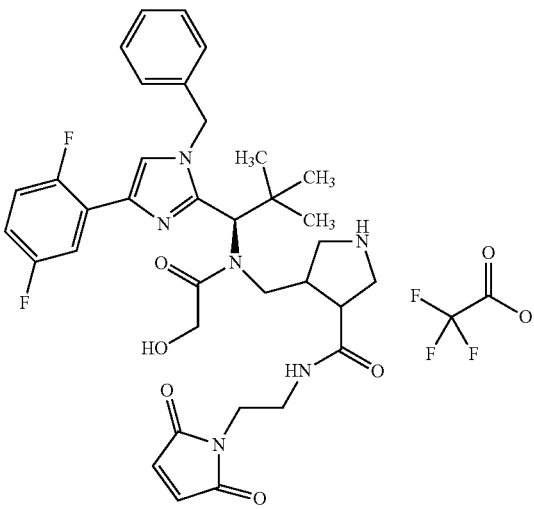

40.5 mg (0.06 mmol) of 4-{[{(1R)-1-[1-benzyl-4-(2,5-difluorophenyl)-1H-imidazol-2-yl]-2,2-dimethylpropyl}(glycoloyl)amino]methyl}-1-(tert-butoxycarbonyl)pyrrolidine-3-carboxylic acid (Intermediate C25) and 14.5 mg (0.08 mmol) of 1-(2-aminoethyl)-1H-pyrrole-2,5-dione hydrochloride (1:1) were initially charged in 1.0 ml of acetonitrile, and 64.4 mg (0.51 mmol) of N,N-diisopropylethylamine and 50.0 mg (0.08 mmol) of T3P were added and the mixture was stirred at RT for 16 h. The same amount of 1-(2-aminoethyl)-1H-pyrrole-2,5-dione hydrochloride (1:1), N,N-diisopropylethylamine and T3P were added again, and the mixture was stirred at RT for a further 4 h. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 7.2 mg (15% of theory) of the compound tert-butyl 3-{[{(1R)-1-[1-benzyl-4-(2,5-difluorophenyl)-1H-imidazol-2-yl]-2,2-dimethylpropyl}(glycoloyl)amino]methyl}-4-[2-(2,5-dioxo-2,5-dihydro-1H-pyrrol-1-yl)ethyl]carbamoyl pyrrolidine-1-carboxylate.

LC-MS (Method 1): $R_t$=1.30 min; MS (ESIpos): m/z=763 [M+H]$^+$.

7.2 mg (0.01 mmol) of tert-butyl 3-{[{(1R)-1-[1-benzyl-4-(2,5-difluorophenyl)-1H-imidazol-2-yl]-2,2-dimethylpropyl}(glycoloyl)amino]methyl}-4-[2-(2,5-dioxo-2,5-dihydro-1H-pyrrol-1-yl)ethyl]carbamoyl pyrrolidine-1-carboxylate were initially charged in 1.0 ml of dichloromethane, and 43.0 mg (0.38 mmol) of TFA were added. The reaction mixture was stirred at RT for 16 h. The solvent was evaporated under reduced pressure and the residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.5 mg (50% of theory) of the title compound.

LC-MS (Method 1): $R_t$=0.92 min; MS (ESIpos): m/z=663 [M+H]$^+$.

Intermediate F43

N-[19-(2,5-Dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide

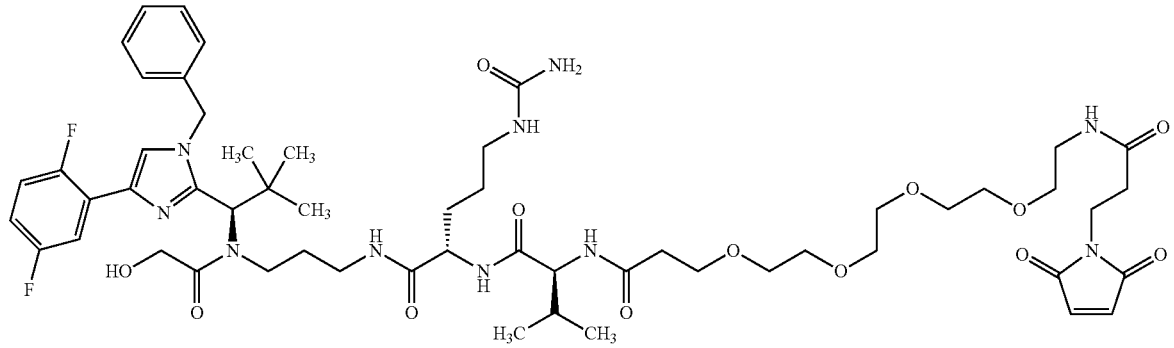 [SMILES: CC(C)[C@H](NC(=O)CCOCCOCCOCCOCCNC(=O)CCN1C(=O)C=CC1=O)C(=O)N[C@@H](CCCNC(N)=O)C(=O)NCCCN(C(=O)CO)[C@@H](c1nc(-c2cc(F)ccc2F)cn1Cc1ccccc1)C(C)(C)C]

22.4 mg (0.03 mmol) of N-[19-(2,5-dioxo-2,5-dihydro-1H-pyrrol-1-yl)-17-oxo-4,7,10,13-tetraoxa-16-azanonadecan-1-oyl]-L-valyl-N5-carbamoyl-L-ornithine (Intermediate L42) were dissolved in 2.0 ml of DMF, and 4.5 mg (0.03 mmol) of HOAt, 15.8 mg (0.04 mmol) of HATU and 15.7 mg (0.03 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) were added. 8.6 mg (0.07 mmol) of N,N-diisopropylethylamine were added and the reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 16.7 mg (45% of theory) of the title compound.

LC-MS (Method 4): $R_t$=1.34 min; MS (ESIpos): m/z=1125 [M+H]$^+$.

Intermediate F44

Trifluoroacetic acid/N-[(4-{[{(1R)-1-[1-benzyl-4-(2,5-difluorophenyl)-1H-imidazol-2-yl]-2,2-dimethylpropyl}(glycoloyl)amino]methyl}pyrrolidin-3-yl)methyl]-19-(2,5-dioxo-2,5-dihydro-1H-pyrrol-1-yl)-17-oxo-4,7,10,13-tetraoxa-16-azanonadecan-1-amide (1:1)

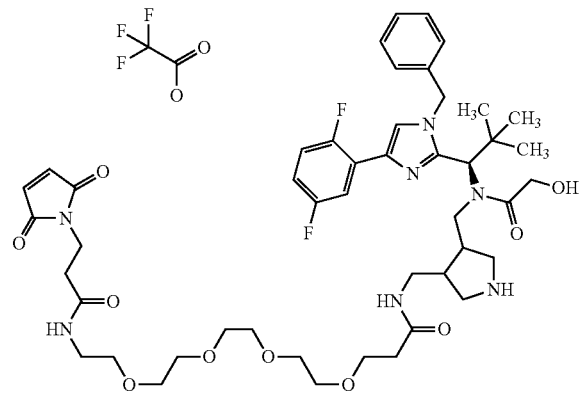 [SMILES: CC(C)(C)[C@H](c1nc(-c2cc(F)ccc2F)cn1Cc1ccccc1)N(CC1CNCC1CNC(=O)CCOCCOCCOCCOCCNC(=O)CCN1C(=O)C=CC1=O)C(=O)CO ; O=C(O)C(F)(F)F]

The title compound was prepared analogously to the synthesis of Intermediate F40. 25.0 mg (0.04 mmol) of trifluoroacetic acid/tert-butyl 3-(aminomethyl)-4-{[{(1R)-1-[1-benzyl-4-(2,5-difluorophenyl)-1H-imidazol-2-yl]-2,2-dimethylpropyl}(glycoloyl)amino]methyl}pyrrolidine-1-carboxylate (1:1) (Intermediate C24).

20.5 mg (0.04 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide.

This gave 21.8 mg (48% of theory) of the compound tert-butyl 3-{[[{(1R)-1-[1-benzyl-4-(2,5-difluorophenyl)-1H-imidazol-2-yl]-2,2-dimethylpropyl}(glycoloyl)amino]methyl}-4-[21-(2,5-dioxo-2,5-dihydro-1H-pyrrol-1-yl)-3,19-dioxo-6,9,12,15-tetraoxa-2,18-diazahenicos-1-yl]pyrrolidine-1-carboxylate.

LC-MS (Method 1): $R_t$=1.22 min; MS (ESIpos): m/z=1025 [M+H]$^+$.

21.0 mg (0.02 mmol) of tert-butyl 3-{[[{(1R)-1-[1-benzyl-4-(2,5-difluorophenyl)-1H-imidazol-2-yl]-2,2-dimethylpropyl}(glycoloyl)amino]methyl}-4-[21-(2,5-dioxo-2,5-dihydro-1H-pyrrol-1-yl)-3,19-dioxo-6,9,12,15-tetraoxa-2,18-diazahenicos-1-yl]pyrrolidine-1-carboxylate. 168.3 mg (1.48 mmol) of TFA.

This gave 17.3 mg (90% of theory) of the title compound.

LC-MS (Method 1): $R_t$=0.92 and 0.94 min; MS (ESIpos): m/z=924 [M+H]$^+$.

Intermediate F45

Trifluoroacetic acid/N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-lysinamide (1:1)

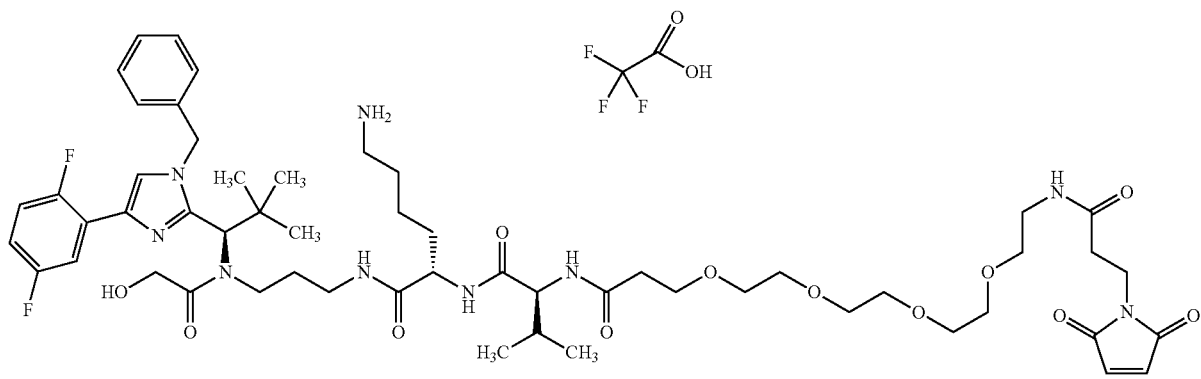 [SMILES: CC(C)[C@H](NC(=O)CCOCCOCCOCCOCCNC(=O)CCN1C(=O)C=CC1=O)C(=O)N[C@@H](CCCCN)C(=O)NCCCN(C(=O)CO)[C@@H](c1nc(-c2cc(F)ccc2F)cn1Cc1ccccc1)C(C)(C)C ; O=C(O)C(F)(F)F]

The synthesis was carried out analogously to the synthesis of Intermediate F46.

22.9 mg (0.05 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40).

36.2 mg (0.05 mmol) of N-[19-(2,5-dioxo-2,5-dihydro-1H-pyrrol-1-yl)-17-oxo-4,7,10,13-tetraoxa-16-azanonadecan-1-oyl]-L-valyl-$N^6$-(tert-butoxycarbonyl)-L-lysine (Intermediate L41).

This gave 19.8 mg (34%) of the compound N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-$N^6$-(tert-butoxycarbonyl)-L-lysinamide.

LC-MS (Method 1): $R_t$=1.20 min; MS (ESIpos): m/z=1196 [M+H]$^+$.

17.0 mg (0.01 mmol) of N-[19-(2,5-dioxo-2,5-dihydro-1H-pyrrol-1-yl)-17-oxo-4,7,10,13-tetraoxa-16-azanonadecan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-$N^6$-(tert-butoxycarbonyl)-L-lysinamide.

This gave 13.6 mg (79% of theory) of the title compound.

LC-MS (Method 1): $R_t$=0.94 min; MS (ESIpos): m/z=1096 [M+H]$^+$.

Intermediate F46

Trifluoroacetic acid/N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-lysinamide (1:1)

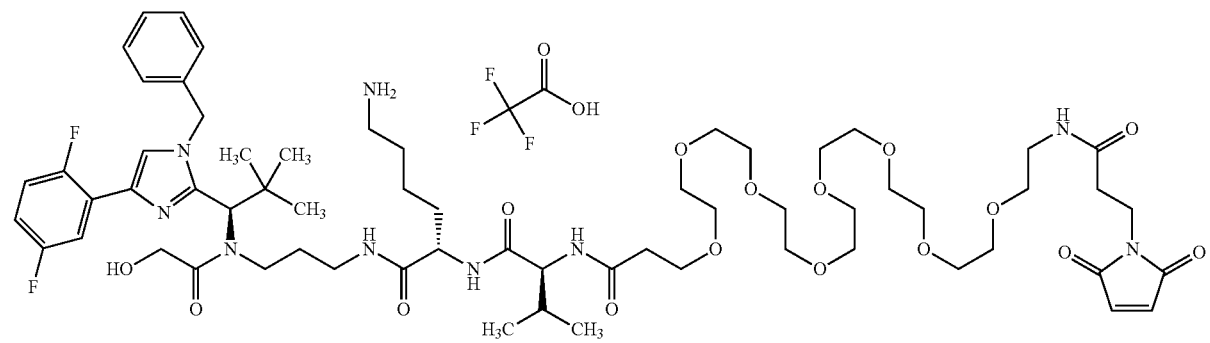 [SMILES: CC(C)[C@H](NC(=O)CCOCCOCCOCCOCCOCCOCCOCCOCCNC(=O)CCN1C(=O)C=CC1=O)C(=O)N[C@@H](CCCCN)C(=O)NCCCN(C(=O)CO)[C@@H](c1nc(-c2cc(F)ccc2F)cn1Cc1ccccc1)C(C)(C)C ; O=C(O)C(F)(F)F]

Under argon and at 0° C., 49.0 mg (0.05 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine (Intermediate L40), 7.3 mg (0.05 mmol) of HOAt and 25.3 mg (0.07 mmol) of HATU were added to 25.1 mg (0.05 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) in 2.0 ml of DMF. 18.6 µl (0.11 mmol) of N,N-diisopropylethylamine were then added, and the reaction was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 29.2 mg (37% of theory) of the compound N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N⁶-(tert-butoxycarbonyl)-L-lysinamide.

LC-MS (Method 4): $R_t$=1.51 min; MS (ESIpos): m/z=1372 [M+H]⁺.

25.2 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N6-(tert-butoxycarbonyl)-L-lysinamide were initially charged in 3.0 ml of dichloromethane, and 83.7 mg (0.73 mmol) of TFA were added. The reaction solution was stirred at RT for 48 h. The solvent was evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 24.5 mg (96% of theory) of the title compound.

LC-MS (Method 1): $R_t$=0.95 min; MS (ESIpos): m/z=1272 [M+H]⁺.

Intermediate F47

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide 15.2 mg (0.01 mmol) of N-[67-(2,5-dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N5-carbamoyl-L-ornithine (Intermediate L43) were dissolved in 1.0 ml of DMF, and 1.5 mg (0.01 mmol) of HOAt, 5.2 mg (0.01 mmol) of HATU and 5.2 mg (0.01 mmol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) were added. 2.9 mg (0.02 mmol) of N,N-diisopropylethylamine were added and the reaction mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 6.8 mg (33% of theory) of the title compound.

LC-MS (Method 4): $R_t$=1.37 min; MS (ESIpos): m/z=1831 [M+H]⁺.

Intermediate F48

Trifluoroacetic acid/N1-(3-aminopropyl)-N1-{(1R)-1-[1-benzyl-4-(2,5-difluorophenyl)-1H-imidazol-2-yl]-2,2-dimethylpropyl}-N18-[2-(2,5-dioxo-2,5-dihydro-1H-pyrrol-1-yl)ethyl]-6,9,12,15-tetraoxa-3-thiaoctadecane-1,18-diamide (1:1)

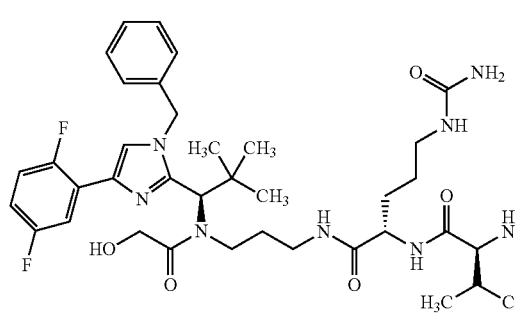

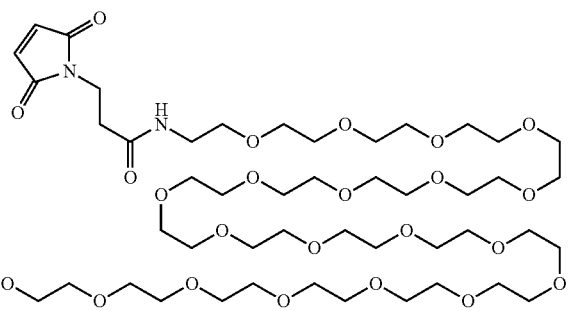

16.1 mg (0.02 mmol) of tert-butyl [22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazapentacosan-25-yl]carbamate (Intermediate C18) were initially charged in 1.5 ml of dichloromethane, and 26 µl (0.34 mmol) of TFA were added. The mixture was stirred at RT overnight, and another 26 µl (0.34 mmol) of TFA were then added. The mixture was once more stirred at RT overnight. The solvent was evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was taken up in water and lyophilized. This gave 10.8 mg (66% of theory) of the title compound.

LC-MS (Method 1): $R_t$=0.98 min; MS (ESIpos): m/z=857 [M+H]$^+$.

Intermediate F49

(25S)-25-Amino-22-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-4,21-dioxo-7,10,13,16-tetraoxa-19-thia-3,22-diazahexacosan-26-oic acid/trifluoroacetic acid (1:1)

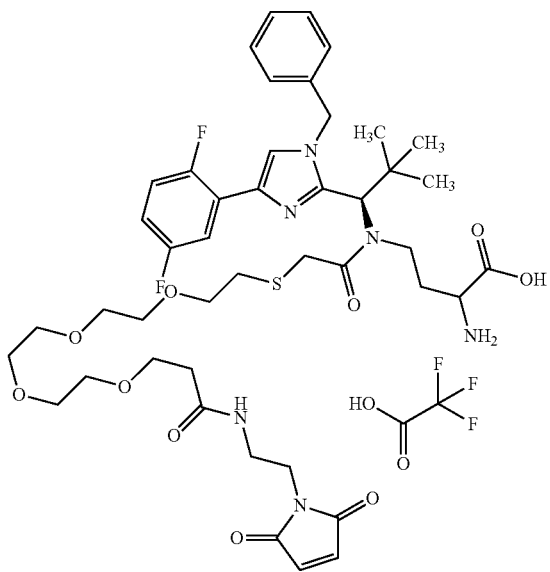

The synthesis of the compound tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate was carried out analogously to the synthesis of Intermediate C16.

50.0 mg (0.08 mmol) of Intermediate C2
20.3 mg (0.18 mmol) of chloroacetyl chloride
19.0 mg (0.19 mmol) of triethylamine
This gave 43.1 mg (77% of theory) of the compound tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate.

LC-MS (Method 1): $R_t$=1.55 min; MS (ESIpos): m/z=689 [M+H]$^+$.

The synthesis of the compound (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid was carried out analogously to the synthesis of Intermediate C17.

38.8 mg (0.06 mmol) of tert-butyl (2S)-4-[{(1R)-1-[1-benzyl-4-(2,5-difluorophenyl)-1H-imidazol-2-yl]-2,2-dimethylpropyl}(chloroacetyl)amino]-2-[(tert-butoxycarbonyl)amino]butanoate.

19.1 mg (0.07 mmol) of 1-sulphanyl-3,6,9,12-tetraoxapentadecan-15-oic acid 45.9 mg (0.14 mmol) of caesium carbonate This gave 40.7 mg (77% of theory) of the compound (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid.

LC-MS (Method 1): $R_t$=1.45 min; MS (ESIpos): m/z=935 [M+H]$^+$.

The synthesis of the compound tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate was carried out analogously to the synthesis of Intermediate C18.

37.4 mg (0.04 mmol) of (6S)-9-{(1R)-1-[1-benzyl-4-(2,5-difluorophenyl)-1H-imidazol-2-yl]-2,2-dimethylpropyl}-6-(tert-butoxycarbonyl)-2,2-dimethyl-4,10-dioxo-3,15,18,21,24-pentaoxa-12-thia-5,9-diazaheptacosan-27-oic acid.

9.2 mg (0.05 mmol) of 1-(2-aminoethyl)-1H-pyrrole-2,5-dione hydrochloride (1:1).

This gave 23.4 mg (49% of theory) of the compound tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate.

LC-MS (Method 1): $R_t$=1.47 min; MS (ESIpos): m/z=1057 [M+H]$^+$.

The synthesis of the title compound was carried out analogously to the synthesis of Intermediate F38. 20.8 mg (0.02 mmol) of tert-butyl (25S)-22-{(1R)-1-[1-benzyl-4-(2,5-difluorophenyl)-1H-imidazol-2-yl]-2,2-dimethylpropyl}-25-[(tert-butoxycarbonyl)amino]-1-(2,5-dioxo-2,5-dihydro-1H-pyrrol-1-yl)-4,21-dioxo-7,10,13,16-tetraoxa-19-thia-3,22-diazahexacosan-26-oate. 157.0 mg (1.37 mmol) of TFA.

This gave 13.0 mg (65%) of the title compound.

LC-MS (Method 1): $R_t$=0.93 min; MS (ESIpos): m/z=901 [M+H]$^+$.

Intermediate F50

Trifluoroacetic acid/1-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopropanecarboxamide (1:1)

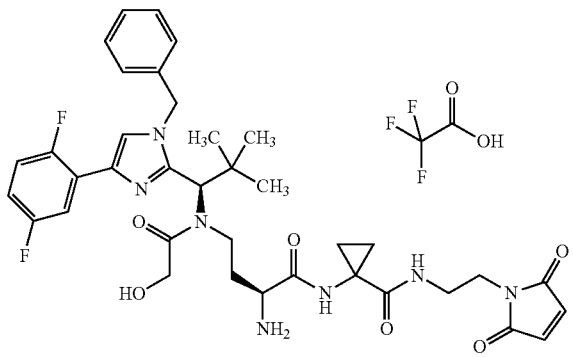 [SMILES: CC(C)(C)[C@H](c1nc(-c2cc(F)ccc2F)cn1Cc1ccccc1)N(CC[C@H](N)C(=O)NC1(C(=O)NCCN2C(=O)C=CC2=O)CC1)C(=O)CO ; O=C(O)C(F)(F)F]

15 mg (0.024 mmol) of Intermediate C5 were dissolved in 6.5 ml of DCM, and 19 mg (0.049 mmol) of Intermediate L24, 13 µl of N,N-diisopropylethylamine and 10 mg (0.037 mmol) of 2-bromo-1-ethylpyridinium tetrafluoroborate were added. The reaction was stirred at RT for 3 h and then dried under reduced pressure. The residue was purified by preparative HPLC, giving 2.4 mg of the protected intermediate.

These were then taken up in 1 ml of DCM and deprotected with 0.1 ml of trifluoroacetic acid. Lyophilization from acetonitrile/water gave 2.6 mg (11% of theory over 2 steps) of the title compound.

HPLC (Method 11): $R_t$=2.4 min

LC-MS (Method 1): $R_t$=1.25 min; MS (ESIpos): m/z=819 [M+H]$^+$.

Intermediate F51

3-{3-[(3-Amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 1)

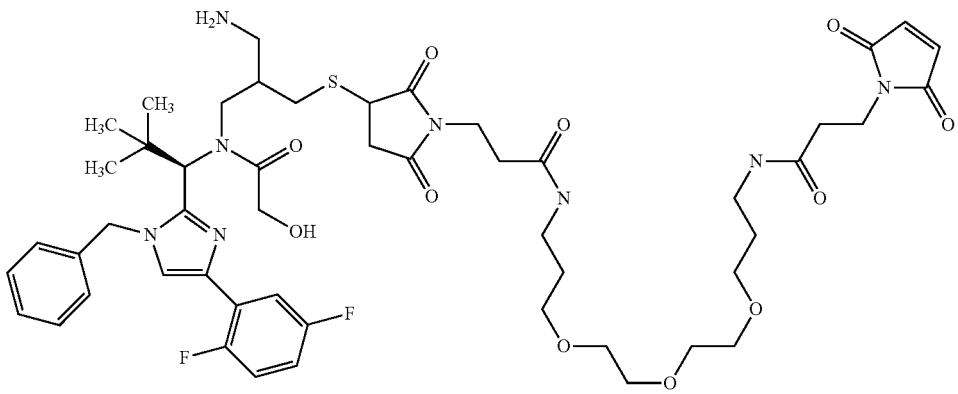 [SMILES: CC(C)(C)[C@H](c1nc(-c2cc(F)ccc2F)cn1Cc1ccccc1)N(CC(CN)CSC1CC(=O)N(CCC(=O)NCCCOCCOCCOCCCNC(=O)CCN2C(=O)C=CC2=O)C1=O)C(=O)CO]

10.0 mg (18.079 µmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1) were initially charged in 100 µl of PBS buffer (Sigma D8537) and 200 µl of ACN. 17.1 mg (32.543 µmol) of 3-(2,5-dioxo-2,5-dihydro-1H-pyrrol-1-yl)-N-[17-(2,5-dioxo-2,5-dihydro-1H-pyrrol-1-yl)-15-oxo-4,7,10-trioxa-14-azaheptadec-1-yl]propanamide were added, and the mixture was stirred at RT for 16 h. The reaction solution was purified by preparative HPLC (mobile phase: ACN/water+0.1% TFA, gradient) and lyophilized. This gave 14.0 mg (75% of theory) of the target compound.

Isomer 1

LC-MS (Method 1): $R_t$=0.94 min; MS (ESIpos): m/z=1039 [M+H]$^+$.

Intermediate F52

3-{3-[(3-Amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 2)

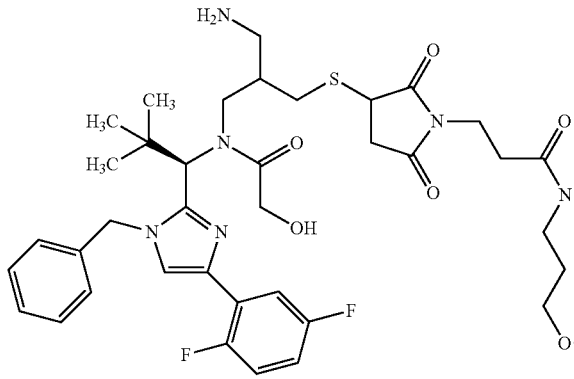
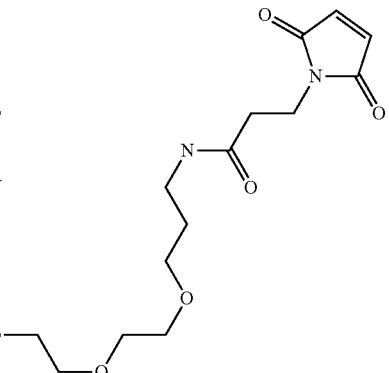

6.5 mg (10.694 μmol, LC/MS purity=91%) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2) were initially charged in 100 μl of PBS buffer (Sigma D8537) and 200 μl of ACN. 10.1 mg (19.249 μmol) of 3-(2,5-dioxo-2,5-dihydro-1H-pyrrol-1-yl)-N-[17-(2,5-dioxo-2,5-dihydro-1H-pyrrol-1-yl)-15-oxo-4,7,10-trioxa-14-azaheptadec-1-yl]propanamide were added, and the mixture was stirred at RT for 16 h. The reaction solution was purified by preparative HPLC (mobile phase: ACN/water+0.1% TFA, gradient) and lyophilized. This gave 5.0 mg (45% of theory) of the target compound.

Isomer 2

LC-MS (Method 5): $R_t$=2.87 min; MS (ESIpos): m/z=1039 [M+H]$^+$.

Intermediate F53

N-{3-Amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 1)

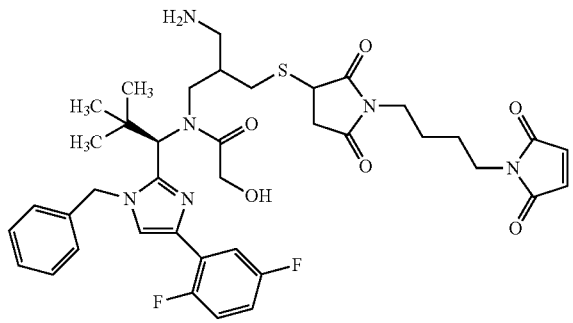 [SMILES: CC(C)(C)[C@H](c1nc(-c2cc(F)ccc2F)cn1Cc1ccccc1)N(CC(CN)CSC1CC(=O)N(CCCCN2C(=O)C=CC2=O)C1=O)C(=O)CO]

10.0 mg (18.079 μmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1) were initially charged in 200 μl of PBS buffer (Sigma D8537) and 400 μl of ACN. 8.1 mg (32.543 μmol) of 1,1'-butane-1,4-diylbis(1H-pyrrole-2,5-dione) were added, and the mixture was stirred at RT for 1 h. 300 μl of DMF were then added, and the mixture was stirred for a further 1.5 h. The reaction solution was purified by preparative HPLC (mobile phase: ACN/water+0.1% TFA, gradient) and lyophilized. This gave 4.0 mg (29% of theory) of the target compound.

Isomer 1

LC-MS (Method 1): $R_t$=0.97 min; MS (ESIpos): m/z=765 [M+H]$^+$.

Intermediate F54

N-{3-Amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 2)

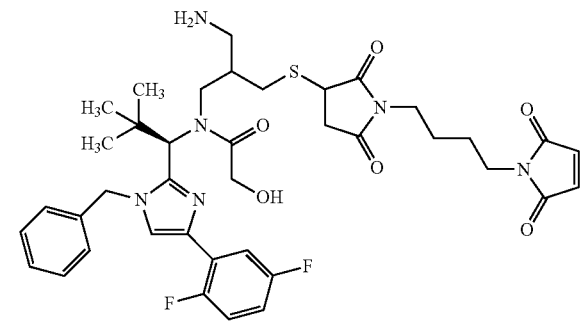 [SMILES: CC(C)(C)[C@H](c1nc(-c2cc(F)ccc2F)cn1Cc1ccccc1)N(CC(CN)CSC1CC(=O)N(CCCCN2C(=O)C=CC2=O)C1=O)C(=O)CO]

5.0 mg (9.040 μmol) of N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2) were initially charged in 500 μl of DMF. 4.0 mg (16.271 μmol) of 1,1'-butane-1,4-diylbis(1H-pyrrole-2,5-dione) were added, and the mixture was stirred at RT for 16 h. The reaction solution was purified by preparative HPLC (mobile phase: ACN/water+0.1% TFA, gradient) and lyophilized. This gave 1.1 mg (16% of theory) of the target compound.

Isomer 2

LC-MS (Method 6): $R_t$=2.41 min; MS (ESIpos): m/z=765 [M+H]$^+$.

Intermediate F55

N-[19-(2,5-Dioxo-2,5-dihydro-1H-pyrrol-1-yl)-17-oxo-4,7,10,13-tetraoxa-16-azanonadecan-1-oyl]-L-valyl-N-{4-[(3-aminopropyl){(1R)-1-[1-benzyl-4-(2,5-difluorophenyl)-1H-imidazol-2-yl]-2,2-dimethylpropyl}carbamoyl]phenyl}-L-alaninamide

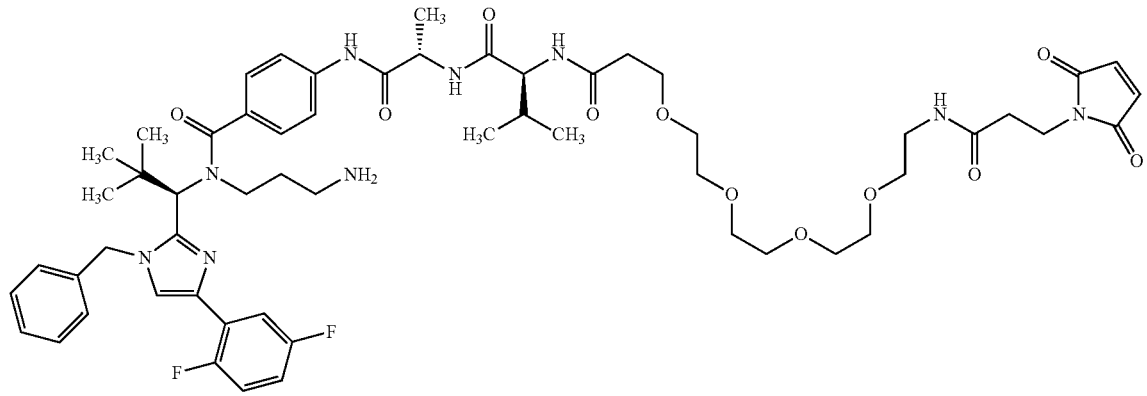 [SMILES: CC(C)[C@H](NC(=O)CCOCCOCCOCCOCCNC(=O)CCN1C(=O)C=CC1=O)C(=O)N[C@@H](C)C(=O)Nc1ccc(C(=O)N(CCCN)[C@@H](c2nc(-c3cc(F)ccc3F)cn2Cc2ccccc2)C(C)(C)C)cc1]

6.5 mg (4.5 µmol) of N-[19-(2,5-dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-imidazol-2-yl]-2,2-dimethylpropyl}{3-[(tert-butoxycarbonyl)amino]propyl}carbamoyl)phenyl]-L-alaninamide were dissolved in 441 µl of dichloromethane, and 44 µl (573.1 µmol) of trifluoroacetic acid were added. The reaction was concentrated on a rotary evaporator at RT, taken up in water and ACN and lyophilized. This gave 5.6 mg (94% of theory, purity according to LC/MS=92%) of the target compound.

LC-MS (Method 1): $R_t$=1.01 min; MS (ESIpos): m/z=1100.6 [M+H]$^+$.

Intermediate F56

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[(2S)-1-{[2-(2,5-dioxo-2,5-dihydro-1H-pyrrol-1-yl)ethyl]amino}-1-oxopropan-2-yl]butanamide (1:1)

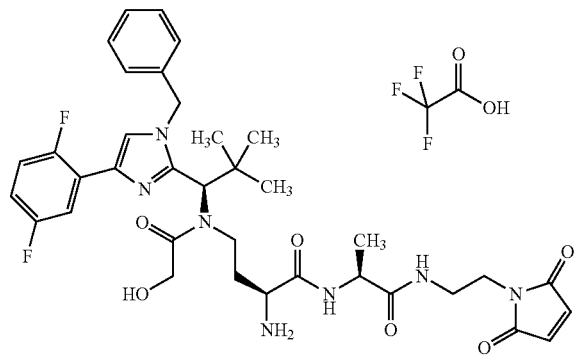 [SMILES: C[C@H](NC(=O)[C@@H](N)CCN(C(=O)CO)[C@@H](c1nc(-c2cc(F)ccc2F)cn1Cc1ccccc1)C(C)(C)C)C(=O)NCCN1C(=O)C=CC1=O ; O=C(O)C(F)(F)F]

The title compound was prepared analogously to Intermediate F50.

LC-MS (Method 1): $R_t$=0.9 min; MS (EIpos): m/z=708 [M+H]$^+$.

Intermediate F57

Trifluoroacetic acid/(2S)-2-amino-4-[{(1R)-1-[1-benzyl-4-(2,5-difluorophenyl)-1H-imidazol-2-yl]-2,2-dimethylpropyl}(glycoloyl)amino]-N-[(2R)-1-{[2-(2,5-dioxo-2,5-dihydro-1H-pyrrol-1-yl)ethyl]amino}-1-oxopropan-2-yl]butanamide (1:1)

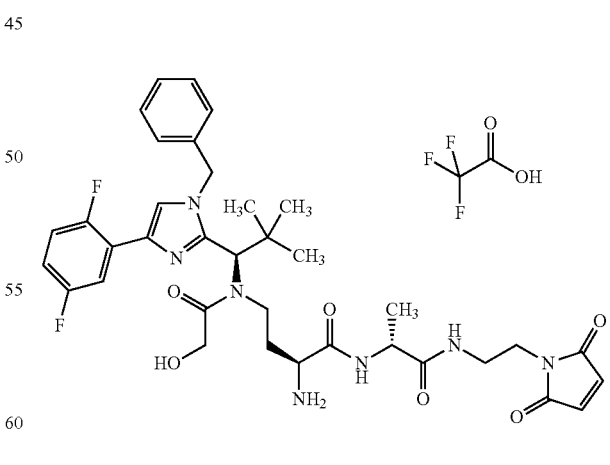

The title compound was prepared analogously to Intermediate F56.

LC-MS (Method 1): $R_t$=0.91 min; MS (EIpos): m/z=708 [M+H]$^+$.

Intermediate F58

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide

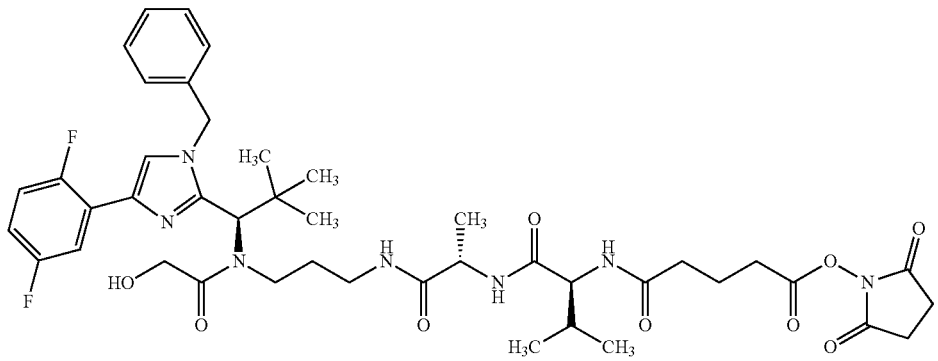 [SMILES: CC(C)[C@H](NC(=O)CCCC(=O)ON1C(=O)CCC1=O)C(=O)N[C@@H](C)C(=O)NCCCN(C(=O)CO)[C@@H](c1nc(-c2cc(F)ccc2F)cn1Cc1ccccc1)C(C)(C)C]

16.2 mg (0.02 mmol) of trifluoroacetic acid/L-valyl-N-{3-[{(1R)-1-[1-benzyl-4-(2,5-difluorophenyl)-1H-imidazol-2-yl]-2,2-dimethylpropyl}(glycoloyl)amino]propyl}-L-alaninamide (1:1) (Intermediate C41) were initially charged in 1.0 ml of DMF, and 8.3 mg (0.06 mmol) of N,N-diisopropylethylamine and 12.6 mg (0.04 mmol) of 1,1'-[(1,5-dioxopentan-1,5-diyl)bis(oxy)]dipyrrolidine-2,5-dione were added. The reaction mixture was stirred at RT overnight and purified directly by preparative RP-HPLC (column: Reprosil 250×30; 10μ, flow rate: 50 ml/min, MeCN/water). The solvents were evaporated under reduced pressure and the residue was dried under high vacuum. This gave 11.0 mg (60% of theory) of the title compound.

LC-MS (Method 1): $R_t$=1.18 min; MS (ESIpos): m/z=852 [M+H]$^+$.

Intermediate F82

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{1-[1-benzyl-4-(2,5-difluorophenyl)-1H-pyrrol-2-yl]-2,2-dimethylpropyl}(glycoloyl)amino]propyl}-L-alaninamide

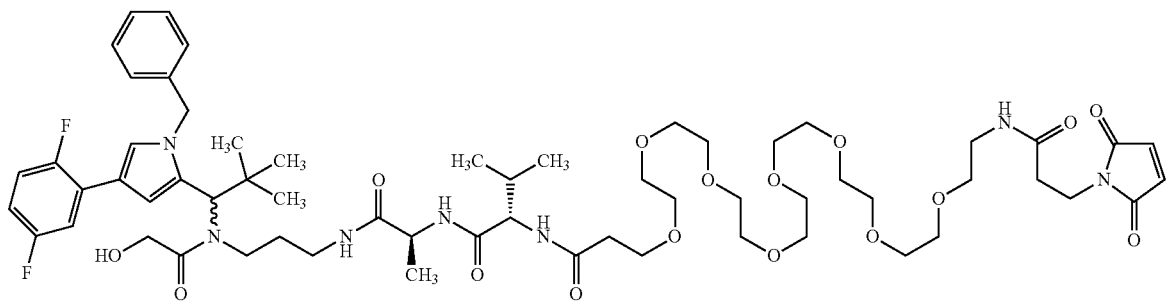 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)C(c1cc(-c2cc(F)ccc2F)cn1Cc1ccccc1)C(C)(C)C]

The synthesis of the title compound was carried out analogously to the synthesis of Intermediate F83. The racemic intermediates used were obtained analogously to the corresponding R-isomer intermediates.

LC-MS (Method 2): R$_t$=7.07 min; MS (EIpos): m/z=1236 [M+Na]$^+$.

Intermediate F83

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

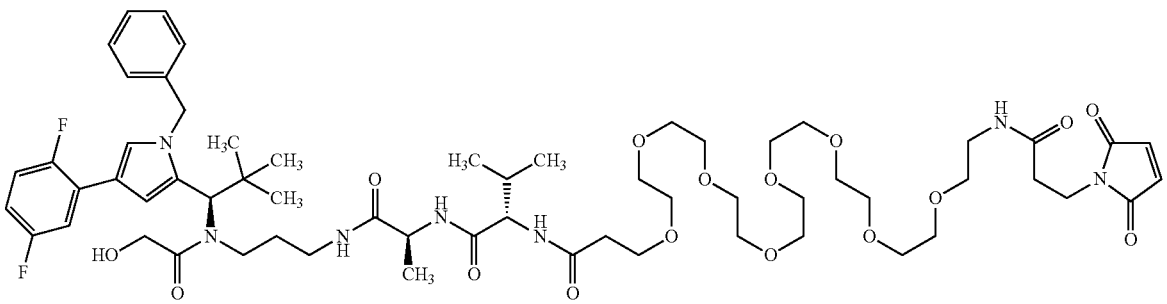 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCCN(C(=O)CO)[C@@H](c1cc(-c2cc(F)ccc2F)cn1Cc1ccccc1)C(C)(C)C]

30.0 mg (0.06 mmol) of N-(3-aminopropyl)-N-{(1R)-1-[1-benzyl-4-(2,5-difluorophenyl)-1H-pyrrol-2-yl]-2,2-dimethylpropyl}-2-hydroxyacetamide (Example 98) and 26.1 mg (0.06 mmol) of 2,5-dioxopyrrolidin-1-yl-N-[(9H-fluoren-9-ylmethoxy)carbonyl]-L-alaninate were initially charged in 2.0 ml of DMF, and 19.4 mg (0.19 mmol) of 4-methylmorpholine were added. The reaction mixture was stirred at RT overnight, and 11.5 mg (0.19 mmol) of HOAc were added. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 41.9 mg (79% of theory) of the compound 9H-fluoren-9-ylmethyl [(2S)-1-({3-[{(1R)-1-[1-benzyl-4-(2,5-difluorophenyl)-1H-pyrrol-2-yl]-2,2-dimethylpropyl}(glycoloyl)amino]propyl}amino)-1-oxopropan-2-yl]carbamate.

LC-MS (Method 1): R$_t$=1.44 min; MS (ESIpos): m/z=763 [M+H]$^+$.

37.2 mg (0.05 mmol) of 9H-fluoren-9-ylmethyl [(2S)-1-({3-[{(1R)-1-[1-benzyl-4-(2,5-difluorophenyl)-1H-pyrrol-2-yl]-2,2-dimethylpropyl}(glycoloyl)amino]propyl}amino)-1-oxopropan-2-yl]carbamate were dissolved in 1.5 ml of DMF, and 124.6 mg (1.46 mmol) of 2-aminoethanol were added. The reaction mixture was stirred at RT overnight. The reaction mixture was partitioned between ethyl acetate and water and the organic phase was washed twice with water and once with saturated NaCl solution. After drying over magnesium sulphate, the solvent was evaporated under reduced pressure and the residue was purified on silica gel (mobile phase: dichloromethane/methanol 10:1). The solvents were evaporated under reduced pressure and the residue was dried under high vacuum. This gave 14.2 mg (50% of theory) of the compound N-{3-[{(1R)-1-[1-benzyl-4-(2,5-difluorophenyl)-1H-pyrrol-2-yl]-2,2-dimethylpropyl}(glycoloyl)amino]propyl}-L-alaninamide LC-MS (Method 1): R$_t$=0.92 min; MS (ESIpos): m/z=541 [M+H]$^+$.

14.1 mg (0.03 mmol) of N-{3-[{(1R)-1-[1-benzyl-4-(2,5-difluorophenyl)-1H-pyrrol-2-yl]-2,2-dimethylpropyl}(glycoloyl)amino]propyl}-L-alaninamide and 11.4 (0.03 mmol) of 2,5-dioxopyrrolidin-1-yl N-[(9H-fluoren-9-ylmethoxy)carbonyl]-L-valinate were dissolved in 1.5 ml of DMF, and 7.9 mg (0.08 mmol) of 4-methylmorpholine were added. The reaction mixture was stirred at RT overnight, and 4.7 mg (0.08 mmol) of HOAc were added. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 15.9 mg (71% of theory) of the compound N-[(9H-fluoren-9-ylmethoxy)carbonyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide.

LC-MS (Method 1): R$_t$=1.46 min; MS (ESIpos): m/z=862 (M+H)$^+$.

14.9 mg (0.02 mmol) of N-[(9H-fluoren-9-ylmethoxy)carbonyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide were dissolved in 1.5 ml of DMF, and 44.2 mg (0.52 mmol) of 2-aminoethanol were added. The reaction mixture was stirred at RT overnight. The reaction mixture was partitioned between ethyl acetate and water and the organic phase was washed twice with water and once with saturated NaCl solution. After drying over magnesium sulphate, the solvent was evaporated under reduced pressure and the residue was purified on silica gel (mobile phase: dichloromethane/methanol 10:1). The solvents were evaporated under reduced pressure and the residue was dried under high vacuum. This gave 5.7 mg (52% of theory) of the compound L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide LC-MS (Method 1): R$_t$=0.92 min; MS (ESIpos): m/z=640 (M+H)$^+$.

5.5 mg (8.6 µmol) of L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide and 6.5 mg (6.5 µmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.0 ml of DMF, and 0.9 mg (8.6 mmol) of 4-methylmorpholine was added. The reaction mixture was stirred at RT overnight, and 0.8 mg (0.01 mmol) of HOAc was added. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 7.7 mg (74% of theory) of the title compound.

LC-MS (Method 1): R$_t$=1.10 min; MS (ESIpos): m/z=1214 (M+H)$^+$.

Intermediate F84

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

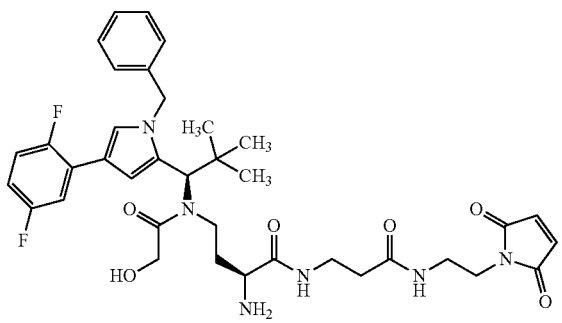 [SMILES: CC(C)(C)[C@H](c1cc(-c2cc(F)ccc2F)cn1Cc1ccccc1)N(CC[C@H](N)C(=O)NCCC(=O)NCCN1C(=O)C=CC1=O)C(=O)CO]

First, 16.5 mg (0.02 mmol) of Intermediate C54 were taken up in 5 ml of DMF and reacted with 10.4 mg (0.041 mmol) of trifluoroacetic acid/1-(2-aminoethyl)-1H-pyrrole-2,5-dione (1:1) in the presence of 11.7 mg (0.03 mmol) of HATU and 18 µl of N,N-diisopropylethylamine After 5 min of stirring at RT, the mixture was concentrated and the residue was taken up in acetonitrile/water 1:1. The pH was adjusted to 2 with trifluoroacetic acid and the reaction was concentrated again. The residue that remained was purified by preparative HPLC. This gave 8 mg (42% of theory) of the protected intermediate.

LC-MS (Method 1): $R_t$=1.38 min; MS (EIpos): m/z=929 [M+H]$^+$.

7.6 mg (0.008 mmol) of this intermediate were taken up in 3 ml of DMF, and 92 mg (0.82 mmol) of 1,4-diazabicyclo[2.2.2]octane were added. The reaction was treated in an ultrasonic bath for 1 h. 31 µl of acetic acid were then added and the reaction was concentrated under high vacuum. The residue was purified by preparative HPLC. This gave 3 mg (45% of theory) of the title compound.

LC-MS (Method 1): $R_t$=0.86 min; MS (EIpos): m/z=707 [M+H]$^+$.

$^1$H NMR (500 MHz, DMSO-d$_6$): δ=8.15 (t, 1H), 7.9-8.1 (m, 4H), 7.6 (m, 1H), 7.5 (s, 1H), 7.15-7.35 (m, 6H), 6.9-7.0 (m, 3H), 6.85 (s, 1H), 5.6 (s, 1H), 4.9 and 5.2 (2d, 2H), 4.05 and 4.2 (2d, 2H), 3.1-3.2 (m, 4H), 2.15 (m, 2H), 0.7 and 1.45 (2m, 2H), 0.8 (s, 9H).

Intermediate F85

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2,5-dioxo-2,5-dihydro-1H-pyrrol-1-yl)ethyl]butanamide (1:1)

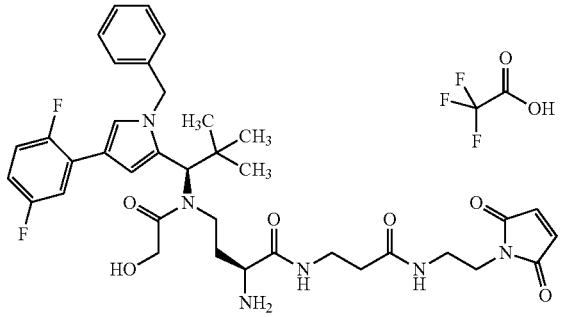 [SMILES: CC(C)(C)[C@H](c1cc(-c2cc(F)ccc2F)cn1Cc1ccccc1)N(CC[C@H](N)C(=O)NCCC(=O)NCCN1C(=O)C=CC1=O)C(=O)CO ; O=C(O)C(F)(F)F]

First, 10 mg (0.014 mmol) of Intermediate C53 were taken up in 3.4 ml of DMF and reacted with 7 mg (0.027 mmol) of trifluoroacetic acid/1-(2-aminoethyl)-1H-pyrrole-2,5-dione (1:1) in the presence of 7.8 mg (0.02 mmol) of HATU and 12 µl of N,N-diisopropylethylamine After 15 min of stirring at RT, the mixture was concentrated and the residue was purified by preparative HPLC. This gave 6.6 mg (57% of theory) of the protected intermediate.

LC-MS (Method 1): $R_t$=1.4 min; MS (EIpos): m/z=858 [M+H]$^+$.

6.6 mg (0.008 mmol) of this intermediate were taken up in 2 ml of DMF, and 86 mg (0.77 mmol) of 1,4-diazabicyclo[2.2.2]octane were added. The reaction was treated in an ultrasonic bath for 2 h. 44 µl of acetic acid were then added and the reaction was concentrated under high vacuum. The residue was purified by preparative HPLC. This gave 3.3 mg (53% of theory) of the title compound.

LC-MS (Method 1): $R_t$=0.88 min; MS (EIpos): m/z=636 [M+H]$^+$.

Intermediate F86

Trifluoroacetic acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

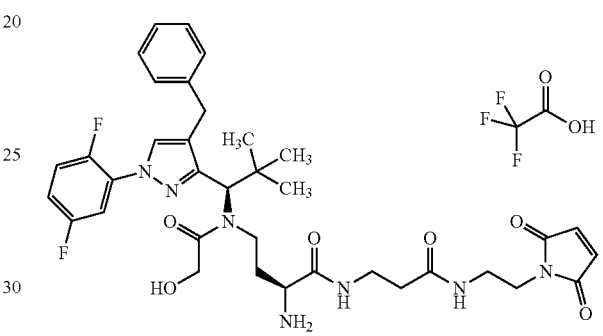

The title compound was prepared from 8 mg (0.012 mmol) of Intermediate C51 by reaction with 4.5 mg (0.017 mmol) of trifluoroacetic acid/1-(2-aminoethyl)-1H-pyrrole-2,5-dione (1:1) in the presence of 5.8 mg (0.015 mmol) of HATU and 10 µl of N,N-diisopropylethylamine and subsequent deprotection with trifluoroacetic acid. This gave 7 mg (78% of theory over 2 steps).

LC-MS (Method 1): $R_t$=0.83 min; MS (EIpos): m/z=708 [M+H]$^+$.

Intermediate F87

Trifluoroacetic acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-(3-{[2-(2,5-dioxo-2,5-dihydro-1H-pyrrol-1-yl)ethyl]amino}-3-oxopropyl)butanamide (1:1)

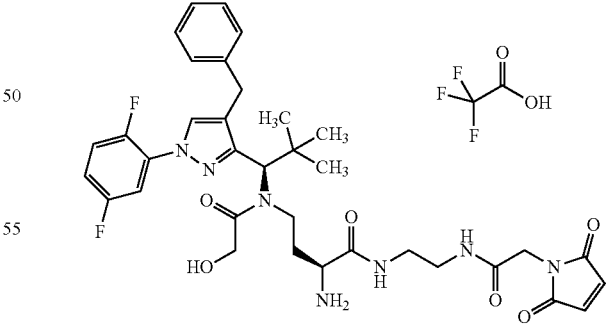

The title compound was prepared analogously to Intermediate F2 from 16 mg (0.025 mmol) of Intermediate C49 by reaction with 24 mg (0.076 mmol) of Intermediate L1 in the presence of EDCI/HOBT and N,N-diisopropylethylamine and subsequent deprotection with trifluoroacetic acid. This gave 3 mg of the title compound (14% of theory over 2 steps).

LC-MS (Method 1): $R_t$=0.88 min; MS (EIpos): m/z=694 [M+H]$^+$.

Intermediate F88

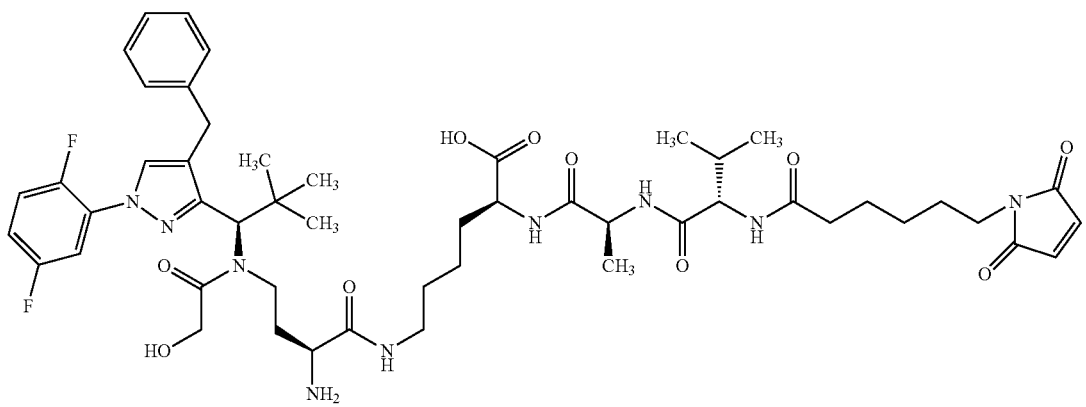 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O]

The compound was prepared analogously to Intermediate F8.
LC-MS (Method 5): $R_t$=2.97 min; MS (EIpos): m/z=1006 [M+H]$^+$.

Intermediate F89

Trifluoroacetic acid/N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N$^5$-carbamoyl-N-[4-(2,5-dioxo-2,5-dihydro-1H-pyrrol-1-yl)phenyl]-L-ornithinamide (1:1)

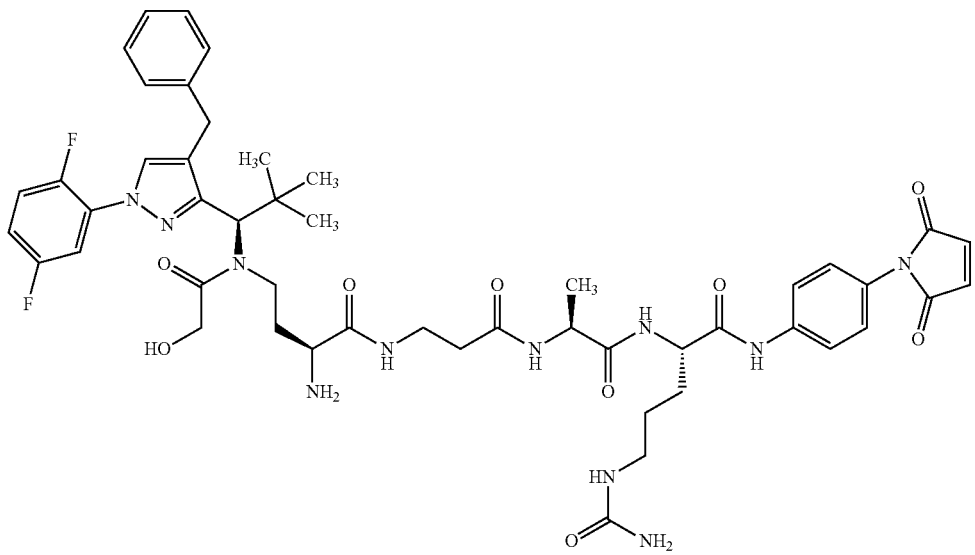 [SMILES: C[C@H](NC(=O)CCNC(=O)[C@@H](N)CCN(C(=O)CO)[C@@H](c1nn(-c2cc(F)ccc2F)cc1Cc1ccccc1)C(C)(C)C)C(=O)N[C@@H](CCCNC(N)=O)C(=O)Nc1ccc(N2C(=O)C=CC2=O)cc1]

The title compound was prepared from 8 mg (0.012 mmol) of Intermediate C51 by reaction with 7.4 mg (0.014 mmol) of Intermediate L8 in the presence of 5.8 mg (0.015 mmol) of HATU and 10 µl of N,N-diisopropylethylamine and subsequent deprotection with trifluoroacetic acid. This gave 10 mg (78% of theory over 2 steps).
LC-MS (Method 1): $R_t$=0.87 min; MS (EIpos): m/z=984 [M+H]$^+$.

Intermediate F90

N-[6-(2,5-Dioxo-2,5-dihydro-1H-pyrrol-1-yl)hexanoyl]-L-valyl-$N^5$-carbamoyl-L-ornithyl-$N^6$-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine/trifluoroacetic acid (1:1)

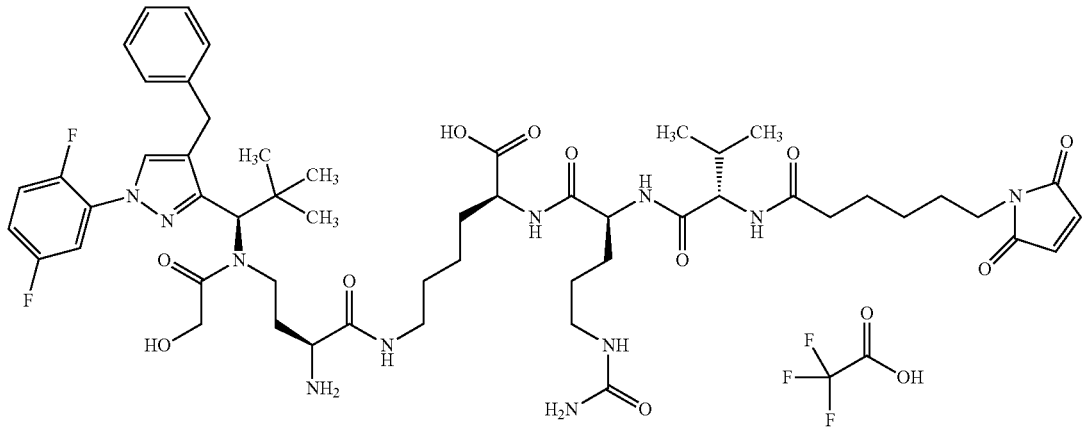 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

The title compound was prepared from 11 mg (0.018 mmol) of Intermediate C49 by reaction with 13.7 mg (0.018 mmol) of Intermediate L17 in the presence of 34 mg (0.089 mmol) of HATU and 19 µl of N,N-diisopropylethylamine and subsequent deprotection with trifluoroacetic acid. This gave 7.5 mg (35% of theory over 2 steps).

LC-MS (Method 8): $R_t$=6.78 min; MS (EIpos): m/z=1092 [M+H]$^+$.

Intermediate F91

Trifluoroacetic acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-[2-(2,5-dioxo-2,5-dihydro-1H-pyrrol-1-yl)ethyl]butanamide (1:1)

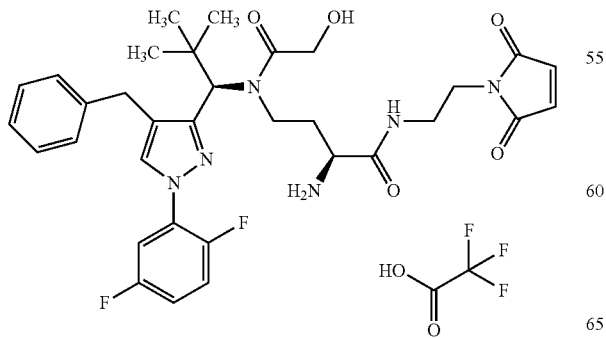

9.3 mg (0.01 mmol) of tert-butyl [(2S)-4-[{(1R)-1-[4-benzyl-1-(2,5-difluorophenyl)-1H-pyrazol-3-yl]-2,2-dimethylpropyl}(glycoloyl)amino]-1-{[2-(2,5-dioxo-2,5-dihydro-1H-pyrrol-1-yl)ethyl]amino}-1-oxobutan-2-yl]carbamate were dissolved in 2 ml of dichloromethane, and 740 mg (6.49 mmol, 0.50 ml) of trifluoroacetic acid were added and the mixture was stirred at RT for 1.5 h. The reaction mixture was then concentrated and the residue was taken up in acetonitrile and water and lyophilized. This gave 9.2 mg (96% of theory) of the target compound.

LC-MS (Method 1): $R_t$=0.88 min; MS (EIpos): m/z=637 [M+H]$^+$.

Intermediate F103

N-[19-(2,5-Dioxo-2,5-dihydro-1H-pyrrol-1-yl)-17-oxo-4,7,10,13-tetraoxa-16-azanonadecan-1-oyl]-L-valyl-N-(3-{[(1R)-1-(3-benzyl-7-chloro-4-oxo-3,4-dihydroquinazolin-2-yl)-2-methylpropyl](4-methylbenzoyl)amino}propyl)-L-alaninamide

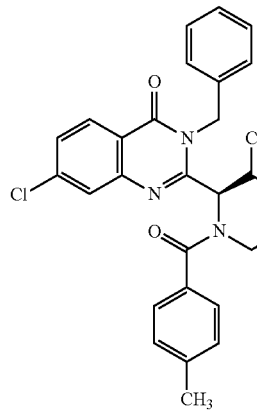

The title compound was prepared from 10 mg (0.019 mmol) of N-(3-aminopropyl)-N-[(1R)-1-(3-benzyl-7-chloro-4-oxo-3,4-dihydroquinazolin-2-yl)-2-methylpropyl]-4-methylbenzamide by reaction with 11.3 mg (0.019 mmol) of Intermediate L44 in the presence of 8.8 mg (0.023 mmol) of HATU and 10 μl of N,N-diisopropylethylamine Purification was by preparative HPLC.

Yield: 8.5 mg (35% of theory)

LC-MS (Method 5): $R_t$=3.82 min; MS (EIpos): m/z=1085 [M+H]$^+$.

Intermediate F104

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

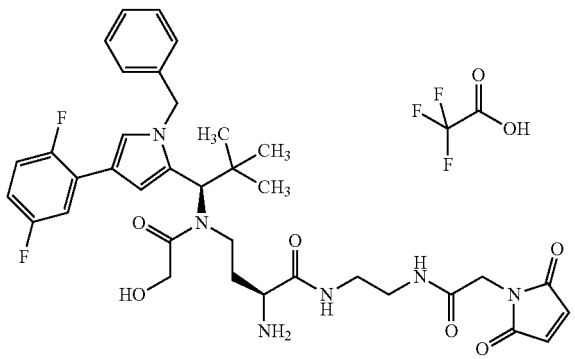 [SMILES: CC(C)(C)[C@H](c1cc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

10 mg (0.014 mmol) of Intermediate C53 were dissolved in 3.3 ml of DMF, and 8.5 mg (0.027 mmol) of Intermediate L1, 7.8 mg (0.02 mmol) of HATU and 12 μl of N,N-diisopropylethylamine were added. The reaction was stirred at RT for 15 min and then concentrated. The residue was purified by preparative HPLC giving, after lyophilization, 5.6 mg (38% of theory) of the protected intermediate.

LC-MS (Method 1): $R_t$=1.32 min; MS (ESIpos): m/z=915 (M+H)$^+$.

5.6 mg (0.006 mmol) of this intermediate were taken up in 2 ml of DMF, and 69 mg (0.61 mmol) of 1,4-diazabicyclo[2.2.2]octane were added. The reaction was treated in an ultrasonic bath for 2 h. 35 μl of acetic acid were then added and the reaction was concentrated under high vacuum. The residue was purified by preparative HPLC. This gave 2.4 mg (48% of theory) of the title compound.

LC-MS (Method 1): $R_t$=0.84 min; MS (EIpos): m/z=693 [M+H]$^+$.

HPLC (Method 11): $R_t$=1.91 min;

Alternatively, the title compound was also prepared from Intermediate C58. 15 mg (0.023 mmol) of Intermediate C58 were initially reacted with 11 mg (0.036 mmol) of Intermediate L1 in the presence of 13 mg (0.034 mmol) of HATU and 10 μl of N,N-diisopropylethylamine After 60 min of stirring at RT, the mixture was concentrated and the residue was purified by preparative HPLC. This gave 12.3 mg (63% of theory) of the protected intermediate.

LC-MS (Method 1): $R_t$=1.3 min; MS (EIpos): m/z=837 [M+H]$^+$.

In the second step, this intermediate was dissolved in 3 ml of 2,2,2-trifluoroethanol. 12 mg (0.088 mmol) of zinc chloride were added, and the reaction was stirred at 50° C. for 2 h. 26 mg (0.088 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 8.1 mg (68% of theory) of the title compound.

LC-MS (Method 1): $R_t$=0.89 min; MS (ESIpos): m/z=693 (M+H)$^+$.

Intermediate F105

N$^2$-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-N-[2-(2,5-dioxo-2,5-dihydro-1H-pyrrol-1-yl)ethyl]-L-glutamine/trifluoroacetic acid (1:1)

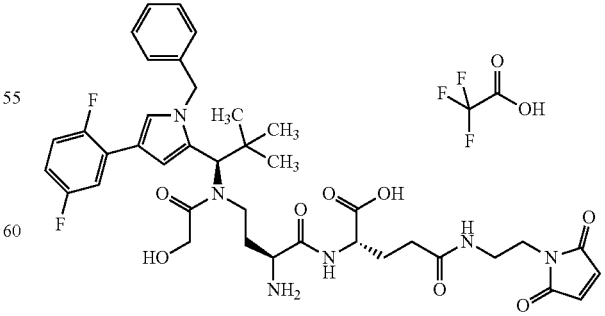

The title compound was prepared analogously to Intermediate F32 from Intermediate C5 and Intermediate L46.

LC-MS (Method 1): $R_t$=0.82 min; MS (EIpos): m/z=766 [M+H]$^+$.

Intermediate F106

Trifluoroacetic acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-alanyl-N5-carbamoyl-N-[4-(2,5-dioxo-2,5-dihydro-1H-pyrrol-1-yl)phenyl]-L-ornithinamide (1:1)

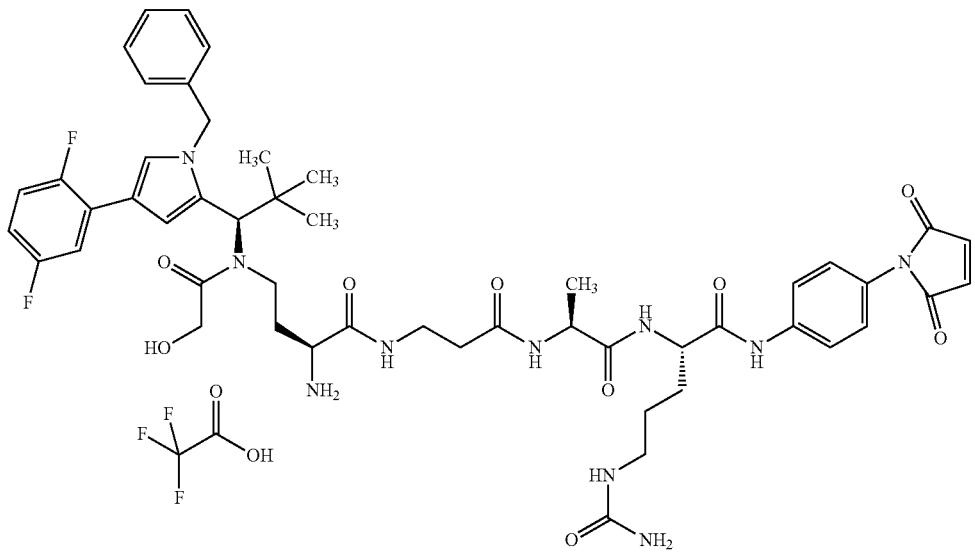 [SMILES: C[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](CCCNC(N)=O)C(=O)Nc1ccc(N2C(=O)C=CC2=O)cc1 ; O=C(O)C(F)(F)F]

The title compound was prepared analogously to Intermediate F104 from Intermediate C53 and Intermediate L47.
HPLC (Method 11): $R_t$=1.85 min;
LC-MS (Method 1): $R_t$=0.86 min; MS (ESIpos): m/z=983 (M+H)+.

Intermediate F107

Trifluoroacetic acid/(1R,2S)-2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

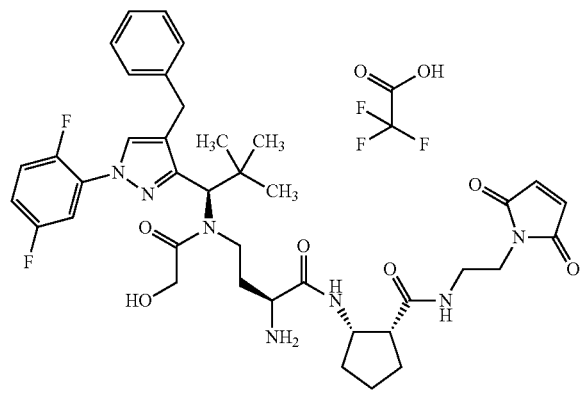 [SMILES: CC(C)(C)[C@H](c1nn(-c2cc(F)ccc2F)cc1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared from 15 mg (0.024 mmol) of Intermediate C49 by reaction with 22.3 mg (0.049 mmol) of Intermediate L48 in the presence of 14 mg (0.037 mmol) of HATU and 21 µl of N,N-diisopropylethylamine and subsequent deprotection with trifluoroacetic acid. This gave 13 mg (60% of theory over 2 steps).
LC-MS (Method 1): $R_t$=0.9 min; MS (EIpos): m/z=748 [M+H]+.

Intermediate F108

Trifluoroacetic acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

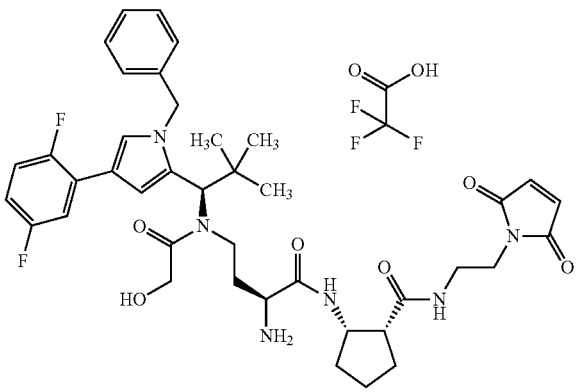 [SMILES: CC(C)(C)[C@H](c1cc(-c2cc(F)ccc2F)cn1Cc1ccccc1)N(CC[C@H](N)C(=O)N[C@H]1CCC[C@H]1C(=O)NCCN1C(=O)C=CC1=O)C(=O)CO ; O=C(O)C(F)(F)F]

The title compound was prepared analogously to Intermediate F104 from 20 mg (0.027 mmol) of Intermediate C53 and 24 mg (0.054 mmol) of Intermediate L48. This gave 3 mg (14% of theory over 2 steps).

LC-MS (Method 1): $R_t$=0.93 min; MS (EIpos): m/z=747 [M+H]$^+$.

Intermediate F109

Trifluoroacetic acid/(2S)-2-amino-4-[{(1R)-1-[4-benzyl-1-(2,5-difluorophenyl)-1H-pyrazol-3-yl]-2,2-dimethylpropyl}(glycoloyl)amino]-N-{2-[(bromoacetyl)amino]ethyl}butanamide (1:1)

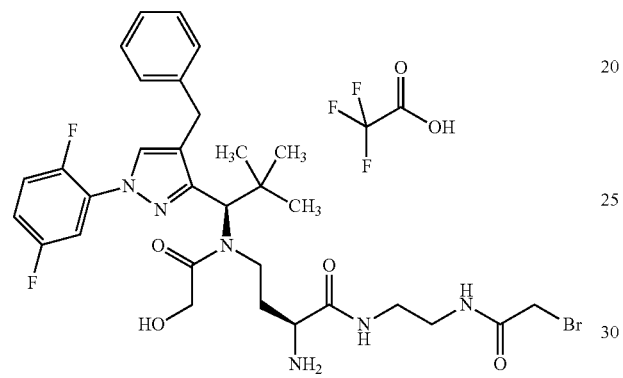

17 mg (0.026 mmol) of Intermediate C57 were taken up in 3 ml of DMF and reacted with 7 mg (0.027 mmol) of commercially available 1-(2-bromoacetoxy)pyrrolidine-2,5-dione in the presence of 14 µl of N,N-diisopropylethylamine After 15 min of stirring at RT, the mixture was concentrated and the residue was purified by preparative HPLC. This gave 7 mg (33% of theory) of this intermediate.

LC-MS (Method 1): $R_t$=1.29 min; MS (ESIpos): m/z=777 and 779 (M+H)$^+$.

This intermediate was taken up in 1 ml of dichloromethane and deprotected with 1 ml of trifluoroacetic acid. After concentration and lyophilization from acetonitrile/water, 6 mg (88% of theory) of the title compound were obtained.

LC-MS (Method 1): $R_t$=0.86 min; MS (ESIpos): m/z=677/679 (M+H)$^+$.

Intermediate F110

N-(Bromoacetyl)-L-valyl-L-alanyl-N6-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine/trifluoroacetic acid (1:1)

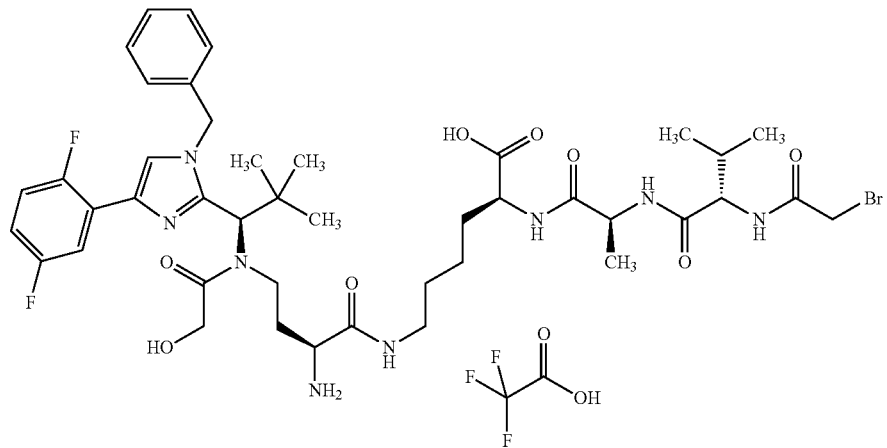 [SMILES: CC(C)[C@H](NC(=O)CBr)C(=O)N[C@@H](C)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F109 from 16 mg (0.023 mmol) of Intermediate C5 and 17 mg (0.025 mmol) of Intermediate L49. This gave 6 mg (24% of theory over 2 steps) of the title compound.

HPLC (Method 11): $R_t$=1.93 min;
LC-MS (Method 1): $R_t$=0.88 min; MS (ESIpos): m/z=933 and 935 (M+H)$^+$.

Intermediate F111

Trifluoroacetic acid/(1S,3R)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

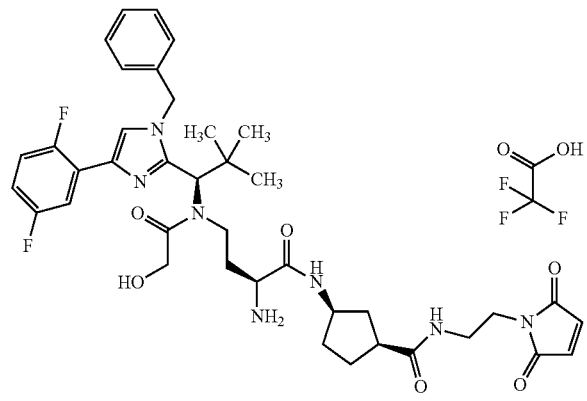 [SMILES: CC(C)(C)[C@H](c1nc(-c2cc(F)ccc2F)cn1Cc1ccccc1)N(CC[C@H](N)C(=O)N[C@@H]1CC[C@H](C(=O)NCCN2C(=O)C=CC2=O)C1)C(=O)CO ; O=C(O)C(F)(F)F]

The title compound was prepared from 15 mg (0.022 mmol) of Intermediate C5 by reaction with 16 mg (0.044 mmol) of Intermediate L50 in the presence of 12.5 mg (0.032 mmol) of HATU and 19 µl of N,N-diisopropylethylamine and subsequent deprotection with trifluoroacetic acid. This gave 13 mg (67% of theory over 2 steps).

LC-MS (Method 1): $R_t$=0.89 min; MS (EIpos): m/z=748 [M+H]$^+$.

Intermediate F112

Trifluoroacetic acid/(1S,3R)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

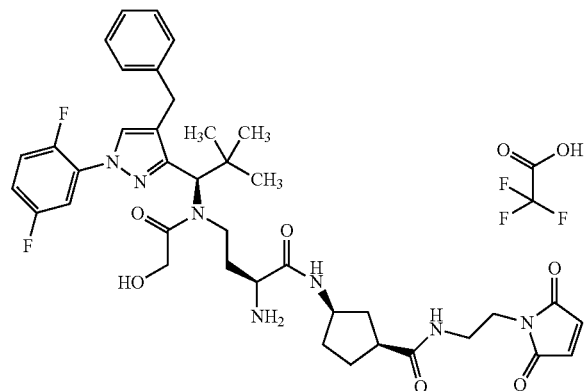 [SMILES: CC(C)(C)[C@H](c1nn(-c2cc(F)ccc2F)cc1Cc1ccccc1)N(CC[C@H](N)C(=O)N[C@@H]1CC[C@H](C(=O)NCCN2C(=O)C=CC2=O)C1)C(=O)CO ; O=C(O)C(F)(F)F]

The title compound was prepared from 15 mg (0.024 mmol) of Intermediate C49 by reaction with 18 mg (0.049 mmol) of Intermediate L50 in the presence of 14 mg (0.037 mmol) of HATU and 21 µl of N,N-diisopropylethylamine and subsequent deprotection with trifluoroacetic acid. This gave 12 mg (51% of theory over 2 steps).

LC-MS (Method 1): $R_t$=0.89 min; MS (EIpos): m/z=748 [M+H]$^+$.

Intermediate F113

Trifluoroacetic acid/(1S,3R)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

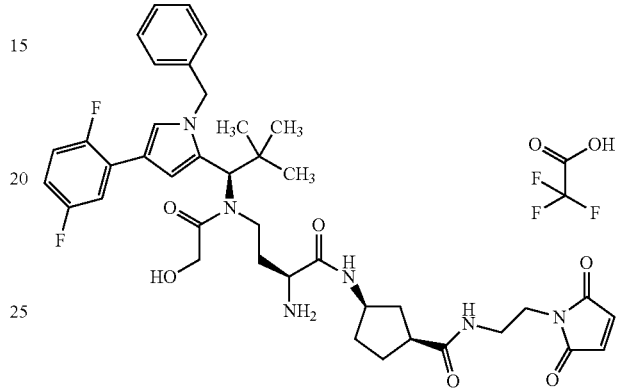

The title compound was prepared from 15 mg (0.019 mmol) of Intermediate C53 by reaction with 14 mg (0.038 mmol) of Intermediate L50 in the presence of 11 mg (0.029 mmol) of HATU and 17 µl of N,N-diisopropylethylamine and subsequent deprotection with 133 mg of DABCO in 2 ml of DMF. Purification by HPLC gave 4 mg (24% of theory over 2 steps).

LC-MS (Method 5): $R_t$=2.77 min; MS (EIpos): m/z=747 [M+H]$^+$.

Intermediate F114

Trifluoroacetic acid/(1R,3R)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

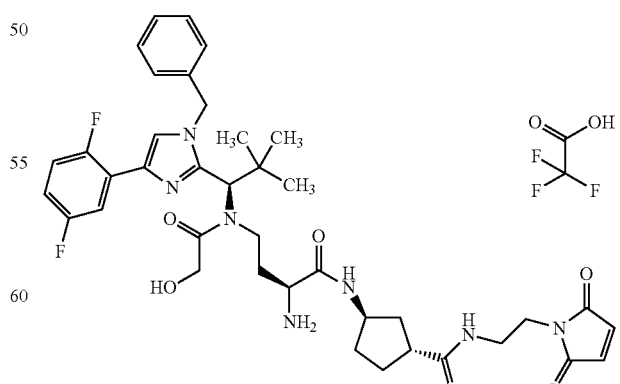

The title compound was prepared from 15 mg (0.022 mmol) of Intermediate C5 by reaction with 16 mg (0.044 mmol) of Intermediate L51 in the presence of 12.6 mg (0.032 mmol) of HATU and 19 µl of N,N-diisopropylethylamine and subsequent deprotection with trifluoroacetic acid. This gave 11 mg (53% of theory over 2 steps).

LC-MS (Method 1): $R_t$=0.89 min; MS (EIpos): m/z=748 [M+H]$^+$.

Intermediate F115

Trifluoroacetic acid/(1R,3R)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

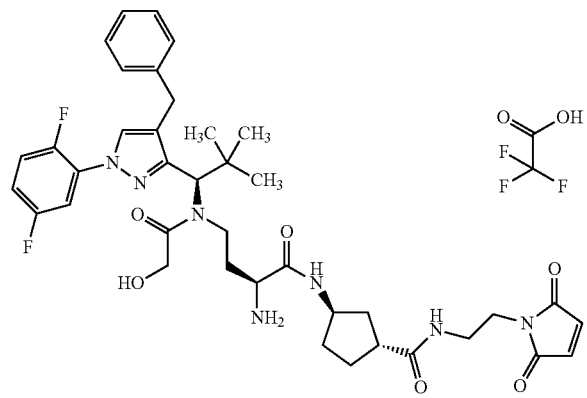 [SMILES: CC(C)(C)[C@H](c1nn(-c2cc(F)ccc2F)cc1Cc1ccccc1)N(CC[C@H](N)C(=O)N[C@@H]1CC[C@@H](C(=O)NCCN2C(=O)C=CC2=O)C1)C(=O)CO ; O=C(O)C(F)(F)F]

The title compound was prepared from 15 mg (0.024 mmol) of Intermediate C49 by reaction with 18 mg (0.047 mmol) of Intermediate L51 in the presence of 13 mg (0.035 mmol) of HATU and 21 µl of N,N-diisopropylethylamine and subsequent deprotection with trifluoroacetic acid. This gave 12 mg (51% of theory over 2 steps).

LC-MS (Method 1): $R_t$=0.87 min; MS (EIpos): m/z=748 [M+H]$^+$.

Intermediate F116

Trifluoroacetic acid/(1R,3R)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

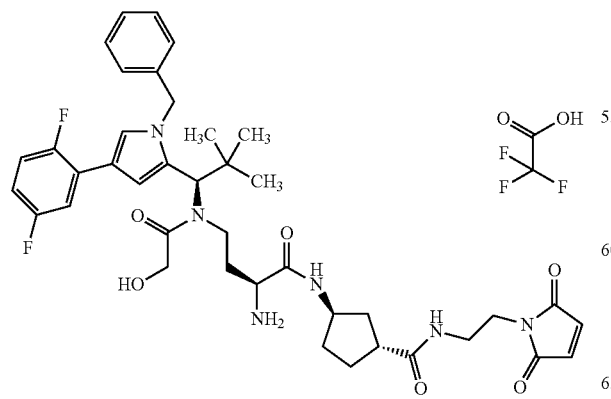

The title compound was prepared from 11 mg (0.014 mmol) of Intermediate C51 by reaction with 11 mg (0.028 mmol) of Intermediate L51 in the presence of 8 mg (0.021 mmol) of HATU and 12 µl of N,N-diisopropylethylamine and subsequent deprotection with 87 mg of DABCO in 2 ml of DMF. Purification by HPLC gave 3.3 mg (28% of theory over 2 steps).

LC-MS (Method 1): $R_t$=0.92 min; MS (EIpos): m/z=747 [M+H]$^+$.

Intermediate F117

Trifluoroacetic acid/N-[(3S)-3-amino-4-{2-[6-(2,5-dioxo-2,5-dihydro-1H-pyrrol-1-yl)hexanoyl]hydrazino}-4-oxobutyl]-N-{(1R)-1-[4-benzyl-1-(2,5-difluorophenyl)-1H-pyrazol-3-yl]-2,2-dimethylpropyl}-2-hydroxyacetamide (1:1)

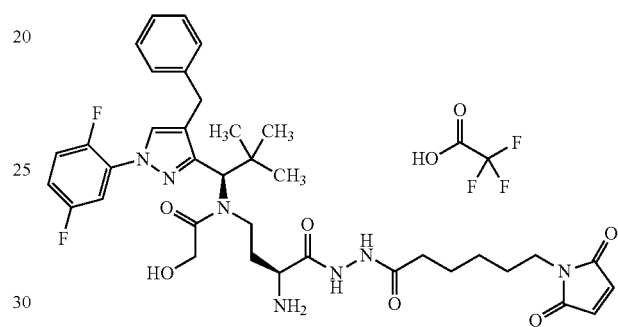

The title compound was prepared according to classical methods of peptide chemistry from Intermediate C49. First, C49 was coupled with 9H-fluoren-9-ylmethyl hydrazinecarboxylate in the presence of HATU. The Fmoc protective group was then removed with piperidine in DMF and the hydrazide obtained was coupled with 6-(2,5-dioxo-2,5-dihydro-1H-pyrrol-1-yl)hexanoic acid in the presence of HATU. In the last step, the Boc protective group was removed with TFA in dichloromethane.

LC-MS (Method 1): $R_t$=0.93 min; MS (EIpos): m/z=722 [M+H]$^+$.

Intermediate F118

Trifluoroacetic acid N-[(3S)-3-amino-4-{2-[6-(2,5-dioxo-2,5-dihydro-1H-pyrrol-1-yl)hexanoyl]hydrazino -4-oxobutyl]-N-{(1R)-1-[1-benzyl-4-(2,5-difluorophenyl)-1H-pyrrol-2-yl]-2,2-dimethylpropyl}-2-hydroxyacetamide (1:1)

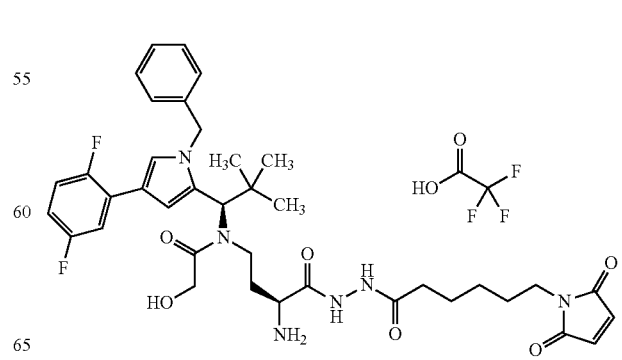

In the first step, the title compound was prepared analogously to Intermediate F3 from 15 mg (0.019 mmol) of Intermediate C53 by coupling with commercially available 6-(2,5-dioxo-2,5-dihydro-1H-pyrrol-1-yl)hexanehydrazide in the presence of HATU. The Fmoc protective group was then removed with 142 mg of DABCO in DMF. Purification by HPLC gave 3 mg (19% of theory) of the title compound.

LC-MS (Method 1): $R_t$=0.90 min; MS (EIpos): m/z=721 [M+H]$^+$.

Intermediate F119

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(bromoacetyl)amino]ethyl}butanamide (1:1)

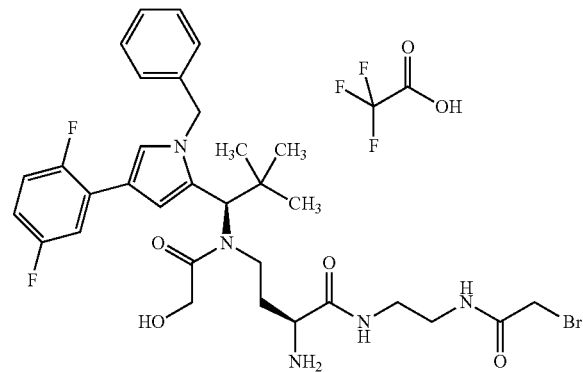 [SMILES: CC(C)(C)[C@H](c1cc(-c2cc(F)ccc2F)cn1Cc1ccccc1)N(CC[C@H](N)C(=O)NCCNC(=O)CBr)C(=O)CO ; O=C(O)C(F)(F)F]

29 mg (0.044 mmol) of Intermediate C58 were taken up in 3.4 ml of DMF, and 36 mg (0.087 mmol) of Intermediate L52, 25 mg (0.065 mmol) of HATU and 19 µl of N,N-diisopropylethylamine were added. After 60 min of stirring at RT, the mixture was concentrated and the residue was purified by preparative HPLC. This gave 26.4 mg (73% of theory) of the intermediate.

LC-MS (Method 1): $R_t$=1.34 min; MS (ESIpos): m/z=820 and 822 (M+H)$^+$.

This intermediate was dissolved in 3 ml of 2,2,2-trifluoroethanol. 6.5 mg (0.048 mmol) of zinc chloride were added, and the reaction was stirred at 50° C. for 4 h. 13.9 mg (0.048 mmol) of ethylenediamine-N,N,N',N'-tetraacetic acid and 2 ml of a 0.1% strength aqueous trifluoroacetic acid solution were added. The reaction was purified by preparative HPLC. Concentration of the appropriate fractions and lyophilization of the residue from acetonitrile/water gave 14.4 mg (58% of theory) of the title compound.

LC-MS (Method 1): $R_t$=0.88 min; MS (ESIpos): m/z=676 and 678 (M+H)$^+$.

Intermediate F120

Trifluoroacetic acid/(1S,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

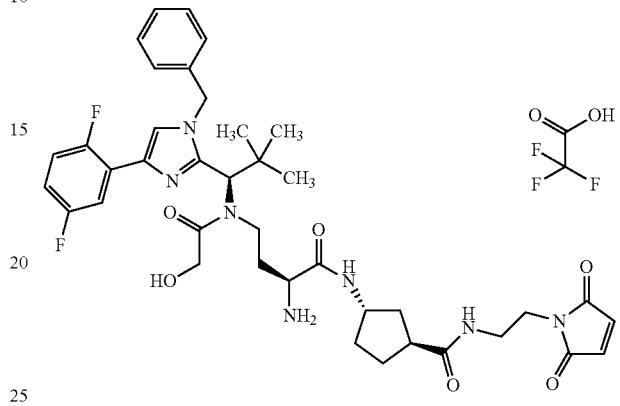

The title compound was prepared from 10 mg (0.015 mmol) of Intermediate C5 by reaction with 11 mg (0.03 mmol) of Intermediate L53 in the presence of 8.4 mg (0.022 mmol) of HATU and 13 µl of N,N-diisopropylethylamine and subsequent deprotection with trifluoroacetic acid. This gave 7.5 mg (59% of theory over 2 steps).

LC-MS (Method 1): $R_t$=0.85 min; MS (EIpos): m/z=748 [M+H]$^+$.

Intermediate F121

Trifluoroacetic acid/(1S,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

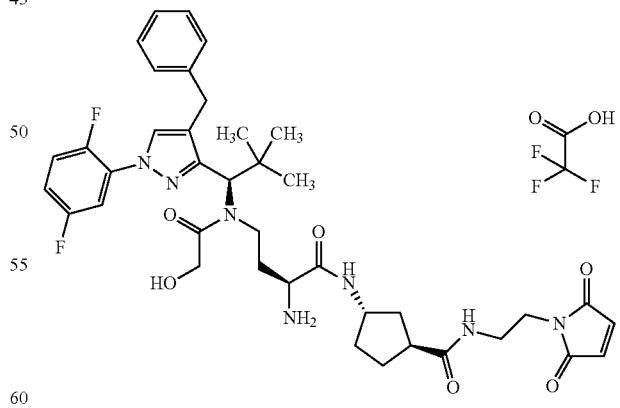

The title compound was prepared from 10 mg (0.016 mmol) of Intermediate C49 by reaction with 11.5 mg (0.031 mmol) of Intermediate L53 in the presence of 9 mg (0.024 mmol) of HATU and 14 µl of N,N-diisopropylethylamine and subsequent deprotection with trifluoroacetic acid. This gave 9 mg (61% of theory over 2 steps).

LC-MS (Method 1): R$_t$=0.84 min; MS (EIpos): m/z=748 [M+H]$^+$.

Intermediate F122

Trifluoroacetic acid/(1S,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

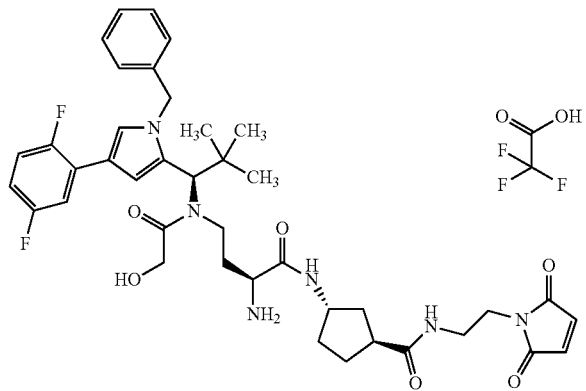 [SMILES: CC(C)(C)[C@H](c1cc(-c2cc(F)ccc2F)cn1Cc1ccccc1)N(CC[C@H](N)C(=O)N[C@H]1CC[C@H](C(=O)NCCN2C(=O)C=CC2=O)C1)C(=O)CO ; O=C(O)C(F)(F)F]

The title compound was prepared from 15 mg (0.019 mmol) of Intermediate C53 by reaction with 14 mg (0.038 mmol) of Intermediate L53 in the presence of 11 mg (0.029 mmol) of HATU and 17 µl of N,N-diisopropylethylamine and subsequent deprotection with 202 mg of DABCO in 3 ml of DMF. Purification by HPLC gave 4 mg (24% of theory over 2 steps).

LC-MS (Method 1): R$_t$=0.87 min; MS (EIpos): m/z=747 [M+H]$^+$.

Intermediate F123

Trifluoroacetic acid/(1R,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

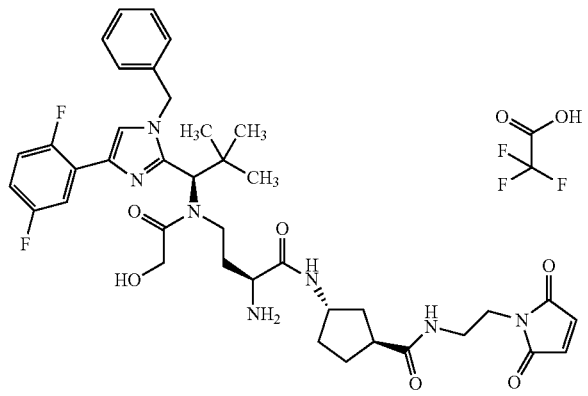 [SMILES: CC(C)(C)[C@H](c1nc(-c2cc(F)ccc2F)cn1Cc1ccccc1)N(CC[C@H](N)C(=O)N[C@H]1CC[C@H](C(=O)NCCN2C(=O)C=CC2=O)C1)C(=O)CO ; O=C(O)C(F)(F)F]

The title compound was prepared from 10 mg (0.015 mmol) of Intermediate C5 by reaction with 11 mg (0.030 mmol) of Intermediate L54 in the presence of 8.4 mg (0.022 mmol) of HATU and 13 µl of N,N-diisopropylethylamine and subsequent deprotection with trifluoroacetic acid. This gave 4 mg (31% of theory over 2 steps).

LC-MS (Method 1): R$_t$=0.86 min; MS (EIpos): m/z=748 [M+H]$^+$.

Intermediate F124

Trifluoroacetic acid/(1R,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

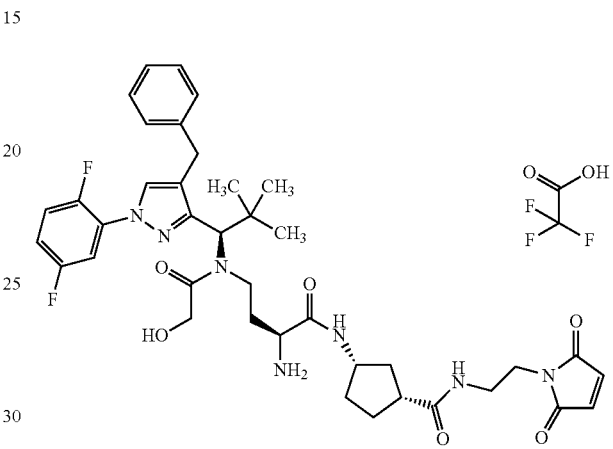

The title compound was prepared from 10 mg (0.016 mmol) of Intermediate C49 by reaction with 11.5 mg (0.031 mmol) of Intermediate L54 in the presence of 9 mg (0.024 mmol) of HATU and 14 µl of N,N-diisopropylethylamine and subsequent deprotection with trifluoroacetic acid. This gave 9 mg (66% of theory over 2 steps).

LC-MS (Method 1): R$_t$=0.84 min; MS (EIpos): m/z=748 [M+H]$^+$.

Intermediate F125

Trifluoroacetic acid/(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-[2-(2,5-dioxo-2,5-dihydro-1H-pyrrol-1-yl)ethyl]cyclopentanecarboxamide (1:1)

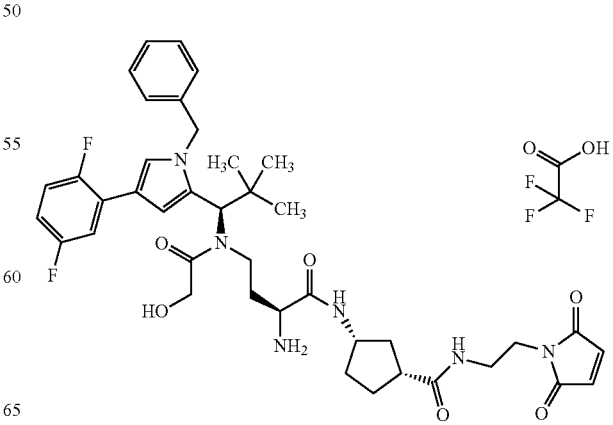

The title compound was prepared from 15 mg (0.019 mmol) of Intermediate C53 by reaction with 14 mg (0.038 mmol) of Intermediate L54 in the presence of 11 mg (0.029 mmol) of HATU and 17 μl of N,N-diisopropylethylamine and subsequent deprotection with 127 mg of DABCO in 3 ml of DMF. Purification by HPLC gave 3 mg (17% of theory over 2 steps).

LC-MS (Method 4): $R_t$=1.08 min; MS (EIpos): m/z=769 [M+Na]$^+$.

Intermediate F126

N-(Bromoacetyl)-L-valyl-L-alanyl-N$^6$-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine/trifluoroacetic acid (1:1)

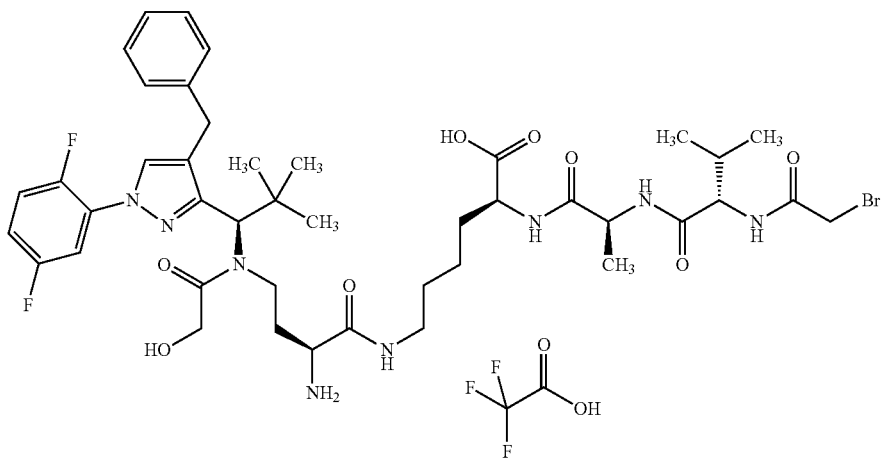 [SMILES: CC(C)[C@H](NC(=O)CBr)C(=O)N[C@@H](C)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

The title compound was prepared analogously to Intermediate F110 from 18 mg (0.027 mmol) of Intermediate C49 and 21 mg (0.027 mmol) of Intermediate L49. This gave 8.7 mg (30% of theory over 2 stages) of the title compound.

HPLC (Method 11): $R_t$=1.94 min;

LC-MS (Method 1): $R_t$=0.86 min; MS (ESIpos): m/z=933 and 935 (M+H)$^+$.

Intermediate F127

Trifluoroacetic acid/(2S)-2-amino-({(1R)-1-[1-benzyl-4-(2,5-difluorophenyl)-1H-pyrrol-2-yl]-2,2-dimethylpropyl}[(2S)-2-methoxypropanoyl]amino)-N-(2-{[2,5-dioxo-2,5-dihydro-1H-pyrrol-1-yl)acetyl]amino}ethyl)butanamide (1:1)

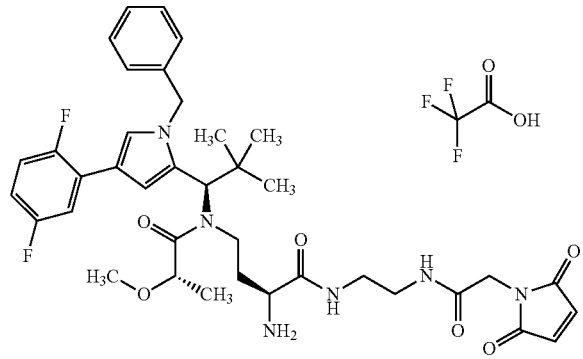 [SMILES: CO[C@@H](C)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

12 mg (0.015 mmol) of Intermediate C59 were dissolved in 2.4 ml of DMF, and 14.6 mg (0.046 mmol) of Intermediate L1, 6 mg (0.031 mmol) of 1-(3-dimethylaminopropyl)-3-ethylcarbodiimide hydrochloride, 5.9 mg (0.039 mmol) of 1-hydroxy-1H-benzotriazole hydrate and 8 μl of N,N-diisopropylethylamine were added. After 1 h of stirring at RT, the mixture was concentrated and the residue was purified by preparative HPLC. This gave 11 mg (70% of theory) of this intermediate.

LC-MS (Method 1): $R_t$=1.34 min; MS (ESIpos): m/z=942 (M+H)$^+$.

11 mg (0.011 mmol) of this intermediate were taken up in 2 ml of DMF, and 123 mg (1.1 mmol) of 1,4-diazabicyclo[2.2.2]octane were added. The reaction was treated in an ultrasonic bath for 2 h. 63 μl of acetic acid were then added and the reaction was concentrated under high vacuum. The residue was purified by preparative HPLC. This gave 2 mg (22% of theory) of the title compound.

LC-MS (Method 1): $R_t$=0.89 min; MS (EIpos): m/z=721 [M+H]$^+$.

HPLC (Method 11): $R_t$=1.95 min;

Intermediate F128

N⁶-(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-D-alanyl)-N²-{N-[6-(2,5-dioxo-2,5-dihydro-1H-pyrrol-1-yl)hexanoyl]-L-valyl-L-alanyl}-L-lysine/trifluoroacetic acid (1:1)

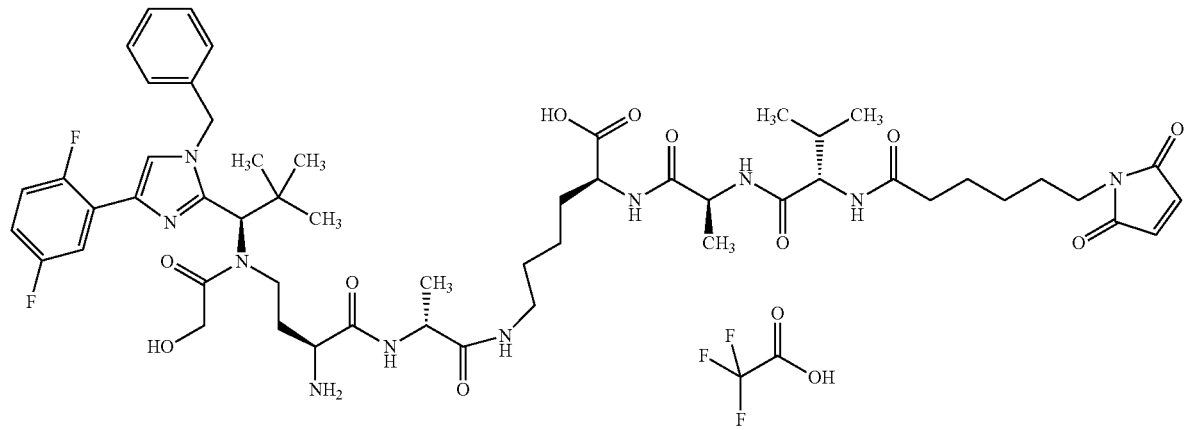 [SMILES: CC(C)[C@H](NC(=O)CCCCCN1C(=O)C=CC1=O)C(=O)N[C@@H](C)C(=O)N[C@@H](CCCCNC(=O)[C@@H](C)NC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared from 3 mg (0.005 mmol) of Intermediate C5 by reaction with 2.5 mg (0.003 mmol) of Intermediate L55 in the presence of 2.5 mg (0.007 mmol) of HATU and 3 µl of N,N-diisopropylethylamine and subsequent deprotection with trifluoroacetic acid. This gave 1.4 mg (32% of theory over 2 steps).

LC-MS (Method 1): R$_t$=0.93 min; MS (EIpos): m/z=1077 [M+H]⁺.

Intermediate F129

N-[6-(2,5-Dioxo-2,5-dihydro-1H-pyrrol-1-yl)hexanoyl]-L-valyl-L-alanyl-N⁶-{[(1R,3S)-3-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)cyclopentyl]carbonyl}-L-lysine/trifluoroacetic acid

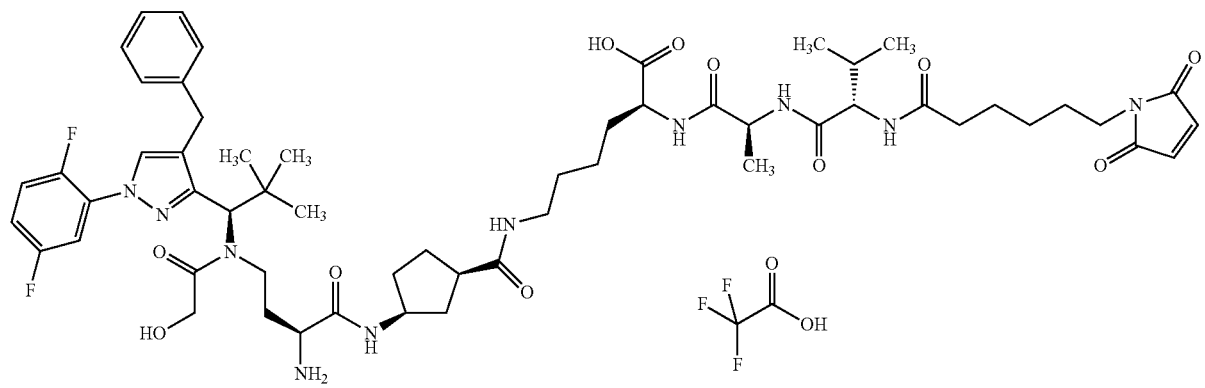 [SMILES: CC(C)[C@H](NC(=O)CCCCCN1C(=O)C=CC1=O)C(=O)N[C@@H](C)C(=O)N[C@@H](CCCCNC(=O)[C@@H]1CC[C@H](NC(=O)[C@@H](N)CCN(C(=O)CO)[C@@H](c2nn(-c3cc(F)ccc3F)cc2Cc2ccccc2)C(C)(C)C)C1)C(=O)O ; O=C(O)C(F)(F)F]

The title compound was prepared analogously to Intermediate F128 from 10 mg (0.016 mmol) of Intermediate C49 by reaction with 19 mg (0.024 mmol) of Intermediate L56 in the presence of 12 mg (0.031 mmol) of HATU and 14 µl of N,N-diisopropylethylamine and subsequent deprotection with trifluoroacetic acid. This gave 13.5 mg (70% of theory over 2 steps).

LC-MS (Method 1): R$_t$=0.9 min; MS (EIpos): m/z=1117 [M+H]⁺.

Intermediate F142

R/S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-homocysteine/trifluoroacetic acid (1:1)

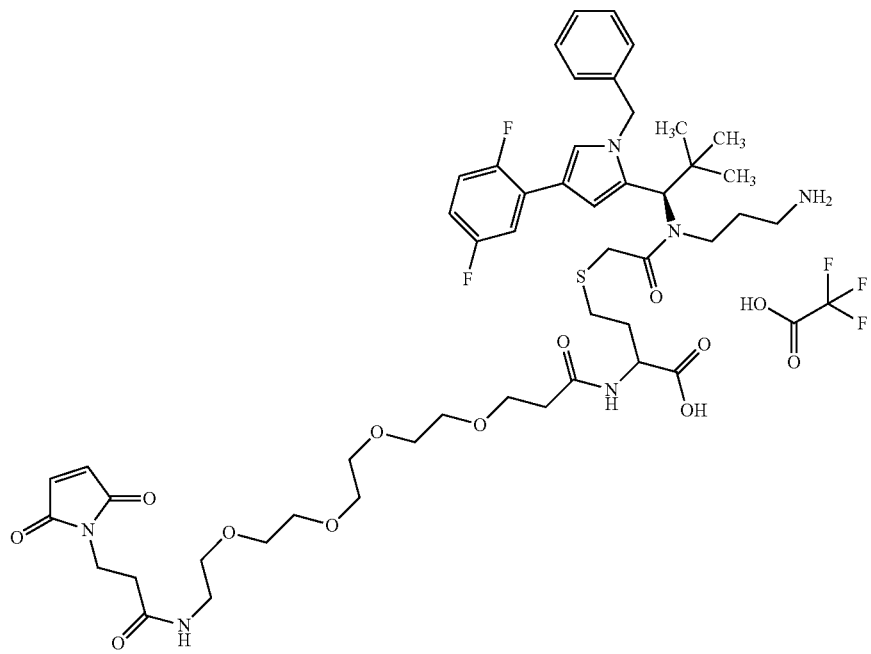 [SMILES: CC(C)(C)[C@H](c1cc(-c2cc(F)ccc2F)cn1Cc1ccccc1)N(CCCN)C(=O)CSCCC(NC(=O)CCOCCOCCOCCOCCNC(=O)CCN1C(=O)C=CC1=O)C(=O)O ; O=C(O)C(F)(F)F]

20.0 mg (23.7 µmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetic acid (1:1) and 13.4 mg (26.04 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.0 ml of DMF, and 4.8 mg (47.34 µmol) of 4-methylmorpholine were added. The reaction mixture was stirred at RT overnight. 3.6 mg (0.06 mmol) of acetic acid were added and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 12.4 mg (44% of theory) of the compound R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]homocysteine.

LC-MS (Method 1): $R_1$=1.30 min; MS (ESIpos): m/z=1129 (M+H)$^+$.

10.0 mg (8.85 µmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-homocysteine were dissolved in trifluoroethanol, and 3.1 mg (22.71 µmol) of zinc dichloride were added. The reaction mixture was stirred at 50° C. overnight. 3.9 mg (0.01 mmol) of ethylenediamine-N,N,N',N'-tetraacetic acid were added, the reaction mixture was stirred briefly and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was lyophilized with a little water. This gave 7.6 mg (78% of theory) of the title compound.

LC-MS (Method 1): $R_t$=0.94 min; MS (ESIpos): m/z=983 (M+H)$^+$.

$^1$H NMR (400 MHz, DMSO-d$_6$): δ [ppm]=0.50 (m, 1H), 0.81 (s, 9H), 1.49 (m, 1H), 1.89 (m, 1H), 2.05 (m, 1H), 2.29-2.43 (m, 4H), 2.45-2.55 (m, 2H), 2.58-2.74 (m, 2H), 3.10-3.20 (m, 2H), 3.21-3.40 (m, 2H), 3.42-3.54 (m, 16H), 3.55-3.65 (m, 4H), 4.28 (m, 1H), 4.91 (dd, 1H), 5.18 (dd, 1H), 5.60 (s, 1H), 6.95 (m, 1H), 7.00 (s, 2H), 7.15-7.38 (m, 7H), 7.53 (s, 1H), 7.68 (m, 1H), 8.00 (m, 2H).

Intermediate F143

Trifluoroacetic acid/6-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl)-N-[2-(2,5-dioxo-2,5-dihydro-1H-pyrrol-1-yl)ethyl]hexanamide (1:1)

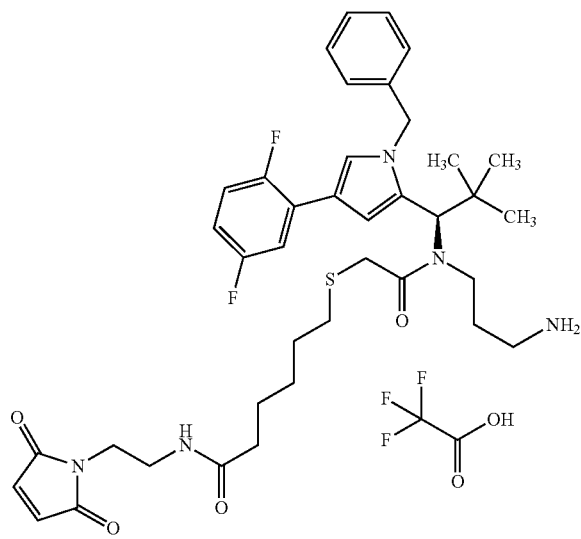 [SMILES: CC(C)(C)[C@H](c1cc(-c2cc(F)ccc2F)cn1Cc1ccccc1)N(CCCN)C(=O)CSCCCCCC(=O)NCCN1C(=O)C=CC1=O ; O=C(O)C(F)(F)F]

30.0 mg (0.05 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate and 13.5 mg (0.07 mmol) of 6-(acetylsulphanyl)hexanoic acid were initially charged in 2.0 ml of methanol with a drop of water. 23.0 mg (0.17 mmol) of potassium carbonate were added. The reaction mixture was stirred at 50° C. for 4 h. Ethyl acetate was added to the reaction mixture. The organic phase was washed with saturated NaCl solution and dried over magnesium sulphate. The solvent was evaporated under reduced pressure. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 54.2 mg (90% of theory) of the compound 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaicosan-20-oic acid.

LC-MS (Method 1): $R_t$=1.49 min; MS (ESIpos): m/z=1106 (M+H)$^+$.

54.0 mg (0.07 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaicosan-20-oic acid and 16.7 mg (0.09 mmol) of 1-(2-\minoethyl)-1H-pyrrole-2,5-dione hydrochloride (1:1) were initially charged in 3.0 ml of acetonitrile, and 75.0 mg (0.58 mmol) of N,N-diisopropylethylamine were added. 60.0 mg (0.09 mmol) of T3P (50% in acetonitrile) were added and the mixture was stirred at RT overnight. The reaction was quenched with water and the reaction mixture was purified directly by preparative RP-HPLC (column: Reprosil 125× 30; 10μ, flow rate: 50 ml/min, MeCN/water). The solvents were evaporated under reduced pressure and the residue was dried under high vacuum. This gave 42.8 mg (68% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{[(6-{[2-(2,5-dioxo-2,5-dihydro-1H-pyrrol-1-yl)ethyl]amino}-6-oxohexyl)sulphanyl]acetyl}amino)propyl]carbamate.

LC-MS (Method 1): $R_t$=1.48 min; MS (ESIpos): m/z=866 (M+H)$^+$.

20.0 mg (0.02 mmol) of 2-(trimethylsilyl)ethyl [3-({(1R)-1-[1-benzyl-4-(2,5-difluorophenyl)-1H-pyrrol-2-yl]-2,2-dimethylpropyl}{[(6-{[2-(2,5-dioxo-2,5-dihydro-1H-pyrrol-1-yl)ethyl]amino}-6-oxohexyl)sulphanyl]acetyl}amino)propyl]carbamate were dissolved in 2.0 ml of trifluoroethanol, and 4.7 mg (0.04 mmol) of zinc dichloride were added. The reaction mixture was stirred at 50° C. overnight, and 10.1 mg (0.04 mmol) of ethylenediamine-N,N,N',N'-tetraacetic acid were then added and the mixture was stirred for 10 min Water (0.1% TFA) was added and the reaction mixture was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.2 mg (48% of theory) of the title compound.

LC-MS (Method 1): $R_t$=0.98 min; MS (ESIpos): m/z=722 (M+H)$^+$.

Intermediate F144

Trifluoroacetic acid/N-(3-aminopropyl)-N-{(1R)-1-[1-benzyl-4-(2,5-difluorophenyl)-1H-imidazol-2-yl]-2,2-dimethylpropyl}-6-(2,5-dioxo-2,5-dihydro-1H-pyrrol-1-yl)hexanamide (1:1)

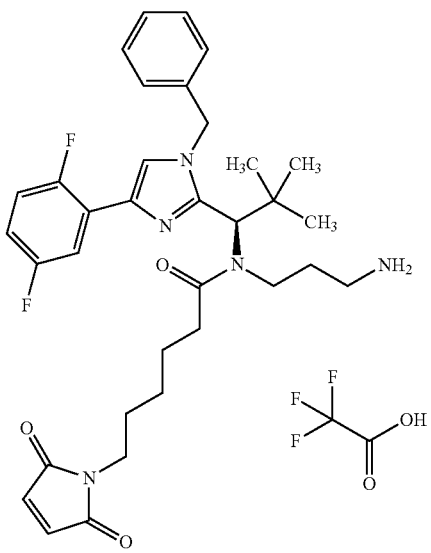 [SMILES: CC(C)(C)[C@H](c1nc(-c2cc(F)ccc2F)cn1Cc1ccccc1)N(CCCN)C(=O)CCCCCN1C(=O)C=CC1=O ; O=C(O)C(F)(F)F]

50.0 mg (0.1 mmol) of tert-butyl [3-({(1R)-1-[1-benzyl-4-(2,5-difluorophenyl)-1H-imidazol-2-yl]-2,2-dimethylpropyl}amino)propyl]carbamate (Intermediate C15) were initially charged in 2.0 ml of dichloromethane, and 22.7 mg (0.22 mmol) of triethylamine and 49.3 mg (0.22 mmol) of 6-(2,5-dioxo-2,5-dihydro-1H-pyrrol-1-yl) hexanoyl chloride (Intermediate L60) WISV1648-1-1 were added. The reaction mixture was stirred at RT overnight. Every 2 h (three times) 1 equivalent of Intermediate L60 and 1.2 equivalents of triethylamine were added, and the mixture was then stirred at RT overnight. This procedure was repeated two more times. The solvent was removed under reduced pressure and the residue was purified by preparative RP-HPLC (column: Reprosil 125×30; 10μ, flow rate: 50 ml/min, MeCN/water). The solvents were evaporated under reduced pressure and the residue was dried under high vacuum. This gave 30.9 mg (43% of theory) of the compound tert-butyl [3-({(1R)-1-[1-benzyl-4-(2,5-difluorophenyl)-1H-imidazol-2-yl]-2,2-dimethylpropyl}[6-(2,5-dioxo-2,5-dihydro-1H-pyrrol-1-yl)hexanoyl]amino)propyl] carbamate.

LC-MS (Method 1): $R_t$=1.51 min; MS (ESIpos): m/z=706 (M+H)$^+$.

24.6 mg (0.04 mmol) of tert-butyl [3-({(1R)-1-[1-benzyl-4-(2,5-difluorophenyl)-1H-imidazol-2-yl]-2,2-dimethylpropyl}[6-(2,5-dioxo-2,5-dihydro-1H-pyrrol-1-yl)hexanoyl] amino)propyl]carbamate were dissolved in 3.0 ml of dichloromethane, 79.5 mg (0.7 mmol) of TFA were added and the mixture was stirred at RT for 6 h. Another 79.5 mg (0.7 mmol) of TFA were added and the mixture was stirred at RT overnight. The solvent was removed under reduced pressure and the residue was co-distilled three times with dichloromethane. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 24.2 mg (97% of theory) of the title compound.

LC-MS (Method 1): $R_t$=1.02 min; MS (ESIpos): m/z=606 (M+H)$^+$.

Intermediate F145

Trifluoroacetic acid/6-({2-[(3-aminopropyl){(1R)-1-[1-benzyl-4-(2,5-difluorophenyl)-1H-imidazol-2-yl]-2,2-dimethylpropyl}amino]-2-oxoethyl}sulphanyl)-N-[2-(2,5-dioxo-2,5-dihydro-1H-pyrrol-1-yl)ethyl] hexanamide

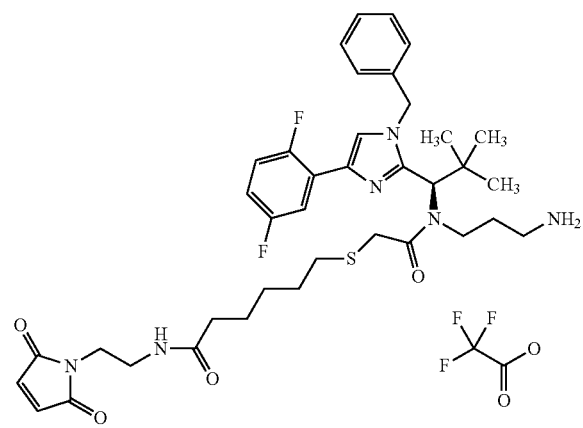 [SMILES: CC(C)(C)[C@H](c1nc(-c2cc(F)ccc2F)cn1Cc1ccccc1)N(CCCN)C(=O)CSCCCCCC(=O)NCCN1C(=O)C=CC1=O ; O=C(O)C(F)(F)F]

90.0 mg (0.15 mmol) of tert-butyl {3-[{(1R)-1-[1-benzyl-4-(2,5-difluorophenyl)-1H-imidazol-2-yl]-2,2-dimethylpropyl}(chloroacetyl)amino]propyl}carbamate (Intermediate C16) and 43.6 mg (0.23 mmol) of 6-(acetylsulphanyl) hexanoic acid were initially charged in 9.0 ml of methanol with a drop of water, and 73.9 mg (0.54 mmol) of potassium carbonate were added. The reaction mixture was stirred at RT for 4 h, and ethyl acetate was then added. The organic phase was washed with water/saturated NaCl solution and with saturated NaCl solution. The organic phase was dried over magnesium sulphate and the solvents were evaporated under reduced pressure. The residue was purified on silica gel (mobile phase: dichloromethane/methanol 100:2). The solvents were evaporated under reduced pressure and the residue was dried under high vacuum. This gave 98.7 mg (83% of theory) of the compound 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid.

LC-MS (Method 1): $R_t$=1.44 min; MS (ESIpos): m/z=701 (M+H)$^+$.

20.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid and 6.5 (0.04 mmol) of 1-(2-aminoethyl)-1H-pyrrole-2,5-dione hydrochloride (1:1) were initially charged in 1.5 ml of acetonitrile, and 23.6 mg (0.04 mmol) of T3P and 29.5 mg (0.23 mmol) of N,N-diisopropylethylamine were added. The reaction mixture was stirred at RT overnight, and water was then added. The reaction mixture was purified by preparative RP-HPLC (column: Reprosil 250× 30; 10μ, flow rate: 50 ml/min, MeCN/water). The solvents were evaporated under reduced pressure and the residue was dried under high vacuum. This gave 16.7 mg (99% of theory) of the compound tert-butyl [3-({(1R)-1-[1-benzyl-4-(2,5-difluorophenyl)-1H-imidazol-2-yl]-2,2-dimethylpropyl {[(6-[2-(2,5-dioxo-2,5-dihydro-1H-pyrrol-1-yl)ethyl] amino}-6-oxohexyl)sulphanyl]acetyl}amino)propyl] carbamate.

LC-MS (Method 1): $R_t$=1.40 min; MS (ESIpos): m/z=823 (M+H)$^+$.

14.8 mg (0.02 mmol) of tert-butyl [3-({(1R)-1-[1-benzyl-4-(2,5-difluorophenyl)-1H-imidazol-2-yl]-2,2-dimethylpropyl}{[(6-{-[2-(2,5-dioxo-2,5-dihydro-1H-pyrrol-1-yl)ethyl] amino}-6-oxohexyl)sulphanyl]acetyl}amino)propyl] carbamate were dissolved in 1.5 ml of dichloromethane, and 41.0 mg (0.36 mmol) of TFA were added. The reaction mixture was stirred at RT overnight. Then, two more times in each case 41.0 mg (0.36 mmol) of TFA were added and the mixture was stirred at RT overnight. The solvent was evaporated under reduced pressure and the residue was purified by preparative RP-HPLC (column: Reprosil 250× 30; 10μ, flow rate: 50 ml/min, MeCN/water, 0.1% TFA). The solvents were evaporated under reduced pressure and the residue was taken up in 1,4-dioxane and water and lyophilized. This gave 2.9 mg (19% of theory) of the title compound.

LC-MS (Method 1): $R_t$=0.93 min; MS (ESIpos): m/z=723 (M+H)$^+$.

Intermediate F146

R/S-[2-([(3S)-3-Amino-3-carboxypropyl]{(1R)-1-[1-benzyl-4-(2,5-difluorophenyl)-1H-pyrrol-2-yl]-2,2-dimethylpropyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine/trifluoroacetic acid (1:1)

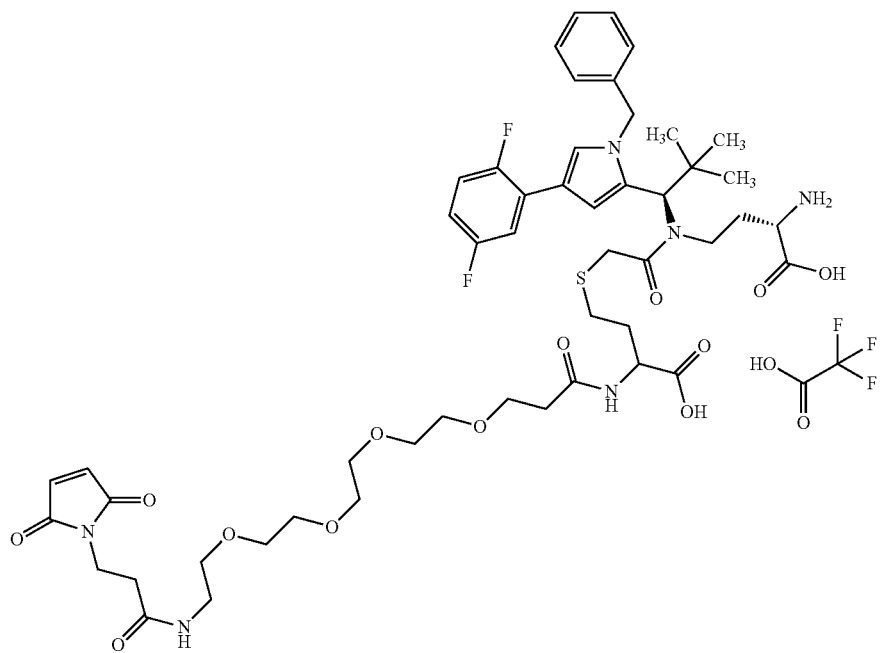

25.0 mg (28.12 µmol) of R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine (Intermediate C12) and 15.9 mg (30.93 µmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 2.0 ml of DMF, and 11.4 mg (112.48 µmol) of 4-methylmorpholine were added. The reaction mixture was stirred at RT overnight. 7.6 mg (0.13 mmol) of acetic acid were added and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 23.9 mg (59% of theory) of the compound R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]-N-[19-(2,5-dioxo-2,5-dihydro-1H-pyrrol-1-yl)-17-oxo-4,7,10,13-tetraoxa-16-azanonadecan-1-oyl]homocysteine.

LC-MS (Method 1): $R_t$=1.26 min; MS (ESIpos): m/z=1173 (M+H)$^+$.

11.8 mg (8.23 µmol) of R/S-[(8S)-11-{(1R)-1-[1-benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]-N-[19-(2,5-dioxo-2,5-dihydro-1H-pyrrol-1-yl)-17-oxo-4,7,10,13-tetraoxa-16-azanonadecan-1-oyl]homocysteine were dissolved in trifluoroethanol, and 1.7 mg (12.35 µmol) of zinc dichloride were added. The reaction mixture was stirred at 50° C. overnight. 3.6 mg (0.01 mmol) of ethylenediamine-N,N,N',N'-tetraacetic acid were added, the reaction mixture was stirred briefly and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 5.8 mg (62% of theory) of the title compound.

LC-MS (Method 4): $R_t$=1.20 min; MS (ESIpos): m/z=1029 (M+H)$^+$.

Intermediate F147

Trifluoroacetic acid/N-(3-aminopropyl)-N-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10-oxo-3,6-dioxa-16-thia-9-azaoctadecan-18-amide (1:1)

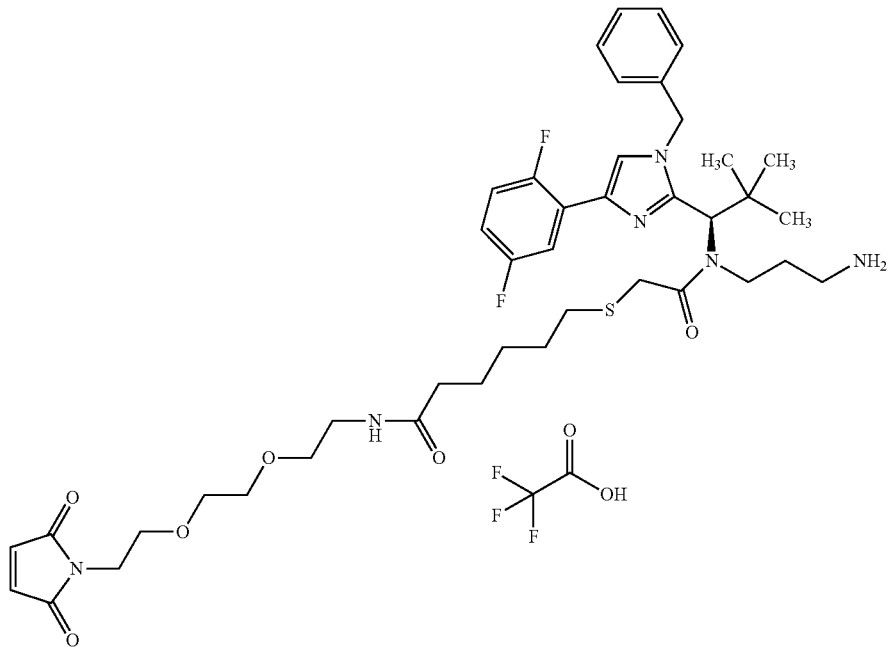

15.0 mg (0.03 mmol) of 9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazaoctadecan-18-oic acid (Intermediate C13) were initially charged in 1.5 ml of acetonitrile, and 22.1 mg (0.17 mmol) of N,N-diisopropylethylamine and then 17.7 mg (0.03 mmol) of T3P were added. The mixture was stirred at RT for 5 min, and 9.5 mg (0.03 mmol) of trifluoroacetic acid/1-{2-[2-(2-aminoethoxy)ethoxy]ethyl}-1H-pyrrole-2,5-dione (1:1) (Intermediate L59) were then added. The reaction mixture was stirred at RT overnight and quenched with water. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 14.8 mg (57% of theory) of the compound tert-butyl [19-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10,18-dioxo-3,6-dioxa-16-thia-9,19-diazadocosan-22-yl]carbamate.

LC-MS (Method 1): $R_t$=1.40 min; MS (ESIpos): m/z=911 (M+H)⁺.

14.2 mg (0.02 mmol) of tert-butyl [19-{(1R)-1-[1-benzyl-4-(2,5-difluorophenyl)-1H-imidazol-2-yl]-2,2-dimethylpropyl}-1-(2,5-dioxo-2,5-dihydro-1H-pyrrol-1-yl)-10,18-dioxo-3,6-dioxa-16-thia-9,19-diazadocosan-22-yl]carbamate were dissolved in 1.5 ml of dichloromethane, 35.5 mg (0.31 mmol) of TFA were added and the mixture was stirred at RT overnight. Another 71.0 mg (0.62 mmol) of TFA were added and the mixture was stirred at RT overnight. The solvents were evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 14.0 mg (97% of theory) of the title compound.

LC-MS (Method 1): $R_t$=1.01 min; MS (ESIpos): m/z=811 (M+H)⁺.

Intermediate F148

Trifluoroacetic acid/6-({2-[(3-aminopropyl){(1R)-1-[1-benzyl-4-(2,5-difluorophenyl)-1H-imidazol-2-yl]-2,2-dimethylpropyl}amino]-2-oxoethyl}sulphinyl)-N-[2-(2,5-dioxo-2,5-dihydro-1H-pyrrol-1-yl)ethyl]hexanamide (1:1)

The title compound was formed as a by-product in the synthesis of Intermediate F145. This gave 8.1 mg (53% of theory) of the title compound.

LC-MS (Method 1): $R_t$=1.25 min; MS (ESIpos): m/z=739 [M+H]⁺.

Intermediate F149

Trifluoroacetic acid/R/S-{2-[(3-aminopropyl){(1R)-1-[1-benzyl-4-(2,5-difluorophenyl)-1H-imidazol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]homocysteine (1:1)

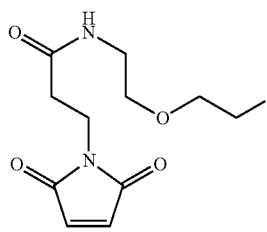

20.0 mg (24.94 μmol) of R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]homocysteine (Intermediate C14) and 14.1 mg (27.44 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were initially charged in 1.0 ml of DMF, and 5.1 mg (49.88 μmol) of 4-methylmorpholine were added. The reaction mixture was stirred overnight. 3.7 mg (0.06 mmol) of acetic acid were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 18.2 mg (67% of theory) of the compound R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine.

LC-MS (Method 1): $R_t$=1.23 min; MS (ESIpos): m/z=1086 (M+H)⁺.

17.6 mg (0.02 mmol) of R/S-[2-({(1R)-1-[1-benzyl-4-(2,5-difluorophenyl)-1H-imidazol-2-yl]-2,2-dimethylpropyl}{3-[(tert-butoxycarbonyl)amino]propyl}amino)-2-oxoethyl]-N-[19-(2,5-dioxo-2,5-dihydro-1H-pyrrol-1-yl)-17-oxo-4,7,10,13-tetraoxa-16-azanonadecan-1-oyl]homocysteine were dissolved in 1.5 ml of dichloromethane, 37.0 mg (0.32 mmol) of TFA were added, and the mixture was stirred at RT overnight. Another 74.0 mg (0.64 mmol) of TFA were added and the mixture was stirred at RT overnight. The solvents were evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was taken up in a little water and lyophilized. This gave 16.0 mg (90% of theory) of the title compound.

LC-MS (Method 1): $R_t$=0.92 min; MS (ESIpos): m/z=986 (M+H)⁺.

Intermediate F150

Trifluoroacetic acid/N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-[2-({2-[(3-aminopropyl){(1R)-1-[1-benzyl-4-(2,5-difluorophenyl)-1H-imidazol-2-yl]-2,2-dimethylpropyl}amino]-2-oxoethyl}sulphanyl)ethyl]-L-alaninamide (1:1)

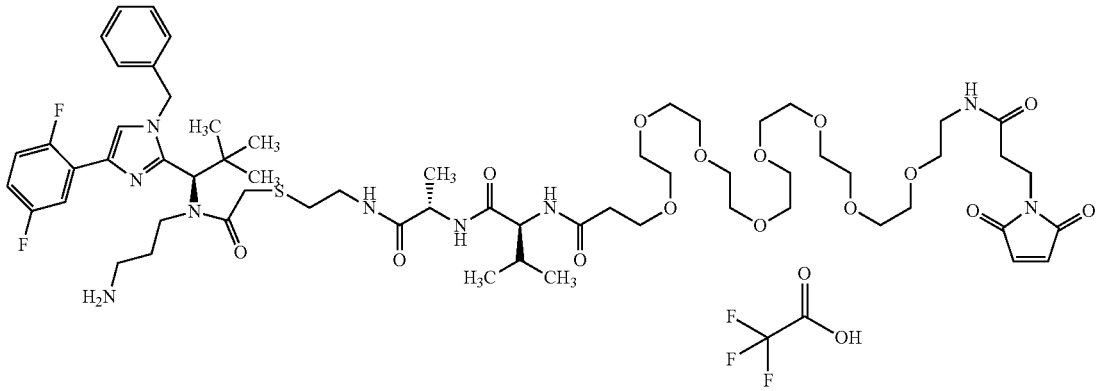 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)NCCSCC(=O)N(CCCN)[C@@H](c1nc(-c2cc(F)ccc2F)cn1Cc1ccccc1)C(C)(C)C ; O=C(O)C(F)(F)F]

Under argon and at 0° C., 10.0 mg (0.02 mmol) of trifluoroacetic acid/tert-butyl [3-({[(2-aminoethyl)sulphanyl]acetyl}{(1R)-1-[1-benzyl-4-(2,5-difluorophenyl)-1H-imidazol-2-yl]-2,2-dimethylpropyl}amino)propyl]carbamate (Intermediate C20) in 1.0 ml of DMF were treated with 12.1 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-L-alanine (Intermediate L25), 2.2 mg (0.02 mmol) of HOAt and 7.6 mg (0.02 mmol) of HATU. 5.5 µl (0.03 mmol) of N,N-diisopropylethylamine were then added, and the reaction was stirred at RT overnight. 1.8 µl of HOAc were added, and the reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 10.4 mg (48% of theory) of the compound N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-(9-{(1R)-1-[1-benzyl-4-(2,5-difluorophenyl)-1H-imidazol-2-yl]-2,2-dimethylpropyl}-2,2-dimethyl-4,10-dioxo-3-oxa-12-thia-5,9-diazatetradecan-14-yl)-L-alaninamide LC-MS (Method 4): $R_t$=1.60 min; MS (ESIpos): m/z=687.5 [M+2]$^{2+}$.

9.5 mg (0.01 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-N-(9-(1R)-1-[1-benzyl-4-(2,5-difluorophenyl)-1H-imidazol-2-yl]-2,2-dimethylpropyl-2,2-dimethyl-4,10-dioxo-3-oxa-12-thia-5,9-diazatetradecan-14-yl)-L-alaninamide were initially charged in 1.0 ml of dichloromethane, 15.8 mg (0.14 mmol) of TFA were added and the mixture was stirred overnight. Another 31.6 mg (0.28 mmol) of TFA were added, and the mixture was stirred overnight. The solvent was evaporated under reduced pressure and the residue was purified by preparative RP-HPLC (column: Reprosil 250×30; 10µ, flow rate: 50 ml/min, MeCN/water, 0.1% TFA). The solvents were evaporated under reduced pressure and the residue was taken up in a little water and lyophilized. This gave 10.2 mg (98% of theory) of the title compound.

LC-MS (Method 4): $R_t$=1.13 min; MS (ESIpos): m/z=637.5 [M+2H]$^{2+}$.

Intermediate F151

N-[19-(2,5-Dioxo-2,5-dihydro-1H-pyrrol-1-yl)-17-oxo-4,7,10,13-tetraoxa-16-azanonadecan-1-oyl]-L-valyl-N-(3-{(2S)-5-(2,5-difluorophenyl)-3-[methoxy(methyl)carbamoyl]-2-phenyl-2,3-dihydro-1,3,4-thiadiazol-2-yl}propyl)-L-alaninamide

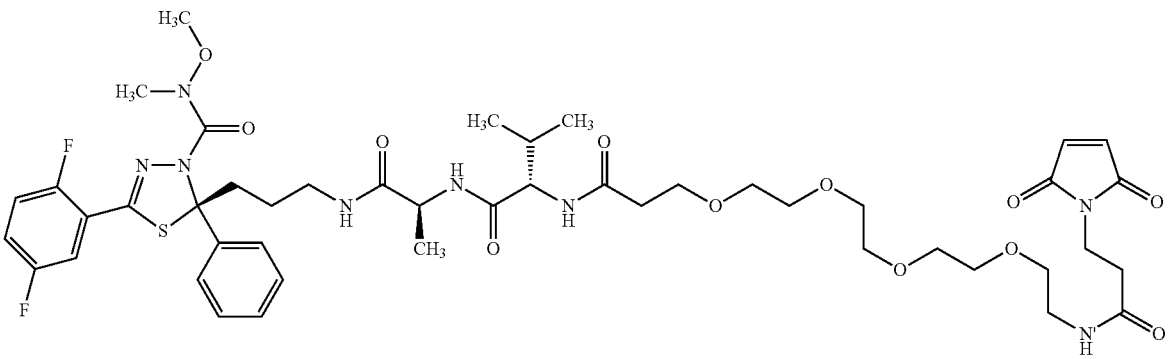

5.0 mg (0.01 mmol) of (2S)-2-(3-aminopropyl)-5-(2,5-difluorophenyl)-N-methoxy-N-methyl-2-phenyl-1,3,4-thiadiazol-3(2H)-carboxamide were initially charged in 1.0 ml of acetonitrile, and 7.7 mg (0.06 mmol) of N,N-diisopropylethylamine and 9.8 (0.02 mmol) of T3P were added. The mixture was stirred at RT for 5 min, and 9.1 mg (0.02 mmol) of N-[19-(2,5-dioxo-2,5-dihydro-1H-pyrrol-1-yl)-17-oxo-4,7,10,13-tetraoxa-16-azanonadecan-1-oyl]-L-valyl-L-alanine (Intermediate L44) were then added. The reaction mixture was stirred at RT overnight. Water was added and the reaction mixture was purified directly by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 4.3 mg (35% of theory) of the title compound.

LC-MS (Method 1): $R_t$=1.02 min; MS (ESIpos): m/z=989 [M+H]$^+$.

Intermediate F152

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N-(3-{(2S)-5-(2,5-difluorophenyl)-3-[methoxy(methyl)carbamoyl]-2-phenyl-2,3-dihydro-1,3,4-thiadiazol-2-yl}propyl)-L-alaninamide

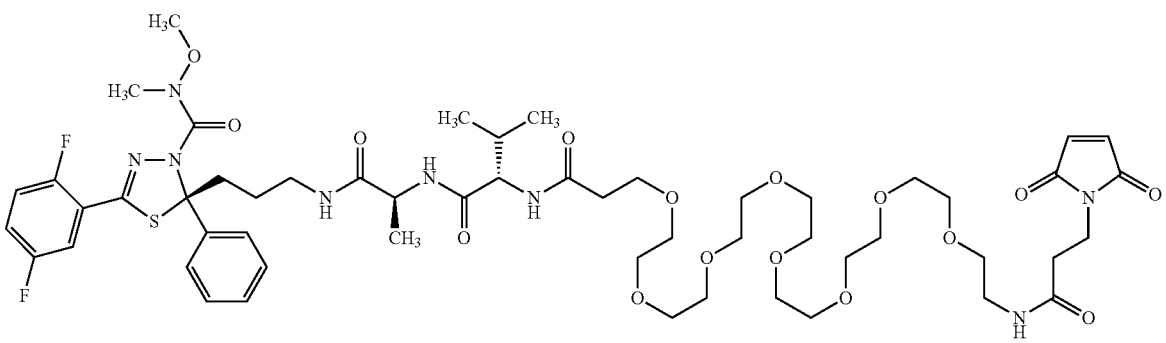 [SMILES: CON(C)C(=O)N1N=C(c2cc(F)ccc2F)S[C@@]1(CCCNC(=O)[C@H](C)NC(=O)[C@@H](NC(=O)CCOCCOCCOCCOCCOCCOCCOCCOCCNC(=O)CCN1C(=O)C=CC1=O)C(C)C)c1ccccc1]

5.0 mg (0.01 mmol) of (2S)-2-(3-aminopropyl)-5-(2,5-difluorophenyl)-N-methoxy-N-methyl-2-phenyl-1,3,4-thiadiazol-3(2H)-carboxamide were initially charged in 1.0 ml of acetonitrile, and 7.7 mg (0.06 mmol) of N,N-diisopropylethylamine and 9.8 (0.02 mmol) of T3P were added. The mixture was stirred at RT for 5 min, and 11.8 mg (0.02 mmol) of N-[31-(2,5-dioxo-2,5-dihydro-1H-pyrrol-1-yl)-29-oxo-4,7,10,13,16,19,22,25-octaoxa-28-azahentriacontan-1-oyl]-L-valyl-L-alanine (Intermediate L25) were then added. The reaction mixture was stirred at RT overnight. Water was added and the reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.7 mg (34% of theory) of the title compound.

LC-MS (Method 4): $R_t$=1.34 min; MS (ESIpos): m/z=1165 [M+H]$^+$.

Intermediate F153

Trifluoroacetic acid/(2S)-2-amino-4-({(1R)-1-[1-benzyl-4-(2,5-difluorophenyl)-1H-pyrrol-2-yl]-2,2-dimethylpropyl}[(2S)-2-hydroxypropanoyl]amino)-N-(2-[(2,5-dioxo-2,5-dihydro-1H-pyrrol-1-yl)acetyl]amino}ethyl)butanamide (1:1)

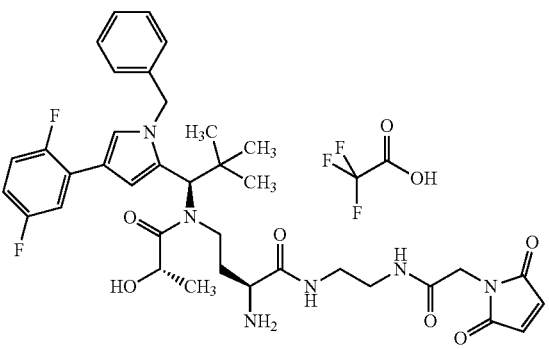 [SMILES: C[C@H](O)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

The synthesis was carried out analogously to Intermediate F104 from Intermediate C60.

LC-MS (Method 1): $R_t$=1.1 min; MS (ESIpos): m/z=707 (M+H)$^+$.

Intermediate F154

N⁶-(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)-N²-{N-[6-(2,5-dioxo-2,5-dihydro-1H-pyrrol-1-yl)hexanoyl]-L-valyl-L-alanyl}-L-lysine/trifluoroacetic acid (1:1)

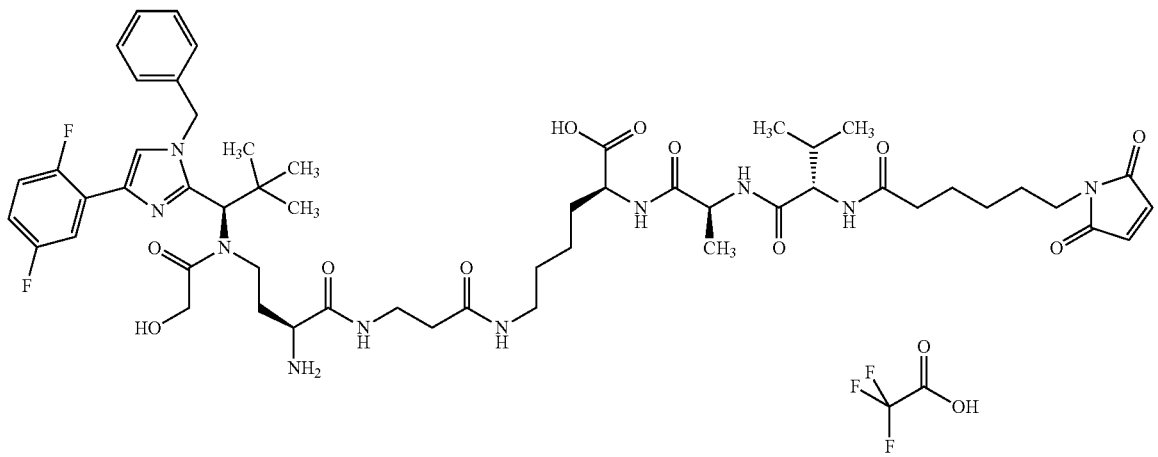 [SMILES: CC(C)[C@H](NC(=O)CCCCCN1C(=O)C=CC1=O)C(=O)N[C@@H](C)C(=O)N[C@@H](CCCCNC(=O)CCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to Intermediate F2 from 10 mg (0.015 mmol) of Intermediate C8 and 15 mg (0.022 mmol) of Intermediate L6.

HPLC (Method 11): $R_t$=1.91 min;
LC-MS (Method 1): $R_t$=0.89 min; MS (ESIpos): m/z=1077 (M+H)⁺.

Intermediate F155

N⁶-(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N²-{N-[6-(2,5-dioxo-2,5-dihydro-1H-pyrrol-1-yl)hexanoyl]-L-valyl-L-alanyl}-L-lysine/trifluoroacetic acid (1:1)

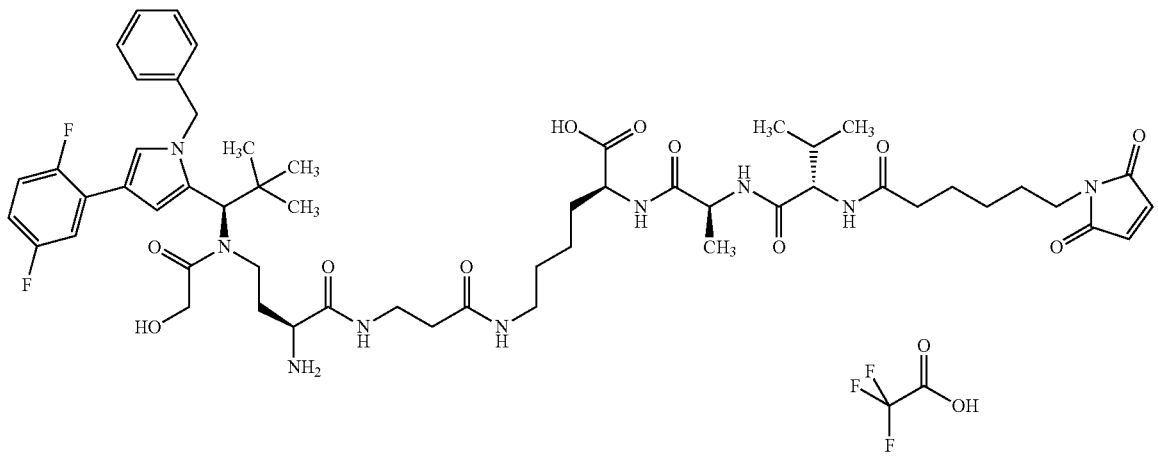 [SMILES: CC(C)[C@H](NC(=O)CCCCCN1C(=O)C=CC1=O)C(=O)N[C@@H](C)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 14 mg (0.019 mmol) of Intermediate C61 with 15 mg (0.021 mmol) of Intermediate L61 in the presence of 8.7 mg (0.023 mmol) of HATU and 17 μl of N,N-diisopropylethylamine and subsequent deprotection with zinc chloride in trifluoroethanol as described for Intermediate F119. Purification by preparative HPLC gave 13 mg (59% of theory over 2 steps) of the title compound.

LC-MS (Method 1): $R_t$=0.86 min; MS (ESIpos): m/z=1076 (M+H)$^+$.

Intermediate F156

N-(Bromoacetyl)-L-valyl-L-alanyl-N$^6$-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine/trifluoroacetic acid (1:1)

adjusted with trifluoroacetic acid to pH 2 and purified by preparative HPLC. After concentration of the appropriate fractions, the residue was taken up in 15 ml of a 5% strength trifluoroacetic acid solution in DCM and stirred at RT for 2 h. The mixture was then concentrated with slight cooling and the residue was lyophilized from acetonitrile/water 1:1. 53 mg (50% of theory) of this intermediate were obtained over 2 steps.

LC-MS (Method 1): $R_t$=0.72 min; MS (ESIpos): m/z=537 and 539 (M+H)$^+$.

For the synthesis of the title compound, 18 mg (0.027 mmol) of this intermediate were taken up in 4 ml of DMF, and 16 mg (0.025 mmol) of Intermediate C61 and 19 mg of HATU and 9 μl of N,N-diisopropylethylamine were added. After 5 min of stirring at RT, a few drops of trifluoroacetic acid were added and the reaction was purified by preparative HPLC. After concentration of the appropriate fractions and lyophilization from acetonitrile/water 1:1, the intermediate

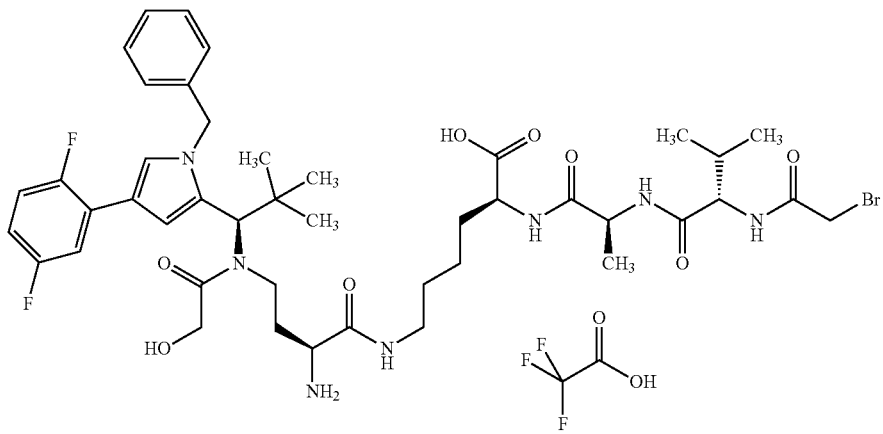

First, the tripeptide derivative 2-trimethylsilyl)ethyl-L-valyl-L-alanyl-N$^6$-(tert-butoxycarbonyl)-L-lysinate was prepared from N$^2$-[(benzyloxy)carbonyl]-N$^6$-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis).

84 mg (0.163 mmol) of this Intermediate were taken up in 2.5 ml of DMF, and 58 mg (0.244 mmol) of 1-(2-bromoacetoxy)pyrrolidine-2,5-dione were added. After 10 min of stirring at RT, the mixture was concentrated, the residue was taken up in acetonitrile/water 1:1 and the mixture was obtained was dissolved in 3 ml of 2,2,2-trifluoroethanol. Following addition of 4.8 mg (0.035 mmol) of zinc chloride, the reaction was stirred at 50° C. for 2.5 h. 10 mg (0.035 mmol) of ethylenediamine-N,N,N',N'-tetraacetic acid were then added, and the reaction was diluted with acetonitrile/water and filtered. Purification was carried out by preparative HPLC. Concentration of the appropriate fractions and lyophilization of the residue from acetonitrile/water gave 3.2 mg (13% of theory) of the title compound over 2 steps.

HPLC (Method 11): $R_t$=1.94 min;

LC-MS (Method 5): $R_t$=2.79 min; MS (ESIpos): m/z=932 and 934 (M+H)$^+$.

Intermediate F163

N-[6-(2,5-Dioxo-2,5-dihydro-1H-pyrrol-1-yl)hexanoyl]-L-valyl-L-alanyl-N6-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine/trifluoroacetic acid (1:1)

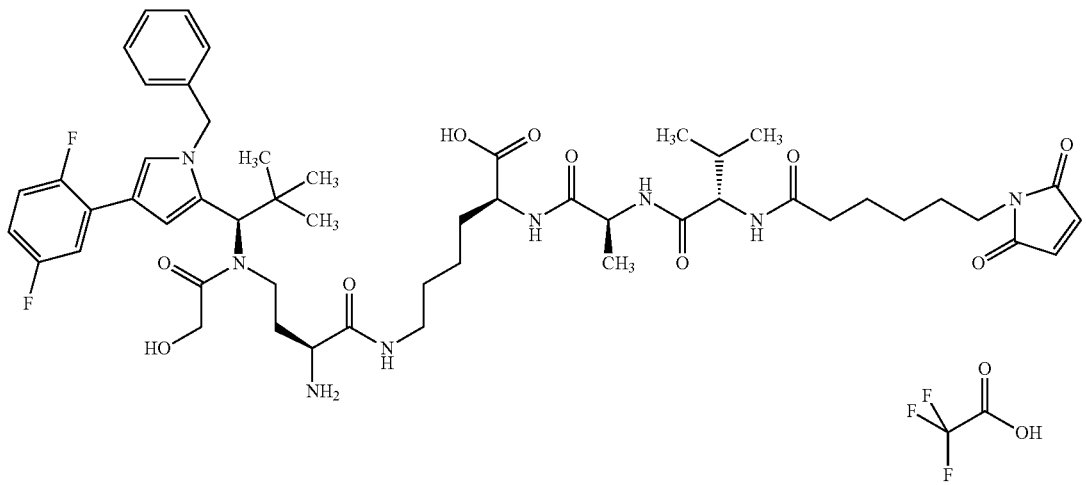 [SMILES: CC(C)[C@H](NC(=O)CCCCCN1C(=O)C=CC1=O)C(=O)N[C@@H](C)C(=O)N[C@@H](CCCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 37 mg (0.056 mmol) of Intermediate C58 and 41 mg (0.056 mmol) of Intermediate L61 in the presence of HATU and subsequent deblocking with zinc chloride as described for Intermediate F119. This gave 12 mg (19% of theory over 2 steps) of the title compound.

HPLC (Method 11): $R_t$=1.49 min;

LC-MS (Method 1): $R_t$=0.89 min; MS (ESIpos): m/z=1005 (M+H)$^+$.

Intermediate F164

N-[6-(2,5-Dioxo-2,5-dihydro-1H-pyrrol-1-yl)hexanoyl]-L-valyl-N5-carbamoyl-L-ornithyl-N6-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-lysine/trifluoroacetic acid (1:1)

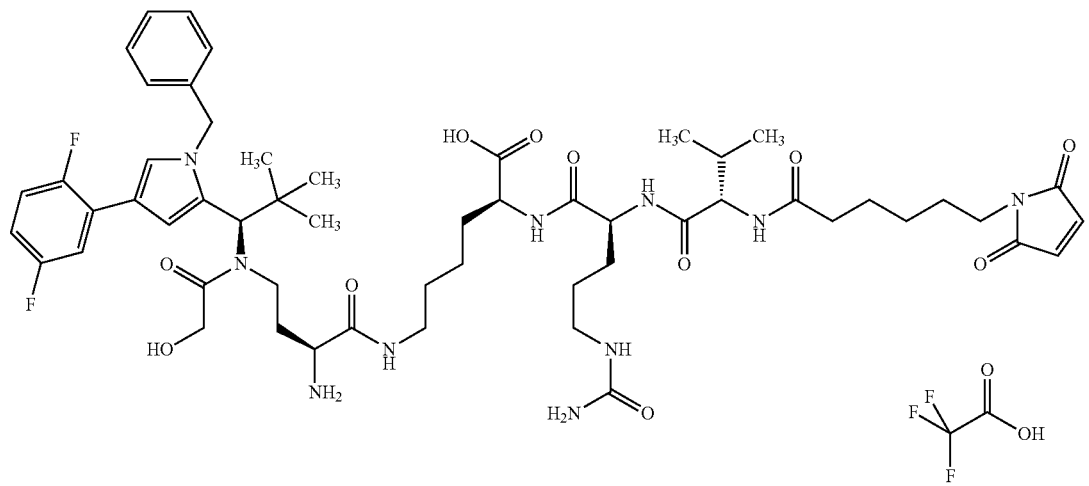 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

463

The title compound was prepared analogously to Intermediate F155 by coupling of 20 mg (0.030 mmol) of Intermediate C58 with 27 mg (0.033 mmol) of Intermediate L62 in the presence of HATU and N,N-diisopropylethylamine and subsequent deprotection with zinc chloride in trifluoroethanol.

HPLC (Method 11): $R_t$=1.92 min;
LC-MS (Method 1): $R_t$=0.87 min; MS (ESIpos): m/z=1091 (M+H)$^+$.

464

Intermediate F165

$N^6$-(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$-{N-[6-(2,5-dioxo-2,5-dihydro-1H-pyrrol-1-yl)hexanoyl]-L-valyl-N5-carbamoyl-L-ornithyl}-L-lysine/trifluoroacetic acid (1:1)

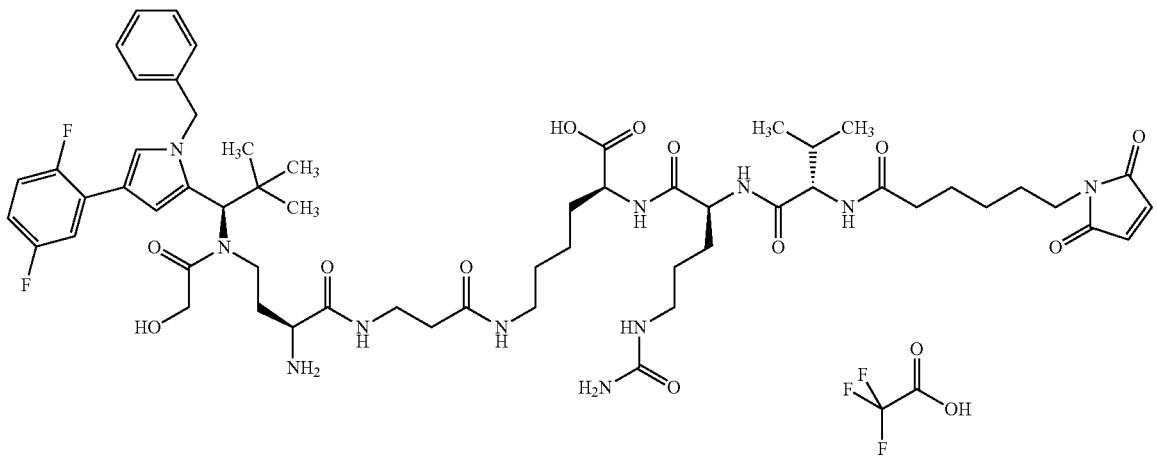 [SMILES: CC(C)[C@H](NC(=O)CCCCCN1C(=O)C=CC1=O)C(=O)N[C@@H](CCCNC(N)=O)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared analogously to Intermediate F155 by coupling of 15 mg (0.021 mmol) of Intermediate C61 with 18 mg (0.023 mmol) of Intermediate L62 in the presence of HATU and subsequent deprotection with zinc chloride in trifluoroethanol.

LC-MS (Method 1): $R_t$=0.88 min; MS (ESIpos): m/z=1162 (M+H)$^+$.

Intermediate F166

N-[6-(2,5-Dioxo-2,5-dihydro-1H-pyrrol-1-yl)hexanoyl]-L-valyl-$N^5$-carbamoyl-L-ornithyl-$N^6$-{[(1R,3S)-3-((2S)-2-amino-4-[{(1R)-1-[1-benzyl-4-(2,5-difluorophenyl)-1H-pyrrol-2-yl]-2,2-dimethylpropyl}(glycoloyl)amino]butanoyl amino)cyclopentyl]carbonyl}-L-lysine/trifluoroacetic acid (1:1)

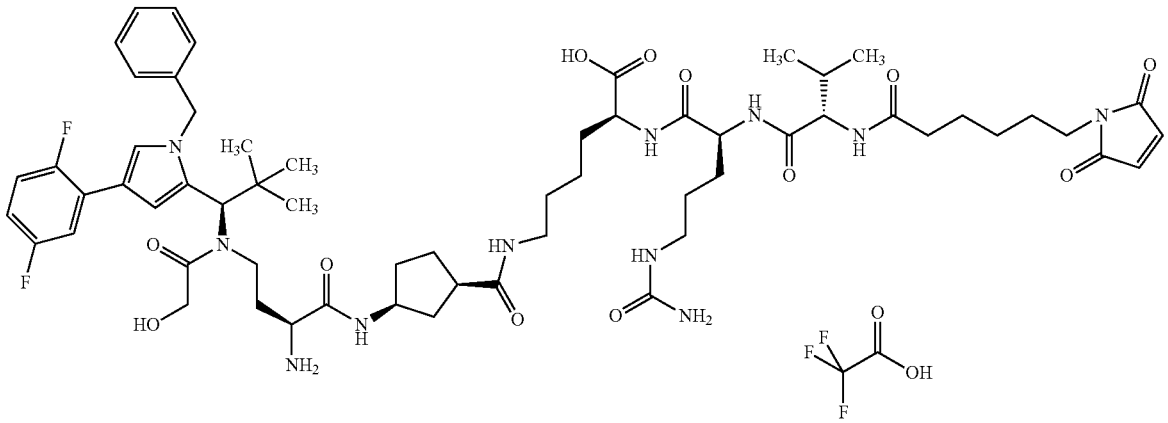 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H]1CC[C@H](NC(=O)[C@@H](N)CCN(C(=O)CO)[C@@H](c2cc(-c3cc(F)ccc3F)cn2Cc2ccccc2)C(C)(C)C)C1)C(=O)O ; O=C(O)C(F)(F)F]

First, trifluoroacetic acid/benzyl (1R,3S)-3-aminocyclopentanecarboxylate (1:1) was prepared from commercially available (1R,3S)-3-[(tert-butoxycarbonyl)amino]cyclopentanecarboxylic acid according to classical methods of peptide chemistry by esterification with benzyl alcohol using EDCI/DMAP and subsequent removal of the tert-butoxycarbonyl protective group with TFA in DCM.

51 mg (0.076 mmol) of this intermediate were taken up in 6 ml of DMF and coupled with 50 mg (0.076 mmol) of Intermediate C58 in the presence of HATU and N,N-diisopropylethylamine After purification by preparative HPLC, the intermediate was taken up in methanol and hydrogenated over 10% palladium on activated carbon at RT under hydrogen standard pressure for 2 h. The catalyst was then filtered off, the solvent was removed under reduced pressure and the product was purified by preparative HPLC. Lyophilization from dioxane gave 21 mg (34% of theory over 2 steps) of (1R,3S)-3-{[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]amino}cyclopentanecarboxylic acid.

The title compound was prepared analogously to Intermediate F155 by coupling of 10.5 mg (0.013 mmol) of this intermediate with 11.4 mg (0.014 mmol) of Intermediate L62 in the presence of HATU and subsequent deprotection with zinc chloride in trifluoroethanol. Purification by preparative HPLC gave 8.6 mg (48% of theory over 2 steps) of the title compound.

LC-MS (Method 1): $R_t$=0.88 min; MS (ESIpos): m/z=1203 (M+H)$^+$.

Intermediate F167

N-[6-(2,5-Dioxo-2,5-dihydro-1H-pyrrol-1-yl)hexanoyl]-L-valyl-L-alanyl-N$^6$-{[(1R,3S)-3-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}-L-lysine/trifluoroacetic acid (1:1)

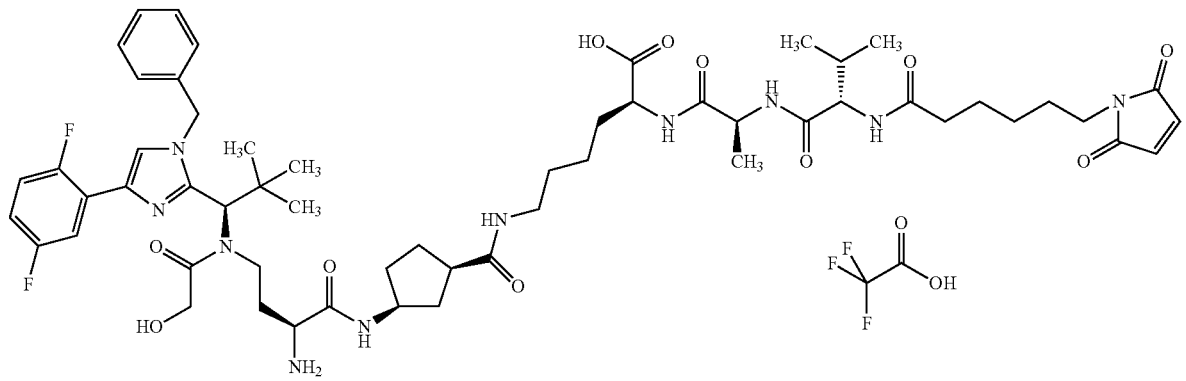 [SMILES: CC(C)[C@H](NC(=O)CCCCCN1C(=O)C=CC1=O)C(=O)N[C@@H](C)C(=O)N[C@@H](CCCCNC(=O)[C@@H]1CC[C@H](NC(=O)[C@@H](N)CCN(C(=O)CO)[C@@H](c2nc(-c3cc(F)ccc3F)cn2Cc2ccccc2)C(C)(C)C)C1)C(=O)O ; O=C(O)C(F)(F)F]

The title compound was prepared analogously to Intermediate F129 from 11 mg (0.016 mmol) of Intermediate C5 by reaction with 20 mg (0.024 mmol) of Intermediate L56 in the presence of 12 mg (0.032 mmol) of HATU and 14 µl of N,N-diisopropylethylamine and subsequent deprotection with trifluoroacetic acid. This gave 11 mg (46% of theory over 2 steps).

LC-MS (Method 4): $R_t$=1.13 min; MS (EIpos): m/z=1117 [M+H]$^+$.

Intermediate F168

N-[6-(2,5-Dioxo-2,5-dihydro-1H-pyrrol-1-yl)
hexanoyl]-L-valyl-L-alanyl-$N^6$-{[(1R,2S)-2-({(2S)-
2-amino-4-[{(1R)-1-[1-benzyl-4-(2,5-difluorophe-
nyl)-1H-pyrrol-2-yl]-2,2-dimethylpropyl}(glycoloyl)
amino]butanoyl}amino)cyclopentyl]carbonyl}-L-
lysine/trifluoroacetic acid (1:1)

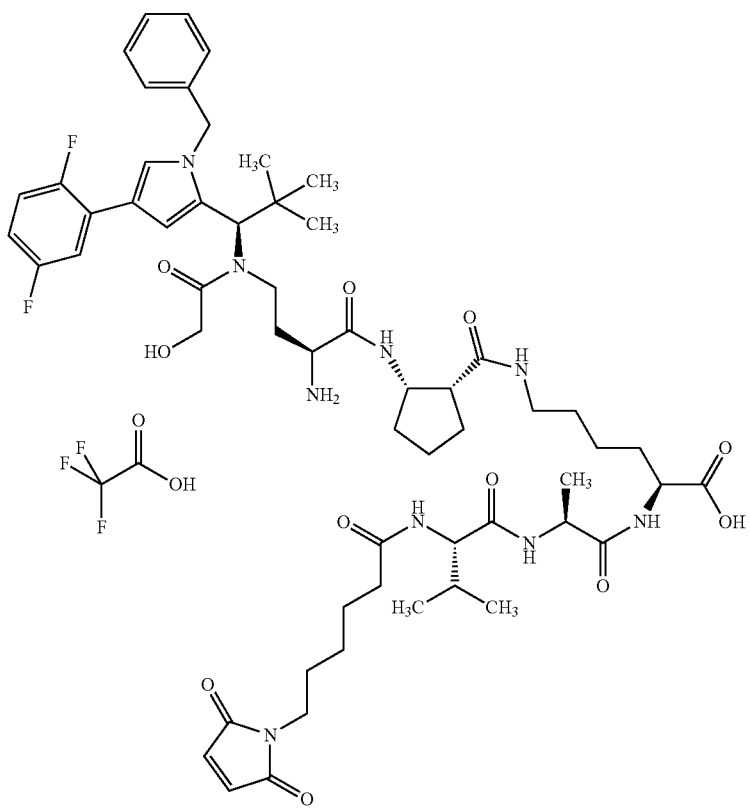 [SMILES: CC(C)[C@H](NC(=O)CCCCCN1C(=O)C=CC1=O)C(=O)N[C@@H](C)C(=O)N[C@@H](CCCCNC(=O)[C@@H]1CCC[C@@H]1NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

First, trifluoroacetic acid/benzyl (1R,2S)-2-aminocyclo-pentanecarboxylate (1:1) was prepared from commercially available (1R,2S)-2-[(tert-butoxycarbonyl) amino]cyclo-pentanecarboxylic acid according to classical methods of peptide chemistry by esterification with benzyl alcohol using EDCI/DMAP and subsequent removal of the tert-butoxy-carbonyl protective group with TFA in DCM.

102 mg (0.305 mmol) of this intermediate were taken up in 12 ml of DMF and coupled with 100 mg (0.152 mmol) of Intermediate C58 in the presence of HATU and N,N-diiso-propylethylamine After purification by preparative HPLC, the intermediate was taken up in methanol and hydrogenated over 10% palladium on activated carbon at RT under hydro-gen standard pressure for 2 h. The catalyst was then filtered off, the solvent was removed under reduced pressure and the product was purified by preparative HPLC. Lyophilization from acetonitrile/water 1:1 gave 70 mg (59% of theory over 2 steps) of (1R,2S)-2-{[(2S)-4-[{(1R)-1-[1-benzyl-4-(2,5-difluorophenyl)-1H-pyrrol-2-yl]-2,2-dimethylpropyl}(gly-coloyl)amino]-2-({[2-(trimethylsilyl)ethoxy] carbonyl}amino)butanoyl]amino}cyclopentanecarboxylic acid.

The title compound was then prepared by coupling of 20 mg (0.013 mmol) of this intermediate with 16.6 mg (0.023 mmol) of Intermediate L61 in the presence of 9.5 mg (0.025 mmol) of HATU and 18 µl of N,N-diisopropylethylamine and subsequent deprotection with zinc chloride in trifluo-roethanol as described for Intermediate F119. Purification by preparative HPLC gave 9.3 mg (30% of theory over 2 steps) of the title compound.

LC-MS (Method 1): $R_t$=0.98 min; MS (ESIpos): m/z=1116 (M+H)$^+$.

Intermediate F169

N-[6-(2,5-Dioxo-2,5-dihydro-1H-pyrrol-1-yl)hexanoyl]-L-valyl-N⁵-carbamoyl-L-ornithyl-N⁶-{[(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}-L-lysine/trifluoroacetic acid (1:1)

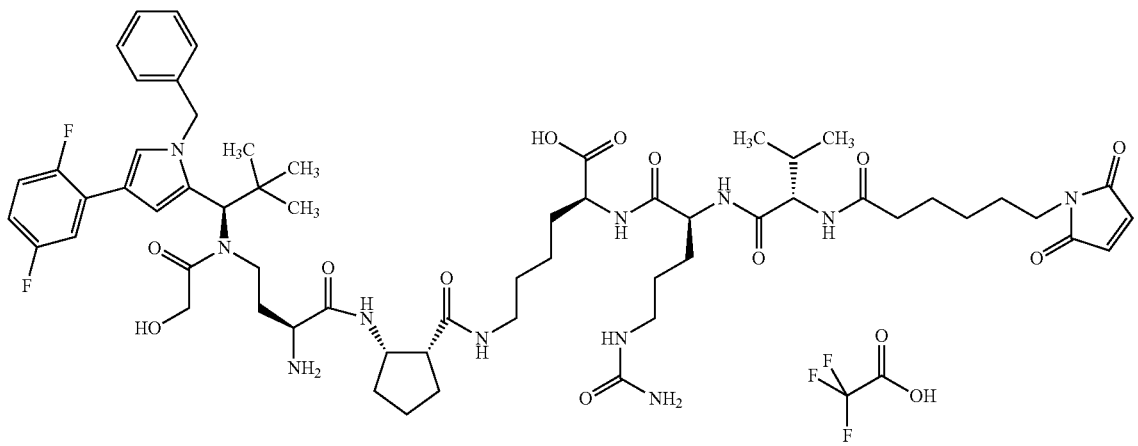 [SMILES: CC(C)[C@H](NC(=O)CCCCCN1C(=O)C=CC1=O)C(=O)N[C@@H](CCCNC(N)=O)C(=O)N[C@@H](CCCCNC(=O)[C@@H]1CCC[C@@H]1NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The synthesis of the title compound was carried out analogously to Intermediate F168 from Intermediates C58 and L62.

LC-MS (Method 1): $R_t$ =0.91 min; MS (ESIpos): m/z=1202 (M+H)⁺.

Intermediate F170

N-[6-(2,5-Dioxo-2,5-dihydro-1H-pyrrol-1-yl)hexanoyl]-L-valyl-N⁵-carbamoyl-L-ornithyl-N⁶-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-D-lysine/trifluoroacetic acid (1:1)

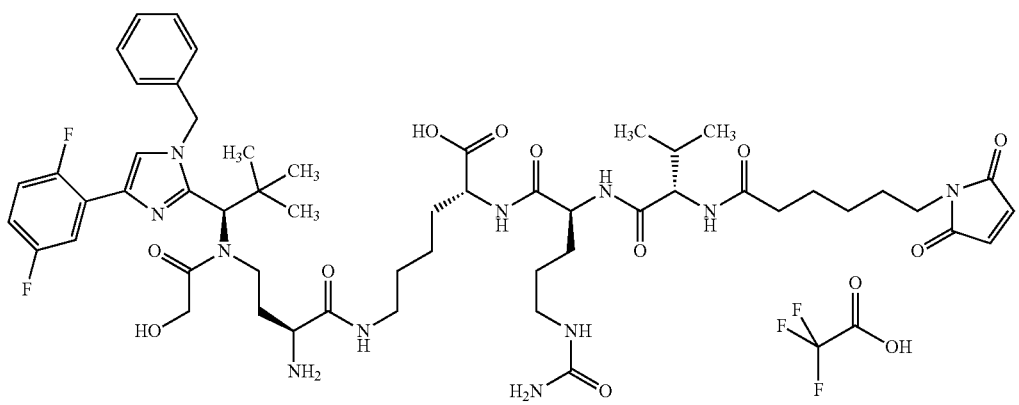 [SMILES: CC(C)[C@H](NC(=O)CCCCCN1C(=O)C=CC1=O)C(=O)N[C@@H](CCCNC(N)=O)C(=O)N[C@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared analogously to its diastereomer Intermediate F23.

HPLC (Method 11): $R_t$=1.9 min;

LC-MS (Method 1): $R_t$=0.83 min; MS (ESIpos): m/z=1092 (M+H)⁺.

Intermediate F171

N⁶-(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-D-alanyl)-N²-{N-[6-(2,5-dioxo-2,5-dihydro-1H-pyrrol-1-yl)hexanoyl]-L-valyl-L-alanyl}-L-lysine/trifluoroacetic acid (1:1)

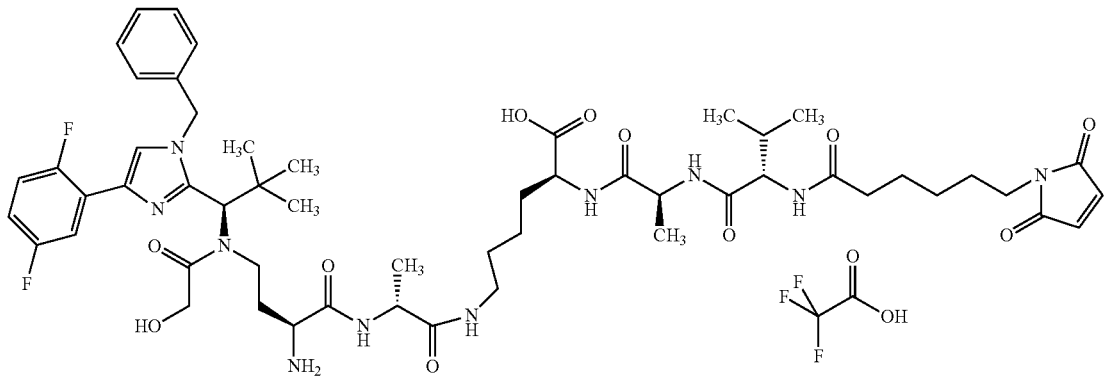 [SMILES: CC(C)[C@H](NC(=O)CCCCCN1C(=O)C=CC1=O)C(=O)N[C@@H](C)C(=O)N[C@@H](CCCCNC(=O)[C@@H](C)NC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The synthesis of the title compound was carried out analogously to Intermediate F155 from Intermediates C62 and L61.

LC-MS (Method 1): $R_t$=0.93 min; MS (ESIpos): m/z=1076 (M+H)⁺.

Intermediate F172

N-[6-(2,5-Dioxo-2,5-dihydro-1H-pyrrol-1-yl)hexanoyl]-L-valyl-L-alanyl-N-[2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]-L-glutamine/trifluoroacetic acid (1:1)

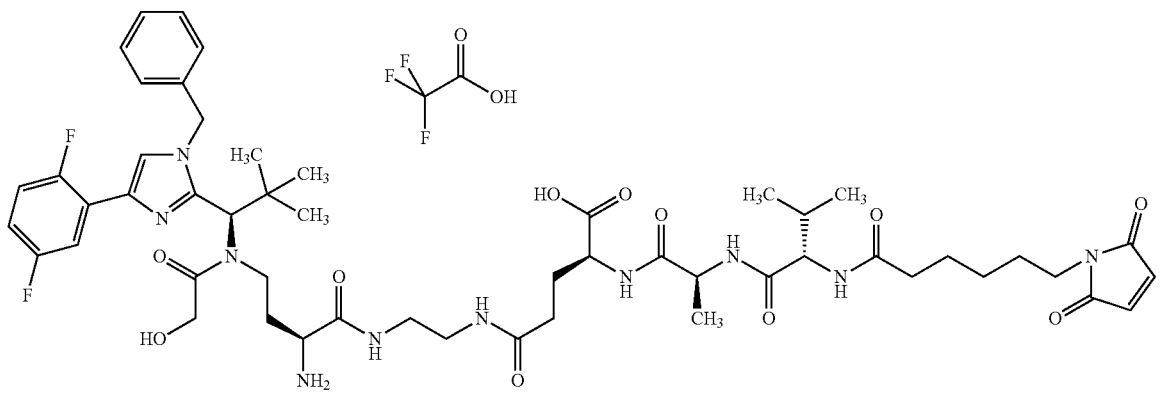 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

The title compound was prepared from 10 mg (0.013 mmol) of Intermediate C63 by coupling with 9 mg (0.014 mmol) of Intermediate L63 in the presence of 5.5 mg (0.014 mmol) of HATU and 11 μl of N,N-diisopropylethylamine and subsequent deprotection by stirring in a solution of trifluoroacetic acid/dichloromethane 1:1 for 2.5 hours. This gave 11 mg (72% of theory over 2 steps).

LC-MS (Method 1): $R_t$=0.9 min; MS (EIpos): m/z=1049 [M+H]⁺.

Intermediate F173

N-[6-(2,5-Dioxo-2,5-dihydro-1H-pyrrol-1-yl)hexanoyl]-L-valyl-L-alanyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1:1)

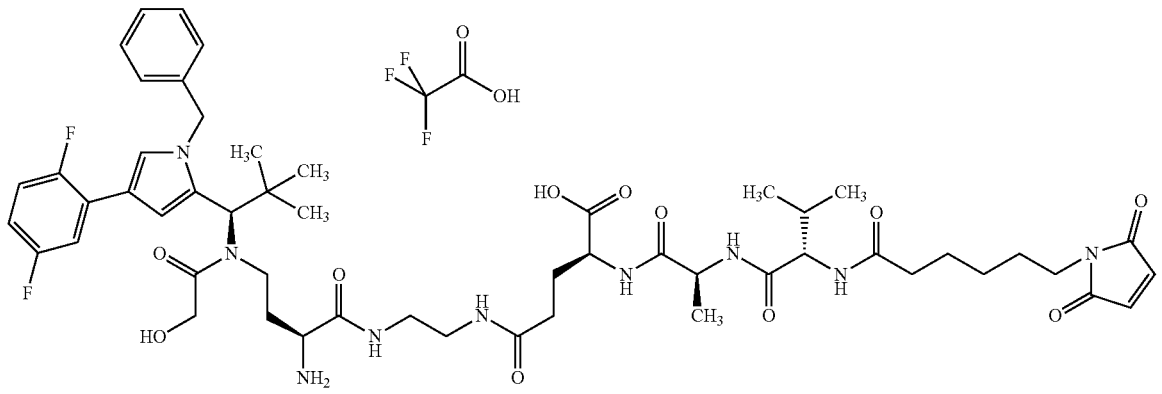 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared from 15 mg (0.018 mmol) of Intermediate C64 by coupling with 12 mg (0.02 mmol) of Intermediate L63 in the presence of 7.7 mg (0.02 mmol) of HATU and 16 μl of N,N-diisopropylethylamine and subsequent deprotection with zinc chloride in trifluoroethanol as described for Intermediate F119. Purification by preparative HPLC gave 12 mg (58% of theory over 2 steps) of the title compound.

LC-MS (Method 1): $R_t$=0.91 min; MS (EIpos): m/z=1048 [M+H]$^+$.

Intermediate F174

N-[6-(2,5-Dioxo-2,5-dihydro-1H-pyrrol-1-yl)hexanoyl]-L-valyl-L-alanyl-N-[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]-L-glutamine/trifluoroacetic acid (1:1)

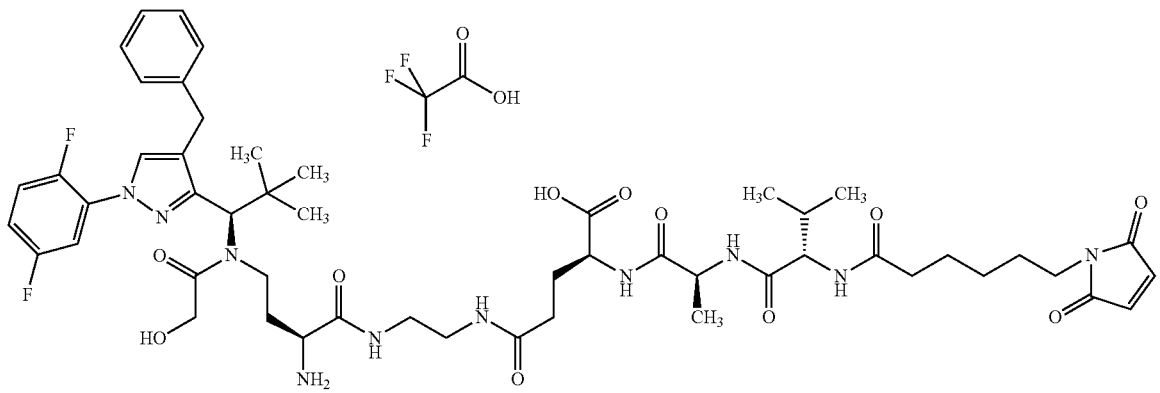 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

The title compound was prepared analogously to Intermediate F172 from Intermediates C57 and L63.

LC-MS (Method 1): $R_1$=0.9 min; MS (EIpos): m/z=1049 [M+H]$^+$.

Intermediate F175

Trifluoroacetic acid/N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-6-(2,5-dioxo-2,5-dihydro-1H-pyrrol-1-yl)hexanamide (1:1)

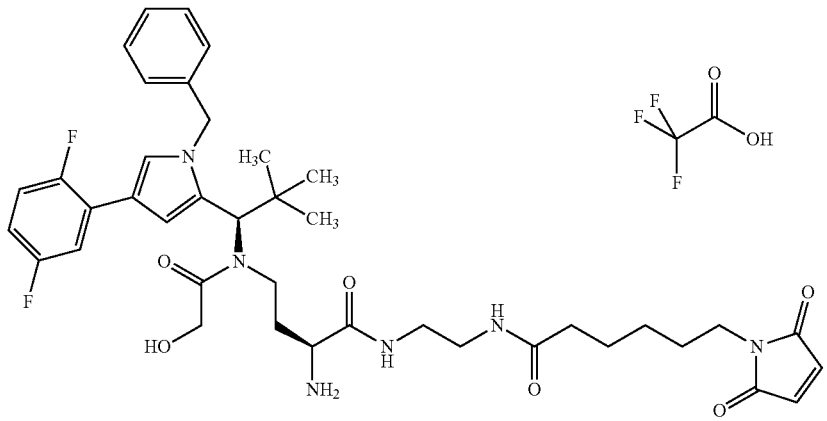 [SMILES: CC(C)(C)[C@H](c1cc(-c2cc(F)ccc2F)cn1Cc1ccccc1)N(CC[C@H](N)C(=O)NCCNC(=O)CCCCCN1C(=O)C=CC1=O)C(=O)CO ; O=C(O)C(F)(F)F]

The title compound was prepared by coupling of 11 mg (0.013 mmol) of Intermediate C64 with 3.4 mg (0.016 mmol) of 6-(2,5-dioxo-2,5-dihydro-1H-pyrrol-1-yl) hexanoic acid in the presence of 6.7 mg (0.018 mmol) of HATU and 9 μl of N,N-diisopropylethylamine and subsequent deprotection with zinc chloride in trifluoroethanol as described for Intermediate F119. Purification by preparative HPLC gave 8 mg (69% of theory over 2 steps) of the title compound.

LC-MS (Method 1): $R_t$=1.35 min; MS (EIpos): m/z=893 [M+H]$^+$.

Intermediate F176

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[1-(2,5-dioxo-2,5-dihydro-1H-pyrrol-1-yl)-12-oxo-3,6,9-trioxa-13-azapentadecan-15-yl]butanamide (1:1)

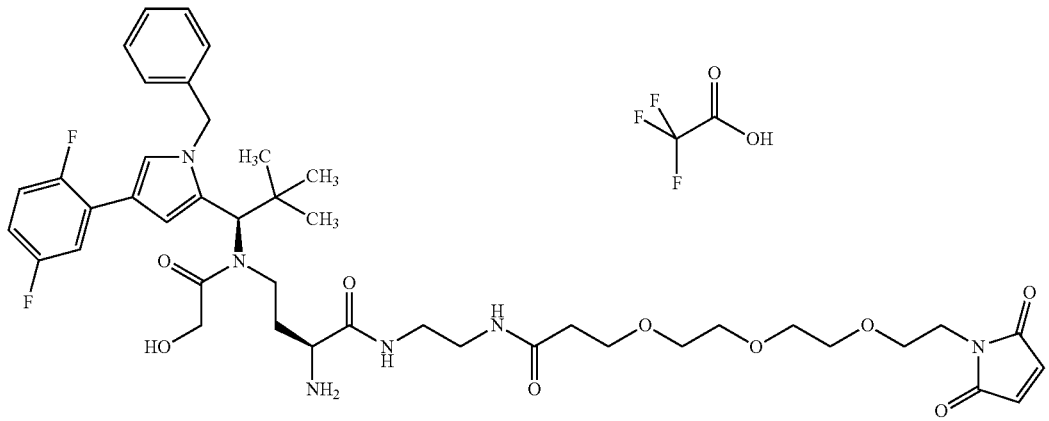 [SMILES: CC(C)(C)[C@H](c1cc(-c2cc(F)ccc2F)cn1Cc1ccccc1)N(CC[C@H](N)C(=O)NCCNC(=O)CCOCCOCCOCCN1C(=O)C=CC1=O)C(=O)CO ; O=C(O)C(F)(F)F]

The title compound was prepared by coupling of 5 mg (0.006 mmol) of Intermediate C64 with 2 mg (0.007 mmol) of 3-(2-{2-[2-(2,5-dioxo-2,5-dihydro-1H-pyrrol-1-yl)ethoxy]ethoxy}ethoxy)propanoic acid, the preparation of which is described under Intermediate L15, in the presence of 3.5 mg (0.009 mmol) of HATU and 4 µl of N,N-diisopropylethylamine and subsequent deprotection with zinc chloride in trifluoroethanol as described for Intermediate F119. Purification by preparative HPLC gave 2 mg (35% of theory over 2 steps) of the title compound.

LC-MS (Method 1): $R_t$=0.86 min; MS (EIpos): m/z=839 [M+H]$^+$.

Intermediate F177

Trifluoroacetic acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-(2-{[(2,5-dioxo-2,5-dihydro-1H-pyrrol-1-yl)acetyl]amino}ethyl)cyclopentanecarboxamide (1:1)

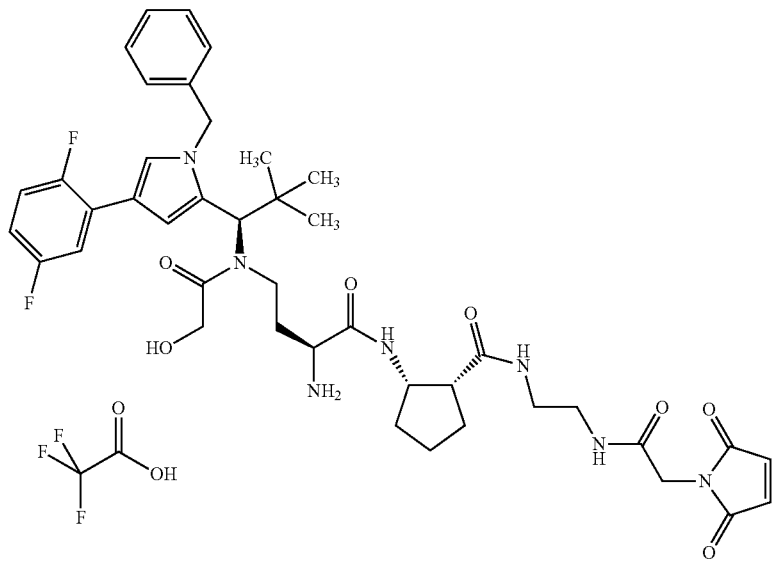 [SMILES: CC(C)(C)[C@H](c1cc(-c2cc(F)ccc2F)cn1Cc1ccccc1)N(CC[C@H](N)C(=O)N[C@H]1CCC[C@H]1C(=O)NCCNC(=O)CN1C(=O)C=CC1=O)C(=O)CO ; O=C(O)C(F)(F)F]

The title compound was prepared analogously to Intermediate F168 using, instead of Intermediate L61, the Intermediate L1.

LC-MS (Method 1): $R_t$=0.86 min; MS (EIpos): m/z=804 [M+H]$^+$.

Intermediate F178

Trifluoroacetic acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-{2-[(bromoacetyl)amino]ethyl}cyclopentanecarboxamide (1:1)

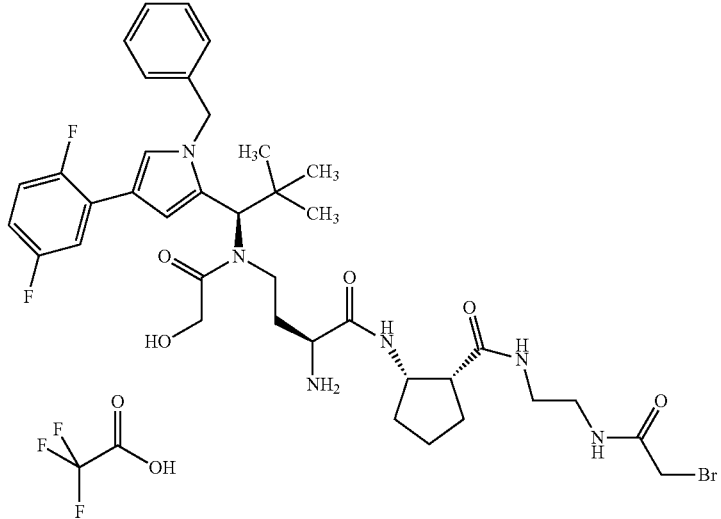 [SMILES: CC(C)(C)[C@H](c1cc(-c2cc(F)ccc2F)cn1Cc1ccccc1)N(CC[C@H](N)C(=O)N[C@H]1CCC[C@H]1C(=O)NCCNC(=O)CBr)C(=O)CO ; O=C(O)C(F)(F)F]

The title compound was prepared analogously to Intermediate F177 using, instead of Intermediate L1, the Intermediate L52.

LC-MS (Method 1): $R_t$=0.89 min; MS (EIpos): m/z=787 and 789 [M+H]$^+$.

Intermediate F179

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[6-(2,5-dioxo-2,5-dihydro-1H-pyrrol-1-yl)hexyl]butanamide (1:1)

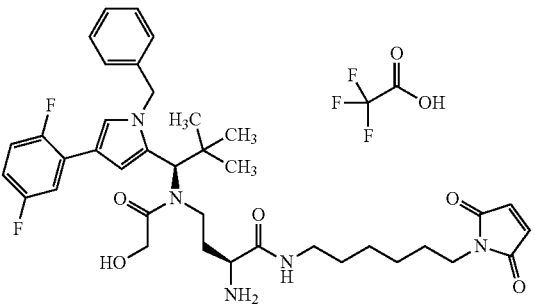 [SMILES: CC(C)(C)[C@H](c1cc(-c2cc(F)ccc2F)cn1Cc1ccccc1)N(CC[C@H](N)C(=O)NCCCCCCN1C(=O)C=CC1=O)C(=O)CO ; O=C(O)C(F)(F)F]

The title compound was prepared by coupling of 15 mg (0.023 mmol) of Intermediate C58 with 6 mg (0.025 mmol) of 1-(6-aminohexyl)-1H-pyrrole-2,5-dione in the presence of 13 mg (0.034 mmol) of HATU and 16 µl of N,N-diisopropylethylamine and subsequent deprotection with zinc chloride in trifluoroethanol as described for Intermediate F119. Purification by preparative HPLC gave 8.5 mg (46% of theory over 2 steps) of the title compound.

LC-MS (Method 6): $R_t$=2.22 min; MS (EIpos): m/z=692 [M+H]$^+$.

Intermediate F180

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2[(2,5-dioxo-2,5-dihydro-1H-pyrrol-1-yl)acetyl]-L-glutamine/trifluoroacetic acid (1:1)

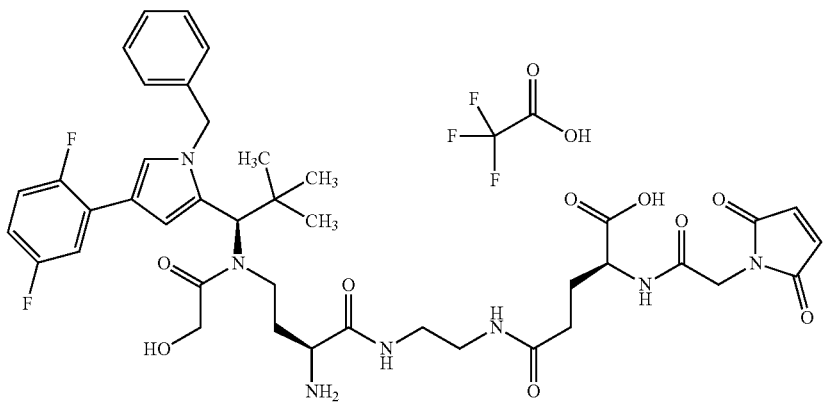 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)CN1C(=O)C=CC1=O)C(=O)O)C(=O)CO ; O=C(O)C(F)(F)F]

The title compound was prepared by coupling of 9.6 mg (0.012 mmol) of Intermediate C64 with 5 mg (0.013 mmol) of Intermediate L64 in the presence of 7 mg (0.018 mmol) of HATU and 6 µl of N,N-diisopropylethylamine and subsequent deprotection with zinc chloride in trifluoroethanol as described for Intermediate F119. Purification by preparative HPLC gave 3.1 mg (28% of theory over 2 steps) of the title compound.

LC-MS (Method 1): $R_t$=0.85 min; MS (EIpos): m/z=822 [M+H]$^+$.

Intermediate F192

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-[{(2,5-dioxo-2,5-dihydro-1H-pyrrol-1-yl)acetyl]amino}-L-alanine/trifluoroacetic acid (1:1)

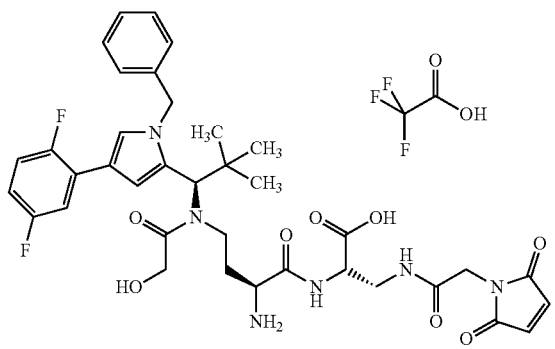

60 mg (0.091 mmol) of Intermediate C58 were taken up in 8 ml of DMF and coupled with 45 mg (0.100 mmol) of Intermediate L65 in the presence of 42 mg (0.11 mmol) of HATU and 64 µl of N,N-diisopropylethylamine After purification by preparative HPLC, the intermediate was taken up in 10 ml of ethanol and hydrogenated over 10% palladium on activated carbon at RT under hydrogen standard pressure for 45 min. The catalyst was then filtered off, the solvent was removed under reduced pressure and the product was purified by preparative HPLC. Lyophilization from acetonitrile/water 1:1 gave 24.5 mg (31% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxyl]carbonyl}amino)butanoyl]-L-alaninate.

LC-MS (Method 1): $R_t$=1.17 min; MS (EIpos): m/z=844 [M+H]$^+$.

The title compound was then prepared by coupling of 10 mg (0.012 mmol) of this intermediate with 2 mg (0.013 mmol) of commercially available (2,5-dioxo-2,5-dihydro-1H-pyrrol-1-yl)acetic acid intermediate in the presence of 5.4 mg (0.014 mmol) of HATU and 8 µl of N,N-diisopropylethylamine and subsequent deprotection with zinc chloride in trifluoroethanol as described for Intermediate F119. Purification by preparative HPLC gave 3.5 mg (33% of theory over 2 steps) of the title compound.

LC-MS (Method 1): $R_t$=0.81 min; MS (ESIpos): m/z=737 (M+H)$^+$.

Intermediate F193

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-D-alanine/trifluoroacetic acid (1:1)

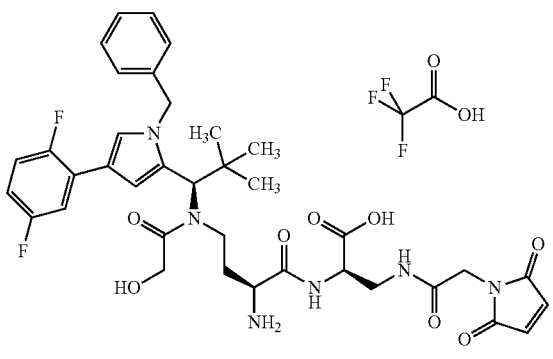 [SMILES: CC(C)(C)[C@H](c1cc(-c2cc(F)ccc2F)cn1Cc1ccccc1)N(CC[C@H](N)C(=O)N[C@H](CNC(=O)CN1C(=O)C=CC1=O)C(=O)O)C(=O)CO ; O=C(O)C(F)(F)F]

The synthesis of the title compound was carried out analogously to Intermediate F192 from 3-{[(benzyloxy)carbonyl]amino}-N-(tert-butoxycarbonyl)-D-alanine/N-cyclohexylcyclohexanamine (1:1).

LC-MS (Method 1): $R_t$=0.87 min; MS (ESIpos): m/z=737 (M+H)$^+$.

Intermediate F194

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

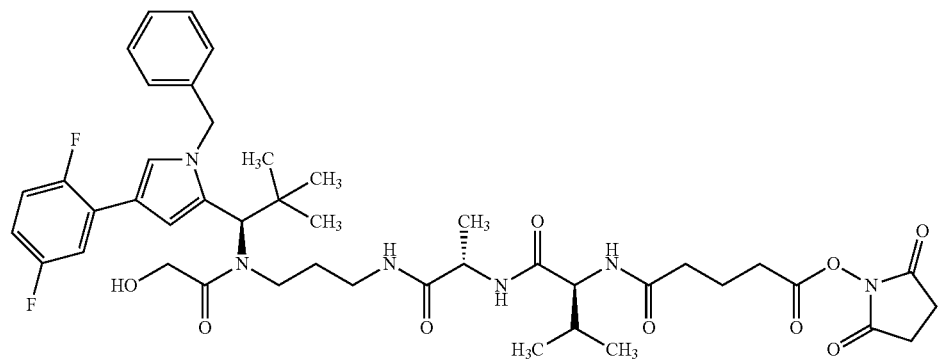 [SMILES: CC(C)[C@H](NC(=O)CCCC(=O)ON1C(=O)CCC1=O)C(=O)N[C@@H](C)C(=O)NCCCN(C(=O)CO)[C@@H](c1cc(-c2cc(F)ccc2F)cn1Cc1ccccc1)C(C)(C)C]

Intermediate F195

Trifluoroacetic acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-[2-(2,5-dioxo-2,5-dihydro-1H-pyrrol-1-yl)ethyl]succinamide (1:1)

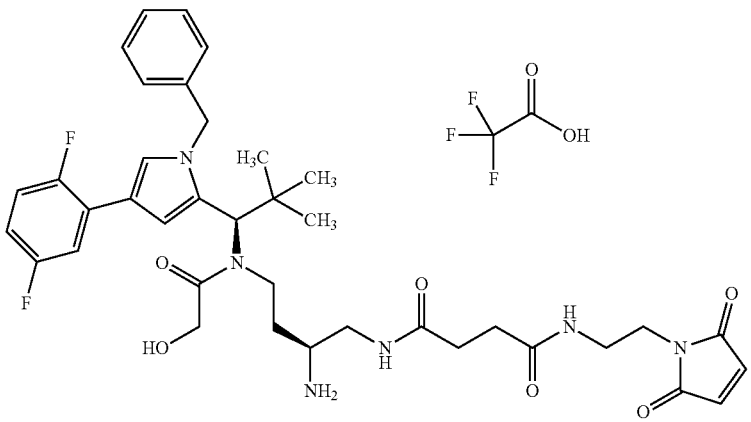 [SMILES: CC(C)(C)[C@H](c1cc(-c2cc(F)ccc2F)cn1Cc1ccccc1)N(CC[C@H](N)CNC(=O)CCC(=O)NCCN1C(=O)C=CC1=O)C(=O)CO ; O=C(O)C(F)(F)F]

The title compound was prepared from Example 98 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate as described for Intermediate F58 by reaction with 1,1'-[(1,5-dioxopentane-1,5-diyl)bis(oxy)]dipyrrolidine-2,5-dione into the title compound.

LC-MS (Method 1): $R_t$=1.19 min; MS (ESIpos): m/z=851 [M+H]$^+$.

The title compound was prepared by coupling of 26 mg (0.035 mmol) of Intermediate C65 with 18 mg (0.07 mmol) of commercially available trifluoroacetic acid/1-(2-aminoethyl)-1H-pyrrole-2,5-dione (1:1) in 8 ml of DMF in the presence of 40 mg (0.1054 mmol) of HATU and 61 µl of N,N-diisopropylethylamine and subsequent deprotection with zinc chloride in trifluoroethanol as described for Intermediate F119. Purification by preparative HPLC gave 16 mg (43% of theory over 2 steps) of the title compound.

LC-MS (Method 1): $R_t$=0.85 min; MS (ESIpos): m/z=721 (M+H)$^+$.

$^1$H NMR (500 MHz, DMSO-d$_6$): δ=7.99 (t, 1H), 7.95 (t, 1H), 7.6-7.75 (m, 4H), 7.5 (s, 1H) 7.2-7.4 (m, 6H), 6.8-7.0 (m, 4H), 5.63 (s, 1H), 4.9 and 5.2 (2d, 2H), 4.26 and 4.0 (2d, 2H), 3.3-3.6 (m, 4H), 3.15-3.25 (m, 3H), 2.85-3.0 (m, 2H), 2.2-2.3 (m, 4H), 0.64 and 1.49 (2m, 2H), 0.81 (s, 9H).

Intermediate F196

Trifluoroacetic acid/2-(2,5-dioxo-2,5-dihydro-1H-pyrrol-1-yl)ethyl-N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alaninate (1:1)

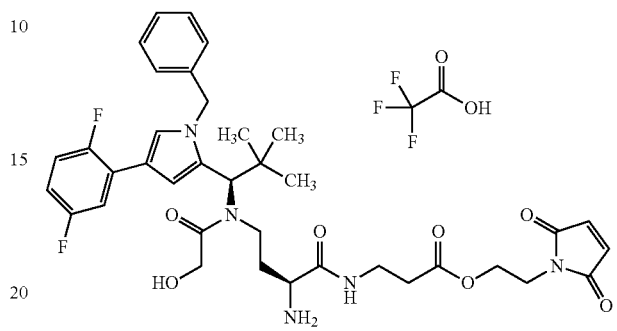

First, 15 mg (0.023 mmol) of Intermediate C58 were taken up in 4 ml of DMF and reacted with 8.2 mg (0.025 mmol) of Intermediate L67 in the presence of 13.0 mg (0.034 mmol) of HATU and 16 µl of N,N-diisopropylethylamine After 30 min of stirring at RT, the mixture was concentrated and the residue was purified by preparative HPLC. After combination of the appropriate fractions and evaporation of the solvent, the residue was lyophilized from acetonitrile/water 1:1. This gave 4.3 mg (20% of theory) of the protected intermediate.

LC-MS (Method 1): $R_t$=1.35 min; MS (EIpos): m/z=852 [M+H]$^+$.

4.3 mg (4.5 µmol) of the intermediate were dissolved in 1 ml of trifluoroethanol and deprotected with 3.65 mg (27 µmol) zinc chloride as described for Intermediate F119. Purification by preparative HPLC gave 1 mg (25% of theory over 2 steps) of the title compound.

LC-MS (Method 1): $R_t$=0.88 min; MS (ESIpos): m/z=708 (M+H)$^+$

Intermediate F204

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[3-(2,5-dioxo-2,5-dihydro-1H-pyrrol-1-yl)propanoyl]amino}ethyl)butanamide (1:1)

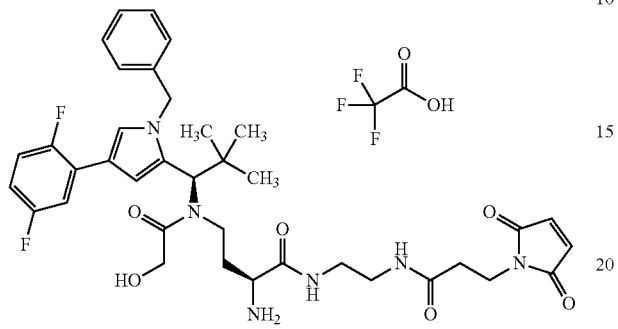

25 mg (0.038 mmol) of Intermediate C58 were initially reacted with 16.5 mg (75% pure) (0.038 mmol) of Intermediate L68 in the presence of 17 mg (0.046 mmol) of HATU and 20 µl of N,N-diisopropylethylamine After 60 min of stirring at RT, the mixture was concentrated and the residue was purified by preparative HPLC. This gave 18.3 mg (56% of theory) of the protected intermediate.

LC-MS (Method 1): $R_t$=1.32 min; MS (EIpos): m/z=851 [M+H]$^+$.

In the second step, this intermediate was dissolved in 3 ml of 2,2,2-trifluoroethanol. 12 mg (0.086 mmol) of zinc chloride were added, and the reaction was stirred at 50° C. for 2 h. 25 mg (0.086 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 11 mg (62% of theory) of the title compound.

LC-MS (Method 1): $R_t$=0.85 min; MS (ESIpos): m/z=707 (M+H)$^+$.

Intermediate F205

Trifluoroacetic acid/1[(2,5-dioxo-2,5-dihydro-1H-pyrrol-1-yl)acetyl]piperidin-4-yl N-(2S)-2-amino-4-[(1R)-1-[1-benzyl-4-(2,5-difluorophenyl)-1H-pyrrol-2-yl]-2,2-dimethylpropyl (glycoloyl)amino]butanoyl -beta-alanyl-L-valyl-N$^5$-carbamoyl-L-ornithinate (1:1)

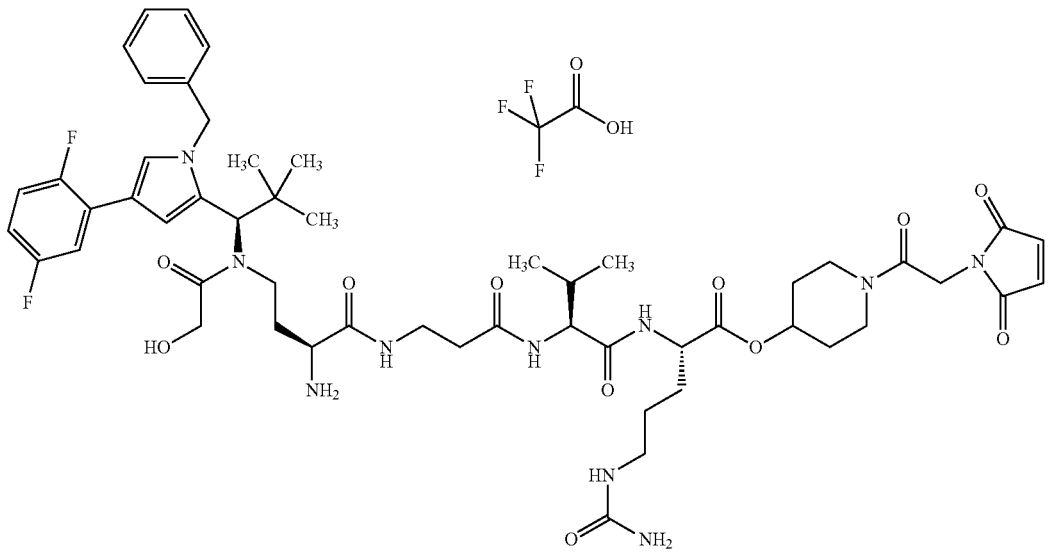 [SMILES: CC(C)[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](CCCNC(N)=O)C(=O)OC1CCN(C(=O)CN2C(=O)C=CC2=O)CC1 ; O=C(O)C(F)(F)F]

The synthesis was carried out by coupling of 25 mg (0.034 mmol) of Intermediate C61 and 29 mg (0.041 mmol) of Intermediate L69 in the presence of HATU and N,N-diisopropylethylamine, followed by hydrogenation with palladium on activated carbon (10%) under standard pressure, then coupling with (2,5-dioxo-2,5-dihydro-1H-pyrrol-1-yl)acetic acid in the presence of HATU and N,N-diisopropylethylamine and finally removal of the 2-(trimethylsilyl)ethoxycarbonyl protective group with zinc chloride. HPLC purification gave 11 mg (26% of theory over 4 steps).

LC-MS (Method 1): $R_t$=0.86 min; MS (ESIpos): m/z=1061 (M+H)$^+$.

Intermediate F206

Trifluoroacetic acid/1[(2,5-dioxo-2,5-dihydro-1H-pyrrol-1-yl)acetyl]piperidin-4-yl N-(2S)-2-amino-4-[(1R)-1-[1-benzyl-4-(2,5-difluorophenyl)-1H-pyrrol-2-yl]-2,2-dimethylpropyl (glycoloyl)amino]butanoyl -beta-alanyl-L-valyl-L-alaninate (1:1)

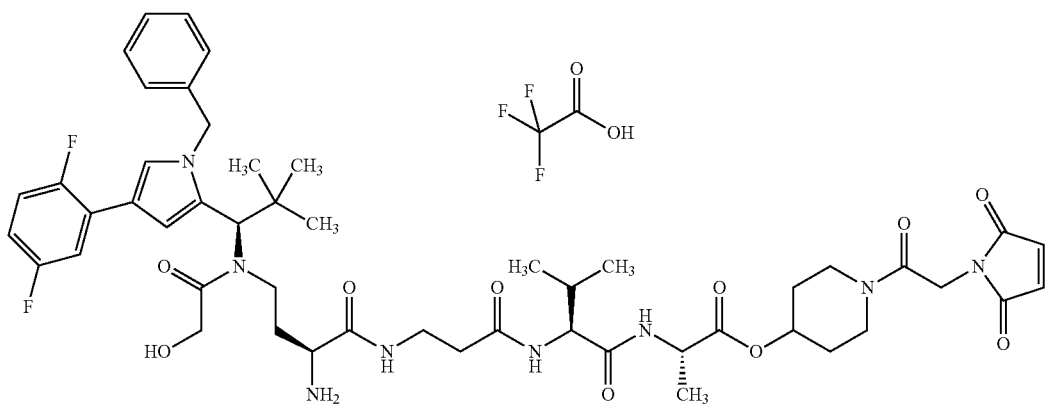 [SMILES: CC(C)[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)N[C@@H](C)C(=O)OC1CCN(C(=O)CN2C(=O)C=CC2=O)CC1 ; O=C(O)C(F)(F)F]

The synthesis was carried out analogously to Intermediate F205.

LC-MS (Method 1): $R_t$=0.86 min; MS (ESIpos): m/z=975 $(M+H)^+$.

Intermediate F207

$N^6$-(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$-{N-[(2,5-dioxo-2,5-dihydro-1H-pyrrol-1-yl)acetyl]-L-valyl-L-alanyl}-L-lysine/trifluoroacetic acid (1:1)

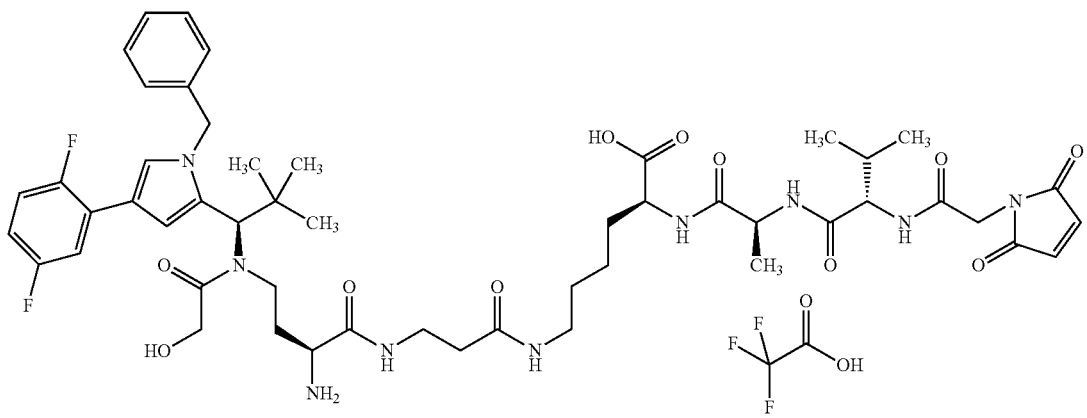

The title compound was prepared analogously to Intermediate F155.

LC-MS (Method 1): $R_t$=0.81 min; MS (ESIpos): m/z=1020 $(M+H)^+$.

Intermediate F209

R-{2[(3-Aminopropyl) {(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/ trifluoroacetic acid (1:1)

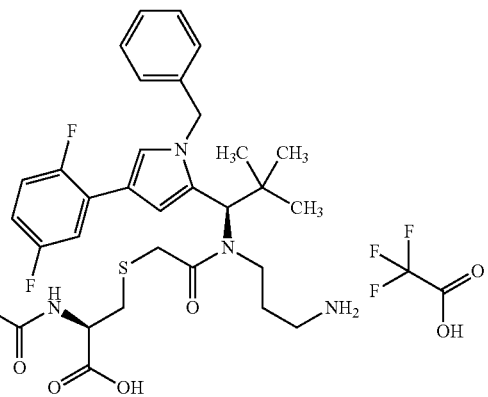

93.9 mg (0.78 mmol) of L-cysteine were suspended in a solution of 93.0 mg (1.11 mmol) of sodium bicarbonate and 0.9 ml of water. 70.0 mg (0.11 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70), dissolved in 6.0 ml of isopropanol, and 202.3 mg (1.33 mmol) of 1,8-diazabicyclo[5.4.0]undec-7-ene were added. The reaction mixture was stirred at 50° C. for 90 min Water (0.1% TFA) was added, and the reaction was purified by preparative RP-HPLC (column: Reprosil 125×30; 10µ, flow rate: 50 ml/min, MeCN/water; 0.1% TFA). The solvents were evaporated under reduced pressure and the residue was dried under high vacuum. This gave 53.9 mg (59% of theory) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/ trifluoroacetic acid (1:1).

LC-MS (Method 1): $R_t$=1.24 min; MS (ESIpos): m/z=717 (M+H)$^+$.

86.0 mg (0.1 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) and 58.5 mg (0.11 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 4.0 ml of DMF, and 20.9 mg (0.21 mmol) of 4-methylmorpholine were added. The reaction mixture was stirred at RT overnight. 15.5 mg (0.26 mmol) of HOAc were added and the reaction mixture was purified directly by preparative RP-HPLC (column: Reprosil 125×30; 10µ, flow rate: 50 ml/min, MeCN/water; 0.1% TFA). The solvents were evaporated under reduced pressure and the residue was dried under high vacuum. This gave 68.6 mg (59% of theory) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteine.

LC-MS (Method 6): $R_t$=2.88 min; MS (ESIpos): m/z=1115 (M+H)$^+$.

46.4 mg (0.04 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteine were dissolved in 2.0 ml of trifluoroethanol, and 17.0 mg (0.13 mmol) of zinc dichloride were added. The reaction mixture was stirred at 50° C. overnight. Another 8.5 mg (0.07 mmol) of zinc dichloride were added, and the mixture was stirred at 50° C. overnight. 36.5 mg (0.13 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 19.4 mg (43% of theory) of the title compound.

LC-MS (Method 1): $R_t$=0.94 min; MS (ESIpos): m/z=971 (M+H)$^+$.

Intermediate F210

5-{2[(3-Aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-D-cysteine/trifluoroacetic acid (1:1)

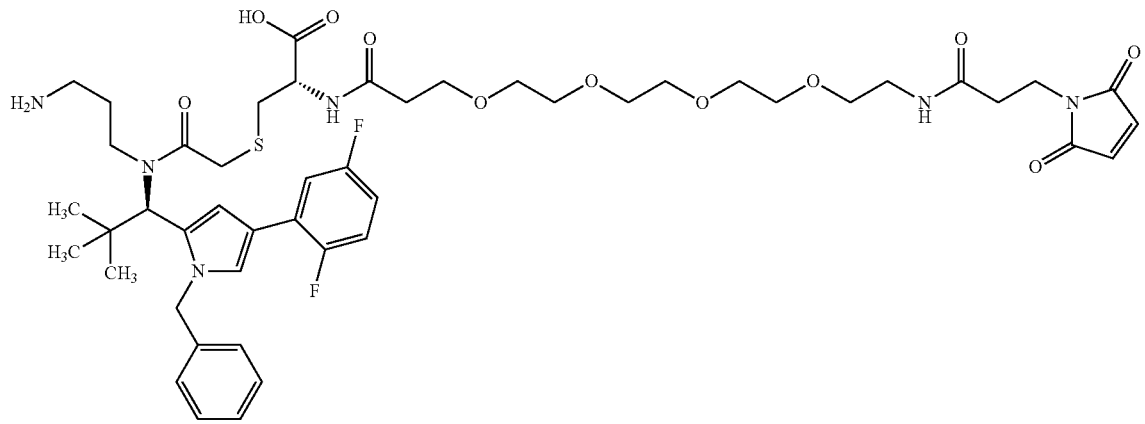 [SMILES: CC(C)(C)[C@H](c1cc(-c2cc(F)ccc2F)cn1Cc1ccccc1)N(CCCN)C(=O)CSC[C@@H](NC(=O)CCOCCOCCOCCOCCNC(=O)CCN1C(=O)C=CC1=O)C(=O)O]

The title compound was prepared analogously to the synthesis of Intermediate F209 using D-cysteine.

LC-MS (Method 1): $R_t$=0.91 min; MS (ESIpos): m/z=971 (M+H)⁺.

Intermediate F211

Trifluoroacetic acid/3-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl)-N-[2-(2,5-dioxo-2,5-dihydro-1H-pyrrol-1-yl)ethyl]propanamide (1:1)

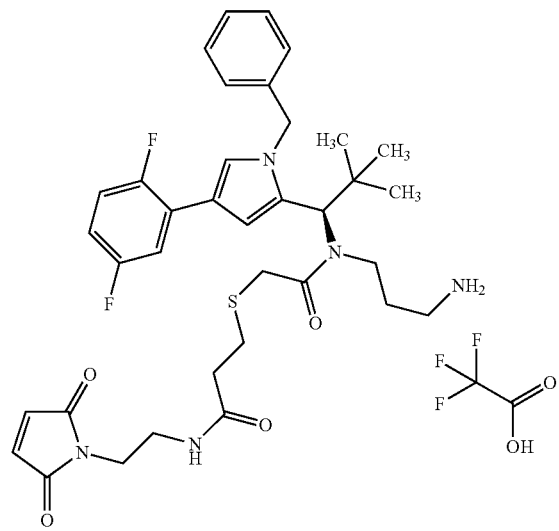

30.0 mg (0.05 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) were initially charged together with 5.5 mg (0.05 mmol) of 3-sulphanylpropanoic acid in 0.5 ml of methanol with a drop of water. 23.0 mg (0.17 mmol) of potassium carbonate were then added, and the reaction mixture was stirred at 50° C. for 4 h. Ethyl acetate was added and the organic phase was washed once with water and once with saturated NaCl solution. The organic phase was dried over magnesium sulphate and the solvent was evaporated under reduced pressure. The residue was used without further purification in the next step of the synthesis. This gave 30.3 mg (86% of theory) of the compound 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid.

LC-MS (Method 1): $R_t$=1.39 min; MS (ESIpos): m/z=702 (M+H)⁺.

30.0 mg (0.04 mol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid and 9.8 mg (0.06 mmol) of 1-(2-aminoethyl)-1H-pyrrole-2,5-dione hydrochloride (1:1) were initially charged in 2.0 ml of acetonitrile, and 44.2 mg (0.34 mmol) of N,N-diisopropylethylamine were added. 35.4 mg (0.06 mmol) T3P (50% in ethyl acetate) were added, and the reaction mixture was stirred at RT overnight. Water was added, and purification was carried out directly by preparative RP-HPLC (column: Reprosil 125×30; 10μ, flow rate: 50 ml/min, MeCN/water). The solvents were evaporated under reduced pressure and the residue was dried under high vacuum. This gave 22.0 mg (63% of theory) of the compound 2-(trimethylsilyl)ethyl [3-[{(1R)-1-[1-benzyl-4-(2,5-difluorophenyl)-1H-pyrrol-2-yl]-2,2-dimethylpropyl}{(3-{[2-(2,5-dioxo-2,5-dihydro-1H-pyrrol-1-yl)ethyl]amino}-3-oxopropyl)sulphanyl]acetyl}amino)propyl]carbamate.

LC-MS (Method 1): $R_t$=1.41 min; MS (ESIpos): m/z=824 (M+H)⁺.

22.0 mg (0.03 mol) of 2-(trimethylsilyl)ethyl [3-({(1R)-1-[1-benzyl-4-(2,5-difluorophenyl)-1H-pyrrol-2-yl]-2,2-dimethylpropyl}{[(3-{[2-(2,5-dioxo-2,5-dihydro-1H-pyrrol-1-yl)ethyl]amino}-3-oxopropyl)sulphanyl]acetyl}amino)propyl]carbamate were dissolved in 1.0 ml of trifluoroethanol, and 9.1 mg (0.07 mmol) of zinc dichloride were added. The reaction mixture was stirred at 50° C. for 5 h. 19.5 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 15.0 mg (71% of theory) of the title compound.

LC-MS (Method 1): $R_t$=0.88 min; MS (ESIpos): m/z=680 (M+H)⁺.

Intermediate F212

Trifluoroacetic acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10-oxo-3,6-dioxa-13-thia-9-azapentadecan-15-amide (1:1)

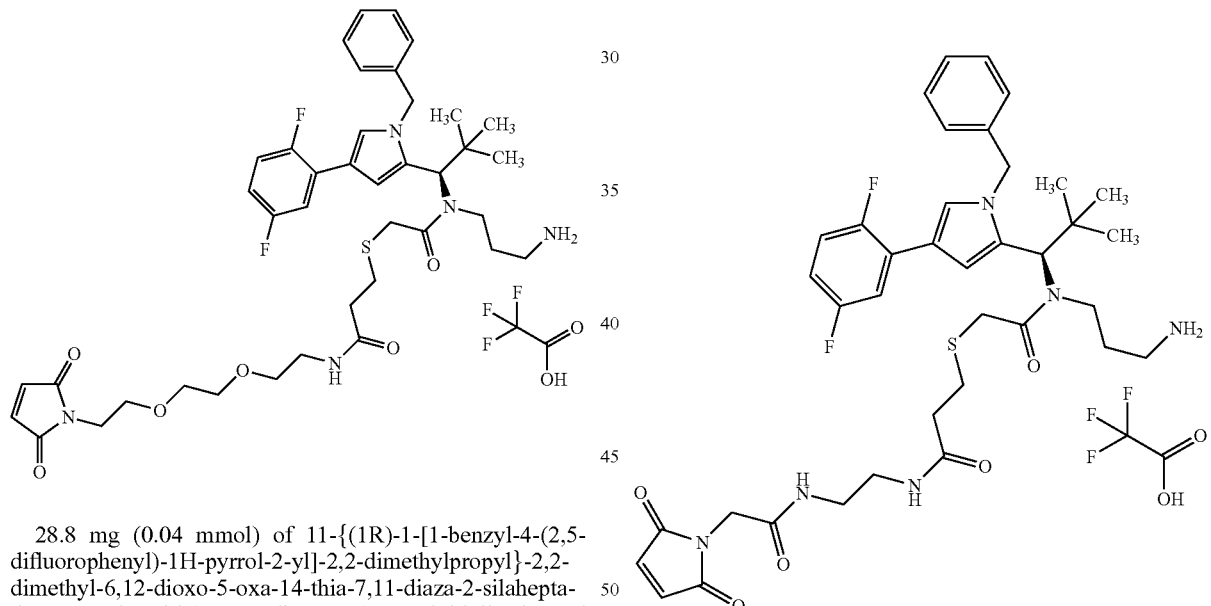

28.8 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 18.3 mg (0.05 mmol) of trifluoroacetic acid/1-{2-[2-(2-aminoethoxy)ethoxy]ethyl}-1H-pyrrole-2,5-dione (1:1) (Intermediate L59) in 1.9 ml of acetonitrile. 42.4 mg (0.33 mmol) of N,N-diisopropylethylamine were then added, and 33.9 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 10.7 mg (26% of theory) of the compound 2-(trimethylsilyl)ethyl [16-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10,15-dioxo-3,6-dioxa-13-thia-9,16-diazanonadecan-19-yl]carbamate.

LC-MS (Method 1): $R_t$=1.44 min; MS (ESIpos): m/z=812 (M+H)⁺.

10.7 mg (0.01 mol) of 2-(trimethylsilyl)ethyl [16-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-10,15-dioxo-3,6-dioxa-13-thia-9,16-diazanonadecan-19-yl]carbamate were dissolved in 0.8 ml of trifluoroethanol, and 8.0 mg (0.06 mmol) of zinc dichloride were added. The reaction mixture was stirred at 50° C. for 5 h. 17.1 mg (0.06 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum.

LC-MS (Method 1): $R_t$=1.03 min; MS (ESIpos): m/z=768 (M+H)⁺.

Intermediate F213

Trifluoroacetic acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-(2-{[(2,5-dioxo-2,5-dihydro-1H-pyrrol-1-yl)acetyl]amino}ethyl)propanamide (1:1)

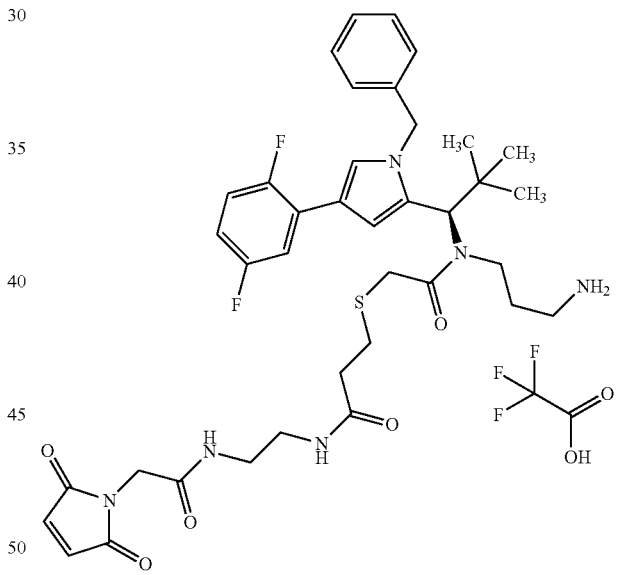

27.5 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 15.9 mg (0.05 mmol) of trifluoroacetic acid/N-(2-aminoethyl)-2-(2,5-dioxo-2,5-dihydro-1H-pyrrol-1-yl)acetamide (1:1) (Intermediate L1) in 1.8 ml of acetonitrile. 32.4 mg (0.31 mmol) of N,N-diisopropylethylamine were then added, and 32.4 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.9 mg (35% of theory) of the compound 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate.

LC-MS (Method 1): $R_t$=1.39 min; MS (ESIpos): m/z=881 (M+H)$^+$.

11.9 mg (0.01 mol) of 2-(trimethylsilyl)ethyl-[13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate were dissolved in 1.0 ml of trifluoroethanol, and 5.5 mg (0.04 mmol) of zinc dichloride were added. The reaction mixture was stirred at 50° C. overnight. 11.8 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.4 mg (60% of theory) of the title compound.

LC-MS (Method 5): $R_t$=2.75 min; MS (ESIpos): m/z=737 (M+H)$^+$.

Intermediate F214

N-[19-(2,5-Dioxo-2,5-dihydro-1H-pyrrol-1-yl)-17-oxo-4,7,10,13-tetraoxa-16-azanonadecan-1-oyl]-L-alpha-glutamyl-S-{2-[(3-aminopropyl {(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 257.0 mg (80% of theory) of the compound (16R)-11-{(1R)-1-[1-benzyl-4-(2,5-difluorophenyl)-1H-pyrrol-2-yl]-2,2-dimethylpropyl}-16-{[(2S)-5-(benzyloxy)-2-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid.

LC-MS (Method 1): $R_t$=1.55 min; MS (ESIpos): m/z=1071 (M+H)$^+$.

Under argon, 24.6 mg (0.11 mmol) of palladium(II) acetate were initially charged in 5.0 ml of dichloromethane, and 33.2 mg (0.33 mmol) of triethylamine and 254.3 mg (2.19 mmol) of triethylsilane were added. The reaction mixture was stirred at RT for 5 min, and 234.1 mg (0.22 mmol) of (16R)-11-{(1R)-1-[1-benzyl-4-(2,5-difluorophenyl)-1H-pyrrol-2-yl]-2,2-dimethylpropyl}-16-{[(2S)-5-(benzyloxy)-2-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid dissolved in 5.0 ml of dichloromethane were added. The reaction mixture was stirred at RT overnight. The reaction mixture was filtered through a cardboard filter and the filter cake was washed with dichloromethane. The solvent was evaporated under reduced pressure without heating. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 177.5 mg (85% of theory) of the compound L-alpha-glutamyl-S-(11-{(1R)-1-[1-benzyl-4-(2,5-difluorophenyl)-1H-pyrrol-2-yl]-2,2-dim-

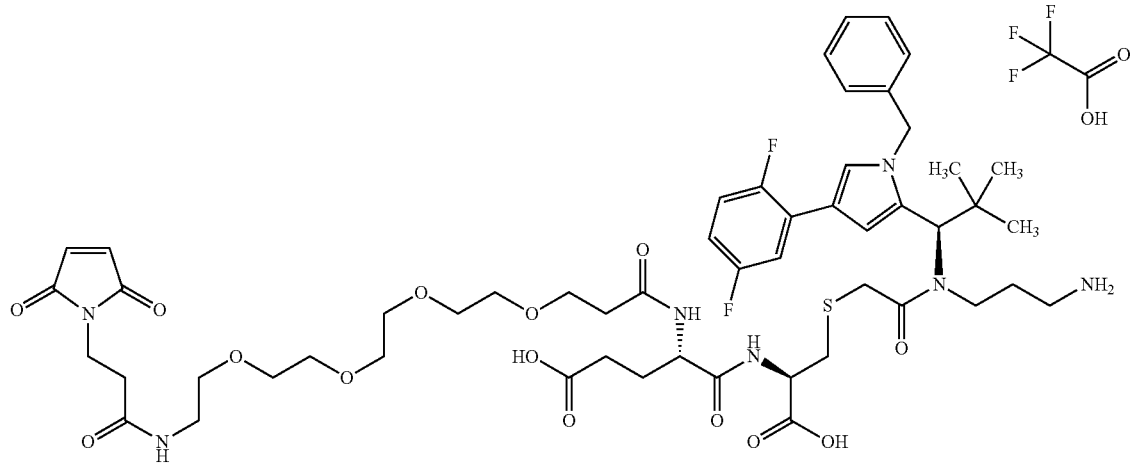 [SMILES: CC(C)(C)[C@H](c1cc(-c2cc(F)ccc2F)cn1Cc1ccccc1)N(CCCN)C(=O)CSC[C@H](NC(=O)[C@H](CCC(=O)O)NC(=O)CCOCCOCCOCCOCCNC(=O)CCN1C(=O)C=CC1=O)C(=O)O ; O=C(O)C(F)(F)F]

111.7 mg (0.30 mmol) of (2S)-5-(benzyloxy)-2-{[(benzyloxy)carbonyl]amino}-5-oxopentanoic acid were initially charged in 3.0 ml of DMF, and 46.1 (0.30 mmol) of HOBt, 96.6 mg (0.30 mmol) of TBTU and 38.9 mg (0.30 mmol) of N,N-diisopropylethylamine were added. The reaction mixture was stirred at RT for 10 min 250.0 mg (0.30 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) dissolved in 116.3 mg (0.9 mmol) of N,N-diisopropylethylamine and 3.0 ml of DMF were then added. The reaction mixture was stirred at RT ethylpropyl}-2,2-dimethyl-6,12-dioxo-5-oxa-7,11-diaza-2-silatridecan-13-yl)-L-cysteine trifluoroacetic acid (1:1).

LC-MS (Method 1): $R_t$=1.07 min; MS (ESIpos): m/z=846 (M+H)$^+$.

20.0 mg (20.83 μmol) L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) were initially charged together with 11.8 mg (22.91 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.5 ml of DMF, and 6.3 mg (62.49

μmol) of 4-methylmorpholine were added. The reaction mixture was stirred at RT overnight, and 4.4 mg (0.07 mmol) of acetic acid were then added.

The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 19.1 mg (74% of theory) of the compound N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.24 min; MS (ESIpos): m/z=1244 (M+H)$^+$.

17.5 mg (14.06 μmol) of N-[19-(2,5-dioxo-2,5-dihydro-1H-pyrrol-1-yl)-17-oxo-4,7,10,13-tetraoxa-16-azanonadecan-1-oyl]-L-alpha-glutamyl-S -(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 1.5 ml of trifluoroethanol, and 11.5 mg (84.37 μmol) of zinc dichloride were added. The reaction mixture was stirred at 50° C. for 4 h. 24.7 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 10.8 mg (63% of theory) of the title compound.

LC-MS (Method 1): $R_t$=0.89 min; MS (ESIpos): m/z=1100 (M+H)$^+$.

Intermediate F215

N-[19-(2,5-Dioxo-2,5-dihydro-1H-pyrrol-1-yl)-17-oxo-4,7,10,13-tetraoxa-16-azanonadecan-1-oyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide 14.9 mg (0.02 mmol) of N-acetyl-S-[2-([3-(L-alanylamino)propyl]{(1R)-1-[1-benzyl-4-(2,5-difluorophenyl)-1H-pyrrol-2-yl]-2,2-dimethylpropyl}amino)-2-oxoethyl]-L-cysteine/trifluoroacetic acid (1:1) (Example 229) and 7.1 mg (0.02 mmol) of 2,5-dioxopyrrolidin-1-yl-N-[(benzyloxy)carbonyl]-L-valinate were initially charged in 1.0 ml of DMF, and 5.7 mg (0.06 mmol) of 4-methylmorpholine were added. The reaction mixture was stirred at RT overnight, and 4.5 mg (0.08 mmol) of acetic acid were then added. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 13.3 mg (78% of theory) of the compound N-[(benzyloxy)carbonyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide.

LC-MS (Method 1): $R_t$=1.24 min; MS (ESIpos): m/z=919 (M+H)$^+$.

11.1 mg (0.01 mmol) of N-[(benzyloxy)carbonyl]-L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide were dissolved in 5.0 ml of ethanol, 1.0 mg of palladium on activated carbon (10%) was added and the mixture was hydrogenated at RT and standard pressure overnight. The reaction mixture was filtered through Celite and the filter cake was washed with an ethanol/THF/water mixture. The solvents were evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (69% of theory) of the compound L-valyl-N-{3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl}-L-alaninamide/trifluoroacetic acid (1:1).

LC-MS (Method 1): $R_t$=0.86 min; MS (ESIpos): m/z=785 (M+H)$^+$.

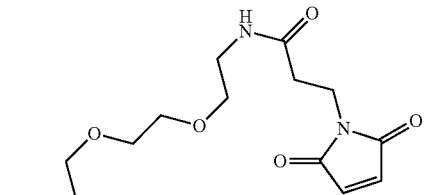
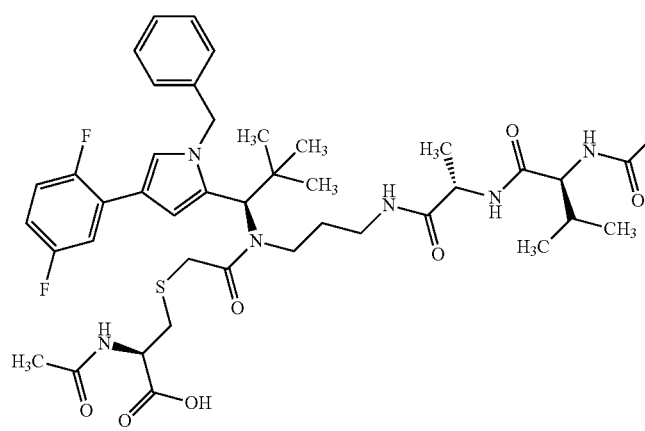

7.3 mg (8.12 µmol) of L-valyl-N-3-[({[(2R)-2-acetamido-2-carboxyethyl]sulphanyl}acetyl){(1R)-1-[1-benzyl-4-(2,5-difluorophenyl)-1H-pyrrol-2-yl]-2,2-dimethylpropyl}amino]propyl-L-alaninamide/trifluoroacetic acid (1:1) were initially charged together with 4.6 mg (8.93 µmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 0.5 ml of DMF, and 2.5 mg (24.36 µmol) of 4-methylmorpholine were added. The reaction mixture was stirred at RT overnight, and 4.4 mg (0.03 mmol) of acetic acid were then added. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 4.9 mg (50% of theory) of the title compound.

LC-MS (Method 1): $R_t$=1.07 min; MS (ESIpos): m/z=1183 (M+H)$^+$.

Intermediate F216

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1)

added, and the reaction mixture was stirred at 50° C. for 1 h. The mixture was diluted with ethyl acetate and the organic phase was extracted with water and saturated sodium bicarbonate solution and washed with saturated NaCl solution. The organic phase was dried over magnesium sulphate and the solvent was evaporated under reduced pressure. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 (M+H)$^+$.

16.5 mg (0.05 mmol) of 4-methylbenzenesulphonic acid/benzyl beta-alaninate (1:1) were initially charged together with 14.0 mg (0.11 mmol) of N,N-diisopropylethylamine in 1.5 ml of acetonitrile. The reaction mixture was stirred at RT for 3 min, and 30.8 mg (0.04 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine dissolved in 1.5 ml of acetonitrile, 23.4 mg (0.18 mmol) of N,N-diisopropylethylamine and 29.9 mg (0.05 mmol) of T3P (50% in ethyl acetate) were then added. The reaction

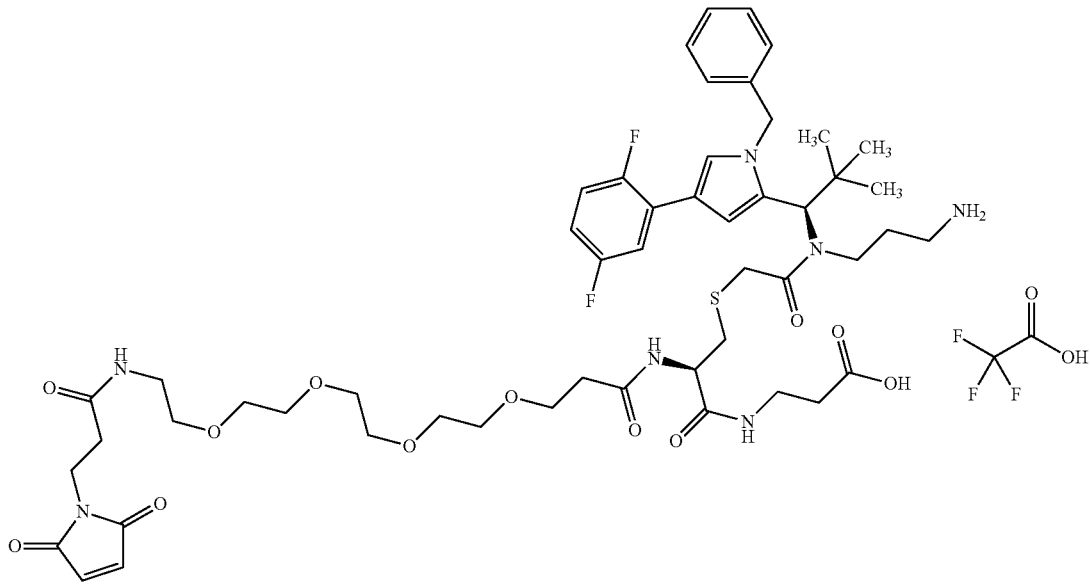 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CCN1C(=O)C=CC1=O)C(=O)NCCC(=O)O ; O=C(O)C(F)(F)F]

Under argon, 30.2 mg (0.06 mmol) of N,N-bis[(benzyloxy)carbonyl]-L-cystine were initially charged in 2.0 ml of water and 2.0 ml of isopropanol, and 56.7 mg (0.20 mmol) of TCEP were added. The reaction mixture was stirred at RT for 30 min 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70), dissolved in 2.0 ml of isopropanol, and 122.2 mg (0.48 mmol) of 1,8-diazabicyclo[5.4.0]undec-7-ene were then added, and the reaction mixture was stirred at 50° C. for 7 h. Another 122.2 mg (0.48 mmol) of 1,8-diazabicyclo[5.4.0]undec-7-ene were then mixture was stirred at RT overnight. Water was added, and the reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. The compound obtained was benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate.

LC-MS (Method 1): $R_t$=1.59 min; MS (ESIpos): m/z=1012 (M+H)$^+$.

43.8 mg (43.3 µmol) of benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate were dissolved in 8.0 ml of ethanol, 4.4 mg of palladium on activated carbon (10%) were added and the mixture was hydrogenated at RT and standard pressure overnight. The reaction mixture was filtered through a cardboard filter and the filter cake was washed with ethanol. The solvent was evaporated under reduced pressure. Two more times, the residue was treated as just described. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.08 min; MS (ESIpos): m/z=788 (M+H)$^+$.

14.5 mg (16.1 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) were initially charged together with 9.1 mg (17.7 µmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.9 mg (48.2 µmol) of 4-methylmorpholine were added. The reaction mixture was stirred at RT overnight, and 3.4 mg (0.06 mmol) of acetic acid were then added. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.28 min; MS (ESIpos): m/z=1186 (M+H)$^+$.

14.1 mg (11.9 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1) were dissolved in 1.5 ml of trifluoroethanol, and 9.7 mg (71.3 µmol) of zinc dichloride were added. The reaction mixture was stirred at 50° C. for 3 h. Another 9.7 mg (71.3 µmol) of zinc dichloride were added, and the reaction mixture was stirred at 50° C. for 3 h. Another 9.7 mg (71.3 µmol) of zinc dichloride were added, and the reaction mixture was stirred at 70° C. for 4 h. 20.8 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was lyophilized. This gave 6.2 mg (44% of theory) of the title compound.

LC-MS (Method 1): $R_t$=0.82 min; MS (ESIpos): m/z=1042 (M+H)$^+$.

Intermediate F217

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[(2,5-dioxo-2,5-dihydro-1H-pyrrol-1-yl)acetyl]-L-cysteine/ trifluoroacetic acid (1:1)

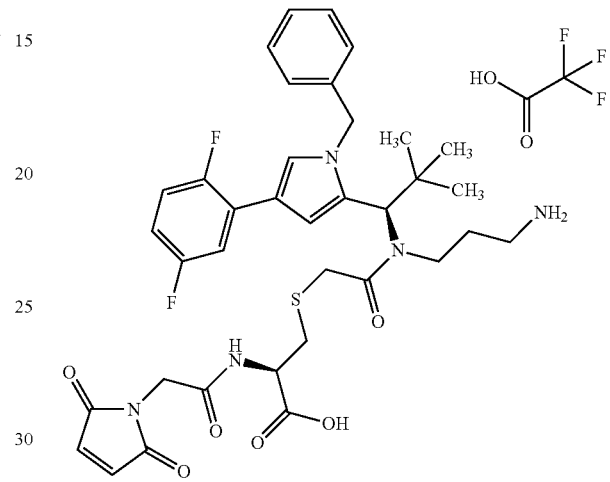

Under argon, 7.5 mg (0.05 mmol) of (2,5-dioxo-2,5-dihydro-1H-pyrrol-1-yl)acetic acid were initially charged in 1.5 ml of DMF, and 7.5 mg (0.05 mmol) of HOBt, 15.5 mg (0.05 mmol) of TBTU and 6.2 mg (0.05 mmol) of N,N-diisopropylethylamine were added. The reaction mixture was stirred at RT for 10 min 40.0 mg (0.05 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71), dissolved in 1.5 ml of DMF, and 18.7 mg (0.14 mmol) of N,N-diisopropylethylamine were then added, and the reaction mixture was stirred at RT overnight. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 11.2 mg (25% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine.

LC-MS (Method 1): $R_t$=1.37 min; MS (ESIpos): m/z=854 (M+H)$^+$.

10.9 mg (12.8 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine were dissolved in 2.0 ml of trifluoroethanol, and 10.4 mg (76.6 µmol) zinc dichloride were added. The reaction mixture was stirred at 50° C. for 4 h. 22.4 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250× 30; 10μ, flow rate: 50 ml/min, MeCN/water, 0.1% TFA). The solvents were evaporated under reduced pressure and the residue was lyophilized. This gave 7.5 mg (65% of theory) of the title compound.

LC-MS (Method 1): $R_t$=0.92 min; MS (ESIpos): m/z=710 (M+H)$^+$.

Intermediate F218

N-[19-(2,5-Dioxo-2,5-dihydro-1H-pyrrol-1-yl)-17-oxo-4,7,10,13-tetraoxa-16-azanonadecan-1-oyl]-L-gamma-glutamyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

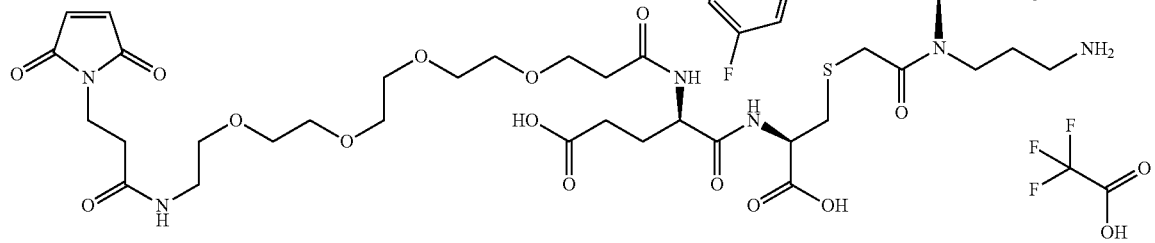

Under argon, 22.9 mg (0.06 mmol) of (4S)-5-(benzyloxy)-4-{[(benzyloxy)carbonyl]amino}-5-oxopentanoic acid were initially charged in 2.0 ml of DMF, and 9.4 mg (0.05 mmol) of HOBt, 19.8 mg (0.06 mmol) of TBTU and 8.0 mg (0.06 mmol) of N,N-diisopropylethylamine were added. The reaction mixture was stirred at RT for 10 min 51.2 mg (0.06 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine (Intermediate C71), dissolved in 1.0 ml of DMF, and 23.9 mg (0.19 mmol) of N,N-diisopropylethylamine were then added, and the reaction mixture was stirred at RT overnight. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound (16R)-11-{(1R)-1-[1-benzyl-4-(2,5-difluorophenyl)-1H-pyrrol-2-yl]-2,2-dimethylpropyl}-16-[{(4S)-5-(benzyloxy)-4-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid.

LC-MS (Method 1): $R_t$=1.52 min; MS (ESIpos): m/z=1070 (M+H)$^+$.

Under argon, 3.9 mg (0.02 mmol) of palladium(II) acetate were initially charged in 1.0 ml of dichloromethane, and 5.3 mg (0.05 mmol) of triethylamine and 254.3 mg (2.19 mmol) of triethylsilane were added. The reaction mixture was stirred at RT for 5 min, and 18.6 mg (0.02 mmol) of (16R)-11-{(1R)-1-[1-benzyl-4-(2,5-difluorophenyl)-1H-pyrrol-2-yl]-2,2-dimethylpropyl}-16-{[(4S)-5-(benzyloxy)-4-{[(benzyloxy)carbonyl]amino}-5-oxopentanoyl]amino}-2,2-dimethyl-6,12-dioxo-5-oxa-14-thia-7,11-diaza-2-silaheptadecan-17-oic acid dissolved in 1.0 ml of dichloromethane were added. The solvent was evaporated under reduced pressure without heating. The residue was taken up in acetonitrile, filtered through a syringe filter and purified by preparative RP-HPLC (column: Reprosil 250× 30; 10μ, flow rate: 50 ml/min, MeCN/water, 0.1% TFA). The solvents were evaporated under reduced pressure and the residue was dried under high vacuum. This gave 11.0 mg (66% of theory) of the compound L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1).

LC-MS (Method 1): $R_t$=1.14 min; MS (ESIpos): m/z=846 (M+H)$^+$.

15.0 mg (15.6 μmol) of L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) were initially charged together with 8.8 mg (17.2 μmol) of 3-(2,5-dioxo-2,5-dihydro-1H-pyrrol-1-yl)-N-15-[(2,5-dioxopyrrolidin-1-yl)oxy]-15-oxo-3,6,9,12-tetraoxapentadec-1-yl propanamide in 1.0 ml of DMF, and 4.7 mg (46.9 μmol) of 4-methylmorpholine were added. The reaction mixture was stirred at RT overnight, and 3.3 mg (0.06 mmol) of acetic acid were then added.

The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 14.2 mg (70% of theory) of the compound N-[19-(2,5-dioxo-2,5-dihydro-1H-pyrrol-1-yl)-17-oxo-4,7,10,13-tetraoxa-16-azanonadecan-1-oyl]-L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 4) $R_t$=1.24 min; MS (ESIpos): m/z=1244 (M+H)$^+$.

13.8 mg (11.1 µmol) of N-[19-(2,5-dioxo-2,5-dihydro-1H-pyrrol-1-yl)-17-oxo-4,7,10,13-tetraoxa-16-azanonadecan-1-oyl]-L-gamma-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 9.1 mg (66.5 µmol) zinc dichloride were added. The reaction mixture was stirred at 50° C. for 4 h. 19.4 mg (0.07 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 6.9 mg (50% of theory) of the title compound.

LC-MS (Method 1): $R_t$=0.89 min; MS (ESIpos): m/z=1100 (M+H)$^+$.

Intermediate F235

Trifluoroacetic acid/N-[19-(2,5-dioxo-2,5-dihydro-1H-pyrrol-1-yl)-17-oxo-4,7,10,13-tetraoxa-16-azanonadecan-1-oyl]-L-valyl-N-{4-[(3-aminopropyl){(1R)-1-[1-benzyl-4-(2,5-difluorophenyl)-1H-pyrrol-2-yl]-2,2-dimethylpropyl}carbamoyl]phenyl}-L-alaninamide (1:1)

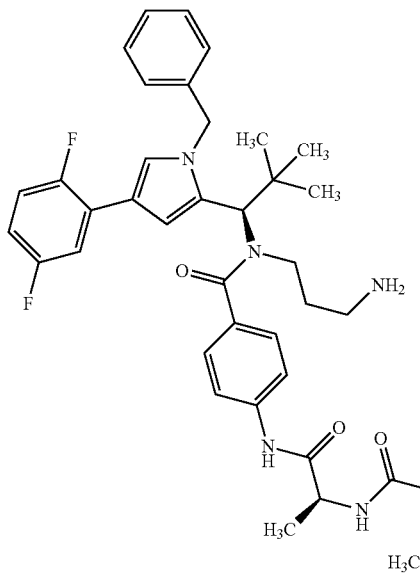
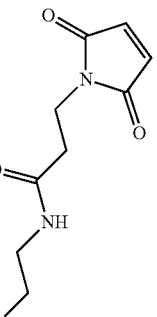

120.0 mg (0.22 mmol) of 2-(trimethylsilyl)ethyl [3-{(1R)-1-[1-benzyl-4-(2,5-difluorophenyl)-1H-pyrrol-2-yl]-2,2-dimethylpropyl}amino)propyl]carbamate (see synthesis of Intermediate C11) and 52.1 mg (0.28 mmol) of 4-nitrobenzoyl chloride were dissolved in 8.0 ml of dichloromethane, and 28.4 mg (0.28 mmol) of triethylamine were added. The reaction mixture was stirred at RT overnight. The solvent was evaporated under reduced pressure and the residue was purified by preparative RP-HPLC (column: Reprosil 125×30; 10µ, flow rate: 50 ml/min, MeCN/water, 0.1% TFA). This gave 97.7 mg (64% of theory) of the compound 2-(trimethylsilyl)ethyl {3-[({(1R)-1-[1-benzyl-4-(2,5-difluorophenyl)-1H-pyrrol-2-yl]-2,2-dimethylpropyl}(4-nitrobenzoyl)amino]propyl}carbamate.

LC-MS (Method 1): $R_t$=1.54 min; MS (ESIpos): m/z=705 (M+H)$^+$.

97.0 mg (0.14 mmol) of 2-(trimethylsilyl)ethyl {3-[{(1R)-1-[1-benzyl-4-(2,5-difluorophenyl)-1H-pyrrol-2-yl]-2,2-dimethylpropyl}(4-nitrobenzoyl)amino]propyl}carbamate were dissolved in 5.0 ml of ethanol, 9.7 mg of palladium on activated carbon (10%) were added and the mixture was hydrogenated at standard pressure for 5 h. The reaction mixture was filtered through a cardboard filter and the filter cake was washed with ethanol. The solvent was evaporated under reduced pressure. The residue was used without further purification in the next step of the synthesis. This gave 87.4 mg (88% of theory) of the compound 2-(trimethylsilyl)ethyl {3-[(4-aminobenzoyl){(1R)-1-[1-benzyl-4-(2,5-difluorophenyl)-1H-pyrrol-2-yl]-2,2-dimethylpropyl}amino]propyl}carbamate.

LC-MS (Method 1): $R_t$=1.47 min; MS (ESIpos): m/z=675 (M+H)$^+$.

59.3 mg (0.09 mmol) of 2-(trimethylsilyl)ethyl {3-[(4-aminobenzoyl){(1R)-1-[1-benzyl-4-(2,5-difluorophenyl)-1H-pyrrol-2-yl]-2,2-dimethylpropyl}amino]propyl}carbamate and 25.5 mg (0.11 mmol) of N-[(benzyloxy)carbonyl]-L-alanine were initially charged together with 68.1 mg (0.53 mmol) of N,N-diisopropylethylamine in 5.0 ml of acetonitrile. 72.7 mg (0.11 mmol) of T3P (50% in ethyl acetate) were added slowly. The reaction mixture was stirred at RT overnight. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 52.2 mg (68% of theory) of the compound benzyl [(2S)-1-{[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]amino}-1-oxopropan-2-yl]carbamate.

LC-MS (Method 1): $R_t$=1.48 min; MS (ESIpos): m/z=880 (M+H)$^+$.

23.9 mg (0.03 mmol) of benzyl [(2S)-1-{[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]amino}-1-oxopropan-2-yl] carbamate were dissolved in 3.0 ml of ethyl acetate, 2.4 mg of palladium on activated carbon (10%) were added and the mixture was hydrogenated at standard pressure for 2 h. The reaction mixture was filtered through a paper filter and the filter cake was washed with ethyl acetate. The solvent was evaporated under reduced pressure. The residue was used without further purification in the next step of the synthesis. This gave 20.1 mg (90% of theory) of the compound 2-(trimethylsilyl)ethyl [3-([4-(L-alanylamino)benzoyl]{(1R)-1-[1-benzyl-4-(2,5-difluorophenyl)-1H-pyrrol-2-yl]-2,2-dimethylpropyl}amino)propyl]carbamate LC-MS (Method 1): $R_t$=1.13 min; MS (ESIpos): m/z=746 (M+H)$^+$.

20.0 mg (0.03 mmol) of 2-(trimethylsilyl)ethyl [3-([4-(L-alanylamino)benzoyl]{(1R)-1-[1-benzyl-4-(2,5-difluorophenyl)-1H-pyrrol-2-yl]-2,2-dimethylpropyl}amino)propyl]carbamate were initially charged together with 14.9 mg (0.04 mmol) of 2,5-dioxopyrrolidin-1-yl N-[(benzyloxy)carbonyl]-L-valinate in 2.0 ml of DMF, and 5.4 mg (0.05 mmol) of 4-methylmorpholine were added. The reaction mixture was purified directly by preparative RP-HPLC (column: Reprosil 125×30; 10µ, flow rate: 50 ml/min, MeCN/water). The solvents were evaporated under reduced pressure and the residue was dried under high vacuum. This gave the compound N-[(benzyloxy)carbonyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

LC-MS (Method 1): $R_t$=1.49 min; MS (ESIpos): m/z=979 (M+H)$^+$.

17.0 mg (17.4 µmol) of N-[(benzyloxy)carbonyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were dissolved in 2.5 ml of ethyl acetate, 1.7 mg of palladium on activated carbon (10%) were added and the mixture was hydrogenated at standard pressure overnight. The reaction mixture was filtered through a paper filter and the filter cake was washed with ethyl acetate. The solvent was evaporated under reduced pressure and the residue was dried under high vacuum. This gave 15.3 mg (60% of theory) of the compound L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

LC-MS (Method 1): $R_t$=1.15 min; MS (ESIpos): m/z=845 (M+H)$^+$.

15.3 mg (0.01 mmol) of L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were initially charged together with 7.9 mg (0.02 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 2.4 ml of DMF, and 1.9 mg (0.02 mmol) of 4-methylmorpholine were added. The reaction mixture was stirred at RT overnight, and 1.4 mg (0.02 mmol) of acetic acid were then added. The reaction mixture was purified directly by preparative RP-HPLC (column: Reprosil 125×30; 10µ, flow rate: 50 ml/min, MeCN/water). The solvents were evaporated under reduced pressure and the residue was dried under high vacuum. This gave 11.7 mg (70% of theory) of the compound N-[19-(2,5-dioxo-2,5-dihydro-1H-pyrrol-1-yl)-17-oxo-4,7,10,13-tetraoxa-16-azanonadecan-1-oyl]-L-valyl-N-4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide.

11.7 mg (0.01 mmol) of N-[19-(2,5-dioxo-2,5-dihydro-1H-pyrrol-1-yl)-17-oxo-4,7,10,13-tetraoxa-16-azanonadecan-1-oyl]-L-gamma-glutamyl-S-(11-{(1R)-1-[1-N-[19-(2,5-dioxo-2,5-dihydro-1H-pyrrol-1-yl)-17-oxo-4,7,10,13-tetraoxa-16-azanonadecan-1-oyl]-L-valyl-N-[4-({(1R)-1-[1-benzyl-4-(2,5-difluorophenyl)-1H-pyrrol-2-yl]-2,2-dimethylpropyl}[3-({[2-(trimethylsilyl)ethoxy]carbonyl}amino)propyl]carbamoyl)phenyl]-L-alaninamide were dissolved in 2.0 ml of trifluoroethanol, and 3.9 mg (0.03 mmol) of zinc dichloride were added. The reaction mixture was stirred at 50° C. overnight. 8.3 mg (0.03 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 5.4 mg (47% of theory) of the title compound.

LC-MS (Method 1): $R_t$=0.94 min; MS (ESIpos): m/z=1100 (M+H)$^+$.

Intermediate F236

(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-4-{[(2,5-dioxo-2,5-dihydro-1H-pyrrol-1-yl)acetyl]amino}butanoic acid/trifluoroacetic acid (1:1)

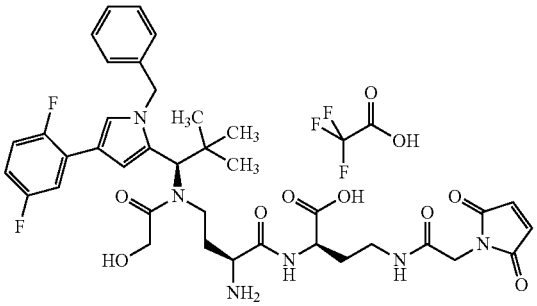

The synthesis of the title compound was carried out analogously to Intermediate F192 from (2R)-4-{[(benzyloxy)carbonyl]amino}-2-[(tert-butoxycarbonyl)amino]butanoic acid/N-cyclohexylcyclohexanamine (1:1).

LC-MS (Method 4): $R_t$=1.1 min; MS (ESIpos): m/z=751 (M+H)$^+$.

Intermediate F238

Trifluoroacetic acid/N-{(2S)-1-amino-3-[{(1R)-1-[1-benzyl-4-(2,5-difluorophenyl)-1H-pyrrol-2-yl]-2,2-dimethylpropyl}(glycoloyl)amino]propan-2-yl}-N'-[2-(2,5-dioxo-2,5-dihydro-1H-pyrrol-1-yl)ethyl]succinamide (1:1)

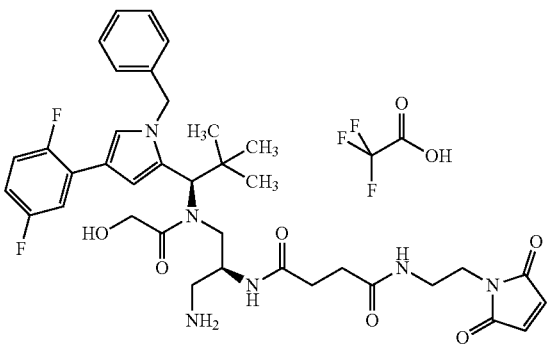 [SMILES: CC(C)(C)[C@H](c1cc(-c2cc(F)ccc2F)cn1Cc1ccccc1)N(C[C@H](CN)NC(=O)CCC(=O)NCCN1C(=O)C=CC1=O)C(=O)CO ; O=C(O)C(F)(F)F]

18 mg (0.025 mmol) of Intermediate C72 were taken up in 6 ml of DMF and coupled with 7.5 mg (0.03 mmol) of trifluoroacetic acid/1-(2-aminoethyl)-1H-pyrrole-2,5-dione (1:1) in the presence of 11.3 mg (0.03 mmol) of HATU and 22 µl of N,N-diisopropylethylamine After 1 h of stirring at RT, the reaction was concentrated and the residue was purified by preparative HPLC. The appropriate fractions were concentrated and the residue was lyophilized from acetonitrile/water 1:1. This gave 15 mg (67% of theory) of the intermediate.

LC-MS (Method 4): R$_t$=1.71 min; MS (EIpos): m/z=873 [M+Na]$^+$.

The title compound was then prepared from this intermediate by deprotection with zinc chloride in 4 ml of trifluoroethanol as described for Intermediate F119. Purification by preparative HPLC gave 8.5 mg (63% of theory) of the title compound.

LC-MS (Method 1): R$_t$=0.86 min; MS (ESIpos): m/z=707 (M+Na)$^+$.

Intermediate F241

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[N-(bromoacetyl)glycyl]amino}ethyl)butanamide (1:1)

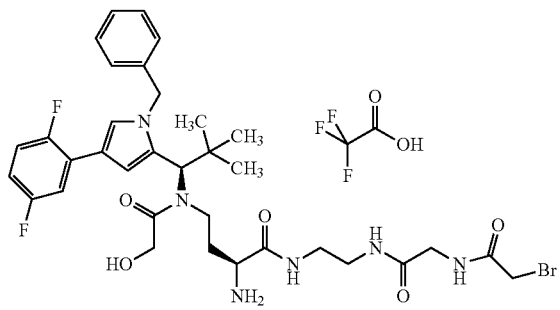 [SMILES: CC(C)(C)[C@H](c1cc(-c2cc(F)ccc2F)cn1Cc1ccccc1)N(CC[C@H](N)C(=O)NCCNC(=O)CNC(=O)CBr)C(=O)CO ; O=C(O)C(F)(F)F]

The title compound was prepared analogously from Intermediate C66 by coupling with commercially available 1-(2-bromoacetoxy)pyrrolidine-2,5-dione and subsequent deblocking with zinc chloride.

LC-MS (Method 1): R$_t$=0.84 min; MS (EIpos): m/z=733 and 735 [M+H]$^+$.

Intermediate F242

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[(2,5-dioxo-2,5-dihydro-1H-pyrrol-1-yl)acetyl]amino}propyl)butanamide (1:1)

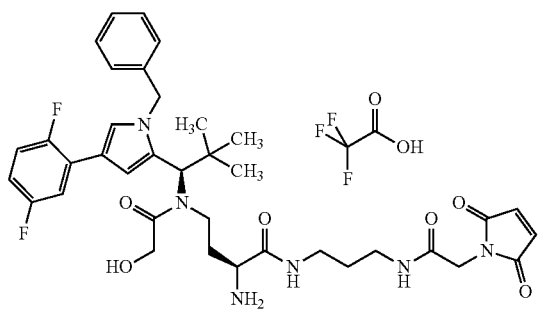 [SMILES: CC(C)(C)[C@H](c1cc(-c2cc(F)ccc2F)cn1Cc1ccccc1)N(CC[C@H](N)C(=O)NCCCNC(=O)CN1C(=O)C=CC1=O)C(=O)CO ; O=C(O)C(F)(F)F]

The synthesis of the title compound was carried out analogously to Intermediate F104.

LC-MS (Method 1): R$_t$=0.84 min; MS (ESIpos): m/z=707 (M+H)$^+$.

Intermediate F243

Trifluoroacetic acid/(2S)-2-amino-4-{[(1R)-1-[1-benzyl-4-(2,5-difluorophenyl)-1H-pyrrol-2-yl]-2,2-dimethylpropyl}(glycoloyl)amino]-N-[2-(2-{[(2,5-dioxo-2,5-dihydro-1H-pyrrol-1-yl)acetyl]amino}ethoxy)ethyl]butanamide (1:1)

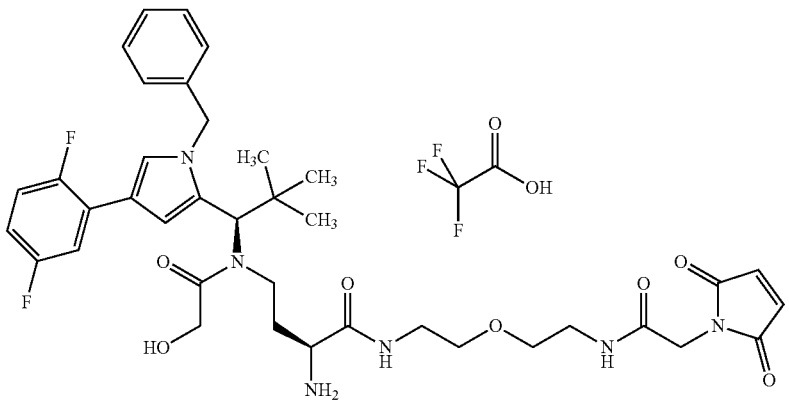 [SMILES: CC(C)(C)[C@H](c1cc(-c2cc(F)ccc2F)cn1Cc1ccccc1)N(CC[C@H](N)C(=O)NCCOCCNC(=O)CN1C(=O)C=CC1=O)C(=O)CO ; O=C(O)C(F)(F)F]

The synthesis of the title compound was carried out analogously to Intermediate F242.

LC-MS (Method 1): $R_t$=0.81 min; MS (ESIpos): m/z=737 (M+H)$^+$.

Intermediate F244

N-{2-[(S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-L-cysteinyl)amino]ethyl}-6-(2,5-dioxo-2,5-dihydro-1H-pyrrol-1-yl)hexanamide

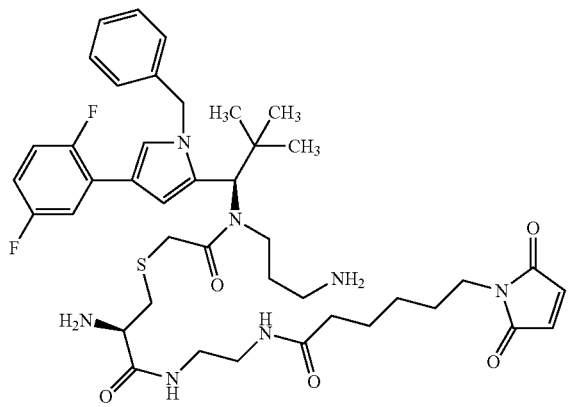 [SMILES: CC(C)(C)[C@H](c1cc(-c2cc(F)ccc2F)cn1Cc1ccccc1)N(CCCN)C(=O)CSC[C@H](N)C(=O)NCCNC(=O)CCCCCN1C(=O)C=CC1=O]

100 mg (about 0.101 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine (Intermediate C 73) were initially charged in 88 ml of dimethylformamide, and with 107 mg (about 0.15 mmol) of N-(2-aminoethyl)-6-(2,5-dioxo-2,5-dihydro-1H-pyrrol-1-yl)hexanamide (Intermediate L73), 46 mg (0.12 mmol) of HATU and 88 µl (0.50 mmol) of were added. The reaction mixture was stirred at RT for 15 minutes. Water/dichloromethane was added to the mixture, and the organic phase was then washed with water and brine, dried over magnesium sulphate, concentrated on a rotary evaporator and dried under high vacuum. The residue was used further without further purification. This gave 92 mg (59%, purity 72%) of the title compound.

LC-MS (Method 1): $R_t$=1.59 min; MS (ESIpos): m/z=1096 (M+H)$^+$.

Under argon, 40 mg (0.30 mmol) of zinc chloride were added to a solution of 91 mg (about 0.06 mmol) of 2-(trimethylsilyl)ethyl [(9R)-4-{(1R)-1-[1-benzyl-4-(2,5-difluorophenyl)-1H-pyrrol-2-yl]-2,2-dimethylpropyl}-20-(2,5-dioxo-2,5-dihydro-1H-pyrrol-1-yl)-5,10,15-trioxo-9-{[3-(trimethylsilyl)propanoyl]amino}-7-thia-4,11,14-triazaicos-1-yl]carbamate in 1.45 ml of trifluoroethanol. The reaction mixture was stirred at 50° C. for 2 h. 30 mg (0.22 mmol) of zinc chloride were then added, and the mixture was stirred at RT for another 1 h. 52 mg (0.18 mmol) of EDTA were added, and after 10 minutes of stirring at RT the mixture was diluted slightly with water/acetonitrile and purified by preparative HPLC (mobile phase: ACN/water+0.1% TFA, gradient). This gave 17 mg (31%) of the title compound.

LC-MS (Method 1): $R_t$=0.80 min; MS (ESIpos): m/z=808 (M+H)$^+$.

Intermediate F245

Trifluoroacetic acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-(2-{[(2,5-dioxo-2,5-dihydro-1H-pyrrol-1-yl)acetyl]amino}ethyl)succinamide (1:1)

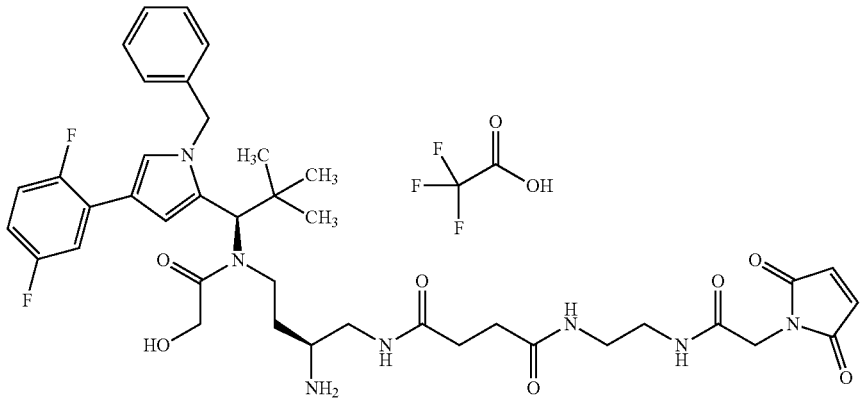 [SMILES: CC(C)(C)[C@H](c1cc(-c2cc(F)ccc2F)cn1Cc1ccccc1)N(CC[C@H](N)CNC(=O)CCC(=O)NCCNC(=O)CN1C(=O)C=CC1=O)C(=O)CO ; O=C(O)C(F)(F)F]

The title compound was prepared by coupling of 10 mg (0.0135 mmol) of Intermediate C65 with 8 mg (0.027 mmol) of Intermediate L1 in 8 ml of DMF in the presence of 15 mg (0.04 mmol) of HATU and 9 µl of N,N-diisopropylethylamine and subsequent deprotection with zinc chloride in trifluoroethanol as described for Intermediate F119. Purification by preparative HPLC gave 8.8 mg (58% of theory over 2 steps) of the title compound.

LC-MS (Method 1): $R_t$=0.84 min; MS (ESIpos): m/z=778 (M+H)$^+$.

Intermediate F247

Trifluoroacetic acid/methyl 4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-bromo-4-oxobutanoate (1:1)

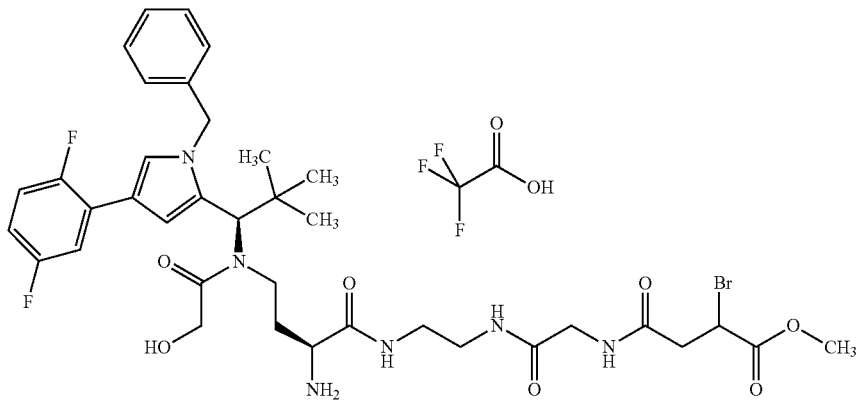 [SMILES: COC(=O)C(Br)CC(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

14 mg (0.018 mmol) of Intermediate C66 were dissolved in 14 ml of DCM, and with 10.1 mg (0.037 mmol) of 2-bromo-1-ethylpyridinium tetrafluoroborate (BEP) and, a little at a time, a total of 250 μl of pyridine were added, the pH being kept between 5 and 6. The pH was then adjusted to 4 with acetic acid, the reaction was concentrated and the residue was purified by preparative HPLC. Combination of the appropriate fractions, lyophilization and drying gave 4 mg (21% of theory) the protected intermediate, which were then deprotected at the amino function with zinc chloride. HPLC purification and lyophilisation gave 3 mg (72% of theory) of the title compound as a colourless foam.

LC-MS (Method 1): $R_t$=0.88 min; MS (ESIpos): m/z=805 and 807(M+H)$^+$.

The title compound was prepared by coupling of 10 mg (0.015 mmol) of Intermediate C58 with 5 mg (0.017 mmol) of Intermediate L12 in the presence of HATU and subsequent deprotection with zinc chloride. This gave 6.5 mg (52% of theory over 2 steps) of the title compound.

LC-MS (Method 1): $R_t$=0.91 min; MS (ESIpos): m/z=680 (M+H)$^+$.

Intermediate F248

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[2-(2,5-dioxo-2,5-dihydro-1H-pyrrol-1-yl)ethoxy]ethyl}butanamide (1:1)

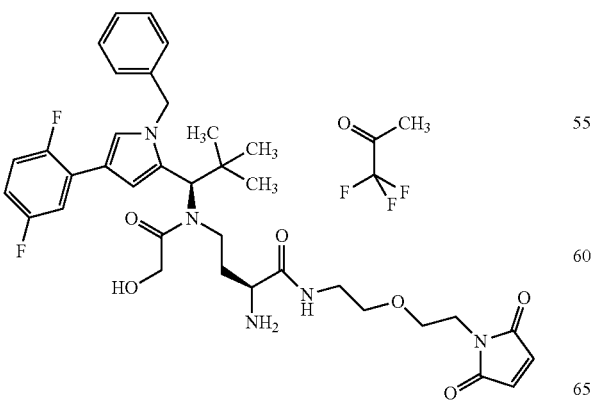

515

Intermediate F254

Trifluoroacetic acid/methyl (3S)-4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-bromo-4-oxobutanoate (1:1)

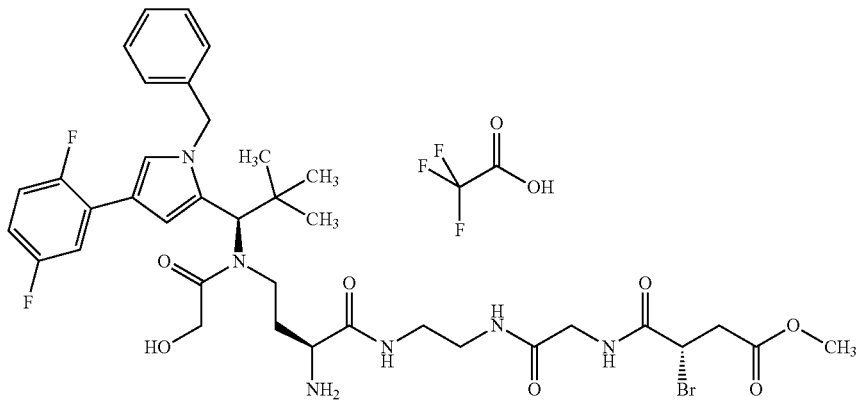 [SMILES: COC(=O)C[C@H](Br)C(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

The title compound was prepared analogously to Intermediate 247 by coupling of 15 mg (0.02 mmol) of Intermediate C66 with 21 mg (0.099 mmol) of (2S)-2-bromo-4-methoxy-4-oxobutanoic acid which had been synthesized as described in (J. Org. Chem. 200, 65, 517-522) from (2S)-2-amino-4-methoxy-4-oxobutanoic acid hydrochloride (1:1).

LC-MS (Method 1): $R_t$=0.89 min; MS (ESIpos): m/z=805 and 807 (M+H)$^+$.

B: Preparation of Antibody/Active Compound Conjugates (ADC)

B-1. General Process for Generating Anti-TWEAKR Antibodies

The anti-TWEAKR antibodies were generated, for example, by screening of a phage display library for recombinant human TWEAKR SEQ ID NO: 138 and murine TWEAKR SEQ ID NO: 137. The antibodies obtained in this manner were reformatted into the human IgG1 format and used for the working examples described here. In addition, antibodies which bind to TWEAKR are known to the person skilled in the art, see, for example, WO2009/020933(A2) or WO2009140177 (A2).

SEQ ID NO: 138 (polypeptide):
EQAPGTAPCSRGSSWSADLDKCMDCASCRARPHSDFCLGCAAAPPAPFRL

LWPRSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK

SEQ ID NO: 137 (polypeptide):
EQAPGTSPCSSGSSWSADLDKCMDCASCPARPHSDFCLGCAAAPPAHFRL

LWPRSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK

B-2. General Process for Expressing Anti-TWEAKR Antibodies in Mammalian Cells The antibodies, for example TPP-2090, were produced in transient mammalian cell cultures as described by Tom et al., Chapter 12 in Methods Express: Expression Systems edited by Micheal R. Dyson and Yves Durocher, Scion Publishing Ltd, 2007 (see AK-Example 1).

B-3. General Process for Purifying Antibodies from Cell Supernatants

The antibodies, for example TPP-2090, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The commercially available antibody cetuximab (trade name Erbitux) was purified from the commercial product by standard chromatographic methods (protein A, preparative SEC).

The commercially available antibody trastuzumab (trade name Herceptin) was purified from the commercial product by standard chromatographic methods (protein A, preparative SEC).

From the commercial product (trade name CIMAher), the antibody nimotuzumab was purified from the commercial product by standard chromatographic methods (protein A, preparative SEC).

From the commercial product (trade name Vectibix), the antibody panitumumab was purified from the commercial product by standard chromatographic methods (protein A, preparative SEC).

B-4. General Process for Coupling to Cysteine Side Chains

The following antibodies were used for the coupling reactions:
cetuximab (anti EGFR AK)
anti-TWEAKR AK 1 (TPP-2090)
trastuzumab (anti-Her2 AK)
nimotuzumab (anti-EGFR AK)
panitumumab (anti-EGFR AK)

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 10 mg/ml to 15 mg/ml, and the mixture was stirred at RT for 1 h. For this purpose, the solution of the respective antibody used can be employed at the concentrations stated in the working examples, or it may optionally also be diluted with PBS buffer to about half of the stated starting concentrations in order to get into the preferred concentration range. Subsequently, depending on the intended loading from 2 to 12 equivalents, preferably about 5-10 equivalents of the maleinimide precursor compound or halide precursor compound to be coupled can be added as a solution in DMSO. Here, the amount of DMSO should not exceed 10% of the total volume. The reaction was stirred in the case of maleinimide precursors for 60-240 min at RT and in the case of halide precursors between 8 and 24 h at RT and then applied to PBS-equilibrated PD 10 columns (Sephadex® G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

Unless indicated otherwise, the immunoconjugates shown in the examples were prepared by this process. Depending on the linker, the ADCs shown in the examples may also be present to a lesser or higher degree in the form of the hydrolysed open-chain succinamides attached to the antibodies.

In particular the KSP-I-ADCs attached though the linker substructure

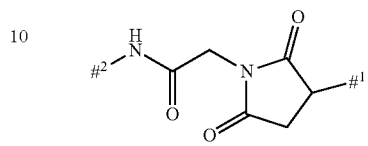

to thiol groups of the antibodies may optionally also be prepared in a targeted manner by rebuffering after the coupling and stirring at pH 8 for about 20 h according to Scheme 26 via the ADCs attached via open-chain succinamides.

$^1$ represents the sulphur bridge to the antibody, and #$^2$ the point of attachment to the modified KSP inhibitor Such ADCs where the linker is attached to the antibodies through hydrolysed open-chain succinamides may optionally also be prepared in a targeted manner by an exemplary procedure as follows:

Under argon, a solution of 0.344 mg TCEP in 100 µl of PBS buffer was added to 60 mg of the antibody in question in 5 ml of PBS buffer (c~12 mg/ml). The reaction was stirred at RT for 30 min, and 0.003 mmol of a maleinimide precursor compound dissolved in 600 µl of DMSO was then added. After a further 1.5 h -2 h of stirring at RT, the reaction was diluted with 1075 µl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

Other potentially hydrolysis-sensitive thianylsuccinimide bridges to the antibody in the working examples contain the following linker substructures, where #$^1$ represents the thioether linkage to the antibody and #$^2$ the point of attachment to the modified KSP inhibitor:

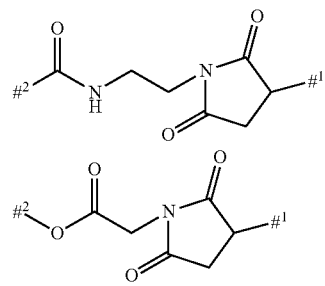

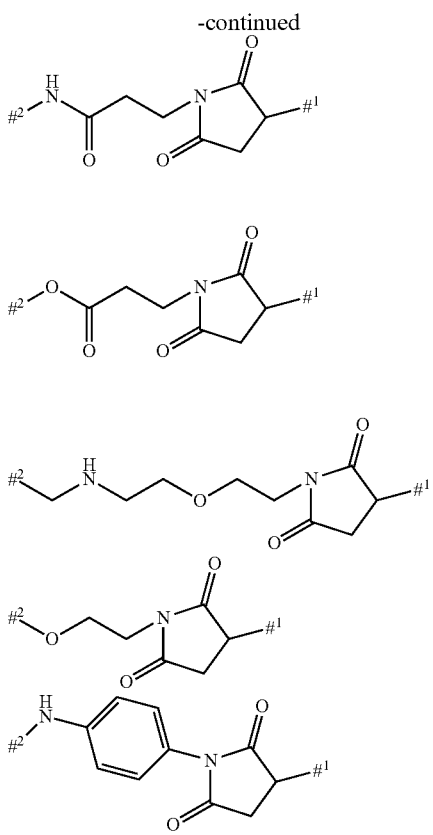

These linker substructures represent the linking unit to the antibody and have (in addition to the linker composition) a significant effect on the structure and the profile of the metabolites formed in the tumour cells.

In the structural formulae shown, $AK_{1A}$, $AK_{1B}$, $AK_{1E}$, $AK_{1I}$, $AK_{1H}$, $AK_{1K}$ have the following meanings:

$AK_{1A}$=cetuximab (partially reduced)–$S\S^1$ $AK_{1B}$=anti-TWEAKR AK-1 (partially reduced)–$S\S^1$ $AK_{1E}$=trastuzumab (partially reduced)–$S\S^1$ $AK_{1I}$=nimotuzumab (partially reduced)–$S\S^1$ $AK_{1H}$=panitumumab (partially reduced)–$S\S^1$ where
$\S^1$ represents the linkage to the succinimide group or to any isomeric hydrolysed open-chain succinamides or the alkylene radical resulting therefrom,
and
S represents the sulphur atom of a cysteine residue of the partially reduced antibody.

B-5. General Process for Coupling to Lysine Side Chains

The following antibodies were used for the coupling reactions:
cetuximab (anti EGFR AK)
anti-TWEAKR AK 1 (TPP-2090)
trastuzumab (anti-Her2 AK)
nimotuzumab (anti-EGFR AK)
panitumumab (anti-EGFR AK)

From 2 to 8 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After 30 min to 6 h of stirring at RT, the same amount of precursor compound in DMSO was added again. Here, the amount of DMSO should not exceed 10% of the total volume. After a further 30 min to 6 h of stirring at RT, the reaction was applied to PD 10 columns (Sephadex® G-25, GE Healthcare) equilibrated with PBS and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-7.

In the structural formulae shown, $AK_{2A}$, $AK_{2B}$, $AK_{2G}$, $AK_{2E}$, $AK_{2I}$, $AK_{2H}$, $AK_{2K}$ have the following meanings:

$AK_{2A}$=cetuximab (anti-EGFR AK)–$NH\S^2$ $AK_{2B}$=anti-TWEAKR AK-1–$NH\S^2$ $AK_{2E}$=trastuzumab–$NH\S^2$ $AK_{2I}$=nimotuzumab–$NH\S^2$ $AK_{2H}$=panitumumab–$NH\S^2$ where
$\S^2$ represents the linkage to the carbonyl group
and
NH represents the side-chain amino group of a lysine residue of the antibody.

B-6a. General Process for Preparing Closed Succinimide-Cysteine Adducts

In an exemplary embodiment, 10 µmol of the maleinimide precursor compounds described above were taken up in 3-5 ml of DMF, and 2.1 mg (20 µmol) of L-cysteine were added. The reaction mixture was stirred at RT for 2 h to 24 h, then dried under reduced pressure and then purified by preparative HPLC.

B-6aa. General Process for Preparing Isomeric Open Succinamide-Cysteine Adducts In an exemplary embodiment, 68 µmol of the maleinimide precursor compounds described above were taken up in 15 ml of DMF, and with 36 mg (136 µmol) of N-{[2-(trimethylsilyl)ethoxy]carbonyl}-L-cysteine were added. The reaction mixture was stirred at RT for ~20 h, then dried under reduced pressure and then purified by preparative HPLC.

The appropriate fractions were combined and the solvents were evaporated under reduced pressure, and the residue was then dissolved in 15 ml of THF/water 1:1. 131 μl of a 2M aqueous lithium hydroxide solution were added, and the reaction was stirred at RT for 1 h. The reaction was then neutralized with a 1M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave the hydrolysed open sulphanylsuccinamides as a regioisomer mixture.

B-6b. General Process for Preparing Lysine Adducts

In an exemplary embodiment, 10 μmol of the activated ester precursor compounds described above were taken up in 3-5 ml of DMF, and α-amino-protected L-lysine was added in the presence of 30 μmol of N,N-diisopropylethylamine. The reaction mixture was stirred at RT for 2 h to 24 h, then dried under reduced pressure and then purified by preparative HPLC. The protective group was then removed by known methods.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophilized.

B-7. Determination of the Antibody, the Toxophor Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophor loading of the PBS buffer solutions obtained of the conjugates described in the working example was determined as follows:

Determination of toxophor loading of lysine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTofQ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

The toxophor loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 μA) were added to the ADC solution (1 mg/ml, 50 μA). The mixture was incubated at 55° C. for one hour and analysed by HPLC.

HPLC analysis was carried out on an Agilent 1260HPLC system with detection at 220 nm A Polymer Laboratories PLRP-S polymeric reversed-phase column (catalogue number PL1912-3802) (2.1×150 mm, 8 μl particle size, 1000 Å) was used at a flow rate of 1 ml/min with the following gradient: 0 min, 25% B; 3 min, 25% B; 28 min, 50% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophor (L1) and the heavy chains with one, two and three toxophors (H1, H2, H3).

Average loading of the antibody with toxophors was calculated from the peak areas determined by integration as double the sum of the toxophor number weighed integration results of all peaks divided by the sum of the singly weighed integration results of all peaks. In individual cases, it may be possible that, owing to co-elution of some peaks, it is not possible to determine toxophor loading accurately.

In the cases where light and heavy chains could not be separated sufficiently by HPLC, determination of toxophor loading of cysteine-linked conjugates was carried out by mass spectrometric determination of the molecular weights of the individual conjugate species at light and heavy chain.

Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated for one hour at 55° C. and analysed by mass spectrometry after online desalting using ESI-MicroTof$_Q$ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. The average loading of the antibody with toxophores was calculated by integration of certain molecular weight areas as double the sum of the toxophor number weighed integration results of all peaks divided by the sum of the singly weighed integration results of all peaks.

To determine the proportion of the open cysteine adduct, the molecular weight area ratio of closed to open cysteine adduct (molecular weight delta 18 Dalton) of all singly conjugated light and heavy chains was determined. The mean of all variants yielded the proportion of the open cysteine adduct.

B-8. Checking the Antigen-Binding of the ADCs

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

WORKING EXAMPLES ADCS

Example 1A

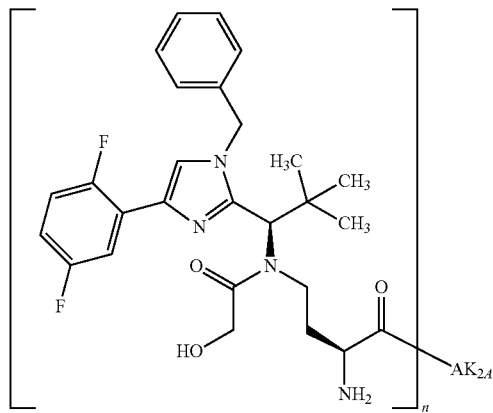

Here, 70 mg of cetuximab in PBS (c=5.1 mg/ml) were used for coupling with Intermediate F1, and the reaction was, after Sephadex purification, concentrated by ultracentrifugation, rediluted with PBS and concentrated again.
Protein concentration: 10.8 mg/ml
Drug/mAb ratio: 2.6
Parenthesis
In Example 1A, the compound of the formula

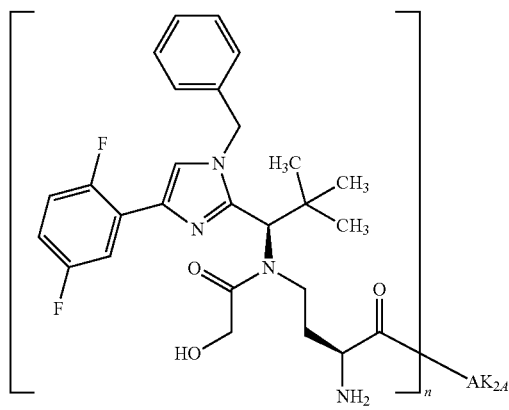

with n=2.6 and a certain antibody (cetuximab) was obtained. However, the invention provides not only this particular conjugate having exactly this antibody in this drug/mAB ratio, but also other binder conjugates having this formula, that is conjugates in which cetuximab is replaced by a different antibody or derivative thereof (such as cysteine) and n=2.6 is replaced by any value in the range from n=1 to 20, preferably n=1-10.

This applies correspondingly in the examples below.

Example 2A

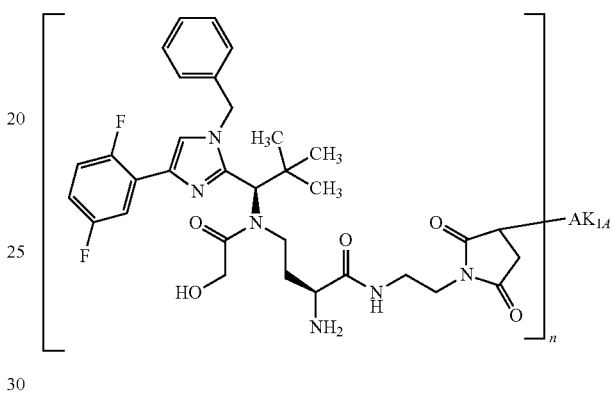

Here, 80 mg of cetuximab in PBS (c=5.1 mg/ml) were used for coupling with Intermediate F2, and the reaction was, after Sephadex purification, concentrated by ultracentrifugation, rediluted with PBS and concentrated again. Some of the ADC may also be present in the form of the hydrolysed open-chain succinamides attached to the antibody.
Protein concentration: 11.0 mg/ml
Drug/mAb ratio: 2.5

Example 2B

Here, 50 mg of anti-TWEAKR AK-1 in PBS (c=10.1 mg/ml) were used for coupling with Intermediate F2, and the reaction was, after Sephadex purification, concentrated by ultracentrifugation, rediluted with PBS and concentrated again. Some of the ADC may also be present in the form of the hydrolysed open-chain succinamides attached to the antibody.
Protein concentration: 11.7 mg/ml
Drug/mAb ratio: 3.7

Example 2E

Here, 5 mg of trastuzumab in PBS (c=13.4 mg/ml) were used for coupling with Intermediate F2, and the reaction was, after Sephadex purification, concentrated by ultracentrifugation and rediluted with PBS. Some of the ADC may also be present in the form of the hydrolysed open-chain succinamides attached to the antibody.
Protein concentration: 2.77 mg/ml
Drug/mAb ratio: 2.6

Example 3A

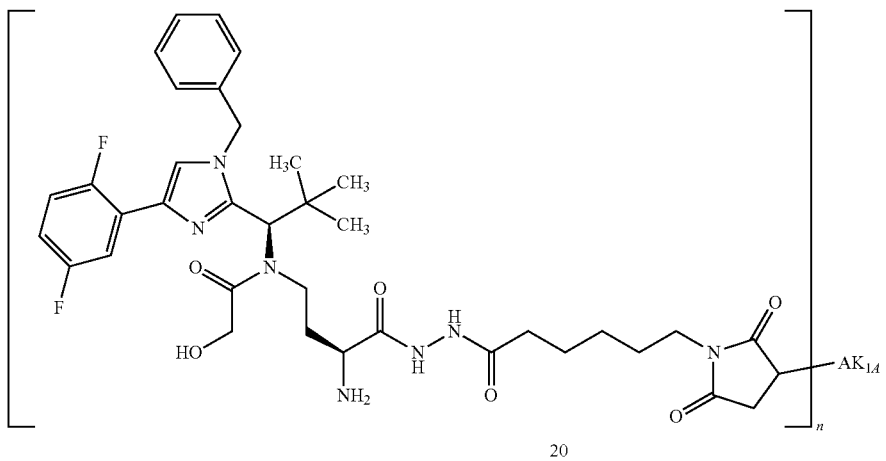

Here, 5 mg of cetuximab in PBS (c=5.1 mg/ml) were used for coupling with Intermediate F3, and the reaction was, after Sephadex purification, concentrated by ultracentrifugation and rediluted with PBS.
Protein concentration: 2.87 mg/ml
Drug/mAb ratio: 2.0

Example 3B

Here, 5 mg of anti-TWEAKR AK-1 in PBS (c=16.5 mg/ml) were used for coupling with Intermediate F3, and the reaction was, after Sephadex purification, concentrated by ultracentrifugation and rediluted with PBS.
Protein concentration: 2.13 mg/ml
Drug/mAb ration: 2.1

Example 4A

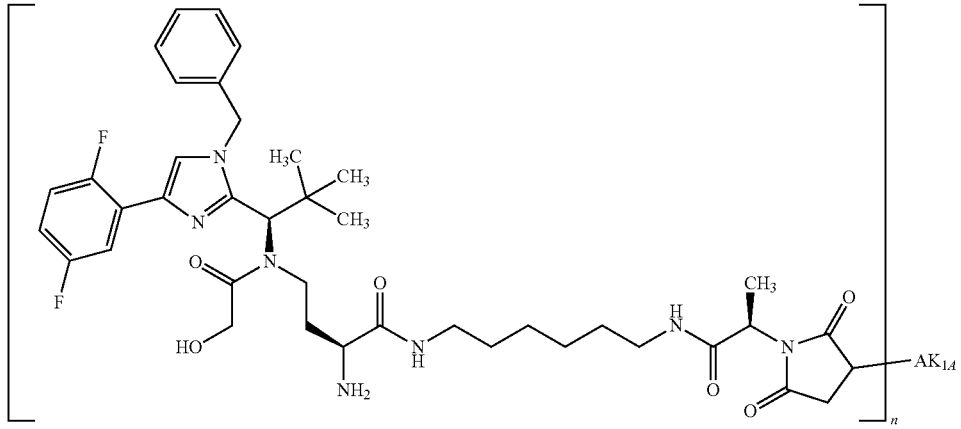

Here, 5 mg of cetuximab in PBS (c=5.1 mg/ml) were used for coupling with Intermediate F4, and the reaction was, after Sephadex purification, concentrated by ultracentrifugation and rediluted with PBS.
Protein concentration: 2.11 mg/ml
Drug/mAb ratio: 2.4

Example 4B

Here, 5 mg of anti-TWEAKR AK-1 in PBS (c=16.5 mg/ml) were used for coupling with Intermediate F4, and the reaction was, after Sephadex purification, concentrated by ultracentrifugation and rediluted with PBS.
Protein concentration: 1.69 mg/ml
Drug/mAb ratio: 2.9

Example 5A

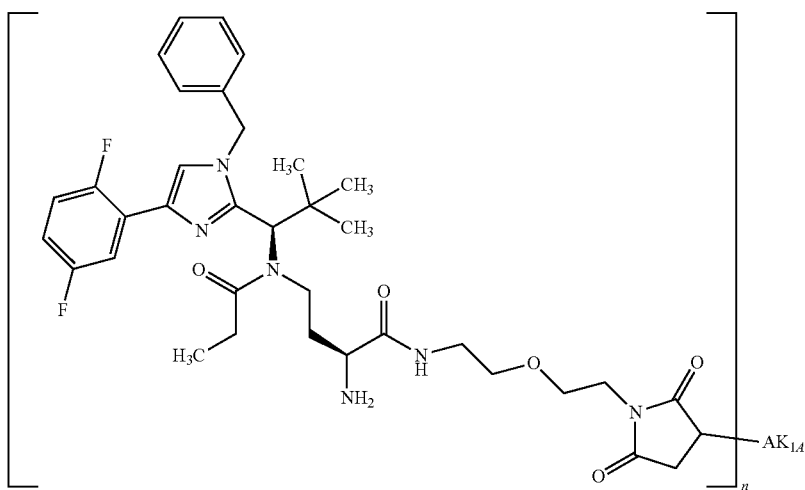

Here, 5 mg of cetuximab in PBS (c=5.1 mg/ml) were used for coupling with Intermediate F5, and the reaction was, after Sephadex purification, concentrated by ultracentrifugation and rediluted with PBS. Some of the ADC may also be present in the form of the hydrolysed open-chain succinamides attached to the antibody.
Protein concentration: 2.16 mg/ml
Drug/mAb ratio: 2.1

Example 5B

Here, 5 mg of anti-TWEAKR AK-1 in PBS (c=16.5 mg/ml) were used for coupling with Intermediate F5, and the reaction was, after Sephadex purification, concentrated by ultracentrifugation and rediluted with PBS. Some of the ADC may also be present in the form of the hydrolysed open-chain succinamides attached to the antibody.
Protein concentration: 1.5 mg/ml
Drug/mAb ratio: 2.6

Example 6A

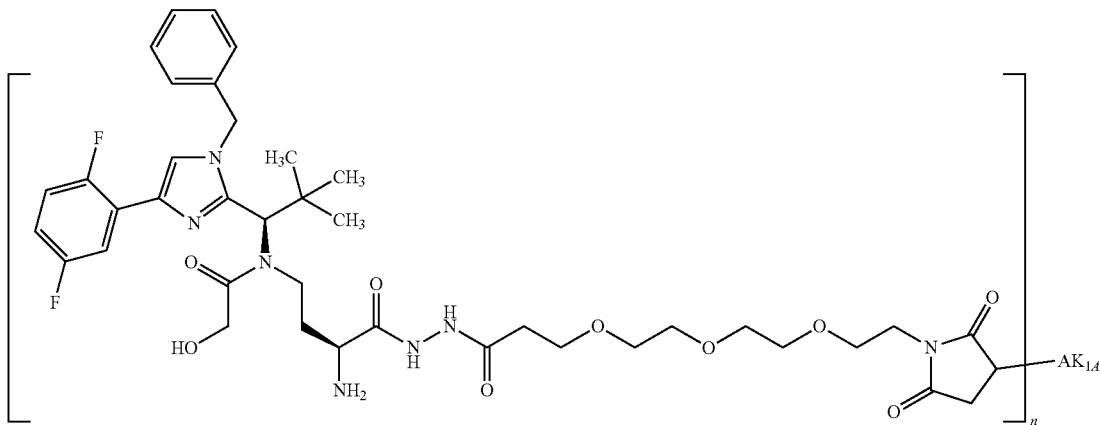

Here, 5 mg of cetuximab in PBS (c=5.1 mg/ml) were used for coupling with Intermediate F6, and the reaction was, after Sephadex purification, concentrated by ultracentrifugation and rediluted with PBS. Some of the ADC may also be present in the form of the hydrolysed open-chain succinamides attached to the antibody.
Protein concentration: 2.24 mg/ml
Drug/mAb ratio: 2.3

Example 6B

Here, 5 mg of anti-TWEAKR AK-1 in PBS (c=16.5 mg/ml) were used for coupling with Intermediate F6, and the reaction was, after Sephadex purification, concentrated by ultracentrifugation and rediluted with PBS. Some of the ADC may also be present in the form of the hydrolysed open-chain succinamides attached to the antibody.
Protein concentration: 1.88 mg/ml
Drug/mAb ratio: 2.1

Example 7A

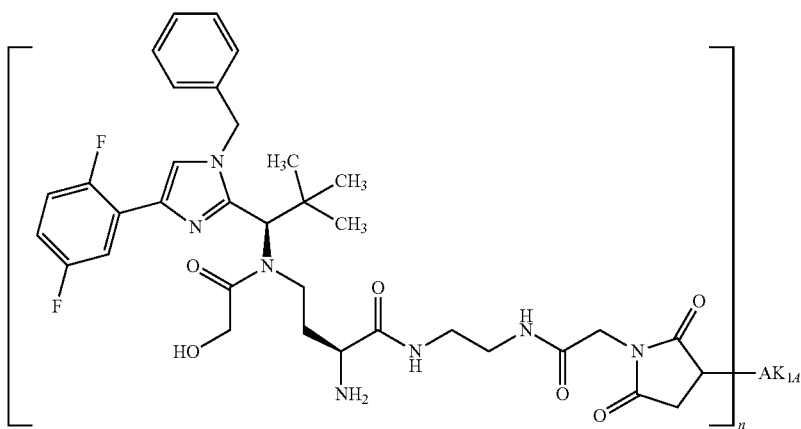

Here, 5 mg of cetuximab in PBS (c=5.9 mg/ml) were used for coupling with Intermediate F7, and the reaction was, after Sephadex purification, concentrated by ultracentrifugation and rediluted with PBS. Some of the ADC may also be present in the form of the hydrolysed open-chain succinamides attached to the antibody.
Protein concentration: 2.46 mg/ml
Drug/mAb ratio: 2.9

Example 7B

Here, 40 mg of anti-TWEAKR AK-1 in PBS (c=12.9 mg/ml) were used for coupling with Intermediate F7, and the reaction was, after Sephadex purification, concentrated by ultracentrifugation, rediluted with PBS and concentrated again. Some of the ADC may also be present in the form of the hydrolysed open-chain succinamides attached to the antibody.
Protein concentration: 11.27 mg/ml
Drug/mAb ratio: 3.0

Example 8A

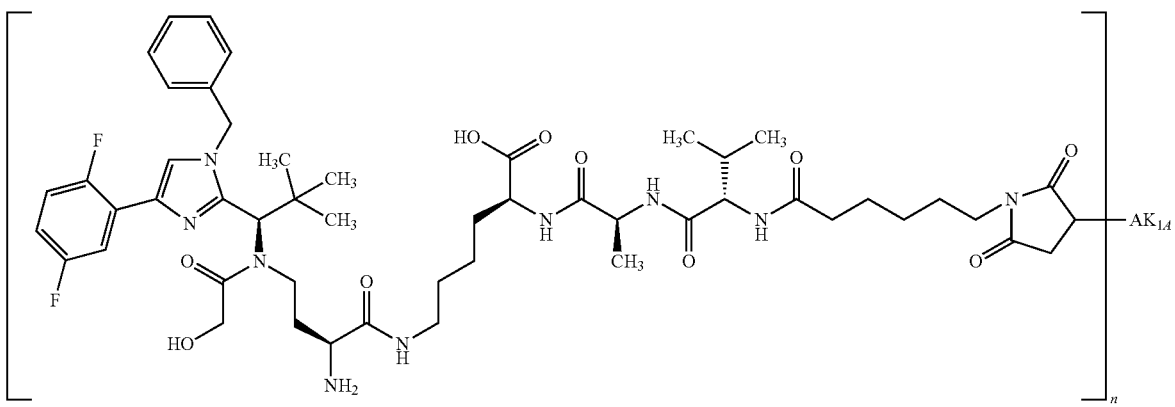

Here, 5 mg of cetuximab in PBS (c=12.7 mg/ml) were used for coupling with Intermediate F8, and the reaction was, after Sephadex purification, concentrated by ultracentrifugation and rediluted with PBS.
Protein concentration: 1.91 mg/ml
Drug/mAb ratio: 3.6

Example 8B

Here, 40 mg of anti-TWEAKR AK-1 in PBS (c=12.9 mg/ml) were used for coupling with Intermediate F8, and the reaction was, after Sephadex purification, concentrated by ultracentrifugation, rediluted with PBS and concentrated again.
Protein concentration: 11.54 mg/ml
Drug/mAb ratio: 2.9

Example 8E

Here, 5 mg of trastuzumab in PBS (c=13.4 mg/ml) were used for coupling with Intermediate F8, and the reaction was, after Sephadex purification, concentrated by ultracentrifugation and rediluted with PBS.
Protein concentration: 1.97 mg/ml
Drug/mAb ratio: 3.5

Example 8H

Here, 5.0 mg of panitumumab in PBS (c=10 mg/ml) were used for coupling with Intermediate F8. The time for the reduction with TCEP was increased to 4 h and stirring time for the ADC coupling was increased to 20 h. The reaction was then, after Sephadex purification, concentrated by ultracentrifugation and rediluted.
Protein concentration: 1.79 mg/ml
Drug/mAb ratio: 2.4

Example 9A

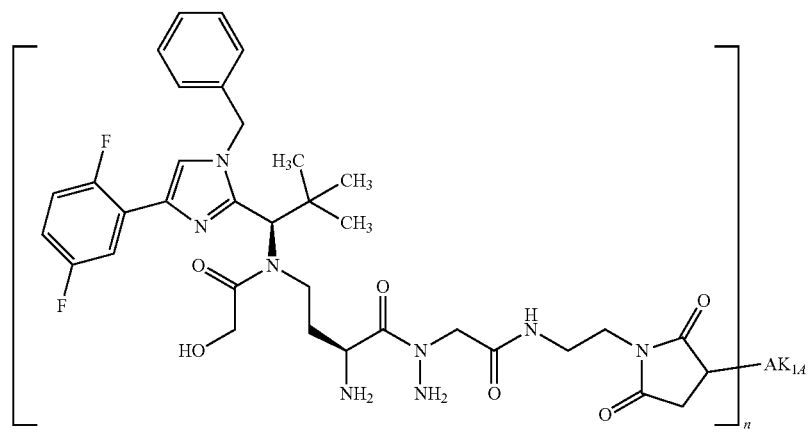

Here, 5 mg of cetuximab in PBS (c=13.6 mg/ml) were used for coupling with Intermediate F9, and the reaction was, after Sephadex purification, concentrated by ultracentrifugation and rediluted with PBS. Some of the ADC may also be present in the form of the hydrolysed open-chain succinamides attached to the antibody.
Protein concentration: 2.05 mg/ml
Drug/mAb ratio: 2.1

Example 9B

Here, 5 mg of anti-TWEAKR AK-1 in PBS (c=12.2 mg/ml) were used for coupling with Intermediate F9, and the reaction was, after Sephadex purification, concentrated by ultracentrifugation and rediluted with PBS. Some of the ADC may also be present in the form of the hydrolysed open-chain succinamides attached to the antibody.
Protein concentration: 1.84 mg/ml
Drug/mAb ratio: 2.1

Example 10A

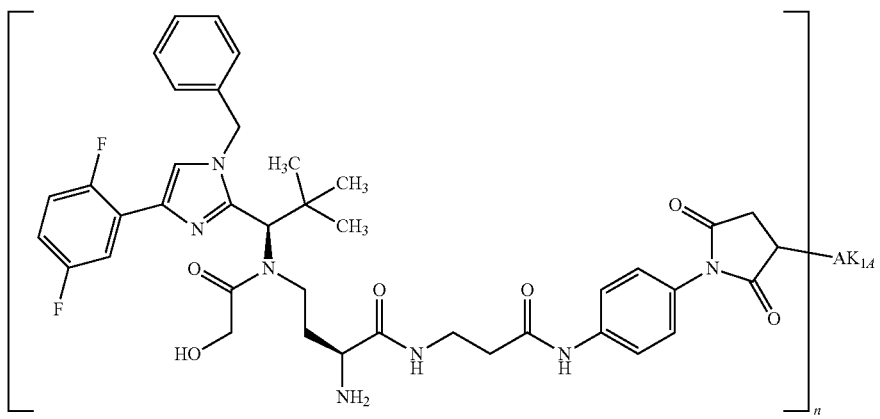

Here, 5 mg of cetuximab in PBS (c=5.9 mg/ml) were used for coupling with Intermediate F10, and the reaction was, after Sephadex purification, concentrated by ultracentrifugation and rediluted with PBS. Some of the ADC may also be present in the form of the hydrolysed open-chain succinamides attached to the antibody.

Protein concentration: 2.04 mg/ml
Drug/mAb ratio: 1.8

Example 10B

Here, 5 mg of anti-TWEAKR AK-1 in PBS (c=12.2 mg/ml) were used for coupling with Intermediate F10, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.2

Example 11A

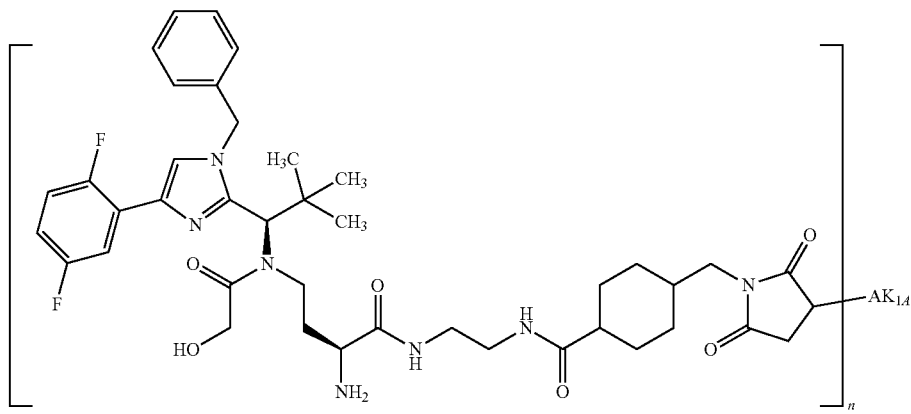

Here, 5 mg of cetuximab in PBS (c=5.9 mg/ml) were used for coupling with Intermediate F11, and the reaction was, after Sephadex purification, concentrated by ultracentrifugation and rediluted with PBS.

Protein concentration: 1.97 mg/ml
Drug/mAb ratio: 2.0

Example 11B

Here, 5 mg of anti-TWEAKR AK-1 in PBS (c=12.2 mg/ml) were used for coupling with Intermediate F11, and the reaction was, after Sephadex purification, concentrated by ultracentrifugation and rediluted with PBS.

Protein concentration: 1.86 mg/ml
Drug/mAb ratio: 2.0

Example 12A

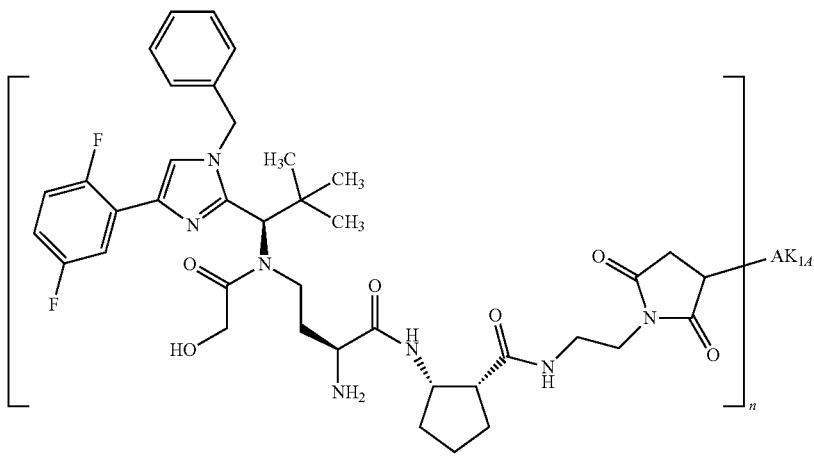

Here, 5 mg of cetuximab in PBS (c=5.9 mg/ml) were used for coupling with Intermediate F12, and the reaction was, after Sephadex purification, concentrated by ultracentrifugation and rediluted with PBS. Some of the ADC may also be present in the form of the hydrolysed open-chain succinamides attached to the antibody.

Protein concentration: 1.98 mg/ml
Drug/mAb ratio: 1.9

Example 12B

Here, 40 mg of anti-TWEAKR AK-1 in PBS (c=12.9 mg/ml) were used for coupling with Intermediate F12, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 9.9 mg/ml
Drug/mAb ratio: 2.5

Example 13A

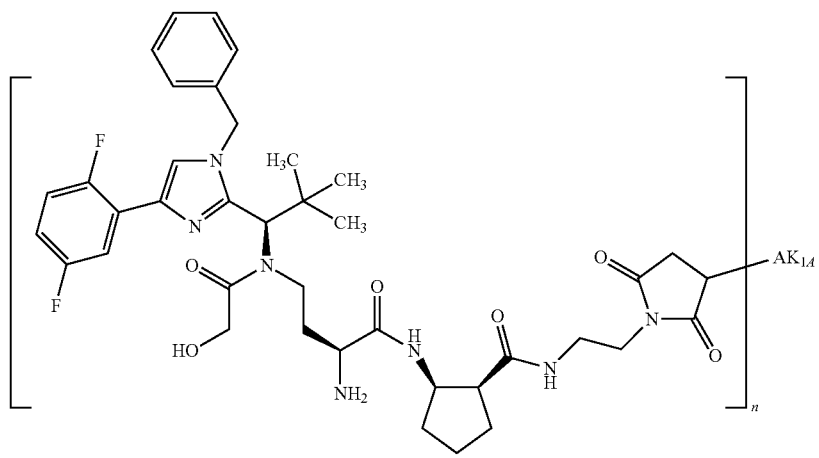

Here, 5 mg of cetuximab in PBS (c=5.9 mg/ml) were used for coupling with Intermediate F13, and the reaction was, after Sephadex purification, concentrated by ultracentrifugation and rediluted with PBS. Some of the ADC may also be present in the form of the hydrolysed open-chain succinamides attached to the antibody.

Protein concentration: 1.87 mg/ml
Drug/mAb ratio: 2.1

Example 13B

Here, 5 mg of anti-TWEAKR AK-1 in PBS (c=12.2 mg/ml) were used for coupling with Intermediate F13, and the reaction was, after Sephadex purification, concentrated by ultracentrifugation and rediluted with PBS. Some of the ADC may also be present in the form of the hydrolysed open-chain succinamides attached to the antibody.

Protein concentration: 1.84 mg/ml
Drug/mAb ratio: 2.2

Example 14A

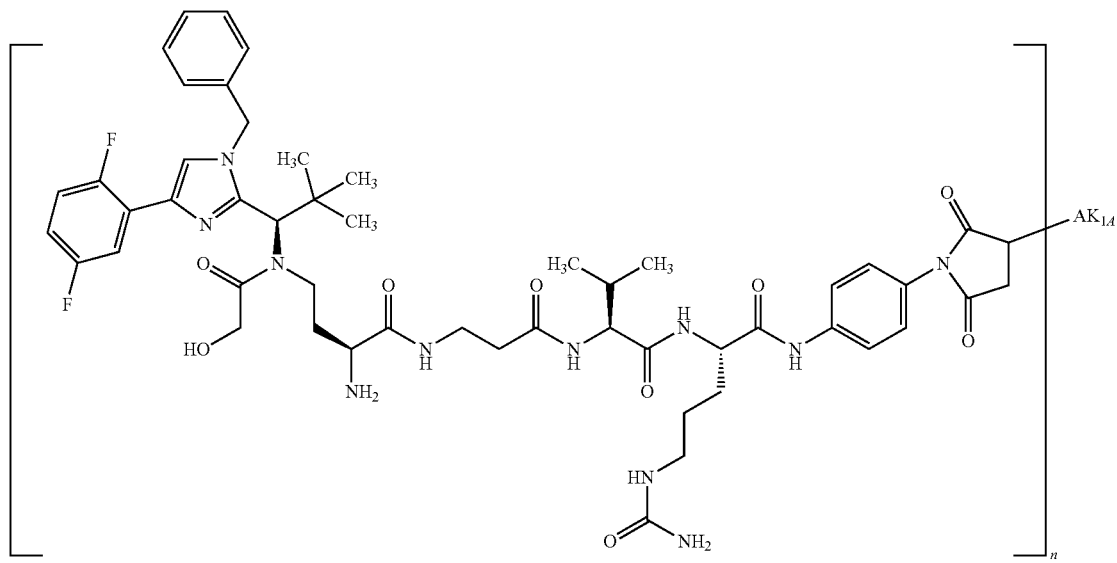

Here, 5 mg of cetuximab in PBS (c=13.2 mg/ml) were used for coupling with Intermediate F14, and the reaction was, after Sephadex purification, concentrated by ultracentrifugation and rediluted with PBS.

Some of the ADC may also be present in the form of the hydrolysed open-chain succinamides attached to the antibody.

Protein concentration: 2.32 mg/ml
Drug/mAb ratio: 3.8

Example 14B

Here, 5 mg of anti-TWEAKR AK-1 in PBS (c=12.2 mg/ml) were used for coupling with Intermediate F14, and the reaction was, after Sephadex purification, concentrated by ultracentrifugation and rediluted with PBS. Some of the ADC may also be present in the form of the hydrolysed open-chain succinamides attached to the antibody.

Protein concentration: 1.23 mg/ml
Drug/mAb ratio: 2.1

Example 14E

Here, 5 mg of trastuzumab in PBS (c=13.4 mg/ml) were used for coupling with Intermediate F14, and the reaction was, after Sephadex purification, concentrated by ultracentrifugation and rediluted with PBS. Some of the ADC may also be present in the form of the hydrolysed open-chain succinamides attached to the antibody.

Protein concentration: 2.21 mg/ml
Drug/mAb ratio: 2.6

Example 15A

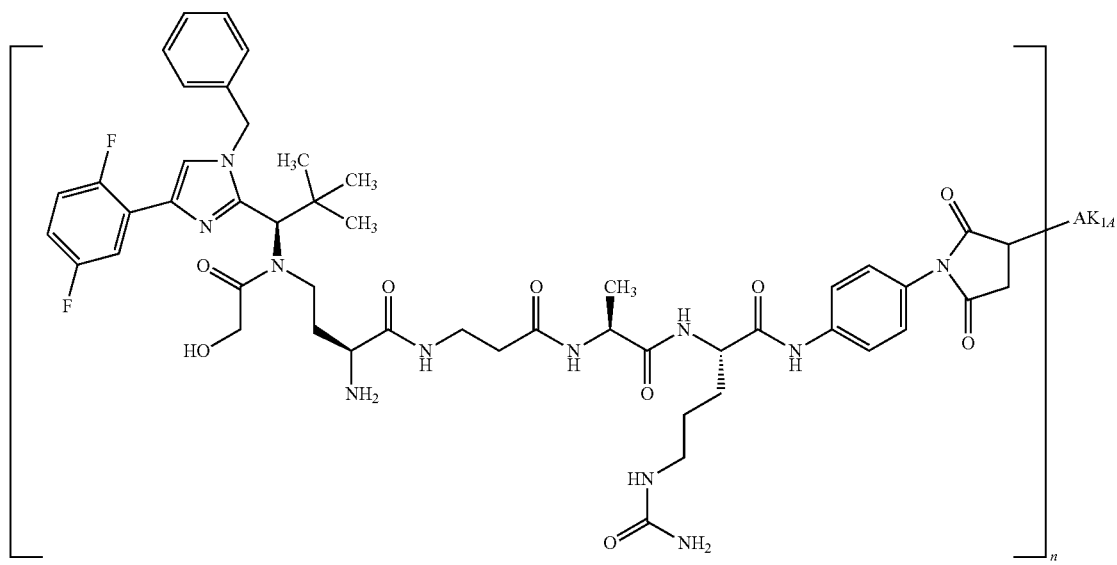

Here, 5 mg of cetuximab in PBS (c=13.2 mg/ml) were used for coupling with Intermediate F15, and the reaction was, after Sephadex purification, concentrated by ultracentrifugation and rediluted with PBS. Some of the ADC may also be present in the form of the hydrolysed open-chain succinamides attached to the antibody.

Protein concentration: 2.39 mg/ml
Drug/mAb ratio: 3.7

Example 15B

Here, 32 mg of anti-TWEAKR AK-1 in PBS (c=10.1 mg/ml) were used for coupling with Intermediate F15, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 11.82 mg/ml
Drug/mAb ratio: 3.7

Example 15E

Here, 5 mg of trastuzumab in PBS (c=13.4 mg/ml) were used for coupling with Intermediate F15, and the reaction was, after Sephadex purification, concentrated by ultracentrifugation and rediluted with PBS. Some of the ADC may also be present in the form of the hydrolysed open-chain succinamides attached to the antibody.

Protein concentration: 2.57 mg/ml
Drug/mAb ratio: 3.0

Example 16A

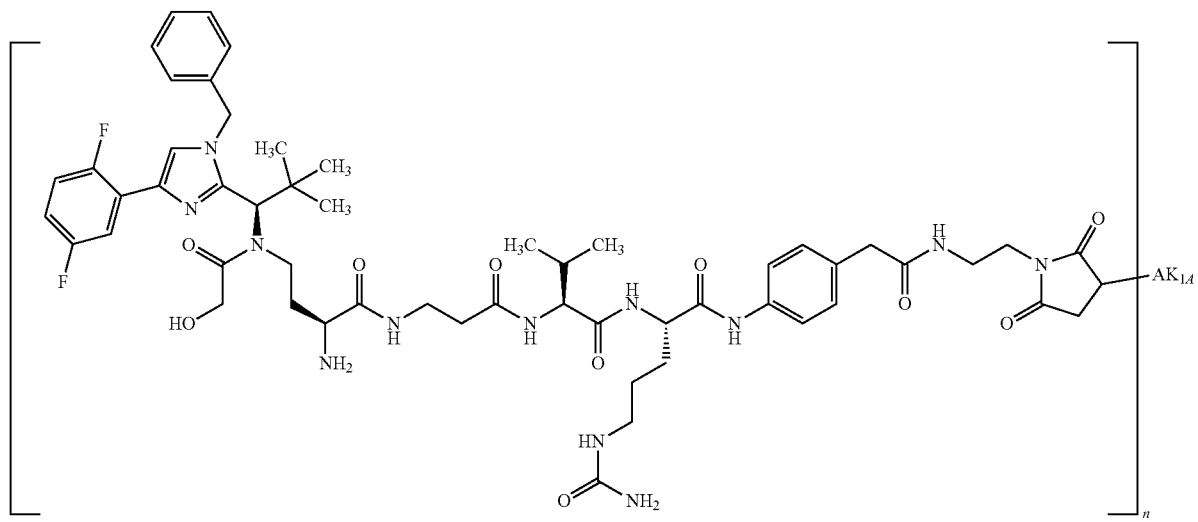

Here, 5 mg of cetuximab in PBS (c=13.2 mg/ml) were used for coupling with Intermediate F16, and the reaction was, after Sephadex purification, concentrated by ultracentrifugation and rediluted with PBS. Some of the ADC may also be present in the form of the hydrolysed open-chain succinamides attached to the antibody.

Protein concentration: 2.15 mg/ml
Drug/mAb ratio: 3.1

Example 16B

Here, 30 mg of anti-TWEAKR AK-1 in PBS (c=12.9 mg/ml) were used for coupling with Intermediate F16, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 9.54 mg/ml
Drug/mAb ratio: 2.8

Example 16E

Here, 5 mg of trastuzumab in PBS (c=13.4 mg/ml) were used for coupling with Intermediate F16, and the reaction was, after Sephadex purification, concentrated by ultracentrifugation and rediluted with PBS. Some of the ADC may also be present in the form of the hydrolysed open-chain succinamides attached to the antibody.

Protein concentration: 2.26 mg/ml
Drug/mAb ratio: 3.4

Example 17A

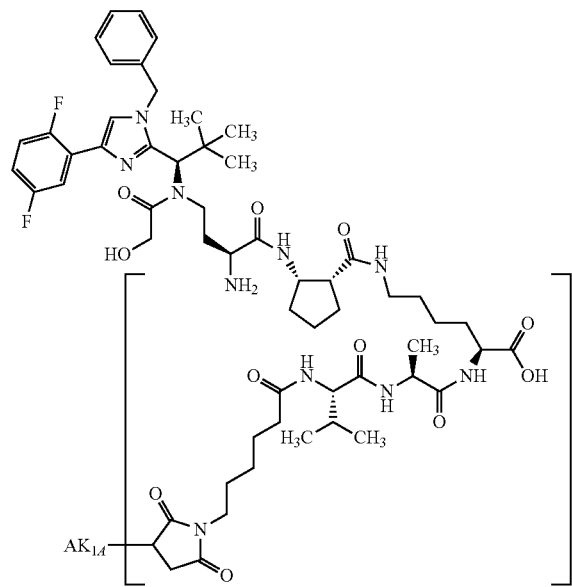

Here, 5 mg of cetuximab in PBS (c=13.6 mg/ml) were used for coupling with Intermediate F17, and the reaction was, after Sephadex purification, concentrated by ultracentrifugation and rediluted with PBS.

Protein concentration: 2.02 mg/ml
Drug/mAb ratio: nd

Example 17B

Here, 5 mg of anti-TWEAKR AK-1 in PBS (c=12.2 mg/ml) were used for coupling with Intermediate F17, and the reaction was, after Sephadex purification, concentrated by ultracentrifugation and rediluted with PBS.

Protein concentration: 1.64 mg/ml
Drug/mAb ratio: 2.9

Example 18A

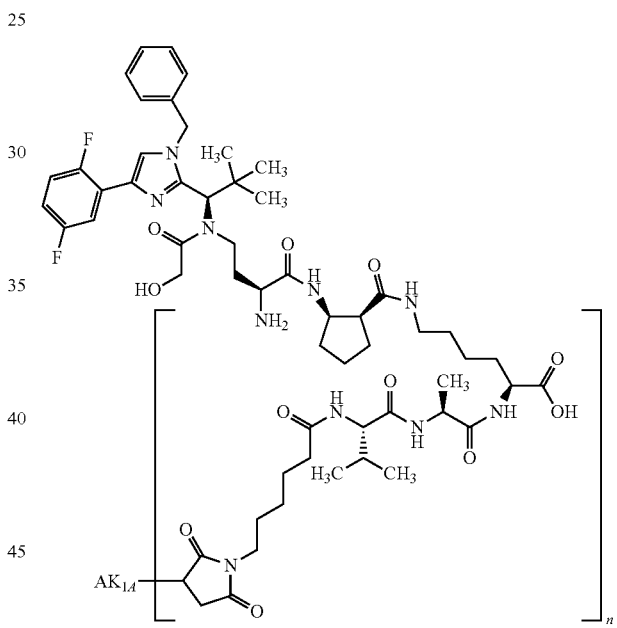

Here, 5 mg of cetuximab in PBS (c=13.6 mg/ml) were used for coupling with Intermediate F18, and the reaction was, after Sephadex purification, concentrated by ultracentrifugation and rediluted with PBS.

Protein concentration: 1.8 mg/ml
Drug/mAb ratio: 2.7

Example 18B

Here, 5 mg of anti-TWEAKR AK-1 in PBS (c=12.2 mg/ml) were used for coupling with Intermediate F18, and the reaction was, after Sephadex purification, concentrated by ultracentrifugation and rediluted with PBS.

Protein concentration: 1.74 mg/ml
Drug/mAb ratio: 2.7

Example 19A

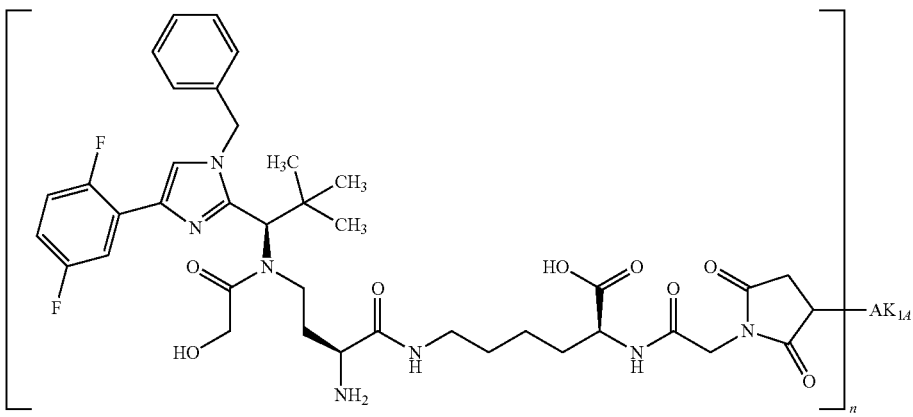

Here, 5 mg of cetuximab in PBS (c=5.9 mg/ml) were used for coupling with Intermediate F19, and the reaction was, after Sephadex purification, concentrated by ultracentrifugation and rediluted with PBS. Some of the ADC may also be present in the form of the hydrolysed open-chain succinamides attached to the antibody.

Protein concentration: 1.94 mg/ml
Drug/mAb ratio: 2.2

Example 19B

Here, 5 mg of anti-TWEAKR AK-1 in PBS (c=12.2 mg/ml) were used for coupling with Intermediate F19, and the reaction was, after Sephadex purification, concentrated by ultracentrifugation and rediluted with PBS. Some of the ADC may also be present in the form of the hydrolysed open-chain succinamides attached to the antibody.

Protein concentration: 1.9 mg/ml
Drug/mAb ratio: 2.8

Example 20A

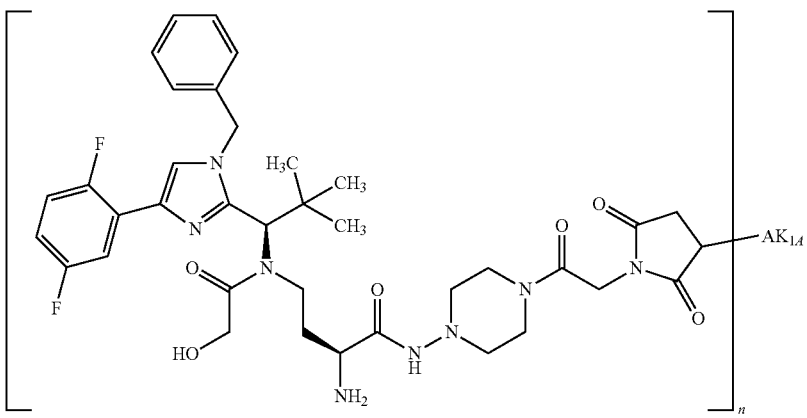

Here, 5 mg of cetuximab in PBS (c=5.9 mg/ml) were used for coupling with Intermediate F20, and the reaction was, after Sephadex purification, concentrated by ultracentrifugation and rediluted with PBS. Some of the ADC may also be present in the form of the hydrolysed open-chain succinamides attached to the antibody.

Protein concentration: 1.99 mg/ml
Drug/mAb ratio: 2.6

Example 20B

Here, 5 mg of anti-TWEAKR AK-1 in PBS (c=10.1 mg/ml) were used for coupling with Intermediate F20, and the reaction was, after Sephadex purification, concentrated by ultracentrifugation and rediluted with PBS. Some of the ADC may also be present in the form of the hydrolysed open-chain succinamides attached to the antibody.
Protein concentration: 2.03 mg/ml
Drug/mAb ratio: 2.5

Example 21A

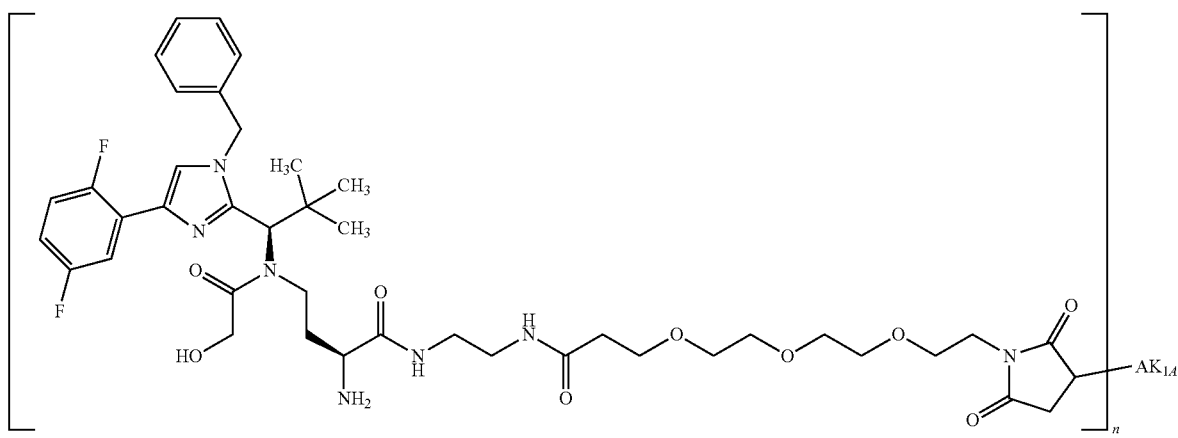

Here, 5 mg of cetuximab in PBS (c=5.9 mg/ml) were used for coupling with Intermediate F21, and the reaction was, after Sephadex purification, concentrated by ultracentrifugation and rediluted with PBS. Some of the ADC may also be present in the form of the hydrolysed open-chain succinamides attached to the antibody.
Protein concentration: 1.76 mg/ml
Drug/mAb ratio: 2.4

Example 21B

Here, 5 mg of anti-TWEAKR AK-1 in PBS (c=10.1 mg/ml) were used for coupling with Intermediate F21, and the reaction was, after Sephadex purification, concentrated by ultracentrifugation and rediluted with PBS. Some of the ADC may also be present in the form of the hydrolysed open-chain succinamides attached to the antibody.
Protein concentration: 1.8 mg/ml
Drug/mAb ratio: 2.3

Example 22A

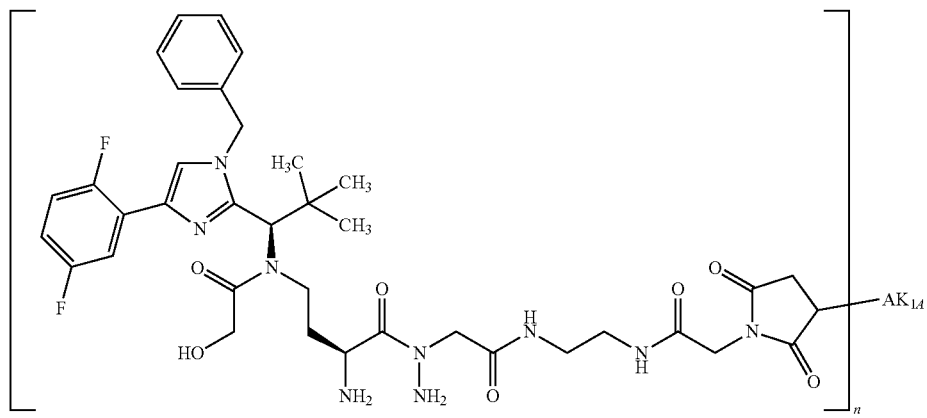

Here, 5 mg of cetuximab in PBS (c=13.56 mg/ml) were used for coupling with Intermediate F22, and the reaction was, after Sephadex purification, concentrated by ultracentrifugation and rediluted with PBS. Some of the ADC may also be present in the form of the hydrolysed open-chain succinamides attached to the antibody.

Protein concentration: 1.99 mg/ml
Drug/mAb ratio: 2.9

Example 22B

Here, 5 mg of anti-TWEAKR AK-1 in PBS (c=12.9 mg/ml) were used for coupling with Intermediate F22, and the reaction was, after Sephadex purification, concentrated by ultracentrifugation and rediluted with PBS. Some of the ADC may also be present in the form of the hydrolysed open-chain succinamides attached to the antibody.

Protein concentration: 1.77 mg/ml
Drug/mAb ratio: 3.0

Example 22E

Here, 5 mg of trastuzumab in PBS (c=13.4 mg/ml) were used for coupling with Intermediate F22, and the reaction was, after Sephadex purification, concentrated by ultracentrifugation and rediluted with PBS. Some of the ADC may also be present in the form of the hydrolysed open-chain succinamides attached to the antibody.

Protein concentration: 1.89 mg/ml
Drug/mAb ratio: 3.0

Example 23A

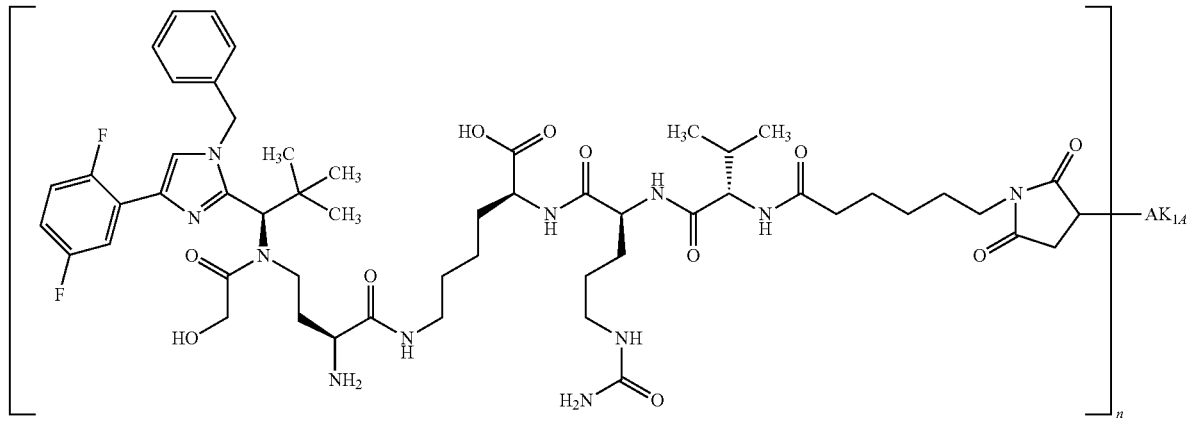

Here, 5 mg of cetuximab in PBS (c=13.56 mg/ml) were used for coupling with Intermediate F23, and the reaction was, after Sephadex purification, concentrated by ultracentrifugation and rediluted with PBS.

Protein concentration: 1.32 mg/ml
Drug/mAb ratio: 3.4

Example 23B

Here, 5 mg of anti-TWEAKR AK-1 in PBS (c=12.9 mg/ml) were used for coupling with Intermediate F23, and the reaction was, after Sephadex purification, concentrated by ultracentrifugation and rediluted with PBS.

Protein concentration: 1.83 mg/ml
Drug/mAb ratio: 3.7

Example 24A

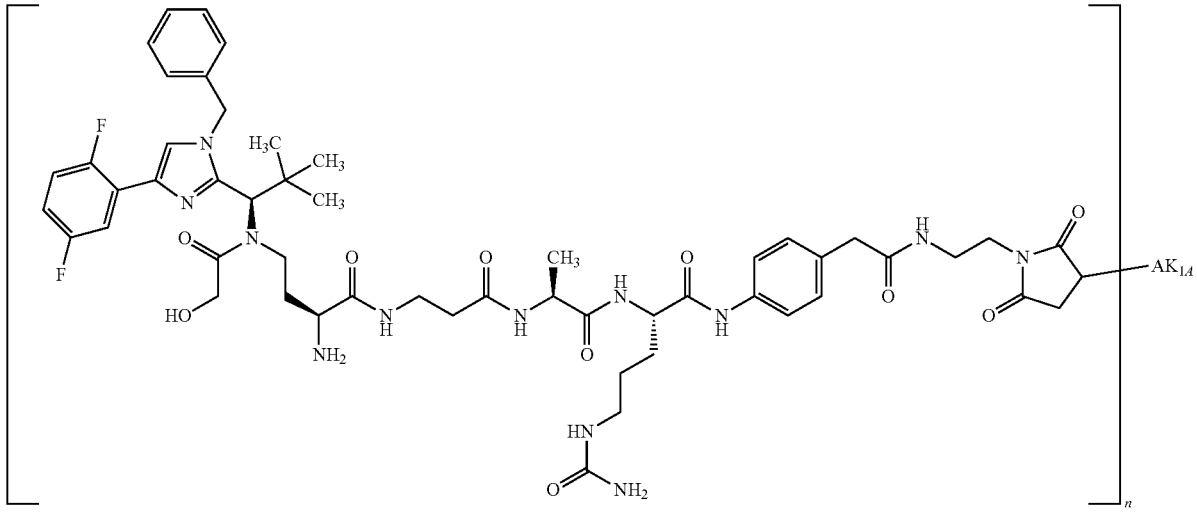

Here, 5 mg of cetuximab in PBS (c=13.56 mg/ml) were used for coupling with Intermediate F24, and the reaction was, after Sephadex purification, concentrated by ultracentrifugation and rediluted with PBS. Some of the ADC may also be present in the form of the hydrolysed open-chain succinamides attached to the antibody.
  Protein concentration: 1.83 mg/ml
  Drug/mAb ratio: 2.9

Example 24B

Here, 5 mg of anti-TWEAKR AK-1 in PBS (c=10.1 mg/ml) were used for coupling with Intermediate F24, and the reaction was, after Sephadex purification, concentrated by ultracentrifugation and rediluted with PBS. Some of the ADC may also be present in the form of the hydrolysed open-chain succinamides attached to the antibody.
  Protein concentration: 1.83 mg/ml
  Drug/mAb ratio: 2.9

Example 25A

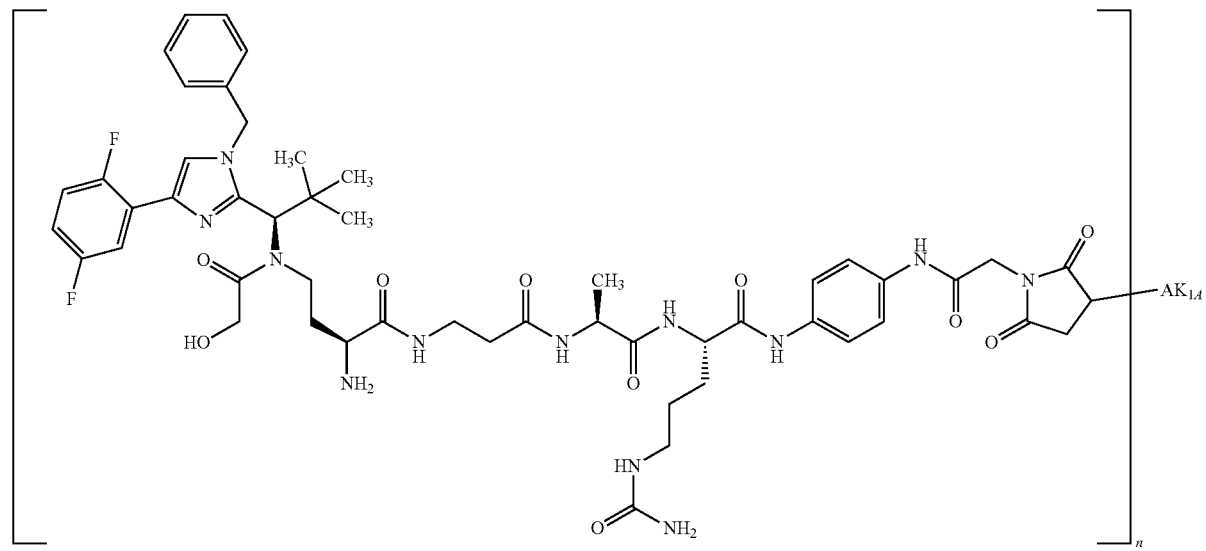

Here, 5 mg of cetuximab in PBS (c=13.56 mg/ml) were used for coupling with Intermediate F25, and the reaction was, after Sephadex purification, concentrated by ultracentrifugation and rediluted with PBS. Some of the ADC may also be present in the form of the hydrolysed open-chain succinamides attached to the antibody.
  Protein concentration: 2.17 mg/ml
  Drug/mAb ratio: 3.2

Example 25B

Here, 5 mg of anti-TWEAKR AK-1 in PBS (c=10.1 mg/ml) were used for coupling with Intermediate F25, and the reaction was, after Sephadex purification, concentrated by ultracentrifugation and rediluted with PBS. Some of the ADC may also be present in the form of the hydrolysed open-chain succinamides attached to the antibody.
  Protein concentration: 1.78 mg/ml
  Drug/mAb ratio: 3.2

Example 26A

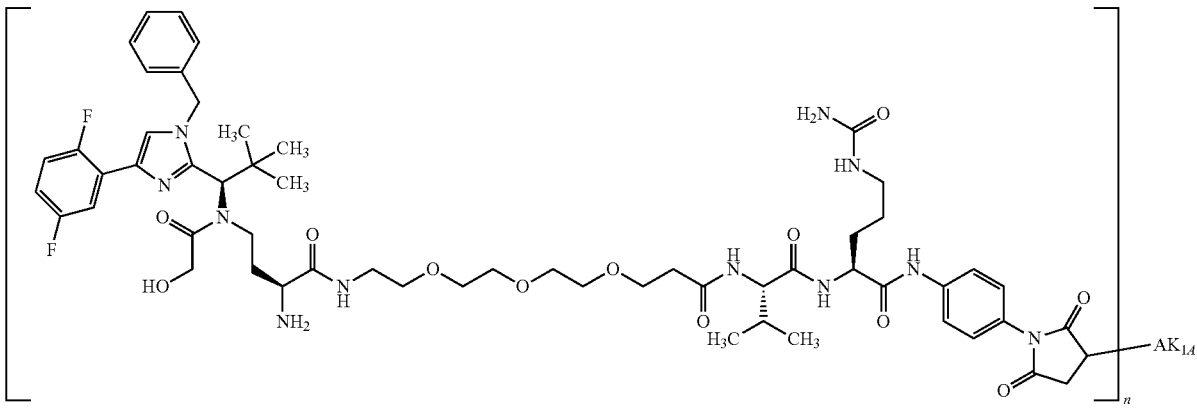

Here, 5 mg of cetuximab in PBS (c=13.56 mg/ml) were used for coupling with Intermediate F26, and the reaction was, after Sephadex purification, concentrated by ultracentrifugation and rediluted with PBS. Some of the ADC may also be present in the form of the hydrolysed open-chain succinamides attached to the antibody.

Protein concentration: 1.8 mg/ml
Drug/mAb ratio: nd

Example 26B

Here, 5 mg of anti-TWEAKR AK-1 in PBS (c=12.9 mg/ml) were used for coupling with Intermediate F26, and the reaction was, after Sephadex purification, concentrated by ultracentrifugation and rediluted with PBS. Some of the ADC may also be present in the form of the hydrolysed open-chain succinamides attached to the antibody.

Protein concentration: 2.02 mg/ml
Drug/mAb ratio: 2.7

Example 27A

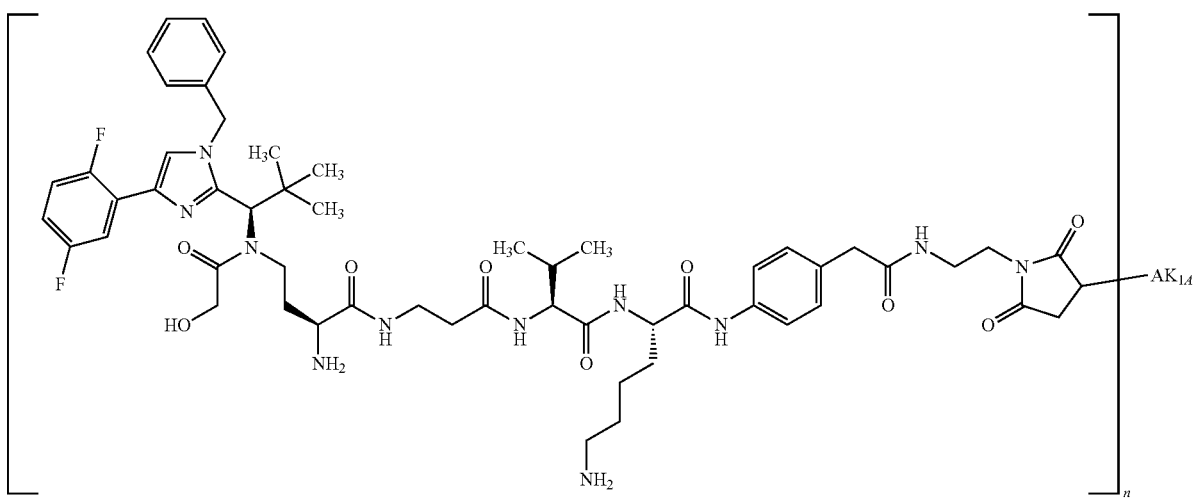

Here, 5 mg of cetuximab in PBS (c=5.9 mg/ml) were used for coupling with Intermediate F27, and the reaction was, after Sephadex purification, concentrated by ultracentrifugation and rediluted with PBS. Some of the ADC may also be present in the form of the hydrolysed open-chain succinamides attached to the antibody.

Protein concentration: 1.91 mg/ml
Drug/mAb ratio: 2.1

Example 27B

Here, 5 mg of anti-TWEAKR AK-1 in PBS (c=10.1 mg/ml) were used for coupling with Intermediate F27, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.1

Example 28A

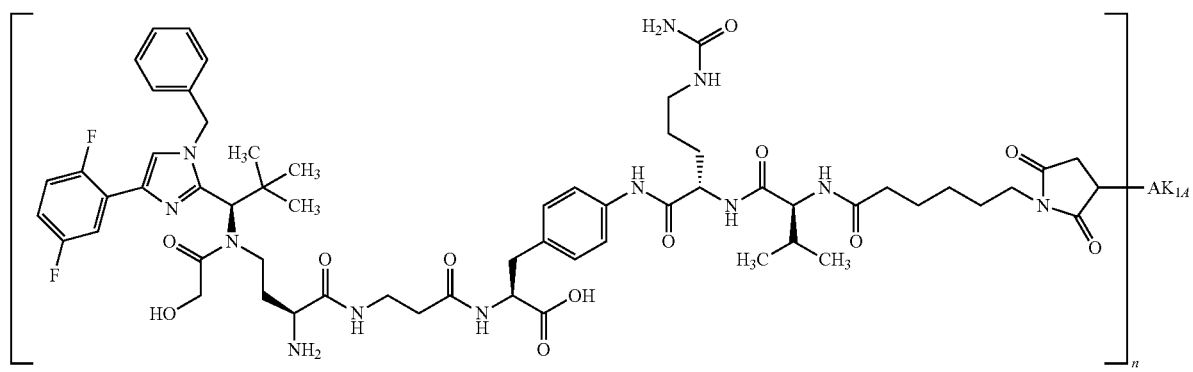

Here, 5 mg of cetuximab in PBS (c=11.59 mg/ml) were used for coupling with Intermediate F28, and the reaction was, after Sephadex purification, concentrated by ultracentrifugation and rediluted with PBS.

Protein concentration: 2.13 mg/ml
Drug/mAb ratio: 3.6

Example 28B

Here, 5 mg of anti-TWEAKR AK-1 in PBS (c=10.1 mg/ml) were used for coupling with Intermediate F28, and the reaction was, after Sephadex purification, concentrated by ultracentrifugation and rediluted with PBS.

Protein concentration: 1.95 mg/ml
Drug/mAb ratio: 3.5

Example 29A

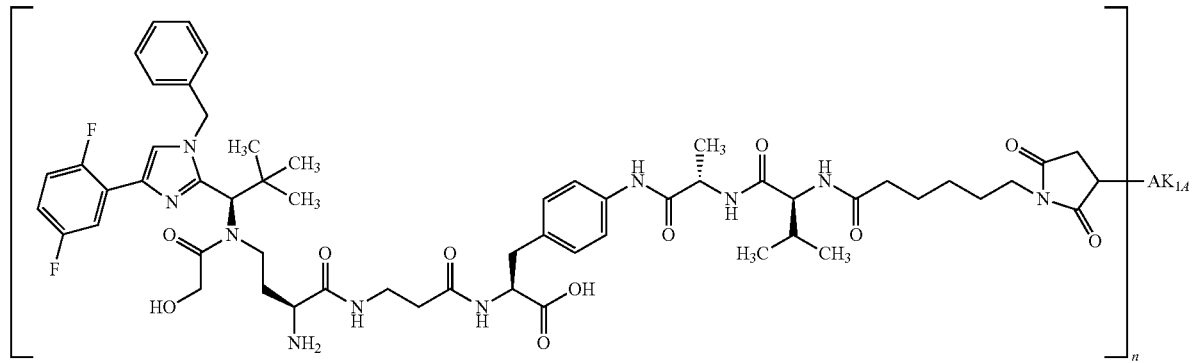

Here, 5 mg of cetuximab in PBS (c=11.59 mg/ml) were used for coupling with Intermediate F29, and the reaction was, after Sephadex purification, concentrated by ultracentrifugation and rediluted with PBS.

Protein concentration: 2.49 mg/ml
Drug/mAb ratio: 3.7

Example 29B

Here, 5 mg of anti-TWEAKR AK-1 in PBS (c=10.1 mg/ml) were used for coupling with Intermediate F29, and the reaction was, after Sephadex purification, concentrated by ultracentrifugation and rediluted with PBS.

Protein concentration: 1.82 mg/ml
Drug/mAb ratio: 3.1

Example 30A

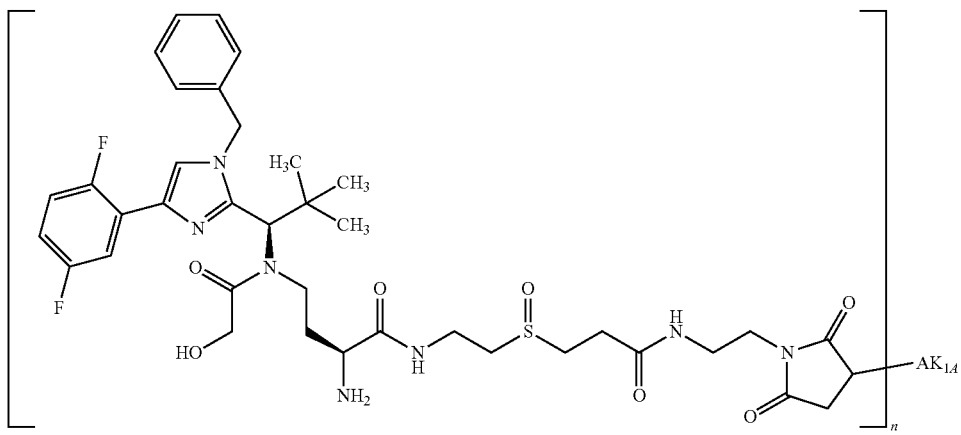

Here, 5 mg of cetuximab in PBS (c=11.59 mg/ml) were used for coupling with Intermediate F30, and the reaction was, after Sephadex purification, concentrated by ultracentrifugation and rediluted with PBS. Some of the ADC may also be present in the form of the hydrolysed open-chain succinamides attached to the antibody.

Protein concentration: 2.04 mg/ml
Drug/mAb ratio: 2.8

Example 30B

Here, 5 mg of anti-TWEAKR AK-1 in PBS (c=10.1 mg/ml) were used for coupling with Intermediate F30, and the reaction was, after Sephadex purification, concentrated by ultracentrifugation and rediluted with PBS. Some of the ADC may also be present in the form of the hydrolysed open-chain succinamides attached to the antibody.

Protein concentration: 1.85 mg/ml
Drug/mAb ratio: 2.9

Example 31A

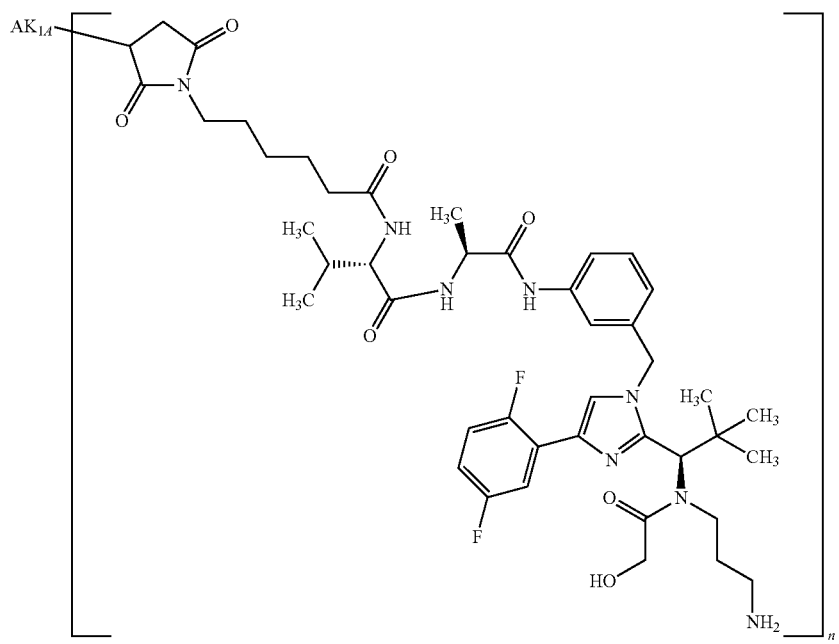

Here, 5 mg of cetuximab in PBS (c=5.1 mg/ml) were used for coupling with Intermediate F31, and the reaction was, after Sephadex purification, concentrated by ultracentrifugation and rediluted with PBS.
Protein concentration: 2.21 mg/ml
Drug/mAb ratio: 2.1

Example 31B

Here, 5 mg of anti-TWEAKR AK-1 in PBS (c=16.54 mg/ml) were used for coupling with Intermediate F31, and the reaction was, after Sephadex purification, concentrated by ultracentrifugation and rediluted with PBS.
Protein concentration: 1.59 mg/ml
Drug/mAb ratio: 2.4

Example 32A

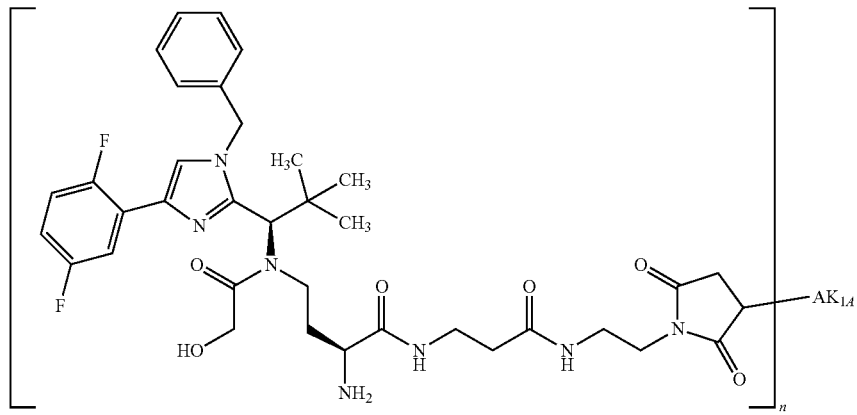

Here, 5 mg of cetuximab in PBS (c=11.59 mg/ml) were used for coupling with Intermediate F32, and the reaction was, after Sephadex purification, concentrated by ultracentrifugation and rediluted with PBS. Some of the ADC may also be present in the form of the hydrolysed open-chain succinamides attached to the antibody.
Protein concentration: 1.91 mg/ml
Drug/mAb ratio: 3.6

Example 32B

Here, 5 mg of anti-TWEAKR AK-1 in PBS (c=10.1 mg/ml) were used for coupling with Intermediate F32, and the reaction was, after Sephadex purification, concentrated by ultracentrifugation and rediluted with PBS. Some of the ADC may also be present in the form of the hydrolysed open-chain succinamides attached to the antibody.

Protein concentration: 1.78 mg/ml
Drug/mAb ratio: 3.6

Example 33A

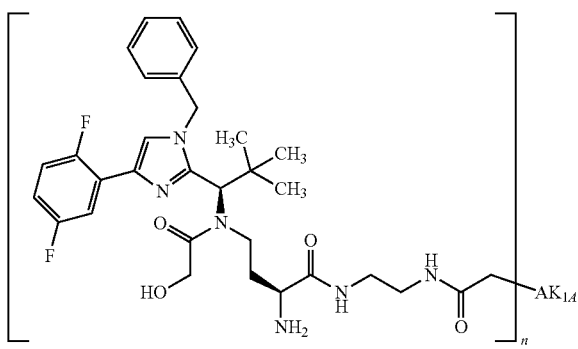

Here, 5 mg of cetuximab in PBS (c=8.95 mg/ml) were used for coupling with Intermediate F33. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.78 mg/ml
Drug/mAb ratio: 3.3

Example 33B

Here, 5 mg of anti-TWEAKR AK-1 in PBS (c=12.87 mg/ml) were used for coupling with Intermediate F33. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.46 mg/ml
Drug/mAb ratio: 3.9

Example 34A

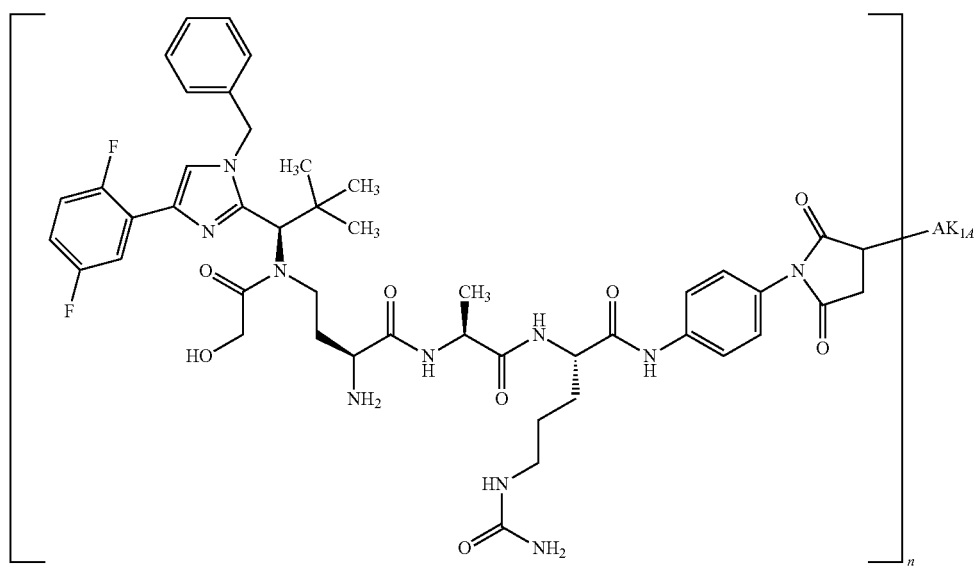

Here, 5 mg of cetuximab in PBS (c=8.95 mg/ml) were used for coupling with Intermediate F34, and the reaction was, after Sephadex purification, concentrated by ultracentrifugation and rediluted with PBS. Some of the ADC may also be present in the form of the hydrolysed open-chain succinamides attached to the antibody.

Protein concentration: 2.21 mg/ml
Drug/mAb ratio: 3.5

Example 34B

Here, 5 mg of anti-TWEAKR AK-1 in PBS (c=12.87 mg/ml) were used for coupling with Intermediate F34, and the reaction was, after Sephadex purification, concentrated by ultracentrifugation and rediluted with PBS. Some of the ADC may also be present in the form of the hydrolysed open-chain succinamides attached to the antibody.

Protein concentration: 1.4 mg/ml
Drug/mAb ratio: 3.3

Example 35A

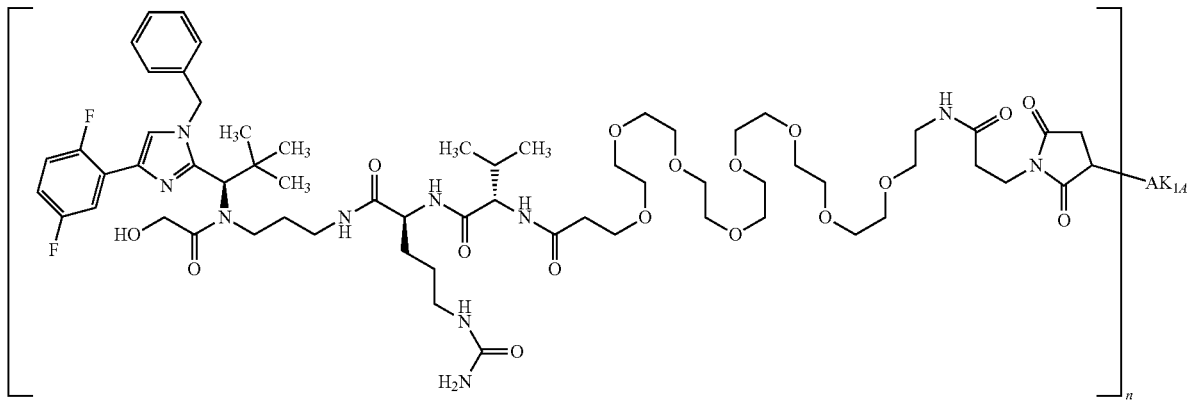

Here, 5.0 mg of cetuximab in PBS (c=5.90 mg/ml) were used for coupling with Intermediate F35, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 14.30 mg/ml
Drug/mAb ratio: 1.4

Example 35B

Here, 5.0 mg of anti-TWEAKR AK-1 antibody in PBS (c=16.54 mg/ml) were used for coupling with Intermediate F35, and the reaction was, after Sephadex purification, concentrated by ultracentrifugation and rediluted. Some of the ADC may also be present in the form of the hydrolysed open-chain succinamides attached to the antibody.

Protein concentration: 0.93 mg/ml
Drug/mAb ratio: 2.2

Example 35E

Here, 5.0 mg of trastuzumab antibody in PBS (c=8.23 mg/ml) were used for coupling with Intermediate F35, and the reaction was, after Sephadex purification, concentrated by ultracentrifugation and rediluted. Some of the ADC may also be present in the form of the hydrolysed open-chain succinamides attached to the antibody.

Protein concentration: 1.61 mg/ml
Drug/mAb ratio: 2.1

Example 36A

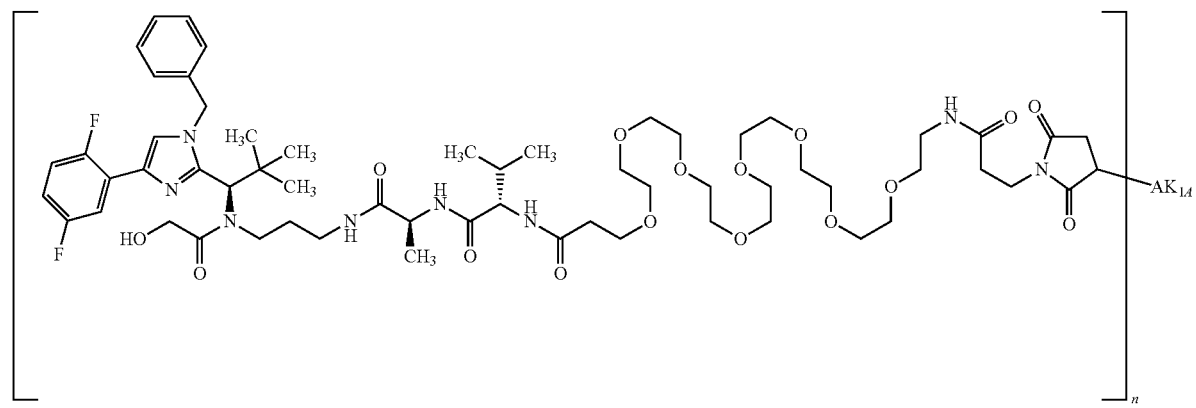

Here, 5.0 mg of cetuximab in PBS (c=5.9 mg/ml) were used for coupling with Intermediate F36, and the reaction was, after Sephadex purification, concentrated by ultracentrifugation, rediluted with PBS and concentrated again.

Protein concentration: 1.98 mg/ml
Drug/mAb ratio: 1.9

Example 37A

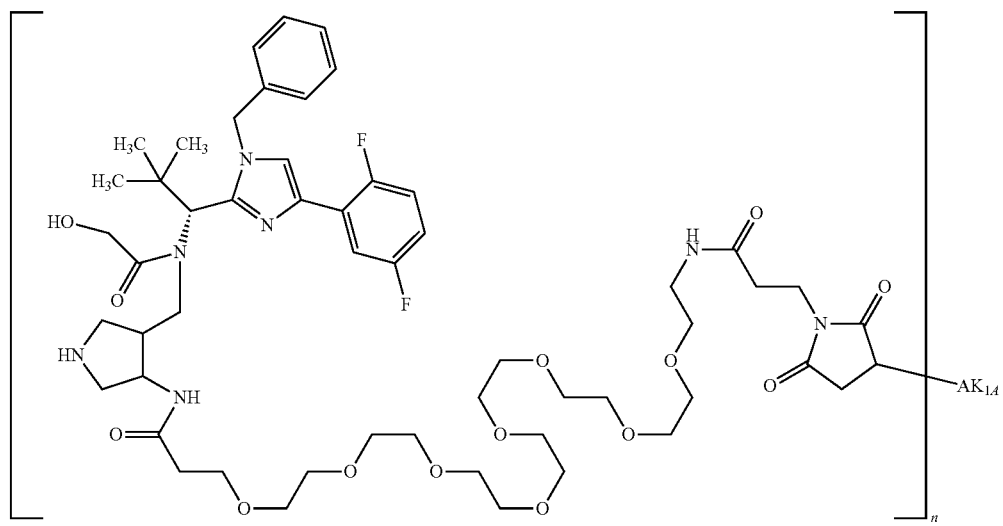

Some of the ADC may also be present in the form of the hydrolysed open-chain succinamides attached to the antibody.

Protein concentration: 13.86 mg/ml
Drug/mAb ratio: 2.9

Example 36B

Here, 5.0 mg of anti-TWEAKR AK-1 antibody in PBS (c=16.54 mg/ml) were used for coupling with Intermediate F36, and the reaction was, after Sephadex purification, concentrated by ultracentrifugation and rediluted. Some of the ADC may also be present in the form of the hydrolysed open-chain succinamides attached to the antibody.

Protein concentration: 1.08 mg/ml
Drug/mAb ratio: 2.0

Example 36E

Here, 5.0 mg of trastuzumab antibody in PBS (c=8.23 mg/ml) were used for coupling with Intermediate F36, and the reaction was, after Sephadex purification, concentrated by ultracentrifugation and rediluted. Some of the ADC may also be present in the form of the hydrolysed open-chain succinamides attached to the antibody.

Here, 5.0 mg of cetuximab in PBS (c=5.08 mg/ml) were used for coupling with Intermediate F37, and the reaction was, after Sephadex purification, concentrated by ultracentrifugation and rediluted with PBS. Some of the ADC may also be present in the form of the hydrolysed open-chain succinamides attached to the antibody.

Protein concentration: 2.52 mg/ml
Drug/mAb ratio: 1.5

Example 37B

Here, 5.0 mg of anti-TWEAKR AK-1 antibody in PBS (c=16.54 mg/ml) were used for coupling with Intermediate F37, and the reaction was, after Sephadex purification, concentrated by ultracentrifugation and rediluted. Some of the ADC may also be present in the form of the hydrolysed open-chain succinamides attached to the antibody.

Protein concentration: 1.91 mg/ml
Drug/mAb ratio: 2.0

Example 37E

Here, 5.0 mg of trastuzumab antibody in PBS (c=8.23 mg/ml) were used for coupling with Intermediate F37, and the reaction was, after Sephadex purification, concentrated by ultracentrifugation and rediluted. Some of the ADC may also be present in the form of the hydrolysed open-chain succinamides attached to the antibody.

Protein concentration: 2.23 mg/ml
Drug/mAb ratio: 1.5

Example 38A

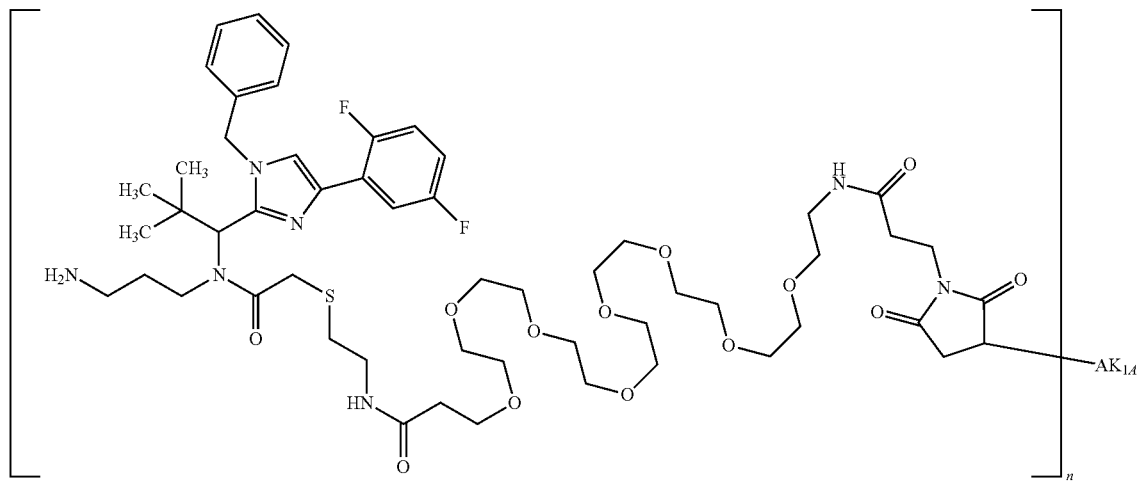

Here, 5.0 mg of cetuximab in PBS (c=5.08 mg/ml) were used for coupling with Intermediate F38, and the reaction was, after Sephadex purification, concentrated by ultracentrifugation and rediluted with PBS. Some of the ADC may also be present in the form of the hydrolysed open-chain succinamides attached to the antibody.

Protein concentration: 2.45 mg/ml
Drug/mAb ratio: 1.9

Example 38B

Here, 5.0 mg of anti-TWEAKR AK-1 antibody in PBS (c=12.23 mg/ml) were used for coupling with Intermediate F38, and the reaction was, after Sephadex purification, concentrated by ultracentrifugation and rediluted. Some of the ADC may also be present in the form of the hydrolysed open-chain succinamides attached to the antibody.

Protein concentration: 1.54 mg/ml
Drug/mAb ratio: 2.2

Example 38E

Here, 5.0 mg of trastuzumab antibody in PBS (c=13.39 mg/ml) were used for coupling with Intermediate F38, and the reaction was, after Sephadex purification, concentrated by ultracentrifugation and rediluted. Some of the ADC may also be present in the form of the hydrolysed open-chain succinamides attached to the antibody.

Protein concentration: 1.90 mg/ml
Drug/mAb ratio: 2.4

Example 39A

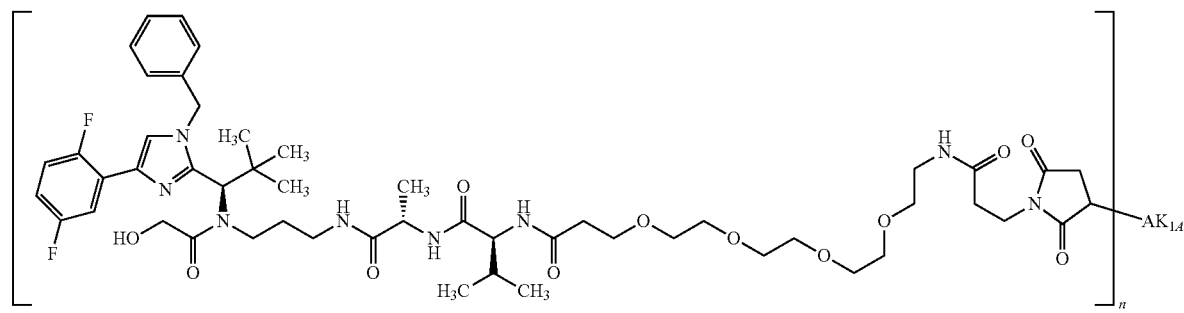

Here, 5.0 mg of cetuximab in PBS (c=5.90 mg/ml) were used for coupling with Intermediate F39, and the reaction was, after Sephadex purification, concentrated by ultracentrifugation and rediluted with PBS. Some of the ADC may also be present in the form of the hydrolysed open-chain succinamides attached to the antibody.

Protein concentration: 1.98 mg/ml
Drug/mAb ratio: 2.0

Example 39B

Here, 5.0 mg of anti-TWEAKR AK-1 antibody in PBS (c=12.23 mg/ml) were used for coupling with Intermediate F39, and the reaction was, after Sephadex purification, concentrated by ultracentrifugation and rediluted. Some of the ADC may also be present in the form of the hydrolysed open-chain succinamides attached to the antibody.

Protein concentration: 1.40 mg/ml
Drug/mAb ratio: 1.4

Example 39E

Here, 5.0 mg of trastuzumab antibody in PBS (c=13.39 mg/ml) were used for coupling with Intermediate F39, and the reaction was, after Sephadex purification, concentrated by ultracentrifugation and rediluted. Some of the ADC may also be present in the form of the hydrolysed open-chain succinamides attached to the antibody.

Protein concentration: 2.04 mg/ml
Drug/mAb ratio: 2.1

Example 40A

Here, 5.0 mg of cetuximab in PBS (c=5.90 mg/ml) were used for coupling with Intermediate F40, and the reaction was, after Sephadex purification, concentrated by ultracentrifugation and rediluted with PBS. Some of the ADC may also be present in the form of the hydrolysed open-chain succinamides attached to the antibody.

Protein concentration: 2.0 mg/ml
Drug/mAb ratio: 2.5

Example 40B

Here, 5.0 mg of anti-TWEAKR AK-1 antibody in PBS (c=12.23 mg/ml) were used for coupling with Intermediate F40, and the reaction was, after Sephadex purification, concentrated by ultracentrifugation and rediluted. Some of the ADC may also be present in the form of the hydrolysed open-chain succinamides attached to the antibody.

Protein concentration: 1.81 mg/ml
Drug/mAb ratio: 2.5

Example 40E

Here, 5.0 mg of trastuzumab antibody in PBS (c=13.39 mg/ml) were used for coupling with Intermediate F40, and the reaction was, after Sephadex purification, concentrated by ultracentrifugation and rediluted. Some of the ADC may also be present in the form of the hydrolysed open-chain succinamides attached to the antibody.

Protein concentration: 1.98 mg/ml
Drug/mAb ratio: 2.3

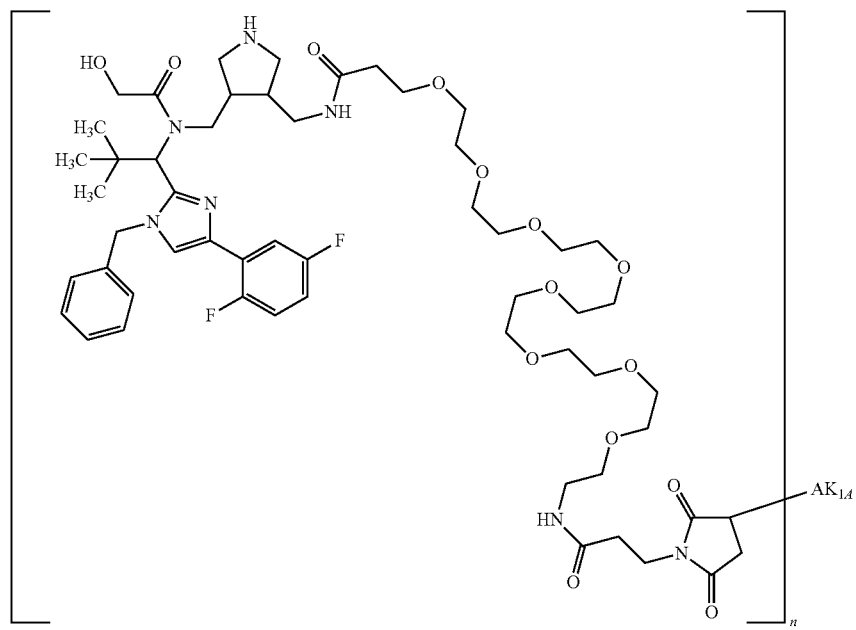

Example 41A

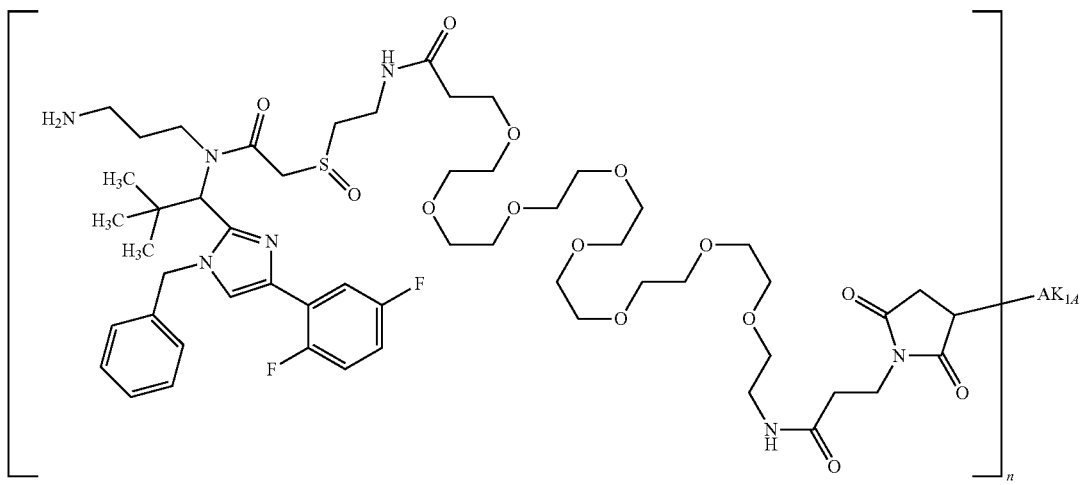

Here, 5.0 mg of cetuximab in PBS (c=5.08 mg/ml) were used for coupling with Intermediate F41, and the reaction was, after Sephadex purification, concentrated by ultracentrifugation and rediluted with PBS. Some of the ADC may also be present in the form of the hydrolysed open-chain succinamides attached to the antibody.

Protein concentration: 2.53 mg/ml

Drug/mAb ratio: 1.9

Example 41B

Here, 5.0 mg of anti-TWEAKR AK-1 antibody in PBS (c=12.23 mg/ml) were used for coupling with Intermediate F41, and the reaction was, after Sephadex purification, concentrated by ultracentrifugation and rediluted. Some of the ADC may also be present in the form of the hydrolysed open-chain succinamides attached to the antibody.

Protein concentration: 1.73 mg/ml

Drug/mAb ratio: 2.5

Example 41E

Here, 5.0 mg of trastuzumab antibody in PBS (c=13.39 mg/ml) were used for coupling with Intermediate F39, and the reaction was, after Sephadex purification, concentrated by ultracentrifugation and rediluted. Some of the ADC may also be present in the form of the hydrolysed open-chain succinamides attached to the antibody.

Protein concentration: 2.09 mg/ml

Drug/mAb ratio: 2.5

Example 42A

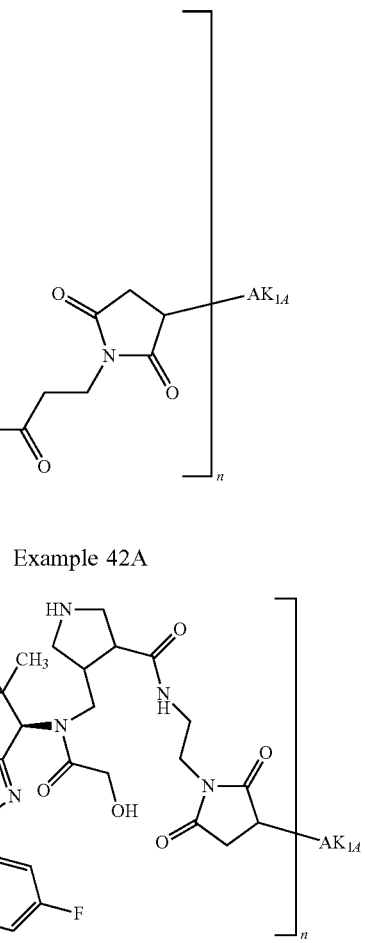

Here, 5.0 mg of cetuximab in PBS (c=5.90 mg/ml) were used for coupling with Intermediate F42, and the reaction was, after Sephadex purification, concentrated by ultracentrifugation and rediluted with PBS. Some of the ADC may also be present in the form of the hydrolysed open-chain succinamides attached to the antibody.

Protein concentration: 2.05 mg/ml

Drug/mAb ratio: 2.1

Example 42B

Here, 5.0 mg of anti-TWEAKR AK-1 antibody in PBS (c=12.23 mg/ml) were used for coupling with Intermediate F42, and the reaction was, after Sephadex purification, concentrated by ultracentrifugation and rediluted. Some of the ADC may also be present in the form of the hydrolysed open-chain succinamides attached to the antibody.

Protein concentration: 1.64 mg/ml

Drug/mAb ratio: 2.3

Example 42E

Here, 5.0 mg of trastuzumab antibody in PBS (c=13.39 mg/ml) were used for coupling with Intermediate F42, and the reaction was, after Sephadex purification, concentrated by ultracentrifugation and rediluted. Some of the ADC may also be present in the form of the hydrolysed open-chain succinamides attached to the antibody.

Protein concentration: 1.80 mg/ml

Drug/mAb ratio: 2.0

Example 43A

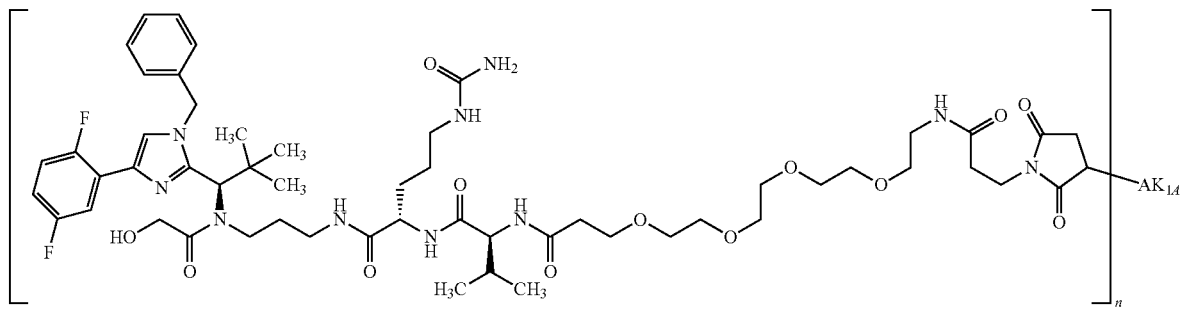

Here, 5.0 mg of cetuximab in PBS (c=5.90 mg/ml) were used for coupling with Intermediate F43, and the reaction was, after Sephadex purification, concentrated by ultracentrifugation and rediluted with PBS. Some of the ADC may also be present in the form of the hydrolysed open-chain succinamides attached to the antibody.

Protein concentration: 1.90 mg/ml
Drug/mAb ratio: 1.3

Example 43B

Here, 5.0 mg of anti-TWEAKR AK-1 antibody in PBS (c=12.23 mg/ml) were used for coupling with Intermediate F43, and the reaction was, after Sephadex purification, concentrated by ultracentrifugation and rediluted. Some of the ADC may also be present in the form of the hydrolysed open-chain succinamides attached to the antibody.

Protein concentration: 0.85 mg/ml
Drug/mAb ratio: 1.3

Example 43E

Here, 5.0 mg of trastuzumab antibody in PBS (c=13.39 mg/ml) were used for coupling with Intermediate F43, and the reaction was, after Sephadex purification, concentrated by ultracentrifugation and rediluted. Some of the ADC may also be present in the form of the hydrolysed open-chain succinamides attached to the antibody.

Protein concentration: 1.97 mg/ml
Drug/mAb ratio: 2.1

Example 44A

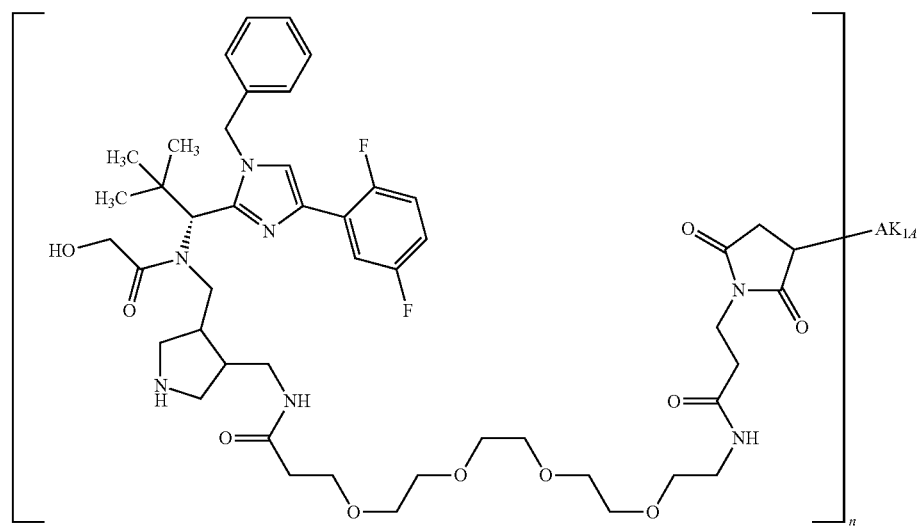

Here, 5.0 mg of cetuximab in PBS (c=5.90 mg/ml) were used for coupling with Intermediate F44, and the reaction was, after Sephadex purification, concentrated by ultracentrifugation and rediluted with PBS. Some of the ADC may also be present in the form of the hydrolysed open-chain succinamides attached to the antibody.

Protein concentration: 1.99 mg/ml
Drug/mAb ratio: 2.5

Example 44B

Here, 5.0 mg of anti-TWEAKR AK-1 antibody in PBS (c=12.23 mg/ml) were used for coupling with Intermediate F44, and the reaction was, after Sephadex purification, concentrated by ultracentrifugation and rediluted. Some of the ADC may also be present in the form of the hydrolysed open-chain succinamides attached to the antibody.

Protein concentration: 1.65 mg/ml
Drug/mAb ratio: 2.5

Example 44E

Here, 5.0 mg of trastuzumab antibody in PBS (c=13.39 mg/ml) were used for coupling with Intermediate F44, and the reaction was, after Sephadex purification, concentrated by ultracentrifugation and rediluted. Some of the ADC may also be present in the form of the hydrolysed open-chain succinamides attached to the antibody.

Protein concentration: 1.95 mg/ml
Drug/mAb ratio: 2.4

Example 45A

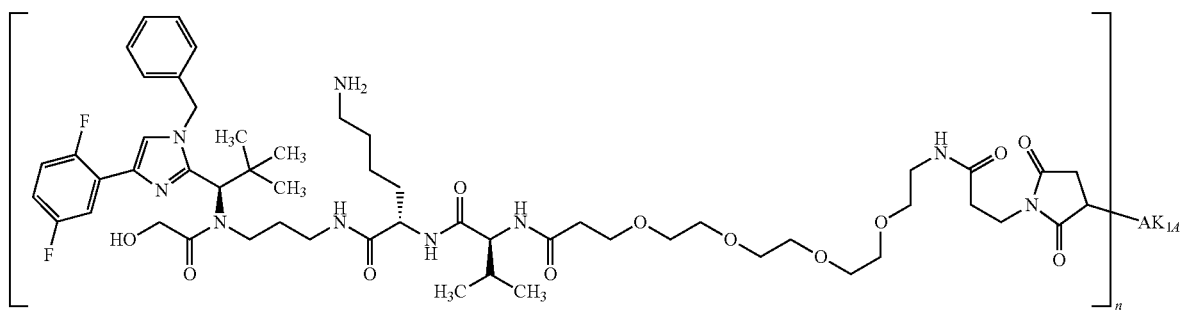

Here, 5.0 mg of cetuximab in PBS (c=5.90 mg/ml) were used for coupling with Intermediate F45, and the reaction was, after Sephadex purification, concentrated by ultracentrifugation and rediluted with
PBS. Some of the ADC may also be present in the form of the hydrolysed open-chain succinamides attached to the antibody.

Protein concentration: 1.92 mg/ml
Drug/mAb ratio: 2.3

Example 45B

Here, 5.0 mg of anti-TWEAKR AK-1 antibody in PBS (c=12.23 mg/ml) were used for coupling with Intermediate F45, and the reaction was, after Sephadex purification, concentrated by ultracentrifugation and rediluted. Some of the ADC may also be present in the form of the hydrolysed open-chain succinamides attached to the antibody.

Protein concentration: 1.27 mg/ml
Drug/mAb ratio: 1.8

Example 45E

Here, 5.0 mg of trastuzumab antibody in PBS (c=13.39 mg/ml) were used for coupling with Intermediate F45, and the reaction was, after Sephadex purification, concentrated by ultracentrifugation and rediluted. Some of the ADC may also be present in the form of the hydrolysed open-chain succinamides attached to the antibody.

Protein concentration: 1.91 mg/ml
Drug/mAb ratio: 2.1

Example 46A

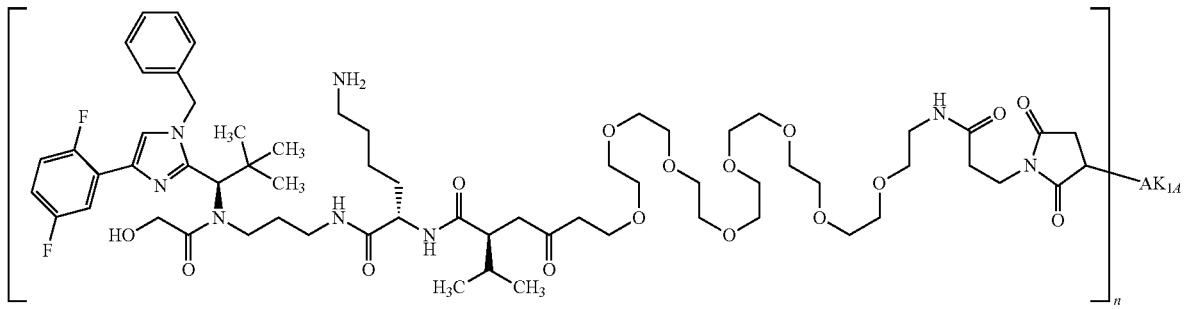

Here, 5.0 mg of cetuximab in PBS (c=5.90 mg/ml) were used for coupling with Intermediate F46, and the reaction was, after Sephadex purification, concentrated by ultracentrifugation and rediluted with PBS. Some of the ADC may also be present in the form of the hydrolysed open-chain succinamides attached to the antibody.

Protein concentration: 2.0 mg/ml

Drug/mAb ratio: 2.2

Example 46B

Here, 5.0 mg of anti-TWEAKR AK-1 antibody in PBS (c=12.23 mg/ml) were used for coupling with Intermediate F46, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 11.21 mg/ml

Drug/mAb ratio: 2.1

Example 46E

Here, 5.0 mg of trastuzumab antibody in PBS (c=13.39 mg/ml) were used for coupling with Intermediate F46, and the reaction was, after Sephadex purification, concentrated by ultracentrifugation and rediluted. Some of the ADC may also be present in the form of the hydrolysed open-chain succinamides attached to the antibody.

Protein concentration: 1.84 mg/ml

Drug/mAb ratio: 2.4

Example 47A

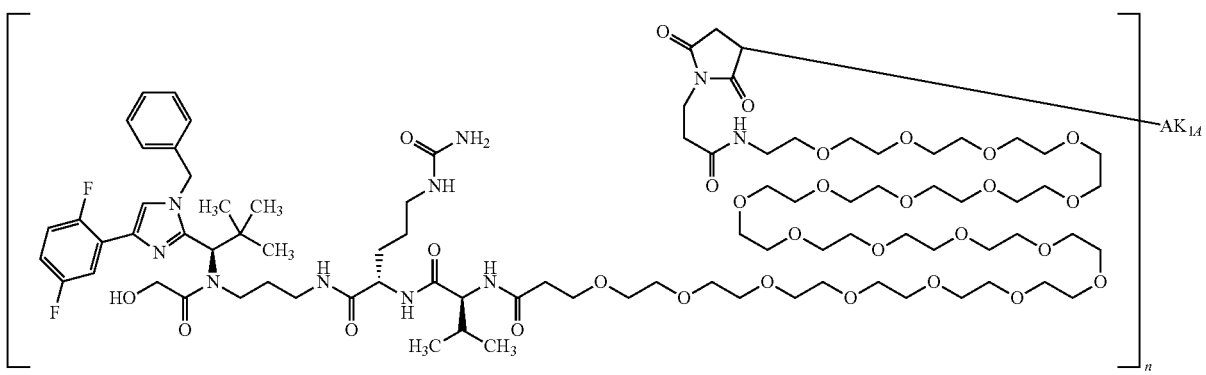

Here, 5.0 mg of cetuximab in PBS (c=5.90 mg/ml) were used for coupling with Intermediate F47, and the reaction was, after Sephadex purification, concentrated by ultracentrifugation and rediluted with PBS. Some of the ADC may also be present in the form of the hydrolysed open-chain succinamides attached to the antibody.
Protein concentration: 1.51 mg/ml
Drug/mAb ratio: 2.1

Example 47B

Here, 5.0 mg of anti-TWEAKR AK-1 antibody in PBS (c=12.23 mg/ml) were used for coupling with Intermediate F47, and the reaction was, after Sephadex purification, concentrated by ultracentrifugation and rediluted. Some of the ADC may also be present in the form of the hydrolysed open-chain succinamides attached to the antibody.
Protein concentration: 0.89 mg/ml
Drug/mAb ratio: 1.7

Example 47E

Here, 5.0 mg of trastuzumab antibody in PBS (c=13.39 mg/ml) were used for coupling with Intermediate F47, and the reaction was, after Sephadex purification, concentrated by ultracentrifugation and rediluted. Some of the ADC may also be present in the form of the hydrolysed open-chain succinamides attached to the antibody.
Protein concentration: 1.97 mg/ml
Drug/mAb ratio: 2.9

Example 48A

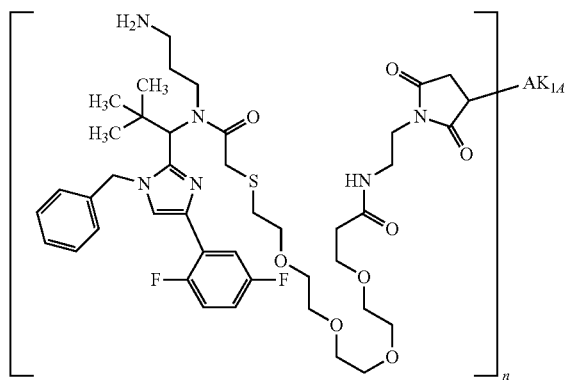

Here, 5.0 mg of cetuximab in PBS (c=5.90 mg/ml) were used for coupling with Intermediate F48, and the reaction was, after Sephadex purification, concentrated by ultracentrifugation and rediluted with PBS. Some of the ADC may also be present in the form of the hydrolysed open-chain succinamides attached to the antibody.
Protein concentration: 2.10 mg/ml
Drug/mAb ratio: 2.4

Example 48B

Here, 5.0 mg of anti-TWEAKR AK-1 antibody in PBS (c=10.10 mg/ml) were used for coupling with Intermediate F48, and the reaction was, after Sephadex purification, concentrated by ultracentrifugation and rediluted. Some of the ADC may also be present in the form of the hydrolysed open-chain succinamides attached to the antibody.
Protein concentration: 1.73 mg/ml
Drug/mAb ratio: 1.8

Example 48E

Here, 5.0 mg of trastuzumab antibody in PBS (c=13.39 mg/ml) were used for coupling with Intermediate F48, and the reaction was, after Sephadex purification, concentrated by ultracentrifugation and rediluted. Some of the ADC may also be present in the form of the hydrolysed open-chain succinamides attached to the antibody.
Protein concentration: 1.95 mg/ml
Drug/mAb ratio: 2.7

Example 49A

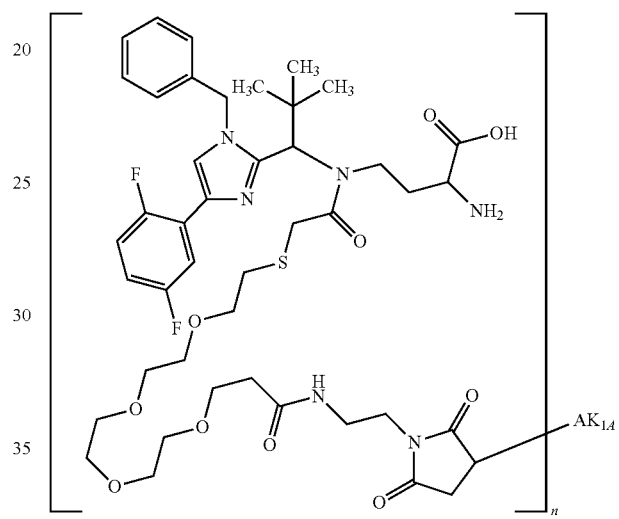

Here, 5.0 mg of cetuximab in PBS (c=5.90 mg/ml) were used for coupling with Intermediate F49, and the reaction was, after Sephadex purification, concentrated by ultracentrifugation and rediluted with PBS. Some of the ADC may also be present in the form of the hydrolysed open-chain succinamides attached to the antibody.
Protein concentration: 2.09 mg/ml
Drug/mAb ratio: 2.0

Example 49B

Here, 5.0 mg of anti-TWEAKR AK-1 antibody in PBS (c=12.87 mg/ml) were used for coupling with Intermediate F49, and the reaction was, after Sephadex purification, concentrated by ultracentrifugation and rediluted. Some of the ADC may also be present in the form of the hydrolysed open-chain succinamides attached to the antibody.
Protein concentration: 1.95 mg/ml
Drug/mAb ratio: 2.1

Example 49E

Here, 5.0 mg of trastuzumab antibody in PBS (c=13.5 mg/ml) were used for coupling with Intermediate F49, and the reaction was, after Sephadex purification, concentrated by ultracentrifugation and rediluted. Some of the ADC may also be present in the form of the hydrolysed open-chain succinamides attached to the antibody.
Protein concentration: 1.96 mg/ml
Drug/mAb ratio: 2.4

Example 50A

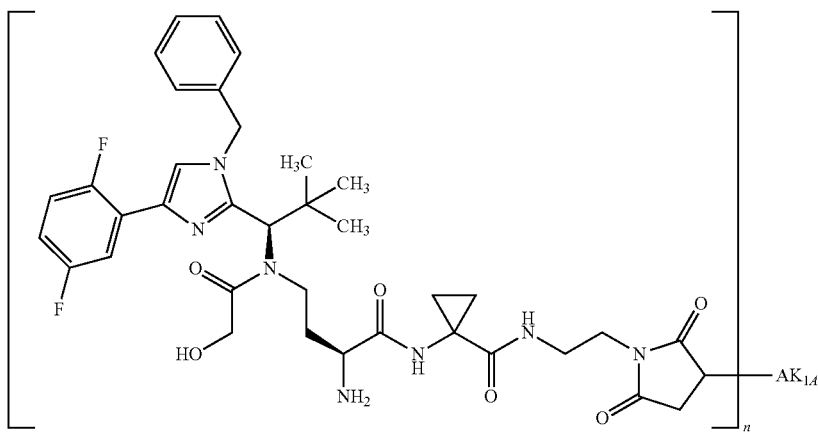

Here, 5 mg of cetuximab in PBS (c=11.02 mg/ml) were used for coupling with Intermediate F50, and the reaction was, after Sephadex purification, concentrated by ultracentrifugation and rediluted with PBS. Some of the ADC may also be present in the form of the hydrolysed open-chain succinamides attached to the antibody.

Protein concentration: 1.89 mg/ml
Drug/mAb ratio: 3.0

Example 50B

Here, 5 mg of anti-TWEAKR AK-1 in PBS (c=12.87 mg/ml) were used for coupling with Intermediate F50, and the reaction was, after Sephadex purification, concentrated by ultracentrifugation and rediluted with PBS. Some of the ADC may also be present in the form of the hydrolysed open-chain succinamides attached to the antibody.

Protein concentration: 1.82 mg/ml
Drug/mAb ratio: 2.9

Example 51A

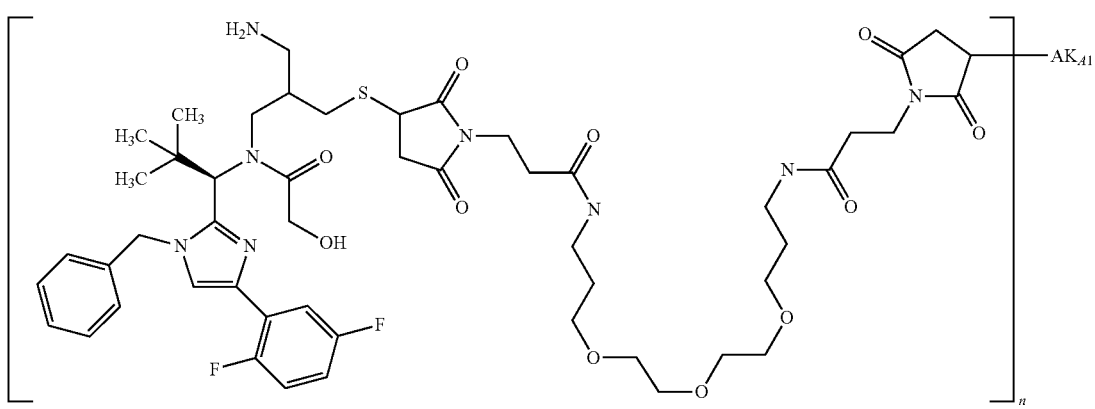

Here, 5 mg of cetuximab in PBS (c=5.1 mg/ml) were used for coupling with the intermediate 3-{3-[(3-amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 1), and the reaction was, after Sephadex purification, concentrated by ultracentrifugation and rediluted with PBS. Some of the ADC may also be present in the form of the hydrolysed open-chain succinamides attached to the antibody.

Protein concentration: 2.16 mg/ml

Example 51B

Here, 5 mg of anti-TWEAKR AK-1 in PBS (c=16.5 mg/me were used for coupling with the intermediate 3-{3-[(3-amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 1), and the reaction was, after Sephadex purification, concentrated by ultracentrifugation and rediluted with PBS. Some of the ADC may also be present in the form of the hydrolysed open-chain succinamides attached to the antibody.

Protein concentration: 1.74 mg/ml
Drug/mAb ratio: 1.7

Example 51E

Here, 5 mg of trastuzumab in PBS (c=8.2 mg/ml) were used for coupling with the intermediate 3-{3-[(3-amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 1), and the reaction was, after Sephadex purification, concentrated by ultracentrifugation and rediluted with PBS. Some of the ADC may also be present in the form of the hydrolysed open-chain succinamides attached to the antibody.

Protein concentration: 1.67 mg/ml
Drug/mAb ratio: 2.4

Example 52A

Here, 5 mg of cetuximab in PBS (c=5.1 mg/ml) were used for coupling with the intermediate 3-{3-[(3-amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 2), and the reaction was, after Sephadex purification, concentrated by ultracentrifugation and rediluted with PBS. Some of the ADC may also be present in the form of the hydrolysed open-chain succinamides attached to the antibody.

Protein concentration: 2.41 mg/ml
Drug/mAb ratio: 2.3

Example 52B

Here, 5 mg of anti-TWEAKR AK-1 in PBS (c=16.5 mg/me were used for coupling with the intermediate 3-{3-{[{(3-amino-2-[(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 2), and the reaction was, after Sephadex purification, concentrated by ultracentrifugation and rediluted with PBS. Some of the ADC may also be present in the form of the hydrolysed open-chain succinamides attached to the antibody.

Protein concentration: 1.34 mg/ml
Drug/mAb ratio: 1.6

Example 52E

Here, 5 mg of trastuzumab in PBS (c=8.2 mg/ml) were used for coupling with the intermediate 3-{3-[(3-amino-2-{[{(1R)-1-[1-benzyl-4-(2,5-difluorophenyl)-1H-imidazol-2-yl]-2,2-dimethylpropyl}(glycoloyl)amino]methyl}propyl)sulphanyl]-2,5-dioxopyrrolidin-1-yl}-N-[17-(2,5-dioxo-2,5-dihydro-1H-pyrrol-1-yl)-15-oxo-4,7,10-trioxa-14-azaheptadec-1-yl]propanamide (Isomer 2), and the reaction was, after Sephadex purification, concentrated by ultracentrifugation and rediluted with PBS. Some of the ADC may also be present in the form of the hydrolysed open-chain succinamides attached to the antibody.

Protein concentration: 2.16 mg/ml
Drug/mAb ratio: 2.6

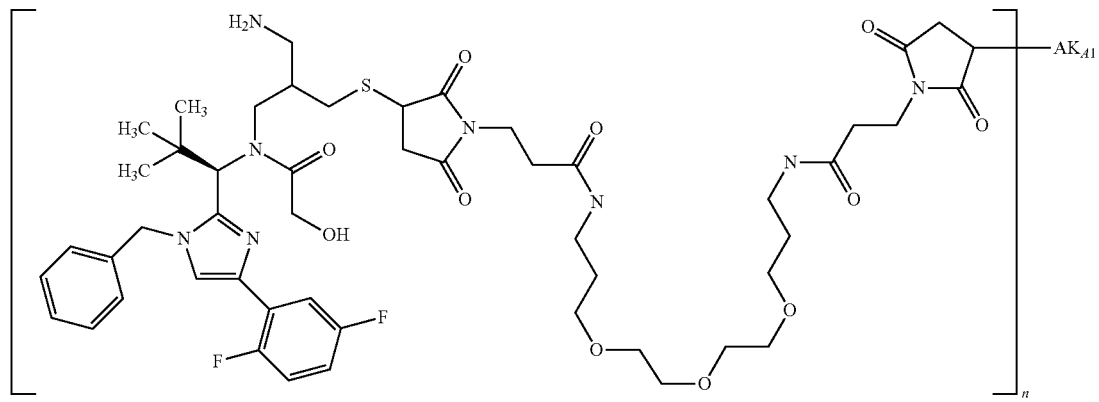

Example 53A

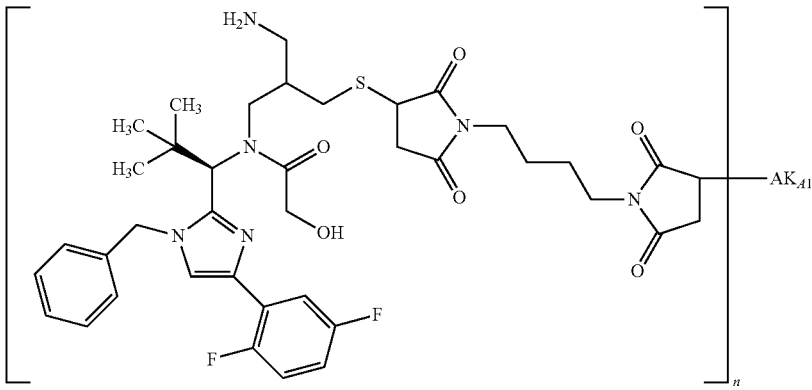

Here, 5 mg of cetuximab in PBS (c=5.1 mg/ml) were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 1), and the reaction was, after Sephadex purification, concentrated by ultracentrifugation and rediluted with PBS.

Protein concentration: 2.09 mg/ml
Drug/mAb ratio: 2.1

Example 53B

Here, 5 mg of anti-TWEAKR AK-1 in PBS (c=16.5 mg/me were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 1), and the reaction was, after Sephadex purification, concentrated by ultracentrifugation and rediluted with PBS.

Protein concentration: 1.95 mg/ml
Drug/mAb ratio: 1.8

Example 53E

Here, 5 mg of trastuzumab in PBS (c=8.2 mg/ml) were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 1), and the reaction was, after Sephadex purification, concentrated by ultracentrifugation and rediluted with PBS.

Protein concentration: 2.15 mg/ml
Drug/mAb ratio: 2.4

Example 54A

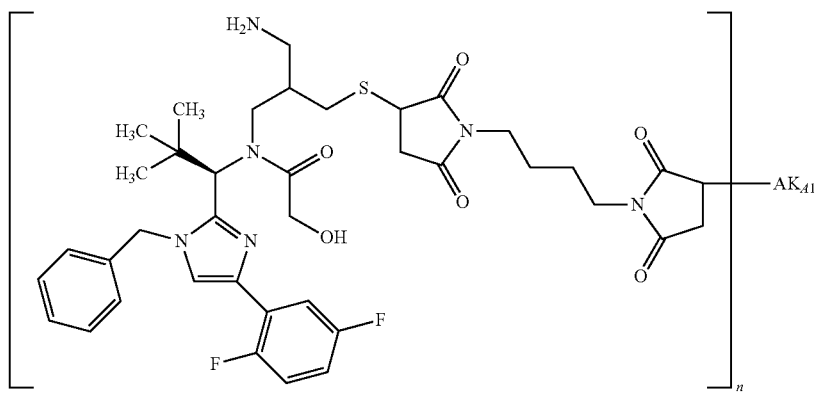

Here, 5 mg of cetuximab in PBS (c=5.1 mg/ml) were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 2), and the reaction was, after Sephadex purification, concentrated by ultracentrifugation and rediluted with PBS.

Protein concentration: 2.17 mg/ml
Drug/mAb ratio: 1.9

Example 54B

Here, 5 mg of anti-TWEAKR AK-1 in PBS (c=16.5 mg/me were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 2), and the reaction was, after Sephadex purification, concentrated by ultracentrifugation and rediluted with PBS.

Protein concentration: 1.95 mg/ml
Drug/mAb ratio: 2.0

Example 54E

Here, 5 mg of trastuzumab in PBS (c=8.2 mg/ml) were used for coupling with the intermediate N-{3-amino-2-[({1-[4-(2,5-dioxo-2,5-dihydro-1H-pyrrol-1-yl)butyl]-2,5-dioxopyrrolidin-3-yl}sulphanyl)methyl]propyl}-N-{(1R)-1-[1-benzyl-4-(2,5-difluorophenyl)-1H-imidazol-2-yl]-2,2-dimethylpropyl}-2-hydroxyacetamide (Isomer 2), and the reaction was, after Sephadex purification, concentrated by ultracentrifugation and rediluted with PBS.

Protein concentration: 1.90 mg/ml
Drug/mAb ratio: 1.8

Example 55A

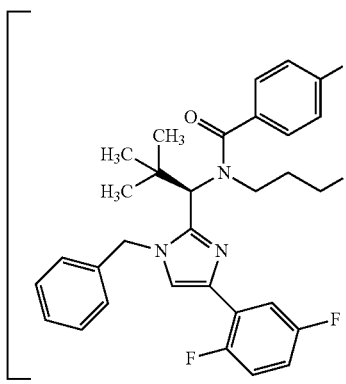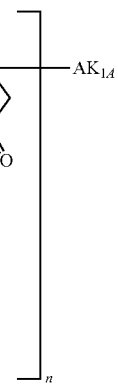

Here, 5 mg of cetuximab in PBS (c=5.1 mg/ml) were used for coupling with the intermediate N-[19-(2,5-dioxo-2,5-dihydro-1H-pyrrol-1-yl)-17-oxo-4,7,10,13-tetraoxa-16-azanonadecan-1-oyl]-L-valyl-N-{4-[(3-aminopropyl){(1R)-1-[1-benzyl-4-(2,5-difluorophenyl)-1H-imidazol-2-yl]-2,2-dimethylpropyl}carbamoyl]penyl}-L-alaninamide, and the reaction was, after Sephadex purification, concentrated by ultracentrifugation and rediluted with PBS. Some of the ADC may also be present in the form of the hydrolysed open-chain succinamides attached to the antibody.

Protein concentration: 0.47 mg/ml
Drug/mAb ratio: nd

Example 55B

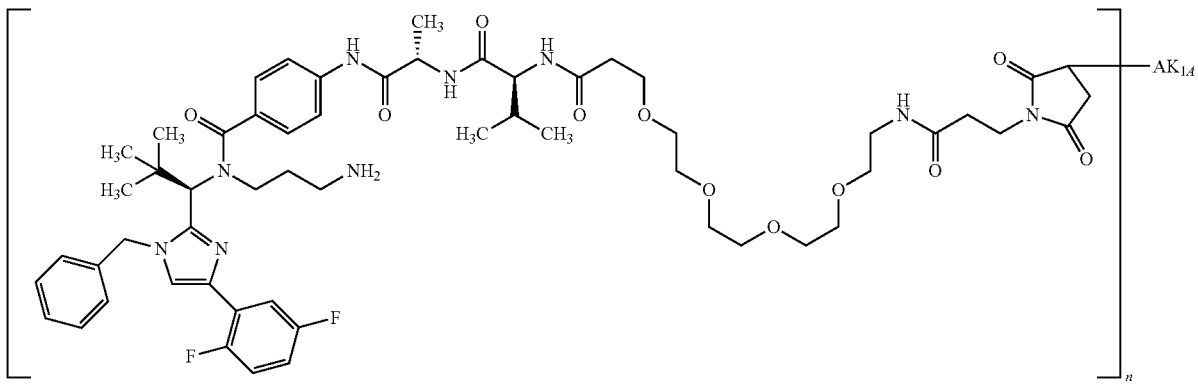

Here, 5 mg of anti-TWEAKR AK-1 in PBS (c=12.2 mg/me were used for coupling with the intermediate N-[19-(2,5-dioxo-2,5-dihydro-1H-pyrrol-1-yl)-17-oxo-4,7,10,13-tetraoxa-16-azanonadecan-1-oyl]-L-valyl-N-{4-[(3-aminopropyl){(1R)-1-[1-benzyl-4-(2,5-difluorophenyl)-1H-imidazol-2-yl]-2,2-dimethylpropyl}carbamoyl]phenyl}-L-alaninamide, and the reaction was, after Sephadex purification, concentrated by ultracentrifugation and rediluted with PBS. Some of the ADC may also be present in the form of the hydrolysed open-chain succinamides attached to the antibody.

Protein concentration: 1.26 mg/ml
Drug/mAb ratio: 1.8

Example 56A

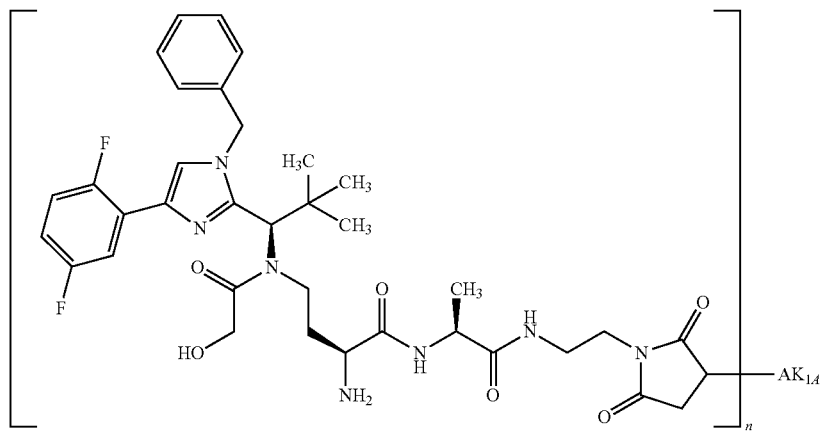

Example 56B

Here, 5 mg of anti-TWEAKR AK-1 in PBS (c=12.87 mg/ml) were used for coupling with Intermediate F56, and the reaction was, after Sephadex purification, concentrated by ultracentrifugation and rediluted with PBS. Some of the ADC may also be present in the form of the hydrolysed open-chain succinamides attached to the antibody.

Protein concentration: 1.74 mg/ml
Drug/mAb ratio: 2.8

Here, 5 mg of cetuximab in PBS (c=15.33 mg/ml) were used for coupling with Intermediate F56, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml
Drug/mAb ratio: 2.8

Example 57A

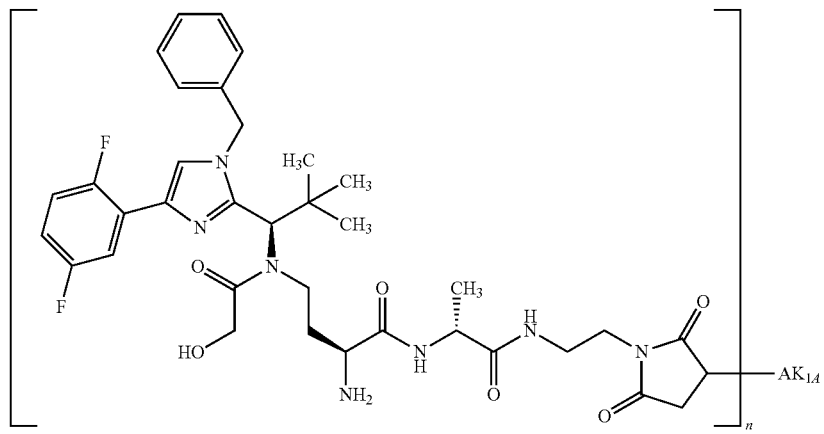

Here, 5 mg of cetuximab in PBS (c=15.33 mg/ml) were used for coupling with Intermediate F57, and the reaction was, after Sephadex purification, concentrated by ultracentrifugation and rediluted with PBS. Some of the ADC may also be present in the form of the hydrolysed open-chain succinamides attached to the antibody.

Protein concentration: 2.04 mg/ml

Drug/mAb ratio: 3.3

Example 57B

Here, 5 mg of anti-TWEAKR AK-1 in PBS (c=12.87 mg/ml) were used for coupling with Intermediate F57, and the reaction was, after Sephadex purification, concentrated by ultracentrifugation and rediluted with PBS. Some of the ADC may also be present in the form of the hydrolysed open-chain succinamides attached to the antibody.

Protein concentration: 1.93 mg/ml

Drug/mAb ratio: 3.3

Example 58A

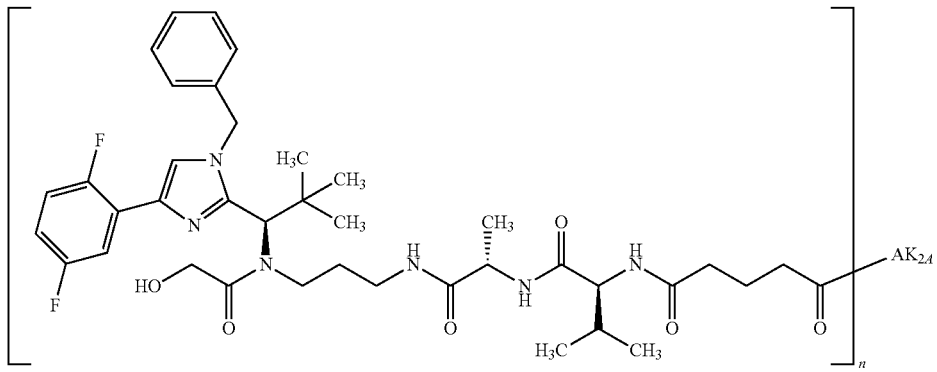

Here, 20 mg of cetuximab in PBS (c=21.32 mg/ml) were used for coupling with Intermediate F58, and the reaction was, after Sephadex purification, concentrated by ultracentrifugation and rediluted with PBS.

Protein concentration: 1.33 mg/ml

Drug/mAb ratio: 2.0

Example 58B

Here, 20.0 mg of anti-TWEAKR AK-1 antibody in PBS (c=18.6 mg/ml) were used for coupling with Intermediate F58, and the reaction was, after Sephadex purification, concentrated by ultracentrifugation and rediluted with PBS.

Protein concentration: 1.54 mg/ml

Drug/mAb ratio: 4.6

Example 58E

Here, 5.0 mg of trastuzumab antibody in PBS (c=13.5 mg/ml) were used for coupling with Intermediate F58, and the reaction was, after Sephadex purification, concentrated by ultracentrifugation and rediluted with PBS.

Protein concentration: 1.15 mg/ml

Example 59

$N^6$-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-L-lysine trifluoroacetic acid (1:1)

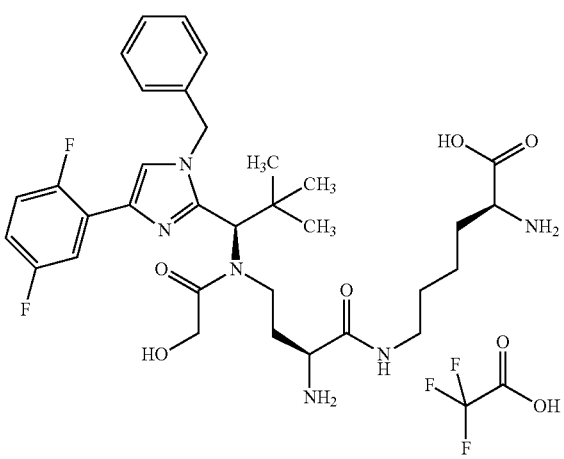

8 mg (15 μmol) of Intermediate F1 were taken up in 1.7 ml of DCM, and 7.3 mg (30 μmol) of N2-(tert-butoxycarbonyl)-L-lysine and 13 μl of N,N-diisopropylethylamine were added. The reaction mixture was stirred at RT for 15 min, then concentrated under reduced pressure and then purified by preparative HPLC. The intermediate was then taken up in 1 ml of DCM and deprotected using 1 ml of TFA. The reaction was concentrated and the residue was lyophilized from acetonitrile/water 1:1.

LC-MS (Method 1): $R_t$=0.8 min; MS (ESIpos): m/z=643 $(M+H)^+$.

Example 60

S-{1-[6-(2-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}hydrazino)-6-oxohexyl]-2,5-dioxopyrrolidin-3-yl}-L-cysteine

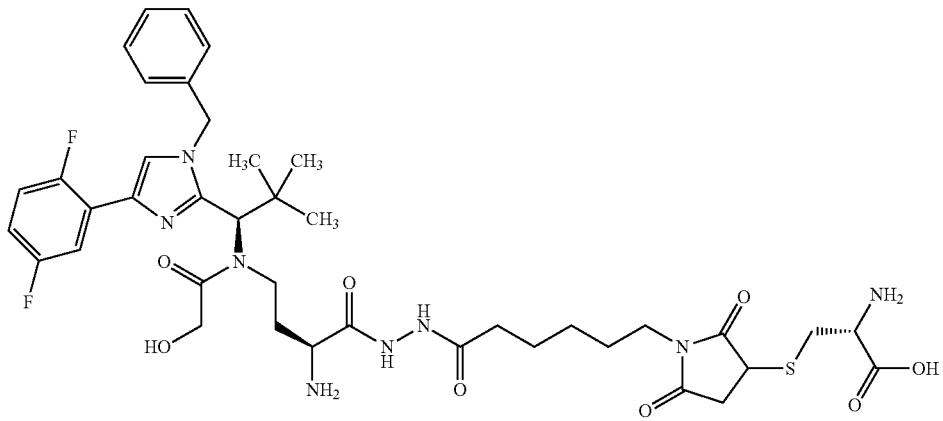 [SMILES: CC(C)(C)[C@H](c1nc(-c2cc(F)ccc2F)cn1Cc1ccccc1)N(CC[C@H](N)C(=O)NNC(=O)CCCCCN1C(=O)CC(SC[C@H](N)C(=O)O)C1=O)C(=O)CO]

4 mg (5 µmol) of Intermediate F3 were taken up in 1 ml of DCM, and 1.2 mg (10 µmol) of L-cysteine were added. The reaction mixture was stirred at RT for 20 h, then concentrated under reduced pressure and then purified by preparative HPLC.

LC-MS (Method 1): $R_t$=0.85 min; MS (ESIpos): m/z=843 (M+H)$^+$.

Example 61

S-{1-[2-({(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]-2,5-dioxopyrrolidin-3-yl}-L-cysteine

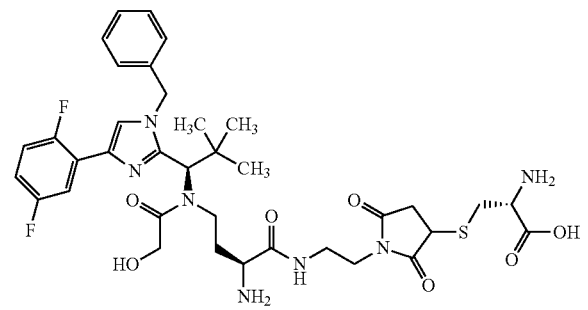 [SMILES: CC(C)(C)[C@H](c1nc(-c2cc(F)ccc2F)cn1Cc1ccccc1)N(CC[C@H](N)C(=O)NCCN1C(=O)CC(SC[C@H](N)C(=O)O)C1=O)C(=O)CO]

7 mg (9 µmol) of Intermediate F2 were taken up in 1.75 ml of DMF, and 2.3 mg (19 µmol) of L-cysteine were added. The reaction mixture was stirred at RT for 20 h, then concentrated under reduced pressure and then purified by preparative HPLC.

LC-MS (Method 1): $R_t$=0.84 min; MS (ESIpos): m/z=758 (M+H)$^+$.

Example 62

S-(1-{2-[2-({(2S)-2-Amino-4-[{(1R)-1-[1-benzyl-4-(2,5-difluorophenyl)-1H-imidazol-2-yl]-2,2-dimethylpropyl}(propionyl)amino]butanoyl}amino)ethoxy]ethyl}-2,5-dioxopyrrolidin-3-yl)-L-cysteine

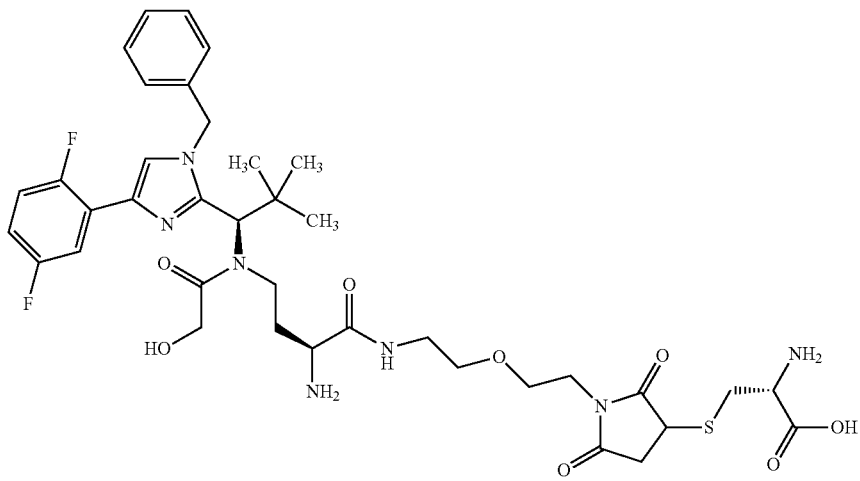 [SMILES: CC(C)(C)[C@H](c1nc(-c2cc(F)ccc2F)cn1Cc1ccccc1)N(CC[C@H](N)C(=O)NCCOCCN1C(=O)CC(SC[C@H](N)C(=O)O)C1=O)C(=O)CO]

2.9 mg (3.6 µmol) of Intermediate F5 were taken up in 1 ml of DMF, and 0.9 mg (7.3 µmol) of L-cysteine was added. The reaction mixture was stirred at RT for 3d, and the same amount of cysteine was then added. After stirring at RT for a further 24 h, the mixture was concentrated under reduced pressure and the product was purified by preparative HPLC.

LC-MS (Method 1): $R_t$=0.84 min; MS (ESIpos): m/z=802 (M+H)$^+$.

Example 63

N-[6-(3-{[(2R)-2-Amino-2-carboxyethyl]sulfanyl}-2,5-dioxopyrrolidin-1-yl)hexanoyl]-L-valyl-L-alanyl-N$^6$-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-L-lysine trifluoroacetic acid (1:1)

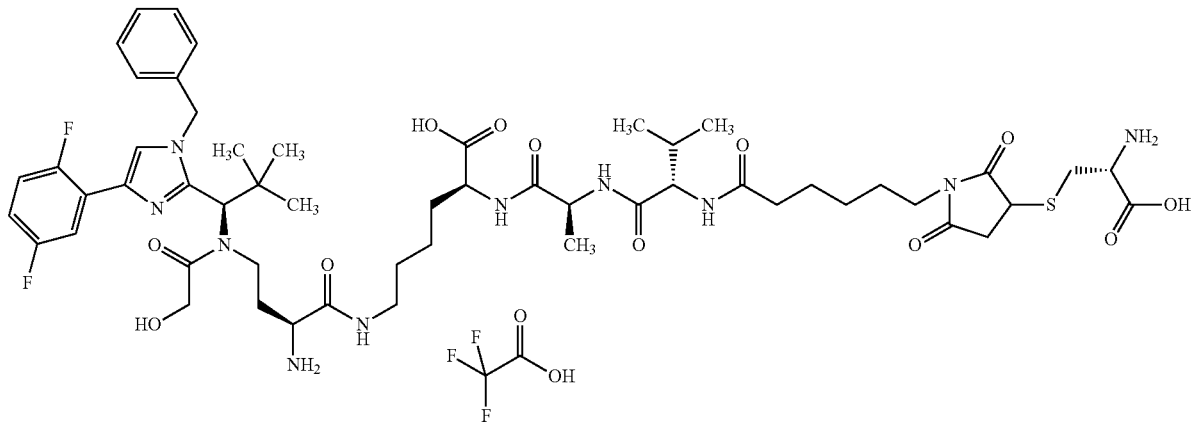 [SMILES: CC(C)[C@H](NC(=O)CCCCCN1C(=O)CC(SC[C@H](N)C(=O)O)C1=O)C(=O)N[C@@H](C)C(=O)N[C@@H](CCCCNC(=O)[C@@H](N)CCN(C(=O)CO)[C@@H](c1nc(-c2cc(F)ccc2F)cn1Cc1ccccc1)C(C)(C)C)C(=O)O ; O=C(O)C(F)(F)F]

3 mg (3 µmol) of Intermediate F5 were taken up in 2 ml of DMF, and 1 mg (8 µmol) of L-cysteine was added. The reaction mixture was stirred at RT for 10 min, 500 µl of water were added and the mixture was adjusted to pH 2 using TFA and then concentrated under reduced pressure and then purified by preparative HPLC.

LC-MS (Method 1): $R_t$=0.82 min; MS (ESIpos): m/z=1127 (M+H)$^+$.

Example 64

S-[1-(2-{[2-({(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]amino}-2-oxoethyl)-2,5-dioxopyrrolidin-3-yl]-L-cysteine trifluoroacetic acid (1:1)

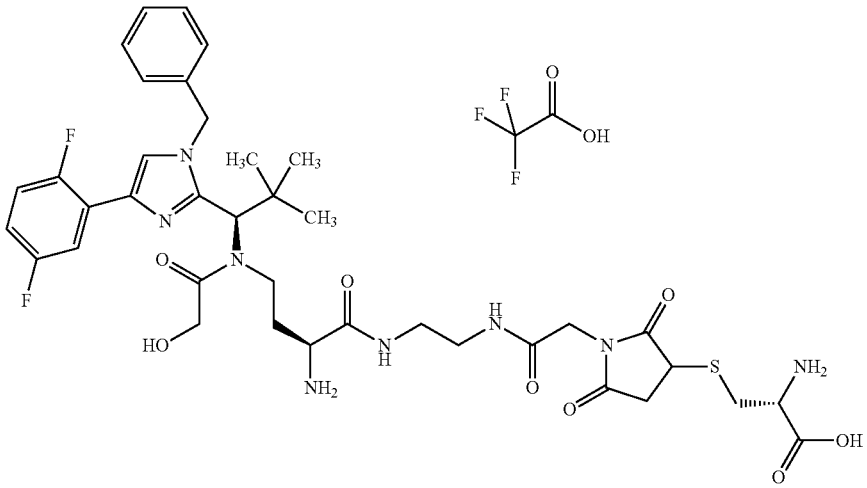 [SMILES: CC(C)(C)[C@H](c1nc(-c2cc(F)ccc2F)cn1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

5.6 mg (7 µmol) of Intermediate F7 were taken up in 1 ml of DMF, and 1.7 mg (14 µmol) of L-cysteine were added. The reaction mixture was stirred at RT for 20 h and then concentrated under reduced pressure, and the product was purified by preparative HPLC.

LC-MS (Method 1): $R_t$=0.81 min; MS (ESIpos): m/z=815 (M+H)$^+$.

Example 65

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N-(4-{[(3-{[(2R)-2-amino-2-carboxyethyl]sulphanyl}-2,5-dioxopyrrolidin-1-yl)acetyl]amino}phenyl)-N$^5$-carbamoyl-L-ornithinamide

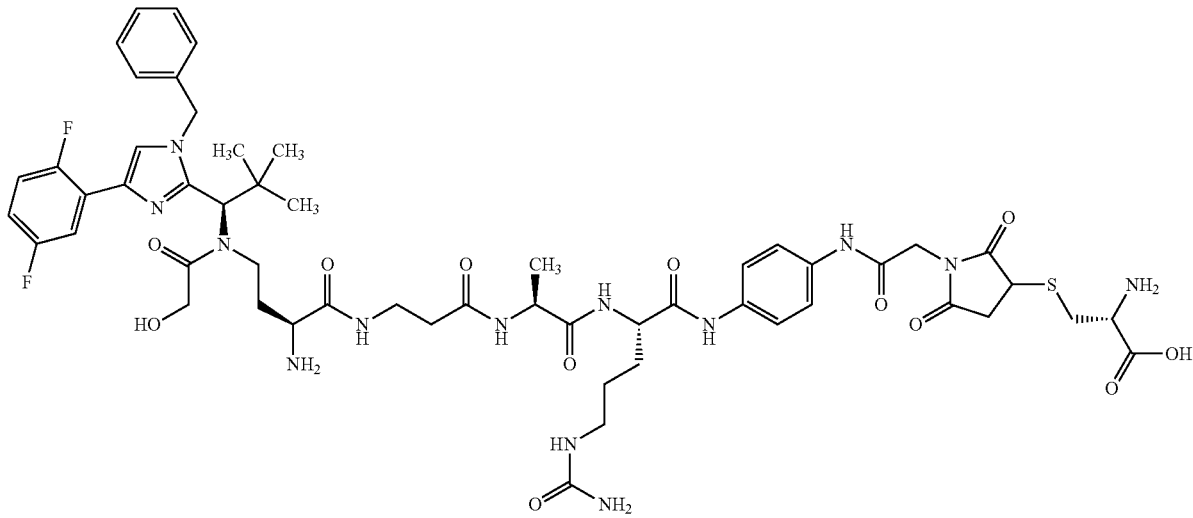 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(NC(=O)CN2C(=O)CC(SC[C@H](N)C(=O)O)C2=O)cc1]

3 mg (3 μmol) of Intermediate F25 were taken up in 2 ml of DMF and 200 μl of water, and 1 mg (8 μmol) of L-cysteine was added. The reaction mixture was stirred at RT for 4 h, 500 μl of water were added and the mixture was adjusted to pH 2 using TFA and then concentrated under reduced pressure and then purified by preparative HPLC.

LC-MS (Method 1): $R_t$=0.76 min; MS (ESIpos): m/z=1162 (M+H)$^+$.

Example 66

S-(1-{4-[(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)amino]phenyl}-2,5-dioxopyrrolidin-3-yl)-L-cysteine

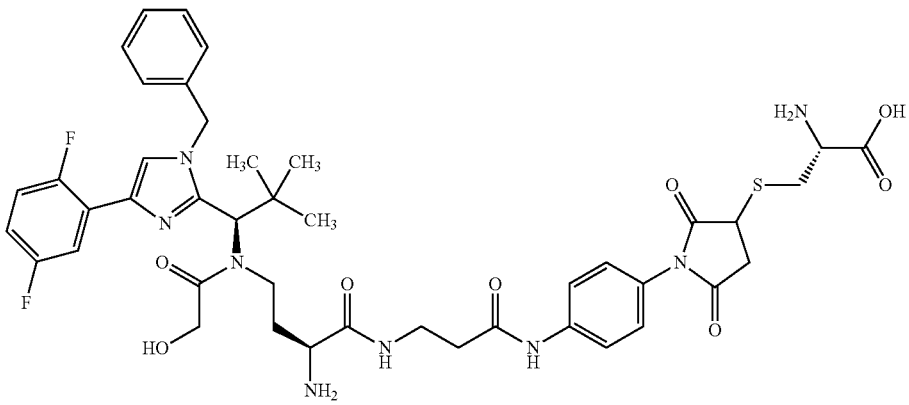 [SMILES: CC(C)(C)[C@H](c1nc(-c2cc(F)ccc2F)cn1Cc1ccccc1)N(CC[C@H](N)C(=O)NCCC(=O)Nc1ccc(N2C(=O)CC(SC[C@H](N)C(=O)O)C2=O)cc1)C(=O)CO]

3.5 mg (3.8 μmol) of Intermediate F10 were taken up in 1 ml of DMF, and 1.4 mg (11 μmol) of L-cysteine were added. The reaction mixture was stirred at RT for 23 h, and the same amount of cysteine was then added. After stirring at RT for a further 24 h, the mixture was concentrated under reduced pressure and the product was purified by preparative HPLC.

LC-MS (Method 1): $R_t$=0.82 min; MS (ESIpos): m/z=877 (M+H)$^+$.

Example 67

S-{1-[2-({[(1R,2S)-2-({(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine

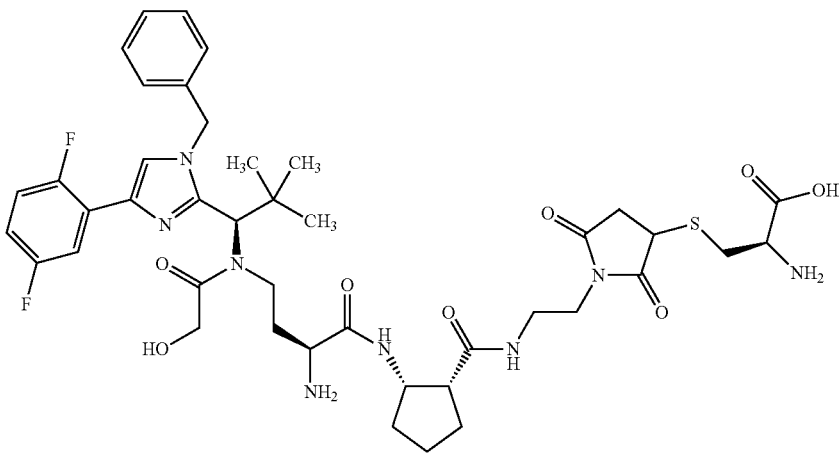 [SMILES: CC(C)(C)[C@H](c1nc(-c2cc(F)ccc2F)cn1Cc1ccccc1)N(CC[C@H](N)C(=O)N[C@H]1CCC[C@H]1C(=O)NCCN1C(=O)CC(SC[C@H](N)C(=O)O)C1=O)C(=O)CO]

3.3 mg (4 μmol) of Intermediate F12 were taken up in 1 ml of DMF, and 1.4 mg (11 μmol) of L-cysteine were added. The reaction mixture was stirred at RT for 3 h. 500 μl of water were then added, the mixture was concentrated under reduced pressure and the product was purified by preparative HPLC.

LC-MS (Method 1): $R_t$=0.82 min; MS (ESIpos): m/z=869 (M+H)$^+$.

Example 68

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N$^5$-carbamoyl-L-ornithinamide

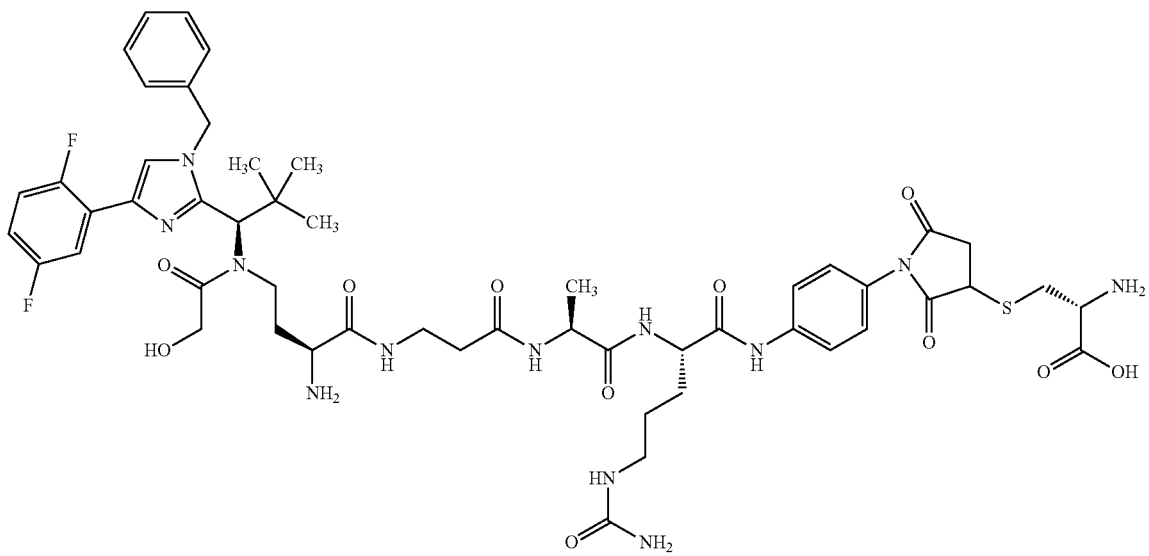 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(N2C(=O)CC(SC[C@H](N)C(=O)O)C2=O)cc1]

3 mg (3 μmol) of Intermediate F15 were taken up in 2 ml of DMF, and 1 mg (8 μmol) of L-cysteine was added. The reaction mixture was stirred at RT for 4 h. 500 μl of water were then added to the reaction, and the mixture was adjusted to pH 2 using TFA. The mixture was then concentrated under reduced pressure, and the product was purified by preparative HPLC.

LC-MS (Method 1): $R_t$=0.76 min; MS (ESIpos): m/z=1105 (M+H)$^+$.

Example 69

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N-[4-(2-{[2-(3-{[(2R)-2-amino-2-carboxyethyl]sulphanyl}-2,5-dioxopyrrolidin-1-yl)ethyl]amino}-2-oxoethyl)phenyl]-N$^5$-carbamoyl-L-ornithinamide

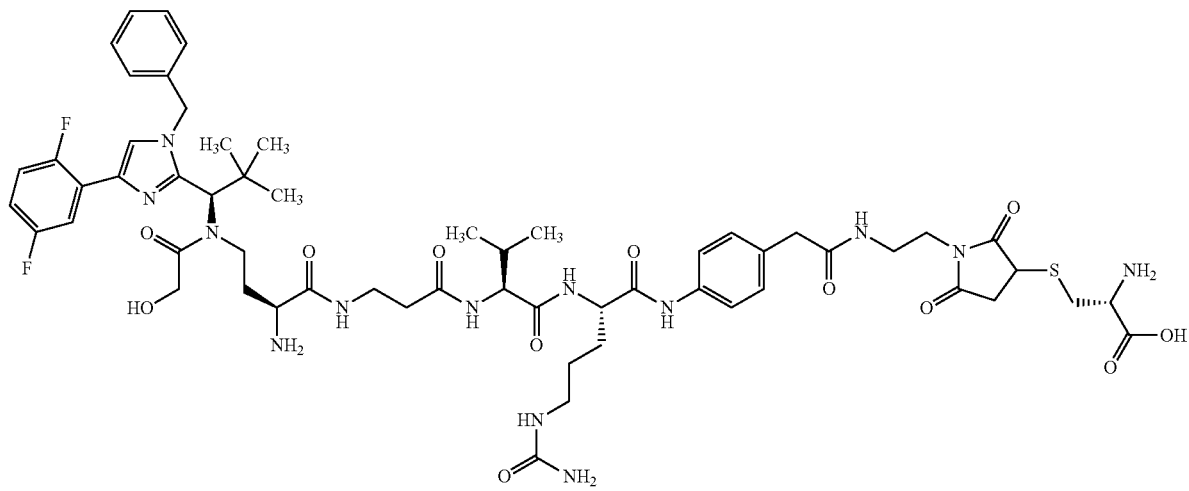 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)CC(SC[C@H](N)C(=O)O)C2=O)cc1]

3 mg (2 μmol) of Intermediate F16 were taken up in 2 ml of DMF, and 0.8 mg (7 μmol) of L-cysteine was added. The reaction mixture was stirred at RT for 4 h. 500 μl of water were then added to the reaction, and the mixture was adjusted to pH 2 using TFA. The mixture was then concentrated under reduced pressure, and the product was purified by preparative HPLC.

LC-MS (Method 1): $R_t$=0.82 min; MS (ESIpos): m/z=1218 (M+H)$^+$.

Example 70

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N-[4-(2-{[2-(3-{[(2R)-2-amino-2-carboxyethyl]sulphanyl}-2,5-dioxopyrrolidin-1-yl)ethyl]amino}-2-oxoethyl)phenyl]-N$^5$-carbamoyl-L-ornithinamide

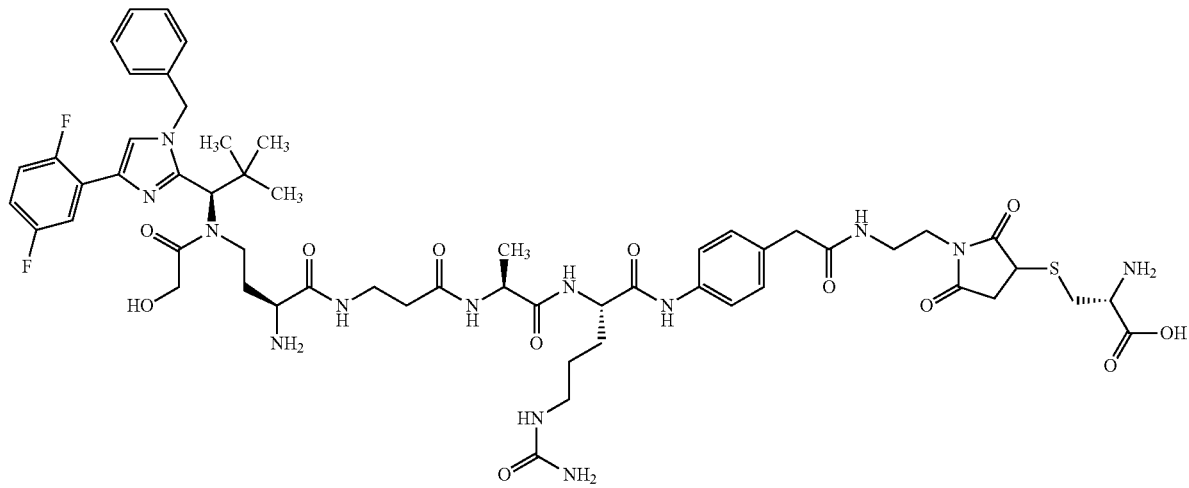 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)Nc1ccc(CC(=O)NCCN2C(=O)CC(SC[C@H](N)C(=O)O)C2=O)cc1]

3 mg (3 μmol) of Intermediate F24 were taken up in 2 ml of DMF and 200 μl of water, and 0.9 mg (8 μmol) of L-cysteine was added. The reaction mixture was stirred at RT for 4 h. 500 μl of water were then added to the reaction, and the mixture was adjusted to pH 2 using TFA. The mixture was then concentrated under reduced pressure, and the product was purified by preparative HPLC.

LC-MS (Method 1): $R_t$=0.77 min; MS (ESIpos): m/z=1190 (M+H)$^+$.

Example 71

(15S,19R)-15-Amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oic acid/trifluoroacetic acid (1:1)

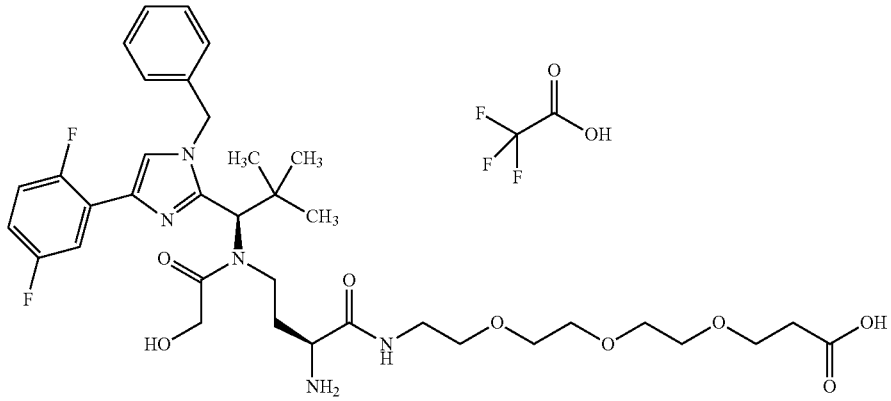 [SMILES: CC(C)(C)[C@H](c1nc(-c2cc(F)ccc2F)cn1Cc1ccccc1)N(CC[C@H](N)C(=O)NCCOCCOCCOCCC(=O)O)C(=O)CO ; O=C(O)C(F)(F)F]

In the first step, 70 mg (0.114 mmol) of Intermediate C5 were coupled with 32 mg (0.114 mmol) of tert-butyl 3-{2-[2-(2-aminoethoxy)ethoxy]ethoxy}propanoate in 15 ml of DMF in the presence of 44 mg (0.228 mmol) of 1-(3-dimethylaminopropyl)-3-ethylcarbodiimide hydrochloride, 35 mg (0.228 mmol) of 1-hydroxy-1H-benzotriazole hydrate and 60 μl of N,N-diisopropylethylamine. The reaction was stirred at RT overnight and the product was purified by preparative HPLC. This gave 33 mg (33% of theory) of the protected intermediate. This was stirred with 1.1 ml of trifluoroacetic acid in 11 ml of dichloromethane for 1 h giving, after work-up, 26 mg (98%) of the title compound.

LC-MS (Method 1): $R_t$=0.91 min; MS (ESIpos): m/z=718 (M+H)$^+$.

Example 72

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-$N^5$-carbamoyl-L-ornithine/trifluoroacetic acid (1:1)

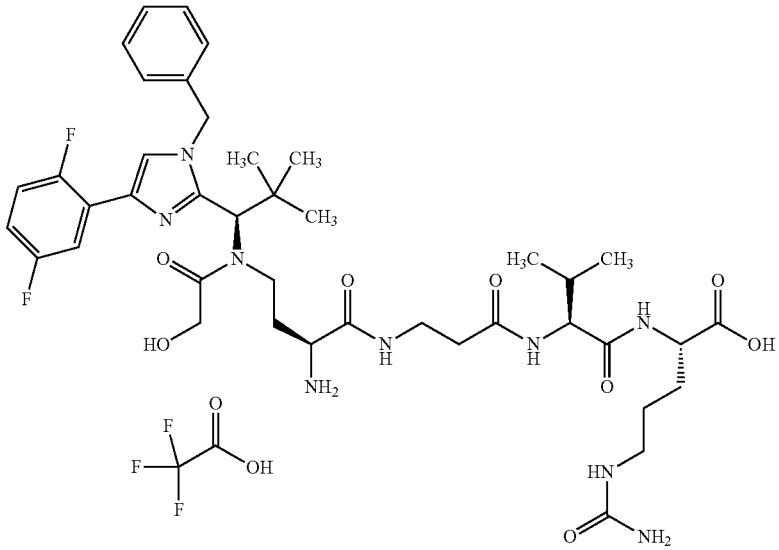 [SMILES: CC(C)[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)O ; O=C(O)C(F)(F)F]

The title compound was prepared from Intermediate C3 using classical methods of peptide chemistry.

LC-MS (Method 1): $R_t$=0.87 min; MS (ESIpos): m/z=842 (M+H)$^+$.

Example 73

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-$N^5$-carbamoyl-L-ornithine/trifluoroacetic acid (1:1)

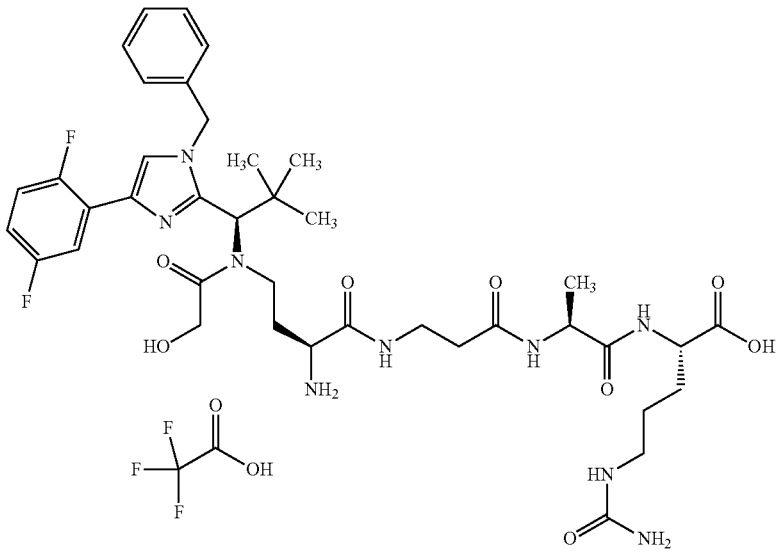 [SMILES: C[C@H](NC(=O)CCNC(=O)[C@@H](N)CCN(C(=O)CO)[C@@H](c1nc(-c2cc(F)ccc2F)cn1Cc1ccccc1)C(C)(C)C)C(=O)N[C@@H](CCCNC(N)=O)C(=O)O ; O=C(O)C(F)(F)F]

The title compound was prepared analogously to Example 72 from Intermediate C3 using classical methods of peptide chemistry.

LC-MS (Method 1): $R_t$=0.82 min; MS (ESIpos): m/z=814 (M+H)$^+$.

Example 74

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-amino-L-phenylalanine/trifluoroacetic acid (1:2)

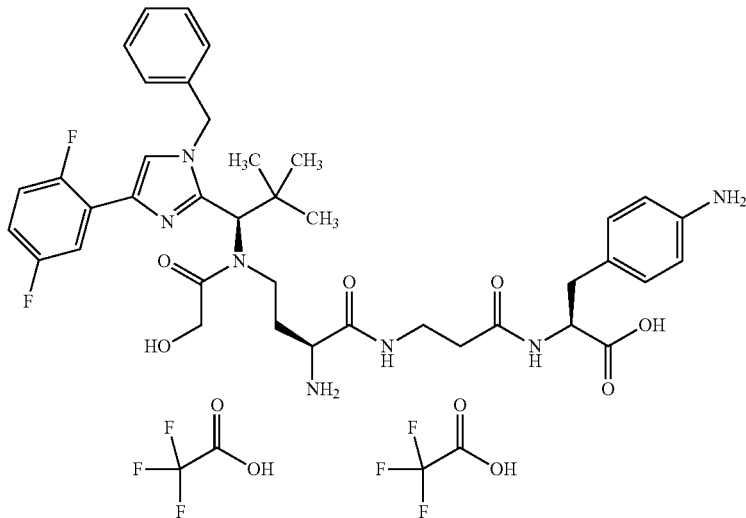

The title compound was synthesized from Intermediate C8 and trifluoroacetic acid/methyl 4-amino-L-phenylalaninate (1:1) which was prepared using classical methods of peptide chemistry from commercially available N-(tert-butoxycarbonyl)-4-nitro-L-phenylalanine.

LC-MS (Method 1): $R_t$=0.82 min; MS (ESIpos): m/z=748 (M+H)$^+$.

Example 75

Trifluoroacetic acid/N-{(1R)-1-[1-(3-aminobenzyl)-4-(2,5-difluorophenyl)-1H-imidazol-2-yl]-2,2-dimethylpropyl}-N-(3-aminopropyl)-2-hydroxyacetamide (1:1)

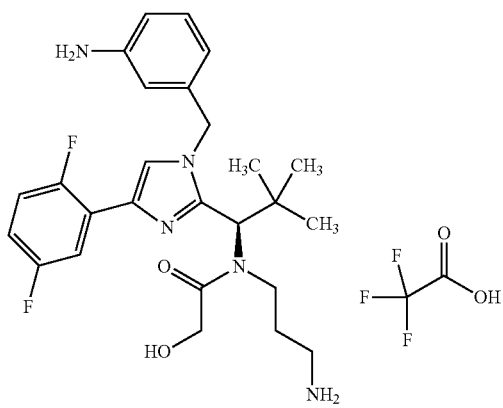 [SMILES: CC(C)(C)[C@H](c1nc(-c2cc(F)ccc2F)cn1Cc1cccc(N)c1)N(CCCN)C(=O)CO ; O=C(O)C(F)(F)F]

The title compound was prepared from Intermediate C10 by deprotection with trifluoroacetic acid.

LC-MS (Method 1): $R_t$=0.81 min; MS (ESIpos): m/z=486 (M+H)$^+$.

Example 76

(2S)-2-Amino-4-[{(1R)-1-[1-benzyl-4-(2,5-difluorophenyl)-1H-imidazol-2-yl]-2,2-dimethylpropyl}(glycoloyl)amino]butanoic acid/trifluoroacetic acid (1:1)

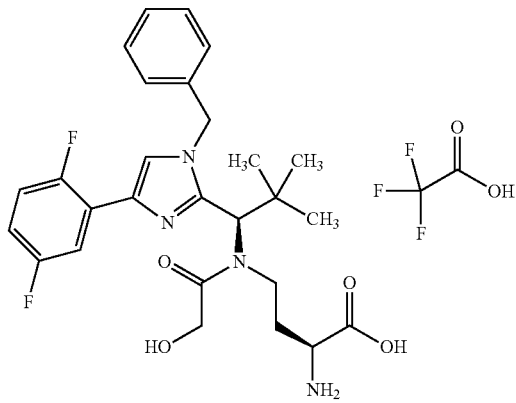 [SMILES: CC(C)(C)[C@H](c1nc(-c2cc(F)ccc2F)cn1Cc1ccccc1)N(CC[C@H](N)C(=O)O)C(=O)CO ; O=C(O)C(F)(F)F]

The title compound was prepared from Intermediate C5 by deprotection with trifluoroacetic acid.

LC-MS (Method 1): $R_t$=0.93 min; MS (ESIpos): m/z=515 (M+H)$^+$.

Example 77

Trifluoroacetic acid/N-[(3S)-3-amino-4-hydrazino-4-oxobutyl]-N-{(1R)-1-[1-benzyl-4-(2,5-difluorophenyl)-1H-imidazol-2-yl]-2,2-dimethylpropyl}-2-hydroxyacetamide (1:1)

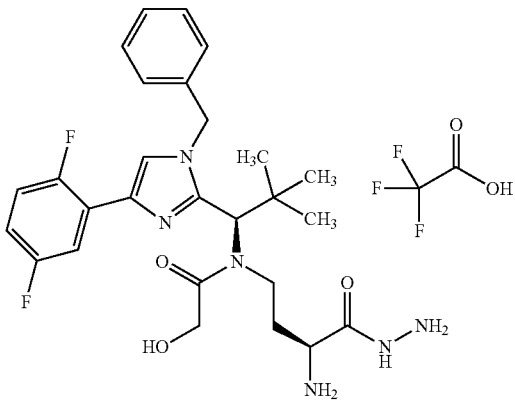 [SMILES: CC(C)(C)[C@H](c1nc(-c2cc(F)ccc2F)cn1Cc1ccccc1)N(CC[C@H](N)C(=O)NN)C(=O)CO ; O=C(O)C(F)(F)F]

The title compound was prepared from Intermediate C6 by deprotection with trifluoroacetic acid.
LC-MS (Method 1): $R_t$=0.88 min; MS (ESIpos): m/z=529 (M+H)$^+$.

Example 78

Trifluoroacetic acid/N-{(1R)-1-[1-benzyl-4-(2,5-difluorophenyl)-1H-imidazol-2-yl]-2,2-dimethylpropyl}-N-[(3S)-3,4-diaminobutyl]-2-hydroxyacetamide (1:1)

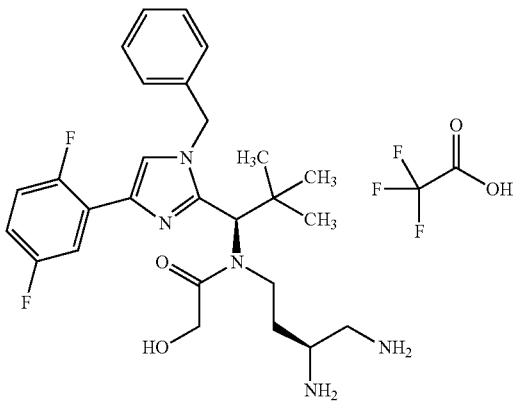 [SMILES: CC(C)(C)[C@H](c1nc(-c2cc(F)ccc2F)cn1Cc1ccccc1)N(CC[C@H](N)CN)C(=O)CO ; O=C(O)C(F)(F)F]

In the first step, Intermediate C1 was reacted with benzyl tert-butyl-[(2S)-4-oxobutan-1,2-diyl]biscarbamate analogously to Intermediate C2. The aldehyde employed was prepared from commercially available (3S)-3-{[(benzyloxy)carbonyl]amino}-4-[(tert-butoxycarbonyl)amino]butanoic acid by reduction and subsequent oxidation analogously to Intermediate C2.

In the second step, N-acylation was carried out analogously to Intermediate C3, finally followed by complete deprotection initially with 33% strength hydrobromic acid in glacial acetic acid and then with lithium hydroxide.
LC-MS (Method 1): $R_t$=0.78 min; MS (ESIpos): m/z=500 (M+H)$^+$.

Example 79

N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanine

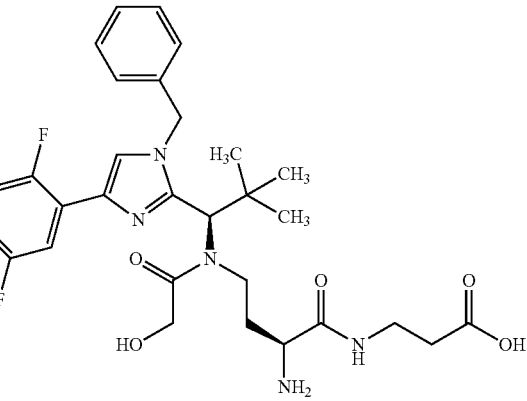

The title compound was prepared from Intermediate C8 by deprotection with trifluoroacetic acid.
LC-MS (Method 1): $R_t$=0.84 min; MS (ESIpos): m/z=586 (M+H)$^+$.

Example 80

Trifluoroacetic acid/(2S)-2-amino-N-(2-aminoethyl)-4-[{(1R)-1-[1-benzyl-4-(2,5-difluorophenyl)-1H-imidazol-2-yl]-2,2-dimethylpropyl}(glycoloyl)amino]butanamide (2:1)

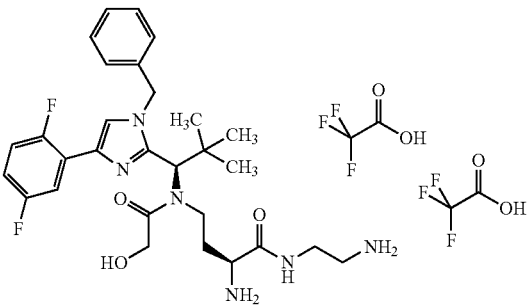 [SMILES: CC(C)(C)[C@H](c1nc(-c2cc(F)ccc2F)cn1Cc1ccccc1)N(CC[C@H](N)C(=O)NCCN)C(=O)CO ; O=C(O)C(F)(F)F ; O=C(O)C(F)(F)F]

The title compound was prepared from Intermediate C5 using classical methods of peptide chemistry.
LC-MS (Method 1): $R_t$=0.72 min; MS (ESIpos): m/z=557 (M+H)$^+$.

Example 81

(1-{(2S)-2-Amino-4-[{(1R)-1-[1-benzyl-4-(2,5-difluorphenyl)-1H-imidazol-2-yl]-2,2-dimethylpropyl}(glycoloyl)amino]butanoyl}hydrazino)acetic acid/trifluoroacetic acid (1:2)

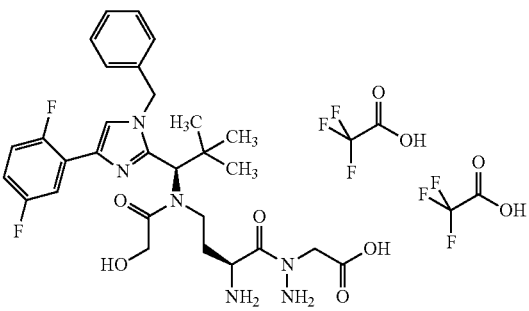 [SMILES: CC(C)(C)[C@H](c1nc(-c2cc(F)ccc2F)cn1Cc1ccccc1)N(CC[C@H](N)C(=O)N(N)CC(=O)O)C(=O)CO ; O=C(O)C(F)(F)F ; O=C(O)C(F)(F)F]

The title compound was prepared from Intermediate C7 by deprotection with trifluoroacetic acid.
LC-MS (Method 1): $R_t$=0.89 min; MS (ESIpos): m/z=587 (M+H)$^+$.

Example 82A

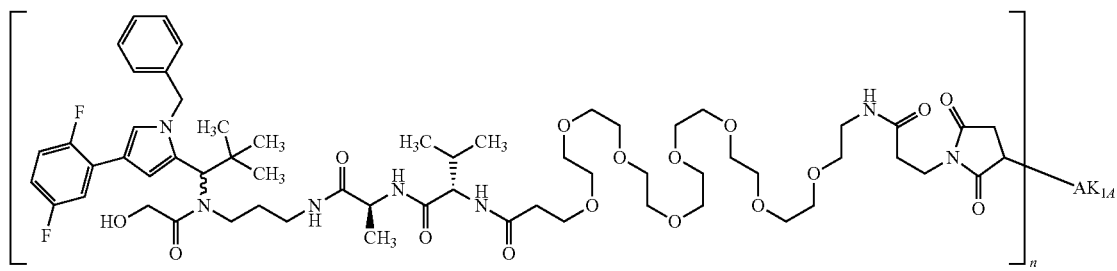

Here, 5.0 mg of cetuximab in PBS (c=5.90 mg/ml) were used for coupling with Intermediate F82, and the reaction was, after Sephadex purification, concentrated by ultracentrifugation and rediluted with PBS. Some of the ADC may also be present in the form of the hydrolysed open-chain succinamides attached to the antibody.
Protein concentration: 1.59 mg/ml
Drug/mAb ratio: 2.3

Example 82B

Here, 5.0 mg of anti-TWEAKR AK-1 antibody in PBS (c=10.10 mg/ml) were used for coupling with Intermediate F82, and the reaction was, after Sephadex purification, concentrated by ultracentrifugation and rediluted. Some of the ADC may also be present in the form of the hydrolysed open-chain succinamides attached to the antibody.
Protein concentration: 1.59 mg/ml
Drug/mAb ratio: 1.8

Example 82E

Here, 5.0 mg of trastuzumab antibody in PBS (c=11.50 mg/ml) were used for coupling with Intermediate F82, and the reaction was, after Sephadex purification, concentrated by ultracentrifugation and rediluted. Some of the ADC may also be present in the form of the hydrolysed open-chain succinamides attached to the antibody.
Protein concentration: 2.15 mg/ml
Drug/mAb ratio: 2.7

Example 83A also be present in the form of the hydrolysed open-chain succinamides attached to the antibody.
Protein concentration: 1.77 mg/ml
Drug/mAb ratio: 2.0

Example 83B

Here, 5.0 mg of anti-TWEAKR AK-1 antibody in PBS (c=12.87 mg/ml) were used for coupling with Intermediate F83, and the reaction was, after Sephadex purification, concentrated by ultracentrifugation and rediluted. Some of the ADC may also be present in the form of the hydrolysed open-chain succinamides attached to the antibody.
Protein concentration: 1.29 mg/ml
Drug/mAb ratio: 1.3

Example 83E

Here, 5.0 mg of trastuzumab antibody in PBS (c=13.50 mg/ml) were used for coupling with Intermediate F83, and the reaction was, after Sephadex purification, concentrated by ultracentrifugation and rediluted. Some of the ADC may also be present in the form of the hydrolysed open-chain succinamides attached to the antibody.
Protein concentration: 1.91 mg/ml
Drug/mAb ratio: 2.1

Example 83H

Here, 5.0 mg of panitumumab in PBS (c=10 mg/ml) were used for coupling with Intermediate F83. The time for the reduction with TCEP was increased to 4 h and stirring time for the ADC coupling was increased to 20 h. The reaction was then, after Sephadex purification, concentrated by ultra-

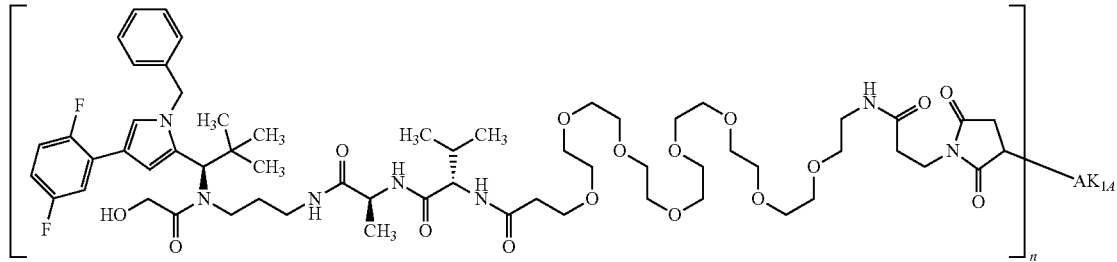

Here, 5.0 mg of cetuximab in PBS (c=5.90 mg/ml) were used for coupling with Intermediate F83, and the reaction was, after Sephadex purification, concentrated by ultracentrifugation and rediluted with PBS. Some of the ADC may centrifugation and rediluted with PBS. Some of the ADC may also be present in the form of the hydrolysed open-chain succinamides attached to the antibody.
Protein concentration: 1.57 mg/ml
Drug/mAb ratio: 0.9

Example 84A

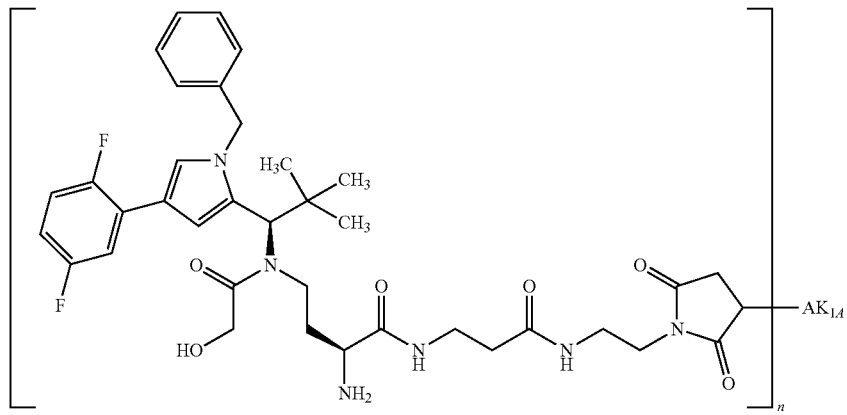

Here, 5 mg of cetuximab in PBS (c=11.02 mg/ml) were used for coupling with Intermediate F84, and the reaction was, after Sephadex purification, concentrated by ultracentrifugation and rediluted with PBS. Some of the ADC may also be present in the form of the hydrolysed open-chain succinamides attached to the antibody.
Protein concentration: 1.94 mg/ml
Drug/mAb ratio: 2.9

Example 84B

Here, 5 mg of anti-TWEAKR AK-1 in PBS (c=12.9 mg/ml) were used for coupling with Intermediate F84, and the reaction was, after Sephadex purification, concentrated by ultracentrifugation and rediluted with PBS. Some of the ADC may also be present in the form of the hydrolysed open-chain succinamides attached to the antibody.
Protein concentration: 1.77 mg/ml
Drug/mAb ratio: 3.0

Example 85A

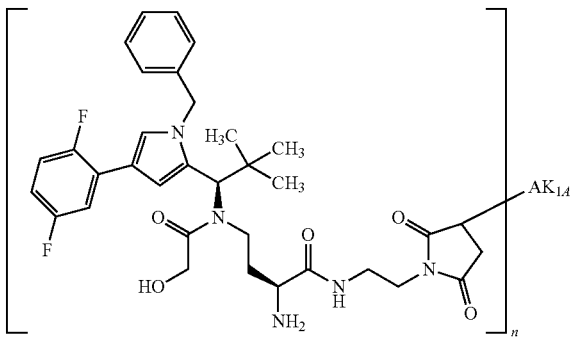

Here, 5 mg of cetuximab in PBS (c=11.02 mg/ml) were used for coupling with Intermediate F85, and the reaction was, after Sephadex purification, concentrated by ultracentrifugation and rediluted with PBS. Some of the ADC may also be present in the form of the hydrolysed open-chain succinamides attached to the antibody.
Protein concentration: 2.13 mg/ml
Drug/mAb ratio: 3.4

Example 85B

Here, 5 mg of anti-TWEAKR AK-1 in PBS (c=12.9 mg/ml) were used for coupling with Intermediate F85, and the reaction was, after Sephadex purification, concentrated by ultracentrifugation and rediluted with PBS. Some of the ADC may also be present in the form of the hydrolysed open-chain succinamides attached to the antibody.
Protein concentration: 1.63 mg/ml
Drug/mAb ratio: 3.2

Example 86A

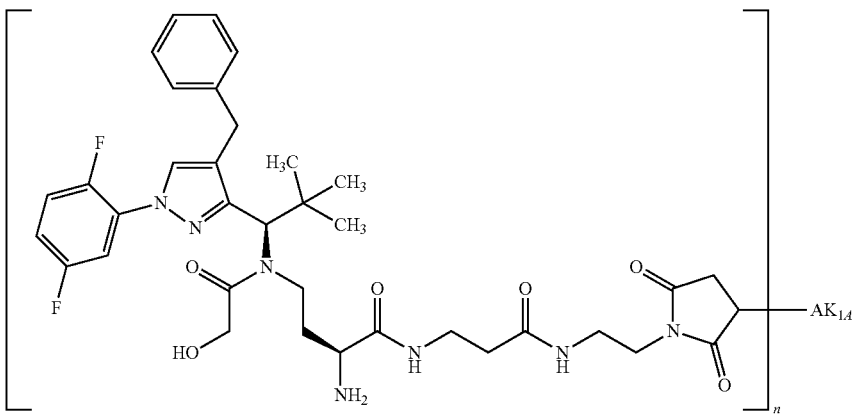

Here, 5 mg of cetuximab in PBS (c=11.59 mg/ml) were used for coupling with Intermediate F86, and the reaction was, after Sephadex purification, concentrated by ultracentrifugation and rediluted with PBS. Some of the ADC may also be present in the form of the hydrolysed open-chain succinamides attached to the antibody.

Protein concentration: 1.96 mg/ml
Drug/mAb ratio: 3.2

Example 86B

Here, 5 mg of anti-TWEAKR AK-1 in PBS (c=12.9 mg/ml) were used for coupling with Intermediate F86, and the reaction was, after Sephadex purification, concentrated by ultracentrifugation and rediluted with PBS. Some of the ADC may also be present in the form of the hydrolysed open-chain succinamides attached to the antibody.

Protein concentration: 2.55 mg/ml
Drug/mAb ratio: 2.8

Example 87A

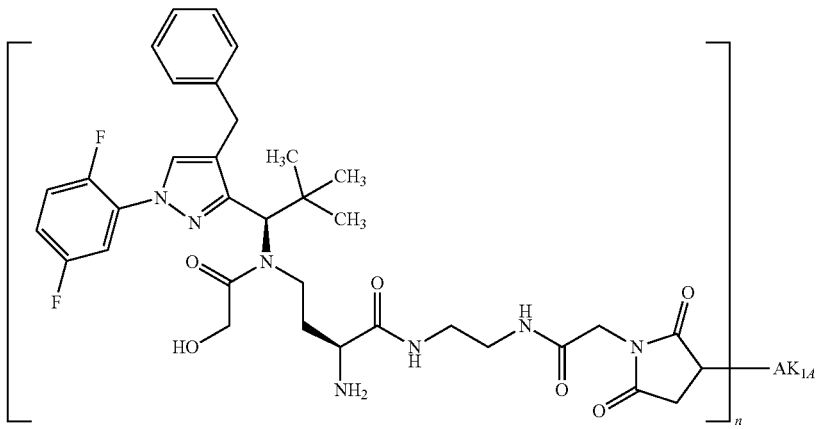

Here, 5 mg of cetuximab in PBS (c=8.95 mg/ml) were used for coupling with Intermediate F87, and the reaction was, after Sephadex purification, concentrated by ultracentrifugation and rediluted with PBS. Some of the ADC may also be present in the form of the hydrolysed open-chain succinamides attached to the antibody.

Protein concentration: 2.08 mg/ml
Drug/mAb ratio: 3.5

Example 87B

Here, 5 mg of anti-TWEAKR AK-1 in PBS (c=12.9 mg/ml) were used for coupling with Intermediate F87, and the reaction was, after Sephadex purification, concentrated by ultracentrifugation and rediluted with PBS. Some of the ADC may also be present in the form of the hydrolysed open-chain succinamides attached to the antibody.

Protein concentration: 1.93 mg/ml
Drug/mAb ratio: 2.2

Example 88A

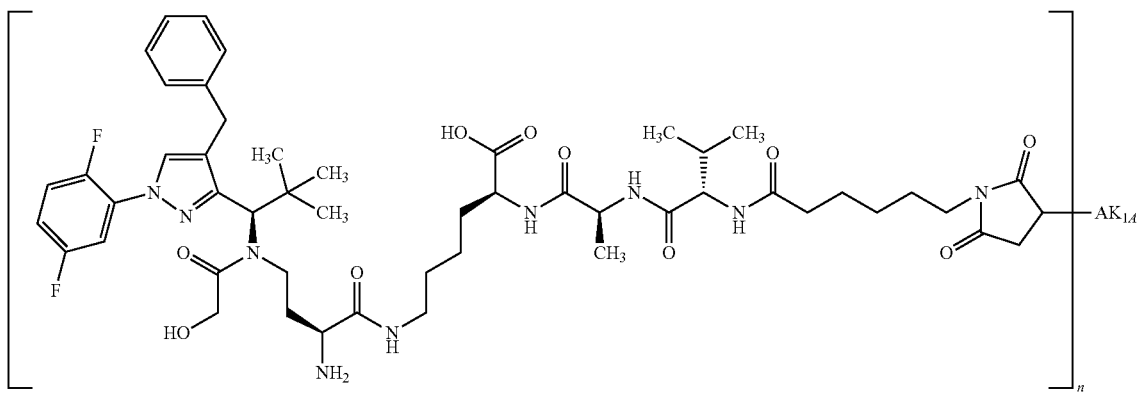

Here, 5 mg of cetuximab in PBS (c=11.02 mg/ml) were used for coupling with Intermediate F88, and the reaction was, after Sephadex purification, concentrated by ultracentrifugation and rediluted with PBS.
Protein concentration: 2.03 mg/ml
Drug/mAb ratio: 3.1

Example 88B

Here, 5 mg of anti-TWEAKR AK-1 in PBS (c=12.9 mg/ml) were used for coupling with Intermediate F88, and the reaction was, after Sephadex purification, concentrated by ultracentrifugation and rediluted with PBS.
Protein concentration: 1.9 mg/ml
Drug/mAb ratio: 3.3

Example 89A

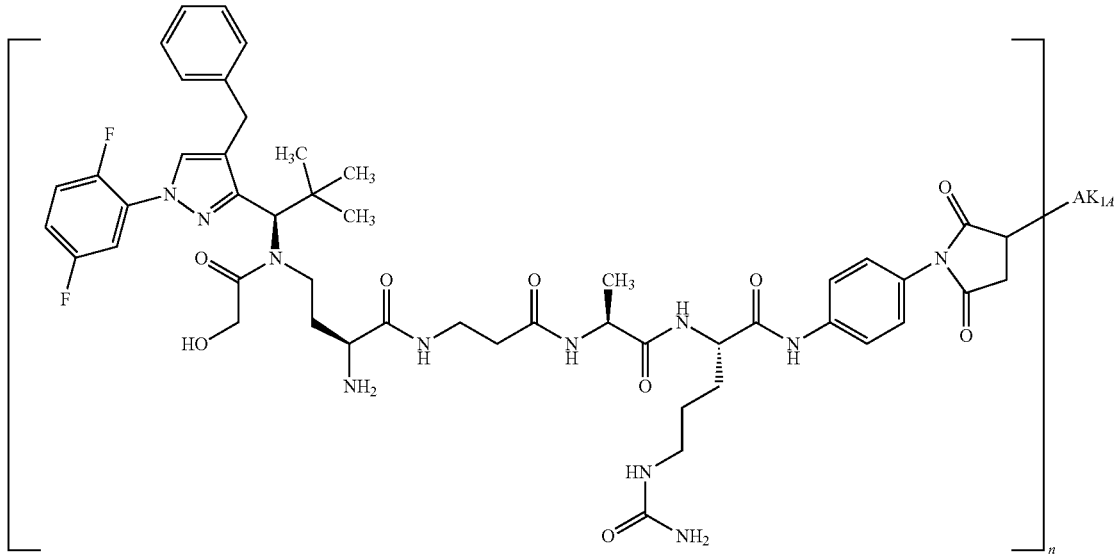

Here, 5 mg of cetuximab in PBS (c=11.02 mg/ml) were used for coupling with Intermediate F89, and the reaction was, after Sephadex purification, concentrated by ultracentrifugation and rediluted with PBS. Some of the ADC may also be present in the form of the hydrolysed open-chain succinamides attached to the antibody.
Protein concentration: 2.2 mg/ml
Drug/mAb ratio: 3.3

Example 89B

Here, 5 mg of anti-TWEAKR AK-1 in PBS (c=12.9 mg/ml) were used for coupling with Intermediate F89, and the reaction was, after Sephadex purification, concentrated by ultracentrifugation and rediluted with PBS. Some of the ADC may also be present in the form of the hydrolysed open-chain succinamides attached to the antibody.

Protein concentration: 2.03 mg/ml
Drug/mAb ratio: 3.4

Example 90A

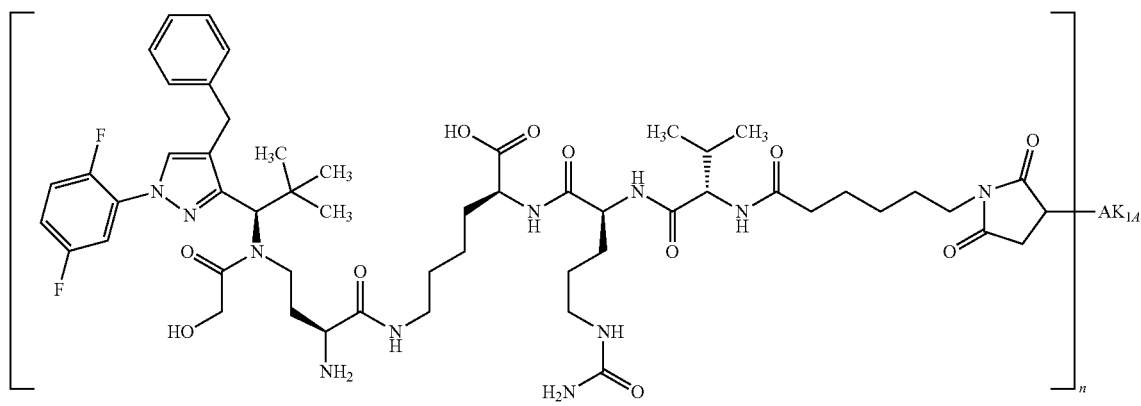

Here, 5 mg of cetuximab in PBS (c=13.33 mg/ml) were used for coupling with Intermediate F90, and the reaction was, after Sephadex purification, concentrated by ultracentrifugation and rediluted with PBS.

Protein concentration: 2.19 mg/ml
Drug/mAb ratio: 3.0

Example 90B

Here, 5 mg of anti-TWEAKR AK-1 in PBS (c=12.9 mg/ml) were used for coupling with Intermediate F90, and the reaction was, after Sephadex purification, concentrated by ultracentrifugation and rediluted with PBS.

Protein concentration: 1.97 mg/ml
Drug/mAb ratio: 2.9

Example 91A

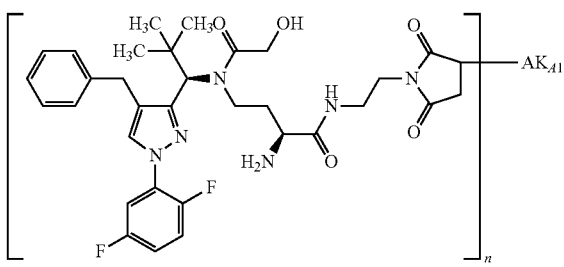

Here, 80 mg of cetuximab in PBS (c=5.9 mg/ml) were used for coupling with Intermediate F91, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 12.75 mg/ml
Drug/mAb ratio: 3.7

Example 91B

Here, 5 mg of anti-TWEAKR AK-1 in PBS (c=12.9 mg/ml) were used for coupling with Intermediate F91, and the reaction was, after Sephadex purification, concentrated by ultracentrifugation and rediluted with PBS. Some of the ADC may also be present in the form of the hydrolysed open-chain succinamides attached to the antibody.

Protein concentration: 5.71 mg/ml
Drug/mAb ratio: 4.0

Example 92

S-(1-{2-[N-{(2S)-2-Amino-4-[{(1R)-1-[4-benzyl-1-(2,5-difluorophenyl)-1H-pyrazol-3-yl]-2,2-dimethyl-propyl}(glycoloyl)amino]butanoyl}-beta-alanyl)amino]ethyl}-2,5-dioxopyrrolidin-3-yl)-L-cysteine trifluoroacetic acid (1:1)

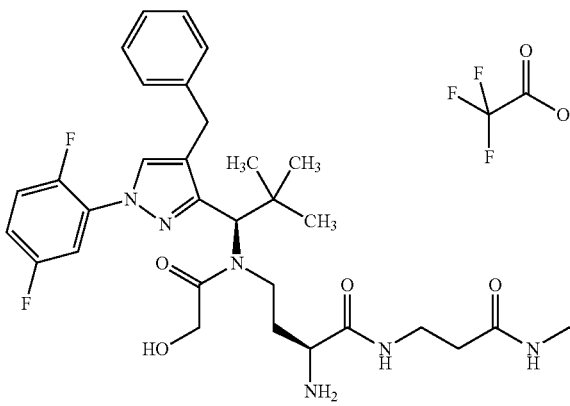
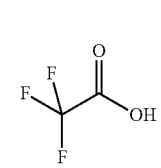

3 mg (4 µmol) of Intermediate F86 were taken up in 3 ml of DCM/water 10:1, and 1.3 mg (11 µmol) of L-cysteine were added. The reaction mixture was stirred at RT for 10 min, then concentrated under reduced pressure and then purified by preparative HPLC.

LC-MS (Method 1): $R_t$=0.77 min; MS (EIpos): m/z=829 [M+H]$^+$.

Example 93

N-[3-Amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 1)

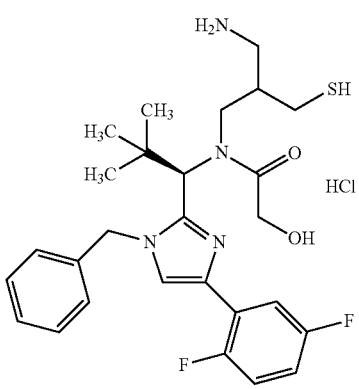 [SMILES: CC(C)(C)[C@H](c1nc(-c2cc(F)ccc2F)cn1Cc1ccccc1)N(CC(CN)CS)C(=O)CO ; Cl]

The compound was obtained according to Intermediate C32 (Isomer 1).

Example 94

Intermediate C33 (Isomer 2) N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1) (Isomer 2)

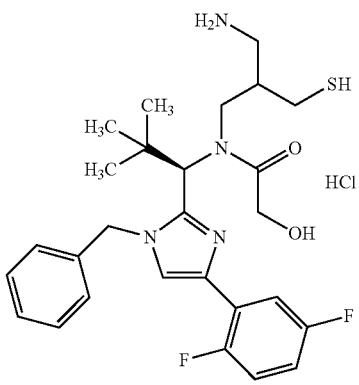 [SMILES: CC(C)(C)[C@H](c1nc(-c2cc(F)ccc2F)cn1Cc1ccccc1)N(CC(CN)CS)C(=O)CO ; Cl]

The compound was obtained according to Intermediate C33 (Isomer 2).

Example 95

Trifluoroacetic acid/4-amino-N-(3-aminopropyl)-N-{(1R)-1-[1-benzyl-4-(2,5-difluorophenyl)-1H-imidazol-2-yl]-2,2-dimethylpropyl}benzamide (2:1)

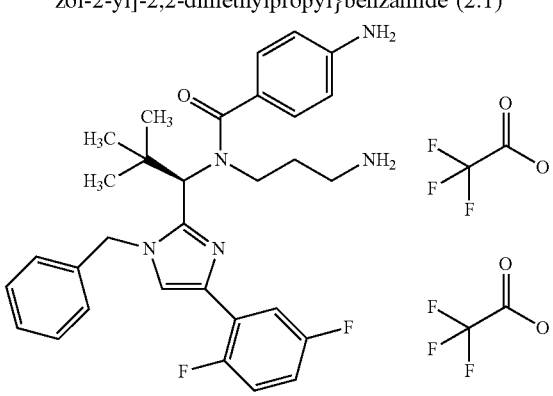

The title compound was obtained from tert-butyl {3-[(4-aminobenzoyl){(1R)-1-[1-benzyl-4-(2,5-difluorophenyl)-1H-imidazol-2-yl]-2,2-dimethylpropyl}amino]propyl}carbamate by deprotection with trifluoroacetic acid.

LC-MS (Method 1): $R_t$=0.93 min; MS (EIpos): m/z=532 [M+H]$^+$.

Example 96

N-(3-Aminopropyl)-N-{(1R)-1-[4-benzyl-1-(2,5-difluorophenyl)-1H-pyrazol-3-yl]-2,2-dimethylpropyl}-2-hydroxyacetamide

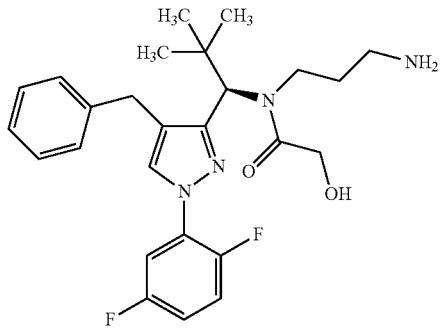 [SMILES: CC(C)(C)[C@H](c1nn(-c2cc(F)ccc2F)cc1Cc1ccccc1)N(CCCN)C(=O)CO]

101 mg (0.16 mmol) of 2-({(1R)-1-[4-benzyl-1-(2,5-difluorphenyl)-1H-pyrazol-3-yl]-2,2-dimethylpropyl}[3-(1,3-dioxo-1,3-dihydro-2H-isoindol-2-yl)propyl]amino)-2-oxoethyl acetate were initially charged in 2 ml of absolute ethanol, and 244 mg (3.14 mmol, 225 µl) of a 40% strength solution of methylamine in water were added. The mixture was stirred at 50° C. for 1 h, another 244 mg (3.14 mmol, 225 µl) of a 40% strength solution of methylamine in water were then added and after a total of 3.5 h the mixture was purified directly by preparative HPLC (mobile phase: ACN/water+1.0% NEt$_3$, gradient). This gave 52 mg (70% of theory) of the target compound.

LC-MS (Method 3): $R_t$=2.56 min; MS (EIpos): m/z=471 [M+H]$^+$.

Example 97

S-(2-{[2-({(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]amino}-2-oxoethyl)-L-cysteine/trifluoroacetic acid (1:1)

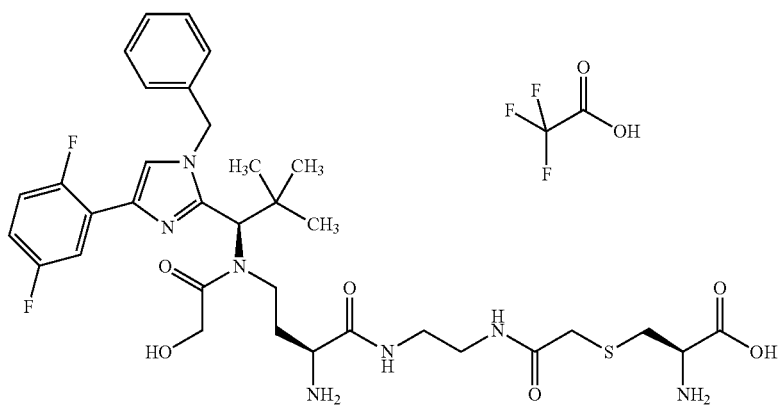 [SMILES: CC(C)(C)[C@H](c1nc(-c2cc(F)ccc2F)cn1Cc1ccccc1)N(CC[C@H](N)C(=O)NCCNC(=O)CSC[C@H](N)C(=O)O)C(=O)CO ; O=C(O)C(F)(F)F]

3 mg (4 µmol) of Intermediate F33 were taken up in 2 ml of DMF and 200 µl of water, and 1.4 mg (12 µmol) of L-cysteine was added. The reaction mixture was stirred at RT for 1 h. The reaction was then concentrated under reduced pressure, and the product was purified by preparative HPLC.

LC-MS (Method 1): $R_t$=0.81 min; MS (ESIpos): m/z=718 (M+H)$^+$.

Example 98

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

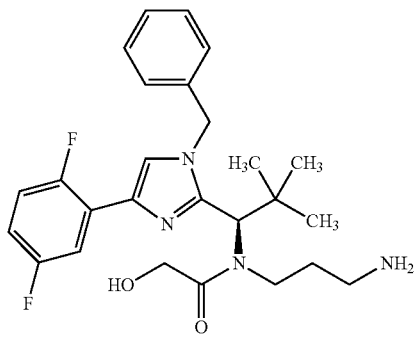

150.0 mg (0.42 mmol) of (1R)-1-[1-benzyl-4-(2,5-difluorophenyl)-1H-pyrrol-2-yl]-2,2-dimethylpropan-1-amine (Intermediate C52) were initially charged in 2.0 ml of dichloromethane, and 29.2 mg (0.49 mmol) of HOAc and 125.6 mg (0.59 mmol) of sodium triacetoxyborohydride were added and the mixture was stirred at RT for 5 min 98.9 mg (0.49 mmol) of 3-(1,3-dioxo-1,3-dihydro-2H-isoindol-2-yl)propanal were added. The reaction mixture was stirred at RT overnight. The reaction mixture was then diluted with ethyl acetate and the organic phase was washed twice with saturated sodium carbonate solution and once with saturated NaCl solution. After drying over magnesium sulphate, the solvent was evaporated under reduced pressure and the residue was purified using silica gel (mobile phase: dichloromethane/methanol 100:1). The solvents were evaporated under reduced pressure and the residue was dried under high vacuum. This gave 188.6 mg (74%) of the compound 2-[3-({(1R)-1-[1-benzyl-4-(2,5-difluorophenyl)-1H-pyrrol-2-yl]-2,2-dimethylpropyl}amino)propyl]-1H-isoindole-1,3 (2H)-dione.

LC-MS (Method 1): $R_t$=1.00 min; MS (ESIpos): m/z=541 [M+H]$^+$.

171.2 mg (0.32 mmol) of 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione were initially charged in 5.0 ml of dichloromethane, and 73.6 mg (0.73 mmol) of triethylamine were added. At 0° C., 94.9 mg (0.70 mmol) of acetoxyacetyl chloride were added, and the reaction mixture was stirred at RT overnight. The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified using Biotage Isolera (silica gel, column 10 g SNAP, flow rate 12 ml/min, ethyl acetate/cyclohexane 1:3). The solvents were evaporated under reduced pressure and the residue was dried under high vacuum. This gave 159.0 mg (77%) of the compound 2-(({1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate.

LC-MS (Method 1): $R_t$=1.35 min; MS (ESIpos): m/z=642 [M+H]$^+$.

147.2 mg (0.23 mmol) of 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate were initially charged in 4.0 ml of ethanol, and 356.2 mg (4.59 mmol) of methanamine (40% in water) were added. The reaction mixture was stirred at 50° C. overnight. The solvent was evaporated under reduced pressure and the residue was co-distilled with toluene three times. The residue was purified using silica gel (mobile phase: dichloromethane/methanol 10:1). The solvents were evaporated under reduced pressure and the residue was dried under high vacuum. This gave 67.4 mg (63%) of the title compound.

LC-MS (Method 1): $R_t$=0.91 min; MS (ESIpos): m/z=470 [M+H]$^+$.

Example 99

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1)

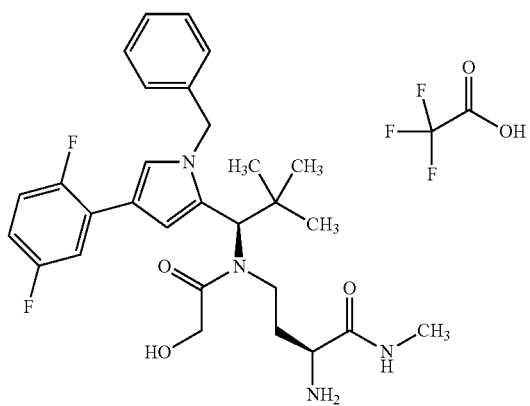 [SMILES: CNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

First, Intermediate C52 was reductively alkylated with benzyl (2S)-2-{[(benzyloxy)carbonyl]amino}-4-oxobutanoate analogously to C2. The secondary amino group was then acylated with 2-chloro-2-oxoethyl acetate as described in Intermediate C27. 190 mg (0.244 mmol) of this intermediate were taken up in 7.5 ml of ethanol, and 0.35 ml of a 40% strength solution of methanamine in water was added. The reaction was stirred at 50° C. for 3 h, and the same amount of methanamine was then added again. After a further 5 h of stirring at 50° C., the reaction was concentrated and the residue was purified by preparative HPLC. This gave 78 mg (48% of theory) of this title compound.

LC-MS (Method 1): $R_t$=1.32 min; MS (EIpos): m/z=661 [M+H]$^+$.

78 mg (0.118 mmol) of this intermediate were dissolved in 8 ml of ethanol and, after addition of 15 mg of 10% palladium on activated carbon, hydrogenated under standard hydrogen pressure at RT for 3 min. The catalyst was then filtered off, the solvent was removed under reduced pressure and the product was purified by preparative HPLC. After lyophilization from acetonitrile/water, 33 mg (44% of theory) of the title compound were obtained.

LC-MS (Method 1): $R_t$=0.88 min; MS (ESIpos): m/z=527 (M+H)$^+$.

$^1$H NMR (500 MHz, DMSO-$d_6$): δ=8.1 (m, 1H), 8.0 (m, 3H), 7.9 (m, 1H), 7.65 (m, 1H), 7.5 (s, 1H), 7.15-7.35 (m, 5H) 7.0 (m, 1H), 6.85 (m, 1H), 5.6 (s, 1H), 4.9 and 5.2 (2d, 2H), 4.02 and 4.22 (2d, 2H), 3.2-3.5 (m, 6H), 0.7 and 1.46 (2m, 2H), 0.8 (s, 9H).

Example 100

Trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1)

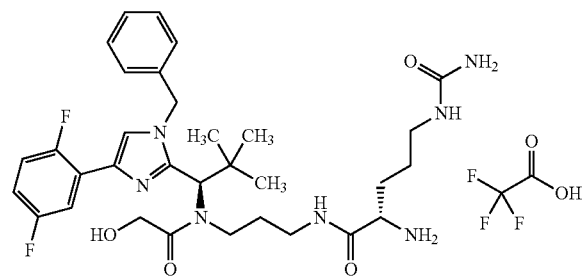 [SMILES: CC(C)(C)[C@H](c1nc(-c2cc(F)ccc2F)cn1Cc1ccccc1)N(CCCNC(=O)[C@@H](N)CCCNC(N)=O)C(=O)CO ; O=C(O)C(F)(F)F]

100.0 mg (0.21 mol) of N-(3-aminopropyl)-N-{(1R)-1-[1-benzyl-4-(2,5-difluorophenyl)-1H-imidazol-2-yl]-2,2-dimethylpropyl}-2-hydroxyacetamide (Intermediate C40) and 109.8 mg (0.28 mmol) of N5-carbamoyl-N2-[(9H-fluoren-9-ylmethoxy)carbonyl]-L-ornithine were initially charged in 5.0 ml of acetonitrile, and 137.3 mg (1.06 mmol) of N,N-diisopropylethylamine and 175.8 mg (0.28 mmol) of T3P were added. The reaction mixture was stirred at RT overnight. The reaction mixture was partitioned between saturated ammonium chloride solution and ethyl acetate. The organic phase was washed twice with water and once with saturated NaCl solution. After drying over magnesium sulphate, the solvent was evaporated under reduced pressure. The residue was purified by preparative RP-HPLC (column: Reprosil 250×30; 10μ, flow rate: 50 ml/min, MeCN/water). The solvents were evaporated under reduced pressure and the residue was dried under high vacuum. This gave 118.9 mg (66%) of the compound N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-N2-[(9H-fluoren-9-ylmethoxy)carbonyl]-L-ornithinamide.

LC-MS (Method 1): $R_t$=1.31 min; MS (ESIpos): m/z=850 [M+H]$^+$.

97.3 mg (0.11 mmol) of N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-N2-[(9H-fluoren-9-ylmethoxy)carbonyl]-L-ornithinamide were initially charged in 4.0 ml of DMF, and 194.9 mg (2.29 mmol) of piperidine were added. The reaction mixture was stirred at RT for 2 h and then neutralized with HOAc. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 101.4 mg of the title compound.

LC-MS (Method 1): $R_t$=0.87 min; MS (ESIpos): m/z=628 [M+H]$^+$.

Example 101

Trifluoroacetic acid/L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1)

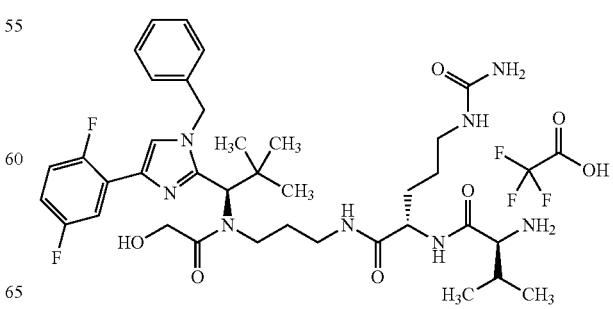

96.2 mg (0.13 mmol) of trifluoroacetic acid/N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1) (Example 100) and 40.8 mg (0.13 mmol) of 2,5-dioxopyrrolidin-1-yl-N-(tert-butoxycarbonyl)-L-valinate were initially charged in 2.0 ml of DMF, and 39.4 mg (0.39 mmol) of 4-methylmorpholine were added. The reaction mixture was stirred at RT overnight. A further 59.1 mg (0.59 mmol) of 4-methylmorpholine were added, and the mixture was stirred at RT overnight. The reaction mixture was partitioned between ethyl acetate and saturated ammonium chloride solution. The organic phase was washed once with saturated NaCl solution and dried over magnesium sulphate. The solvent was evaporated under reduced pressure and the residue was purified by preparative RP-HPLC (column: Reprosil 250×30; 10μ, flow rate: 50 ml/min, MeCN/water). The solvents were evaporated under reduced pressure and the residue was dried under high vacuum. This gave 74.1 mg (69%) of the compound N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide.

LC-MS (Method 1): $R_t$=1.27 min; MS (ESIpos): m/z=827 [M+H]$^+$.

68.1 mg (0.08 mmol) of N-(tert-butoxycarbonyl)-L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide were dissolved in 4.0 ml of dichloromethane, and 187.8 mg (1.65 mmol) of TFA were added. The reaction mixture was stirred at RT overnight, another 187.8 mg (1.65 mmol) of TFA were added and the reaction mixture was once more stirred at RT overnight. The solvent was evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 67.2 mg (97%) of the title compound.

LC-MS (Method 1): $R_t$=0.97 min; MS (ESIpos): m/z=727 [M+H]$^+$.

Example 102

N-(3-Aminopropyl)-N-{(1S)-1-[1-benzyl-4-(2,5-difluorophenyl)-1H-pyrrol-2-yl]-2,2-dimethylpropyl}-2-hydroxyacetamide

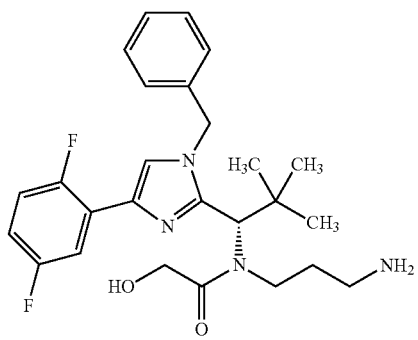 [SMILES: CC(C)(C)[C@@H](c1nc(-c2cc(F)ccc2F)cn1Cc1ccccc1)N(CCCN)C(=O)CO]

The synthesis was carried out analogously to the synthesis of Example 98 using the corresponding S-isomer intermediate.

LC-MS (Method 1): $R_t$=0.92 min; MS (ESIpos): m/z=470 [M+H]$^+$.

Example 103A

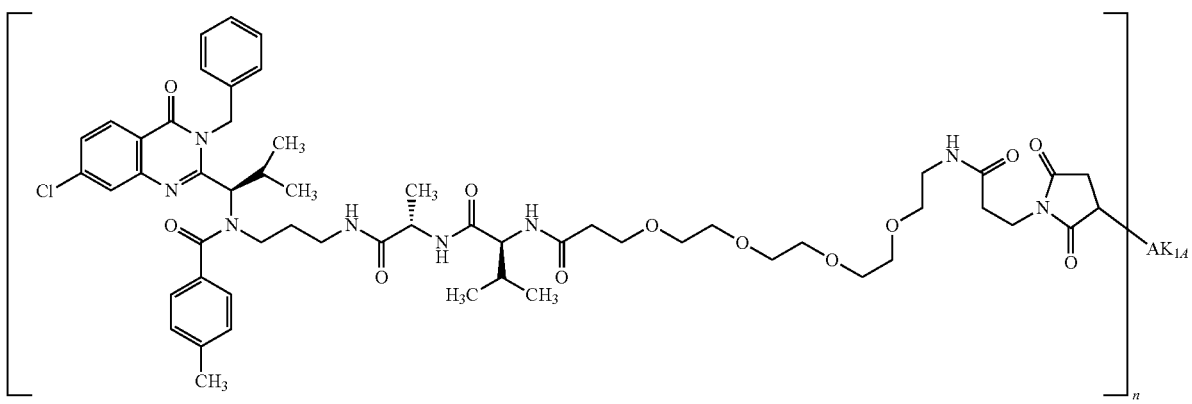

Here, 5.0 mg of cetuximab in PBS (c=15.33 mg/ml) were used for coupling with Intermediate F103, and the reaction was, after Sephadex purification, concentrated by ultracentrifugation and rediluted with PBS. Some of the ADC may also be present in the form of the hydrolysed open-chain succinamides attached to the antibody.

Protein concentration: 0.9 mg/ml
Drug/mAb ratio: 2.2

Example 103B

Here, 5 mg of anti-TWEAKR AK-1 in PBS (c=12.9 mg/ml) were used for coupling with Intermediate F103, and the reaction was, after Sephadex purification, concentrated by ultracentrifugation and rediluted with PBS. Some of the ADC may also be present in the form of the hydrolysed open-chain succinamides attached to the antibody.

Protein concentration: 0.95 mg/ml
Drug/mAb ratio: 2.0

Example 103E

Here, 5.0 mg of trastuzumab antibody in PBS (c=8.23 mg/ml) were used for coupling with Intermediate F103, and the reaction was, after Sephadex purification, concentrated by ultracentrifugation and rediluted with PBS. Some of the ADC may also be present in the form of the hydrolysed open-chain succinamides attached to the antibody.

Protein concentration: 2.05 mg/ml
Drug/mAb ratio: 2.7

Example 104A

Example 104B

Here, 35 mg of anti-TWEAKR AK-1 in PBS (c=12.9 mg/ml) were used for coupling with Intermediate F104, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 10.93 mg/ml
Drug/mAb ratio: 3.2

Example 104E

Here, 5.0 mg of trastuzumab antibody in PBS (c=8.23 mg/ml) were used for coupling with Intermediate F104, and the reaction was, after Sephadex purification, concentrated by ultracentrifugation and rediluted with PBS. Some of the ADC may also be present in the form of the hydrolysed open-chain succinamides attached to the antibody.

Protein concentration: 2.11 mg/ml
Drug/mAb ratio: 2.8

Example 104I

Here, 5.0 mg of nimotuzumab in PBS (c=13.1 mg/ml) were used for coupling with Intermediate F104, and the reaction was, after Sephadex purification, concentrated by ultracentrifugation and rediluted with PBS. Some of the ADC may also be present in the form of the hydrolysed open-chain succinamides attached to the antibody.

Protein concentration: 1.89 mg/ml
Drug/mAb ratio: 3.5

Example 104H

Here, 5.0 mg of panitumumab in PBS (c=12 mg/ml) were used for coupling with Intermediate F104. The time for the

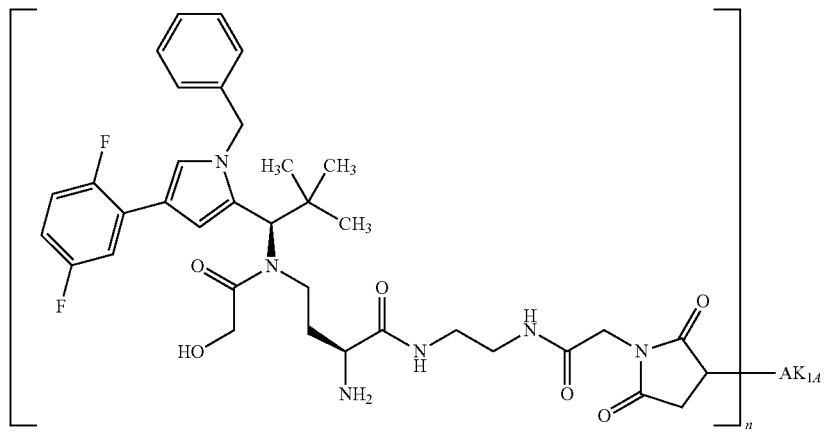

Here, 5 mg of cetuximab in PBS (c=15.33 mg/ml) were used for coupling with Intermediate F104, and the reaction was, after Sephadex purification, concentrated by ultracentrifugation and rediluted with PBS. Some of the ADC may also be present in the form of the hydrolysed open-chain succinamides attached to the antibody.

Protein concentration: 1.95 mg/ml
Drug/mAb ratio: 3.7 reduction with TCEP was increased to 4 h and stirring time for the ADC coupling was increased to 20 h. The reaction was then, after Sephadex purification, concentrated by ultracentrifugation and rediluted with PBS. Some of the ADC may also be present in the form of the hydrolysed open-chain succinamides attached to the antibody.

Protein concentration: 1.79 mg/ml
Drug/mAb ratio: 2.2

Example 105A

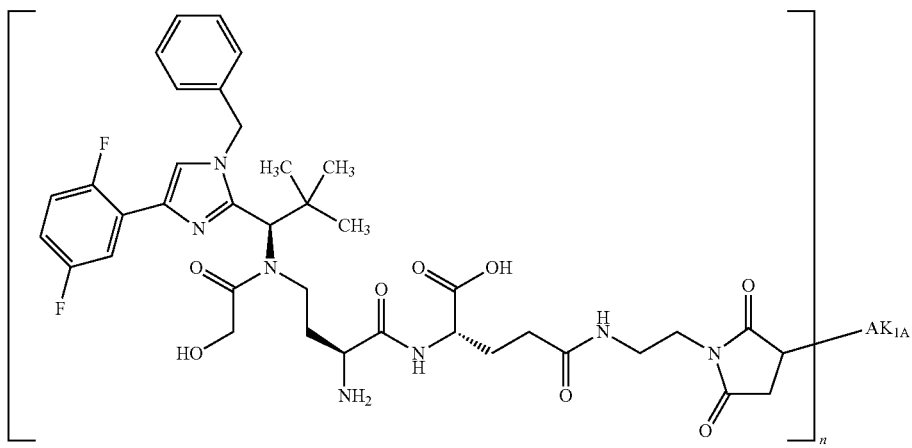

Here, 5 mg of cetuximab in PBS (c=5.9 mg/ml) were used for coupling with Intermediate F105, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.7

Example 105B

Here, 5 mg of anti-TWEAKR AK-1 in PBS (c=12.23 mg/ml) were used for coupling with Intermediate F105, and the reaction was, after Sephadex purification, concentrated by ultracentrifugation and rediluted with PBS. Some of the ADC may also be present in the form of the hydrolysed open-chain succinamides attached to the antibody.

Protein concentration: 2.01 mg/ml
Drug/mAb ratio: 2.6

Example 106A

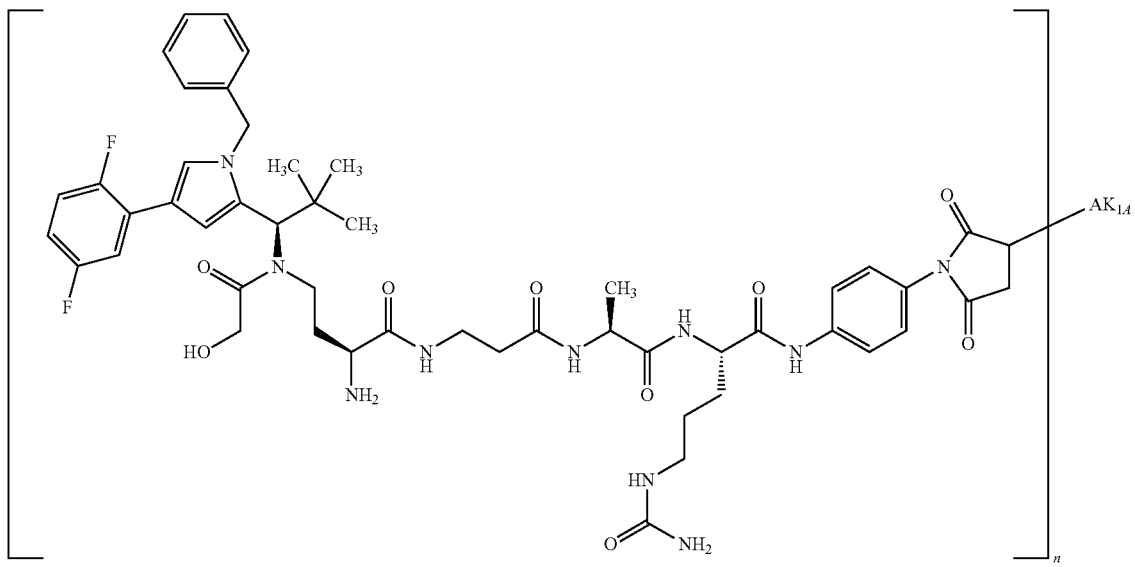

Here, 5 mg of cetuximab in PBS (c=15.33 mg/ml) were used for coupling with Intermediate F106, and the reaction was, after Sephadex purification, concentrated by ultracentrifugation and rediluted with PBS. Some of the ADC may also be present in the form of the hydrolysed open-chain succinamides attached to the antibody.

Protein concentration: 1.91 mg/ml

Drug/mAb ratio: 3.3

Example 106B

Here, 5 mg of anti-TWEAKR AK-1 in PBS (c=12.87 mg/ml) were used for coupling with Intermediate F106, and the reaction was, after Sephadex purification, concentrated by ultracentrifugation and rediluted with PBS. Some of the ADC may also be present in the form of the hydrolysed open-chain succinamides attached to the antibody.

Protein concentration: 1.76 mg/ml

Drug/mAb ratio: 3.0

Example 106E

Here, 5 mg of trastuzumab in PBS (c=8.23 mg/ml) were used for coupling with Intermediate F106, and the reaction was, after Sephadex purification, concentrated by ultracentrifugation and rediluted with PBS. Some of the ADC may also be present in the form of the hydrolysed open-chain succinamides attached to the antibody.

Protein concentration: 2.5 mg/ml

Drug/mAb ratio: 2.4

Example 107A

Here, 5 mg of cetuximab in PBS (c=12.3 mg/ml) were used for coupling with Intermediate F107, and the reaction was, after Sephadex purification, concentrated by ultracentrifugation and rediluted with PBS. Some of the ADC may also be present in the form of the hydrolysed open-chain succinamides attached to the antibody.

Protein concentration: 2.16 mg/ml

Drug/mAb ratio: 3.3

Example 107B

Here, 5 mg of anti-TWEAKR AK-1 in PBS (c=12.9 mg/ml) were used for coupling with Intermediate F107, and the reaction was, after Sephadex purification, concentrated by ultracentrifugation and rediluted with PBS. Some of the ADC may also be present in the form of the hydrolysed open-chain succinamides attached to the antibody.

Protein concentration: 1.9 mg/ml

Drug/mAb ratio: 3.1

Example 107E

Here, 5 mg of trastuzumab in PBS (c=8.23 mg/ml) were used for coupling with Intermediate F107, and the reaction was, after Sephadex purification, concentrated by ultracentrifugation and rediluted with PBS. Some of the ADC may also be present in the form of the hydrolysed open-chain succinamides attached to the antibody.

Protein concentration: 2.48 mg/ml

Drug/mAb ratio: 2.9

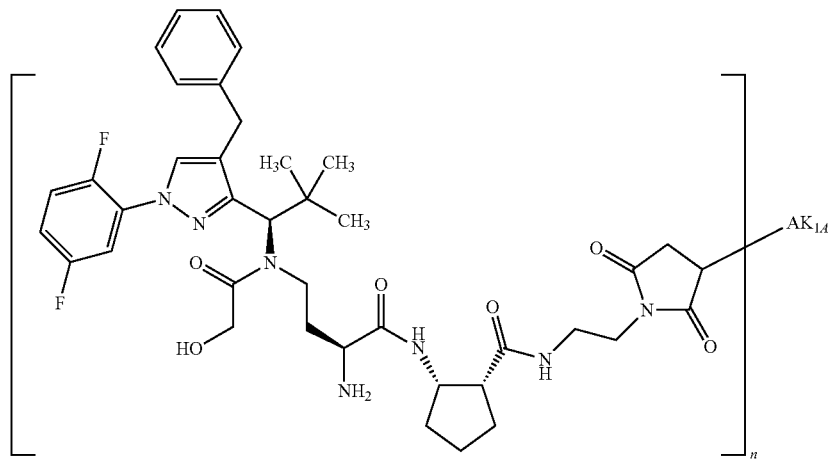

Example 108A

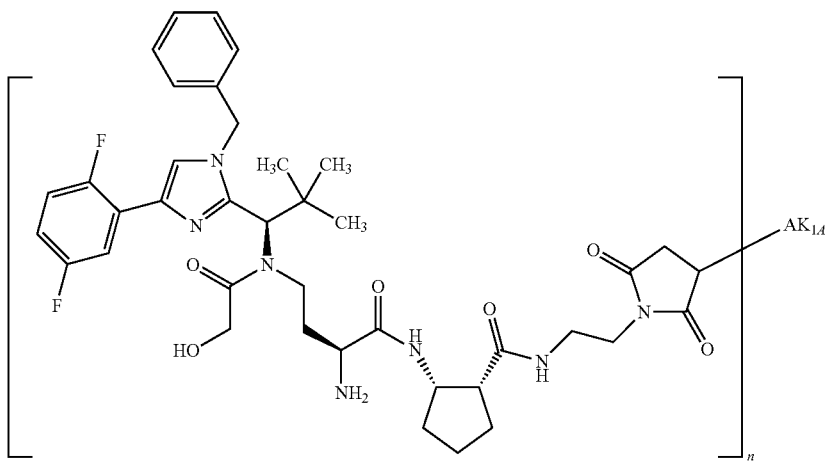

Here, 5 mg of cetuximab in PBS (c=15.3 mg/ml) were used for coupling with Intermediate F108, and the reaction was, after Sephadex purification, concentrated by ultracentrifugation and rediluted with PBS. Some of the ADC may also be present in the form of the hydrolysed open-chain succinamides attached to the antibody.
Protein concentration: 1.98 mg/ml
Drug/mAb ratio: 3.2

Example 108B

Here, 5 mg of anti-TWEAKR AK-1 in PBS (c=12.9 mg/ml) were used for coupling with Intermediate F108, and the reaction was, after Sephadex purification, concentrated by ultracentrifugation and rediluted with PBS. Some of the ADC may also be present in the form of the hydrolysed open-chain succinamides attached to the antibody.
Protein concentration: 1.22 mg/ml
Drug/mAb ratio: 2.1

Example 109A

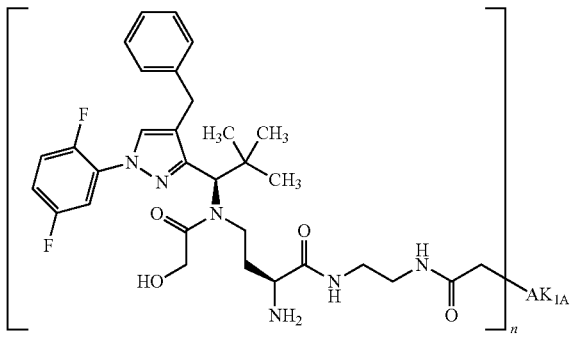

Here, 5 mg of cetuximab in PBS (c=12.33 mg/ml) were used for coupling with Intermediate F109. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 2.1 mg/ml
Drug/mAb ratio: 3.1

Example 109B

Here, 5 mg of anti-TWEAKR AK-1 in PBS (c=34.4 mg/ml) were used for coupling with Intermediate F109. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 1.63 mg/ml
Drug/mAb ratio: 2.7

Example 110A

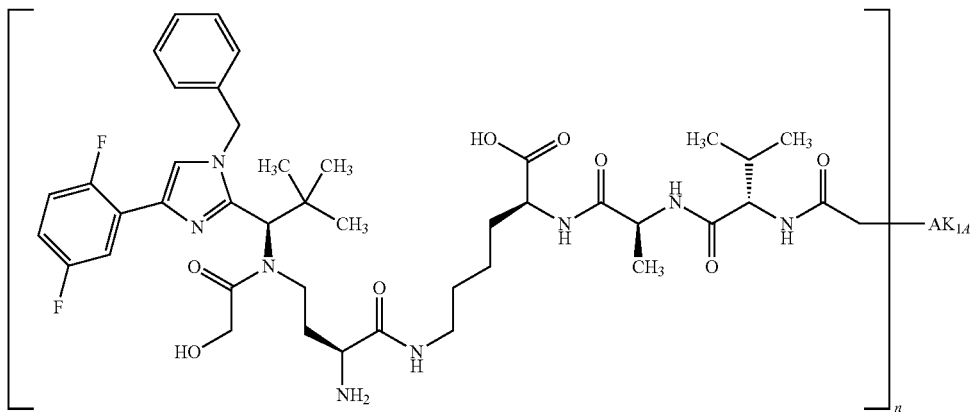

Here, 5 mg of cetuximab in PBS (c=15.33 mg/ml) were used for coupling with Intermediate F110. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.86 mg/ml
Drug/mAb ratio: 3.8

Example 110B

Here, 5 mg of anti-TWEAKR AK-1 in PBS (c=12.9 mg/ml) were used for coupling with Intermediate F110. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.64 mg/ml
Drug/mAb ratio: 3.7

Example 110E

Here, 5 mg of trastuzumab in PBS (c=8.23 mg/ml) were used for coupling with Intermediate F110. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 2.23 mg/ml
Drug/mAb ratio: 2.4

Example 111A

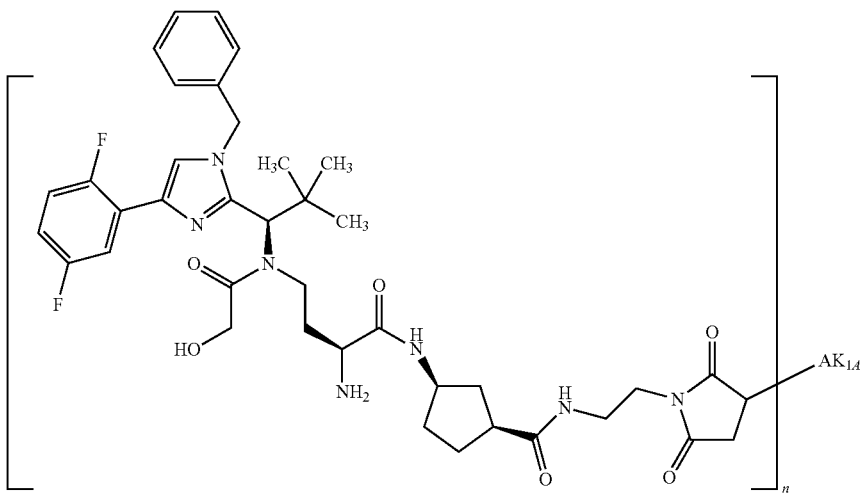

Here, 5 mg of cetuximab in PBS (c=12.33 mg/ml) were used for coupling with Intermediate F111, and the reaction was, after Sephadex purification, concentrated by ultracentrifugation and rediluted with PBS. Some of the ADC may also be present in the form of the hydrolysed open-chain succinamides attached to the antibody.

Protein concentration: 2.4 mg/ml
Drug/mAb ratio: 3

Example 111B

Here, 5 mg of anti-TWEAKR AK-1 in PBS (c=34.4 mg/ml) were used for coupling with Intermediate F111, and the reaction was, after Sephadex purification, concentrated by ultracentrifugation and rediluted with PBS. Some of the ADC may also be present in the form of the hydrolysed open-chain succinamides attached to the antibody.

Protein concentration: 1.71 mg/ml
Drug/mAb ratio: 2.5

Example 112A

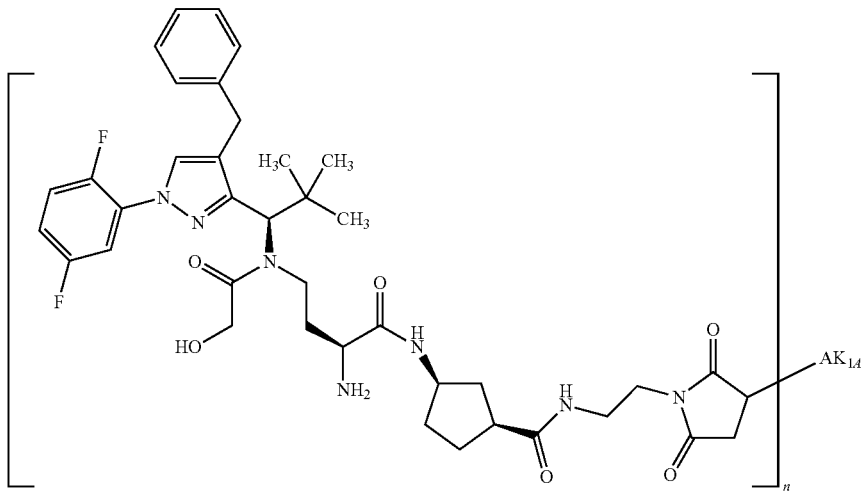

Here, 5 mg of cetuximab in PBS (c=12.33 mg/ml) were used for coupling with Intermediate F122, and the reaction was, after Sephadex purification, concentrated by ultracentrifugation and rediluted with PBS. Some of the ADC may also be present in the form of the hydrolysed open-chain succinamides attached to the antibody.

Protein concentration: 2.2 mg/ml
Drug/mAb ratio: 3

Example 112B

Here, 5 mg of anti-TWEAKR AK-1 in PBS (c=34.4 mg/ml) were used for coupling with Intermediate F112, and the reaction was, after Sephadex purification, concentrated by ultracentrifugation and rediluted with PBS. Some of the ADC may also be present in the form of the hydrolysed open-chain succinamides attached to the antibody.

Protein concentration: 2.39 mg/ml
Drug/mAb ratio: 2.1

Example 113A

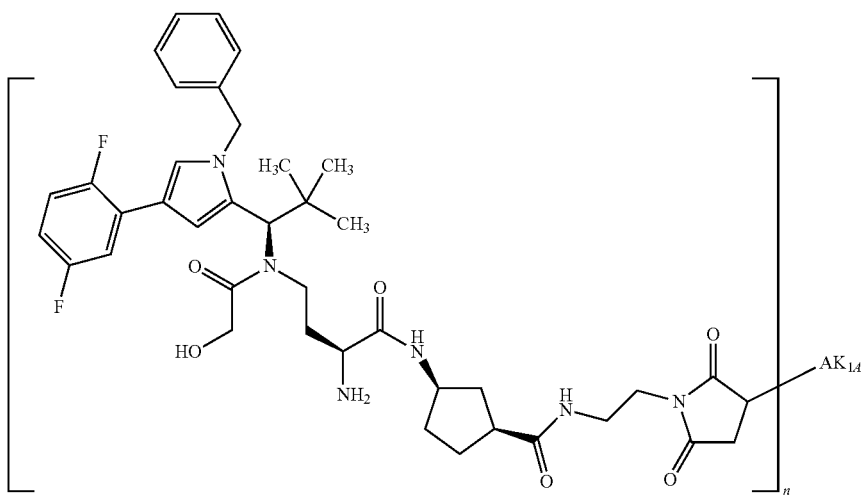

Here, 5 mg of cetuximab in PBS (c=12.33 mg/ml) were used for coupling with Intermediate F113, and the reaction was, after Sephadex purification, concentrated by ultracentrifugation and redituted with PBS. Some of the ADC may also be present in the form of the hydrolysed open-chain succinamides attached to the antibody.

Protein concentration: 1.95 mg/ml
Drug/mAb ratio: 2.2

Example 113B

Here, 5 mg of anti-TWEAKR AK-1 in PBS (c=34.4 mg/ml) were used for coupling with Intermediate F113, and the reaction was, after Sephadex purification, concentrated by ultracentrifugation and redituted with PBS. Some of the ADC may also be present in the form of the hydrolysed open-chain succinamides attached to the antibody.

Protein concentration: 1.8 mg/ml
Drug/mAb ratio: 2.2

Example 114A

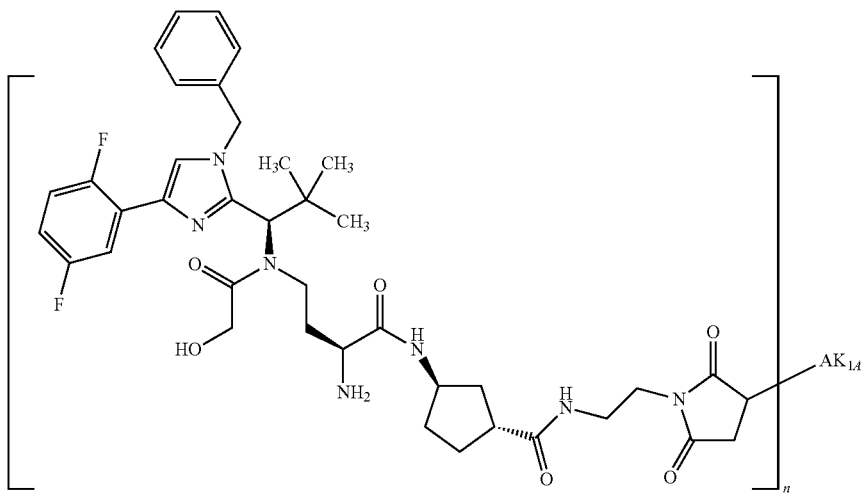

Here, 5 mg of cetuximab in PBS (c=12.33 mg/ml) were used for coupling with Intermediate F114, and the reaction was, after Sephadex purification, concentrated by ultracentrifugation and rediluted with PBS. Some of the ADC may also be present in the form of the hydrolysed open-chain succinamides attached to the antibody.

Protein concentration: 2.07 mg/ml
Drug/mAb ratio: 2.8

Example 114B

Here, 5 mg of anti-TWEAKR AK-1 in PBS (c=34.4 mg/ml) were used for coupling with Intermediate F114, and the reaction was, after Sephadex purification, concentrated by ultracentrifugation and rediluted with PBS. Some of the ADC may also be present in the form of the hydrolysed open-chain succinamides attached to the antibody.

Protein concentration: 1.9 mg/ml
Drug/mAb ratio: 2.4

Example 115A

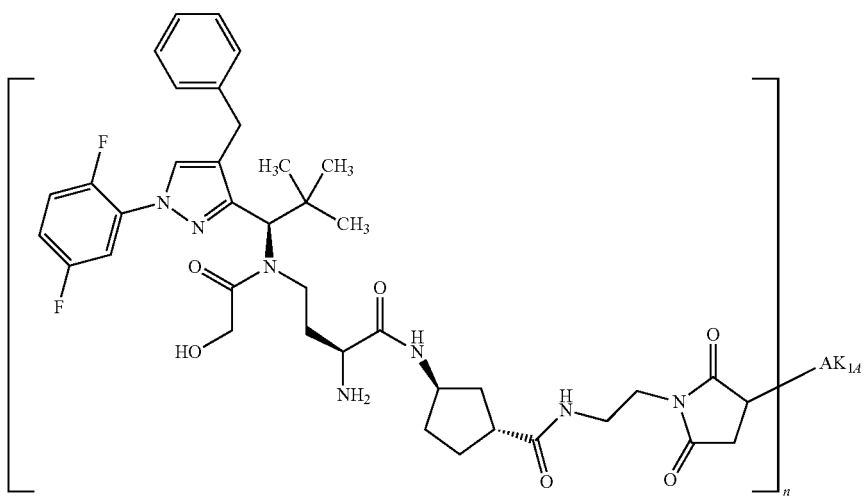

Here, 5 mg of cetuximab in PBS (c=12.33 mg/ml) were used for coupling with Intermediate F115, and the reaction was, after Sephadex purification, concentrated by ultracentrifugation and rediluted with PBS. Some of the ADC may also be present in the form of the hydrolysed open-chain succinamides attached to the antibody.

Protein concentration: 2.18 mg/ml
Drug/mAb ratio: 3.7

Example 115B

Here, 5 mg of anti-TWEAKR AK-1 in PBS (c=34.4 mg/ml) were used for coupling with Intermediate F115, and the reaction was, after Sephadex purification, concentrated by ultracentrifugation and rediluted with PBS. Some of the ADC may also be present in the form of the hydrolysed open-chain succinamides attached to the antibody.

Protein concentration: 2.0 mg/ml
Drug/mAb ratio: 3.0

Example 116A

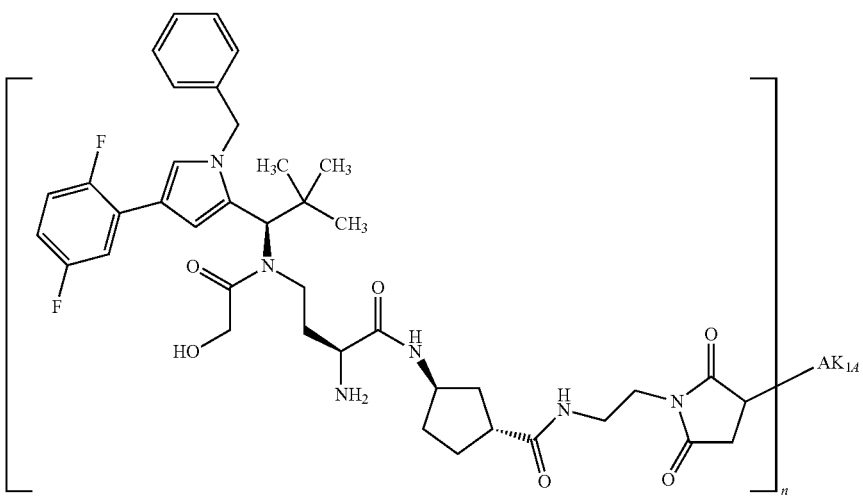

Here, 5 mg of cetuximab in PBS (c=12.33 mg/ml) were used for coupling with Intermediate F116, and the reaction was, after Sephadex purification, concentrated by ultracentrifugation and rediluted with PBS. Some of the ADC may also be present in the form of the hydrolysed open-chain succinamides attached to the antibody.
Protein concentration: 2.03 mg/ml
Drug/mAb ratio: 4.4

Example 116B

Here, 5 mg of anti-TWEAKR AK-1 in PBS (c=34.4 mg/ml) were used for coupling with Intermediate F116, and the reaction was, after Sephadex purification, concentrated by ultracentrifugation and rediluted with PBS. Some of the ADC may also be present in the form of the hydrolysed open-chain succinamides attached to the antibody.
Protein concentration: 1.96 mg/ml
Drug/mAb ratio: 2.9

Example 117A

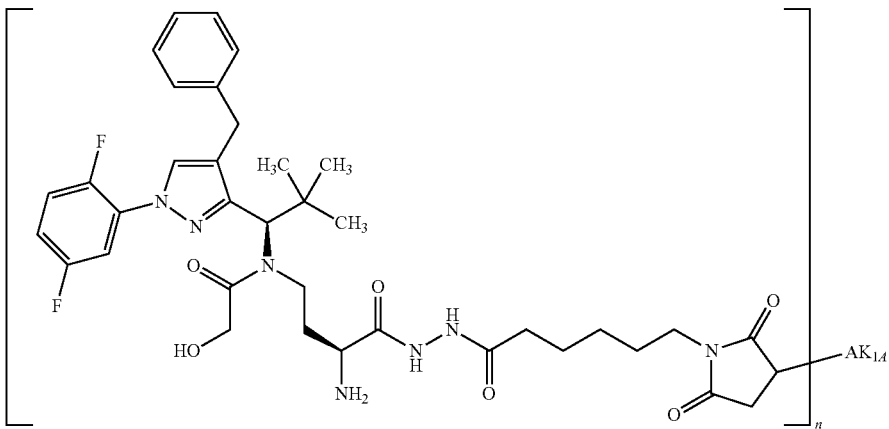

Here, 5 mg of cetuximab in PBS (c=12.33 mg/ml) were used for coupling with Intermediate F117, and the reaction was, after Sephadex purification, concentrated by ultracentrifugation and rediluted with PBS.

Protein concentration: 2.02 mg/ml
Drug/mAb ratio: 2.7

Example 117B

Here, 5 mg of anti-TWEAKR AK-1 in PBS (c=34.4 mg/ml) were used for coupling with Intermediate F117, and the reaction was, after Sephadex purification, concentrated by ultracentrifugation and rediluted with PBS.

Protein concentration: 1.77 mg/ml
Drug/mAb ratio: 2.7

Example 118A

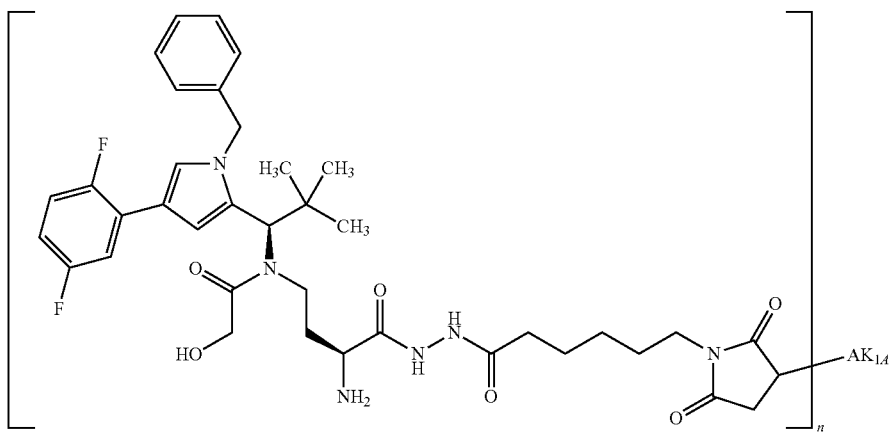

Here, 5 mg of cetuximab in PBS (c=26.84 mg/ml) were used for coupling with Intermediate F118, and the reaction was, after Sephadex purification, concentrated by ultracentrifugation and rediluted with PBS.

Protein concentration: 2.38 mg/ml
Drug/mAb ratio: 3.6

Example 118B

Here, 5 mg of anti-TWEAKR AK-1 in PBS (c=12.87 mg/ml) were used for coupling with Intermediate F118, and the reaction was, after Sephadex purification, concentrated by ultracentrifugation and rediluted with PBS.

Protein concentration: 1.14 mg/ml
Drug/mAb ratio: 2.9

Example 118E

Here, 5 mg of trastuzumab in PBS (c=8.23 mg/ml) were used for coupling with Intermediate F118, and the reaction was, after Sephadex purification, concentrated by ultracentrifugation and rediluted with PBS.

Protein concentration: 2.27 mg/ml
Drug/mAb ratio: 3

Example 119A

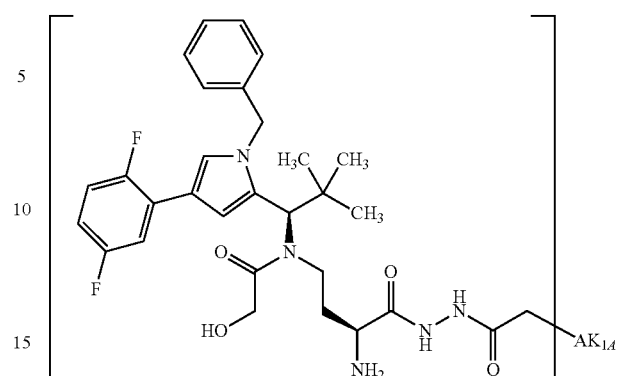

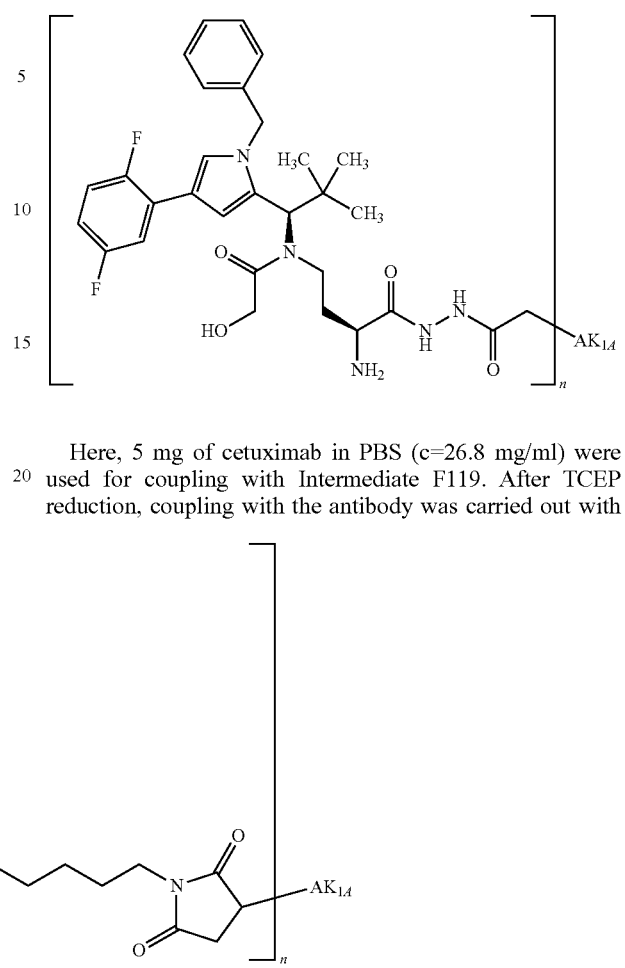

Here, 5 mg of cetuximab in PBS (c=26.8 mg/ml) were used for coupling with Intermediate F119. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 2.14 mg/ml
Drug/mAb ratio: 3.9

Example 119B

Here, 5 mg of anti-TWEAKR AK-1 in PBS (c=12.87 mg/ml) were used for coupling with Intermediate F119. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 0.91 mg/ml
Drug/mAb ratio: 4.1

Example 119E

Here, 5 mg of trastuzumab in PBS (c=13.5 mg/ml) were used for coupling with Intermediate F119. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.69 mg/ml
Drug/mAb ratio: 4.4

Example 120A

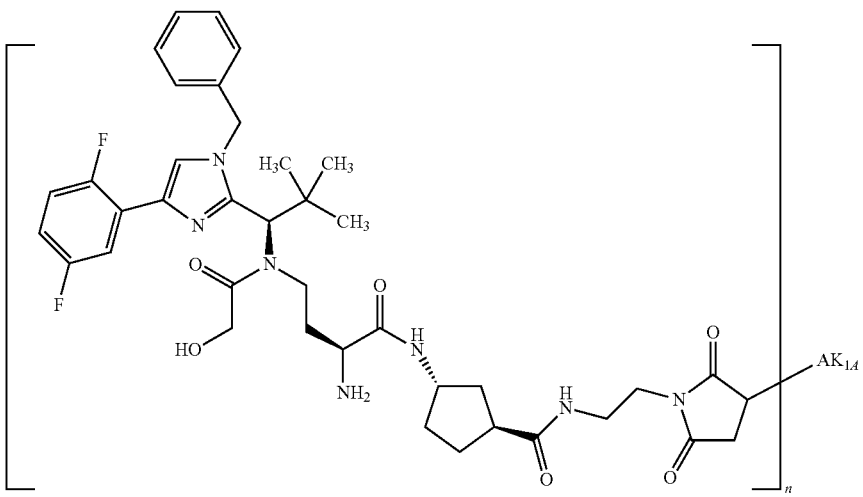

Here, 5 mg of cetuximab in PBS (c=26.84 mg/ml) were used for coupling with Intermediate F120, and the reaction was, after Sephadex purification, concentrated by ultracentrifugation and rediluted with PBS. Some of the ADC may also be present in the form of the hydrolysed open-chain succinamides attached to the antibody.

Protein concentration: 1.95 mg/ml
Drug/mAb ratio: 3.4

Example 120B

Here, 5 mg of anti-TWEAKR AK-1 in PBS (c=12.87 mg/ml) were used for coupling with Intermediate F120, and the reaction was, after Sephadex purification, concentrated by ultracentrifugation and rediluted with PBS. Some of the ADC may also be present in the form of the hydrolysed open-chain succinamides attached to the antibody.

Protein concentration: 1.71 mg/ml
Drug/mAb ratio: 3.3

Example 121A

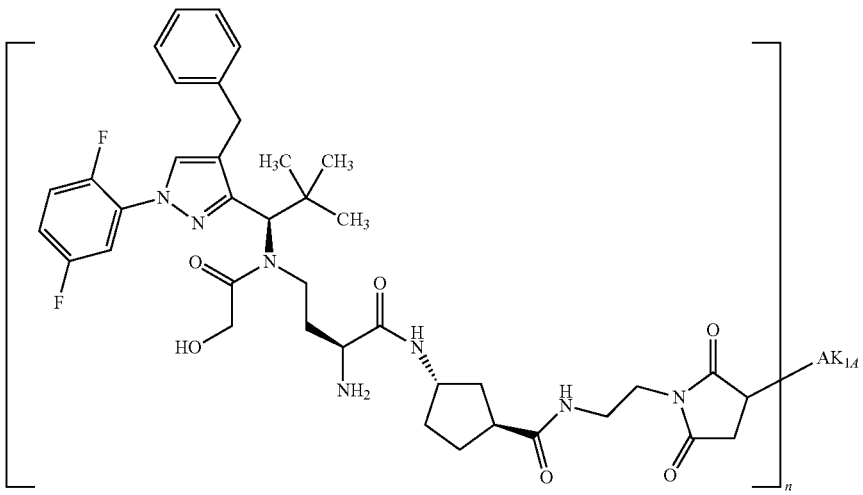

Here, 5 mg of cetuximab in PBS (c=26.84 mg/ml) were used for coupling with Intermediate F121, and the reaction was, after Sephadex purification, concentrated by ultracentrifugation and rediluted with PBS. Some of the ADC may also be present in the form of the hydrolysed open-chain succinamides attached to the antibody.

Protein concentration: 2.1 mg/ml

Drug/mAb ratio: 3.2

Example 121B

Here, 5 mg of anti-TWEAKR AK-1 in PBS (c=12.87 mg/ml) were used for coupling with Intermediate F121, and the reaction was, after Sephadex purification, concentrated by ultracentrifugation and rediluted with PBS. Some of the ADC may also be present in the form of the hydrolysed open-chain succinamides attached to the antibody.

Protein concentration: 1.88 mg/ml

Drug/mAb ratio: 3.4

Example 122A

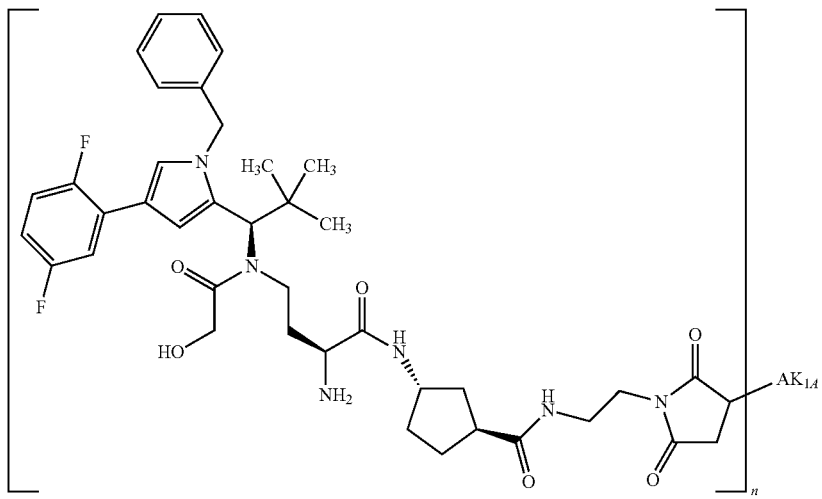

Here, 5 mg of cetuximab in PBS (c=26.84 mg/ml) were used for coupling with Intermediate F122, and the reaction was, after Sephadex purification, concentrated by ultracentrifugation and rediluted with PBS. Some of the ADC may also be present in the form of the hydrolysed open-chain succinamides attached to the antibody.

Protein concentration: 1.78 mg/ml

Drug/mAb ratio: 3.2

Example 122B

Here, 5 mg of anti-TWEAKR AK-1 in PBS (c=12.87 mg/ml) were used for coupling with Intermediate F122, and the reaction was, after Sephadex purification, concentrated by ultracentrifugation and rediluted with PBS. Some of the ADC may also be present in the form of the hydrolysed open-chain succinamides attached to the antibody.

Protein concentration: 1.64 mg/ml

Drug/mAb ratio: 3.4

Example 123A

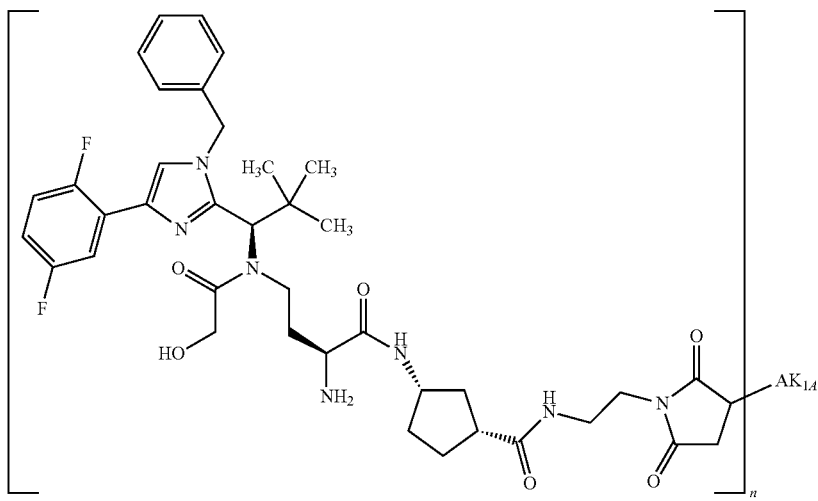

Here, 5 mg of cetuximab in PBS (c=26.84 mg/ml) were used for coupling with Intermediate F123, and the reaction was, after Sephadex purification, concentrated by ultracentrifugation and rediluted with PBS. Some of the ADC may also be present in the form of the hydrolysed open-chain succinamides attached to the antibody.
Protein concentration: 1.98 mg/ml
Drug/mAb ratio: 2.9

Example 123B

Here, 5 mg of anti-TWEAKR AK-1 in PBS (c=12.87 mg/ml) were used for coupling with Intermediate F123, and the reaction was, after Sephadex purification, concentrated by ultracentrifugation and rediluted with PBS. Some of the ADC may also be present in the form of the hydrolysed open-chain succinamides attached to the antibody.
Protein concentration: 1.84 mg/ml
Drug/mAb ratio: 3.0

Example 124A

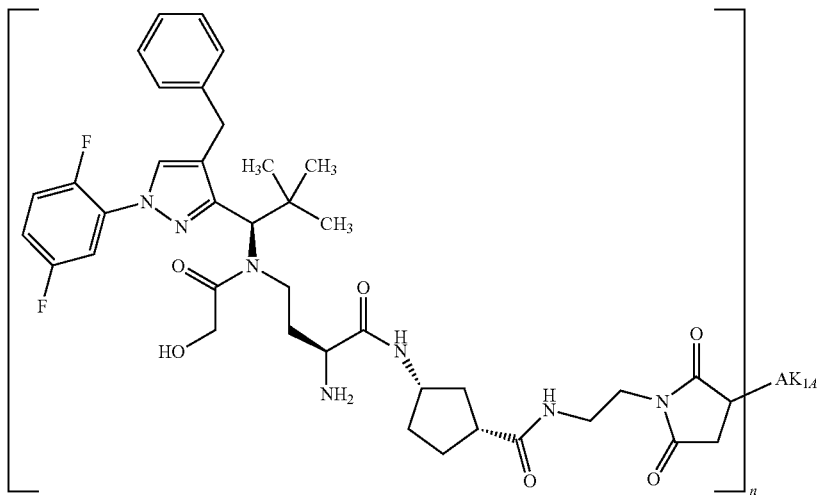

Here, 5 mg of cetuximab in PBS (c=26.84 mg/ml) were used for coupling with Intermediate F124, and the reaction was, after Sephadex purification, concentrated by ultracentrifugation and rediluted with PBS. Some of the ADC may also be present in the form of the hydrolysed open-chain succinamides attached to the antibody.

Protein concentration: 1.93 mg/ml
Drug/mAb ratio: 2.8

Example 124B

Here, 5 mg of anti-TWEAKR AK-1 in PBS (c=12.87 mg/ml) were used for coupling with Intermediate F124, and the reaction was, after Sephadex purification, concentrated by ultracentrifugation and rediluted with PBS. Some of the ADC may also be present in the form of the hydrolysed open-chain succinamides attached to the antibody.

Protein concentration: 1.84 mg/ml
Drug/mAb ratio: 3.0

Example 125A

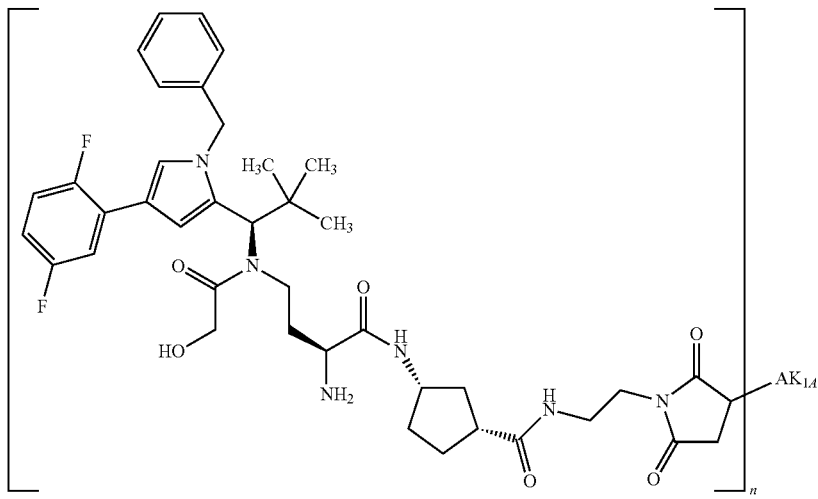

Here, 5 mg of cetuximab in PBS (c=26.84 mg/ml) were used for coupling with Intermediate F125, and the reaction was, after Sephadex purification, concentrated by ultracentrifugation and rediluted with PBS. Some of the ADC may also be present in the form of the hydrolysed open-chain succinamides attached to the antibody.

Protein concentration: 2.14 mg/ml
Drug/mAb ratio: 2.9

Example 125B

Here, 5 mg of anti-TWEAKR AK-1 in PBS (c=12.87 mg/ml) were used for coupling with Intermediate F125, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.3

Example 126A

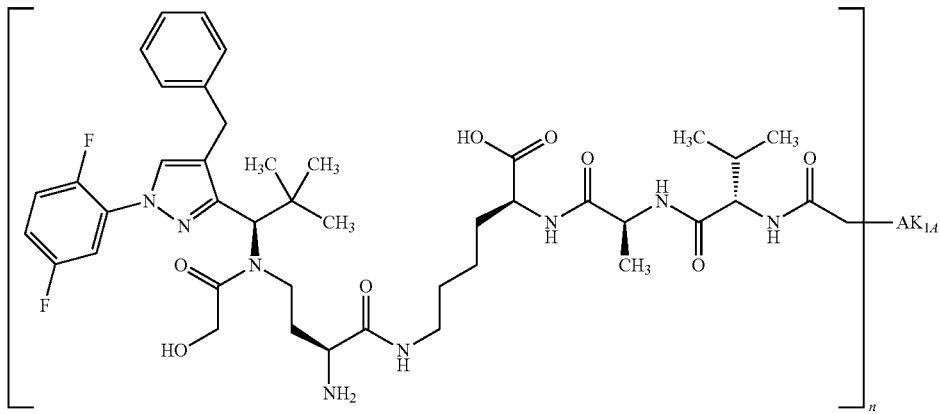

Here, 5 mg of cetuximab in PBS (c=26.84 mg/ml) were used for coupling with Intermediate F126. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.89 mg/ml
Drug/mAb ratio: 2.5

Example 126B

Here, 5 mg of anti-TWEAKR AK-1 in PBS (c=12.9 mg/ml) were used for coupling with Intermediate F126. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.62 mg/ml
Drug/mAb ratio: 2.8

Example 126E

Here, 5 mg of trastuzumab in PBS (c=8.23 mg/ml) were used for coupling with Intermediate F126. After TCEP reduction, coupling with the antibody was carried out with stirring overnight, followed by further work-up by Sephadex purification. After Sephadex purification, the reaction was concentrated by ultracentrifugation and rediluted with PBS.

Protein concentration: 1.93 mg/ml
Drug/mAb ratio: 1.9

Example 127A

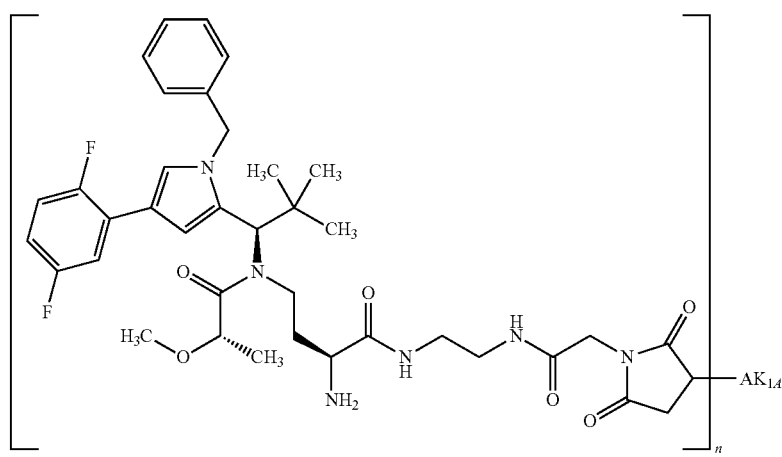

Here, 5 mg of cetuximab in PBS (c=26.84 mg/ml) were used for coupling with Intermediate F127, and the reaction was, after Sephadex purification, concentrated by ultracentrifugation and rediluted with PBS. Some of the ADC may also be present in the form of the hydrolysed open-chain succinamides attached to the antibody.

Protein concentration: 1.54 mg/ml
Drug/mAb ratio: 3.3

Example 127B

Here, 5 mg of anti-TWEAKR AK-1 in PBS (c=12.9 mg/ml) were used for coupling with Intermediate F127, and the reaction was, after Sephadex purification, concentrated by ultracentrifugation and rediluted with PBS. Some of the ADC may also be present in the form of the hydrolysed open-chain succinamides attached to the antibody.

Protein concentration: 1.62 mg/ml
Drug/mAb ratio: 3.3

Example 127E

Here, 5.0 mg of trastuzumab antibody in PBS (c=13.5 mg/ml) were used for coupling with Intermediate F127, and the reaction was, after Sephadex purification, concentrated by ultracentrifugation and rediluted with PBS. Some of the ADC may also be present in the form of the hydrolysed open-chain succinamides attached to the antibody.

Protein concentration: 2.07 mg/ml
Drug/mAb ratio: 3.6

Example 128A

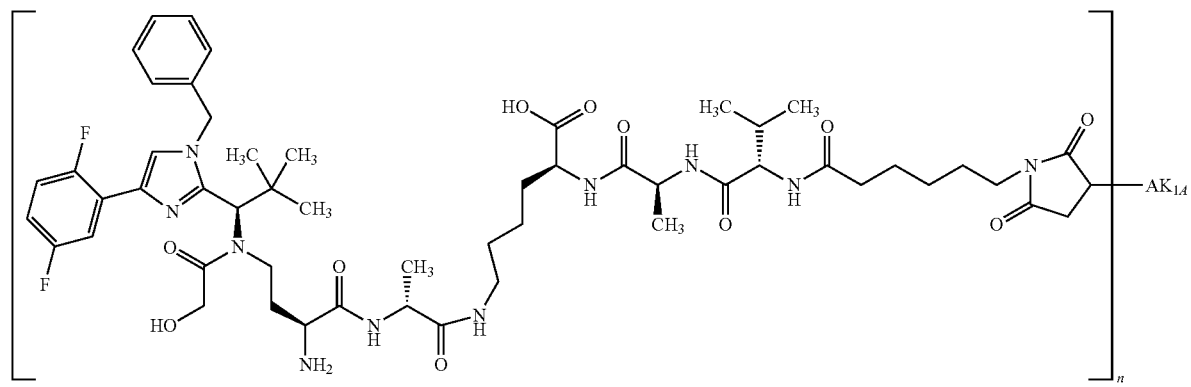

Here, 5 mg of cetuximab in PBS (c=26.84 mg/ml) were used for coupling with Intermediate F128, and the reaction was, after Sephadex purification, concentrated by ultracentrifugation and rediluted with PBS.

Protein concentration: 1.99 mg/ml
Drug/mAb ratio: 2.7

Example 128B

Here, 5 mg of anti-TWEAKR AK-1 in PBS (c=12.9 mg/ml) were used for coupling with Intermediate F128, and the reaction was, after Sephadex purification, concentrated by ultracentrifugation and rediluted with PBS.

Protein concentration: 1.99 mg/ml
Drug/mAb ratio: 3.4

Example 129A

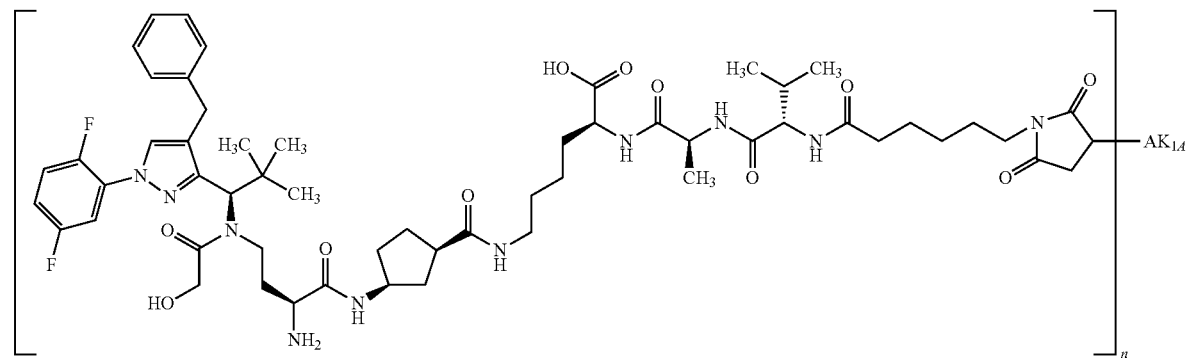

Here, 5 mg of cetuximab in PBS (c=26.84 mg/ml) were used for coupling with Intermediate F129, and the reaction was, after Sephadex purification, concentrated by ultracentrifugation and rediluted with PBS.

Protein concentration: 2.28 mg/ml
Drug/mAb ratio: 2.9

Example 129B

Here, 5 mg of anti-TWEAKR AK-1 in PBS (c=12.9 mg/ml) were used for coupling with Intermediate F129, and the reaction was, after Sephadex purification, concentrated by ultracentrifugation and rediluted with PBS.

Protein concentration: 2.06 mg/ml
Drug/mAb ratio: 3.2

Example 129E

Here, 5 mg of trastuzumab in PBS (c=13.5 mg/ml) were used for coupling with Intermediate F129, and the reaction was, after Sephadex purification, concentrated by ultracentrifugation and rediluted with PBS.

Protein concentration: 2.0 mg/ml
Drug/mAb ratio: 3.4

Example 130

S-(1-{2-[(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)amino]ethyl}-2,5-dioxopyrrolidin-3-yl)-L-cysteine/trifluoroacetic acid (1:1)

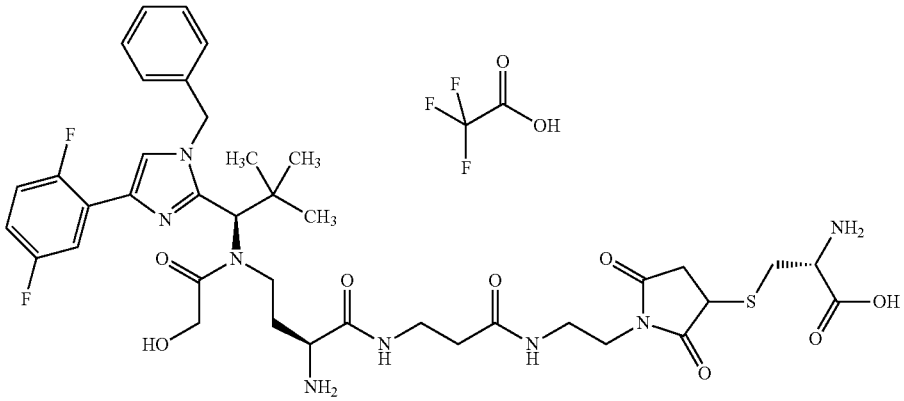 [SMILES: CC(C)(C)[C@H](c1nc(-c2cc(F)ccc2F)cn1Cc1ccccc1)N(CC[C@H](N)C(=O)NCCC(=O)NCCN1C(=O)CC(SC[C@H](N)C(=O)O)C1=O)C(=O)CO ; O=C(O)C(F)(F)F]

4.2 mg (5 µmol) of Intermediate F32 were taken up in 2 ml of DCM/water 10:1, and 1.8 mg (15 µmol) of L-cysteine were added. The reaction mixture was stirred at RT for 2 h, then concentrated under reduced pressure and then purified by preparative HPLC.

LC-MS (Method 1): $R_t$=0.8 min; MS (EIpos): m/z=829 [M+H]$^+$.

Example 131

S-[1-(2-{[2-({(2S)-2-Amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-2,5-dioxopyrrolidin-3-yl]-L-cysteine/trifluoroacetic acid (1:1)

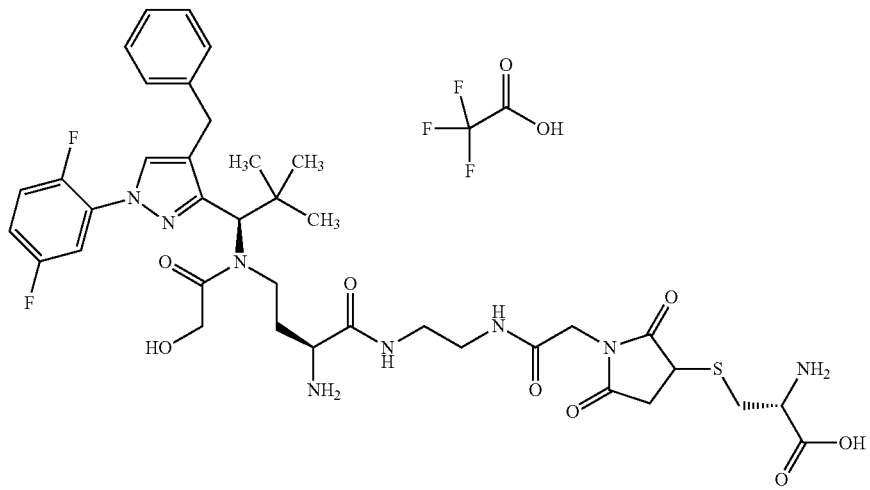 [SMILES: CC(C)(C)[C@H](c1nn(-c2cc(F)ccc2F)cc1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

5 mg (6 µmol) of Intermediate F87 were taken up in 1 ml of DMF, and 7.5 mg (62 µmol) of L-cysteine were added. The reaction mixture was stirred at RT for 20 h, then concentrated under reduced pressure and then purified by preparative HPLC.

LC-MS (Method 1): $R_t$=0.81 min; MS (EIpos): m/z=815 [M+H]$^+$.

Example 132

N-{(2S)-2-Amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N$^5$-carbamoyl-L-ornithinamide/trifluoroacetic acid (1:1)

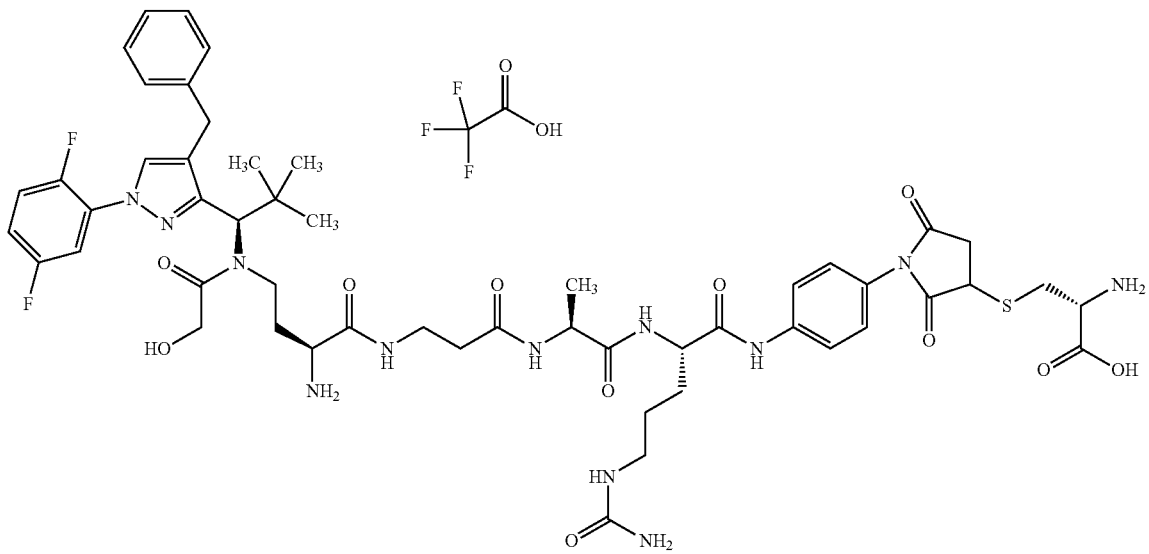 [SMILES: C[C@H](NC(=O)CCNC(=O)[C@@H](N)CCN(C(=O)CO)[C@@H](c1nn(-c2cc(F)ccc2F)cc1Cc1ccccc1)C(C)(C)C)C(=O)N[C@@H](CCCNC(N)=O)C(=O)Nc1ccc(N2C(=O)CC(SC[C@H](N)C(=O)O)C2=O)cc1 ; O=C(O)C(F)(F)F]

5 mg (5 µmol) of Intermediate F89 were taken up in 2 ml of DMF/water 10:1, and 1.7 mg (14 µmol) of L-cysteine were added. The reaction mixture was stirred at RT for 1 h and then concentrated under reduced pressure. The residue was taken up in acetonitrile/water, and the mixture was adjusted to pH 2 using TFA and then concentrated under reduced pressure and then purified by preparative HPLC. The appropriate fractions were concentrated, giving, after lyophilization of the residue from acetonitrile/water, 3 mg of the title compound as a white foam.

LC-MS (Method 4): $R_t$=0.93 min; MS (EIpos): m/z=1105 [M+H]$^+$.

Example 133

S-(1-{2-[(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine/trifluoroacetic acid (1:1)

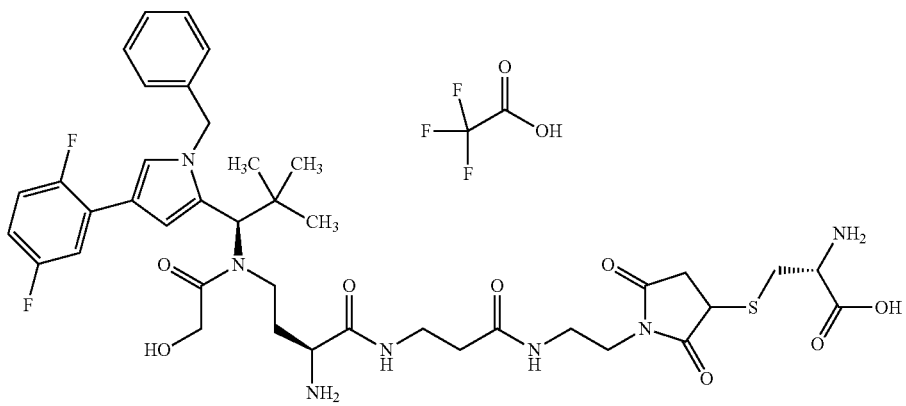 [SMILES: CC(C)(C)[C@H](c1cc(-c2cc(F)ccc2F)cn1Cc1ccccc1)N(CC[C@H](N)C(=O)NCCC(=O)NCCN1C(=O)CC(SC[C@H](N)C(=O)O)C1=O)C(=O)CO ; O=C(O)C(F)(F)F]

1.6 mg (2 μmol) of Intermediate F84 were taken up in 1.5 ml of DMF/water 10:1, and 0.74 mg (6 μmol) of L-cysteine were added. The reaction mixture was stirred at RT for 10 min and then concentrated under reduced pressure. The residue was taken up in acetonitrile/water, and the mixture was adjusted to pH 2 using TFA and then concentrated under reduced pressure and then purified by preparative HPLC. The appropriate fractions were concentrated, giving, after lyophilization of the residue from acetonitrile/water, 1.9 mg (89% of theory) of the title compound as a white foam.

LC-MS (Method 1): $R_t$=0.8 min; MS (EIpos): m/z=828 [M+H]$^+$.

Example 134

N-[6-(3-{[(2R)-2-Amino-2-carboxyethyl]sulpha-nyl}-2,5-dioxopyrrolidin-1-yl)hexanoyl]-L-valyl-N$^5$-carbamoyl-L-ornithyl-N$^6$-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine/trifluoroacetic acid (1:1)

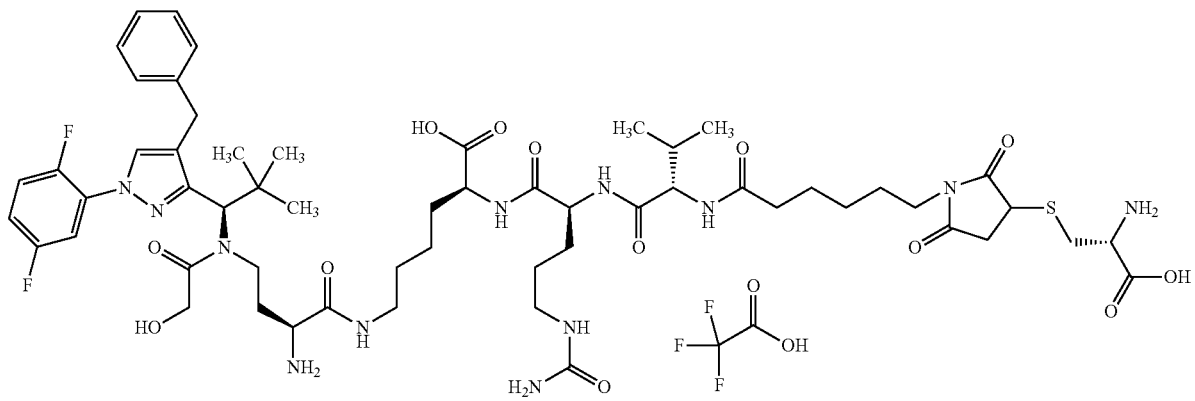 [SMILES: CC(C)[C@H](NC(=O)CCCCCN1C(=O)CC(SC[C@H](N)C(=O)O)C1=O)C(=O)N[C@@H](CCCNC(N)=O)C(=O)N[C@@H](CCCCNC(=O)[C@@H](N)CCN(C(=O)CO)[C@@H](c1nn(-c2cc(F)ccc2F)cc1Cc1ccccc1)C(C)(C)C)C(=O)O ; O=C(O)C(F)(F)F]

3.8 mg (3 μmol) of Intermediate F90 were taken up in 1.5 ml of DMF/water 10:1, and 1.2 mg (9 μmol) of L-cysteine were added. The reaction mixture was stirred at RT for 15 min and then concentrated under reduced pressure. The residue was taken up in acetonitrile/water 1:1, concentrated again and then purified by preparative HPLC. The appropriate fractions were concentrated, giving, after lyophilization of the residue from acetonitrile/water, 2.3 mg (56% of theory) of the title compound as a white foam.

LC-MS (Method 4): $R_t$=1.0 min; MS (EIpos): m/z=1213 [M+H]$^+$.

Example 135

S-[1-(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)-2,5-dioxopyrrolidin-3-yl]-L-cysteine/trifluoroacetic acid (1:1)

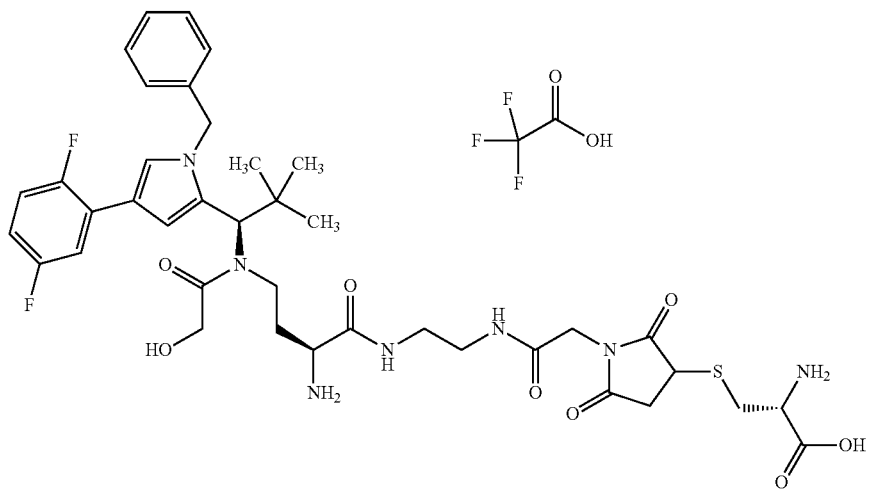 [SMILES: CC(C)(C)[C@H](c1cc(-c2cc(F)ccc2F)cn1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

1.8 mg (2 µmol) of Intermediate F104 were taken up in 1 ml of DMF, and 2.7 mg (22 µmol) of L-cysteine were added. The reaction mixture was stirred at RT for 20 h, then concentrated under reduced pressure and then purified by preparative HPLC. 0.6 mg (26% of theory) of the title compound remained as a colourless foam.

LC-MS (Method 1): $R_t$=0.80 min; MS (EIpos): m/z=814 [M+H]$^+$.

Example 136

S-(2-{[2-({(2S)-2-Amino-4-[{(1R)-1-[4-benzyl-1-(2,5-difluorophenyl)-1H-pyrazol-3-yl]-2,2-dimethyl-propyl}(glycoloyl)amino]butanoyl}amino)ethyl]amino}-2-oxoethyl)-L-cysteine/trifluoroacetic acid (1:1)

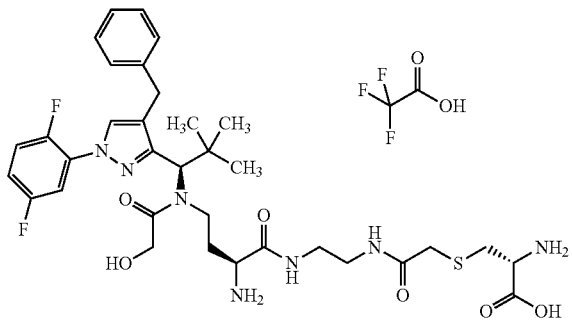 [SMILES: CC(C)(C)[C@H](c1nn(-c2cc(F)ccc2F)cc1Cc1ccccc1)N(CC[C@H](N)C(=O)NCCNC(=O)CSC[C@H](N)C(=O)O)C(=O)CO ; O=C(O)C(F)(F)F]

3.3 mg (4 µmol) of Intermediate F109 were taken up in 2 ml of DMF/water 10:1, and 1.5 mg (13 µmol) of L-cysteine were added. The reaction mixture was stirred at RT for 30 min and then concentrated under reduced pressure. The residue was taken up in acetonitrile/water 1:1, concentrated again and then purified by preparative HPLC. The appropriate fractions were concentrated, giving, after lyophilization of the residue from acetonitrile/water, 1.9 mg (55% of theory) of the title compound as a white foam.

LC-MS (Method 1): $R_t$=0.75 min; MS (EIpos): m/z=718 [M+H]$^+$.

Example 137

S-{1-[6-(2-{(2S)-2-Amino-4-[{(1R)-1-[4-benzyl-1-(2,5-difluorophenyl)-1H-pyrazol-3-yl]-2,2-dimethyl-propyl}(glycoloyl)amino]butanoyl}hydrazino)-6-oxohexyl]-2,5-dioxopyrrolidin-3-yl}-L-cysteine/trifluoroacetic acid (1:1)

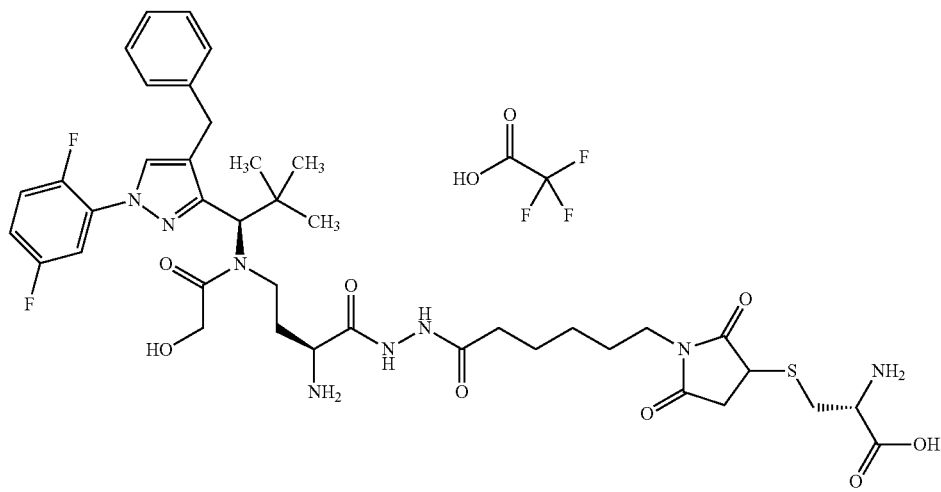 [SMILES: CC(C)(C)[C@H](c1nn(-c2cc(F)ccc2F)cc1Cc1ccccc1)N(CC[C@H](N)C(=O)NNC(=O)CCCCCN1C(=O)CC(SC[C@H](N)C(=O)O)C1=O)C(=O)CO ; O=C(O)C(F)(F)F]

3.2 mg (4 µmol) of Intermediate F117 were taken up in 2 ml of DMF/water 10:1, and 1.6 mg (13 µmol) of L-cysteine were added. The reaction mixture was stirred at RT for 30 min and then concentrated under reduced pressure. The residue was taken up in acetonitrile/water 1:1, concentrated again and then purified by preparative HPLC. The appropriate fractions were concentrated, giving, after lyophilization of the residue from acetonitrile/water, 2 mg (47% of theory) of the title compound as a white foam.

LC-MS (Method 1): $R_t$=0.76 min; MS (EIpos): m/z=843 [M+H]$^+$.

Example 138

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine/trifluoroacetic acid (1:1)

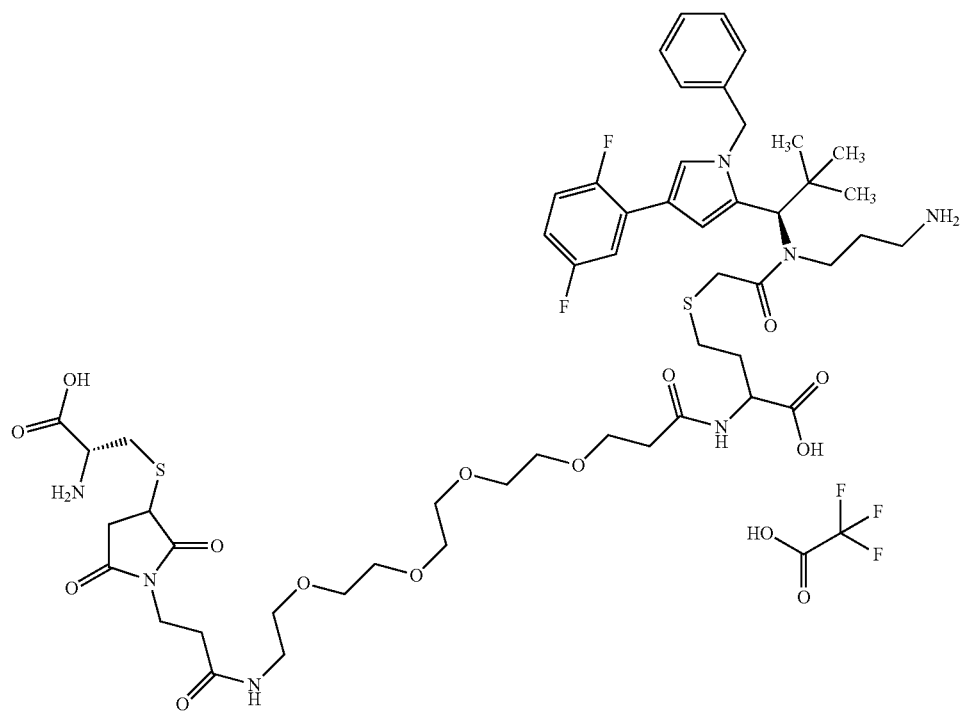

6.0 mg (0.01 mmol) of R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-homocysteine/trifluoroacetic acid (1:1) (Intermediate F146) were initially charged in 2.2 ml of DMF/water (10:1), 2.0 mg (0.02 mmol) of L-cysteine were added and the mixture was stirred at RT for 10 min. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 5.5 mg (76% of theory) of the title compound.

LC-MS (Method 4): $R_t$=1.07 min; MS (ESIpos): m/z=1106 (M+H)$^+$.

Example 139

S-{(3R/S)-1-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-2,5-dioxopyrrolidin-3-yl}-L-cysteine/trifluoroacetic acid (1:2)

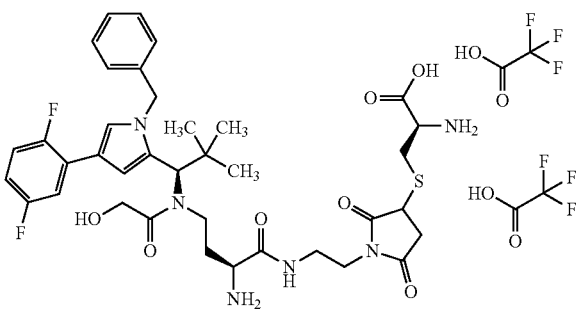 [SMILES: CC(C)(C)[C@H](c1cc(-c2cc(F)ccc2F)cn1Cc1ccccc1)N(CC[C@H](N)C(=O)NCCN1C(=O)CC(SC[C@H](N)C(=O)O)C1=O)C(=O)CO ; O=C(O)C(F)(F)F ; O=C(O)C(F)(F)F]

The synthesis was carried out analogously to the synthesis of compound Example 138. 6.0 mg (0.01 mmol) of trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2,5-dioxo-2,5-dihydro-1H-pyrrol-1-yl)ethyl]butanamide (1:1). 2.6 mg (0.02 mmol) of L-cysteine.

This gave 3.4 mg (43% of theory) of the title compound.

LC-MS (Method 1): $R_t$=0.82 min; MS (ESIpos): m/z=757 $(M+H)^+$.

Example 140

N-[19-(3(R/S)-[{(2R)-2-Amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-imidazol-2-yl]-2,2-dimethylpropyl}amino]-2-oxoethyl}homocysteine/ trifluoroacetic acid (1:2)

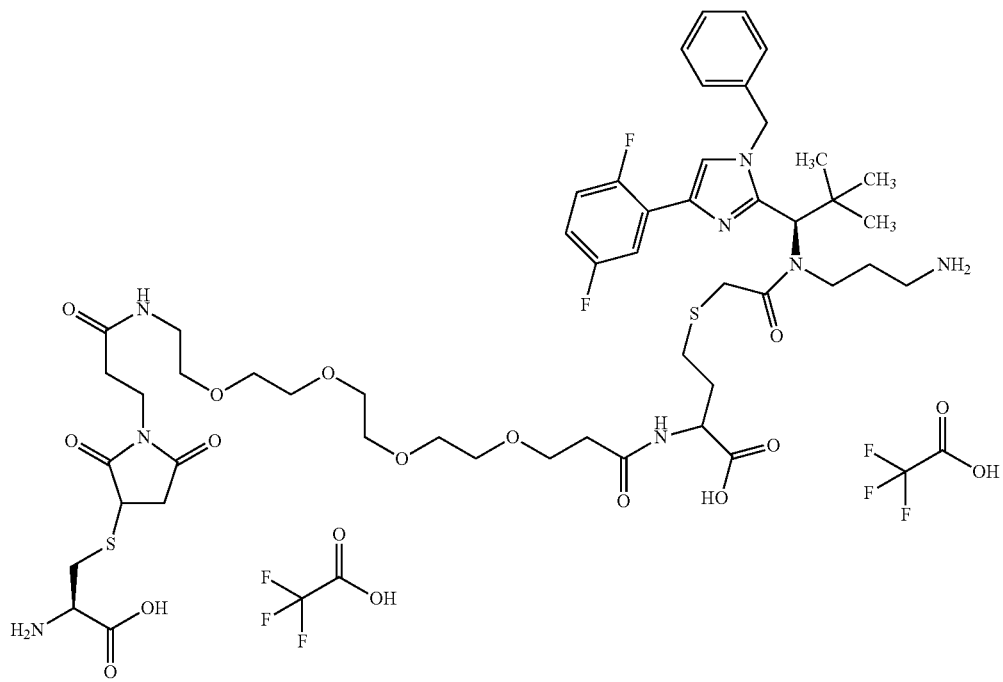 [SMILES: CC(C)(C)[C@H](c1nc(-c2cc(F)ccc2F)cn1Cc1ccccc1)N(CCCN)C(=O)CSCCC(NC(=O)CCOCCOCCOCCOCCNC(=O)CCN1C(=O)CC(SC[C@H](N)C(=O)O)C1=O)C(=O)O ; O=C(O)C(F)(F)F ; O=C(O)C(F)(F)F]

The synthesis was carried out analogously to the synthesis of compound Example 138. 6.0 mg (0.01 mmol) of trifluoroacetic acid/R/S-{2-[(3-aminopropyl){(1R)-1-[1-benzyl-4-(2,5-difluorophenyl)-1H-imidazol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]homocysteine (1:1)

Intermediate F149

2.0 mg (0.02 mmol) of L-cysteine.

This gave 6.1 mg (84% of theory) of the title compound.

LC-MS (Method 1): $R_t$=0.85 min; MS (ESIpos): m/z=1107 $(M+H)^+$.

Example 141

S-[(3R/S)-1-(2-{[6-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulphanyl)hexanoyl]amino}ethyl)-2,5-dioxopyrrolidin-3-yl]-L-cysteine/trifluoroacetic acid (1:2)

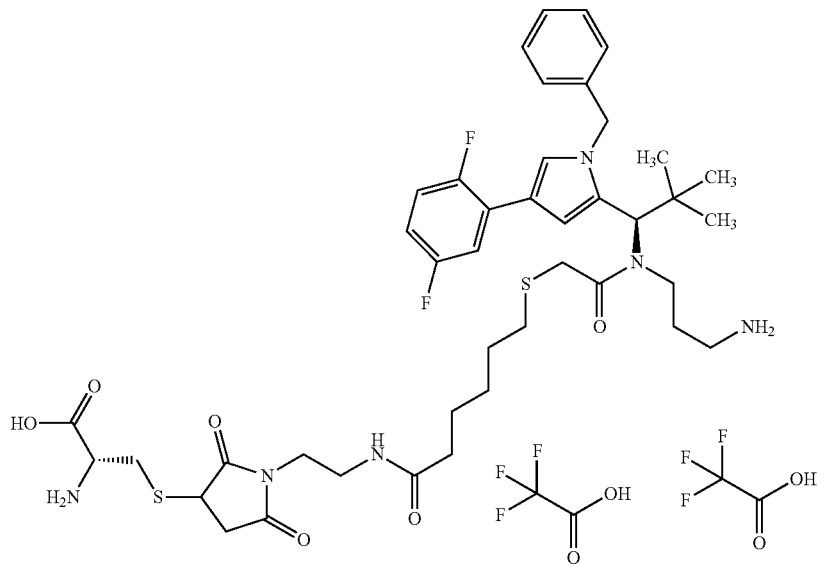

The synthesis was carried out analogously to the synthesis of compound Example 138. 10.07 mg (0.01 mmol) of trifluoroacetic acid/6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-[2-(2,5-dioxo-2,5-dihydro-1H-pyrrol-1-yl)ethyl]hexanamide (1:1) (Intermediate F143). 9.3 mg (0.08 mmol) of L-cysteine.

This gave 9.2 mg (67% of theory) of the title compound.
LC-MS (Method 4): $R_t$=1.05 min; MS (ESIpos): m/z=843 (M+H)⁺.

Example 142A

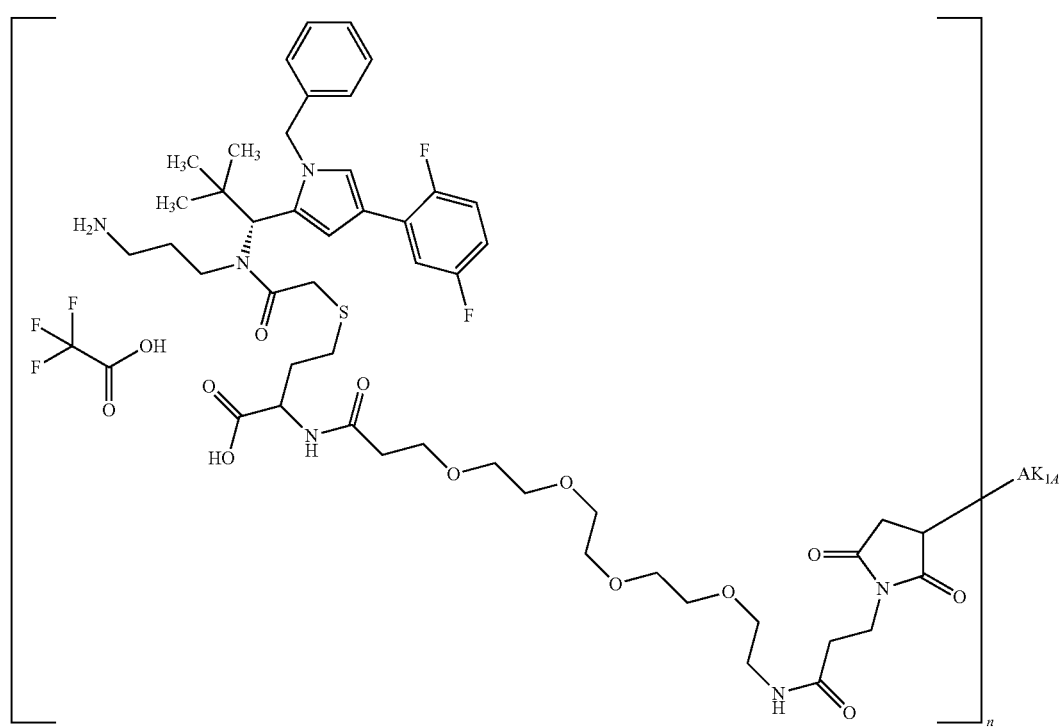

Here, 5.0 mg of cetuximab in PBS (c=12.33 mg/ml) were used for coupling with Intermediate F142, and the reaction was, after Sephadex purification, concentrated by ultracentrifugation and rediluted with PBS. Some of the ADC may also be present in the form of the hydrolysed open-chain succinamides attached to the antibody.

Protein concentration: 2.08 mg/ml

Drug/mAb ratio: 2.1

Example 142B

Here, 5.0 mg of anti-TWEAKR AK-1 antibody in PBS (c=34.42 mg/ml) were used for coupling with Intermediate F142, and the reaction was, after Sephadex purification, concentrated by ultracentrifugation and rediluted. Some of the ADC may also be present in the form of the hydrolysed open-chain succinamides attached to the antibody.

Protein concentration: 1.84 mg/ml

Drug/mAb ratio: 2.0

Example 142E

Here, 5.0 mg of trastuzumab antibody in PBS (c=13.50 mg/ml) were used for coupling with Intermediate F142, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml

Drug/mAb ratio: 2.3

Example 142I

Here, 5.0 mg of nimotuzumab in PBS (c=13.8 mg/ml) were used for coupling with Intermediate F142, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml

Drug/mAb ratio: 2.5

Example 142H

Here, 5.0 mg of panitumumab in PBS (c=2.1 mg/ml) were used for coupling with Intermediate F142. The reduction time with TCEP was 1 h and the stirring time for the ADC coupling was 1.5 h. After Sephadex purification, the reaction was concentrated by ultracentrifugation and rediluted with PBS. Some of the ADC may also be present in the form of the hydrolysed open-chain succinamides attached to the antibody.

Protein concentration: 1.7 mg/ml

Drug/mAb ratio: 2.2

Example 143A

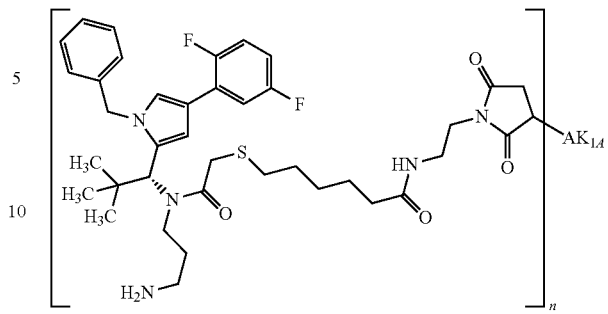

Here, 5.0 mg of cetuximab in PBS (c=12.33 mg/ml) were used for coupling with Intermediate F143, and the reaction was, after Sephadex purification, concentrated by ultracentrifugation and rediluted with PBS. Some of the ADC may also be present in the form of the hydrolysed open-chain succinamides attached to the antibody.

Protein concentration: 1.84 mg/ml

Drug/mAb ratio: 2.5

Example 143B

Here, 5.0 mg of anti-TWEAKR AK-1 antibody in PBS (c=34.42 mg/ml) were used for coupling with Intermediate F143, and the reaction was, after Sephadex purification, concentrated by ultracentrifugation and rediluted. Some of the ADC may also be present in the form of the hydrolysed open-chain succinamides attached to the antibody.

Protein concentration: 1.05 mg/ml

Drug/mAb ratio: 1.6

Example 143E

Here, 5.0 mg of trastuzumab antibody in PBS (c=13.50 mg/ml) were used for coupling with Intermediate F143, and the reaction was, after Sephadex purification, concentrated by ultracentrifugation and rediluted. Some of the ADC may also be present in the form of the hydrolysed open-chain succinamides attached to the antibody.

Protein concentration: 1.95 mg/ml

Drug/mAb ratio: 2.3

Example 144B

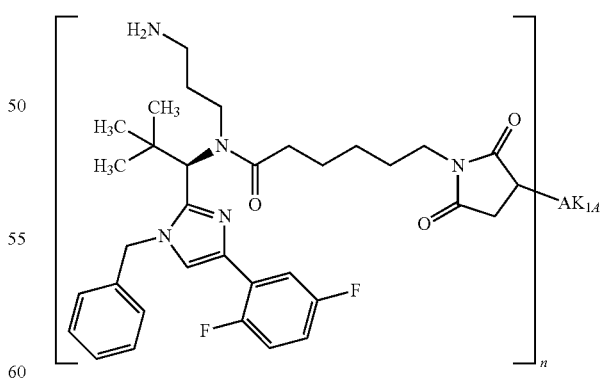

Here, 5.0 mg of anti-TWEAKR AK-1 antibody in PBS (c=12.87 mg/ml) were used for coupling with Intermediate F144, and the reaction was, after Sephadex purification, concentrated by ultracentrifugation and rediluted.

Protein concentration: 1.53 mg/ml

Drug/mAb ratio: 2.0

Example 145A

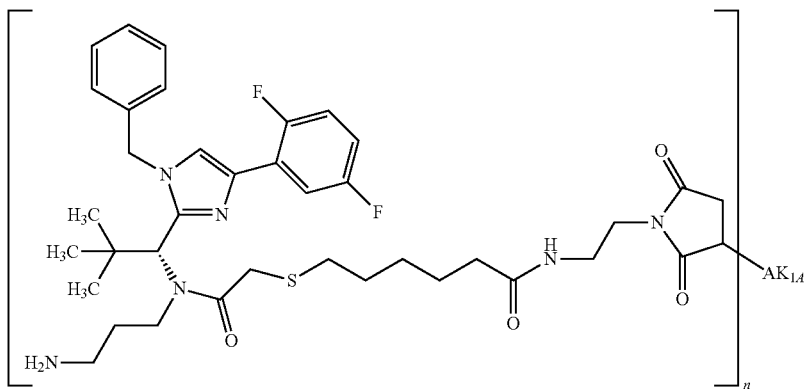

Here, 5.0 mg of cetuximab in PBS (c=5.90 mg/ml) were used for coupling with Intermediate F145, and the reaction was, after Sephadex purification, concentrated by ultracentrifugation and rediluted with PBS. Some of the ADC may also be present in the form of the hydrolysed open-chain succinamides attached to the antibody.

Protein concentration: 2.00 mg/ml
Drug/mAb ratio: 2.0

Example 145B

Here, 5.0 mg of anti-TWEAKR AK-1 antibody in PBS (c=12.87 mg/ml) were used for coupling with Intermediate F145, and the reaction was, after Sephadex purification, concentrated by ultracentrifugation and rediluted. Some of the ADC may also be present in the form of the hydrolysed open-chain succinamides attached to the antibody.

Protein concentration: 1.54 mg/ml
Drug/mAb ratio: 1.9

Example 145E

Here, 5.0 mg of trastuzumab antibody in PBS (c=13.50 mg/ml) were used for coupling with Intermediate F145, and the reaction was, after Sephadex purification, concentrated by ultracentrifugation and rediluted with PBS. Some of the ADC may also be present in the form of the hydrolysed open-chain succinamides attached to the antibody.

Protein concentration: 1.86 mg/ml
Drug/mAb ratio: 2.4

Example 146A

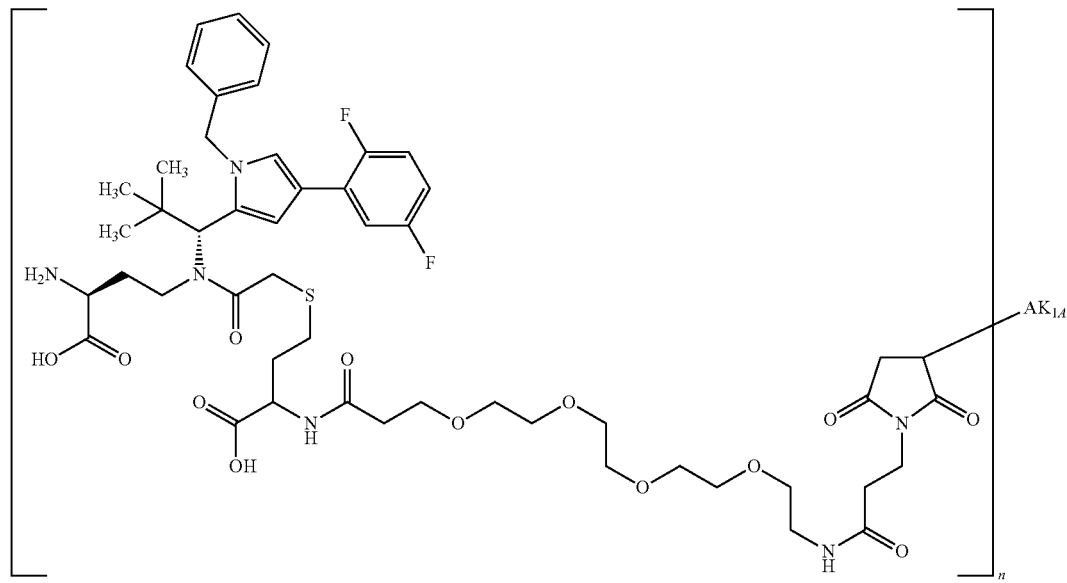

Here, 5.0 mg of cetuximab in PBS (c=12.33 mg/ml) were used for coupling with Intermediate F146, and the reaction was, after Sephadex purification, concentrated by ultracentrifugation and rediluted with PBS. Some of the ADC may also be present in the form of the hydrolysed open-chain succinamides attached to the antibody.

Protein concentration: 2.02 mg/ml
Drug/mAb ratio: 2.4

Example 146B

Here, 5.0 mg of anti-TWEAKR AK-1 antibody in PBS (c=34.42 mg/ml) were used for coupling with Intermediate F146, and the reaction was, after Sephadex purification, concentrated by ultracentrifugation and rediluted. Some of the ADC may also be present in the form of the hydrolysed open-chain succinamides attached to the antibody.

Protein concentration: 1.87 mg/ml
Drug/mAb ratio: 2.4

Example 146E

Here, 5.0 mg of trastuzumab antibody in PBS (c=13.50 mg/ml) were used for coupling with Intermediate F146, and the reaction was, after Sephadex purification, concentrated by ultracentrifugation and rediluted. Some of the ADC may also be present in the form of the hydrolysed open-chain succinamides attached to the antibody.

Protein concentration: 1.92 mg/ml
Drug/mAb ratio: 2.5

Example 147A

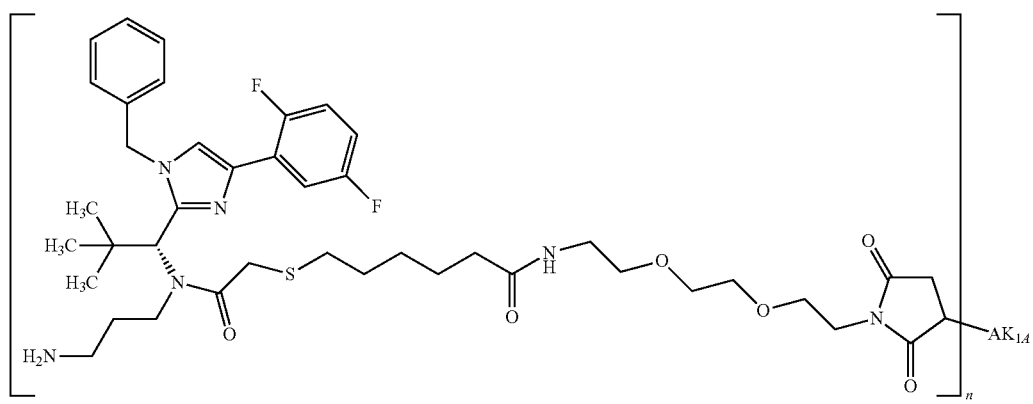

Here, 5.0 mg of cetuximab in PBS (c=5.90 mg/ml) were used for coupling with Intermediate F147, and the reaction was, after Sephadex purification, concentrated by ultracentrifugation and rediluted with PBS. Some of the ADC may also be present in the form of the hydrolysed open-chain succinamides attached to the antibody.

Protein concentration: 2.04 mg/ml
Drug/mAb ratio: 2.2

Example 147B

Here, 5.0 mg of anti-TWEAKR AK-1 antibody in PBS (c=12.87 mg/ml) were used for coupling with Intermediate F147, and the reaction was, after Sephadex purification, concentrated by ultracentrifugation and rediluted. Some of the ADC may also be present in the form of the hydrolysed open-chain succinamides attached to the antibody.

Protein concentration: 1.31 mg/ml
Drug/mAb ratio: 1.8

Example 147E

Here, 5.0 mg of trastuzumab antibody in PBS (c=13.50 mg/ml) were used for coupling with Intermediate F147, and the reaction was, after Sephadex purification, concentrated by ultracentrifugation and rediluted. Some of the ADC may also be present in the form of the hydrolysed open-chain succinamides attached to the antibody.

Protein concentration: 1.86 mg/ml
Drug/mAb ratio: 2.6

Example 148A

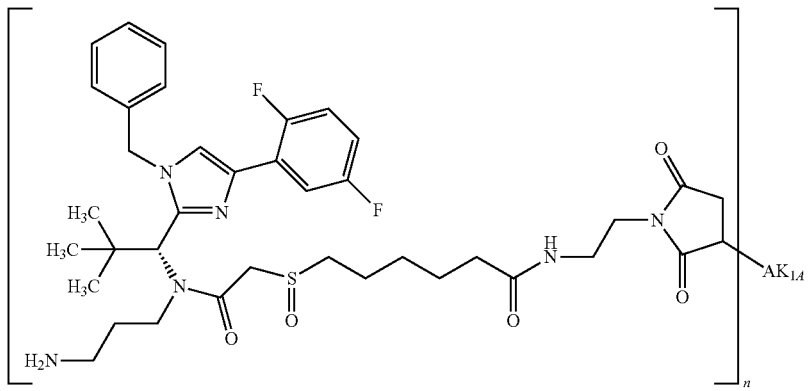

Here, 5.0 mg of cetuximab in PBS (c=5.90 mg/ml) were used for coupling with Intermediate F148, and the reaction was, after Sephadex purification, concentrated by ultracentrifugation and rediluted with PBS. Some of the ADC may also be present in the form of the hydrolysed open-chain succinamides attached to the antibody.
Protein concentration: 2.11 mg/ml
Drug/mAb ratio: 2.3

Example 148B

Here, 5.0 mg of anti-TWEAKR AK-1 antibody in PBS (c=12.87 mg/ml) were used for coupling with Intermediate F148, and the reaction was, after Sephadex purification, concentrated by ultracentrifugation and rediluted. Some of the ADC may also be present in the form of the hydrolysed open-chain succinamides attached to the antibody.
Protein concentration: 1.95 mg/ml
Drug/mAb ratio: 2.0

Example 148E

Here, 5.0 mg of trastuzumab antibody in PBS (c=13.50 mg/ml) were used for coupling with Intermediate F148, and the reaction was, after Sephadex purification, concentrated by ultracentrifugation and rediluted. Some of the ADC may also be present in the form of the hydrolysed open-chain succinamides attached to the antibody.
Protein concentration: 2.62 mg/ml
Drug/mAb ratio: 2.5

Example 149A

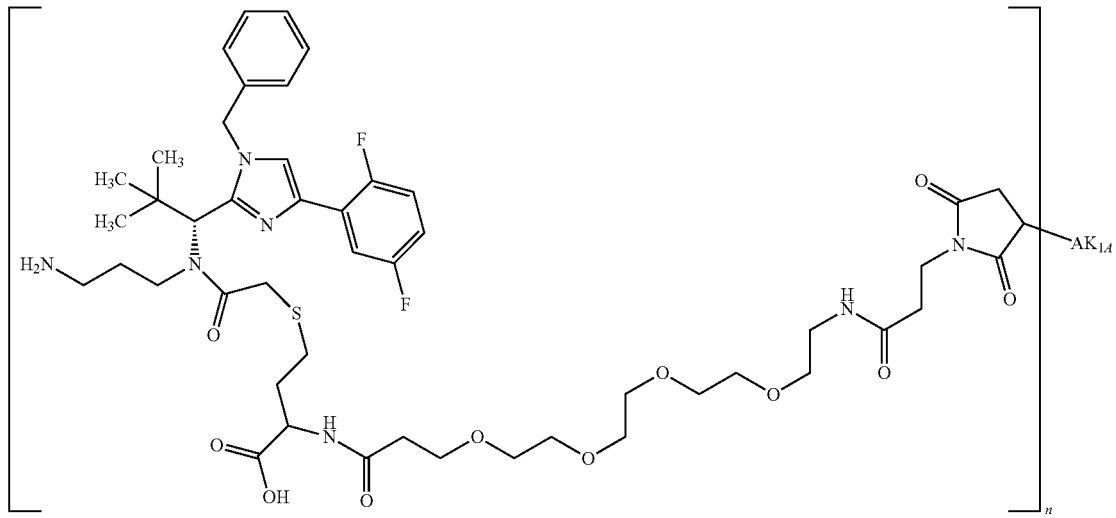

Here, 5.0 mg of cetuximab in PBS (c=5.90 mg/ml) were used for coupling with Intermediate F149, and the reaction was, after Sephadex purification, concentrated by ultracentrifugation and rediluted with PBS. Some of the ADC may also be present in the form of the hydrolysed open-chain succinamides attached to the antibody.

Protein concentration: 2.09 mg/ml
Drug/mAb ratio: 2.3

Example 149B

Here, 40 mg of anti-TWEAKR AK-1 in PBS (c=34.42 mg/ml) were used for coupling with Intermediate F149, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 9.61 mg/ml
Drug/mAb ratio: 2.6

Example 149E

Here, 5.0 mg of trastuzumab antibody in PBS (c=13.50 mg/ml) were used for coupling with Intermediate F149, and the reaction was, after Sephadex purification, concentrated by ultracentrifugation and rediluted with PBS. Some of the ADC may also be present in the form of the hydrolysed open-chain succinamides attached to the antibody.

Protein concentration: 1.93 mg/ml
Drug/mAb ratio: 2.7

Example 150A

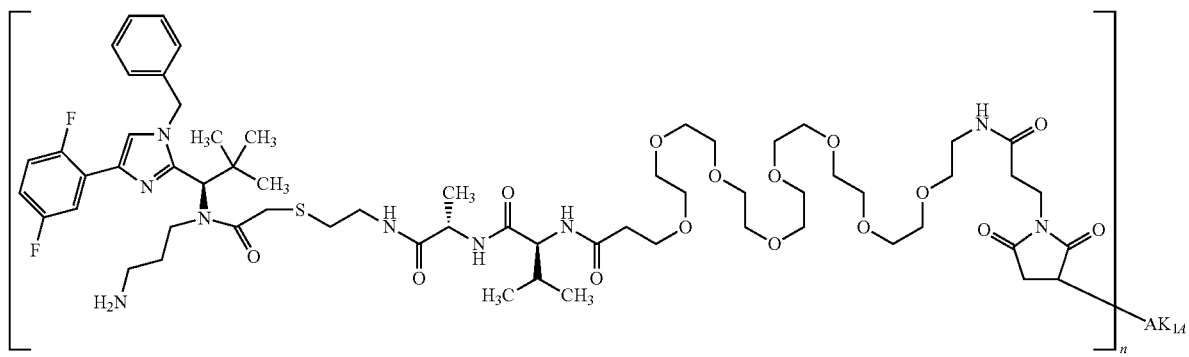

Here, 5.0 mg of cetuximab in PBS (c=15.33 mg/ml) were used for coupling with Intermediate F150, and the reaction was, after Sephadex purification, concentrated by ultracentrifugation and rediluted with PBS. Some of the ADC may also be present in the form of the hydrolysed open-chain succinamides attached to the antibody.

Protein concentration: 1.91 mg/ml
Drug/mAb ratio: 2.1

Example 150B

Here, 5.0 mg of anti-TWEAKR AK-1 antibody in PBS (c=12.87 mg/ml) were used for coupling with Intermediate F150, and the reaction was, after Sephadex purification, concentrated by ultracentrifugation and rediluted. Some of the ADC may also be present in the form of the hydrolysed open-chain succinamides attached to the antibody.

Protein concentration: 1.81 mg/ml
Drug/mAb ratio: 2.1

Example 150E

Here, 5.0 mg of trastuzumab antibody in PBS (c=13.50 mg/ml) were used for coupling with Intermediate F150, and the reaction was, after Sephadex purification, concentrated by ultracentrifugation and rediluted with PBS. Some of the ADC may also be present in the form of the hydrolysed open-chain succinamides attached to the antibody.

Protein concentration: 1.84 mg/ml
Drug/mAb ratio: 2.6

Example 151A

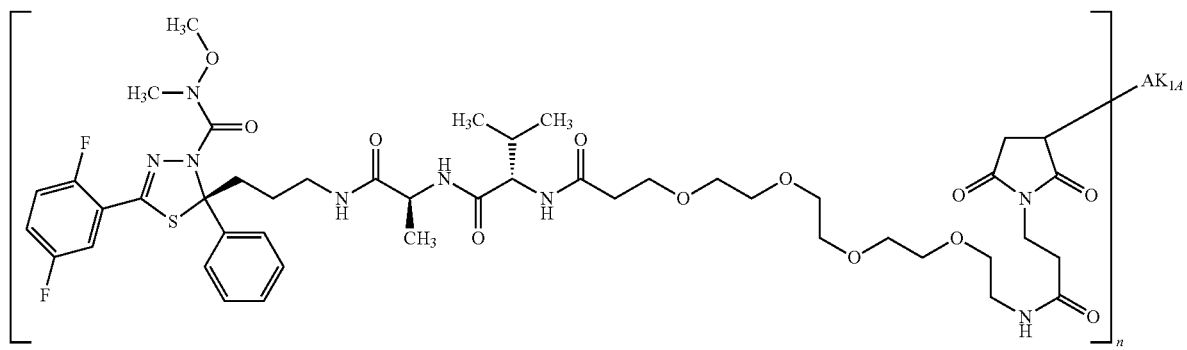

Here, 5.0 mg of cetuximab in PBS (c=16.90 mg/ml) were used for coupling with Intermediate F151, and the reaction was, after Sephadex purification, concentrated by ultracentrifugation and rediluted with PBS. Some of the ADC may also be present in the form of the hydrolysed open-chain succinamides attached to the antibody.

Protein concentration: 1.86 mg/ml
Drug/mAb ratio: 2.3

Example 151B

Here, 5.0 mg of anti-TWEAKR AK-1 antibody in PBS (c=12.87 mg/ml) were used for coupling with Intermediate F151, and the reaction was, after Sephadex purification, concentrated by ultracentrifugation and rediluted. Some of the ADC may also be present in the form of the hydrolysed open-chain succinamides attached to the antibody.

Protein concentration: 1.78 mg/ml
Drug/mAb ratio: 2.2

Example 151E

Here, 5.0 mg of trastuzumab antibody in PBS (c=16.90 mg/ml) were used for coupling with Intermediate F151, and the reaction was, after Sephadex purification, concentrated by ultracentrifugation and rediluted. Some of the ADC may also be present in the form of the hydrolysed open-chain succinamides attached to the antibody.

Protein concentration: 1.74 mg/ml
Drug/mAb ratio: 1.9

Example 152A

Here, 5.0 mg of cetuximab in PBS (c=16.90 mg/ml) were used for coupling with Intermediate F152, and the reaction was, after Sephadex purification, concentrated by ultracentrifugation and rediluted with PBS. Some of the ADC may also be present in the form of the hydrolysed open-chain succinamides attached to the antibody.

Protein concentration: 1.80 mg/ml
Drug/mAb ratio: 2.3

Example 152B

Here, 5.0 mg of anti-TWEAKR AK-1 antibody in PBS (c=12.87 mg/ml) were used for coupling with Intermediate F152, and the reaction was, after Sephadex purification, concentrated by ultracentrifugation and rediluted. Some of the ADC may also be present in the form of the hydrolysed open-chain succinamides attached to the antibody.

Protein concentration: 1.77 mg/ml
Drug/mAb ratio: 2.3

Example 152E

Here, 5.0 mg of trastuzumab antibody in PBS (c=16.90 mg/ml) were used for coupling with Intermediate F152, and the reaction was, after Sephadex purification, concentrated by ultracentrifugation and rediluted. Some of the ADC may also be present in the form of the hydrolysed open-chain succinamides attached to the antibody.

Protein concentration: 1.69 mg/ml
Drug/mAb ratio: 2.9

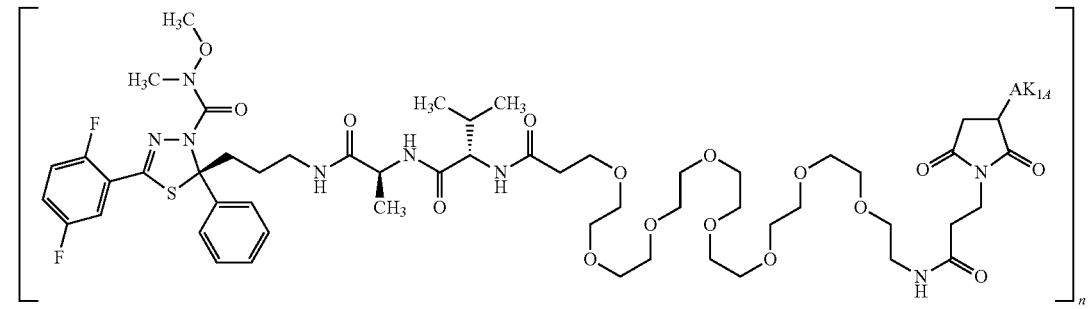

Example 153A

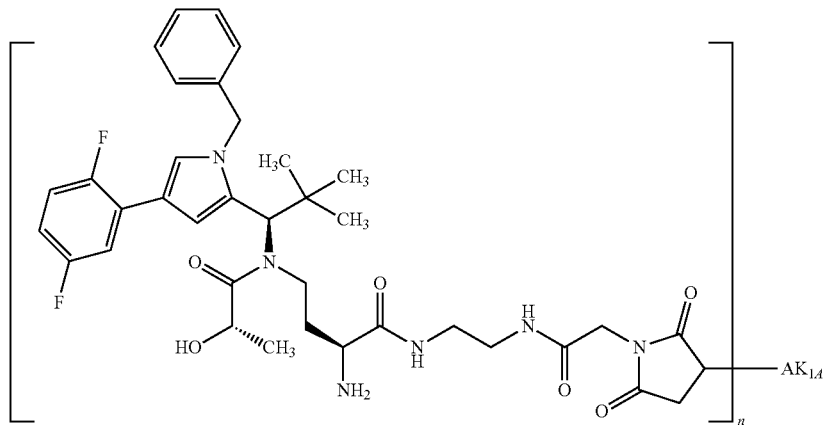

Here, 5 mg of cetuximab in PBS (c=21.32 mg/ml) were used for coupling with Intermediate F153, and the reaction was, after Sephadex purification, concentrated by ultracentrifugation and rediluted with PBS. Some of the ADC may also be present in the form of the hydrolysed open-chain succinamides attached to the antibody.
Protein concentration: 1.93 mg/ml
Drug/mAb ratio: 3.2

Example 153B

Here, 5 mg of anti-TWEAKR AK-1 in PBS (c=18.6 mg/ml) were used for coupling with Intermediate F153, and the reaction was, after Sephadex purification, concentrated by ultracentrifugation and rediluted with PBS. Some of the ADC may also be present in the form of the hydrolysed open-chain succinamides attached to the antibody.
Protein concentration: 1.71 mg/ml
Drug/mAb ratio: 2.8

Example 154A

Here, 5 mg of cetuximab in PBS (c=26.8 mg/ml) were used for coupling with Intermediate F154, and the reaction was, after Sephadex purification, concentrated by ultracentrifugation and rediluted with PBS.
Protein concentration: 2.34 mg/ml
Drug/mAb ratio: 3.6

Example 154B

Here, 5 mg of anti-TWEAKR AK-1 in PBS (c=12.9 mg/ml) were used for coupling with Intermediate F154, and the reaction was, after Sephadex purification, concentrated by ultracentrifugation and rediluted with PBS.
Protein concentration: 1.83 mg/ml
Drug/mAb ratio: 3.8

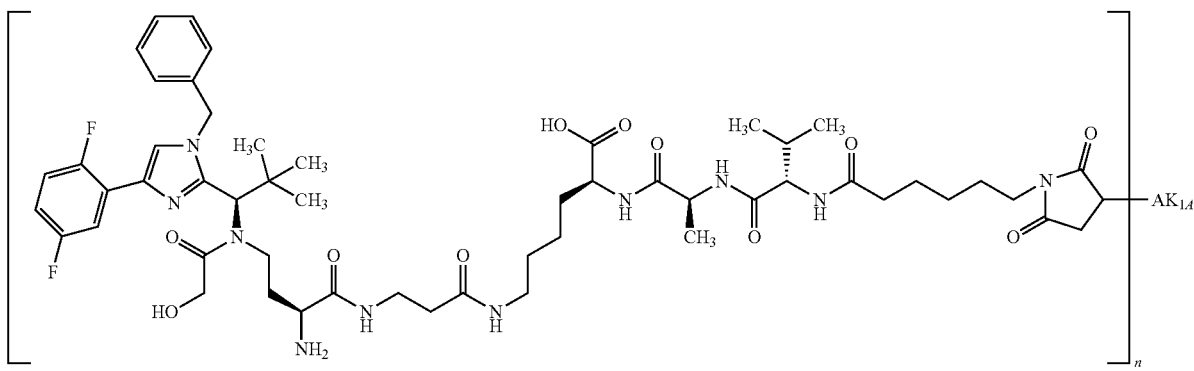

Example 155A

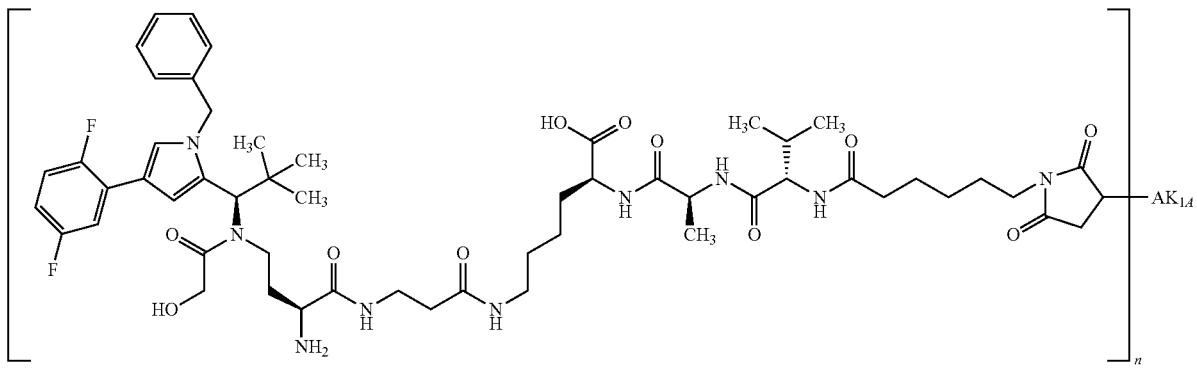

Here, 50 mg of cetuximab in PBS (c=8.51 mg/ml) were used for coupling with Intermediate F155, and the reaction was, after Sephadex purification, concentrated by ultracentrifugation, rediluted with PBS and concentrated again.
Protein concentration: 14.85 mg/ml
Drug/mAb ratio: 2.5

Example 155B

Here, 40 mg of anti-TWEAKR AK-1 in PBS (c=18.6 mg/ml) were used for coupling with Intermediate F155, and the reaction was, after Sephadex purification, concentrated by ultracentrifugation, rediluted with PBS and concentrated again.
Protein concentration: 11.25 mg/ml
Drug/mAb ratio: 3.1

Example 156A

Here, 5 mg of cetuximab in PBS (c=21.3 mg/ml) were used for coupling with Intermediate F156. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 1.83 mg/ml
Drug/mAb ratio: 3.6

Example 156B

Here, 5 mg of anti-TWEAKR AK-1 in PBS (c=18.6 mg/ml) were used for coupling with Intermediate F156, and the reaction was, after Sephadex purification, concentrated by ultracentrifugation and rediluted with PBS.
Protein concentration: 1.79 mg/ml
Drug/mAb ratio: 3.9

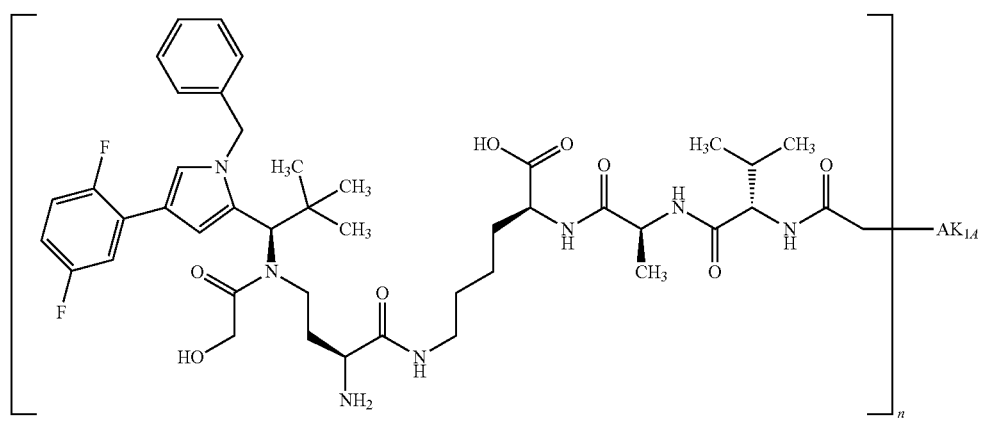

Example 156E

Here, 5 mg of trastuzumab in PBS (c=13.5 mg/ml) were used for coupling with Intermediate F156, and the reaction was, after Sephadex purification, concentrated by ultracentrifugation and rediluted with PBS.

Protein concentration: 1.91 mg/ml
Drug/mAb ratio: 4.2

Example 157

S-{1-[2-({[(1R,3S)-3-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine/trifluoroacetic acid (1:1)

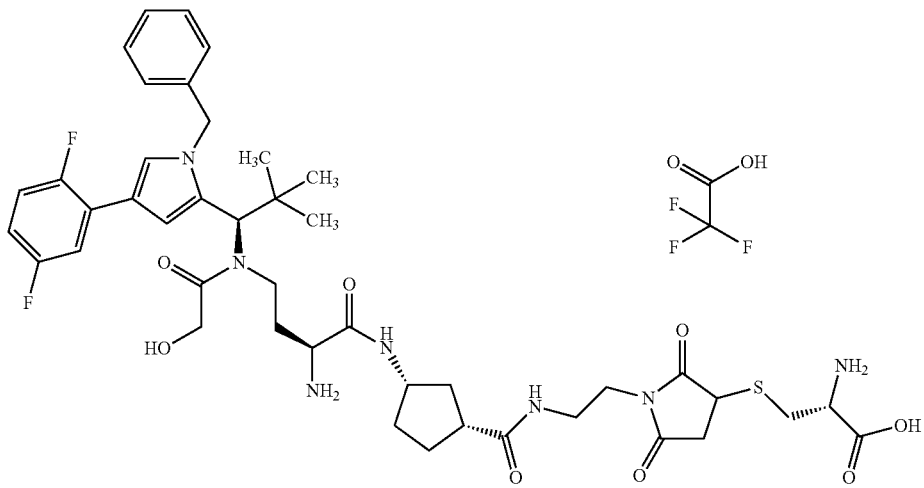 [SMILES: CC(C)(C)[C@H](c1cc(-c2cc(F)ccc2F)cn1Cc1ccccc1)N(CC[C@H](N)C(=O)N[C@H]1CC[C@@H](C(=O)NCCN2C(=O)CC(SC[C@H](N)C(=O)O)C2=O)C1)C(=O)CO ; O=C(O)C(F)(F)F]

2 mg (2 µmol) of Intermediate F125 were taken up in 2 ml of DMF/water 10:1, and 0.8 mg (6 µmol) of L-cysteine were added. The reaction mixture was stirred at RT for 20 h, then concentrated under reduced pressure and then purified by preparative HPLC.

LC-MS (Method 1): $R_t$=0.81 min; MS (EIpos): m/z=868 [M+H]$^+$.

Example 158

S-(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine/trifluoroacetic acid (1:1)

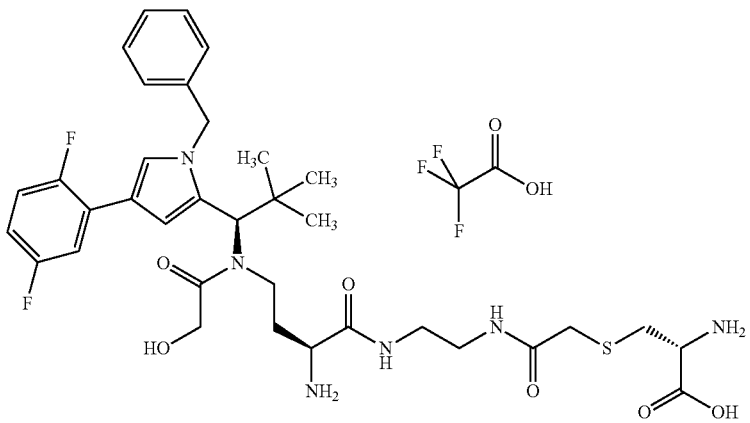 [SMILES: CC(C)(C)[C@H](c1cc(-c2cc(F)ccc2F)cn1Cc1ccccc1)N(CC[C@H](N)C(=O)NCCNC(=O)CSC[C@H](N)C(=O)O)C(=O)CO ; O=C(O)C(F)(F)F]

6 mg (8 μmol) of Intermediate F119 were taken up in 3 ml of DMF, and 1.8 mg (15 μmol) of L-cysteine were added. The reaction mixture was stirred at RT for 6 h and then allowed to stand at RT for 3 days. The reaction was then concentrated under reduced pressure, and the product was purified by preparative HPLC.

LC-MS (Method 1): $R_t$=0.81 min; MS (ESIpos): m/z=717 (M+H)$^+$.

Example 159

N$^6$-(N-{(2S)-2-Amino-4-[{(1R)-1-[1-benzyl-4-(2,5-difluorophenyl)-1H-imidazol-2-yl]-2,2-dimethylpropyl}(glycoloyl)amino]butanoyl}-D-alanyl)-L-lysine/trifluoroacetic acid (1:1)

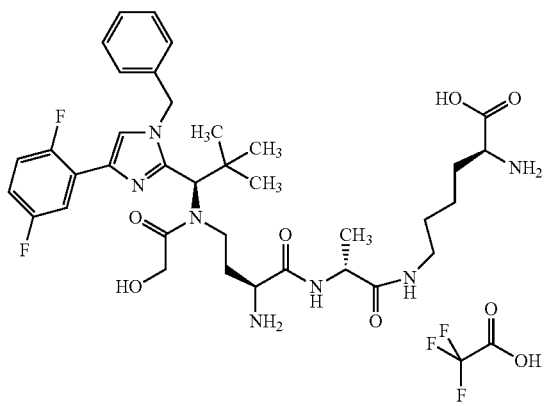 [SMILES: C[C@@H](NC(=O)[C@@H](N)CCN(C(=O)CO)[C@@H](c1nc(-c2cc(F)ccc2F)cn1Cc1ccccc1)C(C)(C)C)C(=O)NCCCC[C@H](N)C(=O)O ; O=C(O)C(F)(F)F]

First, starting with 2,5-dioxopyrrolidin-1-yl-N-[(benzyloxy)carbonyl]-D-alaninate and methyl N2-(tert-butoxycarbonyl)-L-lysinate, methyl N6-D-alanyl-N2-(tert-butoxycarbonyl)-L-lysinate was prepared using classical methods of peptide chemistry.

For the synthesis of the title compound, 8.4 mg (0.022 mmol) of this Intermediate were taken up in 4 ml of DMF, and 10 mg (0.015 mmol) of Intermediate C5 and 11 mg of HATU and 13 μl of N,N-diisopropylethylamine were added. After stirring at RT for 5 h, the reaction was purified by preparative HPLC. After concentration of the appropriate fractions and drying under a high vacuum, the intermediate obtained was dissolved in 4 ml of methanol, 83 μl of a 2M lithium hydroxide solution were added and the mixture was stirred at RT overnight. Another 167 μl of the lithium hydroxide solution were added, and the mixture was stirred for a further 4 h. The mixture was then diluted with water and adjusted to pH=5 with 5% strength citric acid. After concentration, the residue was purified by preparative HPLC. Concentration of the appropriate fractions and lyophilization of the residue from acetonitrile/water gave 3.5 mg (26% of theory) of the Boc-protected intermediate. By deprotection with 1 ml of trifluoroacetic acid in 2 ml of DCM, this gave 3 mg (95% of theory) of the title compound.

HPLC (Method 11): $R_t$=1.76 min;

LC-MS (Method 1): $R_t$=0.75 min; MS (ESIpos): m/z=714 (M+H)$^+$.

Example 160

N$^6$-(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N$^2$-N-{[6-(3-{[(2R)-2-amino-2-carboxyethyl]sulfanyl}-2,5-dioxopyrrolidin-1-yl)hexanoyl]-L-valyl-L-alanyl}-L-lysine/trifluoroacetic acid (1:1)

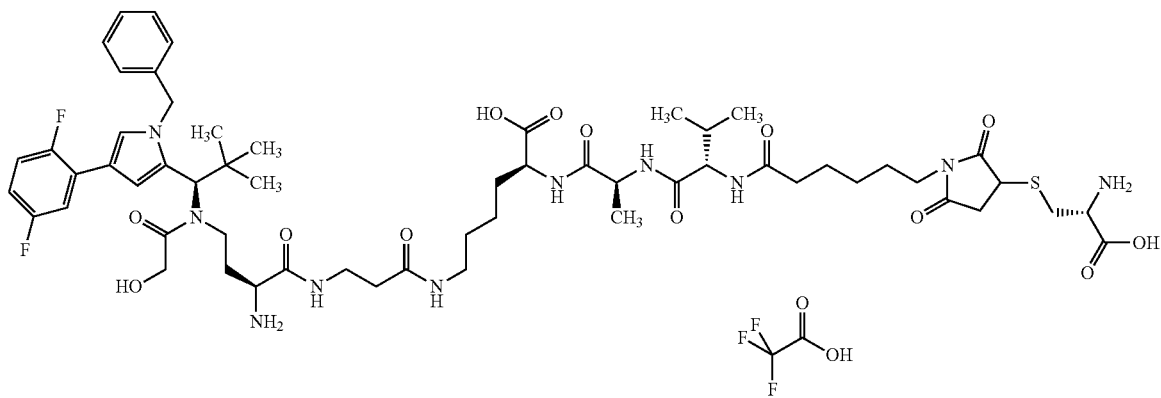 [SMILES: CC(C)[C@H](NC(=O)CCCCCN1C(=O)CC(SC[C@H](N)C(=O)O)C1=O)C(=O)N[C@@H](C)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

4 mg (3 μmol) of Intermediate F155 were taken up in 2.5 ml of DMF/water 10:1, and 1.2 mg (10 μmol) of L-cysteine were added. The reaction mixture was stirred at RT for 30 min, then concentrated under reduced pressure, taken up in acetonitrile/water 1:1 and then purified by preparative HPLC.

LC-MS (Method 1): $R_t$=0.81 min; MS (EIpos): m/z=1197 [M+H]$^+$.

Example 161

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1:1)

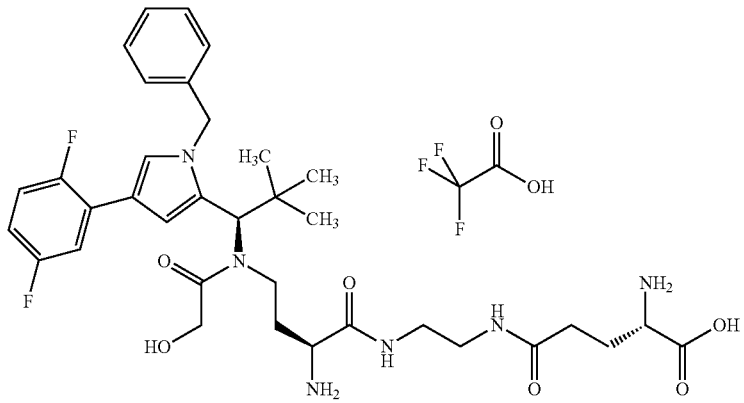 [SMILES: CC(C)(C)[C@H](c1cc(-c2cc(F)ccc2F)cn1Cc1ccccc1)N(CC[C@H](N)C(=O)NCCNC(=O)CC[C@H](N)C(=O)O)C(=O)CO ; O=C(O)C(F)(F)F]

First, trifluoroacetic acid/benzyl N-(2-aminoethyl)-$N^2$-[(benzyloxy)carbonyl]-L-glutaminate (1:1) was prepared using classical methods of peptide chemistry. In the presence of HATU, this intermediate was then coupled with Intermediate C58. Subsequently, first the benzyloxycarbonyl protective group and the benzyl ester were removed by hydrogenolytic cleavage, and then the 2-(trimethylsilyl)ethoxycarbonyl protective group was removed using zinc chloride.

LC-MS (Method 6): $R_t$=1.91 min; MS (EIpos): m/z=685 [M+H]$^+$.

Example 162

$N^6$-(N-(2S)-2-Amino-4-[{(1R)-1-[1-benzyl-4-(2,5-difluorophenyl)-1H-pyrrol-2-yl]-2,2-dimethylpropyl(glycoloyl)amino]butanoyl}-beta-alanyl)-L-lysine/trifluoroacetic acid (1:1)

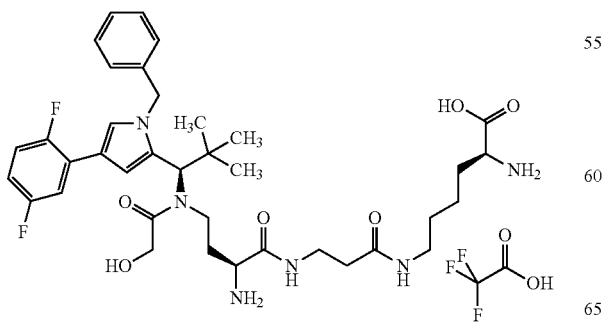

Initially, trifluoroacetic acid/2-(trimethylsilyl)ethyl-N2-[(benzyloxy)carbonyl]-L-lysinate (1:1) was prepared using classical protective group operations known in peptide chemistry. In the presence of HATU, this intermediate was then coupled with Intermediate C61. Subsequently, first the 2-(trimethylsilyl)ethoxycarbonyl protective group and the 2-(trimethylsilyl)ethyl ester were cleaved using zinc chloride. Finally, the title compound was obtained by hydrogenolytical cleavage of the benzyloxycarbonyl protective group and purification by preparative HPLC.

HPLC (Method 11): $R_t$=1.65 min;

LC-MS (Method 1): $R_t$=0.76 min; MS (EIpos): m/z=713 [M+H]$^+$.

Example 163A

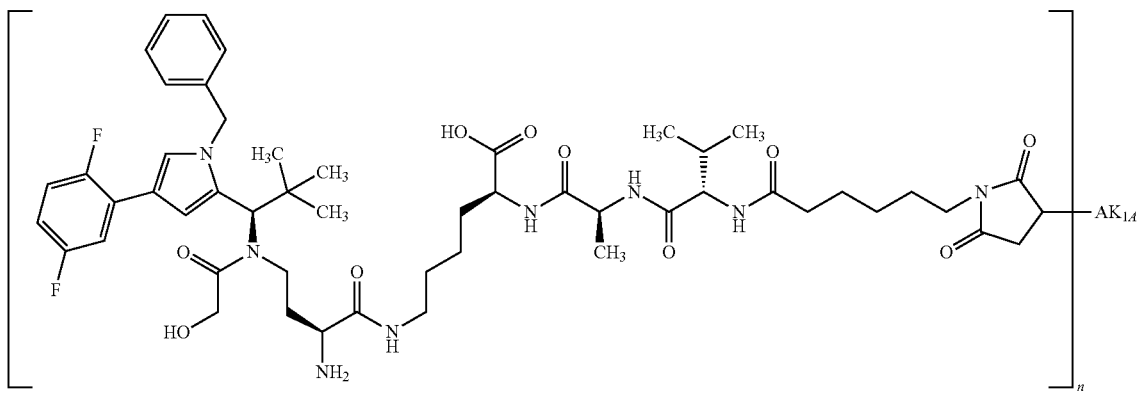

Here, 5 mg of cetuximab in PBS (c=11.3 mg/ml) were used for coupling with Intermediate F163, and the reaction was, after Sephadex purification, concentrated by ultracentrifugation and rediluted with PBS.

Protein concentration: 2.02 mg/ml
Drug/mAb ratio: 3.3

Example 163B

Here, 5 mg of anti-TWEAKR AK-1 in PBS (c=12.9 mg/ml) were used for coupling with Intermediate F163, and the reaction was, after Sephadex purification, concentrated by ultracentrifugation and rediluted with PBS.

Protein concentration: 1.76 mg/ml
Drug/mAb ratio: 2.5

Example 163H

Here, 5.0 mg of panitumumab in PBS (c=10 mg/ml) were used for coupling with Intermediate F163. The reduction time with TCEP was 30 min and the stirring time for the ADC coupling was 2 h. After Sephadex purification, the reaction was concentrated by ultracentrifugation and rediluted with PBS.

Protein concentration: 1.61 mg/ml
Drug/mAb ratio: 2.6

Example 164A

Here, 5 mg of cetuximab in PBS (c=16.9 mg/ml) were used for coupling with Intermediate F164, and the reaction was, after Sephadex purification, concentrated by ultracentrifugation and rediluted with PBS.

Protein concentration: 2.15 mg/ml
Drug/mAb ratio: 3.5

Example 164B

Here, 30 mg of anti-TWEAKR AK-1 in PBS (c=18.6 mg/ml) were used for coupling with Intermediate F164, and the reaction was, after Sephadex purification, concentrated by ultracentrifugation, rediluted with PBS and concentrated again.

Protein concentration: 14.8 mg/ml
Drug/mAb ratio: 2.8

Example 164E

Here, 5 mg of trastuzumab in PBS (c=13.5 mg/ml) were used for coupling with Intermediate F164, and the reaction was, after Sephadex purification, concentrated by ultracentrifugation and rediluted with PBS.

Protein concentration: 2.11 mg/ml
Drug/mAb ratio: 3.8

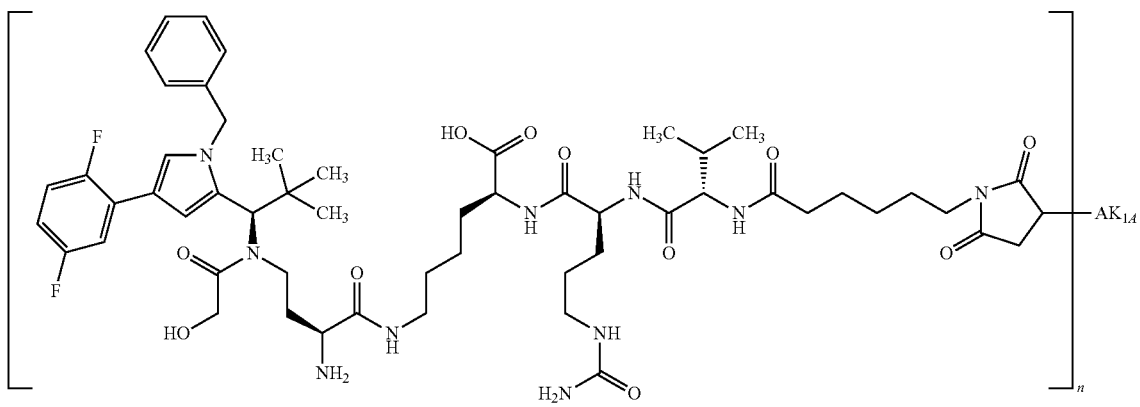

Example 165A

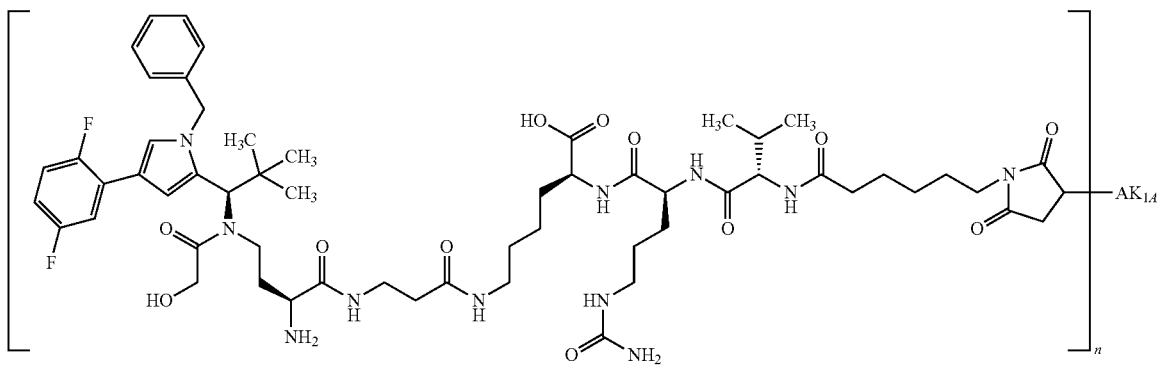

Here, 5 mg of cetuximab in PBS (c=16.9 mg/ml) were used for coupling with Intermediate F165, and the reaction was, after Sephadex purification, concentrated by ultracentrifugation and rediluted with PBS.
Protein concentration: 1.93 mg/ml
Drug/mAb ratio: 3.4

Example 165B

Here, 40 mg of anti-TWEAKR AK-1 in PBS (c=12.9 mg/ml) were used for coupling with Intermediate F165, and the reaction was, after Sephadex purification, concentrated by ultracentrifugation, rediluted with PBS and concentrated again.
Protein concentration: 12.02 mg/ml
Drug/mAb ratio: 3.3

Example 165E

Here, 5 mg of trastuzumab in PBS (c=13.5 mg/ml) were used for coupling with Intermediate F165, and the reaction was, after Sephadex purification, concentrated by ultracentrifugation and rediluted with PBS.
Protein concentration: 1.94 mg/ml
Drug/mAb ratio: 3.5

Example 166A

Here, 5 mg of cetuximab in PBS (c=21.3 mg/ml) were used for coupling with Intermediate F166, and the reaction was, after Sephadex purification, concentrated by ultracentrifugation and rediluted with PBS.
Protein concentration: 2.0 mg/ml
Drug/mAb ratio: 3.0

Example 166B

Here, 5 mg of anti-TWEAKR AK-1 in PBS (c=18.6 mg/ml) were used for coupling with Intermediate F166, and the reaction was, after Sephadex purification, concentrated by ultracentrifugation and rediluted with PBS.
Protein concentration: 1.76 mg/ml
Drug/mAb ratio: 3.4

Example 166E

Here, 5 mg of trastuzumab in PBS (c=13.5 mg/ml) were used for coupling with Intermediate F166, and the reaction was, after Sephadex purification, concentrated by ultracentrifugation and rediluted with PBS.
Protein concentration: 2.01 mg/ml
Drug/mAb ratio: 3.6

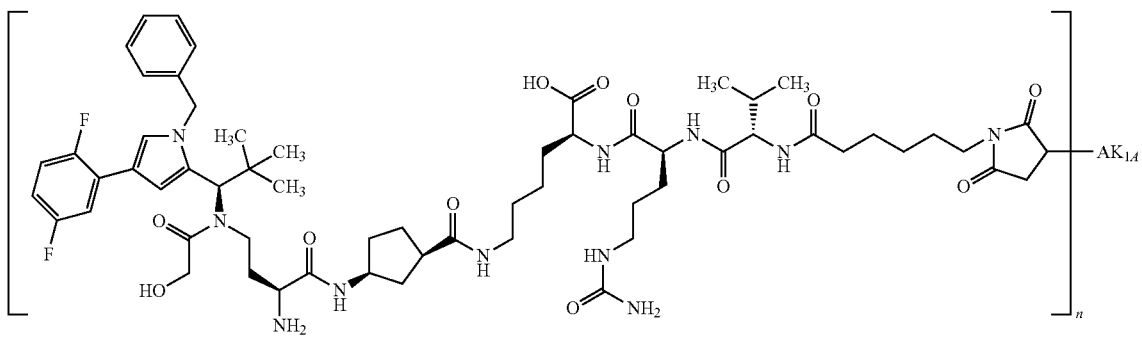

Example 167A

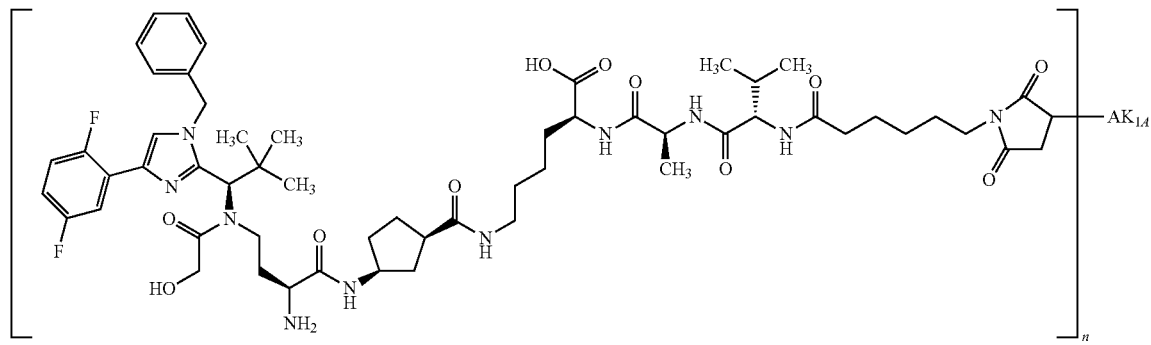

Here, 5 mg of cetuximab in PBS (c=16.9 mg/ml) were used for coupling with Intermediate F167, and the reaction was, after Sephadex purification, concentrated by ultracentrifugation and rediluted with PBS.

Protein concentration: 2.05 mg/ml
Drug/mAb ratio: 3.0

Example 167B

Here, 5 mg of anti-TWEAKR AK-1 in PBS (c=12.9 mg/ml) were used for coupling with Intermediate F167, and the reaction was, after Sephadex purification, concentrated by ultracentrifugation and rediluted with PBS.

Protein concentration: 1.76 mg/ml
Drug/mAb ratio: 2.9

Example 167E

Here, 5 mg of trastuzumab in PBS (c=13.5 mg/ml) were used for coupling with Intermediate F167, and the reaction was, after Sephadex purification, concentrated by ultracentrifugation and rediluted with PBS.

Protein concentration: 1.9 mg/ml
Drug/mAb ratio: 3.6

Example 168A

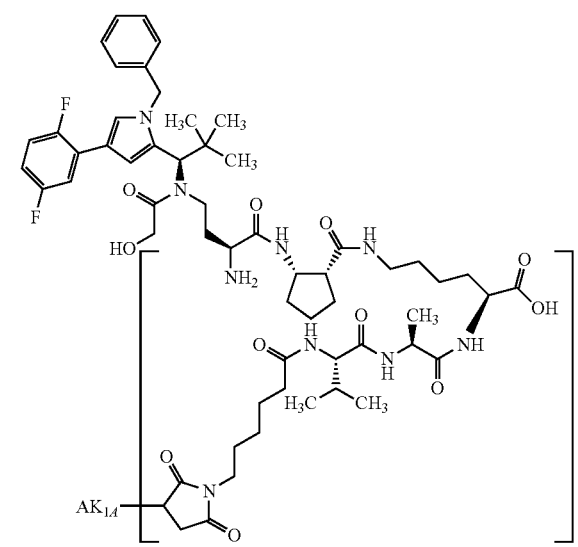

Here, 5 mg of cetuximab in PBS (c=11.3 mg/ml) were used for coupling with Intermediate F168, and the reaction was, after Sephadex purification, concentrated by ultracentrifugation and rediluted with PBS.

Protein concentration: 1.94 mg/ml
Drug/mAb ratio: 3.0

Example 168B

Here, 5 mg of anti-TWEAKR AK-1 in PBS (c=12.9 mg/ml) were used for coupling with Intermediate F168, and the reaction was, after Sephadex purification, concentrated by ultracentrifugation and rediluted with PBS.

Protein concentration: 1.33 mg/ml
Drug/mAb ratio: 2.8

Example 168E

Here, 5 mg of trastuzumab in PBS (c=13.5 mg/ml) were used for coupling with Intermediate F168, and the reaction was, after Sephadex purification, concentrated by ultracentrifugation and rediluted with PBS.

Protein concentration: 1.89 mg/ml
Drug/mAb ratio: 3.0

Example 168H

Here, 5.0 mg of panitumumab in PBS (c=10 mg/ml) were used for coupling with Intermediate F168. The reduction time with TCEP was 4 h and the stirring time for the ADC coupling was 20 h. After Sephadex purification, the reaction was concentrated by ultracentrifugation and rediluted with PBS.

Protein concentration: 1.76 mg/ml
Drug/mAb ratio: 2.8

Example 169A

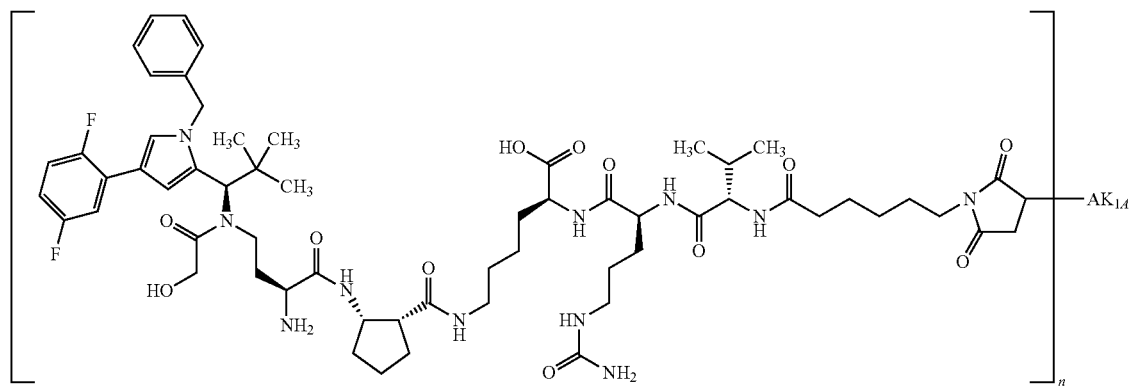

Here, 5 mg of cetuximab in PBS (c=16.9 mg/ml) were used for coupling with Intermediate F169, and the reaction was, after Sephadex purification, concentrated by ultracentrifugation and rediluted with PBS.
Protein concentration: 1.98 mg/ml
Drug/mAb ratio: 3.4

Example 169B

Here, 40 mg of anti-TWEAKR AK-1 in PBS (c=18.6 mg/ml) were used for coupling with Intermediate F169, and the reaction was, after Sephadex purification, concentrated by ultracentrifugation, rediluted with PBS and concentrated again.
Protein concentration: 11.2 mg/ml
Drug/mAb ratio: 2.4

Example 169E

Here, 5 mg of trastuzumab in PBS (c=13.5 mg/ml) were used for coupling with Intermediate F169, and the reaction was, after Sephadex purification, concentrated by ultracentrifugation and rediluted with PBS.
Protein concentration: 1.95 mg/ml
Drug/mAb ratio: 3.7

Example 170A

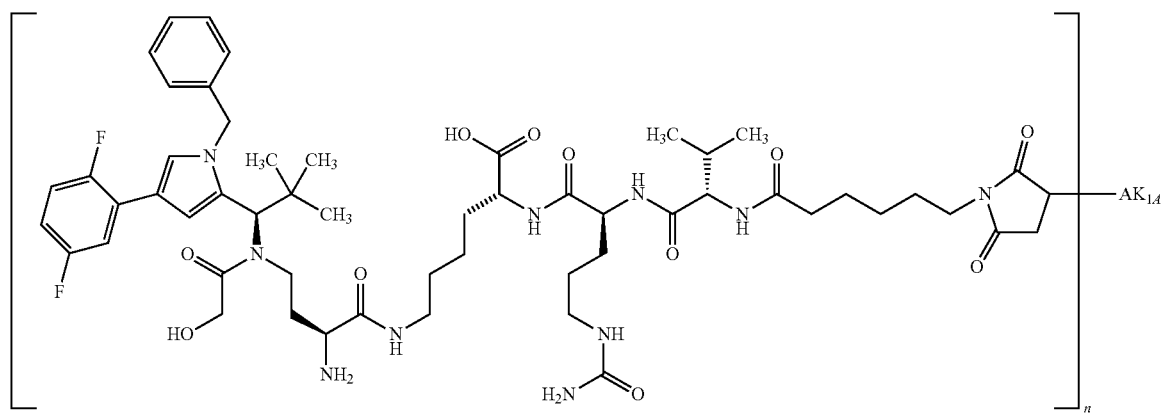

Here, 5 mg of cetuximab in PBS (c=16.9 mg/ml) were used for coupling with Intermediate F170, and the reaction was, after Sephadex purification, concentrated by ultracentrifugation and rediluted with PBS.
Protein concentration: 1.91 mg/ml
Drug/mAb ratio: 2.9

Example 170B

Here, 5 mg of anti-TWEAKR AK-1 in PBS (c=12.9 mg/ml) were used for coupling with Intermediate F170, and the reaction was, after Sephadex purification, concentrated by ultracentrifugation and rediluted with PBS.

Protein concentration: 1.72 mg/ml
Drug/mAb ratio: 3.07

Example 170E

Here, 5 mg of trastuzumab in PBS (c=13.5 mg/ml) were used for coupling with Intermediate F170, and the reaction was, after Sephadex purification, concentrated by ultracentrifugation and rediluted with PBS.
Protein concentration: 1.84 mg/ml
Drug/mAb ratio: 3.3

Example 171A

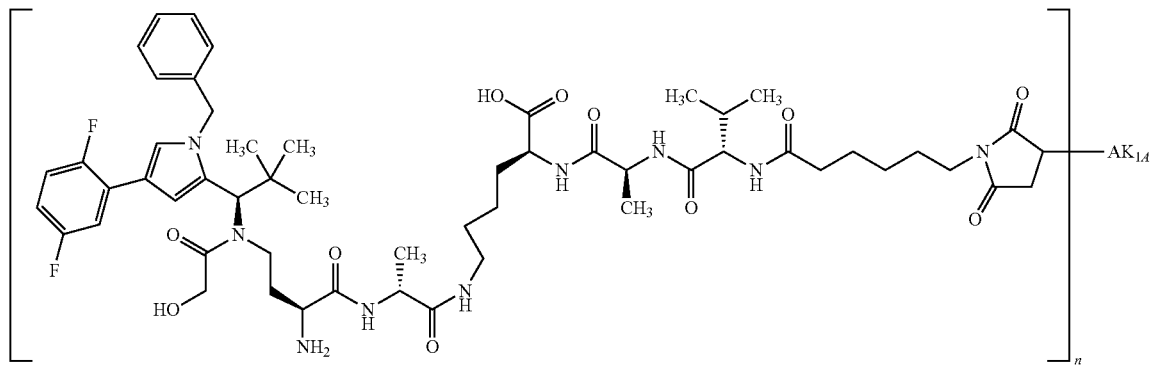

Here, 5 mg of cetuximab in PBS (c=11.3 mg/ml) were used for coupling with Intermediate F171, and the reaction was, after Sephadex purification, concentrated by ultracentrifugation and rediluted with PBS.
Protein concentration: 1.94 mg/ml
Drug/mAb ratio: 2.5

Example 171B

Here, 5 mg of anti-TWEAKR AK-1 in PBS (c=12.9 mg/ml) were used for coupling with Intermediate F171, and the reaction was, after Sephadex purification, concentrated by ultracentrifugation and rediluted with PBS.
Protein concentration: 1.58 mg/ml
Drug/mAb ratio: 2.7

Example 172A

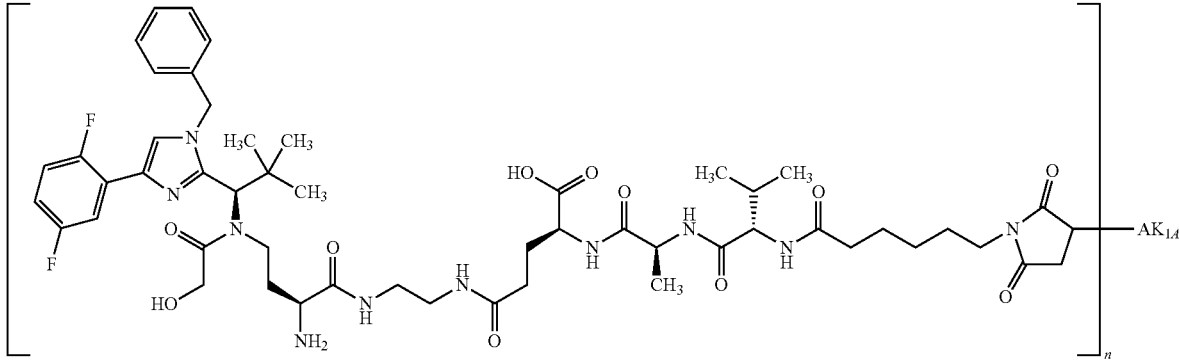

Here, 5 mg of cetuximab in PBS (c=11.3 mg/ml) were used for coupling with Intermediate F172, and the reaction was, after Sephadex purification, concentrated by ultracentrifugation and rediluted with PBS.
Protein concentration: 1.96 mg/ml
Drug/mAb ratio: 3.1

Example 172B

Here, 5 mg of anti-TWEAKR AK-1 in PBS (c=18.6 mg/ml) were used for coupling with Intermediate F172, and the reaction was, after Sephadex purification, concentrated by ultracentrifugation and rediluted with PBS.
Protein concentration: 1.85 mg/ml
Drug/mAb ratio: 3.1

Example 172E

Here, 5 mg of trastuzumab in PBS (c=13.5 mg/ml) were used for coupling with Intermediate F172, and the reaction was, after Sephadex purification, concentrated by ultracentrifugation and rediluted with PBS.
Protein concentration: 1.92 mg/ml
Drug/mAb ratio: 3.3

Example 173A

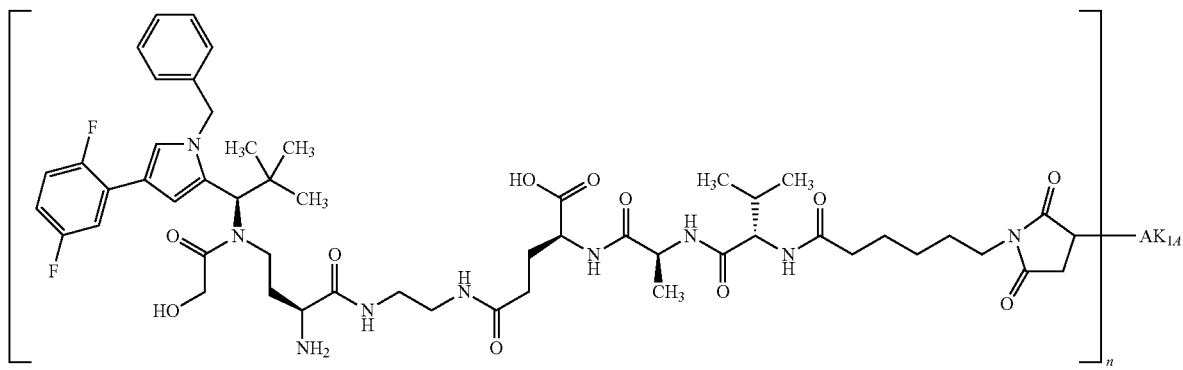

Here, 5 mg of cetuximab in PBS (c=11.3 mg/ml) were used for coupling with Intermediate F173, and the reaction was, after Sephadex purification, concentrated by ultracentrifugation and rediluted with PBS.
Protein concentration: 2.1 mg/ml
Drug/mAb ratio: 3.6

Example 173B

Here, 5 mg of anti-TWEAKR AK-1 in PBS (c=18.6 mg/ml) were used for coupling with Intermediate F173, and the reaction was, after Sephadex purification, concentrated by ultracentrifugation, rediluted with PBS and concentrated again.

Protein concentration: 12.26 mg/ml
Drug/mAb ratio: 3.4

Example 173E

Here, 5 mg of trastuzumab in PBS (c=13.5 mg/ml) were used for coupling with Intermediate F173, and the reaction was, after Sephadex purification, concentrated by ultracentrifugation and rediluted with PBS.
Protein concentration: 2.33 mg/ml
Drug/mAb ratio: 3.9

Example 174A

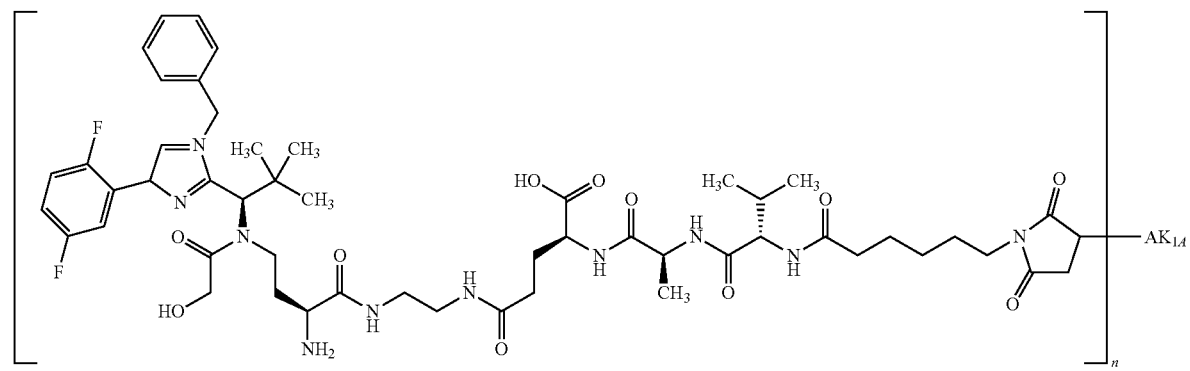

Here, 5 mg of cetuximab in PBS (c=11.3 mg/ml) were used for coupling with Intermediate F174, and the reaction was, after Sephadex purification, concentrated by ultracentrifugation and rediluted with PBS.
Protein concentration: 2.18 mg/ml
Drug/mAb ratio: 3.1

Example 174B

Here, 5 mg of anti-TWEAKR AK-1 in PBS (c=18.6 mg/ml) were used for coupling with Intermediate F174, and the reaction was, after Sephadex purification, concentrated by ultracentrifugation and rediluted with PBS.
Protein concentration: 1.99 mg/ml
Drug/mAb ratio: 3.1

Example 174E

Here, 5 mg of trastuzumab in PBS (c=13.5 mg/ml) were used for coupling with Intermediate F174, and the reaction was, after Sephadex purification, concentrated by ultracentrifugation and rediluted with PBS.
Protein concentration: 2.03 mg/ml
Drug/mAb ratio: 3.5

Example 175A

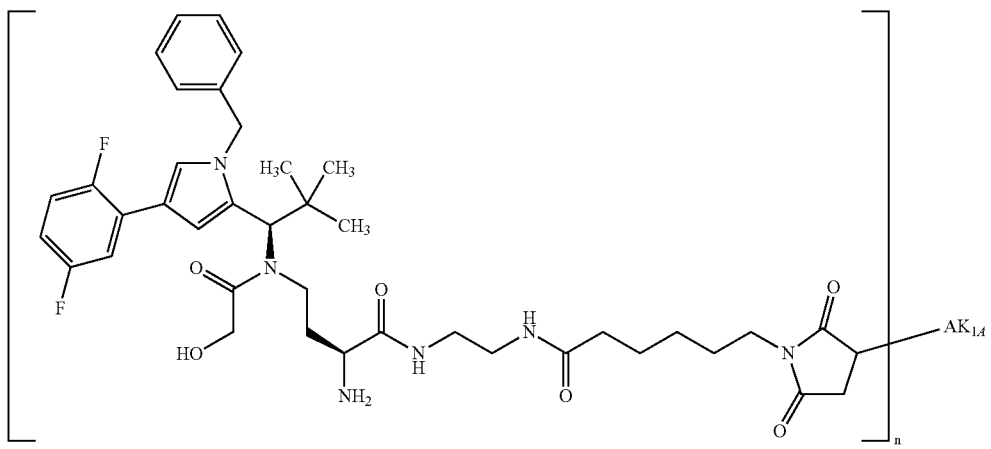

Here, 5 mg of cetuximab in PBS (c=16.9 mg/ml) were used for coupling with Intermediate F175, and the reaction was, after Sephadex purification, concentrated by ultracentrifugation and rediluted with PBS.
Protein concentration: 1.98 mg/ml
Drug/mAb ratio: 3.8

Example 175B

Here, 40 mg of anti-TWEAKR AK-1 in PBS (c=18.6 mg/ml) were used for coupling with Intermediate F175, and the reaction was, after Sephadex purification, concentrated by ultracentrifugation, rediluted with PBS and concentrated again.
Protein concentration: 9.8 mg/ml
Drug/mAb ratio: 2.8

Example 175E

Here, 5.0 mg of trastuzumab antibody in PBS (c=13.5 mg/ml) were used for coupling with Intermediate F175, and the reaction was, after Sephadex purification, concentrated by ultracentrifugation and rediluted with PBS.
Protein concentration: 1.97 mg/ml
Drug/mAb ratio: 4.2

Example 176A

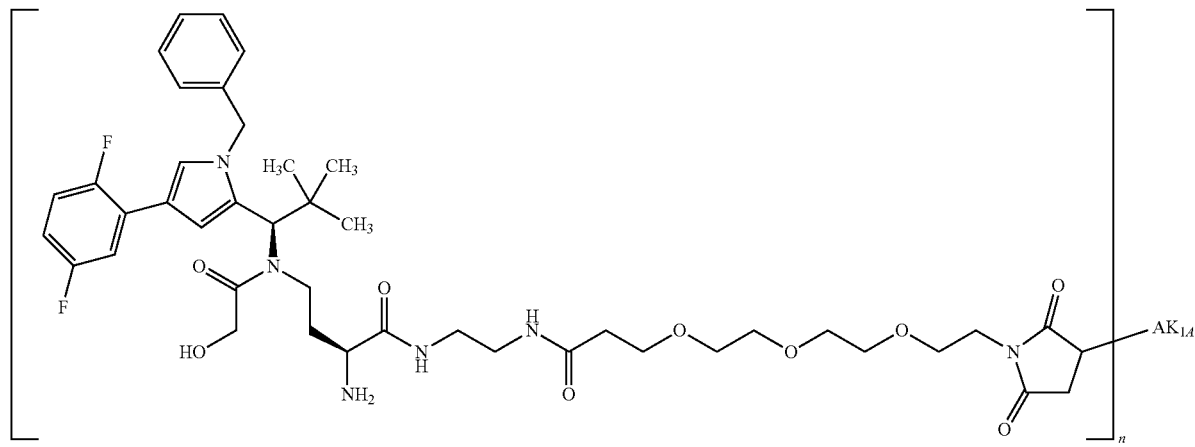

Here, 5 mg of cetuximab in PBS (c=21.3 mg/ml) were used for coupling with Intermediate F176, and the reaction was, after Sephadex purification, concentrated by ultracentrifugation and rediluted with PBS. Some of the ADC may also be present in the form of the hydrolysed open-chain succinamides attached to the antibody.
Protein concentration: 1.98 mg/ml
Drug/mAb ratio: 2.6

Example 176B

Here, 5 mg of anti-TWEAKR AK-1 in PBS (c=18.6 mg/ml) were used for coupling with Intermediate F176, and the reaction was, after Sephadex purification, concentrated by ultracentrifugation and rediluted with PBS. Some of the ADC may also be present in the form of the hydrolysed open-chain succinamides attached to the antibody.

Protein concentration: 1.93 mg/ml
Drug/mAb ratio: 2.8

Example 176E

Here, 5.0 mg of trastuzumab antibody in PBS (c=13.5 mg/ml) were used for coupling with Intermediate F176, and the reaction was, after Sephadex purification, concentrated by ultracentrifugation and rediluted with PBS. Some of the ADC may also be present in the form of the hydrolysed open-chain succinamides attached to the antibody.
Protein concentration: 1.85 mg/ml
Drug/mAb ratio: 3.3

Example 177A

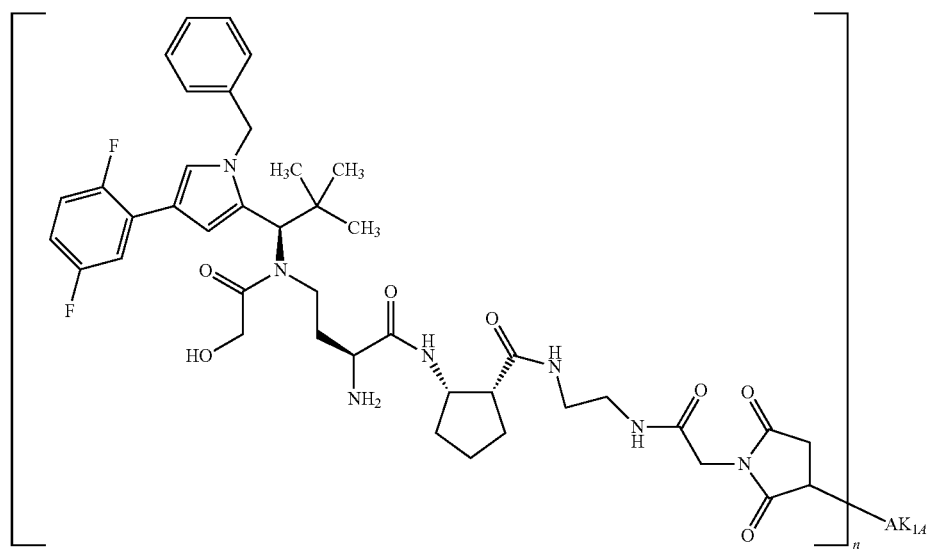

Here, 5 mg of cetuximab in PBS (c=21.3 mg/ml) were used for coupling with Intermediate F177, and the reaction was, after Sephadex purification, concentrated by ultracentrifugation and rediluted with PBS. Some of the ADC may also be present in the form of the hydrolysed open-chain succinamides attached to the antibody.
Protein concentration: 1.96 mg/ml
Drug/mAb ratio: 2.8

Example 177B

Here, 5 mg of anti-TWEAKR AK-1 in PBS (c=18.6 mg/ml) were used for coupling with Intermediate F177, and the reaction was, after Sephadex purification, concentrated by ultracentrifugation and rediluted with PBS. Some of the ADC may also be present in the form of the hydrolysed open-chain succinamides attached to the antibody.
Protein concentration: 1.2 mg/ml
Drug/mAb ratio: 2.3

Example 177E

Here, 5 mg of trastuzumab in PBS (c=13.5 mg/ml) were used for coupling with Intermediate F177, and the reaction was, after Sephadex purification, concentrated by ultracentrifugation and rediluted with PBS. Some of the ADC may also be present in the form of the hydrolysed open-chain succinamides attached to the antibody.
Protein concentration: 1.83 mg/ml
Drug/mAb ratio: 3.1

Example 178A

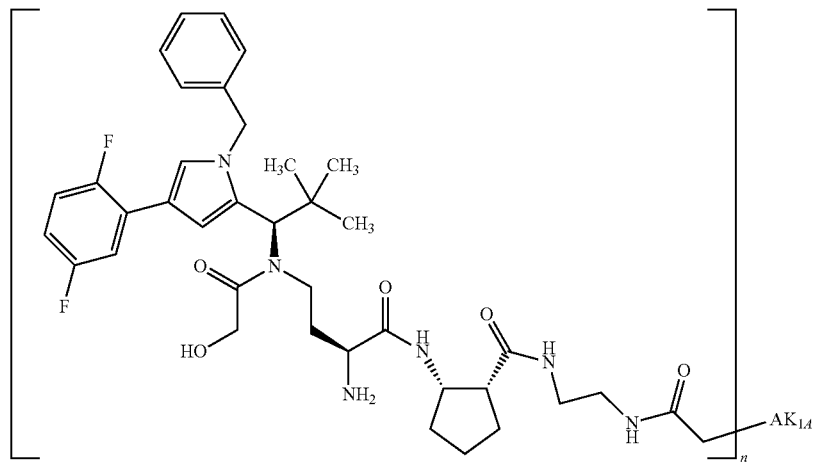

Here, 5 mg of cetuximab in PBS (c=21.3 mg/ml) were used for coupling with Intermediate F178, and the reaction was, after Sephadex purification, concentrated by ultracentrifugation and rediluted with PBS.
Protein concentration: 1.8 mg/ml
Drug/mAb ratio: 2.1

Example 178B

Here, 5 mg of anti-TWEAKR AK-1 in PBS (c=18.6 mg/ml) were used for coupling with Intermediate F178, and the reaction was, after Sephadex purification, concentrated by ultracentrifugation and rediluted with PBS.
Protein concentration: 1.45 mg/ml
Drug/mAb ratio: 2.4

Example 178E

Here, 5 mg of trastuzumab in PBS (c=13.5 mg/ml) were used for coupling with Intermediate F178, and the reaction was, after Sephadex purification, concentrated by ultracentrifugation and rediluted with PBS.
Protein concentration: 1.8 mg/ml
Drug/mAb ratio: 2.6

Example 179A

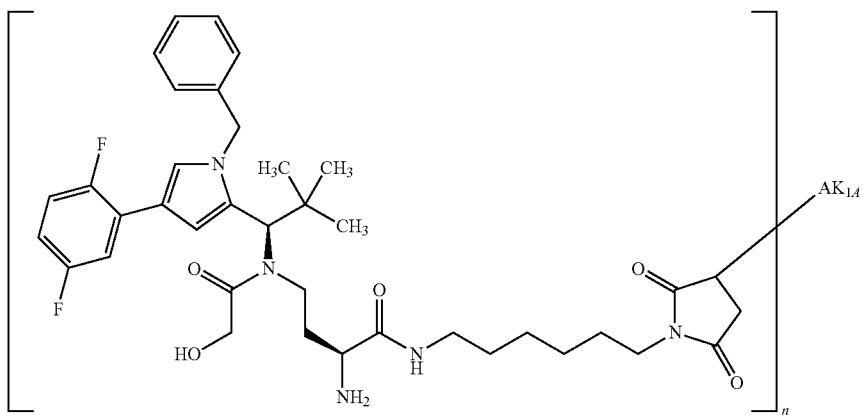

Here, 5 mg of cetuximab in PBS (c=11.3 mg/ml) were used for coupling with Intermediate F179, and the reaction was, after Sephadex purification, concentrated by ultracentrifugation and rediluted with PBS.
Protein concentration: 2.04 mg/ml
Drug/mAb ratio: 3.1

Example 179B

Here, 5 mg of anti-TWEAKR AK-1 in PBS (c=18.6 mg/ml) were used for coupling with Intermediate F179, and the reaction was, after Sephadex purification, concentrated by ultracentrifugation and rediluted with PBS.
Protein concentration: 1.65 mg/ml
Drug/mAb ratio: 3.1

Example 179E

Here, 5 mg of trastuzumab in PBS (c=13.5 mg/ml) were used for coupling with Intermediate F179, and the reaction was, after Sephadex purification, concentrated by ultracentrifugation and rediluted with PBS.
Protein concentration: 1.89 mg/ml
Drug/mAb ratio: 3.3

Example 180A

Here, 5 mg of cetuximab in PBS (c=8.51 mg/ml) were used for coupling with Intermediate F180, and the reaction was, after Sephadex purification, concentrated by ultracentrifugation and rediluted with PBS. Some of the ADC may also be present in the form of the hydrolysed open-chain succinamides attached to the antibody.
Protein concentration: 1.72 mg/ml
Drug/mAb ratio: 3.5

Example 180B

Here, 5 mg of anti-TWEAKR AK-1 in PBS (c=18.6 mg/ml) were used for coupling with Intermediate F180, and the reaction was, after Sephadex purification, concentrated by ultracentrifugation and rediluted with PBS. Some of the ADC may also be present in the form of the hydrolysed open-chain succinamides attached to the antibody.
Protein concentration: 1.82 mg/ml
Drug/mAb ratio: 3.4

Example 180E

Here, 5 mg of trastuzumab in PBS (c=13.5 mg/ml) were used for coupling with Intermediate F180, and the reaction was, after Sephadex purification, concentrated by ultracentrifugation and rediluted with PBS. Some of the ADC may also be present in the form of the hydrolysed open-chain succinamides attached to the antibody.
Protein concentration: 2.01 mg/ml
Drug/mAb ratio: 4.7

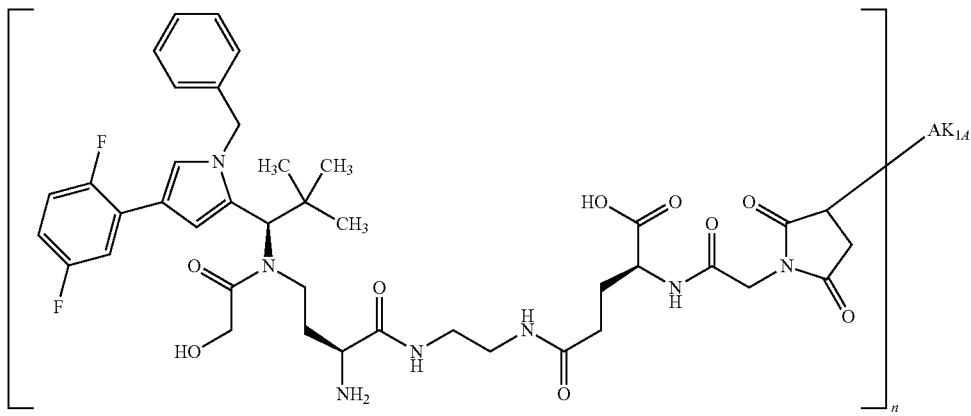

Example 181

N-(3-Aminopropyl)-N-{(1R)-1-[4-benzyl-1-(2,5-difluorophenyl)-1H-pyrazol-3-yl]-2,2-dimethylpropyl}acetamide

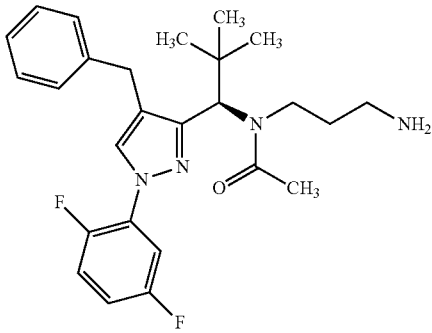 [SMILES: CC(=O)N(CCCN)[C@@H](c1nn(-c2cc(F)ccc2F)cc1Cc1ccccc1)C(C)(C)C]

1.01 g (2.84 mmol) of (1R)-1-[4-benzyl-1-(2,5-difluorophenyl)-1H-pyrazol-3-yl]-2,2-dimethylpropan-1-amine were initially charged in 20 ml of 1,2-dichloroethane, and 0.84 g (3.98 mmol) of sodium triacetoxyborohydride and 2.56 g (42.65 mmol) of acetic acid were added, and the mixture was stirred at RT for 5 min A solution of 0.54 g (3.13 mmol) of tert-butyl (3-oxopropyl)carbamate in 5 ml of 1,2-dichloroethane was then added, and the reaction mixture was stirred overnight. The mixture was then evaporated to dryness, the residue was taken up in ethyl acetate and filtered and the product-containing filtrate was evaporated to dryness.

51.26 mg of the residue were dissolved in 0.8 ml of 1,2-dichloromethane and added to 7.85 mg (0.1 mmol) of acetyl chloride on a deep 96-well multititre plate 25.8 mg (0.2 mmol) of N,N-diisopropylethylamine were then added and the mixture was shaken at RT overnight. The solvent was then removed completely using a centrifugal drier, 0.4 ml of 1,2-dichlorethane and 0.4 ml of trifluoroacetic acid were added and the mixture was shaken overnight. The solvent was then removed completely using a centrifugal drier, and 0.8 ml of DMF were added to the residue. The mixture was then filtered and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. This gave 12.2 mg (27% of theory; purity 100%) of the title compound.

LC-MS (Method 10): $R_t$=0.95 min; MS (ESIpos): m/z=455 [M+H]$^+$

The exemplary compounds shown in Table XA were prepared analogously to Example 181:

Table XA with Examples 182-185

| Example | IUPAC name/structure (Yield) | Analytical data |
| --- | --- | --- |
| 182 | N-(3-aminopropyl)-N-{(1R)-1-[4-benzyl-1-(2,5-difluorophenyl)-1H-pyrazol-3-yl]-2,2-dimethylpropyl}-2-methoxyacetamide | LC-MS (Method 10): $R_t$ = (195 min MS (ESpos): m/z = 485 (M + H)$^+$ |
| | 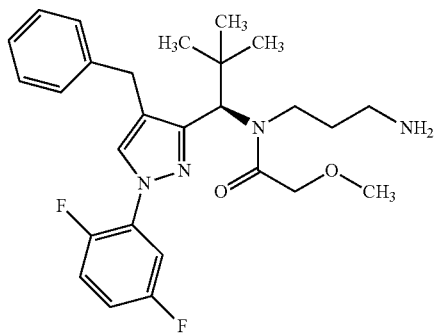 (14% of theory; purity 98%) | |
| 183 | N-(3-aminopropyl)-N-{(1R)-1-[4-benzyl-1-(2,5-difluorophenyl)-1H-pyrazol-3-yl]-2,2-dimethylpropyl}-2,4-difluorobenzamide | LC-MS (Method 10): $R_t$ = 1.02 min MS (ESpos): m/z = 553 (M + H)$^+$ |
| | 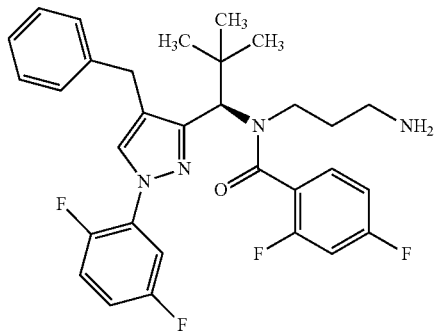 (20% of theory; purity 100%) | |

-continued

Table XA with Examples 182-185

| Example | IUPAC name/structure (Yield) | Analytical data |
|---|---|---|
| 184 | N-(3-aminopropyl)-N-{(1R)-1-[4-benzyl-1-(2,5-difluorophenyl)-1H-pyrazol-3-yl]-2,2-dimethylpropyl}-4-methylbenzamide<br>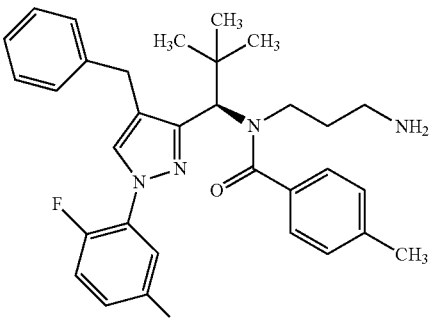<br>(14% of theory; purity 100%) | LC-MS (Method 10): $R_t$ = 1.04 min<br>MS (ESpos): m/z = 531 (M + H)$^+$ |
| 185 | N-(3-aminopropyl)-N-{(1R)-1-[4-benzyl-1-(2,5-difluorophenyl)-1H-pyrazol-3-yl]-2,2-dimethylpropyl}-2-ethoxyacetamide<br>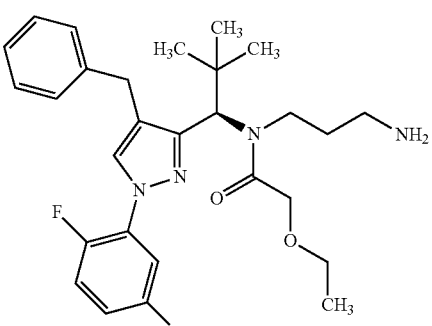<br>(3% of theory; purity 83%) | LC-MS (Method 10): $R_t$ = 0.98 min<br>MS (ESpos): m/z = 499 (M + H)$^+$ |

Example 186

N-(3-Aminopropyl)-N-{(1R)-1-[1-benzyl-4-(2,5-difluorophenyl)-1H-pyrrol-2-yl]-2,2-dimethylpropyl}-3,3,3-trifluoropropanamide

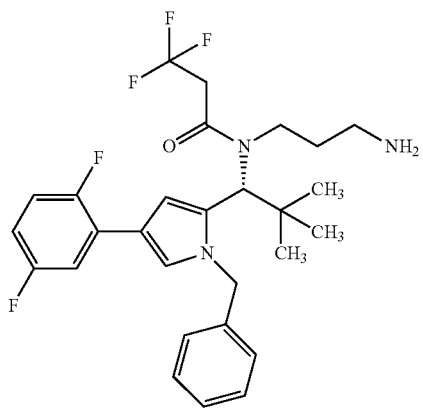 [SMILES: CC(C)(C)[C@H](c1cc(-c2cc(F)ccc2F)cn1Cc1ccccc1)N(CCCN)C(=O)CC(F)(F)F]

1.0 g (2.82 mmol) of (1R)-1-[1-benzyl-4-(2,5-difluorophenyl)-1H-pyrrol-2-yl]-2,2-dimethylpropan-1-amine were initially charged in 20 ml of 1,2-dichloroethane, and 1.4 g (3.95 mmol) of sodium triacetoxyborohydride and 2.54 g (42.32 mmol) of acetic acid were added, and the mixture was stirred at RT for 5 min A solution of 0.54 g (3.10 mmol) of tert-butyl (3-oxopropyl)carbamate in 5 ml of 1,2-dichloroethane was then added, and the reaction mixture was stirred overnight. The mixture was then evaporated to dryness, the residue was taken up in ethyl acetate and filtered and the product-containing filtrate was evaporated to dryness.

51.16 mg of the residue were dissolved in 0.8 ml of 1,2-dichloromethane and added to 14.65 mg (0.1 mmol) of 3,3,3-trifluoropropanoyl chloride on a deep 96-well multititre plate 25.8 mg (0.2 mmol) of N,N-diisopropylethylamine were then added and the mixture was shaken at RT overnight. The solvent was then removed completely using a centrifugal drier, 0.4 ml of 1,2-dichlorethane and 0.4 ml of trifluoroacetic acid were added and the mixture was shaken overnight. The solvent was then removed completely using a centrifugal drier, and 0.8 ml of DMF were added to the residue. The mixture was then filtered and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. This gave 1.0 mg (2% of theory; purity 82%) of the title compound.

LC-MS (Method 10): $R_t$=1.01 min MS (ESIpos): m/z=522 [M+H]$^+$

The exemplary compounds shown in Table XA1 were prepared analogously to Example 186:

| Example | IUPAC (Yield) | name/structure Analytical data |
|---|---|---|
| 187 | N-(3-aminopropyl)-N-{(1R)-1-[1-benzyl-4-(2,5-difluorophenyl)-1H-pyrrol-2-yl]-2,2-dimethylpropyl}-4-fluorobenzamide | LC-MS (Method 10): $R_t$ = 1.01 min MS (ESpos): m/z = 534 (M + H)$^+$ |

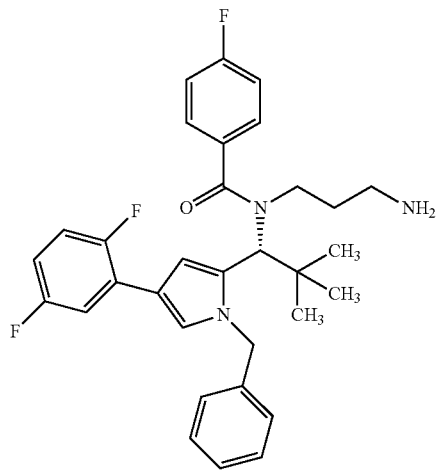

(3% of theory; purity 83%)

| 188 | N-(3-aminopropyl)-N-{(1R)1-[1-benzyl-4-(2,5-difluorophenyl)-1H-pyrrol-2-yl]-2,2-dimethylpropyl}acetamide | LC-MS (Method 10): $R_t$ = 0.94 min MS (ESpos): m/z = 454 (M + H)$^+$ |

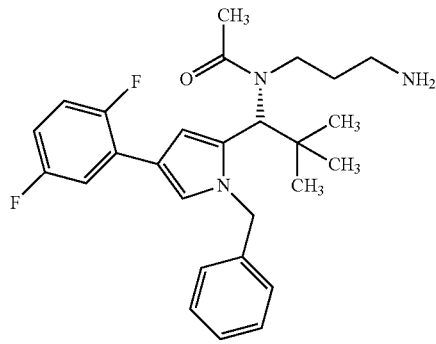

(2% of theory; purity 87%)

-continued

Table XAI with Examples 187-191

| Ex-ample | IUPAC (Yield) | name/structure Analytical data |
|---|---|---|
| 189 | N-(3-aminopropyl)-N-{(1R)-1-[1-benzyl-4-(2,5-difluorophenyl)-1H-pyrrol-2-yl]-2,2-dimethylpropyl}-4-(trifluoromethyl)benzamide | LC-MS (Method 10): $R_t$ = 1.05 min<br>MS (ESpos): m/z = 584 (M + H)$^+$ |

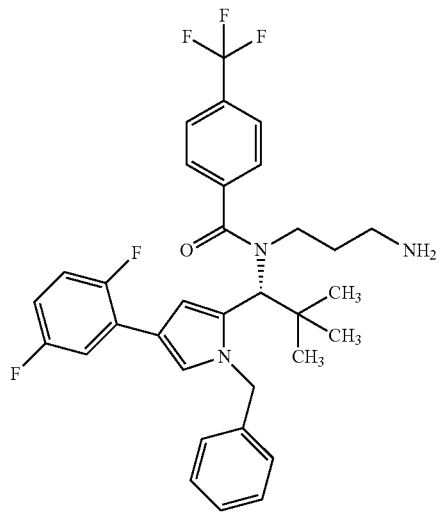

(6% of theory; purity 90%)

| 190 | N-(3-aminopropyl)-N-{(1R)-1-[4-benzyl-1-(2,5-difluorophenyl)-1H-pyrazol-3-yl]-2,2-dimethylpropyl}-2-ethoxyacetamide | LC-MS (Method 10): $R_t$ = 0.98 min<br>MS (ESpos): m/z = 552 (M + H)$^+$ |

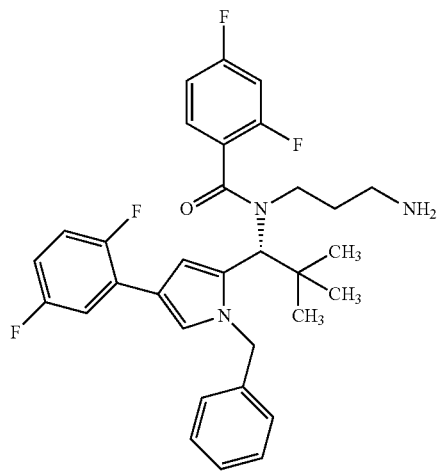

(7% of theory; purity 83%)

Table XAI with Examples 187-191

| Example | IUPAC (Yield) | name/structure Analytical data |
|---|---|---|
| 191 | N-(3-aminopropyl)-N-{(1R)-1-[4-benzyl-1-(2,5-difluorophenyl)-1H-pyrazol-3-yl]-2,2-dimethylpropyl}-2-ethoxyacetamide | LC-MS (Method 10): $R_t$ = 1.02 min<br>MS (ESpos): m/z = 564 (M + H)$^+$ |

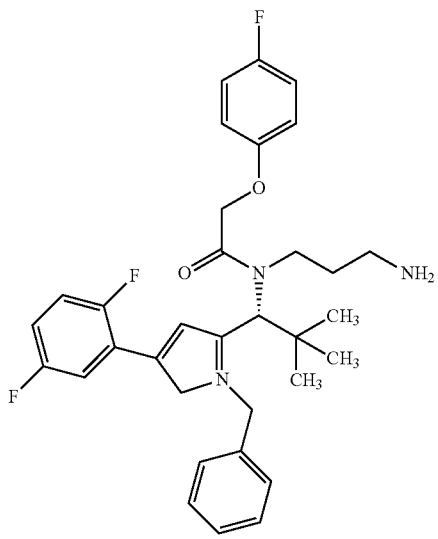

(13% of theory; purity 98%)

Example 192A

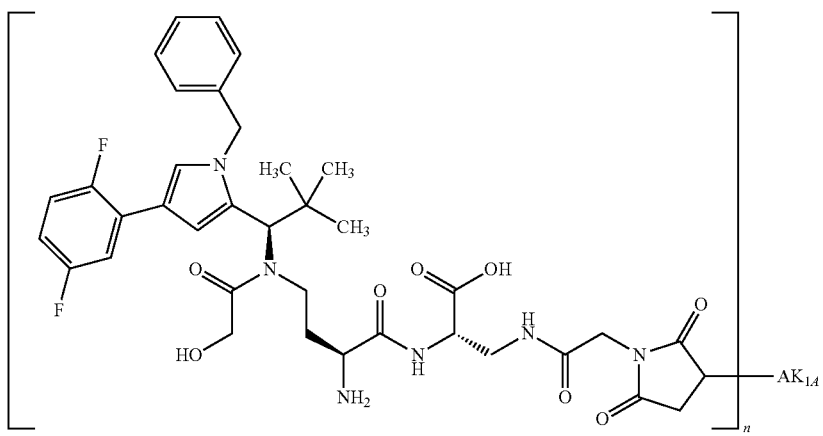

Here, 5 mg of cetuximab in PBS (c=21.3 mg/ml) were used for coupling with Intermediate F192, and the reaction was, after Sephadex purification, concentrated by ultracentrifugation and rediluted with PBS. Some of the ADC may also be present in the form of the hydrolysed open-chain succinamides attached to the antibody.

Protein concentration: 1,968 mg/ml
Drug/mAb ratio: 2.9

Example 192B

Here, 5 mg of anti-TWEAKR AK-1 in PBS (c=18.6 mg/ml) were used for coupling with Intermediate F192, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml
Drug/mAb ratio: 2.6

Example 192E

Here, 5 mg of trastuzumab antibody in PBS (c=13.5 mg/ml) were used for coupling with Intermediate F192, and the reaction was, after Sephadex purification, concentrated by ultracentrifugation and rediluted with PBS. Some of the ADC may also be present in the form of the hydrolysed open-chain succinamides attached to the antibody.

Protein concentration: 2.04 mg/ml
Drug/mAb ratio: 3.3

Example 193A

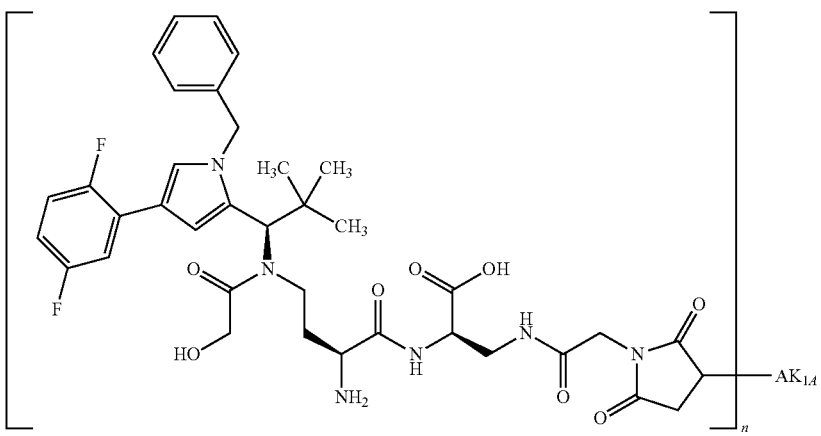

Here, 5 mg of cetuximab in PBS (c=23.1 mg/ml) were used for coupling with Intermediate F193, and the reaction was, after Sephadex purification, concentrated by ultracentrifugation and rediluted with PBS. Some of the ADC may also be present in the form of the hydrolysed open-chain succinamides attached to the antibody.
Protein concentration: 1.98 mg/ml
Drug/mAb ratio: 2.9

Example 193B

Here, 5 mg of anti-TWEAKR AK-1 in PBS (c=18.6 mg/ml) were used for coupling with Intermediate F193, and the reaction was, after Sephadex purification, concentrated by ultracentrifugation and rediluted with PBS. Some of the ADC may also be present in the form of the hydrolysed open-chain succinamides attached to the antibody.
Protein concentration: 2.03 mg/ml
Drug/mAb ratio: 3.2

Example 193E

Here, 5 mg of trastuzumab antibody in PBS (c=13.5 mg/ml) were used for coupling with Intermediate F193, and the reaction was, after Sephadex purification, concentrated by ultracentrifugation and rediluted with PBS. Some of the ADC may also be present in the form of the hydrolysed open-chain succinamides attached to the antibody.

Protein concentration: 1.61 mg/ml
Drug/mAb ratio: 3.3

Example 194A

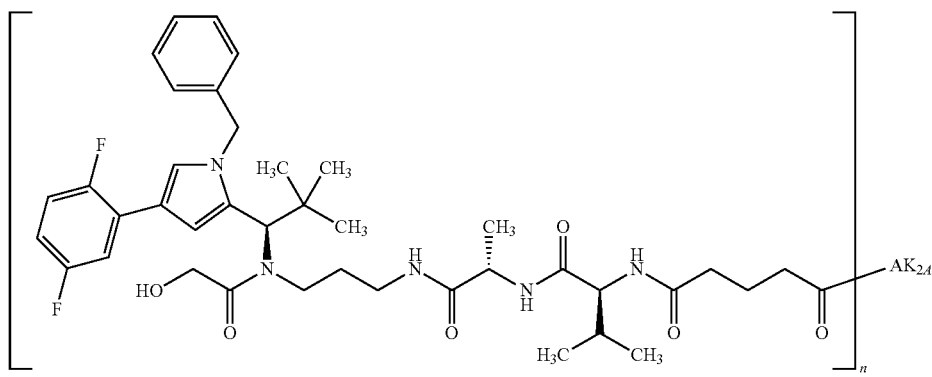

Here, 5 mg of cetuximab in PBS (c=23.1 mg/ml) were used for coupling with Intermediate F194, and the reaction was, after Sephadex purification, concentrated by ultracentrifugation and rediluted with PBS.
Protein concentration: 1.67 mg/ml
Drug/mAb ratio: 1.9

Example 194B

Here, 5.0 mg of anti-TWEAKR AK-1 antibody in PBS (c=18.6 mg/ml) were used for coupling with Intermediate F194, and the reaction was, after Sephadex purification, concentrated by ultracentrifugation and rediluted with PBS.
Protein concentration: 0.99 mg/ml
Drug/mAb ratio: 3.8

Example 194E

Here, 5.0 mg of trastuzumab antibody in PBS (c=13.5 mg/ml) were used for coupling with Intermediate F194, and the reaction was, after Sephadex purification, concentrated by ultracentrifugation and rediluted with PBS.
Protein concentration: 1.39 mg/ml
Drug/mAb ratio: 2.4

Example 195A

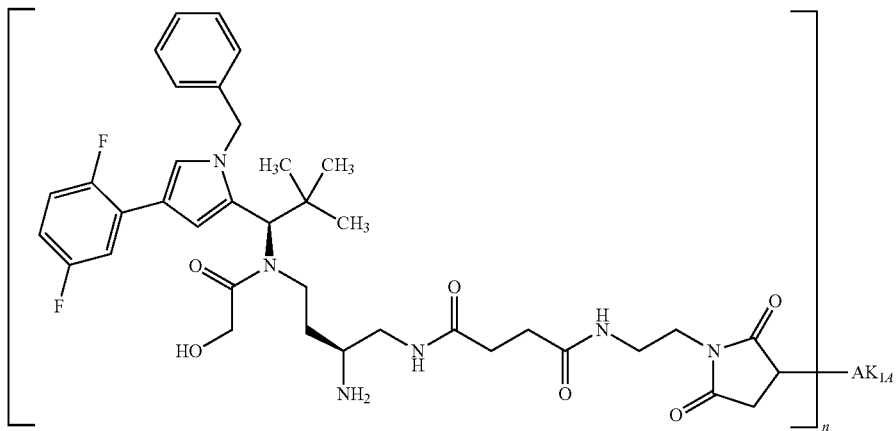

Here, 5 mg of cetuximab in PBS (c=23.1 mg/ml) were used for coupling with Intermediate F195, and the reaction was, after Sephadex purification, concentrated by ultracentrifugation and rediluted with PBS. Some of the ADC may also be present in the form of the hydrolysed open-chain succinamides attached to the antibody.

Protein concentration: 1.79 mg/ml
Drug/mAb ratio: 3.2

Example 195B

Here, 5 mg of anti-TWEAKR AK-1 in PBS (c=18.6 mg/ml) were used for coupling with Intermediate F195, and the reaction was, after Sephadex purification, concentrated by ultracentrifugation and rediluted with PBS. Some of the ADC may also be present in the form of the hydrolysed open-chain succinamides attached to the antibody.

Protein concentration: 1.53 mg/ml
Drug/mAb ratio: 3.3

Example 195E

Here, 5.0 mg of trastuzumab antibody in PBS (c=13.5 mg/ml) were used for coupling with Intermediate F195, and the reaction was, after Sephadex purification, concentrated by ultracentrifugation and rediluted with PBS. Some of the ADC may also be present in the form of the hydrolysed open-chain succinamides attached to the antibody.

Protein concentration: 1.91 mg/ml
Drug/mAb ratio: 3.4

Example 196A

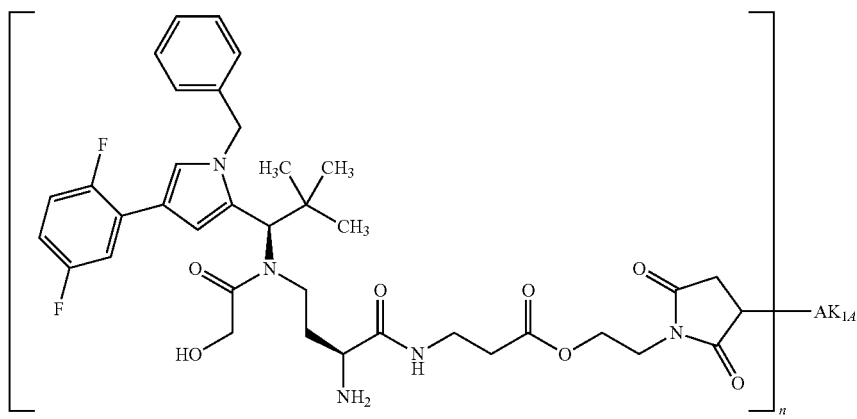

Here, 5 mg of cetuximab in PBS (c=23.1 mg/ml) were used for coupling with Intermediate F196, and the reaction was, after Sephadex purification, concentrated by ultracentrifugation and redilated with PBS. Some of the ADC may also be present in the form of the hydrolysed open-chain succinamides attached to the antibody.

Protein concentration: 1.85 mg/ml
Drug/mAb ratio: 3.0

Example 196B

Here, 5 mg of anti-TWEAKR AK-1 in PBS (c=18.6 mg/ml) were used for coupling with Intermediate F196, and the reaction was, after Sephadex purification, concentrated by ultracentrifugation and redilated with PBS. Some of the ADC may also be present in the form of the hydrolysed open-chain succinamides attached to the antibody.

Protein concentration: 1.73 mg/ml
Drug/mAb ratio: 3.1

Example 196E

Here, 5.0 mg of trastuzumab antibody in PBS (c=13.5 mg/ml) were used for coupling with Intermediate F196, and the reaction was, after Sephadex purification, concentrated by ultracentrifugation and redilated with PBS. Some of the ADC may also be present in the form of the hydrolysed open-chain succinamides attached to the antibody.

Protein concentration: 1.86 mg/ml
Drug/mAb ratio: 3.4

Example 197

(2S)-2-Amino-4-[{(1R)-1-[1-benzyl-4-(2,5-difluorophenyl)-1H-pyrrol-2-yl]-2,2-dimethylpropyl}(glycoloyl)amino]butanoic acid hydrochloride (1:1)

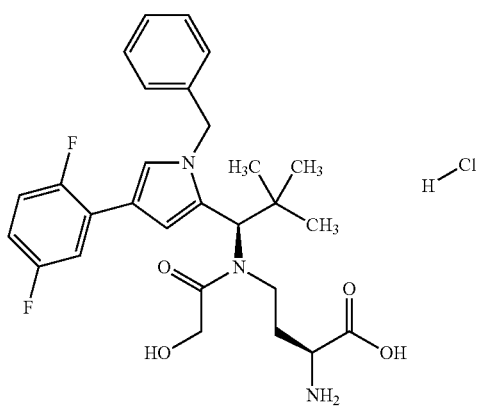 [SMILES: CC(C)(C)[C@H](c1cc(-c2cc(F)ccc2F)cn1Cc1ccccc1)N(CC[C@H](N)C(=O)O)C(=O)CO ; Cl]

150 mg (0.2 mmol) of Intermediate C53 were dissolved in 15 ml of DMF, and 2.29 g (20.39 mmol) of DABCO. The reaction was treated in an ultrasonic bath for 30 min By addition of 1.17 ml of acetic acid, the reaction was then adjusted to pH 3-4, and the mixture was concentrated under reduced pressure. The residue was purified by preparative HPLC and the appropriate fractions were concentrated at RT under reduced pressure. The residue was taken up in acetonitrile/water 1:1, 5 ml of a 4N hydrochloric acid were added and the mixture was then lyophilized. This gave 81 mg (68% of theory) of the title compound.

LC-MS (Method 5): $R_t$=2.69 min; MS (EIpos): m/z=514 $[M+H]^+$.

Example 198

Trifluoroacetic acid/(2S)-2-amino-N-(2-aminoethyl)-4-[(1R)-1-[1-benzyl-4-(2,5-difluorophenyl)-1H-pyrrol-2-yl]-2,2-dimethylpropyl}(glycoloyl)amino]butanamide (1:1)

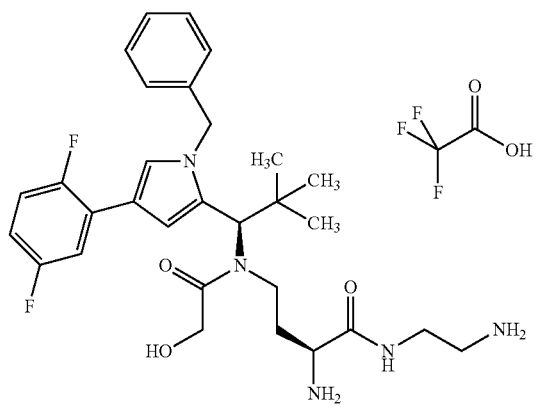 [SMILES: CC(C)(C)[C@H](c1cc(-c2cc(F)ccc2F)cn1Cc1ccccc1)N(CC[C@H](N)C(=O)NCCN)C(=O)CO ; O=C(O)C(F)(F)F]

15 mg (0.018 mmol) of Intermediate C64 were dissolved in 4 ml of 2,2,2-trifluoroethanol. 15 ml (0.110 mmol) of zinc chloride were added, and the reaction was stirred at 50° C. for 2 h. 32 mg (0.110 mmol) of ethylenediamine-N,N,N',N'-tetraacetic acid were then added, and the reaction was concentrated under reduced pressure. The residue was purified by preparative HPLC. Concentration of the appropriate fractions and lyophilization of the residue from acetonitrile/water gave 9.5 mg (77% of theory) of the title compound.

LC-MS (Method 1): $R_t$=0.68 min; MS (ESIpos): m/z=556 $(M+H)^+$.

Example 199

4-[(2-{[2-({(2S)-2-Amino-4-[(1R)-1-[1-benzyl-4-(2,5-difluorophenyl)-1H-pyrrol-2-yl]-2,2-dimethylpropyl}(glycoloyl)amino]butanoyl amino)ethyl]amino}-2-oxoethyl)amino]-3-{[(2R)-2-amino-2-carboxyethyl]sulphanyl}-4-oxobutanoic acid/trifluoroacetic acid (1:1) and 4-[(2-{[2-({(2S)-2-amino-4-[(1R)-1-[1-benzyl-4-(2,5-difluorophenyl)-1H-pyrrol-2-yl]-2,2-dimethylpropyl}(glycoloyl)amino]butanoyl amino)ethyl]amino}-2-oxoethyl)amino]-2-{[(2R)-2-amino-2-carboxyethyl]sulphanyl}-4-oxobutanoic acid/trifluoroacetic acid (1:1)

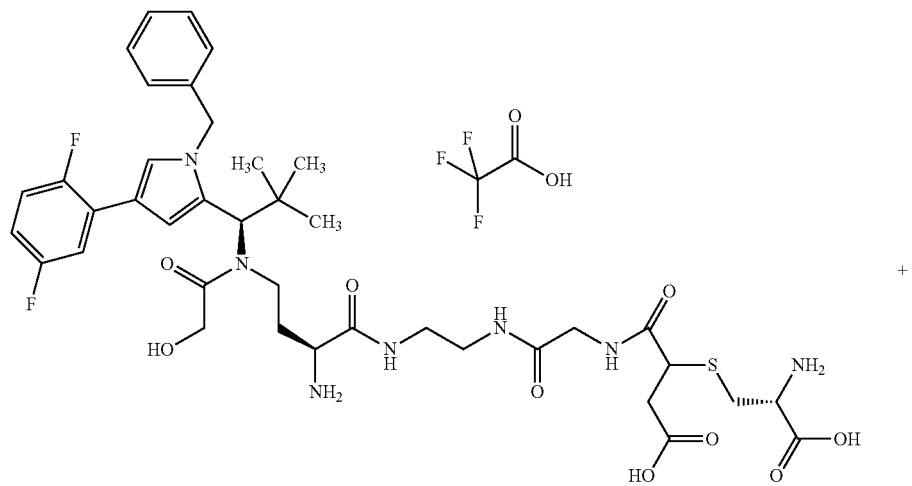

Isomer 1

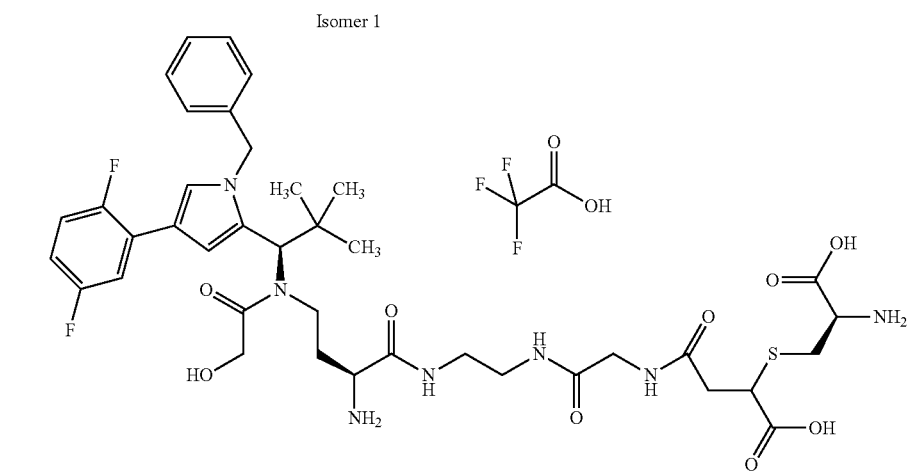

Isomer 2

LC-MS (Method 1): $R_t$=0.80 min; MS (EIpos): m/z=814 [M+H]$^+$.

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

406 mg (1.53 mmol) of N-{[2-(trimethylsilyl)ethoxy]carbonyl}-L-cysteine were dissolved in 10 ml of DMF, 157.5 mg (1.606 mmol) of maleic anhydride were added and the reaction was stirred at RT for 1 hour. 7.5 mg (0.01 mmol) of intermediate C66 were added to 130 µl of this solution, and the reaction was stirred at RT for 5 min. The mixture was then concentrated under reduced pressure, and the residue was purified by preparative HPLC. The solvent was evaporated under reduced pressure and the residue was dried under high vacuum. This gave 10 mg (89%) of the protected intermediate; it was not possible to separate the regioisomers neither by HPLC nor by LC-MS.

LC-MS (Method 1): $R_t$=1.38 min; MS (EIpos): m/z=1120 [M+H]$^+$.

In the last step, the 10 mg of this intermediate were dissolved in 2 ml of 2,2,2-trifluoroethanol. 12 ml (0.088 mmol) of zinc chloride were added, and the reaction was stirred at 50° C. for 30 min 26 mg (0.088 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 8.3 mg (99% of theory) of the title compound as a regioisomer mixture in a ratio of 87:13.

LC-MS (Method 5): $R_t$=2.3 min and 2.43 min; MS (ESIpos): m/z=832 (M+H)$^+$.

$^1$H NMR main isomer: (500 MHz, DMSO-d$_6$): δ=8.7 (m, 1H), 8.5 (m, 2H), 8.1 (m, 1H), 7.6 (m, 1H), 7.5 (s, 1H) 7.4-7.15 (m, 6H), 6.9-7.0 (m, 1H), 6.85 (s, 1H), 5.61 (s, 1H), 4.9 and 5.2 (2d, 2H), 4.26 and 4.06 (2d, 2H), 3.5-3.8 (m, 5H), 3.0-3.4 (m, 5H), 2.75-3.0 (m, 3H), 2.58 and 2.57 (dd, 1H), 0.77 and 1.5 (2m, 2H), 0.81 (s, 9H).

Alternatively, the regioisomeric title compounds were prepared as follows:

To this end, first L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

55 mg (0.068 mmol) of Intermediate F104 and 36 mg (0.136 mmol) of N-{[2-(trimethylsilyl) ethoxy]carbonyl}-L-cysteine were dissolved in 15 ml of DMF, and the mixture was stirred at RT for 20 h. The mixture was then concentrated and the residue was purified by preparative HPLC. The appropriate fractions were combined and the solvents were evaporated under reduced pressure, and the residue was then dissolved in 15 ml of THF/water 1:1. 131 µl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave 37 mg (50% of theory) of the regioisomeric protected intermediates as a colourless foam.

LC-MS (Method 5): $R_t$=3.33 min and 3.36 min; MS (ESIpos): m/z=976 (M+H)$^+$.

In the last step, 25 mg of this intermediate were dissolved in 3 ml of 2,2,2-trifluoroethanol. 12.5 ml (0.092 mmol) of zinc chloride were added, and the reaction was stirred at 50° C. for 4 h. 27 mg (0.092 mmol) of ethylenediamine-N,N, N',N'-tetraacetic acid were then added, and the solvent was evaporated under reduced pressure. The residue was purified by preparative HPLC. Concentration of the appropriate fractions and lyophilization of the residue from acetonitrile/water gave 18.5 mg (85% of theory) of the title compound as a regioisomer mixture in a ratio of 21:79.

LC-MS (Method 5): $R_t$=2.37 min and 3.44 min; MS (ESIpos): m/z=832 (M+H)$^+$.

The targeted preparation of the individual regioisomers of the title compounds was carried out as follows:

Example 199-2

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl] amino}-2-oxoethyl)amino]-2-{[(2R)-2-amino-2-carboxyethyl]sulphanyl}-4-oxobutanoic acid/ trifluoroacetic acid (1:1)

First, methyl L-cysteinate was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate.

53 mg (0.251 mmol) of commercially available 3-bromo-4-methoxy-4-oxobutanoic acid and 70 mg (0.251 mmol) of methyl N-{[2-(trimethylsilyl)ethoxy]carbonyl}-L-cysteinate were dissolved in 5 ml of DMF, and aqueous sodium bicarbonate solution was added while monitoring the pH. After stirring 15 min of stirring at RT, the mixture was adjusted to pH=4.3 with acetic acid and the reaction was concentrated. The residue was purified by preparative HPLC. Combination of the appropriate fractions and evaporation of the solvents under reduced pressure gave 72 mg (70% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 1): $R_t$=0.93 min; MS (ESIpos): m/z=410 (M+H)$^+$.

This intermediate was coupled in the presence of HATU with Intermediate C66 and then deprotected completely as described above first with lithium hydroxide in methanol and then with zinc chloride. The residue was purified by preparative HPLC. Concentration of the appropriate fractions and lyophilization of the residue from acetonitrile/water gave 2 mg of the title compound.

LC-MS (Method 1): $R_t$=0.78 min; MS (ESIpos): m/z=832 (M+H)$^+$.

Isomer 1 can be prepared in an analogous manner

Example 200

N-{(2S)-2-Amino-4-[{(1R)-1-[1-benzyl-4-(2,5-difluorophenyl)-1H-pyrrol-2-yl]-2,2-dimethylpropyl} (glycoloyl)amino]butanoyl}-beta-alanine/trifluoroacetic acid (1:1)

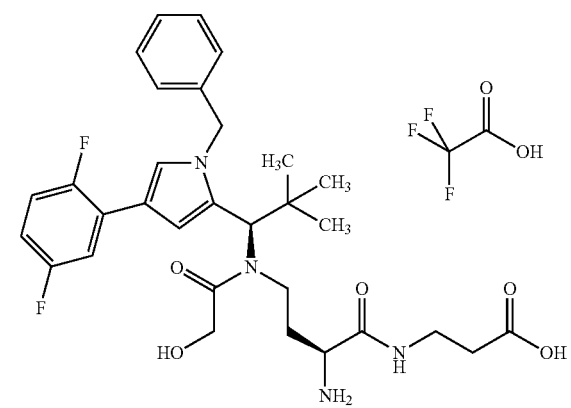 [SMILES: CC(C)(C)[C@H](c1cc(-c2cc(F)ccc2F)cn1Cc1ccccc1)N(CC[C@H](N)C(=O)NCCC(=O)O)C(=O)CO ; O=C(O)C(F)(F)F]

10 mg (0.014 mmol) of Intermediate C61 were dissolved in 3 ml of 2,2,2-trifluoroethanol. 11 ml (0.082 mmol) of zinc chloride were added, and the reaction was stirred at 50° C. for 30 min 24 mg (0.082 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4.2 mg (40% of theory) of the title compound.

LC-MS (Method 1): $R_t$=0.79 min; MS (ESIpos): m/z=585 (M+H)$^+$.

Example 201

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-L-serine/trifluoroacetic acid (1:1)

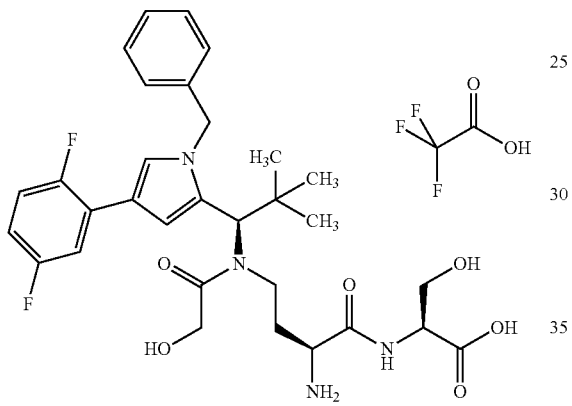

20 mg (0.03 mmol) of Intermediate C58 and 8.5 mg (0.037 mmol) of benzyl L-serinate hydrochloride (1:1) were taken up in 5 ml of DMF, and 17 mg (0.046 mmol) of HATU and 21 µl of N,N-diisopropylethylamine were added. After stirring at RT for 10 minutes, the mixture was concentrated and the residue was purified by preparative HPLC. This gave 12.5 mg (49% of theory) of the intermediate. LC-MS (Method 1): $R_t$=1.42 min; MS (ESIpos): m/z=835 (M+H)$^+$.

12.5 mg (0.015 mmol) of this intermediate were dissolved in 10 ml of ethanol, palladium on carbon (10%) was added and the mixture was hydrogenated at RT with hydrogen at standard pressure for 30 min. The catalyst was filtered off and the solvents were evaporated under reduced pressure giving, after lyophilization of the residue from acetonitrile/water, 7.5 mg (67% of theory) of the intermediate. LC-MS (Method 1): $R_t$=1.28 min; MS (ESIpos): m/z=745 (M+H)$^+$.

7.5 mg (0.01 mmol) of this intermediate were dissolved in 3 ml of 2,2,2-trifluoroethanol. 8 ml (0.06 mmol) of zinc chloride were added, and the reaction was stirred at 50° C. for 4.5 h. 17.7 mg (0.06 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4.2 mg (58% of theory) of the title compound.

LC-MS (Method 1): $R_t$=0.75 min; MS (ESIpos): m/z=601 (M+H)$^+$.

Example 202

N-{(2S)-2-Amino-4-{[(1R)-1-[1-benzyl-4-(2,5-difluorophenyl)-1H-pyrrol-2-yl]-2,2-dimethylpropyl}(glycoloyl)amino]butanoyl}-L-alanine/trifluoroacetic acid (1:1)

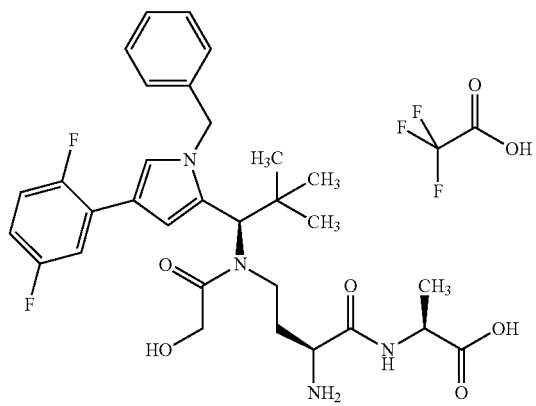 [SMILES: C[C@H](NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared analogously to Example 201 from Intermediate C58 and benzyl L-alaninate hydrochloride (1:1).

LC-MS (Method 1): $R_t$=0.82 min; MS (ESIpos): m/z=585 (M+H)$^+$.

Example 203

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}glycine/trifluoroacetic acid (1:1)

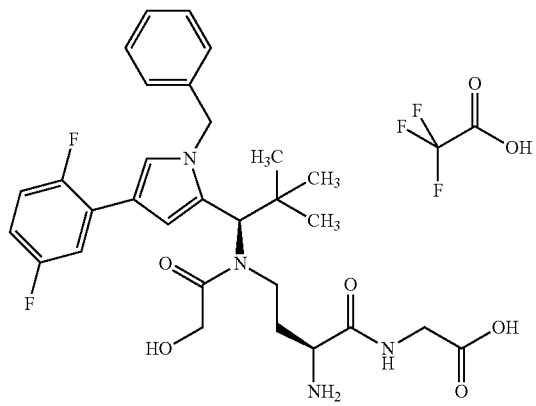 [SMILES: CC(C)(C)[C@H](c1cc(-c2cc(F)ccc2F)cn1Cc1ccccc1)N(CC[C@H](N)C(=O)NCC(=O)O)C(=O)CO ; O=C(O)C(F)(F)F]

The title compound was prepared analogously to Example 201 from Intermediate C58 and benzyl glycinate hydrochloride (1:1).

LC-MS (Method 1): $R_t$=0.82 min; MS (ESIpos): m/z=571 (M+H)$^+$.

Example 204A

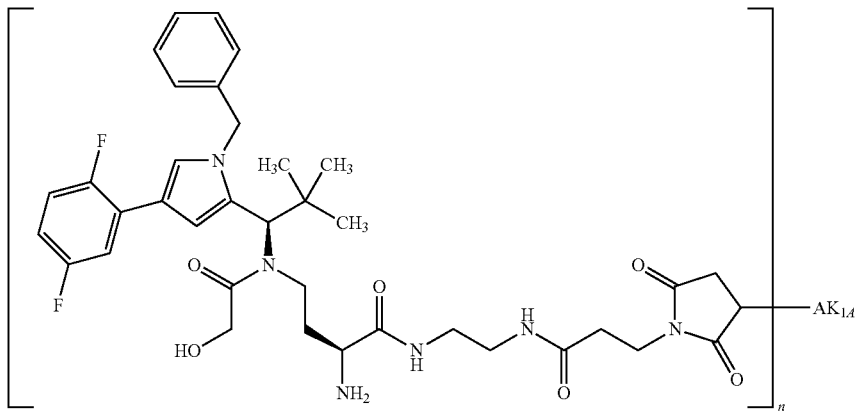

Here, 5 mg of cetuximab in PBS (c=23.1 mg/ml) were used for coupling with Intermediate F204, and the reaction was, after Sephadex purification, concentrated by ultracentrifugation and rediluted with PBS. Some of the ADC may also be present in the form of the hydrolysed open-chain succinamides attached to the antibody.

Protein concentration: 1.88 mg/ml
Drug/mAb ratio: 2.6

Example 204B

Here, 50 mg of anti-TWEAKR AK-1 in PBS (c=18.6 mg/ml) were used for coupling with Intermediate F204, and the reaction was, after Sephadex purification, concentrated by ultracentrifugation, rediluted with PBS and concentrated again. Some of the ADC may also be present in the form of the hydrolysed open-chain succinamides attached to the antibody.

Protein concentration: 12.66 mg/ml
Drug/mAb ratio: 3.5

Example 204E

Here, 5.0 mg of trastuzumab antibody in PBS (c=13.5 mg/ml) were used for coupling with Intermediate F204, and the reaction was, after Sephadex purification, concentrated by ultracentrifugation and rediluted with PBS. Some of the ADC may also be present in the form of the hydrolysed open-chain succinamides attached to the antibody.

Protein concentration: 1.65 mg/ml
Drug/mAb ratio: 3.5

Example 205A

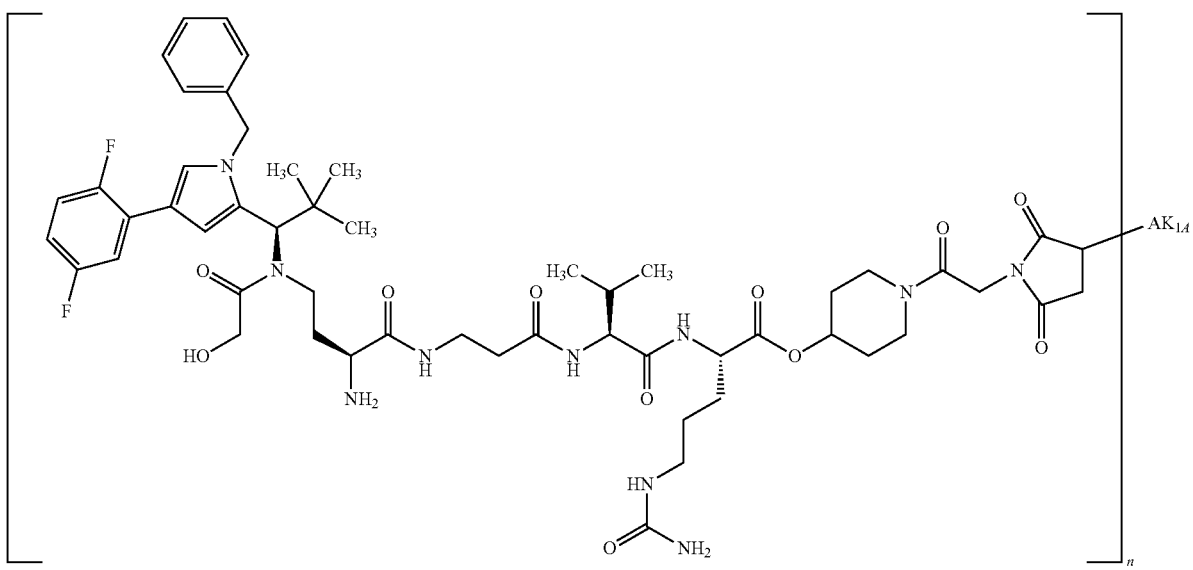

Here, 5 mg of cetuximab in PBS (c=23.1 mg/ml) were used for coupling with Intermediate F205, and the reaction was, after Sephadex purification, concentrated by ultracentrifugation and rediluted with PBS. Some of the ADC may also be present in the form of the hydrolysed open-chain succinamides attached to the antibody.

Protein concentration: 1.99 mg/ml

Drug/mAb ratio: 3.2

Example 205B

Here, 5 mg of anti-TWEAKR AK-1 in PBS (c=18.6 mg/ml) were used for coupling with Intermediate F205, and the reaction was, after Sephadex purification, concentrated by ultracentrifugation and rediluted with PBS. Some of the ADC may also be present in the form of the hydrolysed open-chain succinamides attached to the antibody.

Protein concentration: 0.96 mg/ml

Drug/mAb ratio: 2.6

Example 205E

Here, 5 mg of trastuzumab in PBS (c=13.5 mg/ml) were used for coupling with Intermediate F205, and the reaction was, after Sephadex purification, concentrated by ultracentrifugation and rediluted with PBS. Some of the ADC may also be present in the form of the hydrolysed open-chain succinamides attached to the antibody.

Protein concentration: 1.94 mg/ml

Drug/mAb ratio: 3.6

Example 206A

Here, 5 mg of cetuximab in PBS (c=23.1 mg/ml) were used for coupling with Intermediate F206, and the reaction was, after Sephadex purification, concentrated by ultracentrifugation and rediluted with PBS. Some of the ADC may also be present in the form of the hydrolysed open-chain succinamides attached to the antibody.

Protein concentration: 1.73 mg/ml

Drug/mAb ratio: 2.6

Example 206B

Here, 5 mg of anti-TWEAKR AK-1 in PBS (c=18.6 mg/ml) were used for coupling with Intermediate F206, and the reaction was, after Sephadex purification, concentrated by ultracentrifugation and rediluted with PBS. Some of the ADC may also be present in the form of the hydrolysed open-chain succinamides attached to the antibody.

Protein concentration: 1.21 mg/ml

Drug/mAb ratio: 2.0

Example 206E

Here, 5 mg of trastuzumab in PBS (c=13.5 mg/ml) were used for coupling with Intermediate F206, and the reaction was, after Sephadex purification, concentrated by ultracentrifugation and rediluted with PBS. Some of the ADC may also be present in the form of the hydrolysed open-chain succinamides attached to the antibody.

Protein concentration: 1.84 mg/ml

Drug/mAb ratio: 2.8

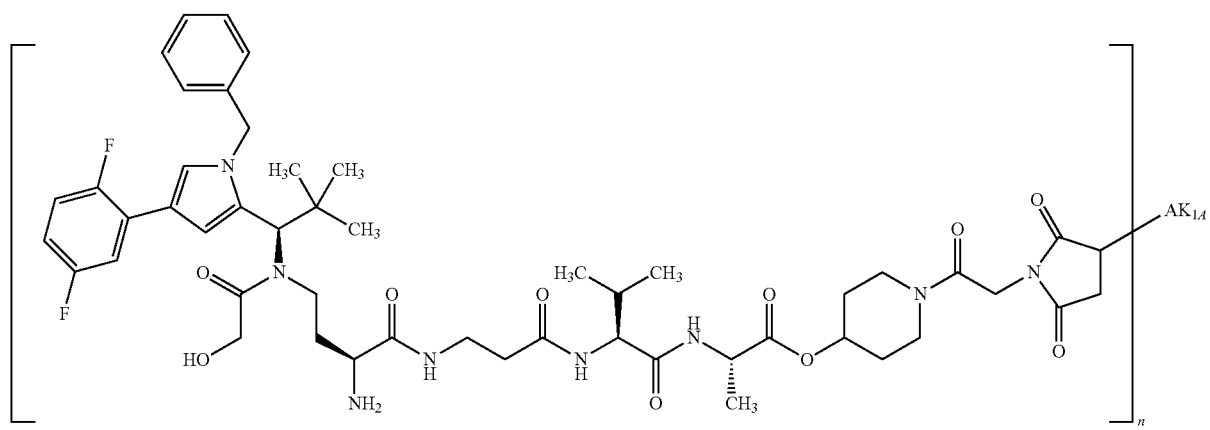

Example 207A

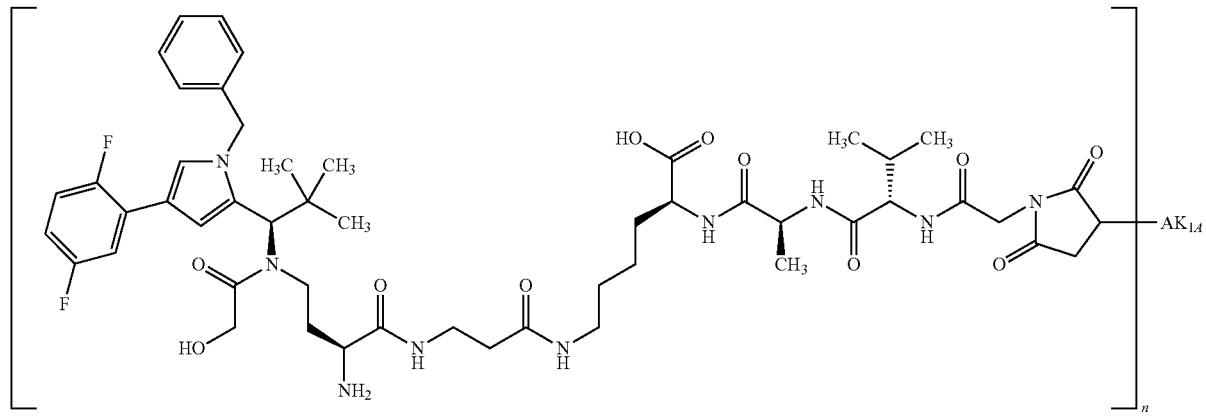

Here, 5 mg of cetuximab in PBS (c=10 mg/ml) were used for coupling with Intermediate F207, and the reaction was, after Sephadex purification, concentrated by ultracentrifugation and rediluted with PBS. Some of the ADC may also be present in the form of the hydrolysed open-chain succinamides attached to the antibody.

Protein concentration: 1.79 mg/ml
Drug/mAb ratio: 3.4

Example 207B

Here, 50 mg of anti-TWEAKR AK-1 in PBS (c=18.6 mg/ml) were used for coupling with Intermediate F207, and the reaction was, after Sephadex purification, concentrated by ultracentrifugation, rediluted with PBS and concentrated again. Some of the ADC may also be present in the form of the hydrolysed open-chain succinamides attached to the antibody. For this ADC preparation, immediately after the synthesis a proportion of 19% was determined for the ring-opened succinamide form.

Protein concentration: 12.99 mg/ml
Drug/mAb ratio: 4.3

Example 207E

Here, 5 mg of trastuzumab in PBS (c=13.5 mg/ml) were used for coupling with Intermediate F207, and the reaction was, after Sephadex purification, concentrated by ultracentrifugation and rediluted with PBS. Some of the ADC may also be present in the form of the hydrolysed open-chain succinamides attached to the antibody.

Protein concentration: 2.39 mg/ml
Drug/mAb ratio: 2.8

Example 207I

Here, 5.0 mg of nimotuzumab in PBS (c=13.1 mg/ml) were used for coupling with Intermediate F207, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml
Drug/mAb ratio: 3.5

Example 207H

Here, 5.0 mg of panitumumab in PBS (c=13.6 mg/ml) were used for coupling with Intermediate F207. The reduction time with TCEP was 4 h and the stirring time for the ADC coupling was 20 h. After Sephadex purification, the reaction was concentrated by ultracentrifugation and rediluted with PBS. Some of the ADC may also be present in the form of the hydrolysed open-chain succinamides attached to the antibody.

Protein concentration: 2.0 mg/ml
Drug/mAb ratio: 1.9

Example 208A

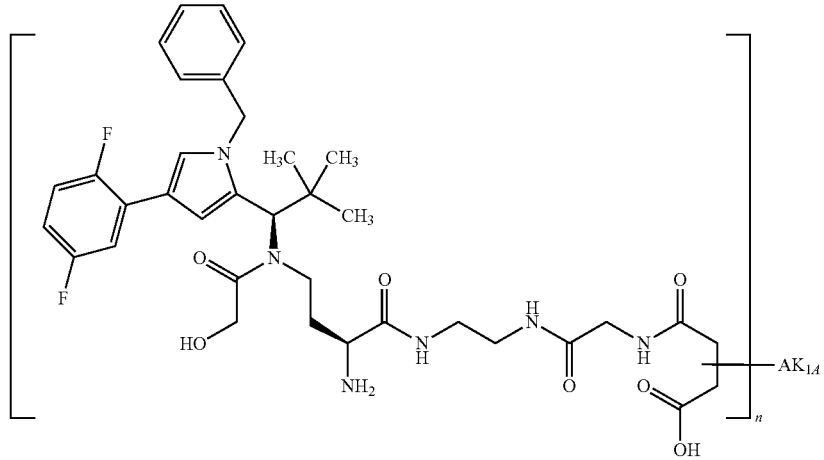

Under argon, a solution of 0.344 mg of TCEP in 100 μl of PBS buffer was added to 60 mg of cetuximab in 5494 μl of PBS (c=10.92 mg/ml). The reaction was stirred at RT for 30 min, and 2.582 mg (0.003 mmol) of Intermediate F104 dissolved in 600 μl of DMSO were then added. After a further 120 min of stirring at RT, the reaction was diluted with 1306 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred under argon at RT overnight and then concentrated by ultracentrifugation, rediluted with PBS buffer (pH 7.2) and reconcentrated again. The ADC batch obtained was characterized as follows:

Protein concentration: 13.36 mg/ml

Drug/mAb ratio: 1.8

For this ADC preparation, a proportion of 94% was determined for the ring-opened succinamide form.

Example 208B

Under argon, 60 mg of anti-TWEAKR AK-1 in 3225 μl of PBS (c=18.6 mg/ml) were diluted with 775 μl of PBS buffer, and a solution of 0.344 mg of TCEP in 100 μl of PBS buffer was then added. The reaction was stirred at RT for 30 min, and 2.582 mg (0.003 mmol) of Intermediate F104 dissolved in 600 μl of DMSO were then added. After a further 120 min of stirring at RT, the reaction was diluted with 300 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred under argon at RT overnight and then concentrated by ultracentrifugation, rediluted with PBS buffer (pH 7.2) and reconcentrated again. The ADC batch obtained was characterized as follows:

Protein concentration: 14.95 mg/ml

Drug/mAb ratio: 3.2

Example 208I

Under argon, a solution of 0.344 mg of TCEP in 100 μl of PBS buffer was added to 60 mg of nimotuzumab in 4587 μl of PBS (c=13.1 mg/ml). The reaction was stirred at RT for 30 min, and 2.582 mg (0.003 mmol) of Intermediate F104 dissolved in 600 μl of DMSO were then added. After a further 120 min of stirring at RT, the reaction was diluted with 2213 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred under argon at RT overnight and then concentrated by ultracentrifugation, rediluted with PBS buffer (pH 7.2) and reconcentrated again. The ADC batch obtained was characterized as follows:

Protein concentration: 14.79 mg/ml

Drug/mAb ratio: 3.1

For this ADC preparation, a proportion of 91% was determined for the ring-opened succinamide form.

Example 208K

Under argon, a solution of 0.23 mg of TCEP in 67 μl of PBS buffer was added to 40 mg of anti-TWEAKR AK-2 in 2759 μl of PBS (c=14.5 mg/ml). The reaction was stirred at RT for 30 min, and 1.72 mg (0.002 mmol) of Intermediate F104 dissolved in 400 μl of DMSO were then added. After a further 120 min of stirring at RT, the reaction was diluted with 1774 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred under argon at RT overnight and then concentrated by ultracentrifugation, rediluted with PBS buffer (pH 7.2) and reconcentrated again. The ADC batch obtained was characterized as follows:

Protein concentration: 11.66 mg/ml

Drug/mAb ratio: 3.1

Example 209A

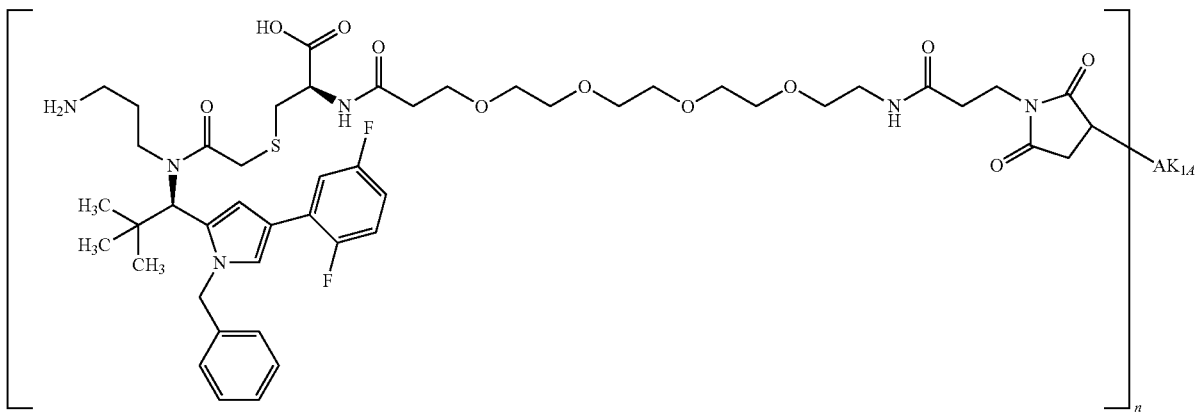

Here, 5.0 mg of cetuximab in PBS (c=21.32 mg/ml) were used for coupling with Intermediate F209, and the reaction was, after Sephadex purification, concentrated by ultracentrifugation and rediluted with PBS. Some of the ADC may also be present in the form of the hydrolysed open-chain succinamides attached to the antibody.

Protein concentration: 1.75 mg/ml
Drug/mAb ratio: 2.4

Example 209B

Here, 5.0 mg of anti-TWEAKR AK-1 antibody in PBS (c=18.60 mg/ml) were used for coupling with Intermediate F209, and the reaction was, after Sephadex purification, Example 209I Here, 5.0 mg of nimotuzumab antibody in PBS (c=13.1 mg/ml) were used for coupling with Intermediate F209, and the reaction was, after Sephadex purification, concentrated by ultracentrifugation and rediluted. Some of the ADC may also be present in the form of the hydrolysed open-chain succinamides attached to the antibody.

Protein concentration: 1.81 mg/ml
Drug/mAb ratio: 2.5

Example 210A

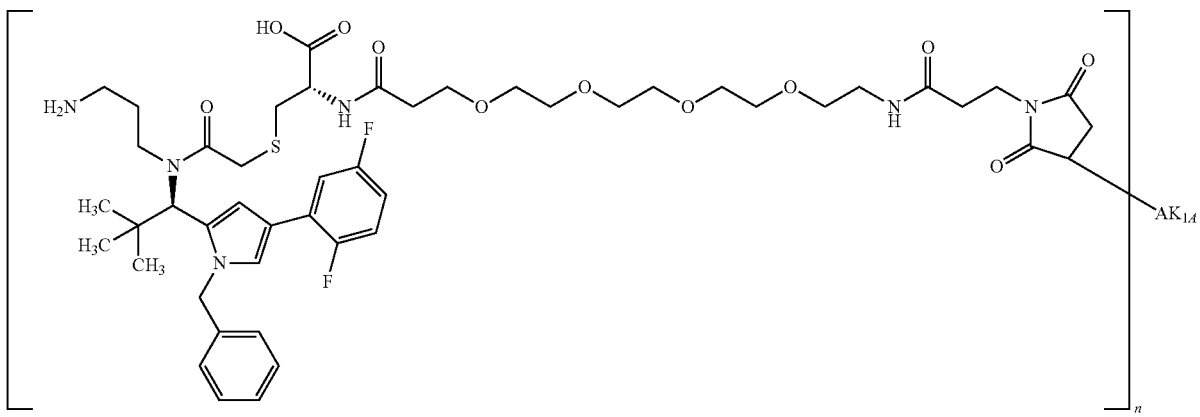

concentrated by ultracentrifugation and rediluted. Some of the ADC may also be present in the form of the hydrolysed open-chain succinamides attached to the antibody.

Protein concentration: 1.30 mg/ml
Drug/mAb ratio: 2.1

Example 209E

Here, 5.0 mg of trastuzumab antibody in PBS (c=13.50 mg/ml) were used for coupling with Intermediate F209, and the reaction was, after Sephadex purification, concentrated by ultracentrifugation and rediluted. Some of the ADC may also be present in the form of the hydrolysed open-chain succinamides attached to the antibody.

Protein concentration: 2.03 mg/ml
Drug/mAb ratio: 2.3

Example 209H

Here, 5.0 mg of panitumumab antibody in PBS (c=70.5 mg/ml) were used for coupling with Intermediate F209, and the reaction was, after Sephadex purification, concentrated by ultracentrifugation and rediluted. Some of the ADC may also be present in the form of the hydrolysed open-chain succinamides attached to the antibody.

Protein concentration: 1.91 mg/ml
Drug/mAb ratio: 1.5

Here, 5.0 mg of cetuximab in PBS (c=21.32 mg/ml) were used for coupling with Intermediate F210, and the reaction was, after Sephadex purification, concentrated by ultracentrifugation and rediluted with PBS. Some of the ADC may also be present in the form of the hydrolysed open-chain succinamides attached to the antibody.

Protein concentration: 1.92 mg/ml
Drug/mAb ratio: 2.9

Example 210B

Here, 5.0 mg of anti-TWEAKR AK-1 antibody in PBS (c=18.60 mg/ml) were used for coupling with Intermediate F210, and the reaction was, after Sephadex purification, concentrated by ultracentrifugation and rediluted. Some of the ADC may also be present in the form of the hydrolysed open-chain succinamides attached to the antibody.

Protein concentration: 1.41 mg/ml
Drug/mAb ratio: 2.5

Example 210E

Here, 5.0 mg of trastuzumab antibody in PBS (c=13.50 mg/ml) were used for coupling with Intermediate F210, and the reaction was, after Sephadex purification, concentrated by ultracentrifugation and rediluted. Some of the ADC may also be present in the form of the hydrolysed open-chain succinamides attached to the antibody.

Protein concentration: 1.79 mg/ml
Drug/mAb ratio: 2.8

Example 211A

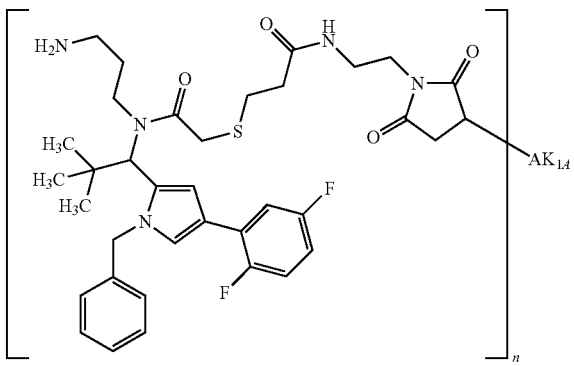

Here, 5.0 mg of cetuximab in PBS (c=12.33 mg/ml) were used for coupling with Intermediate F211, and the reaction was, after Sephadex purification, concentrated by ultracentrifugation and rediluted with PBS. Some of the ADC may also be present in the form of the hydrolysed open-chain succinamides attached to the antibody.

Protein concentration: 1.82 mg/ml
Drug/mAb ratio: 2.0

Example 211B

Here, 5.0 mg of anti-TWEAKR AK-1 antibody in PBS (c=34.42 mg/ml) were used for coupling with Intermediate F211, and the reaction was, after Sephadex purification, concentrated by ultracentrifugation and rediluted. Some of the ADC may also be present in the form of the hydrolysed open-chain succinamides attached to the antibody.

Protein concentration: 1.52 mg/ml
Drug/mAb ratio: 2.4

Example 211E

Here, 5.0 mg of trastuzumab antibody in PBS (c=13.50 mg/ml) were used for coupling with Intermediate F211, and the reaction was, after Sephadex purification, concentrated by ultracentrifugation and rediluted. Some of the ADC may also be present in the form of the hydrolysed open-chain succinamides attached to the antibody.

Protein concentration: 1.84 mg/ml
Drug/mAb ratio: 2.4

Example 212A

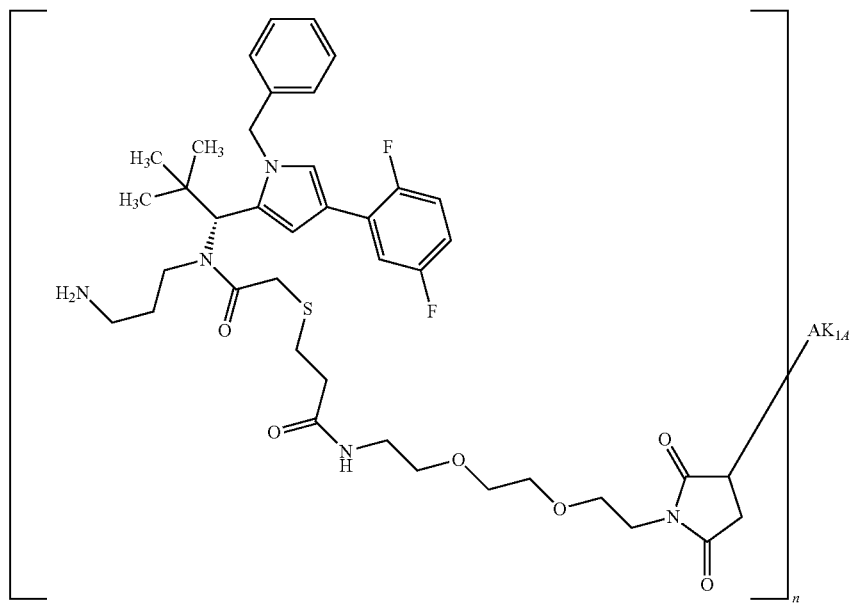

Here, 5.0 mg of cetuximab in PBS (c=11.3 mg/ml) were used for coupling with Intermediate F212, and the reaction was, after Sephadex purification, concentrated by ultracentrifugation and rediluted with PBS. Some of the ADC may also be present in the form of the hydrolysed open-chain succinamides attached to the antibody.

Protein concentration: 1.94 mg/ml
Drug/mAb ratio: 3.3

Example 212B

Here, 5.0 mg of anti-TWEAKR AK-1 antibody in PBS (c=18.6 mg/ml) were used for coupling with Intermediate F212, and the reaction was, after Sephadex purification, concentrated by ultracentrifugation and rediluted. Some of the ADC may also be present in the form of the hydrolysed open-chain succinamides attached to the antibody.

Protein concentration: 0.85 mg/ml
Drug/mAb ratio: 2.0

Example 212E

Here, 5.0 mg of trastuzumab antibody in PBS (c=13.50 mg/ml) were used for coupling with Intermediate F212, and the reaction was, after Sephadex purification, concentrated by ultracentrifugation and rediluted. Some of the ADC may also be present in the form of the hydrolysed open-chain succinamides attached to the antibody.

Protein concentration: 1.55 mg/ml
Drug/mAb ratio: 2.0

Example 213A

Here, 5.0 mg of cetuximab in PBS (c=21.32 mg/ml) were used for coupling with Intermediate F213, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.4

Example 213B

Here, 5.0 mg of anti-TWEAKR AK-1 antibody in PBS (c=18.6 mg/ml) were used for coupling with Intermediate F213, and the reaction was, after Sephadex purification, concentrated by ultracentrifugation and rediluted. Some of the ADC may also be present in the form of the hydrolysed open-chain succinamides attached to the antibody.

Protein concentration: 1.4 mg/ml
Drug/mAb ratio: 2.3

Example 213E

Here, 5.0 mg of trastuzumab antibody in PBS (c=13.50 mg/ml) were used for coupling with Intermediate F213, and the reaction was, after Sephadex purification, concentrated by ultracentrifugation and rediluted. Some of the ADC may also be present in the form of the hydrolysed open-chain succinamides attached to the antibody.

Protein concentration: 1.94 mg/ml
Drug/mAb ratio: 2.5

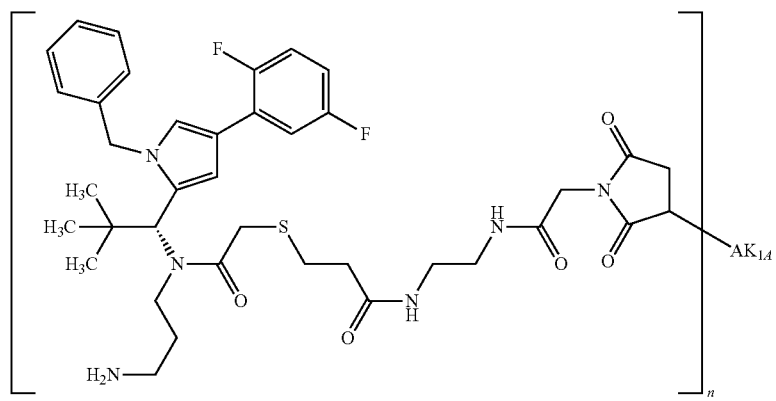

Example 214A

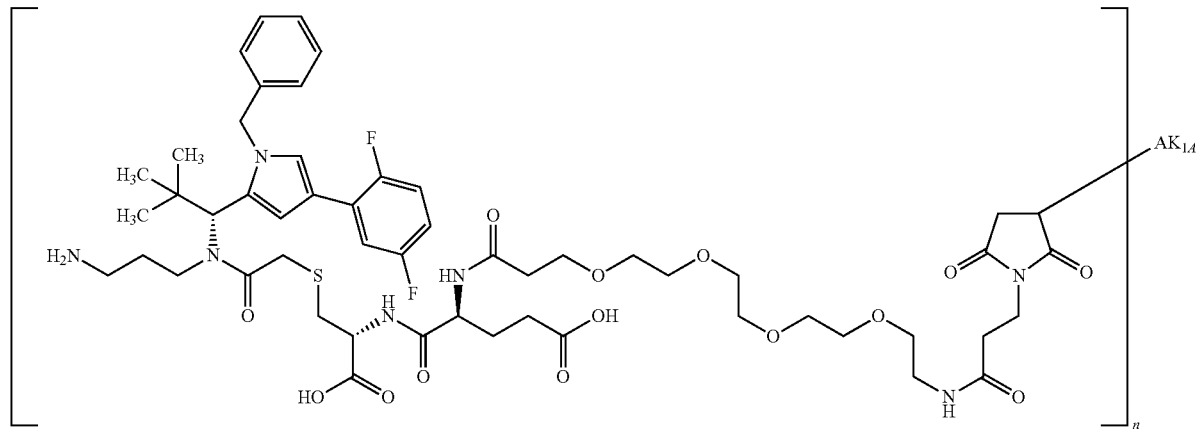

Here, 5.0 mg of cetuximab in PBS (c=15.21 mg/ml) were used for coupling with Intermediate F214, and the reaction was, after Sephadex purification, concentrated by ultracentrifugation and rediluted with PBS. Some of the ADC may also be present in the form of the hydrolysed open-chain succinamides attached to the antibody.
Protein concentration: 2.00 mg/ml
Drug/mAb ratio: 2.6

Example 214B

Here, 5.0 mg of anti-TWEAKR AK-1 antibody in PBS (c=18.6 mg/ml) were used for coupling with Intermediate F214, and the reaction was, after Sephadex purification, concentrated by ultracentrifugation and rediluted. Some of the ADC may also be present in the form of the hydrolysed open-chain succinamides attached to the antibody.

Protein concentration: 2.01 mg/ml
Drug/mAb ratio: 2.6

Example 214E

Here, 5.0 mg of trastuzumab antibody in PBS (c=13.50 mg/ml) were used for coupling with Intermediate F214, and the reaction was, after Sephadex purification, concentrated by ultracentrifugation and rediluted. Some of the ADC may also be present in the form of the hydrolysed open-chain succinamides attached to the antibody.
Protein concentration: 1.86 mg/ml
Drug/mAb ratio: 2.7

Example 215A

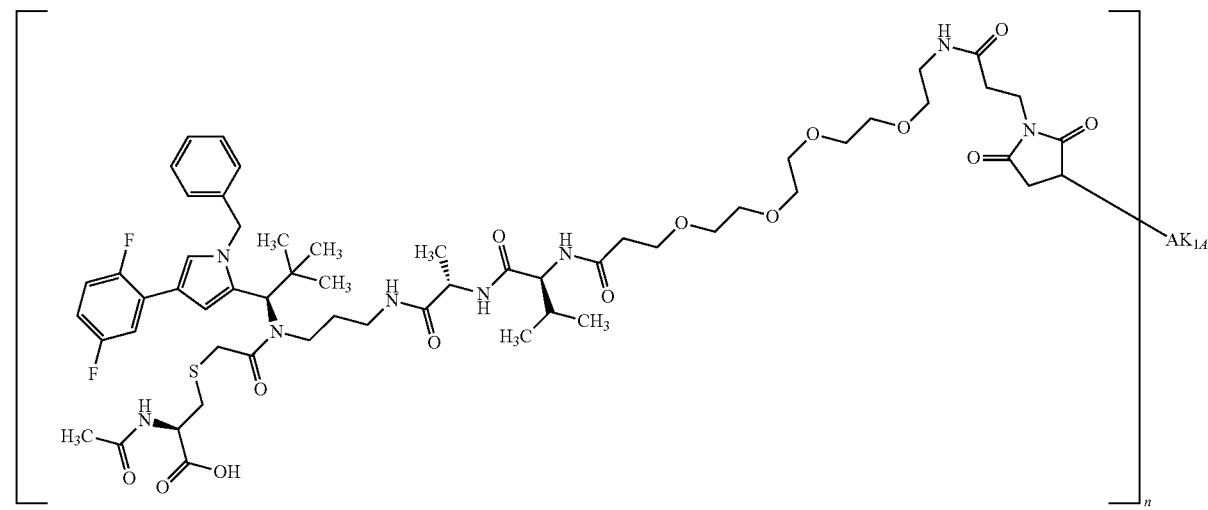

Here, 5.0 mg of cetuximab in PBS (c=15.21 mg/ml) were used for coupling with Intermediate F215, and the reaction was, after Sephadex purification, concentrated by ultracentrifugation and rediluted with PBS. Some of the ADC may also be present in the form of the hydrolysed open-chain succinamides attached to the antibody.

Protein concentration: 1.99 mg/ml
Drug/mAb ratio: 2.7

Example 215B

Here, 5.0 mg of anti-TWEAKR AK-1 antibody in PBS (c=18.6 mg/ml) were used for coupling with Intermediate F215, and the reaction was, after Sephadex purification, Example 215I Here, 5.0 mg of nimotuzumab in PBS (c=13.1 mg/ml) were used for coupling with Intermediate F215, and the reaction was, after Sephadex purification, concentrated by ultracentrifugation and rediluted with PBS. Some of the ADC may also be present in the form of the hydrolysed open-chain succinamides attached to the antibody.

Protein concentration: 1.83 mg/ml
Drug/mAb ratio: 2.6

Example 216A

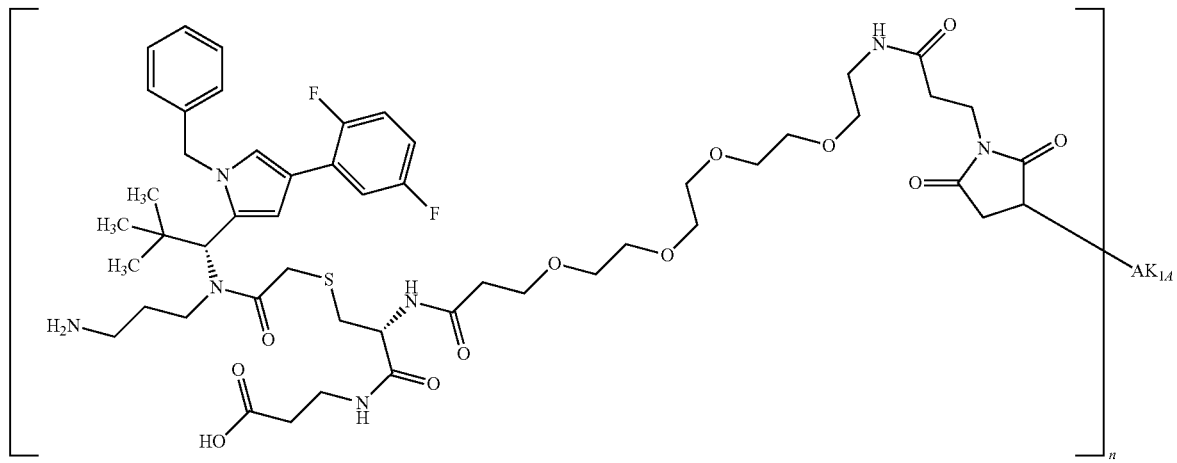

concentrated by ultracentrifugation and rediluted. Some of the ADC may also be present in the form of the hydrolysed open-chain succinamides attached to the antibody.

Protein concentration: 1.64 mg/ml
Drug/mAb ratio: 2.8

Example 215E

Here, 5.0 mg of trastuzumab antibody in PBS (c=13.50 mg/ml) were used for coupling with Intermediate F215, and the reaction was, after Sephadex purification, concentrated by ultracentrifugation and rediluted. Some of the ADC may also be present in the form of the hydrolysed open-chain succinamides attached to the antibody.

Protein concentration: 1.84 mg/ml
Drug/mAb ratio: 2.8

Example 215H

Here, 5.0 mg of panitumumab antibody in PBS (c=70.5 mg/ml) were used for coupling with Intermediate F215, and the reaction was, after Sephadex purification, concentrated by ultracentrifugation and rediluted. Some of the ADC may also be present in the form of the hydrolysed open-chain succinamides attached to the antibody.

Protein concentration: 1.86 mg/ml
Drug/mAb ratio: 1.4

Here, 5.0 mg of cetuximab in PBS (c=15.21 mg/ml) were used for coupling with Intermediate F216, and the reaction was, after Sephadex purification, concentrated by ultracentrifugation and rediluted with PBS. Some of the ADC may also be present in the form of the hydrolysed open-chain succinamides attached to the antibody.

Protein concentration: 1.97 mg/ml
Drug/mAb ratio: 2.8

Example 216B

Here, 5.0 mg of anti-TWEAKR AK-1 antibody in PBS (c=18.6 mg/ml) were used for coupling with Intermediate F216, and the reaction was, after Sephadex purification, concentrated by ultracentrifugation and rediluted. Some of the ADC may also be present in the form of the hydrolysed open-chain succinamides attached to the antibody.

Protein concentration: 1.94 mg/ml
Drug/mAb ratio: 2.5

Example 216E

Here, 5.0 mg of trastuzumab antibody in PBS (c=13.50 mg/ml) were used for coupling with Intermediate F216, and the reaction was, after Sephadex purification, concentrated by ultracentrifugation and rediluted. Some of the ADC may also be present in the form of the hydrolysed open-chain succinamides attached to the antibody.

Protein concentration: 1.90 mg/ml
Drug/mAb ratio: 1.7

Example 217A

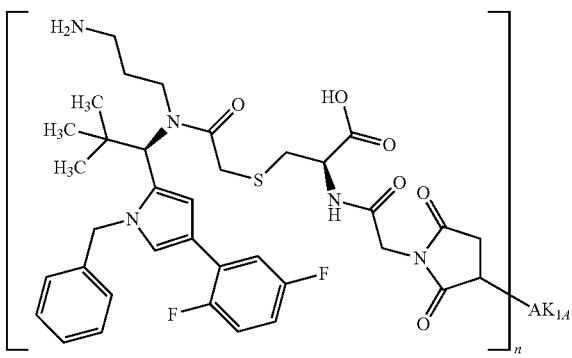

Here, 5.0 mg of cetuximab in PBS (c=15.21 mg/ml) were used for coupling with Intermediate F217, and the reaction was, after Sephadex purification, concentrated by ultracentrifugation and rediluted with PBS. Some of the ADC may also be present in the form of the hydrolysed open-chain succinamides attached to the antibody.

Protein concentration: 2.05 mg/ml
Drug/mAb ratio: 2.7

Example 217B

Here, 5.0 mg of anti-TWEAKR AK-1 antibody in PBS (c=18.6 mg/ml) were used for coupling with Intermediate F217, and the reaction was, after Sephadex purification, concentrated by ultracentrifugation and rediluted. Some of the ADC may also be present in the form of the hydrolysed open-chain succinamides attached to the antibody.

Protein concentration: 1.44 mg/ml
Drug/mAb ratio: 2.4

Example 217E

Here, 5.0 mg of trastuzumab antibody in PBS (c=13.50 mg/ml) were used for coupling with Intermediate F217, and the reaction was, after Sephadex purification, concentrated by ultracentrifugation and rediluted. Some of the ADC may also be present in the form of the hydrolysed open-chain succinamides attached to the antibody.

Protein concentration: 1.85 mg/ml
Drug/mAb ratio: 2.8

Example 218A

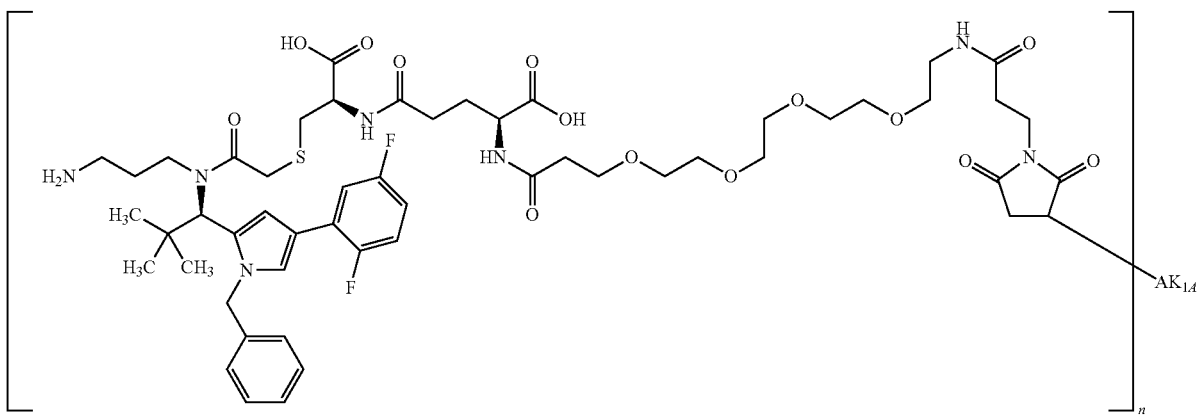

Here, 5.0 mg of cetuximab in PBS (c=15.21 mg/ml) were used for coupling with Intermediate F218, and the reaction was, after Sephadex purification, concentrated by ultracentrifugation and rediluted with PBS. Some of the ADC may also be present in the form of the hydrolysed open-chain succinamides attached to the antibody.

Protein concentration: 2.05 mg/ml
Drug/mAb ratio: 3.0

Example 218B

Here, 5.0 mg of anti-TWEAKR AK-1 antibody in PBS (c=18.6 mg/ml) were used for coupling with Intermediate F218, and the reaction was, after Sephadex purification, concentrated by ultracentrifugation and rediluted. Some of the ADC may also be present in the form of the hydrolysed open-chain succinamides attached to the antibody.

Protein concentration: 1.95 mg/ml
Drug/mAb ratio: 2.9

Example 218E

Here, 5.0 mg of trastuzumab antibody in PBS (c=13.50 mg/ml) were used for coupling with Intermediate F218, and the reaction was, after Sephadex purification, concentrated by ultracentrifugation and rediluted. Some of the ADC may also be present in the form of the hydrolysed open-chain succinamides attached to the antibody.
Protein concentration: 1.84 mg/ml
Drug/mAb ratio: 2.7

Example 218H

Here, 5.0 mg of panitumumab antibody in PBS (c=20 mg/ml) were used for coupling with Intermediate F218. The time for the reduction with TCEP was increased to 4 h and stirring time for the ADC coupling was increased to 20 h. After Sephadex purification, the reaction was concentrated by ultracentrifugation and rediluted. Some of the ADC may also be present in the form of the hydrolysed open-chain succinamides attached to the antibody.
Protein concentration: 1.33 mg/ml
Drug/mAb ratio: 0.8

Example 218I

Here, 5.0 mg of nimotuzumab antibody in PBS (c=13.8 mg/ml) were used for coupling with Intermediate F218, and the reaction was, after Sephadex purification, concentrated by ultracentrifugation and rediluted. Some of the ADC may also be present in the form of the hydrolysed open-chain succinamides attached to the antibody.
Protein concentration: 1.48 mg/ml
Drug/mAb ratio: 3.0

Example 219

Trifluoroacetic acid/N-(3-aminopropyl)-N-{(1R)-1-[1-benzyl-4-(2,5-difluorophenyl)-1H-pyrrol-2-yl]-2,2-dimethylpropyl}-4-methylbenzamide (1:1)

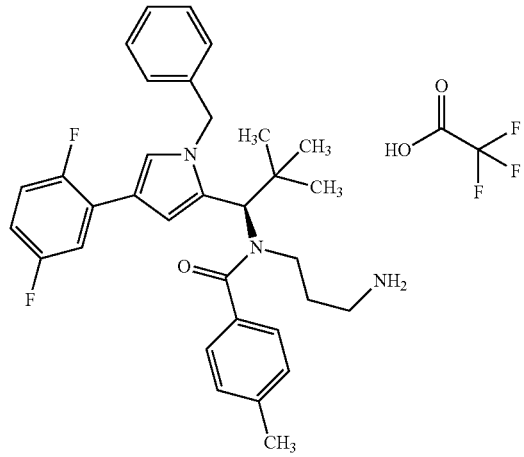 [SMILES: Cc1ccc(C(=O)N(CCCN)[C@@H](c2cc(-c3cc(F)ccc3F)cn2Cc2ccccc2)C(C)(C)C)cc1 ; O=C(O)C(F)(F)F]

70.0 mg (0.09 mmol) of 9H-fluoren-9-ylmethyl-[3-({(1R)-1-[1-benzyl-4-(2,5-difluorophenyl)-1H-pyrrol-2-yl]-2,2-dimethylpropyl}amino)propyl]carbamate (Intermediate C67) were initially charged in 3.0 ml of dichloromethane, and 31.3 mg (0.31 mmol) of triethylamine and 31.8 mg (0.21 mmol) of 4-methylbenzoyl chloride were added. The reaction mixture was stirred at RT overnight. The solvent was evaporated under reduced pressure and the residue was purified directly by preparative RP-HPLC (column: Reprosil 125×30; 10µ, flow rate: 50 ml/min, MeCN/water). The solvents were evaporated under reduced pressure and the residue was dried under high vacuum. This gave 33.4 mg (48% of theory) of the compound 9H-fluoren-9-ylmethyl {3-[{(1R)-1-[1-benzyl-4-(2,5-difluorophenyl)-1H-pyrrol-2-yl]-2,2-dimethylpropyl}(4-methylbenzoyl)amino]propyl}carbamate.

LC-MS (Method 2): $R_t$=11.91 min; MS (ESIpos): m/z=774 (M+Na)$^+$.

33.0 mg (0.04 mmol) of 9H-fluoren-9-ylmethyl {3-[{(1R)-1-[1-benzyl-4-(2,5-difluorophenyl)-1H-pyrrol-2-yl]-2,2-dimethylpropyl}(4-methylbenzoyl)amino]propyl}carbamate in 1.0 ml of DMF were stirred with 20.0 mg (0.23 mmol) of morpholine overnight. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 9.6 mg (34% of theory) of the title compound.

LC-MS (Method 1): $R_t$=1.01 min; MS (ESIpos): m/z=530 (M+H)$^+$.

Example 220

Trifluoroacetic acid/N-(3-aminopropyl)-N-{(1R)-1-[1-benzyl-4-(2,5-difluorophenyl)-1H-pyrrol-2-yl]-2,2-dimethylpropyl}-4-(methylsulphanyl)benzamide (1:1)

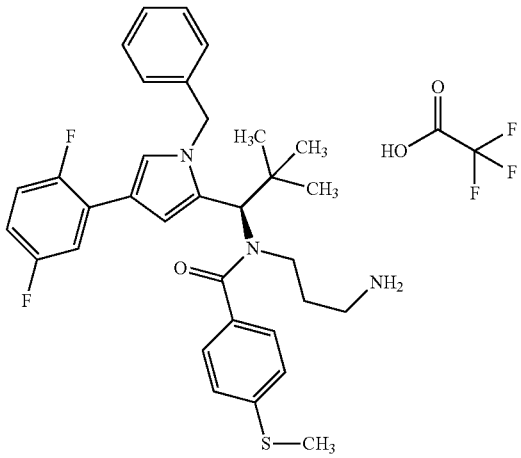 [SMILES: CSc1ccc(C(=O)N(CCCN)[C@@H](c2cc(-c3cc(F)ccc3F)cn2Cc2ccccc2)C(C)(C)C)cc1 ; O=C(O)C(F)(F)F]

50.0 mg (0.07 mmol) of 9H-fluoren-9-ylmethyl-[3-({(1R)-1-[1-benzyl-4-(2,5-difluorophenyl)-1H-pyrrol-2-yl]-2,2-dimethylpropyl}amino)propyl]carbamate (Intermediate C67) were initially charged in 2.0 ml of dichloromethane, and 22.3 mg (0.22 mmol) of triethylamine and 27.5 mg (0.15 mmol) of 4-(methylsulphanyl)benzoyl chloride were added. The reaction mixture was stirred at 40° C. for 4 h, another 10.2 mg (0.10 mmol) of triethylamine and 27.5 mg (0.15 mmol) of 4-(methylsulphanyl)benzoyl chloride were added and the mixture was stirred at RT overnight. Another 14.9 mg (0.15 mmol) of triethylamine and 27.5 mg (0.15 mmol) of 4-(methylsulphanyl)benzoyl chloride were then added, and the mixture was stirred at 40° C. for 2 h. The mixture was diluted with ethyl acetate and the organic phase was washed three times with water and once with saturated NaCl solution. The organic phase was dried over magnesium sulphate and concentrated under reduced pressure. The residue was purified by preparative RP-HPLC (column: Reprosil 125×30; 10µ, flow rate: 50 ml/min, MeCN/water). The solvents were evaporated under reduced pressure and the residue was dried under high vacuum. This gave 39.8 mg (76% of theory) of the compound 9H-fluoren-9-ylmethyl

[3-({(1R)-1-[1-benzyl-4-(2,5-difluorophenyl)-1H-pyrrol-2-yl]-2,2-dimethylpropyl}[4-(methylsulphanyl)benzoyl]amino)propyl]carbamate.

LC-MS (Method 1): $R_t$=1.59 min; MS (ESIpos): m/z=785 (M+H)$^+$.

18.0 mg (0.02 mmol) of 9H-fluoren-9-ylmethyl [3-({(1R)-1-[1-benzyl-4-(2,5-difluorophenyl)-1H-pyrrol-2-yl]-2,2-dimethylpropyl}[4-(methylsulphanyl)benzoyl]amino)propyl]carbamate in 1.0 ml of DMF were stirred with 10.0 mg (0.12 mmol) of morpholine overnight. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.2 mg (40% of theory) of the title compound.

LC-MS (Method 1): $R_t$=0.99 min; MS (ESIpos): m/z=562 (M+H)$^+$.

Example 221

Trifluoroacetic acid/(2S)—N-(3-aminopropyl)-N-{(1R)-1-[1-benzyl-4-(2,5-difluorophenyl)-1H-pyrrol-2-yl]-2,2-dimethylpropyl}-2-hydroxypropanamide (1:1)

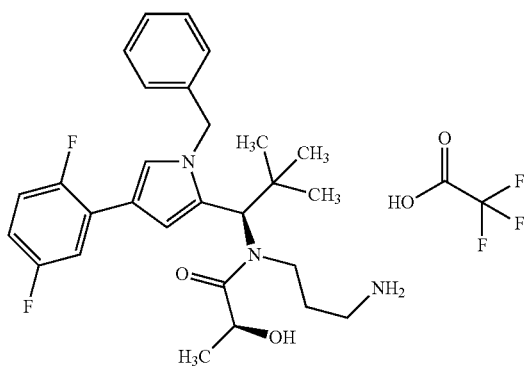 [SMILES: C[C@H](O)C(=O)N(CCCN)[C@@H](c1cc(-c2cc(F)ccc2F)cn1Cc1ccccc1)C(C)(C)C ; O=C(O)C(F)(F)F]

40.0 mg (0.06 mmol) of 9H-fluoren-9-ylmethyl-[3-({(1R)-1-[1-benzyl-4-(2,5-difluorophenyl)-1H-pyrrol-2-yl]-2,2-dimethylpropyl}amino)propyl]carbamate (Intermediate C67) were initially charged in 2.0 ml of dichloromethane, and 9.6 mg (0.10 mmol) of triethylamine and 14.3 mg (0.10 mmol) of (2S)-1-chloro-1-oxopropan-2-yl acetate were added. The reaction mixture was stirred at RT overnight. The solvent was evaporated under reduced pressure and the residue was purified by preparative RP-HPLC (column: Reprosil 125×30; 10μ, flow rate: 50 ml/min, MeCN/water). The solvents were evaporated under reduced pressure and the residue was dried under high vacuum. This gave 39.7 mg (84% of theory) of the compound (2S)-1-[{(1R)-1-[1-benzyl-4-(2,5-difluorophenyl)-1H-pyrrol-2-yl]-2,2-dimethylpropyl}1(3-[(9H-fluoren-9-ylmethoxy)carbonyl]amino}propyl)amino]-1-oxopropan-2-yl acetate.

LC-MS (Method 1): $R_t$=1.51 min; MS (ESIpos): m/z=748 (M+H)$^+$.

37.0 mg (0.05 mmol) of (2S)-1-[{(1R)-1-[1-benzyl-4-(2,5-difluorophenyl)-1H-pyrrol-2-yl]-2,2-dimethylpropyl}(3-{[(9H-fluoren-9-ylmethoxy)carbonyl]amino}propyl)amino]-1-oxopropan-2-yl acetate in 1.0 ml of DMF were stirred with 0.1 ml of morpholine and 3 drops of water at 50° C. for 10 h. Another 0.1 ml of morpholine and 0.1 ml of water were added, and the mixture was stirred at 50° C. for 10 h. After addition of 20.5 mg (0.15 mmol) of potassium carbonate and 72 h of stirring at RT, 0.1 ml of 1N NaOH solution was added and the mixture was stirred at RT overnight. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 20.5 mg (69% of theory) of the title compound.

LC-MS (Method 1): $R_t$=0.89 min; MS (ESIpos): m/z=484 (M+H)$^+$.

Example 222

Trifluoroacetic acid/N-(3-aminopropyl)-N-{(1R)-1-[1-benzyl-4-(2,5-difluorophenyl)-1H-pyrrol-2-yl]-2,2-dimethylpropyl}-2-(methylsulphanyl)acetamide (1:1)

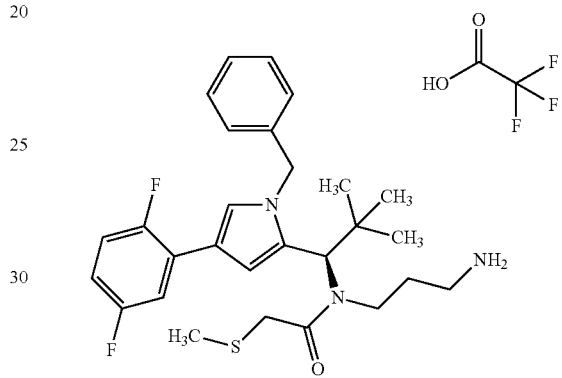

70.0 mg (0.11 mmol) of 2-(trimethylsilyl)ethyl-{3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C 70) were initially charged in 3.0 ml of DMF. 15.5 mg (0.22 mmol) of sodium methanethiolate were added, and the reaction mixture was stirred at 50° C. for 2 h. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 60.0 mg (84% of theory) of the compound 2-(trimethylsilyl)ethyl [3-({(1R)-1-[1-benzyl-4-(2,5-difluorophenyl)-1H-pyrrol-2-yl]-2,2-dimethylpropyl}[(methylsulphanyl)acetyl]amino)propyl]carbamate.

LC-MS (Method 1): $R_t$=1.50 min; MS (ESIpos): m/z=644 (M+H)$^+$.

40.0 mg (0.06 mol) of 2-(trimethylsilyl)ethyl [3-({(1R)-1-[1-benzyl-4-(2,5-difluorophenyl)-1H-pyrrol-2-yl]-2,2-dimethylpropyl}[(methylsulphanyl)acetyl]amino)propyl]carbamate were dissolved in 2.0 ml of trifluoroethanol, and 21.2 mg (0.16 mmol) of zinc dichloride were added. The reaction mixture was stirred at 50° C. overnight. 45.4 mg (0.01 mmol) of ethylenediamin-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 34.6 mg (91% of theory) of the title compound.

LC-MS (Method 1): $R_t$=0.92 min; MS (ESIpos): m/z=500 (M+H)$^+$.

Example 223

Trifluoroacetic acid/(2S)—N-(3-aminopropyl)-N-{(1R)-1-[4-benzyl-1-(2,5-difluorophenyl)-1H-pyrazol-3-yl]-2,2-dimethylpropyl}-2-hydroxypropanamide (1:1)

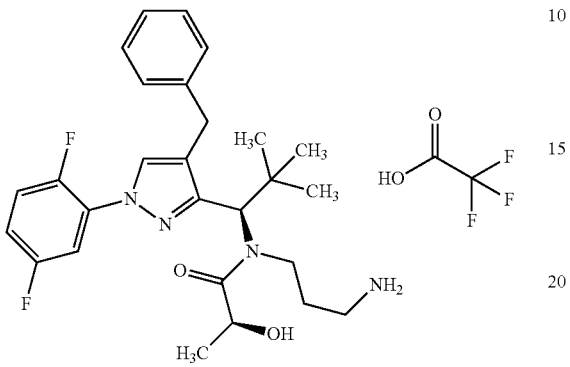

40.0 mg (0.08 mmol) of tert-butyl [3-({(1R)-1-[4-benzyl-1-(2,5-difluorophenyl)-1H-pyrazol-3-yl]-2,2-dimethylpropyl}amino)propyl]carbamate were dissolved in 2.0 ml of dichloromethane, and 19.7 mg (0.20 mmol) of triethylamine and 29.4 mg (0.20 mmol) of (2S)-1-chloro-1-oxopropan-2-yl acetate were added. The reaction mixture was stirred overnight. The solvent was evaporated under reduced pressure and the residue was purified by prep. RP-HPLC (column: Reprosil 125×30; 10µ, flow rate: 50 ml/min, MeCN/water). The solvents were evaporated under reduced pressure and the residue was dried under high vacuum. This gave 21.2 mg (43% of theory) of the compound 2S)-1-((1R)-1-[4-benzyl-1-(2,5-difluorophenyl)-1H-pyrazol-3-yl]-2,2-dimethylpropyl {3-[(tert-butoxycarbonyl)amino]propyl amino)-1-oxopropan-2-yl}acetate.

LC-MS (Method 1): $R_t$=1.46 min; MS (ESIpos): m/z=627 (M+H)$^+$.

21.2 mg (0.03 mmol) of (2S)-1-((1R)-1-[4-benzyl-1-(2,5-difluorophenyl)-1H-pyrazol-3-yl]-2,2-dimethylpropyl {3-[(tert-butoxycarbonyl)amino]propyl}amino)-1-oxopropan-2-yl acetate were dissolved in 1.0 ml of dichloromethane, 77.1 mg (0.68 mmol) of trifluoroacetic acid were added and the mixture was stirred at RT for 2 h. Two more times, a further 77.1 mg (0.68 mmol) of trifluoroacetic acid were added, and in each case the mixture was stirred at RT overnight. The solvent was evaporated under reduced pressure and the residue was repeatedly co-distilled with dichloromethane and then dried under high vacuum. The residue, comprising the substance trifluoroacetic acid/(2S)-[4(3-aminopropyl){(1R)-1-[4-benzyl-1-(2,5-difluorophenyl)-1H-pyrazol-3-yl]-2,2-dimethylpropyl}amino]-1-oxopropan-2-yl acetate (1:1), was reacted further without further purification.

LC-MS (Method 1): $R_t$=0.92 min; MS (ESIpos): m/z=527 (M+H)$^+$.

26.5 mg (0.04 mmol) of trifluoroacetic acid/(2S)-1-[(3-aminopropyl){(1R)-1-[4-benzyl-1-(2,5-difluorophenyl)-1H-pyrazol-3-yl]-2,2-dimethylpropyl}amino]-1-oxopropan-2-yl acetat (1:1) were dissolved in THF/methanol/water (1.0 ml/1.0 ml/0.05 ml), and 17.2 mg of potassium carbonate were added. The reaction mixture was stirred at RT overnight. The reaction mixture was purified directly by preparative RP-HPLC (column: Reprosil 125×30; 10µ, flow rate: 50 ml/min, MeCN/water; 0.1% TFA). The solvents were evaporated under reduced pressure and the residue was dried under high vacuum. This gave 17.3 mg (70% of theory) of the title compound.

LC-MS (Method 1): $R_t$=0.91 min; MS (ESIpos): m/z=485 (M+H)$^+$.

Example 224

Trifluoroacetic acid/methyl 4-[(3-aminopropyl){(1R)-1-[1-benzyl-4-(2,5-difluorophenyl)-1H-pyrrol-2-yl]-2,2-dimethylpropyl}amino]-4-oxobutanoate (1:1)

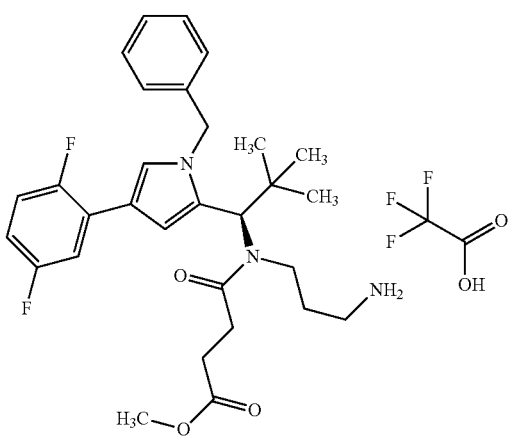

60.0 mg (0.11 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) were dissolved in 1.0 ml of dichloromethane, and 19.6 mg (0.25 mmol) of pyridine and 35.8 mg (0.24 mmol) of methyl 4-chloro-4-oxobutanoate were added. The reaction mixture was stirred at 40° C. overnight. Another 19.6 mg (0.25 mmol) of pyridine and 35.8 mg (0.24 mmol) of methyl 4-chloro-4-oxobutanoate were added and the mixture was stirred at 40° C. overnight. The solvent was evaporated under reduced pressure and the residue was purified by preparative RP-HPLC (column: Reprosil 125×30; 10µ, flow rate: 50 ml/min, MeCN/water). The solvents were evaporated under reduced pressure and the residue was dried under high vacuum. This gave 16.1 mg (22% of theory) of the compound methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate.

LC-MS (Method 1): $R_t$=1.52 min; MS (ESIpos): m/z=670 (M+H)$^+$.

16.1 mg (0.02 mmol) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate were dissolved in 1.0 ml of trifluoroethanol, and 16.4 mg (0.12 mmol) of zinc dichloride were added. The reaction mixture was stirred at 50° C. for 5 h. 35.1 mg (0.12 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 11.1 mg (72% of theory) of the title compound.

LC-MS (Method 1): $R_t$=0.93 min; MS (ESIpos): m/z=526 (M+H)$^+$.

Example 225

4-[(3-Aminopropyl) {(1R)-1-[1-benzyl-4-(2,5-difluorophenyl)-1H-pyrrol-2-yl]-2,2-dimethylpropyl}amino]-4-oxobutanoic acid/trifluoroacetic acid (1:1)

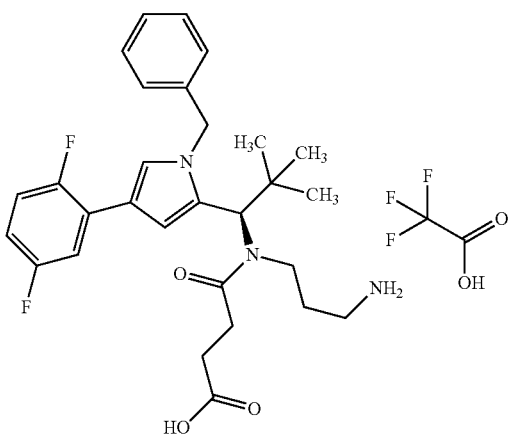

9.7 mg (0.02 mmol) of trifluoroacetic acid/methyl 4-[(3-aminopropyl){(1R)-1-[1-benzyl-4-(2,5-difluorophenyl)-1H-pyrrol-2-yl]-2,2-dimethylpropyl}amino]-4-oxobutanoate (1:1) (Example 224) were initially charged in THF/methanol/water (1.0 ml/0.2 ml/0.04 ml), and 1.3 mg (0.03 mmol) of lithium hydroxide monohydrate were added. The reaction mixture was stirred at RT overnight. A further 1.3 mg (0.03 mmol) of lithium hydroxide monohydrate were added, and the mixture was stirred at RT overnight. 3.6 mg (0.06 mmol) of HOAc were added and the reaction mixture was purified directly by preparative RP-HPLC (column: Reprosil 125× 30; 10µ, flow rate: 50 ml/min, MeCN/water; 0.1% TFA). The solvents were evaporated under reduced pressure and the residue was dried under high vacuum. This gave 5.4 mg (57% of theory) of the title compound.

LC-MS (Method 1): $R_t$=0.90 min; MS (ESIpos): m/z=512 (M+H)$^+$.

Example 226

(2R)-22-[(3R/S)-3-{[(2R)-2-Amino-2-carboxyethyl]sulphanyl}-2,5-dioxopyrrolidin-1-yl]-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-4,20-dioxo-7,10,13,16-tetraoxa-3,19-diazadocosan-1-oic acid/trifluoroacetic (1:2)

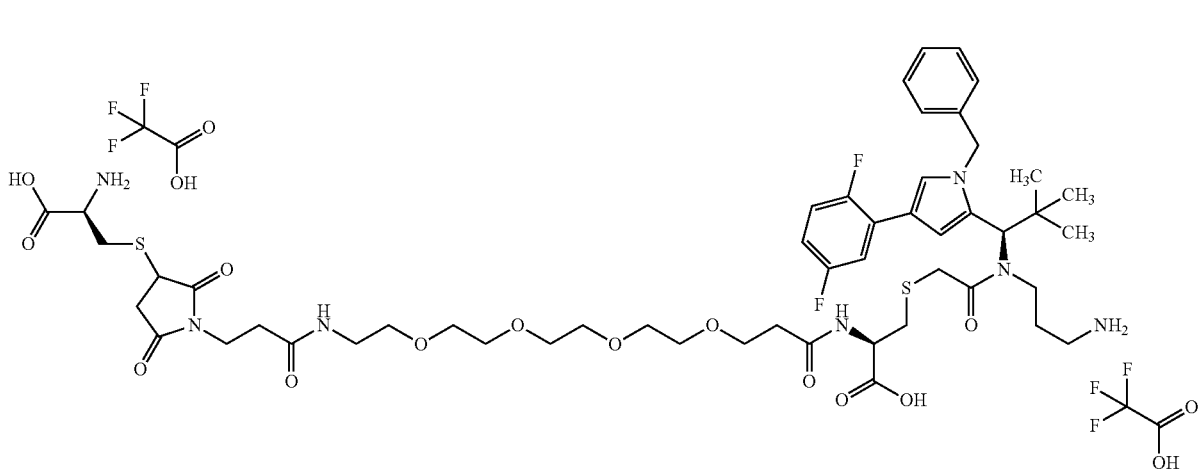

10.3 mg (mmol) of R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic acid (1:1) (Intermediate F209) were initially charged in DMF/water (2.0 ml/0.2 ml), L-cysteine was added and the mixture was stirred at RT for 10 min Water was added and the reaction mixture was purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 10.3 mg (82% of theory) of the title compound.

LC-MS (Method 1): $R_t$=0.84 min; MS (ESIpos): m/z=1092 (M+H)$^+$.

Example 227

Trifluoroacetic acid/4-amino-N-(3-aminopropyl)-N-{(1R)-1-[4-benzyl-1-(2,5-difluorophenyl)-1H-pyrazol-3-yl]-2,2-dimethylpropyl}benzamide (2:1)

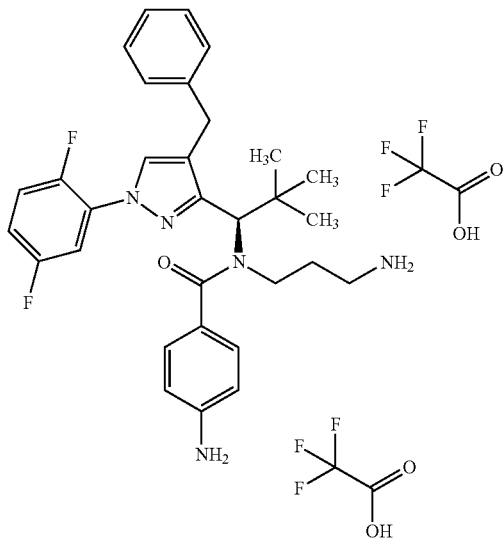 [SMILES: CC(C)(C)[C@H](c1nn(-c2cc(F)ccc2F)cc1Cc1ccccc1)N(CCCN)C(=O)c1ccc(N)cc1 ; O=C(O)C(F)(F)F ; O=C(O)C(F)(F)F]

50.0 mg (0.10 mol) of tert-butyl [3-({(1R)-1-[4-benzyl-1-(2,5-difluorophenyl)-1H-pyrazol-3-yl]-2,2-dimethylpropyl}amino)propyl]carbamate (Intermediate C68) were initially charged in dichloromethane, and 54.9 mg (0.22 mmol) of tert-butyl [4-(chlorocarbonyl)phenyl]carbamate (Intermediate L71) and 22.7 mg (0.22 mmol) of triethylamine were added. The reaction mixture was stirred at RT overnight, and another 54.9 mg (0.22 mmol) of tert-butyl [4-(chlorocarbonyl)phenyl]carbamate (Intermediate L71) and 22.7 mg (0.22 mmol) of triethylamine were added. The reaction mixture was stirred at RT overnight. The solvent was evaporated under reduced pressure and the residue was purified by prep. RP-HPLC (column: Reprosil 250×40; 10μ, flow rate: 50 ml/min, MeCN/water, 0.1% TFA). The solvents were evaporated under reduced pressure and the residue was dried under high vacuum. This gave 26.2 mg (37% of theory) of the compound.

tert-Butyl [3-({(1R)-1-[4-benzyl-1-(2,5-difluorophenyl)-1H-pyrazol-3-yl]-2,2-dimethylpropyl}{4-[(tert-butoxycarbonyl)amino]benzoyl}amino)propyl]carbamate LC-MS (Method 1): $R_t$=5.34 min; MS (ESIpos): m/z=732 (M+H)$^+$.

26.2 mg (0.04 mmol) of tert-butyl [3-({(1R)-1-[4-benzyl-1-(2,5-difluorophenyl)-1H-pyrazol-3-yl]-2,2-dimethylpropyl}{4-[(tert-butoxycarbonyl)amino]benzoyl}amino)propyl]carbamate were dissolved in 2.0 ml of dichloromethane, and 204.1 mg (1.79 mmol) of TFA were added. The reaction mixture was stirred at RT overnight. The solvent was evaporated under reduced pressure and the residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 3.4 mg (13% of theory) of the title compound.

LC-MS (Method 1): $R_t$=0.92 min; MS (ESIpos): m/z=532 (M+H)$^+$.

Example 228

N-Acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

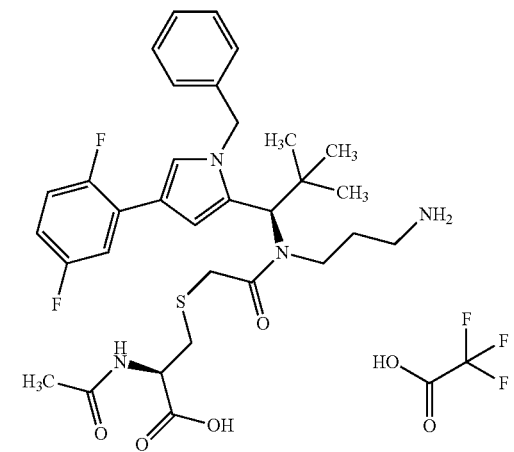 [SMILES: CC(=O)N[C@@H](CSCC(=O)N(CCCN)[C@@H](c1cc(-c2cc(F)ccc2F)cn1Cc1ccccc1)C(C)(C)C)C(=O)O ; O=C(O)C(F)(F)F]

50.0 mg (0.08 mol) of 2-(trimethylsilyl)ethyl-{3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) were suspended in 0.30 ml of water with 66.43 mg of sodium bicarbonate. A solution of 144.47 (0.95 mmol) of 1,8-diazabicyclo(5.4.0)undec-7-ene and 51.62 mg (0.32 mmol) of N-acetyl-L-cysteine in 3.0 ml of isopropanol was added to the suspension. The reaction mixture was stirred at 50° C. for 2.5 h. Water (0.1% TFA) was added and the reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 55.2 mg (92% of theory) of the compound N-acetyl-S -(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.41 min; MS (ESIpos): m/z=759 (M+H)$^+$.

53.1 mg (69.96 μmol) of N-acetyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 5.0 ml of trifluoroethanol, and 57.2 mg (419.76 μmol) of zinc dichloride were added. The reaction mixture was stirred at 50° C. for 4 h. 122.67 mg (0.42 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). This gave 32.5 mg (64% of theory) of the title compound.

LC-MS (Method 1): $R_t$=0.90 min; MS (ESIpos): m/z=615 (M+H)$^+$.

Example 229

N-Acetyl-S-[2-([3-(L-alanylamino)propyl]{(1R)-1-[1-benzyl-4-(2,5-difluorophenyl)-1H-pyrrol-2-yl]-2,2-dimethylpropyl}amino)-2-oxoethyl]-L-cysteine/trifluoroacetic acid (1:1)

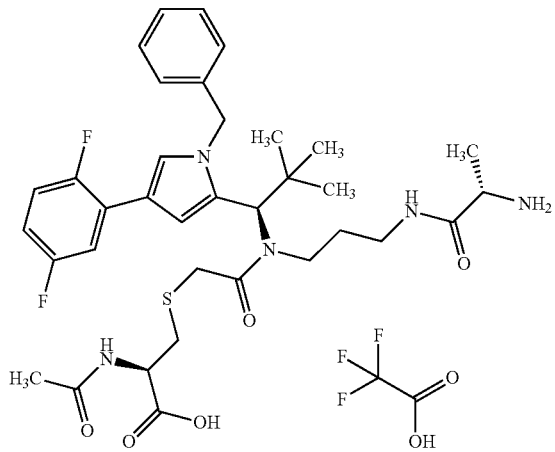 [SMILES: CC(=O)N[C@@H](CSCC(=O)N(CCCNC(=O)[C@H](C)N)[C@@H](c1cc(-c2cc(F)ccc2F)cn1Cc1ccccc1)C(C)(C)C)C(=O)O ; O=C(O)C(F)(F)F]

30.3 mg (41.58 μmol) of N-acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1) (Example 228) were dissolved in 1.5 ml of DMF, and 8.4 mg (83.15 μmol) of 4-methylmorpholine and 14.65 mg (45.73 μmol) of 2,5-dioxopyrrolidin-1-yl-N-[(benzyloxy)carbonyl]-L-alaninate were added. The reaction mixture was stirred at RT overnight, and another 8.4 mg (83.15 μmol) of 4-methylmorpholine were then added. Once more, the reaction mixture was stirred at RT overnight. 10.0 mg (0.17 mmol) of acetic acid were added and the reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 31.2 mg (92% of theory) of the compound N-acetyl-S-[2-({(1R)-1-[1-benzyl-4-(2,5-difluorophenyl)-1H-pyrrol-2-yl]-2,2-dimethylpropyl}[3-({N-[(benzyloxy)carbonyl]-L-alanyl}amino)propyl]amino)-2-oxoethyl]-L-cysteine.

LC-MS (Method 1): $R_t$=1.22 min; MS (ESIpos): m/z=820 (M+H)$^+$.

28.6 mg (0.04 mmol) of N-acetyl-S-[2-({(1R)-1-[1-benzyl-4-(2,5-difluorophenyl)-1H-pyrrol-2-yl]-2,2-dimethylpropyl}[3-({N-[(benzyloxy)carbonyl]-L-alanyl}amino)propyl]amino)-2-oxoethyl]-L-cysteine were dissolved in 5.0 ml of ethanol, and 2.9 mg of palladium on activated carbon (10%) were added. The reaction mixture was hydrogenated at standard pressure and RT overnight. The mixture was filtered through Celite and the filter cake was washed with a mixture of ethanol. The solvents were evaporated under reduced pressure and the residue was purified by preparative RP-HPLC (column: Reprosil 250×30; 10μ, flow rate: 50 ml/min, MeCN/water, 0.1% TFA). The solvents were evaporated under reduced pressure and the residue was lyophilized. This gave 17.4 mg (62% of theory) of the title compound.

LC-MS (Method 1): $R_t$=0.85 min; MS (ESIpos): m/z=686 (M+H)$^+$.

Example 230

Trifluoroacetic acid/(2S)—N-(3-aminopropyl)-N-{(1R)-1-[1-benzyl-4-(2,5-difluorophenyl)-1H-pyrrol-2-yl]-2,2-dimethylpropyl}tetrahydrofuran-2-carboxamide (1:1)

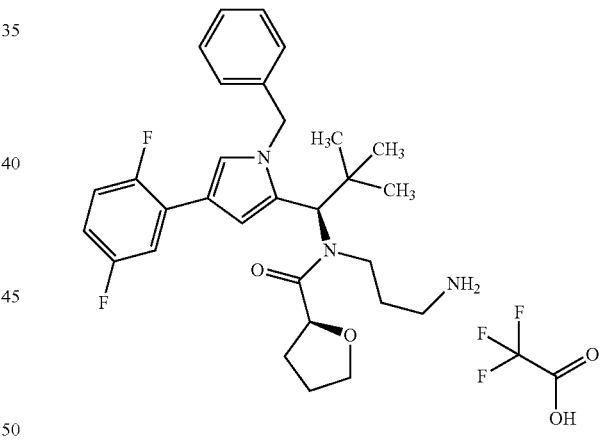

100.0 mg (0.16 mmol) of 9H-fluoren-9-ylmethyl-[3-({(1R)-1-[1-benzyl-4-(2,5-difluorophenyl)-1H-pyrrol-2-yl]-2,2-dimethylpropyl}amino)propyl]carbamate (Intermediate C67) were dissolved in 5.0 ml of dichloromethane with 71.9 mg (0.71 mmol) of triethylamine and added dropwise to a solution of freshly prepared (2S)-tetrahydrofuran-2-carbonyl chloride (preparation: 54.7 mg (0.39 mmol) of (2S)-tetrahydrofuran-2-carboxylic acid were initially charged in 0.7 ml of toluene, 0.04 ml of thionyl chloride were added and the mixture was stirred at 90° C. for 1 h. After cooling, the crude reaction solution was reacted further). The reaction mixture was stirred at RT overnight. The solvents were evaporated under reduced pressure and the residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 44.3 mg (38% of theory) of the compound 9H-fluoren-9-ylmethyl [3-({(1R)-1-[1-benzyl-4-(2,5-difluorophenyl)-1H-pyrrol-2-yl]-2,2-dimethylpropyl}[(2S)-tetrahydrofuran-2-ylcarbonyl]amino)propyl]carbamate.

LC-MS (Method 1): R_t=1.52 min; MS (ESIpos): m/z=776 (M+HCOOH−H)⁻.

26.0 mg (0.04 mmol) of 9H-fluoren-9-ylmethyl [3-({(1R)-1-[1-benzyl-4-(2,5-difluorophenyl)-1H-pyrrol-2-yl]-2,2-dimethylpropyl}[(2S)-tetrahydrofuran-2-ylcarbonyl]amino)propyl]carbamate were dissolved in 2.6 ml of DMF, and 0.26 ml of morpholine were added. The reaction mixture was stirred at RT for 3 h. Purification was carried out directly by preparative RP-HPLC (column: Reprosil 125×30; 10μ, flow rate: 50 ml/min, MeCN/water, 0.1% TFA). This gave 11.7 mg (53% of theory) of the title compound.

LC-MS (Method 1): R_t=0.93 min; MS (ESIpos): m/z=510 (M+H)⁺.

Example 231

3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoic acid/trifluoroacetic acid (1:1)

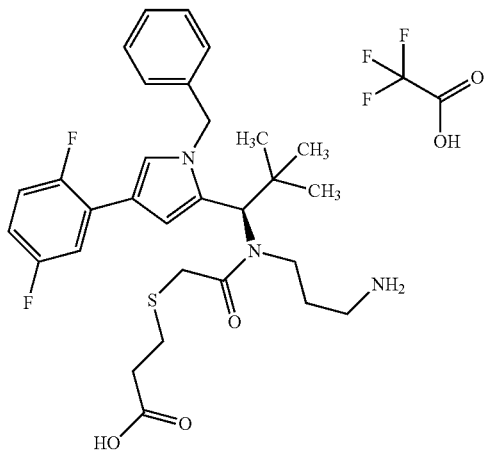 [SMILES: CC(C)(C)[C@H](c1cc(-c2cc(F)ccc2F)cn1Cc1ccccc1)N(CCCN)C(=O)CSCCC(=O)O ; O=C(O)C(F)(F)F]

53.9 mg (0.08 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were dissolved in 4.0 ml of trifluoroethanol, and 31.4 mg (0.23 mmol) of zinc dichloride were added. The reaction mixture was stirred at 50° C. overnight. 67.3 mg (0.23 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). This gave 34.2 mg (66% of theory) of the title compound.

LC-MS (Method 1): R_t=0.91 min; MS (ESIpos): m/z=558 (M+H)⁺.

Example 232

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}homocysteine/trifluoroacetic acid (1:2)

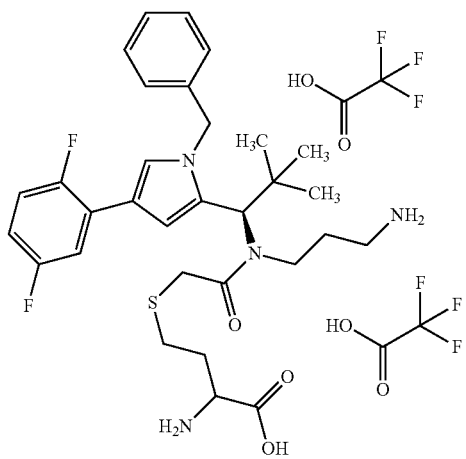

40.0 mg (47.3 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine (Intermediate C11) were dissolved in 3.0 ml of trifluoroethanol, and 38.7 mg (0.28 μmol) of zinc dichloride were added. The reaction mixture was stirred at 50° C. for 6 h. 83 mg (0.28 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). This gave 32.4 mg (84% of theory) of the title compound.

LC-MS (Method 1): R_t=0.81 min; MS (ESIpos): m/z=587 (M+H)⁺.

Example 233

Trifluoroactic acid/4-amino-N-(3-aminopropyl)-N-{(1R)-1-[1-benzyl-4-(2,5-difluorophenyl)-1H-pyrrol-2-yl]-2,2-dimethylpropyl}benzamide (2:1)

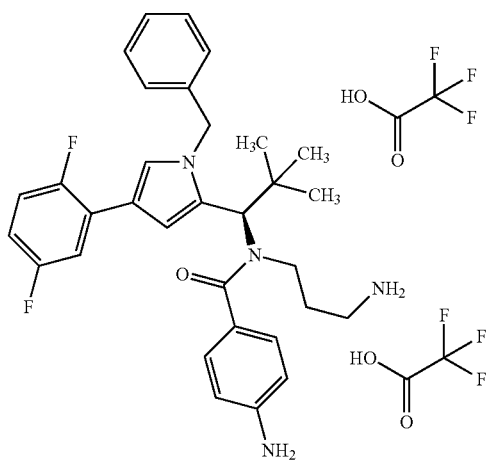

73.0 mg (0.12 mmol) of 9H-fluoren-9-ylmethyl-[3-({(1R)-1-[1-benzyl-4-(2,5-difluorophenyl)-1H-pyrrol-2-yl]-2,2-dimethylpropyl}amino)propyl]carbamate (Intermediate C67) and 27.8 mg (0.15 mmol) of 4-nitrobenzoyl chloride were dissolved in 2.0 ml of dichloromethane, and 15.2 mg (0.15 mmol) of triethylamine were added. The reaction mixture was stirred at RT overnight. The same amount of 4-nitrobenzoyl chloride and triethylamine was added again, and the reaction mixture was stirred at RT overnight. The solvent was evaporated under reduced pressure and the residue was purified by preparative RP-HPLC (column: Reprosil 125×30; 10μ, flow rate: 50 ml/min, MeCN/water, 0.1% TFA). This gave 39.3 mg (44% of theory) of the compound 9H-fluoren-9-ylmethyl {3-[{(1R)-1-[1-benzyl-4-(2,5-difluorophenyl)-1H-pyrrol-2-yl]-2,2-dimethylpropyl}(4-nitrobenzoyl)amino]propyl}carbamate.

LC-MS (Method 1): $R_t$=1.54 min; MS (ESIpos): m/z=783 (M+H)$^+$.

39.3 mg (0.05 mmol) of fluoren-9-ylmethyl-{3-[{(1R)-1-[1-benzyl-4-(2,5-difluorophenyl)-1H-pyrrol-2-yl]-2,2-dimethylpropyl}(4-nitrobenzoyl)amino]propy}carbamate were dissolved in 2.0 ml of ethanol, 3.9 mg of palladium hydroxide on activated carbon (20%) were added and the mixture was hydrogenated at standard pressure overnight. The reaction mixture was filtered through a paper filter and the filter cake was washed with ethanol. The solvent was evaporated under reduced pressure. The residue was purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 32.9 mg (86% of theory) of the title compound. LC-MS (Method 1): $R_t$=0.93 min; MS (ESIpos): m/z=531 (M+H)$^+$.

Example 234A

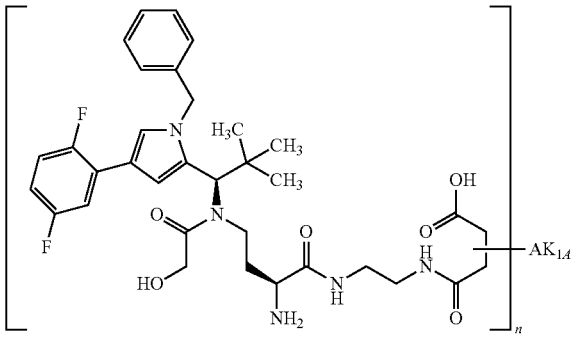

Under argon, a solution of 0.029 mg of TCEP in 50 μl of PBS buffer was added to 5 mg of cetuximab in 500 μl of PBS (c=10 mg/ml). The reaction was stirred at RT for 30 min, and 0.2 mg (0.00027 mmol) of Intermediate F85 dissolved in 50 μl of DMSO were then added. After a further 90 min of stirring at RT, the reaction was diluted with 1900 μl of PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.68 mg/ml
Drug/mAb ratio: 3.8

Example 234B

Under argon, a solution of 0.029 mg of TCEP in 50 μl of PBS buffer was added to 5 mg of anti-TWEAKR AK-1 in 269 μl of PBS (c=18.6 mg/ml). The reaction was stirred at RT for 30 min, and 0.2 mg (0.00027 mmol) of Intermediate F85 dissolved in 50 μl of DMSO were then added. After a further 90 min of stirring at RT, the reaction was diluted with 2130 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.57 mg/ml
Drug/mAb ratio: 3.7

Example 234I

Under argon, a solution of 0.029 mg of TCEP in 50 μl of PBS buffer was added to 5 mg of nimotuzumab in 500 μl of PBS (c=10 mg/ml). The reaction was stirred at RT for 30 min, and 0.2 mg (0.00027 mmol) of Intermediate F85 dissolved in 50 μl of DMSO were then added. After a further 90 min of stirring at RT, the reaction was diluted with 1900 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.93 mg/ml
Drug/mAb ratio: 3.6

Example 234H

Under argon, a solution of 0.029 mg of TCEP in 50 μl of PBS buffer was added to 5 mg of panitumumab in 500 μl of PBS (c=10 mg/ml). The reaction was stirred at RT for 4 h, and 0.2 mg (0.00027 mmol) of Intermediate F85 dissolved in 50 μl of DMSO were then added. After a further 120 min of stirring at RT, the reaction was diluted with 1900 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 2.12 mg/ml
Drug/mAb ratio: 1.4

Example 235A

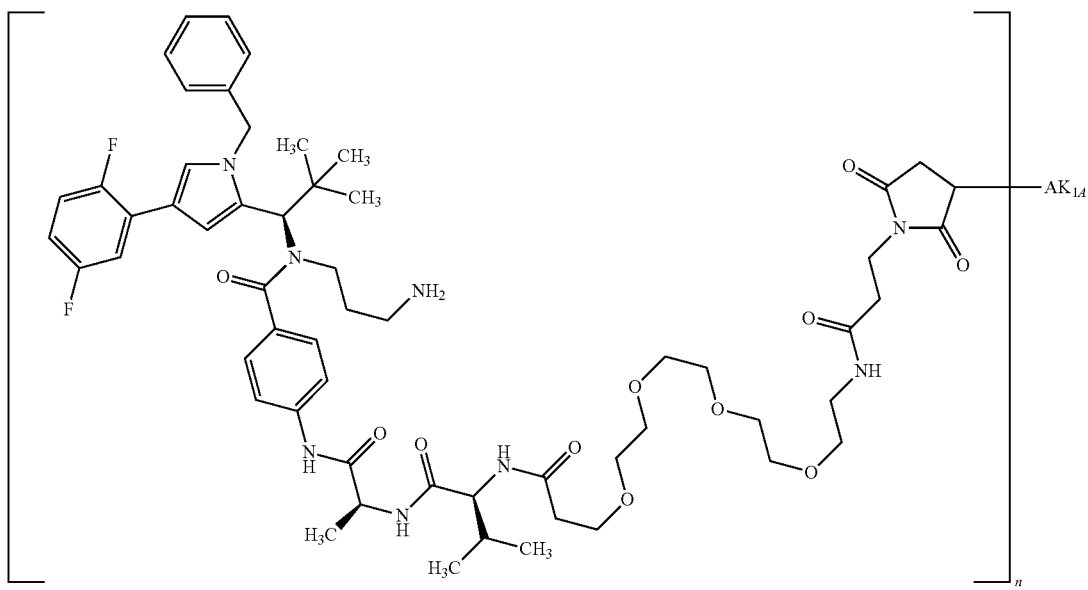

Under argon, a solution of 0.029 mg of TCEP in 50 µl of PBS buffer was added to 5 mg of cetuximab in 329 µl of PBS (c=15.2 mg/ml), and the mixture was then diluted with 2021 µl of PBS buffer which had been adjusted to pH 8 beforehand. The reaction was stirred at RT for 1 h, and 0.28 mg of Intermediate F235 dissolved in 50 µl of DMSO were then added. After a further 90 min of stirring at RT, the reaction was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Some of the ADC prepared in this manner may also be present in the form of the hydrolysed open-chain succinamides attached to the antibody. The ADC batch obtained was characterized as follows:

Protein concentration: 1.5 mg/ml
Drug/mAb ratio: 2.4

Example 235B

Analogously to Example 235A, 5 mg of anti-TWEAKR AK-1 in 269 µl of PBS (c=18.6 mg/ml) were diluted with PBS buffer pH 8 to a concentration of 2 mg/ml and coupled with Intermediate F235. Some of the ADC prepared in this manner may also be present in the form of the hydrolysed open-chain succinamides attached to the antibody. The ADC batch obtained was characterized as follows:

Protein concentration: 0.56 mg/ml
Drug/mAb ratio: 1.0

Example 235E

Analogously to Example 235A, 5 mg of trastuzumab in 370 µl of PBS (c=14.5 mg/ml) were diluted with PBS buffer pH 8 to a concentration of 2 mg/ml and coupled with Intermediate F235. Some of the ADC prepared in this manner may also be present in the form of the hydrolysed open-chain succinamides attached to the antibody. The ADC batch obtained was characterized as follows:

Protein concentration: 1.67 mg/ml
Drug/mAb ratio: 2.9

Example 235I

Analogously to Example 235A, 5 mg of nimotuzumab in 382 µl of PBS (c=13.08 mg/ml) were diluted with PBS buffer pH 8 to a concentration of 2 mg/ml and coupled with Intermediate F235. Some of the ADC prepared in this manner may also be present in the form of the hydrolysed open-chain succinamides attached to the antibody. The ADC batch obtained was characterized as follows:

Protein concentration: 1.81 mg/ml
Drug/mAb ratio: 2.8

Example 235H

Analogously to Example 235A, 5 mg of panitumumab in 74 µl of PBS (c=67.4 mg/ml) were diluted with PBS buffer pH 8 to a concentration of 2 mg/ml and coupled with Intermediate F235. Some of the ADC prepared in this manner may also be present in the form of the hydrolysed open-chain succinamides attached to the antibody. The ADC batch obtained was characterized as follows:

Protein concentration: 1.14 mg/ml
Drug/mAb ratio: 0.9

Example 236A

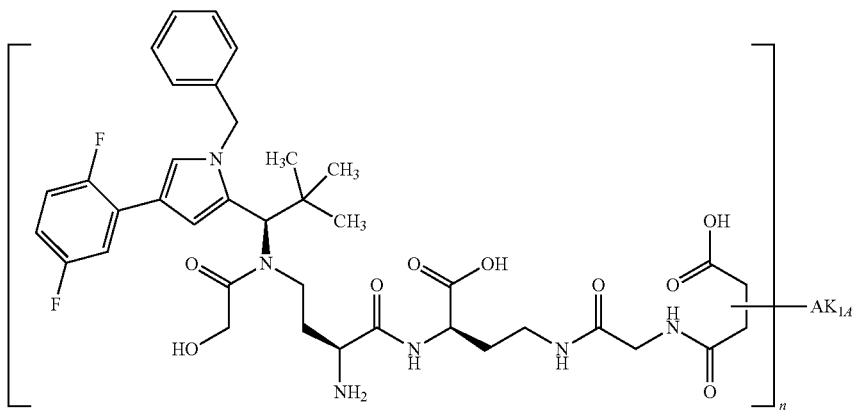

Analogously to Example 234A, 5 mg of cetuximab in 500 µl of PBS (c=10 mg/ml) were coupled with Intermediate F236. Under these conditions, some of the ADCs may also be present in the ring-closed form. The ADC batch obtained was characterized as follows:
Protein concentration: 1.85 mg/ml
Drug/mAb ratio: 3.6

Example 236B

Analogously to Example 234A, 5 mg of anti-TWEAKR AK-1 in 500 µl of PBS (c=10 mg/ml) were coupled with Intermediate F236. Under these conditions, some of the ADCs may also be present in the ring-closed form. The ADC batch obtained was characterized as follows:
Protein concentration: 1.67 mg/ml
Drug/mAb ratio: 3.5

Example 236E

Analogously to Example 234A, 5 mg of trastuzumab in 500 µl of PBS (c=10 mg/ml) were coupled with Intermediate F236. Under these conditions, some of the ADCs may also be present in the ring-closed form. The ADC batch obtained was characterized as follows:
Protein concentration: 1.67 mg/ml
Drug/mAb ratio: 3.9

Example 237A

Under argon, a solution of 0.344 mg of TCEP in 100 µl of PBS buffer was added to 60 mg of cetuximab in 4000 µl of PBS (c=15 mg/ml). The reaction was stirred at RT for 1 h, and 3.04 mg (0.003 mmol) of Intermediate F104 dissolved in 600 µl of DMSO were then added. After a further 90 min of stirring at RT, the reaction was diluted to 15 ml with PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. This solution was stirred under argon at RT overnight and then concentrated by ultracentrifugation, rediluted with PBS buffer (pH 7.2) and reconcentrated again. Under these conditions, some of the ADCs may also be present in the ring-closed form. The ADC batch obtained was characterized as follows:
Protein concentration: 13.78 mg/ml
Drug/mAb ratio: 4.8

Example 237B

Under argon, a solution of 0.287 mg of TCEP in 500 µl of PBS buffer was added to 50 mg of anti-TWEAKR AK-1 in 2688 µl of PBS (c=18.6 mg/ml), and the mixture was then diluted with 8812 µl of PBS buffer which had been adjusted to pH 8 beforehand. The reaction was stirred at RT for 1 h, and 2,894 mg (0.003 mmol) of Intermediate F104 dissolved in 500 µl of DMSO were then added. After a further 90 min of stirring at RT, the reaction was then applied to PD 10

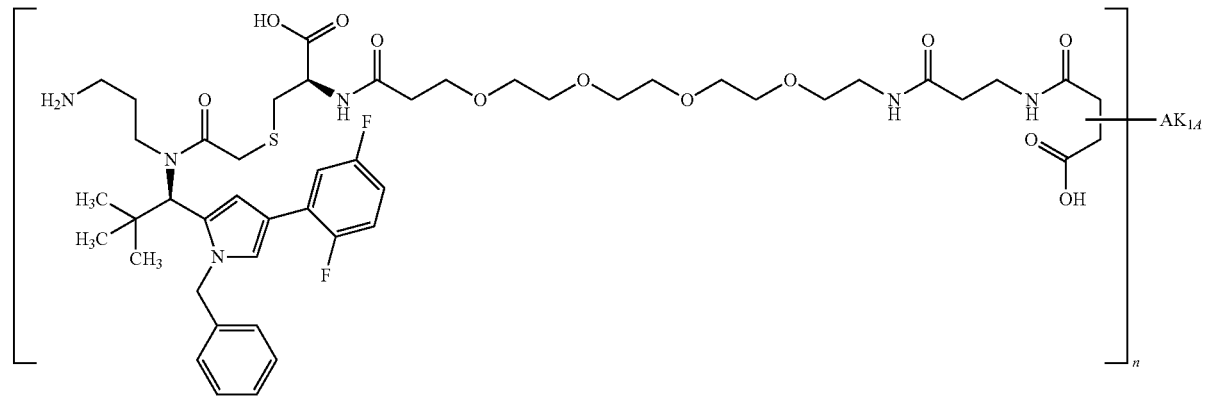

columns (Sephadex® G-25, GE Healthcare) which had been equilibrated with PBS buffer pH 8 and was eluted with PBS buffer pH 8. This solution was stirred under argon at RT overnight and then concentrated by ultracentrifugation, rediluted with PBS buffer (pH 7.2) and reconcentrated again. Under these conditions, some of the ADCs may also be present in the ring-closed form. For this batch, the proportion of the ring-opened form was determined directly after the synthesis to be 23%. The ADC batch obtained was characterized as follows:

Protein concentration: 11.1 mg/ml
Drug/mAb ratio: 3.3

Example 237I

Analogously to Example 237A, 60 mg of nimotuzumab in 4587 µl of PBS (c=13.08 mg/ml) were coupled with Intermediate F209. Under these conditions, some of the ADSs may also be present in the ring-closed form. The ADC batch obtained was characterized as follows:

Protein concentration: 15.88 mg/ml
Drug/mAb ratio: 4.0

Example 238A

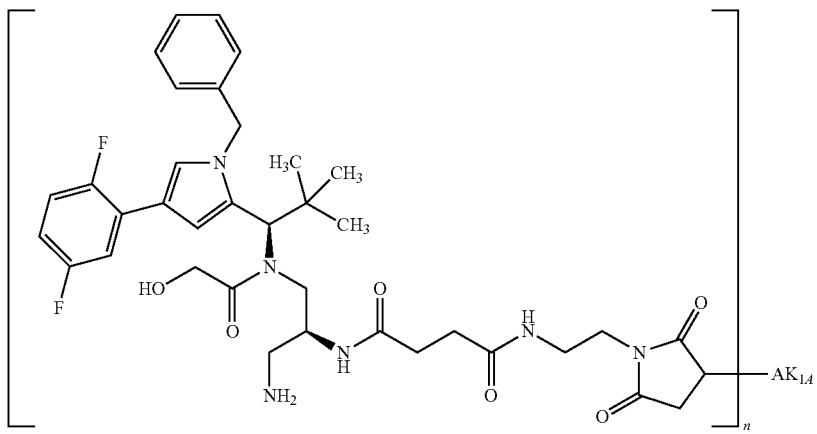

Under argon, a solution of 0.029 mg of TCEP in 50 µl of PBS buffer was added to 5 mg of cetuximab in 500 µl of PBS (c=10 mg/ml). The reaction was stirred at RT for 30 min, and 0.22 mg (0.00027 mmol) of Intermediate F238 dissolved in 50 µl of DMSO were then added. After a further 90 min of stirring at RT, the reaction was diluted with 1900 µl of PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Some of the ADC prepared in this manner may also be present in the form of the hydrolysed open-chain succinamides attached to the antibody. The ADC batch obtained was characterized as follows:

Protein concentration: 1.89 mg/ml
Drug/mAb ratio: 2.9

Example 238B

Analogously to Example 238A, 5 mg of anti-TWEAKR AK-1 in 500 µl of PBS (c=10 mg/ml) were coupled with Intermediate F238. Some of the ADC prepared in this manner may also be present in the form of the hydrolysed open-chain succinamides attached to the antibody. The ADC batch obtained was characterized as follows:

Protein concentration: 1.66 mg/ml
Drug/mAb ratio: 3.1

Under these coupling conditions, 26% of the ADC were present in the form of the hydrolysed open-chain succinamides attached to the antibody.

Example 238E

Analogously to Example 238A, 5 mg of trastuzumab in 500 µl of PBS (c=10 mg/ml) were coupled with Intermediate F238. Some of the ADC prepared in this manner may also be present in the form of the hydrolysed open-chain succinamides attached to the antibody. The ADC batch obtained was characterized as follows:

Protein concentration: 1.84 mg/ml
Drug/mAb ratio: 3.5

Example 239A

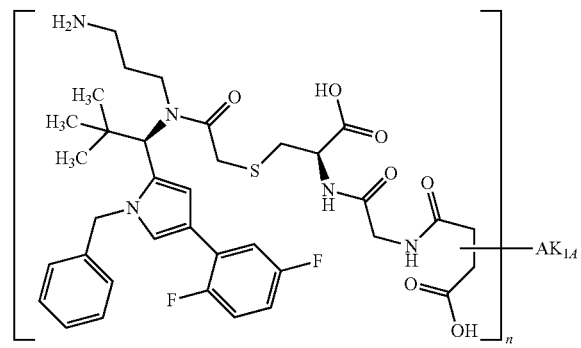

Under argon, a solution of 0.029 mg of TCEP in 50 µl of PBS buffer was added to 5 mg of cetuximab in 458 µl of PBS (c=10.92 mg/ml). The reaction was diluted with 1892 µl of PBS buffer which had been adjusted to pH 8 beforehand and stirred at RT for 1 h. 0.19 mg (0.00027 mmol) of Intermediate F217 dissolved in 100 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.86 mg/ml
Drug/mAb ratio: 2.8

Example 239B

Under argon, a solution of 0.029 mg of TCEP in 50 μl of PBS buffer was added to 5 mg of anti-TWEAKR AK-1 in 269 μl of PBS (c=18.6 mg/ml). The reaction was diluted with 2081 μl of PBS buffer which had been adjusted to pH 8 beforehand and stirred at RT for 1 h. 0.19 mg (0.00027 mmol) of Intermediate F217 dissolved in 100 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.32 mg/ml
Drug/mAb ratio: 2.9

For this ADC preparation, a proportion of 89% was determined for the ring-opened succinamide form.

Example 239H

Under argon, a solution of 0.048 mg of TCEP in 83 μl of PBS buffer was added to 5 mg of panitumumab in 74 μl of PBS (c=67.5 mg/ml). The reaction was diluted with 2243 μl of PBS buffer which had been adjusted to pH 8 beforehand and stirred at RT for 4 h. 0.19 mg (0.00027 mmol) of Intermediate F217 dissolved in 100 μl of DMSO were then added. The reaction was stirred at RT overnight. The solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.33 mg/ml
Drug/mAb ratio: 2.1

Example 240A

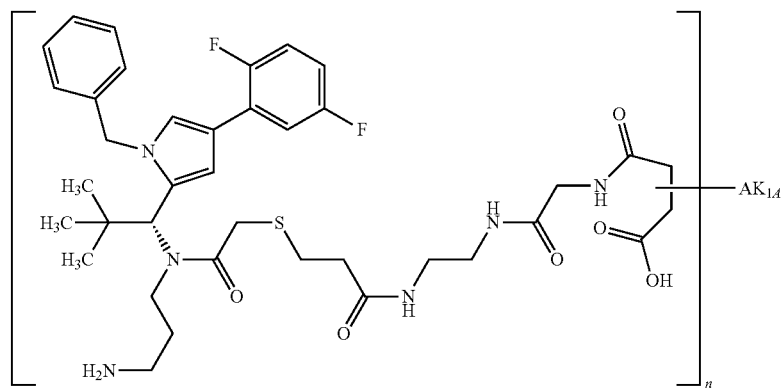

also be present in the ring-closed form. The ADC batch obtained was characterized as follows:

Protein concentration: 1.28 mg/ml
Drug/mAb ratio: 2.6

Example 239I

Under argon, a solution of 0.029 mg of TCEP in 50 μl of PBS buffer was added to 5 mg of nimotuzumab in 382 μl of PBS (c=13.1 mg/ml). The reaction was diluted with 1968 μl of PBS buffer which had been adjusted to pH 8 beforehand and stirred at RT for 1 h. 0.19 mg (0.00027 mmol) of Intermediate F217 dissolved in 100 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2).

Under argon, a solution of 0.29 mg of TCEP in 500 μl of PBS buffer was added to 50 mg of cetuximab in 4579 μl of PBS (c=10.92 mg/ml). The reaction was diluted with 7421 μl of PBS buffer which had been adjusted to pH 8 beforehand and stirred at RT for 1 h. 1.4 mg (0.0027 mmol) of Intermediate F213 dissolved in 500 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 15.63 mg/ml
Drug/mAb ratio: 2.7

Example 240B

Analogously to Example 239A, 5 mg of anti-TWEAKR AK-1 in 500 µl of PBS (c=10 mg/ml) were coupled with Intermediate F213. Under these conditions, some of the ADSs may also be present in the ring-closed form. The ADC batch obtained was characterized as follows:
Protein concentration: 0.9 mg/ml
Drug/mAb ratio: 2.0

Example 240E

Analogously to Example 239A, 5 mg of trastuzumab in 500 µl of PBS (c=10 mg/ml) were coupled with Intermediate F213. Under these conditions, some of the ADSs may also be present in the ring-closed form. The ADC batch obtained was characterized as follows:
Protein concentration: 1.4 mg/ml
Drug/mAb ratio: 2.1

Example 241A

Under argon, a solution of 0.172 mg of TCEP in 300 µl of PBS buffer was added to 30 mg of cetuximab in 3 ml of PBS (c=10 mg/ml). The reaction was stirred at RT for 30 min, and 1.36 mg (1.6 µmol) of Intermediate F241 dissolved in 330 µl of DMSO were then added. After 20 h of stirring at RT, the reaction was diluted with 1.37 ml of PBS buffer and eluted through PD 10 columns (Sephadex® G-25, GE Healthcare) using PBS buffer. The eluate was then concentrated by ultracentrifugation, rediluted with PBS buffer (pH 7.2) and reconcentrated again. The ADC batch obtained was characterized as follows:
Protein concentration: 9.98 mg/ml
Drug/mAb ratio: 3.3

Example 241B

Here, 5 mg of anti-TWEAKR AK-1 in PBS (c=10 mg/ml) were used for coupling with Intermediate F241. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 1.39 mg/ml
Drug/mAb ratio: 3.9

Example 241E

Here, 5 mg of trastuzumab in PBS (c=10 mg/ml) were used for coupling with Intermediate F241. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 1.83 mg/ml
Drug/mAb ratio: 4.7

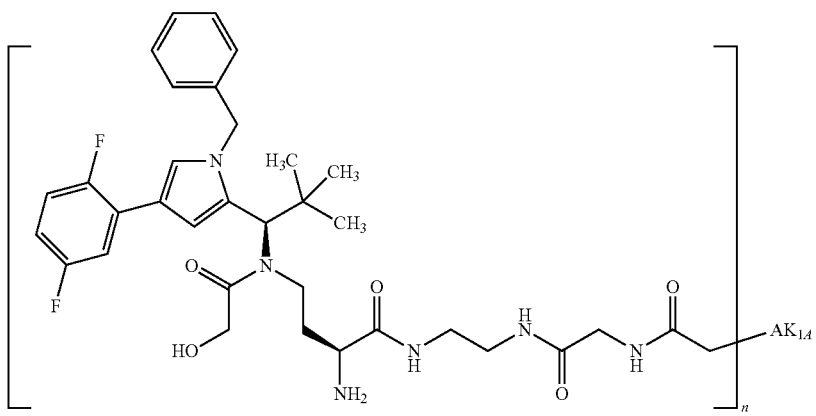

Example 241I

Here, 5 mg of nimotuzumab in PBS (c=10 mg/ml) were used for coupling with Intermediate F241. After TCEP reduction, coupling with the antibody was carried out with stirring overnight, followed by further work-up by Sephadex purification. After Sephadex purification, the reaction was concentrated by ultracentrifugation and rediluted with PBS.
Protein concentration: 1.6 mg/ml
Drug/mAb ratio: 4.0

Example 242A

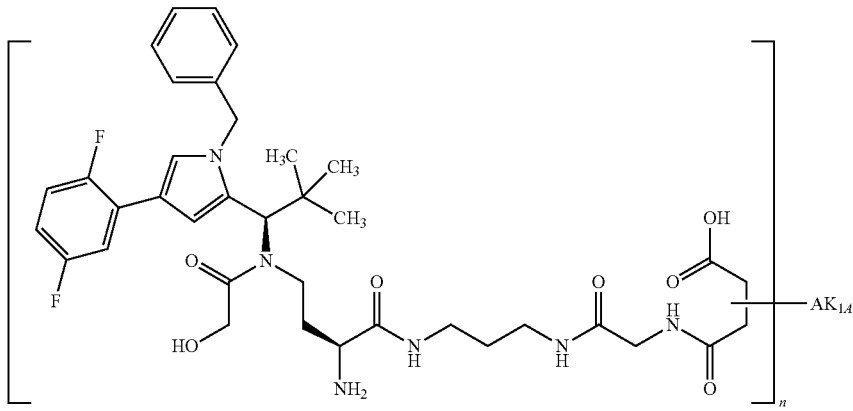

Under argon, a solution of 0.029 mg of TCEP in 50 µl of PBS buffer was added to 5 mg of cetuximab in 500 µl of PBS (c=10 mg/ml). The reaction was stirred at RT for 30 min, and 0.22 mg (0.00027 mmol) of Intermediate F242 dissolved in 50 µl of DMSO were then added. After a further 90 min of stirring at RT, the reaction was diluted with 1900 µl of PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.92 mg/ml
Drug/mAb ratio: 2.7

Example 242B

As described in Example 242A, 5 mg of anti-TWEAKR AK-1 in 500 µl of PBS (c=10 mg/ml) were coupled with 0.22 mg of Intermediate F242. Under these conditions, some of the ADSs may also be present in the ring-closed form. The ADC batch obtained was characterized as follows:

Protein concentration: 1.54 mg/ml
Drug/mAb ratio: 3.1

Example 242E

As described in Example 242A, 5 mg of trastuzumab in 500 µl of PBS (c=10 mg/ml) were coupled with 0.22 mg of Intermediate F242. Under these conditions, some of the ADSs may also be present in the ring-closed form. The ADC batch obtained was characterized as follows:

Protein concentration: 1.76 mg/ml
Drug/mAb ratio: 3.6

Example 243A

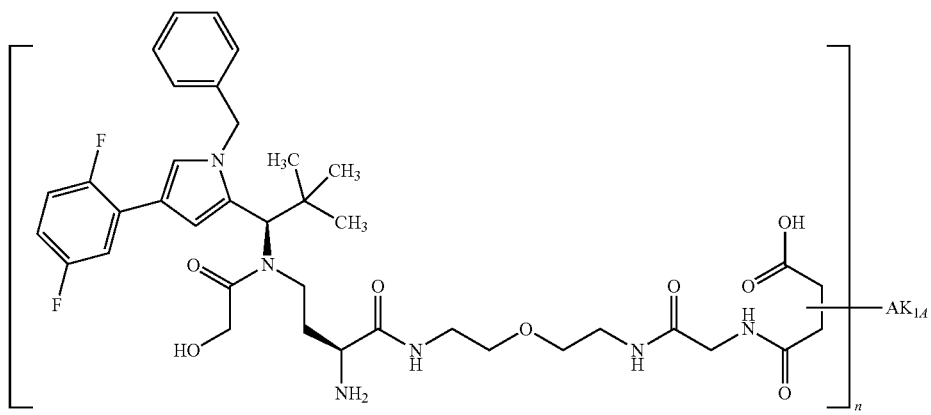

Under argon, a solution of 0.029 mg of TCEP in 50 μl of PBS buffer was added to 5 mg of cetuximab in 500 μl of PBS (c=10 mg/ml). The reaction was stirred at RT for 30 min, and 0.23 mg (0.00027 mmol) of Intermediate F243 dissolved in 50 μl of DMSO were then added. After a further 90 min of stirring at RT, the reaction was diluted with 1900 μl of PBS buffer which had been adjusted to pH 8 beforehand. This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:

Protein concentration: 1.92 mg/ml
Drug/mAb ratio: 2.9

Example 243B

As described in Example 243A, 5 mg of anti-TWEAKR AK-1 in 500 μl of PBS (c=10 mg/ml) were coupled with 0.23 mg of Intermediate F243. Under these conditions, some of the ADSs may also be present in the ring-closed form. The ADC batch obtained was characterized as follows:

Protein concentration: 1.63 mg/ml
Drug/mAb ratio: 3.1

Example 243E

As described in Example 243A, 5 mg of trastuzumab in 500 μl of PBS (c=10 mg/ml) were coupled with 0.23 mg of Intermediate F243. Under these conditions, some of the ADSs may also be present in the ring-closed form. The ADC batch obtained was characterized as follows:

Protein concentration: 1.8 mg/ml
Drug/mAb ratio: 3.5

Example 243I

As described in Example 243A, 5 mg of nimotuzumab in 500 μl of PBS (c=10 mg/ml) were coupled with 0.23 mg of Intermediate F243. Under these conditions, some of the ADSs may also be present in the ring-closed form. The ADC batch obtained was characterized as follows:

Protein concentration: 1.87 mg/ml
Drug/mAb ratio: 3.1

Example 244A

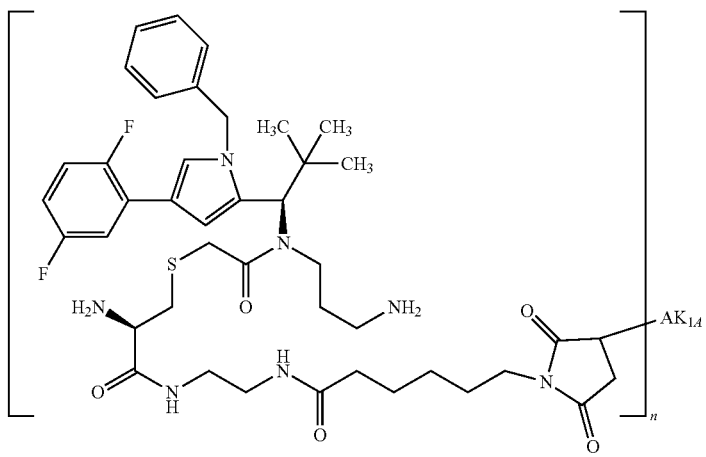

Here, 5.0 mg of cetuximab in PBS (c=23.10 mg/ml) were used for coupling with Intermediate F244, and the reaction was, after Sephadex purification, concentrated by ultracentrifugation and rediluted with PBS.

Protein concentration: 2.12 mg/ml
Drug/mAb ratio: 3.5

Example 244B

Here, 5.0 mg of anti-TWEAK AK-1 in PBS (c=18.60 mg/ml) were used for coupling with Intermediate F244, and the reaction was, after Sephadex purification, concentrated by ultracentrifugation and rediluted with PBS.

Protein concentration: 1.65 mg/ml
Drug/mAb ratio: 3.5

Example 244E

Here, 5.0 mg of trastuzumab in PBS (c=13.50 mg/ml) were used for coupling with Intermediate F244, and the reaction was, after Sephadex purification, concentrated by ultracentrifugation and rediluted with PBS.

Protein concentration: 1.91 mg/ml
Drug/mAb ratio: 3.5

Example 244I

Here, 5.0 mg of nimotuzumab in PBS (c=13.08 mg/ml) were used for coupling with Intermediate F244, and the reaction was, after Sephadex purification, concentrated by ultracentrifugation and rediluted with PBS.

Protein concentration: 1.91 mg/ml
Drug/mAb ratio: 2.9

Example 245A

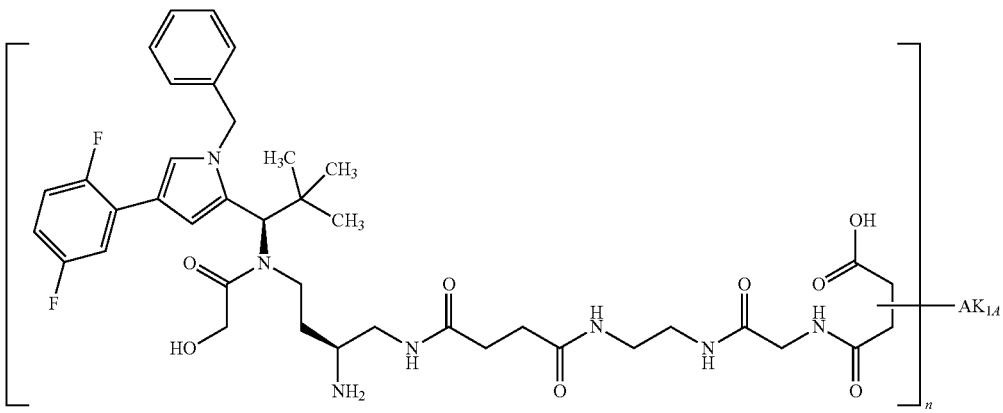

Under argon, a solution of 0.029 mg of TCEP in 50 µl of PBS buffer was added to 5 mg of cetuximab in 500 µl of PBS (c=10 mg/ml). The reaction was stirred at RT for 30 min, and 0.24 mg (0.00027 mmol) of Intermediate F245 dissolved in 50 µl of DMSO were then added. After a further 90 min of stirring at RT, the reaction was diluted with 1900 µl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADSs may also be present in the ring-closed form. The ADC batch obtained was characterized as follows:
Protein concentration: 1.69 mg/ml
Drug/mAb ratio: 2.4

Example 245B

As described in Example 245A, 5 mg of anti-TWEAKR AK-1 in 500 µl of PBS (c=10 mg/ml) were coupled with 0.24 mg of Intermediate F245. Under these conditions, some of the ADSs may also be present in the ring-closed form. The ADC batch obtained was characterized as follows:
Protein concentration: 1.51 mg/ml
Drug/mAb ratio: 2.5

Example 245E

As described in Example 245A, 5 mg of trastuzumab in 500 µl of PBS (c=10 mg/ml) were coupled with 0.24 mg of Intermediate F245. Under these conditions, some of the ADSs may also be present in the ring-closed form. The ADC batch obtained was characterized as follows:
Protein concentration: 1.8 mg/ml
Drug/mAb ratio: 3.5

Example 245I

As described in Example 245A, 5 mg of nimotuzumab in 500 µl of PBS (c=10 mg/ml) were coupled with 0.24 mg of Intermediate F245. Under these conditions, some of the ADSs may also be present in the ring-closed form. The ADC batch obtained was characterized as follows:
Protein concentration: 1.65 mg/ml
Drug/mAb ratio: 2.3

Example 246

4-[(2-{[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid/trifluoroacetic acid and 4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic acid/trifluoroacetic acid (1:1)

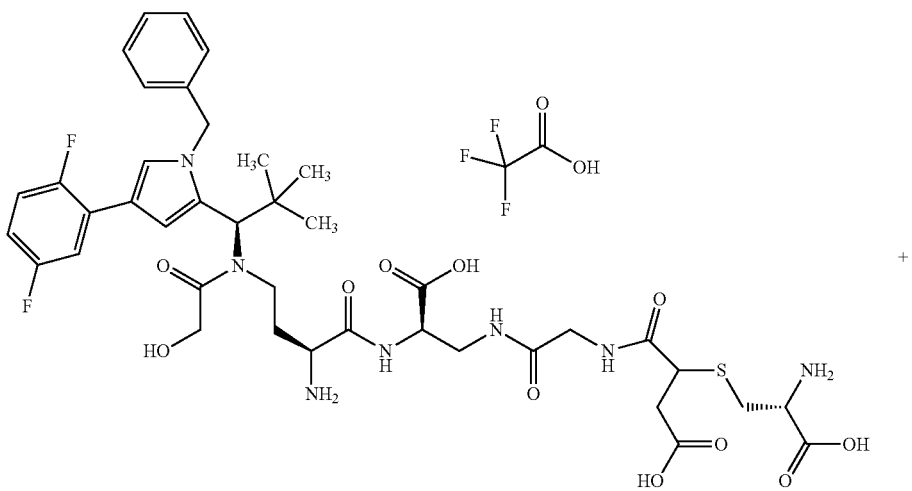

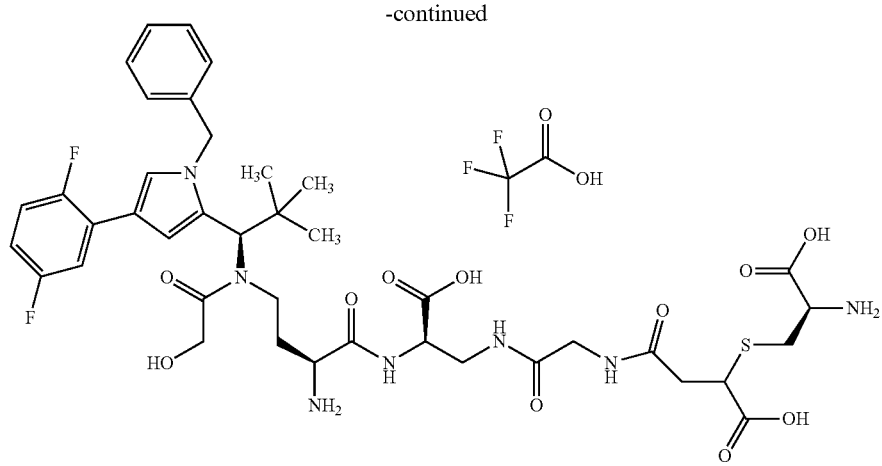

First, L-cysteine was converted with 1-({[2-(trimethylsilyl)ethoxy]carbonyl}oxy)pyrrolidine-2,5-dione in DMF in the presence of N,N-diisopropylethylamine into N-{[2-(trimethylsilyl)ethoxy]carbonyl}-L-cysteine.

11 mg (0.013 mmol) of Intermediate F193 and 8 mg (0.016 mmol) of N-{[2-(trimethylsilyl) ethoxy]carbonyl}-L-cysteine were dissolved in 3 ml of DMF, and the mixture was stirred at RT for 20 h. The mixture was then concentrated and the residue was purified by preparative HPLC.

The appropriate fractions were combined and the solvents were evaporated under reduced pressure, and the residue was then dissolved in 2 ml of THF/water 1:1. 19 μl of a 2M aqueous lithium hydroxide solution were added and the reaction was stirred at RT for 1 h. Another 19 μl of the 2M aqueous lithium hydroxide solution were then added and the reaction was stirred at RT overnight. The mixture was then neutralized with a 1M hydrochloric acid, the solvent was evaporated under reduced pressure and the residue was purified by preparative HPLC. This gave 4.1 mg (38% of theory) of the regioisomeric protected intermediates as a colourless foam.

LC-MS (Method 1): $R_t$=1.03 min (broad); MS (ESIpos): m/z=1020 (M+H)$^+$.

In the last step, 4.1 mg (0.004 mmol) of this intermediate were dissolved in 3 ml of 2,2,2-trifluoroethanol. 3 ml (0.022 mmol) of zinc chloride were added, and the reaction was stirred at 50° C. for 1 h. 6 mg (0.022 mmol) of ethylenediamine-N,N,N',N'-tetraacetic acid and 2 ml of a 0.1% strength aqueous trifluoroacetic acid were then added, and the solvent was evaporated under reduced pressure. The residue was purified by preparative HPLC. Concentration of the appropriate fractions and lyophilization of the residue from acetonitrile/water gave 5 mg (quant.) of the title compound as a regioisomer mixture in a ratio of 20:80.

LC-MS (Method 1): $R_t$=0.78 min (broad); MS (ESIpos): m/z=876 (M+H)$^+$.

LC-MS (Method 5): $R_t$=2.36 min and 2.39 min; MS (ESIpos): m/z=876 (M+H)$^+$.

Example 247A

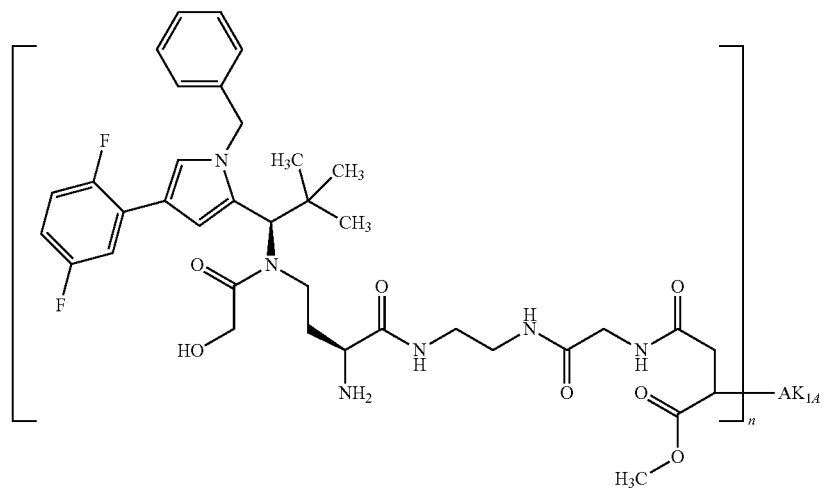

Under argon, a solution of 0.029 mg of TCEP in 50 μl of PBS buffer was added to 5 mg of cetuximab in 500 μl of PBS (c=10 mg/ml). The reaction was stirred at RT for 30 min, and 0.264 mg (0.27 μmol) of Intermediate F247 dissolved in 50 μl of DMSO were then added. After 20 h of stirring at RT, the reaction was diluted with 1.9 ml of PBS buffer and eluted through PD 10 columns (Sephadex® G-25, GE Healthcare) using PBS buffer. The eluate was then concentrated by ultracentrifugation, rediluted with PBS buffer (pH 7.2) and reconcentrated again. The ADC batch obtained was characterized as follows:
Protein concentration: 1.66 mg/ml
Drug/mAb ratio: 2.2

Example 247B

Here, 5 mg of anti-TWEAKR AK-1 in PBS (c=10 mg/ml) were used for coupling with Intermediate F247, and coupling and work-up were carried out as described in Example 247A.
Protein concentration: 1.49 mg/ml
Drug/mAb ratio: 2.6

Example 247E

Here, 5 mg of trastuzumab in PBS (c=10 mg/ml) were used for coupling with Intermediate F247, and coupling and work-up were carried out as described in Example 247A.
Protein concentration: 1.67 mg/ml
Drug/mAb ratio: 2.3

Example 247I

Here, 5 mg of nimotuzumab in PBS (c=10 mg/ml) were used for coupling with Intermediate F247, and coupling and work-up were carried out as described in Example 247A.
Protein concentration: 1.62 mg/ml
Drug/mAb ratio: 2.4

Example 248A

Here, analogously to Example 5A, 5 mg of cetuximab in PBS (c=10.92 mg/ml) were used for coupling with Intermediate F248, and the reaction was, after Sephadex purification, concentrated by ultracentrifugation and rediluted with PBS. Some of the ADC prepared in this manner may also be present in the form of the hydrolysed open-chain succinamides attached to the antibody.

Protein concentration: 2.06 mg/ml

Drug/mAb ratio: 3.8

Example 248B

Here, analogously to Example 5B, 5 mg of anti-TWEAKR AK-1 in PBS (c=18.6 mg/ml) were used for coupling with Intermediate F248, and the reaction was, after Sephadex purification, concentrated by ultracentrifugation and rediluted with PBS. Some of the ADC prepared in this manner may also be present in the form of the hydrolysed open-chain succinamides attached to the antibody.

Protein concentration: 1.84 mg/ml

Drug/mAb ratio: 4.1

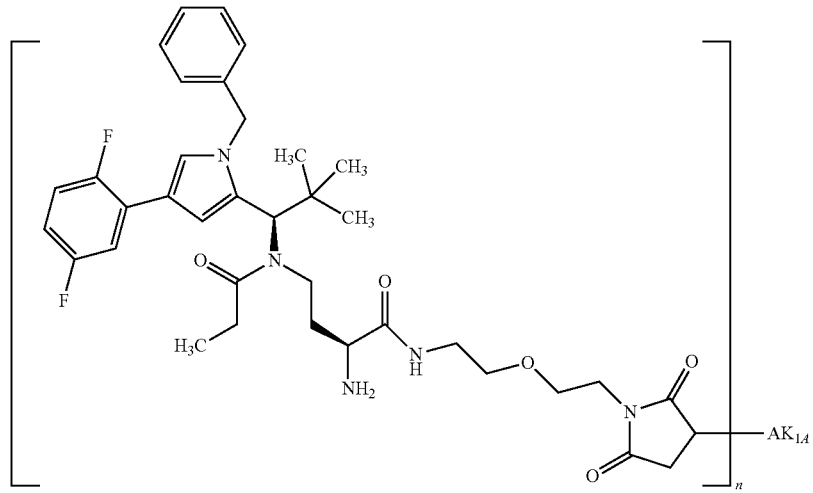

Example 249

S-{1-[6-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)hexyl]-2,5-dioxopyrrolidin-3-yl}-L-cysteine/trifluoroacetic acid (1:1)

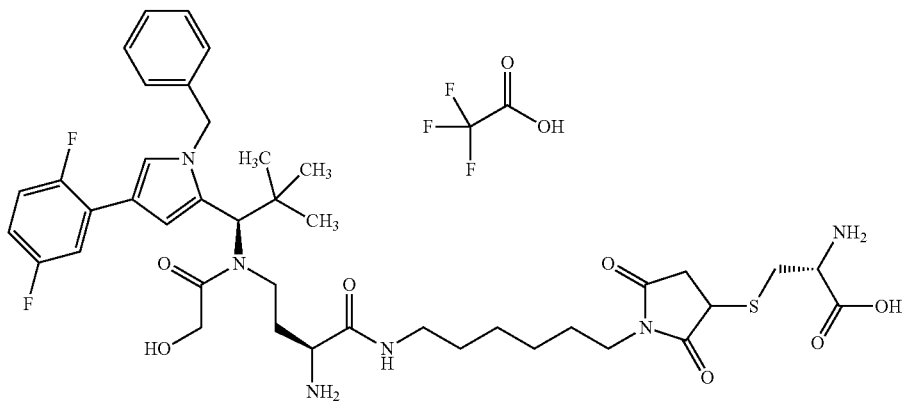 [SMILES: CC(C)(C)[C@H](c1cc(-c2cc(F)ccc2F)cn1Cc1ccccc1)N(CC[C@H](N)C(=O)NCCCCCCN1C(=O)CC(SC[C@H](N)C(=O)O)C1=O)C(=O)CO ; O=C(O)C(F)(F)F]

11 mg (14 µmol) of Intermediate F179 were taken up in 2.2 ml of DMF, and 3.3 mg (27 µmol) of L-cysteine were added. The reaction mixture was stirred at RT for 3 h and then concentrated under reduced pressure. The residue was purified by preparative HPLC. The appropriate fractions were concentrated, giving, after lyophilization of the residue from acetonitrile/water, 7.3 mg (58% of theory) of the title compound as a colourless foam.

LC-MS (Method 4): $R_t$=1.04 min; MS (EIpos): m/z=813 [M+H]$^+$.

Example 250

4-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-3-{[(2R)-2-amino-2-carboxyethyl]sulphanyl}-4-oxobutanoic acid/trifluoroacetic acid (1:1) and 4-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-{[(2R)-2-amino-2-carboxyethyl]sulphanyl}-4-oxobutanoic acid/trifluoroacetic acid (1:1)

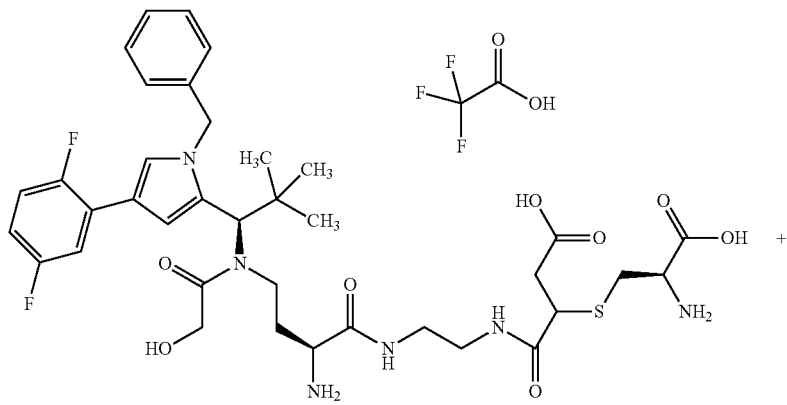

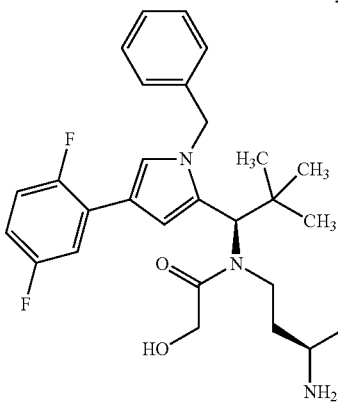
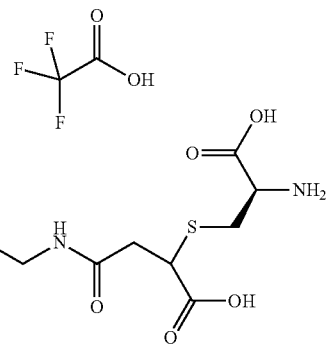

10 mg (0.013 mmol) of Intermediate F85 and 5.3 mg (0.02 mmol) of N-{[2-(trimethylsilyl) ethoxy]carbonyl}-L-cysteine were dissolved in 3 ml of DMF, and the mixture was stirred at RT for 3 days. The mixture was then concentrated and the residue was purified by preparative HPLC. The appropriate fractions were combined and the solvents were evaporated under reduced pressure, and the residue was then dissolved in 2 ml of THF/water 1:1. 9 μl of a 2M aqueous lithium hydroxide solution were added and the reaction was stirred at RT for 1 h. The reaction was then adjusted to a pH of ~3 with a 1M hydrochloric acid, the solvent was evaporated under reduced pressure and the residue was purified by preparative HPLC. This gave 3 mg (24% of theory over 2 steps) of the regioisomeric protected intermediates as a colourless foam.

theory) of the title compound as a regioisomer mixture in a ratio of 43:34. The isomer mixture comprised 23% of a further isomer (RT=2.51).

LC-MS (Method 5): $R_t$=2.57 min and 2.62 min; MS (ESIpos): m/z=775 (M+H)$^+$.

Example 251

S-(1-{2-[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethoxy]ethyl}-2,5-dioxopyrrolidin-3-yl)-L-cysteine/trifluoroacetic acid (1:1)

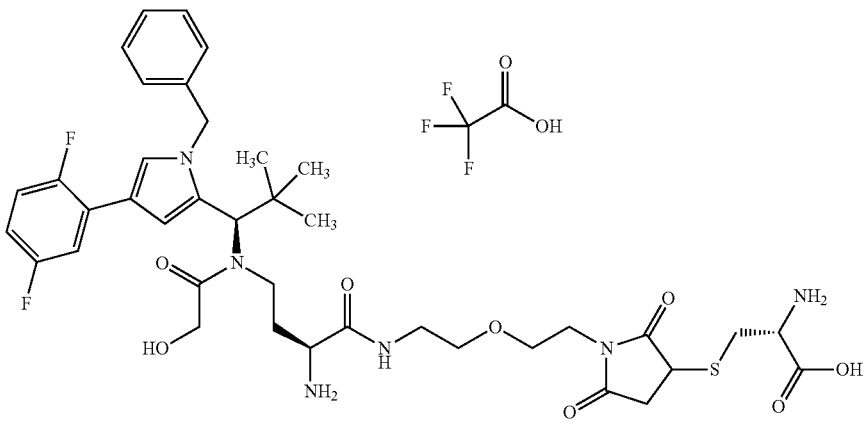 [SMILES: CC(C)(C)[C@H](c1cc(-c2cc(F)ccc2F)cn1Cc1ccccc1)N(CC[C@H](N)C(=O)NCCOCCN1C(=O)CC(SC[C@H](N)C(=O)O)C1=O)C(=O)CO ; O=C(O)C(F)(F)F]

LC-MS (Method 5): $R_t$=3.39 min and 3.43 min; MS (ESIpos): m/z=919 (M+H)$^+$.

In the last step, 3 mg (0.0033 mmol) of this intermediate were dissolved in 3 ml of 2,2,2-trifluoroethanol. 2.2 ml (0.016 mmol) of zinc chloride were added, and the reaction was stirred at 50° C. for 3.5 h. 4.8 mg (0.016 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 1 mg (33% of 3 mg (4 μmol) of Intermediate F248 were taken up in 2 ml of DMF, and 0.9 mg (8 μmol) of L-cysteine were added. The reaction mixture was stirred at RT for 18 h and then concentrated under reduced pressure. The residue was purified by preparative HPLC. The appropriate fractions were concentrated, giving, after lyophilization of the residue from acetonitrile/water, 1.1 mg (32% of theory) of the title compound as a white solid.

LC-MS (Method 1): $R_t$=0.78 min; MS (EIpos): m/z=801 [M+H]$^+$.

Example 252

(3R,7S)-7-Amino-17-{[(2R)-2-amino-2-carboxy-ethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic acid/ trifluoroacetic acid (1:1) and (3R,7S)-7-amino-18-{[(2R)-2-amino-2-carboxy-ethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic acid/ trifluoroacetic acid (1:1)

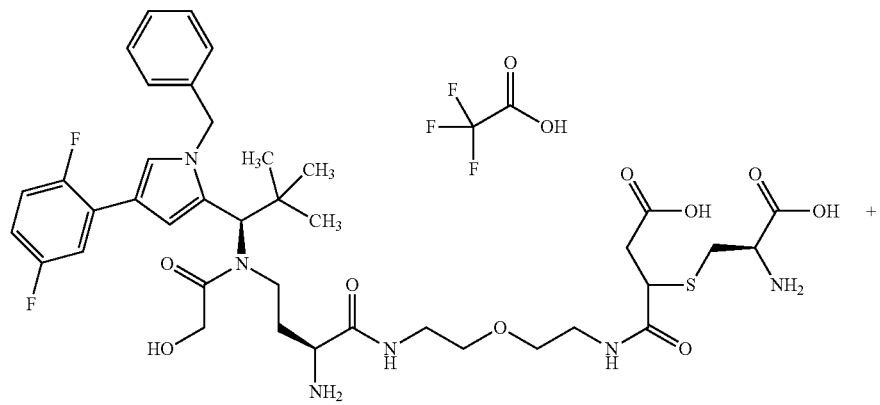

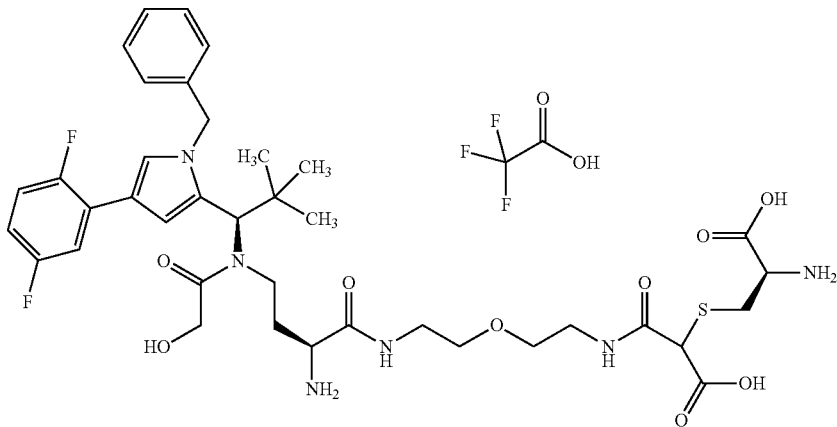

8 mg (0.010 mmol) of the protected intermediate of Intermediate F248 and 5.1 mg (0.02 mmol) of N-{[2-(trimethylsilyl)ethoxy]carbonyl}-L-cysteine were dissolved in 3 ml of DMF, and the mixture was stirred at RT for 18 h and then treated in an ultrasonic bath for 2 h. The mixture was then concentrated and the residue was purified by preparative HPLC. The appropriate fractions were combined and the solvents were evaporated under reduced pressure, and the residue was then dissolved in 2 ml of THF/water 1:1. 15 µl of a 2M aqueous lithium hydroxide solution were added and the reaction was stirred at RT for 15 min. The reaction was then adjusted to a pH of ~3 with a 1M hydrochloric acid, diluted with 20 ml of sodium chloride solution and extracted twice with 20 ml of ethyl acetate. The organic phase was dried over magnesium sulphate and concentrated, and the residue was lyophilized from acetonitrile/water. This gave 8.4 mg (78% of theory over 2 steps) of the regioisomeric protected intermediates as a colourless foam.

LC-MS (Method 1): $R_t$=1.44 min and 3.43 min; MS (ESIpos): m/z=1107 (M+H)$^+$.

In the last step, 8 mg (0.007 mmol) of this intermediate were dissolved in 5 ml of 2,2,2-trifluoroethanol. 9.8 ml (0.072 mmol) of zinc chloride were added, and the reaction was stirred at 50° C. for 1.5 h. Ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4 mg (59% of theory) of the title compound as a regioisomer mixture in a ratio of 31:67.

LC-MS (Method 1): $R_t$=0.79 min and 0.81 min; MS (ESIpos): m/z=819 (M+H)$^+$.

Example 253

4-({2-[(N-{(2S)-2-Amino-4-{[(1R)-1-[1-benzyl-4-(2,5-difluorophenyl)-1H-pyrrol-2-yl]-2,2-dimethyl-propyl}(glycoloyl)amino]butanoyl}-beta-alanyl)amino]ethyl}amino)-3-{[(2R)-2-amino-2-carboxyethyl]sulphanyl}-4-oxobutanoic acid/ trifluoroacetic acid (1:1) and 4-({2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}amino)-2-{[(2R)-2-amino-2-carboxyethyl]sulphanyl}-4-oxobutanoic acid/trifluoroacetic acid (1:1)

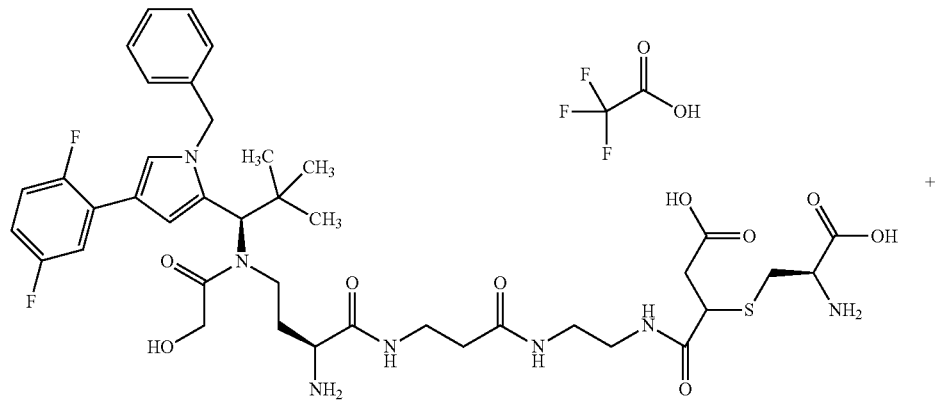

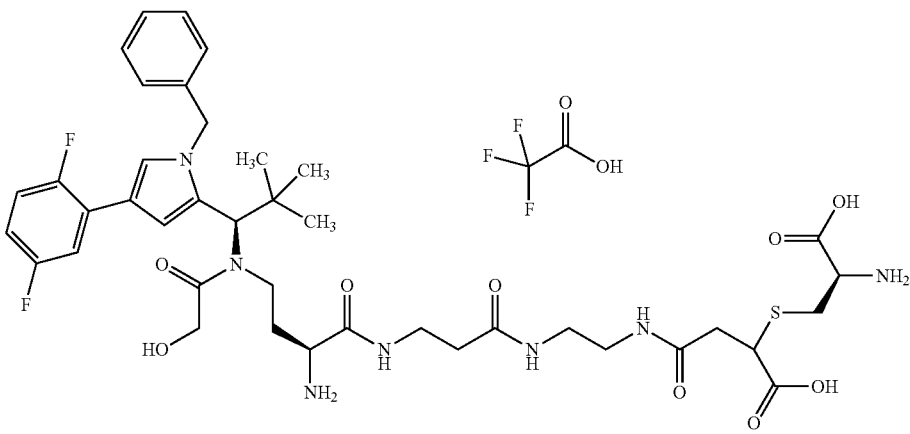

The isomeric title compounds were prepared analogously to Example 250 from Intermediate F84 and N-{[2-(trimethylsilyl)ethoxy]carbonyl}-L-cysteine.

Example 254A

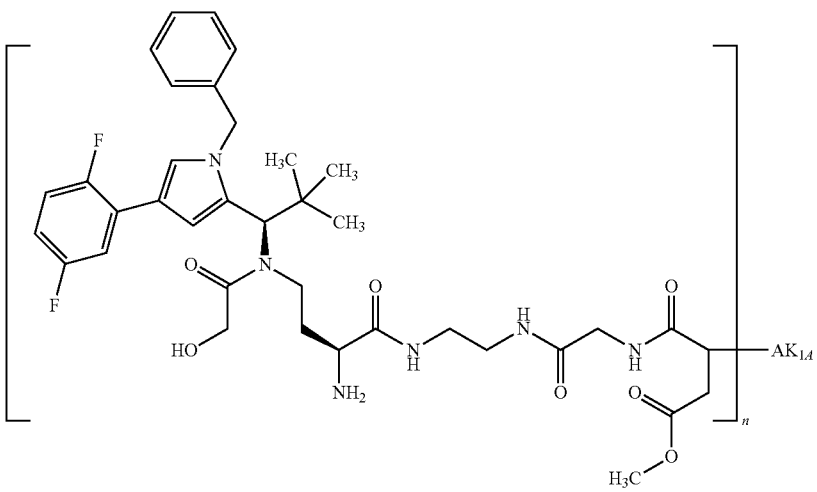

Under argon, a solution of 0.029 mg of TCEP in 50 μl of PBS buffer was added to 5 mg of cetuximab in 500 μl of PBS (c=10 mg/ml). The reaction was stirred at RT for 30 min, and 0.264 mg (0.27 μmol) of Intermediate F254 dissolved in 50 μl of DMSO were then added. After 20 h of stirring at RT, the reaction was diluted with 1.9 ml of PBS buffer and eluted through PD 10 columns (Sephadex® G-25, GE Healthcare) using PBS buffer. The eluate was then concentrated by ultracentrifugation, rediluted with PBS buffer (pH 7.2) and reconcentrated again. The ADC batch obtained was characterized as follows:

Protein concentration: 1.74 mg/ml
Drug/mAb ratio: 2.2

Example 254B

Here, 5 mg of anti-TWEAKR AK-1 in PBS (c=10 mg/ml) were used for coupling with Intermediate F254, and coupling and work-up were carried out as described in Example 254A.

Protein concentration: 1.8 mg/ml
Drug/mAb ratio: 2.5

Example 254E

Here, 5 mg of trastuzumab in PBS (c=10 mg/ml) were used for coupling with Intermediate F254, and coupling and work-up were carried out as described in Example 254A.

Protein concentration: 1.74 mg/ml
Drug/mAb ratio: 2.4

Example 254I

Here, 5 mg of nimotuzumab in PBS (c=10 mg/ml) were used for coupling with Intermediate F254, and coupling and work-up were carried out as described in Example 254A.

Protein concentration: 1.73 mg/ml
Drug/mAb ratio: 2.0

Example 255

(2R,28R)-28-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl) methyl]-25-(carboxymethyl)-4,20,24-trioxo-7,10,13,16-tetraoxa-26-thia-3,19,23-triazanonacosan-1,29-dioic acid/trifluoroacetic acid (1:2) and (1R,28R, 34R)-1-amino-33-(3-aminopropyl)-34-[1-benzyl-4-(2,5-difluorophenyl)-1H-pyrrol-2-yl]-35,35-dimethyl-6,10,26,32-tetraoxo-14,17,20,23-tetraoxa-3,30-dithia-7,11,27,33-tetraazahexatriacontan-1,4,28-tricarboxylic acid/trifluoroacetic acid (1:2)

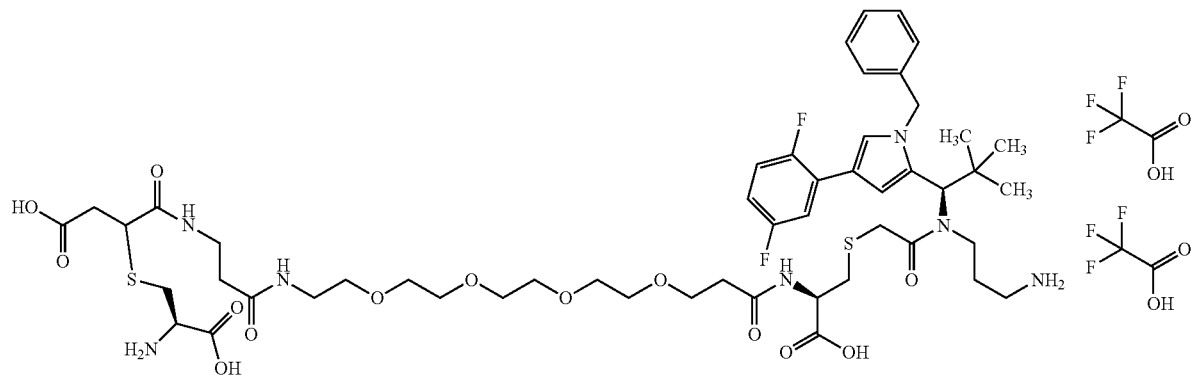

+

-continued

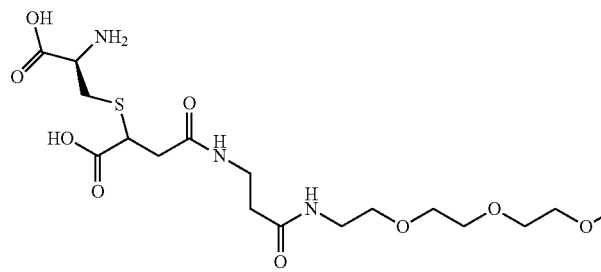

20 mg (0.018 mmol) of R-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic acid (1:1) (Intermediate F209) and 9.78 mg (0.036 mmol) of N-{[2-(trimethylsilyl)ethoxy]carbonyl}-L-cysteine were dissolved in 2 ml of DMF, and the mixture was stirred at RT for 18 h. The reaction mixture was concentrated under reduced pressure. The residue (47.7 mg) was dissolved in 3 ml of THF/water 1:1. 0.08 ml of a 2M aqueous lithium hydroxide solution were added and the reaction was stirred at RT for 1 hour. The reaction was then adjusted to a pH of ~7 using 9.26 mg (0.15 mmol) of acetic acid. The reaction mixture was purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 15.3 mg (29% over 2 steps) of the regioisomeric protected intermediates.

LC-MS (Method 6): $R_t$=12.26 min and 12.30 min; MS (ESIpos): m/z=1254 (M+H)$^+$.

In the last step, 15.3 mg (0.01 mmol) of this intermediate were dissolved in 2 ml of 2,2,2-trifluoroethanol. 6.1 ml (0.05 mmol) of zinc chloride were added, and the reaction was stirred at 50° C. for 2 h. 13.1 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 11.9 mg (79.5%) of the title compound as a regioisomer mixture.

LC-MS (Method 1): $R_t$=0.85 min; MS (ESIpos): m/z=1110 (M+H)$^+$.

Example 256

(3R)-6-{(11S,15R)-11-Amino-15-[1-benzyl-4-(2,5-difluorophenyl)-1H-pyrrol-2-yl]-14-glycoloyl-16,16-dimethyl-2,5,10-trioxo-3,6,9,14-tetraazaheptadec-1-yl}-5-oxothiomorpholine-3-carboxylic acid/trifluoroacetic acid (1:1)

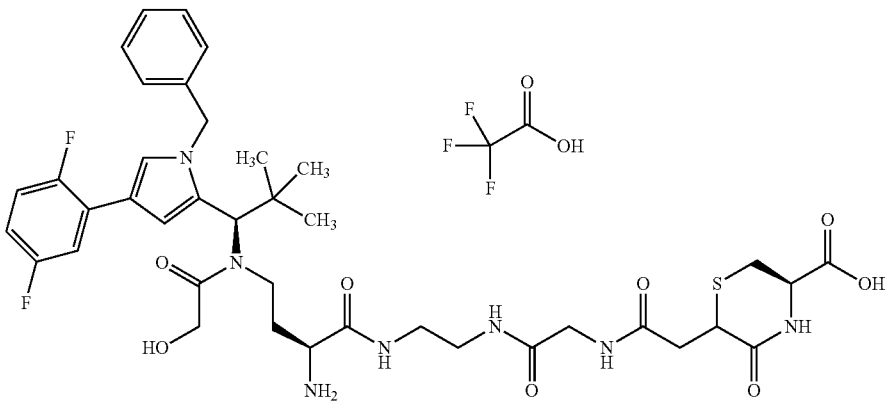

4 mg (0.004 mmol) of the compound from Example 135 were dissolved in 4 ml of THF/water, and 48 μl of a 2-molar aqueous lithium hydroxide solution were added. The reaction was stirred at RT for 1 h and then concentrated and purified by preparative HPLC. Combination, concentration and lyophilization of the appropriate fractions from acetonitrile/water gave 2.4 mg (60% of theory) of the title compound.

LC-MS (Method 1): $R_t$=0.86 min; MS (EIpos): m/z=814 [M+H]+.

C: Assessment of Biological Efficacy

The biological activity of the compounds according to the invention can be shown in the assays described below:

m. C-1a Determination of the Cytotoxic Effects of the ADCs Directed Against TWEAKR The analysis of the cytotoxic effects of the anti-TWEAKR-ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Biochrom; #SO415), TWEAKR-positive, EGFR-positive.

BxPC3: human pancreas carcinoma cells, ATCC-CRL-1687, standard medium: RPMI 1640 (Biochrom; #FG1215, stab. glutamine)+10% FCS (Biochrom; #SO415), TWEAKR-positive.

KPL4: human breast carcinoma cells, standard medium: RPMI 1640+GlutaMAX I+10% FBS, cell bank, Bayer Pharma AG (identity checked and confirmed on 19.7.2012 at DSMZ), Berlin, ERBB2-positive.

The cells are cultivated by a standard method, as indicated in the American Tissue Type Collection (ATCC) for the respective cell lines.

MTT Assay

The test is carried out by detaching the cells with a solution of Accutase in PBS (Biochrom AG #L2143), pelleting, resuspending in culture medium, counting and sowing into a 96-well culture plate with white bottom (Costar #3610) (1000-2000 cells in 100 μl/well depending on the cell used) and incubating in an incubator at 37° C. and 5% carbon dioxide. After 48 h, the antibody drug conjugates are added in 10 μl of culture medium in concentrations of from $10^5$M to $10^{-13 M}$ to the cells (triplicates) and incubated in an incubator at 37° C. and 5% carbon dioxide. After 72 h, the proliferation is detected using the MTT assay (ATCC, Manassas, Va., USA, catalogue No. 30-1010K). At the end of the selected incubation time, the MTT reagent is incubated with the cells for 4 h, followed by lysis of the cells overnight by addition of the detergent. The dye formed was detected at 570 nm. The proliferation of cells which were not treated with test substance but were otherwise identically treated was defined as the 100% figure.

CTG Assay

The cells were cultivated according to the standard method using the growth media listed under C-1. The test was carried out by detaching the cells with a solution of trypsin (0.05%) and EDTA (0.02%) in PBS (Biochrom AG #L2143), pelleting, resuspending in culture medium, counting and sowing into a 96-well culture plate with white bottom (Costar #3610) (at 75 μl/well, the following cell numbers are per well: NCI-H292: 2500 cells/well, BxPC3 2500 cells/well) and incubating in an incubator at 37° C. and 5% carbon dioxide. After 24 h, the antibody drug conjugates were added in 25 μl of culture medium (concentrated four-fold) to the cells to give final antibody drug conjugate concentrations of $3 \times 10^{-7}$ M to $3 \times 10^{11}$ M on the cells (triplicates). The cells were then incubated in an incubator at 37° C. and 5% carbon dioxide. On a parallel plate, the cell activity at the start of the active compound treatment (day 0) was determined using the Cell Titer Glow (CTG) luminescent cell viability assay (Promega #G7573 and #G7571). To this end, per cell batch 100 μl of the substrate were added, the plates were then covered with aluminium foil, shaken on the plate shaker at 180 rpm for 2 minutes, allowed to stand on the laboratory bench for 8 minutes and then measured using a luminometer (Victor X2, Perkin Elmer). The substrate detects the ATP content of the living cells generating a luminescence signal whose intensity is directly proportional to the viability of the cells. After 72 h of incubation with the antibody drug conjugates, the viability of these cells was then also determined using the Cell Titer Glow luminescent cell viability assay as described above. From the data measured, the $IC_{50}$ of the growth inhibition was calculated in comparison to day 0 using the DRC (Dose Response Curve) analysis spreadsheets and a 4-parameter fit. The DRC analysis spreadsheet is a biobook spreadsheet developed by Bayer Pharma AG and Bayer Business Services on the IDBS E-WorkBook Suite platform (IDBS: ID Business Solutions Ltd., Guildford, UK).

The Tables 1a, 1b and 1c list the $IC_{50}$ values of representative working examples using the anti-TWEAKR antibody from this assay:

TABLE 1a

| Example | BxPC3 $IC_{50}$ [M] CTG | NCI-H292 $IC_{50}$ [M] CTG |
|---|---|---|
| 02b | 1.88E−09 | 5.41E−10 |
| 03b | 1.92E−08 | — |
| 05b | — | — |
| 06b | 4.96E−08 | — |
| 07b | 6.56E−10 | 3.06E−10 |
| 08b | 1.20E−09 | 4.73E−10 |
| 09b | 1.18E−08 | 1.05E−08 |
| 10b | 1.43E−08 | — |
| 11b | 1.32E−08 | — |
| 12b | 1.32E−09 | 6.54E−10 |
| 13b | 9.65E−09 | — |
| 14b | 1.96E−09 | 4.13E−07 |
| 15b | 2.26E−09 | 6.00E−07 |
| 16b | 2.82E−09 | 6.00E−07 |
| 17b | 8.47E−10 | 3.52E−10 |
| 18b | 6.00E−07 | 6.00E−07 |
| 19b | 7.73E−08 | — |
| 20b | — | — |
| 21b | 1.11E−08 | 9.53E−09 |
| 22b | 6.89E−09 | 2.73E−09 |
| 23b | 8.43E−10 | 4.04E−10 |
| 24b | 2.26E−09 | 6.00E−07 |
| 25b | 1.76E−09 | 6.00E−07 |
| 26b | 1.08E−08 | 6.00E−07 |
| 27b | 2.75E−09 | 6.00E−07 |
| 28b | 5.15E−08 | 6.00E−07 |
| 29b | 2.06E−07 | 6.00E−07 |
| 30b | 2.05E−09 | 8.53E−10 |
| 31b | — | — |
| 32b | 3.04E−09 | 8.20E−10 |
| 33b | 1.01E−09 | 5.36E−10 |
| 34b | 5.43E−09 | 6.00E−07 |
| 35b | 9.27E−09 | 5.42E−09 |
| 36b | 1.83E−09 | — |
| 37b | — | — |
| 38b | 1.41E−09 | 2.61E−10 |
| 39b | 2.74E−09 | — |
| 40b | 3.76E−09 | — |
| 41b | 1.98E−09 | — |
| 42b | 5.53E−09 | — |
| 43b | — | — |
| 44b | 3.07E−09 | 1.44E−09 |
| 45b | 5.64E−09 | — |
| 46b | 1.72E−09 | 2.57E−09 |
| 47b | 4.34E−09 | — |
| 48b | 2.90E−09 | 8.46E−10 |
| 49b | 9.76E−09 | 6.37E−08 |
| 50b | 2.39E−09 | 1.86E−07 |
| 51b | — | — |
| 52b | — | — |
| 53b | — | — |
| 54b | — | — |
| 55b | 2.73E−08 | 2.59E−08 |
| 56b | 6.29E−09 | 6.00E−07 |
| 57b | 1.52E−09 | 5.02E−09 |
| 58b | 5.32E−09 | 5.76E−09 |
| 82b | 4.26E−09 | 6.00E−07 |
| 83b | 4.68E−09 | 1.97E−08 |
| 84b | 1.00E−09 | 8.58E−10 |
| 85b | 2.03E−09 | 8.84E−10 |
| 86b | 2.96E−09 | 8.68E−09 |
| 87b | 2.16E−09 | 1.33E−09 |
| 88b | 2.0E−08 | 8.34E−09 |
| 89b | 1.87E−09 | 6.00E−07 |
| 90b | 2.12E−08 | 8.49E−09 |
| 91b | 9.98E−09 | 3.07E−09 |

TABLE 1b

| Example | BxPC3 IC$_{50}$ [M] CTG | NCI-H292 IC$_{50}$ [M] CTG |
|---|---|---|
| 103b | 6.00E−07 | 6.00E−07 |
| 104b | 5.88E−10 | 1.44E−10 |
| 105b | 5.03E−09 | — |
| 106b | 2.43E−09 | 6.00E−07 |
| 107b | 4.19E−09 | 4.52E−09 |
| 108b | 2.38E−09 | 1.32E−09 |
| 109b | 9.26E−08 | 1.61E−07 |
| 110b | 1.32E−09 | 9.99E−10 |
| 111b | 1.92E−08 | 9.22E−08 |
| 112b | 6.00E−07 | 6.00E−07 |
| 113b | 2.48E−08 | 7.36E−08 |
| 114b | 1.61E−08 | 1.17E−08 |
| 115b | 2.43E−07 | 6.00E−07 |
| 116b | 1.01E−08 | 6.00E−07 |
| 117b | 6.00E−07 | 6.00E−07 |
| 118b | 6.00E−07 | 6.00E−07 |
| 119b | 8.90E−09 | 9.14E−10 |
| 120b | 3.78E−08 | 5.70E−09 |
| 121b | 6.00E−07 | 6.00E−07 |
| 122b | 6.00E−07 | 1.03E−08 |
| 123b | 6.90E−09 | 1.44E−09 |
| 124b | 6.00E−07 | 6.00E−07 |
| 125b | 2.99E−08 | 3.58E−09 |
| 126b | 6.00E−07 | 6.00E−07 |
| 127b | 3.31E−08 | 1.94E−09 |
| 128b | 7.83E−09 | 1.02E−09 |
| 129b | 6.00E−07 | 6.00E−07 |
| 142b | 1.41E−09 | 6.92E−10 |
| 143b | 1.04E−09 | 4.33E−09 |
| 144b | 1.17E−08 | 8.29E−08 |
| 145b | 2.64E−09 | 3.24E−10 |
| 146b | 4.85E−08 | 1.05E−08 |
| 147b | 1.17E−09 | 2.26E−09 |
| 148b | 1.06E−09 | 2.05E−10 |
| 149b | 9.52E−10 | 3.74E−10 |
| 150b | 9.25E−09 | 6.00E−07 |
| 151b | 6.00E−07 | 6.00E−07 |
| 152b | 6.00E−07 | 6.00E−07 |
| 153b | 1.44E−09 | 1.17E−08 |
| 154b | 5.05E−09 | 5.77E−10 |
| 155b | 9.44E−10 | 5.09E−10 |
| 156b | 1.39E−09 | 6.00E−07 |

TABLE 1c

| Example | BxPC3 IC$_{50}$ [M] CTG | NCI-H292 IC$_{50}$ [M] CTG |
|---|---|---|
| 163b | 3.80E−09 | 1.21E−08 |
| 164b | 8.54E−09 | 4.10E−09 |
| 165b | 9.14E−10 | 8.95E−10 |
| 166b | 3.72E−09 | 9.27E−08 |
| 167b | 6.00E−07 | 3.40E−09 |
| 168b | 9.12E−10 | 5.78E−09 |
| 169b | 2.04E−09 | 3.19E−09 |
| 170b | 1.71E−09 | 1.29E−09 |
| 171b | 6.00E−07 | 4.25E−09 |
| 172b | 2.28E−09 | 5.46E−09 |
| 173b | 1.39E−09 | 1.07E−09 |
| 174b | 5.27E−09 | 6.00E−07 |
| 175b | 9.58E−09 | 6.00E−07 |
| 176b | 3.84E−09 | 6.00E−07 |
| 177b | 2.00E−08 | 5.11E−08 |
| 178b | 1.78E−08 | 3.78E−08 |
| 179b | 2.29E−08 | 6.00E−07 |
| 180b | 4.39E−09 | 2.34E−09 |
| 192b | 6.29E−09 | 6.00E−07 |
| 193b | 1.85E−09 | 8.98E−09 |
| 194b | 3.96E−09 | 2.92E−09 |
| 195b | 4.07E−09 | 2.95E−09 |
| 196b | 5.73E−09 | 1.58E−09 |
| 204b | 6.42E−09 | 1.25E−09 |

TABLE 1c-continued

| Example | BxPC3 IC$_{50}$ [M] CTG | NCI-H292 IC$_{50}$ [M] CTG |
|---|---|---|
| 205b | 1.45E−09 | 5.17E−08 |
| 206b | 3.89E−09 | 3.01E−08 |
| 207b | 1.36E−09 | 3.33E−10 |
| 208b | 2.55E−09 | 6.98E−10 |
| 209b | 7.07E−10 | 1.42E−09 |
| 210b | 8.53E−10 | 1.89E−08 |
| 211b | 5.94E−09 | 3.75E−09 |
| 212b | 3.65E−08 | 3.31E−08 |
| 213b | 6.02E−09 | 2.16E−09 |
| 214b | 3.86E−09 | 3.82E−09 |
| 215b | 1.14E−09 | 5.94E−09 |
| 216b | 7.15E−10 | 5.28E−10 |
| 217b | 5.60E−09 | 1.33E−08 |
| 218b | 9.73E−10 | 1.53E−08 |
| 234b | 8.17E−09 | 1.82E−09 |
| 235b | 1.31E−07 | 5.91E−08 |
| 236b | 1.93E−07 | 2.38E−07 |
| 237b | 1.05E−09 | 3.74E−10 |
| 238b | 6.00E−07 | 6.03E−08 |
| 239b | 2.52E−08 | 7.04E−09 |
| 240b | 1.13E−08 | 8.69E−08 |
| 241b | 1.10E−08 | 1.15E−09 |
| 242b | 8.54E−09 | 1.21E−09 |
| 243b | 9.99E−09 | 1.18E−09 |
| 244b | 4.63E−08 | 3.28E−08 |
| 245b | 1.05E−08 | 1.30E−09 |
| 247b | 6.19E−10 | 3.63E−10 |
| 248b | 1.53E−08 | 1.28E−09 |
| 254b | 3.46E−09 | 3.37E−10 |

The activity data reported relate to the working examples described in the present experimental section, with the drug/mAB ratios indicated. The values may possibly deviate for different drug/mAB ratios. The I050 values are means of several independent experiments or individual values. The action of the TWEAKR antibody drug conjugates was selective for the respective isotype control comprising the respective linker and toxophor.

Table 2 below lists the I050 values of representative working examples with the cetuximab antibody from the MTT assay:

TABLE 2

| Example | NCI-H292 IC$_{50}$ [M] MTT |
|---|---|
| 1a | 5.94E−10 |
| 2a | 3.02E−10 |
| 3a | 9.40E−11 |
| 4a | 6.88E−09 |
| 5a | 7.00E−09 |
| 6a | 1.09E−09 |
| 7a | 2.35E−10 |
| 8a | 2.30E−10 |
| 9a | 1.93E−10 |
| 10a | 4.70E−09 |
| 11a | 4.50E−09 |
| 12a | 8.00E−10 |
| 13a | 2.00E−09 |
| 14a | 1.01E−09 |
| 15a | 8.98E−10 |
| 16a | 5.49E−10 |
| 17a | 1.79E−11 |
| 18a | 8.77E−10 |
| 19a | 1.80E−09 |
| 20a | 5.07E−10 |
| 21a | 5.05E−10 |
| 22a | 6.12E−11 |
| 23a | 5.95E−10 |
| 24a | 4.68E−09 |

TABLE 2-continued

| Example | NCI-H292 IC$_{50}$ [M] MTT |
|---|---|
| 25a | 7.52E-09 |
| 26a | 7.32E-09 |
| 27a | 1.76E-08 |
| 28a | 2.85E-09 |
| 29a | 4.25E-09 |
| 30a | 7.93E-09 |
| 31a | 6.12E-10 |
| 32a | 7.28E-10 |
| 33a | 6.00E-10 |
| 34a | 5.00E-09 |
| 35a | 5.15E-09 |
| 36a | 1.65E-10 |
| 37a | 1.31E-10 |
| 38a | 1.70E-09 |
| 39a | 3.36E-10 |
| 40a | 2.45E-09 |
| 41a | 1.76E-08 |
| 42a | 3.97E-09 |
| 43a | 5.14E-10 |
| 44a | 4.31E-08 |
| 45a | 5.45E-10 |
| 46a | 3.81E-10 |
| 47a | 2.69E-10 |
| 48a | 3.49E-11 |
| 49a | 1.27E-08 |
| 50a | 4.00E-09 |
| 51a | 1.47E-09 |
| 52a | 4.19E-09 |
| 53a | 9.88E-9 |
| 54a | 6.30E-09 |
| 55a | 1.98E-09 |
| 56a | 2.11E-09 |
| 82a | 4.37E-09 |
| 83a | 1.07E-09 |
| 84a | 9.43E-10 |
| 85a | 3.40E-10 |
| 86a | 1.05E-08 |
| 87a | 4.34E-09 |
| 88a | 1.32E-09 |
| 89a | 3.78E-09 |
| 90a | 2.35E-09 |
| 91a | 1.45E-10 |
| 96 | 2.09E-09 |
| 98 | 1.65E-09 |
| 99 | 8.51E-10 |
| 102 | 3.29E-08 |
| 103a | 1.52E-09 |
| 104a | 1.85E-10 |
| 104h | 4.60E-10 |
| 104i | 1.47E-09 |
| 105a | 2.52E-07 |
| 106a | 7.89E-11 |
| 107a | 4.02E-11 |
| 108a | 1.04E-11 |
| 109a | 2.63E-10 |
| 110a | 6.27E-12 |
| 111a | 2.00E-09 |
| 112a | 1.80E-10 |
| 113a | 1.97E-10 |
| 114a | 1.61E-10 |
| 115a | 2.39E-10 |
| 116a | 8.99E-11 |
| 117a | 1.09E-10 |
| 118a | 8.33E-09 |
| 119a | 8.39E-10 |
| 120a | 1.94E-10 |
| 121a | 8.78E-11 |
| 122a | 2.01E-10 |
| 123a | 1.00E-10 |
| 124a | 5.75E-11 |
| 125a | 9.11E-11 |
| 126a | 8.38E-09 |
| 127a | 5.97E-10 |
| 128a | 4.87E-10 |
| 129a | 1.70E-09 |
| 130 | 1.78E-07 |
| 131 | 5.00E-07 |
| 132 | 5.00E-07 |
| 133 | 1.55E-07 |
| 134 | 5.00E-07 |
| 135 | 5.00E-07 |
| 136 | 5.00E-07 |
| 137 | 5.00E-07 |
| 138 | 5.00E-07 |
| 139 | 1.34E-07 |
| 140 | 5.00E-07 |
| 141 | 1.61E-08 |
| 142a | 4.95E-11 |
| 142h | 6.50E-10 |
| 142i | 3.62E-09 |
| 143a | 1.21E-10 |
| 145a | 2.55E-09 |
| 146a | 6.44E-11 |
| 147a | 4.30E-09 |
| 148a | 3.71E-09 |
| 149a | 8.31E-10 |
| 150a | 1.65E-09 |
| 153a | 2.40E-12 |
| 154a | 8.57E-11 |
| 155a | 7.34E-11 |
| 156a | 3.74E-11 |
| 157 | 5.00E-07 |
| 158 | 2.22E-08 |
| 159 | 1.14E-07 |
| 160 | 5.00E-07 |
| 161 | 3.55E-08 |
| 162 | 1.21E-07 |
| 163a | 7.24E-10 |
| 163h | 6.03E-10 |
| 164a | 1.29E-10 |
| 165a | 3.26E-11 |
| 166a | 1.08E-10 |
| 167a | 4.99E-10 |
| 168a | 1.23E-10 |
| 168h | 1.57E-10 |
| 169a | 1.86E-10 |
| 170a | 7.39E-10 |
| 171a | 5.05E-10 |
| 172a | 3.57E-12 |
| 173a | 3.16E-11 |
| 174a | 5.41E-10 |
| 175a | 4.72E-10 |
| 176a | 2.19E-10 |
| 177a | 1.87E-11 |
| 178a | 1.99E-10 |
| 179a | 1.51E-09 |
| 180a | 2.32E-10 |
| 181 | 7.72E-09 |
| 182 | 1.20E-09 |
| 183 | 3.29E-08 |
| 184 | 2.78E-08 |
| 185 | 1.20E-08 |
| 186 | 9.29E-09 |
| 187 | 1.98E-09 |
| 188 | 9.28E-10 |
| 189 | 8.76E-09 |
| 190 | 5.42E-09 |
| 191 | 9.36E-10 |
| 192a | 5.18E-10 |
| 193a | 3.10E-10 |
| 193h | 2.52E-10 |
| 194a | 6.17E-11 |
| 195a | 8.27E-10 |
| 196a | 3.67E-09 |
| 197 | 7.35E-09 |
| 198 | 1.95E-08 |
| 199 | 3.23E-07 |
| 199-2 | |
| 200 | 1.40E-07 |
| 201 | |
| 202 | 4.22E-07 |
| 203 | |

TABLE 2-continued

| Example | NCI-H292 IC$_{50}$ [M] MTT |
|---|---|
| 204a | 3.60E−09 |
| 205a | 6.64E−10 |
| 206a | 1.37E−09 |
| 207a | 1.05E−10 |
| 207h | 2.39E−09 |
| 207i | 6.87E−10 |
| 208a | 1.16E−08 |
| 208i | 8.22E−09 |
| 209a | 2.02E−11 |
| 209h | 1.35E−09 |
| 209i | 1.37E−09 |
| 210a | 1.30E−11 |
| 211a | 4.71E−10 |
| 212a | 4.43E−10 |
| 213a | 1.95E−11 |
| 214a | 6.83E−10 |
| 215a | 5.20E−10 |
| 215h | 5.18E−10 |
| 215i | 1.58E−08 |
| 216a | 1.12E−10 |
| 217a | 1.27E−09 |
| 218a | 3.44E−10 |
| 218h | 9.42E−10 |
| 218i | 1.37E−08 |
| 219 | 3.48E−09 |
| 220 | 1.97E−10 |
| 221 | 1.00E−10 |
| 222 | 3.30E−09 |
| 223 | 7.70E−12 |
| 224 | 3.37E−12 |
| 225 | 1.51E−09 |
| 226 | 2.22E−07 |
| 227 | 1.82E−09 |
| 228 | 5.36E−09 |
| 229 | 5.00E−07 |
| 230 | 1.21E−11 |
| 231 | 9.18E−10 |
| 232 | 1.55E−08 |
| 233 | 9.63E−10 |
| 234a | 2.10E−09 |
| 234h | 7.28E−09 |
| 234i | 6.97E−09 |
| 235a | 4.6E−08 |
| 235h | 3.04E−10 |
| 235i | 1.45E−08 |
| 236a | 5.98E−09 |
| 237a | 1.51E−09 |
| 237i | 5.94E−09 |
| 238a | 3.49E−10 |
| 239a | 7.78E−11 |
| 239h | 1.65E−09 |
| 239i | 6.48E−09 |
| 240a | 3.66E−11 |
| 241a | 5.91E−11 |
| 241i | 5.80E−10 |
| 242a | 8.26E−11 |
| 243a | 3.37E−10 |
| 243i | 3.22E−09 |
| 244a | 3.70E−10 |
| 244i | 4.50E−09 |
| 245a | 5.30E−11 |
| 245i | 2.50E−08 |
| 246 | 9.38E−09 |
| 247a | <1.00E−10 |
| 247i | 1.53E−10 |
| 248a | |
| 249 | 2.66E−08 |
| 252 | |
| 254a | |
| 254i | |

The activity data reported relate to the working examples described in the present experimental section, with the drug/mAB ratios indicated. The values may possibly deviate for different drug/mAB ratios. The IC50 values are means of several independent experiments or individual values. The action of the cetuximab antibody drug conjugates was selective for the respective isotype control comprising the respective linker and toxophor.

Table 3 below lists the 1050 values of representative working examples with the trastuzumab antibody from the MTT assay:

TABLE 3

| Example | KPL4 IC$_{50}$ [M] MTT |
|---|---|
| 2e | 2.00E−10 |
| 8e | 1.49E−10 |
| 14e | 5.00E−09 |
| 15e | 1.45E−08 |
| 16e | 3.41E−10 |
| 22e | 4.99E−09 |
| 35e | 2.00E−09 |
| 36e | 2.89E−09 |
| 37e | 1.99E−09 |
| 38e | 1.87E−10 |
| 39e | 3.40E−10 |
| 40e | 9.84E−09 |
| 41e | 7.99E−09 |
| 42e | 3.10E−10 |
| 43e | 5.33E−10 |
| 44e | 4.49E−08 |
| 45e | 4.78E−10 |
| 46e | 2.91E−10 |
| 47e | 3.89E−10 |
| 48e | 5.64E−10 |
| 49e | 3.02E−10 |
| 51e | 1.00E−06 |
| 52e | 4.76E−10 |
| 53e | 5.0E−07 |
| 54e | 1.50E−09 |
| 82e | 9.53E−08 |
| 83e | 5.81E−09 |
| 103e | 4.16E−07 |
| 104e | 2.09E−10 |
| 106e | 5.00E−05 |
| 110e | 5.00E−05 |
| 118e | 5.0E−07 |
| 126e | 5.0E−07 |
| 127e | 1.22E−09 |
| 129e | 5.0E−07 |
| 142e | 1.53E−07 |
| 143e | 5.0E−07 |
| 145e | 1.00E−09 |
| 146e | 5.0E−07 |
| 147e | 3.38E−09 |
| 148e | 5.89E−10 |
| 149e | 3.02E−10 |
| 150e | 2.71E−08 |
| 156e | 5.00E−07 |
| 164e | 5.85E−10 |
| 165e | 7.44E−11 |
| 166e | 5.00E−07 |
| 167e | 1.00E−09 |
| 168e | 3.50E−10 |
| 169e | 6.27E−08 |
| 170e | 3.59E−10 |
| 172e | 3.08E−11 |
| 173e | 8.07E−10 |
| 175e | 5.00E−07 |
| 176e | 2.55E−08 |
| 179e | 1.21E−07 |
| 180e | 4.13E−10 |
| 192e | 5.00E−07 |
| 193e | 1.23E−09 |
| 194e | 1.55E−08 |
| 195e | 7.27E−10 |
| 196e | 5.49E−10 |
| 204e | 1.66E−10 |
| 205e | 3.24E−10 |
| 206e | 1.13E−08 |
| 207e | 1.55E−10 |

TABLE 3-continued

| Example | KPL4 IC$_{50}$ [M] MTT |
|---|---|
| 210e | 5.00E−07 |
| 211e | 1.06E−07 |
| 212e | 5.03E−09 |
| 213e | 5.00E−07 |
| 214e | 8.48E−09 |
| 215e | 1.89E−10 |
| 216e | 9.64E−11 |
| 217e | 1.47E−10 |
| 218e | 1.67E−09 |
| 235e | 8.0E−08 |
| 236e | 8.40E−08 |
| 238e | 2.30E−08 |
| 240e | 1.90E−11 |
| 241e | 1.90E−10 |
| 242e | 6.288E−11 |
| 243e | 2.92E−10 |
| 244e | 8.30E−09 |
| 245e | 4.48E−10 |
| 247e | 1.43E−10 |
| 254e | 1.09E−10 |

The activity data reported relate to the working examples described in the present experimental section, with the drug/mAB ratios indicated. The values may possibly deviate for different drug/mAB ratios. The IC50 values are means of several independent experiments or individual values. The action of the trastuzumab antibody drug conjugates was selective for the respective isotype control comprising the respective linker and toxophor.

C-1b Determination of the Inhibition of the Kinesin Spindle Protein KSP/Eg5 by Selected Examples The motor domain of the human kinesin spindle protein KSP/Eg5 (from tebu-bio/Cytoskeleton Inc, No. 027EG01-XL) is incubated at a concentration of 10 nM with 50 μg/ml taxol- (from Sigma No. T7191-5MG) stabilized microtubuli (bovine or porcine, from tebu-bio/Cytoskeleton Inc) for 5 min at RT in 15 mM PIPES, pH 6.8 (5 mM MgCl$_2$ and 10 mM DTT, from Sigma). The freshly prepared mixture is aliquoted into a 384-well MTP. The inhibitors to be examined at concentrations of $1.0 \times 10^{-6}$ M to $1.0 \times 10^{-13}$ and ATP (final concentration 500 μM, from Sigma) are then added. Incubation is at RT for 2 h. ATPase activity is detected by detecting the inorganic phosphate formed using malachite green (from Biomol). After addition of the reagent, the assay was incubated at RT for 50 minutes prior to detection of the absorption at a wavelength of 620 nm Monastrol and Ispinesib (from Adooq A10486) are used as positive control. The individual data of the dose-activity curve are eight-fold determinations. The IC50 values are means of three independent experiments. The 100% control was the sample which had not been treated with inhibitors.

Table 4 below summarizes the IC50 values of representative working examples from the assay described: In an exemplary manner, they confirm the high potency at the target of the toxophors and ADC methods described.

TABLE 4

| Examples | KSP assay IC$_{50}$ [M] |
|---|---|
| 59 | 4.27E−09 |
| 60 | n.a |
| 61 | 6.78E−09 |
| 61 | 1.16E−09 |
| 62 | n.d. |
| 63 | 2.88E−09 |
| 64 | 3.06E−09 |
| 65 | 2.03E−09 |
| 66 | 8.08E−09 |
| 67 | 8.07E−09 |
| 68 | 3.22E−09 |
| 69 | 4.82E−09 |
| 70 | 3.18E−09 |
| 71 | 1.22E−09 |
| 72 | 4.85E−09 |
| 73 | 4.52E−09 |
| 74 | 6.13E−09 |
| 75 | n.d |
| 76 | 2.33E−09 |
| 77 | n.d |
| 78 | 4.95E−09 |
| 79 | 2.11E−09 |
| 80 | 3.72E−09 |
| 81 | 1.42E−09 |
| 93 | 2.52E−09 |
| 94 | 5.14E−09 |
| 95 | 3.05E−09 |
| 96 | 7.80E−09 |
| 97 | 2.13E−09 |
| 98 | 1.80E−09 |
| 99 | n.d. |
| 100 | 5.99E−09 |
| 101 | 4.28E−09 |
| 102 | 4.70E−09 |
| 130 | 1.66E−09 |
| 131 | 1.24E−09 |
| 132 | 1.65E−09 |
| 133 | 4.13E−09 |
| 134 | 4.35E−09 |
| 135 | 2.04E−09 |
| 136 | 3.28E−10 |
| 137 | 7.78E−10 |
| 138 | 1.01E−9 |
| 139 | 1.82E−09 |
| 140 | 2.51E−09 |
| 141 | 9.02E−10 |
| 157 | 9.61E−09 |
| 158 | 6.20E−10 |
| 159 | 3.11E−10 |
| 160 | 6.81E−10 |
| 161 | 5.17E−09 |
| 162 | 2.58E−09 |
| 181 | 7.90E−09 |
| 182 | 1.04E−08 |
| 183 | 6.21E−09 |
| 184 | 1.43E−08 |
| 185 | 1.80E−08 |
| 186 | 2.53E−08 |
| 187 | 1.41E−08 |
| 188 | 1.01E−08 |
| 189 | 1.12E−08 |
| 190 | 9.61E−09 |
| 191 | 1.26E−08 |
| 197 | 4.17E−09 |
| 198 | 1.07E−08 |
| 199 | 6.00E−09 |
| 199-2 | 9.09E−10 |
| 200 | 1.08E−10 |
| 201 | 1.79E−10 |
| 202 | 2.56E−10 |
| 203 | 2.30E−10 |
| 219 | 1.13E−09 |
| 220 | 1.45E−09 |
| 221 | 1.12E−10 |
| 222 | 1.58E−09 |
| 223 | 2.89E−10 |
| 224 | 1.96E−10 |
| 225 | 4.25E−10 |
| 226 | 1.49E−09 |
| 227 | 1.78E−09 |

TABLE 4-continued

| Examples | KSP assay IC$_{50}$ [M] |
|---|---|
| 228 | 3.07E-09 |
| 229 | 4.44E-09 |
| 230 | 3.41E-09 |
| 231 | 1.67E-09 |
| 232 | 2.20E-09 |
| 233 | 3.88E-09 |
| 246 | 2.69E-09 |
| 249 | 9.15E-10 |
| 250 | 3.26E-09 |
| 251 | 2.71E-10 |
| 252 | 4.57E-10 |
| 256 | 1.64E-08 |

The activity data reported relate to the working examples described in the present experimental section.

C-2 Internalisation Assay

Internalisation is a key process which enables specific and efficient provision of the cytotoxic payload in antigen-expressing cancer cells via antibody drug conjugates (ADC). This process is monitored via fluorescent labelling of specific TWEAKR antibodies and an isotype control antibody (M014). First, the fluorescent dye is conjugated to lysines of the antibody. Conjugation is carried out using a two-fold molar excess of CypHer 5E mono NHS ester (Batch 357392, GE Healthcare) at pH 8.3. After the coupling, the reaction mixture is dialysed at 4° C. (sSlide-A-Lyser Dialysis Cassettes MWCD 10 kD, from Pierce) overnight to remove excess dye and to adjust the pH, and the protein solution is then concentrated (VIVASPIN 500, from Sartorius stedim biotec). Determination of the dye load of the antibody is by spectrophotometric analysis (NanoDrop) and subsequent calculation (D: $P = A_{dye} \varepsilon_{protein} \cdot (A_{280} - 0.16 A_{dye}) \varepsilon_{dye}$). The dye load of the TWEAKR antibody examined here and the isotype control were of a comparable order. In cell binding assays, it is confirmed that the conjugation did not lead to a change in the affinity of the antibody.

The labelled antibodies are used for the internalisation assay. Prior to the start of the treatment, the cells ($2 \times 10^4$/well) are sown in 100 µl medium in a 96-well MTP (fat, black, clear bottom No 4308776, from Applied Biosystems). After 18 h of incubation at 37° C./5% CO$_2$, the medium is replaced and labelled anti-TWEAKR antibodies are added in different concentrations (10, 5, 2.5, 1, 0.1 µg/ml). The same treatment protocol is applied to the labelled isotype control (negative control). The chosen incubation times are 0, 0.25 h, 0.5 h, 1 h, 1.5 h, 2 h, 3 h, 6 h and 24 h. The fluorescence measurement is carried out using the InCellanalyser 1000 (from GE Healthcare). This was followed by kinetic evaluation via measurement of the parameters granule counts/cell and totale granule intensity/cell.

Following binding to the TWEAKR, TWEAKR antibodies were examined for the internalisation ability. For this purpose, cells with different TWEAKR expression levels were chosen. A target-mediated specific internalisation was observed with the TWEAKR antibodies, whereas the isotype control showed no internalisation.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective working example was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropol mass spectrometer API 4000 (Applied Biosystems Applera, Darmstadt, Germany) The permeability was evaluated on the basis of a Papp value, which was calculated using the formula published by Schwab et al. [D. Schwab et al., J. Med. Chem. 46, 1716-1725 (2003)]. A substance was classified as actively transported when the ratio of $P_{app}$ (B-A) to $P_{app}$ (A-B) (efflux ratio) was >2 or <0.5.

Of critical importance for toxophores which are released intracellularly is the permeability from B to A [$P_{app}$(B-A)] and the ratio of $P_{app}$(B-A) to $P_{app}$(A-B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 5 below sets out permeability data for representative working examples from this assay:

TABLE 5

| Working Example | $P_{app}$ (B-A) [nm/s] | Efflux ratio |
|---|---|---|
| 59 | 22 | 4.8 |
| 61 | 44 | 7.4 |
| 62 | 50 | 6 |
| 63 | 0.98 | 1.1 |
| 64 | 10 | 2.8 |
| 65 | 1.2 | 2.3 |
| 66 | 27 | 12 |
| 67 | 25 | 15 |
| 68 | 1.8 | 1.9 |
| 69 | 1.5 | 2 |
| 70 | 1.6 | 1.9 |
| 71 | 280 | 280 |
| 72 | 2.5 | 2.1 |
| 73 | 4.6 | 2.7 |
| 74 | 26 | 15 |
| 76 | 55 | 27 |
| 77 | 480 | 47 |
| 78 | 140 | 44 |
| 79 | 58 | 16 |
| 80 | 200 | 22 |
| 92 | 4 | 3 |
| 96 | 285 | 16 |
| 97 | 5.6 | 2 |
| 98 | 213 | 16 |
| 99 | 303 | 8.7 |
| 130 | 10 | 6.7 |
| 131 | 9 | 10 |
| 132 | 1.6 | 1 |
| 133 | 4.3 | 6 |
| 134 | 2.9 | 0.5 |
| 135 | 7.8 | 4 |
| 136 | 9.1 | 8.5 |
| 137 | 17 | 19 |
| 138 | 1.7 | 1.6 |
| 139 | 21 | 7.7 |
| 140 | 1.7 | 1 |
| 141 | 30 | 35 |

TABLE 5-continued

| Working Example | $P_{app}$ (B-A) [nm/s] | Efflux ratio |
|---|---|---|
| 157 | 7.7 | 7.2 |
| 158 | 5.6 | 2.2 |
| 159 | 7 | 6.1 |
| 160 | 1.6 | 1 |
| 161 | 1.6 | 2 |
| 162 | 2 | 2.9 |
| 197 | 93 | 81 |
| 198 | 519 | 34 |
| 199 | 4.8 | 6.4 |
| 226 | 3 | 0.2 |
| 232 | 49 | 14 |
| 246 | 1.4 | 1.3 |
| 251 | 21 | 19 |
| 252 | 20 | 26 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany) The permeability was evaluated on the basis of a Papp value, which was calculated using the formula published by Schwab et al. [D. Schwab et al., *J. Med. Chem.* 46, 1716-1725 (2003)]. A substance was classified as P=gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmakokinetics

C5a: Identification of the ADC Metabolites after Internalisation In Vitro

Description of the Method:

Internalisation studies with immunoconjugates are carried out to analyse metabolites formed intracellularly. To this end, human lung tumour cells NCI H292 ($3 \times 10^5$/well) are sown in 6-well plates and incubated overnight (37° C., 5% $CO_2$). The cells are treated with 10 µg/ml of the ADC to be examined Internalisation is carried out at 37° C. and 5% $CO_2$. At various time points (0, 4, 24, 48, 72 h), cell samples are taken for further analysis. First, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined After another washing, a defined number of cells ($2 \times 10^5$) is treated with 100 µl of lysis buffer (Mammalian Cell Lysis Kit (Sigma MCL1) and incubated with continuous shaking (Thermomixer, 15 min, 4° C., 650 rpm) in Protein LoBind tubes (eppendorf Cat. No. 0030 108.116). After the incubation, the lysate is centrifuged (10 min, 4° C., 12000 g, eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For work-up of 50 µl of culture supernatant/cell lysate, 150 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-200 µg/l are added to the supernatant of untreated tumours. The detection limit is 4 µg/l. The linear range extends from 4 to 200 µg/l.

Quality controls for testing validity contain 5 and 50 µg/l.

NCI-H292 cells were incubated with in each case 10 µg/ml of the ADCs from Examples 104b, 119b, 155b, 165b and 173b. After 72 h, the cells were washed with PBS, lysed and deep-frozen (−80° C.). Using the method described above, the cell lysates and cell culture supernatants were worked up, and after extraction the following metabolites were identified and quantified:

| Incubated ADC Example | Isolated metabolite | Metabolite concentration in the cell lysate [µg/l] | Metabolite concentration in the supernatant [µg/l] |
|---|---|---|---|
| 104b | 199 | 11.6 | <1 |
| 104b | 198 | <2 | <2 |
| 104b | 135 | <0.2 | <0.2 |
| 104b | 197 | <1 | <1 |
| 104b | 256 | <0.2 | <0.2 |
| 119b | 158 | 14 | <0.2 |
| 155b | 162 | 10 | <0.2 |
| 165b | 162 | 8.8 | <0.2 |
| 173b | 161 | 18 | <0.2 |

NCI-H292 cells were incubated with in each case 10 µg/ml of the ADCs from Examples 179a, 226a, 85b and 208b. After 72 h, the cells were washed with PBS, lysed and deep-frozen (−80° C.). Using the method described above, the cell lysates and cell culture supernatants were worked up, and after extraction the following metabolites were identified and quantified:

| Incubated ADC Example | Isolated metabolite | Metabolite concentration in the cell lysate [µg/l] | Metabolite concentration in the supernatant [µg/l] |
|---|---|---|---|
| 179a | 249 | <1 | 5.6 |
| 226a | 226 | <1 | 9.1 |
| 226a | 255 | <1 | 2.5 |
| 85b | 139 | 1.5 | 3.2 |
| 85b | 250 | 7.4 | 1.8 |
| 208b | 199 | 13.5 | 2.3 |
| 208b | 198 | <1 | <1 |

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

Analysis for Quantification of any Metabolites Occurring

Measurement of the compounds in plasma and tumour is carried out after precipitation of the proteins with methanol or acetonitrile by high-pressure liquid chromatography (HPLC) coupled to a triple-quadrupole mass spectrometer (MS).

For work-up of 50 µl of plasma, 250 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

During the work-up of a tumour, the latter is treated with 3 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulphonyl fluoride (Sigma, St. Louis, Mo.) in a final concentration of 1 mM. The sample is homogenized twice for 20 minutes in a Tissuelyser II (Qiagen), at maximum stroke number. 50 µl of the homogenate are transferred into an autosampler vial and made up with 150 µl of methanol including ISTD. After 3 minutes of centrifugation at 16000 g, 10 µl of the supernatant are made up with 180 µl of a buffer suitable for the mobile phase and shaken again. The tumour sample is then ready for measuring.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-2000 µg/l are added to the supernatant of untreated tumours. The detection limit is 5 µg/l. The linear range extends from 5 to 200 µg/l.

Quality controls for testing validity contain 5 and 50 µg/l, in plasma additionally 500 µg/l.

Following administration of 10 mg/kg of the ADCs from Examples 119b and 104b in the control groups from the xenograft models with NCI-H292, the mice were sacrificed after 24 h, blood was removed and the tumours were isolated. Using the method described above, the plasma and tumour samples were worked up, and after extraction the following metabolites were identified and quantified:

| ADC administered Example (Number) | Isolated metabolite (Example Number) | Metabolite concentration in the tumour [µg/l] | Metabolite concentration in the plasma [µg/l] |
|---|---|---|---|
| 119b | 158 | 155 | <5 |
| 104b | 199 | 147 | <5 |
| 104b | 198 | 27.4 | <5 |
| 104b | 135 | 5.23 | <5 |
| 104b | 197 | 7.75 | <5 |

Analysis for Quantification of the Antibodies Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG(H+L) antibody and horseradish peroxidase (HRP). After a further washing step, the HRP substrate was added to OPD and the colour development was monitored via absorption at 490 nm Standard samples having a known IgG concentration were fitted using a 4-parameter equation. Within the lower (LLOQ) and upper (ULOQ) quantification limits, the unknown concentrations were determined by interpolation.

C-6 Activity Test In Vivo

The activity of the conjugates according to the invention was tested, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6):2358-64). To this end, a tumour cell line expressing the target molecule of the binder was implanted into rodents (for example mice). A conjugate according to the invention, an isotype control conjugate, a control antibody or isotonic saline was then administered to the implant animals. The administration took place once or more than once. Following an incubation time of several days, the size of the tumour was determined by comparing conjugate-treated animals and the control group. The conjugate-treated animals displayed a smaller tumour size.

C-6a. Growth Inhibition/Regression of Experimental Tumours in the Mouse

Human tumour cells expressing the antigen for the antibody drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 mm$^2$ To examine the effect on larger tumours, treatment may be initiated only at a tumour size of 50-100 mm$^2$.

Treatment with ADCs is carried out via the intravenouse route into the tail vein of the mouse. The ADC is administered in a volume of 5 ml/kg.

The treatment protocol depends on the pharmacokinetics of the antibody. As standard, treatment takes place three times in succession every fourth day. For a quick assessment, a protocol with a single treatment may be employed. However, the treatment may also be continued, or a second cycle of three treatment days may follow at a later time.

As standard, 8 animals are used per treatment group. In addition to the groups to which the active substances are administered, one group is treated as control group only with the buffer, according to the same protocol.

During the experiment, the tumour area is measured regularly in two dimensions (length×width) using a caliper. The tumour area is determined as length×width. The ratio of the mean tumour area of the treatment group to that of the control group is stated as T/C area.

When after the end of the treatment all groups of the experiment are terminated at the same time, the tumours can be removed and weighed. The ratio of the mean tumour weights of the treatment group to that of the control group is stated as T/C weight.

C-6b. Efficacy of the Anti-EGFR Antibody Drug Conjugates in the NCI-H292 Tumour Model on Repeat Treatment 1 million NCI-H292 cells are inoculated subcutaneously into the flank of female NMRI-nude mice (Janvier). At a tumour size of 35 mm$^2$ on day 7, treatment is initiated intravenously at a dosage of 3 or 10 mg/kg (day 7, 11, 15). After the treatment, the tumour growth is monitored up to day 105.

Treatment with the antibody drug conjugates according to Examples 01a and 02a results in a marked inhibition of the growth of the tumours compared to the vehicle and isotype control groups. Initially independently of the dosage, there is a regression of most tumours. Table 6 shows the T/C area values determined via the tumour area on day 35. Treatment with a control conjugate (isotype antibody against an irrelevant antigen) results in a markedly weaker tumour growth-inhibiting action. Treatment with the unconjugated antibody likewise results in an inhibition of growth; however, this was less than in the case of the antibody drug conjugate.

TABLE 6

| Example | Dosage | T/C area |
| --- | --- | --- |
| 01a | 3 mg/kg | 0.09 |
| 01a | 10 mg/kg | 0.11 |
| isotype control | 10 mg/kg | 0.87 |
| 02a | 3 mg/kg | 0.13 |
| 02a | 10 mg/kg | 0.13 |
| isotype control | 10 mg/kg | 1.01 |
| cetuximab | 3 mg/kg | 0.23 |

C-6c. Efficacy of the Anti-EGFR Antibody Drug Conjugates in the NCI-H292 Tumour Model on Single Treatment 1 million NCI-H292 cells are inoculated subcutaneously into the flank of female NMRI-nude mice (Janvier). At a tumour size of ~37 mm$^2$ on day 9, the animals are treated once with a dose of 3 mg/kg of ADC or 2.5 mg/kg toxophor A (N-(3-aminopropyl)-N-{(1R)-1-[1-benzyl-4-(2,5-difluorophenyl)-1H-imidazol-2-yl]-2,2-dimethylpropyl}-2-hydroxyacetamide) or toxophor B (N-[(3R)-3-amino-4-fluorobutyl]-N-{(1R)-1-[1-benzyl-4-(2,5-difluorophenyl)-1H-imidazol-2-yl]-2,2-dimethylpropyl}-2-hydroxyacetamide). After the treatment, the tumour growth is monitored up to day 25.

Treatment with the antibody drug conjugates according to Examples 35A and 02A results in a marked inhibition of the growth of the tumours compared to the control group. During the treatment with 3 mg/kg, there is a regression of most tumours. Table 7 shows the T/C values determined for tumour weights and tumour area on day 25. Here, the antibody drug conjugate 35A shows better efficacy than cetuximab and than toxophor A or toxophor B.

TABLE 7

| Example | Dosage | T/C weight | T/C area |
| --- | --- | --- | --- |
| 35A | 3 mg/kg | 0.33 | 0.49 |
| 36A | 3 mg/kg | 0.77 | 0.84 |
| 52A | 3 mg/kg | 0.54 | 0.54 |
| Isotype control for 52A | 3 mg/kg | 0.55 | 0.79 |
| 02A | 3 mg/kg | 0.07 | 0.24 |
| Toxophor A | 2.5 mg/kg | 0.82 | 0.87 |
| Toxophor B | 2.5 mg/kg | 0.40 | 0.57 |
| cetuximab | 3 mg/kg | 0.47 | 0.54 |

C-6d. Efficacy of Anti-EGFR and Anti-TWEAKR Antibody Drug Conjugates in the NCI-H292 Tumour Model on Single Treatment 1 million NCI-H292 cells are inoculated subcutaneously into the flank of female NMRI-nude mice (Janvier). At a tumour size of 37 mm$^2$ on day 7, treatment is carried out once intravenously at a dose of 3 or 10 mg/kg of antibody drug conjugate. After the treatment, the tumour growth is monitored up to day 24.

Single treatment with the anti-TWEAKR antibody drug conjugate 02B results in a marked and long-lasting inhibition of growth of the tumours compared to the control group and the unconjugated anti-TWEAKR antibody. Table 8 shows the T/C values determined for tumour weights and tumour area on day 24.

TABLE 8

| Example | Dosage | T/C weight | T/C area |
| --- | --- | --- | --- |
| isotype control for 02A | 10 mg/kg | 1.06 | 0.96 |
| 02A | 3 mg/kg | n.d. | 0.66 |
| 91A | 3 mg/kg | n.d. | 0.78 |
| 02B | 10 mg/kg | 0.08 | 0.27 |
| anti-TWEAKR antibody | 10 mg/kg | 0.99 | 1.01 |
| cetuximab | 3 mg/kg | n.d. | 0.67 |
| nimotuzumab | 3 mg/kg | n.d. | 0.95 |
| 237i | 3 mg/kg | n.d. | 0.47 |
| 208i | 3 mg/kg | n.d. | 0.69 |

C-6e. Efficacy of the Anti-TWEAKR Antibody Drug Conjugates in the BxPC3 Tumour Model on Repeat Treatment 2 million BxPC3 cells are inoculated subcutaneously into the flank of female NMRI-nude mice (Janvier). At a tumour size of 45 mm$^2$ on day 10, treatment is initiated intravenously at a dosage of 10 mg/kg (day 10, 14, 18). After the treatment, the tumour growth is monitored up to day 42.

Treatment with the antibody drug conjugates according to Examples 07B, 08B, 12B, 15B and 46B results in a marked inhibition of the growth of the tumours compared to the control group. Table 9 shows the T/C values determined for tumour weights and tumour area on day 42. Treatment with the respective control conjugate (isotype antibody against an irrelevant antigen) results in a markedly weaker tumour growth-inhibiting action. Treatment with the unconjugated antibodies likewise results in an in some cases weaker inhibition of the growth of the tumours.

TABLE 9

| Example | Dosage | T/C weight | T/C area |
|---|---|---|---|
| 07B | 10 mg/kg | 0.27 | 0.50 |
| isotype control for 07B | 10 mg/kg | 0.77 | 0.84 |
| 08B | 10 mg/kg | 0.48 | 0.69 |
| isotype control for 08B | 10 mg/kg | 0.61 | 0.81 |
| 12B | 10 mg/kg | 0.18 | 0.54 |
| isotype control for 12B | 10 mg/kg | 0.64 | 0.74 |
| 15B | 10 mg/kg | 0.37 | 0.53 |
| isotype control for 15B | 10 mg/kg | 0.95 | 0.89 |
| 46B | 10 mg/kg | 0.47 | 0.57 |
| isotype control for 46B | 10 mg/kg | 0.87 | 0.93 |
| anti-TWEAKR antibody | 10 mg/kg | 0.50 | 0.55 |

C-6f. Efficacy of the Anti-TWEAKR Antibody Drug Conjugates in the NCI-H292 Tumour Model on Single Treatment (2 Independent Experiments)

In both experiments, 1 million NCI-H292 cells are inoculated subcutaneously into the flank of female NMRI-nude mice (Janvier). At a tumour size of 45 mm² on day 10 (experiment 1) or day 8 (experiment 2), treatment is carried out once intravenously at a dose of 3 mg/kg of antibody drug conjugate. After the treatment, the tumour growth is monitored up to day 18 (Experiment 1) or day 24 (Experiment 2).

Single treatment with the anti-TWEAKR antibody drug conjugates 02B, 07B and 08B in Experiment 1 results in a marked inhibition of growth of the tumours compared to the control group and the unconjugated anti-TWEAKR antibody. Table 10 (Experiment 1) shows the T/C values determined for tumour weights and tumour area on day 18. Single treatment with the anti-TWEAKR antibody drug conjugates 155B, 173B, 165B and 085B in Experiment 2 likewise results in a marked inhibition of growth of the tumours compared to the control group and the respective isotype control (not shown). Table 11 (Experiment 2) shows the T/C values determined for the tumour area on day 24.

TABLE 10

| Example | Dosage | T/C weight | T/C area |
|---|---|---|---|
| 02B | 10 mg/kg | 0.27 | 0.36 |
| 07B | 10 mg/kg | 0.26 | 0.38 |
| 08B | 10 mg/kg | 0.24 | 0.38 |
| 91B | 10 mg/kg | 0.52 | 0.58 |
| isotype control for 07B | 10 mg/kg | 1.05 | 0.93 |
| anti-TWEAKR antibody | 10 mg/kg | 0.68 | 0.84 |

TABLE 11

| Example | Dosage | T/C weight | T/C area |
|---|---|---|---|
| 155B | 10 mg/kg | / | 0.32 |
| 173B | 10 mg/kg | / | 0.32 |
| 165B | 10 mg/kg | / | 0.30 |
| 085B | 10 mg/kg | / | 0.24 |

C-6g. Efficacy of the Anti-TWEAKR Antibody Drug Conjugates in the A375 Tumour Model on Repeat Treatment 5 million A375 (human melanoma) cells are inoculated subcutaneously into the flank of female NMRI-nude mice (Janvier). At a tumour size of 41 mm² on day 10, treatment is initiated intravenously at a dosage of 10 mg/kg (day 10, 14, 18). After the treatment, the tumour growth is monitored up to day 22.

Treatment with the antibody drug conjugates according to Examples 38B and 104B results in a marked inhibition of the growth of the tumours compared to the control group. Table 10 shows the T/C values determined for tumour weights and tumour area on day 22. Treatment with the respective control conjugate (isotype antibody against an irrelevant antigen) results in a markedly weaker tumour growth-inhibiting action. Treatment with the unconjugated antibodies likewise results in an in some cases weaker inhibition of the growth of the tumours.

TABLE 10

| Example | Dosage | T/C weight | T/C area |
|---|---|---|---|
| anti-TWEAKR antibody | 10 mg/kg | 0.32 | 0.52 |
| isotype control for 104B | 10 mg/kg | 0.94 | 0.96 |
| 104B | 10 mg/kg | 0.14 | 0.29 |
| isotype control for 38B | 10 mg/kg | 0.86 | 0.98 |
| 38B | 10 mg/kg | 0.31 | 0.58 |

C-6h. Efficacy of the Anti-TWEAKR Antibody Drug Conjugates in the LoVo Tumour Model on Repeat Treatment 5 million LoVo (human colon carcinoma) cells are inoculated subcutaneously into the flank of female NMRI-nude mice (Janvier). At a tumour size of 43 mm² on day 7, treatment is initiated intravenously at a dosage of 10 mg/kg (day 7, 11, 15). After the treatment, the tumour growth is monitored up to day 45.

Treatment with the antibody drug conjugates according to Examples 07B, 87B and 104B results in a marked inhibition of the growth of the tumours compared to the control group. Table 11 shows the T/C values determined for the tumour area on day 45. Treatment with the control conjugate for 07B (isotype antibody against an irrelevant antigen) results in a markedly weaker tumour growth-inhibiting action.

TABLE 11

| Example | Dosage | T/C area |
|---|---|---|
| 07B | 10 mg/kg | 0.40 |
| isotype control for 07B | 10 mg/kg | 0.82 |
| 104B | 10 mg/kg | 0.43 |
| 87B | 10 mg/kg | 0.52 |

D. Working Examples of Pharmaceutical Compositions

The compounds according to the invention can be converted to pharmaceutical formulations as follows:

i.v. solution:
The compound according to the invention is dissolved in a concentration below the saturation solubility in a physiologically acceptable solvent (e.g. isotonic saline solution, D-PBS, or a formulation with glycine and sodium chloride in citrate buffer with addition of polysorbate 80). The solution is subjected to sterile filtration and dispensed into sterile and pyrogen-free injection vessels.

i.v. solution:

The compounds according to the invention can be converted to the administration forms mentioned. This can be accomplished in a manner known per se by "mixing with" or "dissolving in" inert, non-toxic, pharmaceutically suitable excipients (e.g. buffer substances, stabilizers, solubilizers, preservatives). The following, for example, may be present: amino acids (glycine, histidine, methionine, arginine, lysine, leucine, isoleucine, threonine, glutamic acid, phenylalanine and others), sugars and related compounds (glucose, saccharose, mannitol, trehalose, sucrose, mannose, lactose, sorbitol), glycerol, sodium salts, potassium, ammonium salts and calcium salts (e.g. sodium chloride, potassium chloride or disodiumhydrogenphosphate and many others), acetate/acetic acid buffer systems, phosphate buffer systems, citric acid and citrate buffer systems, trometamol (TRIS and TRIS salts), Polysorbates (e.g. Polysorbate 80 and Polysorbate 20), Poloxamers (e.g. Poloxamer 188 and Poloxamer 171), Macrogols (PEG derivatives, e.g. 3350), Triton X-100, EDTA salts, glutathione, albumins (e.g. human), urea, benzyl alcohol, phenol, chlorocresol, metacresol, benzalkonium chloride and many others.

Lyophilizate for Subsequent Conversion into an i.v., s.c. or i.m. Solution:

Alternatively the compounds of the invention may be converted into a stable lyophilizate (possibly with the aid of abovementioned excipients) and, before being administered, reconstituted with a suitable solvent (e.g. injection-grade water, isotonic saline solution) and administered.

Working examples of anti-TWEAKR antibodies

All examples were carried out using standard methods known to the person skilled in the art, unless described here in detail. Routine methods of molecular biology of the examples that follow can be carried out as described in standard laboratory textbooks such as Sambrook et al., Molecular Cloning: a Laboratory Manual, 2. Edition; Cold Spring Harbor Laboratory Press, Cold Spring Harbor, N.Y., 1989.

AK Example 1: Antibody Preparation Using an Antibody Library

A complete human phage display library (Hoet R M et al, Nat Biotechnol 2005; 23(3):344-8) was employed to isolate TWEAKR-specific human monoclonal antibodies of the present invention by protein panning (Hoogenboom H. R., Nat Biotechnol 2005; 23(3):1105-16), where dimeric Fc-fused extracellular domains of human and murine TWEAKR were immobilized as target.

TABLE AK-1

List of recombinant antigens used for antibody selection

| Nomenclature | Description | SEQ ID NO |
|---|---|---|
| TPP-599 | HUMAN-TNFRSF12Aaa28-80-hIgG1-Fc | 138 |
| TPP-601 | MURIN-TNFRSF12Aaa28-80-hIgG1-Fc | 137 |

The antigens were biotinylated using an about 2-fold molar excess of biotin-LC-NHS (Pierce; Cat. No. 21347) according to the instructions of the manufacturer and desalted using Zeba desalting columns (Pierce; Cat. No. 89889). Washed magnetic beads (DynaBeads) were incubated overnight with 200 nM biotinylated antigen at 4° C. and blocked for 1 h at 4° C. with blocking buffer (PBS with 3% BSA, 0.05% Tween-20). The blocked Fab phage library was added to the blocked TWEAKR beads (DynaBeads Streptavidin-M280—Invitrogen 112-06D) and incubated at room temperature for 30 min After stringent washing (3× with blocking buffer and 9× with PBS (150 mM NaCl; 8 mM Na2HPO4; 1.5 mM KH2PO4; adjusted to pH=7.4-7.6) with 0.05% Tween-20), Fab phages binding specifically to biotinylated TWEAKR beads (DynaBeads Streptavidin-M280—Invitrogen 112-06D) were resuspended in PBS and, for amplification, used directly for infecting Escherichia coli strain TG1. In the second selection round, two murine TWEAKR (200 nM) were used to select for cross-reactive binders, and in the third selection round the concentration of human TWEAKR was reduced (100 nM) to increase the selection pressure for high-affinity binders.

11 different Fab phages were identified and the corresponding antibodies were cloned into a mammalian IgG expression vector which provided the missing CH2-CH3 domains not present in the soluble Fab. The resulting IgGs were expressed transiently in mammalian cells as described in Tom et al., Chapter 12 in Methods Express: Expression Systems edited by Micheal R. Dyson and Yves Durocher, Scion Publishing Ltd, 2007. Briefly, a CMV promoter-based expression plasmid was transfected into HEK293-6E cells and incubated in Fernbach bottles or Wave bags. Expression took place at 37° C. for 5 to 6 days in F17 medium (Invitrogen). 1% Ultra-Low IgG FCS (Invitrogen) and 0.5 mM valproic acid (Sigma) were added as supplements 24 h after the transfection. The antibodies were purified by protein-A chromatography and characterized further by their binding affinity to soluble monomeric TWEAKR using ELISA and BIAcore analysis, as described in AK-Example 2.

TABLE AK-2

List of recombinant antigen used for the affinity measurement

| Nomenclature | Description | Origin | Cat. No. (Fitzgerald Inc) | SEQ ID NO |
|---|---|---|---|---|
| TPP-2305 | hTNFRSF12 amino acids a28-80 | human | 30R-AT080 | 168 |

To determine the cell binding characteristics of the anti-TWEAKR antibodies, binding to a number of cell lines (HT29, HS68, HS578) was examined by flow cytometry. The cells were suspended in dilutions of the antibodies (5 µg/ml) in FACS buffer and incubated on ice for 1 h. A second antibody (PE goat-anti-human IgG, Dianova #109-115-098) was then added. After 1 h of incubation on ice, the cells were analysed by flow cytometry using an FACS array (BD Biosciences).

NF-kappaB reporter gene assays were carried out to assess the agonistic activity of all 11 antibodies identified (human IgG1). HEK293 cells were transiently transfected with an NF-kappaB reporter construct (BioCat, Cat. No. LR-0051-PA) using 293fectin according to the instructions of the manufacturer. Transfected cells were sown in F17 media (serum-free; Invitrogen) at 37 C, 5% CO2 into white polylysine-coated 384-well plates (BD). The next day, the cells were stimulated with various concentrations of purified antibodies for 6 h, and a luciferase assay was then carried out using standard methods.

Internalisation was monitored via fluorescence labelling of anti-TWEAKR antibodies (CypHer 5E mono NHS ester; GE Healthcare). Prior to the treatment, HT29 cells were sown ($2\times10^4$/well) in 100 µl of medium in 96-well MTP plates (thick, black, transparent bottom, No. 4308776, Applied Biosystems). After 18 h of incubation at 37° C./5% $CO_2$, the medium was replaced and labelled anti-TWEAKR antibodies were added in different concentrations (10, 5, 2.5, 1, 0.1 µg/ml). The chosen incubation time was 0, 0.25, 0.5, 1, 1,5, 2, 3, 6 and 24h. Fluorescence measurement was carried out in an InCell-analyser 1000 (GE Healthcare).

The antibody having the highest in vitro activity (TPP-883) was selected for further activity and affinity maturation.

TPP-883
SEQ ID NO. 71
AQDIQMTQSPATLSASVGDRVTITC<u>RASQSISSYLN</u>WYQQKPGKAPKLLI

Y<u>AASSLQS</u>GVPSRFSGSGSGTDFTLTISSLQPEDFATYYC<u>QQSYSSPGIT</u>

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC

SEQ ID NO. 72
EVQLLESGGGLVQPGGSLRLSCAASGFTFS<u>PYPMMW</u>VRQAPGKGLEWVS<u>Y</u>

<u>ISPSGGKTHYADSVKG</u>RFTISRDNSKNTLYLQMNSLRAEDTAVYYCAR<u>GG</u>

<u>DGYFDYFDY</u>WGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.71) and heavy (SEQ ID NO.72) chains of TPP-883; CDRs both of the heavy and the light chain are underlined.

Maturation was carried out in a first mutations collection round, followed by recombination of those amino acid modifications which increased affinity and activity most. For collecting mutations NNK (N=AGCT, K=G or T), randomization was carried out at the following individual amino acid positions by site-directed mutagenesis using synthetic oligonucleotides including NNK codon diversification (continuous amino acid nomenclature): S35, S36, Y37 and N39 in CDR-L1; A51, S53, S54, Q56 and S57 in CDR-L2; S92, Y93, S94, S95, G97 and I98 in CDR-L3; P31, Y32, P33, M34 and M35 in CDR-H1; Y50, S52, P53, S54, G56, K57 and H59 in CDR-H2; G99, G100, D101, G102, Y103, F104, D105 and Y106 in CDR-H3. The DNA of all individual NNK saturation mutagenesis libraries was cloned into a mammalian IgG expression vector for activity maturation or into a phagemid vector for affinity maturation. Affinity maturation was carried out by phage panning Washed magnetic beads (DynaBeads) were incubated overnight with 10 nM, 1 nM, 100 pM or 10 pM biotinylated antigen at 4° C. and blocked for 1 h at 4° C. with blocking buffer (PBS with 3% BSA, 0.05% Tween-20). The blocked Fab phage library was added in 10000-fold, 1000-fold or 100-fold excess, compared to the theoretical library complexity, to the blocked TWEAKR-DynaBeads and incubated at room temperature for 30 min That means that 12 strategies were followed in total (4 antigen concentrations x 3 Fab phage titres). After stringent washing (3× with blocking buffer and 9× with PBS with 0.05% Tween-20), Fab phages binding specifically to biotinylated TWEAKR DynaBeads (DynaBeads Streptavidin-M280-Invitrogen 112-06D) were resuspended in PBS and, for amplification, used directly for infecting *Escherichia coli* strain TG1. In selection round two, the concentration of human TWEAKR-Fc was reduced (1 nM, 100 pM, 10 pM and 1 pM), and the same Fab phage titre was used for all 12 strategies ($4.4\times10^{11}$). For the expression of soluble Fab, the phagemid vector was digested with MluI to remove the gene-III membrane anchor sequence required for the Fab display on the phage, and the vector was re-ligated. 96 variants of each of the 12 selection pools were expressed as soluble Fabs and examined in an ELISA format. To this end, 2.5 nM biotinylated TWEAKR-Fc were antigen-coated, and binding of soluble Fabs was demonstrated using anti-c-Myc antibodies (Abcam ab62928). 7 single substitution variants (consecutive amino acid nomenclature) with improved binding to TWEAKR-Fc (Seq ID No 138) were demonstrated: S36G of CDR-L1, A51Q and S57K of CDR-L2, S94T and G97F of CDR-L3, M35I of CDR-H1 and G102T of CDR-H3. For the activity maturation, HEK293 cells were transfected with an NF-kappaB reporter (BioCat, Cat. No. LR-0051-PA). Transfected cells were sown in F17 media (serum-free; Invitrogen) in white, polylysine-coated 384-well plates (BD), and individual variants of the NNK-diversified position antibodies (human IgG1) libraries were expressed transiently in mammalian cells. The next day, NF-kappaB reporter cells were stimulated with the individual NNK antibody variants expressed for 6 h, and a luciferase assay was then carried out using standard methods. 1 single substitution variant having improved agonistic activity was detected: G102T of CDR-H3. This variant was also obtained by affinity maturation, and there, too, it showed the highest enhancement of affinity. After mutation collection by affinity and activity screening, all 7 favourable individual substitutions (library complexity: 128 variants) were recombined into a recombination library. To this end, oligonucleotides were synthesized to introduce selected mutations or the corresponding wild type amino acid at each selected position. The library was established using successive rounds of overlap extension PCR. The final PCR product was ligated into a bacterial soluble Fab expression vector, and 528 variants were selected at random (~4-fold excess of the sample taken) for an equilibrium ELISA screen with soluble Fabs, as described above. In the end, 7 variants were selected based on increased affinity compared to the best single substitution variant G102T. The corresponding DNA of these was cloned into a mammalian IgG expression vector and examined for functional activity in the abovementioned NF-kappaB reporter cell assay. Finally, the sequences obtained were compared with human germ line sequences, and deviations without any significant effect on the affinity and the efficacy were adapted. Antibodies having the sequences below were obtained by antibody library screening and by affinity and/or activity maturation:

TPP-2090
SEQ ID NO. 1:
DIQMTQSPSSLSASVGDRVTITC<u>RASQSISGYLN</u>WYQQKPGKAPKLLIYQ

<u>ASSLQS</u>GVPSRFSGSGSGTDFTLTISSLQPEDFATYYC<u>QQSYTSPFIT</u>FG

```
QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO. 2:
EVQLLESGGGLVQPGGSLRLSCAASGFTFSPYPMIWVRQAPGKGLEWVSY

ISPSGGSTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.1) and heavy (SEQ ID NO.2) chains of TPP-2090; CDRs both of the heavy and the light chain are underlined.

TPP-2149

```
                                         SEQ ID NO. 11
DIQMTQSPATLSASVGDRVTITCRASQSISGYLNWYQQKPGKAPKLLIYQ

ASSLQSGVPSRFSGSGSGTDFTLTISSLQPEDFATYYCQQSYTSPFITFG

PGTKVEIKRTVAAPSVFIFPPSDEQLKSGTASVVCLLNNFYPREAKVQWK

VDNALQSGNSQESVTEQDSKDSTYSLSSTLTLSKADYEKHKLYACEVTHQ

GLSSPVTKSFNRGEC

SEQ ID NO. 12
EVQLLESGGGLVQPGGSLRLSCAASGFTFSPYPMIWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.11) and heavy (SEQ ID NO.12) chains of TPP-2149; CDRs both of the heavy and the light chain are underlined.

TPP-2093

```
                                         SEQ ID NO. 21
DIQMTQSPSSLSASVGDRVTITCRASQSISSYLNWYQQKPGKAPKLLIYQ

ASSLQSGVPSRFSGSGSGTDFTLTISSLQPEDFATYYCQQSYTSPFITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO. 22
EVQLLESGGGLVQPGGSLRLSCAASGFTFSPYPMMWVRQAPGKGLEWVSY

ISPSGGSTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.21) and heavy (SEQ ID NO.22) chains of TPP-2093; CDRs both of the heavy and the light chain are underlined.

TPP-2148

```
                                         SEQ ID NO. 31
DIQMTQSPATLSASVGDRVTITCRASQSISSYLNWYQQKPGKAPKLLIYQ

ASSLQSGVPSRFSGSGSGTDFTLTISSLQPEDFATYYCQQSYTSPFITFG

PGTKVEIKRTVAAPSVFIFPPSDEQLKSGTASVVCLLNNFYPREAKVQWK

VDNALQSGNSQESVTEQDSKDSTYSLSSTLTLSKADYEKHKLYACEVTHQ

GLSSPVTKSFNRGEC

SEQ ID NO. 32
EVQLLESGGGLVQPGGSLRLSCAASGFTFSPYPMMWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.31) and heavy (SEQ ID NO.32) chains of TPP-2148; CDRs both of the heavy and the light chain are underlined.

TPP-2084

```
                                         SEQ ID NO. 41
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPGITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO. 42
EVQLLESGGGLVQPGGSLRLSCAASGFTFSPYPMMWVRQAPGKGLEWVSY

ISPSGGSTHYADSVKGRFTISRDNSKNTLYLQMNSLRAEDTAVYYCARGG

DTYFDYFDYWGQGTLVTVSSASTKGPSVFPLAPSSKSTSGGTAALGCLVK
```

-continued
```
DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.41) and heavy (SEQ ID NO.42) chains of TPP-2084; CDRs both of the heavy and the light chain are underlined.

TPP-2077

SEQ ID NO. 51
```
DIQMTQSPATLSASVGDRVTITCRASQSISSYLNWYQQKPGKAPKLLIYA

ASSLQSGVPSRFSGSGSGTDFTLTISSLQPEDFATYYCQQSYSSPGITFG

PGTKVEIKRTVAAPSVFIFPPSDEQLKSGTASVVCLLNNFYPREAKVQWK

VDNALQSGNSQESVTEQDSKDSTYSLSSTLTLSKADYEKHKLYACEVTHQ

GLSSPVTKSFNRGEC
```

SEQ ID NO. 52
```
EVQLLESGGGLVQPGGSLRLSCAASGFTFSPYPMMWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.51) and heavy (SEQ ID NO.52) chains of TPP-2077; CDRs both of the heavy and the light chain are underlined.

TPP-1538

SEQ ID NO. 61
```
AQDIQMTQSPATLSASVGDRVTITCRASQSISSYLNWYQQKPGKAPKLLI

YAASSLQSGVPSRFSGSGSGTDFTLTISSLQPEDFATYYCQQSYSSPGIT

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC
```

SEQ ID NO. 62
```
EVQLLESGGGLVQPGGSLRLSCAASGFTFSPYPMMWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.61) and heavy (SEQ ID NO.62) chains of TPP-1538; CDRs both of the heavy and the light chain are underlined.

TPP-1854

SEQ ID NO. 81
```
AQDIQMTQSPATLSASVGDRVTITCRASQSISGYLNWYQQKPGKAPKLLI

YNASSLQSGVPSRFSGSGSGTDFTLTISSLQPEDFATYYCQQSYTSPFIT

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC
```

SEQ ID NO. 82
```
EVQLLESGGGLVQPGGSLRLSCAASGFTFSPYPMIWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.81) and heavy (SEQ ID NO.82) chains of TPP-1854; CDRs both of the heavy and the light chain are underlined.

TPP-1853

SEQ ID NO. 91
```
AQDIQMTQSPATLSASVGDRVTITCRASQSISSYLNWYQQKPGKAPKLLI

YNASSLQSGVPSRFSGSGSGTDFTLTISSLQPEDFATYYCQQSYTSPGIT

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC
```

SEQ ID NO. 92
```
EVQLLESGGGLVQPGGSLRLSCAASGFTFSPYPMMWVRQAPGKGLEWVSY

ISPSGGKTHYADSVKGRFTISRDNSKNTLYLQMNSLRAEDTAVYYCARGG

DTYFDYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG
```

Amino acid sequences of the light (SEQ ID NO.91) and heavy (SEQ ID NO.92) chains of TPP-1853; CDRs both of the heavy and the light chain are underlined.

TPP-1857

SEQ ID NO. 101
AQDIQMTQSPATLSASVGDRVTITC<u>RASQSISGYLN</u>WYQQKPGKAPKLLI

Y<u>NASSLQS</u>GVPSRFSGSGSGTDFTLTISSLQPEDFATYYC<u>QQSYTSPGIT</u>

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC

SEQ ID NO. 102
EVQLLESGGGLVQPGGSLRLSCAASGFTFS<u>PYPMM</u>WVRQAPGKGLEWVS<u>Y</u>

<u>ISPSGGKTHYADSVKG</u>RFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.101) and heavy (SEQ ID NO.102) chains of TPP-1857; CDRs both of the heavy and the light chain are underlined.

TPP-1858

SEQ ID NO. 111
AQDIQMTQSPATLSASVGDRVTITC<u>RASQSISSYLN</u>WYQQKPGKAPKLLI

Y<u>NASSLQS</u>GVPSRFSGSGSGTDFTLTISSLQPEDFATYYC<u>QQSYTSPFIT</u>

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC

SEQ ID NO. 112
EVQLLESGGGLVQPGGSLRLSCAASGFTFS<u>PYPMM</u>WVRQAPGKGLEWVS<u>Y</u>

<u>ISPSGGKTHYADSVKG</u>RFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.111) and heavy (SEQ ID NO.112) chains of TPP-1858; CDRs both of the heavy and the light chain are underlined.

Example 2: Biochemical Characteristics of the Antibodies

Determination of Binding Affinities by Biacore Analysis:

Binding affinities of anti-TWEAKR antibodies were examined using surface plasmon resonance analysis on a Biacore T100 instrument (GE Healthcare Biacore, Inc.). The antibodies were immobilized on a CM5 sensor chip using an indirect capture reagent, anti-human IgG(Fc). Reagents of the "Human Antibody Capture Kit" (BR-1008-39, GE Healthcare Biacore, Inc.) were used as described by the manufacturer. Anti-TWEAKR antibodies were injected at a concentration of 10 µg/ml at 10 µg/min for 10 sec.

TABLE AK-3

List of recombinant antigen (TWEAKR) used for affinity measurement

| Nomenclature | Description | Origin | Cat. No. (Fitzgerald Inc) | SEQ ID NO |
|---|---|---|---|---|
| TPP-2305 | hTNFRSF12 amino acids a28-80 | human | 30R-AT080 | 168 |

TABLE AK-4

List of antibodies used for the affinity measurement

| | | SEQ ID NO | |
|---|---|---|---|
| Nomenclature | Description | Light chain | Heavy chain |
| P3G5(TPP-2195) | murine IgG2a | 121 | 122 |
| P4A8(TPP-1324) | human IgG1 | 125 | 126 |
| P2D3(TPP-2196) | murine IgG2a | 131 | 132 |
| 136.1(TPP-2194) | murine IgG2a | 123 | 124 |
| PDL-192(TPP-1104) | human IgG1 | 127 | 128 |
| 18.3.3(TPP-2193) | murine IgG2a | 129 | 130 |
| TPP-883 | human IgG1 | 71 | 72 |
| TPP-1538 | human IgG1 | 61 | 62 |
| TPP-2077 | human IgG1 | 51 | 52 |
| TPP-2084 | human IgG1 | 41 | 42 |
| TPP-2148 | human IgG1 | 31 | 32 |
| TPP-2093 | human IgG1 | 21 | 22 |
| TPP-2149 | human IgG1 | 11 | 12 |
| TPP-2090 | human IgG1 | 1 | 2 |

TABLE AK-5

List of commercially available antibodies used for the affinity measurement

| Nomenclature | Description | Cat. No. (Abcam) |
|---|---|---|
| ITEM-1 | murine IgG1 | ab21359 |
| ITEM-4 | murine IgG1 | ab21127 |

Various concentrations (200 nM, 100 nM, 50 nM, 25 nM, 12.5 nM, 6.25 nM, 3.12 nM, 1.56 nM) of purified recombinant human TWEAKR protein (TPP-2305, SEQ ID NO:168) in HEPES-EP buffer (GE Healthcare Biacore, Inc.) were injected over immobilised anti-TWEAKR antibodies at a flow rate of 60 µl/min for 3 minutes, the dissociation time being 5 minutes. Sensorgrams were generated after in-line reference cell correction, followed by subtraction of the buffer sample. The dissociation constant ($K_D$) was calculated based on the ratio of association ($k_{on}$) and dissociation ($k_{off}$) constants, obtained by fitting sensorgrams using a 1:1 first order binding model.

TABLE AK-6

Monovalent $K_D$ values of anti-TWEAKR antibodies measured using Biacore with TWEAKR protein (TPP-2305 (SEQ ID NO: 168)).

|  | ka (1/Ms) | kd (1/s) | $K_D$ (n M) |
|---|---|---|---|
| TPP-883 | 4.40E+06 | 9.10E-01 | 205.9 |
| TPP-1538 | 4.20E+06 | 1.10E-01 | 27.6 |
| TPP-2077 | 3.00E+06 | 8.60E-02 | 28.9 |
| TPP-2084 | 4.20E+06 | 1.10E-01 | 27.6 |
| TPP-2148 | 5.10E+06 | 1.30E-01 | 24.5 |
| TPP-2093 | 4.10E+06 | 9.00E-02 | 22.1 |
| TPP-2149 | 8.40E+06 | 1.00E-01 | 12.1 |
| TPP 2090 | 9.10E+06 | 1.10E-01 | 12.4 |
| PDL-192(TPP-1104) | 1.10E+07 | 3.80E-01 | 3.7 |
| 136.1(TPP-2194) | 3.84E+07 | 3.24E-02 | 0.8 |
| 18.3.3(TPP-2193) | 1.64E+07 | 2.85E-02 | 1.7 |
| P4A8(TPP-1324) | 1.20E+06 | 2.70E-03 | 2.3 |
| P3G5(TPP-2195) | 2.31E+06 | 1.22E-03 | 0.5 |
| P2D3(TPP-2196) | 1.32E+06 | 5.64E-04 | 0.4 |
| ITEM-1 | 3.80E+06 | 1.10E-02 | 2.9 |
| ITEM-4 | 2.80E+06 | 2.00E-03 | 0.7 |

It was determined that the antibodies of the invention bind TWEAKR with moderate affinity ($K_D$ 10-200 nM), whereas some comparative antibodies (e.g. PDL-192(TPP-1104), 136.1(TPP-2194), 18.3.3(TPP-2193), P4A8(TPP-1324), P3G5(TPP-2195), P2D3(TPP-2196), ITEM-1, ITEM-4) show high-affinity binding (0.7-3.7 nM). The sequences of the variable domains of the antibodies PDL-192, 136.1, 18.3.3, P4A8, P3G5 snd P2D3 were obtained from the patent literature WO2009/020933 and WO2009/140177, and the sequences coding for the constant region of human IgG1 and murine IgG2 were added, resulting in full-length IgGs PDL-192(TPP-1104), 136.1(TPP-2194), 18.3.3(TPP-2193), P4A8(TPP-1324), P3G5(TPP-2195), P2D3(TPP-2196). The range of the affinities measured in this study agrees well with published data: for PDL-192, 18.3.3 and 136.1, KD values of 5.5, 0.2 and 0.7 nM have been published (WO2009/020933); for P4A8 2.6 nM (WO2009/140177). For comparison: the native ligand TWEAK binds TWEAKR with a $K_D$ value of 0.8-2.4 nM (Immunity. 2001 November; 15(5):837-46; Biochem J. 2006 Jul. 15; 397(2): 297-304; Arterioscler Thromb Vasc Biol. 2003 Apr. 1; 23(4): 594-600).

As a result, it can be recorded that the antibodies of the invention (TPP-883, TPP-1538, TPP-2077, TPP-2084, TPP-2148, TPP-2093, TPP-2149 and TPP-2090) bind TWEAKR with moderate affinity ($K_D$ 10-200 nM).

Figure 2:
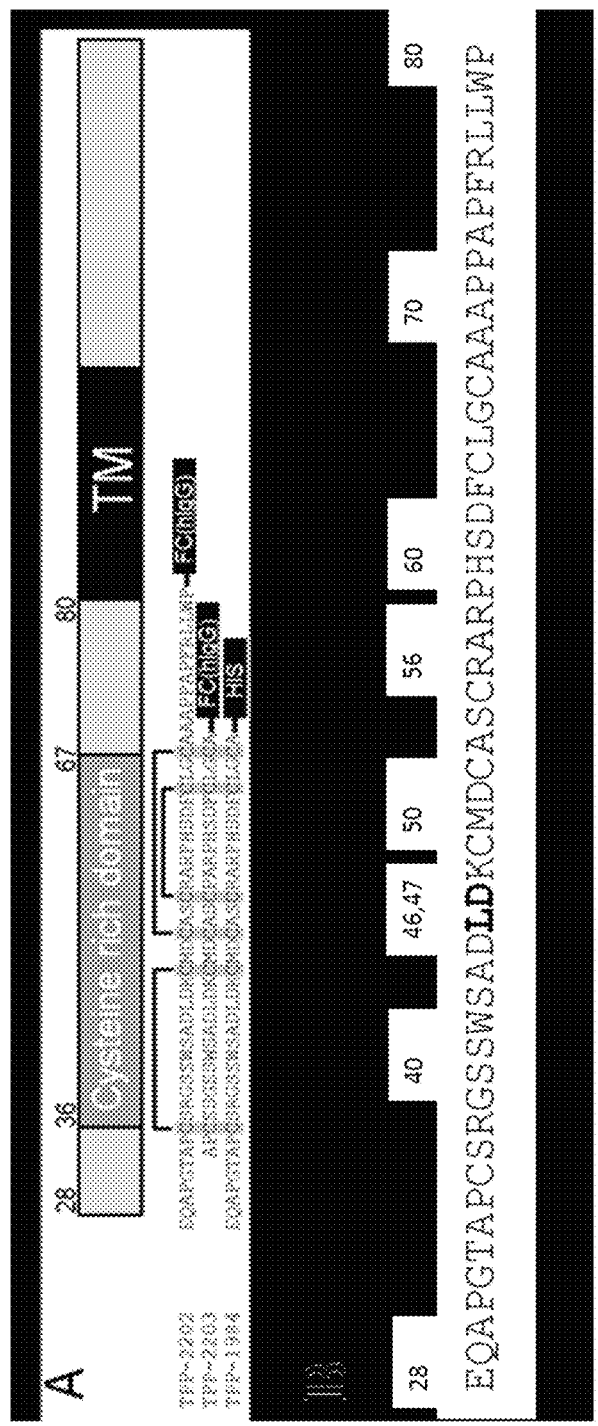
FIG. 2: A—Schematic diagram of the structure of TWEAKR (SEQ ID NO: 169). The diagram shows the extracellular domain (amino acids 28-80) (SEQ ID NO: 168) including the cysteine-rich domain (36-67), the transmembrane domain—TM (81-101) and the intracellular domain (102-129). TPP-2202—the complete ectodomain (28-80), fused to the Fc domain of hIgG1. TPP-2203—extracellular domain with N- and C-terminal truncation (34-68), fused to the Fc domain of hIgG1. Disulphide bridges Cys36-Cys49, Cys52-Cys67 and Cys55-Cys64 are indicated by black bars. N-terminally and C-terminally, TPP-2203 contains two amino acids more and one amino acid more, respectively, than the unmodified cysteine-rich domain to ensure proper folding. TPP-1984— extracellular domain having C-terminal truncation (28-68), fused to an HIS6 tag. All three constructs show comparable binding to the antibodies according to the invention and PDL-192 (TPP-1104). P4A8 (TPP-1324) binds only to the full-length extracellular domain (TPP-2202).

Characterization of the Binding Epitope of TPP-2090 Using N- and C-Terminally Truncated Variants of the TWEAKR Ectodomain:

The alignment of the cysteine-rich domain of TWEAKR (amino acids 34-68) of different species (FIG. 1—Alignment) shows that it is well conserved in all 6 species analysed. PDL-192 binds depending on R56 (WO2009/020933: FIG. 2B) and does therefore not bind to rat, pig and mouse TWEAKR. TPP-2090 binds depending on the conserved amino acid D47, and therefore binds to all species shown.

In a first approach to characterizing the binding epitope of the antibodies mentioned above, a N- and C-terminally truncated mutant of the TWEAKR ectodomain was generated and examined for its ability to bind the various anti-TWEAKR antibodies. Amino acids 28 to 33 were deleted N-terminally and amino acids 69 to 80 were deleted C-terminally, such that the cysteine-rich domains with disulphide bridges between Cys36-Cys49, Cys52-Cys67 and Cys55-Cys64 remained intact (compare FIG. 2). Both constructs, the full ectodomain 28-80 including N- and C-terminus and the truncated ectodomain 34-68, were expressed and purified as Fc fusion proteins TPP-2202 and TPP-2203, respectively.

To analyse the binding, 1 µg/ml of the corresponding dimeric TWEAKR Fc construct was coated, and 0.3 µg/ml and 0.08 µg/ml of biotinylated IgG were used as soluble binding partner. Detection was carried out using streptavidin-HRP and Amplex Red substrate. IgGs were biotinylated using an about 2-fold molar excess of biotin-LC-NHS (Pierce; Cat. No. 21347) according to the instructions of the manufacturer and desalted using Zeba desalting columns (Pierce; Cat. No. 89889). At all concentrations used of the soluble ligand, the antibodies of the present invention displayed saturated binding to both constructs, whereas the antibodies P4A8(TPP-1324), P3G5(TPP-2195) and Item-4 showed saturated binding only to the full-length ectodomain, but worsened binding to the N- and C-terminally truncated constructs (FIG. 3 & FIG. 4). This shows that the binding epitope of the antibodies of the present invention is located in the cysteine-rich domain between amino acids 34-68. To analyse whether the N-terminus or the C-terminus of the TWEAKR ectodomain is required for P4A8(TPP-1324) and P3G5(TPP-2195) binding, a monomeric ectodomain having the C-terminal deletion of amino acids 69 to 80 was generated. Binding of P4A8(TPP-1324) and P3G5 (TPP-2195) to the C-terminally truncated TWEAKR ectodomain is likewise worsened, whereas the antibodies of the present invention show saturated binding (FIG. 5).

TABLE AK-9

List of recombinant antigens used in the ELISA analysis for epitope profiling

| Nomenclature | Description | SEQ ID NO |
|---|---|---|
| TPP-2202 | TWEAKR-ECD-28-80-hIgGFc-His | 139 |
| TPP-2203 | TWEAKR-ECD-34-68-hIgGFc-His | 140 |
| TPP-1984 | hTNFRSF12 amino acids 28-68-CT-His | 141 |

TABLE AK-10

List of antibodies used in the ELISA analysis for epitope profiling

|  |  | SEQ ID NO | |
|---|---|---|---|
| Nomenclature | Description | Light chain | Heavy chain |
| P3G5(TPP-2195) | murine IgG2a | 121 | 122 |
| P4A8(TPP-1324) | human IgG1 | 125 | 126 |
| 136.1(TPP-2194) | murine IgG2a | 123 | 124 |
| PDL-192(TPP-1104) | human IgG1 | 127 | 128 |
| TPP 2090 | human IgG1 | 1 | 2 |
| TPP-2084 | human IgG1 | 41 | 42 |

Thus, the binding epitope of TPP-2090, TPP-2084, PDL-192(TPP-1104) and 136.1(TPP-2194) in the cysteine-rich domain and the binding epitope of P4A8(TPP-1324) and P3G5(TPP-2195) are located at least partially outside of the cysteine-rich domain Effect of TWEAKR-Fc Muteins on the Antibody Affinity To examine the binding characteristics of the antibodies of the invention in more detail, certain muteins of TWEAKR suggested to be of relevance for the activity of known agonistic antibodies (WO2009/140177) were investigated.

To this end, the full-length ectodomain (amino acids 28-80) having the individual amino acid substitutions below were expressed and purified as Fc fusion proteins: T33Q; S40R; W42A; M50A; R56P; H60K; L65Q.

TABLE AK-11

List of recombinant proteins used in the ELISA analysis for mutein binding

| Nomenclature | Description | SEQ ID NO |
|---|---|---|
| TPP-1990 | hTNFRSF12 amino acids a28-80-L65Q-hIgG1-Fc | 142 |
| TPP-1989 | hTNFRSF12 amino acids a28-80-H60K-hIgG1-Fc | 143 |
| TPP-2683 | hTNFRSF12 amino acids a28-80-R56P-hIgG1-Fc | 144 |
| TPP-1988 | hTNFRSF12 amino acids a28-80-M50A-hIgG1-Fc | 145 |
| TPP-1985 | hTNFRSF12 amino acids a28-80-W42A-hIgG1-Fc | 146 |
| TPP-1987 | hTNFRSF12 amino acids a28-80-S40R-hIgG1-Fc | 147 |
| TPP-1986 | hTNFRSF12 amino acids a28-80-T33Q-hIgG1-Fc | 148 |
| TPP-599 | hTNFRSF12 amino acids a28-80-hIgG1-Fc | 138 |

To obtain dose-reaction data, the different TWEAKR-Fc muteins were coated at a low concentration (62 ng/ml) onto a 384-well Maxisorb ELISA plate, and a serial 2-fold dilution of biotinylated IgG beginning with a concentration of 100 nM was used as a soluble binding partner. Detection was carried out using streptavidin-HRP and Amplex Red. The IgGs examined were TPP-2090 and TPP-2084 of the present invention, PDL-192, 136.1 and 18.3.3 of WO2009/020933, P4A8 and P3G5 of WO2009/140177, and ITEM-1 and ITEM-4 of Nakayama et al [Biochem Biophys Res Corn 306: 819-825].

TABLE AK-12

List of antibodies used in the ELISA analysis for mutein binding

| | | SEQ ID NO | |
|---|---|---|---|
| Nomenclature | Description | Light chain | Heavy chain |
| P3G5(TPP-2195) | murine IgG2a | 121 | 122 |
| P4A8(TPP-1324) | human IgG1 | 125 | 126 |
| 136.1(TPP-2194) | murine IgG2a | 123 | 124 |
| PDL-192(TPP-1104) | human IgG1 | 127 | 128 |
| 18.3.3(TPP-2193) | murine IgG2a | 129 | 130 |
| TPP 2090 | human IgG1 | 1 | 2 |
| TPP-2084 | human IgG1 | 41 | 42 |

TABLE AK-13

List of commercially available antibodies used in the ELISA for mutein binding

| Nomenclature | Description | Cat. No. (Abcam) |
|---|---|---|
| ITEM-1 | murine IgG1 | ab21359 |
| ITEM-4 | murine IgG1 | ab21127 |

IgGs were biotinylated using an about 2-fold molar excess of biotin-LC-NHS (Pierce; Cat. No. 21347) according to the instructions of the manufacturer and desalted using Zeba desalting columns (Pierce; Cat. No. 89889). The dose-reaction data were fitted and the IC50s were determined. To illustrate the results, a table was generated; "−" marks IC50s over 50 nM, "+" marks IC50s in the range from 1 to 150 pM.

TABLE AK-14

Effect of muteins on antibody binding

| | T33Q | S40R | W42A | M50A | R56P | H60K | L65Q | WT |
|---|---|---|---|---|---|---|---|---|
| TPP-2084 | + | + | − | + | + | + | + | + |
| TPP-2090 | + | + | − | + | + | + | + | + |
| PDL-192 (TPP-1104) | + | + | − | + | − | + | + | + |
| 136.1 (TPP-2194) | + | + | − | + | − | + | + | + |
| 18.3.3 (TPP-2193) | + | + | − | + | − | + | + | + |
| P4A8 (TPP-1324) | + | + | − | + | + | + | + | + |
| P3G5 (TPP-2195) | + | + | − | + | + | + | + | + |
| ITEM1 | + | + | | + | − | + | + | + |
| ITEM4 | + | + | − | + | + | − | + | + |

As already published, ITEM-4 shows worsened binding to the H60K mutein [WO2009/140177: FIG. 23F] and PDL-192 to the R56P mutein [WO2009/020933: FIG. 22B]. In contrast to published data, ITEM-1 shows worsened binding to R56P, and all antibodies to W42A [WO2009/140177: FIG. 23E, FIG. 23F]. These differences can be explained by the methods chosen.

In contrast to ITEM-1, ITEM-4, PDL-192, 136.1 and 18.3.3, the antibodies of the present invention bind independently of all substitutions except for W42A.

Alanine Scan of the Cysteine-Rich Domain:

An alanine scan of the cysteine-rich domain (amino acids 34-68) was carried out in order to locate the binding site of the antibodies of the invention. FIG. 6 shows that N- and C-terminally truncated variants of the full-length ectodomain of TWEAKR do not worsen binding of the antibodies of the invention. Accordingly, the binding epitope is located in the cysteine-rich domain. The substitutions below were introduced into the TWEAKR(34-68) Fc construct: S37A, R38A, S40A, S41A, W42A, S43A, D45A, D47A, K48A, D51A, S54A, R56A, R58A, P59A, H60A, S61A, D62A, F63A and L65A.

TABLE AK-15

List of TWEAKR mutein constructs for the alanine scan of the cysteine-rich domain

| Nomenclature | Description | SEQ ID NO |
|---|---|---|
| TPP-2203 | TweakR-ECD-34-68-hIgGFc-His | 140 |
| TPP-2625 | TweakR-ECD-34-68-hIgGFc-His-L65A | 149 |
| TPP-2624 | TweakR-ECD-34-68-hIgGFc-His-F63A | 150 |
| TPP-2623 | TweakR-ECD-34-68-hIgGFc-His-D62A | 151 |
| TPP-2622 | TweakR-ECD-34-68-hIgGFc-His-S61A | 152 |
| TPP-2621 | TweakR-ECD-34-68-hIgGFc-His-H60A | 153 |
| TPP-2620 | TweakR-ECD-34-68-hIgGFc-His-P59A | 154 |
| TPP-2619 | TweakR-ECD-34-68-hIgGFc-His-R58A | 155 |
| TPP-2618 | TweakR-ECD-34-68-hIgGFc-His-R56A | 156 |
| TPP-2617 | TweakR-ECD-34-68-hIgGFc-His-S54A | 157 |
| TPP-2616 | TweakR-ECD-34-68-hIgGFc-His-D51A | 158 |
| TPP-2615 | TweakR-ECD-34-68-hIgGFc-His-K48A | 159 |
| TPP-2614 | TweakR-ECD-34-68-hIgGFc-His-D47A | 160 |
| TPP-2613 | TweakR-ECD-34-68-hIgGFc-His-D45A | 161 |
| TPP-2612 | TweakR-ECD-34-68-hIgGFc-His-S43A | 162 |
| TPP-2611 | TweakR-ECD-34-68-hIgGFc-His-W42A | 163 |

TABLE AK-15-continued

List of TWEAKR mutein constructs for the alanine scan of the cysteine-rich domain

| Nomenclature | Description | SEQ ID NO |
|---|---|---|
| TPP-2610 | TweakR-ECD-34-68-hIgGFc-His-S41A | 164 |
| TPP-2609 | TweakR-ECD-34-68-hIgGFc-His-S40A | 165 |
| TPP-2608 | TweakR-ECD-34-68-hIgGFc-His-R38A | 166 |
| TPP-2607 | TweakR-ECD-34-68-hIgGFc-His-S37A | 167 |

These TWEAKR(34-68) Fc muteins were expressed in HEK293 cells. To obtain dose-reaction data, IgGs were coated at a concentration of 1 µg/ml onto a 384-well Maxisorp ELISA plate, and a serial 2-fold dilution of the supernatant comprising the TWEAKR mutein was used as soluble binding partner. Detection was carried out using anti-HIS-HRP and Amplex Red. The IgGs examined were TPP-2090 of the present invention, PDL-192 of WO2009/020933 and P4A8 of WO2009/140177.

TABLE AK-16

List of antibodies used for the alanine scan of the cysteine-rich domain

| | | SEQ ID NO | |
|---|---|---|---|
| Nomenclature | Description | Light chain | Heavy chain |
| P4A8(TPP-1324) | human IgG1 | 125 | 126 |
| PDL-192(TPP-1104) | human IgG1 | 127 | 128 |
| TPP 2090 | human IgG1 | 1 | 2 |

To assess the relevance of the TWEAKR mutein for binding to various IgGs, a correlation blot at a certain mutein concentration was prepared. By way of example, FIG. 6 shows the correlation blots for the 8-fold diluted supernatants of the TWEAKR expression broth, with PDL-192 (TPP-1104) on the X axis and TPP-2090 on the Y axis. The blot shows that binding of TPP-2090 was worsened by substitution D47A, and binding of PDL-192(TPP-1104) was worsened by substitution R56A. Binding to P4A8(TPP-1324) was demonstrated for none of the constructs, which agrees with the results obtained above (FIG. 6). Thus, the P4A8 epitope is localized at least partially outside of the cysteine-rich domain. The dependencies identified for certain TWEAKR amino acids for antibody interaction correlates with the agonistic activity determined for these antibodies. The native ligand TWEAK shows an effective activation of the TWEAKR and binds depending on leucine 46 in the cysteine-rich domain of TWEAKR (Pellegrini et al, FEBS 280:1818-1829). P4A8 displays a very low agonistic activity and interacts at least partially with domains outside of the cysteine-rich domain of TWEAKR. PDL-192 displays a moderate agonistic activity and binds depending on R56 to the cysteine-rich domain, but opposite the TWEAK ligand site. TPP-2090 and TWEAK binding depends on D47 and L46, respectively, and they therefore bind to a similar binding site (FIG. 7).

It can be concluded the the antibodies of the invention (e.g. TPP-2090) bind to TWEAKR in a manner depending on D47.

The dependencies identified for certain TWEAKR amino acids for antibody interaction correlates with the agonistic activity determined for these antibodies. The native ligand TWEAK shows an effective activation of the TWEAKR and binds depending on leucine 46 in the cysteine-rich domain of TWEAKR (Pellegrini et al, FEBS 280:1818-1829). P4A8 displays a very low agonistic activity and interacts at least partially with domains outside of the cysteine-rich domain of TWEAKR. PDL-192 displays a moderate agonistic activity and binds depending on R56 to the cysteine-rich domain, but opposite the TWEAK ligand site. Antibodies of the present invention (Example TPP-2090) bind in a manner depending on D47, and TWEAK binds in a manner depending on L46, and binds to a similar, but distinct, binding site (FIG. 7). Accordingly, the antibodies of the present invention displaying strong agonistic activity bind to a novel epitope (D47-dependent) for antibodies associated with very high agonistic activity. It is interesting to note that Michaelson et al. (see page 369, left column in Michaelson J S et al, MAbs. 2011 July-August; 3(4):362-75) gave an explanation for the fact that all agonistic antibodies examined by them have weaker agonistic activity than the natural ligand TWEAK. They conclude that reduced efficacy could be a function of the dimeric binding interaction of the antibodies with TWEAKR, with TWEAK probably entering into a trimeric interaction. It is therefore a surprising result that an antibody of the invention, in spite of its dimeric interaction with TWEAKR, has an even higher agonistic activity. This surprising activity is linked to the specific binding properties of the antibodies of the invention, i.e. the specific binding to D47 of TWEAKR.

Further Embodiments

1. Conjugate of a binder or derivative thereof with one or more active compound molecules, the active compound molecule being a kinesin spindle protein inhibitor attached to the binder via a linker L.
2. Conjugate according to Item 1 where the binder or derivative thereof is a binder peptide or protein or a derivative of a binder peptide or protein.
3. Conjugate according to Item 2 where each active compound molecule is attached to different amino acids of the binder peptide or protein or derivative thereof via the linker
4. Conjugate according to one or more of the preceding items where the conjugate has on average 1.2 to 20 active compound molecules per binder.
5. Conjugate according to one or more of Items 2 to 4 where the binder peptide or protein represents an antibody or the derivative of the binder peptide or protein

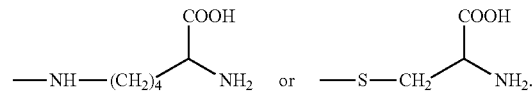

6. Conjugate according to one or more of the preceding items where the binder binds to a cancer target molecule.
7. Conjugate according to Item 6 where the binder binds to an extracellular target molecule.
8. Conjugate according to Item 7 where the binder, after binding to the extracellular target molecule, is internalized and processed intracellularly (preferably lysosomally) by the cell expressing the target molecule.
9. Conjugate according to one or more of Items 2 to 8 where the binder peptide or protein is a human, humanized or chimeric monoclonal antibody or an antigen-binding fragment thereof.

10. Conjugate according to Item 9 where the binder peptide or protein is an anti-HER2 antibody, an anti-EGFR antibody, an anti-TWEAKR antibody or an antigen-binding fragment thereof.

11. Conjugate according to Item 10 where the anti-TWEAKR antibody binds specifically to amino acid D in position 47 (D47) of TWEAKR (SEQ ID NO:169), preferably the anti-TWEAKR antibody TPP-2090.

12. Conjugate according to one or more of the preceding items where the kinesin spindle protein inhibitor has the substructure below:

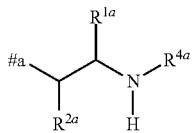

where a represents a bond to the remainder of the molecule;

$R^{1a}$ represents H or —$(CH_2)_{0-3}$Z, where Z represents —H, —$OY^3$, —$SY^3$, —$NHY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}$Z' or —CH($CH_2$W)Z', and $Y^3$ represents H or —$(CH_2)_{0-3}$Z', where Z' represents H, $SO_3H$, $NH_2$, COOH, —NH—CO—$CH_2$—$CH_2$—CH($NH_2$)COOH or —(CO—NH—$CHY^4$)$_{1-3}$COOH, where W represents H or OH, where $Y^4$ independently of one another represents straight-chain or branched $C_{1-6}$-alkyl which is optionally substituted by —$NHCONH_2$, or represents aryl or benzyl which are optionally substituted by —$NH_2$;

$R^{2a}$ and $R^{4a}$ independently of one another represent H, —CO—$CHY^4$—$NHY^5$ or —$(CH_2)_{0-3}$Z, or $R^{2a}$ and $R^{4a}$ together (with formation of a pyrrolidine ring) represent —$CH_2$—$CHR^{10}$— or —$CHR^{10}$—$CH_2$—, where $R^{10}$ represents H, $NH_2$, COOH, $SO_3H$, SH or OH, where Z represents —H, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;

where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

where the kinesin spindle protein inhibitor is attached to the linker by substitution of a hydrogen atom at $R^{1a}$, $R^{2a}$, $R^{4a}$ or at the pyrrolidine ring formed by $R^{2a}$ and $R^{4a}$, and the salts, solvates and salts of the solvates thereof.

13. Conjugate according to one or more of the preceding items where the kinesin spindle protein inhibitor is represented by general formula (I):

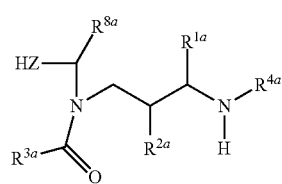

where $R^{1a}$ represents H or —$(CH_2)_{0-3}$Z, where Z represents —H, —$OY^3$, —$SY^3$, —$NHY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}$Z' or —CH($CH_2$W)Z', and $Y^3$ represents H or —$(CH_2)_{0-3}$Z', where Z' represents H, $SO_3H$, $NH_2$, COOH, —NH—CO—$CH_2$—$CH_2$—CH($NH_2$)COOH or —(CO—NH—$CHY^4$)$_{1-3}$COOH, where W represents H or OH, where $Y^4$ independently of one another represents straight-chain or branched $C_{1-6}$-alkyl which is optionally substituted by —$NHCONH_2$, or represents aryl or benzyl which are optionally substituted by —$NH_2$;

$R^{2a}$ and $R^{4a}$ independently of one another represent H, —CO—$CHY^4$—$NHY^5$ or —$(CH_2)_{0-3}$Z, or $R^{2a}$ and $R^{4a}$ together (with formation of a pyrrolidine ring) represent —$CH_2$—$CHR^{10}$— or —$CHR^{10}$—$CH_2$—, where $R^{10}$ represents H, $SO_3H$, $NH_2$, COOH, SH or OH, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;

where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^{3a}$ represents an optionally substituted alkyl, aryl, heteroaryl, heteroalkyl or heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl- or $C_{5-10}$-heterocycloalkyl group, which may be substituted by 1-3 —OH groups, 1-3 halogen atoms, 1-3 halogenated alkyl groups (which may each have 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —$(CH_2)_{0-3}$Z groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}$Z' and $Y^3$ represents H, —$(CH_2)_{0-3}$—CH($NHCOCH_3$)Z', —$(CH_2)_{0-3}$—CH($NH_2$)Z' or —$(CH_2)_{0-3}$Z', where Z' represents H, $SO_3H$, $NH_2$ or COOH (where "alkyl" preferably represents $C_{1-10}$-alkyl);

$R^{8a}$ represents $C_{1-10}$-alkyl;

HZ represents a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen;

where the kinesin spindle protein inhibitor is attached to the linker by substitution of a hydrogen atom at $R^{1a}$, $R^{2a}$, $R^{3a}$, $R^{4a}$, $R^{8a}$ or at the pyrrolidine ring formed by $R^{2a}$ and $R^{4a}$, and the salts, solvates and salts of the solvates thereof.

14. Conjugate according to one or more of the preceding items where the active compound molecule linker is represented by general formula (II):

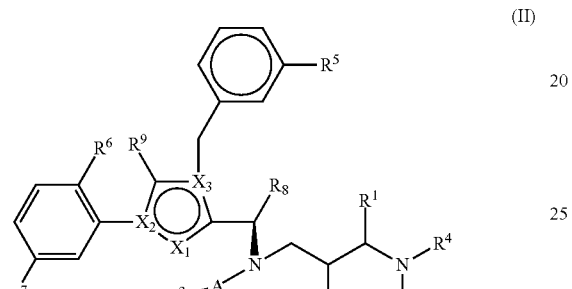

(II)

where $X_1$ represents N, $X_2$ represents N and $X_3$ represents C; or $X_1$ represents N, $X_2$ represents C and $X_3$ represents N; or $X_1$ represents CH, $X_2$ represents C and $X_3$ represents N; or $X_1$ represents NH, $X_2$ represents C and $X_3$ represents C; or $X_1$ represents CH, $X_2$ represents N and $X_3$ represents C $R^1$ represents H, —L-#$^1$ or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH, where Y$^4$ independently of one another represents straight-chain or branched C$_{1-6}$-alkyl which is optionally substituted by —NHCONH$_2$, or represents aryl or benzyl which are optionally substituted by —NH$_2$;

R$^2$ and R$^4$ independently of one another represent —L-#$^1$, H, —CO—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—, where R$^{10}$ represents L-#$^1$, H, NH$_2$, SO$_3$H, COOH, SH or OH, where Z represents —H, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

A represents CO, SO, SO$_2$, SO$_2$NH or CNNH;

R$^3$ represents —L-#$^1$ or an optionally substituted alkyl, aryl, heteroaryl, heteroalkyl or heterocycloalkyl group, preferably —L-#$^1$ or a C$_{1-10}$-alkyl, C$_{6-10}$-aryl, C$_{6-10}$-aralkyl, C$_{5-10}$-heteroalkyl, C$_{1-10}$-alkyl-O—C$_{6-10}$-aryl- or C$_{5-10}$-heterocycloalkyl group, which may be substituted by 1-3 —OH groups, 1-3 halogen atoms, 1-3 halogenated alkyl groups (which may each have 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

R$^5$ represents —L-#$^1$, H, F, NH$_2$, NO$_2$, halogen, SH or —(CH$_2$)$_{0-3}$Z, where Z represents —H, OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where one of the substituents R$^1$, R$^2$, R$^3$, R$^4$ and R$^5$ represents —L-#$^1$, L represents the linker and #$^1$ represents the bond to the binder or derivative thereof, R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen, R$^8$ represents (optionally fluorinated) C$_{1-10}$-alkyl, (optionally fluorinated) C$_{4-10}$-cycloalkyl or optionally substituted oxetane; and R$^9$ represents H, F, CH$_3$, CF$_3$, CH$_2$F or CHF$_2$;

and the salts, solvates and salts of the solvates thereof.

15. Conjugate according to Item 14 where R$^1$ represents —L-#$^1$, H, —(CH$_2$)$_{0-3}$Z, where Z represents —H, —CO—NY$^1$Y$^2$, NHY$^3$, OY$^3$, —SY$^3$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' or —CH(CH$_2$W)Z', and Y$^3$ represents H or —(CH$_2$)$_{0-3}$Z', where Z' represents H, NH$_2$, COOH, —NH—CO—CH$_2$—CH$_2$—CH(NH$_2$)COOH or —(CO—NH—CHY$^4$)$_{1-3}$COOH, where W represents H or OH, where Y$^4$ independently of one another represents straight-chain or branched C$_{1-6}$-alkyl which is optionally substituted by —NHCONH$_2$, or represents aryl or benzyl which are optionally substituted by —NH$_2$;

R² and R⁴ independently of one another represent
—L-#¹, —CO—CHY⁴—NHY⁵ or H or R² and R⁴
together (with formation of a pyrrolidine ring) represent —CH₂—CHR¹⁰—, where R¹⁰ represents H,
—L-#¹, NH₂, COOH, SH, OH or SO₃H,
where Y⁴ independently of one another represents
straight-chain or branched C₁₋₆ alkyl which is
optionally substituted by —NHCONH₂, or represents aryl or benzyl which are optionally substituted
by —NH₂, and Y⁵ represents H or —CO—CHY⁶—
NH₂, where Y⁶ represents straight-chain or branched
C₁₋₆-alkyl;
A represents CO,
R³ represents —(CH₂)OH or —L-#¹, and
R⁵ represents —L-#¹ or H,
where one of the substituents R¹, R², R³, R⁴ and R⁵
represents —L-#¹.

16. Conjugate according to Item 14 or 15
where R⁶ and R⁷ independently of one another represent H, C₁₋₃-alkyl or halogen.

17. Conjugate according to one or more of Items 14 to 16
where R⁸ represents C₁₋₄-alkyl (preferably tea-butyl).

18. Conjugate according to one or more of Items 14 to 17
where R⁹ represents H.

19. Conjugate according to one or more of Items 14 to 18
where R⁶ and R⁷ represent F.

20. Conjugate according to one or more of the preceding items where the linker -L- has one of the basic structures (i) to (iv) below:
(i) —(CO)ₘ—SG1-L1-L2-
(ii) —(CO)ₘ-L1-SG-L1-L2-
(iii) —(CO)ₘ-L1-L2-
(iv) —(CO)ₘ-L1-SG-L2
where m is 0 or 1, SG and SG1 are in vivo cleavable groups, L1 independently of one another represent organic groups not cleavable in vivo, and L2 represents a coupling group to the binder.

21. Conjugate according to Item 20 where the in vivo cleavable group SG is a 2-8 oligopeptide group, preferably a dipeptide group or a disulphide, a hydrazone, an acetal or an aminal and SG1 is a 2-8 oligopeptide group, preferably a dipeptide group.

22. Conjugate according to one or more of Items 2 to 21
where the linker is attached to a cysteine side chain or a cysteine residue and has the formula below:

§-(CO)ₘ-L1-L2-§§ where
m is 0 or 1;
§ represents the bond to the active compound molecule and
§§ represents the bond to the binder peptide or protein, and
-L2- represents

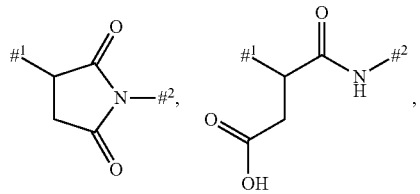

-continued

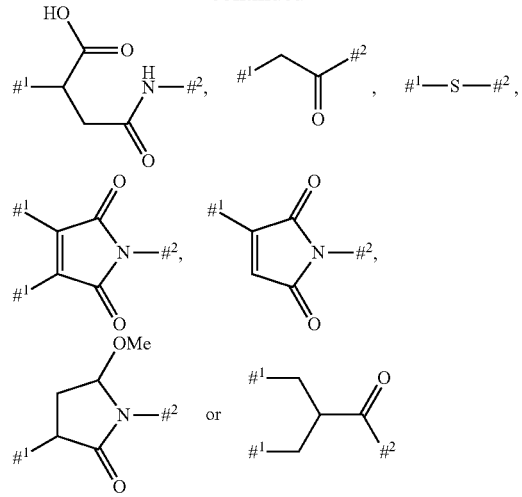

where
¹ denotes the point of attachment to the sulphur atom of the binder,
² denotes the point of attachment to group L1,
L1 represents —(NR¹⁰)ₙ-(G1)ₒ-G2-,
where R¹⁰ represents H, NH₂ or C₁-C₃-alkyl;
G1 represents —NHCO— or

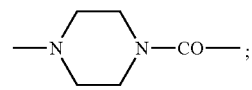

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, —SO₂—, —NH—, —CO—, —NMe—, —NHNH—, —SO₂NHNH—, —NHCO—, —CONH—, —CONHNH— and a 5- to 10-membered aromatic or non-aromatic heterocycle having up to 4 heteroatoms selected from the group consisting of N, O and S, —SO— or —SO₂— (preferably

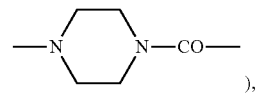

), where the side chains, if present, may be substituted by —NHCONH₂, —COOH, —OH, —NH₂, NH—CNNH₂, sulphonamide, sulphone, sulphoxide or sulphonic acid, or represents one of the groups below:

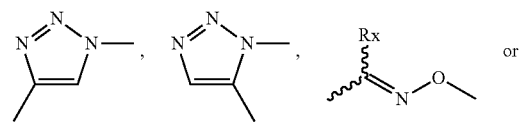

-continued

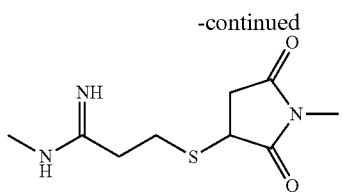

where Rx represents H, $C_1$-$C_3$-alkyl or phenyl.

23. Conjugate according to Item 22 where the hydrocarbon chain is interrupted by one of the groups below:

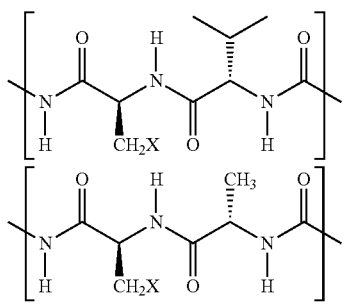

where X represents H or a $C_{1-10}$-alkyl group which may optionally be substituted by —NHCONH$_2$, —COOH, —OH, NH$_2$, —NH—CNNH$_2$, sulphone, sulphoxide or sulphonic acid.

24. Conjugate according to Item 22 where the linker has the formula below:

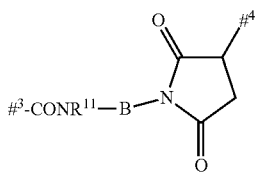

where
$^3$ represents the bond to the active compound molecule,
$^4$ represents the bond to the binder peptide or protein,
$R^{11}$ represents H or NH$_2$;
B represents —[(CH$_2$)$_x$—(X$^4$)$_y$]$_w$—(CH$_2$)$_z$—,
w=0 to 20;
x=0 to 5;
x=0 to 5;
y=0 or 1;
z=0 to 5; and
X$^4$ represents —O—, —CONH— or —NHCO—

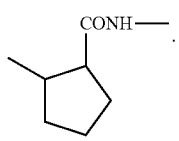

25. Conjugate according to Item 24 where $R^1$ or $R^4$ represents —L-#$^1$.
26. Conjugate according to one or more of Items 21 to 25 where the conjugate has one of the formulae below:

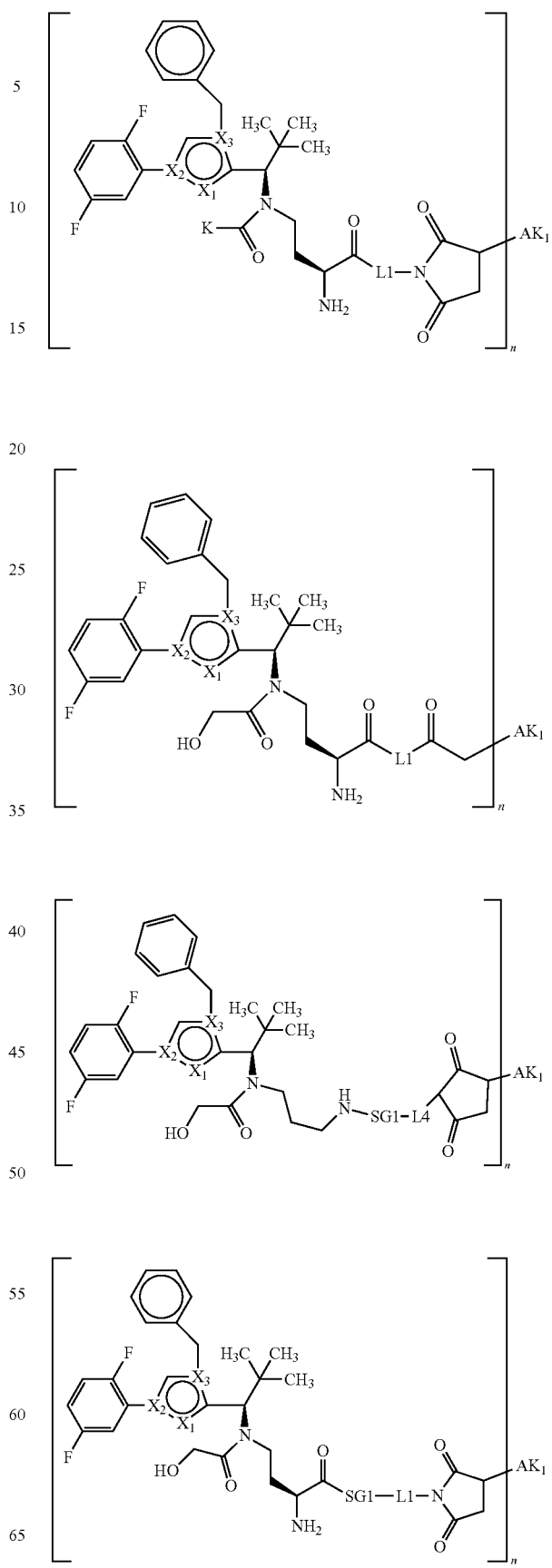

-continued

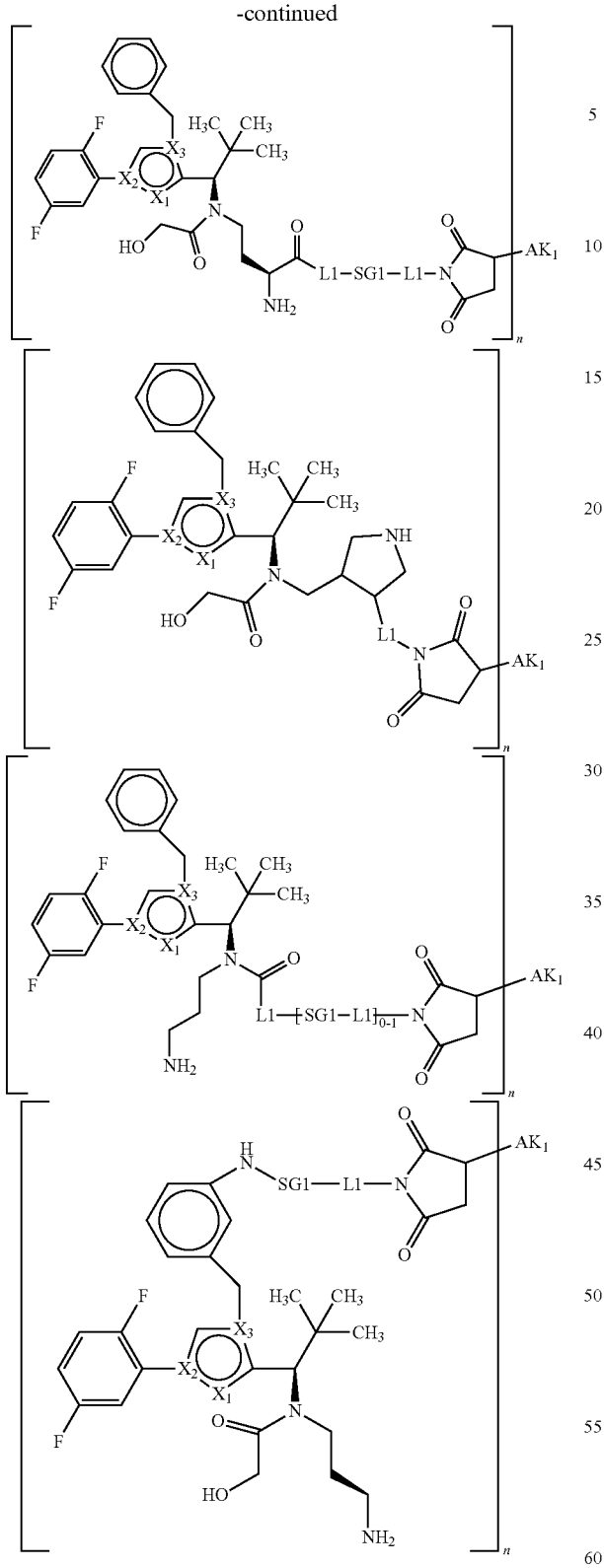

where
X₁, X₂ and X₃ have the same meaning as in Item 14, AK₁ represents a binder peptide or protein which is attached via a sulphur atom of the binder; n represents a number from 1 to 20; and L1 represents an optionally branched hydrocarbon group having 1 to 70 carbon atoms, which represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —CONH—, —NHCO—, —NMe—, —NHNH—, —$SO_2$NHNH—, —CONHNH— and a 5- to 10-membered aromatic or non-aromatic heterocycle having up to 4 heteroatoms selected from the group consisting of N, O and S, or —SO— or —$SO_2$— (preferably

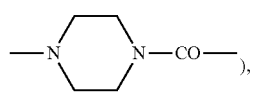

where the side chains, if present, may be substituted by —NHCONH₂, —COOH, —OH, —NH₂, NH—CNNH₂, sulphonamide, sulphone, sulphoxide or sulphonic acid, and SG1 is a 2-8 oligopeptide, preferably a dipeptide; L4 is a single bond or a group —(CO)$_y$-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe—, —NHNH—, —$SO_2$NHNH—, —CONHNH— and a 5- to 10-membered aromatic or non-aromatic heterocycle having up to 4 heteroatoms selected from the group consisting of N, O and S, —SO— or —$SO_2$— (preferably

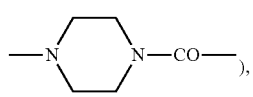

where the side chains, if present, may be substituted by —NHCONH₂, —COOH, —OH, —NH₂, NH—CNNH₂, sulphonamide, sulphone, sulphoxide or sulphonic acid.

27. Conjugate according to one or more of Items 1 to 21 where the linker -L- is attached to a cysteine side chain or a cysteine residue and has the formula below:

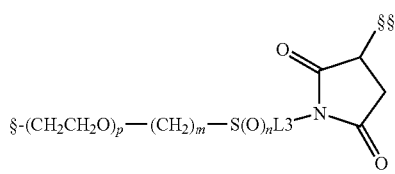

where
§ represents the bond to the active compound molecule and
§§ represents the bond to the binder peptide or protein,
m is 0, 1, 2 or 3;
n is 0, 1 or 2;

p is 0 to 20; and
L3 represents

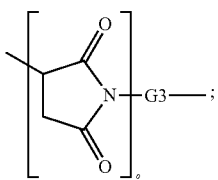

where
o is 0 or 1;
and
G3 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH— and a 5- to 10-membered aromatic or non-aromatic heterocycle having up to 4 heteroatoms selected from the group consisting of N, O and S, —NMe—, —NHNH—, —$SO_2$NHNH—, —CONHNH—, —SO— or —$SO_2$— (preferably

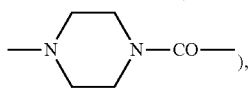

where the side chains, if present, may be substituted by —$NHCONH_2$, —COOH, —OH, sulphone, sulphoxide or sulphonic acid.

28. Conjugate according to Item 27 where the linker -L- is attached to a cysteine side chain or a cysteine residue and has the formula below:

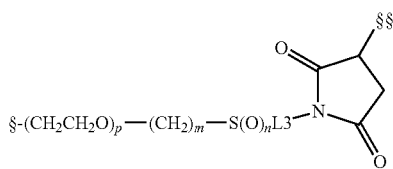

where
§ represents the bond to the active compound molecule and
§§ represents the bond to the binder peptide or protein,
m is 1;
p is 0;
n is 0;
and L3 represents

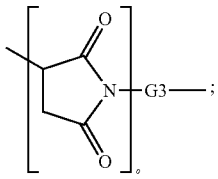

where
o is 0 or 1; and
G3 represents —$(CH_2CH_2O)_s(CH_2)_t(CONH)_u(CH_2CH_2O)_v(CH_2)_w$—, where
s, t, v and w each independently of one another are from 0 to 20 and u is 0 or 1.

29. Conjugate according to Item 27 or 28 where $R^2$ or $R^3$ represents —L-#$^1$.

30. Conjugate according to Item 29 where the conjugate has one of the formulae below:

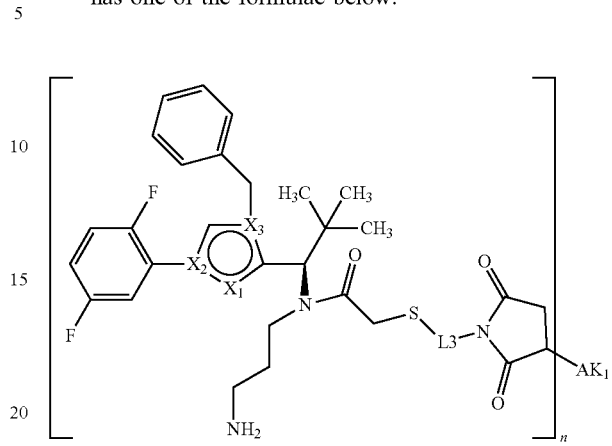

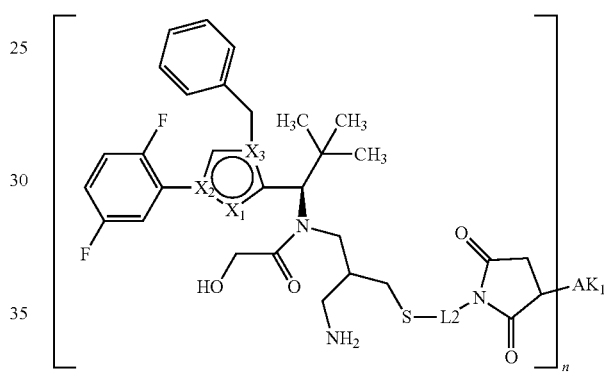

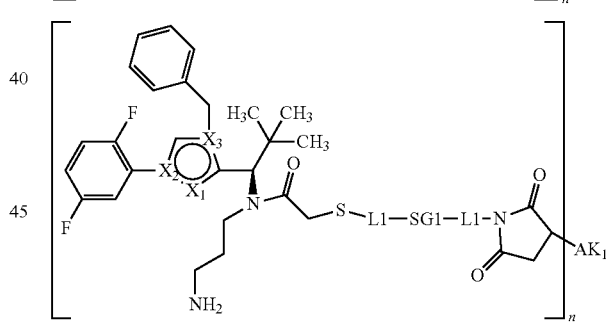

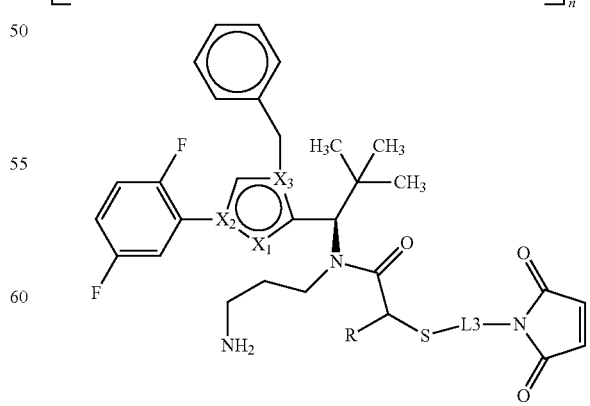

TFA

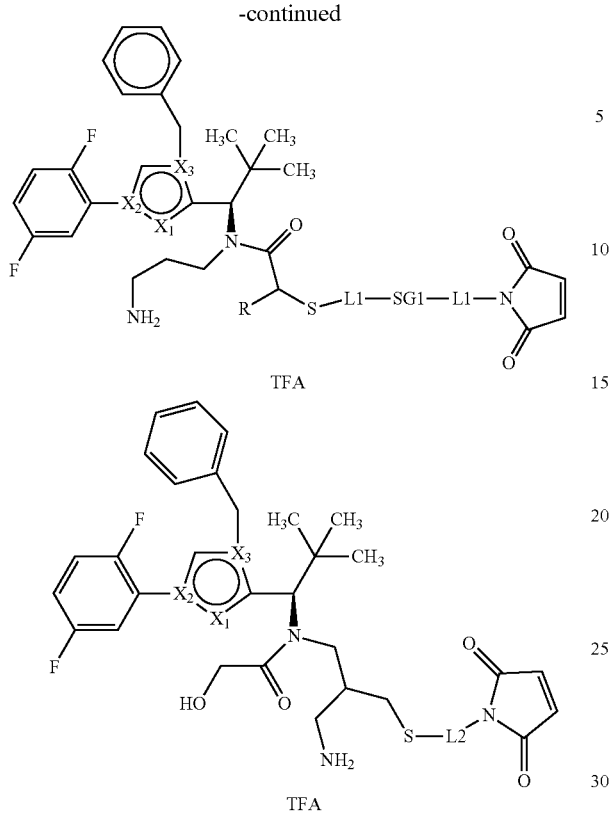

TFA

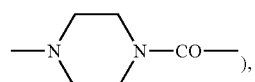

TFA where
$X_1$, $X_2$ and $X_3$ have the same meaning as in Item 14,
AK$_1$ represents a binder peptide or protein which is attached via a sulphur atom of the binder; n represents a number from 1 to 20; and L2 and L3 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NMe—, —NHNH—, —SO$_2$NHNH—, —NHCO—, —CONH—, —CONHNH— and a 5- to 10-membered aromatic or non-aromatic heterocycle having up to 4 heteroatoms selected from the group consisting of N, O and S, —SO— or —SO$_2$— (preferably

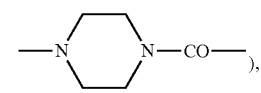

where the side chains, if present, may be substituted by —NHCONH$_2$, —COOH, —OH, —NH$_2$, NH—CNNH$_2$, sulphonamide, sulphone, sulphoxide or sulphonic acid.

31. Conjugate according to one or more of Items 1 to 21 where the linker -L- is attached to a lysine side chain and has the formula below:

-§-(SG)$_x$-L4-CO-§§ where
§ represents the bond to the active compound molecule and
§§ represents the bond to the binder peptide or protein, x represents 0 or 1,
SG represents a cleavable group, preferably a 2-8 oligopeptide, particularly preferably a dipeptide, and
L4 represents a single bond or a group —(CO)$_y$-G4-, where y represents 0 or 1, and
G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe—, —NHNH—, —SO$_2$NHNH—, —CONHNH— and a 5- to 10-membered aromatic or non-aromatic heterocycle having up to 4 heteroatoms selected from the group consisting of N, O and S, or —SO— (preferably

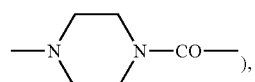

where the side chains, if present, may be substituted by —NHCONH$_2$, —COOH, —OH, —NH$_2$, NH—CNNH$_2$, sulphonamide, sulphone, sulphoxide or sulphonic acid.

32. Conjugate of a binder peptide or protein according to Item 31 where the conjugate has one of the formulae below:

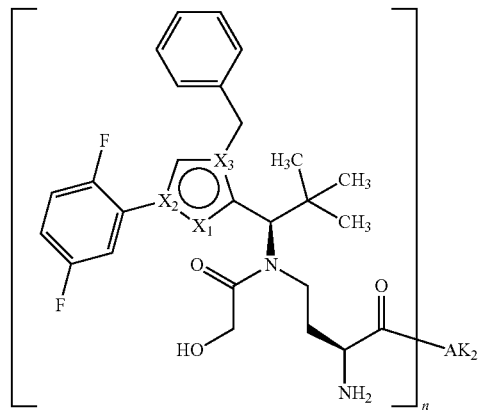

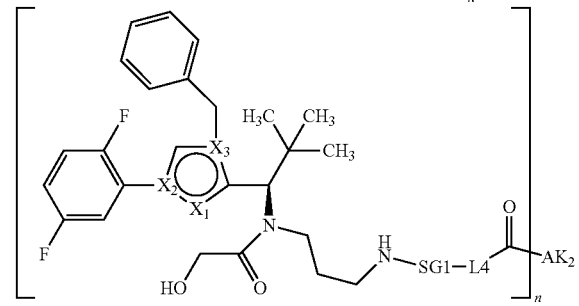

where
$X_1$, $X_2$ and $X_3$ have the same meaning as in Item 14,
AK$_2$ represents a binder peptide or protein which is attached via a sulphur atom of the binder; n represents a number from 1 to 20; and L4 represents an optionally straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NMe—, —NHNH—, —SO₂NHNH—, —NHCO—, —CONH—, —CONHNH— and a 5- to 10-membered aromatic or non-aromatic heterocycle having up to 4 heteroatoms selected from the group consisting of N, O and S, —SO— or —SO₂— (preferably

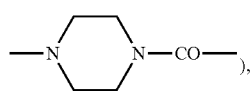

), where the side chains, if present, may be substituted by —NHCONH₂, —COOH, —OH, —NH₂, NH—CNNH₂, sulphonamide, sulphone, sulphoxide or sulphonic acid, and SG1 represents a cleavable group, preferably a 2-8 oligopeptide, particularly preferably a dipeptide.

33. Conjugate according to one or more of Items 10 to 32 where the anti-TWEAKR antibody is an agonistic antibody.

34. Conjugate according to one or more of Items 10 to 33 which comprises:
    a variable heavy chain comprising:
    a. a CDR1 of the heavy chain encoded by an amino acid sequence comprising the formula PYPMX (SEQ ID NO: 171), where X is I or M;
    b. a CDR2 of the heavy chain encoded by an amino acid sequence comprising the formula YISPSGGXTHYADSVKG (SEQ ID NO: 172), where X is S or K; and
    c. a CDR3 of the heavy chain encoded by an amino acid sequence comprising the formula GGDTYFDYFDY (SEQ ID NO: 173);
    and a variable light chain comprising:
    d. a CDR1 of the light chain encoded by an amino acid sequence comprising the formula RASQSISXYLN (SEQ ID NO: 174), where X is G or S;
    e. a CDR2 of the light chain encoded by an amino acid sequence comprising the formula XASSLQS (SEQ ID NO: 175), where X is Q, A or N; and
    f. a CDR3 of the light chain encoded by an amino acid sequence comprising the formula QQSYXXPXIT (SEQ ID NO: 176), where X at position 5 is T or S, X at position 6 is T or S and X at position 8 is G or F.

35. Conjugate according to one or more of Items 10 to 34 which comprises:
    a. a variable sequence of the heavy chain, as shown in SEQ ID NO:10, and also a variable sequence of the light chain, as shown in SEQ ID NO:9, or
    b. a variable sequence of the heavy chain, as shown in SEQ ID NO:20, and also a variable sequence of the light chain, as shown in SEQ ID NO:19, or
    c. a variable sequence of the heavy chain, as shown in SEQ ID NO:30, and also a variable sequence of the light chain, as shown in SEQ ID NO:29, or
    d. a variable sequence of the heavy chain, as shown in SEQ ID NO:40, and also a variable sequence of the light chain, as shown in SEQ ID NO:39, or
    e. a variable sequence of the heavy chain, as shown in SEQ ID NO:50, and also a variable sequence of the light chain, as shown in SEQ ID NO:49, or
    f. a variable sequence of the heavy chain, as shown in SEQ ID NO:60, and also a variable sequence of the light chain, as shown in SEQ ID NO:59, or
    g. a variable sequence of the heavy chain, as shown in SEQ ID NO:70, and also a variable sequence of the light chain, as shown in SEQ ID NO:69, or
    h. a variable sequence of the heavy chain, as shown in SEQ ID NO:80, and also a variable sequence of the light chain, as shown in SEQ ID NO:79, or
    i. a variable sequence of the heavy chain, as shown in SEQ ID NO:90, and also a variable sequence of the light chain, as shown in SEQ ID NO:89, or
    j. a variable sequence of the heavy chain, as shown in SEQ ID NO:100, and also a variable sequence of the light chain, as shown in SEQ ID NO:99, or
    k. a variable sequence of the heavy chain, as shown in SEQ ID NO:110, and also a variable sequence of the light chain, as shown in SEQ ID NO:109, or
    l. a variable sequence of the heavy chain, as shown in SEQ ID NO:120, and also a variable sequence of the light chain, as shown in SEQ ID NO:119.

36. Conjugate according to one or more of Items 10 to 35 where the antibody is an IgG antibody.

37. Conjugate according to one or more of Items 10 to 36 which comprises:
    a. a sequence of the heavy chain, as shown in SEQ ID NO:2, and also a sequence of the light chain, as shown in SEQ ID NO:1, or
    b. a sequence of the heavy chain, as shown in SEQ ID NO:12, and also a sequence of the light chain, as shown in SEQ ID NO:11, or
    c. a sequence of the heavy chain, as shown in SEQ ID NO:22, and also a sequence of the light chain, as shown in SEQ ID NO:21, or
    d. a sequence of the heavy chain, as shown in SEQ ID NO:32, and also a sequence of the light chain, as shown in SEQ ID NO:31, or
    e. a sequence of the heavy chain, as shown in SEQ ID NO:42, and also a sequence of the light chain, as shown in SEQ ID NO:41, or
    f. a sequence of the heavy chain, as shown in SEQ ID NO:52, and also a sequence of the light chain, as shown in SEQ ID NO:51, or
    g. a sequence of the heavy chain, as shown in SEQ ID NO:62, and also a sequence of the light chain, as shown in SEQ ID NO:61, or
    h. a sequence of the heavy chain, as shown in SEQ ID NO:72, and also a sequence of the light chain, as shown in SEQ ID NO:71, or
    i. a sequence of the heavy chain, as shown in SEQ ID NO:82, and also a sequence of the light chain, as shown in SEQ ID NO:81, or
    j. a sequence of the heavy chain, as shown in SEQ ID NO:92, and also a sequence of the light chain, as shown in SEQ ID NO:91, or
    k. a sequence of the heavy chain, as shown in SEQ ID NO:102, and also a sequence of the light chain, as shown in SEQ ID NO:101, or
    l. a sequence of the heavy chain, as shown in SEQ ID NO:112, and also a sequence of the light chain, as shown in SEQ ID NO:111.

38. Spindle conjugate according to one or more of the preceding Items where the conjugate has 1 to 10, preferably 2 to 8 active compound molecules per binder peptide or protein.

39. Process for preparing the conjugate according to Item 26 or 30 where a compound of one of the formulae below, preferably in the form of its trifluoroacetic acid salt, is attached to a cysteine residue of a binder peptide or protein which is optionally partially reduced beforehand, where the compound is preferably employed in a 2- to 12-fold molar excess with respect to the binder peptide or protein:

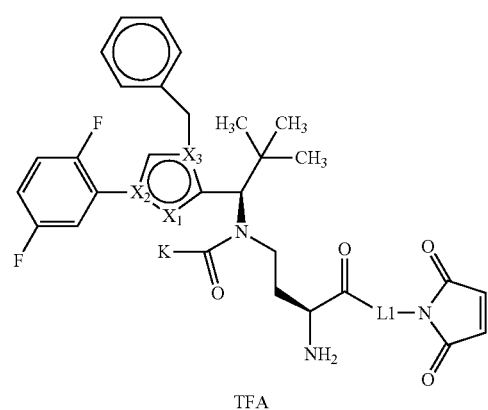

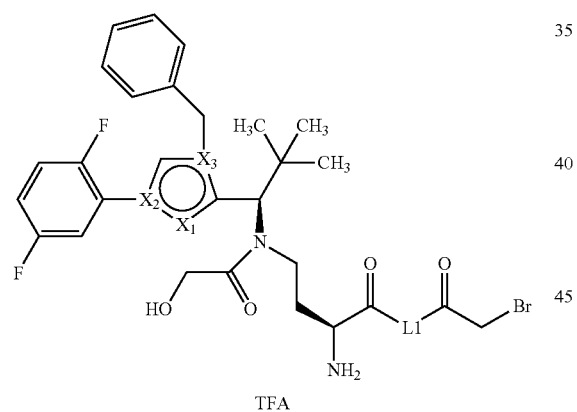

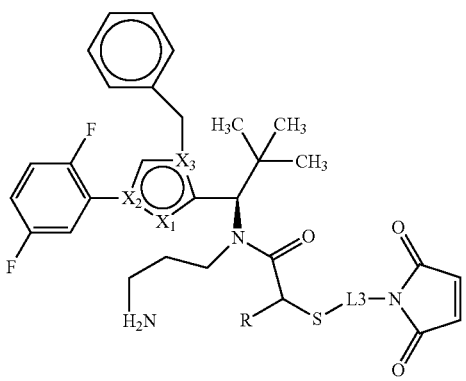

-continued

861
-continued

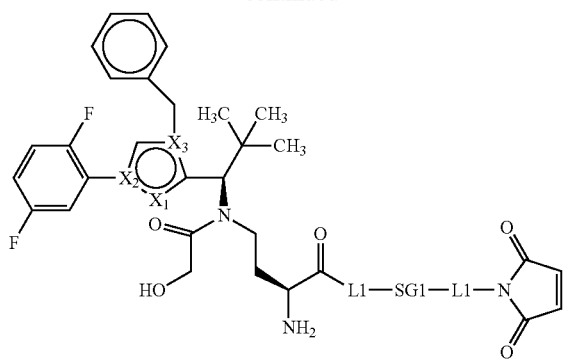

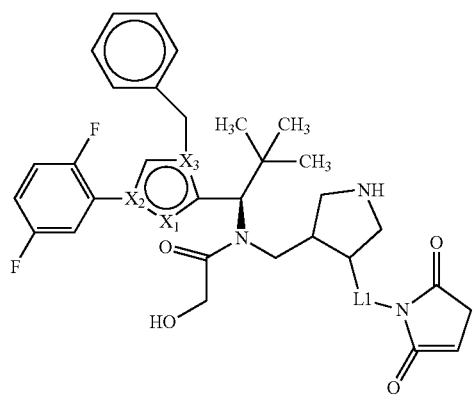

TFA

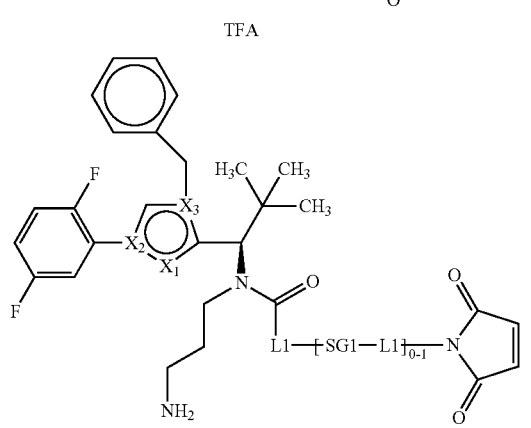

TFA

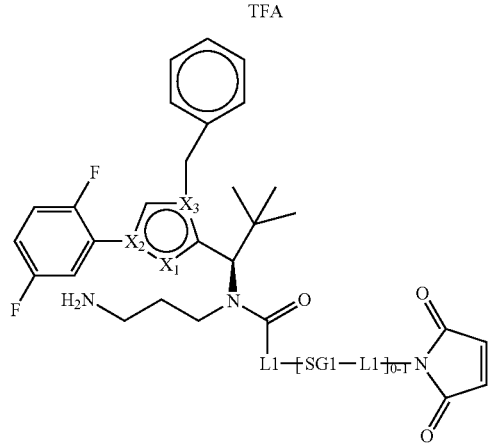

TFA

862
-continued

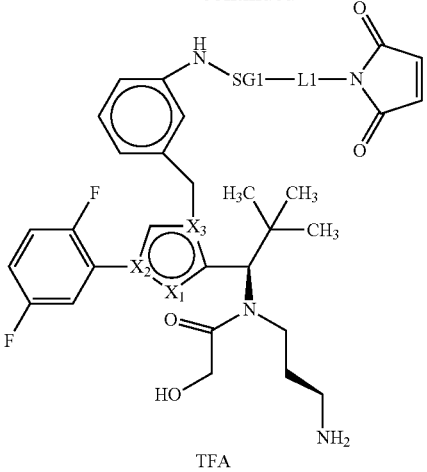

TFA where R represents —H or —COOH,
where K represents straight-chain or branched optionally substituted by $C_1$-$C_6$-alkoxy or —OH—$C_1$-$C_6$-alkyl, and
where $X_1$, $X_2$, $X_3$, SG1, L1, L2, L3 and L4 have the same meaning as in Item 26 or 30.

40. Process for preparing the conjugate according to Item 32 where a compound of one of the formulae below, preferably in the form of its trifluoroacetic acid salt, is attached to a lysine residue of a binder peptide or protein, where the compound is preferably employed in a 2- to 12-fold molar excess with respect to the binder peptide or protein:

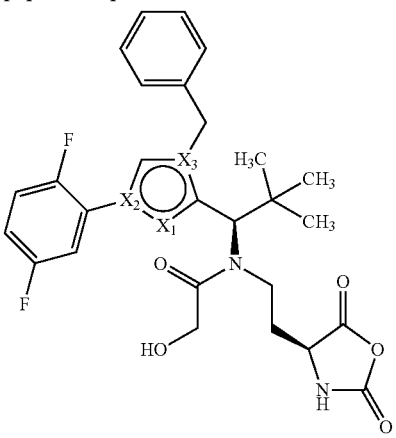

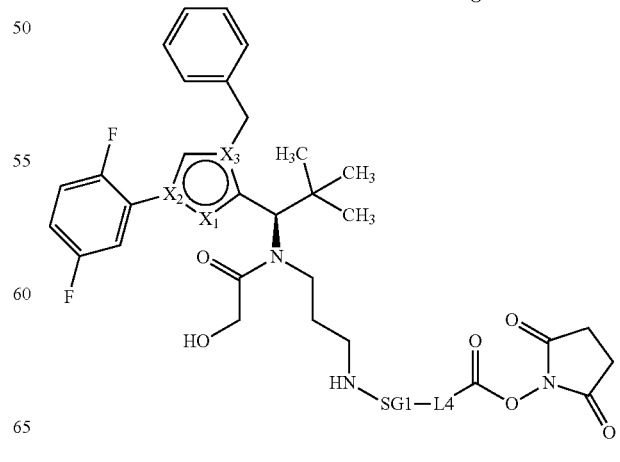

where $X_1$, $X_2$, $X_3$, SG1 and L4 have the same meaning as in Item 32.
41. Compound of one of the formulae below:
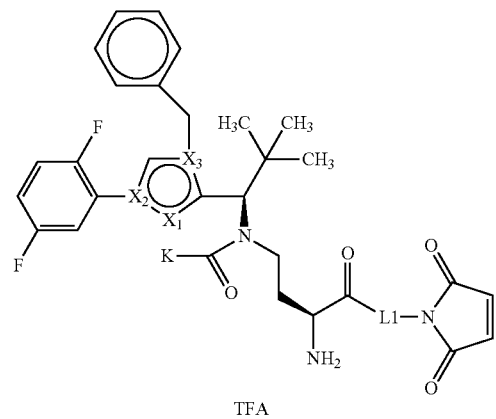
TFA
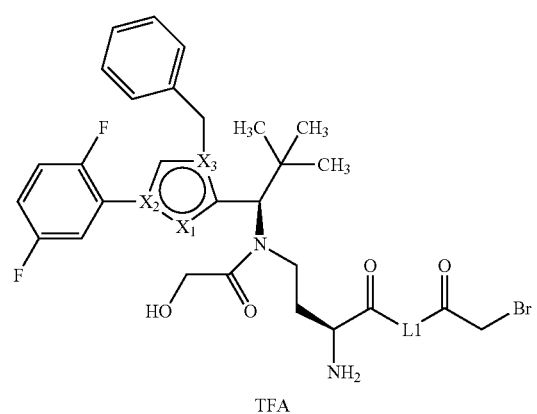
TFA
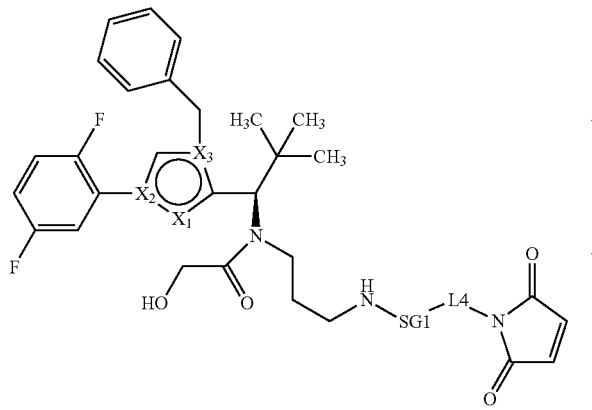
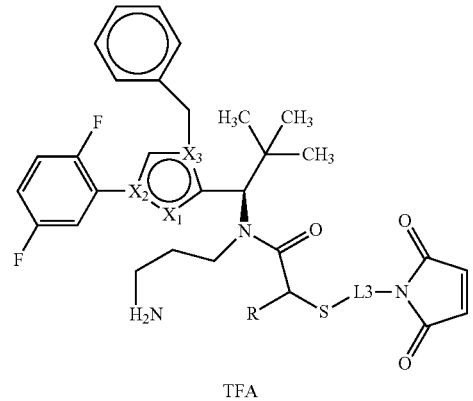
TFA
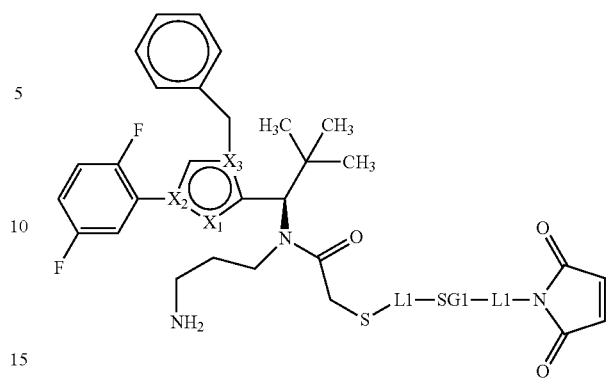
TFA
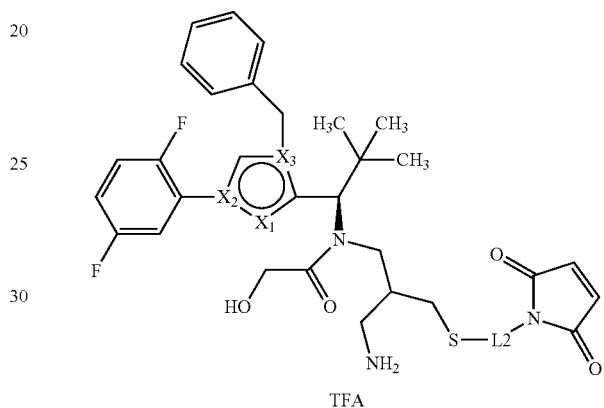
TFA
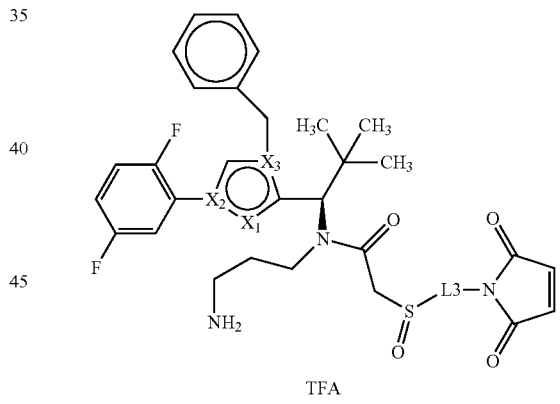
TFA
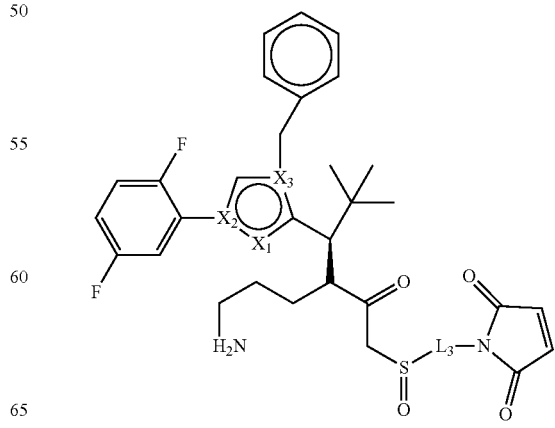

865
-continued
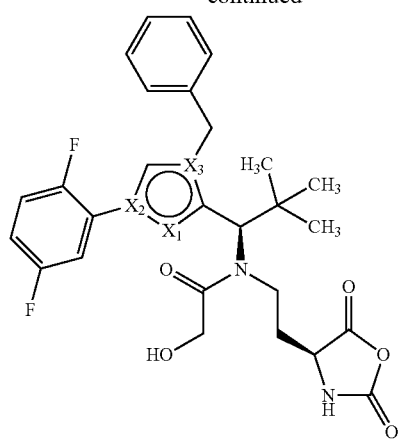
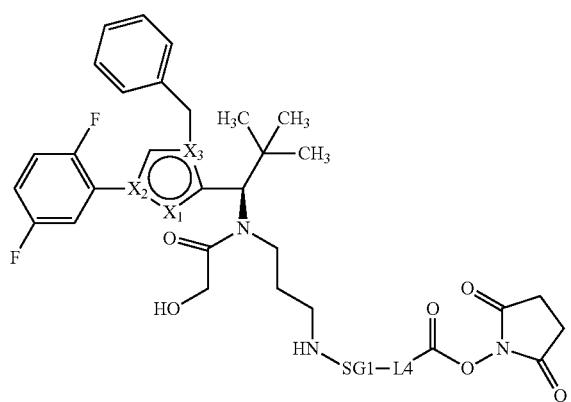
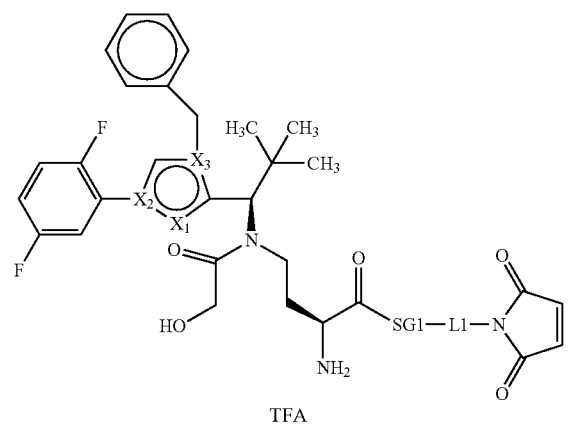
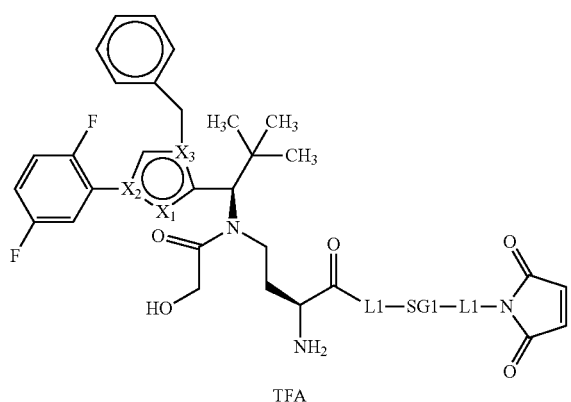
TFA
866
-continued
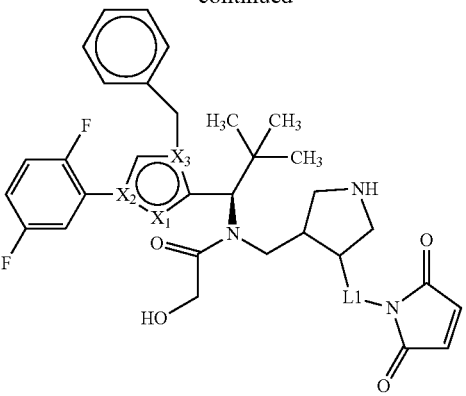
TFA
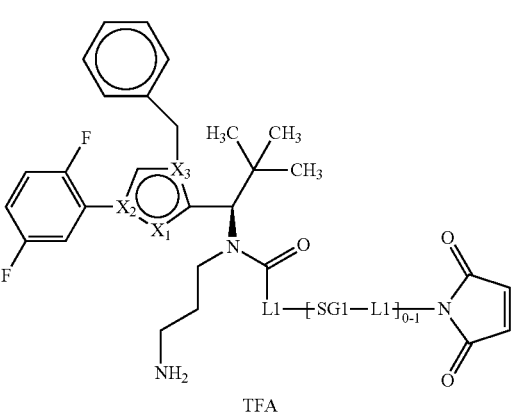
TFA
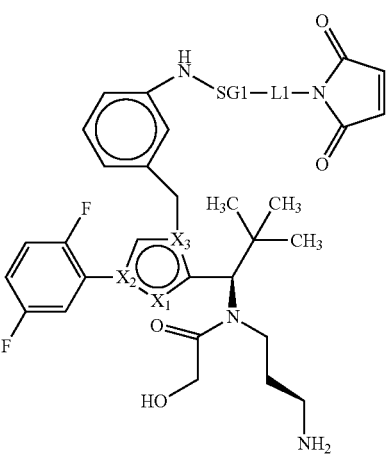
TFA
where R represents —H or —COOH,
where K represents straight-chain or branched optionally substituted by $C_1$-$C_6$-alkoxy or —OH—$C_1$-$C_6$-alkyl, and
where $X_1$, $X_2$, $X_3$, SG1, L1, L2, L3 and L4 have the same meaning as in Item 26, 30 or 32.

42. Compounds of the general formula (III):

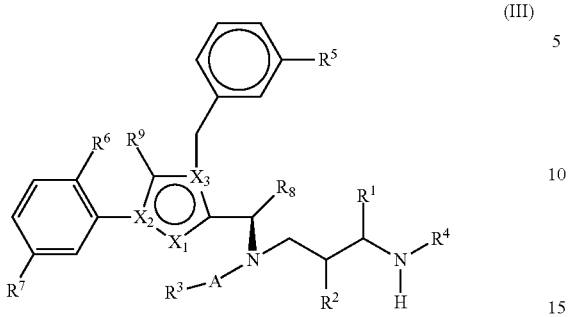

where
$X_1$ represents N, $X_2$ represents N and $X_3$ represents C, or $X_1$ represents CH, $X_2$ represents C and $X_3$ represents N or $X_1$ represents NH, $X_2$ represents C and $X_3$ represents C, or $X_1$ represents CH, $X_2$ represents N and $X_3$ represents C;

$R^1$ represents -L-BINDER, H or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ or —$CH(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)$COOH or —(CO—NH—$CHY^4)_{1-3}$COOH; where W represents H or OH;

where $Y^4$ independently of one another represents straight-chain or branched $C_{1-6}$-alkyl which is optionally substituted by —$NHCONH_2$, or represents aryl or benzyl which are optionally substituted by —$NH_2$;

$R^2$ and $R^4$ independently of one another represent -L-BINDER, H, —CO—$CHY^4$—$NHY^5$ or —$(CH_2)_{0-3}Z$, or $R^2$ and $R^4$ together (with formation of a pyrrolidine ring) represent —$CH_2$—$CHR^{10}$— or —$CHR^{10}$—$CH_2$—, where $R^{10}$ represents L-#$^1$, H, $NH_2$, $SO_3H$, COOH, SH or OH, where Z represents —H, halogen, —$OY^3$, —$SY^3$, $NHY^3$, —CO—$NY^1Y^2$ or -OO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ independently of one another represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

A represents CO, SO, $SO_2$, $SO_2NH$ or CNNH;

$R^3$ represents -L-BINDER or an optionally substituted alkyl, aryl, heteroaryl, heteroalkyl, heterocycloalkyl group, preferably —L-#$^1$, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH— alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z^4$, —$(CH_2)_{0-3}$—$CH(NH_2)Z^4$ or —$(CH_2)_{0-3}Z'$, where Z' represents H, $SO_3H$, $NH_2$ or COOH (where "alkyl" preferably represents $C_{1-10}$-alkyl);

$R^5$ represents -L-BINDER, H, F, $NH_2$, $NO_2$, halogen, SH or —$(CH_2)_{0-3}Z$, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where L represents a linker and BINDER represents a binder or a derivative thereof, where the binder may optionally be attached to a plurality of active compound molecules, $R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen, $R^8$ represents (optionally fluorinated) $C_{1-10}$-alkyl, (optionally fluorinated) $C_{4-10}$-cycloalkyl or optionally substituted oxetane; and $R^9$ represents H, F, $CH_3$, $CF_3$, $CH_2F$ or $CHF_2$;

and the salts, solvates and salts of the solvates thereof.

43. Compounds of the general formula (IV):

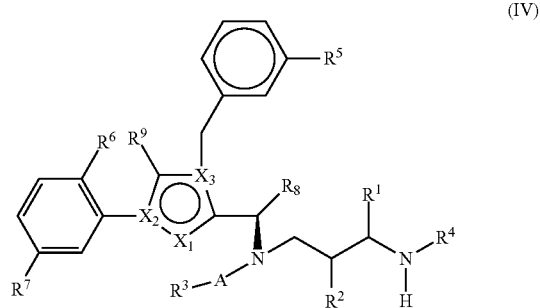

where
$X_1$ represents N, $X_2$ represents C and $X_3$ represents N;

$R^1$ represents -L-BINDER, H or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ or —$CH(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)$COOH or —(CO—NH—$CHY^4)_{1-3}$COOH; where W represents H or OH;

where $Y^4$ independently of one another represents straight-chain or branched $C_{1-6}$-alkyl which is optionally substituted by —$NHCONH_2$, or represents aryl or benzyl which are optionally substituted by —$NH_2$;

$R^2$ and $R^4$ independently of one another represent -L-BINDER, H, —CO—CHY$^4$—NHY$^5$ or —(CH$_2$)$_{0-3}$Z, or $R^2$ and $R^4$ together (with formation of a pyrrolidine ring) represent —CH$_2$—CHR$^{10}$— or —CH$^{10}$—CH$_2$—, where R$^{10}$ represents L-#$^1$, H, NH$_2$, SO$_3$H, COOH, SH or OH, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

A represents CO, SO, SO$_2$, SO$_2$NH or CNNH;

R$^3$ represents -L-BINDER or an optionally substituted alkyl, aryl, heteroaryl, heteroalkyl or heterocycloalkyl group, preferably —L-#$^1$ or a C$_{1-10}$-alkyl, C$_{6-10}$-aryl, C$_{6-10}$-aralkyl, C$_{5-10}$-heteroalkyl, C$_{1-10}$-alkyl-O—C$_{6-10}$-aryl- or C$_{5-10}$-heterocycloalkyl group, which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH, (where "alkyl" preferably represents C$_{1-10}$-alkyl);

R$^5$ represents -L-BINDER, H, F, NH$_2$, NO$_2$, halogen, SH or —(CH$_2$)$_{0-3}$Z, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where L represents a linker and BINDER represents a binder or a derivative thereof, where the binder may optionally be attached to a plurality of active compound molecules, R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen, R$^8$ represents (optionally fluorinated) C$_{1-10}$-alkyl, (optionally fluorinated) C$_{4-10}$-cycloalkyl or optionally substituted oxetane; and R$^9$ represents H, F, CH$_3$, CF$_3$, CH$_2$F or CHF$_2$;

and the salts, solvates and salts of the solvates thereof; with the proviso that R$^1$, R$^2$ and R$^4$ do not simultaneously represent H.

44. Compound according to Item 43 where Z represents Cl or Br.

45. Compound according to Item 43 where R$^1$ represents —(CH$_2$)$_{0-3}$Z, where Z represents —CO—NY$^1$Y$^2$, where Y$^2$ represents —(CH$_2$CH$_2$O)$_{0-3}$—(CH$_2$)$_{0-3}$Z' and Y$^1$ represents H, NH$_2$ or —(CH$_2$CH$_2$O)$_{0-3}$—(CH$_2$)$_{0-3}$Z'—

46. Compound according to one or more of Items 43-44, where Y$^1$ represents H, Y$^2$ represents —(CH$_2$CH$_2$O)$_3$—CH$_2$CH$_2$Z' and Z' represents —COOH.

47. Compound according to one or more of Items 43-44, where Y$^1$ represents H, Y$^2$ represents —CH$_2$CH$_2$Z' and Z' represents —(CONHCHY$^4$)$_2$COOH.

48. Compound according to Item 47 where Y$^4$ represents straight-chain or branched C$_{1-6}$-alkyl which is optionally substituted by —NHCONH$_2$.

49. Compound according to Item 48 where at least one Y$^4$ representative is selected from the group consisting of i-propyl and —CH$_3$.

50. Compound according to one or more of Items 43 and 45 where Y$^1$ represents H, Y$^2$ represents —CH$_2$CH$_2$Z', Z' represents —CONHCHY$^4$COOH and Y$^4$ represents aryl or benzyl which are optionally substituted by —NH$_2$.

51. Compound according to Item 50 where Y$^4$ represents aminobenzyl.

52. Compound according to Item 43 where R$^2$ represents —(CH$_2$)$_{0-3}$Z and Z represents —SY$^3$.

53. Compound according to Item 43 where R$^4$ represents —CO—CHY$^4$—NHY$^5$ and Y$^5$ represents H.

54. Compound according to Item 43 where R$^4$ represents —CO—CHY$^4$—NHY$^5$ and Y$^5$ represents —CO—CHY$^6$—NH$_2$.

55. Compound according to one or more of Items 53 and 54 where Y$^4$ represents straight-chain or branched C$_{1-6}$-alkyl which is optionally substituted by —NHCONH$_2$.

56. Compound according to one or more of Items 43 to 55 where the compound has one of the formulae below:

(15S,19R)-15-amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oic acid;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-N$^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-N$^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-amino-L-phenylalanine;

N-{(1R)-1-[1-(3-aminobenzyl)-4-(2,5-difluorophenyl)-1H-imidazol-2-yl]-2,2-dimethylpropyl}-N-(3-aminopropyl)-2-hydroxyacetamide (1:1);

(2S)-2-amino-4-[{(1R)-1-[1-benzyl-4-(2,5-difluorophenyl)-1H-imidazol-2-yl]-2,2-dimethylpropyl}(glycoloyl)amino]butanoic acid;

N-[(3S)-3-amino-4-hydrazino-4-oxobutyl]-N-{(1R)-1-[1-benzyl-4-(2,5-difluorophenyl)-1H-imidazol-2-yl]-2,2-dimethylpropyl}-2-hydroxyacetamide (1:1);

N-{(1R)-1-[1-benzyl-4-(2,5-difluorophenyl)-1H-imidazol-2-yl]-2,2-dimethylpropyl}-N-[(3S)-3,4-diaminobutyl]-2-hydroxyacetamide (1:1);

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanine;

(2S)-2-amino-N-(2-aminoethyl)-4-[{(1R)-1-[1-benzyl-4-(2,5-difluorophenyl)-1H-imidazol-2-yl]-2,2-dimethylpropyl}(glycoloyl)amino]butanamide (2:1);

(1-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}hydrazino)acetic acid;

N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1);

4-amino-N-(3-aminopropyl)-N-{(1R)-1-[1-benzyl-4-(2,5-difluorophenyl)-1H-imidazol-2-yl]-2,2-dimethylpropyl}benzamide (2:1);

N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1).

57. Pharmaceutical composition comprising a conjugate according to one or more of Items 1 to 38 or a compound according to Items 42-56 in combination with an inert non-toxic pharmaceutically suitable auxiliary.

58. Conjugate according to one or more of Items 1 to 38 or compound according to Items 42-56 for use in a method for the treatment and/or prophylaxis of diseases.

59. Conjugate according to one or more of Items 1 to 38 or compound according to Items 42-56 for use in a method for the treatment of hyperproliferative and/or angiogenic disorders.

60. Conjugate according to one or more of Items 1 to 38 or compound according to Items 42-56 where $R^{1a}$ or $R^3$ represents -L-BINDER or a substituted alkyl, aryl or heteroaryl group, preferably —L-#$^1$ or a $C_{1-10}$-alkyl, $C_{6-10}$-aryl or $C_{6-10}$-aralkyl group or $C_{5-10}$-heteroalkyl, which may be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$, NH$_2$ or —(CH$_2$)$_{0-3}$Z, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H or —(CH$_2$)$_{0-3}$Z', where Z' represents H, SO$_3$H, NH$_2$ or COOH, (where "alkyl" preferably represents $C_{1-10}$-alkyl).

61. Method for the treatment and/or prophylaxis of hyperproliferative and/or angiogenic disorders in humans and animals using an effective amount of at least one conjugate according to one or more of Items 1 to 38 or compound according to Items 42-56.

---

The invention claimed is:

1. A conjugate of a binder or derivative thereof, wherein the derivative thereof comprises a cysteine residue or a lysine residue, with one or more active compound molecules, the active compound molecule being a kinesin spindle protein inhibitor attached to the binder via a linker L, where the kinesin spindle protein inhibitor has the formula (IIa) below:

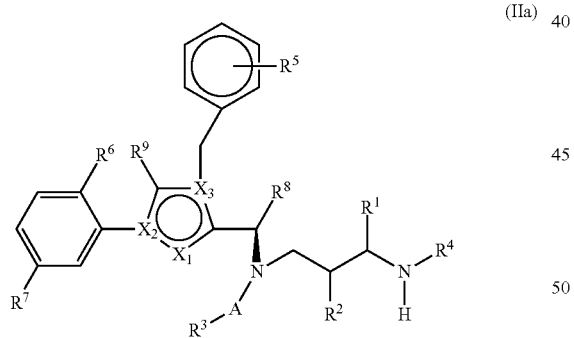

(IIa)

where
$X_1$ represents N, $X_2$ represents N and $X_3$ represents C; or
$X_1$ represents CH or CF, $X_2$ represents C and $X_3$ represents N; or
$X_1$ represents NH, $X_2$ represents C and $X_3$ represents C; or
$X_1$ represents CH, $X_2$ represents N and $X_3$ represents C;
$R^1$ represents H, L-#$^1$, MOD or —(CH$_2$)$_{0-3}$Z, where Z represents —H, —NHY$^3$, —OY$^3$, —SY$^3$, halogen, —CO—NY$^1$Y$^2$ or —CO—OY$^3$,
where $Y^1$ and $Y^2$ independently of one another represent H, NH$_2$, —(CH$_2$CH$_2$O)$_{0-3}$—(CH$_2$)$_{0-3}$Z' or —CH(CH$_2$W)Z', and $Y^3$ represents H or —(CH$_2$)$_{0-3}$Z', where Z' represents H, NH$_2$, SO$_2$H, COOH, —NH—CO— CH$_2$—CH$_2$—CH(NH$_2$)COOH or —(CO—NH— CHY$^4$)$_{1-3}$COOH, where W represents H or OH,
where $Y^4$ independently of one another represents straight-chain or branched C$_{1-6}$-alkyl which is optionally substituted by —NHCONH$_2$, or represents aryl or benzyl which are optionally substituted by —NH$_2$;
$R^2$ represents —L-#$^1$, H, -MOD, —CO—CHY$^4$—NHY$^5$ or —(CH$_2$)$_{0-3}$Z, or $R^2$ and $R^4$ together (with formation of a pyrrolidine ring) represent —CH$_2$—CHR$^{10}$— or —CHR$^{10}$—CH$_2$—,
where $R^{10}$ represents L-#$^1$, H, NH$_2$, SO$_3$H, COOH, SH, or OH;
where Z represents —H, halogen, —OY$^3$, —SY$^3$, NHY$^3$, —CO—NY$^1$Y$^2$ or —CO—OY$^3$,
where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;
where $Y^4$ independently of one another represents straight-chain or branched C$_{1-6}$ alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched C$_{1-6}$-alkyl;
$R^4$ represents —L-#$^1$, H, —CO—CHY$^4$—NHY$^5$ or —(CH$_2$)$_{0-3}$Z,
where Z represents —H, halogen, —OY$^3$, —SY$^3$, NHY$^3$, —CO—NY$^1$Y$^2$ or —CO—OY$^3$,
where $Y^1$ and $Y^2$ independently of one another represent H, NH$_2$ or —(CH$_2$)$_{0-3}$Z', and $Y^3$ represents H or —(CH$_2$)$_{0-3}$Z', where Z' represents H, SO$_3$H, NH$_2$ or COOH;
where $Y^4$ independently of one another represents straight-chain or branched C$_{1-6}$ alkyl which is optionally substituted by —NHCONH$_2$, or represents aryl or benzyl which are optionally substituted by —NH$_2$, and $Y^5$ represents H or —CO—CHY$^6$—NH$_2$, where $Y^6$ represents straight-chain or branched C$_{1-6}$-alkyl;

or $R^2$ and $R^4$ together (with formation of a pyrrolidine ring) represent —$CH_2$—$CHR^{10}$— or —$CHR^{10}$—$CH_2$—, where $R^{10}$ represents L-#$^1$, H, $NH_2$, $SO_3H$, COOH, SH or OH;

A represents CO, SO, $SO_2$, $SO_2NH$ or CNNH;

$R^3$ represents —L-#$^1$, MOD or an optionally substituted alkyl, cycloalkyl, aryl, heteroaryl, heteroalkyl, heterocycloalkyl group;

$R^5$ represents —L-#$^1$, H, $NH_2$, $NO_2$, halogen, —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen, $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —$(CH_2)_{0-2}$-($HZ^2$), where $HZ^2$ represents a 4- to 7-membered heterocycle having up to two heteroatoms selected from the group consisting of N, O and S, where each of these groups may be substituted by —OH, $CO_2H$ or $NH_2$ or —L-#$^1$;

where one or none of the substituents $R^1$, $R^2$, $R^3$, $R^4$ $R^5$, $R^8$ and $R^{10}$ represents or (in the case of $R^8$) contains —L-#$^1$, L represents the linker and #$^1$ represents the bond to the binder or derivative thereof, $R^9$ represents H, F, $CH_3$, $CF_3CH_2F$ or $CHF_2$;

where MOD represents —$(NR^{10})_n$-(G1)$_o$-G2-H, where $R^{10}$ represents H or $C_1$-$C_3$-alkyl;

G1 represents —NHCO—, —CONH— or

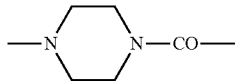

(where, if G1 represents —NHCO— or

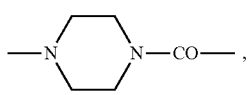

$R^{10}$ does not represent $NH_2$);

n is 0 or 1;

o is 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by —NHCONH$_2$, —COOH, —OH, —NH$_2$, NH—CNNH$_2$, sulphonamide, sulphone, sulphoxide or sulphonic acid), —CO—, —$CR^x$=N—O— (where $R^x$ represents H, $C_1$-$C_3$-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid;

and the salts, solvates and salts of the solvates thereof.

2. The conjugate according to claim 1 where the active compound molecule linker is represented by general formula (II):

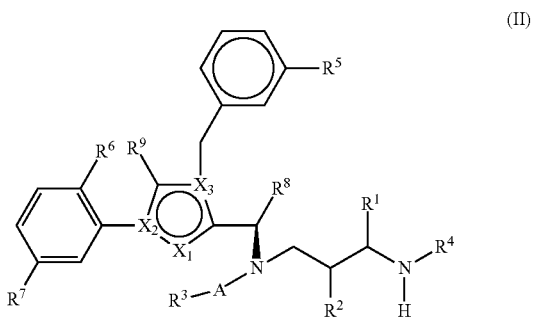

(II)

where $X_1$ represents N, $X_2$ represents N and $X_3$ represents C; or $X_1$ represents CH, $X_2$ represents C and $X_3$ represents N; or $X_1$ represents NH, $X_2$ represents C and $X_3$ represents C; or $X_1$ represents CH, $X_2$ represents N and $X_3$ represents C $R^1$ represents H, —L-#$^1$ or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ or —CH$(CH_2W)Z'$, and $Y^3$ represents H or —$(CH_2)_{0-3}Z'$, where Z' represents H, $NH_2$, $SO_3H$, COOH, —NH—CO—$CH_2$—$CH_2$—$CH(NH_2)COOH$ or —(CO—NH—$CHY^4)_{1-3}COOH$, where W represents H or OH, where $Y^4$ independently of one another represents straight-chain or branched $C_{1-6}$-alkyl which is optionally substituted by —NHCONH$_2$, or represents aryl or benzyl which are optionally substituted by —NH$_2$;

$R^2$ and $R^4$ independently of one another represent —L-#$^1$, H, —CO—$CHY^4$—$NHY^5$ or —$(CH_2)_{0-3}Z$, or $R^2$ and $R^4$ together (with formation of a pyrrolidine ring) represent —$CH_2$—$CHR^{10}$— or —$CHR^{10}$—$CH_2$—, where $R^{10}$ represents L-#$^1$, H, $NH_2$, $SO_3H$, COOH, SH or OH, where Z represents —H, $OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ independently of one another represents straight-chain or branched $C_{1-6}$ alkyl which is optionally substituted by —NHCONH$_2$, or represents aryl or benzyl which are optionally substituted by —NH$_2$, and $Y^5$ represents H or —CO—$CHY^6$—$NH_2$, where $Y^6$ represents straight-chain or branched $C_{1-6}$-alkyl;

A represents CO, SO, $SO_2$, $SO_2NH$ or CNNH;

$R^3$ represents —L-#$^1$ or an optionally substituted alkyl, aryl, heteroaryl, heteroalkyl or heterocycloalkyl group;

R⁵ represents —L-#¹, H, F, NH₂, NO₂, halogen, SH or —(CH₂)₀₋₃Z, where Z represents —H, OY³, —SY³, halogen, NHY³, —CO—NY¹Y² or —CO—OY³, where Y¹ and Y² independently of one another represent H, NH₂ or —(CH₂)₀₋₃Z', and Y³ represents H or —(CH₂)₀₋₃Z', where Z' represents H, SO₃H, NH₂ or COOH;

where one of the substituents R¹, R², R³, R⁴ and R⁵ represents —L-#¹,

L represents the linker and #¹ represents the bond to the binder or derivative thereof, R⁶ and R⁷ independently of one another represent H, cyano, (optionally fluorinated) C₁₋₁₀-alkyl, (optionally fluorinated) C₂₋₁₀-alkenyl, (optionally fluorinated) C₂₋₁₀-alkynyl, hydroxy or halogen, R⁸ represents (optionally fluorinated) C₁₋₁₀-alkyl, (optionally fluorinated) C₄₋₁₀-cycloalkyl or optionally substituted oxetane; and R⁹ represents H, F, CH₃, CF₃, CH₂F or CHF₂;
and the salts, solvates and salts of the solvates thereof.

3. The Conjugate according to claim 1 where the conjugate has on average 1.2 to 20 active compound molecules per binder.

4. The Conjugate according to claim 3 where the binder or derivative thereof is an antibody or the derivative of a binder peptide or protein

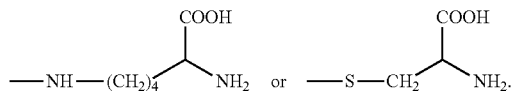

5. The Conjugate according to claim 4 where the binder or derivative thereof is an anti-HER2 antibody, an anti-EGFR antibody, an anti-TWEAKR antibody or an antigen-binding fragment thereof.

6. The Conjugate according to claim 5 where the anti-TWEAKR antibody binds specifically to amino acid D in position 47 (D47) of TWEAKR (SEQ ID NO:169).

7. The Conjugate according to claim 5 where the binder is an anti-EGFR antibody and R³ represents —L-#¹.

8. The Conjugate according to claim 1 where the linker -L- has one of the basic structures (i) to (iv) below:
   (i) —(CO)ₘ-SG1-L1-L2-
   (ii) —(CO)ₘ-L1-SG-L1-L2-
   (iii) —(CO)ₘ-L1-L2-
   (iv) —(CO)ₘ-L1-SG-L2 where m is 0 or 1, SG and SG1 are in vivo cleavable groups, L1 independently of one another represent organic groups not cleavable in vivo, and L2 represents a coupling group to the binder.

9. The Conjugate according to claim 8 where the in vivo cleavable group SG is a 2-8 oligopeptide group a hydrazone, an acetal or an aminal and SG1 is a 2-8 oligopeptide group.

10. The Conjugate according to claim 1 where the linker is attached to a cysteine side chain or a cysteine residue and has the formula below:

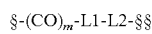

where
m is 0 or 1;
§ represents the bond to the active compound molecule and
§§ represents the bond to the binder peptide or protein, and L2- represents

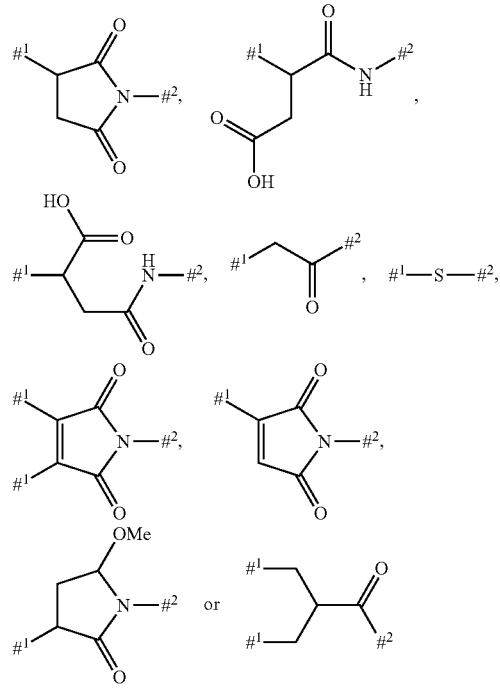

where
¹ denotes the point of attachment to the sulphur atom of the binder,
² denotes the point of attachment to group L1,
L1 represents —(NR¹⁰)ₙ-(G1)ₒ-G2-,
where R¹⁰ represents H, NH₂ or C₁-C₃-alkyl;
G1 represents —NHCO— or

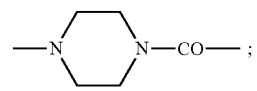

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NMe-, —NHNH—, —SO₂NHNH—, —NHCO—, —CONH—, —CONHNH— and a 5- to 10-membered aromatic or non-aromatic heterocycle having up to 4 heteroatoms selected from the group consisting of N, O and S, —SO— or —SO₂—, where the side chains, if present, may be substituted by —NHCONH₂, —COOH, —OH, —NH₂, NH—CNNH₂, sulphonamide, sulphone, sulphoxide or sulphonic acid, or represents one of the groups below:

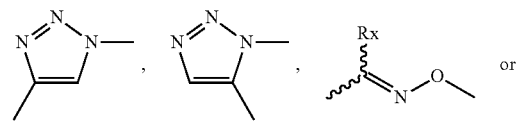

-continued

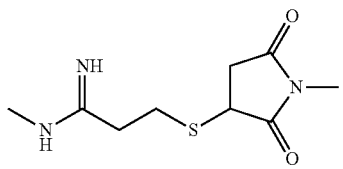

where R$^x$ represents H, C$_1$-C$_3$-alkyl or phenyl.

11. The Conjugate according to claim 10 where L2 is represented by one or both of the formulae below:

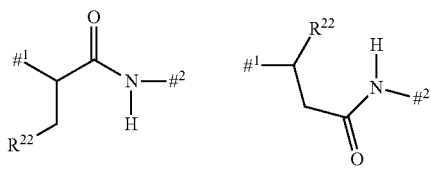

where #$^1$ denotes the point of attachment to the sulphur atom of the binder, #$^2$ denotes the point of attachment to group L1, R$^{22}$ represents COOH and more than 80% (based on the total number of bonds of the linker to the binder) of the bonds to the sulphur atom of the binder are present in one of these two structures.

12. The Conjugate according to claim 10 where the linker has the formula below:

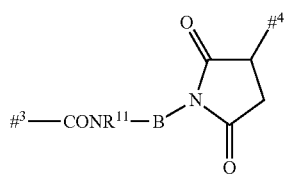

where
$^3$ represents the bond to the active compound molecule,
$^4$ represents the bond to the binder peptide or protein,
R$^{11}$ represents H or NH$_2$;
B represents —[(CH$_2$)$_x$—(X$^4$)$_y$]$_w$—(CH$_2$)$_z$—,
w=0 to 20;
x=0 to 5;
x=0 to 5;
y=0 or 1;
z=0 to 5; and
X$^4$ represents —O—, —CONH— or —NHCO—

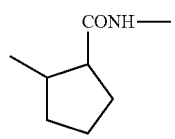

13. The Conjugate according to claim 10 where the conjugate has one of the formulae below:

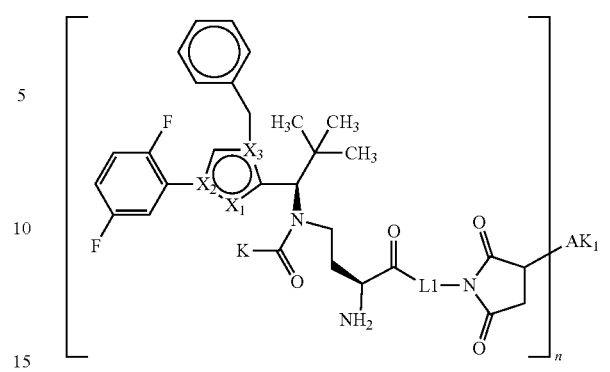

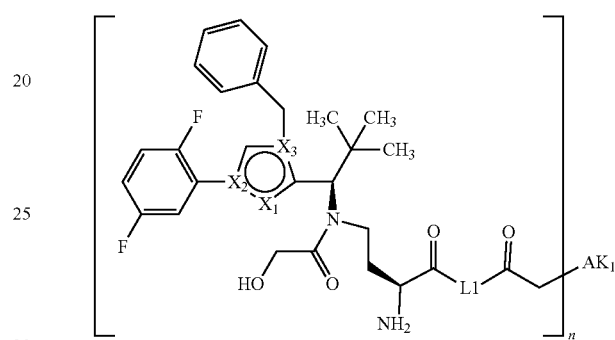

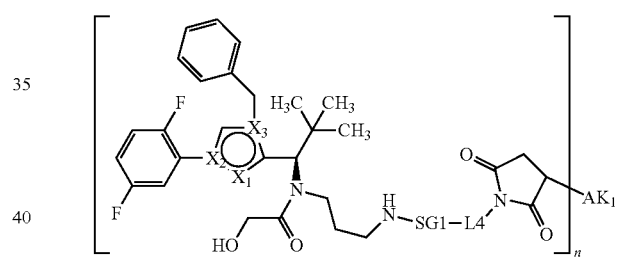

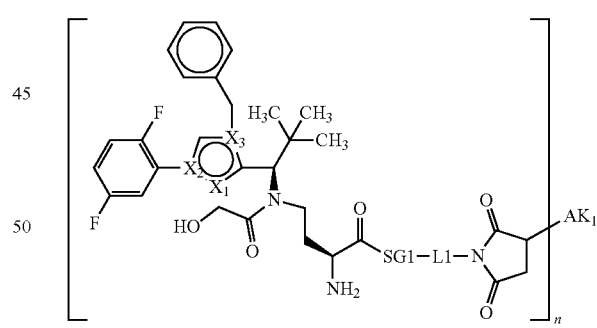

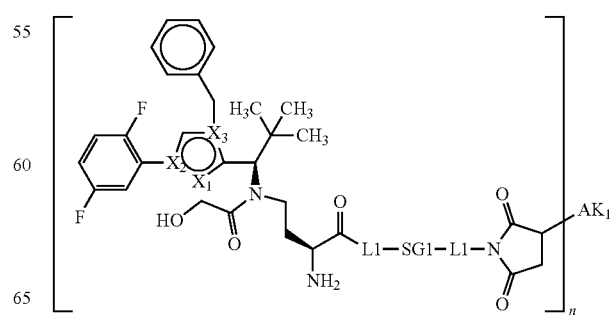

-continued

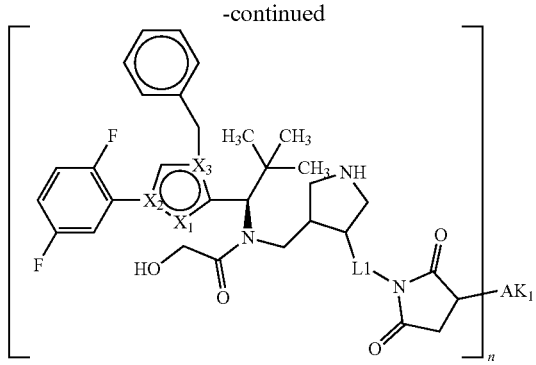

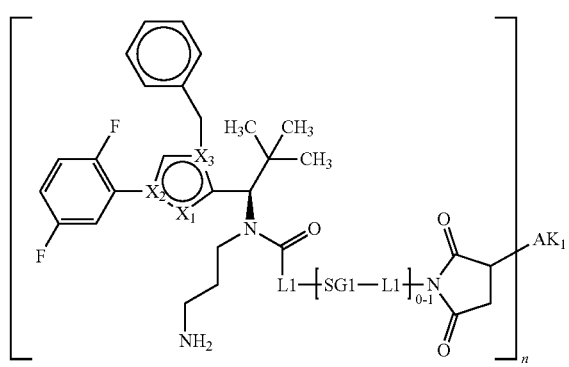

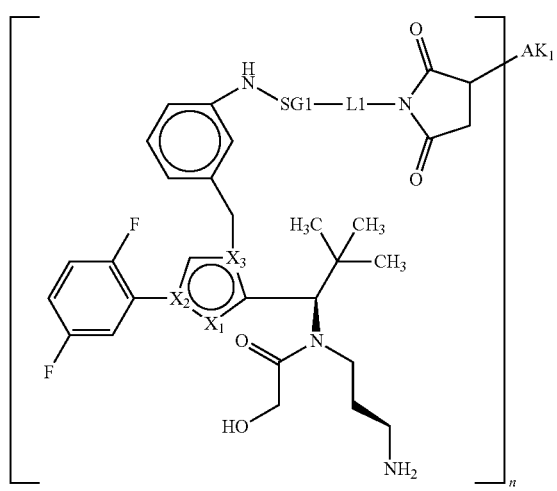

$X_1$, $X_2$ and $X_3$ have the same meaning as in claim 10, $AK_1$ represents a binder peptide or protein which is attached via a sulphur atom of the binder; n represents a number from 1 to 20; and L1 represents an optionally branched hydrocarbon group having 1 to 70 carbon atoms, which represents a straight-chain or branched chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —CONH—, —NHCO—, —NMe-, —NHNH—, —$SO_2NHNH$—, —CONHNH— and a 5- to 10-membered aromatic or non-aromatic heterocycle having up to 4 heteroatoms selected from the group consisting of N, O and S, or —SO— or —$SO_2$— and SG1 is a 2-8 oligopeptide;

L4 is a single bond or a group —(CO)-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2NHNH$—, —CONHNH— and a 5- to 10-membered aromatic or non-aromatic heterocycle having up to 4 heteroatoms selected from the group consisting of N, O and S, or —SO— or —$SO_2$—.

14. The conjugate of a binder or derivative thereof with one or more active compound molecules where the conjugate has one or both of the formulae below:

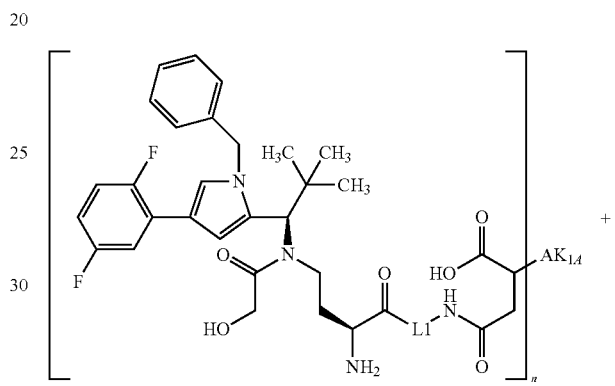

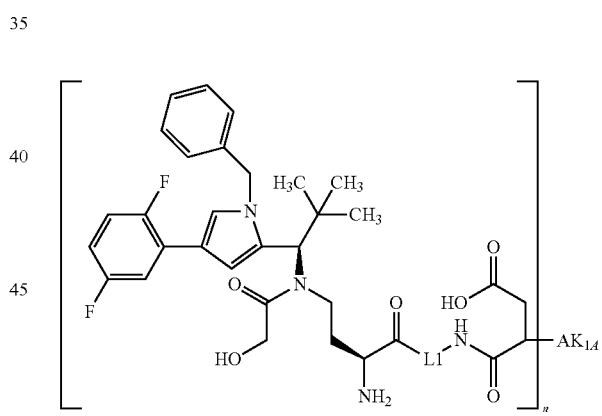

where $AK_{1A}$ represents a binder peptide or protein which is attached via a sulphur atom of the binder; n represents a number from 1 to 20; and L1 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —CONH—, —NHCO—, —NMe-, —NHNH—, —$SO_2NHNH$—, —CONHNH— and a 5- to 10-membered aromatic or non-aromatic heterocycle selected from the group consisting of N, O and 5, —SO— or —$SO_2$—.

15. The conjugate according to claim 1 where the linker -L- is attached to a cysteine side chain or a cysteine residue and has the formula below:

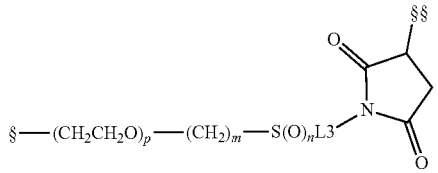

where
§ represents the bond to the active compound molecule and
§§ represents the bond to the binder peptide or protein,
m is 0, 1, 2 or 3;
n is 0, 1 or 2;
p is 0 to 20; and
L3 represents

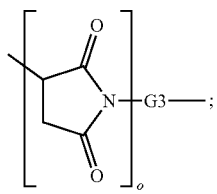

where
o is 0 or 1;
and
G3 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH— and a 5- to 10-membered aromatic or non-aromatic heterocycle having up to 4 heteroatoms selected from the group consisting of N, O and S, —NMe-, —NHNH—, —$SO_2$NHNH—, —CONHNH—, —SO— or —$SO_2$—.

16. The conjugate according to claim 15 where the linker -L- is attached to a cysteine side chain or a cysteine residue and has the formula below:

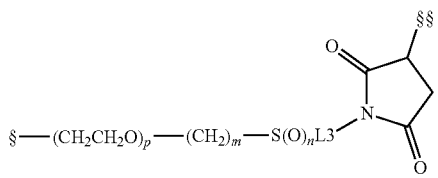

where
§ represents the bond to the active compound molecule and
§§ represents the bond to the binder peptide or protein,
m is 1;
p is 0;
n is 0;

and L3 represents

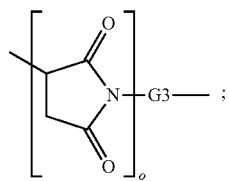

where
o is 0 or 1; and
G3 represents —$(CH_2CH_2O)_s(CH_2)t(CONH)_u(CH_2CH_2O)_v(CH_2)_w$—, where
s, t, v and w each independently of one another are from 0 to 20 and u is 0 or 1.

17. The conjugate according to claim 15 where $R^2$ or $R^3$ represents —L-#$^1$.

18. The conjugate according to claim 17 where the conjugate has one of the formulae below:

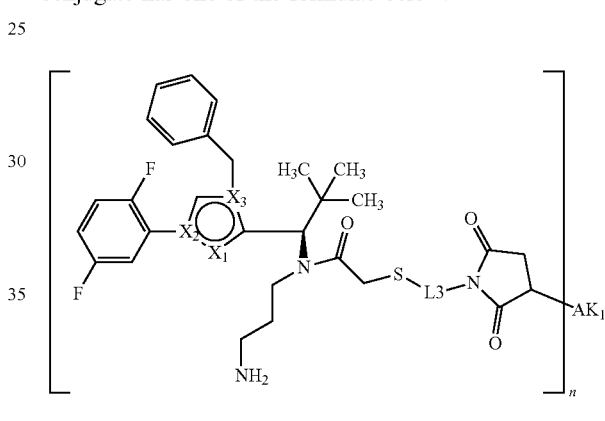

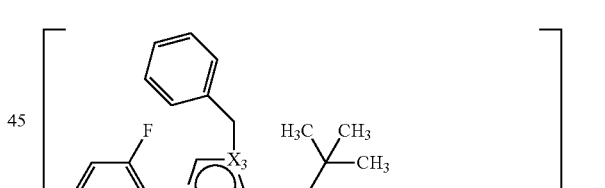

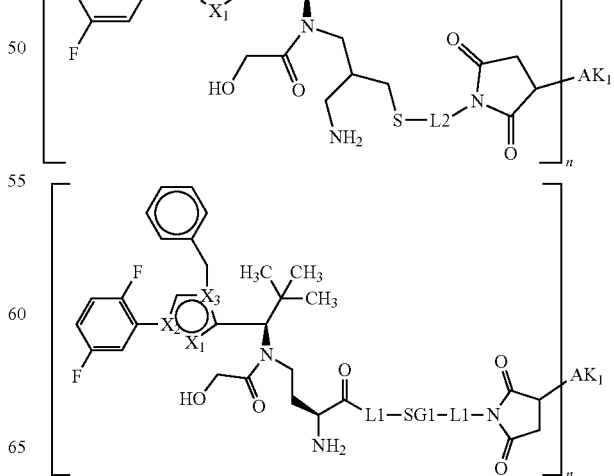

1087
-continued

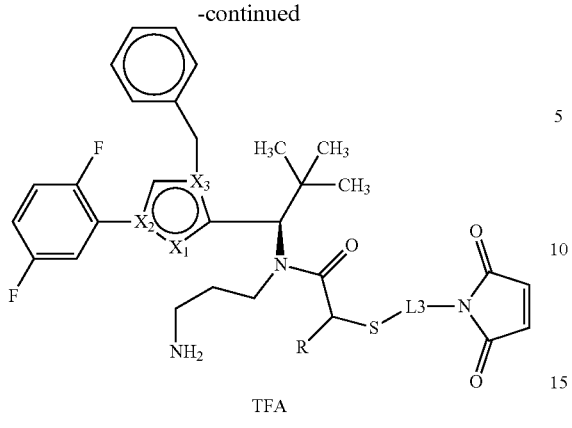

TFA

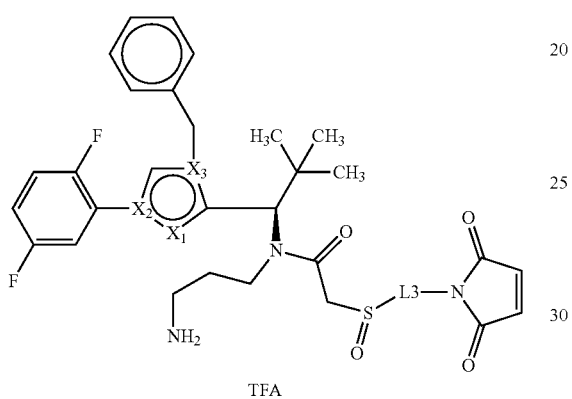

TFA

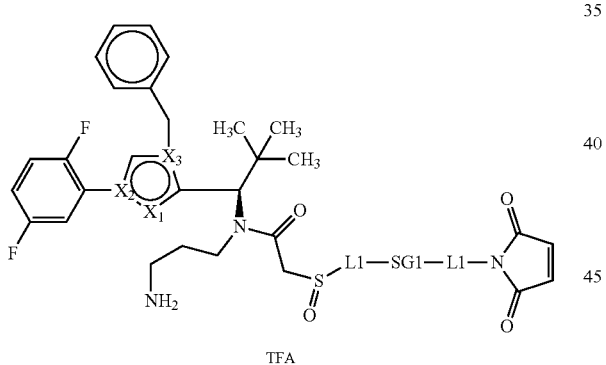

TFA

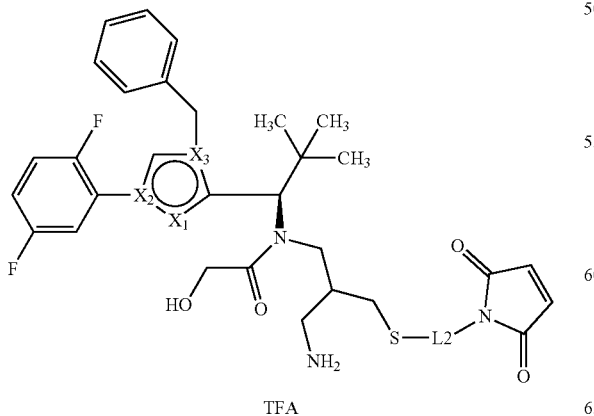

TFA

1088 where $X_1$, $X_2$ and $X_3$ have the same meaning as in claim 17, $AK_1$ represents a binder peptide or protein which is attached via a sulphur atom of the binder; n represents a number from 1 to 20; and L2 and L3 represent a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NMe-, —NHNH—, —$SO_2$NHNH—, —NHCO—, —CONH—, —CONHNH— and a 5- to 10-membered aromatic or non-aromatic heterocycle having up to 4 heteroatoms selected from the group consisting of N, O and S, —SO— or —$SO_2$—.

19. The conjugate according to claim 1 where the linker -L- is attached to a lysine side chain and has the formula below:

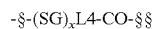

where

§ represents the bond to the active compound molecule and

§§ represents the bond to the binder peptide or protein, x represents 0 or 1,

SG represents a cleavable group, and

L4 represents a single bond or a group —(CO)$_y$-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 5- to 10-membered aromatic or non-aromatic heterocycle having up to 4 heteroatoms selected from the group consisting of N, O and S, or —SO—.

20. The conjugate of a binder peptide or protein according to claim 19 where the conjugate has one of the formulae below:

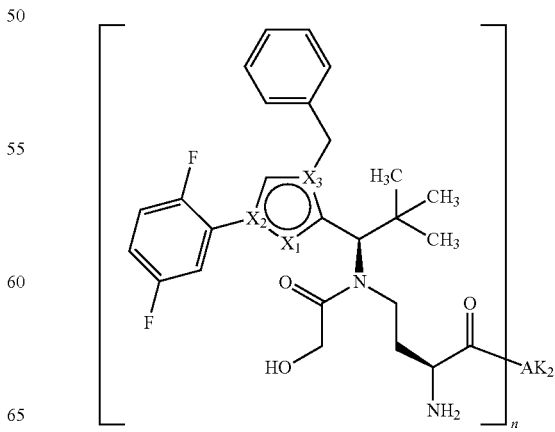

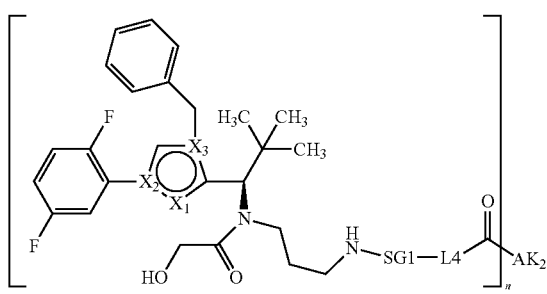

where
X₁, X₂ and X₃ have the same meaning as in claim 19,
AK₂ represents a binder peptide or protein which is attached via a sulphur atom of the binder; n represents a number from 1 to 20; and L4 represents an optionally straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO₂, —NH—, —CO—, —NMe-, —NHNH—, —SO₂NHNH—, —NHCO—, —CONH—, —CONHNH— and a 5- to 10-membered aromatic or non-aromatic heterocycle having up to 4 heteroatoms selected from the group consisting of N, O and S, —SO— or —SO₂— and SG1 represents a cleavable group.

21. The conjugate according to claim 5 where the anti-TWEAKR antibody is an agonistic antibody.

22. The conjugate according to claim 5 which comprises:
a variable heavy chain comprising:
a. a CDR1 of the heavy chain encoded by an amino acid sequence comprising the formula PYPMX (SEQ ID NO: 171), where X is I or M;
b. a CDR2 of the heavy chain encoded by an amino acid sequence comprising the formula YISPSGGXTHY-ADSVKG (SEQ ID NO: 172), where X is S or K; and
c. a CDR3 of the heavy chain encoded by an amino acid sequence comprising the formula GGDTYFDYFDY (SEQ ID NO: 173);
and a variable light chain comprising:
d. a CDR1 of the light chain encoded by an amino acid sequence comprising the formula RASQSISXYLN (SEQ ID NO: 174), where X is G or S;
e. a CDR2 of the light chain encoded by an amino acid sequence comprising the formula XASSLQS (SEQ ID NO: 175), where X is Q, A or N; and
f. a CDR3 of the light chain encoded by an amino acid sequence comprising the formula QQSYXXPXIT (SEQ ID NO: 176), where X at position 5 is T or S, X at position 6 is T or S and X at position 8 is G or F.

23. The conjugate according to claim 5 which comprises:
a. a variable sequence of the heavy chain, as shown in SEQ ID NO:10, and also a variable sequence of the light chain, as shown in SEQ ID NO:9, or
b. a variable sequence of the heavy chain, as shown in SEQ ID NO:20, and also a variable sequence of the light chain, as shown in SEQ ID NO:19, or
c. a variable sequence of the heavy chain, as shown in SEQ ID NO:30, and also a variable sequence of the light chain, as shown in SEQ ID NO:29, or
d. a variable sequence of the heavy chain, as shown in SEQ ID NO:40, and also a variable sequence of the light chain, as shown in SEQ ID NO:39, or
e. a variable sequence of the heavy chain, as shown in SEQ ID NO:50, and also a variable sequence of the light chain, as shown in SEQ ID NO:49, or
f. a variable sequence of the heavy chain, as shown in SEQ ID NO:60, and also a variable sequence of the light chain, as shown in SEQ ID NO:59, or
g. a variable sequence of the heavy chain, as shown in SEQ ID NO:70, and also a variable sequence of the light chain, as shown in SEQ ID NO:69, or
h. a variable sequence of the heavy chain, as shown in SEQ ID NO:80, and also a variable sequence of the light chain, as shown in SEQ ID NO:79, or
i. a variable sequence of the heavy chain, as shown in SEQ ID NO:90, and also a variable sequence of the light chain, as shown in SEQ ID NO:89, or
j. a variable sequence of the heavy chain, as shown in SEQ ID NO:100, and also a variable sequence of the light chain, as shown in SEQ ID NO:99, or
k. a variable sequence of the heavy chain, as shown in SEQ ID NO:110, and also a variable sequence of the light chain, as shown in SEQ ID NO:109, or
l. a variable sequence of the heavy chain, as shown in SEQ ID NO:120, and also a variable sequence of the light chain, as shown in SEQ ID NO:119.

24. The conjugate according to claim 5 where the antibody is an IgG antibody.

25. The conjugate according to claim 5 which comprises:
a. a sequence of the heavy chain, as shown in SEQ ID NO:2, and also a sequence of the light chain, as shown in SEQ ID NO:1, or
b. a sequence of the heavy chain, as shown in SEQ ID NO:12, and also a sequence of the light chain, as shown in SEQ ID NO:11, or
c. a sequence of the heavy chain, as shown in SEQ ID NO:22, and also a sequence of the light chain, as shown in SEQ ID NO:21, or
d. a sequence of the heavy chain, as shown in SEQ ID NO:32, and also a sequence of the light chain, as shown in SEQ ID NO:31, or
e. a sequence of the heavy chain, as shown in SEQ ID NO:42, and also a sequence of the light chain, as shown in SEQ ID NO:41, or
f. a sequence of the heavy chain, as shown in SEQ ID NO:52, and also a sequence of the light chain, as shown in SEQ ID NO:51, or
g. a sequence of the heavy chain, as shown in SEQ ID NO:62, and also a sequence of the light chain, as shown in SEQ ID NO:61, or
h. a sequence of the heavy chain, as shown in SEQ ID NO:72, and also a sequence of the light chain, as shown in SEQ ID NO:71, or
i. a sequence of the heavy chain, as shown in SEQ ID NO:82, and also a sequence of the light chain, as shown in SEQ ID NO:81, or
j. a sequence of the heavy chain, as shown in SEQ ID NO:92, and also a sequence of the light chain, as shown in SEQ ID NO:91, or
k. a sequence of the heavy chain, as shown in SEQ ID NO:102, and also a sequence of the light chain, as shown in SEQ ID NO:101, or
l. a sequence of the heavy chain, as shown in SEQ ID NO:112, and also a sequence of the light chain, as shown in SEQ ID NO:111.

26. A process for preparing the conjugate according to claim 13 where a compound of one of the formulae below is attached to a cysteine residue of a binder peptide or protein which is optionally partially reduced beforehand:

1091
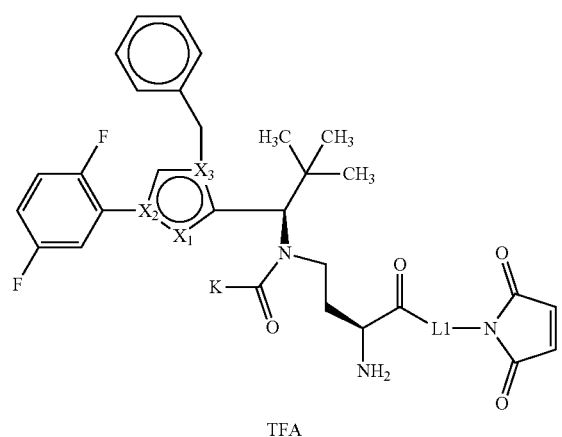
TFA
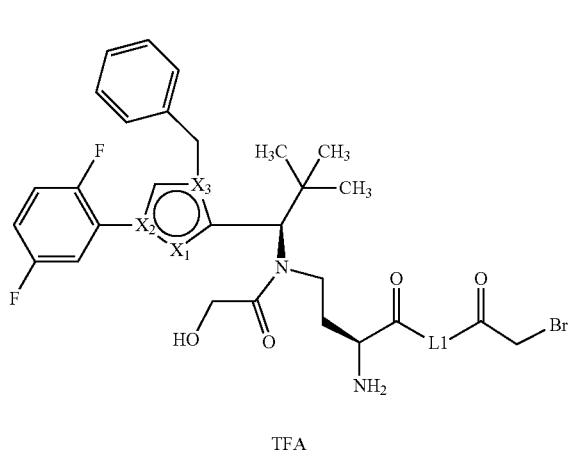
TFA
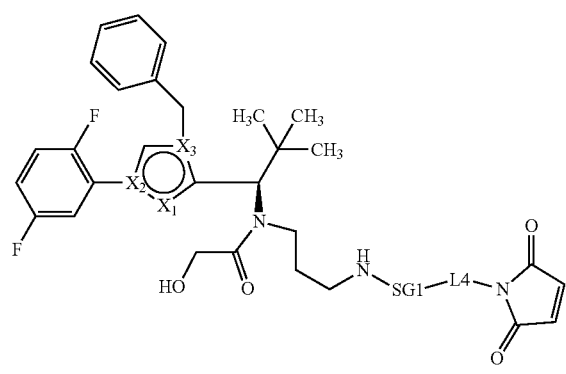
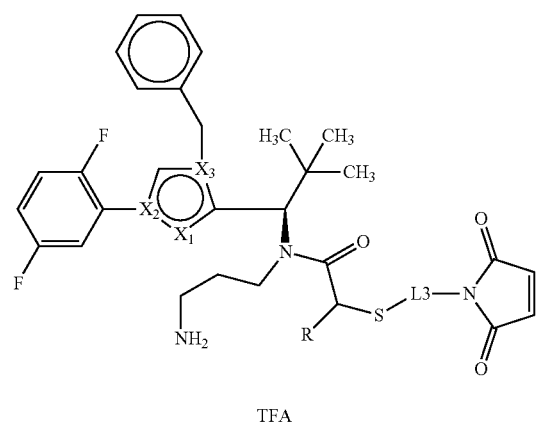
TFA
1092
-continued
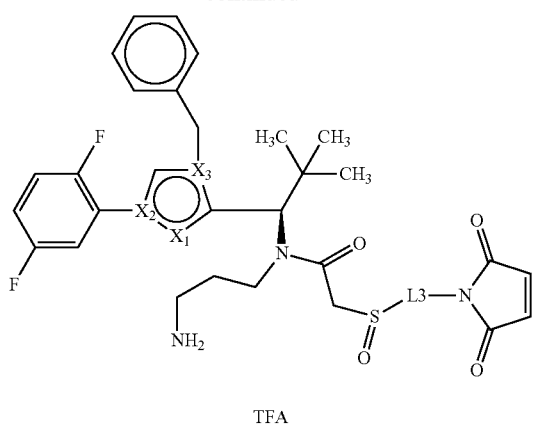
TFA
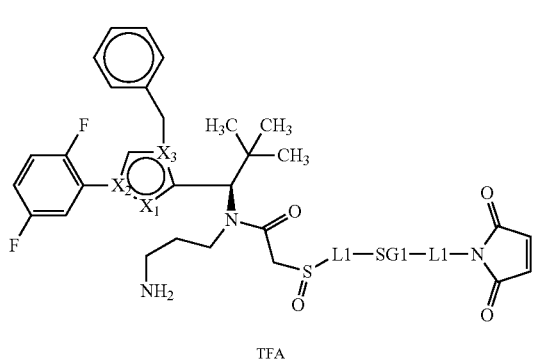
TFA
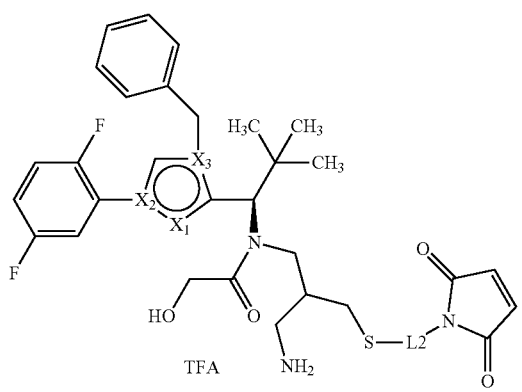
TFA
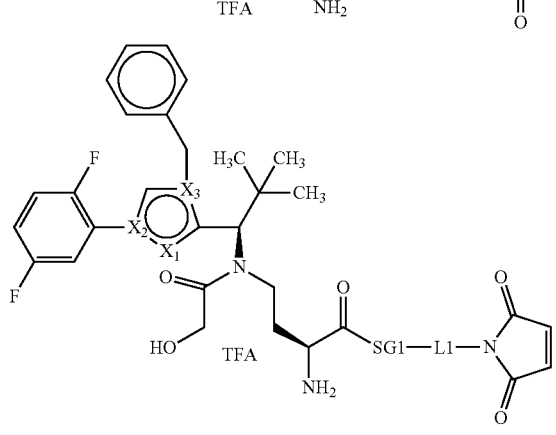

-continued

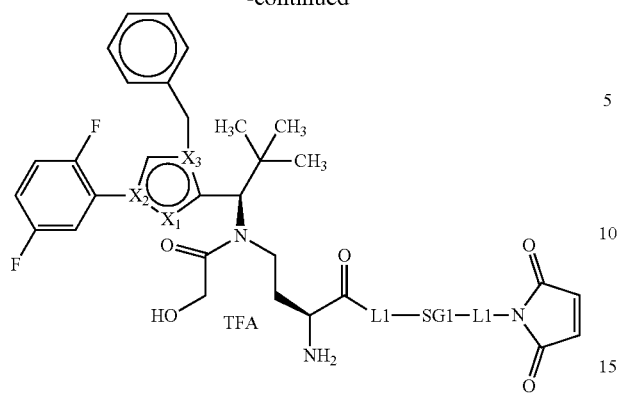

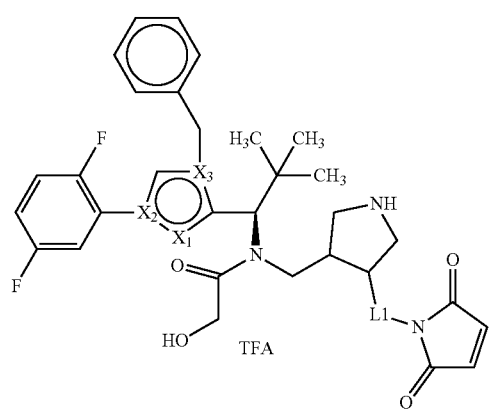

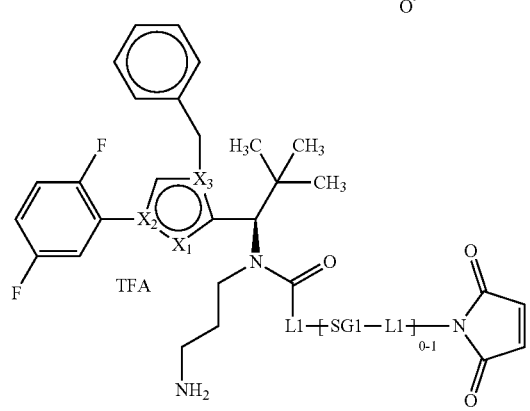

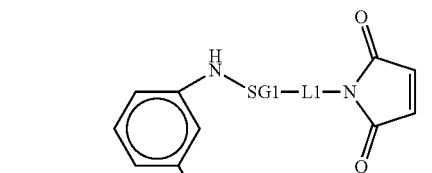

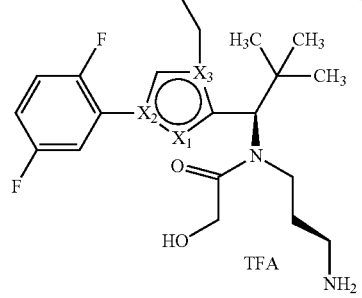

where R represents —H or —COOH, where K represents straight-chain or branched optionally substituted by $C_1$-$C_6$-alkoxy or —OH—$C_1$-$C_6$-alkyl, and where $X_1$, $X_2$, $X_3$, SG1, L1, L2, L3 and L4 have the same meaning as in claim 13.

27. The process for preparing the conjugate according to claim 26 comprising attaching a compound of one of the formulae below to lysine residue of a binder peptide or protein:

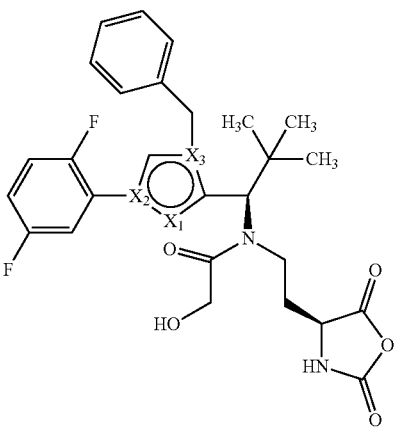

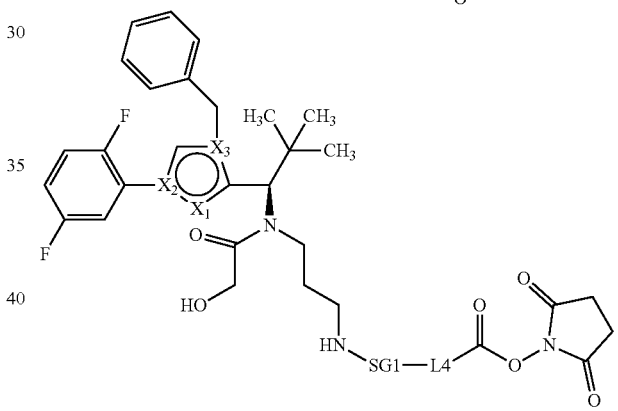

where $X_1$ represents N, $X_2$ represents N and $X_3$ represents C; or $X_1$ represents CH or CF $X_2$ represents C and $X_3$ represents N; or $X_1$ represents NH, $X_2$ represents C and $X_3$ represents C; or $X_1$ represents CH, $X_2$ represents N and $X_3$ represents C;

SG1 is a cleavable group; and

L4 is a single bond or a group —(CO)$_y$-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 5- to 10-membered aromatic or non-aromatic heterocycle having up to 4 heteroatoms selected from the group consisting of N, O and S, or —SO—.

28. A compound of one of the formulae below:
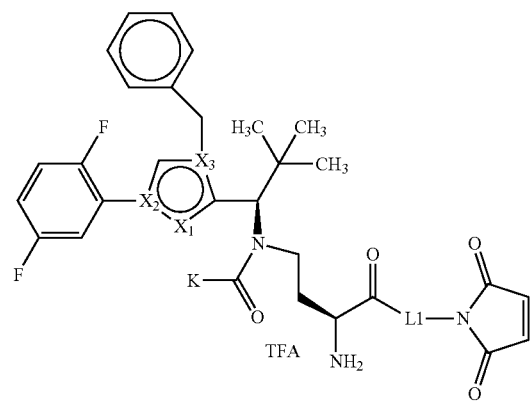
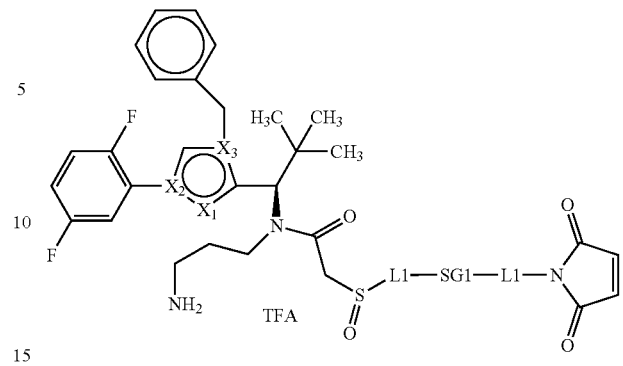
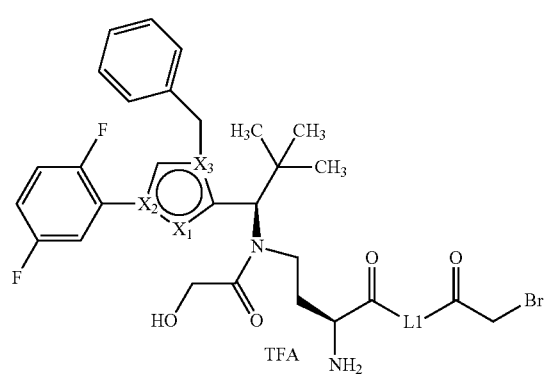
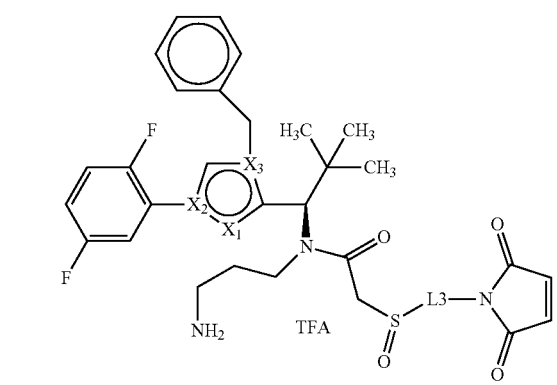
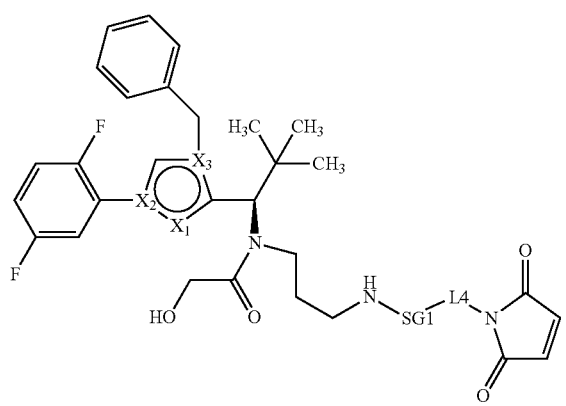
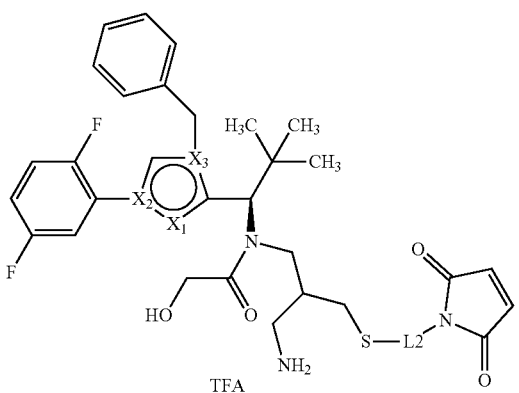
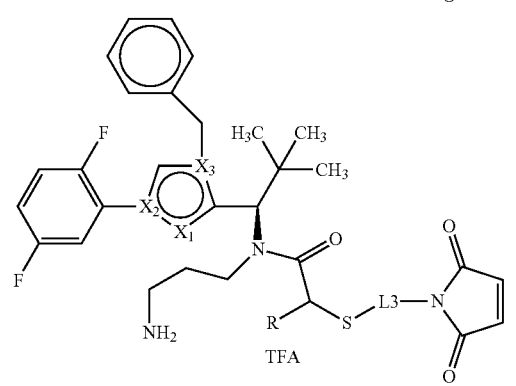
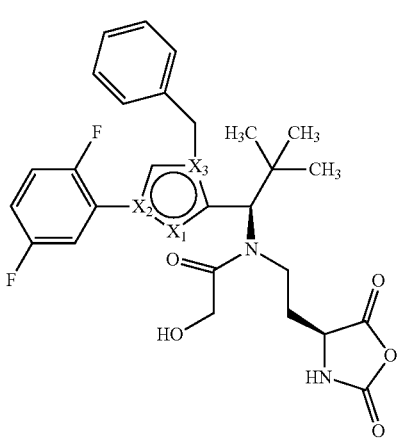

1097
-continued

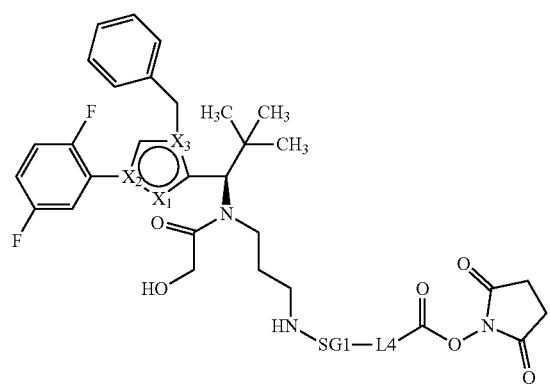

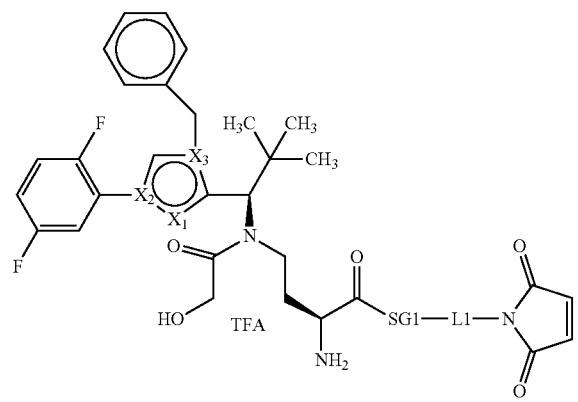

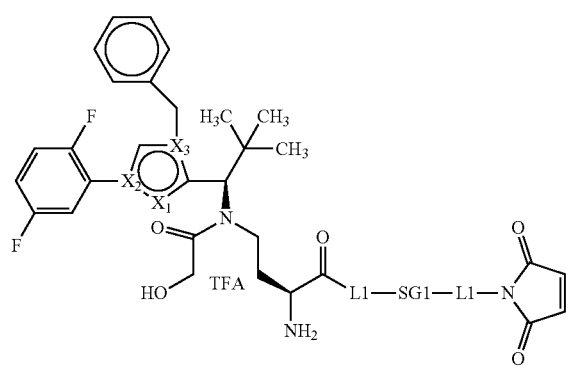

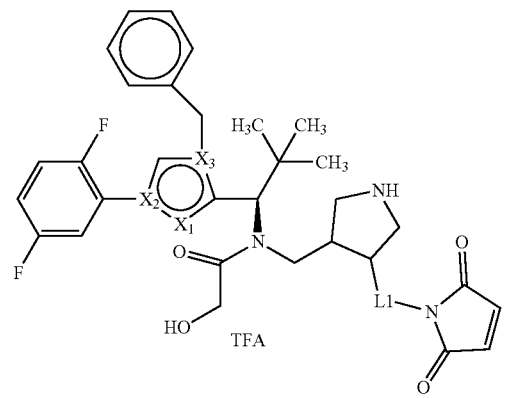

1098
-continued

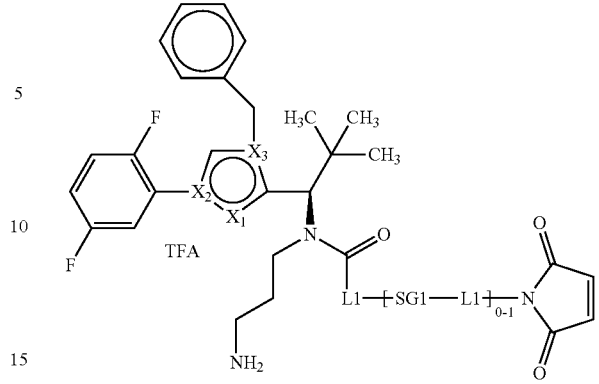

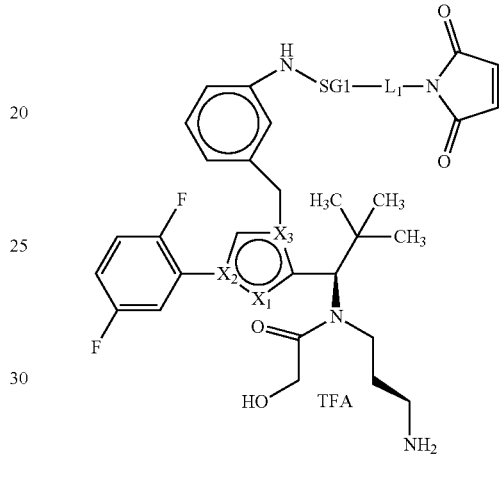

where R represents —H or —COOH,
where K represents straight-chain or branched optionally substituted by $C_1$-$C_6$-alkoxy or —OH $C_1$-$C_6$-alkyl, and where
$X_1$ represents N, $X_2$ represents N and $X_3$ represents C; or
$X_1$ represents CH or CF, $X_2$ represents C and $X_3$ represents N; or
$X_1$ represents NH, $X_2$ represents C and $X_3$ represents C; or
$X_1$ represents CH, $X_2$ represents N and $X_3$ represents C;
L1 represents —(NR$^{10}$)$_n$-(G1)$_o$-G2-
where R$^{10}$ represents H, NH$_2$ or $C_1$-$C_3$-alkyl;
G1 represents —NHCO— or

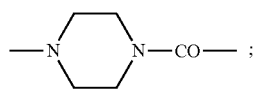

n is 0 or 1;
o is 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NMe-, —NHNH—, —SO$_2$NHNH—, —NHCO—, —CONH—, —CONHNH— and a 5- to 10-membered aromatic or non-aromatic heterocycle having up to 4 heteroatoms selected from the group consisting of N, O and S, —SO— or —SO$_2$—, where the side chains, if present, may be substituted by —NHCONH$_2$, —COOH, —OH, —NH$_2$, NH—CNNH$_2$, sulphonamide, sulphone, sulphoxide or sulphonic acid, or represents one of the groups below:

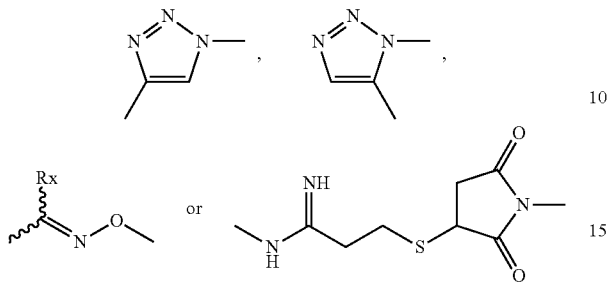

where Rx represents H, C$_1$-C$_3$-alkyl or phenyl;
L2 is represented by one or both of the formulae below:

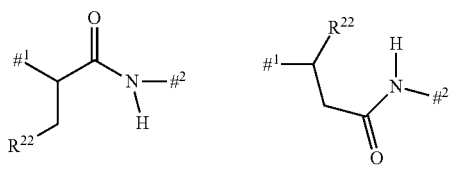

where #$^1$ denotes the point of attachment to the sulphur atom of the binder, #$^2$ denotes the point of attachment to group L1, R$^{22}$ represents COOH and more than 80% (based on the total number of bonds of the linker to the binder) of the bonds to the sulphur atom of the binder are present in one of these two structures;
L3 represents

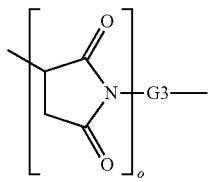

where
o is 0 or 1;
and
G3 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH— and a 5- to 10-membered aromatic or non-aromatic heterocycle having up to 4 heteroatoms selected from the group consisting of N, O and S, —NMe-, —NHNH—, —SO$_2$NHNH—, —CONHNH—, —SO— or —SO$_2$—, and
L4 is a single bond or a group —(CO)$_y$-G4-, where y represents 0 or 1, and G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, —SO$_2$, —NH—, —CO—, —NHCO—, —CONH—, —NMe-, —NHNH—, —SO$_2$NHNH—, —CONHNH— and a 5- to 10-membered aromatic or non-aromatic heterocycle having up to 4 heteroatoms selected from the group consisting of N, O and S, or —SO— or —SO$_2$—.

29. Compounds of the general formula (III):

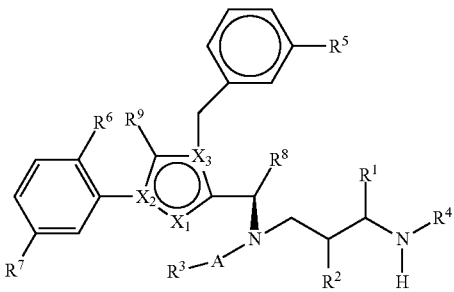

where
X$_1$ represents N, X$_2$ represents N and X$_3$ represents C, or X$_1$ represents CH, X$_2$ represents C and X$_3$ represents N or X$_1$ represents NH, X$_2$ represents C and X$_3$ represents C, or X$_1$ represents CH, X$_2$ represents N and X$_3$ represents C;

R$^1$ represents -L-BINDER, H or —(CH$_2$)$_{0-3}$Z, where Z represents —H, —NHY$^3$, —OY$^3$, —SY$^3$, halogen, —CO—NY$^1$Y$^2$ or —CO—OY$^3$, where Y$^1$ and Y$^2$ independently of one another represent H, NH$_2$, —(CH$_2$CH$_2$O)$_{0-3}$—(CH$_2$)$_{0-3}$Z' or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or —(CO—NH—CHY$^4$)$_{1-3}$COOH; where W represents H or OH;

where Y$^4$ independently of one another represents straight-chain or branched C$_{1-6}$-alkyl which is optionally substituted by —NHCONH$_2$, or represents aryl or benzyl which are optionally substituted by —NH$_2$;

R$^2$ and R$^4$ independently of one another represent -L-BINDER, H, —CO—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—, where R$^{10}$ represents L-#$^1$, H, NH$_2$, SO$_3$H, COOH, SH or OH, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

where Y$^4$ independently of one another represents straight-chain or branched C$_{1-6}$ alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;

A represents CO, SO, SO$_2$, SO$_2$NH or CNNH;
R$^3$ represents -L-BINDER or an optionally substituted alkyl, aryl, heteroaryl, heteroalkyl, heterocycloalkyl group;
R$^5$ represents -L-BINDER, H, F, NH$_2$, NO$_2$, halogen, SH or —(CH$_2$)$_{0-3}$Z, where Z represents —H, halogen, —OY$^3$, —SY$^3$, —NHY$^3$, —CO—NY$^1$Y$^2$ or —CO—OY$^3$, where $Y^1$ and $Y^2$ independently of one another represent H, $NH_2$ or $-(CH_2)_{0-3}Z'$, and $Y^3$ represents H or $-(CH_2)_{0-3}Z'$, where $Z'$ represents H, $SO_3H$, $NH_2$ or COOH;

where L represents a linker and BINDER represents a binder or a derivative thereof, where the binder may optionally be attached to a plurality of active compound molecules, $R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen, $R^8$ represents (optionally fluorinated) $C_{1-10}$-alkyl, (optionally fluorinated) $C_{4-10}$-cycloalkyl or optionally substituted oxetane; and $R^9$ represents H, F, $CH_3$, $CF_3$, $CH_2F$ or $CHF_2$;

and the salts, solvates and salts of the solvates thereof.

30. Compounds of the general formula (IV):

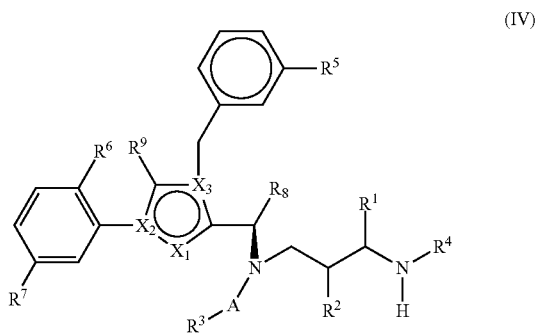

(IV)

where $X_1$ represents CH, $X_2$ represents C and $X_3$ represents N;

$R^1$ represents -L-BINDER, H or $-(CH_2)_{0-3}Z$, where Z represents $-H$, $-NHY^3$, $-OY^3$, $-SY^3$, halogen, $-CO-NY^1Y^2$ or $-CO-OY^3$, where $Y^1$ and $Y^2$ independently of one another represent H, $NH_2$, $-(CH_2CH_2O)_{0-3}-(CH_2)_{0-3}Z'$ or $-CH(CH_2W)Z'$, and $Y^3$ represents H or $-(CH_2)_{0-3}Z'$, where $Z'$ represents H, $NH_2$, $SO_3H$, COOH, $-NH-CO-CH_2-CH_2-CH(NH_2)COOH$ or $-(CO-NH-CHY^4)_{1-3}COOH$; where W represents H or OH;

where $Y^4$ independently of one another represents straight-chain or branched $C_{1-6}$-alkyl which is optionally substituted by $-NHCONH_2$, or represents aryl or benzyl which are optionally substituted by $-NH_2$;

$R^2$ and $R^4$ independently of one another represent -L-BINDER, H, $-CO-CHY^4-NHY^5$ or $-(CH_2)_{0-3}Z$, or $R^2$ and $R^4$ together (with formation of a pyrrolidine ring) represent $-CH_2-CHR^{10}-$ or $-CHR^{10}-CH_2-$, where $R^{10}$ represents L-#$^1$, H, $NH_2$, $SO_3H$, COOH, SH or OH, where Z represents $-H$, halogen, $-OY^3$, $-SY^3$, $NHY^3$, $-CO-NY^1Y^2$ or $-CO-OY^3$, where $Y^1$ and $Y^2$ independently of one another represent H, $NH_2$ or $-(CH_2)_{0-3}Z'$, and $Y^3$ represents H or $-(CH_2)_{0-3}Z'$, where $Z'$ represents H, $SO_3H$, $NH_2$ or COOH;

where $Y^4$ independently of one another represents straight-chain or branched $C_{1-6}$ alkyl which is optionally substituted by $-NHCONH_2$, or represents aryl or benzyl which are optionally substituted by $-NH_2$, and $Y^5$ represents H or $-CO-CHY^6-NH_2$, where $Y^6$ represents straight-chain or branched $C_{1-6}$-alkyl;

A represents CO, SO, $SO_2$, $SO_2NH$ or CNNH;

$R^3$ represents -L-BINDER or an optionally substituted alkyl, aryl, heteroaryl, heteroalkyl or heterocycloalkyl group;

$R^5$ represents -L-BINDER, H, F, $NH_2$, $NO_2$, halogen, SH or $-(CH_2)_{0-3}Z$, where Z represents $-H$, halogen, $-OY^3$, $-SY^3$, $-NHY^3$, $-CO-NY^1Y^2$ or $-CO-OY^3$, where $Y^1$ and $Y^2$ independently of one another represent H, $NH_2$ or $-(CH_2)_{0-3}Z'$, and $Y^3$ represents H or $-(CH_2)_{0-3}Z'$, where $Z'$ represents H, $SO_3H$, $NH_2$ or COOH;

where L represents a linker and BINDER represents a binder or a derivative thereof, where the binder may optionally be attached to a plurality of active compound molecules, $R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen, $R^8$ represents (optionally fluorinated) $C_{1-10}$-alkyl, (optionally fluorinated) $C_{4-10}$-cycloalkyl or optionally substituted oxetane; and $R^9$ represents H, F, $CH_3$, $CF_3$, $CH_2F$ or $CHF_2$;

and the salts, solvates and salts of the solvates thereof.

31. The compound according to claim 30 where the compound has one of the formulae below:

N-(3-aminopropyl)-N-{(1R)-1-[4-benzyl-1-(2,5-difluorophenyl)-1H-pyrazol-3-yl]-2,2-dimethylpropyl}-2-hydroxyacetamide;

N-(3-aminopropyl)-N-{(1R)-1-[1-benzyl-4-(2,5-difluorophenyl)-1H-pyrrol-2-yl]-2,2-dimethylpropyl}-2-hydroxyacetamide;

(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1);

N-(3-aminopropyl)-N-{(1S)-1-[1-benzyl-4-(2,5-difluorophenyl)-1H-pyrrol-2yl]-2,2-dimethylpropyl}acetamide;

(15S,19R)-15-amino-19-[1-benzyl-4-(2,5-difluorophenyl)-1H-imidazol-2-yl]-18-glycoloyl-20,20-dimethyl-14-oxo-4,7,10-trioxa-13,18-diazahenicosan-1-oic acid;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-valyl-$N^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-L-alanyl-$N^5$-carbamoyl-L-ornithine;

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl-4-amino-L-phenylalanine;

N-{(1R)-1-[1-(3-aminobenzyl)-4-(2,5-difluorophenyl)-1H-imidazol-2-yl]-2,2-dimethylpropyl}-N-(3-aminopropyl)-2-hydroxyacetamide (1:1);

(2S)-2-amino-4-[{(1R)-1-[1-benzyl-4-(2,5-difluorophenyl)-1H-imidazol-2-yl]-2,2-dimethylpropyl}(glycoloyl)amino]butanoic acid;

N-[(3S)-3-amino-4-hydrazino-4-oxobutyl]-N-{(1R)-1-[1-benzyl-4-(2,5-difluorophenyl)-1H-imidazol-2-yl]-2,2-dimethylpropyl}-2-hydroxyacetamide (1:1);

N-{(1R)-1-[1-benzyl-4-(2,5-difluorophenyl)-1H-imidazol-2-yl]-2,2-dimethylpropyl}-N-[(3S)-3,4-diaminobutyl]-2-hydroxyacetamide (1:1);

N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanine;

(2S)-2-amino-N-(2-aminoethyl)-4-[{(1R)-1-[1-benzyl-4-(2,5-difluorophenyl)-1H-imidazol-2-yl]-2,2-dimethylpropyl}(glycoloyl)amino]butanamide (2:1);

(1-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}hydrazino)acetic acid;

N-[3-amino-2-(sulphanylmethyl)propyl]-N-{(1R)-1-[1-benzyl-4-(2,5-difluorophenyl)-1H-imidazol-2-yl]-2,2-dimethylpropyl}-2-hydroxyacetamide hydrochloride (1:1);

4-amino-N-(3-aminopropyl)-N-{(1R)-1-[1-benzyl-4-(2,5-difluorophenyl)-1H-imidazol-2-yl]-2,2-dimethylpropyl}benzamide (2:1);

N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

L-valyl-N-{3-[{(1R)-1-[1-benzyl-4-(2,5-difluorophenyl)-1H-imidazol-2-yl]-2,2-dimethylpropyl}(glycoloyl)amino]propyl}-N5-carbamoyl-L-ornithinamide (1:1);

N-(3-aminopropyl)-N-{(1S)-1-[1-benzyl-4-(2,5-difluorophenyl)-1H-pyrrol-2-yl]-2,2-dimethylpropyl}-2-hydroxyacetamide;

S-(1-{2-[(N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-2,5-dioxopyrrolidin-3-yl]-L-cysteine;

N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N⁵-carbamoyl-L-ornithinamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-2,5-dioxopyrrolidin-3-yl]-L-cysteine; N-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-beta-alanyl-L-alanyl-N-[4-(3-{[(2R)-2-amino-2-carboxyethyl]sulphanyl}-2,5-dioxopyrrolidin-1-yl)phenyl]-N⁵-carbamoyl-L-ornithinamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

N-[6-(3-{[(2R)-2-amino-2-carboxyethyl]sulphanyl}-2,5-dioxopyrrolidin-1-yl)hexanoyl]-L-valyl-N⁵-carbamoyl-L-ornithyl-N⁶-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}-L-lysine;

S-[1-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-2,5-dioxopyrrolidin-3-yl]-L-cysteine;

S-(2-{[2-({(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}amino)ethyl]amino}-2-oxoethyl)-L-cysteine;

S-{1-[6-(2-{(2S)-2-amino-4-[{(1R)-1-[4-benzyl-1-(2,5-difluorophenyl)-1H-pyrazol-3-yl]-2,2-dimethylpropyl}(glycoloyl)amino]butanoyl}hydrazino)-6-oxohexyl]-2,5-dioxopyrrolidin-3-yl}-L-cysteine;

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine;

S-{(3R/S)-1-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-2,5-dioxopyrrolidin-3-yl}-L-cysteine;

N-[19-(3(R/S)-{[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-imidazol-2-yl]-2,2-dimethylpropyl}amino]-2-oxoethyl}homocysteine;

S-[(3R/S)-1-(2-{[6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)hexanoyl]amino}ethyl)-2,5-dioxopyrrolidin-3-yl]-L-cysteine;

S-{1-[2-({[(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine;

S-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine;

N⁶-(N-{(2S)-2-amino-4-[{(1R)-1-[1-benzyl-4-(2,5-difluorophenyl)-1H-imidazol-2-yl]-2,2-dimethylpropyl}(glycoloyl)amino]butanoyl}-D-alanyl)-L-lysine;

N⁶-(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N²-{N-[6-(3-{[(2R)-2-amino-2-carboxyethyl]sulphanyl}-2,5-dioxopyrrolidin-1-yl)hexanoyl]-L-valyl-L-alanyl}-L-lysine;

N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine;

N⁶-(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine;

N-(3-aminopropyl)-N-{(1R)-1-[4-benzyl-1-(2,5-difluorophenyl)-1H-pyrazol-3-yl]-2,2-dimethylpropyl}acetamide;

N-(3-aminopropyl)-N-{(1R)-1-[4-benzyl-1-(2,5-difluoro-phenyl)-1H-pyrazol-3-yl]-2,2-dimethylpropyl}-2-methoxyacetamide;

N-(3-aminopropyl)-N-{(1R)-1-[4-benzyl-1-(2,5-difluoro-phenyl)-1H-pyrazol-3-yl]-2,2-dimethylpropyl}-2,4-difluorobenzamide;

N-(3-aminopropyl)-N-{(1R)-1-[4-benzyl-1-(2,5-difluoro-phenyl)-1H-pyrazol-3-yl]-2,2-dimethylpropyl}-4-methylbenzamide;

N-(3-aminopropyl)-N-{(1R)-1-[4-benzyl-1-(2,5-difluoro-phenyl)-1H-pyrazol-3-yl]-2,2-dimethylpropyl}-2-ethoxyacetamide;

N-(3-aminopropyl)-N-{(1R)-1-[1-benzyl-4-(2,5-difluoro-phenyl)-1H-pyrrol-2-yl]-2,2-dimethylpropyl}-3,3,3-trifluoropropanamide;

N-(3-aminopropyl)-N-{(1R)-1-[1-benzyl-4-(2,5-difluoro-phenyl)-1H-pyrrol-2-yl]-2,2-dimethylpropyl}-4-fluorobenzamide;

N-(3-aminopropyl)-N-{(1R)-1-[1-benzyl-4-(2,5-difluoro-phenyl)-1H-pyrrol-2-yl]-2,2-dimethylpropyl}acetamide;

N-(3-aminopropyl)-N-{(1R)-1-[1-benzyl-4-(2,5-difluoro-phenyl)-1H-pyrrol-2-yl]-2,2-dimethylpropyl}-4-(trifluoromethyl)benzamide;

N-(3-aminopropyl)-N-{(1R)-1-[4-benzyl-1-(2,5-difluoro-phenyl)-1H-pyrazol-3-yl]-2,2-dimethylpropyl}-2-ethoxyacetamide;

N-(3-aminopropyl)-N-{(1R)-1-[4-benzyl-1-(2,5-difluoro-phenyl)-1H-pyrazol-3-yl]-2,2-dimethylpropyl}-2-ethoxyacetamide;

(2S)-2-amino-4-[{(1R)-1-[1-benzyl-4-(2,5-difluorophe-nyl)-1H-pyrrol-2-yl]-2,2-dimethylpropyl} (glycoloyl)amino]butanoic acid;

(2S)-2-amino-N-(2-aminoethyl)-4-[{(1R)-1-[1-benzyl-4-(2,5-difluorophenyl)-1H-pyrrol-2-yl]-2,2-dimethylpropyl}(glycoloyl)amino]butanamide;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid;

N-{(2S)-2-amino-4-[{(1R)-1-[1-benzyl-4-(2,5-difluoro-phenyl)-1H-pyrrol-2-yl]-2,2-dimethylpropyl}(glycoloyl)amino]butanoyl}-beta-alanine;

N-{(2S)-2-amino-4-[{(1R)-1-[1-benzyl-4-(2,5-difluoro-phenyl)-1H-pyrrol-2-yl]-2,2-dimethylpropyl}(glycoloyl)amino]butanoyl}-L-serine;

N-{(2S)-2-amino-4-[{(1R)-1-[1-benzyl-4-(2,5-difluoro-phenyl)-1H-pyrrol-2-yl]-2,2-dimethylpropyl}(glycoloyl)amino]butanoyl}-L-alanine;

N-{(2S)-2-amino-4-[{(1R)-1-[1-benzyl-4-(2,5-difluoro-phenyl)-1H-pyrrol-2-yl]-2,2-dimethylpropyl}(glycoloyl)amino]butanoyl}glycine;

N-(3-aminopropyl)-N-{(1R)-1-[1-benzyl-4-(2,5-difluoro-phenyl)-1H-pyrrol-2-yl]-2,2-dimethylpropyl}-4-methylbenzamide;

N-(3-aminopropyl)-N-{(1R)-1-[1-benzyl-4-(2,5-difluoro-phenyl)-1H-pyrrol-2-yl]-2,2-dimethylpropyl}-4-(methylsulphanyl)benzamide;

(2S)—N-(3-aminopropyl)-N-{(1R)-1-[1-benzyl-4-(2,5-difluorophenyl)-1H-pyrrol-2-yl]-2,2-dimethylpropyl}-2-hydroxypropanamide;

N-(3-aminopropyl)-N-{(1R)-1-[1-benzyl-4-(2,5-difluoro-phenyl)-1H-pyrrol-2-yl]-2,2-dimethylpropyl}-2-(methylsulphanyl)acetamide;

(2S)—N-(3-aminopropyl)-N-{(1R)-1-[4-benzyl-1-(2,5-difluorophenyl)-1H-pyrazol-3-yl]-2,2-dimethylpropyl}-2-hydroxypropanamide;

methyl 4-[(3-aminopropyl){(1R)-1-[1-benzyl-4-(2,5-difluorophenyl)-1H-pyrrol-2-yl]-2,2-dimethylpropyl}amino]-4-oxobutanoate;

4-[(3-aminopropyl){(1R)-1-[1-benzyl-4-(2,5-difluoro-phenyl)-1H-pyrrol-2-yl]-2,2-dimethylpropyl}amino]-4-oxobutanoic acid;

(2R)-22-[(3R/S)-3-{[(2R)-2-amino-2-carboxyethyl]sul-phanyl}-2, 5-dioxopyrrolidin-1-yl]-2-[({2-[(3-amino-propyl){(1R)-1-[1-benzyl-4-(2,5-difluorophenyl)-1H-pyrrol-2-yl]-2,2-dimethylpropyl}amino]-2-oxoethyl}sulphanyl)methyl]-4,20-dioxo-7,10,13,16-tetraoxa-3,19-diazadocosan-1-oic acid;

4-amino-N-(3-aminopropyl)-N-{(1R)-1-[4-benzyl-1-(2,5-difluorophenyl)-1H-pyrazol-3-yl]-2,2-dimethylpropyl}benzamide;

N-acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine;

N-acetyl-S-[2-([3-(L-alanylamino)propyl]{(1R)-1-[1-benzyl-4-(2,5-difluorophenyl)-1H-pyrrol-2-yl]-2,2-dimethylpropyl}amino)-2-oxoethyl]-L-cysteine;

(2S)—N-(3-aminopropyl)-N-{(1R)-1-[1-benzyl-4-(2,5-difluorophenyl)-1H-pyrrol-2-yl]-2,2-dimethylpropyl}tetrahydrofuran-2-carboxamide;

3-({2-[(3-aminopropyl){(1R)-1-[1-benzyl-4-(2,5-difluoro-phenyl)-1H-pyrrol-2-yl]-2,2-dimethylpropyl}amino]-2-oxoethyl}sulphanyl)propanoic acid;

S-{2-[(3-aminopropyl){(1R)-1-[1-benzyl-4-(2,5-difluoro-phenyl)-1H-pyrrol-2-yl]-2,2-dimethylpropyl}amino]-2-oxoethyl}homocysteine;

4-amino-N-(3-aminopropyl)-N-{(1R)-1-[1-benzyl-4-(2,5-difluorophenyl)-1H-pyrrol-2-yl]-2,2-dimethylpropyl}benzamide;

4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid.

32. Pharmaceutical composition comprising a conjugate according to claim 1 in combination with an inert non-toxic pharmaceutically suitable auxiliary.

33. The conjugate according to claim 1 where $R^{3a}$ or $R^3$ represents -L-BINDER or a substituted alkyl, aryl or heteroaryl group.

34. The method for the treatment and/or prophylaxis of hyperproliferative and/or angiogenic disorders in humans and animals comprising administering an effective amount of at least one conjugate according to claim 1 to a human or animal in need thereof.

35. An antibody drug conjugate (ADC) according to one of the formulae below, where n is a A number from 1 to 20 and $AK_{1A}$ and $AK_{2A}$ represent the antibody:

1107                                   1108
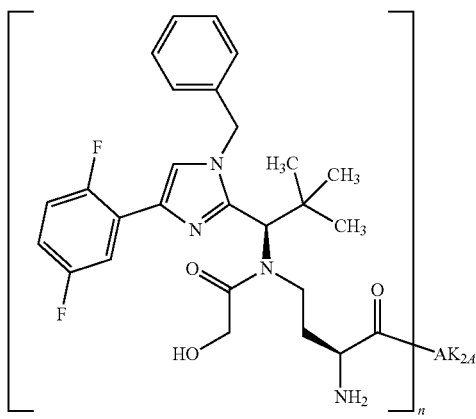
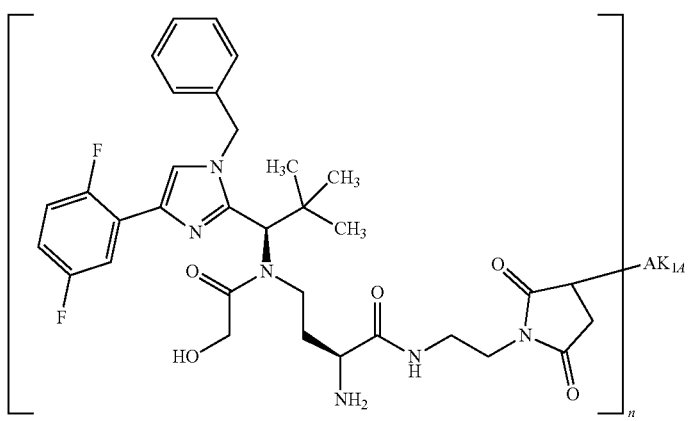
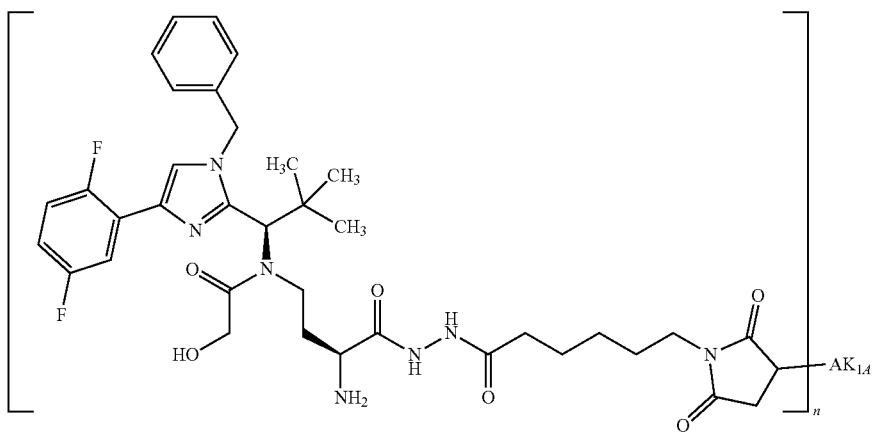
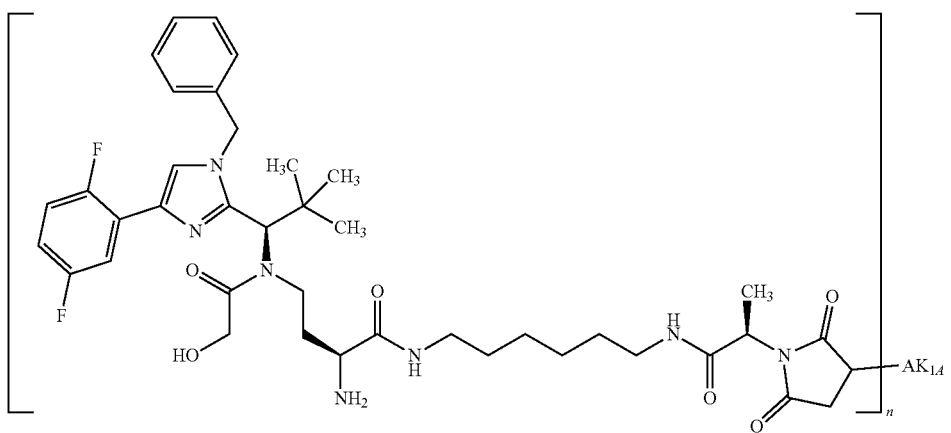

-continued
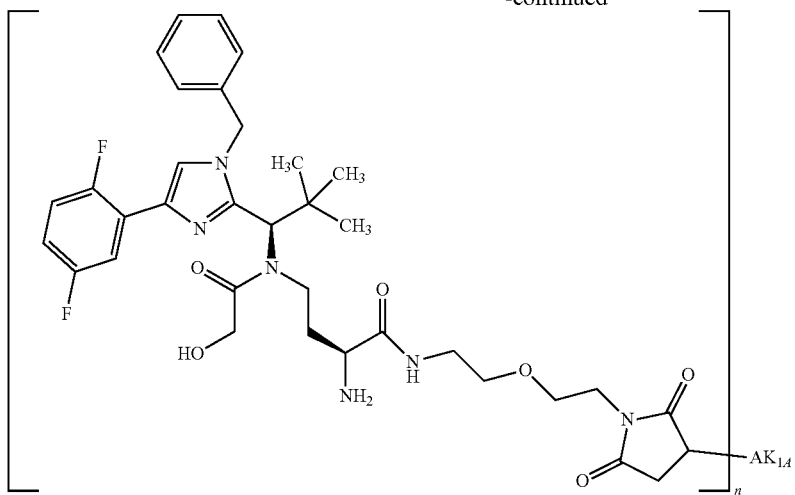
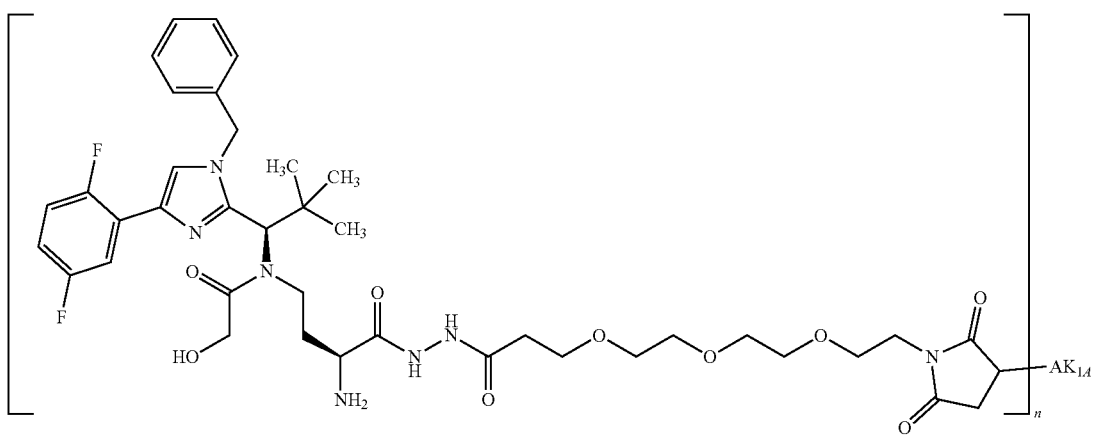
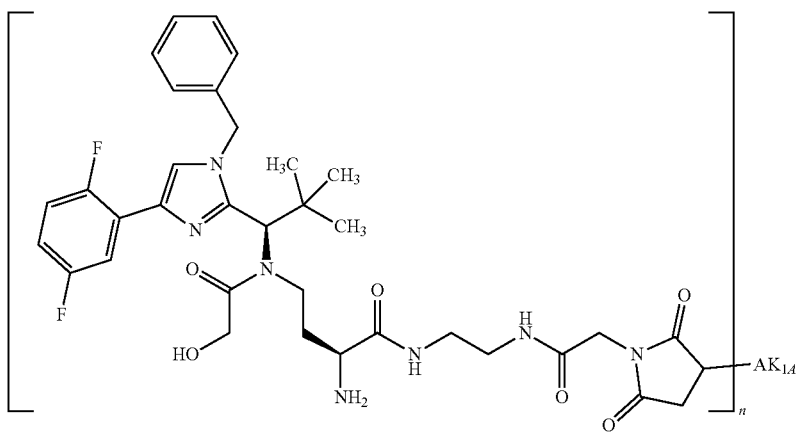

1111 1112
-continued
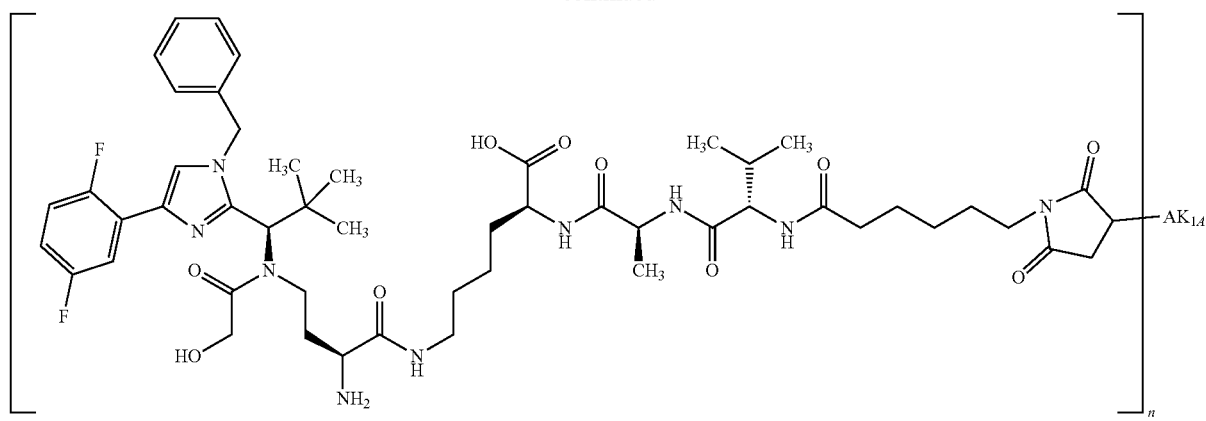
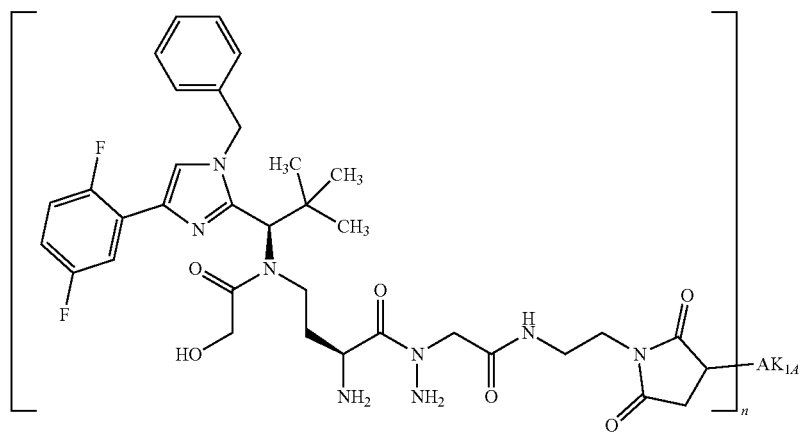
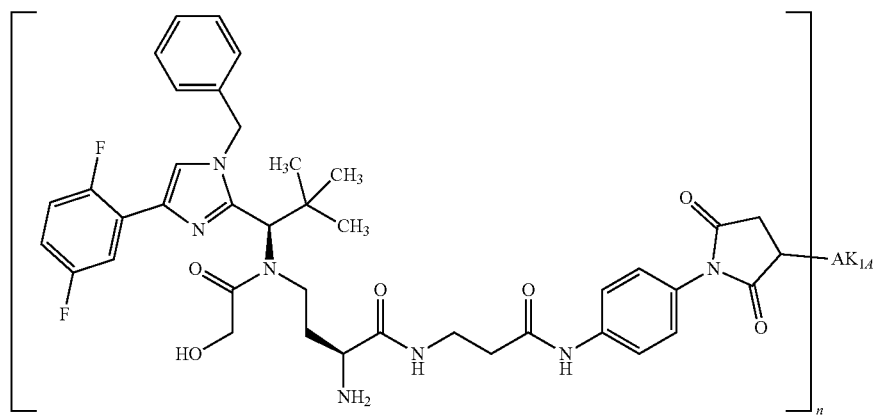
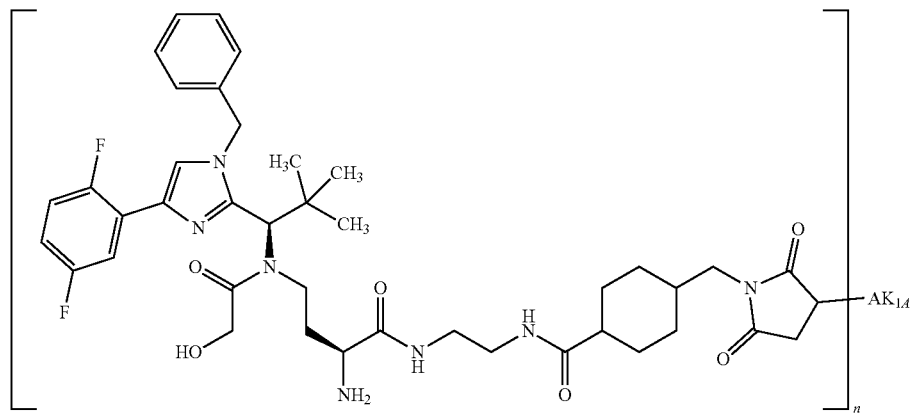

1113
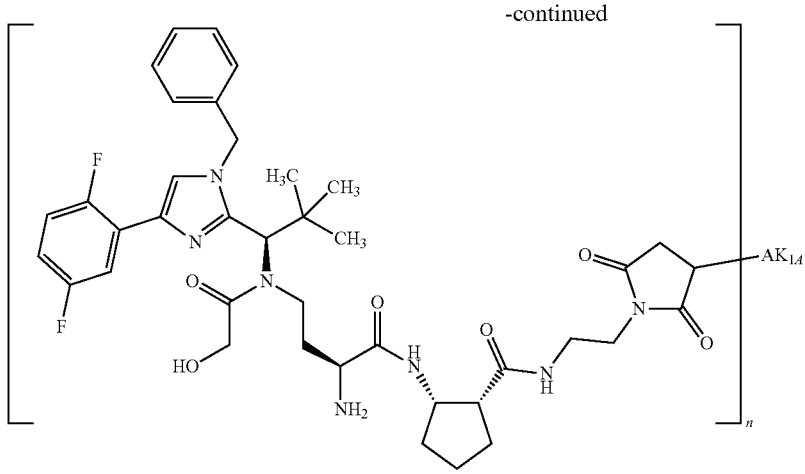
1114
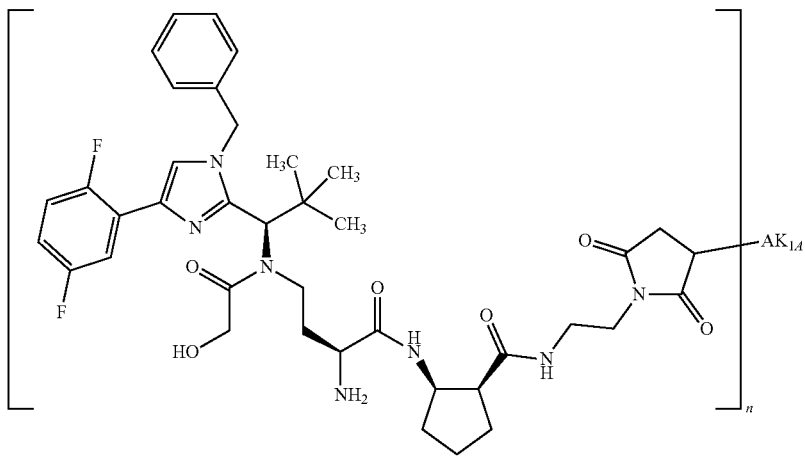
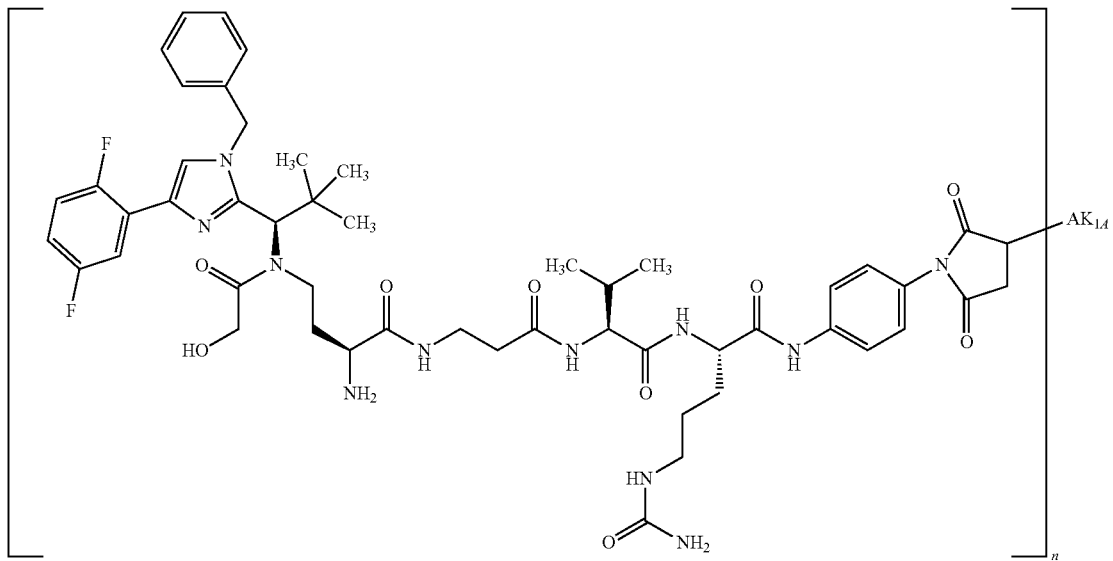

1115 1116
-continued
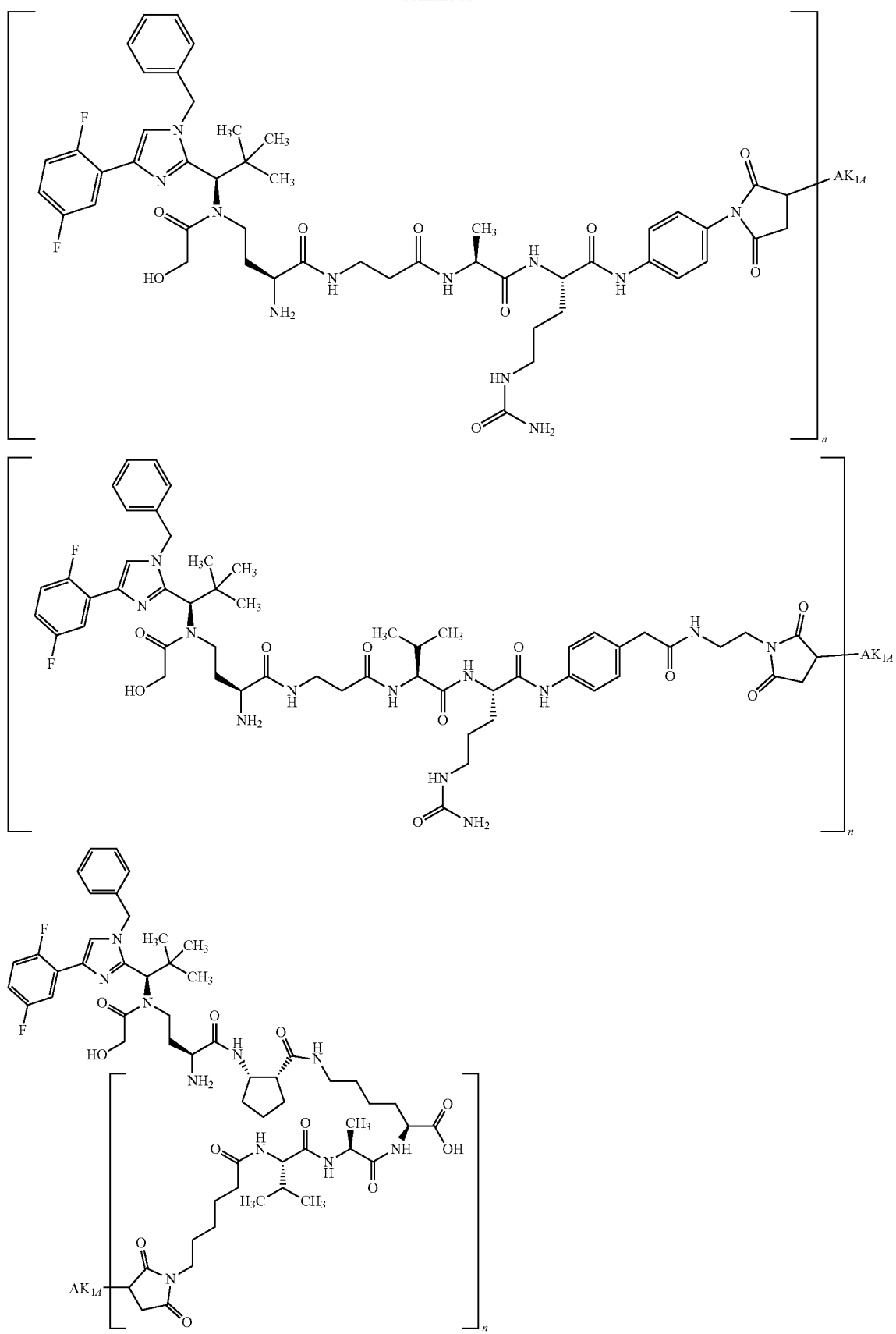

1117 1118
-continued
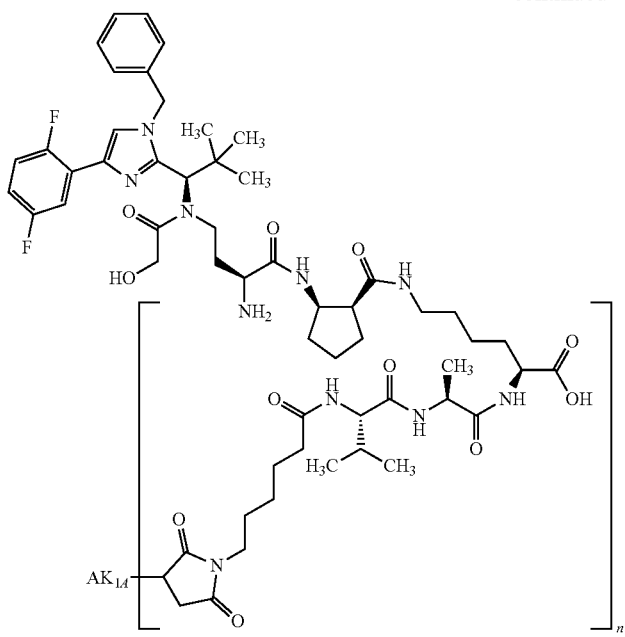
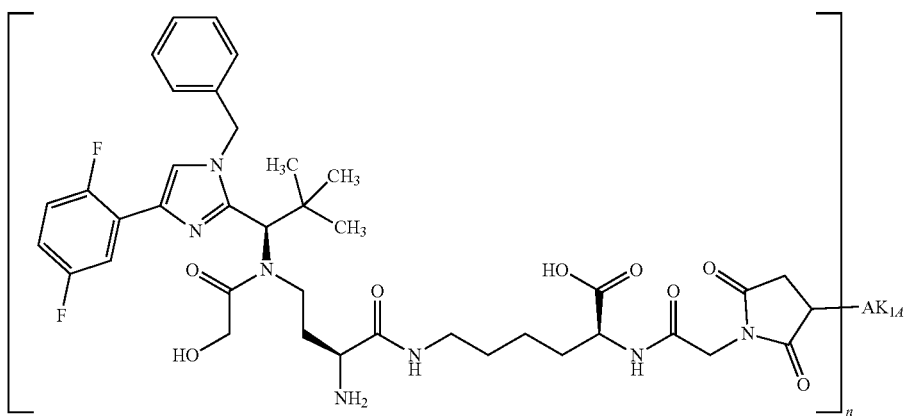
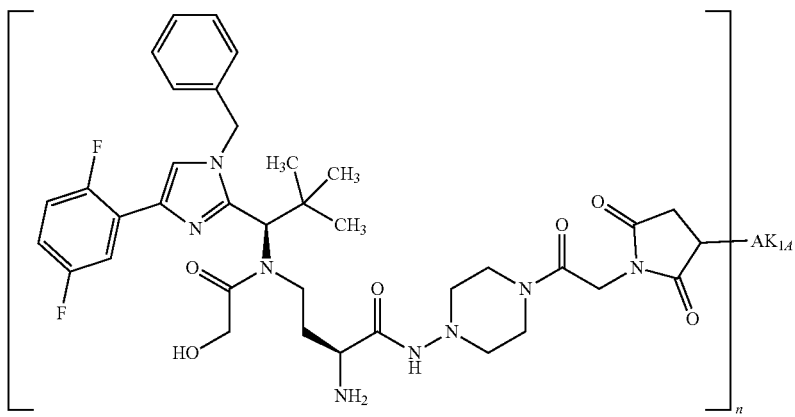

1119
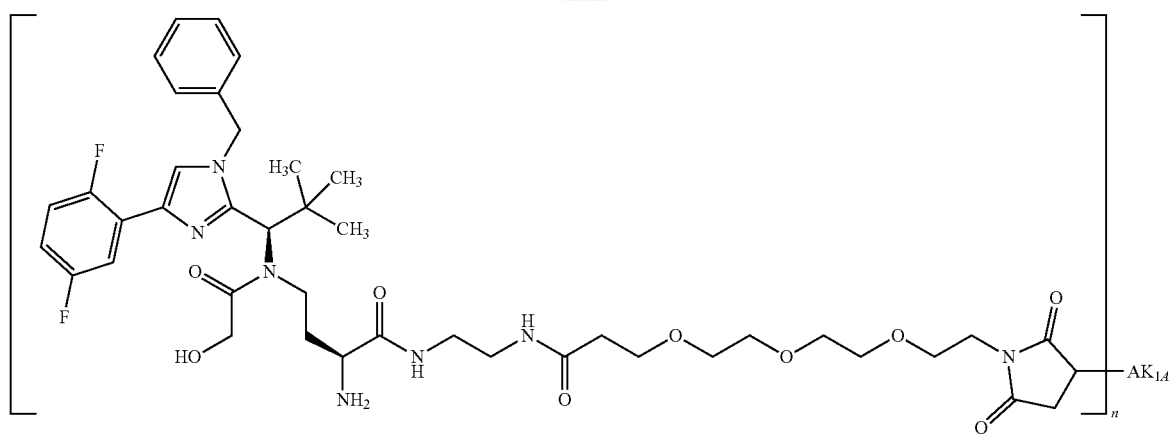
1120
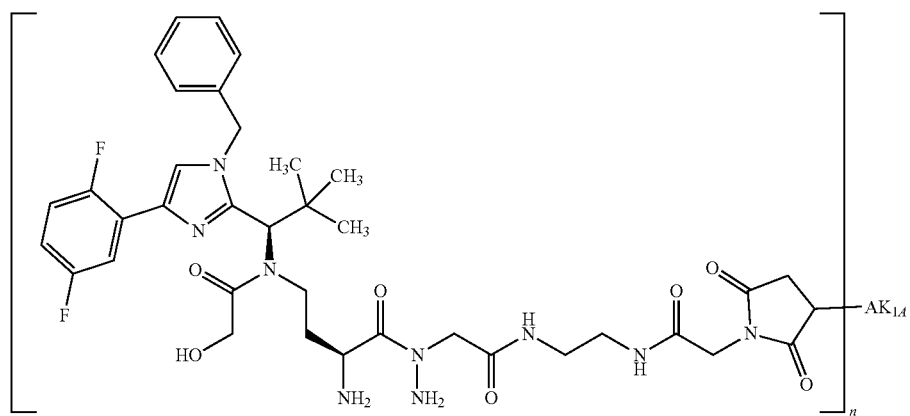
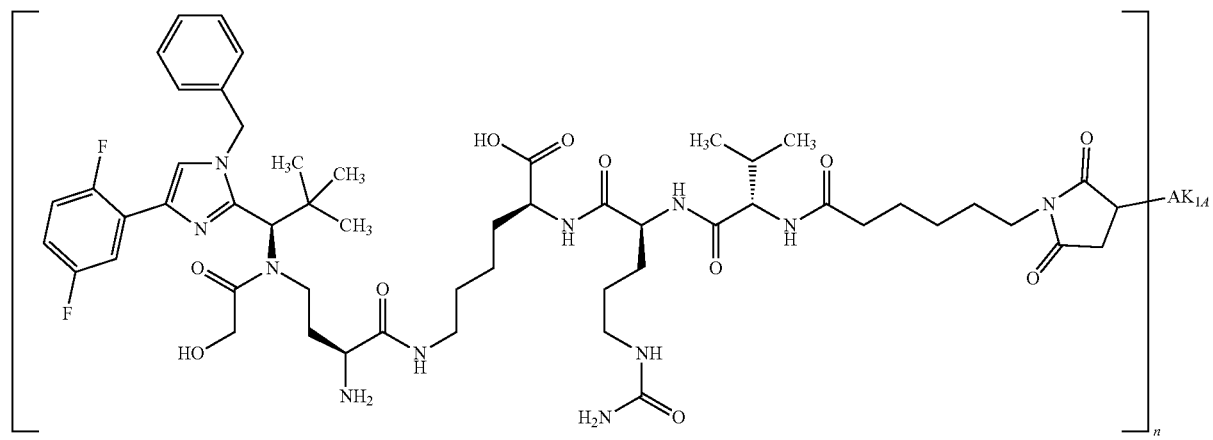

1121 1122
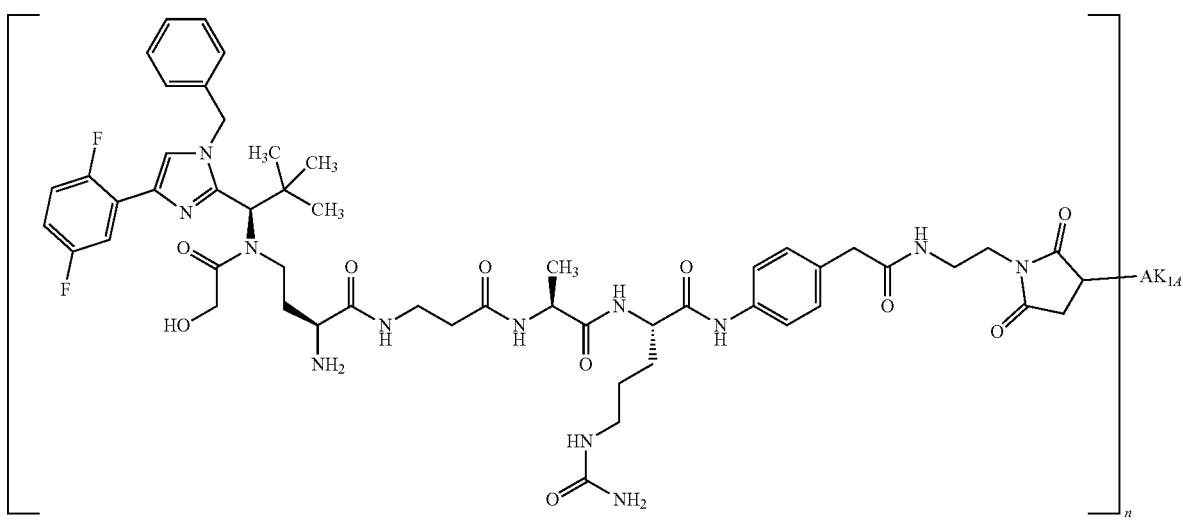
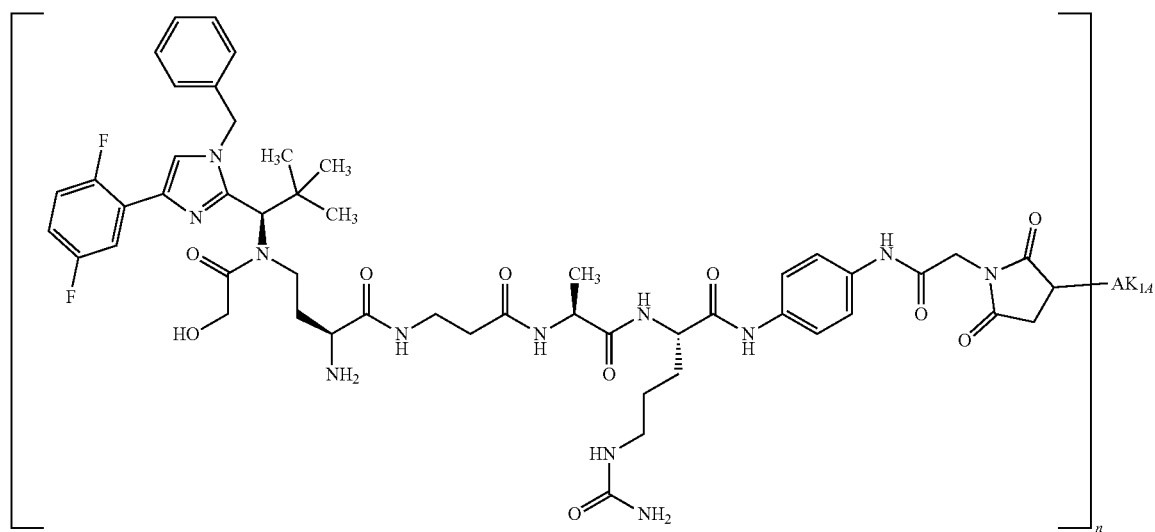
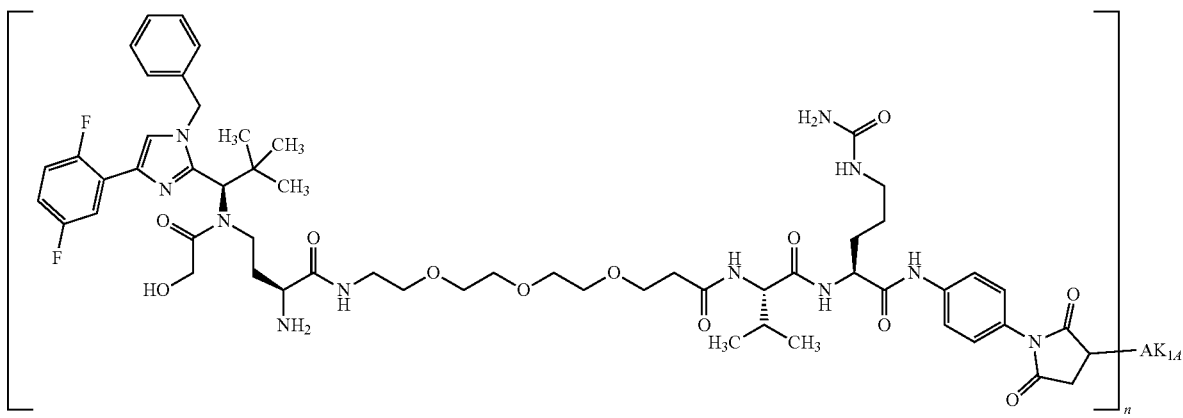

-continued
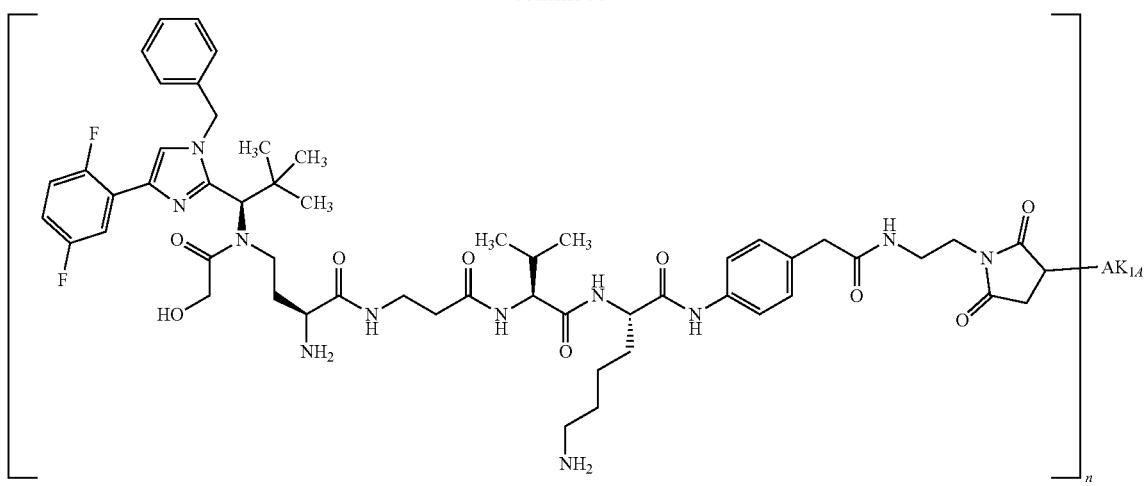
1123
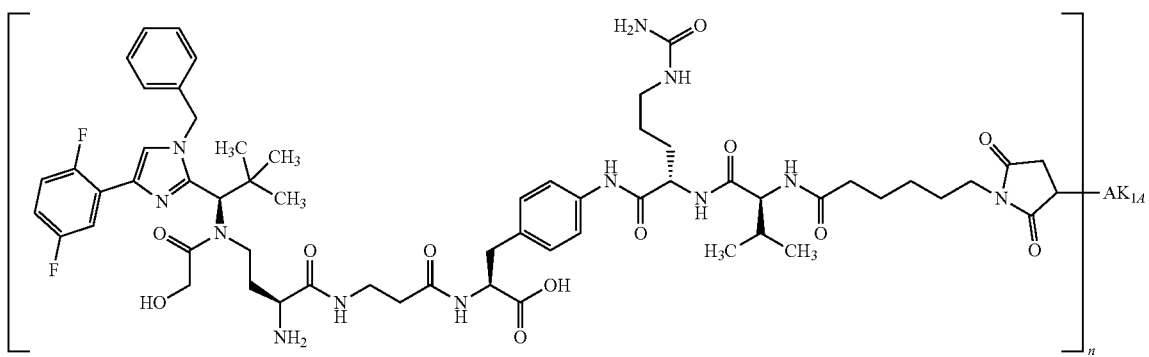
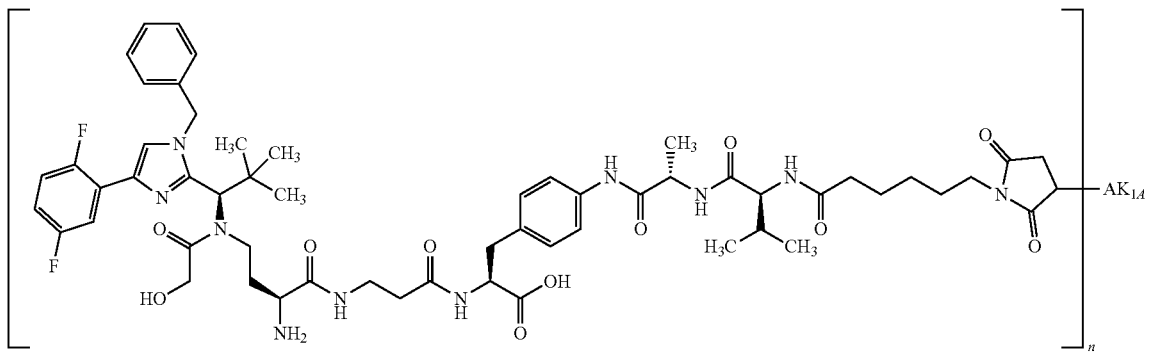
1124
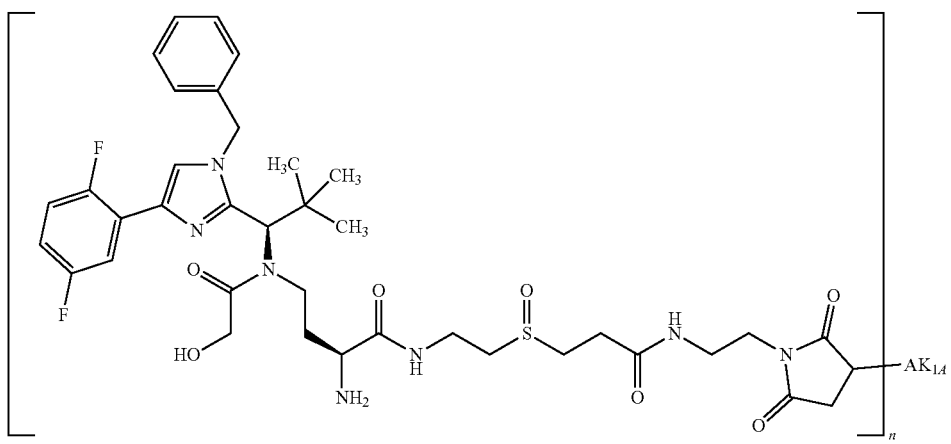

-continued
1125
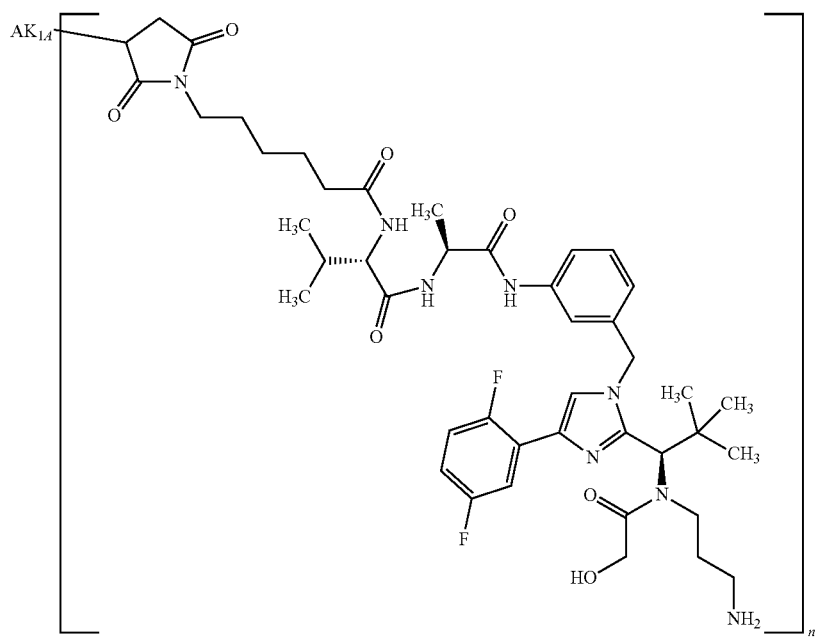
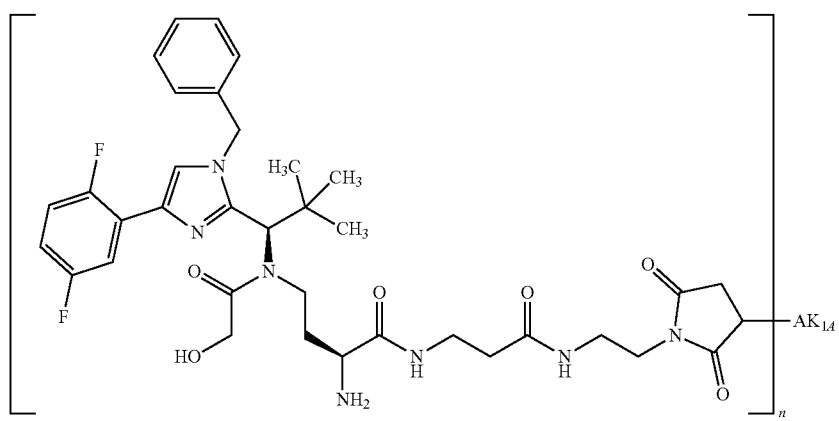
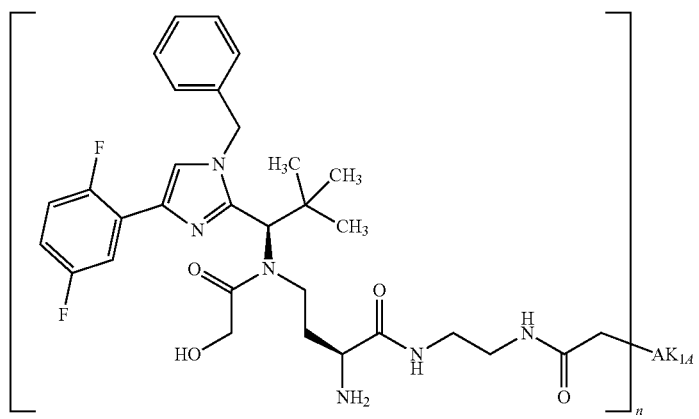

-continued
1127
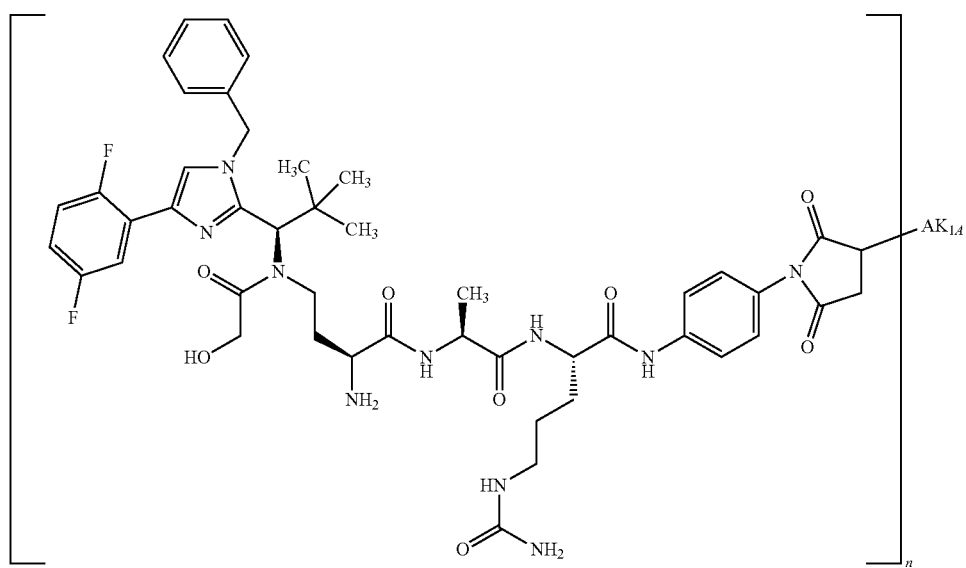
1128
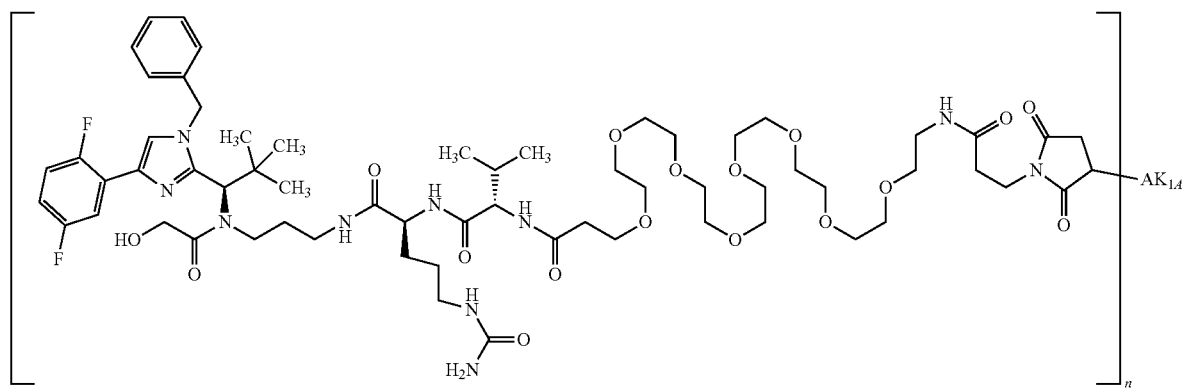
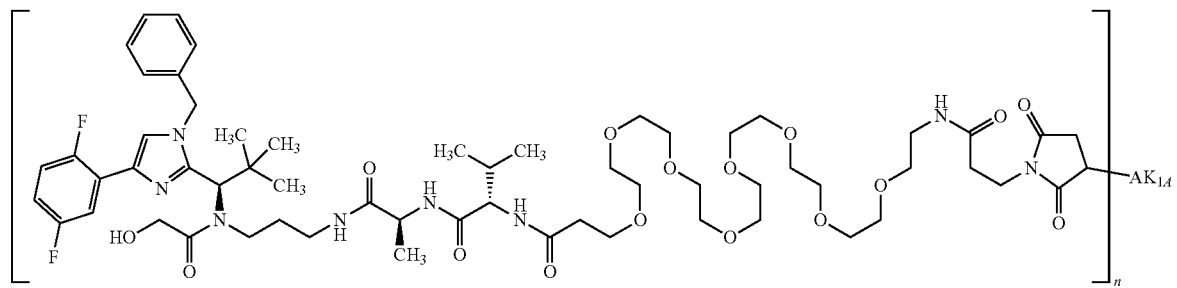

1129 1130
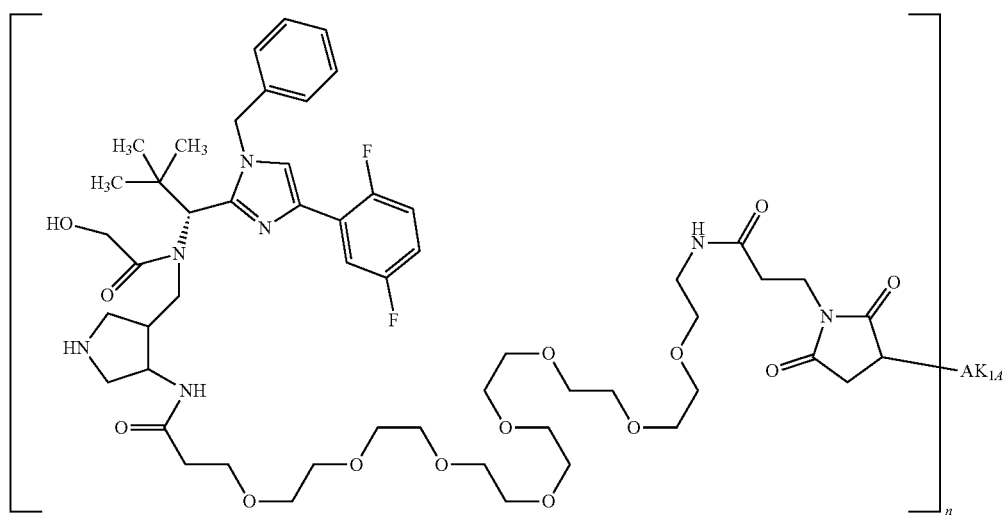
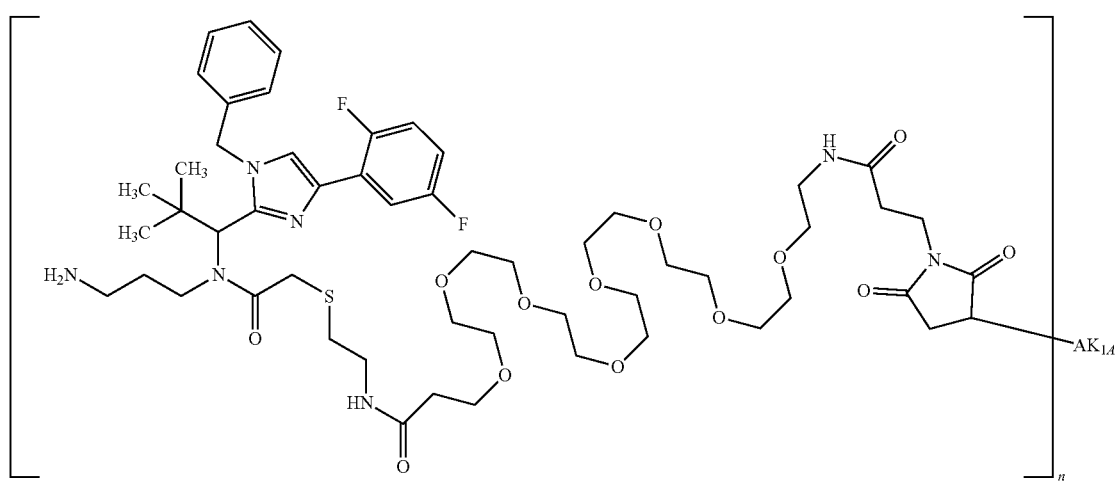
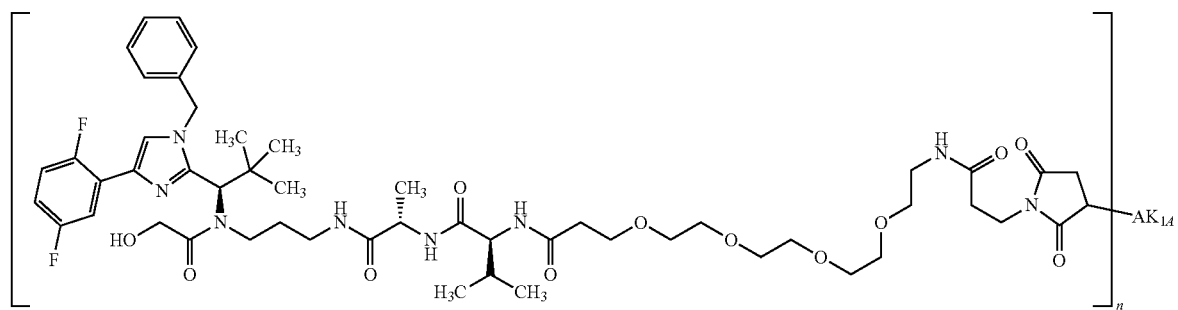

-continued
1131
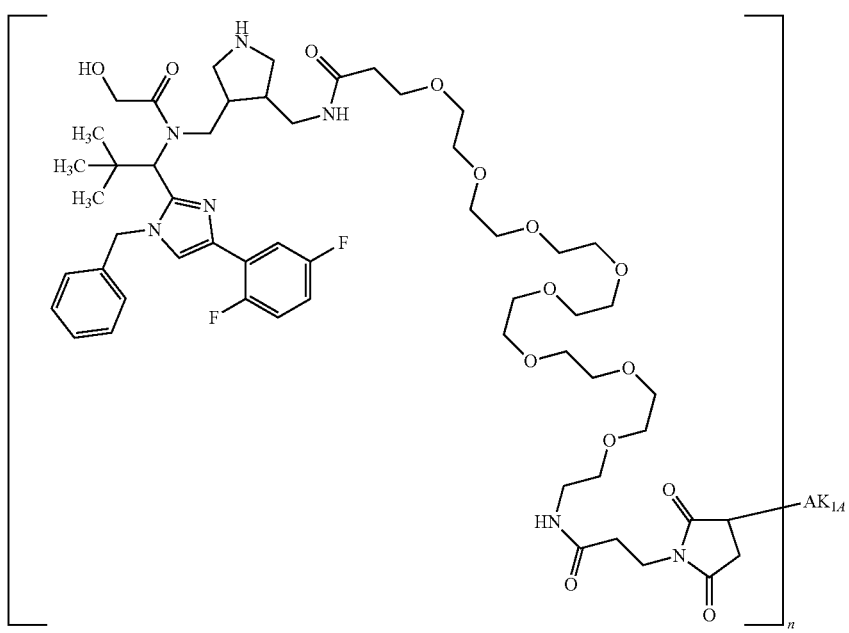
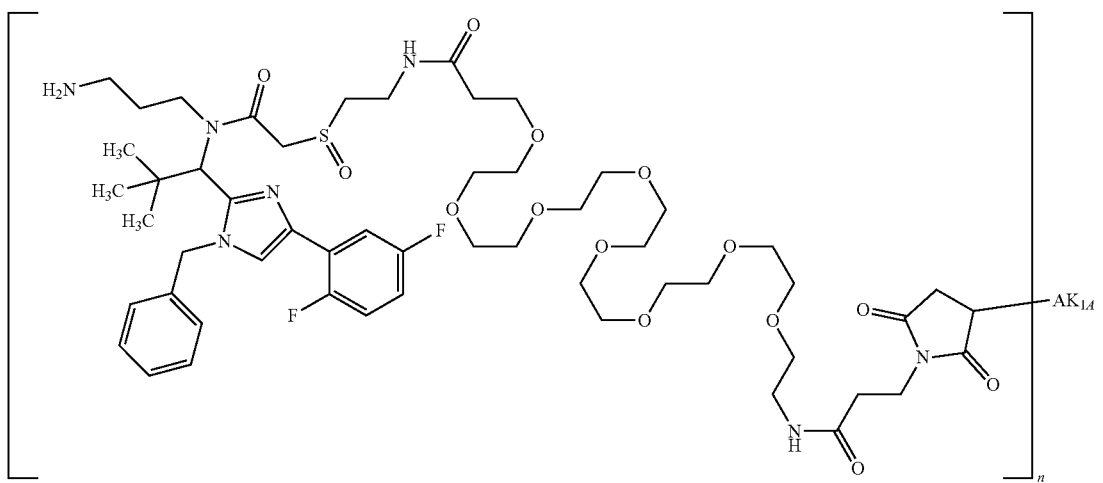
1132
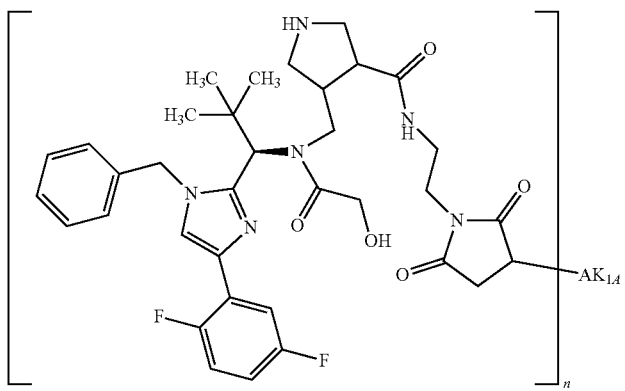

1133
1134
-continued
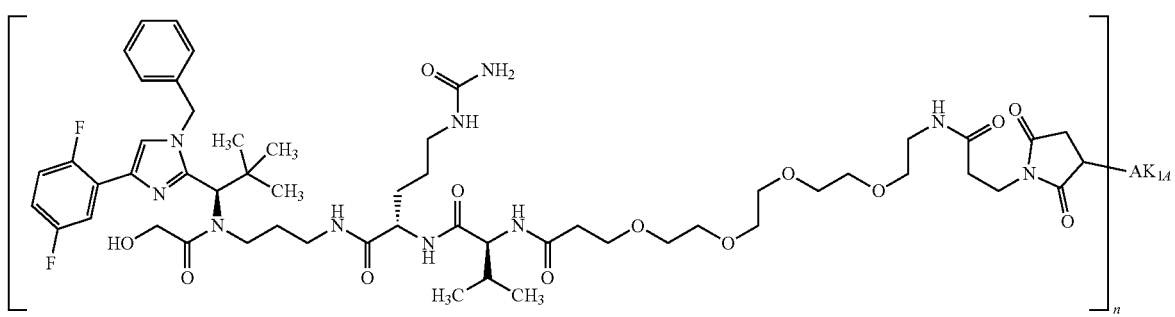
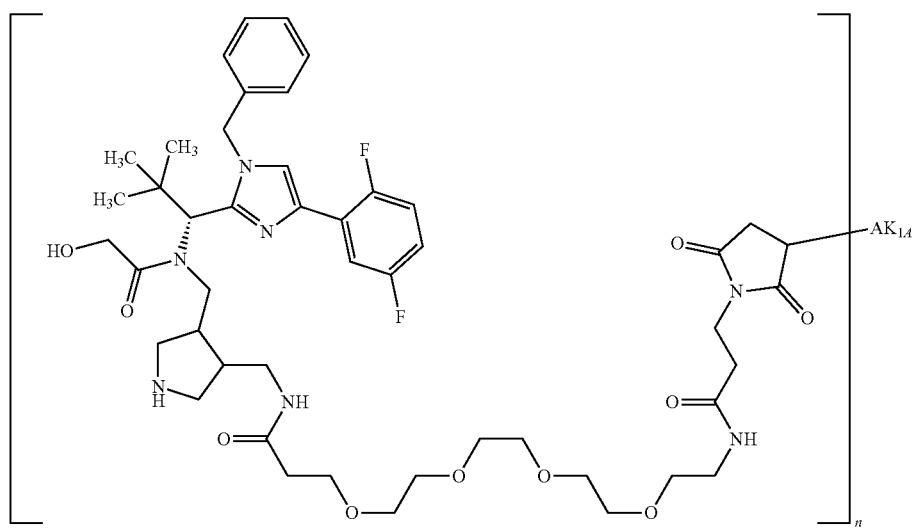
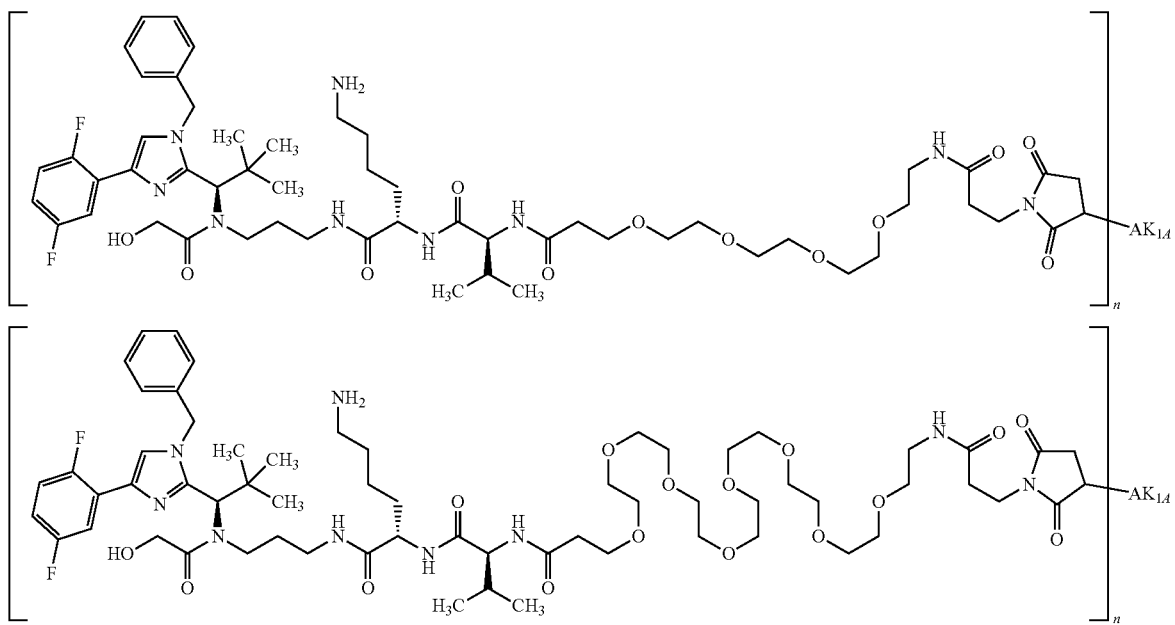

1135
-continued
1136
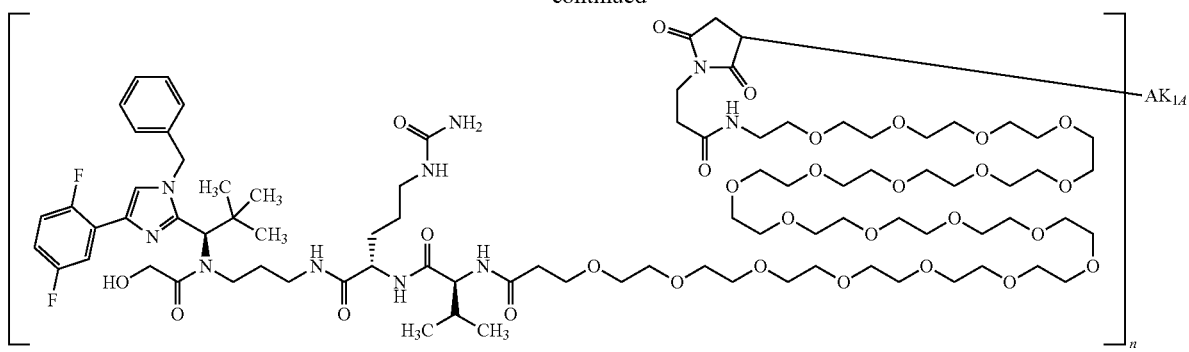
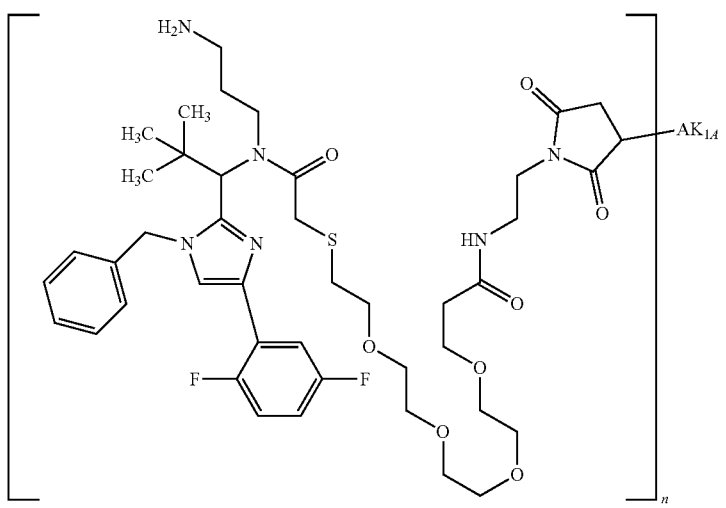
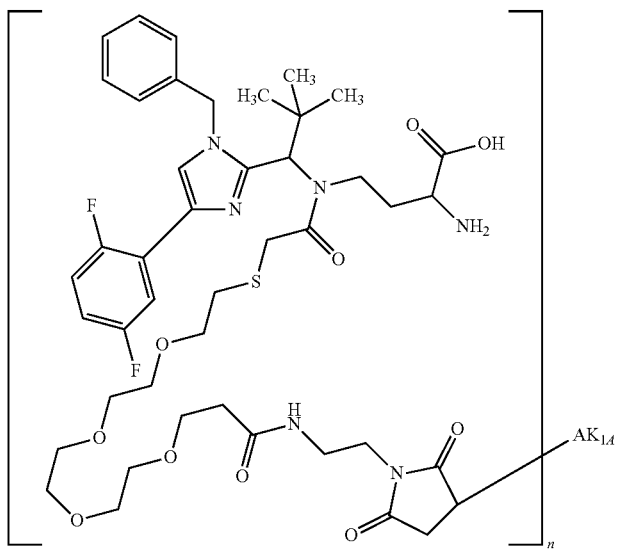

1137
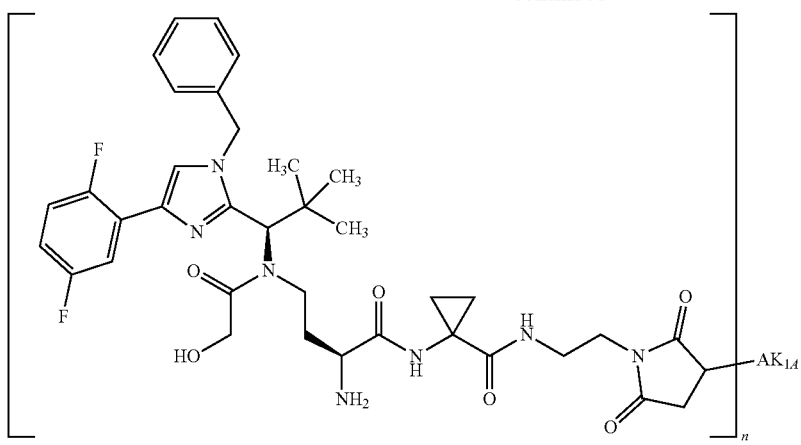
1138
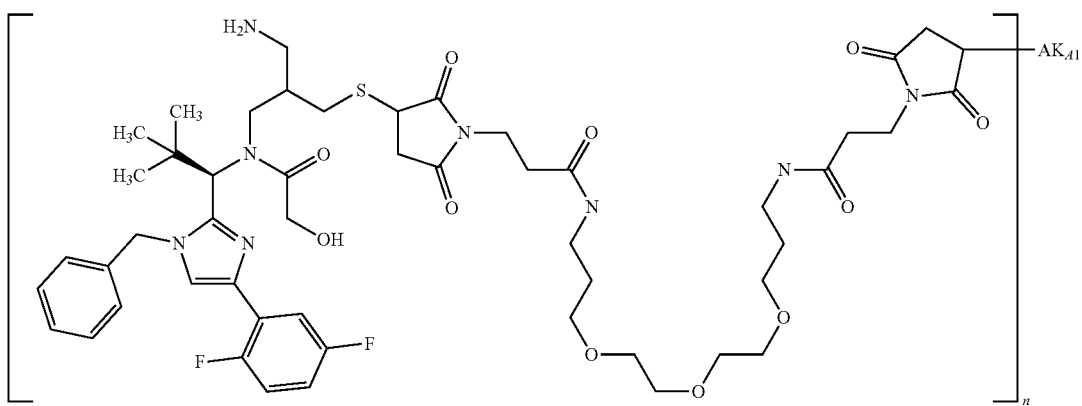
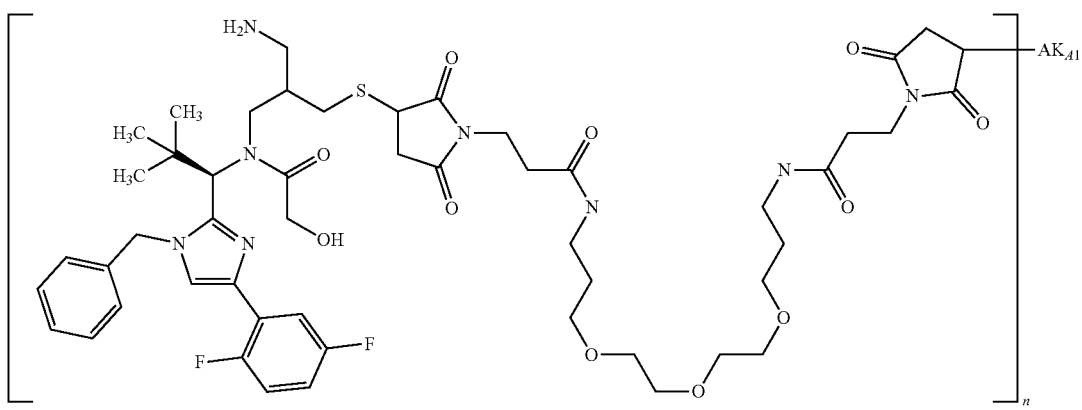
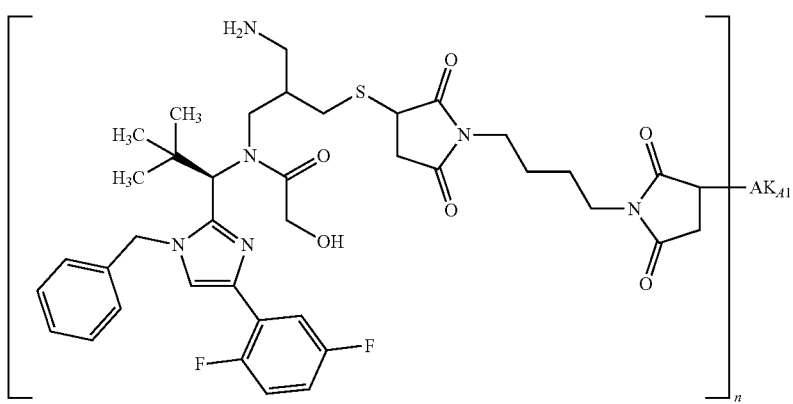

-continued
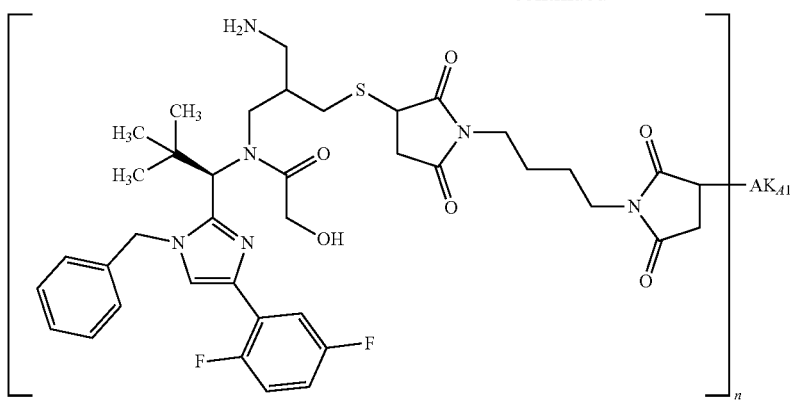
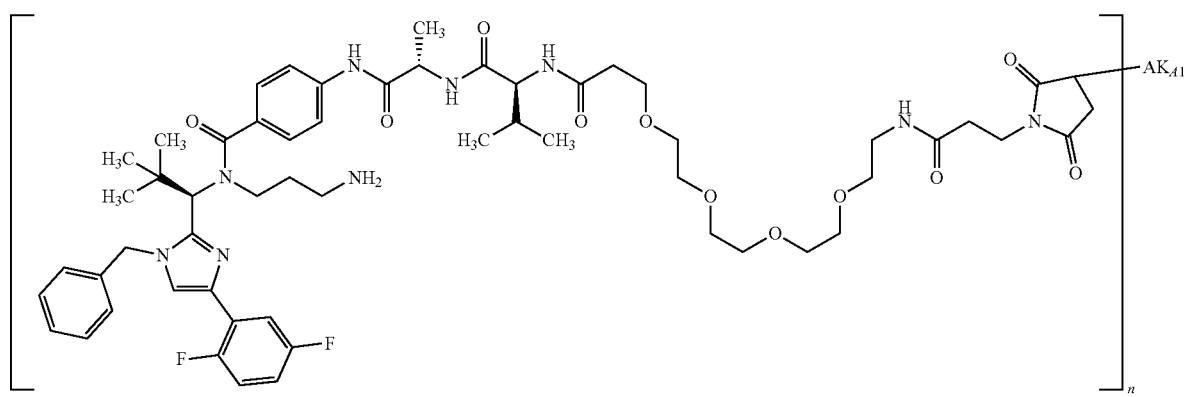
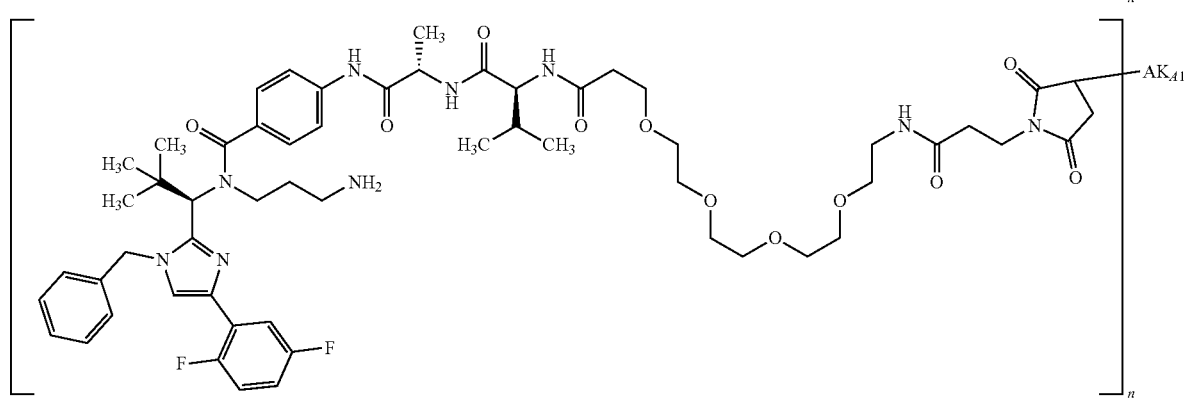
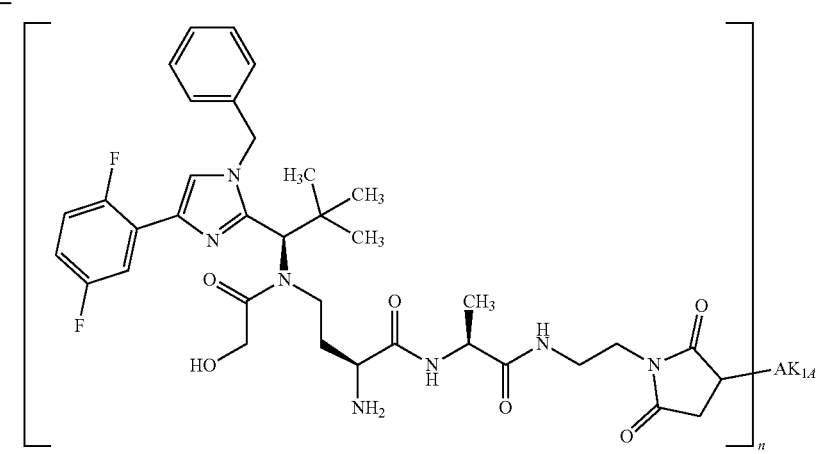

-continued
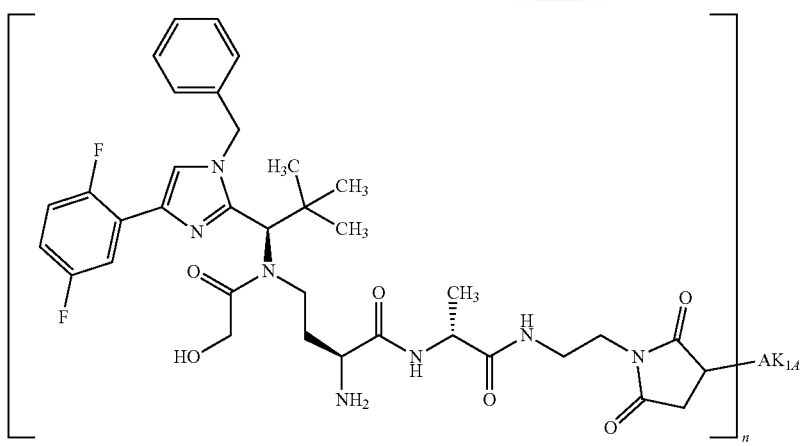
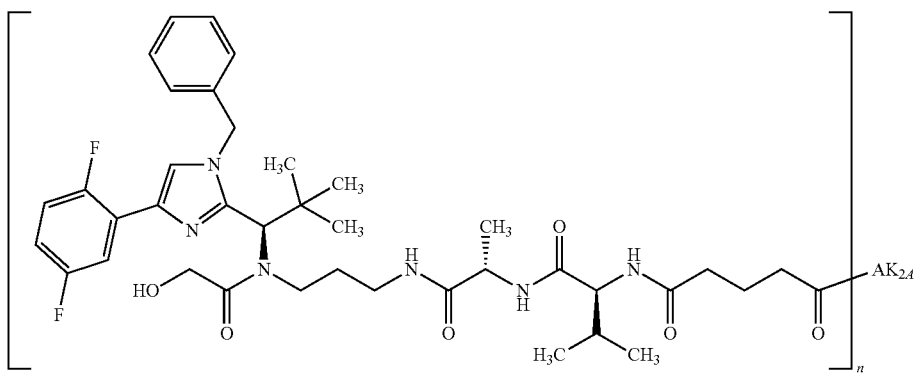
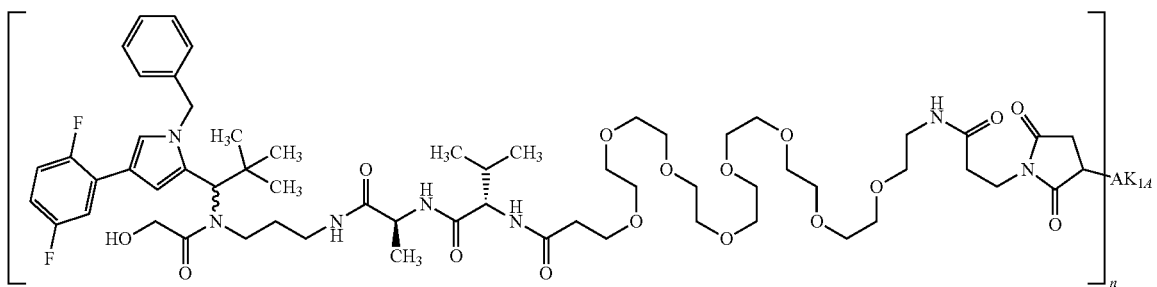
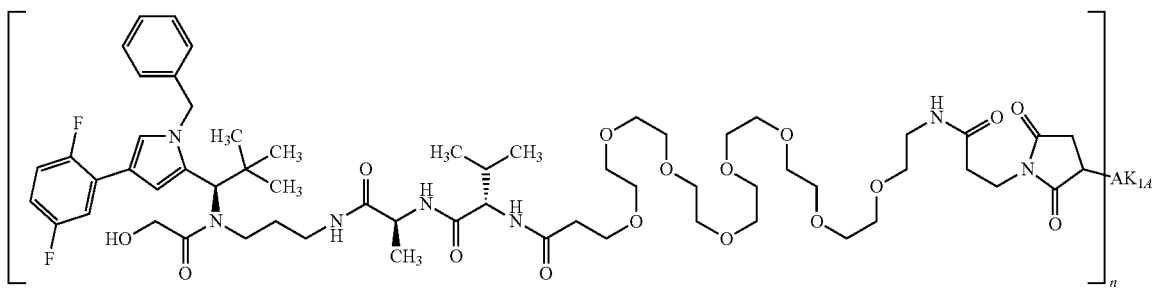

1143 1144
-continued
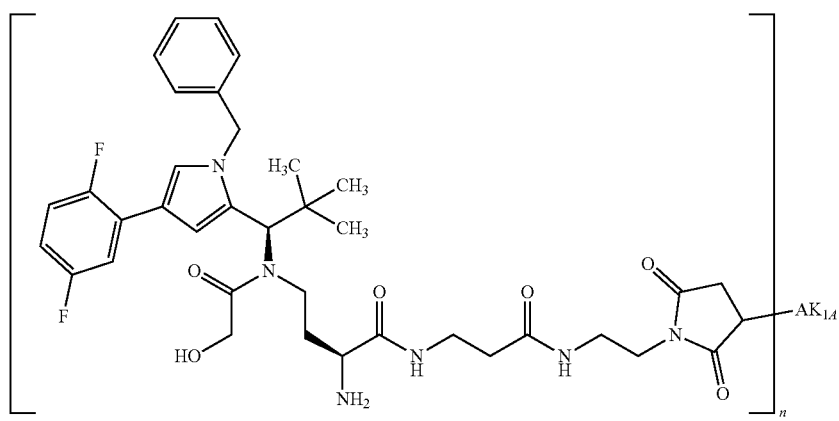
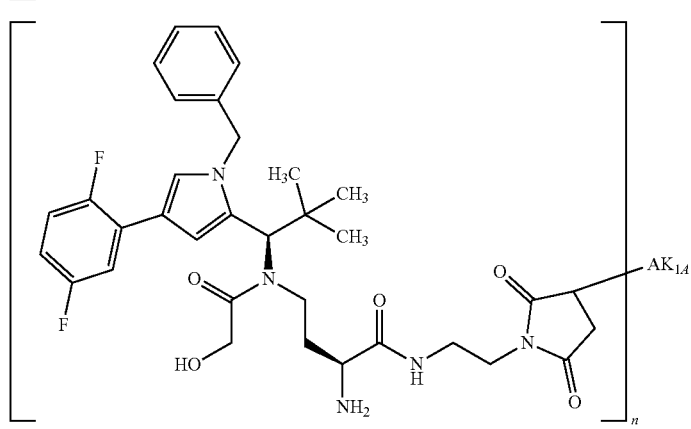
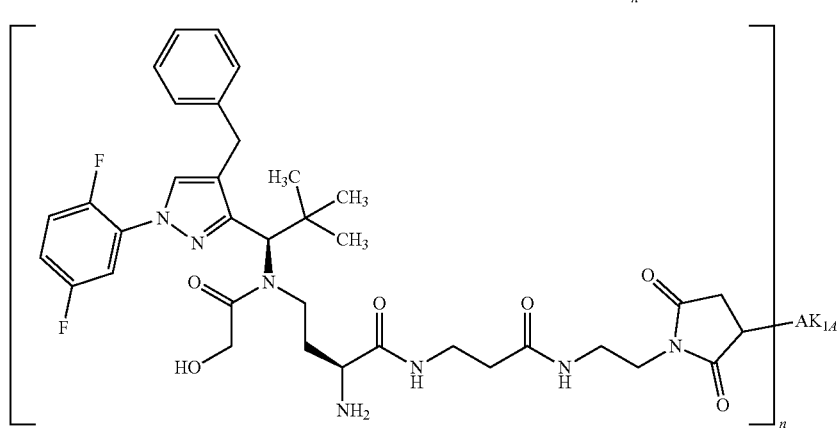
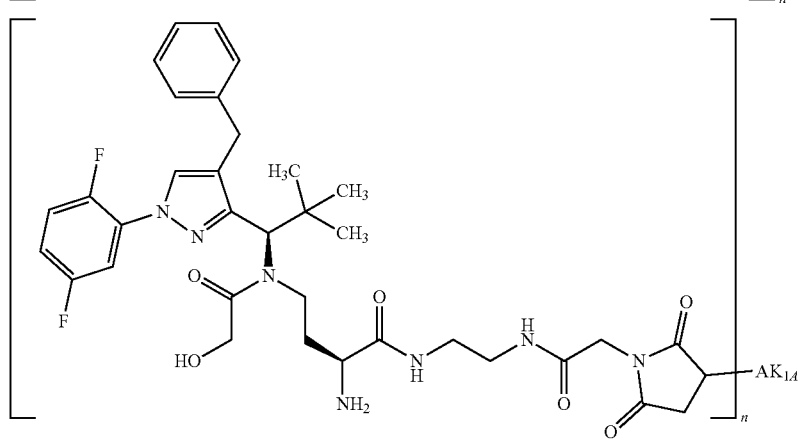

-continued
1145
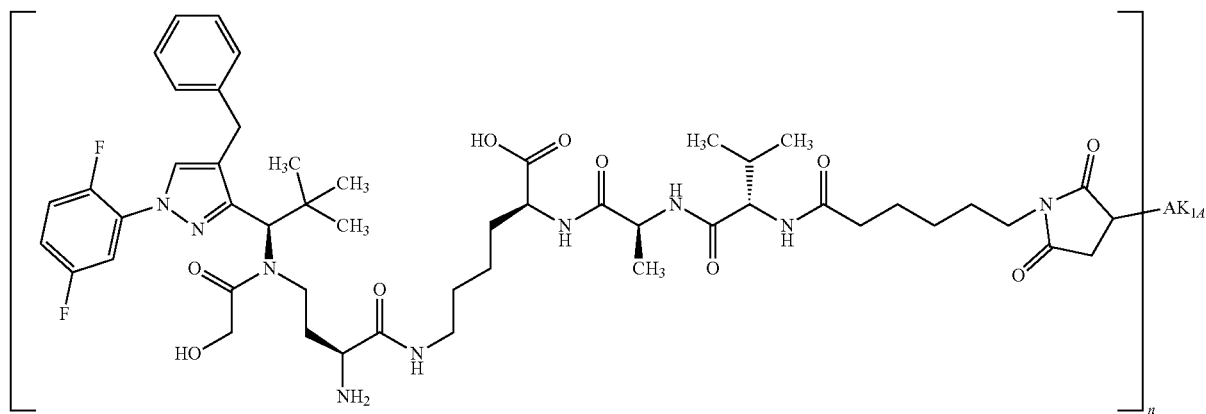
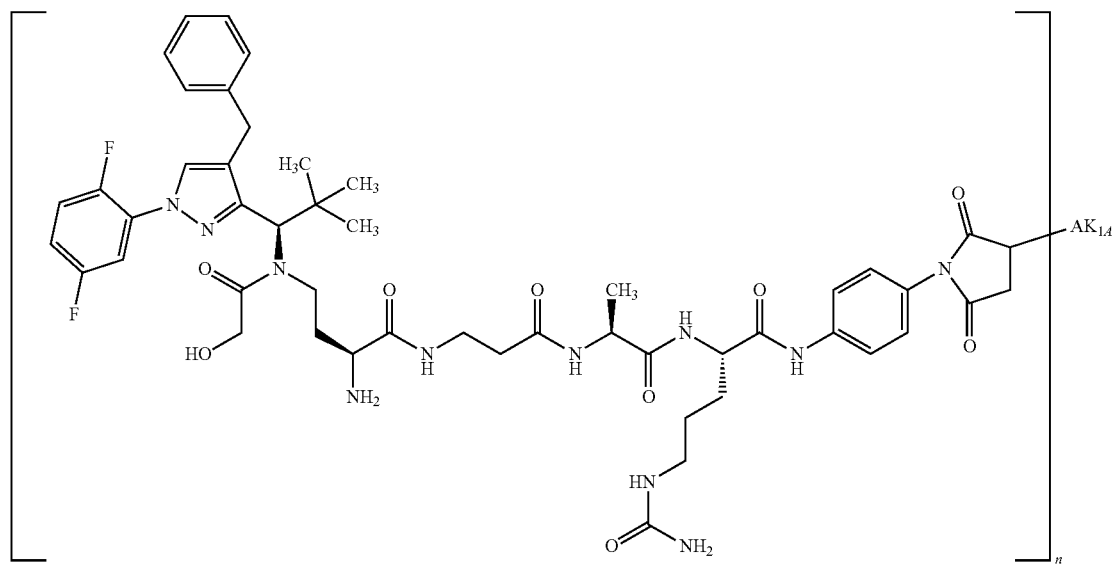
1146
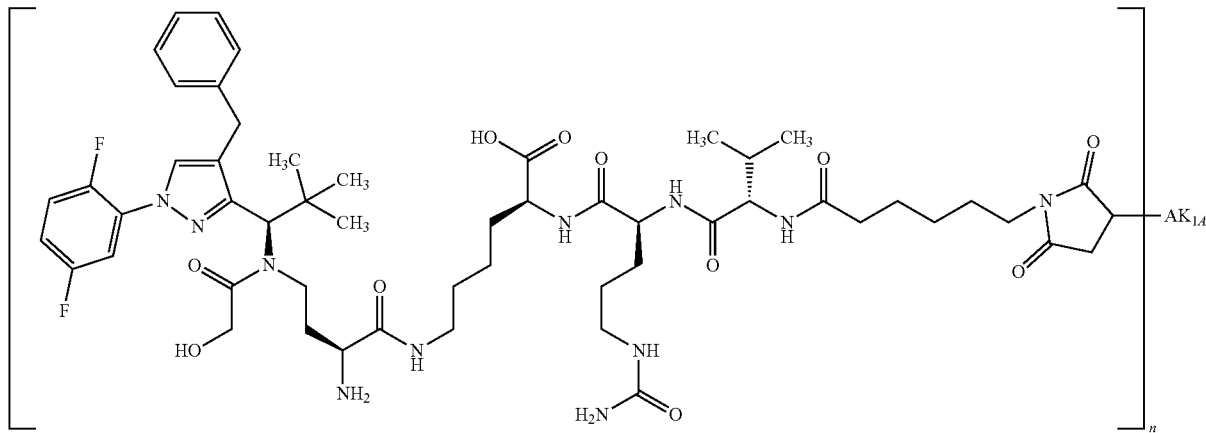

-continued
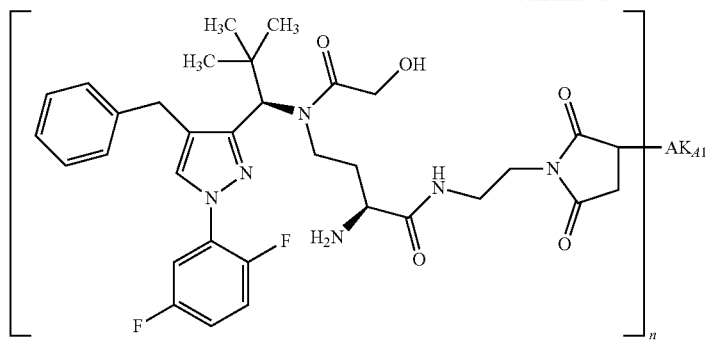
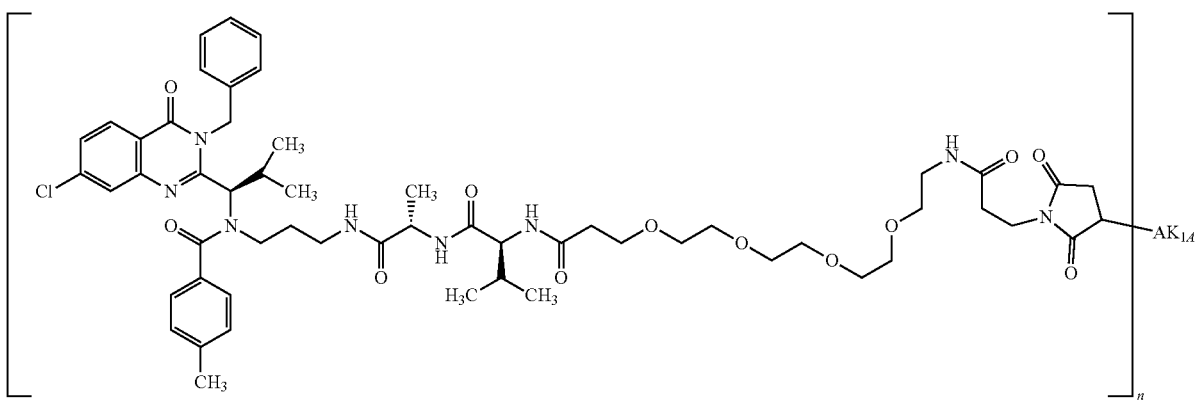
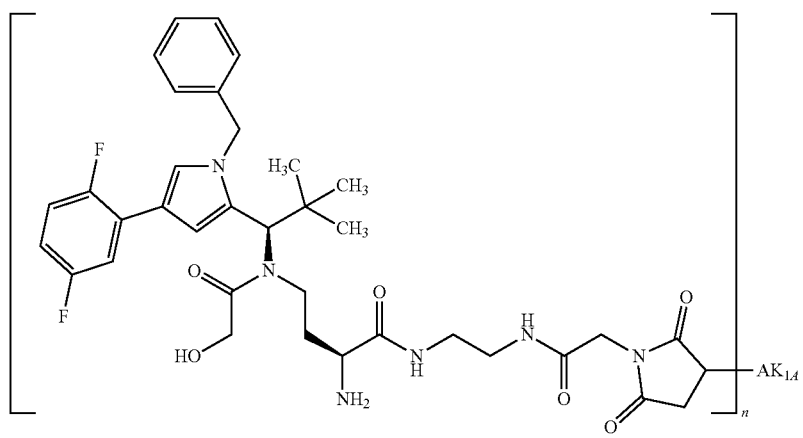
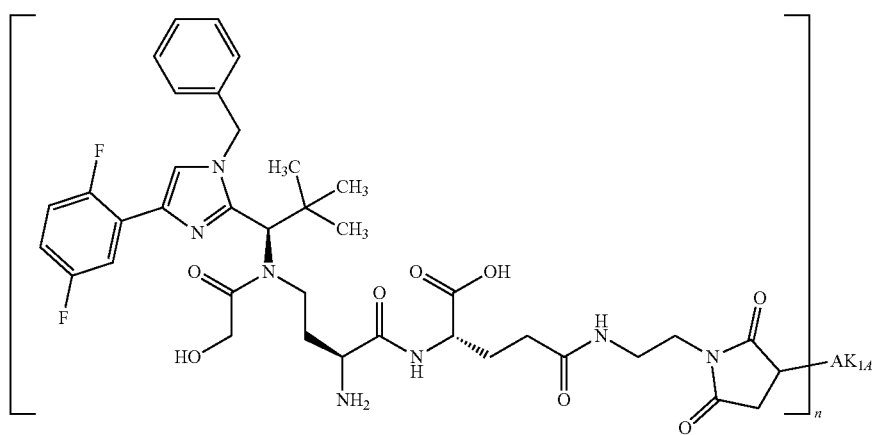

-continued
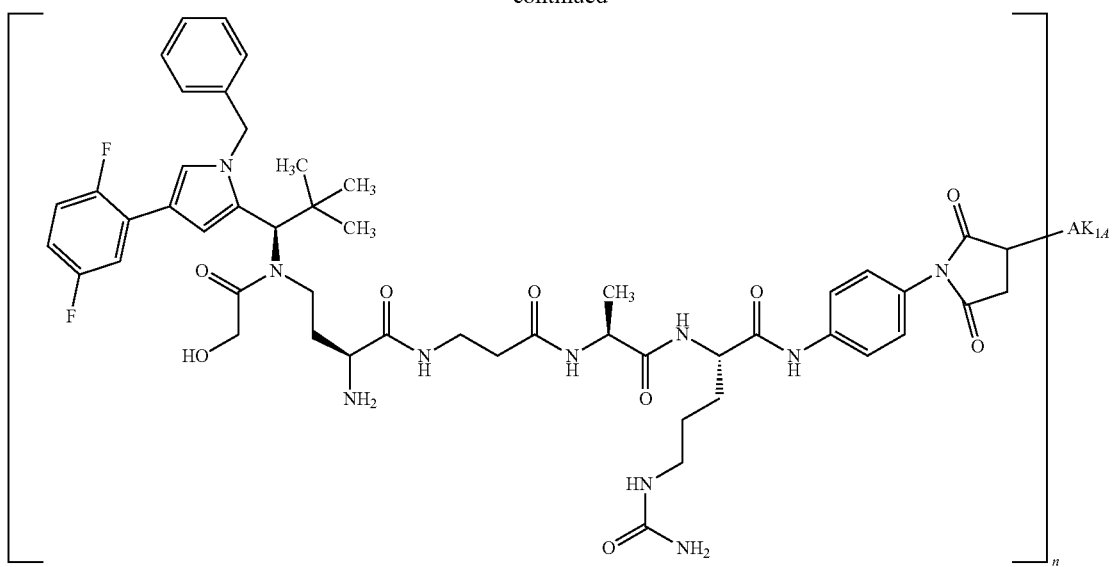
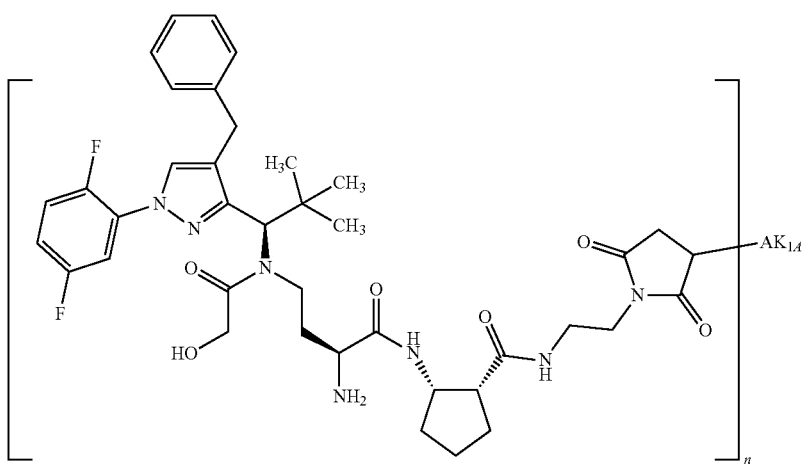
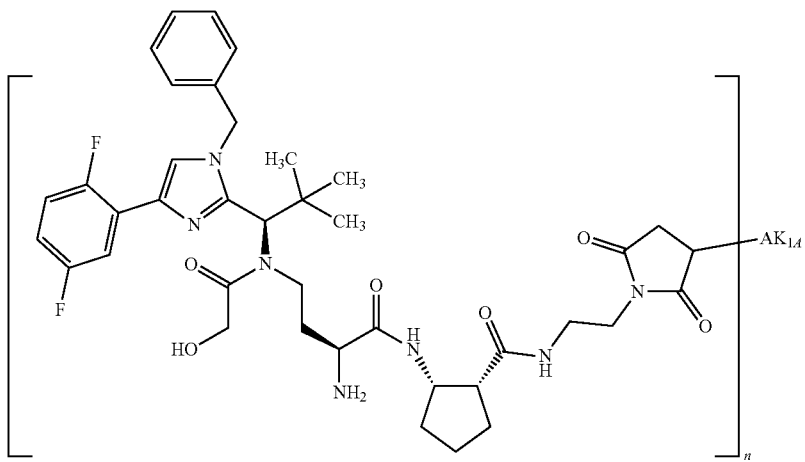

-continued
1151
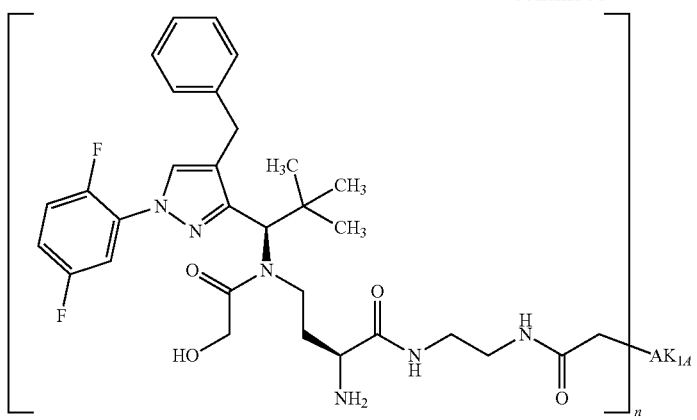
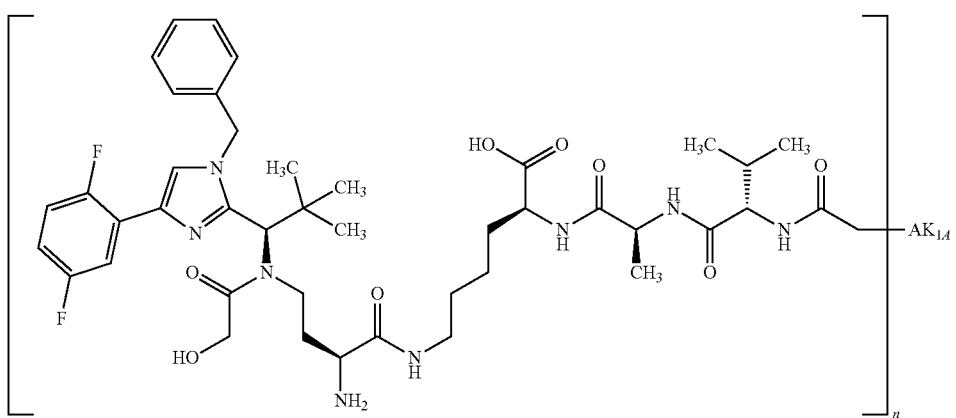
1152
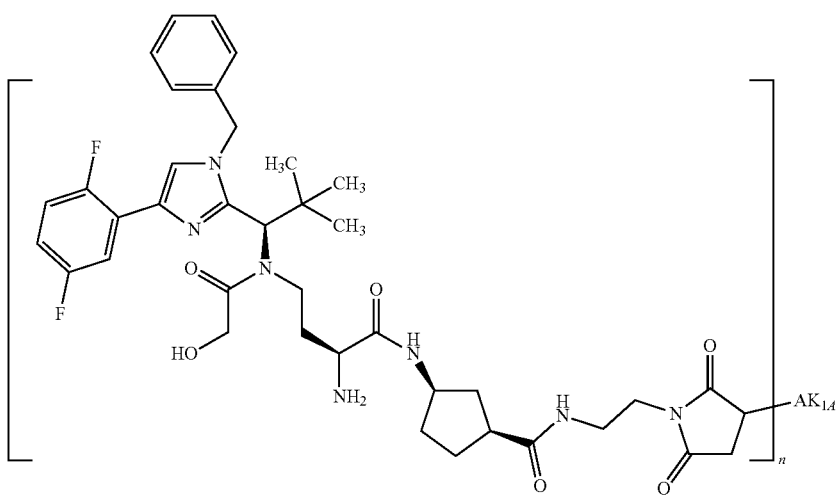

1153
-continued
1154
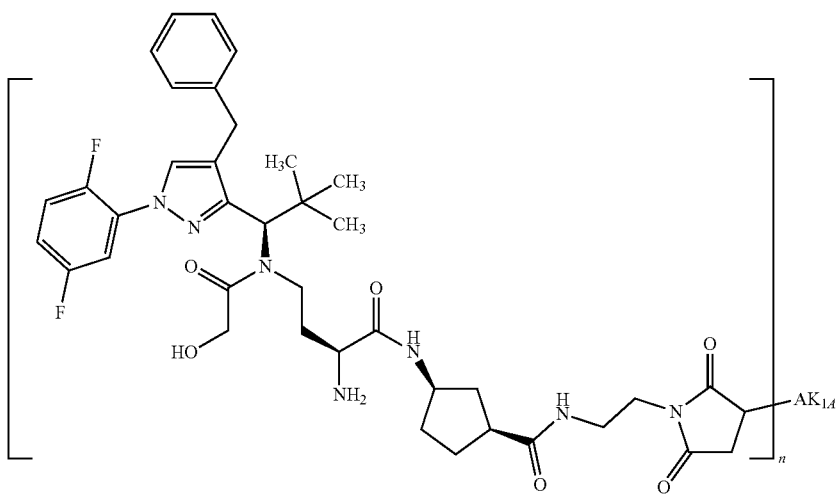
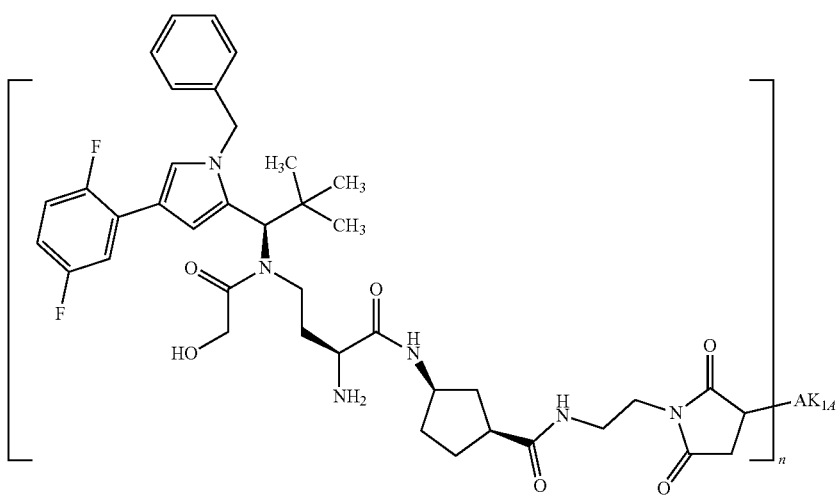
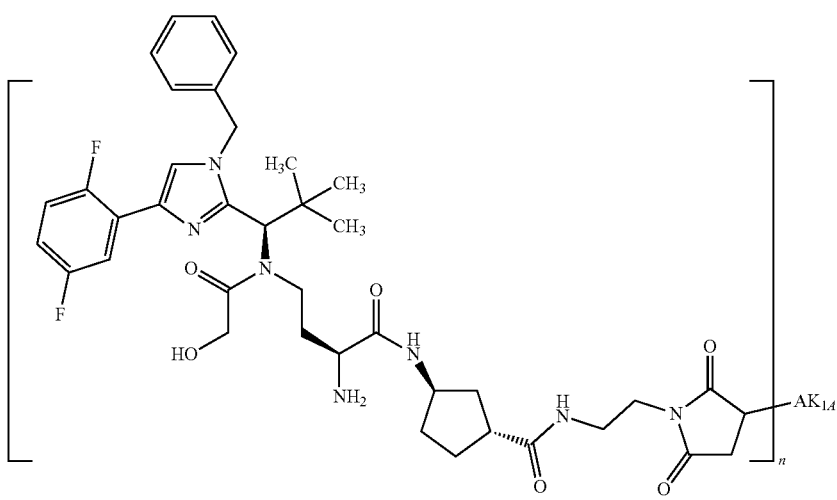

-continued
1155
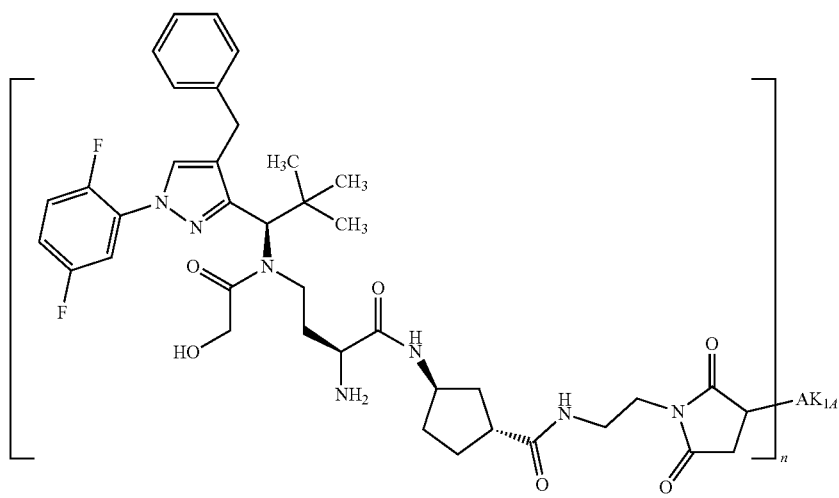
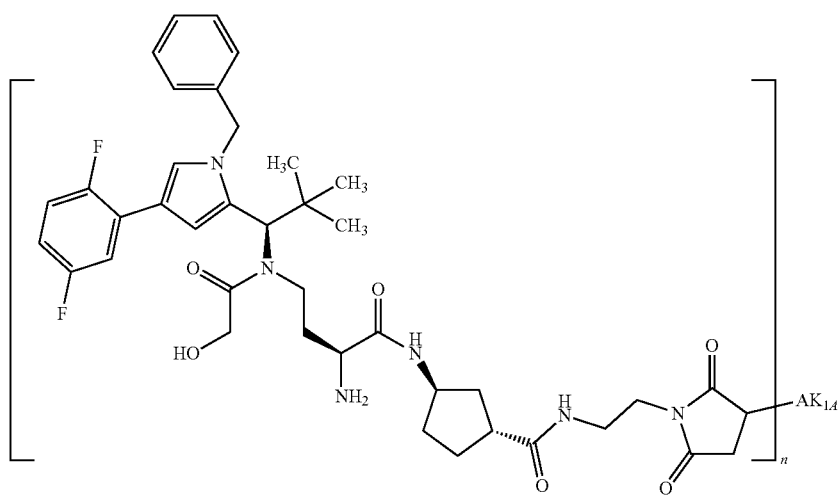
1156
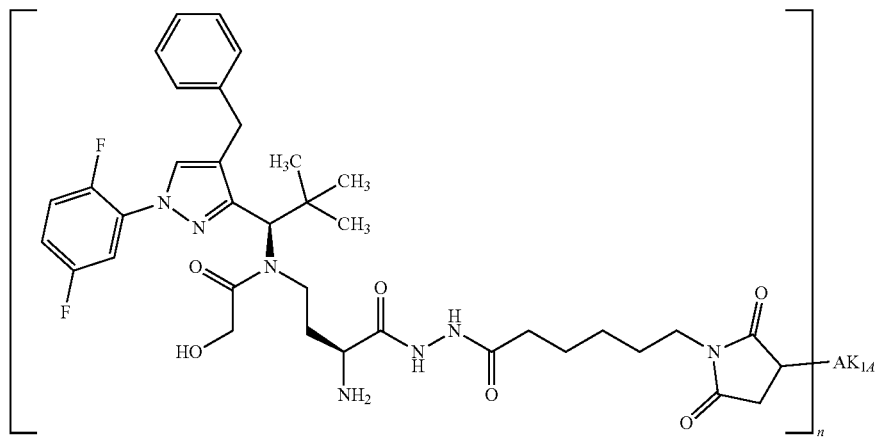

1157
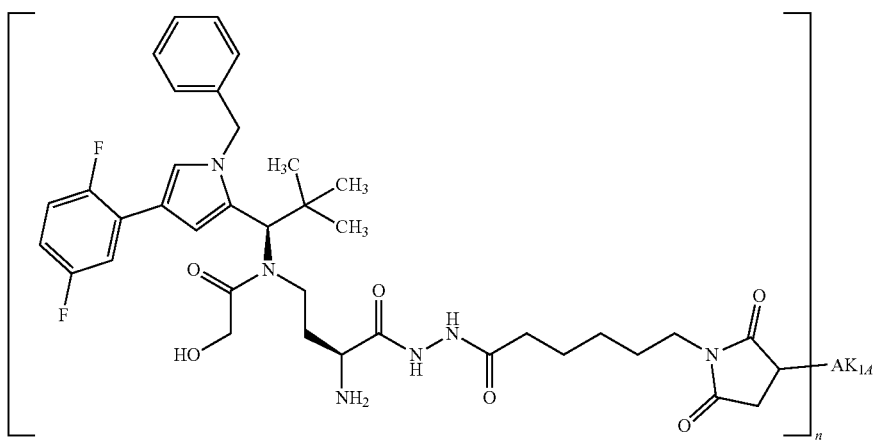
1158
-continued
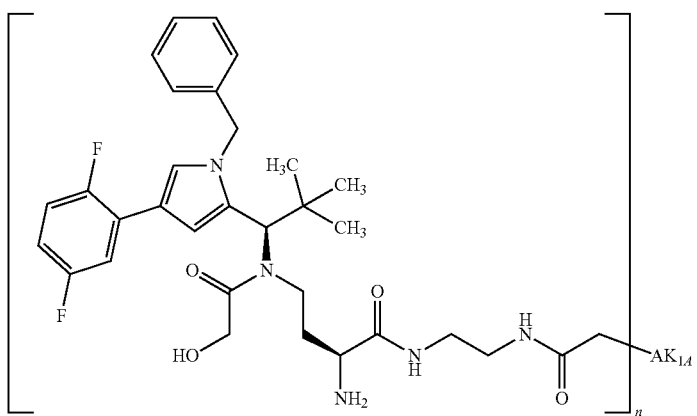
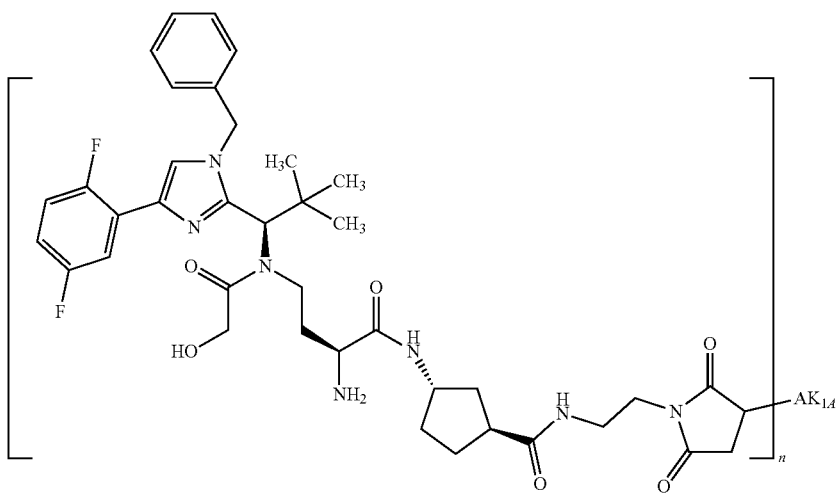

1159
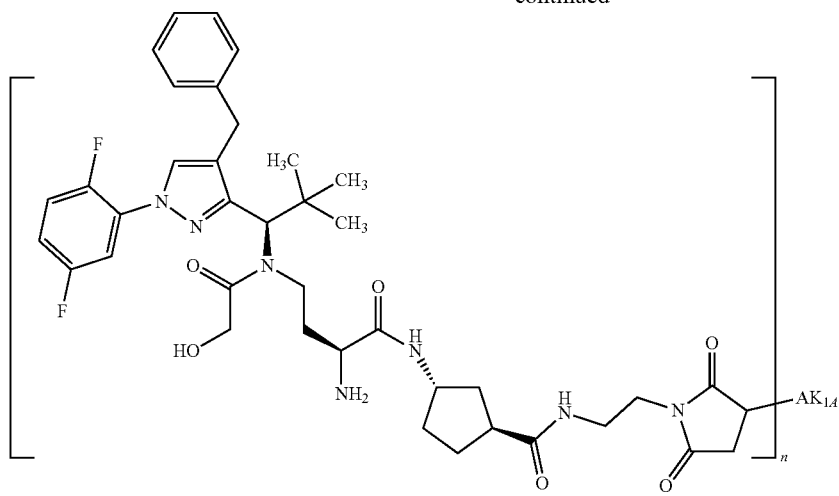
1160
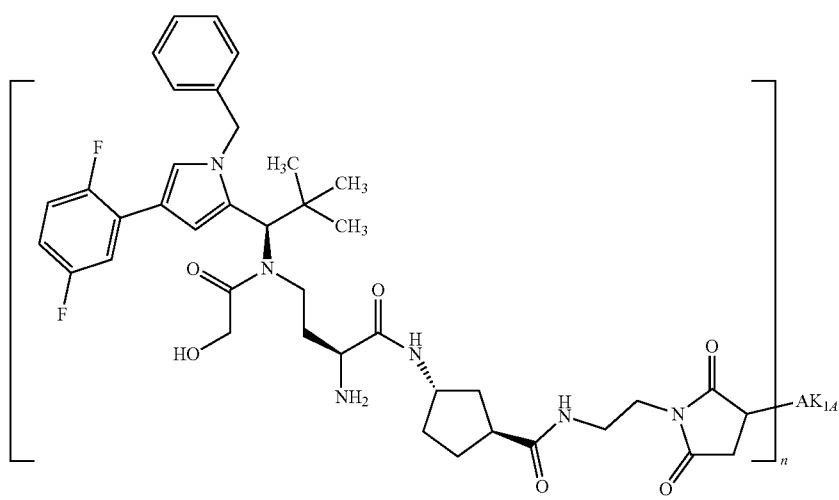
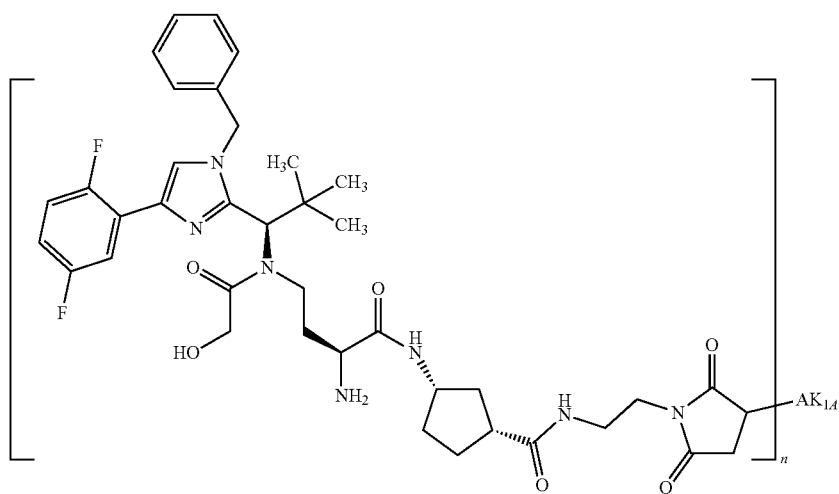

1161
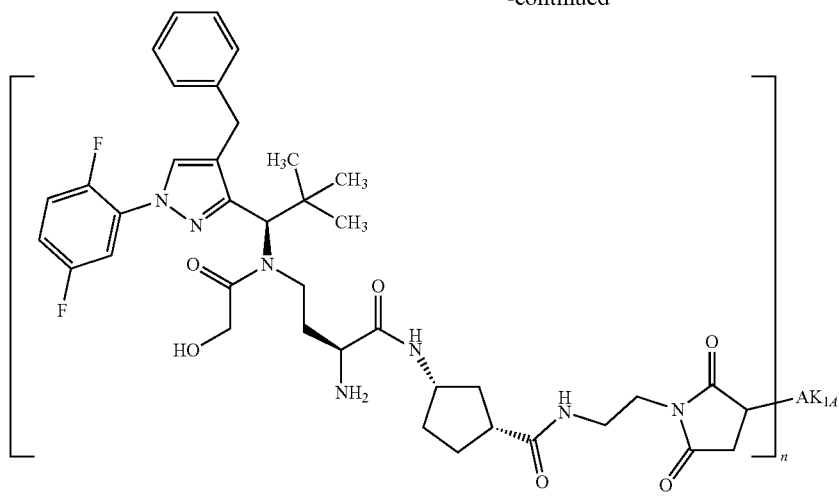
1162
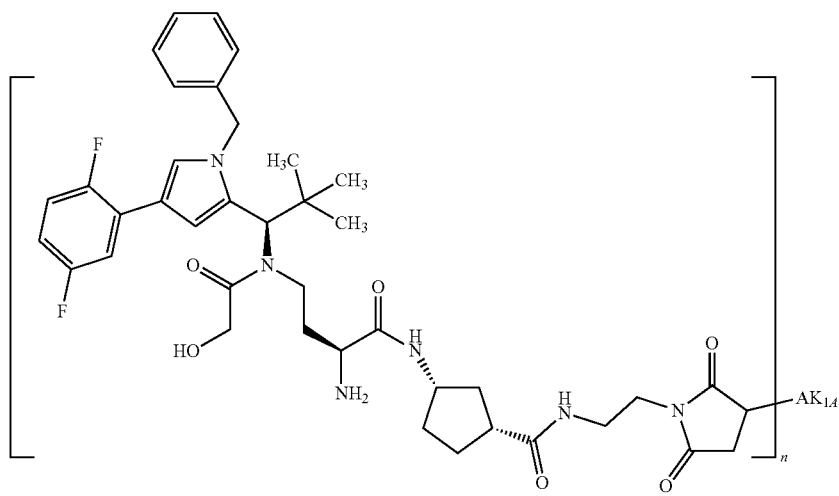
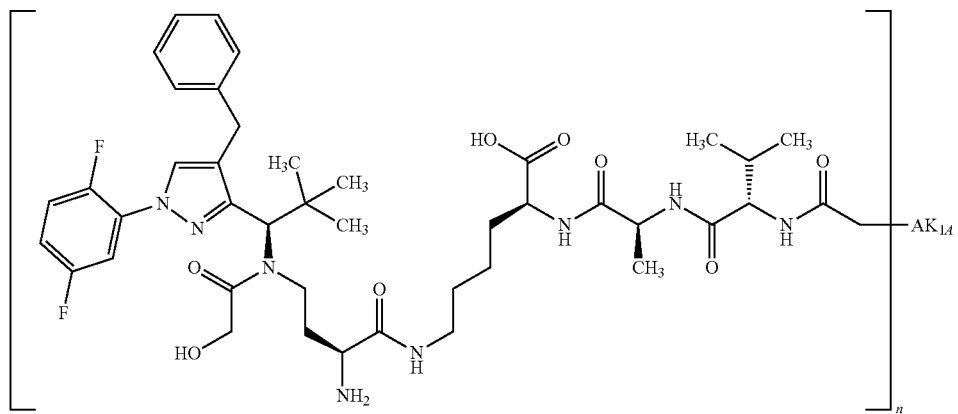

1163
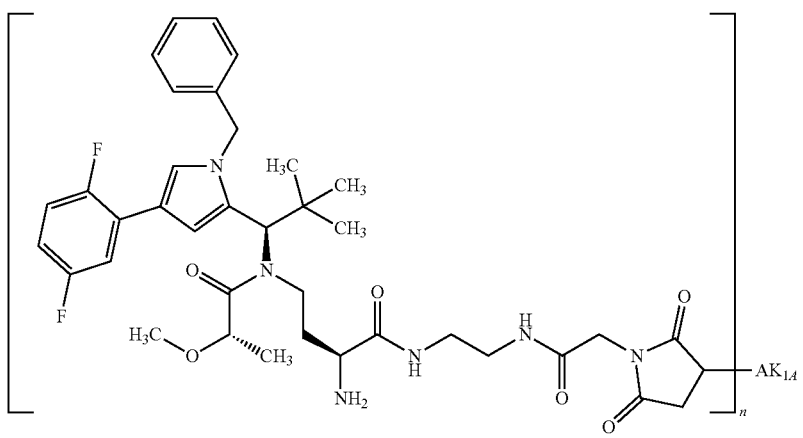
1164
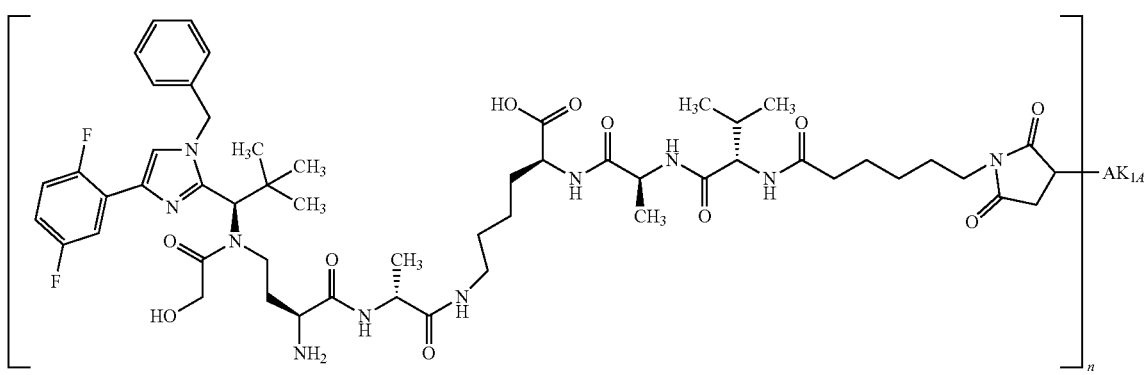
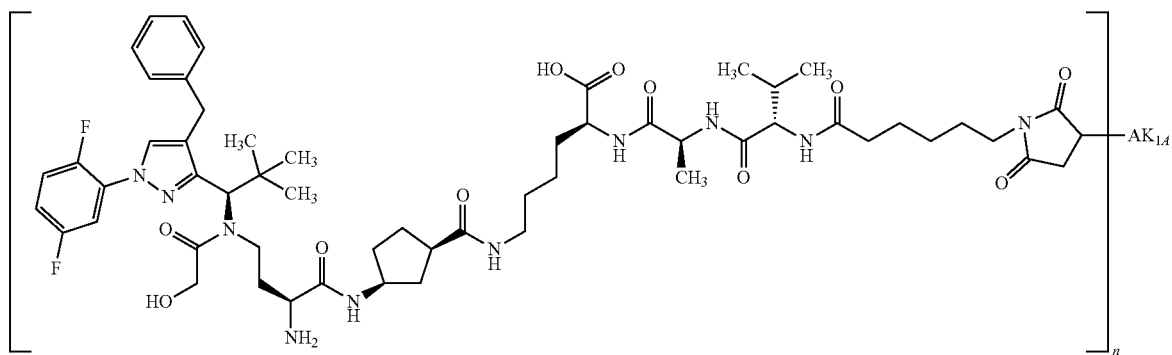

1165
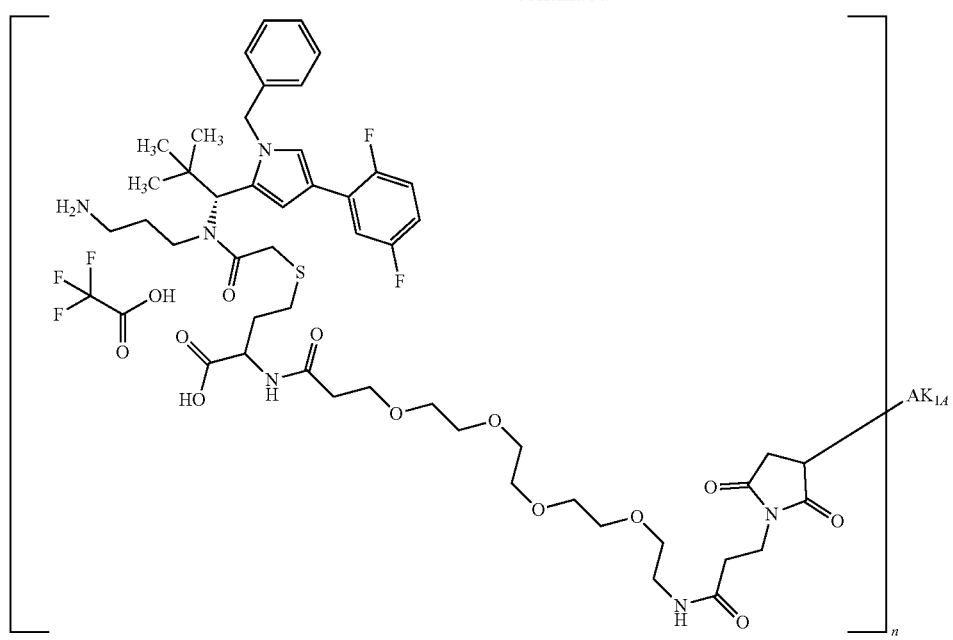
-continued
1166
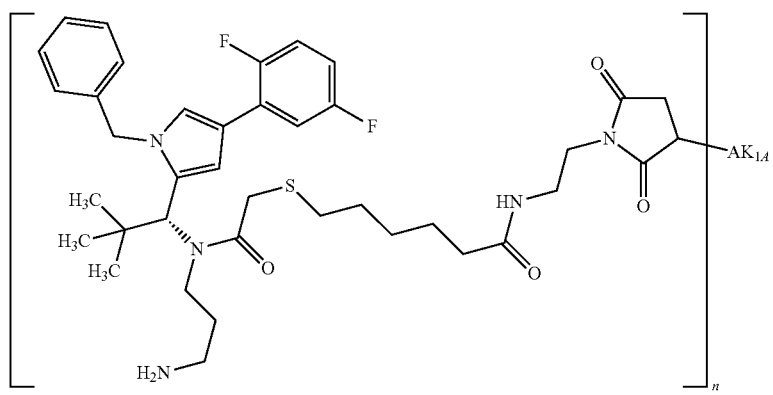
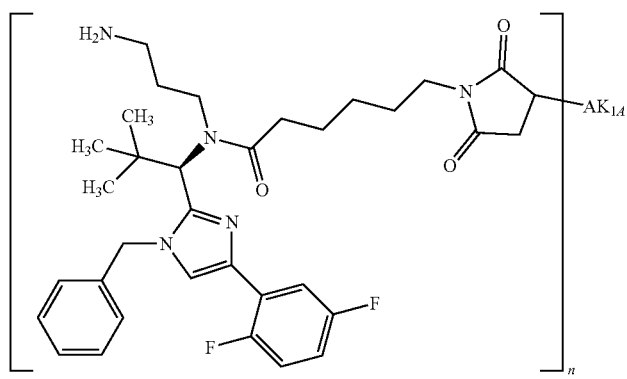

-continued
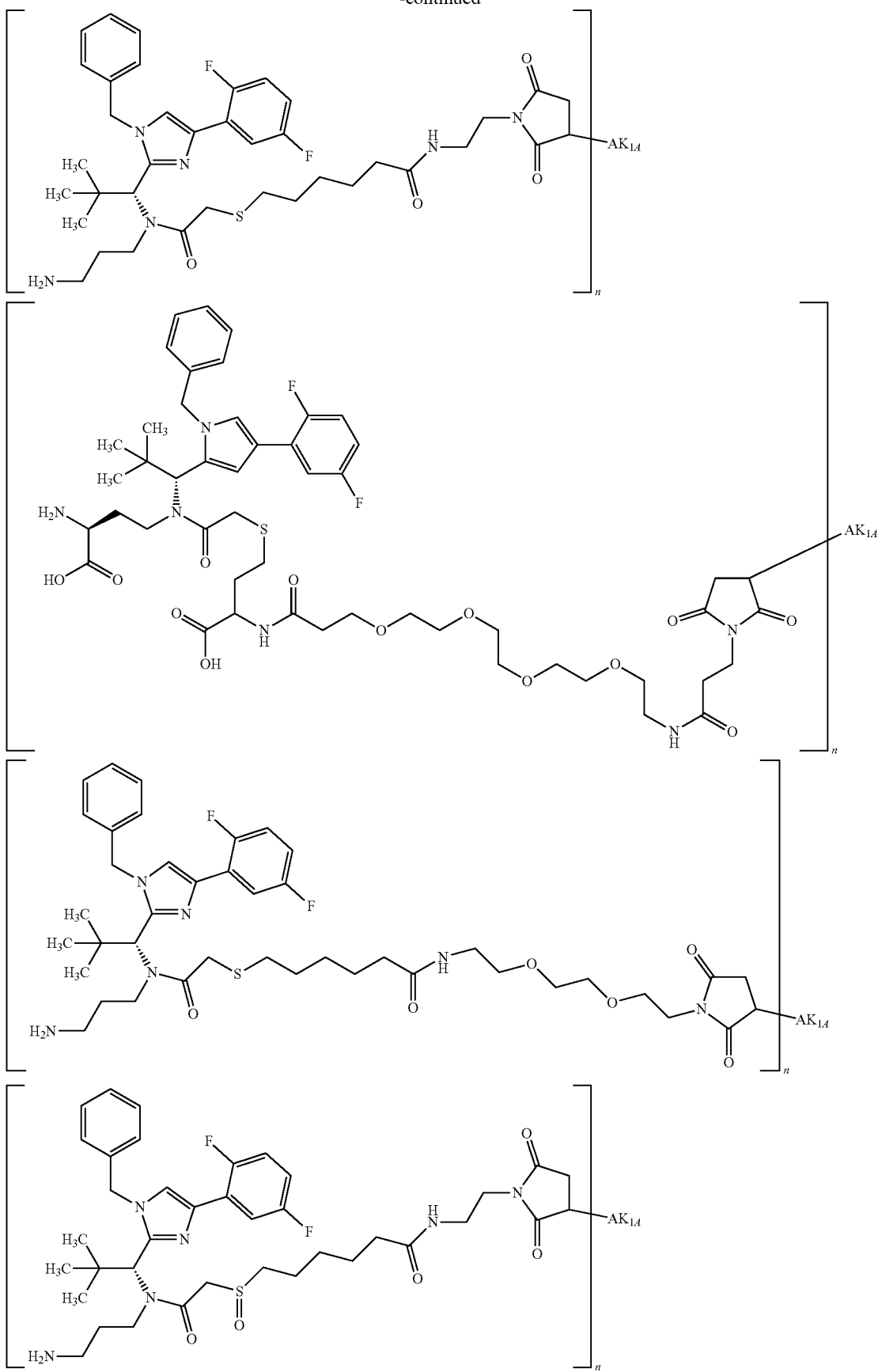

-continued
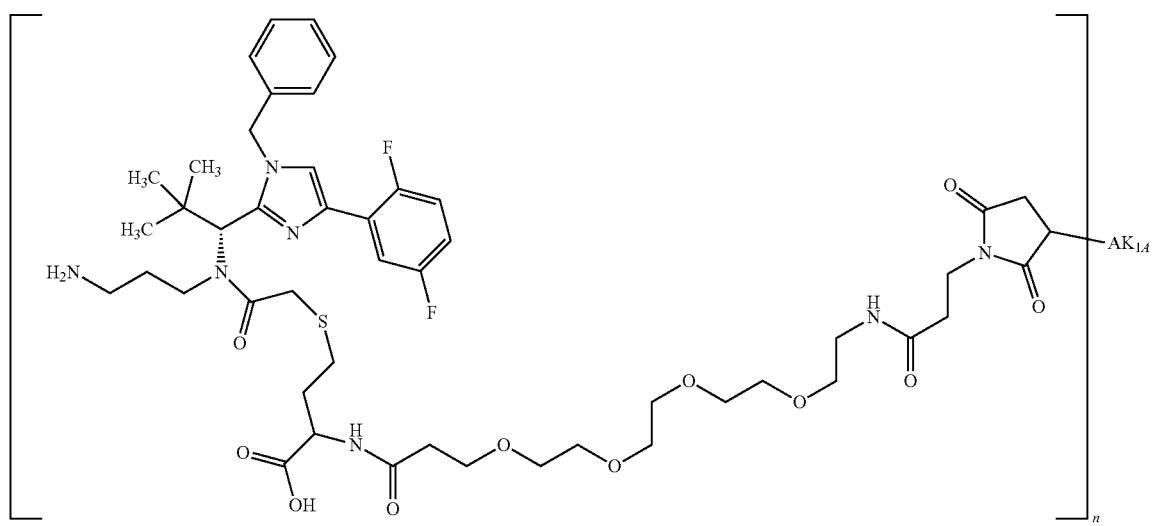
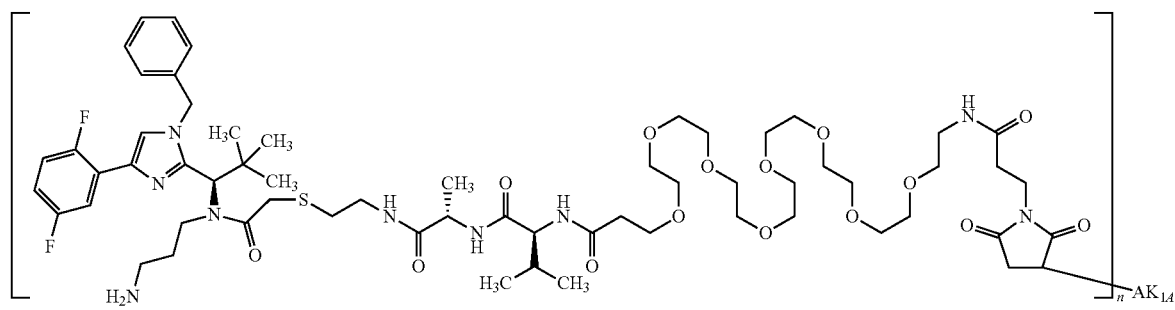
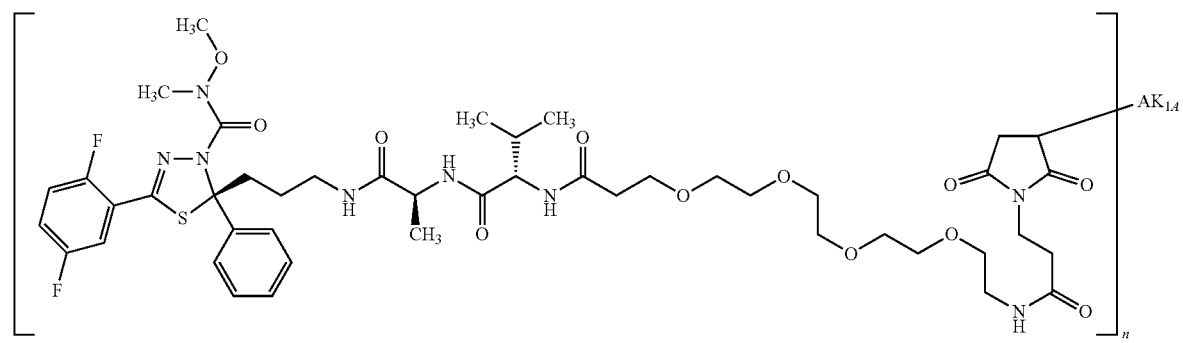
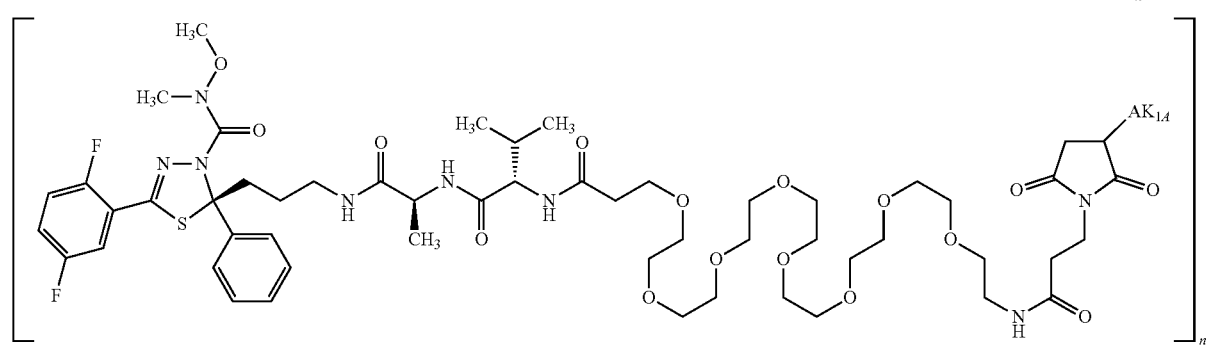

1171    1172
-continued
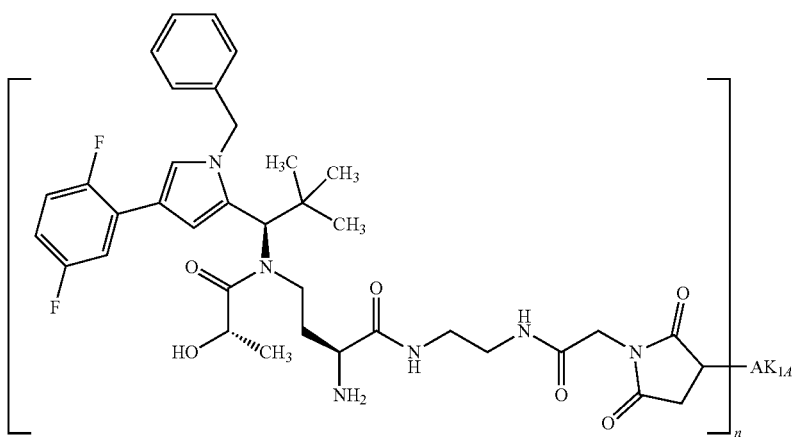
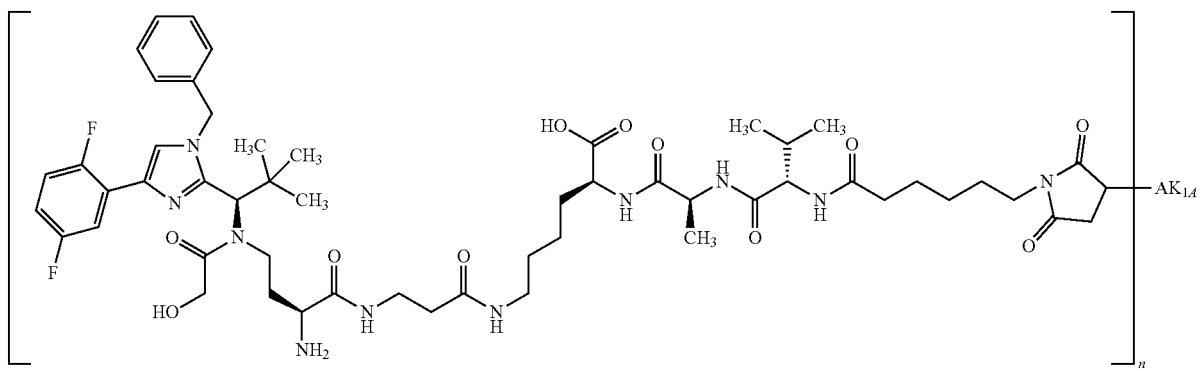
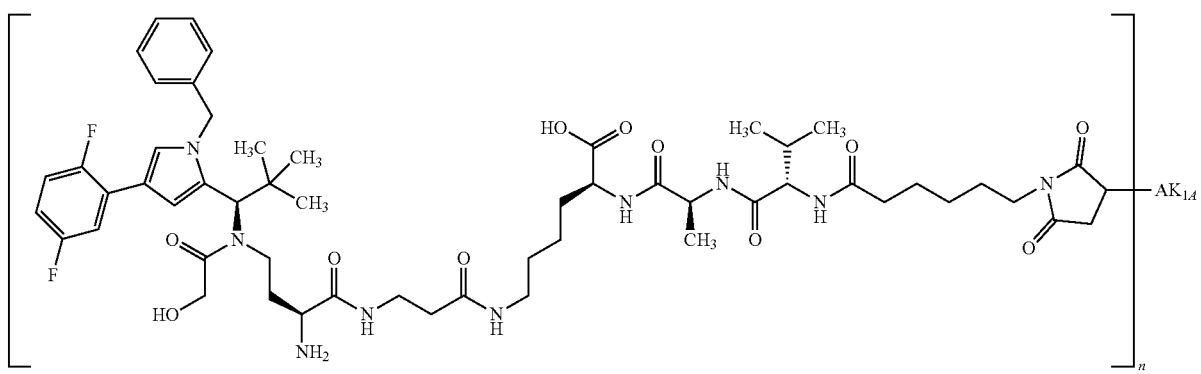
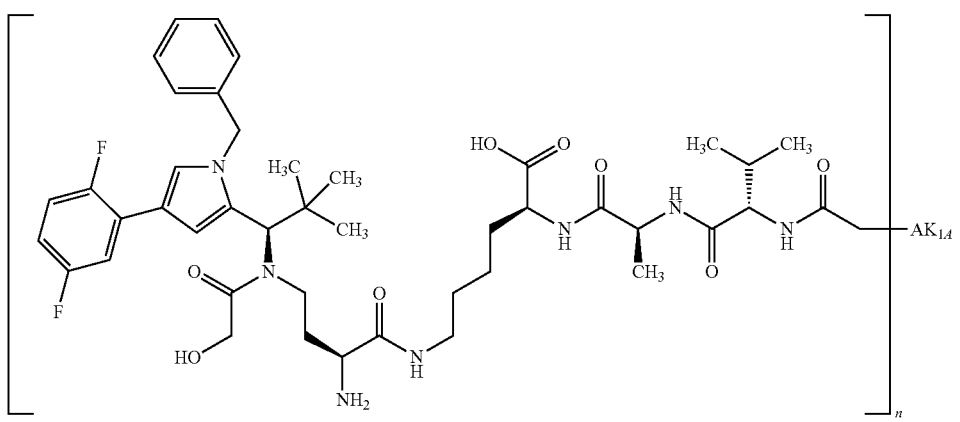

-continued
1173
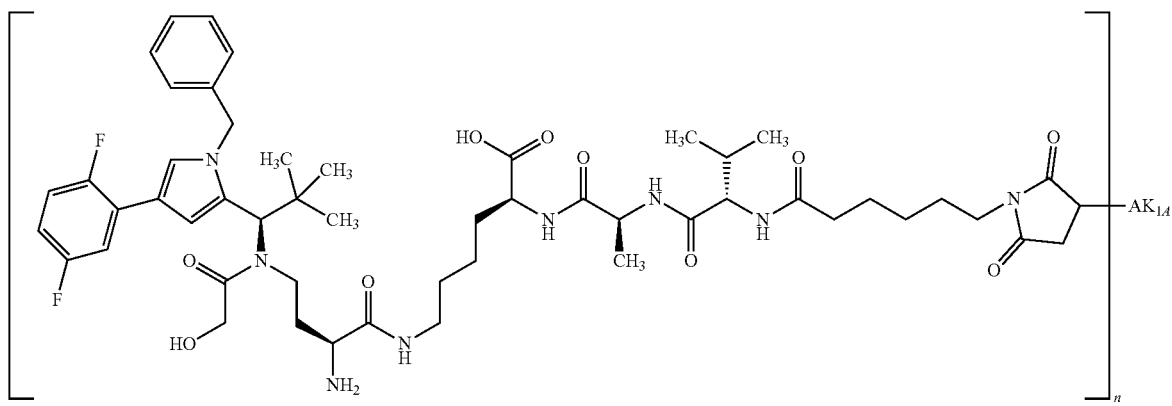
1174
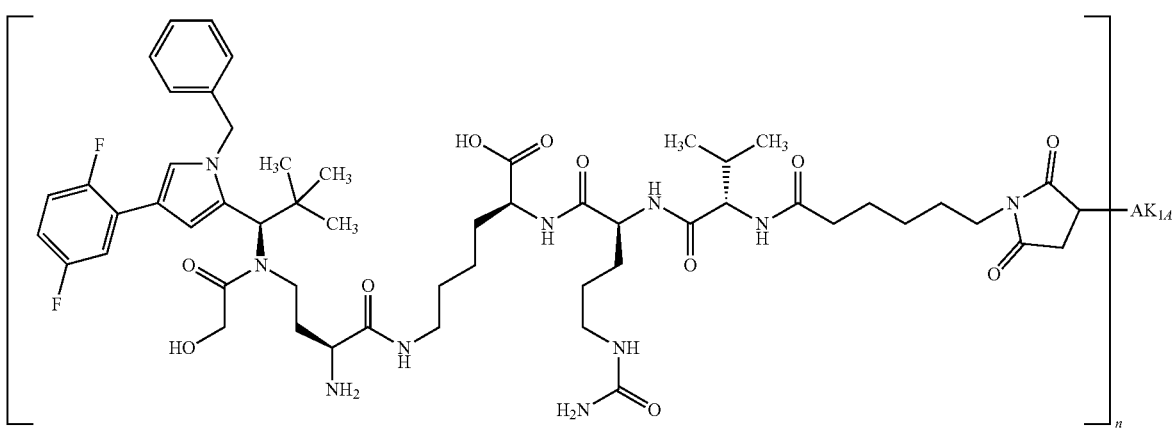
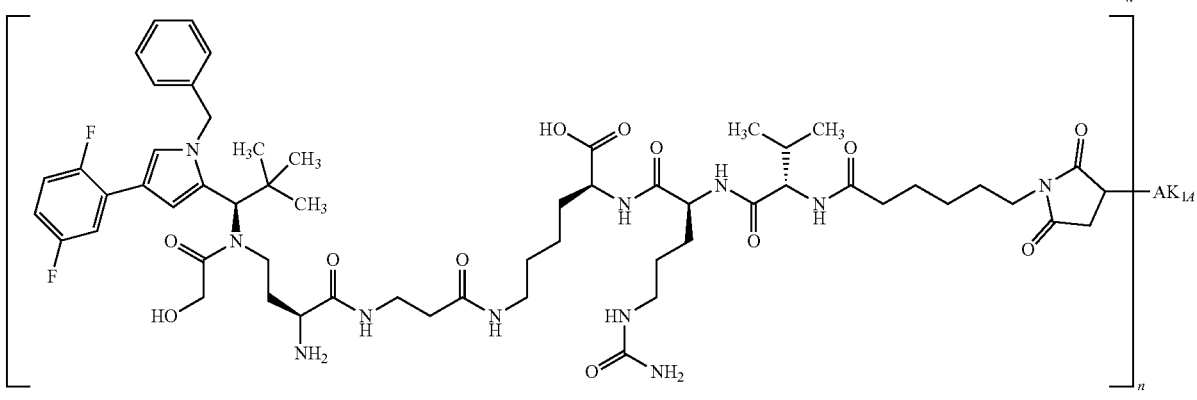
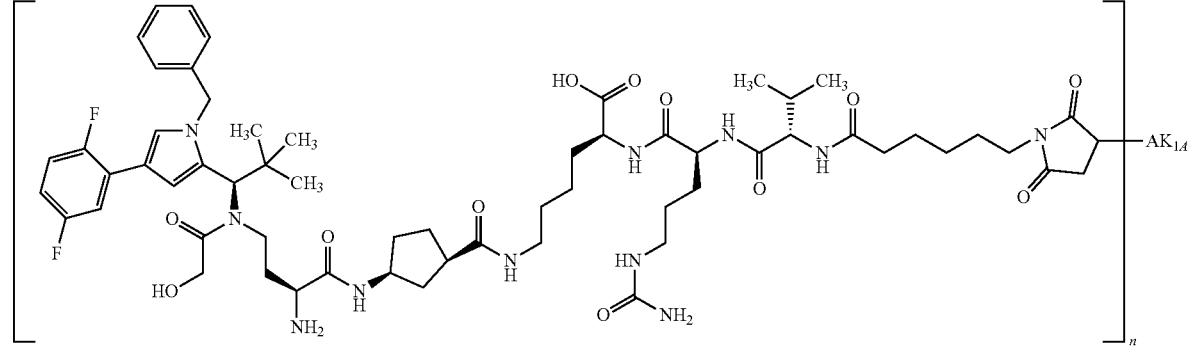

1175                                            1176
-continued
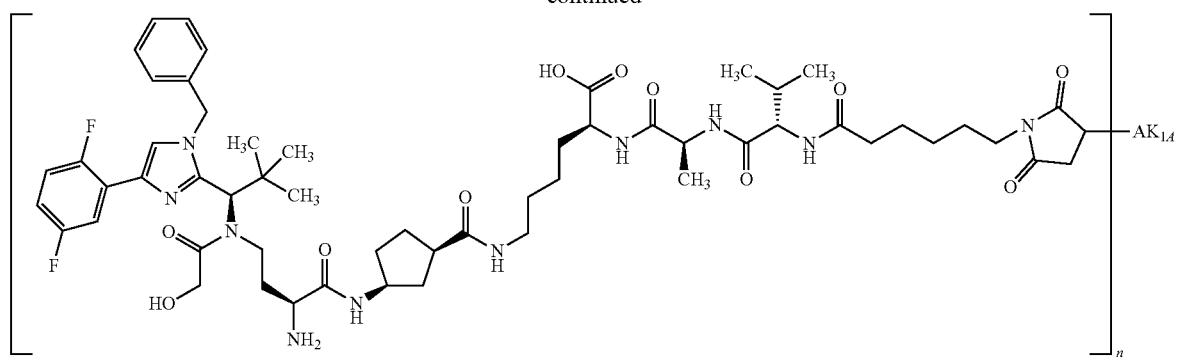
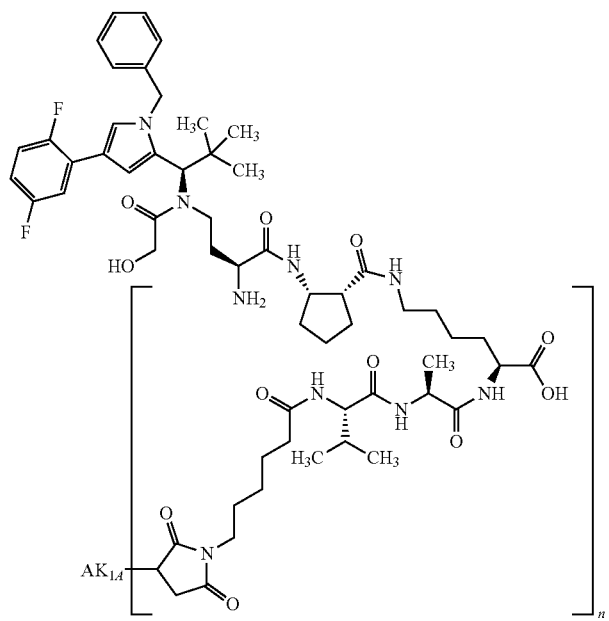
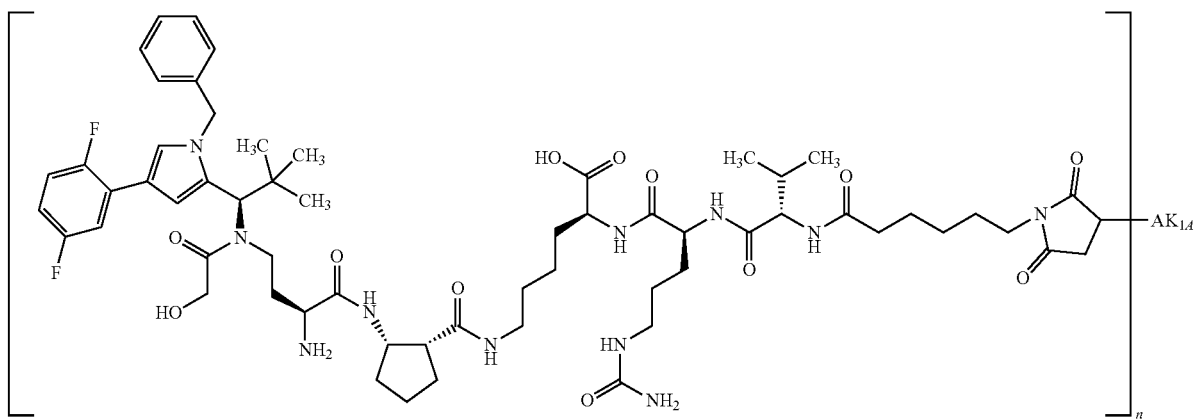

1177 1178
-continued
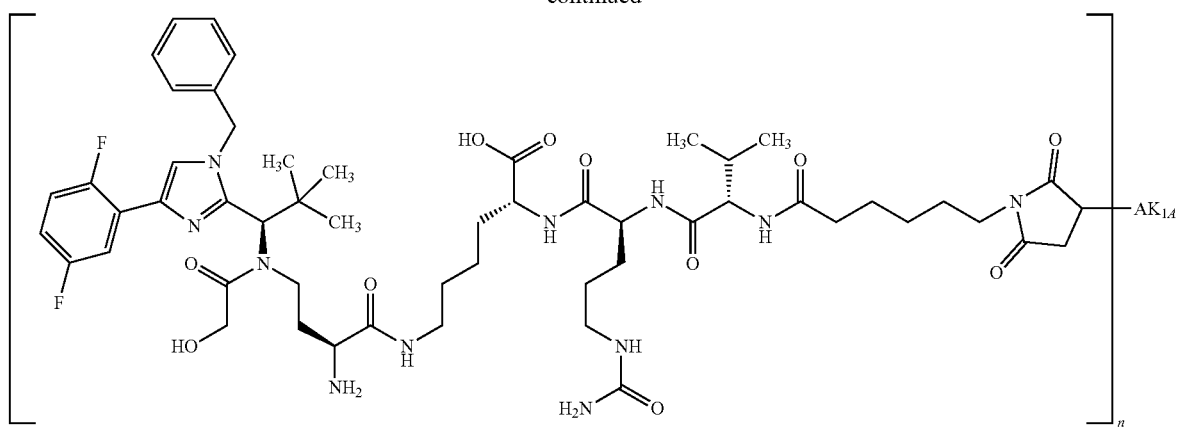
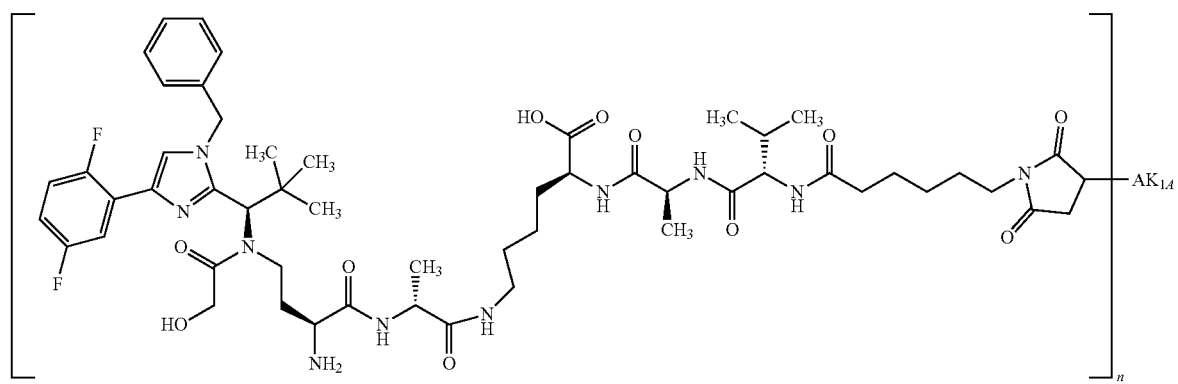
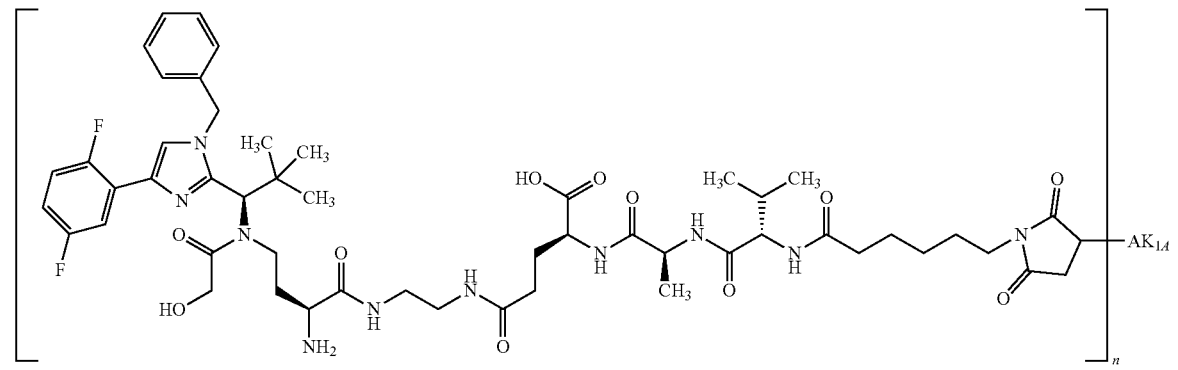
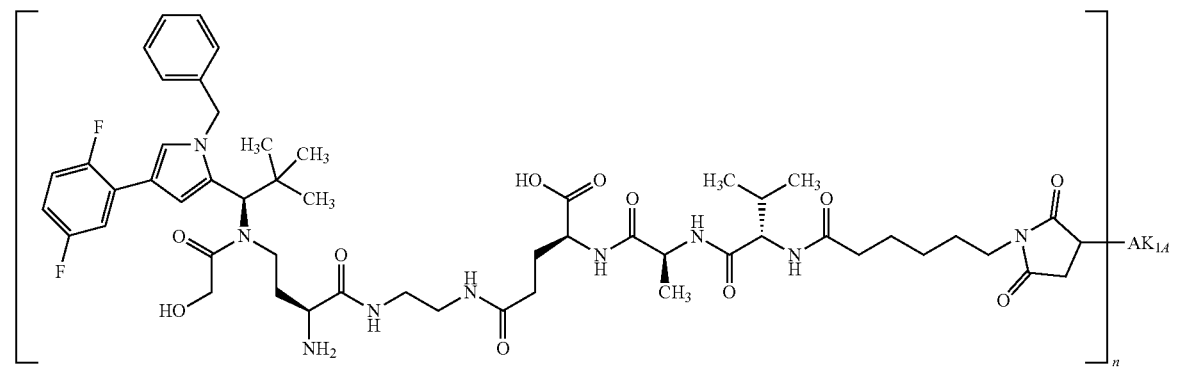

-continued
1179
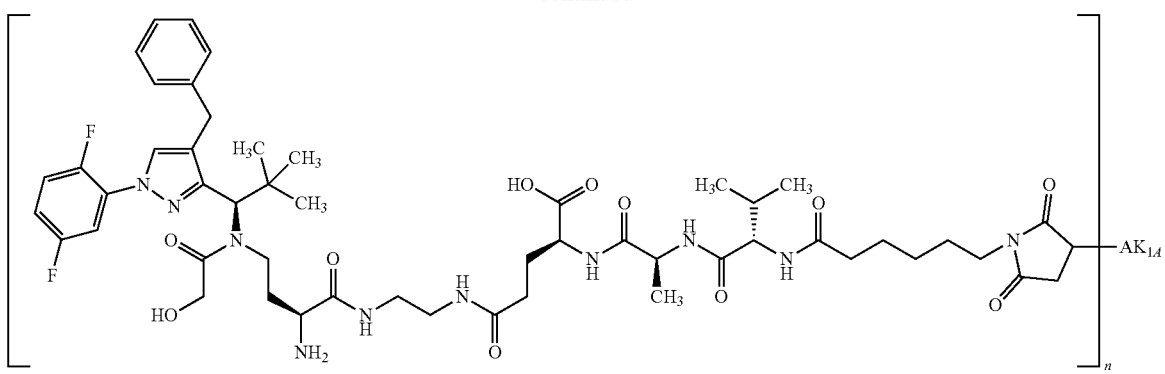
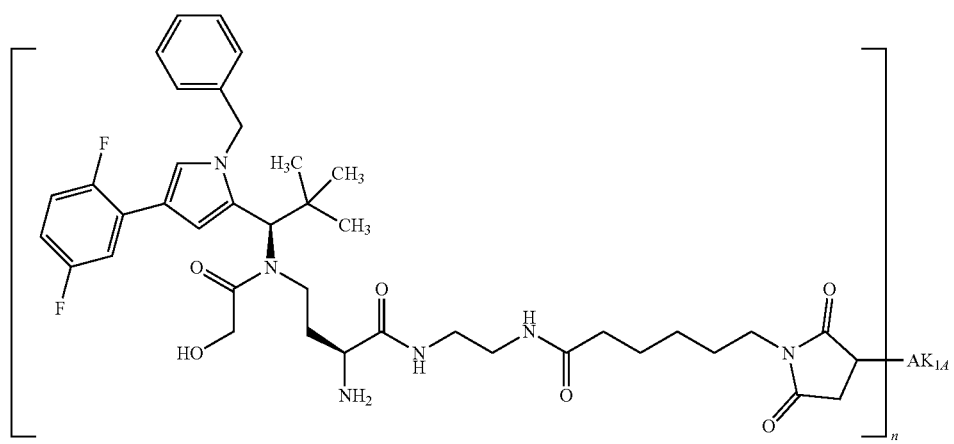
1180
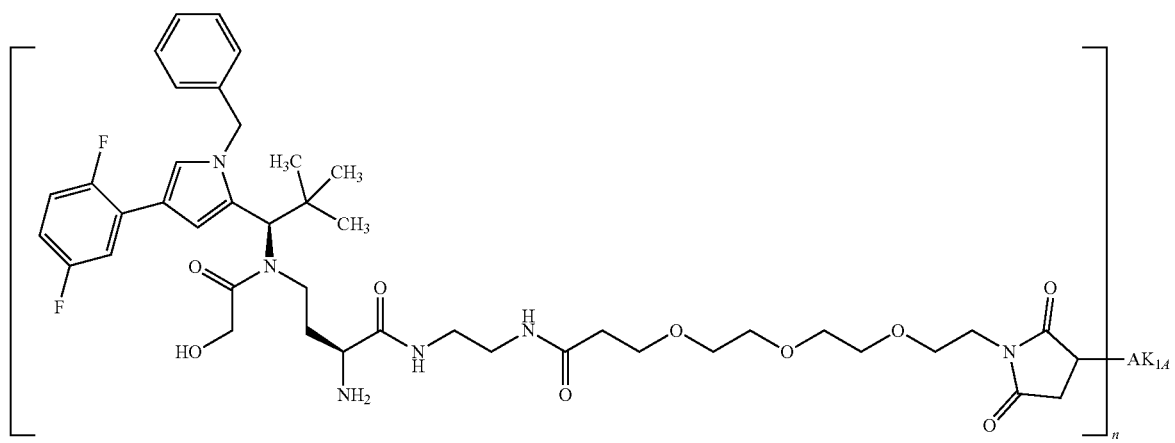

1181
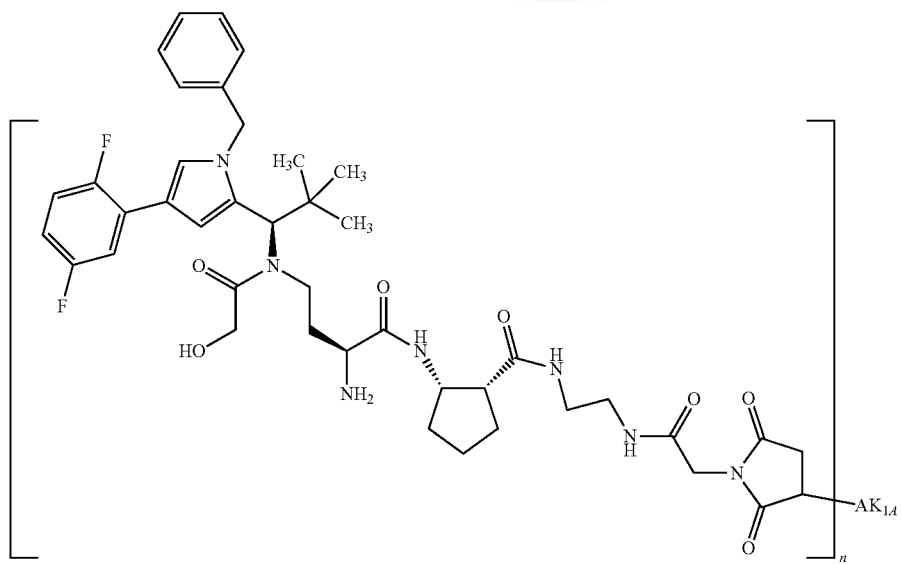
1182
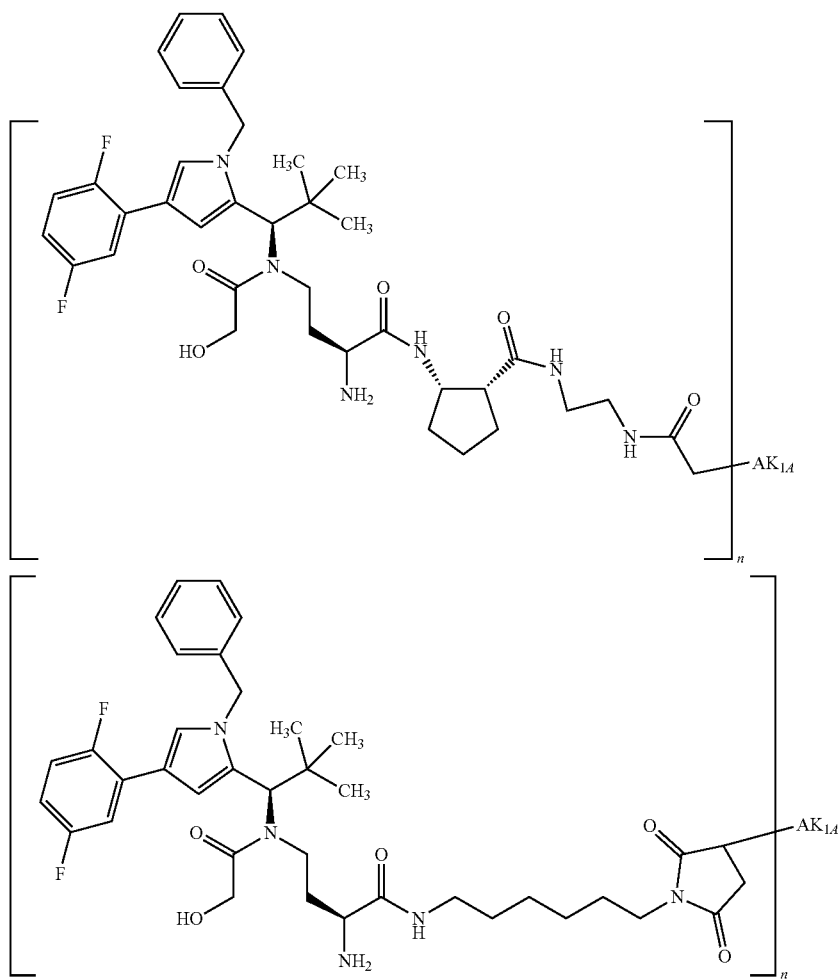

-continued
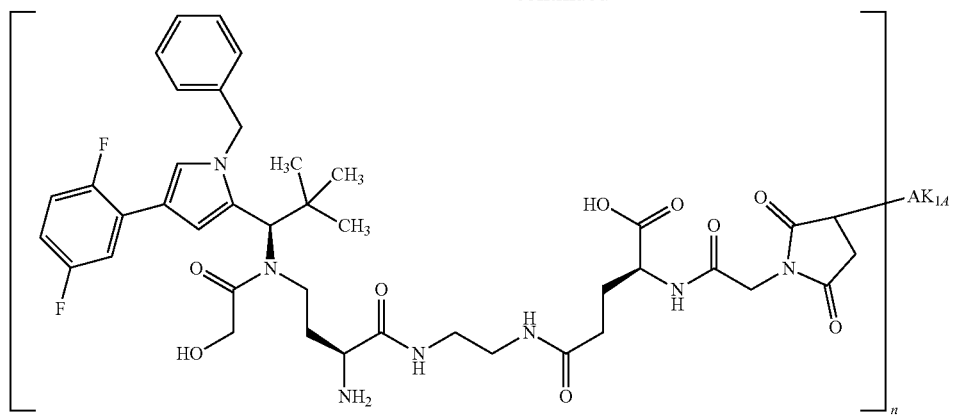
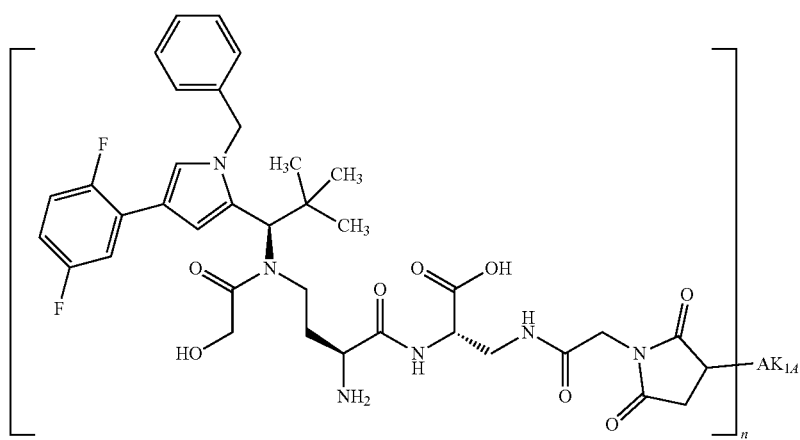
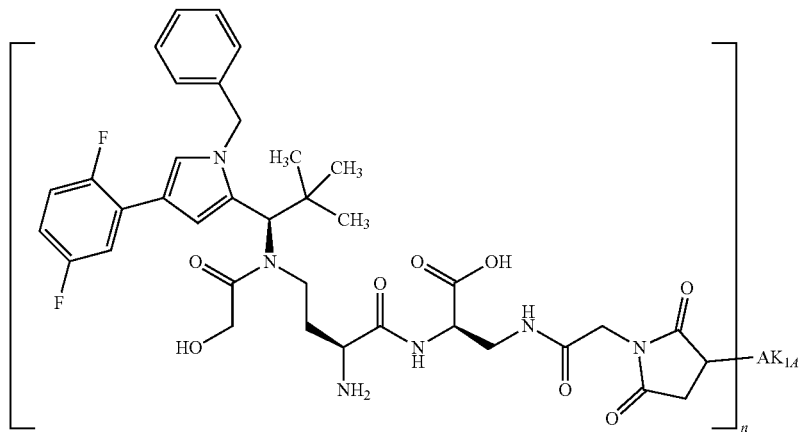
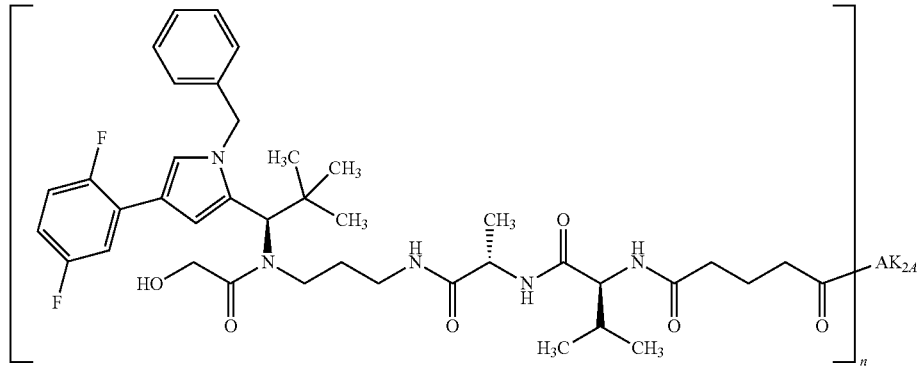

1185
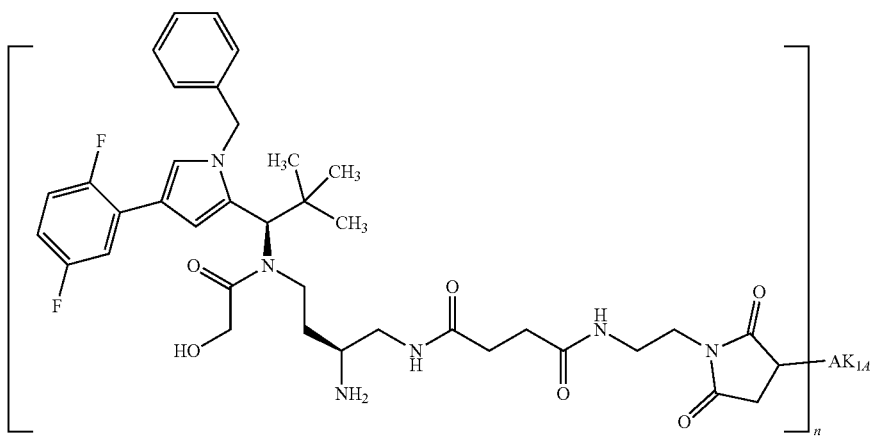
1186
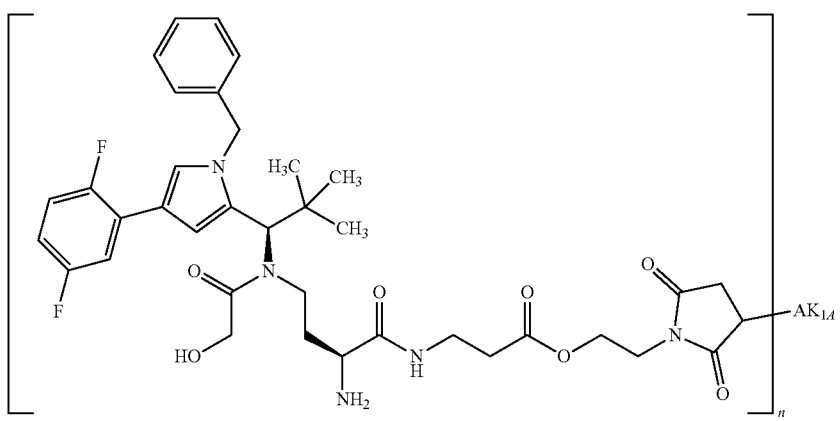
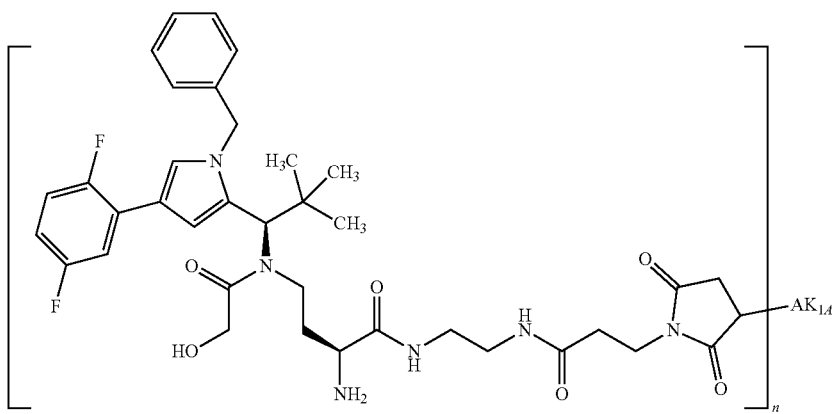

-continued
1187
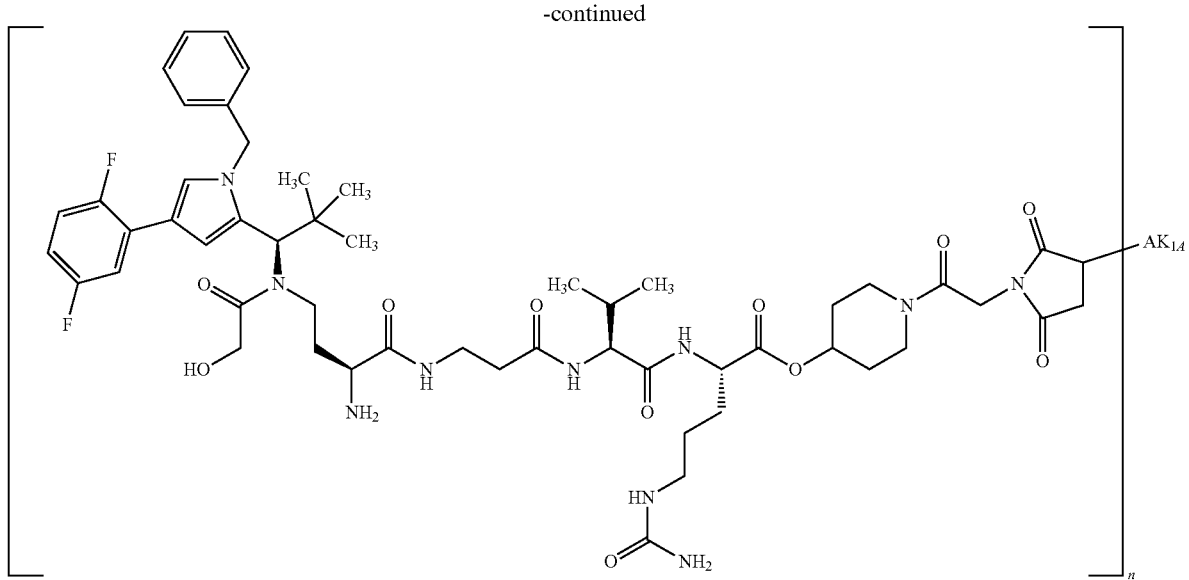
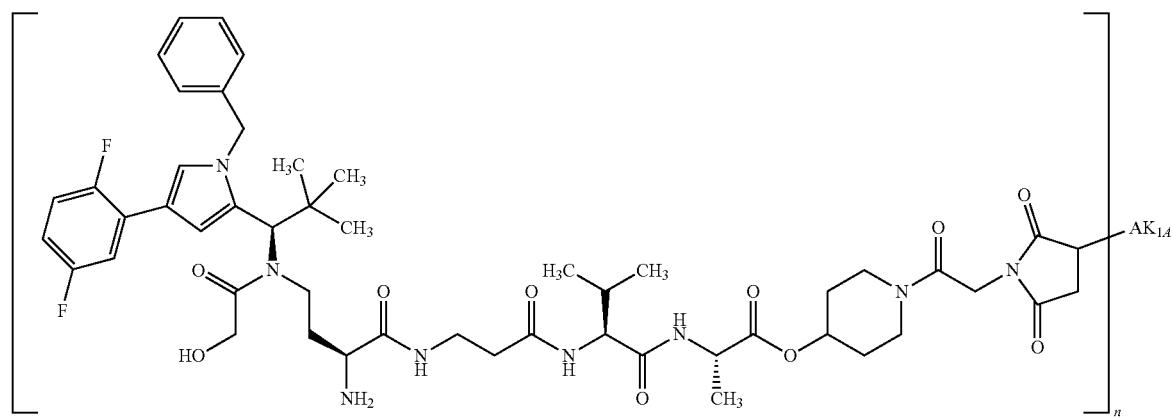
1188
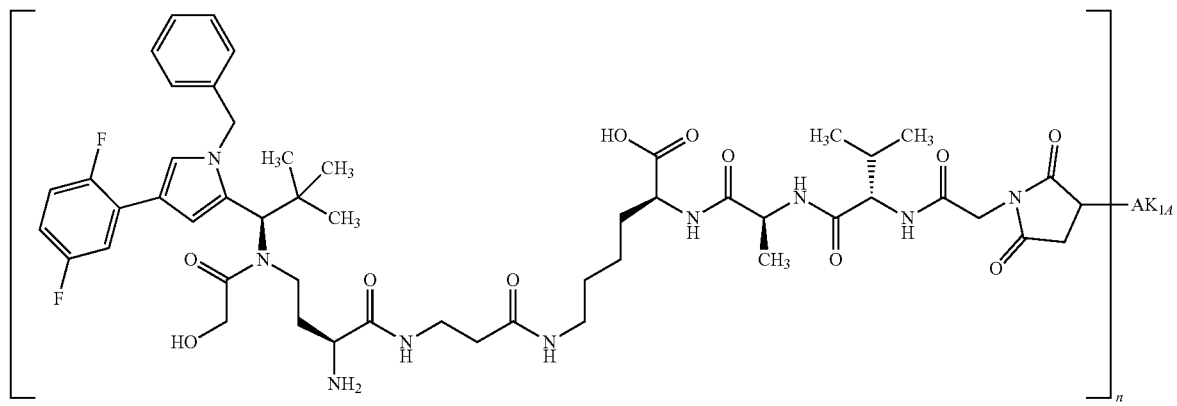

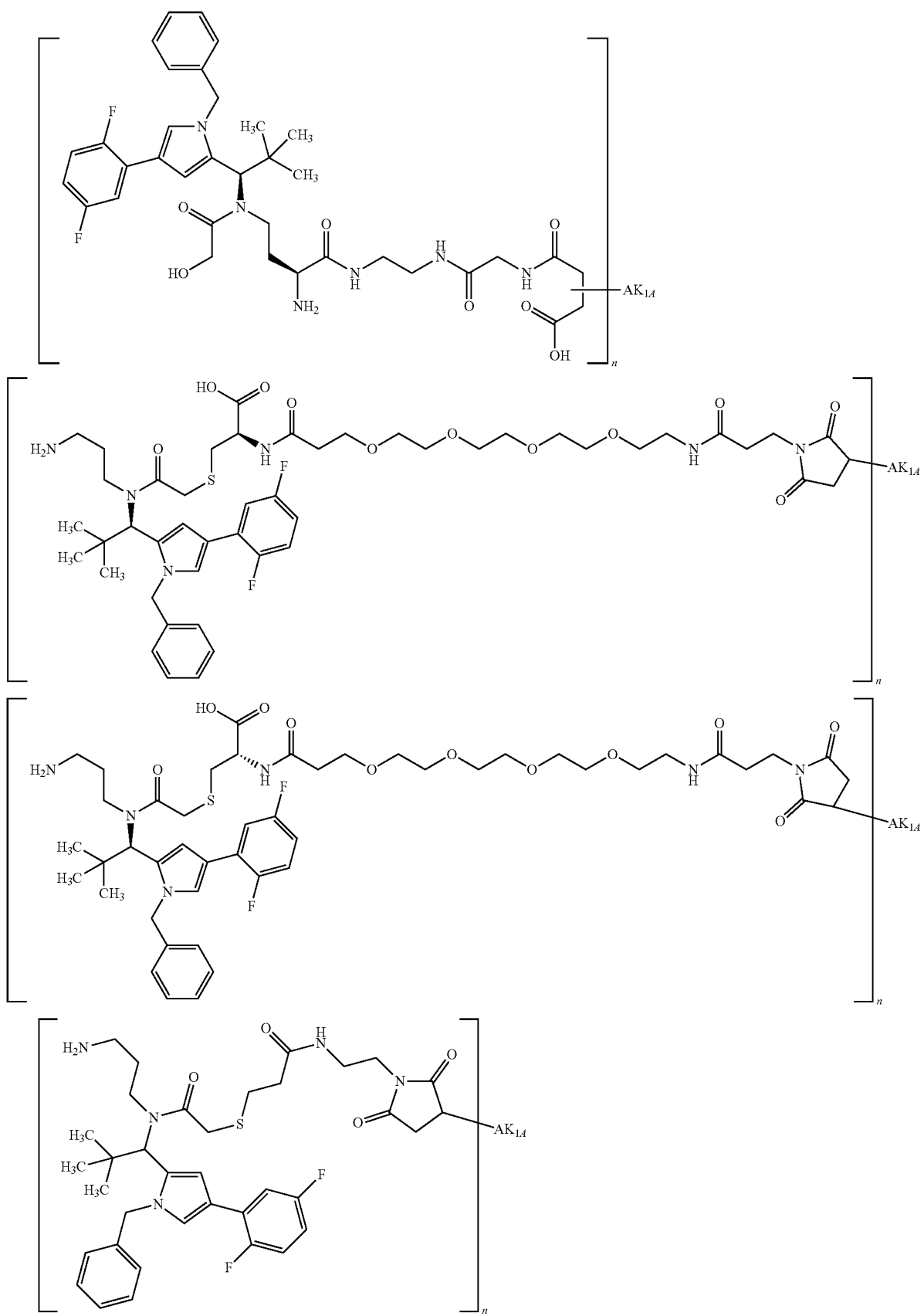

1191
1192
-continued
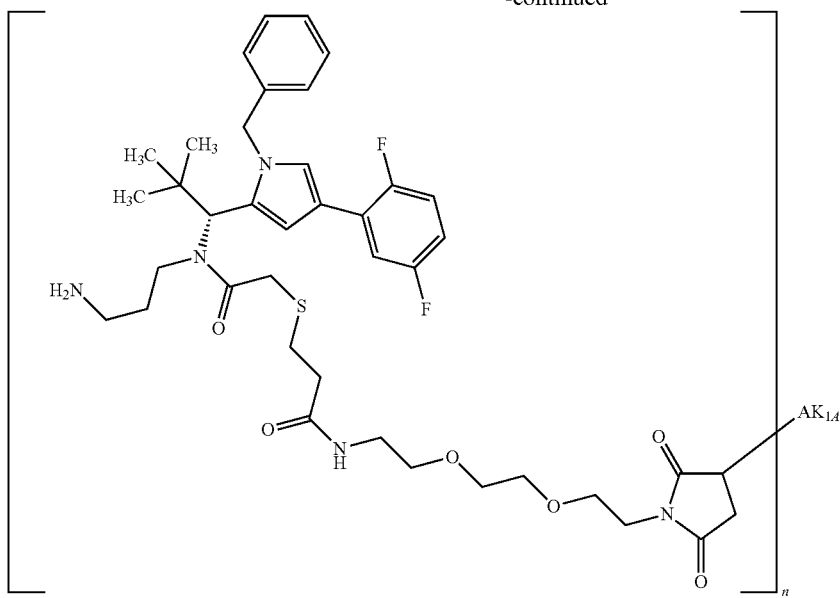
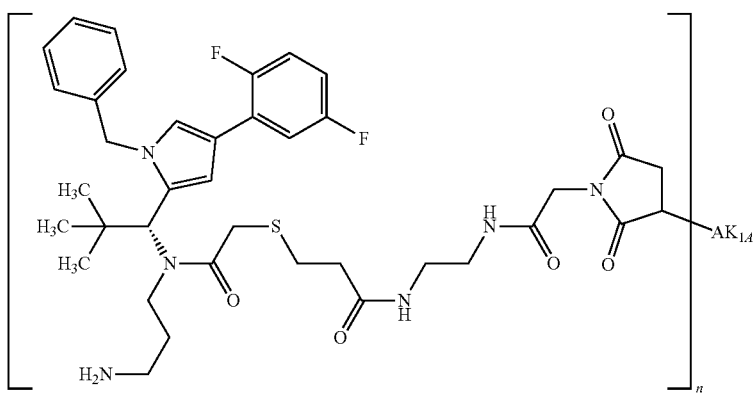
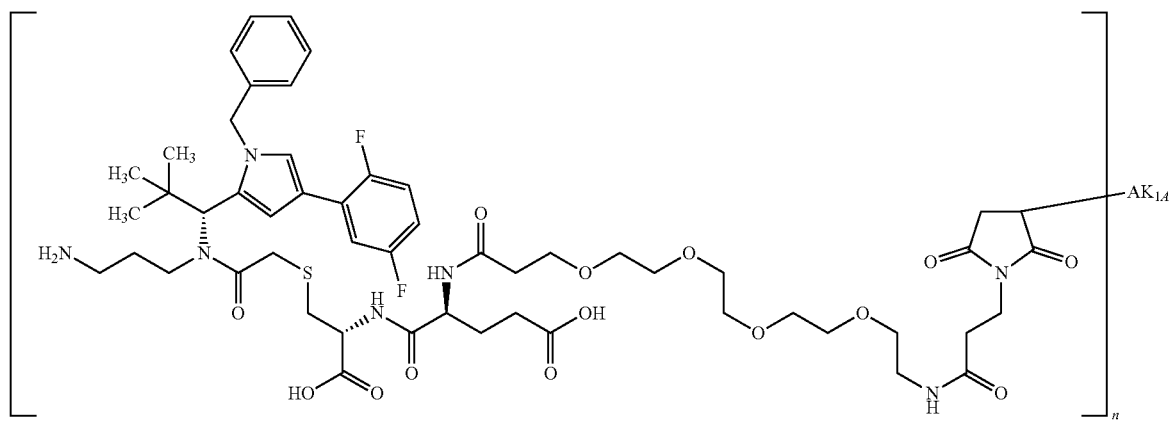

1193 1194
-continued
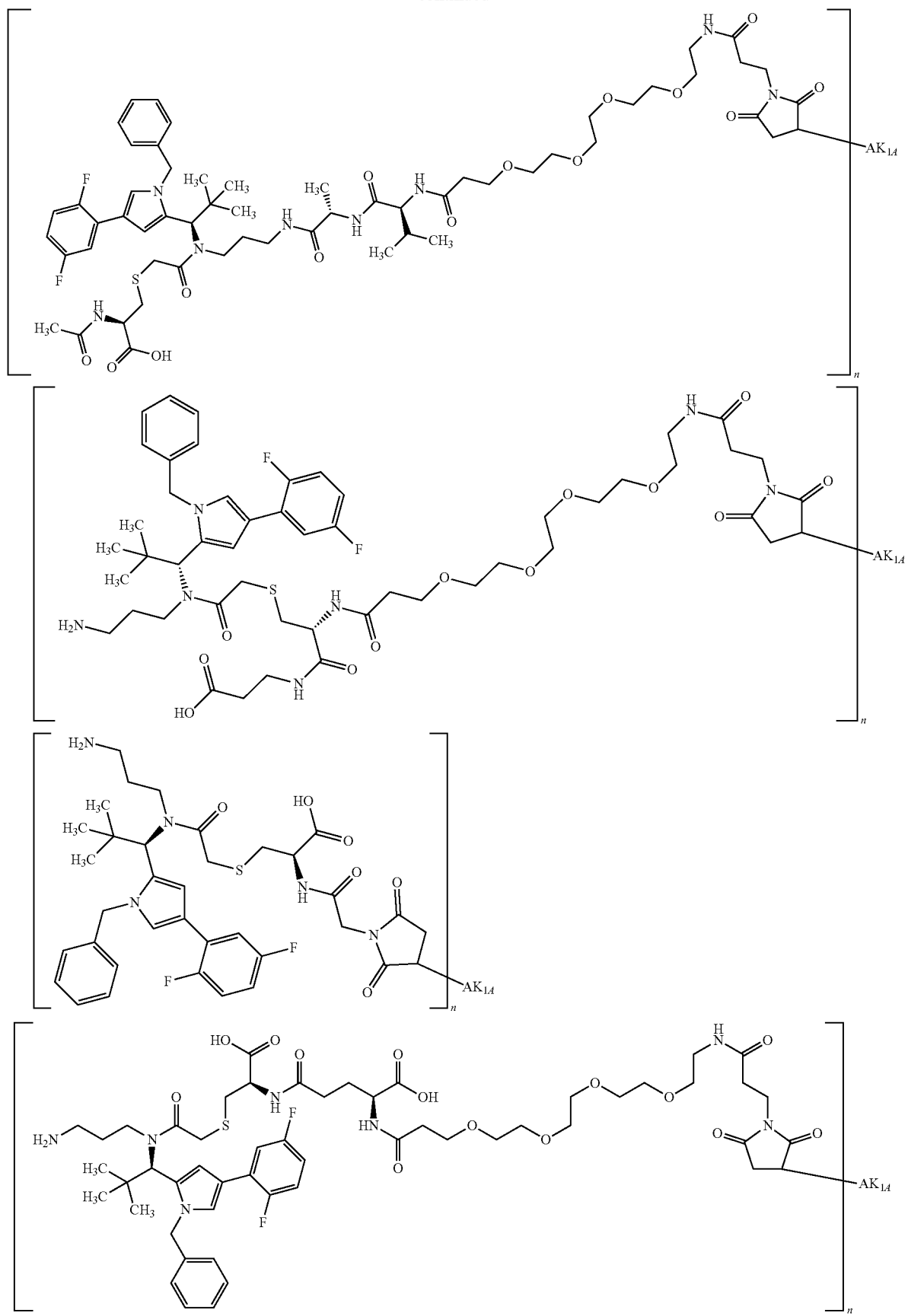

1195
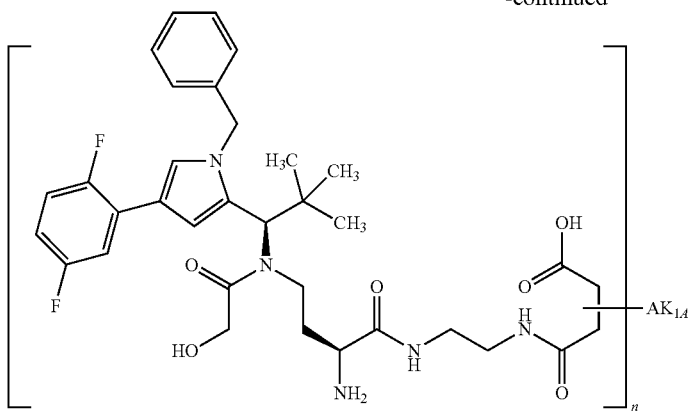
1196
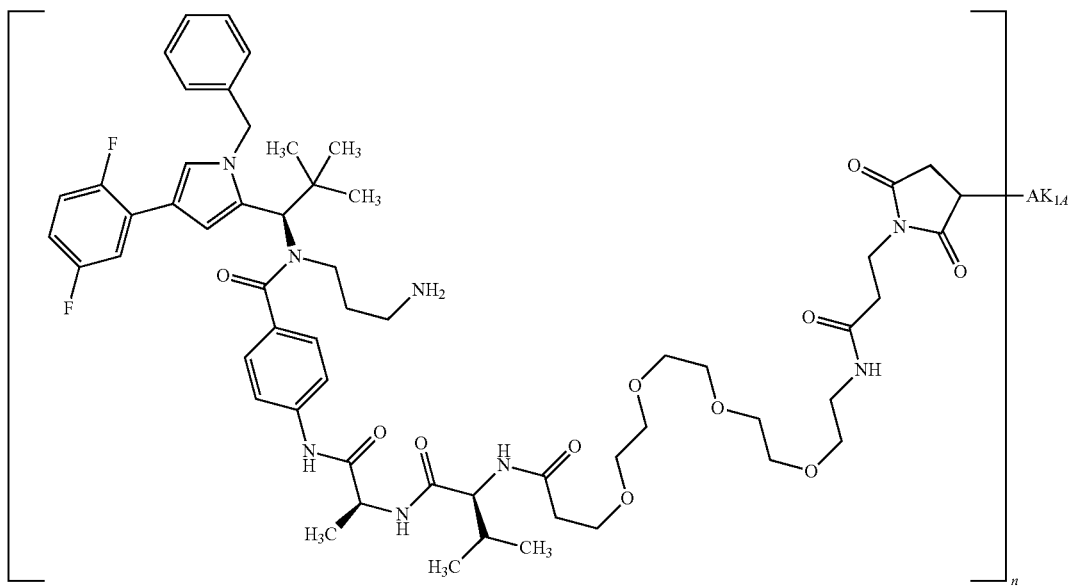
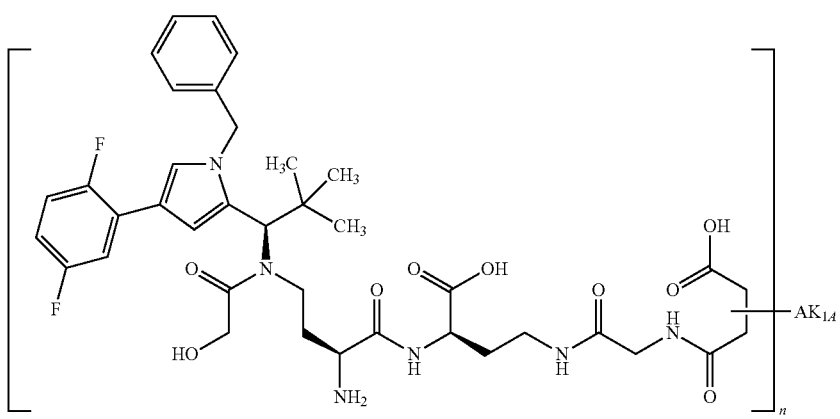

1197 1198
-continued
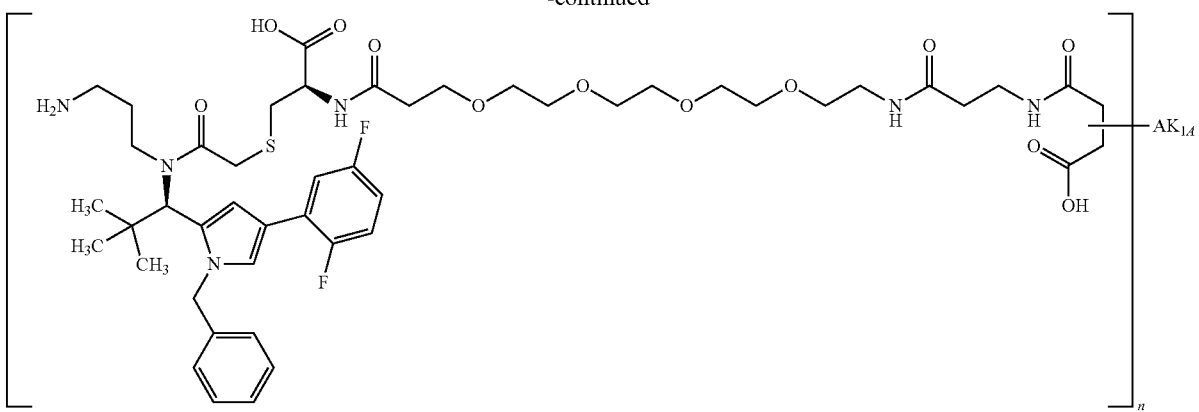
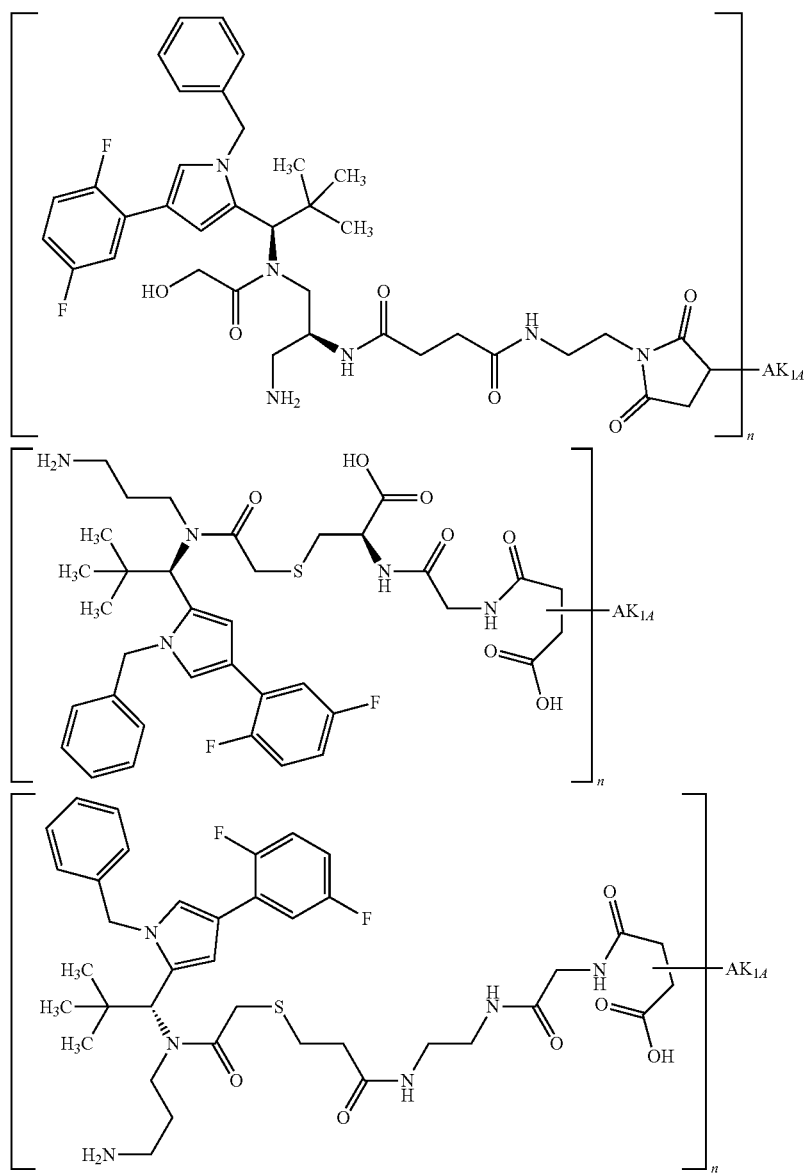

1199
-continued
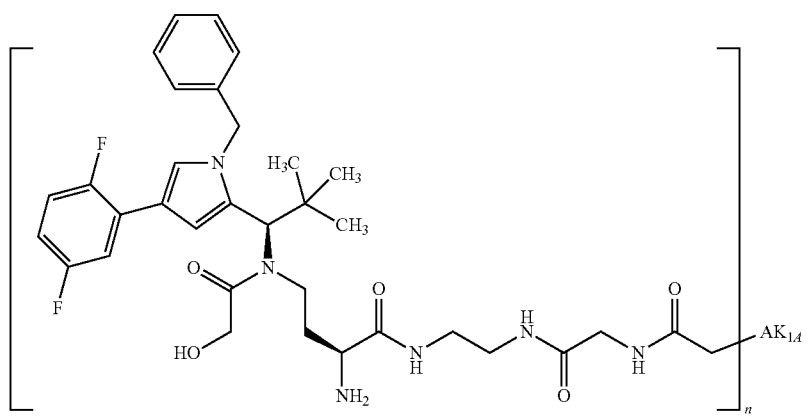
1200
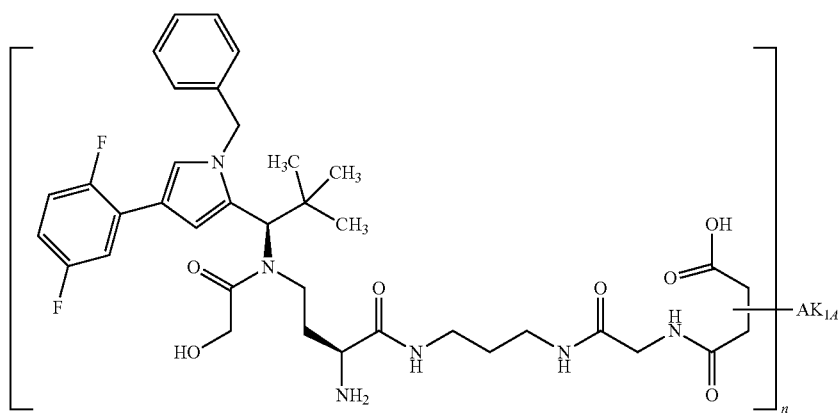
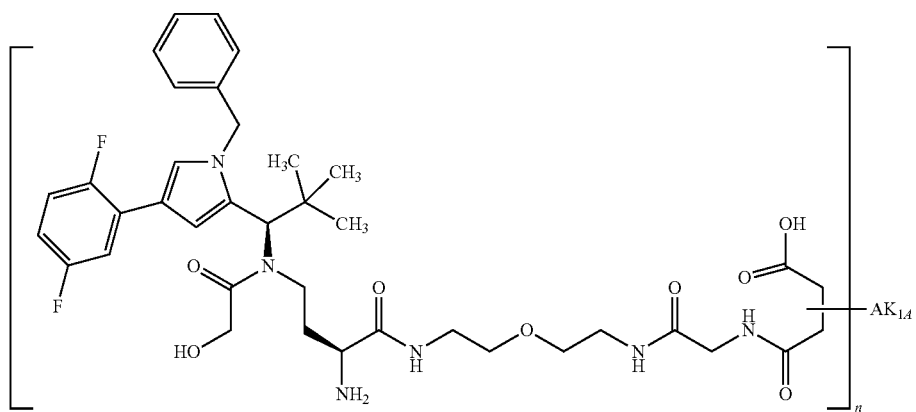

-continued
1201
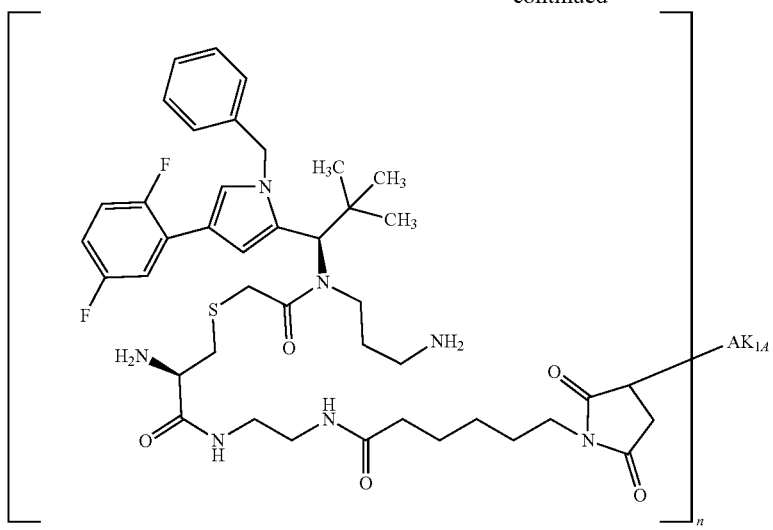
1202
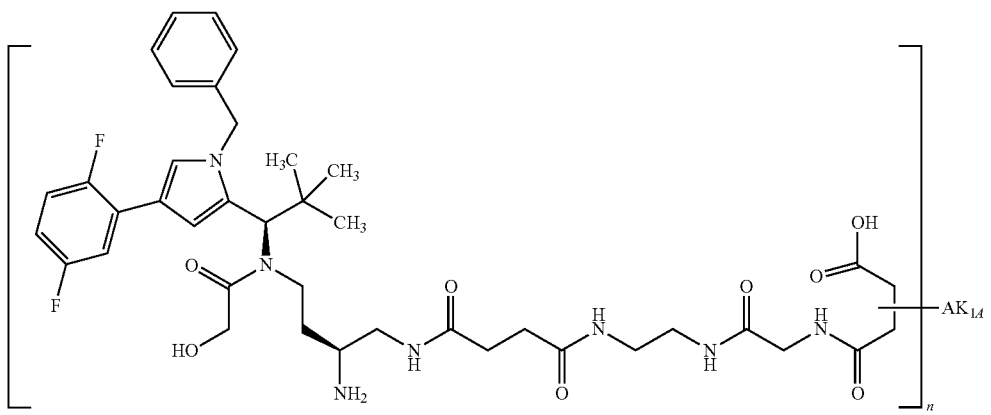
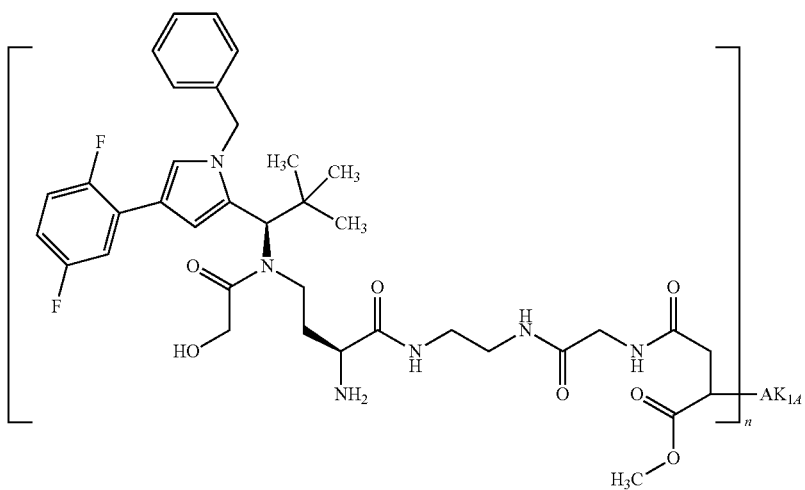

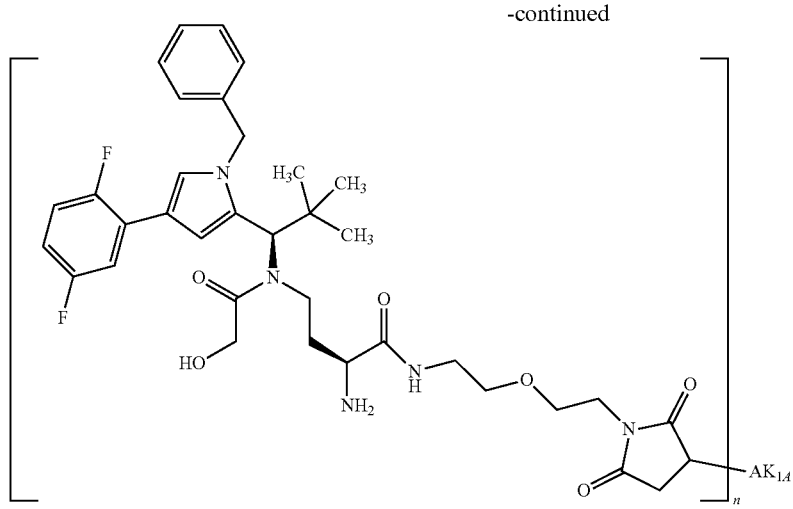

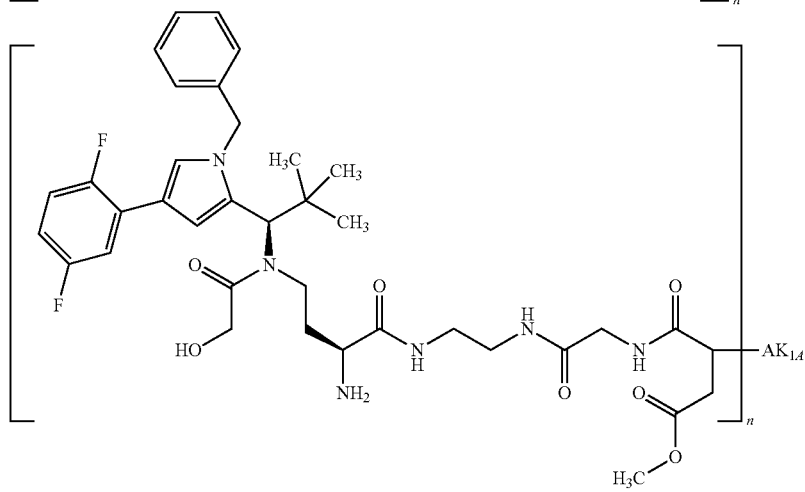

where the ADC, if attached via a group

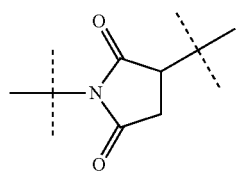

to the antibody, may also be present instead of this group at least partially in the form of the hydrolysed open-chain succinamides.

36. A binder-active compound of the general formula below:

where BINDER represents the binder or a derivative thereof, L represents the linker, WS represents the active compound, m represents a number from 1 to 2, n represents a number from 1 to 50, where L has the structure as set forth in Formula A Formula A

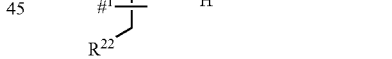

where $\#^1$ denotes the point of attachment to the sulphur atom of the binder, $\#^2$ denotes the point of attachment to the active compound and $R^{22}$ represents COOH, COOR, COR (where R in each case represents $C_{1-3}$-alkyl), CONH$_2$, Br;

$L_5$ is a group selected from —(CH$_2$)$_m$—(CHR$^S$)$_n$—(OCH$_2$CH$_2$)$_o$—(X)$_p$—(CH$_2$)$_q$—, where m, n, o, p and q independently of one another have the following values: m=0-10; n=0 or 1; o=0-10; p=0 or 1; and q=0-10, where m+n+o=1-15, X represents a 5- or 6-membered aromatic or nonaromatic hetero- or homo-cycle, $R^S$ represents an acid group,

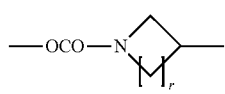

$L_6$ is a group selected from —CONH—, —OCONH—, —NHCO—, —NHCOO—, and

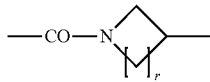

where r is 1, 2 or 3

$L_7$ is a single bond or a group selected from a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, $SO_2$, —$NR^y$—, —$NR^yCO$—, —$C(NH)NR^y$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$=N—O— (where $R^x$ represents H, $C_1$-$C_3$-alkyl or phenyl) and/or a 3- to 10-membered aromatic or non-aromatic heterocycle having up to 4 heteroatoms selected from the group consisting of N, O and S, —SO— or —$SO_2$— where the hydrocarbon chain including any side chains may be substituted by —$NHCONH_2$, —COOH, —OH, —$NH_2$, NH—$CNNH_2$, sulphonamide, sulphone, sulphoxide or sulphonic acid.

37. The conjugate according to claim 35 where the antibody is a human, humanized or chimeric monoclonal antibody or an antigen-binding fragment thereof.

38. The conjugate according to claim 37 where the antibody is an anti-HER2 antibody, and anti-EGFR antibody, an anti-TWEAKR antibody or an antigen-binding fragment thereof.

39. The conjugate according to claim 38 where the anti-TWEAKR antibody binds specifically to amino acid D in position 47 (D47) of TWEAKR (SEQ ID NO:169).

* * * * *

SEQUENCE LISTING

```
<160> NUMBER OF SEQ ID NOS: 213

<210> SEQ ID NO 1
<211> LENGTH: 215
<212> TYPE: PRT
<213> ORGANISM: Homo Sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

-continued

```
Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 2
<211> LENGTH: 449
<212> TYPE: PRT
<213> ORGANISM: Homo Sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                        325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 3
<211> LENGTH: 11
<212> TYPE: PRT
<213> ORGANISM: Homo Sapiens

<400> SEQUENCE: 3

Arg Ala Ser Gln Ser Ile Ser Gly Tyr Leu Asn
1               5                   10

<210> SEQ ID NO 4
<211> LENGTH: 7
<212> TYPE: PRT
<213> ORGANISM: Homo Sapiens

<400> SEQUENCE: 4

Gln Ala Ser Ser Leu Gln Ser
1               5

<210> SEQ ID NO 5
<211> LENGTH: 10
<212> TYPE: PRT
<213> ORGANISM: Homo Sapiens

<400> SEQUENCE: 5

Gln Gln Ser Tyr Thr Ser Pro Phe Ile Thr
1               5                   10

<210> SEQ ID NO 6
<211> LENGTH: 5
<212> TYPE: PRT
<213> ORGANISM: Homo Sapiens

<400> SEQUENCE: 6

Pro Tyr Pro Met Ile
1               5

<210> SEQ ID NO 7
<211> LENGTH: 17
<212> TYPE: PRT
<213> ORGANISM: Homo Sapiens

<400> SEQUENCE: 7

Tyr Ile Ser Pro Ser Gly Gly Ser Thr His Tyr Ala Asp Ser Val Lys
1               5                   10                  15
```

Gly

<210> SEQ ID NO 8
<211> LENGTH: 11
<212> TYPE: PRT
<213> ORGANISM: Homo Sapiens

<400> SEQUENCE: 8

Gly Gly Asp Thr Tyr Phe Asp Tyr Phe Asp Tyr
1               5                   10

<210> SEQ ID NO 9
<211> LENGTH: 108
<212> TYPE: PRT
<213> ORGANISM: Homo Sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
                20                  25                  30

Leu Asn Trp Tyr Gln Gln Lys Pro Gly Lys Ala Pro Lys Leu Leu Ile
            35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 10
<211> LENGTH: 121
<212> TYPE: PRT
<213> ORGANISM: Homo Sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Ile Trp Val Arg Gln Ala Pro Gly Lys Gly Leu Glu Trp Val
            35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 11
<211> LENGTH: 215
<212> TYPE: PRT

<213> ORGANISM: Homo Sapiens

<400> SEQUENCE: 11

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 12
<211> LENGTH: 449
<212> TYPE: PRT
<213> ORGANISM: Homo Sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala

-continued

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 13
<211> LENGTH: 11
<212> TYPE: PRT
<213> ORGANISM: Homo Sapiens

<400> SEQUENCE: 13

Arg Ala Ser Gln Ser Ile Ser Gly Tyr Leu Asn
1               5                   10

<210> SEQ ID NO 14
<211> LENGTH: 7
<212> TYPE: PRT
<213> ORGANISM: Homo Sapiens

<400> SEQUENCE: 14
```

Gln Ala Ser Ser Leu Gln Ser
1               5

<210> SEQ ID NO 15
<211> LENGTH: 10
<212> TYPE: PRT
<213> ORGANISM: Homo Sapiens

<400> SEQUENCE: 15

Gln Gln Ser Tyr Thr Ser Pro Phe Ile Thr
1               5                   10

<210> SEQ ID NO 16
<211> LENGTH: 5
<212> TYPE: PRT
<213> ORGANISM: Homo Sapiens

<400> SEQUENCE: 16

Pro Tyr Pro Met Ile
1               5

<210> SEQ ID NO 17
<211> LENGTH: 17
<212> TYPE: PRT
<213> ORGANISM: Homo Sapiens

<400> SEQUENCE: 17

Tyr Ile Ser Pro Ser Gly Gly Lys Thr His Tyr Ala Asp Ser Val Lys
1               5                   10                  15

Gly

<210> SEQ ID NO 18
<211> LENGTH: 11
<212> TYPE: PRT
<213> ORGANISM: Homo Sapiens

<400> SEQUENCE: 18

Gly Gly Asp Thr Tyr Phe Asp Tyr Phe Asp Tyr
1               5                   10

<210> SEQ ID NO 19
<211> LENGTH: 108
<212> TYPE: PRT
<213> ORGANISM: Homo Sapiens

<400> SEQUENCE: 19

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105

<210> SEQ ID NO 20
<211> LENGTH: 121
<212> TYPE: PRT
<213> ORGANISM: Homo Sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 21
<211> LENGTH: 215
<212> TYPE: PRT
<213> ORGANISM: Homo Sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 22
<211> LENGTH: 449
<212> TYPE: PRT
<213> ORGANISM: Homo Sapiens

<400> SEQUENCE: 22

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Pro Tyr
        20                  25                  30

Pro Met Met Trp Val Arg Gln Ala Pro Gly Lys Gly Leu Glu Trp Val
            35                  40                  45

Ser Tyr Ile Ser Pro Ser Gly Ser Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

```
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 23
<211> LENGTH: 11
<212> TYPE: PRT
<213> ORGANISM: Homo Sapiens

<400> SEQUENCE: 23

Arg Ala Ser Gln Ser Ile Ser Ser Tyr Leu Asn
1               5                   10

<210> SEQ ID NO 24
<211> LENGTH: 7
<212> TYPE: PRT
<213> ORGANISM: Homo Sapiens

<400> SEQUENCE: 24

Gln Ala Ser Ser Leu Gln Ser
1               5

<210> SEQ ID NO 25
<211> LENGTH: 10
<212> TYPE: PRT
<213> ORGANISM: Homo Sapiens

<400> SEQUENCE: 25

Gln Gln Ser Tyr Thr Ser Pro Phe Ile Thr
1               5                   10

<210> SEQ ID NO 26
<211> LENGTH: 5
<212> TYPE: PRT
<213> ORGANISM: Homo Sapiens

<400> SEQUENCE: 26

Pro Tyr Pro Met Met
1               5

<210> SEQ ID NO 27
<211> LENGTH: 17
<212> TYPE: PRT
<213> ORGANISM: Homo Sapiens

<400> SEQUENCE: 27

Tyr Ile Ser Pro Ser Gly Gly Ser Thr His Tyr Ala Asp Ser Val Lys
1               5                   10                  15
Gly

<210> SEQ ID NO 28
<211> LENGTH: 11
<212> TYPE: PRT
```

```
<213> ORGANISM: Homo Sapiens

<400> SEQUENCE: 28

Gly Gly Asp Thr Tyr Phe Asp Tyr Phe Asp Tyr
1               5                   10

<210> SEQ ID NO 29
<211> LENGTH: 108
<212> TYPE: PRT
<213> ORGANISM: Homo Sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 30
<211> LENGTH: 121
<212> TYPE: PRT
<213> ORGANISM: Homo Sapiens

<400> SEQUENCE: 30

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 31
<211> LENGTH: 215
<212> TYPE: PRT
<213> ORGANISM: Homo Sapiens

<400> SEQUENCE: 31

Asp Ile Gln Met Thr Gln Ser Pro Ala Thr Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Gln Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
         195                 200                 205

Ser Phe Asn Arg Gly Glu Cys
210                 215

<210> SEQ ID NO 32
<211> LENGTH: 449
<212> TYPE: PRT
<213> ORGANISM: Homo Sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
         35                  40                  45

Ser Tyr Ile Ser Pro Ser Gly Gly Lys Thr His Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 33
<211> LENGTH: 11
<212> TYPE: PRT
<213> ORGANISM: Homo Sapiens

<400> SEQUENCE: 33

Arg Ala Ser Gln Ser Ile Ser Ser Tyr Leu Asn
1               5                   10

<210> SEQ ID NO 34
<211> LENGTH: 7
<212> TYPE: PRT
<213> ORGANISM: Homo Sapiens

<400> SEQUENCE: 34

Gln Ala Ser Ser Leu Gln Ser
1               5

<210> SEQ ID NO 35
<211> LENGTH: 10

<212> TYPE: PRT
<213> ORGANISM: Homo Sapiens

<400> SEQUENCE: 35

```
Gln Gln Ser Tyr Thr Ser Pro Phe Ile Thr
1               5                   10
```

<210> SEQ ID NO 36
<211> LENGTH: 5
<212> TYPE: PRT
<213> ORGANISM: Homo Sapiens

<400> SEQUENCE: 36

```
Pro Tyr Pro Met Met
1               5
```

<210> SEQ ID NO 37
<211> LENGTH: 17
<212> TYPE: PRT
<213> ORGANISM: Homo Sapiens

<400> SEQUENCE: 37

```
Tyr Ile Ser Pro Ser Gly Gly Lys Thr His Tyr Ala Asp Ser Val Lys
1               5                   10                  15

Gly
```

<210> SEQ ID NO 38
<211> LENGTH: 11
<212> TYPE: PRT
<213> ORGANISM: Homo Sapiens

<400> SEQUENCE: 38

```
Gly Gly Asp Thr Tyr Phe Asp Tyr Phe Asp Tyr
1               5                   10
```

<210> SEQ ID NO 39
<211> LENGTH: 108
<212> TYPE: PRT
<213> ORGANISM: Homo Sapiens

<400> SEQUENCE: 39

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105
```

<210> SEQ ID NO 40
<211> LENGTH: 121
<212> TYPE: PRT
<213> ORGANISM: Homo Sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
            115                 120

<210> SEQ ID NO 41
<211> LENGTH: 215
<212> TYPE: PRT
<213> ORGANISM: Homo Sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 42
<211> LENGTH: 449
<212> TYPE: PRT

<213> ORGANISM: Homo Sapiens

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 43
<211> LENGTH: 11
<212> TYPE: PRT
<213> ORGANISM: Homo Sapiens

<400> SEQUENCE: 43

Arg Ala Ser Gln Ser Ile Ser Ser Tyr Leu Asn
1               5                   10

<210> SEQ ID NO 44
<211> LENGTH: 7
<212> TYPE: PRT
<213> ORGANISM: Homo Sapiens

<400> SEQUENCE: 44

Ala Ala Ser Ser Leu Gln Ser
1               5

<210> SEQ ID NO 45
<211> LENGTH: 10
<212> TYPE: PRT
<213> ORGANISM: Homo Sapiens

<400> SEQUENCE: 45

Gln Gln Ser Tyr Ser Thr Pro Gly Ile Thr
1               5                   10

<210> SEQ ID NO 46
<211> LENGTH: 5
<212> TYPE: PRT
<213> ORGANISM: Homo Sapiens

<400> SEQUENCE: 46

Pro Tyr Pro Met Met
1               5

<210> SEQ ID NO 47
<211> LENGTH: 17
<212> TYPE: PRT
<213> ORGANISM: Homo Sapiens

<400> SEQUENCE: 47

Tyr Ile Ser Pro Ser Gly Gly Ser Thr His Tyr Ala Asp Ser Val Lys
1               5                   10                  15

Gly

<210> SEQ ID NO 48
<211> LENGTH: 11
<212> TYPE: PRT
<213> ORGANISM: Homo Sapiens

<400> SEQUENCE: 48

Gly Gly Asp Thr Tyr Phe Asp Tyr Phe Asp Tyr
1               5                   10

<210> SEQ ID NO 49
<211> LENGTH: 108
<212> TYPE: PRT
<213> ORGANISM: Homo Sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Ile Thr Phe Gly Gln Gly Thr Lys Val Glu Ile Lys
            100                 105

<210> SEQ ID NO 50
<211> LENGTH: 121
<212> TYPE: PRT
<213> ORGANISM: Homo Sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 51
<211> LENGTH: 215
<212> TYPE: PRT
<213> ORGANISM: Homo Sapiens

<400> SEQUENCE: 51

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ser Pro Gly
                 85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 52
<211> LENGTH: 449
<212> TYPE: PRT
<213> ORGANISM: Homo Sapiens

<400> SEQUENCE: 52

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Tyr
             20                  25                  30

Pro Met Met Trp Val Arg Gln Ala Pro Gly Lys Gly Leu Glu Trp Val
         35                  40                  45

Ser Tyr Ile Ser Pro Ser Gly Gly Lys Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 53
<211> LENGTH: 11
<212> TYPE: PRT
<213> ORGANISM: Homo Sapiens

<400> SEQUENCE: 53

Arg Ala Ser Gln Ser Ile Ser Ser Tyr Leu Asn
1               5                   10

<210> SEQ ID NO 54
<211> LENGTH: 7
<212> TYPE: PRT
<213> ORGANISM: Homo Sapiens

<400> SEQUENCE: 54

Ala Ala Ser Ser Leu Gln Ser
1               5

<210> SEQ ID NO 55
<211> LENGTH: 10
<212> TYPE: PRT
<213> ORGANISM: Homo Sapiens

<400> SEQUENCE: 55

Gln Gln Ser Tyr Ser Ser Pro Gly Ile Thr
1               5                   10
```

<210> SEQ ID NO 56
<211> LENGTH: 5
<212> TYPE: PRT
<213> ORGANISM: Homo Sapiens

<400> SEQUENCE: 56

Pro Tyr Pro Met Met
1               5

<210> SEQ ID NO 57
<211> LENGTH: 17
<212> TYPE: PRT
<213> ORGANISM: Homo Sapiens

<400> SEQUENCE: 57

Tyr Ile Ser Pro Ser Gly Gly Lys Thr His Tyr Ala Asp Ser Val Lys
1               5                  10                  15

Gly

<210> SEQ ID NO 58
<211> LENGTH: 11
<212> TYPE: PRT
<213> ORGANISM: Homo Sapiens

<400> SEQUENCE: 58

Gly Gly Asp Thr Tyr Phe Asp Tyr Phe Asp Tyr
1               5                  10

<210> SEQ ID NO 59
<211> LENGTH: 108
<212> TYPE: PRT
<213> ORGANISM: Homo Sapiens

<400> SEQUENCE: 59

Asp Ile Gln Met Thr Gln Ser Pro Ala Thr Leu Ser Ala Ser Val Gly
1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Gly
                85                  90                  95

Ile Thr Phe Gly Pro Gly Thr Lys Val Glu Ile Lys
            100                 105

<210> SEQ ID NO 60
<211> LENGTH: 121
<212> TYPE: PRT
<213> ORGANISM: Homo Sapiens

<400> SEQUENCE: 60

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Pro Tyr
                20                  25                  30

Pro Met Met Trp Val Arg Gln Ala Pro Gly Lys Gly Leu Glu Trp Val
         35                  40                  45

Ser Tyr Ile Ser Pro Ser Gly Gly Lys Thr His Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
             100                 105                 110

Gly Thr Leu Val Thr Val Ser Ser Ala
        115                 120

<210> SEQ ID NO 61
<211> LENGTH: 217
<212> TYPE: PRT
<213> ORGANISM: Homo Sapiens

<400> SEQUENCE: 61

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
             20                  25                  30

Ser Tyr Leu Asn Trp Tyr Gln Gln Lys Pro Gly Lys Ala Pro Lys Leu
         35                  40                  45

Leu Ile Tyr Ala Ala Ser Ser Leu Gln Ser Gly Val Pro Ser Arg Phe
 50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                 85                  90                  95

Pro Gly Ile Thr Phe Gly Pro Gly Thr Lys Val Glu Ile Lys Arg Thr
             100                 105                 110

Val Ala Ala Pro Ser Val Phe Ile Phe Pro Pro Ser Asp Glu Gln Leu
         115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 62
<211> LENGTH: 449
<212> TYPE: PRT
<213> ORGANISM: Homo Sapiens

<400> SEQUENCE: 62

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Pro Tyr
         20                  25                  30

Pro Met Met Trp Val Arg Gln Ala Pro Gly Lys Gly Leu Glu Trp Val
         35                  40                  45

Ser Tyr Ile Ser Pro Ser Gly Gly Lys Thr His Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
```

```
                435                 440                 445

Gly

<210> SEQ ID NO 63
<211> LENGTH: 11
<212> TYPE: PRT
<213> ORGANISM: Homo Sapiens

<400> SEQUENCE: 63

Arg Ala Ser Gln Ser Ile Ser Ser Tyr Leu Asn
1               5                   10

<210> SEQ ID NO 64
<211> LENGTH: 7
<212> TYPE: PRT
<213> ORGANISM: Homo Sapiens

<400> SEQUENCE: 64

Ala Ala Ser Ser Leu Gln Ser
1               5

<210> SEQ ID NO 65
<211> LENGTH: 10
<212> TYPE: PRT
<213> ORGANISM: Homo Sapiens

<400> SEQUENCE: 65

Gln Gln Ser Tyr Ser Ser Pro Gly Ile Thr
1               5                   10

<210> SEQ ID NO 66
<211> LENGTH: 5
<212> TYPE: PRT
<213> ORGANISM: Homo Sapiens

<400> SEQUENCE: 66

Pro Tyr Pro Met Met
1               5

<210> SEQ ID NO 67
<211> LENGTH: 17
<212> TYPE: PRT
<213> ORGANISM: Homo Sapiens

<400> SEQUENCE: 67

Tyr Ile Ser Pro Ser Gly Gly Lys Thr His Tyr Ala Asp Ser Val Lys
1               5                   10                  15

Gly

<210> SEQ ID NO 68
<211> LENGTH: 11
<212> TYPE: PRT
<213> ORGANISM: Homo Sapiens

<400> SEQUENCE: 68

Gly Gly Asp Thr Tyr Phe Asp Tyr Phe Asp Tyr
1               5                   10

<210> SEQ ID NO 69
<211> LENGTH: 110
<212> TYPE: PRT
<213> ORGANISM: Homo Sapiens

<400> SEQUENCE: 69
```

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
            85                  90                  95

Pro Gly Ile Thr Phe Gly Pro Gly Thr Lys Val Glu Ile Lys
        100                 105                 110

<210> SEQ ID NO 70
<211> LENGTH: 121
<212> TYPE: PRT
<213> ORGANISM: Homo Sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Thr Tyr Phe Asp Tyr Phe Asp Tyr Trp Gly Gln
        100                 105                 110

Gly Thr Leu Val Thr Val Ser Ser Ala
        115                 120

<210> SEQ ID NO 71
<211> LENGTH: 217
<212> TYPE: PRT
<213> ORGANISM: Homo Sapiens

<400> SEQUENCE: 71

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
            85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 72
<211> LENGTH: 449
<212> TYPE: PRT
<213> ORGANISM: Homo Sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
            35                  40                  45

Ser Tyr Ile Ser Pro Ser Gly Gly Lys Thr His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile

```
                        245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 73
<211> LENGTH: 11
<212> TYPE: PRT
<213> ORGANISM: Homo Sapiens

<400> SEQUENCE: 73

Arg Ala Ser Gln Ser Ile Ser Ser Tyr Leu Asn
1               5                   10

<210> SEQ ID NO 74
<211> LENGTH: 7
<212> TYPE: PRT
<213> ORGANISM: Homo Sapiens

<400> SEQUENCE: 74

Ala Ala Ser Ser Leu Gln Ser
1               5

<210> SEQ ID NO 75
<211> LENGTH: 10
<212> TYPE: PRT
<213> ORGANISM: Homo Sapiens

<400> SEQUENCE: 75

Gln Gln Ser Tyr Ser Ser Pro Gly Ile Thr
1               5                   10

<210> SEQ ID NO 76
<211> LENGTH: 5
<212> TYPE: PRT
<213> ORGANISM: Homo Sapiens
```

```
<400> SEQUENCE: 76

Pro Tyr Pro Met Met
1               5

<210> SEQ ID NO 77
<211> LENGTH: 17
<212> TYPE: PRT
<213> ORGANISM: Homo Sapiens

<400> SEQUENCE: 77

Tyr Ile Ser Pro Ser Gly Gly Lys Thr His Tyr Ala Asp Ser Val Lys
1               5                   10                  15

Gly

<210> SEQ ID NO 78
<211> LENGTH: 11
<212> TYPE: PRT
<213> ORGANISM: Homo Sapiens

<400> SEQUENCE: 78

Gly Gly Asp Gly Tyr Phe Asp Tyr Phe Asp Tyr
1               5                   10

<210> SEQ ID NO 79
<211> LENGTH: 110
<212> TYPE: PRT
<213> ORGANISM: Homo Sapiens

<400> SEQUENCE: 79

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
                20                  25                  30

Ser Tyr Leu Asn Trp Tyr Gln Gln Lys Pro Gly Lys Ala Pro Lys Leu
            35                  40                  45

Leu Ile Tyr Ala Ala Ser Ser Leu Gln Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys
            100                 105                 110

<210> SEQ ID NO 80
<211> LENGTH: 121
<212> TYPE: PRT
<213> ORGANISM: Homo Sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Met Trp Val Arg Gln Ala Pro Gly Lys Gly Leu Glu Trp Val
            35                  40                  45

Ser Tyr Ile Ser Pro Ser Gly Gly Lys Thr His Tyr Ala Asp Ser Val
        50                  55                  60

Lys Gly Arg Phe Thr Ile Ser Arg Asp Asn Ser Lys Asn Thr Leu Tyr
```

```
              65                  70                  75                  80
Leu Gln Met Asn Ser Leu Arg Ala Glu Asp Thr Ala Val Tyr Tyr Cys
                    85                  90                  95

Ala Arg Gly Gly Asp Gly Tyr Phe Asp Tyr Phe Asp Tyr Trp Gly Gln
                100                 105                 110

Gly Thr Leu Val Thr Val Ser Ser Ala
            115                 120
```

<210> SEQ ID NO 81
<211> LENGTH: 217
<212> TYPE: PRT
<213> ORGANISM: Homo Sapiens

<400> SEQUENCE: 81

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
                20                  25                  30

Gly Tyr Leu Asn Trp Tyr Gln Gln Lys Pro Gly Lys Ala Pro Lys Leu
            35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 82
<211> LENGTH: 449
<212> TYPE: PRT
<213> ORGANISM: Homo Sapiens

<400> SEQUENCE: 82

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Ile Trp Val Arg Gln Ala Pro Gly Lys Gly Leu Glu Trp Val
            35                  40                  45

Ser Tyr Ile Ser Pro Ser Gly Gly Lys Thr His Tyr Ala Asp Ser Val
```

```
                50              55              60
Lys Gly Arg Phe Thr Ile Ser Arg Asp Asn Ser Lys Asn Thr Leu Tyr
 65                      70                      75                      80

Leu Gln Met Asn Ser Leu Arg Ala Glu Asp Thr Ala Val Tyr Tyr Cys
                         85                      90                      95

Ala Arg Gly Gly Asp Thr Tyr Phe Asp Tyr Phe Asp Tyr Trp Gly Gln
                        100                     105                     110

Gly Thr Leu Val Thr Val Ser Ala Ser Thr Lys Gly Pro Ser Val
                115                     120                     125

Phe Pro Leu Ala Pro Ser Ser Lys Ser Thr Ser Gly Gly Thr Ala Ala
130                     135                     140

Leu Gly Cys Leu Val Lys Asp Tyr Phe Pro Glu Pro Val Thr Val Ser
145                     150                     155                     160

Trp Asn Ser Gly Ala Leu Thr Ser Gly Val His Thr Phe Pro Ala Val
                        165                     170                     175

Leu Gln Ser Ser Gly Leu Tyr Ser Leu Ser Ser Val Val Thr Val Pro
                        180                     185                     190

Ser Ser Ser Leu Gly Thr Gln Thr Tyr Ile Cys Asn Val Asn His Lys
                        195                     200                     205

Pro Ser Asn Thr Lys Val Asp Lys Lys Val Glu Pro Lys Ser Cys Asp
210                     215                     220

Lys Thr His Thr Cys Pro Pro Cys Pro Ala Pro Glu Leu Leu Gly Gly
225                     230                     235                     240

Pro Ser Val Phe Leu Phe Pro Pro Lys Pro Lys Asp Thr Leu Met Ile
                245                     250                     255

Ser Arg Thr Pro Glu Val Thr Cys Val Val Val Asp Val Ser His Glu
                260                     265                     270

Asp Pro Glu Val Lys Phe Asn Trp Tyr Val Asp Gly Val Glu Val His
                275                     280                     285

Asn Ala Lys Thr Lys Pro Arg Glu Glu Gln Tyr Asn Ser Thr Tyr Arg
290                     295                     300

Val Val Ser Val Leu Thr Val Leu His Gln Asp Trp Leu Asn Gly Lys
305                     310                     315                     320

Glu Tyr Lys Cys Lys Val Ser Asn Lys Ala Leu Pro Ala Pro Ile Glu
                325                     330                     335

Lys Thr Ile Ser Lys Ala Lys Gly Gln Pro Arg Glu Pro Gln Val Tyr
                340                     345                     350

Thr Leu Pro Pro Ser Arg Asp Glu Leu Thr Lys Asn Gln Val Ser Leu
                355                     360                     365

Thr Cys Leu Val Lys Gly Phe Tyr Pro Ser Asp Ile Ala Val Glu Trp
370                     375                     380

Glu Ser Asn Gly Gln Pro Glu Asn Asn Tyr Lys Thr Thr Pro Pro Val
385                     390                     395                     400

Leu Asp Ser Asp Gly Ser Phe Phe Leu Tyr Ser Lys Leu Thr Val Asp
                405                     410                     415

Lys Ser Arg Trp Gln Gln Gly Asn Val Phe Ser Cys Ser Val Met His
                420                     425                     430

Glu Ala Leu His Asn His Tyr Thr Gln Lys Ser Leu Ser Leu Ser Pro
                435                     440                     445

Gly

<210> SEQ ID NO 83
<211> LENGTH: 11
```

```
<212> TYPE: PRT
<213> ORGANISM: Homo Sapiens

<400> SEQUENCE: 83

Arg Ala Ser Gln Ser Ile Ser Gly Tyr Leu Asn
1               5                   10

<210> SEQ ID NO 84
<211> LENGTH: 7
<212> TYPE: PRT
<213> ORGANISM: Homo Sapiens

<400> SEQUENCE: 84

Asn Ala Ser Ser Leu Gln Ser
1               5

<210> SEQ ID NO 85
<211> LENGTH: 10
<212> TYPE: PRT
<213> ORGANISM: Homo Sapiens

<400> SEQUENCE: 85

Gln Gln Ser Tyr Thr Ser Pro Phe Ile Thr
1               5                   10

<210> SEQ ID NO 86
<211> LENGTH: 5
<212> TYPE: PRT
<213> ORGANISM: Homo Sapiens

<400> SEQUENCE: 86

Pro Tyr Pro Met Ile
1               5

<210> SEQ ID NO 87
<211> LENGTH: 17
<212> TYPE: PRT
<213> ORGANISM: Homo Sapiens

<400> SEQUENCE: 87

Tyr Ile Ser Pro Ser Gly Gly Lys Thr His Tyr Ala Asp Ser Val Lys
1               5                   10                  15

Gly

<210> SEQ ID NO 88
<211> LENGTH: 11
<212> TYPE: PRT
<213> ORGANISM: Homo Sapiens

<400> SEQUENCE: 88

Gly Gly Asp Thr Tyr Phe Asp Tyr Phe Asp Tyr
1               5                   10

<210> SEQ ID NO 89
<211> LENGTH: 110
<212> TYPE: PRT
<213> ORGANISM: Homo Sapiens

<400> SEQUENCE: 89

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30
```

```
Gly Tyr Leu Asn Trp Tyr Gln Gln Lys Pro Gly Lys Ala Pro Lys Leu
            35                  40                  45

Leu Ile Tyr Asn Ala Ser Ser Leu Gln Ser Gly Val Pro Ser Arg Phe
         50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys
            100                 105                 110

<210> SEQ ID NO 90
<211> LENGTH: 121
<212> TYPE: PRT
<213> ORGANISM: Homo Sapiens

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
            35                  40                  45

Ser Tyr Ile Ser Pro Ser Gly Lys Thr His Tyr Ala Asp Ser Val
         50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
            115                 120

<210> SEQ ID NO 91
<211> LENGTH: 217
<212> TYPE: PRT
<213> ORGANISM: Homo Sapiens

<400> SEQUENCE: 91

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
            35                  40                  45

Leu Ile Tyr Asn Ala Ser Ser Leu Gln Ser Gly Val Pro Ser Arg Phe
         50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125
```

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 92
<211> LENGTH: 449
<212> TYPE: PRT
<213> ORGANISM: Homo Sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 93
<211> LENGTH: 11
<212> TYPE: PRT
<213> ORGANISM: Homo Sapiens

<400> SEQUENCE: 93

Arg Ala Ser Gln Ser Ile Ser Ser Tyr Leu Asn
1               5                   10

<210> SEQ ID NO 94
<211> LENGTH: 7
<212> TYPE: PRT
<213> ORGANISM: Homo Sapiens

<400> SEQUENCE: 94

Asn Ala Ser Ser Leu Gln Ser
1               5

<210> SEQ ID NO 95
<211> LENGTH: 10
<212> TYPE: PRT
<213> ORGANISM: Homo Sapiens

<400> SEQUENCE: 95

Gln Gln Ser Tyr Thr Ser Pro Gly Ile Thr
1               5                   10

<210> SEQ ID NO 96
<211> LENGTH: 5
<212> TYPE: PRT
<213> ORGANISM: Homo Sapiens

<400> SEQUENCE: 96

Pro Tyr Pro Met Met
1               5

<210> SEQ ID NO 97

<211> LENGTH: 17
<212> TYPE: PRT
<213> ORGANISM: Homo Sapiens

<400> SEQUENCE: 97

Tyr Ile Ser Pro Ser Gly Gly Lys Thr His Tyr Ala Asp Ser Val Lys
1               5                   10                  15

Gly

<210> SEQ ID NO 98
<211> LENGTH: 11
<212> TYPE: PRT
<213> ORGANISM: Homo Sapiens

<400> SEQUENCE: 98

Gly Gly Asp Thr Tyr Phe Asp Tyr Phe Asp Tyr
1               5                   10

<210> SEQ ID NO 99
<211> LENGTH: 110
<212> TYPE: PRT
<213> ORGANISM: Homo Sapiens

<400> SEQUENCE: 99

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
                20                  25                  30

Ser Tyr Leu Asn Trp Tyr Gln Gln Lys Pro Gly Lys Ala Pro Lys Leu
            35                  40                  45

Leu Ile Tyr Asn Ala Ser Ser Leu Gln Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys
            100                 105                 110

<210> SEQ ID NO 100
<211> LENGTH: 121
<212> TYPE: PRT
<213> ORGANISM: Homo Sapiens

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Met Trp Val Arg Gln Ala Pro Gly Lys Gly Leu Glu Trp Val
            35                  40                  45

Ser Tyr Ile Ser Pro Ser Gly Gly Lys Thr His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

-continued

```
Gly Thr Leu Val Thr Val Ser Ser Ala
        115                 120

<210> SEQ ID NO 101
<211> LENGTH: 217
<212> TYPE: PRT
<213> ORGANISM: Homo Sapiens

<400> SEQUENCE: 101

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 102
<211> LENGTH: 449
<212> TYPE: PRT
<213> ORGANISM: Homo Sapiens

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Lys Thr His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 103
<211> LENGTH: 11
<212> TYPE: PRT
<213> ORGANISM: Homo Sapiens

<400> SEQUENCE: 103

Arg Ala Ser Gln Ser Ile Ser Gly Tyr Leu Asn
1               5                   10
```

<210> SEQ ID NO 104
<211> LENGTH: 7
<212> TYPE: PRT
<213> ORGANISM: Homo Sapiens

<400> SEQUENCE: 104

Asn Ala Ser Ser Leu Gln Ser
1               5

<210> SEQ ID NO 105
<211> LENGTH: 10
<212> TYPE: PRT
<213> ORGANISM: Homo Sapiens

<400> SEQUENCE: 105

Gln Gln Ser Tyr Thr Ser Pro Gly Ile Thr
1               5                   10

<210> SEQ ID NO 106
<211> LENGTH: 5
<212> TYPE: PRT
<213> ORGANISM: Homo Sapiens

<400> SEQUENCE: 106

Pro Tyr Pro Met Met
1               5

<210> SEQ ID NO 107
<211> LENGTH: 17
<212> TYPE: PRT
<213> ORGANISM: Homo Sapiens

<400> SEQUENCE: 107

Tyr Ile Ser Pro Ser Gly Gly Lys Thr His Tyr Ala Asp Ser Val Lys
1               5                   10                  15

Gly

<210> SEQ ID NO 108
<211> LENGTH: 11
<212> TYPE: PRT
<213> ORGANISM: Homo Sapiens

<400> SEQUENCE: 108

Gly Gly Asp Thr Tyr Phe Asp Tyr Phe Asp Tyr
1               5                   10

<210> SEQ ID NO 109
<211> LENGTH: 110
<212> TYPE: PRT
<213> ORGANISM: Homo Sapiens

<400> SEQUENCE: 109

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu

```
                65                  70                  75                  80
Gln Pro Glu Asp Phe Ala Thr Tyr Tyr Cys Gln Gln Ser Tyr Thr Ser
                    85                  90                  95

Pro Gly Ile Thr Phe Gly Pro Gly Thr Lys Val Glu Ile Lys
                100                 105                 110
```

<210> SEQ ID NO 110
<211> LENGTH: 121
<212> TYPE: PRT
<213> ORGANISM: Homo Sapiens

<400> SEQUENCE: 110

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
                100                 105                 110

Gly Thr Leu Val Thr Val Ser Ser Ala
            115                 120
```

<210> SEQ ID NO 111
<211> LENGTH: 217
<212> TYPE: PRT
<213> ORGANISM: Homo Sapiens

<400> SEQUENCE: 111

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                       165                 170                 175
Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 112
<211> LENGTH: 449
<212> TYPE: PRT
<213> ORGANISM: Homo Sapiens

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
            35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 113
<211> LENGTH: 11
<212> TYPE: PRT
<213> ORGANISM: Homo Sapiens

<400> SEQUENCE: 113

Arg Ala Ser Gln Ser Ile Ser Ser Tyr Leu Asn
1               5                   10

<210> SEQ ID NO 114
<211> LENGTH: 7
<212> TYPE: PRT
<213> ORGANISM: Homo Sapiens

<400> SEQUENCE: 114

Asn Ala Ser Ser Leu Gln Ser
1               5

<210> SEQ ID NO 115
<211> LENGTH: 10
<212> TYPE: PRT
<213> ORGANISM: Homo Sapiens

<400> SEQUENCE: 115

Gln Gln Ser Tyr Thr Ser Pro Phe Ile Thr
1               5                   10

<210> SEQ ID NO 116
<211> LENGTH: 5
<212> TYPE: PRT
<213> ORGANISM: Homo Sapiens

<400> SEQUENCE: 116

Pro Tyr Pro Met Met
1               5

<210> SEQ ID NO 117
<211> LENGTH: 17
<212> TYPE: PRT
<213> ORGANISM: Homo Sapiens

<400> SEQUENCE: 117

Tyr Ile Ser Pro Ser Gly Gly Lys Thr His Tyr Ala Asp Ser Val Lys

```
1               5                  10                 15
Gly

<210> SEQ ID NO 118
<211> LENGTH: 11
<212> TYPE: PRT
<213> ORGANISM: Homo Sapiens

<400> SEQUENCE: 118

Gly Gly Asp Thr Tyr Phe Asp Tyr Phe Asp Tyr
1               5                  10

<210> SEQ ID NO 119
<211> LENGTH: 110
<212> TYPE: PRT
<213> ORGANISM: Homo Sapiens

<400> SEQUENCE: 119

Ala Gln Asp Ile Gln Met Thr Gln Ser Pro Ala Thr Leu Ser Ala Ser
1               5                  10                 15

Val Gly Asp Arg Val Thr Ile Thr Cys Arg Ala Ser Gln Ser Ile Ser
                20                 25                 30

Ser Tyr Leu Asn Trp Tyr Gln Gln Lys Pro Gly Lys Ala Pro Lys Leu
            35                 40                 45

Leu Ile Tyr Asn Ala Ser Ser Leu Gln Ser Gly Val Pro Ser Arg Phe
        50                 55                 60

Ser Gly Ser Gly Ser Gly Thr Asp Phe Thr Leu Thr Ile Ser Ser Leu
65                  70                 75                 80

Gln Pro Glu Asp Phe Ala Thr Tyr Tyr Cys Gln Gln Ser Tyr Thr Ser
                85                 90                 95

Pro Phe Ile Thr Phe Gly Pro Gly Thr Lys Val Glu Ile Lys
            100                105                110

<210> SEQ ID NO 120
<211> LENGTH: 121
<212> TYPE: PRT
<213> ORGANISM: Homo Sapiens

<400> SEQUENCE: 120

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Pro Tyr
                20                 25                 30

Pro Met Met Trp Val Arg Gln Ala Pro Gly Lys Gly Leu Glu Trp Val
            35                 40                 45

Ser Tyr Ile Ser Pro Ser Gly Lys Thr His Tyr Ala Asp Ser Val
        50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Thr Ala Val Tyr Tyr Cys
                85                 90                 95

Ala Arg Gly Gly Asp Thr Tyr Phe Asp Tyr Phe Asp Tyr Trp Gly Gln
            100                105                110

Gly Thr Leu Val Thr Val Ser Ser Ala
        115                120

<210> SEQ ID NO 121
<211> LENGTH: 218
```

```
<212> TYPE: PRT
<213> ORGANISM: Mus Musculus

<400> SEQUENCE: 121

Asp Ile Val Leu Thr Gln Ser Pro Ala Ser Leu Ala Val Ser Leu Gly
1               5                   10                  15

Gln Arg Ala Thr Ile Ser Cys Arg Ala Asn Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 122
<211> LENGTH: 450
<212> TYPE: PRT
<213> ORGANISM: Mus Musculus

<400> SEQUENCE: 122

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Gly Ile His Trp Val Lys Gln Ser His Ala Lys Ser Leu Glu Trp Ile
        35                  40                  45

Gly Val Ile Ser Thr Tyr Asn Gly Tyr Thr Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Ser Val Thr Val Ser Ser Ala Lys Thr Thr Ala Pro Ser
        115                 120                 125
```

```
Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Ser Val Thr Val Thr
                180                 185                 190

Ser Ser Thr Trp Pro Ser Gln Ser Ile Thr Cys Asn Val Ala His Pro
            195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
            275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Glu Glu Glu Met Thr Lys Lys Gln Val Thr
            355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His Thr Thr Lys Ser Phe Ser Arg Thr
    435                 440                 445

Pro Gly
    450

<210> SEQ ID NO 123
<211> LENGTH: 218
<212> TYPE: PRT
<213> ORGANISM: Mus Musculus

<400> SEQUENCE: 123

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met Gln Trp Tyr Gln Gln Arg Pro Gly Gln Pro Pro
        35                  40                  45
```

Lys Leu Leu Ile Lys Tyr Ala Thr Asn Leu Asp Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Trp
                 85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 124
<211> LENGTH: 448
<212> TYPE: PRT
<213> ORGANISM: Mus Musculus

<400> SEQUENCE: 124

Glu Val Lys Leu Glu Glu Ser Gly Gly Gly Leu Val Gln Pro Gly Gly
 1                   5                  10                  15

Ser Met Lys Leu Ser Cys Val Ala Ser Gly Phe Thr Phe Asn Asn Tyr
                20                  25                  30

Trp Met Ser Trp Val Arg Gln Ser Pro Glu Lys Gly Leu Glu Trp Leu
            35                  40                  45

Ala Glu Ile Arg Leu Lys Ser Asp Asn Tyr Ala Thr His Tyr Ala Glu
 50                  55                  60

Ser Val Lys Gly Lys Phe Thr Ile Ser Arg Asp Asp Ser Lys Ser Arg
 65                  70                  75                  80

Leu Tyr Leu Gln Met Asn Asn Leu Arg Ala Glu Asn Thr Gly Ile Tyr
                85                  90                  95

Tyr Cys Thr Gly Gly Phe Ala Asp Tyr Phe Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser

-continued

```
                195                 200                 205
Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

<210> SEQ ID NO 125
<211> LENGTH: 218
<212> TYPE: PRT
<213> ORGANISM: Homo Sapiens

<400> SEQUENCE: 125

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln His Ser Arg
                85                  90                  95

Glu Leu Pro Phe Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 126
<211> LENGTH: 450
<212> TYPE: PRT
<213> ORGANISM: Homo Sapiens

<400> SEQUENCE: 126

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Gly Met His Trp Val Arg Gln Ala Pro Gly Gln Gly Leu Glu Trp Met
            35                  40                  45

Gly Val Ile Ser Thr Tyr Asn Gly Tyr Thr Asn Tyr Asn Gln Lys Phe
    50                  55                  60

Lys Gly Arg Val Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 127
<211> LENGTH: 218
<212> TYPE: PRT
<213> ORGANISM: Homo Sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Ser Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
```

```
                195                 200                 205
Val Thr Lys Ser Phe Asn Arg Gly Glu Cys
    210                 215
```

<210> SEQ ID NO 128
<211> LENGTH: 449
<212> TYPE: PRT
<213> ORGANISM: Homo Sapiens

<400> SEQUENCE: 128

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Gly Tyr Tyr Ala Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 129
<211> LENGTH: 218
<212> TYPE: PRT
<213> ORGANISM: Mus Musculus

<400> SEQUENCE: 129

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Ser Thr Ser
            20                  25                  30

Thr Tyr Ser Tyr Met Gln Trp Tyr Gln Gln Arg Pro Gly Gln Ser Pro
        35                  40                  45

Lys Leu Leu Ile Lys Tyr Ala Ser Lys Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Leu Pro Tyr Thr Phe Gly Gly Gly Thr Arg Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 130
<211> LENGTH: 448
<212> TYPE: PRT
<213> ORGANISM: Mus Musculus

<400> SEQUENCE: 130

Glu Val Lys Leu Gly Glu Ser Gly Gly Gly Leu Val Gln Pro Gly Gly

-continued

```
  1               5                  10                 15
Ser Met Lys Leu Ser Cys Val Ala Ser Gly Phe Pro Phe Thr Lys Tyr
             20                 25                 30

Trp Met Asn Trp Val Arg Gln Ser Pro Glu Lys Gly Leu Glu Trp Val
             35                 40                 45

Ala Glu Ile Arg Leu Lys Ser Asp Asn Tyr Ala Thr His Tyr Ala Glu
 50                 55                 60

Ser Ala Lys Gly Arg Phe Thr Ile Ser Arg Asp Asp Ser Arg Ser Ser
 65                 70                 75                 80

Val Tyr Leu Gln Met Asn Asn Leu Arg Ala Glu Asp Thr Ala Ile Tyr
             85                 90                 95

Tyr Cys Ser Pro Thr Tyr Ala Asp Thr Met Asp Tyr Trp Gly Gln Gly
            100                105                110

Thr Ser Val Thr Val Ser Ser Ala Lys Thr Thr Ala Pro Ser Val Tyr
            115                120                125

Pro Leu Ala Pro Val Cys Gly Asp Thr Gly Ser Ser Val Thr Leu
130                135                140

Gly Cys Leu Val Lys Gly Tyr Phe Pro Glu Pro Val Thr Leu Thr Trp
145                150                155                160

Asn Ser Gly Ser Leu Ser Ser Gly Val His Thr Phe Pro Ala Val Leu
            165                170                175

Gln Ser Asp Leu Tyr Thr Leu Ser Ser Ser Val Thr Val Thr Ser Ser
            180                185                190

Thr Trp Pro Ser Gln Ser Ile Thr Cys Asn Val Ala His Pro Ala Ser
            195                200                205

Ser Thr Lys Val Asp Lys Lys Ile Glu Pro Arg Gly Pro Thr Ile Lys
210                215                220

Pro Cys Pro Pro Cys Lys Cys Pro Ala Pro Asn Leu Leu Gly Gly Pro
225                230                235                240

Ser Val Phe Ile Phe Pro Pro Lys Ile Lys Asp Val Leu Met Ile Ser
            245                250                255

Leu Ser Pro Ile Val Thr Cys Val Val Val Asp Val Ser Glu Asp Asp
            260                265                270

Pro Asp Val Gln Ile Ser Trp Phe Val Asn Asn Val Glu Val His Thr
            275                280                285

Ala Gln Thr Gln Thr His Arg Glu Asp Tyr Asn Ser Thr Leu Arg Val
290                295                300

Val Ser Ala Leu Pro Ile Gln His Gln Asp Trp Met Ser Gly Lys Glu
305                310                315                320

Phe Lys Cys Lys Val Asn Asn Lys Asp Leu Pro Ala Pro Ile Glu Arg
            325                330                335

Thr Ile Ser Lys Pro Lys Gly Ser Val Arg Ala Pro Gln Val Tyr Val
            340                345                350

Leu Pro Pro Pro Glu Glu Glu Met Thr Lys Lys Gln Val Thr Leu Thr
            355                360                365

Cys Met Val Thr Asp Phe Met Pro Glu Asp Ile Tyr Val Glu Trp Thr
370                375                380

Asn Asn Gly Lys Thr Glu Leu Asn Tyr Lys Asn Thr Glu Pro Val Leu
385                390                395                400

Asp Ser Asp Gly Ser Tyr Phe Met Tyr Ser Lys Leu Arg Val Glu Lys
            405                410                415

Lys Asn Trp Val Glu Arg Asn Ser Tyr Ser Cys Ser Val Val His Glu
            420                425                430
```

Gly Leu His Asn His Thr Thr Lys Ser Phe Ser Arg Thr Pro Gly
        435                 440                 445

<210> SEQ ID NO 131
<211> LENGTH: 218
<212> TYPE: PRT
<213> ORGANISM: Mus Musculus

<400> SEQUENCE: 131

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Thr Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 132
<211> LENGTH: 451
<212> TYPE: PRT
<213> ORGANISM: Mus Musculus

<400> SEQUENCE: 132

Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Pro Asp Tyr Tyr Gly Tyr Tyr Pro Met Asp Tyr
                100                 105                 110

Trp Gly Gln Gly Thr Ser Val Thr Val Ser Ala Lys Thr Thr Ala Pro
            115                 120                 125

Ser Val Tyr Pro Leu Ala Pro Val Cys Gly Asp Thr Thr Gly Ser Ser
        130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
                290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly
    450

<210> SEQ ID NO 133
<211> LENGTH: 282
<212> TYPE: PRT
<213> ORGANISM: Macaca fascicularis

<400> SEQUENCE: 133

Glu Gln Ala Pro Gly Thr Ala Pro Cys Ser His Gly Ser Ser Trp Ser

```
              1               5                  10                 15
Ala Asp Leu Asp Lys Cys Met Asp Cys Ala Ser Cys Arg Ala Arg Pro
              20                 25                 30

His Ser Asp Phe Cys Leu Gly Cys Ser Ala Pro Pro Ala Pro Phe
              35                 40                 45

Arg Leu Leu Trp Pro Arg Ser Asp Lys Thr His Thr Cys Pro Pro Cys
 50                  55                 60

Pro Ala Pro Glu Leu Leu Gly Gly Pro Ser Val Phe Leu Phe Pro Pro
 65                  70                 75                 80

Lys Pro Lys Asp Thr Leu Met Ile Ser Arg Thr Pro Glu Val Thr Cys
                 85                 90                 95

Val Val Val Asp Val Ser His Glu Asp Pro Glu Val Lys Phe Asn Trp
                 100                105                110

Tyr Val Asp Gly Val Glu Val His Asn Ala Lys Thr Lys Pro Arg Glu
                 115                120                125

Glu Gln Tyr Asn Ser Thr Tyr Arg Val Val Ser Val Leu Thr Val Leu
                 130                135                140

His Gln Asp Trp Leu Asn Gly Lys Glu Tyr Lys Cys Lys Val Ser Asn
145                  150                155                160

Lys Ala Leu Pro Ala Pro Ile Glu Lys Thr Ile Ser Lys Ala Lys Gly
                 165                170                175

Gln Pro Arg Glu Pro Gln Val Tyr Thr Leu Pro Pro Ser Arg Glu Glu
                 180                185                190

Met Thr Lys Asn Gln Val Ser Leu Thr Cys Leu Val Lys Gly Phe Tyr
                 195                200                205

Pro Ser Asp Ile Ala Val Glu Trp Glu Ser Asn Gly Gln Pro Glu Asn
                 210                215                220

Asn Tyr Lys Thr Thr Pro Pro Val Leu Asp Ser Asp Gly Ser Phe Phe
225                  230                235                240

Leu Tyr Ser Lys Leu Thr Val Asp Lys Ser Arg Trp Gln Gln Gly Asn
                 245                250                255

Val Phe Ser Cys Ser Val Met His Glu Ala Leu His Asn His Tyr Thr
                 260                265                270

Gln Lys Ser Leu Ser Leu Ser Pro Gly Lys
                 275                280

<210> SEQ ID NO 134
<211> LENGTH: 282
<212> TYPE: PRT
<213> ORGANISM: Rattus norvegicus

<400> SEQUENCE: 134

Glu Gln Ala Pro Gly Asn Ala Pro Cys Ser Ser Gly Ser Ser Trp Ser
 1               5                  10                 15

Ala Asp Leu Asp Lys Cys Met Asp Cys Ala Ser Cys Pro Ala Arg Pro
                 20                 25                 30

His Ser Asp Phe Cys Leu Gly Cys Ala Ala Pro Pro Ala His Phe
                 35                 40                 45

Arg Met Leu Trp Pro Arg Ser Asp Lys Thr His Thr Cys Pro Pro Cys
 50                  55                 60

Pro Ala Pro Glu Leu Leu Gly Gly Pro Ser Val Phe Leu Phe Pro Pro
 65                  70                 75                 80

Lys Pro Lys Asp Thr Leu Met Ile Ser Arg Thr Pro Glu Val Thr Cys
                 85                 90                 95
```

-continued

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 135
<211> LENGTH: 282
<212> TYPE: PRT
<213> ORGANISM: Sus scrofa

<400> SEQUENCE: 135

Glu Arg Val Pro Gly Thr Thr Pro Cys Ser Arg Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Pro Pro Ala Ser Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
        210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 136
<211> LENGTH: 282
<212> TYPE: PRT
<213> ORGANISM: Canis lupus

<400> SEQUENCE: 136

Glu Arg Val Pro Gly Thr Thr Pro Cys Pro Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Thr Ala Ala Pro Pro Ala Pro Phe
        35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys

<210> SEQ ID NO 137
<211> LENGTH: 282
<212> TYPE: PRT
<213> ORGANISM: Mus Musculus

<400> SEQUENCE: 137

```
Glu Gln Ala Pro Gly Thr Ser Pro Cys Ser Ser Gly Ser Ser Trp Ser
1               5                   10                  15
Ala Asp Leu Asp Lys Cys Met Asp Cys Ala Ser Cys Pro Ala Arg Pro
            20                  25                  30
His Ser Asp Phe Cys Leu Gly Cys Ala Ala Pro Pro Ala His Phe
        35                  40                  45
Arg Leu Leu Trp Pro Arg Ser Asp Lys Thr His Thr Cys Pro Pro Cys
    50                  55                  60
Pro Ala Pro Glu Leu Leu Gly Gly Pro Ser Val Phe Leu Phe Pro Pro
65                  70                  75                  80
Lys Pro Lys Asp Thr Leu Met Ile Ser Arg Thr Pro Glu Val Thr Cys
                85                  90                  95
Val Val Val Asp Val Ser His Glu Asp Pro Glu Val Lys Phe Asn Trp
            100                 105                 110
Tyr Val Asp Gly Val Glu Val His Asn Ala Lys Thr Lys Pro Arg Glu
        115                 120                 125
Glu Gln Tyr Asn Ser Thr Tyr Arg Val Val Ser Val Leu Thr Val Leu
    130                 135                 140
His Gln Asp Trp Leu Asn Gly Lys Glu Tyr Lys Cys Lys Val Ser Asn
145                 150                 155                 160
Lys Ala Leu Pro Ala Pro Ile Glu Lys Thr Ile Ser Lys Ala Lys Gly
                165                 170                 175
Gln Pro Arg Glu Pro Gln Val Tyr Thr Leu Pro Pro Ser Arg Glu Glu
            180                 185                 190
Met Thr Lys Asn Gln Val Ser Leu Thr Cys Leu Val Lys Gly Phe Tyr
        195                 200                 205
Pro Ser Asp Ile Ala Val Glu Trp Glu Ser Asn Gly Gln Pro Glu Asn
    210                 215                 220
Asn Tyr Lys Thr Thr Pro Pro Val Leu Asp Ser Asp Gly Ser Phe Phe
225                 230                 235                 240
Leu Tyr Ser Lys Leu Thr Val Asp Lys Ser Arg Trp Gln Gln Gly Asn
                245                 250                 255
Val Phe Ser Cys Ser Val Met His Glu Ala Leu His Asn His Tyr Thr
            260                 265                 270
Gln Lys Ser Leu Ser Leu Ser Pro Gly Lys
        275                 280
```

<210> SEQ ID NO 138
<211> LENGTH: 282
<212> TYPE: PRT
<213> ORGANISM: Homo Sapiens

<400> SEQUENCE: 138

```
Glu Gln Ala Pro Gly Thr Ala Pro Cys Ser Arg Gly Ser Ser Trp Ser
1               5                   10                  15
Ala Asp Leu Asp Lys Cys Met Asp Cys Ala Ser Cys Arg Ala Arg Pro
            20                  25                  30
His Ser Asp Phe Cys Leu Gly Cys Ala Ala Ala Pro Pro Ala Pro Phe
```

```
                35                  40                  45
Arg Leu Leu Trp Pro Arg Ser Asp Lys Thr His Thr Cys Pro Pro Cys
 50                  55                  60

Pro Ala Pro Glu Leu Leu Gly Gly Pro Ser Val Phe Leu Phe Pro Pro
 65                  70                  75                  80

Lys Pro Lys Asp Thr Leu Met Ile Ser Arg Thr Pro Glu Val Thr Cys
                 85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 139
<211> LENGTH: 296
<212> TYPE: PRT
<213> ORGANISM: Homo Sapiens

<400> SEQUENCE: 139

Glu Gln Ala Pro Gly Thr Ala Pro Cys Ser Arg Gly Ser Ser Trp Ser
 1               5                  10                  15

Ala Asp Leu Asp Lys Cys Met Asp Cys Ala Ser Cys Arg Ala Arg Pro
                 20                  25                  30

His Ser Asp Phe Cys Leu Gly Cys Ala Ala Pro Ala Pro Ala Pro Phe
             35                  40                  45

Arg Leu Leu Trp Pro Ile Glu Gly Arg Met Asp Pro Lys Ser Cys Asp
 50                  55                  60

Lys Thr His Thr Cys Pro Pro Cys Pro Ala Pro Glu Leu Leu Gly Gly
 65                  70                  75                  80

Pro Ser Val Phe Leu Phe Pro Pro Lys Pro Lys Asp Thr Leu Met Ile
                 85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125
```

```
Asn Ala Lys Thr Lys Pro Arg Glu Glu Gln Tyr Asn Ser Thr Tyr Arg
130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys His His His His His His
        290                 295

<210> SEQ ID NO 140
<211> LENGTH: 278
<212> TYPE: PRT
<213> ORGANISM: Homo Sapiens

<400> SEQUENCE: 140

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205
```

```
Asn Gly Gln Pro Glu Asn Asn Tyr Lys Thr Thr Pro Pro Val Leu Asp
    210                 215                 220
Ser Asp Gly Ser Phe Phe Leu Tyr Ser Lys Leu Thr Val Asp Lys Ser
225                 230                 235                 240
Arg Trp Gln Gln Gly Asn Val Phe Ser Cys Ser Val Met His Glu Ala
                245                 250                 255
Leu His Asn His Tyr Thr Gln Lys Ser Leu Ser Leu Ser Pro Gly Lys
            260                 265                 270
His His His His His His
            275
```

<210> SEQ ID NO 141
<211> LENGTH: 47
<212> TYPE: PRT
<213> ORGANISM: Homo Sapiens

<400> SEQUENCE: 141

```
Glu Gln Ala Pro Gly Thr Ala Pro Cys Ser Arg Gly Ser Ser Trp Ser
1               5                   10                  15
Ala Asp Leu Asp Lys Cys Met Asp Cys Ala Ser Cys Arg Ala Arg Pro
            20                  25                  30
His Ser Asp Phe Cys Leu Gly Cys Ala His His His His His His
            35                  40                  45
```

<210> SEQ ID NO 142
<211> LENGTH: 282
<212> TYPE: PRT
<213> ORGANISM: Homo Sapiens

<400> SEQUENCE: 142

```
Glu Gln Ala Pro Gly Thr Ala Pro Cys Ser Arg Gly Ser Ser Trp Ser
1               5                   10                  15
Ala Asp Leu Asp Lys Cys Met Asp Cys Ala Ser Cys Arg Ala Arg Pro
            20                  25                  30
His Ser Asp Phe Cys Gln Gly Cys Ala Ala Ala Pro Ala Pro Ala Phe
            35                  40                  45
Arg Leu Leu Trp Pro Arg Ser Asp Lys Thr His Thr Cys Pro Pro Cys
50                  55                  60
Pro Ala Pro Glu Leu Leu Gly Gly Pro Ser Val Phe Leu Phe Pro Pro
65                  70                  75                  80
Lys Pro Lys Asp Thr Leu Met Ile Ser Arg Thr Pro Glu Val Thr Cys
                85                  90                  95
Val Val Val Asp Val Ser His Glu Asp Pro Glu Val Lys Phe Asn Trp
            100                 105                 110
Tyr Val Asp Gly Val Glu Val His Asn Ala Lys Thr Lys Pro Arg Glu
        115                 120                 125
Glu Gln Tyr Asn Ser Thr Tyr Arg Val Val Ser Val Leu Thr Val Leu
    130                 135                 140
His Gln Asp Trp Leu Asn Gly Lys Glu Tyr Lys Cys Lys Val Ser Asn
145                 150                 155                 160
Lys Ala Leu Pro Ala Pro Ile Glu Lys Thr Ile Ser Lys Ala Lys Gly
                165                 170                 175
Gln Pro Arg Glu Pro Gln Val Tyr Thr Leu Pro Pro Ser Arg Glu Glu
            180                 185                 190
Met Thr Lys Asn Gln Val Ser Leu Thr Cys Leu Val Lys Gly Phe Tyr
        195                 200                 205
```

```
Pro Ser Asp Ile Ala Val Glu Trp Glu Ser Asn Gly Gln Pro Glu Asn
    210                 215                 220

Asn Tyr Lys Thr Thr Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly Lys
                275                 280

<210> SEQ ID NO 143
<211> LENGTH: 282
<212> TYPE: PRT
<213> ORGANISM: Homo Sapiens

<400> SEQUENCE: 143

Glu Gln Ala Pro Gly Thr Ala Pro Cys Ser Arg Gly Ser Trp Ser
1               5                   10                  15

Ala Asp Leu Asp Lys Cys Met Asp Cys Ala Ser Cys Arg Ala Arg Pro
                20                  25                  30

Lys Ser Asp Phe Cys Leu Gly Cys Ala Ala Pro Ala Pro Phe
                35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
    195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly Lys
                275                 280
```

<210> SEQ ID NO 144
<211> LENGTH: 282
<212> TYPE: PRT
<213> ORGANISM: Homo Sapiens

<400> SEQUENCE: 144

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Pro Pro Ala Pro Phe
            35                  40                  45

Arg Leu Leu Trp Pro Arg Ser Asp Lys Thr His Thr Cys Pro Pro Cys
        50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 145
<211> LENGTH: 282
<212> TYPE: PRT
<213> ORGANISM: Homo Sapiens

<400> SEQUENCE: 145

```
Glu Gln Ala Pro Gly Thr Ala Pro Cys Ser Arg Gly Ser Ser Trp Ser
1               5                   10                  15

Ala Asp Leu Asp Lys Cys Ala Asp Cys Ala Ser Cys Arg Ala Arg Pro
            20                  25                  30

His Ser Asp Phe Cys Leu Gly Cys Ala Ala Pro Pro Ala Pro Phe
            35                  40                  45

Arg Leu Leu Trp Pro Arg Ser Asp Lys Thr His Thr Cys Pro Pro Cys
```

```
                 50                   55                      60
Pro Ala Pro Glu Leu Leu Gly Gly Pro Ser Val Phe Leu Phe Pro Pro
 65                  70                      75                  80

Lys Pro Lys Asp Thr Leu Met Ile Ser Arg Thr Pro Glu Val Thr Cys
                     85                      90                  95

Val Val Val Asp Val Ser His Glu Asp Pro Glu Val Lys Phe Asn Trp
                100                     105                 110

Tyr Val Asp Gly Val Glu Val His Asn Ala Lys Thr Lys Pro Arg Glu
            115                     120                 125

Glu Gln Tyr Asn Ser Thr Tyr Arg Val Val Ser Val Leu Thr Val Leu
        130                     135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
        260                 265                 270

Gln Lys Ser Leu Ser Leu Ser Pro Gly Lys
    275                 280

<210> SEQ ID NO 146
<211> LENGTH: 282
<212> TYPE: PRT
<213> ORGANISM: Homo Sapiens

<400> SEQUENCE: 146

Glu Gln Ala Pro Gly Thr Ala Pro Cys Ser Arg Gly Ser Ser Ala Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
 65                  70                      75                  80

Lys Pro Lys Asp Thr Leu Met Ile Ser Arg Thr Pro Glu Val Thr Cys
                     85                      90                  95

Val Val Val Asp Val Ser His Glu Asp Pro Glu Val Lys Phe Asn Trp
                100                     105                 110

Tyr Val Asp Gly Val Glu Val His Asn Ala Lys Thr Lys Pro Arg Glu
            115                     120                 125

Glu Gln Tyr Asn Ser Thr Tyr Arg Val Val Ser Val Leu Thr Val Leu
        130                     135                 140
```

```
His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 147
<211> LENGTH: 282
<212> TYPE: PRT
<213> ORGANISM: Homo Sapiens

<400> SEQUENCE: 147

Glu Gln Ala Pro Gly Thr Ala Pro Cys Ser Arg Gly Arg Ser Trp Ser
1               5                   10                  15

Ala Asp Leu Asp Lys Cys Met Asp Cys Ala Ser Cys Arg Ala Arg Pro
                20                  25                  30

His Ser Asp Phe Cys Leu Gly Cys Ala Ala Ala Pro Pro Ala Pro Phe
            35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240
```

```
Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 148
<211> LENGTH: 282
<212> TYPE: PRT
<213> ORGANISM: Homo Sapiens

<400> SEQUENCE: 148

```
Glu Gln Ala Pro Gly Gln Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Ala Pro Ala Phe
            35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 149
<211> LENGTH: 278
<212> TYPE: PRT
<213> ORGANISM: Homo Sapiens

<400> SEQUENCE: 149

```
Ala Pro Cys Ser Arg Gly Ser Ser Trp Ser Asp Leu Asp Lys Cys
 1               5                  10                  15

Met Asp Cys Ala Ser Cys Arg Ala Arg Pro His Ser Asp Phe Cys Ala
            20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 150
<211> LENGTH: 278
<212> TYPE: PRT
<213> ORGANISM: Homo Sapiens

<400> SEQUENCE: 150

Ala Pro Cys Ser Arg Gly Ser Ser Trp Ser Asp Leu Asp Lys Cys
 1               5                  10                  15

Met Asp Cys Ala Ser Cys Arg Ala Arg Pro His Ser Asp Ala Cys Leu
            20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
```

```
            85                  90                  95
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
            115                 120                 125
Ser Val Leu Thr Val Leu His Gln Asp Trp Leu Asn Gly Lys Glu Tyr
            130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
            165                 170                 175
Pro Pro Ser Arg Glu Glu Met Thr Lys Asn Gln Val Ser Leu Thr Cys
            180                 185                 190
Leu Val Lys Gly Phe Tyr Pro Ser Asp Ile Ala Val Glu Trp Glu Ser
            195                 200                 205
Asn Gly Gln Pro Glu Asn Asn Tyr Lys Thr Thr Pro Pro Val Leu Asp
            210                 215                 220
Ser Asp Gly Ser Phe Phe Leu Tyr Ser Lys Leu Thr Val Asp Lys Ser
225                 230                 235                 240
Arg Trp Gln Gln Gly Asn Val Phe Ser Cys Ser Val Met His Glu Ala
            245                 250                 255
Leu His Asn His Tyr Thr Gln Lys Ser Leu Ser Leu Ser Pro Gly Lys
            260                 265                 270
His His His His His His
            275

<210> SEQ ID NO 151
<211> LENGTH: 278
<212> TYPE: PRT
<213> ORGANISM: Homo Sapiens

<400> SEQUENCE: 151

Ala Pro Cys Ser Arg Gly Ser Ser Trp Ser Ala Asp Leu Asp Lys Cys
1               5                   10                  15
Met Asp Cys Ala Ser Cys Arg Ala Arg Pro His Ser Ala Phe Cys Leu
            20                  25                  30
Gly Cys Ala Ile Glu Gly Arg Met Asp Pro Lys Ser Cys Asp Lys Thr
            35                  40                  45
His Thr Cys Pro Pro Cys Pro Ala Pro Glu Leu Leu Gly Gly Pro Ser
            50                  55                  60
Val Phe Leu Phe Pro Pro Lys Pro Lys Asp Thr Leu Met Ile Ser Arg
65                  70                  75                  80
Thr Pro Glu Val Thr Cys Val Val Val Asp Val Ser His Glu Asp Pro
            85                  90                  95
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
            115                 120                 125
Ser Val Leu Thr Val Leu His Gln Asp Trp Leu Asn Gly Lys Glu Tyr
            130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
            165                 170                 175
```

```
Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
            210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 152
<211> LENGTH: 278
<212> TYPE: PRT
<213> ORGANISM: Homo Sapiens

<400> SEQUENCE: 152

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ala Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270
```

```
His His His His His His
        275

<210> SEQ ID NO 153
<211> LENGTH: 278
<212> TYPE: PRT
<213> ORGANISM: Homo Sapiens

<400> SEQUENCE: 153

Ala Pro Cys Ser Arg Gly Ser Ser Trp Ser Ala Asp Leu Asp Lys Cys
1               5                   10                  15

Met Asp Cys Ala Ser Cys Arg Ala Arg Pro Ala Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 154
<211> LENGTH: 278
<212> TYPE: PRT
<213> ORGANISM: Homo Sapiens

<400> SEQUENCE: 154

Ala Pro Cys Ser Arg Gly Ser Ser Trp Ser Ala Asp Leu Asp Lys Cys
1               5                   10                  15

Met Asp Cys Ala Ser Cys Arg Ala Arg Ala His Ser Asp Phe Cys Leu
            20                  25                  30
```

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 155
<211> LENGTH: 278
<212> TYPE: PRT
<213> ORGANISM: Homo Sapiens

<400> SEQUENCE: 155

Ala Pro Cys Ser Arg Gly Ser Ser Trp Ser Ala Asp Leu Asp Lys Cys
1               5                   10                  15

Met Asp Cys Ala Ser Cys Arg Ala Ala Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val

```
            115                 120                 125
Ser Val Leu Thr Val Leu His Gln Asp Trp Leu Asn Gly Lys Glu Tyr
    130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
                165                 170                 175
Pro Pro Ser Arg Glu Glu Met Thr Lys Asn Gln Val Ser Leu Thr Cys
            180                 185                 190
Leu Val Lys Gly Phe Tyr Pro Ser Asp Ile Ala Val Glu Trp Glu Ser
        195                 200                 205
Asn Gly Gln Pro Glu Asn Asn Tyr Lys Thr Thr Pro Pro Val Leu Asp
    210                 215                 220
Ser Asp Gly Ser Phe Phe Leu Tyr Ser Lys Leu Thr Val Asp Lys Ser
225                 230                 235                 240
Arg Trp Gln Gln Gly Asn Val Phe Ser Cys Ser Val Met His Glu Ala
                245                 250                 255
Leu His Asn His Tyr Thr Gln Lys Ser Leu Ser Leu Ser Pro Gly Lys
            260                 265                 270
His His His His His His
            275

<210> SEQ ID NO 156
<211> LENGTH: 240
<212> TYPE: PRT
<213> ORGANISM: Homo Sapiens

<400> SEQUENCE: 156

Ala Pro Cys Ser Arg Gly Ser Ser Trp Ser Ala Asp Leu Asp Lys Cys
1               5                   10                  15
Met Asp Cys Ala Ser Cys Ala Ala Arg Pro His Ser Asp Phe Cys Leu
            20                  25                  30
Gly Cys Ala Ile Glu Gly Arg Met Asp Pro Lys Ser Cys Asp Lys Thr
        35                  40                  45
His Thr Cys Pro Pro Cys Pro Ala Pro Glu Leu Leu Gly Gly Pro Ser
    50                  55                  60
Val Phe Leu Phe Pro Pro Lys Pro Lys Asp Thr Leu Met Ile Ser Arg
65                  70                  75                  80
Thr Pro Glu Val Thr Cys Val Val Val Asp Val Ser His Glu Asp Pro
                85                  90                  95
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
        115                 120                 125
Ser Val Leu Thr Val Leu His Gln Asp Trp Leu Asn Gly Lys Glu Tyr
    130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
                165                 170                 175
Pro Pro Ser Arg Glu Glu Met Thr Lys Asn Gln Val Ser Leu Thr Cys
            180                 185                 190
Leu Val Lys Gly Phe Tyr Pro Ser Asp Ile Ala Val Glu Trp Glu Ser
        195                 200                 205
```

Asn Gly Gln Pro Glu Asn Asn Tyr Lys Thr Thr Pro Val Leu Asp
    210                 215                 220

Ser Asp Gly Ser Phe Phe Leu Tyr Ser Lys Leu Thr Val Asp Lys Ser
225                 230                 235                 240

<210> SEQ ID NO 157
<211> LENGTH: 278
<212> TYPE: PRT
<213> ORGANISM: Homo Sapiens

<400> SEQUENCE: 157

Ala Pro Cys Ser Arg Gly Ser Ser Trp Ser Ala Asp Leu Asp Lys Cys
1               5                   10                  15

Met Asp Cys Ala Ala Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 158
<211> LENGTH: 278
<212> TYPE: PRT
<213> ORGANISM: Homo Sapiens

<400> SEQUENCE: 158

Ala Pro Cys Ser Arg Gly Ser Ser Trp Ser Ala Asp Leu Asp Lys Cys
1               5                   10                  15

Met Ala Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 159
<211> LENGTH: 278
<212> TYPE: PRT
<213> ORGANISM: Homo Sapiens

<400> SEQUENCE: 159

Ala Pro Cys Ser Arg Gly Ser Ser Trp Ser Ala Asp Leu Asp Ala Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

```
Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 160
<211> LENGTH: 278
<212> TYPE: PRT
<213> ORGANISM: Homo Sapiens

<400> SEQUENCE: 160

Ala Pro Cys Ser Arg Gly Ser Ser Trp Ser Ala Asp Leu Ala Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
            85                  90                  95

Glu Val Lys Phe Asn Trp Tyr Val Asp Gly Val Glu Val His Asn Ala
        100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
```

```
                195                 200                 205
Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 161
<211> LENGTH: 278
<212> TYPE: PRT
<213> ORGANISM: Homo Sapiens

<400> SEQUENCE: 161

Ala Pro Cys Ser Arg Gly Ser Ser Trp Ser Ala Ala Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275
```

<210> SEQ ID NO 162
<211> LENGTH: 278
<212> TYPE: PRT
<213> ORGANISM: Homo Sapiens

<400> SEQUENCE: 162

Ala Pro Cys Ser Arg Gly Ser Ser Trp Ala Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
                35                  40                  45

His Thr Cys Pro Pro Cys Pro Ala Pro Glu Leu Leu Gly Gly Pro Ser
            50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 163
<211> LENGTH: 278
<212> TYPE: PRT
<213> ORGANISM: Homo Sapiens

<400> SEQUENCE: 163

Ala Pro Cys Ser Arg Gly Ser Ser Ala Ser Ala Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
                35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 164
<211> LENGTH: 278
<212> TYPE: PRT
<213> ORGANISM: Homo Sapiens

<400> SEQUENCE: 164

Ala Pro Cys Ser Arg Gly Ser Ala Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
                195                 200                 205

Asn Gly Gln Pro Glu Asn Asn Tyr Lys Thr Thr Pro Pro Val Leu Asp
            210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 165
<211> LENGTH: 278
<212> TYPE: PRT
<213> ORGANISM: Homo Sapiens

<400> SEQUENCE: 165

Ala Pro Cys Ser Arg Gly Ala Ser Trp Ser Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Asp Val Ser His Glu Asp Pro
                85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
                195                 200                 205

Asn Gly Gln Pro Glu Asn Asn Tyr Lys Thr Thr Pro Pro Val Leu Asp
            210                 215                 220

Ser Asp Gly Ser Phe Phe Leu Tyr Ser Lys Leu Thr Val Asp Lys Ser

```
                225                 230                 235                 240
Arg Trp Gln Gln Gly Asn Val Phe Ser Cys Ser Val Met His Glu Ala
                    245                 250                 255

Leu His Asn His Tyr Thr Gln Lys Ser Leu Ser Leu Ser Pro Gly Lys
                    260                 265                 270

His His His His His His
        275

<210> SEQ ID NO 166
<211> LENGTH: 278
<212> TYPE: PRT
<213> ORGANISM: Homo Sapiens

<400> SEQUENCE: 166

Ala Pro Cys Ser Ala Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 167
<211> LENGTH: 278
<212> TYPE: PRT
<213> ORGANISM: Homo Sapiens
```

<400> SEQUENCE: 167

Ala Pro Cys Ala Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 168
<211> LENGTH: 53
<212> TYPE: PRT
<213> ORGANISM: Homo Sapiens

<400> SEQUENCE: 168

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Pro Ala Pro Phe
            35                  40                  45

Arg Leu Leu Trp Pro
    50

<210> SEQ ID NO 169
<211> LENGTH: 129

```
<212> TYPE: PRT
<213> ORGANISM: Homo Sapiens

<400> SEQUENCE: 169

Met Ala Arg Gly Ser Leu Arg Arg Leu Leu Arg Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln

<210> SEQ ID NO 170
<211> LENGTH: 959
<212> TYPE: DNA
<213> ORGANISM: Homo Sapiens

<400> SEQUENCE: 170
atggctcggg gctcgctgcg ccggttgctg cggctcctcg tgctggggct ctggctggcg     60
ttgctgcgct ccgtggccgg ggagcaagcg ccaggcaccg ccccctgctc ccgcggcagc    120
tcctggagcg cggacctgga caagtgcatg gactgcgcgt cttgcagggc gcgaccgcac    180
agcgacttct gcctgggctg cgctgcagca cctcctgccc ccttccggct gctttggccc    240
atccttgggg gcgctctgag cctgaccttc gtgctggggc tgctttctgg cttttttggtc   300
tggagacgat gccgcaggag agagaagttc accacccccc tagaggagac cggcggagag    360
ggctgcccag ctgtggcgct gatccagtga caatgtgccc cctgccagcc ggggctcgcc    420
cactcatcat tcattcatcc attctagagc cagtctctgc ctcccagacg cggcgggagc    480
caagctcctc caaccacaag ggggtgggg ggcggtgaat cacctctgag gcctgggccc     540
agggttcagg ggaaccttcc aaggtgtctg gttgccctgc ctctggctcc agaacagaaa    600
gggagcctca cgctggctca cacaaaacag ctgacactga ctaaggaact gcagcatttg    660
cacaggggag ggggtgccc tccttcctta ggacctgggg gccaggctga cttgggggc      720
agacttgaca ctaggcccca ctcactcaga tgtcctgaaa ttccaccacg ggggtcaccc    780
tgggggggtta gggaccctatt tttaacacta ggggctggcc cactaggagg ctggcccta   840
agatacagac cccccaact ccccaaagcg gggaggagat atttattttg gggagagttt    900
ggaggggagg gagaatttat taataaaaga atctttaact ttaaaaaaaa aaaaaaaa      959

<210> SEQ ID NO 171
<211> LENGTH: 5
<212> TYPE: PRT
<213> ORGANISM: Homo Sapiens
<220> FEATURE:
<221> NAME/KEY: misc_feature
<222> LOCATION: (5)..(5)
```

```
<223> OTHER INFORMATION: Xaa can be any naturally occurring amino acid

<400> SEQUENCE: 171

Pro Tyr Pro Met Xaa
1               5

<210> SEQ ID NO 172
<211> LENGTH: 17
<212> TYPE: PRT
<213> ORGANISM: Homo Sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 172

Tyr Ile Ser Pro Ser Gly Gly Xaa Thr His Tyr Ala Asp Ser Val Lys
1               5                   10                  15
Gly

<210> SEQ ID NO 173
<211> LENGTH: 11
<212> TYPE: PRT
<213> ORGANISM: Homo Sapiens

<400> SEQUENCE: 173

Gly Gly Asp Thr Tyr Phe Asp Tyr Phe Asp Tyr
1               5                   10

<210> SEQ ID NO 174
<211> LENGTH: 11
<212> TYPE: PRT
<213> ORGANISM: Homo Sapiens
<220> FEATURE:
<221> NAME/KEY: misc_feature
<222> LOCATION: (8)..(8)
<223> OTHER INFORMATION: Xaa can be any naturally occurring amino acid

<400> SEQUENCE: 174

Arg Ala Ser Gln Ser Ile Ser Xaa Tyr Leu Asn
1               5                   10

<210> SEQ ID NO 175
<211> LENGTH: 7
<212> TYPE: PRT
<213> ORGANISM: Homo Sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 175

Xaa Ala Ser Ser Leu Gln Ser
1               5

<210> SEQ ID NO 176
<211> LENGTH: 10
<212> TYPE: PRT
<213> ORGANISM: Homo Sapiens
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
```

<400> SEQUENCE: 176

Gln Gln Ser Tyr Xaa Xaa Pro Xaa Ile Thr
1               5                   10

<210> SEQ ID NO 177
<211> LENGTH: 645
<212> TYPE: DNA
<213> ORGANISM: Homo Sapiens

<400> SEQUENCE: 177

| | | | | | |
|---|---|---|---|---|---|
| gacatccaga | tgacccagag | ccccagcagc | ctgagcgcct | ccgtgggcga | cagagtgacc | 60 |
| atcacctgtc | gggccagcca | gagcatcagc | ggctacctga | actggtatca | gcagaagccc | 120 |
| ggcaaggccc | ccaagctgct | gatctaccag | gccagctccc | tgcagagcgg | cgtgccaagc | 180 |
| agattcagcg | gcagcggctc | cggcaccgac | ttcaccctga | ccatcagcag | cctgcagccc | 240 |
| gaggacttcg | ccacctacta | ctgccagcag | agctacacca | ccccttcat | caccttcggc | 300 |
| cagggcacca | aggtggaaat | caagcggacc | gtggccgctc | ccagcgtgtt | catcttccca | 360 |
| cccagcgacg | agcagctgaa | gtccggcaca | gccagcgtgg | tctgcctgct | gaacaacttc | 420 |
| taccccgcg | aggccaaggt | gcagtggaag | gtggacaacg | ccctgcagtc | cggcaactcc | 480 |
| caggaaagcg | tgaccgagca | ggacagcaag | gactccacct | acagcctgag | cagcaccctg | 540 |
| accctgagca | aggccgacta | cgagaagcac | aaggtgtacg | cctgcgaagt | gacccaccag | 600 |
| ggcctgtcca | gccccgtgac | caagagcttc | aaccggggcg | agtgc | | 645 |

<210> SEQ ID NO 178
<211> LENGTH: 1347
<212> TYPE: DNA
<213> ORGANISM: Homo Sapiens

<400> SEQUENCE: 178

| | | | | | |
|---|---|---|---|---|---|
| gaagttcaat | tgttagagtc | cggcggaggc | ctggtgcagc | ctggcggcag | cctgagactg | 60 |
| tcttgcgccg | ccagcggctt | cacattcagc | ccctacccca | tgatctgggt | ccgccaggct | 120 |
| ccaggcaagg | gcctggaatg | ggtgtcctac | atcagcccca | gcggcggcag | cacccactac | 180 |
| gccgatagcg | tgaagggccg | gttcaccatc | agccgggaca | acagcaagaa | caccctgtac | 240 |
| ctgcagatga | acagcctgcg | ggccgaggac | accgccgtgt | actattgcgc | cagaggcggc | 300 |
| gacacctact | cgattacttt | cgactactgg | ggccagggca | ccctggtgac | agtgtccagc | 360 |
| gcctccacca | agggcccatc | ggtcttcccg | ctagcaccca | gcagcaagag | caccagcggc | 420 |
| ggaacagccg | ccctgggctg | cctggtgaaa | gactacttcc | ccgagcccgt | gaccgtgtcc | 480 |
| tggaactctg | gcgccctgac | cagcggagtg | cataccttcc | ccgccgtgct | gcagagcagc | 540 |
| ggcctgtaca | gcctgagcag | cgtggtgaca | gtgcccagca | gcagcctggg | aacccagacc | 600 |
| tacatctgca | acgtgaacca | caagcccagc | aacaccaagg | tggacaagaa | ggtggaaccc | 660 |
| aagagctgcg | acaagaccca | cacctgtccc | ccctgccctg | ccctgaact | gctgggcgga | 720 |
| cccagcgtgt | tcctgttccc | cccaaagccc | aaggacaccc | tgatgatcag | ccggacccc | 780 |
| gaagtgacct | gcgtggtggt | ggacgtgtcc | cacgaggacc | cagaagtgaa | gtttaattgg | 840 |
| tacgtggacg | gcgtggaagt | gcataacgcc | aagaccaagc | cagagagga | acagtacaac | 900 |
| agcacctacc | gggtggtgtc | cgtgctgacc | gtgctgcacc | aggactggct | gaacggcaaa | 960 |
| gagtacaagt | gcaaggtctc | caacaaggcc | ctgcctgccc | catcgagaa | aaccatcagc | 1020 |
| aaggccaagg | gccagccccg | cgagcctcag | gtgtacacac | tgccccccag | ccgggatgag | 1080 |

```
ctgaccaaga accaggtgtc cctgacctgt ctggtgaaag gcttctaccc cagcgatatc   1140
gccgtggaat gggagagcaa cggccagccc gagaacaatt acaagaccac ccccctgtg   1200 ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                        1347

<210> SEQ ID NO 179
<211> LENGTH: 645
<212> TYPE: DNA
<213> ORGANISM: Homo Sapiens

<400> SEQUENCE: 179
gacatccaga tgacccagtc tccagccacc ctgtctgcat ctgtaggaga cagagtcacc     60
atcacttgcc gggcaagtca gagcattagc ggctatttaa attggtatca gcagaaacca    120
gggaaagccc ctaagctcct gatctatcag gcatccagtt tgcaaagtgg ggtcccatca    180
aggttcagtg gcagtggatc tgggacagat ttcactctca ccatcagcag tctgcaacct    240
gaagattttg caacttacta ctgtcaacag agctacacta gtccattcat cactttcggc    300
cctgggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaactctacg cctgcgaagt cacccatcag    600
ggcctgagct cgcccgtcac aaagagcttc aacaggggag agtgt                    645

<210> SEQ ID NO 180
<211> LENGTH: 1347
<212> TYPE: DNA
<213> ORGANISM: Homo Sapiens

<400> SEQUENCE: 180
gaagttcaat tgttagagtc tggtggcggt cttgttcagc ctggtggttc tttacgtctt     60
tcttgcgctg cttccggatt cactttctct ccttacccta tgatctgggt tcgccaagct    120
cctggtaaag gtttggagtg ggtttcttat atctctcctt ctggtggcaa gactcattat    180
gctgactccg ttaaaggtcg cttcactatc tctagagaca actctaagaa tactctctac    240
ttgcagatga acagcttaag ggctgaggac acggccgtgt attactgtgc gagagggggt    300
gatacttatt tcgactactt tgactactgg ggccagggaa ccctggtcac cgtctcaagc    360
gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
tggaactctg gcgccctgac cagcggagtg cataccttcc ccgccgtgct gcagagcagc    540
ggcctgtaca gcctgagcag cgtggtgaca gtgcccagca gcctgggaa cccagacc      600 tacatctgca acgtgaacca caagcccagc aacaccaagg tggacaagaa ggtggaaccc    660
aagagctgcg acaagaccca cacctgtccc cctgccctg cccctgaact gctgggcgga    720
cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
tacgtggacg gcgtggaagt gcataacgcc aagaccaagc cagagagga acagtacaac    900 agcacctacc gggtggtgtc cgtgctgacc gtgctgcacc aggactggct gaacggcaaa    960
```

```
gagtacaagt gcaaggtctc caacaaggcc ctgcctgccc ccatcgagaa aaccatcagc      1020
aaggccaagg gccagccccg cgagcctcag gtgtacacac tgcccccag ccgggatgag       1080 ctgaccaaga accaggtgtc cctgacctgt ctggtgaaag gcttctaccc cagcgatatc     1140
gccgtggaat gggagagcaa cggccagccc gagaacaatt acaagaccac ccccctgtg     1200 ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347
```

<210> SEQ ID NO 181
<211> LENGTH: 645
<212> TYPE: DNA
<213> ORGANISM: Homo Sapiens

<400> SEQUENCE: 181

```
gacatccaga tgacccagag ccccagcagc ctgagcgcct ccgtgggcga cagagtgacc      60
atcacctgtc gggccagcca gagcatcagc agctacctga actggtatca gcagaagccc    120
ggcaaggccc ccaagctgct gatctaccag gccagctccc tgcagagcgg cgtgccaagc   180
agattcagcg gcagcggctc cggcaccgac ttcaccctga ccatcagcag cctgcagccc   240
gaggacttcg ccacctacta ctgccagcag agctacacca cccccttcat caccttcggc   300
cagggcacca aggtggaaat caagcggacc gtggccgctc ccagcgtgtt catcttccca   360
cccagcgacg agcagctgaa gtccggcaca gccagcgtgg tctgcctgct gaacaacttc   420 taccccgcg aggccaaggt gcagtggaag gtggacaacg ccctgcagtc cggcaactcc    480
caggaaagcg tgaccgagca ggacagcaag gactccacct acagcctgag cagcaccctg   540
accctgagca aggccgacta cgagaagcac aaggtgtacg cctgcgaagt gacccaccag   600
ggcctgtcca gccccgtgac caagagcttc aaccggggcg agtgc                    645
```

<210> SEQ ID NO 182
<211> LENGTH: 1347
<212> TYPE: DNA
<213> ORGANISM: Homo Sapiens

<400> SEQUENCE: 182

```
gaagttcaat tgttagagtc cggcggaggc ctggtgcagc ctggcggcag cctgagactg      60
tcttgcgccg ccagcggctt cacattcagc ccctacccca tgatgtgggt ccgccaggct    120
ccaggcaagg gcctggaatg ggtgtcctac atcagcccca gcggcggcag cacccactac   180
gccgatagcg tgaagggccg gttcaccatc agccgggaca acagcaagaa caccctgtac   240
ctgcagatga acagcctgcg ggccgaggac accgccgtgt actattgcgc cagaggcggc   300
gacacctact tcgattactt cgactactgg ggccagggca cctggtgac agtgtccagc    360 gcctccacca agggcccatc ggtcttcccg ctagcaccca gcagcaagag caccagcggc   420
ggaacagccg ccctgggctg cctggtgaaa gactacttcc ccgagcccgt gaccgtgtcc   480
tggaactctg gcgccctgac cagcggagtg cataccttcc ccgccgtgct gcagagcagc   540
ggcctgtaca gcctgagcag cgtggtgaca gtgcccagca gcctgggaa cccagacc     600 tacatctgca acgtgaacca caagcccagc aacaccaagg tggacaagaa ggtggaaccc   660
aagagctgcg acaagaccca cacctgtccc cctgccctg cccctgaact gctgggcgga   720
cccagcgtgt tcctgttccc cccaaagccc aaggacaccc tgatgatcag ccggacccc    780
```

| | |
|---|---|
| gaagtgacct gcgtggtggt ggacgtgtcc cacgaggacc cagaagtgaa gtttaattgg | 840 |
| tacgtggacg gcgtggaagt gcataacgcc aagaccaagc ccagagagga acagtacaac | 900 |
| agcacctacc gggtggtgtc cgtgctgacc gtgctgcacc aggactggct gaacggcaaa | 960 |
| gagtacaagt gcaaggtctc caacaaggcc ctgcctgccc ccatcgagaa aaccatcagc | 1020 |
| aaggccaagg gccagccccg cgagcctcag gtgtacacac tgcccccag ccgggatgag | 1080 |
| ctgaccaaga accaggtgtc cctgacctgt ctggtgaaag gcttctaccc cagcgatatc | 1140 |
| gccgtggaat gggagagcaa cggccagccc gagaacaatt acaagaccac ccccctgtg | 1200 |
| ctggacagcg acggctcatt cttcctgtac tccaagctga ccgtggacaa gagccggtgg | 1260 |
| cagcagggca acgtgttcag ctgcagcgtg atgcacgagg ccctgcacaa tcactacacc | 1320 |
| cagaagtccc tgagcctgag ccccggc | 1347 |

<210> SEQ ID NO 183
<211> LENGTH: 645
<212> TYPE: DNA
<213> ORGANISM: Homo Sapiens

<400> SEQUENCE: 183

| | |
|---|---|
| gacatccaga tgacccagtc tccagccacc ctgtctgcat ctgtaggaga cagagtcacc | 60 |
| atcacttgcc gggcaagtca gagcattagc agctatttaa attggtatca gcagaaacca | 120 |
| gggaaagccc ctaagctcct gatctatcag gcatccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcaacag agctacacta gtccattcat cactttcggc | 300 |
| cctgggacca aggtggagat caaacgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaactctacg cctgcgaagt cacccatcag | 600 |
| ggcctgagct cgcccgtcac aaagagcttc aacaggggag agtgt | 645 |

<210> SEQ ID NO 184
<211> LENGTH: 1347
<212> TYPE: DNA
<213> ORGANISM: Homo Sapiens

<400> SEQUENCE: 184

| | |
|---|---|
| gaagttcaat tgttagagtc tggtggcggt cttgttcagc ctggtggttc tttacgtctt | 60 |
| tcttgcgctg cttccggatt cactttctct ccttaccta tgatgtgggt tcgccaagct | 120 |
| cctggtaaag gtttggagtg gtttcttat atctctcctt ctggtggcaa gactcattat | 180 |
| gctgactccg ttaaaggtcg cttcactatc tctagagaca actctaagaa tactctctac | 240 |
| ttgcagatga acagcttaag ggctgaggac acggccgtgt attactgtgc gagaggggt | 300 |
| gatacttatt tcgactactt tgactactgg ggccagggaa ccctggtcac cgtctcaagc | 360 |
| gcctccacca agggcccatc ggtcttcccg ctagcaccca gcagcaagag caccagcggc | 420 |
| ggaacagccg ccctgggctg cctggtgaaa gactacttcc ccgagcccgt gaccgtgtcc | 480 |
| tggaactctg gcgccctgac cagcggagtg cataccttcc ccgccgtgct gcagagcagc | 540 |
| ggcctgtaca gcctgagcag cgtggtgaca gtgcccagca gcagcctggg aacccagacc | 600 |
| tacatctgca acgtgaacca caagcccagc aacaccaagg tggacaagaa ggtggaaccc | 660 |

```
aagagctgcg acaagaccca cacctgtccc ccctgccctg ccctgaact gctgggcgga      720 cccagcgtgt tcctgttccc cccaaagccc aaggacaccc tgatgatcag ccggacccc      780 gaagtgacct gcgtggtggt ggacgtgtcc cacgaggacc cagaagtgaa gtttaattgg    840
tacgtggacg gcgtggaagt gcataacgcc aagaccaagc ccagagagga acagtacaac    900
agcacctacc gggtggtgtc cgtgctgacc gtgctgcacc aggactggct gaacggcaaa    960
gagtacaagt gcaaggtctc caacaaggcc ctgcctgccc catcgagaa aaccatcagc    1020 aaggccaagg gccagccccg cgagcctcag gtgtacacac tgccccccag ccgggatgag   1080
ctgaccaaga accaggtgtc cctgacctgt ctggtgaaag gcttctaccc cagcgatatc   1140
gccgtggaat gggagagcaa cggccagccc gagaacaatt acaagaccac ccccctgtg    1200 ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347

<210> SEQ ID NO 185
<211> LENGTH: 645
<212> TYPE: DNA
<213> ORGANISM: Homo Sapiens

<400> SEQUENCE: 185
gacatccaga tgacccagag ccccagcagc ctgtctgcca gcgtgggcga cagagtgacc     60
atcacctgta gagccagcca gagcatcagc agctacctga actggtatca gcagaagccc    120
ggcaaggccc ccaagctgct gatctatgcc gccagctctc tgcagagcgg agtgcccagc    180
agattttctg gcagcggcag cggcaccgac ttcaccctga caatcagcag cctgcagccc    240
gaggacttcg ccacctacta ctgccagcag agctacagca ccccggcat cacatttggc     300 cagggcacca aggtggaaat caagcggaca gtggccgctc ccagcgtgtt catcttccca    360
cctagcgacg agcagctgaa gtccggcaca gccagcgtcg tgtgcctgct gaacaacttc    420 taccccgcg aggccaaggt gcagtggaag gtggacaatg ccctgcagtc cggcaactcc     480
caggaaagcg tcaccgagca ggacagcaag gactccacct acagcctgag cagcacccct    540
accctgagca aggccgacta cgagaagcac aaggtgtacg cctgcgaagt gacccaccag    600
ggcctgtcta gccccgtgac caagagcttc aaccggggcg agtgt                    645

<210> SEQ ID NO 186
<211> LENGTH: 1347
<212> TYPE: DNA
<213> ORGANISM: Homo Sapiens

<400> SEQUENCE: 186
gaagttcaat tgttagagtc cggcggaggc ctggtgcagc ctggcggatc tctgagactg      60
agctgtgccg ccagcggctt caccttcagc ccctacccta tgatgtgggt ccgacaggcc    120
cctggcaagg gactggaatg ggtgtcctac atctctccca gcggcggcag cacccactac    180
gccgattctg tgaagggccg gttcaccatc agccgggaca acagcaagaa caccctgtac    240
ctgcagatga acagcctgcg ggccgaggac accgccgtgt actattgtgc cagaggcggc    300
gacacctact tcgattactt cgactactgg ggccagggca cctggtcac cgtgtcatct    360 gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
```

```
tggaactctg gcgccctgac cagcggagtg catacctccc ccgccgtgct gcagagcagc    540
ggcctgtaca gcctgagcag cgtggtgaca gtgcccagca gcagcctggg aacccagacc    600
tacatctgca acgtgaacca caagcccagc aacaccaagg tggacaagaa ggtggaaccc    660
aagagctgcg acaagaccca cacctgtccc cctgccctg ccctgaact gctgggcgga    720
cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
tacgtggacg gcgtggaagt gcataacgcc aagaccaagc ccagagagga cagtacaac     900
agcacctacc gggtggtgtc cgtgctgacc gtgctgcacc aggactggct gaacggcaaa    960
gagtacaagt gcaaggtctc caacaaggcc ctgcctgccc ccatcgagaa aaccatcagc   1020
aaggccaagg gccagccccg cgagcctcag gtgtacacac tgcccccag ccgggatgag    1080
ctgaccaaga accaggtgtc cctgacctgt ctggtgaaag gcttctaccc cagcgatatc   1140
gccgtggaat gggagagcaa cggccagccc gagaacaatt acaagaccac ccccctgtg    1200
ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347

<210> SEQ ID NO 187
<211> LENGTH: 645
<212> TYPE: DNA
<213> ORGANISM: Homo Sapiens

<400> SEQUENCE: 187
gacatccaga tgacccagtc tccagccacc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agctactcta gtccagggat cactttcggc    300
cctgggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaactctacg cctgcgaagt cacccatcag    600
ggcctgagct cgcccgtcac aaagagcttc aacaggggag agtgt                    645

<210> SEQ ID NO 188
<211> LENGTH: 1347
<212> TYPE: DNA
<213> ORGANISM: Homo Sapiens

<400> SEQUENCE: 188
gaagttcaat tgttagagtc tggtggcggt cttgttcagc ctggtggttc tttacgtctt     60
tcttgcgctg cttccggatt cactttctct ccttaccta tgatgtgggt tcgccaagct    120
cctggtaaag gtttggagtg ggtttcttat atctctcctt ctggtggcaa gactcattat    180
gctgactccg ttaaaggtcg cttcactatc tctagagaca actctaagaa tactctctac    240
ttgcagatga cagccttaag ggctgaggac acggccgtgt attactgtgc gagagggggt    300
gatacgtatt tcgactactt tgactactgg ggccaggaa ccctggtcac cgtctcaagc    360
```

```
gcctccacca agggcccatc ggtcttcccg ctagcaccca gcagcaagag caccagcggc      420
ggaacagccg ccctgggctg cctggtgaaa gactacttcc ccgagcccgt gaccgtgtcc      480
tggaactctg gcgccctgac cagcggagtg cataccttcc ccgccgtgct gcagagcagc      540
ggcctgtaca gcctgagcag cgtggtgaca gtgcccagca gcagcctggg aacccagacc      600
tacatctgca acgtgaacca caagcccagc aacaccaagg tggacaagaa ggtggaaccc      660
aagagctgcg acaagaccca cacctgtccc cctgccctg ccctgaact gctgggcgga      720 cccagcgtgt tcctgttccc cccaaagccc aaggacaccc tgatgatcag ccggacccc      780 gaagtgacct gcgtggtggt ggacgtgtcc cacgaggacc cagaagtgaa gtttaattgg      840
tacgtggacg gcgtggaagt gcataacgcc aagaccaagc cagagagga acagtacaac      900 agcacctacc gggtggtgtc cgtgctgacc gtgctgcacc aggactggct gaacggcaaa      960
gagtacaagt gcaaggtctc caacaaggcc ctgcctgccc ccatcgagaa aaccatcagc     1020
aaggccaagg gccagccccg cgagcctcag gtgtacacac tgccccccag ccgggatgag     1080
ctgaccaaga accaggtgtc cctgacctgt ctggtgaaag gcttctaccc cagcgatatc     1140
gccgtggaat gggagagcaa cggccagccc gagaacaatt acaagaccac cccccctgtg     1200
ctggacagcg acggctcatt cttcctgtac tccaagctga ccgtggacaa gagccggtgg     1260
cagcagggca acgtgttcag ctgcagcgtg atgcacgagg ccctgcacaa tcactacacc     1320
cagaagtccc tgagcctgag ccccggc                                        1347
```

<210> SEQ ID NO 189
<211> LENGTH: 651
<212> TYPE: DNA
<213> ORGANISM: Homo Sapiens

<400> SEQUENCE: 189

```
gcacaagaca tccagatgac ccagtctcca gccacccctgt ctgcatctgt aggagacaga      60
gtcaccatca cttgccgggc aagtcagagc attagcagct atttaaattg gtatcagcag     120
aaaccaggga aagcccctaa gctcctgatc tatgctgcat ccagtttgca aagtggggtc     180
ccatcaaggt tcagtggcag tggatctggg acagatttca ctctcaccat cagcagtctg     240
caacctgaag attttgcaac ttactactgt caacagagct actctagtcc agggatcact     300
ttcggccctg ggaccaaggt ggagatcaaa cgaactgtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaac tctacgcctg cgaagtcacc     600
catcagggcc tgagctcgcc cgtcacaaag agcttcaaca ggggagagtg t             651
```

<210> SEQ ID NO 190
<211> LENGTH: 1347
<212> TYPE: DNA
<213> ORGANISM: Homo Sapiens

<400> SEQUENCE: 190

```
gaagttcaat tgttagagtc tggtggcggt cttgttcagc ctggtggttc tttacgtctt      60
tcttgcgctg cttccggatt cactttctct ccttaccctta tgatgtgggt tcgccaagct     120
cctggtaaag gtttggagtg ggtttcttat atctctcctt ctggtggcaa gactcattat     180
```

| | | |
|---|---|---|
| gctgactccg ttaaaggtcg cttcactatc tctagagaca actctaagaa tactctctac | 240 |
| ttgcagatga acagcttaag ggctgaggac acggccgtgt attactgtgc gagaggggt | 300 |
| gatacgtatt tcgactactt tgactactgg ggccagggaa ccctggtcac cgtctcaagc | 360 |
| gcctccacca agggcccatc ggtcttcccg ctagcaccca gcagcaagag caccagcggc | 420 |
| ggaacagccg ccctgggctg cctggtgaaa gactacttcc ccgagccgt gaccgtgtcc | 480 |
| tggaactctg gcgccctgac cagcggagtg catacttcc ccgccgtgct gcagagcagc | 540 |
| ggcctgtaca gcctgagcag cgtggtgaca gtgcccagca gcagcctggg aacccagacc | 600 |
| tacatctgca acgtgaacca caagcccagc aacaccaagg tggacaagcg ggtggaaccc | 660 |
| aagagctgcg acaagaccca cacctgtccc cctgccctg cccctgaact gctgggcgga | 720 |
| cccagcgtgt tcctgttccc cccaaagccc aaggacaccc tgatgatcag ccggaccccc | 780 |
| gaagtgacct gcgtggtggt ggacgtgtcc cacgaggacc cagaagtgaa gtttaattgg | 840 |
| tacgtggacg gcgtggaagt gcataacgcc aagaccaagc ccagagagga acagtacaac | 900 |
| agcacctacc gggtggtgtc cgtgctgacc gtgctgcacc aggactggct gaacggcaaa | 960 |
| gagtacaagt gcaaggtctc caacaaggcc ctgcctgccc ccatcgagaa aaccatcagc | 1020 |
| aaggccaagg ccagccccg cgagcctcag gtgtacacac tgccccccag ccgggaagag | 1080 |
| atgaccaaga accaggtgtc cctgacctgt ctggtgaaag gcttctaccc cagcgatatc | 1140 |
| gccgtggaat gggagagcaa cggccagccc gagaacaatt acaagaccac ccccctgtg | 1200 |
| ctggacagcg acggctcatt cttcctgtac tccaagctga ccgtggacaa gagccggtgg | 1260 |
| cagcagggca acgtgttcag ctgcagcgtg atgcacgagg ccctgcacaa tcactacacc | 1320 |
| cagaagtccc tgagcctgag ccccggc | 1347 |

<210> SEQ ID NO 191
<211> LENGTH: 651
<212> TYPE: DNA
<213> ORGANISM: Homo Sapiens

<400> SEQUENCE: 191

| | | |
|---|---|---|
| gcacaagaca tccagatgac ccagtctcca gccacctgt ctgcatctgt aggagacaga | 60 |
| gtcaccatca cttgccgggc aagtcagagc attagcagct atttaaattg gtatcagcag | 120 |
| aaaccaggga aagcccctaa gctcctgatc tatgctgcat ccagtttgca aagtggggtc | 180 |
| ccatcaaggt tcagtggcag tggatctggg acagatttca ctctcaccat cagcagtctg | 240 |
| caacctgaag attttgcaac ttactactgt caacagagct actctagtcc agggatcact | 300 |
| ttcggccctg ggaccaaggt ggagatcaaa cgaactgtgg ctgcaccatc tgtcttcatc | 360 |
| ttcccgccat ctgatgagca gttgaaatct ggaactgcct ctgttgtgtg cctgctgaat | 420 |
| aacttctatc ccagagaggc caaagtacag tggaaggtgg ataacgccct ccaatcgggt | 480 |
| aactcccagg agagtgtcac agagcaggac agcaaggaca gcacctacag cctcagcagc | 540 |
| accctgacgc tgagcaaagc agactacgag aaacacaaac tctacgcctg cgaagtcacc | 600 |
| catcagggcc tgagctcgcc cgtcacaaag agcttcaaca ggggagagtg t | 651 |

<210> SEQ ID NO 192
<211> LENGTH: 1347
<212> TYPE: DNA
<213> ORGANISM: Homo Sapiens

<400> SEQUENCE: 192

| | | |
|---|---|---|
| gaagttcaat tgttagagtc tggtggcggt cttgttcagc ctggtggttc tttacgtctt | 60 |

-continued

```
tcttgcgctg cttccggatt cactttctct ccttaccta tgatgtgggt tcgccaagct      120
cctggtaaag gtttggagtg ggtttcttat atctctcctt ctggtggcaa gactcattat      180
gctgactccg ttaaaggtcg cttcactatc tctagagaca actctaagaa tactctctac      240
ttgcagatga acagcttaag ggctgaggac acggccgtgt attactgtgc gagaggggg       300 gatggttatt tcgactactt tgactactgg ggccagggaa ccctggtcac cgtctcaagc      360
gcctccacca agggcccatc ggtcttcccg ctagcaccca gcagcaagag caccagcggc      420
ggaacagccg ccctgggctg cctggtgaaa gactacttcc ccgagccgt gaccgtgtcc       480 tggaactctg gcgccctgac cagcggagtg catacctcc ccgccgtgct gcagagcagc       540
ggcctgtaca gcctgagcag cgtggtgaca gtgcccagca gcagcctggg aacccagacc      600
tacatctgca acgtgaacca caagcccagc aacaccaagg tggacaagcg ggtggaaccc      660
aagagctgcg acaagaccca cacctgtccc cctgccctg ccctgaact gctgggcgga       720 cccagcgtgt tcctgttccc cccaaagccc aaggacaccc tgatgatcag ccggacccc       780 gaagtgacct gcgtggtggt ggacgtgtcc cacgaggacc cagaagtgaa gtttaattgg      840
tacgtggacg gcgtggaagt gcataacgcc aagaccaagc ccagagagga acagtacaac      900
agcacctacc gggtggtgtc cgtgctgacc gtgctgcacc aggactggct gaacggcaaa      960
gagtacaagt gcaaggtctc caacaaggcc ctgcctgccc catcgagaa aaccatcagc      1020 aaggccaagg gccagcccg cgagcctcag gtgtacacac tgcccccag ccgggaagag       1080 atgaccaaga accaggtgtc cctgacctgt ctggtgaaag gcttctaccc cagcgatatc      1140
gccgtggaat gggagagcaa cggccagccc gagaacaatt acaagaccac ccccctgtg       1200 ctggacagcg acggctcatt cttcctgtac tccaagctga ccgtggacaa gagccggtgg      1260
cagcagggca acgtgttcag ctgcagcgtg atgcacgagg ccctgcacaa tcactacacc      1320
cagaagtccc tgagcctgag ccccggc                                         1347
```

<210> SEQ ID NO 193
<211> LENGTH: 651
<212> TYPE: DNA
<213> ORGANISM: Homo Sapiens

<400> SEQUENCE: 193

```
gcacaagaca tccagatgac ccagtctcca gccacctgt ctgcatctgt aggagacaga      60
gtcaccatca cttgccgggc aagtcagagc attagcggct atttaaattg gtatcagcag      120
aaaccaggga aagcccctaa gctcctgatc tataacgcat ccagtttgca aagtggggtc      180
ccatcaaggt tcagtggcag tggatctggg acagatttca ctctcaccat cagcagtctg      240
caacctgaag attttgcaac ttactactgt caacagagct acactagtcc attcatcact      300
ttcggccctg ggaccaaggt ggagatcaaa cgaactgtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaac tctacgcctg cgaagtcacc      600
catcagggcc tgagctcgcc cgtcacaaag agcttcaaca ggggagagtg t              651
```

<210> SEQ ID NO 194
<211> LENGTH: 1347
<212> TYPE: DNA

<213> ORGANISM: Homo Sapiens

<400> SEQUENCE: 194

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | ccttaccta | tgatctgggt | tcgccaagct | 120 |
| cctggtaaag | gtttggagtg | ggtttcttat | atctctcctt | ctggtggcaa | gactcattat | 180 |
| gctgactccg | ttaaaggtcg | cttcactatc | tctagagaca | actctaagaa | tactctctac | 240 |
| ttgcagatga | acagcttaag | ggctgaggac | acggccgtgt | attactgtgc | gagaggggt | 300 |
| gatacttatt | tcgactactt | tgactactgg | ggccagggaa | ccctggtcac | cgtctcaagc | 360 |
| gcctccacca | agggcccatc | ggtcttcccg | ctagcaccca | gcagcaagag | caccagcggc | 420 |
| ggaacagccg | ccctgggctg | cctggtgaaa | gactacttcc | ccgagcccgt | gaccgtgtcc | 480 |
| tggaactctg | gcgccctgac | cagcggagtg | cataccttcc | ccgccgtgct | gcagagcagc | 540 |
| ggcctgtaca | gcctgagcag | cgtggtgaca | gtgcccagca | gcagcctggg | aacccagacc | 600 |
| tacatctgca | acgtgaacca | caagcccagc | aacaccaagg | tggacaagaa | ggtggaaccc | 660 |
| aagagctgcg | acaagaccca | cacctgtccc | ccctgccctg | ccctgaact | gctgggcgga | 720 |
| cccagcgtgt | tcctgttccc | cccaaagccc | aaggacaccc | tgatgatcag | ccggaccccc | 780 |
| gaagtgacct | gcgtggtggt | ggacgtgtcc | cacgaggacc | cagaagtgaa | gtttaattgg | 840 |
| tacgtggacg | gcgtggaagt | gcataacgcc | aagaccaagc | cagagagga | acagtacaac | 900 |
| agcacctacc | gggtggtgtc | cgtgctgacc | gtgctgcacc | aggactggct | gaacggcaaa | 960 |
| gagtacaagt | gcaaggtctc | caacaaggcc | ctgcctgccc | catcgagaa | aaccatcagc | 1020 |
| aaggccaagg | gccagccccg | cgagcctcag | gtgtacacac | tgcccccag | ccgggatgag | 1080 |
| ctgaccaaga | accaggtgtc | cctgacctgt | ctggtgaaag | gcttctaccc | cagcgatatc | 1140 |
| gccgtggaat | gggagagcaa | cggccagccc | gagaacaatt | acaagaccac | ccccctgtg | 1200 |
| ctggacagcg | acggctcatt | cttcctgtac | tccaagctga | ccgtggacaa | gagccggtgg | 1260 |
| cagcagggca | acgtgttcag | ctgcagcgtg | atgcacgagg | ccctgcacaa | tcactacacc | 1320 |
| cagaagtccc | tgagcctgag | ccccggc | | | | 1347 |

<210> SEQ ID NO 195
<211> LENGTH: 651
<212> TYPE: DNA
<213> ORGANISM: Homo Sapiens

<400> SEQUENCE: 195

| | | | | | |
|---|---|---|---|---|---|
| gcacaagaca | tccagatgac | ccagtctcca | gccaccctgt | ctgcatctgt | aggagacaga | 60 |
| gtcaccatca | cttgccgggc | aagtcagagc | attagcagct | atttaaattg | gtatcagcag | 120 |
| aaaccaggga | aagcccctaa | gctcctgatc | tataacgcat | ccagtttgca | aagtggggtc | 180 |
| ccatcaaggt | tcagtggcag | tggatctggg | acagatttca | ctctcaccat | cagcagtctg | 240 |
| caacctgaag | attttgcaac | ttactactgt | caacagagct | acactagtcc | aggatcact | 300 |
| ttcggccctg | ggaccaaggt | ggagatcaaa | cgaactgtgg | ctgcaccatc | tgtcttcatc | 360 |
| ttcccgccat | ctgatgagca | gttgaaatct | ggaactgcct | ctgttgtgtg | cctgctgaat | 420 |
| aacttctatc | ccagagaggc | caaagtacag | tggaaggtgg | ataacgccct | ccaatcgggt | 480 |
| aactcccagg | agagtgtcac | agagcaggac | agcaaggaca | gcacctacag | cctcagcagc | 540 |
| accctgacgc | tgagcaaagc | agactacgag | aaacacaaac | tctacgcctg | cgaagtcacc | 600 |
| catcagggcc | tgagctcgcc | cgtcacaaag | agcttcaaca | ggggagagtg | t | 651 |

<210> SEQ ID NO 196
<211> LENGTH: 1347
<212> TYPE: DNA
<213> ORGANISM: Homo Sapiens

<400> SEQUENCE: 196

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | ccttacccta | tgatgtgggt | tcgccaagct | 120 |
| cctggtaaag | gtttggagtg | ggtttcttat | atctctcctt | ctggtggcaa | gactcattat | 180 |
| gctgactccg | ttaaaggtcg | cttcactatc | tctagagaca | actctaagaa | tactctctac | 240 |
| ttgcagatga | acagcttaag | ggctgaggac | acggccgtgt | attactgtgc | gagaggggt | 300 |
| gatacttatt | cgactacttt | tgactactgg | ggccagggaa | ccctggtcac | cgtctcaagc | 360 |
| gcctccacca | agggcccatc | ggtcttcccg | ctagcaccca | gcagcaagag | caccagcggc | 420 |
| ggaacagccg | ccctgggctg | cctggtgaaa | gactacttcc | ccgagcccgt | gaccgtgtcc | 480 |
| tggaactctg | gcgccctgac | cagcggagtg | cataccttcc | ccgccgtgct | gcagagcagc | 540 |
| ggcctgtaca | gcctgagcag | cgtggtgaca | gtgcccagca | gcagcctggg | aacccagacc | 600 |
| tacatctgca | acgtgaacca | caagcccagc | aacaccaagg | tggacaagaa | ggtggaaccc | 660 |
| aagagctgcg | acaagaccca | cacctgtccc | ccctgccctg | cccctgaact | gctgggcgga | 720 |
| cccagcgtgt | tcctgttccc | cccaaagccc | aaggacaccc | tgatgatcag | ccggaccccc | 780 |
| gaagtgacct | gcgtggtggt | ggacgtgtcc | cacgaggacc | cagaagtgaa | gtttaattgg | 840 |
| tacgtggacg | gcgtggaagt | gcataacgcc | aagaccaagc | ccagagagga | acagtacaac | 900 |
| agcacctacc | gggtggtgtc | cgtgctgacc | gtgctgcacc | aggactggct | gaacggcaaa | 960 |
| gagtacaagt | gcaaggtctc | caacaaggcc | ctgcctgccc | ccatcgagaa | aaccatcagc | 1020 |
| aaggccaagg | gccagccccg | cgagcctcag | gtgtacacac | tgcccccag | ccgggatgag | 1080 |
| ctgaccaaga | accaggtgtc | cctgacctgt | ctggtgaaag | gcttctaccc | cagcgatatc | 1140 |
| gccgtggaat | gggagagcaa | cggccagccc | gagaacaatt | acaagaccac | cccccctgtg | 1200 |
| ctggacagcg | acggctcatt | cttcctgtac | tccaagctga | ccgtggacaa | gagccggtgg | 1260 |
| cagcagggca | acgtgttcag | ctgcagcgtg | atgcacgagg | ccctgcacaa | tcactacacc | 1320 |
| cagaagtccc | tgagcctgag | ccccggc | | | | 1347 |

<210> SEQ ID NO 197
<211> LENGTH: 651
<212> TYPE: DNA
<213> ORGANISM: Homo Sapiens

<400> SEQUENCE: 197

| | | | | | |
|---|---|---|---|---|---|
| gcacaagaca | tccagatgac | ccagtctcca | gccaccctgt | ctgcatctgt | aggagacaga | 60 |
| gtcaccatca | cttgccgggc | aagtcagagc | attagcggca | ttttaaattg | gtatcagcag | 120 |
| aaaccaggga | aagcccctaa | gctcctgatc | tataacgcat | ccagtttgca | aagtggggtc | 180 |
| ccatcaaggt | tcagtggcag | tggatctggg | acagatttca | ctctcaccat | cagcagtctg | 240 |
| caacctgaag | attttgcaac | ttactactgt | caacagagct | acactagtcc | agggatcact | 300 |
| ttcggccctg | ggaccaaggt | ggagatcaaa | cgaactgtgg | ctgcaccatc | tgtcttcatc | 360 |
| ttcccgccat | ctgatgagca | gttgaaatct | ggaactgcct | ctgttgtgtg | cctgctgaat | 420 |
| aacttctatc | ccagagaggc | caaagtacag | tggaaggtgg | ataacgccct | ccaatcgggt | 480 |

| | |
|---|---|
| aactcccagg agagtgtcac agagcaggac agcaaggaca gcacctacag cctcagcagc | 540 |
| accctgacgc tgagcaaagc agactacgag aaacacaaac tctacgcctg cgaagtcacc | 600 |
| catcagggcc tgagctcgcc cgtcacaaag agcttcaaca ggggagagtg t | 651 |

<210> SEQ ID NO 198
<211> LENGTH: 1347
<212> TYPE: DNA
<213> ORGANISM: Homo Sapiens

<400> SEQUENCE: 198

| | |
|---|---|
| gaagttcaat tgttagagtc tggtggcggt cttgttcagc ctggtggttc tttacgtctt | 60 |
| tcttgcgctg cttccggatt cactttctct ccttacccta tgatgtgggt tcgccaagct | 120 |
| cctggtaaag gtttggagtg gtttcttat atctctcctt ctggtggcaa gactcattat | 180 |
| gctgactccg ttaaaggtcg cttcactatc tctagagaca actctaagaa tactctctac | 240 |
| ttgcagatga acagcttaag ggctgaggac acggccgtgt attactgtgc gagaggggt | 300 |
| gatacttatt tcgactactt tgactactgg ggccagggaa ccctggtcac cgtctcaagc | 360 |
| gcctccacca agggcccatc ggtcttcccg ctagcaccca gcagcaagag caccagcggc | 420 |
| ggaacagccg ccctgggctg cctggtgaaa gactacttcc ccgagcccgt gaccgtgtcc | 480 |
| tggaactctg gcgccctgac cagcggagtg catacccttcc ccgccgtgct gcagagcagc | 540 |
| ggcctgtaca gcctgagcag cgtggtgaca gtgcccagca gcagcctggg aacccagacc | 600 |
| tacatctgca acgtgaacca caagcccagc aacaccaagg tggacaagaa ggtggaaccc | 660 |
| aagagctgcg acaagaccca cacctgtccc cctgccctg cccctgaact gctgggcgga | 720 |
| cccagcgtgt tcctgttccc cccaaagccc aaggacaccc tgatgatcag ccggaccccc | 780 |
| gaagtgacct gcgtggtggt ggacgtgtcc cacgaggacc cagaagtgaa gtttaattgg | 840 |
| tacgtggacg gcgtggaagt gcataacgcc aagaccaagc ccagagagga acagtacaac | 900 |
| agcacctacc gggtggtgtc cgtgctgacc gtgctgcacc aggactggct gaacggcaaa | 960 |
| gagtacaagt gcaaggtctc caacaaggcc ctgcctgccc ccatcgagaa aaccatcagc | 1020 |
| aaggccaagg gccagccccg cgagcctcag gtgtacacac tgcccccag ccgggatgag | 1080 |
| ctgaccaaga accaggtgtc cctgacctgt ctggtgaaag gcttctaccc cagcgatatc | 1140 |
| gccgtggaat gggagagcaa cggccagccc gagaacaatt acaagaccac ccccctgtg | 1200 |
| ctggacagcg acggctcatt cttcctgtac tccaagctga ccgtggacaa gagccggtgg | 1260 |
| cagcagggca acgtgttcag ctgcagcgtg atgcacgagg ccctgcacaa tcactacacc | 1320 |
| cagaagtccc tgagcctgag ccccggc | 1347 |

<210> SEQ ID NO 199
<211> LENGTH: 651
<212> TYPE: DNA
<213> ORGANISM: Homo Sapiens

<400> SEQUENCE: 199

| | |
|---|---|
| gcacaagaca tccagatgac ccagtctcca gccaccctgt ctgcatctgt aggagacaga | 60 |
| gtcaccatca cttgccgggc aagtcagagc attagcagct atttaaattg gtatcagcag | 120 |
| aaaccaggga aagcccctaa gctcctgatc tataacgcat ccagtttgca aagtggggtc | 180 |
| ccatcaaggt tcagtggcag tggatctggg acagatttca ctctcaccat cagcagtctg | 240 |
| caacctgaag attttgcaac ttactactgt caacagagct acactagtcc attcatcact | 300 |
| ttcggccctg ggaccaaggt ggagatcaaa cgaactgtgg ctgcaccatc tgtcttcatc | 360 |

```
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaac tctacgcctg cgaagtcacc      600
catcagggcc tgagctcgcc cgtcacaaag agcttcaaca ggggagagtg t               651
```

<210> SEQ ID NO 200
<211> LENGTH: 1347
<212> TYPE: DNA
<213> ORGANISM: Homo Sapiens

<400> SEQUENCE: 200

```
gaagttcaat tgttagagtc tggtggcggt cttgttcagc tggtggttc tttacgtctt       60 tcttgcgctg cttccggatt cactttctct ccttacccta tgatgtgggt tcgccaagct      120
cctggtaaag gtttggagtg ggtttcttat atctctcctt ctggtggcaa gactcattat      180
gctgactccg ttaaaggtcg cttcactatc tctagagaca actctaagaa tactctctac      240
ttgcagatga acagcttaag ggctgaggac acggccgtgt attactgtgc gagaggggt      300 gatacttatt tcgactactt tgactactgg ggccagggaa ccctggtcac cgtctcaagc      360
gcctccacca agggcccatc ggtcttcccg ctagcaccca gcagcaagag caccagcggc      420
ggaacagccg ccctgggctg cctggtgaaa gactacttcc ccgagcccgt gaccgtgtcc      480
tggaactctg gcgccctgac cagcggagtg catacctttcc ccgccgtgct gcagagcagc      540
ggcctgtaca gcctgagcag cgtggtgaca gtgcccagca gcctggg aacccagacc        600 tacatctgca acgtgaacca caagcccagc aacaccaagg tggacaagaa ggtggaaccc      660
aagagctgcg acaagaccca cacctgtccc cctgccctg cccctgaact gctgggcgga      720
cccagcgtgt tcctgttccc cccaaagccc aaggacaccc tgatgatcag ccggaccccc      780
gaagtgacct gcgtggtggt ggacgtgtcc cacgaggacc cagaagtgaa gtttaattgg      840
tacgtggacg gcgtggaagt gcataacgcc aagaccaagc ccagagagga acagtacaac      900
agcacctacc gggtggtgtc cgtgctgacc gtgctgcacc aggactggct gaacggcaaa      960
gagtacaagt gcaaggtctc caacaaggcc ctgcctgccc ccatcgagaa aaccatcagc      1020
aaggccaagg ccagccccg cgagcctcag gtgtacacac tgcccccag ccgggatgag       1080 ctgaccaaga accaggtgtc cctgacctgt ctggtgaaag gcttctaccc cagcgatatc      1140
gccgtggaat gggagagcaa cggccagccc gagaacaatt acaagaccac ccccctgtg      1200 ctggacagcg acggctcatt cttcctgtac tccaagctga ccgtggacaa gagccggtgg      1260
cagcagggca acgtgttcag ctgcagcgtg atgcacgagg ccctgcacaa tcactacacc      1320
cagaagtccc tgagcctgag ccccggc                                         1347
```

<210> SEQ ID NO 201
<211> LENGTH: 654
<212> TYPE: DNA
<213> ORGANISM: Mus Musculus

<400> SEQUENCE: 201

```
gatatcgtgc tgacacagtc tcccgccagc ctggccgtgt ctctcggcca gagagccacc       60
atcagctgcc gggccaacaa gagcgtgtcc accagcagct acagctacat gcactggtat      120
cagcagaagc ccggccagcc ccccaagctg ctgattaagt acgccagcaa cctggaaagc      180
```

| | |
|---|---|
| ggcgtgcccg ccagattcag cggcagcggc tctggcaccg acttcatcct gaacatccac | 240 |
| cccgtggaag aagaggacgc cgccacctac tactgccagc acagcagaga gctgcccttc | 300 |
| accttcggca gcggcaccaa gctggaaatc aagcgggccg atgccgcccc taccgtgtcc | 360 |
| atcttcccac ccagcagcga gcagctgacc agcggcggag ccagcgtcgt gtgcttcctg | 420 |
| aacaacttct accccaagga catcaacgtg aagtggaaga tcgacggcag cgagcggcag | 480 |
| aacggcgtgc tgaacagctg gaccgaccag gacagcaagg actccaccta cagcatgagc | 540 |
| agcaccctga ccctgaccaa ggacgagtac gagcggcaca cagctacac atgcgaggcc | 600 |
| acccacaaga ccagcaccag ccccatcgtg aagtccttca ccggaacga gtgc | 654 |

<210> SEQ ID NO 202
<211> LENGTH: 1350
<212> TYPE: DNA
<213> ORGANISM: Mus Musculus

<400> SEQUENCE: 202

| | |
|---|---|
| caggtgcagc tgcagcagtc tggccctgaa gtcgtgcggc tggcgtgtc cgtgaagatc | 60 |
| agctgcaagg gcagcggcta caccttcacc gactacggca tccactgggt caagcagagc | 120 |
| cacgccaaga gcctggaatg gatcggcgtg atcagcacct acaacggcta caccaactac | 180 |
| aaccagaagt tcaagggcaa ggccaccatg accgtggaca agagcagcag caccgcctac | 240 |
| atggaactgg cccggctgac cagcgaggac agcgccatct actactgcgc cagagcctac | 300 |
| tacggcaacc tgtactacgc catggactac tggggccagg gcaccagcgt gaccgtgtcc | 360 |
| tctgccaaga ccaccgcccc tagcgtgtac cctctggccc ctgtgtgtgg cgacaccacc | 420 |
| ggcagctctg tgactctggg ctgcctggtc aagggctact cccccgagcc cgtgacactg | 480 |
| acctggaaca gcggcagcct gagcagcggc gtgcacacct tccagccgt gctgcagagc | 540 |
| gacctgtaca ccctgagcag ctccgtgacc gtgacaagca gcacctggcc cagccagagc | 600 |
| atcacctgta acgtggccca ccccgccagc agcaccaagg tggacaagaa gatcgagccc | 660 |
| agaggcccca ccatcaagcc ctgccccct tgcaagtgcc cagcccccaa tctgctgggc | 720 |
| ggacccagcg tgttcatctt cccacccaag atcaaggacg tgctgatgat cagcctgagc | 780 |
| cccatcgtga cctgcgtggt ggtggacgtg tccgaggacg accccgacgt gcagatcagt | 840 |
| tggttcgtga acaacgtgga agtgcacacc gcccagaccc agaccacag agaggactac | 900 |
| aacagcaccc tgcgggtggt gtccgccctg cccatccagc accaggactg gatgagcggc | 960 |
| aaagaattca gtgcaaagt gaacaacaag gacctgcctg cccccatcga gcggaccatc | 1020 |
| agcaagccca agggcagcgt gcgggctccc caggtgtacg tgctgccccc acccgaggaa | 1080 |
| gagatgacca gaagcaggt cacactgacc tgcatggtca ccgacttcat gcccgaggac | 1140 |
| atctacgtgg aatggaccaa caacggcaag accgagctga actacaagaa caccgagcct | 1200 |
| gtgctggaca gcgacggcag ctacttcatg tacagcaagc tgcgggtgga aaagaaaaac | 1260 |
| tgggtggaac ggaacagcta cagctgcagc gtggtgcacg agggcctgca caaccaccac | 1320 |
| accaccaaga gcttcagccg gacccccggc | 1350 |

<210> SEQ ID NO 203
<211> LENGTH: 654
<212> TYPE: DNA
<213> ORGANISM: Mus Musculus

<400> SEQUENCE: 203

| | |
|---|---|
| gatatcgtgc tgacacagag ccccgccagc ctgaccgtgt ctctcggcca gagagccacc | 60 |

```
atcagctgcc gggccagcca gagcgtgtcc accagcagct acagctacat gcagtggtat    120
cagcagcggc ctggccagcc ccccaagctg ctgattaagt acgccaccaa cctggacagc    180
ggcgtgcccg ccagattttc tggcagcggc agcggcacag acttcaccct gaacatccac    240
cccgtggaag aagaggacgc cgccacctac tactgccagc acagctggga gatcccttac    300
accttcggcg gaggcaccaa gctggaaatc aagcgggccg atgccgcccc taccgtgtcc    360
atcttcccac ccagcagcga gcagctgacc agcggcggag ccagcgtcgt gtgcttcctg    420
aacaacttct accccaagga catcaacgtg aagtggaaga tcgacggcag cgagcggcag    480
aacggcgtgc tgaacagctg gaccgaccag gacagcaagg actccaccta cagcatgagc    540
agcaccctga ccctgaccaa ggacgagtac gagcggcaca cagctacac atgcgaggcc    600 acccacaaga ccagcaccag ccccatcgtg aagtccttca ccggaacga gtgc           654

<210> SEQ ID NO 204
<211> LENGTH: 1344
<212> TYPE: DNA
<213> ORGANISM: Mus Musculus

<400> SEQUENCE: 204
gaagtgaagc tggaagagtc tggcggcgga ctggtccagc ctggcggcag catgaagctg     60
agctgcgtgg ccagcggctt caccttcaac aactactgga tgagctgggt ccgacagagc    120
cccgagaagg gcctggaatg gctggccgag atccggctga gtccgacaa ctacgccacc     180 cactacgccg agagcgtgaa gggcaagttc accatcagcc gggacgacag caagagccgg    240
ctgtacctgc agatgaacaa cctgcgggcc gagaacaccg gcatctacta ctgcaccggc    300
ggcttcgccg actacttcga ctactggggc cagggcacca ccctgaccgt gtcctctgcc    360
aagaccaccg cccctagcgt gtaccctctg gcccctgtgt gtggcgacac caccggcagc    420
tctgtgactc tgggctgcct ggtcaagggc tacttccccg agcccgtgac actgacctgg    480
aacagcggca gcctgagcag cggcgtgcac acctttccag ccgtgctgca gagcgacctg    540
tacaccctga gcagctccgt gaccgtgaca agcagcacct ggcccagcca gagcatcacc    600
tgtaacgtgg cccaccccgc cagcagcacc aaggtggaca gaagatcga gcccagaggc    660 cccaccatca gccctgcc ccttgcaag tgcccagcc caatctgct gggcggaccc         720 agcgtgttca tcttcccacc caagatcaag gacgtgctga tgatcagcct gagccccatc    780
gtgacctgcg tggtggtgga cgtgtccgag gacgaccccg acgtgcagat cagttggttc    840
gtgaacaacg tggaagtgca caccgcccag acccagaccc agagagga ctacaacagc      900 accctgcggg tggtgtccgc cctgcccatc cagcaccagg actggatgag cggcaaagaa    960
ttcaagtgca aagtgaacaa caaggacctg cctgccccca tcgagcggac catcagcaag   1020
cccaagggca gcgtgcgggc tcccagtg tacgtgctgc cccacccga ggaagagatg      1080 accaagaagc aggtcacact gacctgcatg gtcaccgact tcatgcccga ggacatctac   1140
gtggaatgga ccaacaacgg caagaccgag ctgaactaca gaacaccga gcctgtgctg    1200 gacagcgacg gcagctactt catgtacagc aagctgcggg tggaaaagaa aaactgggtg   1260
gaacggaaca gctacagctg cagcgtggtg cacgagggcc tgcacaacca ccacaccacc   1320
aagagcttca gccggacccc cggc                                         1344

<210> SEQ ID NO 205
<211> LENGTH: 654
<212> TYPE: DNA
```

<213> ORGANISM: Homo Sapiens

<400> SEQUENCE: 205

| | | | | | |
|---|---|---|---|---|---|
| gacattgtgc | tgacacagtc | tcctgcttcc | ctggctgtat | ctctgggca gagggccacc | 60 |
| atctcatgca | gggccagcaa | aagtgtcagt | acatctagct | atagttatat gcactggtac | 120 |
| caacagaaac | caggacagcc | acccaaactc | ctcatcaaat | atgcatccaa cctagaatct | 180 |
| ggggtccctg | ccaggttcag | tggcagtggg | tctgggacag | acttctccct caacatccat | 240 |
| cccatggagg | aggacgatac | cgcaatgtat | ttctgtcagc | acagtaggga gcttccattc | 300 |
| acgttcggcg | agggacaaa | gttggaaata | aaacgtacgg | tggccgctcc cagcgtgttc | 360 |
| atcttcccac | ccagcgacga | gcagctgaag | tccggcaccg | ccagcgtcgt gtgcctgctg | 420 |
| aacaacttct | accccgcga | ggccaaggtg | cagtggaagg | tggacaacgc cctgcagagc | 480 |
| ggcaacagcc | aggaaagcgt | caccgagcag | gacagcaagg | actccaccta cagcctgtcc | 540 |
| agcaccctga | ccctgagcaa | ggccgactac | gagaagcaca | aggtgtacgc ctgcgaagtg | 600 |
| acccaccagg | gcctgagcag | ccccgtgacc | aagagcttca | ccggggcga gtgc | 654 |

<210> SEQ ID NO 206
<211> LENGTH: 1350
<212> TYPE: DNA
<213> ORGANISM: Homo Sapiens

<400> SEQUENCE: 206

| | | | | | |
|---|---|---|---|---|---|
| caggtccagc | tggtgcagtc | tggggctgag | gtgaagaagc | ctggggcctc agtgaaggtt | 60 |
| tcctgcaagg | gttccggcta | cacattcact | gattatggca | tgcactgggt gcggcaggcc | 120 |
| cctggacaag | ggctagagtg | gatgggagtt | attagtactt | acaatggtta tacaaactac | 180 |
| aaccagaagt | ttaagggcag | agtcacaatg | actgtagaca | aatccacgag cacagcctat | 240 |
| atggaacttc | ggagcttgag | atctgacgat | acggccgtgt | attactgtgc aagagcctac | 300 |
| tatggcaacc | tttactatgc | tatggactac | tggggtcaag | gaaccctggt caccgtctcc | 360 |
| tcagctagca | ccaaaggccc | gagcgtgttt | ccgctggccc | cgagcagcaa gagcaccagc | 420 |
| ggcggaacag | ccgccctggg | ctgcctggtg | aaagactact | ccccgaacc ggtgaccgtg | 480 |
| tcctggaact | ctggcgccct | gaccagcgga | gtgcatacct | tccccgccgt gctgcagagc | 540 |
| agcggcctgt | acagcctgag | cagcgtggtg | acagtgccca | gcagcagcct gggaacccag | 600 |
| acctacatct | gcaacgtgaa | ccacaagccc | agcaacacca | aggtggacaa gaaggtggaa | 660 |
| cccaagagct | gcgacaagac | ccacacctgt | ccccccctgcc | ctgcccctga actgctgggc | 720 |
| ggacccagcg | tgttcctgtt | cccccccaaag | cccaaggaca | ccctgatgat cagccggacc | 780 |
| cccgaagtga | cctgcgtggt | ggtggacgtg | tcccacgagg | acccagaagt gaagtttaat | 840 |
| tggtacgtgg | acggcgtgga | agtgcataac | gccaagacca | gcccagaga ggaacagtac | 900 |
| aacagcacct | accgggtggt | gtccgtgctg | accgtgctgc | accaggactg gctgaacggc | 960 |
| aaagagtaca | agtgcaaggt | ctccaacaag | gccctgcctg | cccccatcga gaaaaccatc | 1020 |
| agcaaggcca | agggccagcc | ccgcgagcct | caggtgtaca | cactgccccc cagccgggat | 1080 |
| gagctgacca | agaaccaggt | gtccctgacc | tgtctggtga | aaggcttcta ccccagcgat | 1140 |
| atcgccgtgg | aatgggagag | caacggccag | cccgagaaca | attacaagac cacccccct | 1200 |
| gtgctggaca | gcgacggctc | attcttcctg | tactccaagc | tgaccgtgga caagagccgg | 1260 |
| tggcagcagg | gcaacgtgtt | cagctgcagc | gtgatgcacg | aggccctgca caatcactac | 1320 |
| acccagaagt | ccctgagcct | gagccccggc | | | 1350 |

<210> SEQ ID NO 207
<211> LENGTH: 654
<212> TYPE: DNA
<213> ORGANISM: Homo Sapiens

<400> SEQUENCE: 207

```
gatatccaga tgacccagag ccccagcagc ctgagcgcca gcgtgggcga cagagtgacc      60
atcacctgtc gggccagcca gagcgtgtcc accagcagct acagctacat gcactggtat     120
cagcagaagc ccggcaaggc ccccaagctg ctgattaagt acgccagcaa cctggaaagc     180
ggcgtgccca gccggtttag cggctctggc agcggcaccg acttcaccct gaccatcagc     240
agtctgcagc ccgaggactt cgccacctac tactgccagc acagctggga tccccttac      300
accttcggcg gaggcaccaa ggtggaaatc aagcgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgtctaa agcagactac gagaaacaca agtctacgc ctgcgaagtc      600
acccatcagg gcctgagctc gcccgtcaca aagagcttca caggggaga gtgt            654
```

<210> SEQ ID NO 208
<211> LENGTH: 1347
<212> TYPE: DNA
<213> ORGANISM: Homo Sapiens

<400> SEQUENCE: 208

```
caggtggaat tggtggaaag cggcggaggc ctggtgcagc ctggcggaag cctgagactg      60
agctgtgccg ccagcggctt caccttcagc agctactgga tgagctgggt ccgacaggct     120
ccaggcaagg gcctggaatg ggtggccgag atccggctga agtccgacaa ctacgccacc     180
cactacgccg agagcgtgaa gggccggttc accatcagcc gggacgacag caagaacagc     240
ctgtacctgc agatgaacag cctgcgggcc gaggacaccg ccgtgtacta ctgcaccggc     300
tactacgccg acgccatgga ctactggggc cagggcaccc tggtcaccgt cagctcagcc     360
tccaccaagg gtccatcggt cttccccctg gcaccctcct ccaagagcac ctctggggc      420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagcgggt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gaccctgag       780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccggg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaagagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
```
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347

<210> SEQ ID NO 209
<211> LENGTH: 654
<212> TYPE: DNA
<213> ORGANISM: Mus Musculus

<400> SEQUENCE: 209
gatatcgtgc tgacacagtc tcccgccagc ctggccgtgt ctctcggcca gagagccacc      60
atcagctgca aggccagcca gagcgtgtcc accagcacct acagctacat gcagtggtat     120
cagcagcggc ctggacagag ccccaagctg ctgattaagt acgccagcaa gctggacagc     180
ggcgtgcccg ccagattttc tggcagcggc agcggcaccg acttcaccct gaacatccac     240
cccgtggaag aagaggacac cgccacctac tactgccagc acagctggga gctgccctac     300
accttcggcg gaggcacccg gctggaaatc aagagggccg atgccgcccc taccgtgtcc     360
atcttcccac ccagcagcga gcagctgacc agcggcggag ccagcgtcgt gtgcttcctg     420
aacaacttct accccaagga catcaacgtg aagtggaaga tcgacggcag cgagcggcag     480
aacggcgtgc tgaacagctg gaccgaccag gacagcaagg actccaccta cagcatgagc     540
agcaccctga ccctgaccaa ggacgagtac gagcggcaca cagctacac atgcgaggcc      600 acccacaaga ccagcaccag ccccatcgtg aagtccttca ccggaacga gtgc             654

<210> SEQ ID NO 210
<211> LENGTH: 1344
<212> TYPE: DNA
<213> ORGANISM: Mus Musculus

<400> SEQUENCE: 210
gaagtgaagc tgggagagtc tggcggcgga ctggtccagc ctggcggcag catgaagctg      60
agctgcgtgg ccagcggctt cccattcacc aaatactgga tgaactgggt ccgacagagc     120
cccgagaagg gcctggaatg ggtggccgag atccggctga gtccgacaa ctacgccacc      180 cactacgccg agagcgccaa gggccggttc accatcagcc gggacgacag ccggtccagc     240
gtgtacctgc agatgaacaa cctgcgggcc gaggacaccg ccatctacta ctgcagcccc     300
acctatgccg acaccatgga ctactggggc cagggcacca gcgtgacagt gtccagcgcc     360
aagaccaccg cccctagcgt gtaccctctg gcccctgtgt gtggcgacac caccggcagc     420
tctgtgactc tgggctgcct ggtcaagggc tacttccccg agcccgtgac actgacctgg     480
aacagcggca gcctgagcag cggcgtgcac acctttccag ccgtgctgca gagcgacctg     540
tacaccctga gcagctccgt gaccgtgaca agcagcacct ggcccagcca gagcatcacc     600
tgtaacgtgg cccaccccgc cagcagcacc aaggtggaca gaagatcga gcccagaggc     660 cccaccatca gccctgcccc ccttgcaag tgcccagccc ccaatctgct gggcggaccc     720
agcgtgttca tcttcccacc caagatcaag gacgtgctga tgatcagcct gagccccatc     780
gtgacctgcg tggtggtgga cgtgtccgag gacgaccccg acgtgcagat cagttggttc     840
gtgaacaacg tggaagtgca caccgcccag acccagaccc acagagagga ctacaacagc     900
accctgcggg tggtgtccgc cctgcccatc cagcaccagg actggatgag cggcaaagaa     960
ttcaagtgca aagtgaacaa caaggacctg cctgccccca tcgagcggac catcagcaag    1020
cccaagggca gcgtgcgggc tccccaggtg tacgtgctgc ccccacccga ggaagagatg    1080

| | |
|---|---|
| accaagaagc aggtcacact gacctgcatg gtcaccgact tcatgcccga ggacatctac | 1140 |
| gtggaatgga ccaacaacgg caagaccgag ctgaactaca agaacaccga gcctgtgctg | 1200 |
| gacagcgacg gcagctactt catgtacagc aagctgcggg tggaaaagaa aaactgggtg | 1260 |
| gaacggaaca gctacagctg cagcgtggtg cacgagggcc tgcacaacca ccacaccacc | 1320 |
| aagagcttca gccggacccc cggc | 1344 |

<210> SEQ ID NO 211
<211> LENGTH: 654
<212> TYPE: DNA
<213> ORGANISM: Mus Musculus

<400> SEQUENCE: 211

| | |
|---|---|
| gatatcgtgc tgacacagtc tcccgccagc ctggccgtgt ctctcggcca gagagccacc | 60 |
| atcagctgcc gggccagcaa gagcgtgtcc accagcagct acagctacat gcactggtat | 120 |
| cagcagaagc ccggccagcc ccccaagctg ctgatcaagt acaccagcaa cctggaaagc | 180 |
| ggcgtgcccg ccagattcag cggaagcggc tccggcaccg acttcatcct gaacatccac | 240 |
| cccgtggaag aagaggacgc cgccacctac tactgccagc acagcagaga gctgccctgg | 300 |
| accttcggcg aggcaccaa gctggaaatc aagcgggccg atgccgcccc taccgtgtcc | 360 |
| atcttcccac ccagcagcga gcagctgacc agcggcggag ccagcgtcgt gtgcttcctg | 420 |
| aacaacttct accccaagga catcaacgtg aagtggaaga tcgacggcag cgagcggcag | 480 |
| aacggcgtgc tgaacagctg gaccgaccag gacagcaagg actccaccta cagcatgagc | 540 |
| agcaccctga ccctgaccaa ggacgagtac gagcggcaca cagctacac atgcgaggcc | 600 |
| acccacaaga ccagcaccag ccccatcgtg aagtccttca ccggaacga gtgc | 654 |

<210> SEQ ID NO 212
<211> LENGTH: 1353
<212> TYPE: DNA
<213> ORGANISM: Mus Musculus

<400> SEQUENCE: 212

| | |
|---|---|
| caggtgtccc tgaaagagag cggccctggc atcctgcagc ctagccagac cctgagcctg | 60 |
| acctgcagct tcagcggctt cagcctgagc accagcggca tgggcgtgtc ctggatcaga | 120 |
| cagcccagcg gcaagggcct ggaatggctg gcccacatct actgggacga cgacaagcgg | 180 |
| tacaacccca gcctgaagtc ccggctgacc atctccaagg acaccagccg gaatcaggtg | 240 |
| ttcctgaaga tcaccagcgt ggacaccgcc gataccgcca cctactactg cgccagaaga | 300 |
| ggccccgact actacggcta ctaccccatg gactattggg gccagggcac cagcgtgacc | 360 |
| gtgtctgcca agaccaccgc ccctagcgtg taccctctgg cccctgtgtg tggcgacacc | 420 |
| accggcagct ctgtgactct gggctgcctg gtcaagggct acttccccga gccgtgaca | 480 |
| ctgacctgga acagcggcag cctgagcagc ggcgtgcaca cctttccagc cgtgctgcag | 540 |
| agcgacctgt acaccctgag cagctccgtg accgtgacaa gcagcacctg gcccagccag | 600 |
| agcatcacct gtaacgtggc ccaccccgcc agcagcacca aggtggacaa gaagatcgag | 660 |
| cccagaggcc ccaccatcaa gccctgcccc ccttgcaagt gcccagcccc caatctgctg | 720 |
| ggcggaccca gcgtgttcat cttcccaccc aagatcaagg acgtgctgat gatcagcctg | 780 |
| agccccatcg tgacctgcgt ggtggtggac gtgtccgagg acgaccccga cgtgcagatc | 840 |
| agttggttcg tgaacaacgt ggaagtgcac accgcccaga cccagaccca cagagaggac | 900 |

-continued

```
tacaacagca ccctgcgggt ggtgtccgcc ctgcccatcc agcaccagga ctggatgagc    960
ggcaaagaat tcaagtgcaa agtgaacaac aaggacctgc ctgcccccat cgagcggacc   1020
atcagcaagc caagggcag cgtgcgggct ccccaggtgt acgtgctgcc cccacccgag   1080
gaagagatga ccaagaagca ggtcacactg acctgcatgg tcaccgactt catgcccgag   1140
gacatctacg tggaatggac caacaacggc aagaccgagc tgaactacaa gaacaccgag   1200
cctgtgctgg acagcgacgg cagctacttc atgtacagca agctgcgggt ggaaaagaaa   1260
aactgggtgg aacggaacag ctacagctgc agcgtggtgc acgagggcct gcacaaccac   1320
cacaccacca gagcttcag ccggaccccc ggc                                1353
```

<210> SEQ ID NO 213
<211> LENGTH: 449
<212> TYPE: PRT
<213> ORGANISM: Homo sapiens

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg

```
                290                 295                 300
Val Val Ser Val Leu Thr Val Leu His Gln Asp Trp Leu Asn Gly Lys
305                     310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                     390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly
```